(10) Patent No.: US 12,662,451 B2

(45) Date of Patent: Jun. 23, 2026

(12) United States Patent
Brnardic et al.

US012662451B2

(54) CHEMICAL COMPOUNDS AND USES THEREOF

(71) Applicants: GLAXOSMITHKLINE INTELLECTUAL PROPERTY (NO.4) LIMITED, Stevenage (GB); IDEAYA BIOSCIENCES, INC., South San Francisco, CA (US)

(72) Inventors: Edward Brnardic, Collegeville, PA (US); Kira A. Campbell, Collegeville, PA (US); Michael P. Demartino, Collegeville, PA (US); Lara K. Leister, Collegeville, PA (US); Tessa Lynch-Colameta, Collegeville, PA (US); James P. Phelan, Collegeville, PA (US); Michael D. Vanheyst, Collegeville, PA (US); Ann M. Rowley, Collegeville, PA (US); Amberly B. Sanford, Collegeville, PA (US); Hongyi Yu, Collegeville, PA (US); Brian T. Jones, South San Francisco, CA (US); Joshua P.G. Taygerly, South San Francisco, CA (US); Daniel L. Severance, San Francisco, CA (US); Jonathon S. Ryan, South San Francisco, CA (US); Muzaffar Alam, South San Francisco, CA (US); Melissa Fleury, South San Francisco, CA (US); Ryan M. Mcfadden, South San Francisco, CA (US); Scott P. Simonovich, Oakland, CA (US)

(73) Assignees: IDEAYA BIOSCIENCES, INC., South San Francisco, CA (US); GLAXOSMITHKLINE INTELLECTUAL PROPERTY (NO.4) LIMITED, Stevenage (GB)

( * ) Notice: Subject to any disclaimer, the term of this patent is extended or adjusted under 35 U.S.C. 154(b) by 0 days.

(21) Appl. No.: 19/320,020

(22) Filed: Sep. 5, 2025

(65) Prior Publication Data

US 2026/0015321 A1 Jan. 15, 2026

Related U.S. Application Data

(63) Continuation of application No. PCT/IB2024/055354, filed on May 31, 2024, and a (Continued)

(51) Int. Cl.

| | |
|---|---|
| ***C07D 403/12*** | (2006.01) |
| ***A61K 31/341*** | (2006.01) |

(Continued)

(52) U.S. Cl.

CPC .......... *C07D 209/08* (2013.01); *A61K 31/341* (2013.01); *A61K 31/343* (2013.01); *A61K 31/351* (2013.01); *A61K 31/381* (2013.01); *A61K 31/4184* (2013.01); *A61K 31/425* (2013.01); *A61K 31/4453* (2013.01); *A61K 31/505* (2013.01); *A61K 31/5375* (2013.01); *A61P 35/00* (2018.01); *C07D 213/56* (2013.01); *C07D 235/08* (2013.01); *C07D 239/26* (2013.01); *C07D 275/02* (2013.01); *C07D 295/112* (2013.01); *C07D 307/36* (2013.01); *C07D 307/79* (2013.01); *C07D 309/04* (2013.01); *C07D 333/10* (2013.01); *C07D 403/12* (2013.01); *C07D 405/12* (2013.01);

(Continued)

(58) Field of Classification Search

None

See application file for complete search history.

(56) References Cited

FOREIGN PATENT DOCUMENTS

| | | | |
|---|---|---|---|
| WO | 2008027990 | A1 | 3/2008 |
| WO | 2016172325 | A1 | 10/2016 |

(Continued)

OTHER PUBLICATIONS

Yang. Journal of Cancer Research and Clinical Oncology, 2019, 145, 2891-2899 (Year: 2019).*

(Continued)

*Primary Examiner* — Noble E Jarrell

(74) *Attorney, Agent, or Firm* — Bryan Cave Leighton Paisner LLP

(57) ABSTRACT

Disclosed herein are certain chemical compounds of Formula (I):

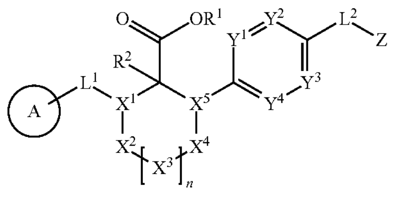

that inhibit Werner Syndrome ATP dependent helicase enzyme (WRN) activity, in particular inhibit WRN helicase domain activity and are therefore useful in treating cancers treatable by inhibition of WRN, including cancers characterized by microsatellite instability (MSI) and/or defective DNA mismatch repair system (dMMR). Also, disclosed are pharmaceutical compositions comprising such compounds, methods of using such compounds, and methods making the same.

14 Claims, 4 Drawing Sheets

Specification includes a Sequence Listing.

Related U.S. Application Data continuation of application No. PCT/IB2024/055353, filed on May 31, 2024.

(60) Provisional application No. 63/583,600, filed on Sep. 19, 2023, provisional application No. 63/505,508, filed on Jun. 1, 2023.

(51) Int. Cl.

| | |
|---|---|
| ***A61K 31/343*** | (2006.01) |
| ***A61K 31/351*** | (2006.01) |
| ***A61K 31/381*** | (2006.01) |
| ***A61K 31/4184*** | (2006.01) |
| ***A61K 31/425*** | (2006.01) |
| ***A61K 31/4453*** | (2006.01) |
| ***A61K 31/505*** | (2006.01) |
| ***A61K 31/5375*** | (2006.01) |
| ***A61P 35/00*** | (2006.01) |
| ***C07D 209/08*** | (2006.01) |
| ***C07D 213/56*** | (2006.01) |
| ***C07D 235/08*** | (2006.01) |
| ***C07D 239/26*** | (2006.01) |
| ***C07D 275/02*** | (2006.01) |
| ***C07D 295/112*** | (2006.01) |
| ***C07D 307/36*** | (2006.01) |
| ***C07D 307/79*** | (2006.01) |
| ***C07D 309/04*** | (2006.01) |
| ***C07D 333/10*** | (2006.01) |
| ***C07D 405/12*** | (2006.01) |
| ***C07D 471/04*** | (2006.01) |
| ***C07D 487/04*** | (2006.01) |
| ***C07D 495/04*** | (2006.01) |

(52) U.S. Cl.

CPC ......... *C07D 471/04* (2013.01); *C07D 487/04* (2013.01); *C07D 495/04* (2013.01)

(56) References Cited

FOREIGN PATENT DOCUMENTS

| | | | |
|---|---|---|---|
| WO | 2019241802 | A2 | 12/2019 |
| WO | 2022249060 | A1 | 12/2022 |
| WO | 2023062575 | A1 | 4/2023 |

OTHER PUBLICATIONS

Olave. Genes Chromosome Cancer, 2022, 61, 314-321 (Year: 2022).*

Abdel-Magid. ACS Medicinal Chemistry Letters, 16, 959-962, published May 20, 2025 (Year: 2025).*

Sommers Joshua et al PLOS ONE 2019 vol. 14 No. 1 pp. 1-23.

Parham William et al Journal of Organic Chemistry 1956 vol. 21 No. 1 pp. 72-77.

Bhoite Shubhangi et al Asian Journal Organic Chemistry 2019 vol. 8 No. 10 99 1907-1911.

Zotova et al Journal of Organic Chemistry 2018 vol. 83 No. 15 pp. 8193-8207.

PCT/IB2024/055353 International Search Report and Written Opinion dated Aug. 20, 2024 15 pages.

PCT/IB2024/055354 International Search Report and Written Opinion dated Aug. 20, 2024 13 pages.

* cited by examiner

CHEMICAL COMPOUNDS AND USES THEREOF

CROSS-REFERENCE TO RELATED APPLICATIONS

This application claims priority to International Application No. PCT/IB2024/055353 filed May 31, 2024 and PCT/IB2024/055354 filed May 31, 2024, which claim the benefit of U.S. provisional application 63/583,600 filed Sep. 19, 2023, and U.S. provisional application 63/505,508 filed Jun. 1, 2023; the contents of each of the four applications are incorporated by reference herein.

FIELD OF THE INVENTION

Disclosed herein are certain compounds that inhibit Werner Syndrome helicase enzyme (WRN) activity, in particular inhibit ATP dependent helicase domain activity and are therefore useful in treating cancers treatable by inhibition of WRN, including cancers characterized by microsatellite instability (MSI) and/or defective DNA mismatch repair system (dMMR). Also, disclosed are pharmaceutical compositions comprising such compounds and methods of making the same.

SEQUENCE LISTING

This application contains a Sequence Listing which has been submitted electronically in XML format and is hereby incorporated by reference in its entirety. Said XML, created on May 29, 2024, is named 70333WO01 Seq List XML 29May2024.xml and is 6,092 bytes in size.

BACKGROUND TO THE INVENTION

Cancer is a leading cause of death throughout the world. A limitation of prevailing therapeutic approaches, e.g., chemotherapy is that their cytotoxic effects are not restricted to cancer cells and adverse side effects can occur within normal tissues. Consequently, novel strategies are needed to better target cancer cells.

Synthetic lethality (SL) arises when a combination of deficiencies in the expression of two or more genes or corresponding loss of function of related gene product proteins (e.g., resulting from one or more chromosomal mutations) leads to cell death, whereas a singular deficiency/loss of function does not. For example, one of the genes (or gene products) can be involved in cell proliferation, whereas the other of the genes (or gene products) can be a non-essential gene. The concept of synthetic lethality originates from studies in *drosophila* model systems in which a combination of mutations in two or more separate genes leads to cell death (in contrast to viability, or even cell proliferation, which occurs when only one of the genes is mutated or deleted). More recently, studies have explored maladaptive genetic changes in cancer cells that render them vulnerable to synthetic-lethality approaches. These tumor-specific genetic defects can create a vulnerability, which enable the use of targeted agents that are synthetically lethal to such tumor-specific genomic defect and induce the death of tumor cells while sparing normal cells.

Disruptions in DNA repair pathways predispose cells to accumulating DNA damage. Various types of tumors are known to accumulate more mutations in DNA as cancers progress. Therefore, pathways involved in DNA repair can be targeted by cytotoxic treatments based on synthetic lethality, turning dysregulated repair processes against themselves to induce tumor death.

Identifying SL interactions that are relevant in cancers is an area of focus for biological discovery efforts. In a yeast screen looking to uncover SL interactions between tumor suppressor genes and drug targets, SGS1, gene encoding a RECQ helicase, was found to be SL with several genes in the screen. In the same study using human cells, Bloom syndrome helicase (BLM), one of five human RECQ helicases, was SL with Check point kinase (CHEK) 1 and 2 (Srivas R, et al., Mol Cell 2016; 63(3):514-25). During DNA damage repair (DDR), BLM participates in homologous recombination (HR). RECQ helicases are 3' to 5' DNA unwinding DNA-dependent ATPases. Three RECQ helicases, BLM, WRN (WRN) and RECQL4, cause human syndromes that overlap, but are also distinct symptomatically, when their expression is altered or lost (de Renty C, Ellis N A. Ageing Res Rev 2017; 33:36-51). This suggests that they may have overlapping, and distinct functions based on when and where they are expressed in cells, their protein-protein interactions and post-translational modifications.

Another study (DRIVE) using approximately 400 cell lines includes data from which it can be shown that WRN is not broadly essential but that MSI cell lines from large intestine, endometrial and stomach tissues of origin are sensitive to WRN shRNAs (McDonald E R, 3rd, de Weck A, Schlabach M R, Billy E, Mavrakis K J, Hoffman G R, et al., Cell 2017; 170(3):577-92). The DepMap study, which derives in part from the DRIVE data, also found a pattern of WRN essentiality in MSI cell lines (Tsherniak A, Vazquez F, Montgomery P G, Weir B A, Kryukov G, Cowley G S, et al., Cell 2017; 170(3):564-76). None of the other human RECQ helicases tested in the study showed this MSI SL interaction.

In confirmation of the DRIVE and DepMap studies, it has been reported by several labs that survival of cancer cells with high microsatellite instability are selectively compromised by knockout of WRN (Behan, F. M. et. al., Nature 2019; 568(7753): 511-16, Chan, E. M. et al., Nature 2019; 568 (551-556), Lieb, S. et al., eLife 2019; 8:e43333, Kategaya, L. et al., iScience 2019; 13:488-497.) WRN is an enzyme that has both an exonuclease domain and an ATP dependent helicase domain. Kategaya, L. et al., supra, identified a synthetic lethality relationship between patients having tumors characterized by high microsatellite instability and, in particular, the ATP dependent helicase domain activity of WRN protein. Identification of patients having tumors characterized by high microsatellite instability, reflecting a high frequency of microsatellite instability, is known in the art, including for example as disclosed by Dudley, Jonathan C., et al., *Clinical Cancer Research,* 22(4): 813-820, 2016.).

These results indicate that WRN inhibitors may provide a novel therapy for cancer patients having tumors with microsatellite instability (MSI) as a marker of DNA mismatch repair (dMMR), including those patients with MSI-high tumors. Microsatellites are repetitive DNA sequences with varying unit lengths (e.g. ranging from one (mononucleotides) to six bases (di-, tri-, tetra-, penta-, esa-nucleotides)) distributed along coding and/or noncoding regions of the genome. Mutations of such microsatellites, for example, repeat length alterations, can represent microsatellite instability. As known in the art and more fully described herein, MSI can be detected (e.g., directly) by molecular testing (e.g., with respect to certain microsatellites) or (e.g., indirectly) by immunohistochemical evaluation (e.g., with respect to expression of certain MMR proteins). Based on a consensus NCI-Reference Panel (Bethesda, 1998), MSI can be assessed by molecular testing of five microsatellites—including two mononucleotides (BAT25 and BAT26) and three dinucleotides (D2S123, D5S346, D17S250). Tumors can be classified into different subtypes based on such a NCI-Reference Panel approach for molecular testing, including MSI-high (MSI-H) if two or more of the microsatellite markers show instability, MSI-low (MSI-L) if only one microsatellite marker shows instability, and MS-stable (MSS) if none of the five microsatellite markers show instability (i.e., each of the five microsatellite markers are determined as stable). In some instances, for example where molecular testing or immunohistochemical evaluation is not able to distinguish between MSI-L and general chromosomal instability, tumors can be classified as a MSS neoplasms.

SUMMARY OF THE INVENTION

In a first aspect, the present invention provides a compound of Formula (I-a):

(I-a)

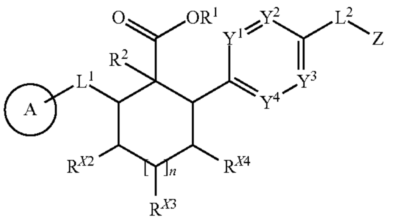

wherein:

- ring A is aryl, heteroaryl, $C_{3-10}$ cycloalkyl, or 3- to 10-membered heterocycloalkyl ring containing one, two, or three heteroatoms independently selected from N, O, and S, wherein ring A is mono- or bicyclic and ring A is optionally substituted with up to three substituents independently selected from halo, cyano, nitro, hydroxy, —$NR^aR^b$, carboxy, —$CONR^aR^b$, $C_{1-3}$ alkyl, $C_{1-3}$ alkoxy, halo($C_{1-3}$)alkyl, halo($C_{1-3}$)alkoxy, hydroxy($C_{1-3}$)alkyl, cyano($C_{1-3}$)alkyl, $C_{1-3}$ alkylsulfonyl, —C(O)O($C_{1-4}$)alkyl, and $C_{3-7}$ cycloalkyl;
- $L^1$ is —$NR^c$—C(O)—, —$OCH_2$—, —$NR^c$—$CH_2$—, or —$CH_2$—;
- n is 0, 1, or 2;
- $R^1$ is hydrogen or $C_{1-3}$ alkyl;
- $R^2$ is hydrogen, halo, or $C_{1-3}$ alkyl;
- $R^{X2}$, $R^{X3}$, and $R^{X4}$ are each independently selected from hydrogen, halo, cyano, —$NR^dR^e$, hydroxy, carboxy, phenoxy, phenyl, $C_{1-3}$alkyl, halo($C_{1-3}$)alkyl, hydroxy($C_{1-3}$)alkyl, $C_{1-3}$alkoxy($C_{1-3}$)alkyl-, $C_{1-3}$ alkoxy, halo($C_{1-3}$)alkoxy, and $L^X$-V;
- $R^{X5}$ is hydrogen, halo, hydroxy, or $C_{1-3}$ alkyl; or
- any two of $R^{X2}$, $R^{X3}$, $R^{X4}$, or $R^{X5}$ taken together with the carbon atoms to which they are attached form a 3- to 6-membered ring which optionally contains one or two heteroatoms independently selected from N, O, and S and which is optionally substituted with up to three substituents independently selected from halo, $C_{1-3}$ alkyl, halo($C_{1-3}$)alkyl, $C_{1-3}$ alkoxy, and halo($C_{1-3}$) alkoxy;
- $L^X$ is a bond, —$CH_2$—, —$NR^d$C(O)—, —$NR^d$—$(CH_2)_w$—, —O—$(CH_2)_w$—, or —S—$(CH_2)_w$—;
- V is independently $C_{3-7}$ cycloalkyl or a 3- to 10-membered heterocycloalkyl ring containing one, two, or three heteroatoms independently selected from N, O, and S, wherein V is optionally substituted with up to three substituents independently selected from halo, $C_{1-3}$ alkyl, halo($C_{1-3}$)alkyl, $C_{1-3}$ alkoxy, and halo($C_{1-3}$) alkoxy;
- $Y^1$, $Y^2$, $Y^3$, and $Y^4$ are each independently N or CRY, and at most two of $Y^1$, $Y^2$, $Y^3$, and $Y^4$ are N;
- $L^2$ is a bond, —NRf—$S(O)_2$—, —NRf—C(O)—, or —$(CH_2)_p$—;
- Z is hydrogen, halo, cyano, hydroxy, —$NR^gR^h$, nitro, carboxy, $C_{1-3}$ alkyl, $C_{1-3}$alkoxy, halo($C_{1-3}$)alkyl, halo($C_{1-3}$)alkoxy, hydroxy($C_{1-3}$)alkyl, cyano($C_{1-3}$)alkyl, $C_{2-5}$ alkenyl, halo($C_{2-5}$)alkenyl, $C_{2-5}$ alkynyl, or halo($C_{2-5}$)alkynyl; or
- Z is ring B, wherein ring B is aryl, heteroaryl, $C_{3-10}$ cycloalkyl, or 3- to 10-membered heterocycloalkyl ring containing one, two, or three heteroatoms independently selected from N, O, and S, wherein ring B is mono- or bicyclic and ring B is optionally substituted with up to three substituents independently selected from halo, cyano, nitro, hydroxy, carboxy, $C_{1-3}$alkyl, $C_{1-3}$ alkoxy, halo($C_{1-3}$)alkyl, halo($C_{1-3}$)alkoxy, hydroxy($C_{1-3}$)alkyl, $C_{2-5}$ alkenyl, $C_{2-5}$ alkynyl, —$C_{1-3}$ alkylene-$NR^gR^h$, —$CONR^gR^h$, —$NR^gR^h$, —$NR^g$C(O)$R^h$, $SO_2NR^gR^h$, and $L^B$-W, or
- two substituents of ring B taken together with the atoms to which they are attached form a 5- or 6-membered ring which optionally contains one or two heteroatoms independently selected from N, O, and S;
- $L^B$ is independently selected from a bond, —$(CH_2)_p$—, —$CH_2O$—, —C(O)—NH—, —C(O)—, and —$CH_2$C(O)NH—;
- W is independently selected from hydrogen, $C_{1-3}$ alkyl, —O($C_{1-4}$)alkyl, $C_{3-7}$ cycloalkyl, 5- or 6-membered heteroaryl, and 4- to 6-membered heterocycloalkyl ring containing one, two, or three heteroatoms independently selected from N, O, and S, wherein W is optionally substituted with up to three substituents independently selected from halo, cyano, nitro, hydroxy, —$NR^mR^n$, carboxy, —$CONR^mR^n$, $C_{1-3}$alkyl, $C_{1-3}$alkoxy, halo($C_{1-3}$)alkyl, halo($C_{1-3}$)alkoxy, hydroxy($C_{1-3}$)alkyl, cyano($C_{1-3}$)alkyl, $C_{1-3}$ alkylsulfonyl, —C(O)O($C_{1-4}$)alkyl, and $C_{3-7}$ cycloalkyl;
- each $R^y$ is independently hydrogen, halo, cyano, nitro, hydroxy, —$NR^jR^k$, carboxy, $C_{1-3}$ alkyl, halo($C_{1-3}$)alkyl, hydroxy($C_{1-3}$)alkyl, cyano($C_{1-3}$)alkyl, $C_{1-3}$ alkoxy, halo($C_{1-3}$)alkoxy, methoxy($C_{1-3}$)alkoxy, $C_{2-5}$ alkenyl, halo($C_{2-5}$)alkenyl, hydroxy($C_{2-5}$)alkenyl, $C_{2-5}$ alkynyl, halo($C_{2-5}$)alkynyl, hydroxy($C_{2-5}$)alkynyl, or 5- or 6-membered heteroaryl containing one, two, or three heteroatoms independently selected from N, O, and S, wherein the heteroaryl is optionally substituted with up to three $C_{1-3}$ alkyl;
- $R^a$, $R^b$, $R^c$, $R^d$, $R^f$, $R^g$, $R^h$, $R^i$, $R^k$, $R^m$, and $R^n$ are each independently hydrogen, $C_{1-3}$ alkyl, or $C_{3-7}$ cycloalkyl; or
- $R^y$ and $R^f$ taken together with the atoms to which they are attached form a 5- or 6-membered ring which contains one or two heteroatoms independently selected from N, O, and S;
- $R^e$ is hydrogen, $C_{1-3}$ alkyl, halo($C_{1-3}$)alkyl, $C_{3-7}$ cycloalkyl, or —C(O)$C_{1-3}$ alkyl;
- each p is independently 1 or 2; and
- each w is independently 0, 1, 2, or 3;
- or a pharmaceutically acceptable salt thereof.

In a second aspect, the present invention provides a pharmaceutical composition comprising a) a compound or pharmaceutically acceptable salt thereof of the invention disclosed herein and b) a pharmaceutically acceptable excipient.

In a third aspect, the present disclosure provides a compound of the invention disclosed herein for use in therapy.

In a fourth aspect, the present disclosure provides a compound of the invention disclosed herein for use in the treatment of cancer.

In a fifth aspect, the present disclosure provides a method of treatment of cancer in a subject in need thereof comprising administering to said subject a therapeutically effective amount of a compound or pharmaceutically acceptable salt thereof of the invention disclosed herein or pharmaceutical composition as disclosed herein.

In a sixth aspect, the present disclosure provides use of a compound of the invention disclosed herein in the manufacture of a medicament for use in the treatment of cancer.

DETAILED DESCRIPTION

Definitions

Figure 1:
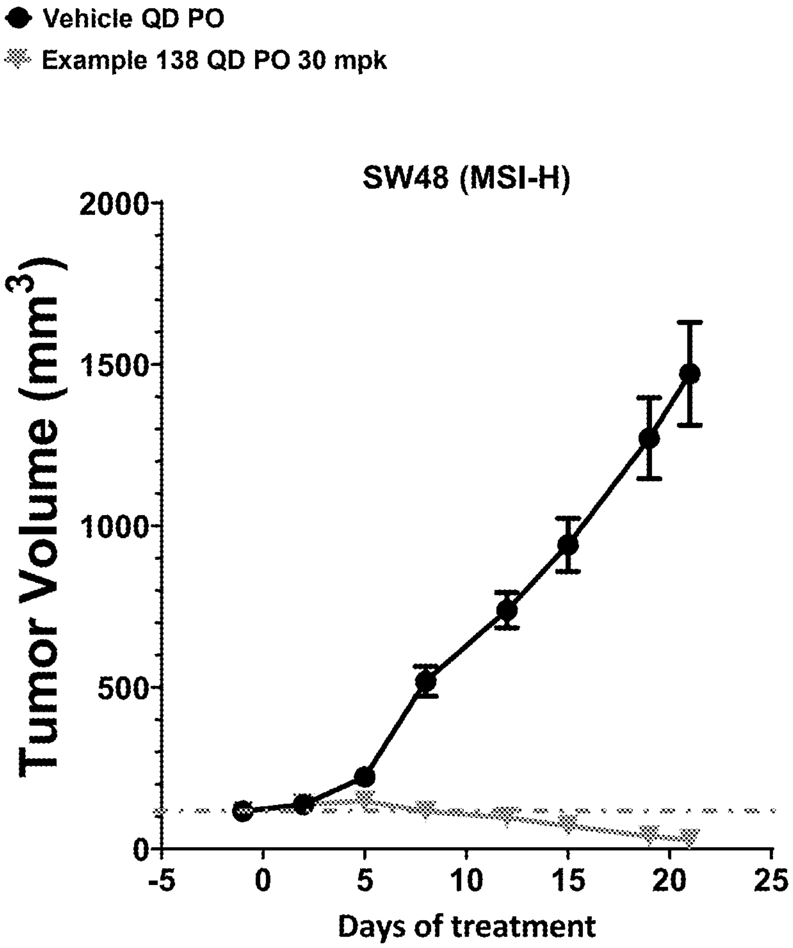
FIG. 1 shows an efficacy study of the compound of Example 138 in mouse model bearing SW48 human colorectal cancer cell line xenografts.

As used herein, the terms "a" and "an" are to be construed to encompass both the singular and plural unless otherwise indicated. For example, the phrase "a pharmaceutically acceptable excipient" refers to one or more pharmaceutically acceptable excipients.

As used herein, the terms "halogen" and "halo" represent chloro, fluoro, bromo, or iodo substituents.

As used herein, the term "cyano" refers to the group —CN.

As used herein, the term "nitro" refers to the group —$NO_2$.

As used herein, the term "hydroxy" or "hydroxyl" refers to the group —OH.

As used herein, the term "carboxy" refers to the group —COOH.

As used herein, the term "alkyl" refers to a saturated hydrocarbon radical, straight or branched, having the specified number of carbon atoms. For example, the term "$C_{1-4}$ alkyl" refers to an alkyl group having 1 to 4 carbon atoms and the term "$C_{1-3}$ alkyl" refers to an alkyl group having 1 to 3 carbon atoms. Exemplary groups include, but are not limited to, methyl, ethyl, propyl (n-propyl and isopropyl), butyl (n-butyl, sec-butyl, isobutyl and tert-butyl).

When the term "alkyl" is used in combination with other substituent groups, such as "halo($C_{1-3}$)alkyl" and "hydroxy ($C_{1-3}$)alkyl" the term "alkyl" is intended to encompass a divalent straight or branched chain hydrocarbon radical, wherein the point of attachment is through the alkyl moiety.

As used herein, the term "halo($C_{1-3}$)alkyl" is intended to mean a radical having one or more halogen atoms, which may be the same or different, at one or more carbon atoms of an alkyl moiety containing from 1 to 3 carbon atoms, which is a straight or branched chain carbon radical. Exemplary groups include, but are not limited to, —$CHF_2$ (difluoromethyl), —$CF_3$ (trifluoromethyl), —$CCl_3$ (trichloromethyl), 1,1-difluoroethyl, 2,2,2-trifluoroethyl, 2-fluoroisopropyl, and hexafluoroisopropyl.

As used herein, the term "hydroxy($C_{1-3}$)alkyl" is intended to mean a radical having one or more hydroxy groups at one or more carbon atoms of an alkyl moiety containing from 1 to 3 carbon atoms, which is a straight or branched chain carbon radical. Exemplary groups include, but are not limited to, hydroxymethyl (—$CH_2OH$), 2-hydroxyethyl (—$CH_2CH_2OH$), and hydroxy-isopropyl. As used herein, the term "cyano($C_{1-3}$)alkyl" is intended to mean a radical having one or more cyano groups at one or more carbon atoms of an alkyl moiety containing 1 to 3 carbon atoms, which is a straight or branched chain carbon radical. Exemplary groups include, but are not limited to, cyanoethyl and cyanopropyl.

As used herein, the term "$C_{1-3}$alkylsulfonyl" refers to the group —$SO_2R$, wherein R is an alkyl group. Exemplary groups include, but are not limited to, methylsulfonyl (i.e., —$SO_2Me$), ethylsulfonyl (i.e., —$SO_2Et$), and n-propylsulfonyl (i.e., —$SO_2{}^nPr$). The term "sulfonyl($C_{1-3}$)alkyl" is used interchangeably with "$C_{1-3}$ alkylsulfonyl" herein.

As used herein, the term "alkenyl" refers to a straight or branched hydrocarbon radical containing the specified number of carbon atoms and at least one double bond. For example, "$C_{2-5}$ alkenyl" has 2 to 5 carbon atoms. Exemplary groups include, but are not limited to, ethenyl and propenyl.

As used herein, the term "halo($C_{2-5}$)alkenyl" is intended to mean a radical having one or more halogen atoms, which may be the same or different, at one or more carbon atoms of an alkenyl moiety containing from 2 to 5 carbon atoms, which is a straight or branched chain carbon radical. Exemplary groups include, but are not limited to, —CH═CHF, —CH═$CF_2$ and —CF═$CF_2$.

As used herein, the term "hydroxy($C_{2-5}$)alkenyl" is intended to mean a radical having one or more hydroxy groups at one or more carbon atoms of an alkenyl moiety containing from 2 to 5 carbon atoms, which is a straight or branched chain carbon radical. Exemplary groups include, but are not limited to, prop-2-enyl-1-ol, but-3-enyl-2-ol, 2-methyl-but-3-enyl-2-ol.

As used herein, the term "alkynyl" refers to a straight or branched hydrocarbon radical containing the specified number of carbon atoms and at least one triple bond. For example, "$C_{2-5}$ alkynyl" has 2 to 5 carbon atoms. Exemplary groups include, but are not limited to, ethynyl and propynyl.

As used herein, the term "halo($C_{2-5}$)alkynyl" is intended to mean a radical having one or more halogen atoms, which may be the same or different, at one or more carbon atoms of an alkynyl moiety containing from 2 to 5 carbon atoms, which is a straight or branched chain carbon radical. Exemplary groups include, but are not limited to, 3-fluoro-prop-1-ynyl, 3-fluoro-but-1-ynyl, 3-fluoro-3-methylbut-1-ynyl.

As used herein, the term "hydroxy($C_{2-5}$)alkynyl" is intended to mean a radical having one or more hydroxy groups at one or more carbon atoms of an alkynyl moiety containing from 2 to 5 carbon atoms, which is a straight or branched chain carbon radical. Exemplary groups include, but are not limited to, prop-2-ynyl-1-ol, but-3-ynyl-2-ol, 2-methyl-but-3-ynyl-2-ol.

As used herein, the term "alkylene" refers to a divalent radical derived from a straight or branched, saturated hydrocarbon group of, for example, 1 to 3 carbon atoms ($C_{1-3}$ alkylene). Exemplary groups include, but are not limited to, $-CH_2-$, $-CH_2CH_2-$, and $-CH_2CH_2CH_2-$.

As used herein, the term "alkoxy" refers to an —O-alkyl group, i.e., an alkyl group which is attached through an oxygen linking atom, wherein "alkyl" is defined above. For example, the term "$C_{1-3}$ alkoxy" refers to an alkoxy group having 1 to 3 carbon atoms. Exemplary groups include, but are not limited to, methoxy, ethoxy, n-propoxy, and isopropoxy.

As used herein, the term "phenoxy" refers to an —O-Ph group, i.e., a phenyl group which is attached through an oxygen linking atom.

As used herein, the term "halo($C_{1-3}$)alkoxy" refers to a straight or branched chain hydrocarbon radical, having at least 1 and up to 3 carbon atoms with one or more halogen atoms, which may be the same or different, attached to one or more carbon atoms, which radical is attached through an oxygen linking atom. Exemplary groups include, but are not limited to, $-OCHF_2$ (difluoromethoxy), $-OCF_3$ (trifluoromethoxy), $-OCH_2CHF_2$ (2,2-difluoroethoxy), and $-OCH(CF_3)_2$ (hexafluoroisopropoxy).

As used herein, the term "cycloalkyl" refers to a non-aromatic, saturated, hydrocarbon ring containing the specified number of carbon atoms, which may be monocyclic or bicyclic. Bicyclic cycloalkyl groups may be bridged, fused, or spiro bicyclic groups. For example, "$C_{3-10}$ cycloalkyl" refers to a cycloalkyl group containing 3 to 10 carbon atoms and the term "$C_{3-7}$ cycloalkyl" refers to a cycloalkyl group having 3 to 7 carbon atoms. Exemplary groups include, but are not limited to, cyclopropyl, cyclobutyl, cyclopentyl, bicyclo[1.1.1]pentyl, cyclohexyl, cycloheptyl, bicyclo[2.2.1]heptyl, cyclooctyl, octahydropentalenyl (such as (3as, 6as)-octahydropentalenyl), spirodecyl (such as spiro[4.5]decyl).

The term "heterocycloalkyl" refers to a saturated or unsaturated 3 to 10 membered monocyclic or bicyclic ring, which must contain at least one heteroatom, which is selected from nitrogen, oxygen, and sulfur. Heterocycloalkyl groups may contain one or more C(O), S(O) or $SO_2$ groups. Bicyclic heterocycloalkyl groups may be bridged, fused, or spiro bicyclic groups. However, heterocycloalkyl groups are not aromatic. Heterocycloalkyl groups containing more than one heteroatom may contain different heteroatoms, i.e. the heteroatoms are independently selected. For example, the term "3- to 10-membered heterocycloalkyl" refers to a saturated or unsaturated 3- to 10-membered monocyclic or bicyclic ring, which must contain one, two, or three non-carbon atoms, which are independently selected from nitrogen, oxygen, and sulfur. Exemplary groups include, but are not limited to, 8-oxabicyclo[3.2.1]octyl, pyrrolidinyl, pyrrolidinyl-2-one, pyrazolidinyl, pyrazolinyl, imidazolidinyl, imidazolinyl, imidazolidinyl-2-one, oxazolinyl, oxetyl, oxepanyl, 1-oxa-6-azaspirooctyl (such as 1-oxa-6-azaspiro[2.5]octyl), thiazolinyl, piperidinyl, piperazinyl, tetrahydrofuranyl, dihydrofuranyl, 1,3-dioxolanyl, tetrahydro-2H-pyranyl, dihydropyranyl (such as 3,4-dihydro-2H-pyranyl), morpholinyl, morpholinyl-3-one, 1,3-dioxanyl, 1,4-dioxanyl, 1,3-oxathiolanyl, 1,3-oxathianyl, 1,3-dithianyl, 1,4-oxathiolanyl, 1,4-oxathianyl, 1,4-dithianyl, piperidyl-2-one, pyrimidinyl-2,4(1H,3H)-dione, thiomorpholinyl, 2-azaspiroheptyl (such as 2-azaspiro[3.3]heptyl), 2,5-dihydrothienyl 1,1-dioxide, tetrahydrothienyl 1,1-dioxide, 3-azabicycloheptyl (such as 3-azabicyclo[4.1.0]heptyl or, more specifically, (1S,6S)-3-azabicyclo[4.1.0]heptyl), 6-oxaspirooctyl (such as 6-oxaspiro[2.5]octyl), and thiomorpholinyl 1,1-dioxide. Exemplary groups also include, but are not limited to, pyrrolidinyl, pyrrolidinyl-2-one, pyrazolidinyl, pyrazolinyl, imidazolidinyl, imidazolinyl, imidazolidinyl-2-one, oxazolinyl, oxetyl, oxepanyl, 1-oxa-6-azaspirooctyl (such as 1-oxa-6-azaspiro[2.5]octyl), thiazolinyl, piperidinyl, piperazinyl, tetrahydrofuranyl, dihydrofuranyl, 1,3-dioxolanyl, tetrahydro-2H-pyranyl, dihydropyranyl (such as 3,4-dihydro-2H-pyranyl), morpholinyl, morpholinyl-3-one, 1,3-dioxanyl, 1,4-dioxanyl, 1,3-oxathiolanyl, 1,3-oxathianyl, 1,3-dithianyl, 1,4-oxathiolanyl, 1,4-oxathianyl, 1,4-dithianyl, piperidyl-2-one, pyrimidinyl-2,4(1H,3H)-dione, thiomorpholinyl, 2-azaspiroheptyl (such as 2-azaspiro[3.3]heptyl), 2,5-dihydrothienyl 1,1-dioxide, tetrahydrothienyl 1,1-dioxide, 3-azabicycloheptyl (such as 3-azabicyclo[4.1.0]heptyl or, more specifically, (1S,6S)-3-azabicyclo[4.1.0]heptyl), 6-oxaspirooctyl (such as 6-oxaspiro[2.5]octyl), and thiomorpholinyl 1,1-dioxide.

The term "aryl" refers to a monocyclic or bicyclic, hydrocarbon, aromatic radical. This term also encompasses bicyclic cycloalkyl-aryl groups containing an aryl ring moiety fused to a cycloalkyl ring moiety. An aryl group may contain 6 to 14 carbon atoms. For example, an aryl may contain 6 to 10 carbon atoms, referred to as $C_{6-10}$ aryl. Aryl includes, for example, phenyl, naphthyl, indenyl, and dihydroindenyl.

The term "heteroaryl" refers to a group or moiety comprising an aromatic monocyclic or bicyclic radical, containing 5 to 10 ring atoms, including at least one heteroatom independently selected from nitrogen, oxygen, and sulfur. This term also encompasses bicyclic heterocycloalkyl-aryl groups containing 5 to 10 ring atoms containing an aryl ring moiety fused to a heterocycloalkyl ring moiety, including at least one heteroatom independently selected from nitrogen, oxygen, and sulfur. Alternatively, the term also encompasses (1) bicyclic heteroaryl-heterocycloalkyl groups containing 5 to 10 ring atoms containing a heteroaryl ring moiety fused to a heterocycloalkyl ring moiety, including at least one heteroatom independently selected from nitrogen, oxygen, and sulfur, and (2) bicyclic heteroaryl-cycloalkyl groups containing 5 to 10 ring atoms containing a heteroaryl ring moiety fused to a cycloalkyl ring moiety. Exemplary groups include, but are not limited to, furanyl, thienyl, pyrrolyl, imidazolyl, pyrazolyl, triazolyl (such as 4H-1,2,4-triazolyl), tetrazolyl, thiazolyl, oxazolyl, isoxazolyl, oxadiazolyl (such as 1,3,4-oxadiazolyl), thiadiazolyl (such as 1,3,4-thiadiazolyl), isothiazolyl, pyridinyl, pyridazinyl, pyrazinyl, pyrimidinyl, triazinyl, benzofuranyl, isobenzofuranyl, 1,3-dihydroisobenzofuranyl, 2,3-dihydrobenzofuranyl, furopyridazinyl (such as furo[2,3-d]pyridazinyl), 1,3-benzodioxolyl, dihydrobenzodioxinyl, benzothienyl, thienopyridinyl (such as thieno[3,2-b]pyridinyl), thienopyrimidinyl (such as thieno[2,3-d]pyrimidinyl), indolizinyl, indolinyl, indolyl, isoindolyl, dihydroindolyl, benzimidazolyl, dihydrobenzimidazolyl, benzooxazolyl, benzooxazolyl-2-one (such as benzo[d]oxazolyl-2(3H)-one), dihydrobenzooxazolyl, dihydrobenzooxazinyl (3,4-dihydro-2H-benzo[b][1,4]oxazinyl), benzthiazolyl, benzoimidazolyl, benzoisothiazolyl, dihydrobenzoisothiazolyl, indazolyl, imidazopyridinyl (such as 3H-imidazo[4,5-c]pyridinyl and 3H-imidazo[4,5-b]pyridinyl), dihydropyrrolopyrazolyl (such as 5,6-dihydro-4H-pyrrolo[1,2-b]pyrazolyl), imidazopyridazinyl (such as imidazo[1,2-b]pyridazinyl), pyrazolopyridinyl, benzothiazolyl, triazolopyridinyl, tetrazolopyridazinyl (such as tetrazolo[1,5-b]pyridazinyl), purinyl, quinoyl, tetrahydroquinolinyl, isoquinolinyl, 1,2,3,4-tetrahydroisoquinolinyl, 1,2,3,4-tetrahydroquinoxalinyl, tetrahydropyridopyridazinyl (such as 5,6,7,8-tetrahydropyrido[3,4-d]pyridazinyl), quinoxalinyl, cinnolinyl, phthalazinyl, quinazolinyl, 1,5-naphthyridinyl, 1,6-naphthyridinyl, 1,7-naphthyridinyl, 1,8-naphthyridinyl, and pteridinyl.

The term "5- or 6-membered heteroaryl" represents a group or moiety comprising an aromatic monovalent monocyclic radical, containing 5 or 6 ring atoms, including at least one carbon atom and containing one, two, or three heteroatoms independently selected from nitrogen, oxygen, and sulfur. Selected 5-membered heteroaryl groups contain three heteroatoms. Exemplary groups include, but are not limited to, furanyl, thienyl, pyrrolyl, imidazolyl, pyrazolyl, triazolyl, tetrazolyl, oxazolyl, thiazolyl, isoxazolyl, isothiazolyl, oxadiazolyl, thiadiazolyl, pyridinyl, pyridazinyl, pyrazinyl, pyrimidinyl, and triazinyl.

As used herein, the term "bicyclic ring" may refer to a bridged, fused, or spiro bicyclic group. For the avoidance of doubt, all bicyclic ring systems may be attached at any suitable position on either ring.

The term "optionally substituted" indicates that a group may be unsubstituted or substituted with one or more substituents as defined herein. The term "substituted" in reference to a group indicates that a hydrogen atom attached to a member atom within a group is replaced by one of the defined substituents. In the case where groups may be selected from a number of alternative groups, the selected groups may be the same or different.

The term "independently selected" means that where more than one substituent is selected from a number of possible substituents, those substituents may be the same or different. Thus, each substituent is separately selected from the entire group of recited possible substituents.

The term "pharmaceutically acceptable" refers to those compounds (including salts), materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

As used herein, the term "pharmaceutically acceptable salt" refers to salts that retain the desired biological activity of the subject compound and exhibit minimal undesired toxicological effects. Such pharmaceutically acceptable salt may be prepared in situ during the final isolation and purification of the compound, or by separately reacting the purified compound in its free acid or free base form with a suitable base or acid, respectively. When compounds disclosed herein contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc. Salts derived from pharmaceutically-acceptable organic bases include salts of primary, secondary and tertiary amines, including substituted amines, cyclic amines, naturally-occurring amines, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogen carbonic, phosphoric, monohydrogen phosphoric, dihydrogen phosphoric, sulfuric, monohydrogen sulfuric, hydriodic, or phosphorous acids, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic. Also included are salts of amino acids such as arginate, and salts of organic acids like glucuronic or galactunoric acids (see, for example, Berge, S. M., et al, "Pharmaceutical Salts", *Journal of Pharmaceutical Science,* 1977, 66, 1-19). Certain specific compounds of the present disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present disclosure.

The present disclosure also includes prodrugs of the compound of Formula (I) or a pharmaceutically acceptable salt thereof. As used herein, the term "prodrug" refers to compounds that readily undergo chemical changes under physiological conditions to provide a pharmacologically active parent compound. The term "prodrug moiety" refers to the chemical moiety of a prodrug that is released under physiological conditions to form the active parent compound. An example, without limitation, of a prodrug would be a compound which is administered as an ester (the "prodrug"), but then is metabolically hydrolyzed to the carboxylic acid, the active entity. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

Certain compounds of Formula (I) can exist in unsolvated forms as well as solvated forms, including hydrated forms. In general, the solvated forms are equivalent to unsolvated forms and are intended to be encompassed within the scope of the present disclosure. Certain compounds of Formula (I) may exist in multiple crystalline or amorphous forms. In general, all physical forms are equivalent for the uses contemplated by the present disclosure and are intended to be within the scope of the present disclosure.

Certain compounds of Formula (I) possess asymmetric carbon atoms (optical centers) or double bonds; the racemates, diastereomers, geometric isomers, regioisomers and individual isomers (e.g., separate enantiomers) are all intended to be encompassed within the scope of the present disclosure. When a stereochemical depiction is shown, it is meant to refer the compound in which one of the isomers is present and substantially free of the other isomer. "Substantially free of" another isomer indicates at least an 80/20 ratio of the two isomers, more preferably 90/10, or 95/5 or more. In some embodiments, one of the isomers will be present in an amount of at least 99%.

Certain compounds of the present disclosure can exist as tautomers and/or geometric isomers. All possible tautomers and cis and trans isomers, as individual forms and mixtures thereof are within the scope of this disclosure. For example, hydroxy substituted compound of Formula (I) can exist as a tautomer as shown below:

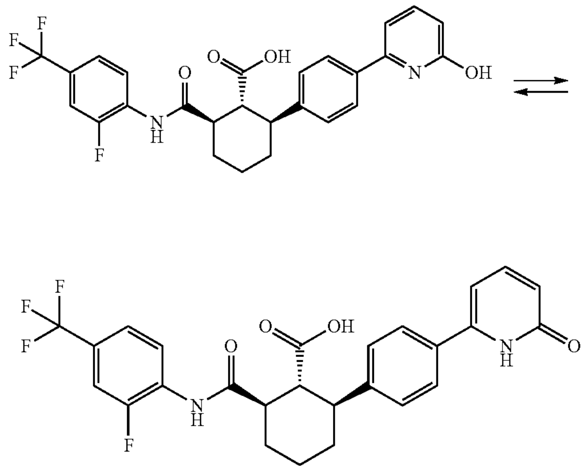

The term "compound(s) of the disclosure" or "compound(s) of the invention" refers to a compound of Formula (I), Formula (I-a), Formula (I-b), Formula (I-c), Formula (I-d), Formula (I-e), Formula (II) or Formula (II-a), or a tautomer thereof, or a pharmaceutically acceptable salt of said compound or tautomer thereof.

The compounds of Formula (I) may also contain unnatural amounts of isotopes at one or more of the atoms that constitute such compounds. Unnatural amounts of an isotope may be defined as ranging from the amount found in nature to an amount 100% of the atom in question. That differ only in the presence of one or more isotopically enriched atoms. Exemplary isotopes that can be incorporated into compounds of the present disclosure, such as a compound of Formula (I) (and any embodiment thereof disclosed herein including specific compounds) include isotopes of hydrogen, carbon, nitrogen, oxygen, phosphorus, sulfur, fluorine, chlorine, and iodine, such as $^{2}H$, $^{3}H$, $^{11}C$, $^{13}C$, $^{14}C$ $^{13}N$, $^{15}N$, $^{15}O$, $^{17}O$, $^{18}O$, $^{32}P$, $^{33}P$, $^{35}S$, $^{18}F$, $^{36}Cl$, $^{123}I$, and $^{125}I$, respectively. Isotopically-labeled compounds (e.g., those labeled with $^{3}H$ and $^{14}C$) can be useful in compound or substrate tissue distribution assays. Tritiated (i.e., $^{3}H$) and carbon-14 (i.e., $^{14}C$) isotopes can be useful for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements). In some embodiments, in compounds disclosed herein, including in Table 1 below one or more hydrogen atoms are replaced by $^{2}H$ or $^{3}H$, or one or more carbon atoms are replaced by $^{13}C$- or $^{14}C$-enriched carbon. Positron emitting isotopes such as $^{15}O$, $^{13}N$, $^{11}C$, and $^{15}F$ are useful for positron emission tomography (PET) studies to examine substrate receptor occupancy. Isotopically labeled compounds can generally be prepared by following procedures analogous to those disclosed in the Schemes or in the Examples herein, by substituting an isotopically labeled reagent for a non-isotopically labeled reagent. Thus, in one embodiment, the present invention includes:

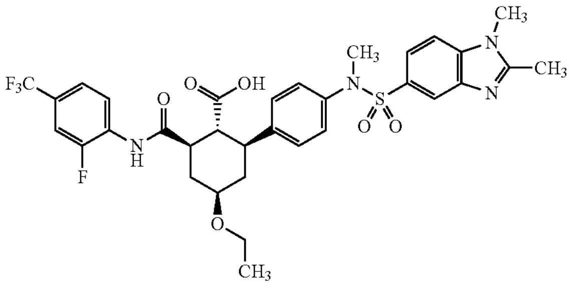

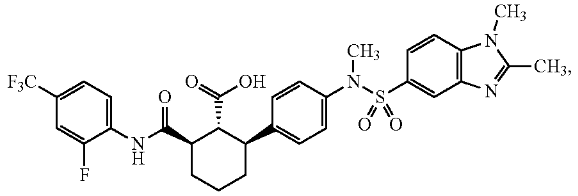

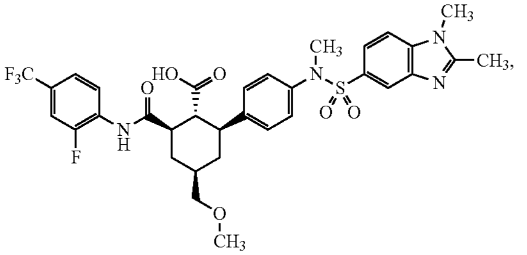

and

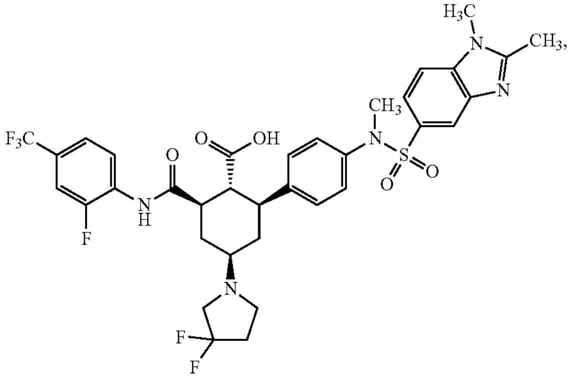

wherein one or more hydrogen atoms attached to carbon atoms are replaced by deuterium.

"Disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

"Patient" is generally synonymous with the term "subject" and as used herein includes all mammals including humans. Examples of patients include humans, livestock such as cows, goats, sheep, pigs, and rabbits, and companion animals such as dogs, cats, rabbits, and horses. Preferably, the patient is a human.

"In need of treatment" as used herein refers to a judgment made by a physician or other caregiver that a subject requires or will benefit from treatment. This judgment is made based on a variety of factors that are in the realm of the physician's or caregiver's expertise.

"Administration" and "administer", as they apply to, for example, a patient, cell, tissue, organ, or biological fluid, refer to contact of, for example, a compound of Formula (I) or a pharmaceutically acceptable salt thereof, a pharmaceutical composition comprising same, or a diagnostic agent to the subject, cell, tissue, organ, or biological fluid. In the context of a cell, administration includes contact (e.g., in vitro or ex vivo) of a reagent to the cell, as well as contact of a reagent to a fluid, where the fluid is in contact with the cell.

"Therapeutically effective amount" as used herein means the amount of a compound of Formula (I) or a pharmaceutically acceptable salt thereof, which will elicit the desired biological response in a human body. It may vary depending on the compound, the disease and its severity and the age and weight of the subject to be treated. The therapeutically effective amount can be ascertained by measuring relevant physiological effects, and it can be adjusted in connection with the dosing regimen and diagnostic analysis of the subject's condition. By way of example, measurement of the serum level of a compound of Formula (I) (or, e.g., a metabolite thereof) at a particular time post-administration may be indicative of whether a therapeutically effective amount has been used.

The term "treatment" refers to ameliorating or stabilising the specified condition, reducing or eliminating the symptoms of the condition, slowing or eliminating the progression of the condition, and preventing or delaying reoccurrence of the condition in a previously afflicted patient or subject.

The term "prevention" refers to avoidance of the stated disease in a subject who is not suffering from the stated disease.

"Inhibiting", "reducing," or any variation of these terms in relation of WRN, includes any measurable decrease or complete inhibition to achieve a desired result. For example, there may be a decrease of about, at most about, or at least about 5%, 10%, 15%, 20%, 25%, 30%, 35%, 40%, 45%, 50%, 55%, 60%, 65%, 70%, 75%, 80%, 85%, 90%, 95%, 99%, or more, or any range derivable therein, reduction of WRN helicase domain activity compared to its normal activity. For the avoidance of doubt, a reference to a compound of Formula (I) encompasses a reference to any one of Formulae (I-a), (I-aa), (I-b), (I-c), (I-cc), (I-ccc), (I-d), (I-dd), (I-e), (I-ee), (I-eee), (II), (II-a), (II-aa), (II-b), (II-bb), (II-c), and (II-cc).

Compounds

In one aspect, the present disclosure provides a compound of Formula (I):

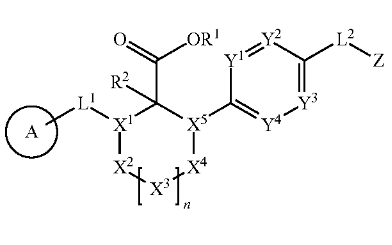

(I)

wherein:

ring A is aryl, heteroaryl, $C_{3-10}$ cycloalkyl, or 3- to 10-membered heterocycloalkyl ring containing one, two, or three heteroatoms independently selected from N, O, and S, wherein ring A is mono- or bicyclic and ring A is optionally substituted with up to three substituents independently selected from halo, cyano, nitro, hydroxy, —$NR^aR^b$, carboxy, —$CONR^aR^b$, $C_{1-3}$ alkyl, $C_{1-3}$ alkoxy, halo($C_{1-3}$)alkyl, halo($C_{1-3}$)alkoxy, hydroxy($C_{1-3}$)alkyl, cyano($C_{1-3}$)alkyl, $C_{1-3}$ alkylsulfonyl, —C(O)O($C_{1-4}$)alkyl, and $C_{3-7}$ cycloalkyl;

$L^1$ is —$NR^c$—C(O)—, —$OCH_2$—, —$NR^c$—$CH_2$—, —$CH_2$—, —S—$CH_2$—, —$CH_2CH_2$—, or —$S(O)_2$—;

n is 0, 1, or 2;

$R^1$ is hydrogen or $C_{1-3}$ alkyl;

$R^2$ is hydrogen, halo, or $C_{1-3}$ alkyl;

$X^1$ and $X^5$ are each independently N or —CH—;

$X^2$, $X^3$, and $X^4$ are each independently —$NR^o$—, —$CR^XR^X$—, —O—, or —C(O)—;

each $R^X$ is independently selected from hydrogen, halo, cyano, —$NR^dR^e$, hydroxy, carboxy, phenoxy, phenyl, $C_{1-3}$ alkyl, halo($C_{1-3}$)alkyl, hydroxy($C_{1-3}$)alkyl, $C_{1-3}$ alkoxy($C_{1-3}$)alkyl, $C_{1-3}$ alkoxy, halo($C_{1-3}$)alkoxy, and $L^X$-V; or any two of $R^o$ and $R^X$ taken together with the atoms to which they are attached form a 3- or 6-membered ring which optionally contains one or two heteroatoms independently selected from N, O, and S and which is optionally substituted with up to three substituents independently selected from halo, $C_{1-3}$alkyl, halo($C_{1-3}$)alkyl, $C_{1-3}$alkoxy, and halo($C_{1-3}$)alkoxy;

$L^X$ is a bond, —$CH_2$—, —$NR^d$C(O)—, —$NR^d$—$(CH_2)_w$—, —O—$(CH_2)_w$—, —S—$(CH_2)_w$—;

V is independently $C_{3-7}$ cycloalkyl or a 3- to 10-membered heterocycloalkyl ring containing one, two, or three heteroatoms independently selected from N, O, and S, wherein V is optionally substituted with up to three substituents independently selected from halo, $C_{1-3}$ alkyl, halo($C_{1-3}$)alkyl, $C_{1-3}$ alkoxy, and halo($C_{1-3}$)alkoxy;

$Y^1$, $Y^2$, $Y^3$, and $Y^4$ are each independently N or CRY, and at most two of $Y^1$, $Y^2$, $Y^3$, and $Y^4$ are N;

$L^2$ is a bond, —NR—$S(O)_2$—, —NR—C(O)—, or —$(CH_2)_p$—;

Z is hydrogen, halo, cyano, hydroxy, —$NR^gR^h$, nitro, carboxy, $C_{1-3}$ alkyl, $C_{1-3}$alkoxy, halo($C_{1-3}$)alkyl, halo($C_{1-3}$)alkoxy, hydroxy($C_{1-3}$)alkyl, cyano($C_{1-3}$)alkyl, $C_{2-5}$ alkenyl, halo($C_{2-5}$)alkenyl, $C_{2-5}$ alkynyl, or halo($C_{2-5}$)alkynyl; or Z is ring B, wherein ring B is aryl, heteroaryl, $C_{3-10}$ cycloalkyl, or 3- to 10-membered heterocycloalkyl ring containing one, two or three heteroatoms independently selected from N, O, and S, wherein ring B is mono- or bicyclic and ring B is optionally substituted with up to three substituents independently selected from halo, cyano, nitro, hydroxy, carboxy, $C_{1-3}$alkyl, $C_{1-3}$ alkoxy, halo($C_{1-3}$)alkyl, halo($C_{1-3}$)alkoxy, hydroxy($C_{1-3}$)alkyl, $C_{2-5}$ alkenyl, $C_{2-5}$ alkynyl, —$C_{1-3}$ alkylene-$NR^gR^h$, —$CONR^gR^h$, —$NR^gR^h$, —$NR^g$C(O)$R^h$, $SO_2NR^gR^h$, and $L^B$-W, or two substituents of ring B taken together with the atoms to which they are attached form a 5- or 6-membered ring which optionally contains one or two heteroatoms independently selected from N, O, and S;

$L^B$ is independently selected from a bond, —$(CH_2)_p$—, —$CH_2$O—, —C(O)—NH—, —C(O)—, and —$CH_2$C(O)NH—;

W is independently selected from hydrogen, $C_{1-3}$ alkyl, —O($C_{1-4}$)alkyl, $C_{3-7}$ cycloalkyl, 5- or 6-membered heteroaryl, and 4- to 6-membered heterocycloalkyl ring containing one, two, or three heteroatoms independently selected from N, O, and S, wherein W is optionally substituted with up to three substituents independently selected from halo, cyano, nitro, hydroxy, —$NR^mR^n$, carboxy, —$CONR^mR^n$, $C_{1-3}$ alkyl, $C_{1-3}$ alkoxy, halo($C_{1-3}$)alkyl, halo($C_{1-3}$)alkoxy, hydroxy($C_{1-3}$)alkyl, cyano($C_{1-3}$)alkyl, $C_{1-3}$ alkylsulfonyl, —C(O)O($C_{1-4}$)alkyl, and $C_{3-7}$ cycloalkyl;

each $R^y$ is independently hydrogen, halo, cyano, nitro, hydroxy, —$NR^iR^k$, carboxy, $C_{1-3}$ alkyl, halo($C_{1-3}$)alkyl, hydroxy($C_{1-3}$)alkyl, cyano($C_{1-3}$)alkyl, $C_{1-3}$ alkoxy, halo($C_{1-3}$)alkoxy, methoxy($C_{1-3}$)alkoxy, $C_{2-5}$ alkenyl, halo($C_{2-5}$)alkenyl, hydroxy($C_{2-5}$)alkenyl, $C_{2-5}$ alkynyl, halo($C_{2-5}$)alkynyl, hydroxy($C_{2-5}$)alkynyl, or 5- or 6-membered heteroaryl containing one, two, or three heteroatoms independently selected from N, O, and S, wherein the heteroaryl is optionally substituted with up to three $C_{1-3}$ alkyl;

$R^a$, $R^b$, $R^c$, $R^d$, $R^f$, $R^g$, $R^h$, $R^i$, $R^k$, $R^m$, and $R^n$ are each independently hydrogen, $C_{1-3}$ alkyl, or $C_{3-7}$ cycloalkyl; or $R^y$ and $R^f$ taken together with the atoms to which they are attached form a 5- or 6-membered ring which contains one or two heteroatoms independently selected from N, O, and S;

$R^o$ is hydrogen, $C_{1-3}$ alkyl, —C(O)$C_{1-3}$ alkyl, or $C_{3-7}$ cycloalkyl;

$R^o$ is hydrogen, $C_{1-3}$ alkyl, halo($C_{1-3}$)alkyl, $C_{3-7}$ cycloalkyl, or —C(O)$C_{1-3}$ alkyl;

each p is independently 1 or 2; and each w is independently 0, 1, 2, or 3;

or a pharmaceutically acceptable salt thereof.

In another aspect, the present disclosure provides a compound of Formula (I):

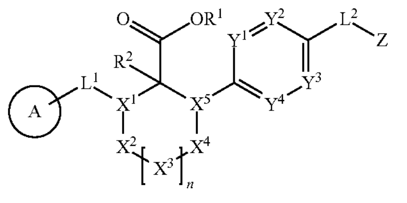

wherein:

ring A is aryl, heteroaryl, $C_{3-10}$ cycloalkyl, or 3- to 10-membered heterocycloalkyl ring containing one, two, or three heteroatoms independently selected from N, O, and S, wherein ring A is mono- or bicyclic and ring A is optionally substituted with up to three substituents independently selected from halo, cyano, nitro, hydroxy, —$NR^aR^b$, carboxy, —$CONR^aR^b$, $C_{1-3}$ alkyl, $C_{1-3}$ alkoxy, halo($C_{1-3}$)alkyl, halo($C_{1-3}$)alkoxy, hydroxy($C_{1-3}$)alkyl, cyano($C_{1-3}$)alkyl, $C_{1-3}$ alkylsulfonyl, —C(O)O($C_{1-4}$)alkyl, and $C_{3-7}$ cycloalkyl;

$L^1$ is —$NR^o$—C(O)—, —$OCH_2$—, —$NR^o$—$CH_2$—, —$CH_2$—, —S—$CH_2$—, —$CH_2CH_2$—, or —$S(O)_2$—;

n is 0, 1, or 2;

$R^1$ is hydrogen or $C_{1-3}$ alkyl;

$R^2$ is hydrogen, halo, or $C_{1-3}$ alkyl;

$X^1$ and $X^5$ are each independently N or —CH—;

$X^2$, $X^3$, and $X^4$ are each independently —$NR^o$—, —$CR^XR^X$—, or —C(O)—;

each $R^X$ is independently selected from hydrogen, halo, —$NR^dR^e$, hydroxy, carboxy, phenoxy, phenyl, $C_{1-3}$ alkyl, halo($C_{1-3}$)alkyl, hydroxy($C_{1-3}$)alkyl, methoxy($C_{1-3}$)alkyl, $C_{1-3}$ alkoxy, and halo($C_{1-3}$)alkoxy, wherein $C_{1-3}$ alkoxy is optionally substituted with $C_{3-7}$ cycloalkyl; or any two of $R^o$ and $R^X$ taken together with the atoms to which they are attached form a 5- or 6-membered ring which optionally contains one or two heteroatoms independently selected from N, O, and S;

$Y^1$, $Y^2$, $Y^3$, and $Y^4$ are each independently N or CRY, and at most two of $Y^1$, $Y^2$, $Y^3$, and $Y^4$ are N;

$L^2$ is a bond, —NR—$S(O)_2$—, —NR—C(O)—, or —$(CH_2)_p$—;

Z is hydrogen, halo, cyano, hydroxy, —$NR^gR^h$, nitro, carboxy, $C_{1-3}$ alkyl, $C_{1-3}$alkoxy, halo($C_{1-3}$)alkyl, halo($C_{1-3}$)alkoxy, hydroxy($C_{1-3}$)alkyl, cyano($C_{1-3}$)alkyl, $C_{2-5}$ alkenyl, halo($C_{2-5}$)alkenyl, $C_{2-5}$ alkynyl, or halo($C_{2-5}$)alkynyl; or Z is ring B, wherein ring B is aryl, heteroaryl, $C_{3-10}$ cycloalkyl, or 3- to 10-membered heterocycloalkyl ring containing one, two or three heteroatoms independently selected from N, O, and S, wherein ring B is mono- or bicyclic and ring B is optionally substituted with up to three substituents independently selected from halo, cyano, nitro, hydroxy, carboxy, $C_{1-3}$alkyl, $C_{1-3}$ alkoxy, halo($C_{1-3}$)alkyl, halo($C_{1-3}$)alkoxy, hydroxy($C_{1-3}$)alkyl, $C_{2-5}$ alkenyl, $C_{2-5}$ alkynyl, —$C_{1-3}$ alkylene-$NR^gR^h$, —$CONR^gR^h$, —$NR^gR^h$, —$NR^gC(O)R^h$, $SO_2NR^gR^h$, and $L^B$-W, or two substituents of ring B taken together with the atoms to which they are attached form a 5- or 6-membered ring which optionally contains one or two heteroatoms independently selected from N, O, and S;

$L^B$ is independently selected from a bond, —$(CH_2)_p$—, —$CH_2O$—, —C(O)—NH—, —C(O)—, and —$CH_2C(O)NH$—;

W is independently selected from hydrogen, $C_{1-3}$ alkyl, —O($C_{1-4}$)alkyl, $C_{3-7}$ cycloalkyl, 5- or 6-membered heteroaryl, and 4- to 6-membered heterocycloalkyl ring containing one, two, or three heteroatoms independently selected from N, O, and S, wherein W is optionally substituted with up to three substituents independently selected from halo, cyano, nitro, hydroxy, —$NR^mR^n$, carboxy, —$CONR^mR^n$, $C_{1-3}$alkyl, $C_{1-3}$alkoxy, halo($C_{1-3}$)alkyl, halo($C_{1-3}$)alkoxy, hydroxy($C_{1-3}$)alkyl, cyano($C_{1-3}$)alkyl, $C_{1-3}$ alkylsulfonyl, —C(O)O($C_{1-4}$)alkyl, and $C_{3-7}$ cycloalkyl;

each $R^y$ is independently hydrogen, halo, cyano, nitro, hydroxy, —$NR^iR^k$, carboxy, $C_{1-3}$ alkyl, halo($C_{1-3}$)alkyl, hydroxy($C_{1-3}$)alkyl, cyano($C_{1-3}$)alkyl, $C_{1-3}$ alkoxy, halo($C_{1-3}$)alkoxy, methoxy($C_{1-3}$)alkoxy, $C_{2-5}$ alkenyl, halo($C_{2-5}$)alkenyl, hydroxy($C_{2-5}$)alkenyl, $C_{2-5}$ alkynyl, halo($C_{2-5}$)alkynyl, hydroxy($C_{2-5}$)alkynyl, or 5- or 6-membered heteroaryl containing one, two, or three heteroatoms independently selected from N, O, and S, wherein the heteroaryl is optionally substituted with up to three $C_{1-3}$ alkyl; or $R^y$ and $R^f$ taken together with the atoms to which they are attached form a 5- or 6-membered ring which contains one or two heteroatoms independently selected from N, O, and S;

each p is independently 1 or 2; and $R^a$, $R^b$, $R^o$, $R^d$, $R^e$, $R^f$, $R^g$, $R^h$, $R^i$, $R^k$, $R^m$, $R^n$, and $R^o$ are each independently hydrogen, $C_{1-3}$ alkyl, or $C_{3-7}$ cycloalkyl;

or a pharmaceutically acceptable salt thereof.

When a moiety in a compound of Formula (I) is divalent, unless otherwise indicated, the moiety is depicted from the left to the right with respect to the remaining parts of the compound. For example, when $L^2$ is —$NR^f$—$S(O)_2$—, the nitrogen atom of $L^2$ is attached to the aromatic ring and the sulfur atom of $L^2$ is attached to Z.

In one aspect, the present disclosure provides a compound of Formula (I), wherein $X^1$ and $X^5$ are —CH—; $X^2$ and $X^4$ are —$CH_2$—; n is 1; and $X^3$ is —$NR^o$—, and wherein $R^1$, $R^2$, $R^o$, ring A, Z, $L^1$, $L^2$, $Y^1$, $Y^2$, $Y^3$, and $Y^4$ are as defined herein. See the structure below.

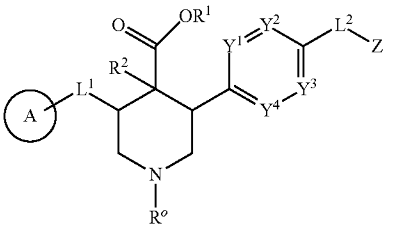

In one aspect, the present disclosure provides a compound of Formula (I), wherein $X^1$ and $X^5$ are —CH—; $X^2$ and $X^4$ are —$CH_2$—; n is 1; and $X^3$ is —O—, and wherein $R^1$, $R^2$, ring A, Z, $L^1$, $L^2$, $Y^1$, $Y^2$, $Y^3$, and $Y^4$ are as defined herein. See the structure below.

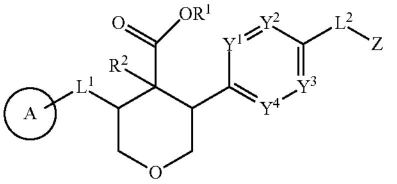

In another aspect, the present disclosure provides a compound of Formula (I-a):

(I-a)

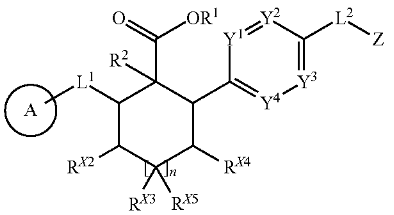

wherein:

ring A is aryl, heteroaryl, $C_{3-10}$ cycloalkyl, or 3- to 10-membered heterocycloalkyl ring containing one, two, or three heteroatoms independently selected from N, O, and S, wherein ring A is mono- or bicyclic and ring A is optionally substituted with up to three substituents independently selected from halo, cyano, nitro, hydroxy, —$NR^aR^b$, carboxy, —$CONR^aR^b$, $C_{1-3}$ alkyl, $C_{1-3}$ alkoxy, halo($C_{1-3}$)alkyl, halo($C_{1-3}$)alkoxy, hydroxy($C_{1-3}$)alkyl, cyano($C_{1-3}$)alkyl, $C_{1-3}$ alkylsulfonyl, —C(O)O($C_{1-4}$)alkyl, and $C_{3-7}$ cycloalkyl;

$L^1$ is —$NR^o$—C(O)—, —$OCH_2$—, —$NR^o$—$CH_2$—, or —$CH_2$—;

n is 0, 1, or 2;

$R^1$ is hydrogen or $C_{1-3}$ alkyl;

$R^2$ is hydrogen, halo, or $C_{1-3}$ alkyl;

$R^{X2}$, $R^{X3}$, and $R^{X4}$ are each independently selected from hydrogen, halo, cyano, —$NR^dR^e$, hydroxy, carboxy, phenoxy, phenyl, $C_{1-3}$ alkyl, halo($C_{1-3}$)alkyl, hydroxy($C_{1-3}$)alkyl, $C_{1-3}$ alkoxy($C_{1-3}$)alkyl-, $C_{1-3}$ alkoxy, halo($C_{1-3}$)alkoxy, and $L^X$-V;

$R^{X5}$ is hydrogen, halo, hydroxy, or $C_{1-3}$alkyl; or any two of $R^{X2}$, $R^{X3}$, $R^{X4}$, or $R^{X5}$ taken together with the carbon atoms to which they are attached form a 3- to 6-membered ring which optionally contains one or two heteroatoms independently selected from N, O, and S and which is optionally substituted with up to three substituents independently selected from halo, $C_{1-3}$ alkyl, halo($C_{1-3}$)alkyl, $C_{1-3}$ alkoxy, and halo($C_{1-3}$) alkoxy;

$L^X$ is a bond, —$CH_2$—, —$NR^d$C(O)—, —$NR^d$—$(CH_2)_w$—, —O—$(CH_2)_w$—, or —S—$(CH_2)_w$—;

V is independently $C_{3-7}$ cycloalkyl or a 3- to 10-membered heterocycloalkyl ring containing one, two, or three heteroatoms independently selected from N, O, and S, wherein V is optionally substituted with up to three substituents independently selected from halo, $C_{1-3}$ alkyl, halo($C_{1-3}$)alkyl, $C_{1-3}$ alkoxy, and halo($C_{1-3}$) alkoxy;

$Y^1$, $Y^2$, $Y^3$, and $Y^4$ are each independently N or CRY, and at most two of $Y^1$, $Y^2$, $Y^3$, and $Y^4$ are N;

$L^2$ is a bond, —NR—$S(O)_2$—, —NR—C(O)—, or —$(CH_2)_p$—;

Z is hydrogen, halo, cyano, hydroxy, —$NR^gR^h$, nitro, carboxy, $C_{1-3}$ alkyl, $C_{1-3}$alkoxy, halo($C_{1-3}$)alkyl, halo ($C_{1-3}$)alkoxy, hydroxy($C_{1-3}$)alkyl, cyano($C_{1-3}$)alkyl, $C_{2-5}$ alkenyl, halo($C_{2-5}$)alkenyl, $C_{2-5}$ alkynyl, or halo ($C_{2-5}$)alkynyl; or Z is ring B, wherein ring B is aryl, heteroaryl, $C_{3-10}$ cycloalkyl, or 3- to 10-membered heterocycloalkyl ring containing one, two, or three heteroatoms independently selected from N, O, and S, wherein ring B is mono- or bicyclic and ring B is optionally substituted with up to three substituents independently selected from halo, cyano, nitro, hydroxy, carboxy, $C_{1-3}$alkyl, $C_{1-3}$ alkoxy, halo($C_{1-3}$)alkyl, halo($C_{1-3}$)alkoxy, hydroxy($C_{1-3}$)alkyl, $C_{2-5}$ alkenyl, $C_{2-5}$ alkynyl, —$C_{1-3}$ alkylene-$NR^gR^h$, —$CONR^gR^h$, —$NR^gR^h$, —$NR^g$C(O) $R^h$, $SO_2NR^gR^h$, and $L^B$-W, or two substituents of ring B taken together with the atoms to which they are attached form a 5- or 6-membered ring which optionally contains one or two heteroatoms independently selected from N, O, and S;

$L^B$ is independently selected from a bond, —$(CH_2)_p$—, —$CH_2$O—, —C(O)—NH—, —C(O)—, and —$CH_2$C (O)NH—;

W is independently selected from hydrogen, $C_{1-3}$ alkyl, —O($C_{1-4}$)alkyl, $C_{3-7}$ cycloalkyl, 5- or 6-membered heteroaryl, and 4- to 6-membered heterocycloalkyl ring containing one, two, or three heteroatoms independently selected from N, O, and S, wherein W is optionally substituted with up to three substituents independently selected from halo, cyano, nitro, hydroxy, —$NR^mR^n$, carboxy, —$CONR^mR^n$, $C_{1-3}$ alkyl, $C_{1-3}$ alkoxy, halo($C_{1-3}$)alkyl, halo($C_{1-3}$)alkoxy, hydroxy($C_{1-3}$)alkyl, cyano($C_{1-3}$)alkyl, $C_{1-3}$ alkylsulfonyl, —C(O)O($C_{1-4}$)alkyl, and $C_{3-7}$ cycloalkyl;

each $R^y$ is independently hydrogen, halo, cyano, nitro, hydroxy, —$NR^iR^k$, carboxy, $C_{1-3}$ alkyl, halo($C_{1-3}$)alkyl, hydroxy($C_{1-3}$)alkyl, cyano($C_{1-3}$)alkyl, $C_{1-3}$ alkoxy, halo($C_{1-3}$)alkoxy, methoxy($C_{1-3}$)alkoxy, $C_{2-5}$ alkenyl, halo($C_{2-5}$)alkenyl, hydroxy($C_{2-5}$)alkenyl, $C_{2-5}$ alkynyl, halo($C_{2-5}$)alkynyl, hydroxy($C_{2-5}$)alkynyl, or 5- or 6-membered heteroaryl containing one, two, or three heteroatoms independently selected from N, O, and S, wherein the heteroaryl is optionally substituted with up to three $C_{1-3}$ alkyl;

$R^a$, $R^b$, $R^o$, $R^d$, $R^f$, $R^g$, $R^h$, $R^i$, $R^k$, $R^m$, and $R^n$ are each independently hydrogen, $C_{1-3}$ alkyl, or $C_{3-7}$ cycloalkyl; or $R^y$ and $R^f$ taken together with the atoms to which they are attached form a 5- or 6-membered ring which contains one or two heteroatoms independently selected from N, O, and S;

$R^e$ is hydrogen, $C_{1-3}$ alkyl, halo($C_{1-3}$)alkyl, $C_{3-7}$ cycloalkyl, or —C(O)$C_{1-3}$ alkyl;

each p is independently 1 or 2; and each w is independently 0, 1, 2, or 3;

or a pharmaceutically acceptable salt thereof.

In an embodiment, $R^{X2}$, $R^{X3}$, and $R^{X4}$ are each independently selected from hydrogen, cyano, —$NR^dR^e$, hydroxy, phenoxy, $C_{1-3}$ alkyl, methoxy($C_{1-3}$)alkyl, halo($C_{1-3}$)alkoxy, and $L^X$-V; or any two of $R^{X2}$, $R^{X3}$, or $R^{X5}$ taken together with the carbon atoms to which they are attached form a 5-membered ring which optionally contains one O;

$L^X$ is —O—$(CH_2)_w$—;

V is independently selected from $C_{1-3}$ alkoxy, $C_{3-4}$ cycloalkyl, or a 3- to 7-membered heterocycloalkyl ring containing one or two heteroatoms independently selected from N or O, wherein V is optionally substituted with one substituent independently selected from $C_{1-3}$ alkyl and $C_{1-3}$ alkoxy; and w is 0 or 1.

In another aspect, the present disclosure provides a compound of Formula (I-aa):

(I-aa)

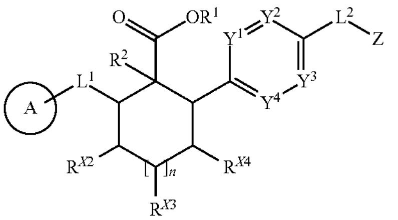

wherein:

ring A is aryl, heteroaryl, $C_{3-10}$ cycloalkyl, or 3- to 10-membered heterocycloalkyl ring containing one, two, or three heteroatoms independently selected from N, O, and S, wherein ring A is mono- or bicyclic and ring A is optionally substituted with up to three substituents independently selected from halo, cyano, nitro, hydroxy, —$NR^aR^b$, carboxy, —$CONR^aR^b$, $C_{1-3}$ alkyl, $C_{1-3}$ alkoxy, halo($C_{1-3}$)alkyl, halo($C_{1-3}$)alkoxy, hydroxy($C_{1-3}$)alkyl, cyano($C_{1-3}$)alkyl, $C_{1-3}$ alkylsulfonyl, —C(O)O($C_{1-4}$)alkyl, and $C_{3-7}$ cycloalkyl;

$L^1$ is —$NR^o$—C(O)—, —$OCH_2$—, —$NR^o$—$CH_2$—, or —$CH_2$—;

n is 0, 1, or 2;

$R^1$ is hydrogen or $C_{1-3}$ alkyl;

$R^2$ is hydrogen, halo, or $C_{1-3}$ alkyl;

$R^{X2}$, $R^{X3}$, and $R^{X4}$ are each independently selected from hydrogen, halo, —$NR^dR^e$, hydroxy, carboxy, phenoxy, phenyl, $C_{1-3}$ alkyl, halo($C_{1-3}$)alkyl, hydroxy($C_{1-3}$)alkyl, methoxy($C_{1-3}$)alkyl, $C_{1-3}$ alkoxy, and halo($C_{1-3}$)alkoxy, wherein $C_{1-3}$ alkoxy is optionally substituted with $C_{3-7}$ cycloalkyl; or any two of $R^{X2}$, $R^{X3}$, or $R^{X4}$ taken together with the carbon atoms to which they are attached form a 5- or 6-membered ring which optionally contains one or two heteroatoms independently selected from N, O, and S;

$Y^1$, $Y^2$, $Y^3$, and $Y^4$ are each independently N or CRY, and at most two of $Y^1$, $Y^2$, $Y^3$, and $Y^4$ are N;

$L^2$ is a bond, —$NR^f$—$S(O)_2$—, —$NR^f$—C(O)—, or —$(CH_2)_p$—;

Z is hydrogen, halo, cyano, hydroxy, —$NR^gR^h$, nitro, carboxy, $C_{1-3}$ alkyl, $C_{1-3}$alkoxy, halo($C_{1-3}$)alkyl, halo($C_{1-3}$)alkoxy, hydroxy($C_{1-3}$)alkyl, cyano($C_{1-3}$)alkyl, $C_{2-5}$ alkenyl, halo($C_{2-5}$)alkenyl, $C_{2-5}$ alkynyl, or halo($C_{2-5}$)alkynyl; or Z is ring B, wherein ring B is aryl, heteroaryl, $C_{3-10}$ cycloalkyl, or 3- to 10-membered heterocycloalkyl ring containing one, two or three heteroatoms independently selected from N, O, and S, wherein ring B is mono- or bicyclic and ring B is optionally substituted with up to three substituents independently selected from halo, cyano, nitro, hydroxy, carboxy, $C_{1-3}$alkyl, $C_{1-3}$ alkoxy, halo($C_{1-3}$)alkyl, halo($C_{1-3}$)alkoxy, hydroxy($C_{1-3}$)alkyl, $C_{2-5}$ alkenyl, $C_{2-5}$ alkynyl, —$C_{1-3}$ alkylene-$NR^gR^h$, —$CONR^gR^h$, —$NR^gR^h$, —$NR^gC(O)R^h$, $SO_2NR^gR^h$, and $L^B$-W, or two substituents of ring B taken together with the atoms to which they are attached form a 5- or 6-membered ring which optionally contains one or two heteroatoms independently selected from N, O, and S;

$L^B$ is independently selected from a bond, —$(CH_2)_p$—, —$CH_2O$—, —C(O)—NH—, —C(O)—, and —$CH_2$C(O)NH—;

W is independently selected from hydrogen, $C_{1-3}$ alkyl, —O($C_{1-4}$)alkyl, $C_{3-7}$ cycloalkyl, 5- or 6-membered heteroaryl, and 4- to 6-membered heterocycloalkyl ring containing one, two, or three heteroatoms independently selected from N, O, and S, wherein W is optionally substituted with up to three substituents independently selected from halo, cyano, nitro, hydroxy, —$NR^mR^n$, carboxy, —$CONR^mR^n$, $C_{1-3}$alkyl, $C_{1-3}$alkoxy, halo($C_{1-3}$)alkyl, halo($C_{1-3}$)alkoxy, hydroxy($C_{1-3}$)alkyl, cyano($C_{1-3}$)alkyl, $C_{1-3}$ alkylsulfonyl, —C(O)O($C_{1-4}$)alkyl, and $C_{3-7}$ cycloalkyl;

each $R^y$ is independently hydrogen, halo, cyano, nitro, hydroxy, —$NR^iR^k$, carboxy, $C_{1-3}$ alkyl, halo($C_{1-3}$)alkyl, hydroxy($C_{1-3}$)alkyl, cyano($C_{1-3}$)alkyl, $C_{1-3}$ alkoxy, halo($C_{1-3}$)alkoxy, methoxy($C_{1-3}$)alkoxy, $C_{2-5}$ alkenyl, halo($C_{2-5}$)alkenyl, hydroxy($C_{2-5}$)alkenyl, $C_{2-5}$ alkynyl, halo($C_{2-5}$)alkynyl, hydroxy($C_{2-5}$)alkynyl, or 5- or 6-membered heteroaryl containing one, two, or three heteroatoms independently selected from N, O, and S, wherein the heteroaryl is optionally substituted with up to three $C_{1-3}$ alkyl; or $R^y$ and $R^f$ taken together with the atoms to which they are attached form a 5- or 6-membered ring which contains one or two heteroatoms independently selected from N, O, and S;

each p is independently 1 or 2; and $R^a$, $R^b$, $R^c$, $R^d$, $R^e$, $R^f$, $R^g$, $R^h$, $R^i$, $R^k$, $R^m$, and $R^n$, are each independently hydrogen, $C_{1-3}$ alkyl, or $C_{3-7}$ cycloalkyl;

or a pharmaceutically acceptable salt thereof.

For the avoidance of doubt, reference to any two of $R^{X2}$, $R^{X3}$, $R^{X4}$, or $R^{X5}$ taken together with the carbon atoms to which they are attached forming a 3- to 6-membered ring encompasses the formation of fused, bridged, and spirocylic bicyclic structures. Reference to any two of $R^{X2}$, $R^{X3}$ or $R^{X4}$ taken together with the carbon atoms to which they are attached forming a 5- or 6-membered ring encompasses the formation of both fused and bridged bicyclic structures.

Reference to $R^y$ and $R^f$ taken together with the atoms to which they are attached forming a 5- or 6-membered ring encompasses the formation of fused structures. Examples include dihydrooxazine derivatives such as that shown below:

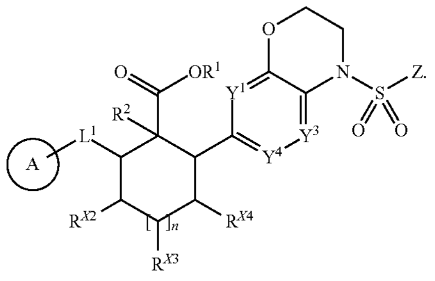

Reference to two optional substituents on ring B taken together with the atoms to which they are attached forming a 5- or 6-membered ring, which optionally contains one or two heteroatoms independently selected from N, O, and S, encompasses the formation of fused structures in combination with ring B (which may be mono- or bicyclic). Examples include 1,2,3,4-tetrahydrobenzimidazopyridine derivatives such as that shown below:

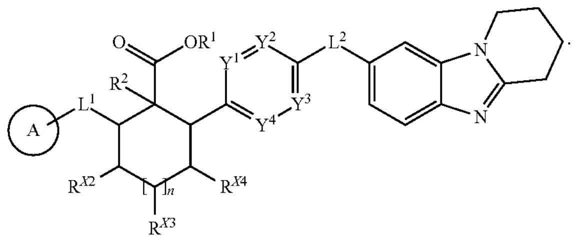

In an embodiment, ring A is optionally substituted with up to three substituents independently selected from halo, hydroxy, $C_{1-3}$ alkyl, halo($C_{1-3}$)alkyl, hydroxy($C_{1-3}$)alkyl, and $C_{3-7}$ cycloalkyl.

In an embodiment, ring A is $C_{6-10}$ aryl, 5- to 10-membered heteroaryl, $C_{3-10}$ cycloalkyl, or 3- to 10-membered heterocycloalkyl ring containing one, two, or three heteroatoms independently selected from N, O, and S, wherein ring A is mono- or bicyclic and ring A is optionally substituted with up to three substituents independently selected from halo, cyano, nitro, hydroxy, —$NR^aR^b$, carboxy, —$CONR^aR^b$, $C_{1-3}$ alkyl, $C_{1-3}$ alkoxy, halo($C_{1-3}$)alkyl, halo($C_{1-3}$)alkoxy, hydroxy($C_{1-3}$)alkyl, cyano($C_{1-3}$)alkyl, $C_{1-3}$ alkylsulfonyl, —C(O)O($C_{1-4}$)alkyl, and $C_{3-7}$ cycloalkyl.

In an embodiment, ring A is phenyl, 5- or 6-membered heteroaryl, $C_{3-10}$ cycloalkyl, or 3- to 10-membered heterocycloalkyl ring containing one, two, or three heteroatoms independently selected from N, O, and S, wherein ring A is mono- or bicyclic, wherein ring A is optionally substituted with up to three substituents independently selected from halo, cyano, nitro, hydroxy, —$NR^aR^b$, carboxy, $CONR^aR^b$, $C_{1-3}$ alkyl, $C_{1-3}$ alkoxy, halo($C_{1-3}$)alkyl, halo($C_{1-3}$)alkoxy, hydroxy($C_{1-3}$)alkyl, cyano($C_{1-3}$)alkyl, $C_{1-3}$ alkylsulfonyl, —C(O)O($C_{1-4}$)alkyl, and $C_{3-7}$ cycloalkyl.

In an embodiment, ring A is phenyl, 5- or 6-membered heteroaryl, $C_{3-10}$ cycloalkyl, or 3- to 10-membered heterocycloalkyl ring containing one, two or three heteroatoms independently selected from N, O, and S, wherein ring A is mono- or bicyclic, wherein ring A is optionally substituted with up to three substituents independently selected from halo, hydroxy, $C_{1-3}$ alkyl, halo($C_{1-3}$)alkyl, hydroxy($C_{1-3}$) alkyl, and $C_{3-7}$ cycloalkyl.

In an embodiment, ring A is phenyl, 6-membered heteroaryl, or $C_{3-10}$ cycloalkyl, wherein ring A is mono- or bicyclic, wherein ring A is optionally substituted with up to three substituents independently selected from halo, cyano, nitro, hydroxy, —$NR^aR^b$, carboxy, —$CONR^aR^b$, $C_{1-3}$ alkyl, $C_{1-3}$ alkoxy, halo($C_{1-3}$)alkyl, halo($C_{1-3}$)alkoxy, hydroxy($C_{1-3}$)alkyl, cyano($C_{1-3}$)alkyl, $C_{1-3}$ alkylsulfonyl, —C(O)O($C_{1-4}$)alkyl, and $C_{3-7}$ cycloalkyl.

In an embodiment, ring A is phenyl, 6-membered heteroaryl, or $C_{3-10}$ cycloalkyl, wherein ring A is mono- or bicyclic, wherein ring A is optionally substituted with up to three substituents independently selected from halo, hydroxy, $C_{1-3}$alkyl, halo($C_{1-3}$)alkyl, hydroxy($C_{1-3}$)alkyl, and $C_{3-7}$ cycloalkyl.

In an embodiment, ring A is phenyl or $C_{3-10}$ cycloalkyl, wherein ring A is mono- or bicyclic, wherein ring A is optionally substituted with up to three substituents independently selected from halo, cyano, nitro, hydroxy, —$NR^aR^b$, carboxy, —$CONR^aR^b$, $C_{1-3}$alkyl, $C_{1-3}$alkoxy, halo($C_{1-3}$)alkyl, halo($C_{1-3}$)alkoxy, hydroxy($C_{1-3}$)alkyl, cyano($C_{1-3}$)alkyl, $C_{1-3}$ alkylsulfonyl, —C(O)O($C_{1-4}$)alkyl, and $C_{3-7}$ cycloalkyl.

In an embodiment, ring A is phenyl, bicyclo[1.1.1]pentyl, or cyclohexyl, wherein ring A is optionally substituted with up to three substituents independently selected from halo, cyano, nitro, hydroxy, —$NR^aR^b$, carboxy, $CONR^aR^b$, $C_{1-3}$alkyl, $C_{1-3}$alkoxy, halo($C_{1-3}$)alkyl, halo($C_{1-3}$)alkoxy, hydroxy($C_{1-3}$)alkyl, cyano($C_{1-3}$)alkyl, $C_{1-3}$ alkylsulfonyl, —C(O)O($C_{1-4}$)alkyl, and $C_{3-7}$ cycloalkyl.

In an embodiment, ring A is phenyl or $C_{3-10}$ cycloalkyl, wherein ring A is mono- or bicyclic, wherein ring A is optionally substituted with up to three substituents independently selected from halo, hydroxy, $C_{1-3}$ alkyl, halo($C_{1-3}$) alkyl, hydroxy($C_{1-3}$)alkyl, and $C_{3-7}$ cycloalkyl.

In an embodiment, ring A is phenyl optionally substituted with up to three substituents independently selected from halo, cyano, nitro, hydroxy, —$NR^aR^b$, carboxy, —$CONR^aR^b$, $C_{1-3}$ alkyl, $C_{1-3}$ alkoxy, halo($C_{1-3}$)alkyl, halo($C_{1-3}$) alkoxy, hydroxy($C_{1-3}$)alkyl, cyano($C_{1-3}$)alkyl, $C_{1-3}$ alkylsulfonyl, —C(O)O($C_{1-4}$)alkyl, and $C_{3-7}$ cycloalkyl.

In an embodiment, ring A is phenyl, optionally substituted with one or two substituents independently selected from halo, hydroxy, $C_{1-3}$ alkyl, and halo($C_{1-3}$)alkyl.

In an embodiment, ring A is phenyl optionally substituted with up to three substituents independently selected from halo, $C_{1-3}$ alkyl, and halo($C_{1-3}$)alkyl.

In an embodiment, ring A is phenyl optionally substituted with up to three substituents independently selected from halo and halo($C_{1-3}$)alkyl.

In an embodiment, ring A is phenyl substituted with fluoro and trifluoromethyl.

In an embodiment, ring A has the structure

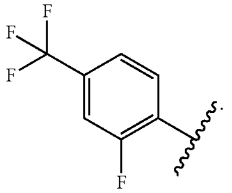 [SMILES: *c1ccc(C(F)(F)F)cc1F]

For the avoidance of doubt, the wavy line represents the point of attachment to the remainder of the compound.

In an embodiment, ring A is phenyl, 2-azaspiro[3.3]heptyl, tetrahydropyranyl, pyridinyl, bicyclo[1.1.1]pentyl, cyclohexyl, spiro[4.5]decyl, (3as,6as)-octahydropentalenyl, bicyclo[2.2.1]heptyl, or 2,3-dihydroindenyl, wherein ring A is optionally substituted with up to three substituents independently selected from halo, cyano, nitro, hydroxy, —$NR^aR^b$, carboxy, $CONR^aR^b$, $C_{1-3}$ alkyl, $C_{1-3}$ alkoxy, halo($C_{1-3}$)alkyl, halo($C_{1-3}$)alkoxy, hydroxy($C_{1-3}$)alkyl, cyano($C_{1-3}$)alkyl, $C_{1-3}$ alkylsulfonyl, —C(O)O($C_{1-4}$)alkyl, and $C_{3-7}$ cycloalkyl.

In an embodiment, ring A is selected from the group consisting of:

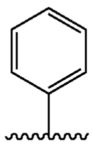
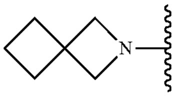
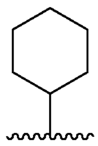
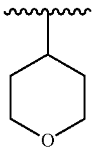
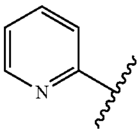
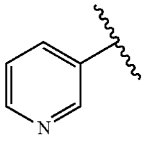
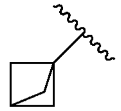
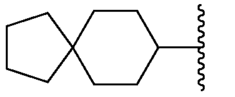
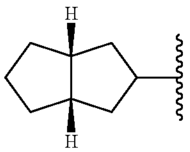
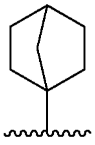
and
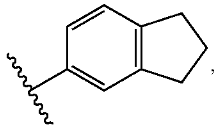
, wherein ring A is optionally substituted with up to three substituents independently selected from halo, cyano, nitro, hydroxy, —$NR^aR^b$, carboxy, —$CONR^aR^b$, $C_{1-3}$alkyl, $C_{1-3}$alkoxy, halo($C_{1-3}$)alkyl, halo($C_{1-3}$)alkoxy, hydroxy($C_{1-3}$)alkyl, cyano($C_{1-3}$)alkyl, $C_{1-3}$ alkylsulfonyl, —C(O)O($C_{1-4}$)alkyl, and $C_{3-7}$ cycloalkyl.

In an embodiment, $L^1$ is —$NR^o$—C(O)— or —$OCH_2$—. In an embodiment, $L^1$ is —$NR^o$—C(O)—. In an embodiment, $L^1$ is —NH—C(O)—. For the avoidance of doubt, the left side of the bivalent $L^1$ moiety (e.g. the N atom of —$NR^c$—C(O)—) is attached to ring A.

In an embodiment, n is 1.

In an embodiment, $R^1$ is hydrogen.

In an embodiment, $R^2$ is hydrogen, fluorine, or methyl. In an embodiment, $R^2$ is hydrogen.

In an embodiment, $L^2$ is —$NR^f$—$S(O)_2$—. For the avoidance of doubt, the left side of the bivalent $L^2$ moiety (e.g. the N atom of —$NR^f$—$S(O)_2$—) is attached to the aromatic ring and the right side is attached to Z.

In an embodiment $R^f$ is H, $CH_3$, or cyclopropane. In an embodiment $R^f$ is $CH_3$.

In an embodiment, $L^2$ is —$NCH_3$—$S(O)_2$—.

In an embodiment, $R^{X2}$, $R^{X3}$, and $R^{X4}$ are each independently selected from hydrogen, fluoro, cyano, hydroxy, methyl, methoxy, ethoxy, propoxy, isopropoxy, phenoxy, difluoromethoxy, cyclobutyloxy, cyclobutylmethoxy, cyclopropylmethoxy, (tetrahydrofuryl)methoxy, oxetylmethoxy, (tetrahydro-2H-pyranyl)methoxy, (8-oxabicyclo[3.2.1]octanyl)methoxy, (methoxybicyclo[1.1.1]pentanyl)methoxy, (methyloxetyl)methoxy, 2,2-difluoroethoxy, (tetrahydrofuryl)oxy, methoxyethoxy, (1,4-dioxanyl)methoxy, methoxymethyl, morpholinyl, difluoropyrrolidinyl, piperidinyl, fluoropiperidinyl, difluoropiperidinyl, —$NH_2$,—NHEt, —$NMe_2$, —N(Me)C(O)Me, —NHC(O)Me, —NHMe, and —$NH(CH_2CF_3)$; or $R^{X5}$ is hydrogen, fluoro, hydroxy, or $C_{1-3}$ alkyl; or any two of $R^{X2}$, $R^{X3}$, or $R^{X5}$ taken together with the carbon atoms to which they are attached form a 5-membered ring which containing O.

In an embodiment, $R^{X5}$ is hydrogen.

In an embodiment, $R^{X2}$, $R^{X3}$, and $R^{X4}$ are each independently selected from hydrogen, halo, cyano, —$NR^dR^e$, hydroxy, carboxy, phenoxy, phenyl, $C_{1-3}$ alkyl, halo($C_{1-3}$)alkyl, hydroxy($C_{1-3}$)alkyl, $C_{1-3}$ alkoxy($C_{1-3}$)alkyl-, $C_{1-3}$ alkoxy, halo($C_{1-3}$)alkoxy, and $L^X$-V, and $R^{X5}$ is hydrogen, halo, hydroxy, and $C_{1-3}$ alkyl.

In an embodiment, any two of $R^{X2}$, $R^{X3}$, $R^{X4}$, or $R^{X5}$ taken together with the carbon atoms to which they are attached form a 3- to 6-membered ring which optionally contains one or two heteroatoms independently selected from N, O, and S and which is optionally substituted with up to three substituents independently selected from halo, $C_{1-3}$ alkyl, halo($C_{1-3}$)alkyl, $C_{1-3}$ alkoxy, and halo($C_{1-3}$)alkoxy.

In an embodiment, $R^{X2}$, $R^{X3}$, and $R^{X4}$ are each independently selected from hydrogen, —$NR^dR^e$, hydroxy, phenoxy, $C_{1-3}$ alkyl, methoxy($C_{1-3}$)alkyl, halo($C_{1-3}$)alkoxy, and $C_{1-3}$ alkoxy, wherein $C_{1-3}$ alkoxy is optionally substituted with $C_{3-7}$ cycloalkyl; or $R^{X2}$ and $R^{X3}$ taken together with the carbon atoms to which they are attached form a 5-membered ring which optionally contains one O.

In an embodiment, $R^{X2}$, $R^{X3}$, and $R^{X4}$ are each independently selected from H, OH, Me, OMe, OEt, OPr, OPh, cyclobutylmethoxy, 2,2-difluoroethoxy, methoxymethyl, —NHEt, —$NMe_2$, and —NHMe; or $R^{X2}$ and $R^{X3}$ taken together with the carbon atoms to which they are attached form a 5-membered ring containing one O.

In an embodiment, $R^{X2}$, $R^{X3}$, and $R^{X4}$ are each independently selected from hydrogen and $C_{1-3}$ alkoxy. In another embodiment, $R^{X2}$ and $R^{X4}$ are hydrogen and $R^{X3}$ is selected from $C_{1-3}$ alkoxy and hydrogen. In another embodiment, $R^{X2}$ and $R^{X4}$ are hydrogen and $R^{X3}$ is selected from ethoxy and hydrogen. In another embodiment, $R^{X2}$, $R^{X3}$, and $R^{X4}$ are hydrogen. In an alternative embodiment, $R^{X2}$ and $R^{X4}$ are hydrogen and $R^{X3}$ is ethoxy.

In an embodiment, $R^{X2}$ and $R^{X3}$ taken together with the carbon atoms to which they are attached form a 5- or 6-membered ring which optionally contains one or two heteroatoms independently selected from N, O, and S and which is optionally substituted with up to three substituents independently selected from halo, $C_{1-3}$ alkyl, halo($C_{1-3}$)alkyl, $C_{1-3}$ alkoxy, and halo($C_{1-3}$)alkoxy.

In an embodiment, $R^{X2}$ and $R^{X3}$ taken together with the carbon atoms to which they are attached form a 5- or 6-membered ring which contains one heteroatoms independently selected from N, O, and S and which is optionally substituted with up to three substituents independently selected from halo, $C_{1-3}$ alkyl, halo($C_{1-3}$)alkyl, $C_{1-3}$ alkoxy, and halo($C_{1-3}$)alkoxy.

In an embodiment, $R^{X3}$ and $R^{X5}$ taken together with the carbon atom to which they are attached form a 3- or 6-membered ring which optionally contains one or two heteroatoms independently selected from N, O, and S and which is optionally substituted with up to three substituents independently selected from halo, $C_{1-3}$ alkyl, halo($C_{1-3}$)alkyl, $C_{1-3}$ alkoxy, and halo($C_{1-3}$)alkoxy.

In an embodiment, $R^{X2}$, $R^{X4}$, and $R^{X5}$ are hydrogen, and $R^{X3}$ is halo, cyano, —$NR^dR^e$, hydroxy, carboxy, phenoxy, phenyl, $C_{1-3}$ alkyl, halo($C_{1-3}$)alkyl, hydroxy($C_{1-3}$)alkyl, $C_{1-3}$ alkoxy($C_{1-3}$)alkyl-, $C_{1-3}$ alkoxy, halo($C_{1-3}$)alkoxy, or $L^X$-V.

In an embodiment, $R^{X2}$, $R^{X4}$, and $R^{X5}$ are hydrogen, and $R^{X3}$ is selected from hydrogen, $C_{1-3}$ alkoxy, and $C_{1-3}$alkoxy($C_{1-3}$)alkyl-. In an embodiment, $R^{X2}$, $R^{X3}$, $R^{X4}$, and $R^{X5}$ are hydrogen. In an embodiment, $R^{X2}$, $R^{X4}$, and $R^{X5}$ are hydrogen, and $R^{X3}$ is ethoxyl. In an embodiment, $R^{X2}$, $R^{X4}$, and $R^{X5}$ are hydrogen, and $R^{X3}$ is methoxylmethyl.

In an embodiment, $R^{X2}$, $R^{X4}$, $R^{X5}$ are hydrogen, and $R^{X3}$ is $L^X$-V.

In an embodiment, $L^X$ is a bond, —$CH_2$—, —$NR^d$—, —$NR^d$C(O)—, —$NR^d$—$(CH_2)_w$—, —O—$(CH_2)_w$—, or —S—$(CH_2)_w$—; and V is independently $C_{3-7}$ cycloalkyl or a 3- to 10-membered heterocycloalkyl ring containing one, two, or three heteroatoms independently selected from N, O, and S, wherein V is optionally substituted with up to three substituents independently selected from halo, $C_{1-3}$ alkyl, halo($C_{1-3}$)alkyl, $C_{1-3}$ alkoxy, and halo($C_{1-3}$)alkoxy.

In an embodiment, $L^X$ is a bond, —$CH_2$—, —$NR^d$—$(CH_2)_w$—, or —O—$(CH_2)_w$—; V is independently selected from $C_{1-3}$ alkoxy, $C_{3-4}$ cycloalkyl, or a 3- to 7-membered heterocycloalkyl ring containing one or two heteroatoms independently selected from N or O, wherein V is optionally substituted with one substituent independently selected from $C_{1-3}$ alkyl and $C_{1-3}$ alkoxy; and w is 0 or 1.

In an embodiment, $L^X$ is a bond or —O—$(CH_2)_w$—; V is $C_{3-7}$ cycloalkyl or a 3- to 6-membered heterocycloalkyl ring containing one heteroatom selected from N and O, wherein V is optionally substituted with up to three substituents independently selected from halo, $C_{1-3}$ alkyl, halo($C_{1-3}$)alkyl, $C_{1-3}$ alkoxy, and halo($C_{1-3}$)alkoxy; and w is 0 or 1.

In an embodiment, $L^X$ is a bond or —O—$(CH_2)_w$—; V is a 3- to 6-membered heterocycloalkyl ring containing one or two heteroatoms selected from N and O, wherein V is optionally substituted with up to three substituents independently selected from halo, $C_{1-3}$ alkyl, halo($C_{1-3}$)alkyl, $C_{1-3}$ alkoxy, and halo($C_{1-3}$)alkoxy; and w is 0 or 1.

In an embodiment, $L^X$ is a bond or —O—$(CH_2)_w$—; V is a 3- to 6-membered heterocycloalkyl ring containing one or two heteroatoms selected from N and O, wherein V is optionally substituted with up to three substituents independently selected from halo, halo($C_{1-3}$)alkyl, $C_{1-3}$ alkoxy, and halo($C_{1-3}$)alkoxy; and w is 0 or 1.

In an embodiment, $L^X$ is a bond or —O—$(CH_2)_w$—; V is a 5- to 6-membered heterocycloalkyl ring containing one or two heteroatoms selected from N and O, wherein V is optionally substituted with up to three substituents independently selected from halo, halo($C_{1-3}$)alkyl, $C_{1-3}$ alkoxy, and halo($C_{1-3}$)alkoxy; and w is 0 or 1.

In an embodiment, $L^X$ is a bond or —O—$(CH_2)_w$—; V is selected from the group consisting of oxetan-3-yl, 3,3-difluoropyrrolidin-1-yl, cyclopropyl, oxolan-3-yl, cyclobutyl, 1,4-dioxan-2-yl, 3-methoxybicyclo[1.1.1]pentan-1-yl, morpholin-4-yl, 4,4-difluoropiperidin-1-yl, 3-fluoropiperidin-1-yl, piperidin-1-yl, 3,3-difluoropiperidin-1-yl, oxan-4-yl, 8-oxabicyclo[3.2.1]octan-3-yl, 3-methyloxetan-3-yl), 3-fluoropyrrolidin-1-yl, and 4-fluoro-2-azabicyclo[2.1.1]hexan-2-yl; and w is 0 or 1. In an embodiment, V is 3,3-difluoropyrrolidin-1-yl.

For the avoidance of doubt, the left side of the bivalent $L^X$ moiety (e.g. the N atom of —$NR^d$C(O)—) is attached to the ring and the right side is attached to V.

In an embodiment, $Y^1$, $Y^2$, $Y^3$, and $Y^4$ are CRY; or $Y^1$, $Y^2$, and $Y^3$ are CRY, and $Y^4$ is N; or $Y^2$ and $Y^4$ are CRY, and $Y^1$ and $Y^3$ are N.

In an embodiment, $Y^1$, $Y^2$, $Y^3$, and $Y^4$ are CRY.

In an embodiment, each $R^y$ is independently selected from hydrogen, halo, cyano, $C_{1-3}$alkyl, $C_{1-3}$ alkoxy, methoxy($C_{1-3}$)alkoxy, hydroxy($C_{2-5}$)alkyl, hydroxy($C_{2-5}$)alkynyl, $C_{2-5}$ alkynyl, and a 5-membered heteroaryl containing up to three heteroatoms independently selected from N, O, and S, wherein the 5-membered heteroaryl is optionally substituted with up to three $C_{1-3}$ alkyl; or $R^y$ and $R^f$ taken together with the atoms to which they are attached form a 6-membered ring which optionally contains an oxygen atom.

In an embodiment, each $R^y$ is independently selected from hydrogen, halo, cyano, $C_{1-3}$alkoxy, methoxy($C_{1-3}$)alkoxy, hydroxy($C_{2-5}$)alkyl, hydroxy($C_{2-5}$)alkynyl, $C_{2-5}$ alkynyl, and a 5-membered heteroaryl containing up to three heteroatoms independently selected from N, O, and S, wherein the 5-membered heteroaryl is optionally substituted with up to three $C_{1-3}$ alkyl; or $R^y$ and $R^f$ taken together with the atoms to which they are attached form a 6-membered ring which optionally contains an oxygen atom.

In an embodiment, each $R^y$ is independently selected from hydrogen, halo, cyano, methyl, methoxy, methoxyethoxy, hydroxymethyl, 2-methylbut-3-ynyl-2-ol, propyl, and 2-methyl-1,3,4-oxadiazolyl; or $R^y$ and $R^f$ taken together with the atoms to which they are attached form a 6-membered ring which contains an oxygen atom.

In an embodiment, each $R^y$ is independently selected from hydrogen, halo, cyano, methoxy, methoxyethoxy, hydroxymethyl, 2-methylbut-3-ynyl-2-ol, propyl, and 2-methyl-1,3,4-oxadiazolyl; or $R^y$ and $R^f$ taken together with the atoms to which they are attached form a 6-membered ring which contains an oxygen atom.

In an embodiment, each $R^y$ is hydrogen. In other words, in an embodiment, $Y^1$, $Y^2$, $Y^3$, and $Y^4$ are each CH.

In an embodiment, Z is halo, $C_{1-3}$ alkyl, halo($C_{1-3}$)alkyl, $C_{2-5}$ alkenyl, halo($C_{2-5}$)alkenyl, or $C_{2-5}$ alkynyl; or Z is ring B, wherein ring B is phenyl, benzimidazolyl, 3-azabicycloheptyl, 1,2,3,4-tetrahydroisoquinolinyl, 1,2,3,4-tetrahydroquinoxalinyl, 1,3,4-thiadiazolyl, 1,3-dihydroisobenzofuranyl, indazolyl, indolyl, 1-oxa-6-azaspirooctyl, 2,3-dihydrobenzofuranyl, 2,5-dihydrofuranyl, 2,5-dihydrothienyl 1,1-dioxide, 3,4-dihydrobenzooxazinyl, 3,4-dihydropyranyl, imidazopyridinyl, 1,2,4-triazolyl, 5,6,7,8-tetrahydropyridopyridazinyl, 5,6-dihydropyrrolopyrazolyl, 6-oxaspirooctyl, benzothienyl, benzoisothiazolyl, benzooxazolyl-2-one, benzooxazolyl, benzothiazolyl, benzofuranyl, cyclohexyl, cyclopentyl, cyclopropyl, furanyl, furopyridazinyl, imidazopyridazinyl, imidazolidinyl-2-one, indolinyl, isoquinolinyl, isothiazolyl, isoxazolyl, oxepanyl, oxetyl, piperidinyl, pyrazolyl, pyridazinyl, pyridinyl, pyrimidinyl, tetrahydrofuranyl, tetrahydrothienyl 1,1-dioxide, tetrazolopyridazinyl, thiazolyl, thienopyrimidinyl, thienopyridinyl, or thienyl, wherein ring B is optionally substituted with up to three substituents independently selected from halo, cyano, nitro, hydroxy, carboxy, $C_{1-3}$alkyl, $C_{1-3}$alkoxy, halo($C_{1-3}$)alkyl, halo($C_{1-3}$)alkoxy, hydroxy($C_{1-3}$)alkyl, $C_{2-5}$ alkenyl, $C_{2-5}$ alkynyl, —$C_{1-3}$alkylene-$NR^gR^h$, —$CONR^gR^h$, —$NR^gR^h$, —$NR^g$C(O)$R^h$, $SO_2NR^gR^h$, and $L^B$-W, or two substituents of ring B taken together with the atoms to which they are attached form a 5- or 6-membered ring which optionally contains one or two heteroatoms independently selected from N, O, and S; and wherein $L^B$, W, $R^g$, and $R^h$ are as defined herein in relation to Formulae (I), (I-a), and (I-aa).

In an embodiment, Z is halo, halo($C_{1-3}$)alkyl, $C_{2-5}$ alkenyl, halo($C_{2-5}$)alkenyl, or $C_{2-5}$ alkynyl; or Z is ring B, wherein ring B is phenyl, benzimidazolyl, 3-azabicycloheptyl, 1,2,3,4-tetrahydroisoquinolinyl, 1,2,3,4-tetrahydroquinoxalinyl, 1,3,4-thiadiazolyl, 1,3-dihydroisobenzofuranyl, indazolyl, indolyl, 1-oxa-6-azaspirooctyl, 2,3-dihydrobenzofuranyl, 2,5-dihydrofuranyl, 2,5-dihydrothienyl 1,1-dioxide, 3,4-dihydrobenzooxazinyl, 3,4-dihydropyranyl, imidazopyridinyl, 1,2,4-triazolyl, 5,6,7,8-tetrahydropyridopyridazinyl, 5,6-dihydropyrrolopyrazolyl, 6-oxaspirooctyl, benzothienyl, benzoisothiazolyl, benzooxazolyl-2-one, benzooxazolyl, benzothiazolyl, benzofuranyl, cyclohexyl, cyclopentyl, cyclopropyl, furanyl, furopyridazinyl, imidazopyridazinyl, imidazolidinyl-2-one, indolinyl, isoquinolinyl, isothiazolyl, isoxazolyl, oxepanyl, oxetyl, piperidinyl, pyrazolyl, pyridazinyl, pyridinyl, pyrimidinyl, tetrahydrofuranyl, tetrahydrothienyl 1,1-dioxide, tetrazolopyridazinyl, thiazolyl, thienopyrimidinyl, thienopyridinyl, or thienyl, wherein ring B is optionally substituted with up to three substituents independently selected from halo, cyano, nitro, hydroxy, carboxy, $C_{1-3}$alkyl, $C_{1-3}$alkoxy, halo($C_{1-3}$)alkyl, halo($C_{1-3}$)alkoxy, hydroxy($C_{1-3}$)alkyl, $C_{2-5}$ alkenyl, $C_{2-5}$ alkynyl, —$C_{1-3}$alkylene-$NR^gR^h$, —$CONR^gR^h$, —$NR^gR^h$, —$NR^gC(O)R^h$, $SO_2NR^gR^h$, and $L^B$-W, or two substituents of ring B taken together with the atoms to which they are attached form a 5- or 6-membered ring which optionally contains one or two heteroatoms independently selected from N, O, and S; and wherein $L^B$, W, $R^g$, and $R^h$ are as defined herein in relation to Formulae (I), (I-a), and (I-aa).

In an embodiment, Z is halo, $C_{1-3}$ alkyl, halo($C_{1-3}$)alkyl, $C_{2-5}$ alkenyl, halo($C_{2-5}$)alkenyl, or $C_{2-5}$ alkynyl.

In an embodiment, Z is halo, halo($C_{1-3}$)alkyl, $C_{2-5}$ alkenyl, halo($C_{2-5}$)alkenyl, or $C_{2-5}$ alkynyl.

In an embodiment, $L^2$ is a bond, —$NR^f$—$S(O)_2$—, or —$NR^f$—C(O)—; and

Z is halo, halo($C_{1-3}$)alkyl, $C_{2-5}$ alkenyl, halo($C_{2-5}$)alkenyl, or $C_{2-5}$ alkynyl.

In an embodiment, Z is bromo, trifluoromethyl, ethenyl, 1-fluoroethenyl, or ethynyl.

In an embodiment, $L^2$ is a bond, —$NR^f$—$S(O)_2$—, or —$NR^f$—C(O)—; and

Z is bromo, trifluoromethyl, ethenyl, 1-fluoroethenyl, or ethynyl.

In an embodiment, Z is ring B, wherein ring B is $C_{6-10}$ aryl, 3- to 10-membered heteroaryl, $C_{3-10}$ cycloalkyl, or 3- to 10-membered heterocycloalkyl, wherein ring B is optionally substituted with up to three substituents independently selected from halo, cyano, nitro, hydroxy, carboxy, $C_{1-3}$ alkyl, $C_{1-3}$ alkoxy, halo($C_{1-3}$)alkyl, halo($C_{1-3}$)alkoxy, hydroxy($C_{1-3}$)alkyl, $C_{2-5}$ alkenyl, $C_{2-5}$ alkynyl, —$C_{1-3}$alkylene-$NR^gR^h$, —$CONR^gR^h$, —$NR^gR^h$, —$NR^gC(O)R^h$, $SO_2NR^gR^h$, and $L^B$-W, wherein $L^B$, W, $R^g$, and $R^h$ are as defined herein in relation to Formulae (I), (I-a), and (I-aa).

In an embodiment, Z is ring B, wherein ring B is phenyl, benzimidazolyl, 3-azabicycloheptyl, 1,2,3,4-tetrahydroisoquinolinyl, 1,2,3,4-tetrahydroquinoxalinyl, 1,3,4-thiadiazolyl, 1,3-dihydroisobenzofuranyl, indazolyl, indolyl, 1-oxa-6-azaspirooctyl, 2,3-dihydrobenzofuranyl, 2,5-dihydrofuranyl, 2,5-dihydrothienyl 1,1-dioxide, 3,4-dihydrobenzooxazinyl, 3,4-dihydropyranyl, imidazopyridinyl, 1,2,4-triazolyl, 5,6,7,8-tetrahydropyridopyridazinyl, 5,6-dihydropyrrolopyrazolyl, 6-oxaspirooctyl, benzothienyl, benzoisothiazolyl, benzooxazolyl-2-one, benzooxazolyl, benzothiazolyl, benzofuranyl, cyclohexyl, cyclopentyl, cyclopropanyl, furanyl, furopyridazinyl, imidazopyridazinyl, imidazolidinyl-2-one, indolinyl, isoquinolinyl, isothiazolyl, isoxazolyl, oxepanyl, oxetyl, piperidinyl, pyrazolyl, pyridazinyl, pyridinyl, pyrimidinyl, tetrahydrofuranyl, tetrahydrothienyl 1,1-dioxide, tetrazolopyridazinyl, thiazolyl, thienopyrimidinyl, thienopyridinyl, or thienyl, wherein ring B is optionally substituted with up to three substituents independently selected from halo, cyano, nitro, hydroxy, carboxy, $C_{1-3}$alkyl, $C_{1-3}$alkoxy, halo($C_{1-3}$)alkyl, halo($C_{1-3}$)alkoxy, hydroxy($C_{1-3}$)alkyl, $C_{2-5}$ alkenyl, $C_{2-5}$ alkynyl, —$C_{1-3}$alkylene-$NR^gR^h$, —$CONR^gR^h$, —$NR^gR^h$, —$NR^gC(O)R^h$, $SO_2NR^gR^h$, and $L^B$-W, or two substituents of ring B taken together with the atoms to which they are attached form a 5- or 6-membered ring which optionally contains one or two heteroatoms independently selected from N, O, and S; and wherein $L^B$, W, $R^g$, and $R^h$ are as defined herein in relation to Formulae (I), (I-a), and (I-aa).

In an embodiment, ring B is selected from the group consisting of:

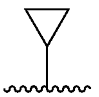 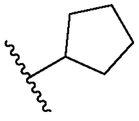 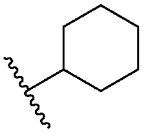 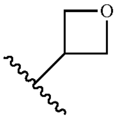

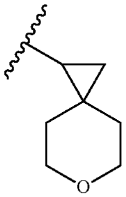 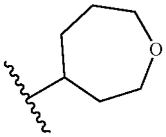 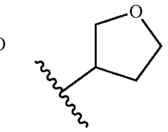

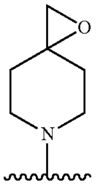 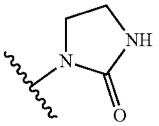 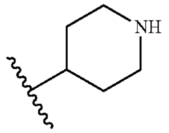

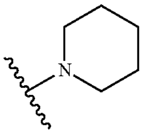 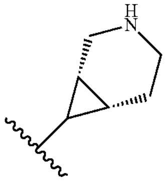 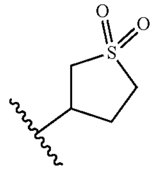

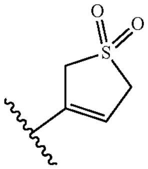 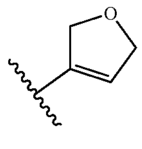 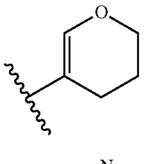

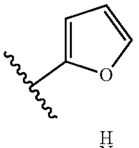 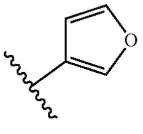 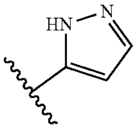

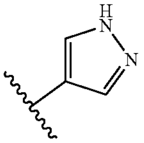 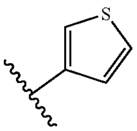 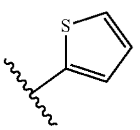

-continued

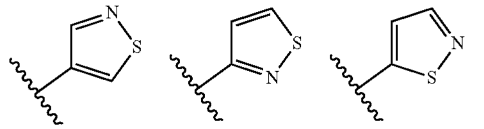
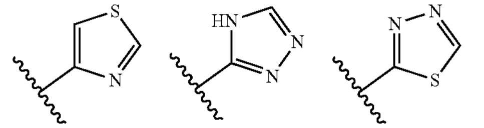
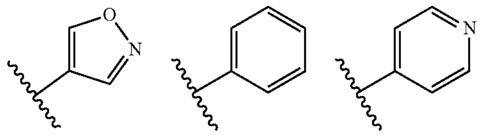
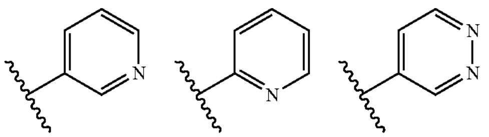
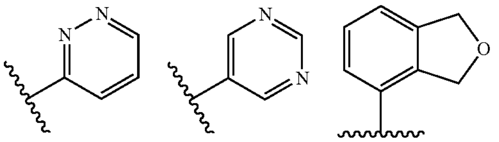
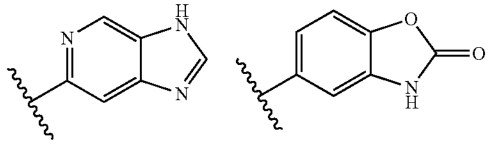
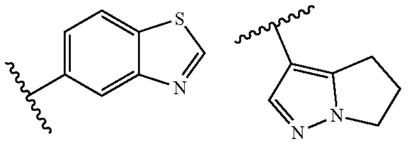
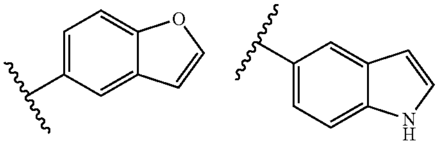
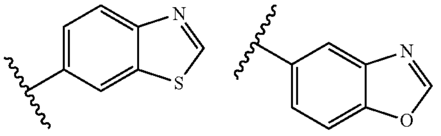
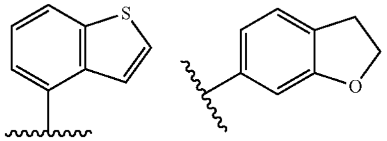
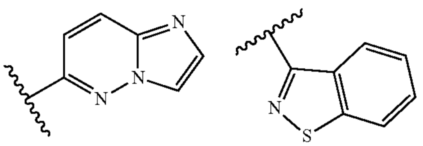
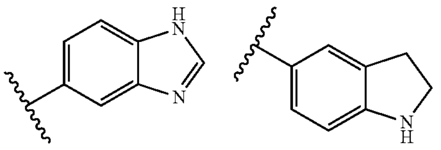

-continued

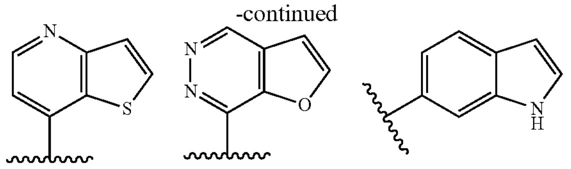
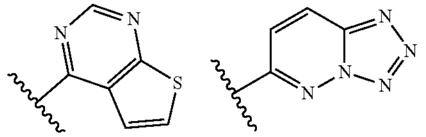
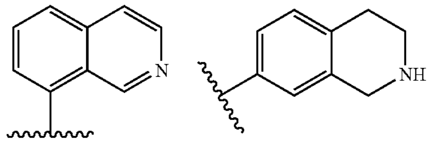
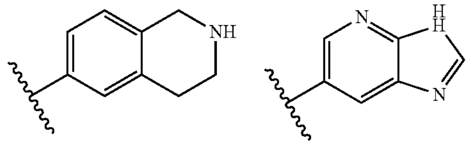
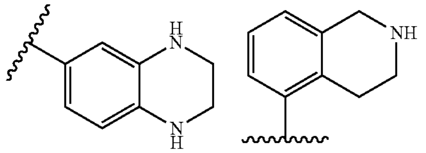
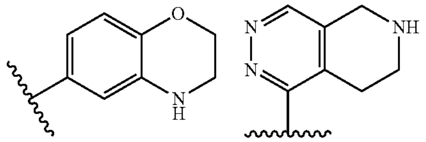

and

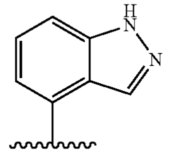

wherein each of the above groups can be substituted with up to three substituents independently selected from halo, cyano, nitro, hydroxy, carboxy, $C_{1-3}$ alkyl, $C_{1-3}$ alkoxy, halo($C_{1-3}$)alkyl, halo($C_{1-3}$)alkoxy, hydroxy($C_{1-3}$)alkyl, $C_{2-5}$ alkenyl, $C_{2-5}$ alkynyl, —$C_{1-3}$ alkylene-$NR^gR^h$, —$CONR^gR^h$, —$NR^gR^h$, —$NR^gC(O)R^h$, $SO_2NR^gR^h$, and $L^B$-W, or two substituents of ring B taken together with the atoms to which they are attached form a 5- or 6-membered ring which optionally contains one or two heteroatoms independently selected from N, O, and S; and wherein $L^B$, W, $R^9$, and $R^h$ are as defined herein in relation to Formulae (I), (1-a), and (I-aa).

In an embodiment, ring B is optionally substituted with up to three substituents independently selected from halo, cyano, hydroxy, $C_{1-3}$ alkyl, $C_{1-3}$ alkoxy, halo($C_{1-3}$)alkyl, hydroxy($C_{1-3}$)alkyl, —$C_{2-5}$alkenyl, —$C_{1-3}$alkylene-$NR^gR^h$, —$NR^gR^h$, —$NR^gC(O)R^h$, $SO_2NR^gR^h$, and $L^B$-W, or two substituents of ring B taken together with the atoms to which they are attached form a 5- or 6-membered ring which optionally contains one or two heteroatoms independently selected from N, O, and S;

$L^B$ is independently selected from a bond, —$(CH_2)_p$—, —$CH_2O$—, —C(O)—, and —$CH_2C(O)NH$—;

W is independently selected from hydrogen, $C_{1-3}$ alkyl, —O($C_{1-4}$)alkyl, $C_{3-7}$ cycloalkyl, 5- or 6-membered heteroaryl, and 4- to 6-membered heterocycloalkyl ring containing one, two, or three heteroatoms independently selected from N, O, and S, wherein W is optionally substituted with up to three substituents independently selected from halo, $C_{1-3}$ alkyl, and —C(O)O($C_{1-4}$)alkyl;

p is 1; and wherein $R^g$ and $R^h$ are each independently hydrogen or $C_{1-3}$ alkyl.

For the avoidance of doubt, the left side of the bivalent $L^B$ moiety (e.g. the C atom of —$CH_2O$—) is attached to ring B and the right side is attached to W.

In an embodiment, Z is ring B, wherein ring B is phenyl, benzoimidazolyl, 1,2,3,4-tetrahydroisoquinolinyl, 1,2,3,4-tetrahydroquinoxalinyl, 1,3,4-thiadiazolyl, 1,3-dihydroisobenzofuranyl, indazolyl, indolyl, 2,3-dihydrobenzofuranyl, 2,5-dihydrofuranyl, 2,5-dihydrothienyl 1,1-dioxide, 3,4-dihydrobenzooxazinyl, 3,4-dihydropyranyl, imidazopyridinyl, 1,2,4-triazolyl, 5,6-dihydropyrrolopyrazolyl, 6-oxaspirooctyl, benzoisothiazolyl, benzooxazolyl-2-one, benzooxazolyl, benzothiazolyl, benzofuranyl, cyclohexyl, cyclopentyl, furanyl, furopyridazinyl, imidazopyridazinyl, indolinyl, isothiazolyl, isoxazolyl, oxepanyl, piperidinyl, pyrazolyl, pyridazinyl, pyridinyl, pyrimidinyl, tetrahydrothienyl 1,1-dioxide, thiazolyl, orthienyl, wherein ring B is optionally substituted with up to three substituents independently selected from halo, cyano, nitro, hydroxy, carboxy, $C_{1-3}$ alkyl, $C_{1-3}$ alkoxy, halo($C_{1-3}$)alkyl, halo($C_{1-3}$)alkoxy, hydroxy($C_{1-3}$)alkyl, $C_{2-5}$alkenyl, $C_{2-5}$alkynyl, —$C_{1-3}$alkylene-$NR^gR^h$, —$CONR^gR^h$, —$NR^gR^h$, —$NR^gC(O)R^h$, $SO_2NR^gR^h$, and $L^B$-W;

$L^B$ and W are as defined herein in relation to Formulae (I), (I-a), and (I-aa); and wherein $R^g$ and $R^h$ are each independently hydrogen or $C_{1-3}$ alkyl.

In an embodiment, ring B is optionally substituted with up to three substituents independently selected from halo, cyano, hydroxy, $C_{1-3}$ alkyl, $C_{1-3}$ alkoxy, halo($C_{1-3}$)alkyl, hydroxy($C_{1-3}$)alkyl, $C_{2-5}$ alkenyl, —$C_{1-3}$alkylene-$NR^gR^h$, —$NR^gR^h$, —$NR^gC(O)R^h$, $SO_2NR^gR^h$, and $L^B$-W;

$L^B$ is independently selected from a bond, —$(CH_2)_p$—, —$CH_2O$—, —C(O)—, and —$CH_2C(O)NH$—;

W is independently selected from hydrogen, $C_{1-3}$ alkyl, —O($C_{1-4}$)alkyl, $C_{3-7}$ cycloalkyl, 5- or 6-membered heteroaryl, and 4- to 6-membered heterocycloalkyl ring containing one, two, or three heteroatoms independently selected from N, O, and S, wherein W is optionally substituted with up to three substituents independently selected from halo, $C_{1-3}$ alkyl, and —C(O)O($C_{1-4}$)alkyl;

p is 1; and wherein $R^g$ and $R^h$ are each independently hydrogen or $C_{1-3}$ alkyl.

In an embodiment, $L^2$ is —$NCH_3SO_2$—;

Z is $C_{2-5}$ alkenyl or $C_{1-3}$ alkyl; or

Z is ring B, wherein ring B is aryl or heteroaryl, wherein ring B is mono- or bicyclic and ring B is optionally substituted with up to three substituents independently selected from halo, hydroxy, $C_{1-3}$alkyl, $C_{1-3}$alkoxy, halo($C_{1-3}$)alkyl, —$C_{1-3}$ alkylene-$NR^gR^h$, —$NR^gR^h$, —$SO_2NR^gR^h$, and $L^B$-W, or two substituents of ring B taken together with the atoms to which they are attached form a 5- or 6-membered ring which optionally contains one or two heteroatoms independently selected from N, O, and S;

$L^B$ is independently selected from a bond and —C(O)—;

W is independently selected from hydrogen, $C_{1-3}$ alkyl, $C_{3-7}$ cycloalkyl, 5- or 6-membered heteroaryl, and 4- to 6-membered heterocycloalkyl ring containing one, two, or three heteroatoms independently selected from N, O, and S, wherein W is optionally substituted with up to three substituents independently selected from halo, $C_{1-3}$ alkyl, and —C(O)O($C_{1-4}$)alkyl; and $R^g$ and $R^h$ are each independently hydrogen or $C_{1-3}$ alkyl.

In an embodiment, $L^2$ is —$NCH_3SO_2$—;

Z is $C_{2-5}$ alkenyl; or

Z is ring B, wherein ring B is aryl or heteroaryl, wherein ring B is mono- or bicyclic and ring B is optionally substituted with up to three substituents independently selected from halo, hydroxy, $C_{1-3}$alkyl, $C_{1-3}$alkoxy, halo($C_{1-3}$)alkyl, —$C_{1-3}$alkylene-$NR^gR^h$, —$NR^gR^h$, $SO_2NR^gR^h$, and $L^B$-W, or two substituents of ring B taken together with the atoms to which they are attached form a 5- or 6-membered ring which optionally contains one or two heteroatoms independently selected from N, O, and S;

$L^B$ is independently selected from a bond and —C(O)—;

W is independently selected from hydrogen, $C_{1-3}$ alkyl, $C_{3-7}$ cycloalkyl, 5- or 6-membered heteroaryl, and 4- to 6-membered heterocycloalkyl ring containing one, two, or three heteroatoms independently selected from N, O, and S, wherein W is optionally substituted with up to three substituents independently selected from halo, $C_{1-3}$ alkyl, and —C(O)O($C_{1-4}$)alkyl; and $R^g$ and $R^h$ are each independently hydrogen or $C_{1-3}$ alkyl.

In an embodiment, $L^2$ is —$NCH_3SO_2$— and Z is ring B; wherein ring B is phenyl, benzimidazolyl, 1,2,4-triazolyl, pyridinyl, benzofuranyl, imidazopyridinyl, benzooxazolyl-2-one, indolyl, benzothiazolyl, benzooxazolyl, indolinyl, 2,3-dihydrobenzofuranyl, 1,2,3,4-tetrahydroisoquinolinyl, 1,2,3,4-tetrahydroquinoxalinyl, or 3,4-dihydrobenzoxazinyl, wherein ring B is optionally substituted with up to three substituents independently selected from halo, hydroxy, $C_{1-3}$ alkyl, $C_{1-3}$ alkoxy, halo($C_{1-3}$)alkyl, —$C_{1-3}$ alkylene-$NR^gR^h$, —$NR^gR^h$, —$SO_2NR^gR^h$, and $L^B$-W;

$L^B$ is independently selected from a bond and —C(O)—;

W is independently selected from hydrogen, $C_{1-3}$ alkyl, $C_{3-7}$ cycloalkyl, 5- or 6-membered heteroaryl, and 4- to 6-membered heterocycloalkyl ring containing one, two, or three heteroatoms independently selected from N, O, and S, wherein W is optionally substituted with up to three substituents independently selected from halo, $C_{1-3}$ alkyl, and —C(O)O($C_{1-4}$)alkyl; and $R^g$ and $R^h$ are each independently hydrogen or $C_{1-3}$ alkyl.

In an embodiment, $L^2$ is a bond;

Z is halo or halo($C_{1-3}$)alkyl; or

Z is ring B, wherein ring B is aryl, heteroaryl, $C_{3-10}$ cycloalkyl, or 3- to 10-membered heterocycloalkyl ring containing one, two or three heteroatoms independently selected from N, O, and S, wherein ring B is mono- or bicyclic and ring B is optionally substituted with up to three substituents independently selected from halo, cyano, hydroxy, $C_{1-3}$ alkyl, $C_{1-3}$ alkoxy, hydroxy($C_{1-3}$)alkyl, $C_{2-5}$ alkenyl, —$NR^gR^h$, and $L^B$-W;

$L^B$ is independently selected from —$(CH_2)_p$—, —$CH_2O$—, —C(O)—, and —$CH_2C(O)NH$—;

W is independently selected from —O($C_{1-4}$)alkyl, $C_{3-7}$ cycloalkyl, 5- or 6-membered heteroaryl, and 4- to 6-membered heterocycloalkyl ring containing one, two, or three heteroatoms independently selected from N, O, and S;

p is 1; and $R^g$ and $R^h$ are each independently hydrogen or $C_{1-3}$ alkyl.

In an embodiment, ring B is mono- or bicyclic. In an embodiment, ring B is bicyclic.

In an embodiment, ring B is benzimidazolyl optionally substituted with up to three substituents independently selected from halo, cyano, hydroxy, carboxy, $C_{1-3}$ alkyl, $C_{1-3}$ alkoxy, halo($C_{1-3}$)alkyl, hydroxy($C_{1-3}$)alkyl, $C_{2-5}$ alkenyl, —$C_{1-3}$alkylene-$NR^gR^h$, —$NR^gR^h$, —$NR^gC(O)R^h$, $SO_2NR^gR^h$ and $L^B$-W, or two substituents of ring B taken together with the atoms to which they are attached form a 5- or 6-membered ring which optionally contains one or two heteroatoms independently selected from N, O, and S;

$L^B$ is independently selected from a bond, —$(CH_2)_p$—, —$CH_2O$—, —C(O)—, and —$CH_2C(O)NH$—;

W is independently selected from hydrogen, $C_{1-3}$ alkyl, —O($C_{1-4}$)alkyl, $C_{3-7}$ cycloalkyl, 5- or 6-membered heteroaryl, and 4- to 6-membered heterocycloalkyl ring containing one, two, or three heteroatoms independently selected from N, O, and S, wherein W is optionally substituted with up to three substituents independently selected from halo, $C_{1-3}$ alkyl, and —C(O)O($C_{1-4}$)alkyl;

p is 1; and $R^g$ and $R^h$ are each independently hydrogen or $C_{1-3}$ alkyl.

In an embodiment, ring B is benzimidazolyl optionally substituted with up to three substituents independently selected from halo, $C_{1-3}$ alkyl, $C_{3-7}$ cycloalkyl, —$C_{1-3}$ alkylene-$NR^gR^h$, —$NR^gR^h$, and a 4- to 6-membered heterocycloalkyl ring containing one or two heteroatoms independently selected from N, O, and S, wherein the heterocycloalkyl ring is optionally substituted with $C_{1-3}$ alkyl; and wherein $R^g$ and $R^h$ are each independently hydrogen or $C_{1-3}$ alkyl.

In an embodiment, ring B is benzimidazolyl optionally substituted with up to three substituents independently selected from halo, $C_{1-3}$alkyl, cyclopropane, —$C_{1-3}$ alkylene-$NR^gR^h$, —$NR^gR^h$ and piperidine; and wherein $R^g$ and $R^h$ are each independently hydrogen or $C_{1-3}$ alkyl.

In an embodiment, ring B is benzimidazolyl linked to $L^2$ through a carbon atom and optionally substituted with up to three substituents independently selected from halo, $C_{1-3}$ alkyl, cyclopropane, —$C_{1-3}$ alkylene-$NR^gR^h$, —$NR^gR^h$ and piperidine; and wherein $R^g$ and $R^h$ are each independently hydrogen or $C_{1-3}$ alkyl.

In an embodiment, ring B is 1H-benzo[d]imidazole-5-yl optionally substituted with up to three substituents independently selected from halo, $C_{1-3}$ alkyl, cyclopropane, —$C_{1-3}$ alkylene-$NR^gR^h$, —$NR^gR^h$, and piperidine; and wherein $R^g$ and $R^h$ are each independently hydrogen or $C_{1-3}$ alkyl.

In an embodiment, when Z is ring B and ring B is benzimidazolyl, it is linked to $L^2$ through a carbon atom, for example through the carbon atom as shown in Formula (II) below.

In an embodiment, ring B is 1,2-dimethyl-1H-benzo[d]imidazol-5-yl.

In an embodiment, the compound of Formula (I) is a compound of Formula (I-b):

(I-b)

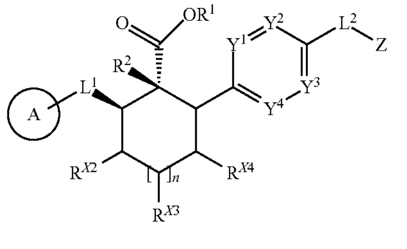

or a pharmaceutically acceptable salt thereof, wherein n, ring A, Z, $L^1$, $L^2$, $R^1$, $R^2$, $R^{X2}$, $R^{X3}$, $R^{X4}$, $Y^1$, $Y^2$, $Y^3$, and $Y^4$ are as defined herein in relation to Formulae (I), (I-a), and (I-aa).

In an embodiment, the compound of Formula (I) is a compound of Formula (I-c):

(I-c)

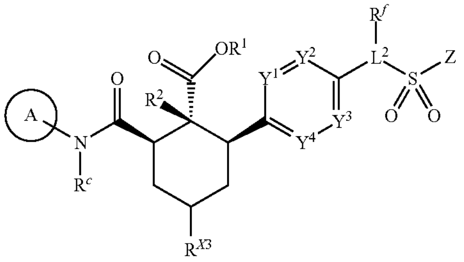

or a pharmaceutically acceptable salt thereof, wherein ring A, Z, $R^1$, $R^2$, $R^{X3}$, $R^o$, $R^f$, $Y^1$, $Y^2$, $Y^3$, and $Y^4$ are as defined herein in relation to Formulae (I), (I-a), and (I-aa).

In an embodiment, the compound of Formula (I) is a compound of Formula (I-cc):

(I-cc)

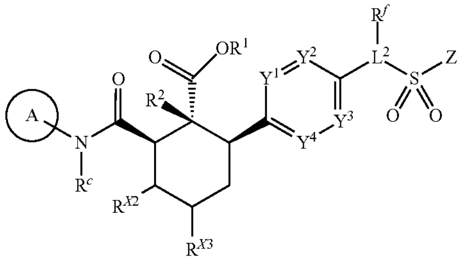

or a pharmaceutically acceptable salt thereof, wherein ring A, Z, $R^1$, $R^2$, $R^{X2}$, $R^{X3}$, $R^o$, $R^f$, $Y^1$, $Y^2$, $Y^3$, and $Y^4$ are as defined herein in relation to Formulae (I), (I-a), and (I-aa).

In an embodiment, the compound of Formula (I) is a compound of Formula (I-ccc):

(I-ccc)

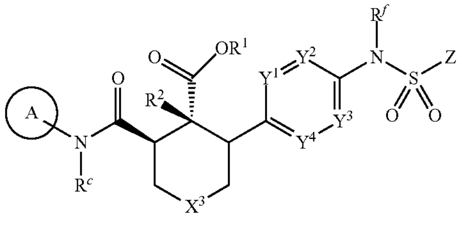

or a pharmaceutically acceptable salt thereof, wherein $X^3$ is —$NR^o$— or —O—, and wherein ring A, Z, $R^1$, $R^2$, $R^o$, $R^c$, $R^f$, $Y^1$, $Y^2$, $Y^3$, and $Y^4$ are as defined herein in relation to Formulae (I), (I-a), and (I-aa).

In an embodiment, the compound of Formula (I) is a compound of Formula (I-d):

(I-d)

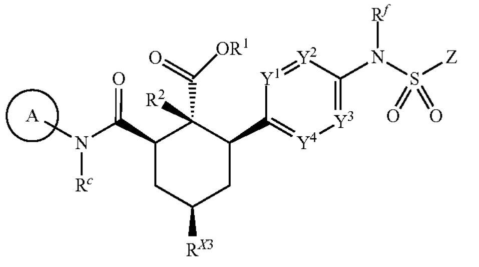

or a pharmaceutically acceptable salt thereof, wherein ring A, Z, $R^1$, $R^2$, $R^{X3}$, $R^c$, $R^f$, $Y^1$, $Y^2$, $Y^3$, and $Y^4$ are as defined herein in relation to Formula (I), (I-a), and (I-aa).

In an embodiment, the compound of Formula (I) is a compound of Formula (I-dd):

(I-dd)

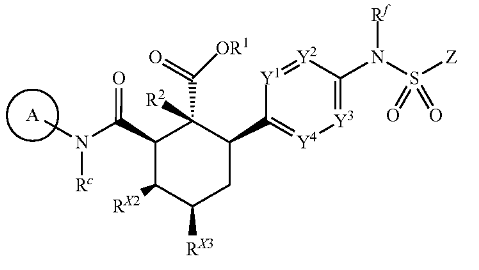

or a pharmaceutically acceptable salt thereof, wherein ring A, Z, $R^1$, $R^2$, $R^{X2}$, $R^{X3}$, $R^c$, $R^f$, $Y^1$, $Y^2$, $Y^3$, and $Y^4$ are as defined herein in relation to Formulae (I), (I-a), and (I-aa).

In an embodiment, the compound of Formula (I) is a compound of Formula (I-e):

(I-e)

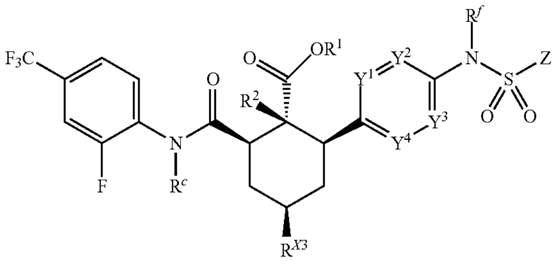

or a pharmaceutically acceptable salt thereof, wherein Z, $R^1$, $R^2$, $R^{X3}$, $R^o$, $R^f$, $Y^1$, $Y^2$, $Y^3$, and $Y^4$ are as defined herein in relation to Formulae (I), (I-a), and (I-aa).

In an embodiment, the compound of Formula (I) is a compound of Formula (I-ee):

(I-ee)

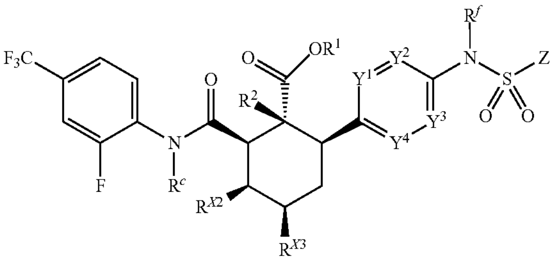

or a pharmaceutically acceptable salt thereof, wherein Z, $R^1$, $R^2$, $R^{X2}$, $R^{X3}$, $R^c$, $R^f$, $Y^1$, $Y^2$, $Y^3$, and $Y^4$ are as defined herein in relation to Formulae (I), (I-a), and (I-aa).

In an embodiment, the compound of Formula (I) is a compound of Formula (I-eee):

(I-eee)

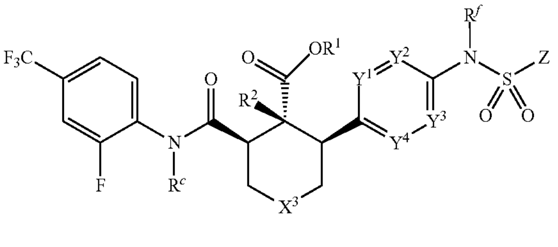

or a pharmaceutically acceptable salt thereof, wherein $X^3$ is —$NR^o$— or —O—, and wherein Z, $R^1$, $R^2$, $R^o$, $R^c$, $R^f$, $Y^1$, $Y^2$, $Y^3$, and $Y^4$ are as defined herein in relation to Formulae (I), (I-a), and (I-aa).

In an embodiment, the compound of Formula (I) is a compound of Formula (II):

(II)

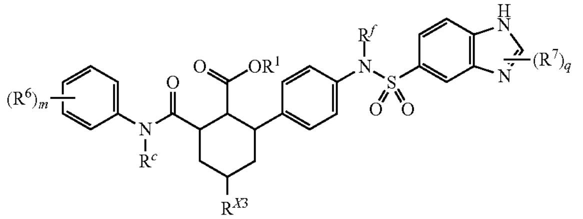

wherein:

m is an integer from 1 to 3;

q is an integer from 1 to 3;

each $R^6$ is independently selected from halo, cyano, nitro, hydroxy, —$NR^aR^b$, carboxy, —$CONR^aR^b$, $C_{1-3}$ alkyl, $C_{1-3}$ alkoxy, halo($C_{1-3}$)alkyl, halo($C_{1-3}$)alkoxy, hydroxy($C_{1-3}$)alkyl, cyano($C_{1-3}$)alkyl, $C_{1-3}$ alkylsulfonyl, —C(O)O($C_{1-4}$)alkyl, and $C_{3-7}$ cycloalkyl;

each $R^7$ is independently selected from halo, cyano, nitro, hydroxy, carboxy, $C_{1-3}$alkyl, $C_{1-3}$ alkoxy, halo($C_{1-3}$) alkyl, halo($C_{1-3}$)alkoxy, hydroxy($C_{1-3}$)alkyl, $C_{2-5}$ alkenyl, $C_{2-5}$ alkynyl, —$C_{1-3}$ alkylene-$NR^gR^h$, —$CONR^gR^h$, —$NR^gR^h$, —$NR^gC(O)R^h$, $SO_2NR^gR^h$, and $L^B$-W, or two $R^7$ taken together with the atoms to which they are attached form a 5- or 6-membered ring which optionally contains one or two heteroatoms independently selected from N, O, and S;

$L^B$ is independently selected from a bond, —$(CH_2)_p$—, —$CH_2O$—, —C(O)—NH—, —C(O)—, and —$CH_2C$(O)NH—;

W is independently selected from hydrogen, $C_{1-3}$ alkyl, —$O(C_{1-4})$alkyl, $C_{3-7}$ cycloalkyl, 5- or 6-membered heteroaryl, and 4- to 6-membered heterocycloalkyl ring containing one, two, or three heteroatoms independently selected from N, O, and S, wherein W is optionally substituted with up to three substituents independently selected from halo, cyano, nitro, hydroxy, —$NR^mR^n$, carboxy, —$CONR^mR^n$, $C_{1-3}$ alkyl, $C_{1-3}$ alkoxy, halo($C_{1-3}$)alkyl, halo($C_{1-3}$)alkoxy, hydroxy($C_{1-3}$)alkyl, cyano($C_{1-3}$)alkyl, $C_{1-3}$ alkylsulfonyl, —$C(O)O(C_{1-4})$alkyl, and $C_{3-7}$ cycloalkyl;

p is 1 or 2;

$R^a$, $R^b$, $R^g$, $R^h$, $R^m$, and $R^n$ are each independently hydrogen, $C_{1-3}$ alkyl or $C_{3-7}$ cycloalkyl; and $R^1$, $R^{X3}$, $R^o$, and $R^f$ are as defined herein in relation to Formulae (I), (I-a), and (I-aa);

or a pharmaceutically acceptable salt thereof.

For the avoidance of doubt, $R^7$ can be attached to any available atom of the benzimidazolyl ring of Formula (II) including the two nitrogen atoms.

In an embodiment, the compound of Formula (I) is a compound of Formula (II):

(II)

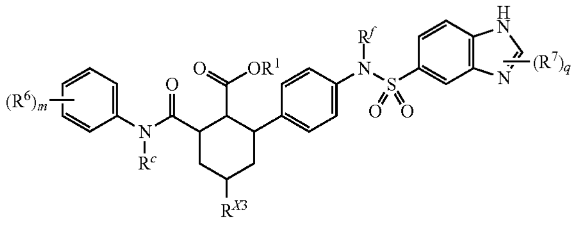

wherein:

m is an integer from 1 to 3;

q is an integer from 1 to 3;

each $R^6$ is independently selected from halo, cyano, nitro, hydroxy, —$NR^aR^b$, carboxy, —$CONR^aR^b$, $C_{1-3}$ alkyl, $C_{1-3}$ alkoxy, halo($C_{1-3}$)alkyl, halo($C_{1-3}$)alkoxy, hydroxy($C_{1-3}$)alkyl, cyano($C_{1-3}$)alkyl, $C_{1-3}$ alkylsulfonyl, —$C(O)O(C_{1-4})$alkyl, and $C_{3-7}$ cycloalkyl;

each $R^7$ is independently selected from halo, cyano, nitro, hydroxy, carboxy, $C_{1-3}$alkyl, $C_{1-3}$ alkoxy, halo($C_{1-3}$)alkyl, halo($C_{1-3}$)alkoxy, hydroxy($C_{1-3}$)alkyl, $C_{2-5}$ alkenyl, $C_{2-5}$ alkynyl, —$C_{1-3}$ alkylene-$NR^gR^h$, —$CONR^gR^h$, —$NR^gR^h$, —$NR^gC(O)R^h$, $SO_2NR^gR^h$, and $L^B$-W, or two $R^7$ taken together with the atoms to which they are attached form a 5- or 6-membered ring which optionally contains one or two heteroatoms independently selected from N, O, and S;

$L^B$ is independently selected from a bond, —$(CH_2)_p$—, —$CH_2O$—, —C(O)—NH—, —C(O)—, and —$CH_2C$(O)NH—;

W is independently selected from hydrogen, $C_{1-3}$ alkyl, —$O(C_{1-4})$alkyl, $C_{3-7}$ cycloalkyl, 5- or 6-membered heteroaryl, and 4- to 6-membered heterocycloalkyl ring containing one, two, or three heteroatoms independently selected from N, O, and S, wherein W is optionally substituted with up to three substituents independently selected from halo, cyano, nitro, hydroxy, —$NR^mR^n$, carboxy, —$CONR^mR^n$, $C_{1-3}$alkyl, $C_{1-3}$ alkoxy, halo($C_{1-3}$)alkyl, halo($C_{1-3}$)alkoxy, hydroxy($C_{1-3}$)alkyl, cyano($C_{1-3}$)alkyl, $C_{1-3}$ alkylsulfonyl, —$C(O)O(C_{1-4})$alkyl, and $C_{3-7}$ cycloalkyl;

p is 1 or 2;

$R^a$, $R^b$, $R^g$, $R^h$, $R^m$, and $R^n$ are each independently hydrogen, $C_{1-3}$ alkyl, or $C_{3-7}$ cycloalkyl;

$R^1$ is hydrogen or $C_{1-3}$ alkyl;

$R^{X3}$ is hydrogen or $C_{1-3}$ alkoxy; and $R^c$ and $R^f$ are each independently hydrogen, $C_{1-3}$ alkyl, or $C_{3-7}$ cycloalkyl;

or a pharmaceutically acceptable salt thereof.

In an embodiment, each $R^6$ is independently selected from halo, hydroxy, $C_{1-3}$alkyl, and halo($C_{1-3}$)alkyl;

Each $R^7$ is independently selected from halo, $C_{1-3}$alkyl, —$C_{1-3}$alkylene-$NR^gR^h$, —$NR^gR^h$ and $L^B$-W;

$L^B$ is a bond;

W is $C_{3-7}$ cycloalkyl or 4- to 6-membered heterocycloalkyl ring containing one, two, or three heteroatoms independently selected from N, O, and S, wherein W is optionally substituted with $C_{1-3}$alkyl; and $R^g$ and $R^h$ are each independently hydrogen or $C_{1-3}$ alkyl.

In an embodiment, the compound of Formula (I) is a compound of Formula (II-a):

(II-a)

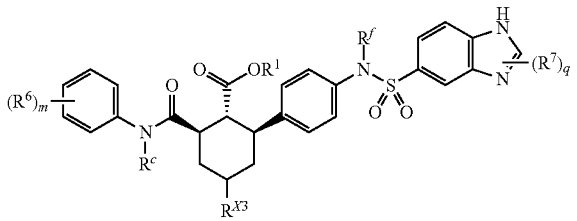

or a pharmaceutically acceptable salt thereof, wherein $R^1$, $R^6$, $R^7$, $R^{X3}$, $R^c$, $R^f$, m, and q are as defined herein in relation to Formulae (I) and (II).

In an embodiment, the compound of Formula (I) is a compound of Formula (II-aa):

(II-aa)

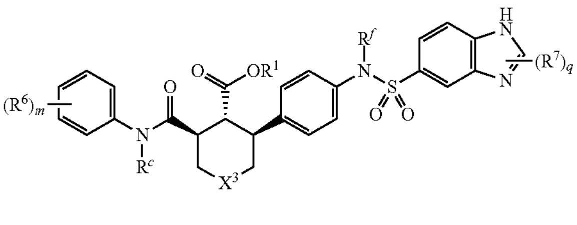

or a pharmaceutically acceptable salt thereof, wherein $X^3$ is —$NR^o$— or —O—, and wherein $R^1$, $R^6$, $R^7$, $R^o$—, $R^c$, $R^f$, m, and q are as defined herein in relation to Formulae (I) and (II).

In an embodiment, the compound of Formula (I) is a compound of Formula (II-b):

(II-b)

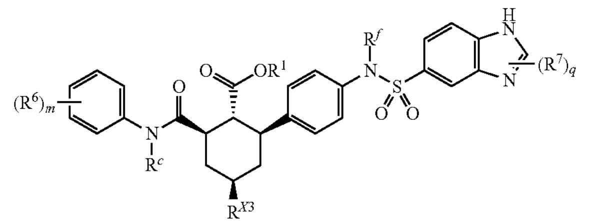

or a pharmaceutically acceptable salt thereof, wherein $R^1$, $R^6$, $R^7$, $R^{X3}$, $R^c$, $R^f$, m, and q are as defined herein in relation to Formulae (I) and (II).

In an embodiment, the compound of Formula (I) is a compound of Formulae (II), (II-a), or (II-b) wherein:

$R^1$ is hydrogen;

$R^c$ is hydrogen;

$R^f$ is methyl; and $R^{X3}$ is hydrogen, $C_{1-3}$ alkoxy, $C_{1-3}$ alkoxy($C_{1-3}$)alkyl-, halo($C_{1-3}$)alkoxy, or 5- or 6-membered heterocycloalkyl ring containing one heteroatom independently selected from N, O, and S.

In an embodiment, the compound of Formula (I) is a compound of Formulae (II), (II-a), or (II-b) wherein:

m is 2;

q is 2;

$R^1$ is hydrogen;

$R^c$ is hydrogen;

$R^f$ is methyl;

$R^{X3}$ is hydrogen, ethoxy, methoxylmethyl, or optionally substituted pyrrolidinyl;

$R^6$ is selected from trifluoromethyl and fluoro; and $R^7$ is methyl.

In an embodiment, the compound of Formula (I) is selected from the compounds in Table 1, or a pharmaceutically acceptable salt thereof.

In an embodiment, the compound of Formula (I) is selected from

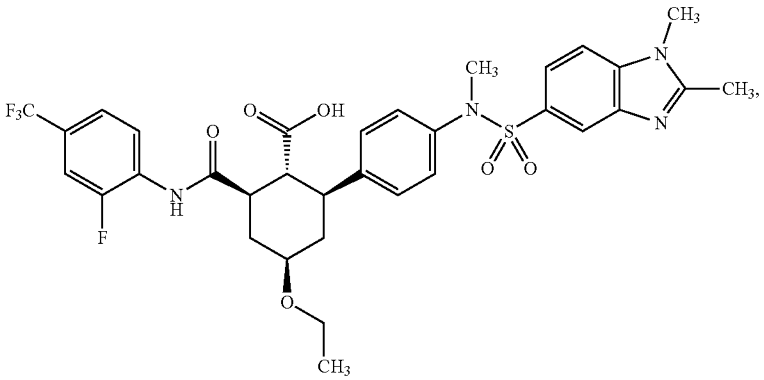

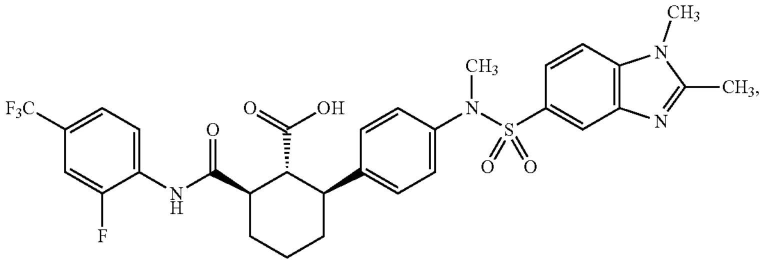

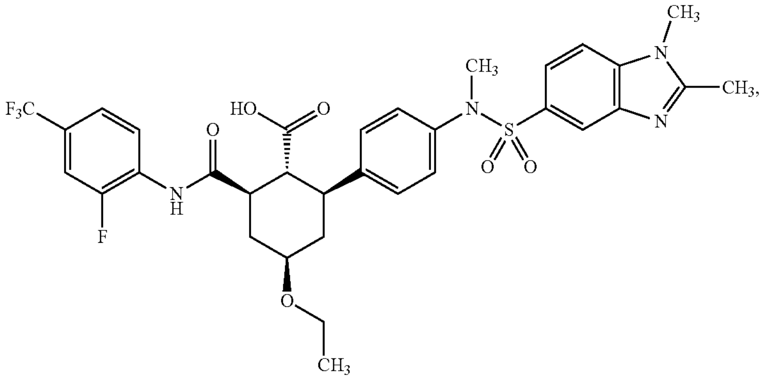

and

-continued

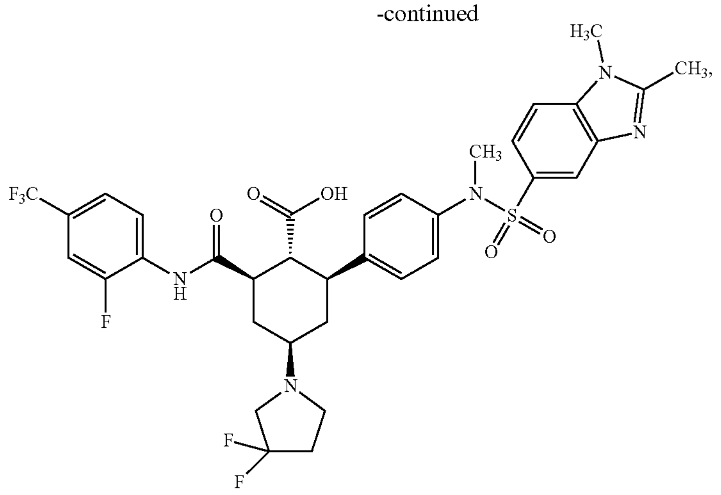

or a pharmaceutically acceptable salt thereof.

The chemical names in the present application are generated from the corresponding structures using either CHEMDRAW, or CHEMAXON. In some instances, chemical names generated from the structures may give a different structure when using the "Convert Name to Structure" function in CHEMDRAW. For example, CHEMDRAW provides the name "(1R,2R,6S)-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylic acid" based on the structure for the compound of Example 83, where the name provides a different structure when using CHEM DRAWs "Convert Name to Structure" function. An alternative name, "(1R,2R,6S)-2-{[2-fluoro-4-(trifluoromethyl)phenyl]carbamoyl}-6-[4-(N-methyl-1,2-dimethyl-1H-1,3-benzodiazole-5-sulfonamido)phenyl]cyclohexane-1-carboxylic acid" provides the correct structure of the Compound of Example 83 in CHEMDRAW. Therefore, when there is a potential ambiguity, the compounds of the present application should be determined by the structures.

The label "&" in the structures in the present disclosure refers to both chiral centers being present in the mixture. When multiple centers are labelled with "&1" the relative stereochemistry between them is determined. The term "rac" in the chemical names denotes a racemic mixture. The label "or" in the structures refers to the specific chiral center being a single undefined isomer but absolute stereochemistry was not determined. When multiple centers are labelled with "or1" the relative stereochemistry between them is determined but not the absolute stereochemistry. The term "rel" in the chemical names denotes relative stereochemistry is defined but the absolute chemistry is not determined.

The label "*" in the chemical name refers to an undefined chiral center in a molecule that also contains other defined chiral centers.

Unless otherwise indicated, Isomer 1 refers to the first eluting isomer and Isomer 2 refers to the second eluting isomer during chiral chromatographic separation.

TABLE 1

| Ex. No. | Structure |
|---|---|
| 1 | 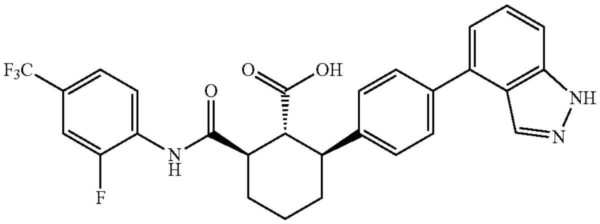 [SMILES: O=C(O)[C@@H]1[C@@H](c2ccc(-c3cccc4[nH]ncc34)cc2)CCC[C@H]1C(=O)Nc1ccc(C(F)(F)F)cc1F] |
| 2 | 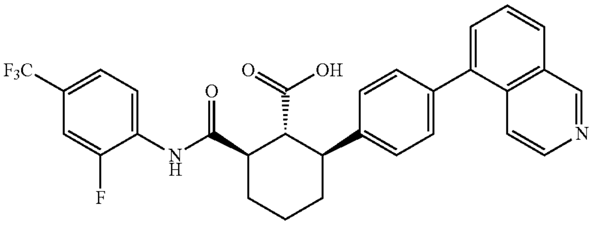 [SMILES: O=C(O)[C@@H]1[C@@H](c2ccc(-c3cccc4cnccc34)cc2)CCC[C@H]1C(=O)Nc1ccc(C(F)(F)F)cc1F] |

TABLE 1-continued
| Ex. No. | Structure |
|---|---|
| 3 | 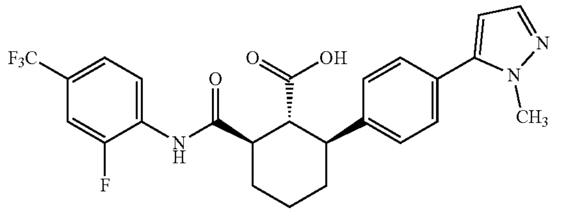 [SMILES: Cn1nccc1-c1ccc([C@H]2CCC[C@@H](C(=O)Nc3ccc(C(F)(F)F)cc3F)[C@@H]2C(=O)O)cc1] |
| 4 | 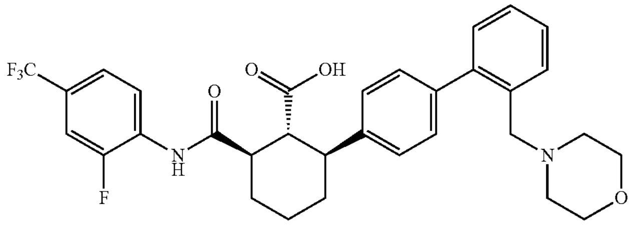 [SMILES: O=C(O)[C@@H]1[C@@H](c2ccc(-c3ccccc3CN3CCOCC3)cc2)CCC[C@H]1C(=O)Nc1ccc(C(F)(F)F)cc1F] |
| 5 | 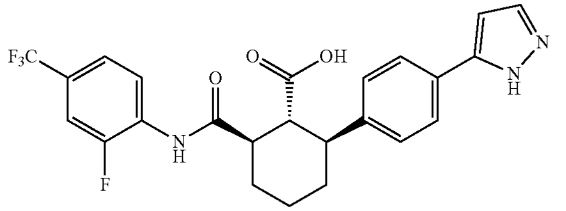 [SMILES: O=C(O)[C@@H]1[C@@H](c2ccc(-c3ccn[nH]3)cc2)CCC[C@H]1C(=O)Nc1ccc(C(F)(F)F)cc1F] |
| 6 | 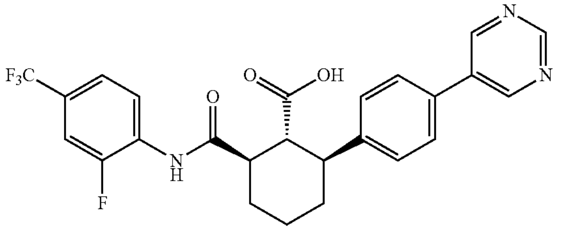 [SMILES: O=C(O)[C@@H]1[C@@H](c2ccc(-c3cncnc3)cc2)CCC[C@H]1C(=O)Nc1ccc(C(F)(F)F)cc1F] |
| 7 | 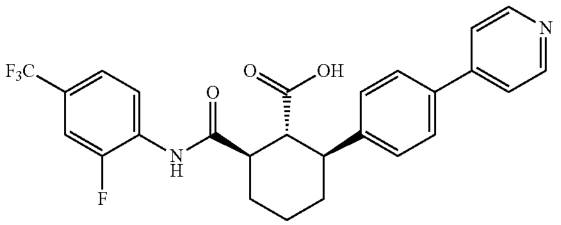 [SMILES: O=C(O)[C@@H]1[C@@H](c2ccc(-c3ccncc3)cc2)CCC[C@H]1C(=O)Nc1ccc(C(F)(F)F)cc1F] |
| 8 | 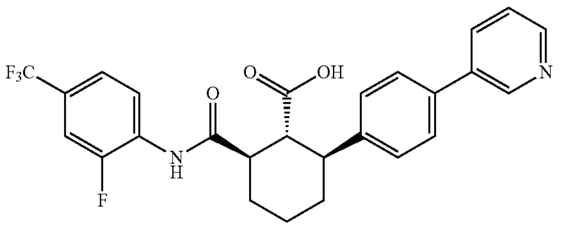 [SMILES: O=C(O)[C@@H]1[C@@H](c2ccc(-c3cccnc3)cc2)CCC[C@H]1C(=O)Nc1ccc(C(F)(F)F)cc1F] |

TABLE 1-continued
| Ex. No. | Structure |
|---|---|
| 9 | 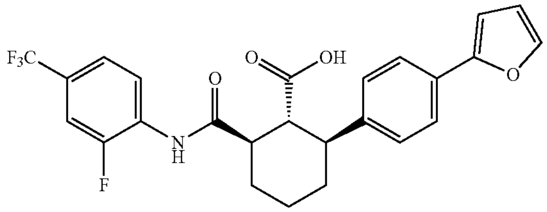 [SMILES: O=C(O)[C@@H]1[C@@H](c2ccc(-c3ccco3)cc2)CCC[C@H]1C(=O)Nc1ccc(C(F)(F)F)cc1F] |
| 10 | 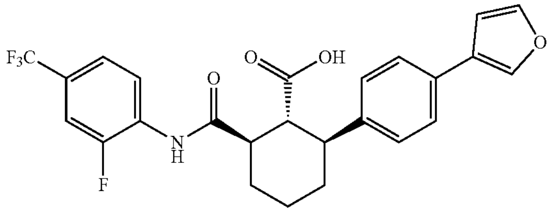 [SMILES: O=C(O)[C@@H]1[C@@H](c2ccc(-c3ccoc3)cc2)CCC[C@H]1C(=O)Nc1ccc(C(F)(F)F)cc1F] |
| 11 | 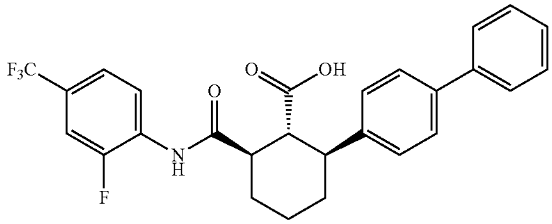 [SMILES: O=C(O)[C@@H]1[C@@H](c2ccc(-c3ccccc3)cc2)CCC[C@H]1C(=O)Nc1ccc(C(F)(F)F)cc1F] |
| 12 | 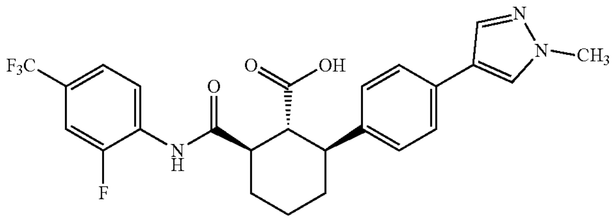 [SMILES: Cn1cc(-c2ccc([C@H]3CCC[C@@H](C(=O)Nc4ccc(C(F)(F)F)cc4F)[C@@H]3C(=O)O)cc2)cn1] |
| 13 | 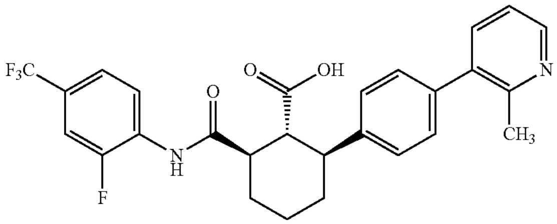 [SMILES: Cc1ncccc1-c1ccc([C@H]2CCC[C@@H](C(=O)Nc3ccc(C(F)(F)F)cc3F)[C@@H]2C(=O)O)cc1] |
| 14 | 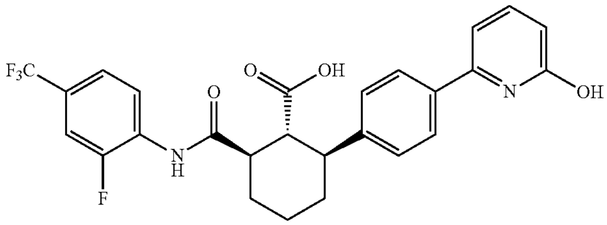 [SMILES: O=C(O)[C@@H]1[C@@H](c2ccc(-c3cccc(O)n3)cc2)CCC[C@H]1C(=O)Nc1ccc(C(F)(F)F)cc1F] |

TABLE 1-continued
| Ex. No. | Structure |
|---|---|
| 15 | 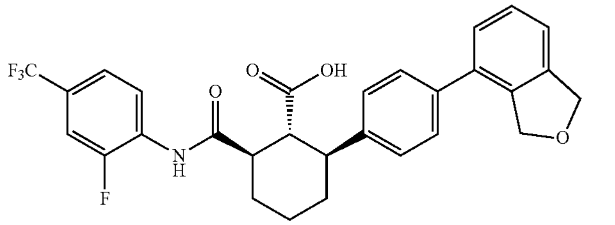 [SMILES: O=C(O)[C@@H]1[C@@H](c2ccc(-c3cccc4c3COC4)cc2)CCC[C@H]1C(=O)Nc1ccc(C(F)(F)F)cc1F] |
| 16 | 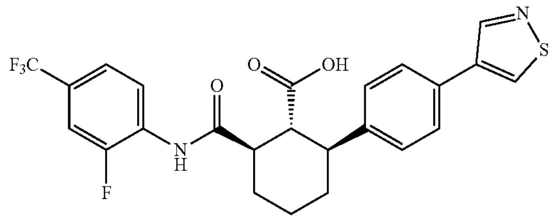 [SMILES: O=C(O)[C@@H]1[C@@H](c2ccc(-c3cnsc3)cc2)CCC[C@H]1C(=O)Nc1ccc(C(F)(F)F)cc1F] |
| 17 | 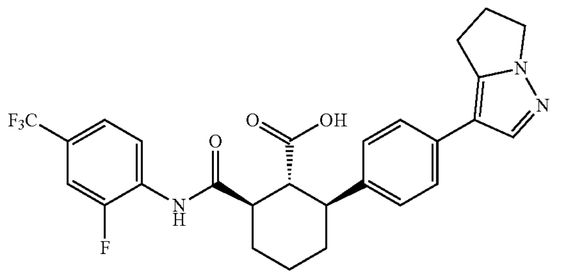 [SMILES: O=C(O)[C@@H]1[C@@H](c2ccc(-c3cnn4c3CCC4)cc2)CCC[C@H]1C(=O)Nc1ccc(C(F)(F)F)cc1F] |
| 18 | 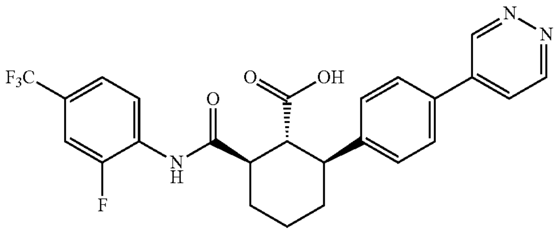 [SMILES: O=C(O)[C@@H]1[C@@H](c2ccc(-c3ccnnc3)cc2)CCC[C@H]1C(=O)Nc1ccc(C(F)(F)F)cc1F] |
| 19 | 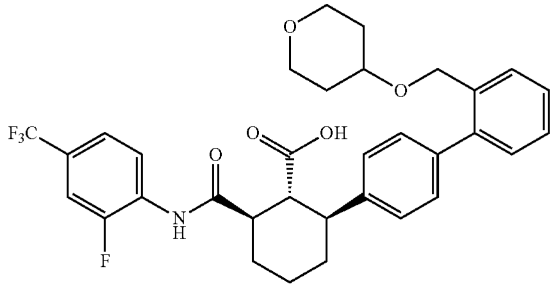 [SMILES: O=C(O)[C@@H]1[C@@H](c2ccc(-c3ccccc3COC3CCOCC3)cc2)CCC[C@H]1C(=O)Nc1ccc(C(F)(F)F)cc1F] |
| 20 | 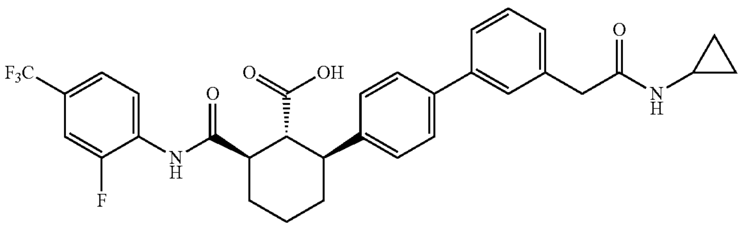 [SMILES: O=C(Cc1cccc(-c2ccc([C@H]3CCC[C@@H](C(=O)Nc4ccc(C(F)(F)F)cc4F)[C@@H]3C(=O)O)cc2)c1)NC1CC1] |

TABLE 1-continued
| Ex. No. | Structure |
|---|---|
| 21 | 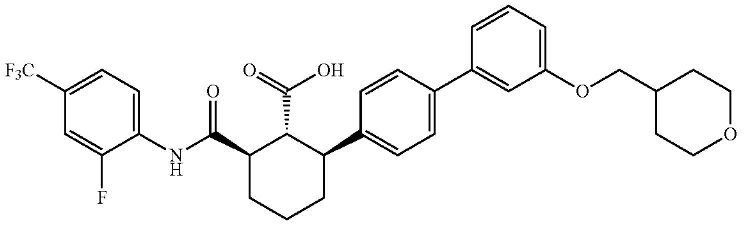 [SMILES: O=C(O)[C@@H]1[C@@H](c2ccc(-c3cccc(OCC4CCOCC4)c3)cc2)CCC[C@H]1C(=O)Nc1ccc(C(F)(F)F)cc1F] |
| 22 | 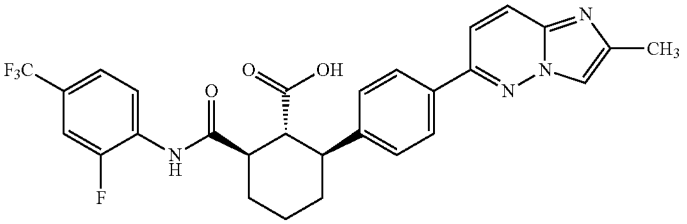 [SMILES: Cc1cn2nc(-c3ccc([C@H]4CCC[C@@H](C(=O)Nc5ccc(C(F)(F)F)cc5F)[C@@H]4C(=O)O)cc3)ccc2n1] |
| 23 | 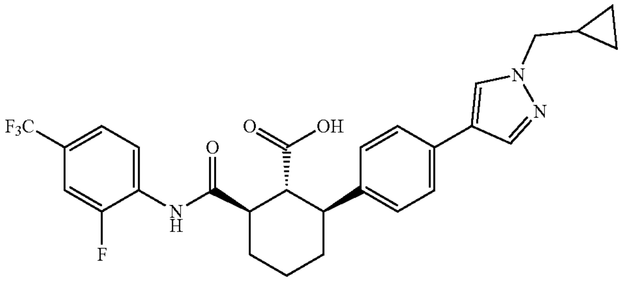 [SMILES: O=C(O)[C@@H]1[C@@H](c2ccc(-c3cnn(CC4CC4)c3)cc2)CCC[C@H]1C(=O)Nc1ccc(C(F)(F)F)cc1F] |
| 24 | 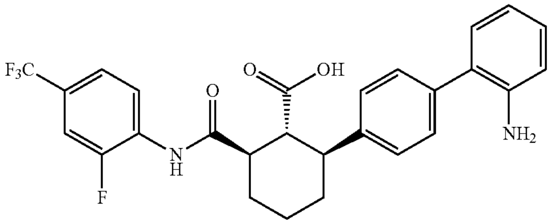 [SMILES: Nc1ccccc1-c1ccc([C@H]2CCC[C@@H](C(=O)Nc3ccc(C(F)(F)F)cc3F)[C@@H]2C(=O)O)cc1] |
| 25 | 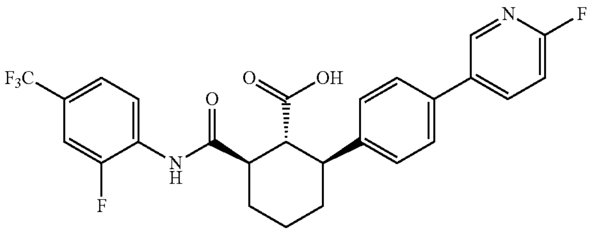 [SMILES: O=C(O)[C@@H]1[C@@H](c2ccc(-c3ccc(F)nc3)cc2)CCC[C@H]1C(=O)Nc1ccc(C(F)(F)F)cc1F] |
| 26 | 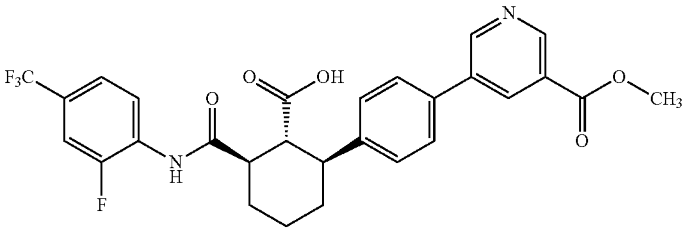 [SMILES: COC(=O)c1cncc(-c2ccc([C@H]3CCC[C@@H](C(=O)Nc4ccc(C(F)(F)F)cc4F)[C@@H]3C(=O)O)cc2)c1] |

TABLE 1-continued
| Ex. No. | Structure |
|---|---|
| 27 | 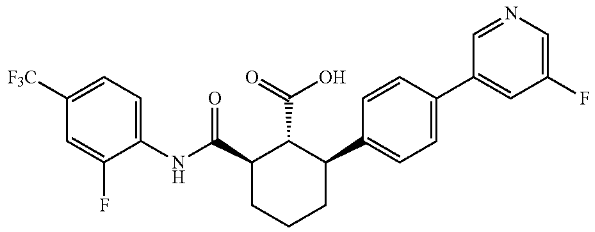 [SMILES: O=C(O)[C@@H]1[C@@H](c2ccc(-c3cncc(F)c3)cc2)CCC[C@H]1C(=O)Nc1ccc(C(F)(F)F)cc1F] |
| 28 | 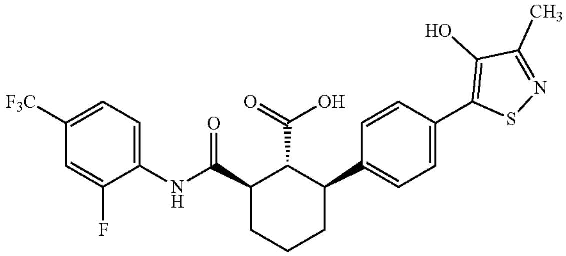 [SMILES: Cc1nsc(-c2ccc([C@H]3CCC[C@@H](C(=O)Nc4ccc(C(F)(F)F)cc4F)[C@@H]3C(=O)O)cc2)c1O] |
| 29 | 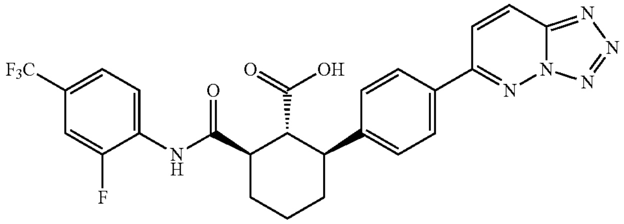 |
| 30 | 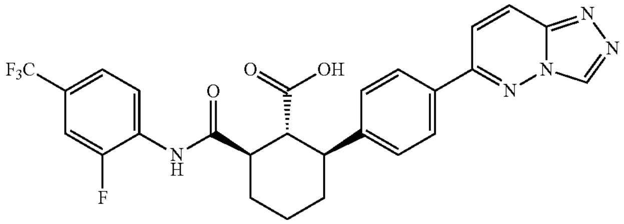 [SMILES: O=C(O)[C@@H]1[C@@H](c2ccc(-c3ccc4nncn4n3)cc2)CCC[C@H]1C(=O)Nc1ccc(C(F)(F)F)cc1F] |
| 31 | 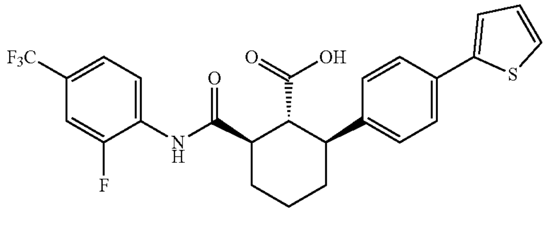 |
| 32 | 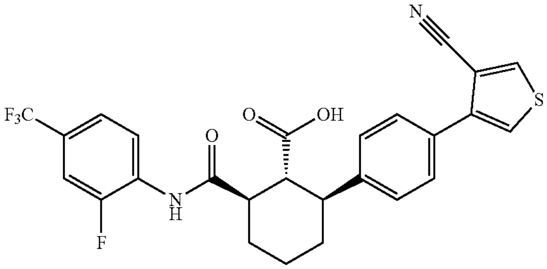 [SMILES: N#Cc1cscc1-c1ccc([C@H]2CCC[C@@H](C(=O)Nc3ccc(C(F)(F)F)cc3F)[C@@H]2C(=O)O)cc1] |

TABLE 1-continued
| Ex. No. | Structure |
| --- | --- |
| 33 | 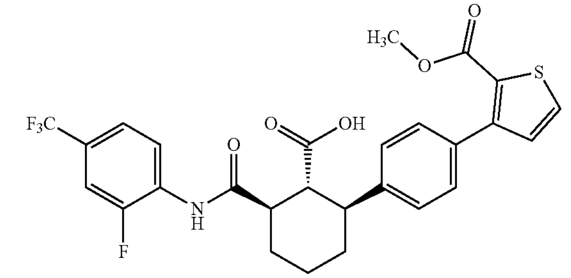 [SMILES: COC(=O)c1sccc1-c1ccc([C@H]2CCC[C@@H](C(=O)Nc3ccc(C(F)(F)F)cc3F)[C@@H]2C(=O)O)cc1] |
| 34 | 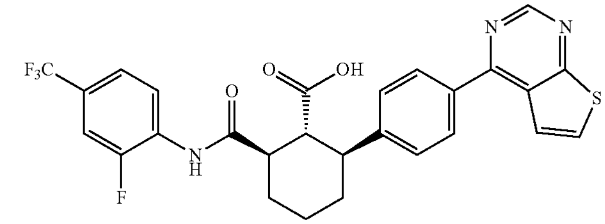 [SMILES: O=C(O)[C@@H]1[C@@H](c2ccc(-c3ncnc4sccc34)cc2)CCC[C@H]1C(=O)Nc1ccc(C(F)(F)F)cc1F] |
| 35 | 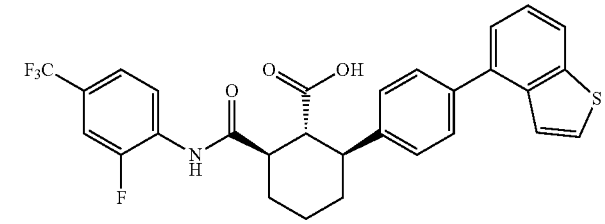 [SMILES: O=C(O)[C@@H]1[C@@H](c2ccc(-c3cccc4sccc34)cc2)CCC[C@H]1C(=O)Nc1ccc(C(F)(F)F)cc1F] |
| 36 | 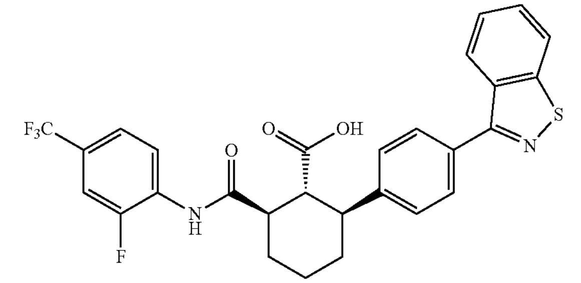 [SMILES: O=C(O)[C@@H]1[C@@H](c2ccc(-c3nsc4ccccc34)cc2)CCC[C@H]1C(=O)Nc1ccc(C(F)(F)F)cc1F] |
| 37 | 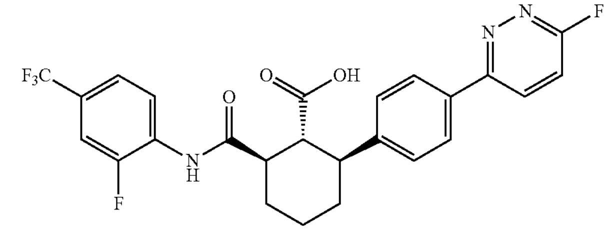 [SMILES: O=C(O)[C@@H]1[C@@H](c2ccc(-c3ccc(F)nn3)cc2)CCC[C@H]1C(=O)Nc1ccc(C(F)(F)F)cc1F] |
| 38 | 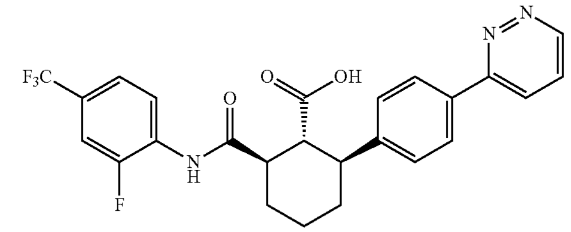 [SMILES: O=C(O)[C@@H]1[C@@H](c2ccc(-c3cccnn3)cc2)CCC[C@H]1C(=O)Nc1ccc(C(F)(F)F)cc1F] |

TABLE 1-continued
| Ex. No. | Structure |
|---|---|
| 39 | 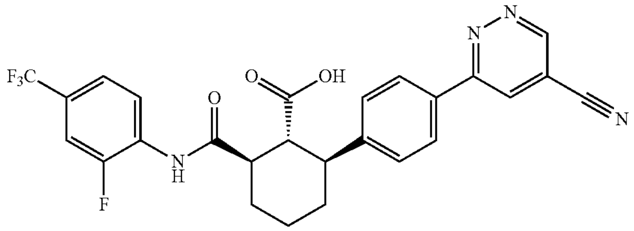 [SMILES: N#Cc1cnnc(-c2ccc([C@H]3CCC[C@@H](C(=O)Nc4ccc(C(F)(F)F)cc4F)[C@@H]3C(=O)O)cc2)c1] |
| 40 | 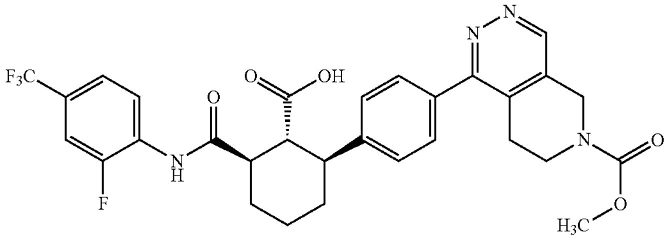 [SMILES: COC(=O)N1CCc2c(cnnc2-c2ccc([C@H]3CCC[C@@H](C(=O)Nc4ccc(C(F)(F)F)cc4F)[C@@H]3C(=O)O)cc2)C1] |
| 41 | 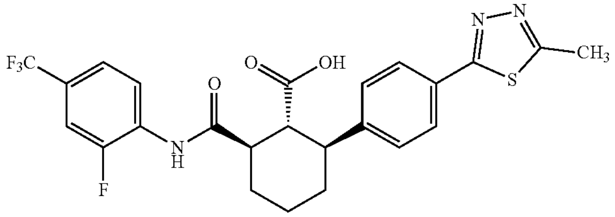 [SMILES: Cc1nnc(-c2ccc([C@H]3CCC[C@@H](C(=O)Nc4ccc(C(F)(F)F)cc4F)[C@@H]3C(=O)O)cc2)s1] |
| 42 | 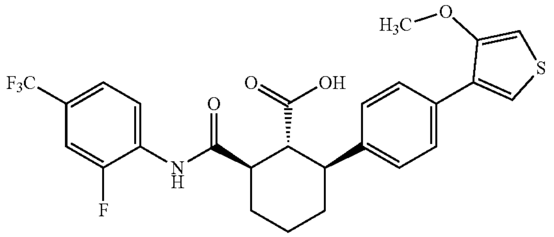 [SMILES: COc1cscc1-c1ccc([C@H]2CCC[C@@H](C(=O)Nc3ccc(C(F)(F)F)cc3F)[C@@H]2C(=O)O)cc1] |
| 43 | 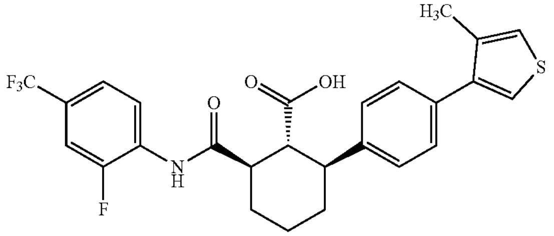 [SMILES: Cc1cscc1-c1ccc([C@H]2CCC[C@@H](C(=O)Nc3ccc(C(F)(F)F)cc3F)[C@@H]2C(=O)O)cc1] |
| 44 | 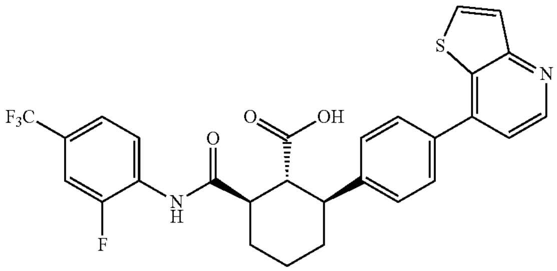 [SMILES: O=C(O)[C@@H]1[C@@H](c2ccc(-c3ccnc4ccsc34)cc2)CCC[C@H]1C(=O)Nc1ccc(C(F)(F)F)cc1F] |

TABLE 1-continued
| Ex. No. | Structure |
| --- | --- |
| 45 | 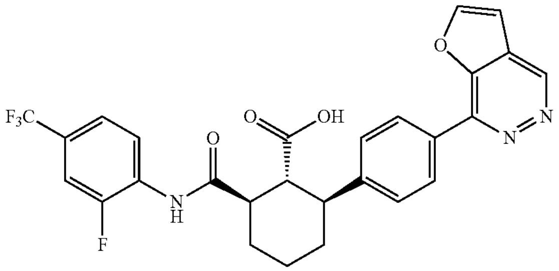 [SMILES: O=C(O)[C@@H]1[C@@H](c2ccc(-c3nncc4ccoc34)cc2)CCC[C@H]1C(=O)Nc1ccc(C(F)(F)F)cc1F] |
| 46 | 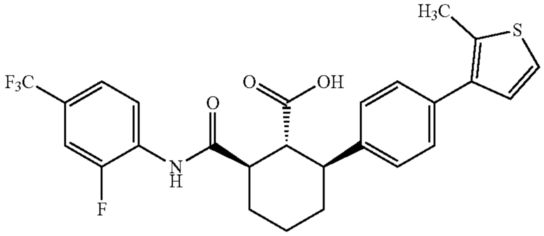 [SMILES: Cc1sccc1-c1ccc([C@H]2CCC[C@@H](C(=O)Nc3ccc(C(F)(F)F)cc3F)[C@@H]2C(=O)O)cc1] |
| 47 | 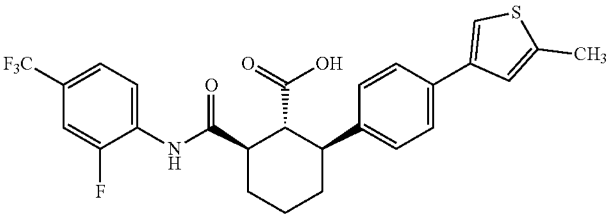 [SMILES: Cc1cc(-c2ccc([C@H]3CCC[C@@H](C(=O)Nc4ccc(C(F)(F)F)cc4F)[C@@H]3C(=O)O)cc2)cs1] |
| 48 | 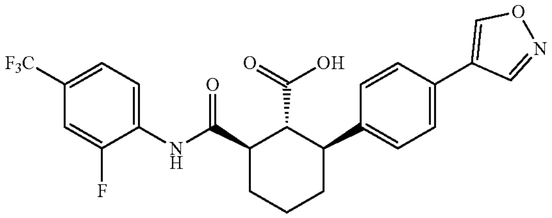 [SMILES: O=C(O)[C@@H]1[C@@H](c2ccc(-c3cnoc3)cc2)CCC[C@H]1C(=O)Nc1ccc(C(F)(F)F)cc1F] |
| 49 | 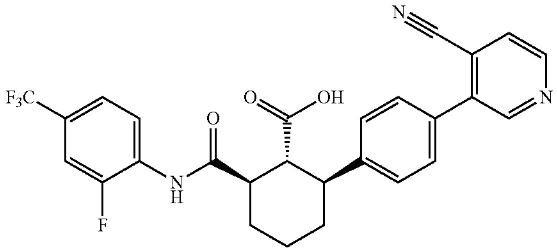 [SMILES: N#Cc1ccncc1-c1ccc([C@H]2CCC[C@@H](C(=O)Nc3ccc(C(F)(F)F)cc3F)[C@@H]2C(=O)O)cc1] |
| 50 | 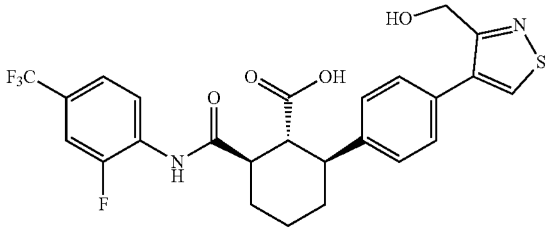 [SMILES: O=C(O)[C@@H]1[C@@H](c2ccc(-c3csnc3CO)cc2)CCC[C@H]1C(=O)Nc1ccc(C(F)(F)F)cc1F] |

TABLE 1-continued
| Ex. No. | Structure |
|---|---|
| 51 | 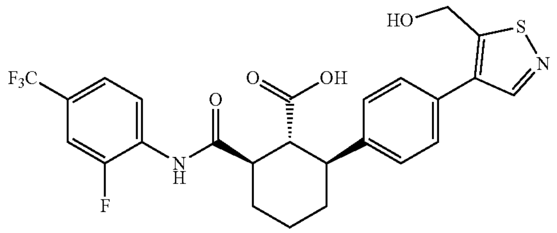 [SMILES: O=C(O)[C@@H]1[C@@H](c2ccc(-c3cnsc3CO)cc2)CCC[C@H]1C(=O)Nc1ccc(C(F)(F)F)cc1F] |
| 52 | 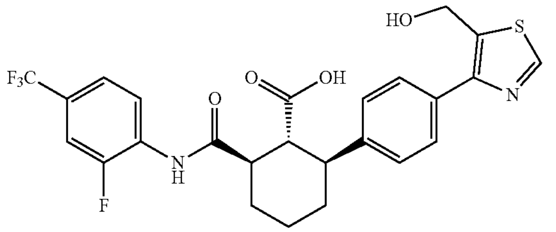 [SMILES: O=C(O)[C@@H]1[C@@H](c2ccc(-c3ncsc3CO)cc2)CCC[C@H]1C(=O)Nc1ccc(C(F)(F)F)cc1F] |
| 53 | 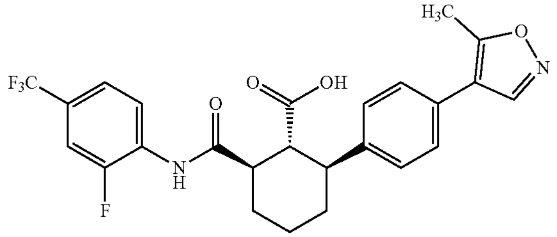 [SMILES: Cc1oncc1-c1ccc([C@H]2CCC[C@@H](C(=O)Nc3ccc(C(F)(F)F)cc3F)[C@@H]2C(=O)O)cc1] |
| 54 | 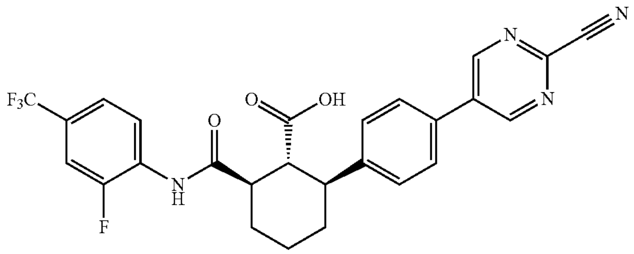 |
| 55 | 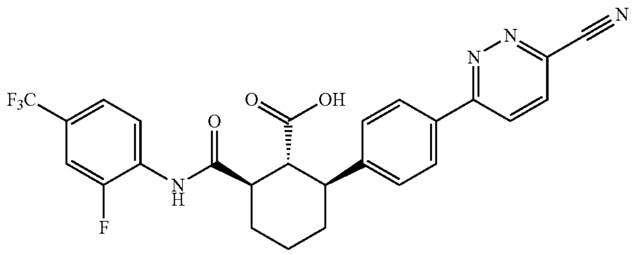 [SMILES: N#Cc1ccc(-c2ccc([C@H]3CCC[C@@H](C(=O)Nc4ccc(C(F)(F)F)cc4F)[C@@H]3C(=O)O)cc2)nn1] |
| 56 | 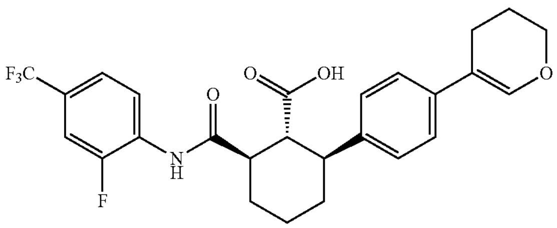 |

TABLE 1-continued
| Ex. No. | Structure |
|---|---|
| 57 | 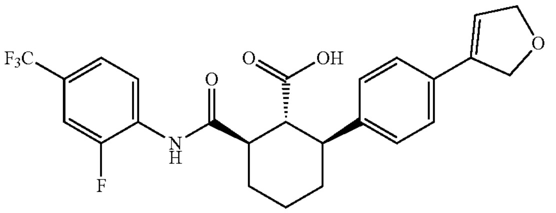 [SMILES: O=C(O)[C@@H]1[C@@H](c2ccc(C3=CCOC3)cc2)CCC[C@H]1C(=O)Nc1ccc(C(F)(F)F)cc1F] |
| 58 | 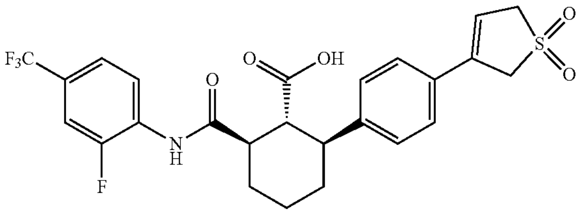 [SMILES: O=C(O)[C@@H]1[C@@H](c2ccc(C3=CCS(=O)(=O)C3)cc2)CCC[C@H]1C(=O)Nc1ccc(C(F)(F)F)cc1F] |
| 59 | 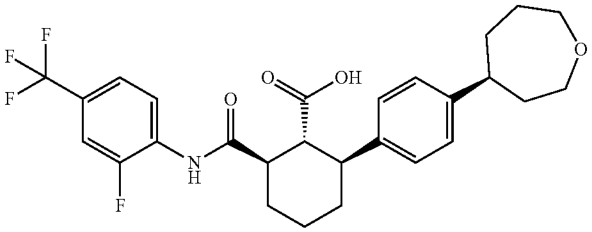 [SMILES: O=C(O)[C@@H]1[C@@H](c2ccc([C@H]3CCCOCC3)cc2)CCC[C@H]1C(=O)Nc1ccc(C(F)(F)F)cc1F]<br>+<br>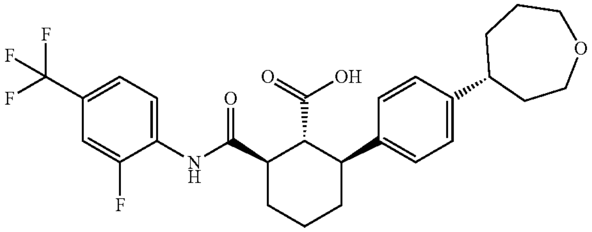 [SMILES: O=C(O)[C@@H]1[C@@H](c2ccc([C@@H]3CCCOCC3)cc2)CCC[C@H]1C(=O)Nc1ccc(C(F)(F)F)cc1F] |
| 60 | 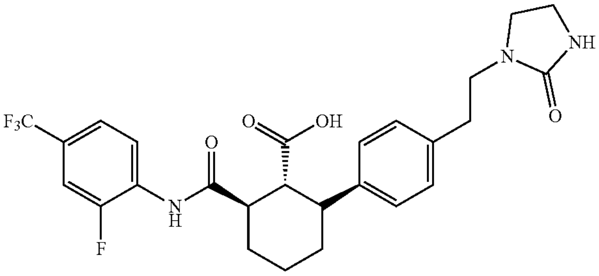 |
| 61 | 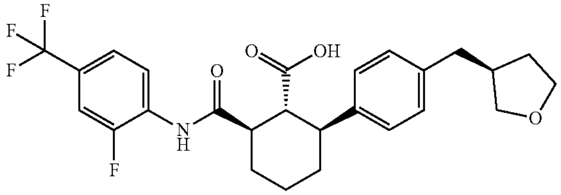 [SMILES: O=C(O)[C@@H]1[C@@H](c2ccc(C[C@H]3CCOC3)cc2)CCC[C@H]1C(=O)Nc1ccc(C(F)(F)F)cc1F]<br>+ |

TABLE 1-continued
| Ex. No. | Structure |
|---|---|
| | 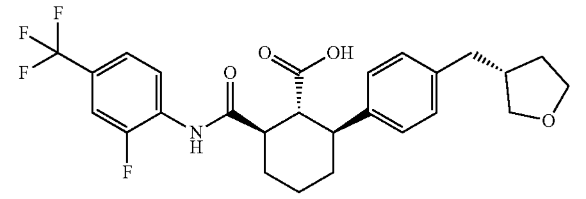 [SMILES: O=C(O)[C@@H]1[C@@H](c2ccc(C[C@@H]3CCOC3)cc2)CCC[C@H]1C(=O)Nc1ccc(C(F)(F)F)cc1F] |
| 62 | 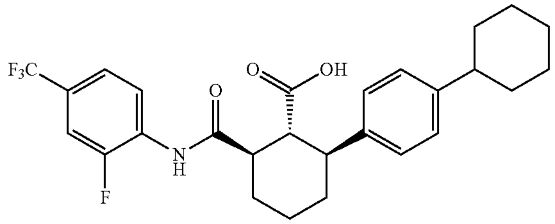 [SMILES: O=C(O)[C@@H]1[C@@H](c2ccc(C3CCCCC3)cc2)CCC[C@H]1C(=O)Nc1ccc(C(F)(F)F)cc1F] |
| 63 | 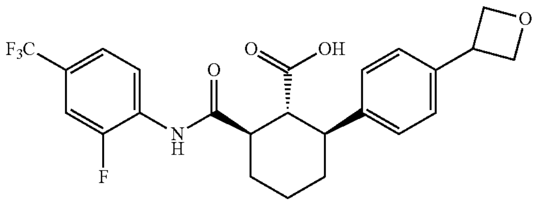 [SMILES: O=C(O)[C@@H]1[C@@H](c2ccc(C3COC3)cc2)CCC[C@H]1C(=O)Nc1ccc(C(F)(F)F)cc1F] |
| 64 | 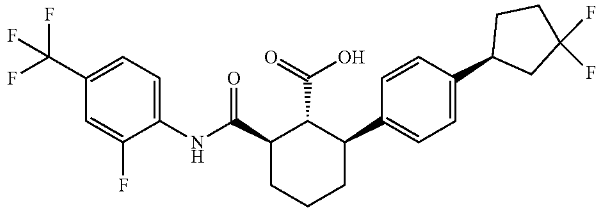 [SMILES: O=C(O)[C@@H]1[C@@H](c2ccc([C@H]3CCC(F)(F)C3)cc2)CCC[C@H]1C(=O)Nc1ccc(C(F)(F)F)cc1F]<br>+<br>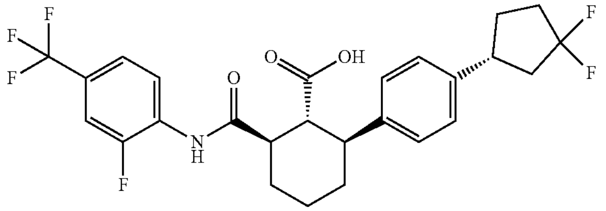 [SMILES: O=C(O)[C@@H]1[C@@H](c2ccc([C@@H]3CCC(F)(F)C3)cc2)CCC[C@H]1C(=O)Nc1ccc(C(F)(F)F)cc1F] |
| 65 | 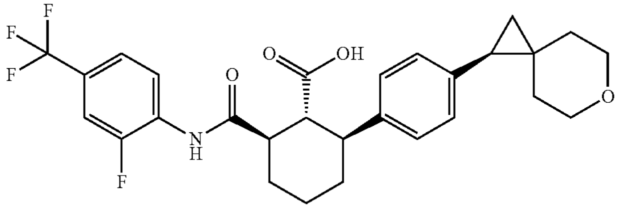 [SMILES: O=C(O)[C@@H]1[C@@H](c2ccc([C@H]3CC34CCOCC4)cc2)CCC[C@H]1C(=O)Nc1ccc(C(F)(F)F)cc1F]<br>+ |

TABLE 1-continued
| Ex. No. | Structure |
|---|---|
| | 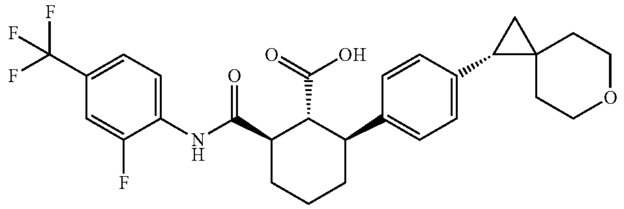 [SMILES: O=C(O)[C@@H]1[C@@H](c2ccc([C@@H]3CC34CCOCC4)cc2)CCC[C@H]1C(=O)Nc1ccc(C(F)(F)F)cc1F] |
| 66 | 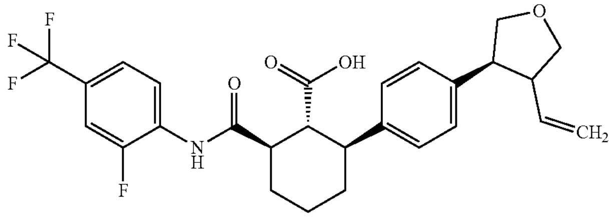 [SMILES: C=CC1COC[C@@H]1c1ccc([C@H]2CCC[C@@H](C(=O)Nc3ccc(C(F)(F)F)cc3F)[C@@H]2C(=O)O)cc1] |
| | + |
| | 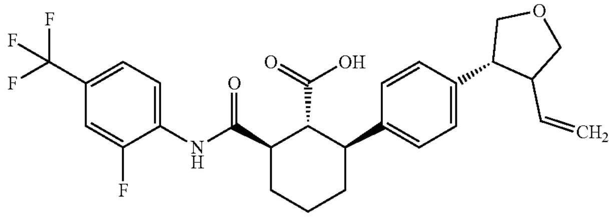 [SMILES: C=CC1COC[C@H]1c1ccc([C@H]2CCC[C@@H](C(=O)Nc3ccc(C(F)(F)F)cc3F)[C@@H]2C(=O)O)cc1] |
| 67 | 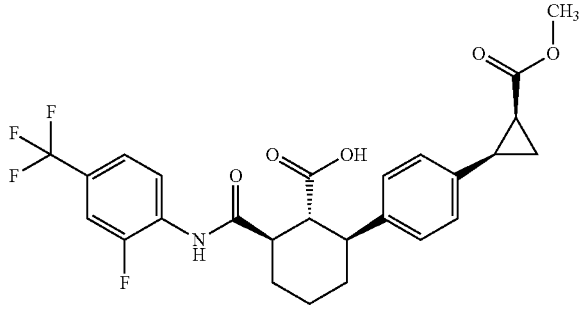 [SMILES: COC(=O)[C@H]1C[C@H]1c1ccc([C@H]2CCC[C@@H](C(=O)Nc3ccc(C(F)(F)F)cc3F)[C@@H]2C(=O)O)cc1] |
| | + |
| | 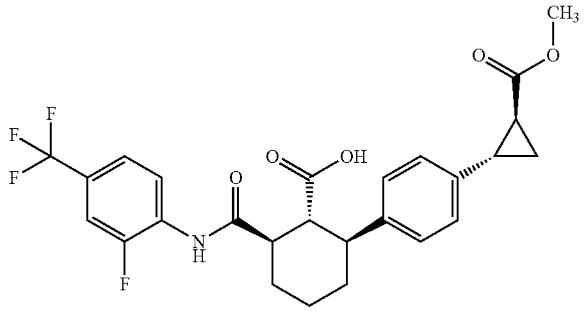 [SMILES: COC(=O)[C@H]1C[C@@H]1c1ccc([C@H]2CCC[C@@H](C(=O)Nc3ccc(C(F)(F)F)cc3F)[C@@H]2C(=O)O)cc1] |

TABLE 1-continued
| Ex. No. | Structure |
|---|---|
| 68 | 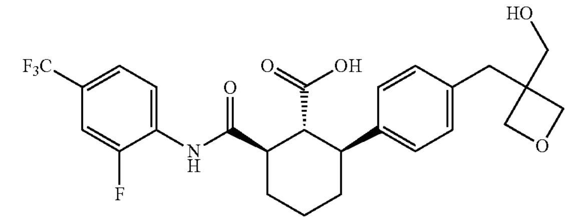 [SMILES: O=C(O)[C@@H]1[C@@H](c2ccc(CC3(CO)COC3)cc2)CCC[C@H]1C(=O)Nc1ccc(C(F)(F)F)cc1F] |
| 69 | 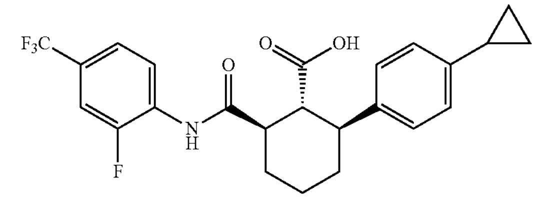 [SMILES: O=C(O)[C@@H]1[C@@H](c2ccc(C3CC3)cc2)CCC[C@H]1C(=O)Nc1ccc(C(F)(F)F)cc1F] |
| 70 | 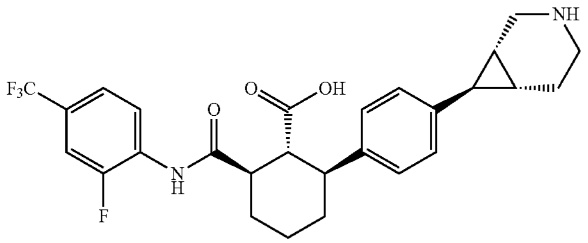 [SMILES: O=C(O)[C@@H]1[C@@H](c2ccc([C@H]3[C@@H]4CNCC[C@@H]43)cc2)CCC[C@H]1C(=O)Nc1ccc(C(F)(F)F)cc1F] + 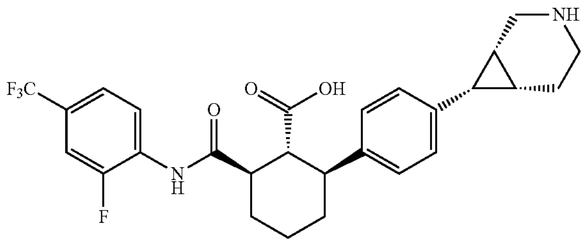 [SMILES: O=C(O)[C@@H]1[C@@H](c2ccc([C@@H]3[C@@H]4CNCC[C@@H]43)cc2)CCC[C@H]1C(=O)Nc1ccc(C(F)(F)F)cc1F] + 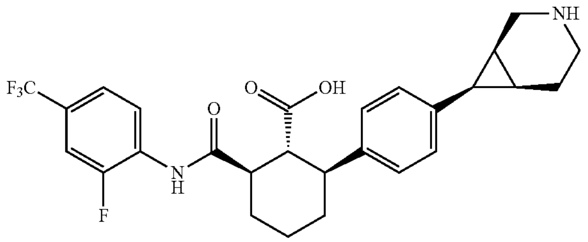 [SMILES: O=C(O)[C@@H]1[C@@H](c2ccc([C@@H]3[C@@H]4CCNC[C@@H]43)cc2)CCC[C@H]1C(=O)Nc1ccc(C(F)(F)F)cc1F] + 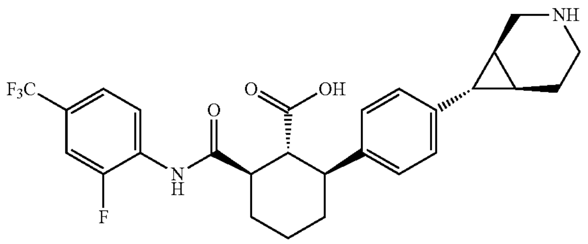 [SMILES: O=C(O)[C@@H]1[C@@H](c2ccc([C@H]3[C@@H]4CCNC[C@@H]43)cc2)CCC[C@H]1C(=O)Nc1ccc(C(F)(F)F)cc1F] |

TABLE 1-continued
| Ex. No. | Structure |
|---|---|
| 71 | 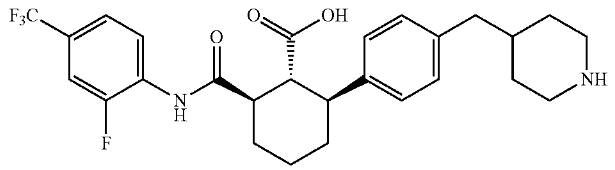 [SMILES: O=C(O)[C@@H]1[C@@H](c2ccc(CC3CCNCC3)cc2)CCC[C@H]1C(=O)Nc1ccc(C(F)(F)F)cc1F] |
| 72 | 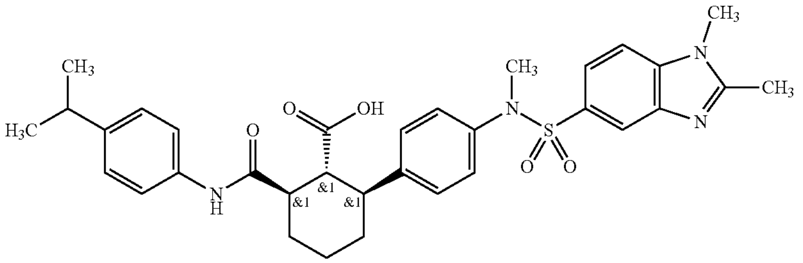 [SMILES: Cc1nc2cc(S(=O)(=O)N(C)c3ccc([C@H]4CCC[C@@H](C(=O)Nc5ccc(C(C)C)cc5)[C@@H]4C(=O)O)cc3)ccc2n1C] |
| 73 | 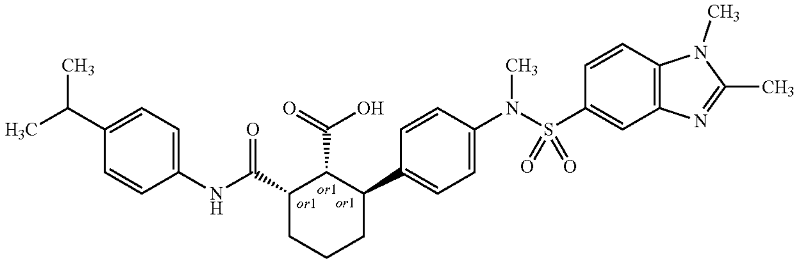 [SMILES: Cc1nc2cc(S(=O)(=O)N(C)c3ccc([C@H]4CCC[C@H](C(=O)Nc5ccc(C(C)C)cc5)[C@@H]4C(=O)O)cc3)ccc2n1C]<br>ISOMER 1 |
| 74 | 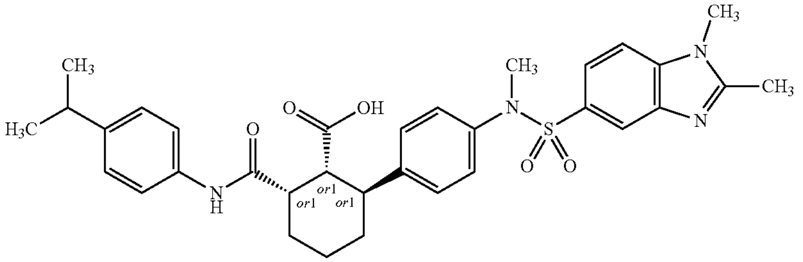 [SMILES: Cc1nc2cc(S(=O)(=O)N(C)c3ccc([C@H]4CCC[C@H](C(=O)Nc5ccc(C(C)C)cc5)[C@@H]4C(=O)O)cc3)ccc2n1C]<br>ISOMER 2 |
| 75 | 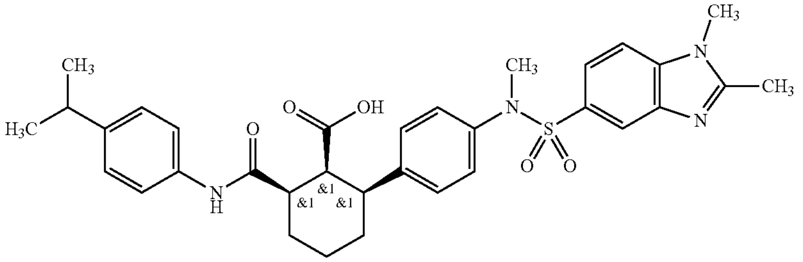 [SMILES: Cc1nc2cc(S(=O)(=O)N(C)c3ccc([C@H]4CCC[C@@H](C(=O)Nc5ccc(C(C)C)cc5)[C@H]4C(=O)O)cc3)ccc2n1C] |

TABLE 1-continued
| Ex. No. | Structure |
|---|---|
| 76 | 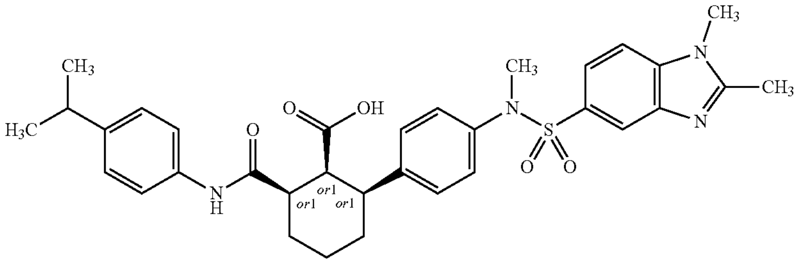 [SMILES: Cc1nc2cc(S(=O)(=O)N(C)c3ccc([C@H]4CCC[C@@H](C(=O)Nc5ccc(C(C)C)cc5)[C@H]4C(=O)O)cc3)ccc2n1C] ISOMER 1 |
| 77 | 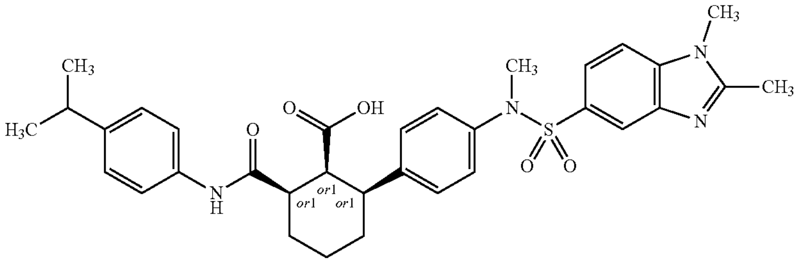 [SMILES: Cc1nc2cc(S(=O)(=O)N(C)c3ccc([C@H]4CCC[C@@H](C(=O)Nc5ccc(C(C)C)cc5)[C@H]4C(=O)O)cc3)ccc2n1C] ISOMER 2 |
| 78 | 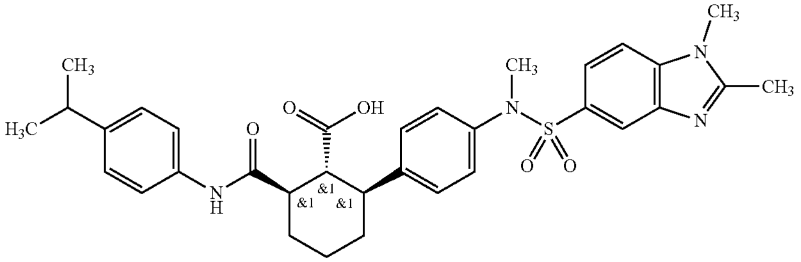 [SMILES: Cc1nc2cc(S(=O)(=O)N(C)c3ccc([C@H]4CCC[C@@H](C(=O)Nc5ccc(C(C)C)cc5)[C@@H]4C(=O)O)cc3)ccc2n1C] |
| 79 | 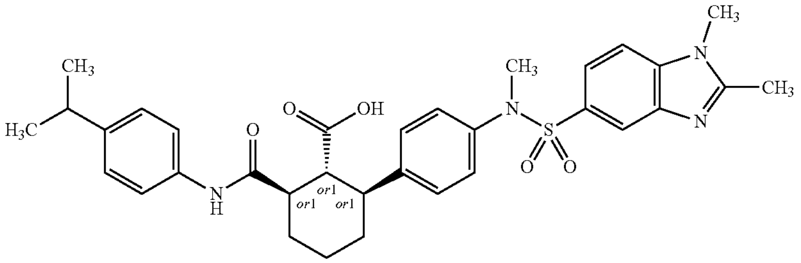 [SMILES: Cc1nc2cc(S(=O)(=O)N(C)c3ccc([C@H]4CCC[C@@H](C(=O)Nc5ccc(C(C)C)cc5)[C@@H]4C(=O)O)cc3)ccc2n1C] ISOMER 1 |
| 80 | 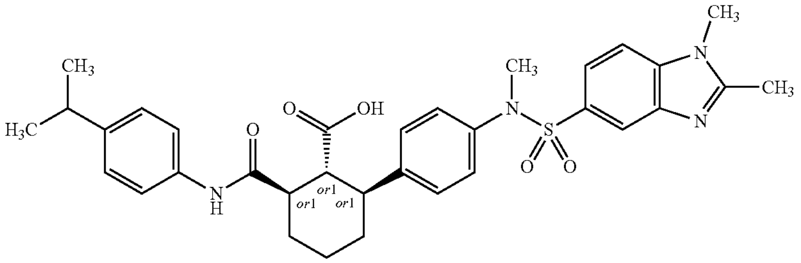 [SMILES: Cc1nc2cc(S(=O)(=O)N(C)c3ccc([C@H]4CCC[C@@H](C(=O)Nc5ccc(C(C)C)cc5)[C@@H]4C(=O)O)cc3)ccc2n1C] ISOMER 2 |

TABLE 1-continued
| Ex. No. | Structure |
|---|---|
| 81 | 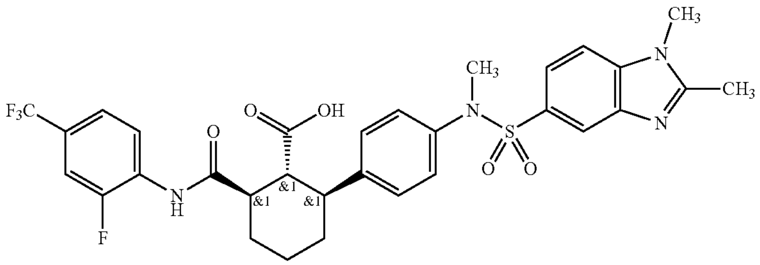 [SMILES: Cc1nc2cc(S(=O)(=O)N(C)c3ccc([C@H]4CCC[C@@H](C(=O)Nc5ccc(C(F)(F)F)cc5F)[C@@H]4C(=O)O)cc3)ccc2n1C] |
| 82 | 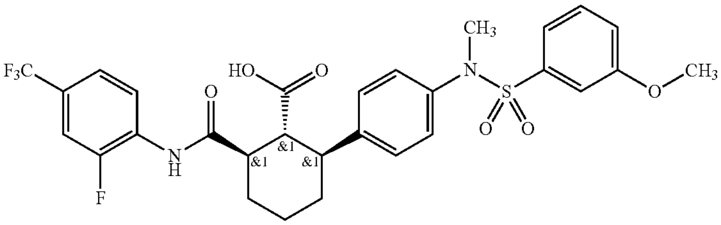 [SMILES: COc1cccc(S(=O)(=O)N(C)c2ccc([C@H]3CCC[C@@H](C(=O)Nc4ccc(C(F)(F)F)cc4F)[C@@H]3C(=O)O)cc2)c1] |
| 83 | 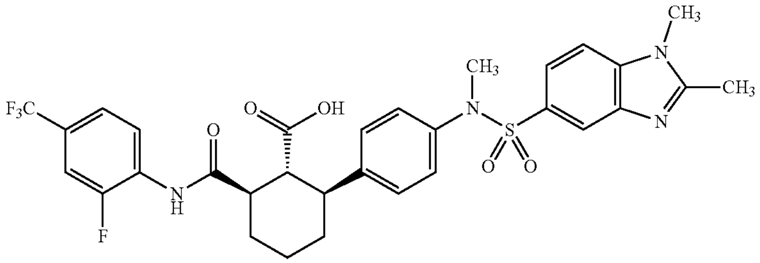 [SMILES: Cc1nc2cc(S(=O)(=O)N(C)c3ccc([C@H]4CCC[C@@H](C(=O)Nc5ccc(C(F)(F)F)cc5F)[C@@H]4C(=O)O)cc3)ccc2n1C] |
| 84 | 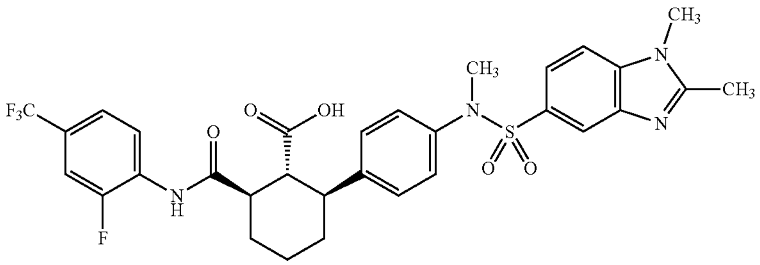 [SMILES: Cc1nc2cc(S(=O)(=O)N(C)c3ccc([C@H]4CCC[C@@H](C(=O)Nc5ccc(C(F)(F)F)cc5F)[C@@H]4C(=O)O)cc3)ccc2n1C] |
| 85 | 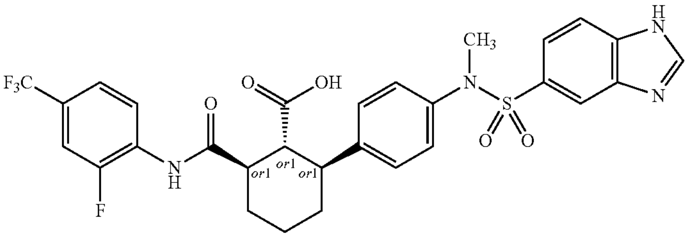 [SMILES: CN(c1ccc([C@H]2CCC[C@@H](C(=O)Nc3ccc(C(F)(F)F)cc3F)[C@@H]2C(=O)O)cc1)S(=O)(=O)c1ccc2[nH]cnc2c1]<br>ISOMER 1 |

TABLE 1-continued
| Ex. No. | Structure |
|---|---|
| 86 | 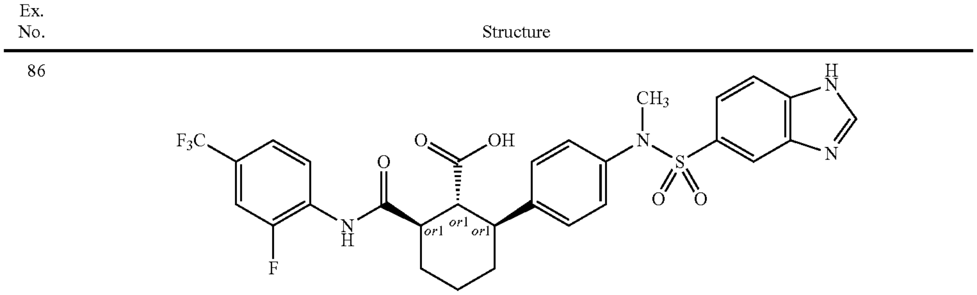 ISOMER 2 |
| 87 | 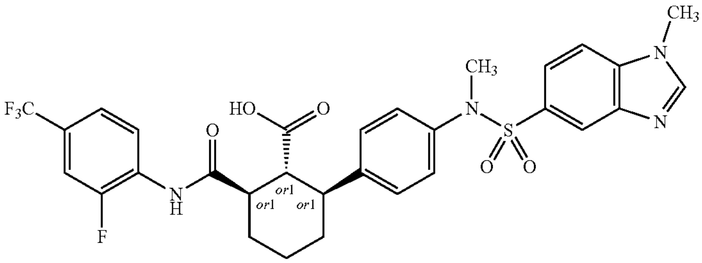 [SMILES: CN(c1ccc([C@H]2CCC[C@@H](C(=O)Nc3ccc(C(F)(F)F)cc3F)[C@@H]2C(=O)O)cc1)S(=O)(=O)c1ccc2c(c1)ncn2C] ISOMER 1 |
| 88 | 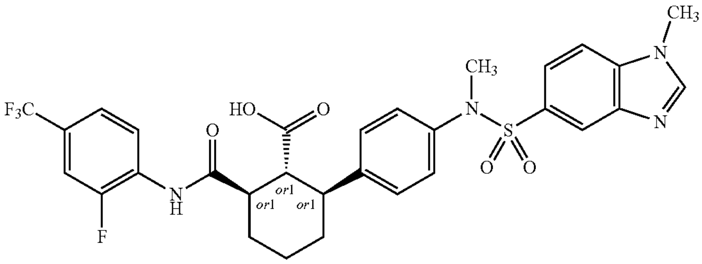 [SMILES: CN(c1ccc([C@H]2CCC[C@@H](C(=O)Nc3ccc(C(F)(F)F)cc3F)[C@@H]2C(=O)O)cc1)S(=O)(=O)c1ccc2c(c1)ncn2C] ISOMER 2 |
| 89 | 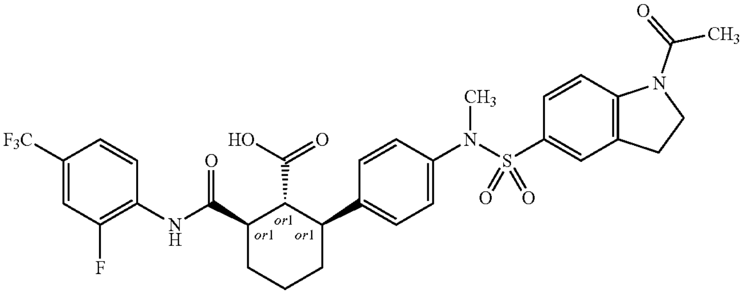 [SMILES: CC(=O)N1CCc2cc(S(=O)(=O)N(C)c3ccc([C@H]4CCC[C@@H](C(=O)Nc5ccc(C(F)(F)F)cc5F)[C@@H]4C(=O)O)cc3)ccc21] ISOMER 1 |
| 90 | 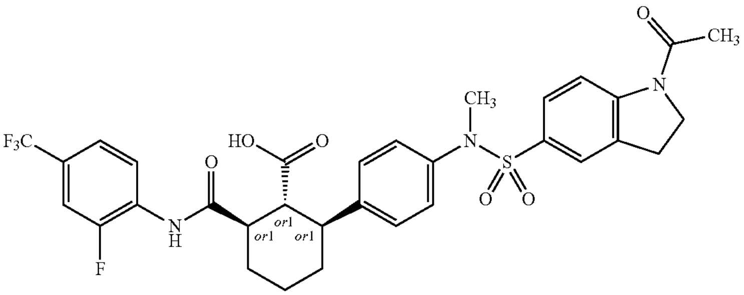 [SMILES: CC(=O)N1CCc2cc(S(=O)(=O)N(C)c3ccc([C@H]4CCC[C@@H](C(=O)Nc5ccc(C(F)(F)F)cc5F)[C@@H]4C(=O)O)cc3)ccc21] ISOMER 2 |

TABLE 1-continued
| Ex. No. | Structure |
|---|---|
| 91 | 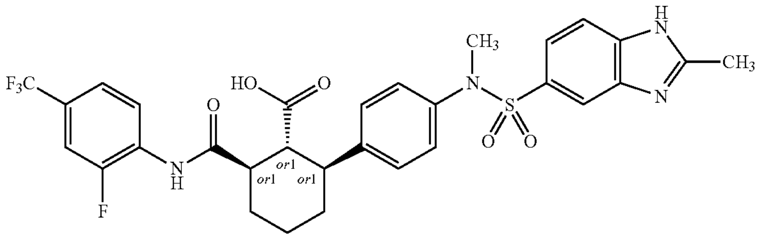 [SMILES: Cc1nc2cc(S(=O)(=O)N(C)c3ccc([C@H]4CCC[C@@H](C(=O)Nc5ccc(C(F)(F)F)cc5F)[C@@H]4C(=O)O)cc3)ccc2[nH]1] ISOMER 1 |
| 92 | 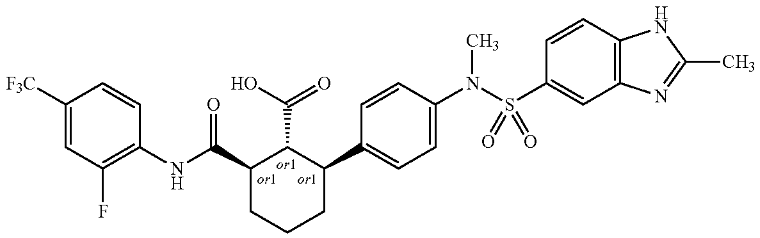 [SMILES: Cc1nc2cc(S(=O)(=O)N(C)c3ccc([C@H]4CCC[C@@H](C(=O)Nc5ccc(C(F)(F)F)cc5F)[C@@H]4C(=O)O)cc3)ccc2[nH]1] ISOMER 2 |
| 93 | 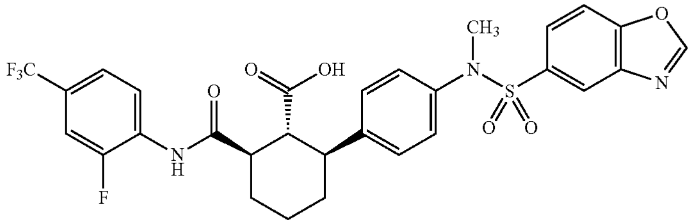 [SMILES: CN(c1ccc([C@H]2CCC[C@@H](C(=O)Nc3ccc(C(F)(F)F)cc3F)[C@@H]2C(=O)O)cc1)S(=O)(=O)c1ccc2ocnc2c1] |
| 94 | 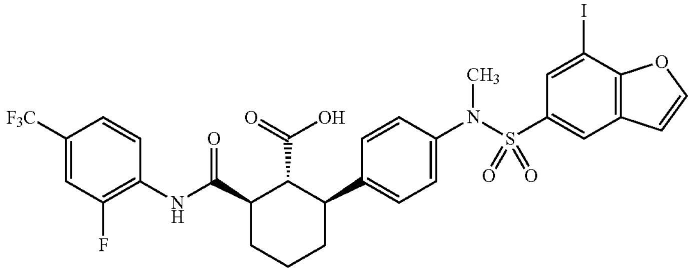 [SMILES: CN(c1ccc([C@H]2CCC[C@@H](C(=O)Nc3ccc(C(F)(F)F)cc3F)[C@@H]2C(=O)O)cc1)S(=O)(=O)c1cc(I)c2occc2c1] |
| 95 | 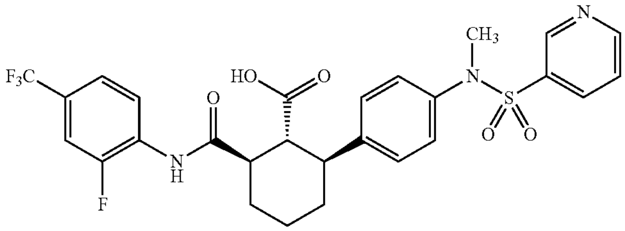 [SMILES: CN(c1ccc([C@H]2CCC[C@@H](C(=O)Nc3ccc(C(F)(F)F)cc3F)[C@@H]2C(=O)O)cc1)S(=O)(=O)c1cccnc1] |
| 96 | 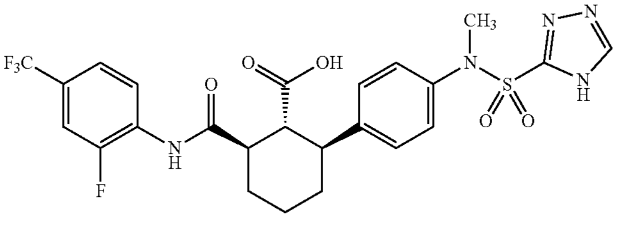 [SMILES: CN(c1ccc([C@H]2CCC[C@@H](C(=O)Nc3ccc(C(F)(F)F)cc3F)[C@@H]2C(=O)O)cc1)S(=O)(=O)c1nnc[nH]1] |

TABLE 1-continued
| Ex. No. | Structure |
| --- | --- |
| 97 | 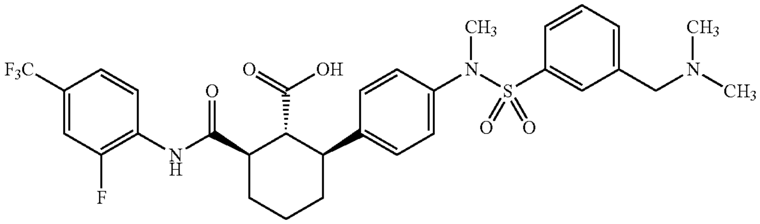 [SMILES: CN(C)Cc1cccc(S(=O)(=O)N(C)c2ccc([C@H]3CCC[C@@H](C(=O)Nc4ccc(C(F)(F)F)cc4F)[C@@H]3C(=O)O)cc2)c1] |
| 98 | 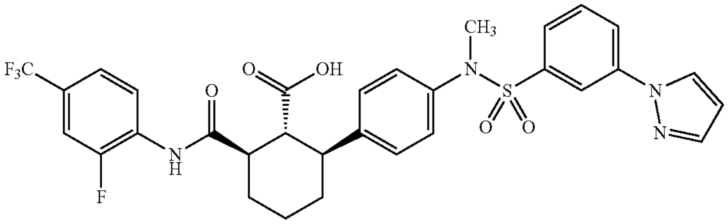 [SMILES: CN(c1ccc([C@H]2CCC[C@@H](C(=O)Nc3ccc(C(F)(F)F)cc3F)[C@@H]2C(=O)O)cc1)S(=O)(=O)c1cccc(-n2cccn2)c1] |
| 99 | 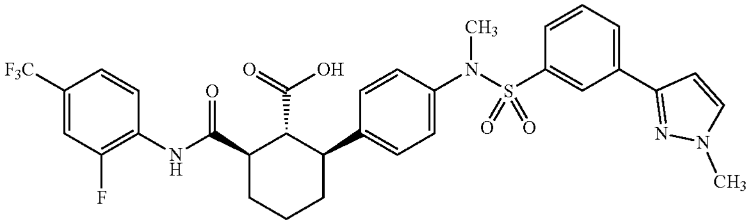 [SMILES: CN(c1ccc([C@H]2CCC[C@@H](C(=O)Nc3ccc(C(F)(F)F)cc3F)[C@@H]2C(=O)O)cc1)S(=O)(=O)c1cccc(-c2ccn(C)n2)c1] |
| 100 | 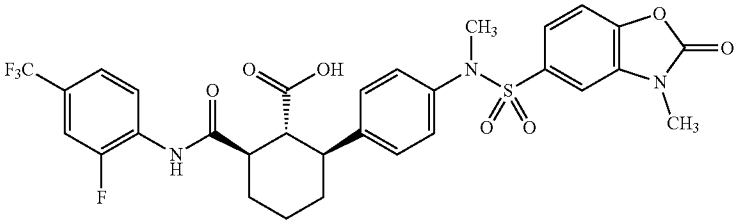 [SMILES: CN(c1ccc([C@H]2CCC[C@@H](C(=O)Nc3ccc(C(F)(F)F)cc3F)[C@@H]2C(=O)O)cc1)S(=O)(=O)c1ccc2oc(=O)n(C)c2c1] |
| 101 | 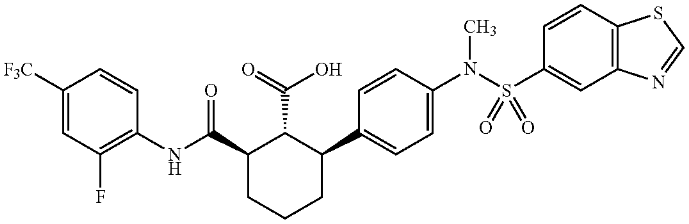 [SMILES: CN(c1ccc([C@H]2CCC[C@@H](C(=O)Nc3ccc(C(F)(F)F)cc3F)[C@@H]2C(=O)O)cc1)S(=O)(=O)c1ccc2scnc2c1] |
| 102 | 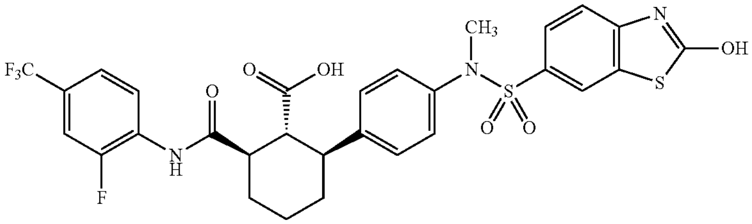 [SMILES: CN(c1ccc([C@H]2CCC[C@@H](C(=O)Nc3ccc(C(F)(F)F)cc3F)[C@@H]2C(=O)O)cc1)S(=O)(=O)c1ccc2nc(O)sc2c1] |

TABLE 1-continued
| Ex. No. | Structure |
|---|---|
| 103 | 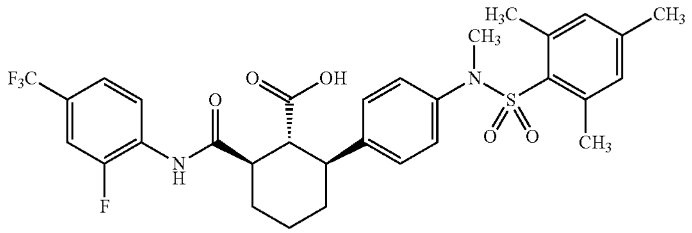 [SMILES: Cc1cc(C)c(S(=O)(=O)N(C)c2ccc([C@H]3CCC[C@@H](C(=O)Nc4ccc(C(F)(F)F)cc4F)[C@@H]3C(=O)O)cc2)c(C)c1] |
| 104 | 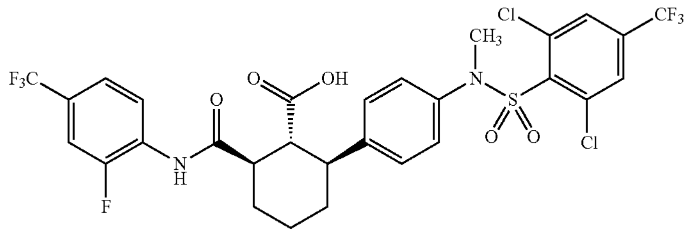 [SMILES: CN(c1ccc([C@H]2CCC[C@@H](C(=O)Nc3ccc(C(F)(F)F)cc3F)[C@@H]2C(=O)O)cc1)S(=O)(=O)c1c(Cl)cc(C(F)(F)F)cc1Cl] |
| 105 | 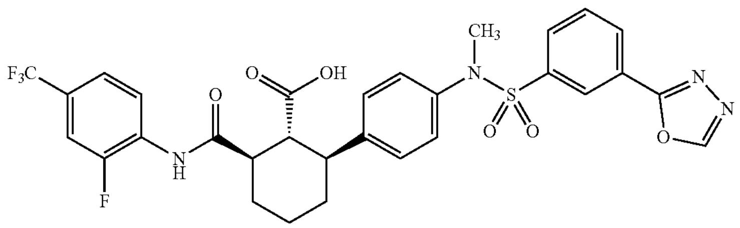 [SMILES: CN(c1ccc([C@H]2CCC[C@@H](C(=O)Nc3ccc(C(F)(F)F)cc3F)[C@@H]2C(=O)O)cc1)S(=O)(=O)c1cccc(-c2nnco2)c1] |
| 106 | 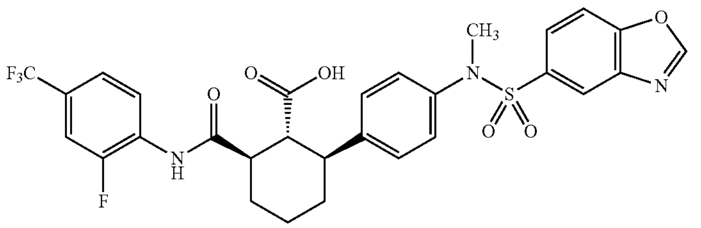 |
| 107 | 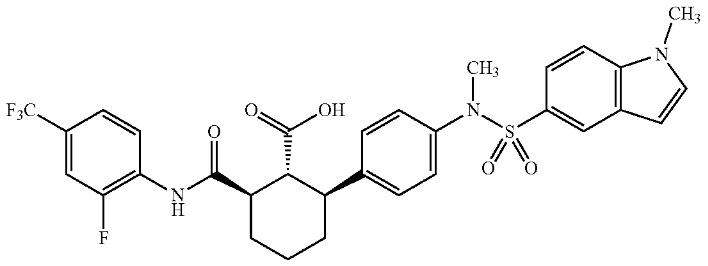 [SMILES: CN(c1ccc([C@H]2CCC[C@@H](C(=O)Nc3ccc(C(F)(F)F)cc3F)[C@@H]2C(=O)O)cc1)S(=O)(=O)c1ccc2c(ccn2C)c1] |
| 108 | 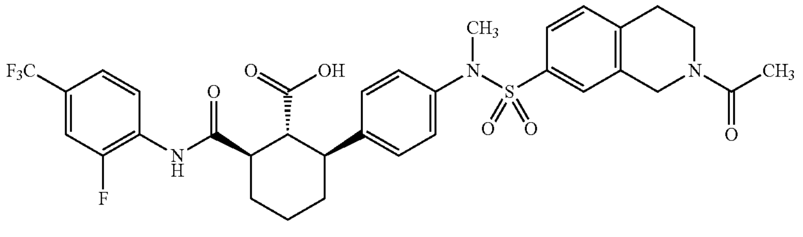 [SMILES: CC(=O)N1CCc2ccc(S(=O)(=O)N(C)c3ccc([C@H]4CCC[C@@H](C(=O)Nc5ccc(C(F)(F)F)cc5F)[C@@H]4C(=O)O)cc3)cc2C1] |

TABLE 1-continued
| Ex. No. | Structure |
|---|---|
| 109 | 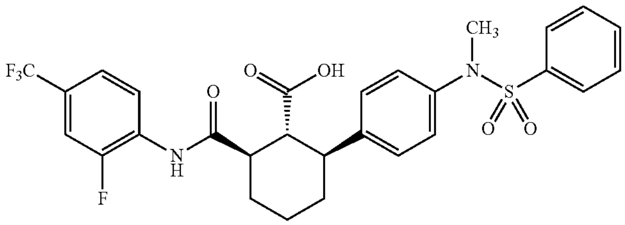 [SMILES: CN(c1ccc([C@H]2CCC[C@@H](C(=O)Nc3ccc(C(F)(F)F)cc3F)[C@@H]2C(=O)O)cc1)S(=O)(=O)c1ccccc1] |
| 110 | 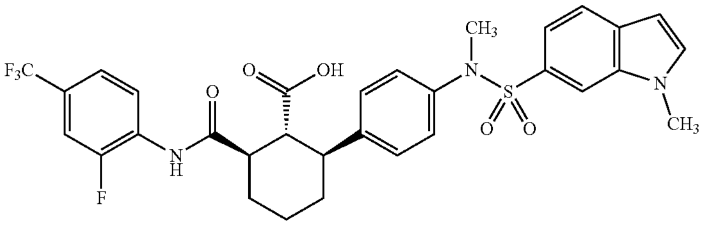 [SMILES: CN(c1ccc([C@H]2CCC[C@@H](C(=O)Nc3ccc(C(F)(F)F)cc3F)[C@@H]2C(=O)O)cc1)S(=O)(=O)c1ccc2ccn(C)c2c1] |
| 111 | 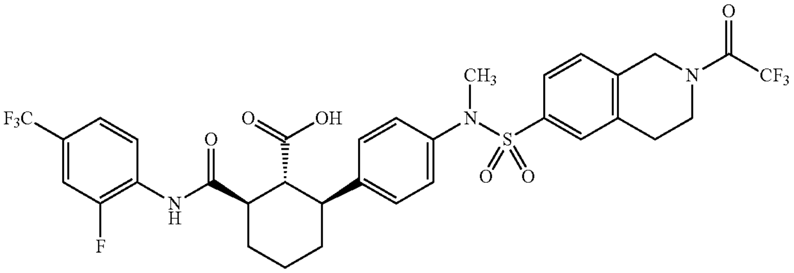 [SMILES: CN(c1ccc([C@H]2CCC[C@@H](C(=O)Nc3ccc(C(F)(F)F)cc3F)[C@@H]2C(=O)O)cc1)S(=O)(=O)c1ccc2c(c1)CCN(C(=O)C(F)(F)F)C2] |
| 112 | 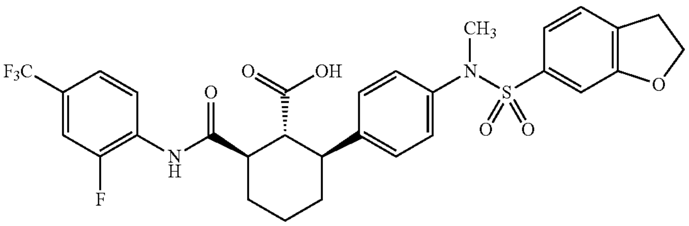 [SMILES: CN(c1ccc([C@H]2CCC[C@@H](C(=O)Nc3ccc(C(F)(F)F)cc3F)[C@@H]2C(=O)O)cc1)S(=O)(=O)c1ccc2c(c1)OCC2] |
| 113 | 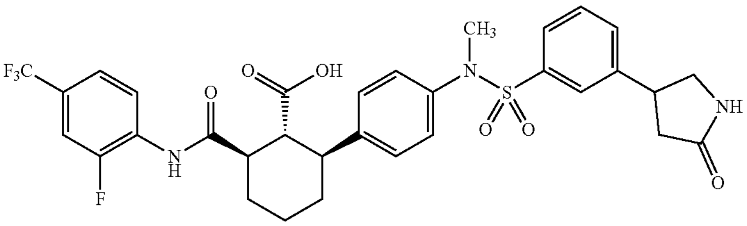 [SMILES: CN(c1ccc([C@H]2CCC[C@@H](C(=O)Nc3ccc(C(F)(F)F)cc3F)[C@@H]2C(=O)O)cc1)S(=O)(=O)c1cccc(C2CNC(=O)C2)c1] |
| 114 | 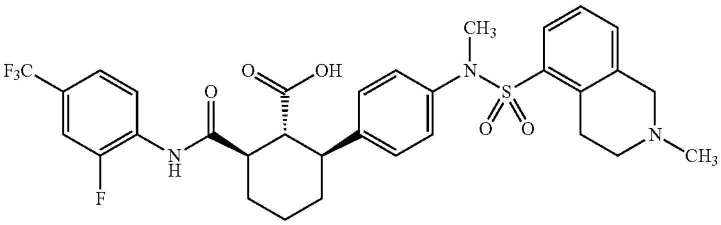 [SMILES: CN1CCc2c(cccc2S(=O)(=O)N(C)c2ccc([C@H]3CCC[C@@H](C(=O)Nc4ccc(C(F)(F)F)cc4F)[C@@H]3C(=O)O)cc2)C1] |

TABLE 1-continued
| Ex. No. | Structure |
|---|---|
| 115 | 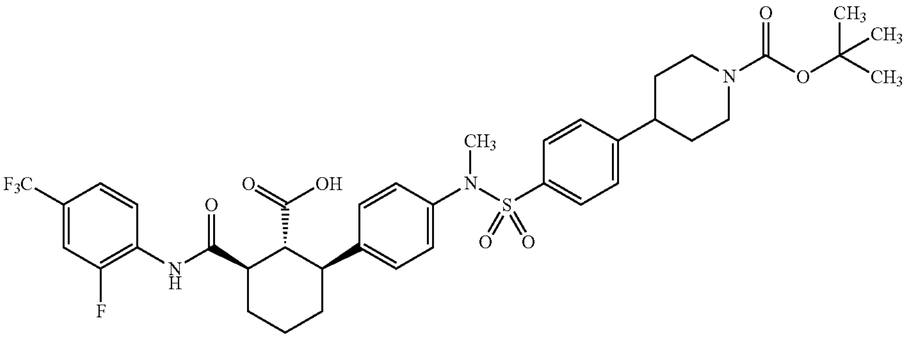 [SMILES: CN(c1ccc([C@H]2CCC[C@@H](C(=O)Nc3ccc(C(F)(F)F)cc3F)[C@@H]2C(=O)O)cc1)S(=O)(=O)c1ccc(C2CCN(C(=O)OC(C)(C)C)CC2)cc1] |
| 116 | 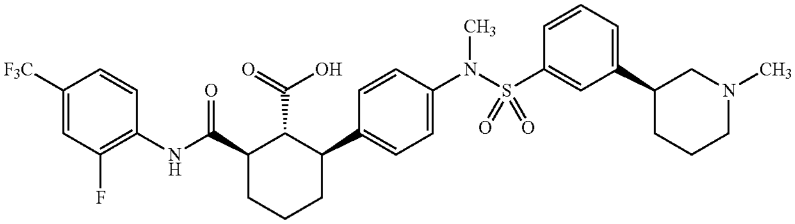 [SMILES: CN1CCC[C@@H](c2cccc(S(=O)(=O)N(C)c3ccc([C@H]4CCC[C@@H](C(=O)Nc5ccc(C(F)(F)F)cc5F)[C@@H]4C(=O)O)cc3)c2)C1] |
| 117 | 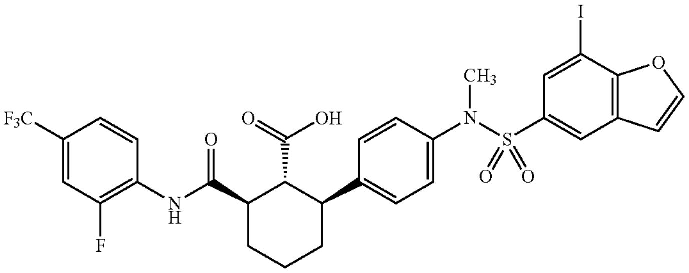 [SMILES: CN(c1ccc([C@H]2CCC[C@@H](C(=O)Nc3ccc(C(F)(F)F)cc3F)[C@@H]2C(=O)O)cc1)S(=O)(=O)c1cc(I)c2occc2c1] |
| 118 | 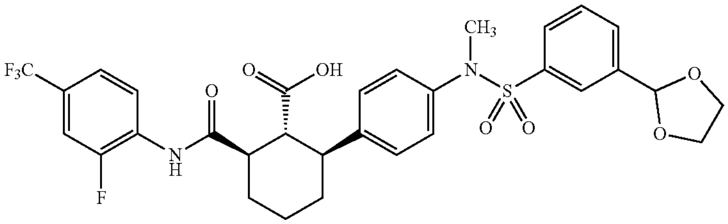 [SMILES: CN(c1ccc([C@H]2CCC[C@@H](C(=O)Nc3ccc(C(F)(F)F)cc3F)[C@@H]2C(=O)O)cc1)S(=O)(=O)c1cccc(C2OCCO2)c1] |
| 119 | 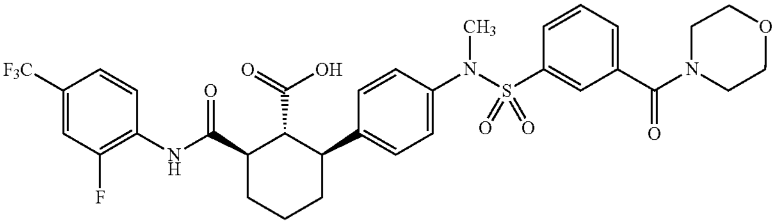 [SMILES: CN(c1ccc([C@H]2CCC[C@@H](C(=O)Nc3ccc(C(F)(F)F)cc3F)[C@@H]2C(=O)O)cc1)S(=O)(=O)c1cccc(C(=O)N2CCOCC2)c1] |
| 120 | 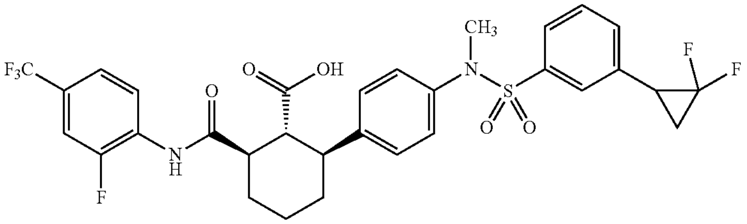 [SMILES: CN(c1ccc([C@H]2CCC[C@@H](C(=O)Nc3ccc(C(F)(F)F)cc3F)[C@@H]2C(=O)O)cc1)S(=O)(=O)c1cccc(C2CC2(F)F)c1] |

TABLE 1-continued
| Ex. No. | Structure |
| --- | --- |
| 121 | 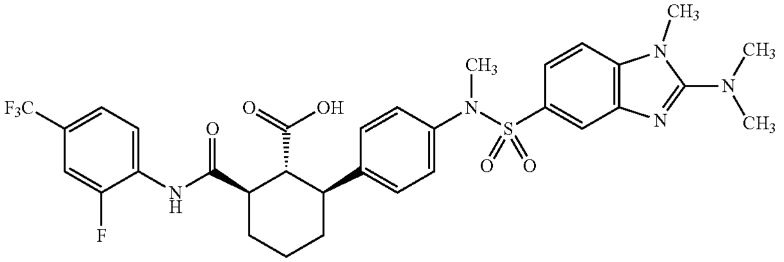 [SMILES: CN(C)c1nc2cc(S(=O)(=O)N(C)c3ccc([C@H]4CCC[C@@H](C(=O)Nc5ccc(C(F)(F)F)cc5F)[C@@H]4C(=O)O)cc3)ccc2n1C] |
| 122 | 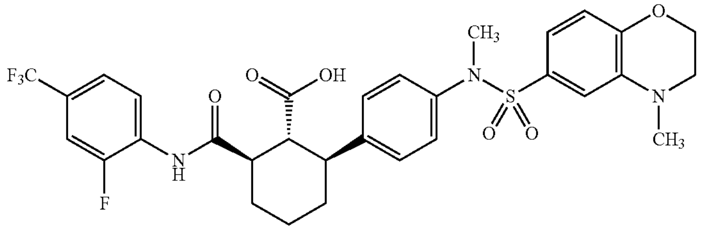 [SMILES: CN1CCOc2ccc(S(=O)(=O)N(C)c3ccc([C@H]4CCC[C@@H](C(=O)Nc5ccc(C(F)(F)F)cc5F)[C@@H]4C(=O)O)cc3)cc21] |
| 123 | 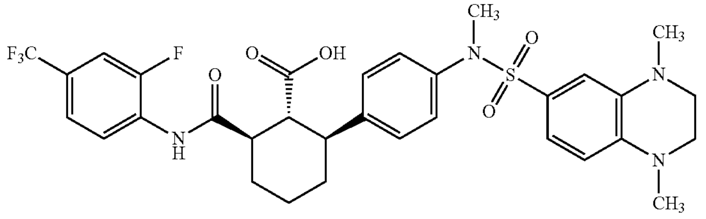 [SMILES: CN1CCN(C)c2cc(S(=O)(=O)N(C)c3ccc([C@H]4CCC[C@@H](C(=O)Nc5ccc(C(F)(F)F)cc5F)[C@@H]4C(=O)O)cc3)ccc21] |
| 124 | 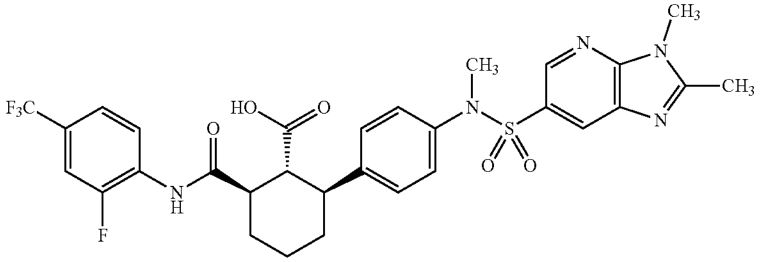 [SMILES: Cc1nc2cc(S(=O)(=O)N(C)c3ccc([C@H]4CCC[C@@H](C(=O)Nc5ccc(C(F)(F)F)cc5F)[C@@H]4C(=O)O)cc3)cnc2n1C] |
| 125 | 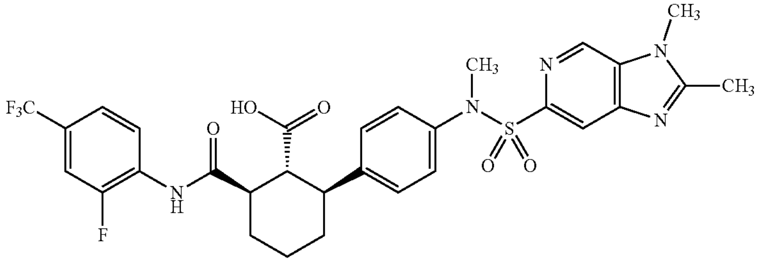 [SMILES: Cc1nc2cc(S(=O)(=O)N(C)c3ccc([C@H]4CCC[C@@H](C(=O)Nc5ccc(C(F)(F)F)cc5F)[C@@H]4C(=O)O)cc3)ncc2n1C] |
| 126 | 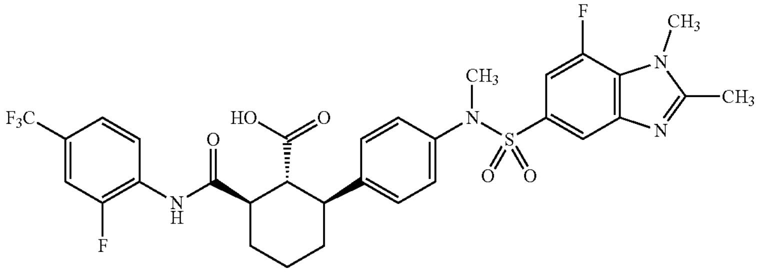 [SMILES: Cc1nc2cc(S(=O)(=O)N(C)c3ccc([C@H]4CCC[C@@H](C(=O)Nc5ccc(C(F)(F)F)cc5F)[C@@H]4C(=O)O)cc3)cc(F)c2n1C] |

TABLE 1-continued
| Ex. No. | Structure |
|---|---|
| 127 | 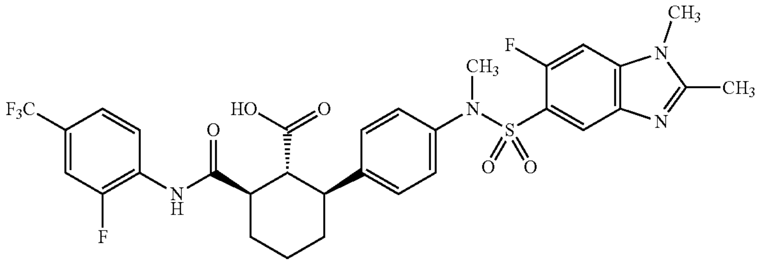 [SMILES: Cc1nc2cc(S(=O)(=O)N(C)c3ccc([C@H]4CCC[C@@H](C(=O)Nc5ccc(C(F)(F)F)cc5F)[C@@H]4C(=O)O)cc3)c(F)cc2n1C] |
| 128 | 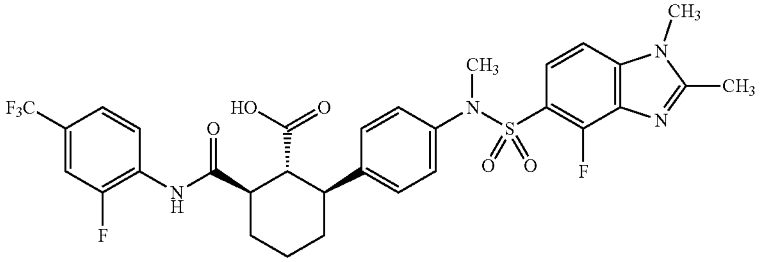 [SMILES: Cc1nc2c(F)c(S(=O)(=O)N(C)c3ccc([C@H]4CCC[C@@H](C(=O)Nc5ccc(C(F)(F)F)cc5F)[C@@H]4C(=O)O)cc3)ccc2n1C] |
| 129 | 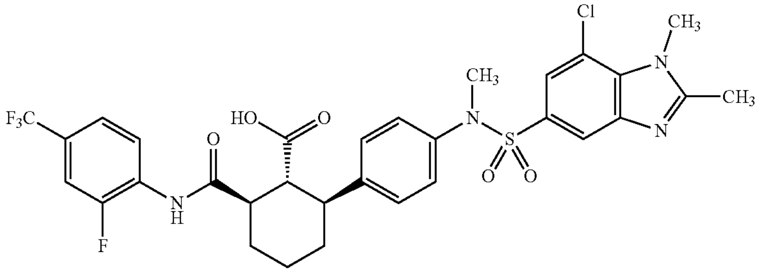 |
| 130 | 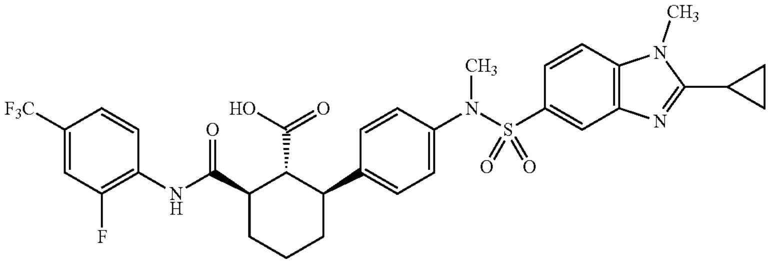 [SMILES: CN(c1ccc([C@H]2CCC[C@@H](C(=O)Nc3ccc(C(F)(F)F)cc3F)[C@@H]2C(=O)O)cc1)S(=O)(=O)c1ccc2c(c1)nc(C1CC1)n2C] |
| 131 | 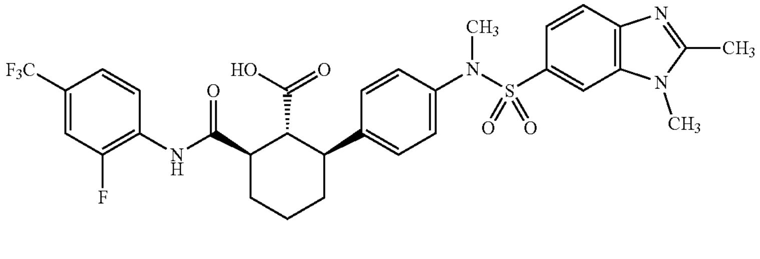 [SMILES: Cc1nc2ccc(S(=O)(=O)N(C)c3ccc([C@H]4CCC[C@@H](C(=O)Nc5ccc(C(F)(F)F)cc5F)[C@@H]4C(=O)O)cc3)cc2n1C] |

TABLE 1-continued
| Ex. No. | Structure |
|---|---|
| 132 | 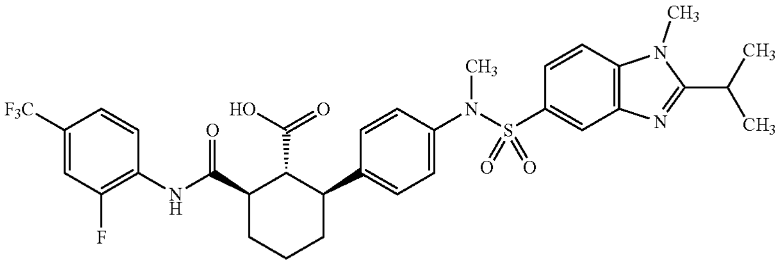 [SMILES: CC(C)c1nc2cc(S(=O)(=O)N(C)c3ccc([C@H]4CCC[C@@H](C(=O)Nc5ccc(C(F)(F)F)cc5F)[C@@H]4C(=O)O)cc3)ccc2n1C] |
| 133 | 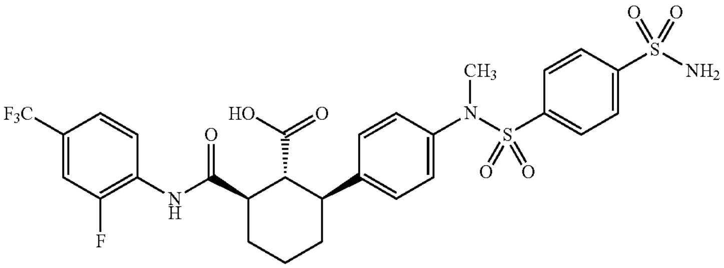 [SMILES: CN(c1ccc([C@H]2CCC[C@@H](C(=O)Nc3ccc(C(F)(F)F)cc3F)[C@@H]2C(=O)O)cc1)S(=O)(=O)c1ccc(S(N)(=O)=O)cc1] |
| 134 | 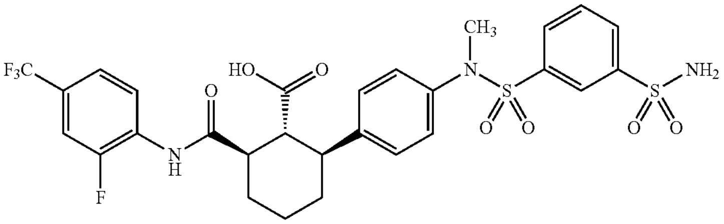 [SMILES: CN(c1ccc([C@H]2CCC[C@@H](C(=O)Nc3ccc(C(F)(F)F)cc3F)[C@@H]2C(=O)O)cc1)S(=O)(=O)c1cccc(S(N)(=O)=O)c1] |
| 135 | 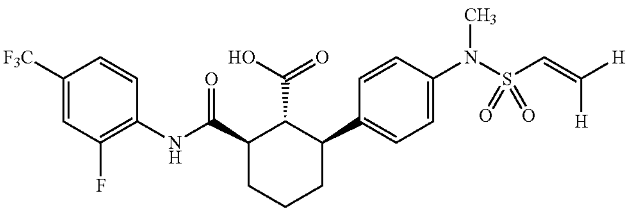 [SMILES: C=CS(=O)(=O)N(C)c1ccc([C@H]2CCC[C@@H](C(=O)Nc3ccc(C(F)(F)F)cc3F)[C@@H]2C(=O)O)cc1] |
| 136 | 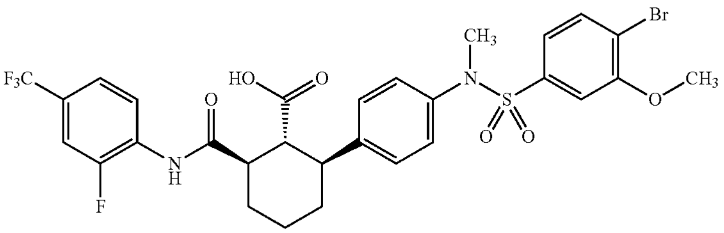 [SMILES: COc1cc(S(=O)(=O)N(C)c2ccc([C@H]3CCC[C@@H](C(=O)Nc4ccc(C(F)(F)F)cc4F)[C@@H]3C(=O)O)cc2)ccc1Br] |

TABLE 1-continued
| Ex. No. | Structure |
|---|---|
| 137 | 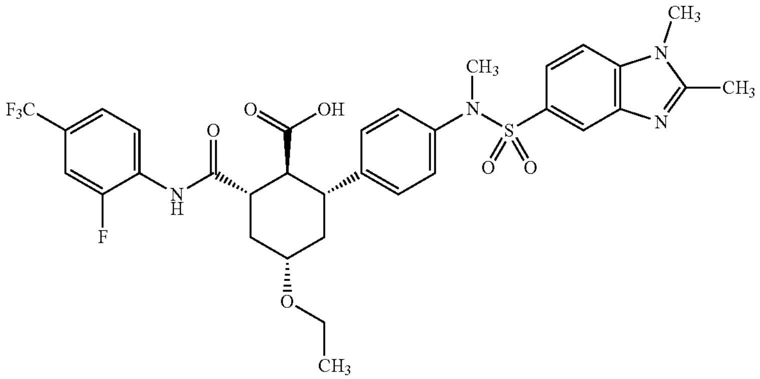 [SMILES: CCO[C@@H]1C[C@H](C(=O)Nc2ccc(C(F)(F)F)cc2F)[C@@H](C(=O)O)[C@H](c2ccc(N(C)S(=O)(=O)c3ccc4c(c3)nc(C)n4C)cc2)C1] |
| 138 | 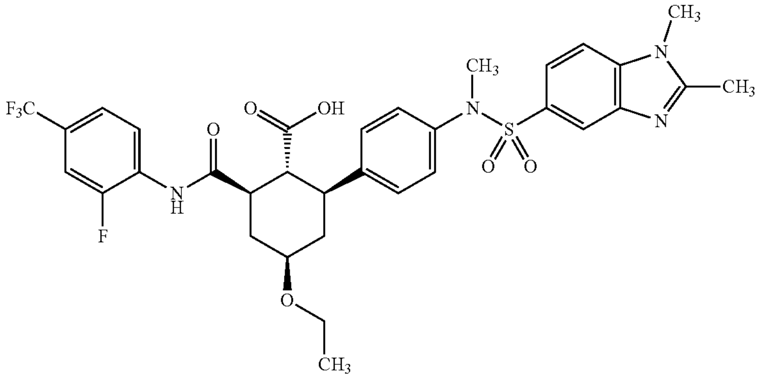 [SMILES: CCO[C@@H]1C[C@H](c2ccc(N(C)S(=O)(=O)c3ccc4c(c3)nc(C)n4C)cc2)[C@@H](C(=O)O)[C@H](C(=O)Nc2ccc(C(F)(F)F)cc2F)C1] |
| 139 | 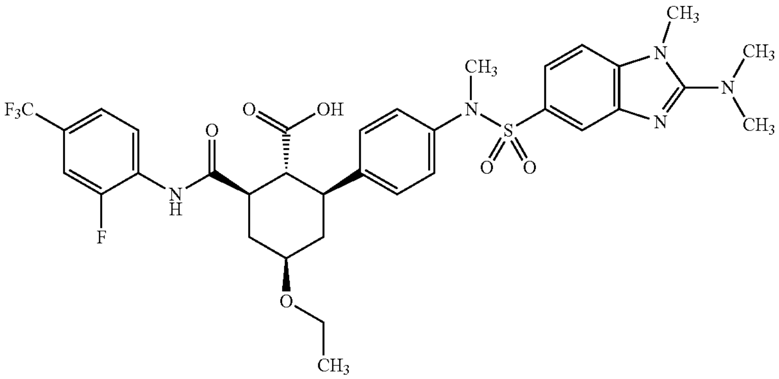 [SMILES: CCO[C@@H]1C[C@H](c2ccc(N(C)S(=O)(=O)c3ccc4c(c3)nc(N(C)C)n4C)cc2)[C@@H](C(=O)O)[C@H](C(=O)Nc2ccc(C(F)(F)F)cc2F)C1] |
| 140 | 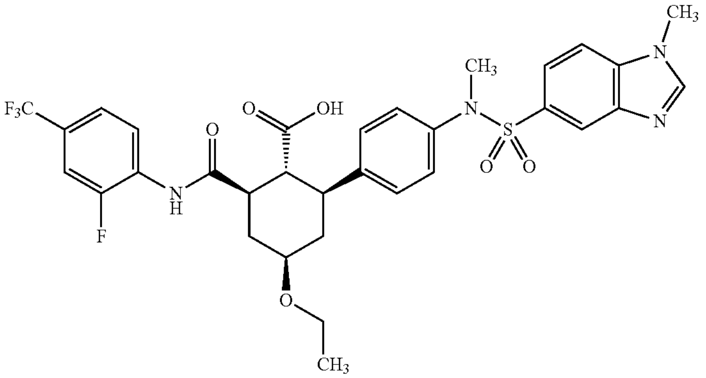 [SMILES: CCO[C@@H]1C[C@H](c2ccc(N(C)S(=O)(=O)c3ccc4c(c3)ncn4C)cc2)[C@@H](C(=O)O)[C@H](C(=O)Nc2ccc(C(F)(F)F)cc2F)C1] |

TABLE 1-continued
| Ex. No. | Structure |
|---|---|
| 141 | 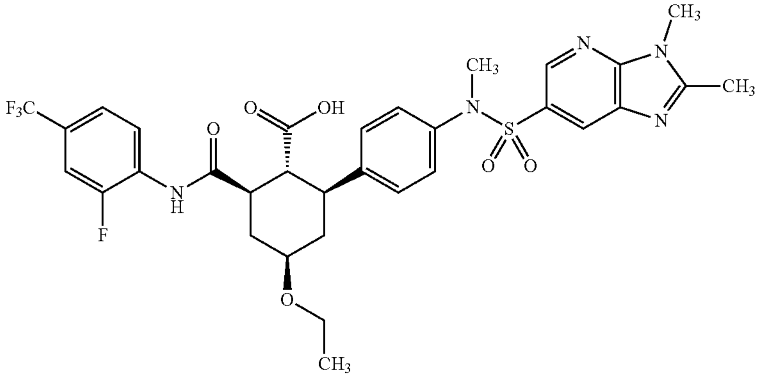 |
| 142 | 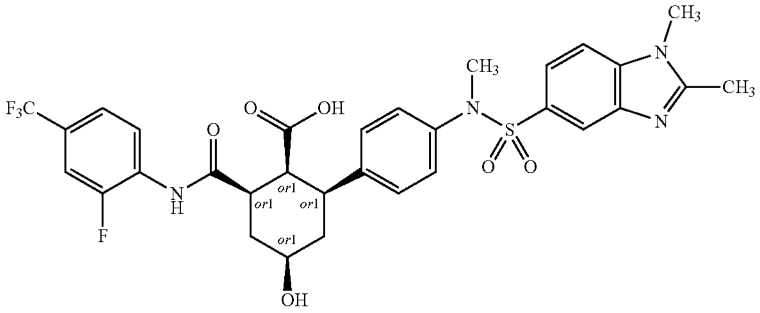 [SMILES: Cc1nc2cc(S(=O)(=O)N(C)c3ccc([C@H]4C[C@@H](O)C[C@@H](C(=O)Nc5ccc(C(F)(F)F)cc5F)[C@H]4C(=O)O)cc3)ccc2n1C]<br>ISOMER 1 |
| 143 | 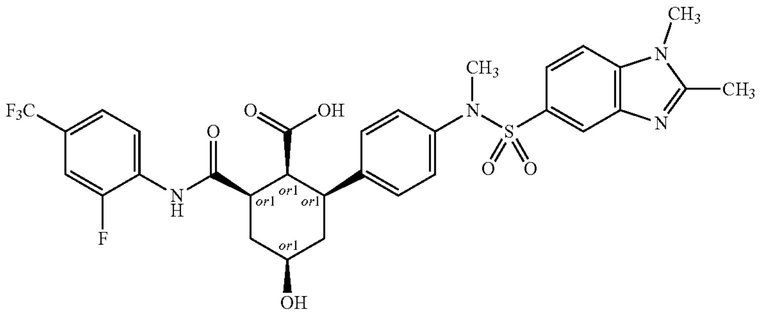 [SMILES: Cc1nc2cc(S(=O)(=O)N(C)c3ccc([C@H]4C[C@@H](O)C[C@@H](C(=O)Nc5ccc(C(F)(F)F)cc5F)[C@H]4C(=O)O)cc3)ccc2n1C]<br>ISOMER 2 |
| 144 | 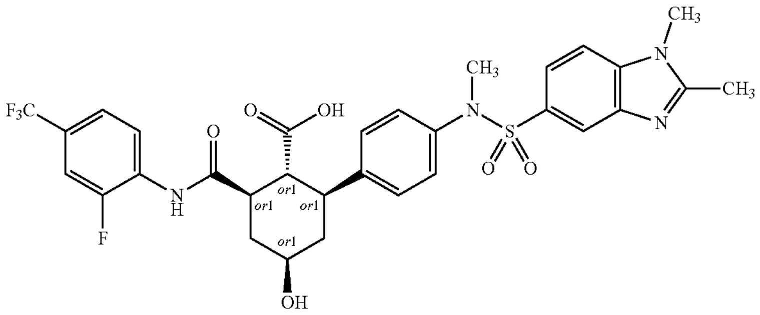 [SMILES: Cc1nc2cc(S(=O)(=O)N(C)c3ccc([C@H]4C[C@@H](O)C[C@@H](C(=O)Nc5ccc(C(F)(F)F)cc5F)[C@@H]4C(=O)O)cc3)ccc2n1C]<br>ISOMER 1 |

TABLE 1-continued
| Ex. No. | Structure |
| --- | --- |
| 145 | 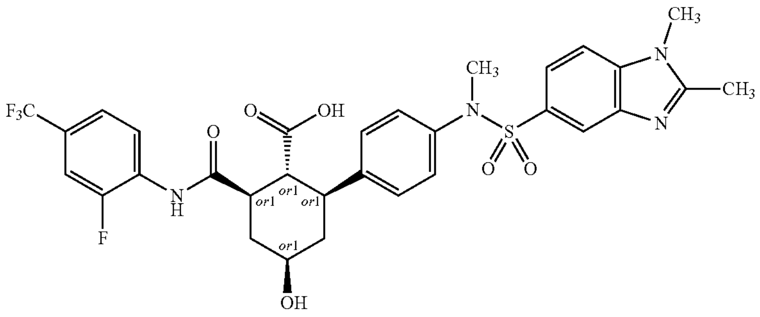 [SMILES: Cc1nc2cc(S(=O)(=O)N(C)c3ccc([C@H]4C[C@@H](O)C[C@@H](C(=O)Nc5ccc(C(F)(F)F)cc5F)[C@@H]4C(=O)O)cc3)ccc2n1C] ISOMER 2 |
| 146 | 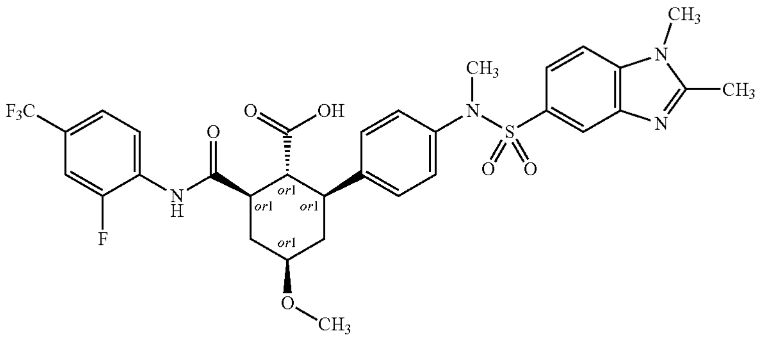 ISOMER 1 |
| 147 | 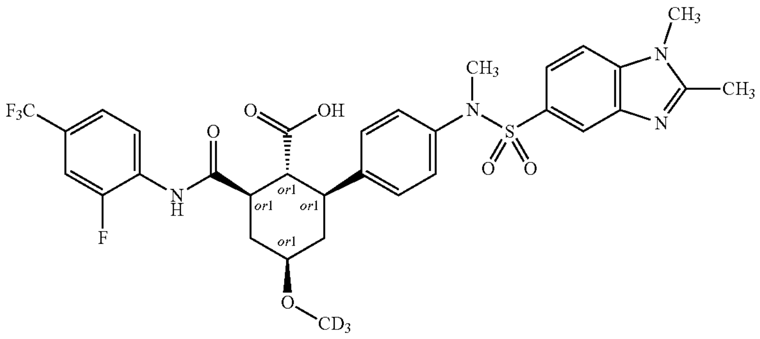 [SMILES: [2H]C([2H])([2H])O[C@@H]1C[C@H](c2ccc(N(C)S(=O)(=O)c3ccc4c(c3)nc(C)n4C)cc2)[C@@H](C(=O)O)[C@H](C(=O)Nc2ccc(C(F)(F)F)cc2F)C1] ISOMER 1 |
| 148 | 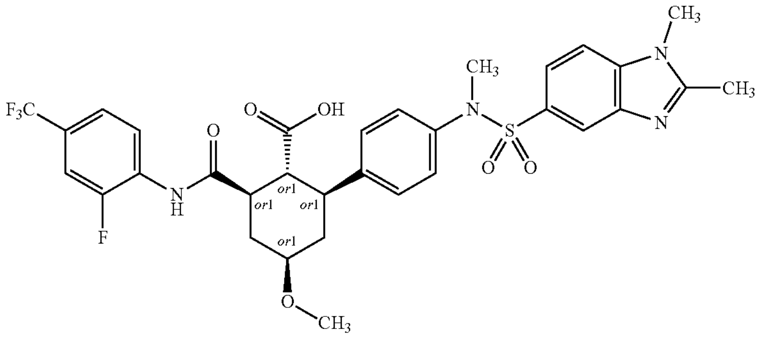 [SMILES: [2H]C([2H])([2H])O[C@@H]1C[C@H](c2ccc(N(C)S(=O)(=O)c3ccc4c(c3)nc(C)n4C)cc2)[C@@H](C(=O)O)[C@H](C(=O)Nc2ccc(C(F)(F)F)cc2F)C1] ISOMER 2 |

TABLE 1-continued
| Ex. No. | Structure |
|---|---|
| 149 | 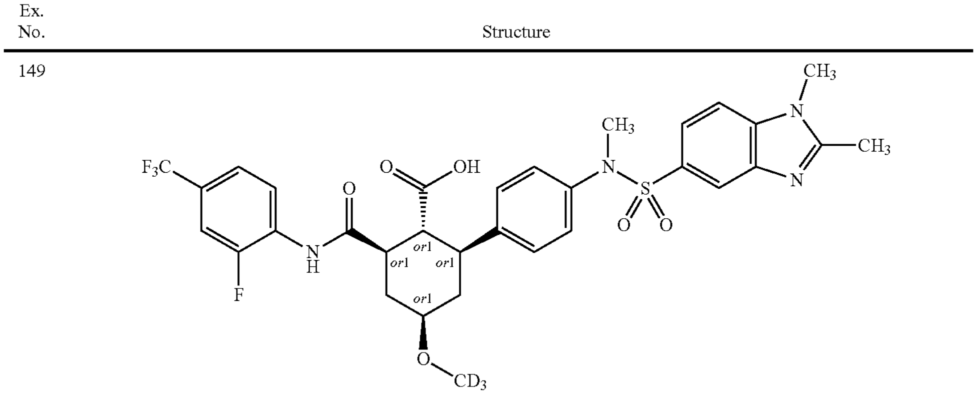 ISOMER 2 |
| 150 | 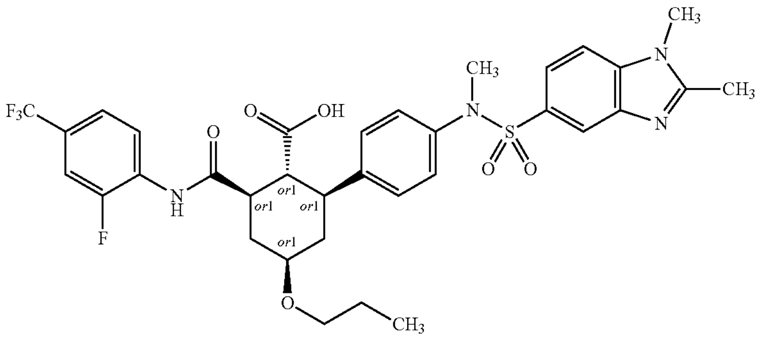 [SMILES: CCCO[C@@H]1C[C@H](c2ccc(N(C)S(=O)(=O)c3ccc4c(c3)nc(C)n4C)cc2)[C@@H](C(=O)O)[C@H](C(=O)Nc2ccc(C(F)(F)F)cc2F)C1] ISOMER 1 |
| 151 | 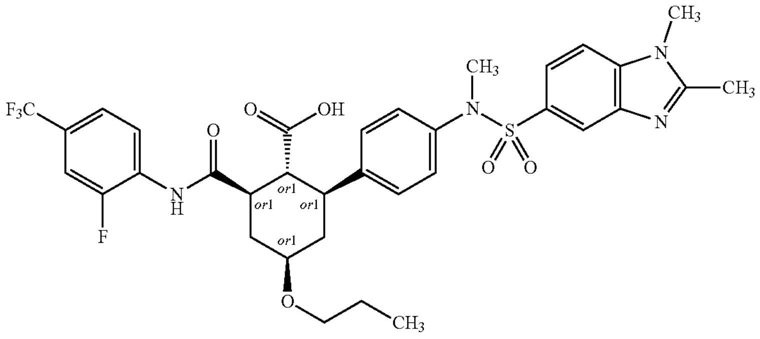 [SMILES: CCCO[C@@H]1C[C@H](c2ccc(N(C)S(=O)(=O)c3ccc4c(c3)nc(C)n4C)cc2)[C@@H](C(=O)O)[C@H](C(=O)Nc2ccc(C(F)(F)F)cc2F)C1] ISOMER 2 |
| 152 | 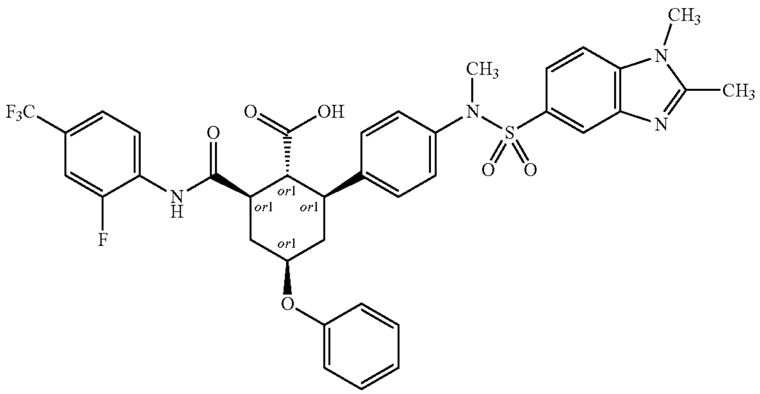 [SMILES: Cc1nc2cc(S(=O)(=O)N(C)c3ccc([C@H]4C[C@@H](Oc5ccccc5)C[C@@H](C(=O)Nc5ccc(C(F)(F)F)cc5F)[C@@H]4C(=O)O)cc3)ccc2n1C] ISOMER 1 |

TABLE 1-continued
| Ex. No. | Structure |
|---|---|
| 153 | 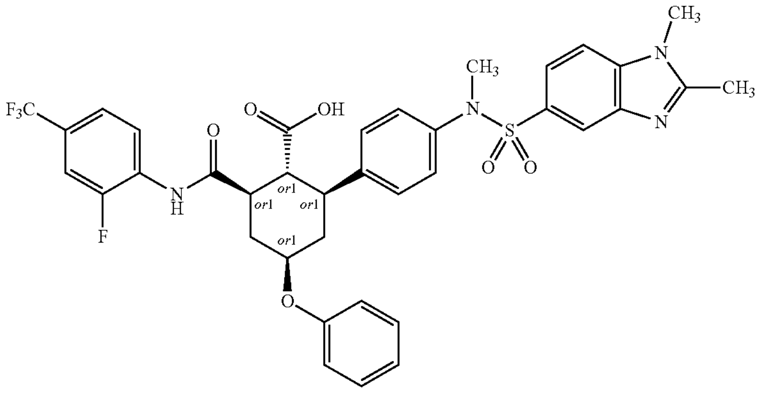 [SMILES: Cc1nc2cc(S(=O)(=O)N(C)c3ccc([C@H]4C[C@@H](Oc5ccccc5)C[C@@H](C(=O)Nc5ccc(C(F)(F)F)cc5F)[C@@H]4C(=O)O)cc3)ccc2n1C] ISOMER 2 |
| 154 | 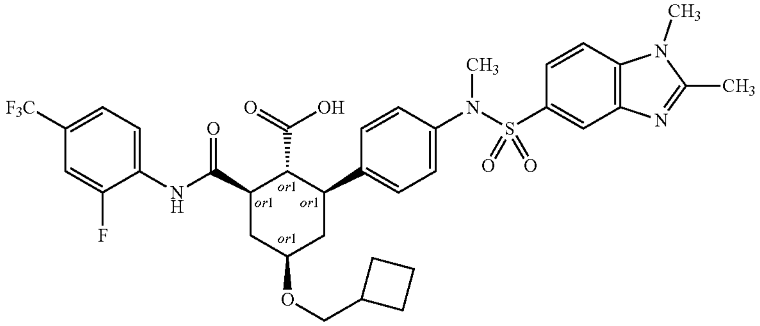 [SMILES: Cc1nc2cc(S(=O)(=O)N(C)c3ccc([C@H]4C[C@@H](OCC5CCC5)C[C@@H](C(=O)Nc5ccc(C(F)(F)F)cc5F)[C@@H]4C(=O)O)cc3)ccc2n1C] ISOMER 1 |
| 155 | 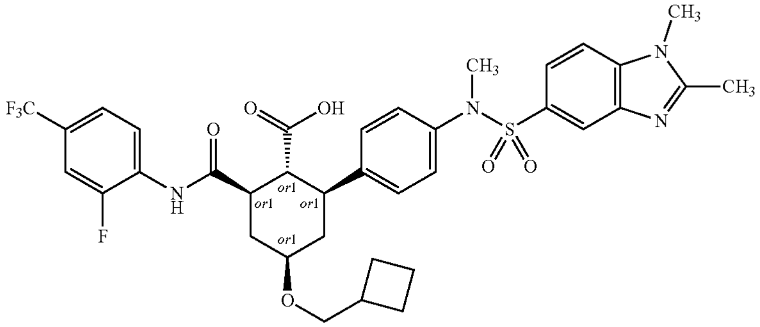 [SMILES: Cc1nc2cc(S(=O)(=O)N(C)c3ccc([C@H]4C[C@@H](OCC5CCC5)C[C@@H](C(=O)Nc5ccc(C(F)(F)F)cc5F)[C@@H]4C(=O)O)cc3)ccc2n1C] ISOMER 2 |
| 156 | 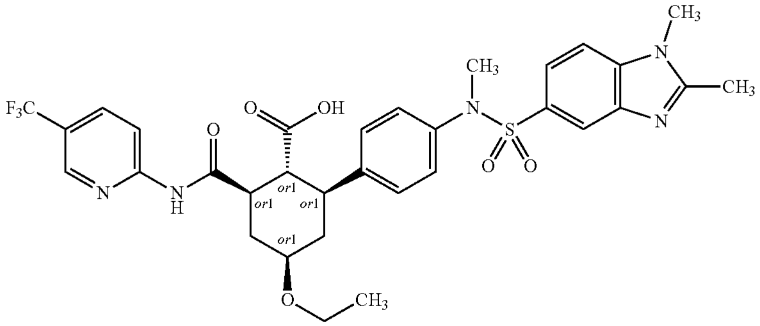 [SMILES: CCO[C@@H]1C[C@H](c2ccc(N(C)S(=O)(=O)c3ccc4c(c3)nc(C)n4C)cc2)[C@@H](C(=O)O)[C@H](C(=O)Nc2ccc(C(F)(F)F)cn2)C1] ISOMER 2 |

TABLE 1-continued
| Ex. No. | Structure |
| --- | --- |
| 157 | 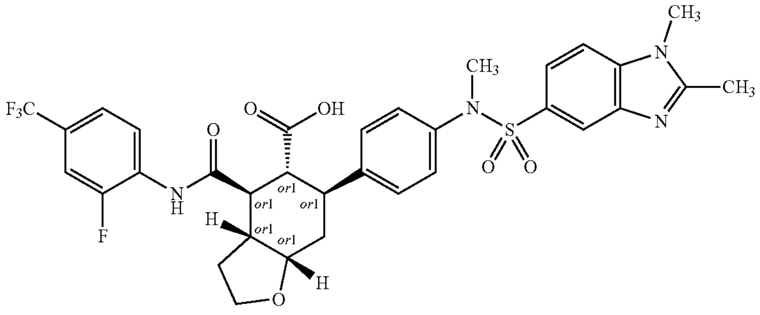 [SMILES: Cc1nc2cc(S(=O)(=O)N(C)c3ccc([C@H]4C[C@@H]5OCC[C@@H]5[C@@H](C(=O)Nc5ccc(C(F)(F)F)cc5F)[C@@H]4C(=O)O)cc3)ccc2n1C]<br>ISOMER 1 |
| 158 | 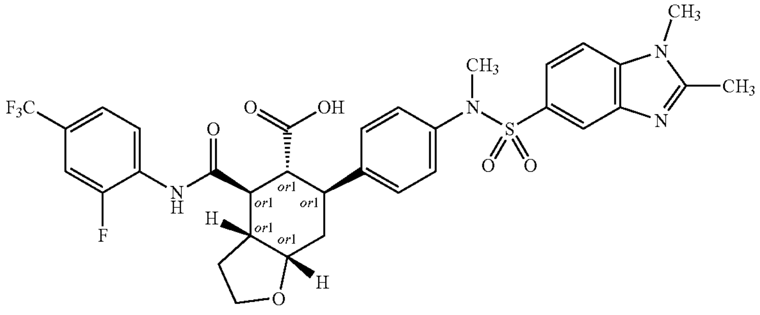 [SMILES: Cc1nc2cc(S(=O)(=O)N(C)c3ccc([C@H]4C[C@@H]5OCC[C@@H]5[C@@H](C(=O)Nc5ccc(C(F)(F)F)cc5F)[C@@H]4C(=O)O)cc3)ccc2n1C]<br>ISOMER 2 |
| 159 | 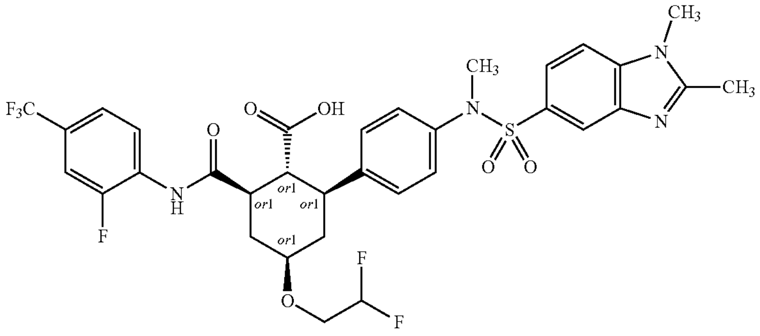 [SMILES: Cc1nc2cc(S(=O)(=O)N(C)c3ccc([C@H]4C[C@@H](OCC(F)F)C[C@@H](C(=O)Nc5ccc(C(F)(F)F)cc5F)[C@@H]4C(=O)O)cc3)ccc2n1C]<br>ISOMER 2 |
| 160 | 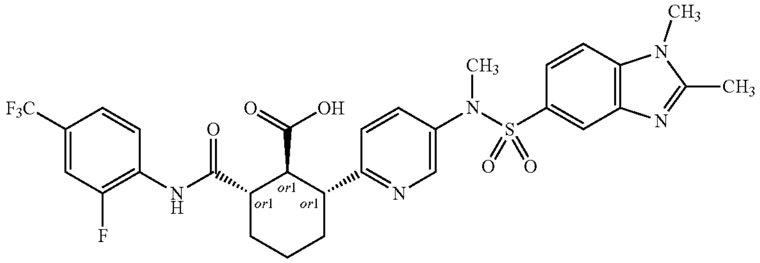 [SMILES: Cc1nc2cc(S(=O)(=O)N(C)c3ccc([C@@H]4CCC[C@H](C(=O)Nc5ccc(C(F)(F)F)cc5F)[C@H]4C(=O)O)nc3)ccc2n1C] |

TABLE 1-continued
| Ex. No. | Structure |
|---|---|
| 161 | 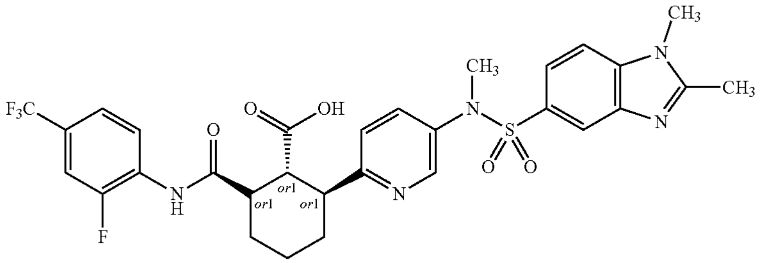 |
| 162 | 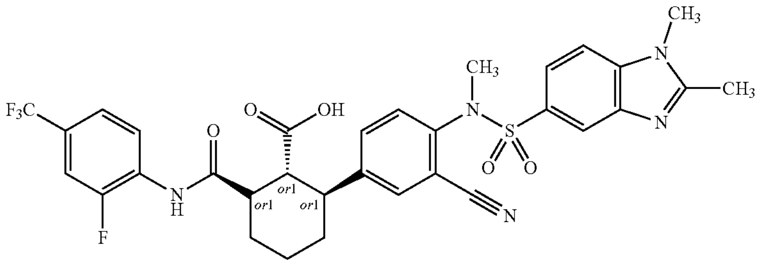 |
| 163 | 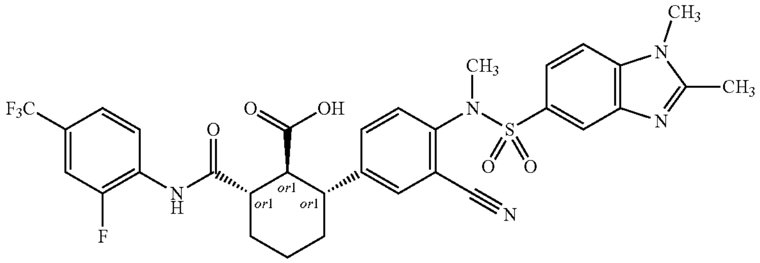 [SMILES: Cc1nc2cc(S(=O)(=O)N(C)c3ccc([C@@H]4CCC[C@H](C(=O)Nc5ccc(C(F)(F)F)cc5F)[C@H]4C(=O)O)cc3C#N)ccc2n1C] |
| 164 | 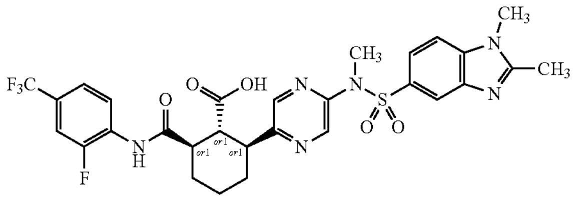 [SMILES: Cc1nc2cc(S(=O)(=O)N(C)c3cnc([C@H]4CCC[C@@H](C(=O)Nc5ccc(C(F)(F)F)cc5F)[C@@H]4C(=O)O)cn3)ccc2n1C] |
| 165 | 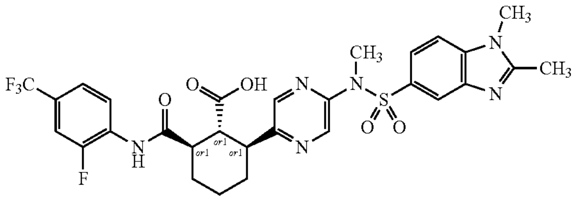 [SMILES: Cc1nc2cc(S(=O)(=O)N(C)c3cnc([C@H]4CCC[C@@H](C(=O)Nc5ccc(C(F)(F)F)cc5F)[C@@H]4C(=O)O)cn3)ccc2n1C] |
| 166 | 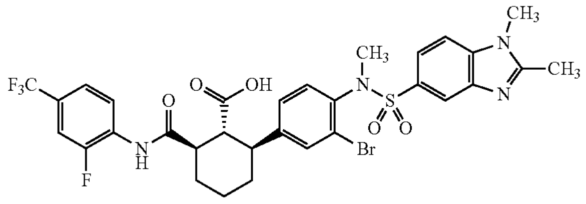 [SMILES: Cc1nc2cc(S(=O)(=O)N(C)c3ccc([C@H]4CCC[C@@H](C(=O)Nc5ccc(C(F)(F)F)cc5F)[C@@H]4C(=O)O)cc3Br)ccc2n1C] |

TABLE 1-continued
| Ex. No. | Structure |
|---|---|
| 167 | 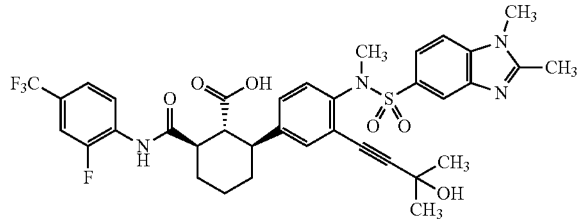 [SMILES: Cc1nc2cc(S(=O)(=O)N(C)c3ccc([C@H]4CCC[C@@H](C(=O)Nc5ccc(C(F)(F)F)cc5F)[C@@H]4C(=O)O)cc3C#CC(C)(C)O)ccc2n1C] |
| 168 | 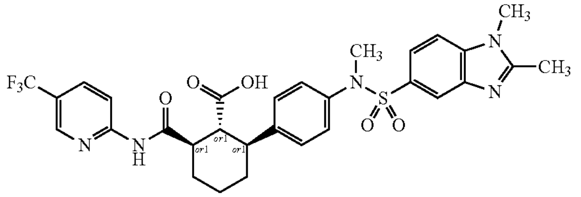 [SMILES: Cc1nc2cc(S(=O)(=O)N(C)c3ccc([C@H]4CCC[C@@H](C(=O)Nc5ccc(C(F)(F)F)cn5)[C@@H]4C(=O)O)cc3)ccc2n1C] |
| 169 | 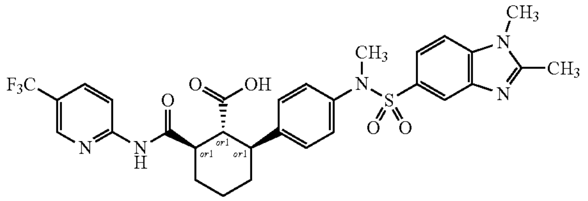 [SMILES: Cc1nc2cc(S(=O)(=O)N(C)c3ccc([C@H]4CCC[C@@H](C(=O)Nc5ccc(C(F)(F)F)cn5)[C@@H]4C(=O)O)cc3)ccc2n1C] |
| 170 | 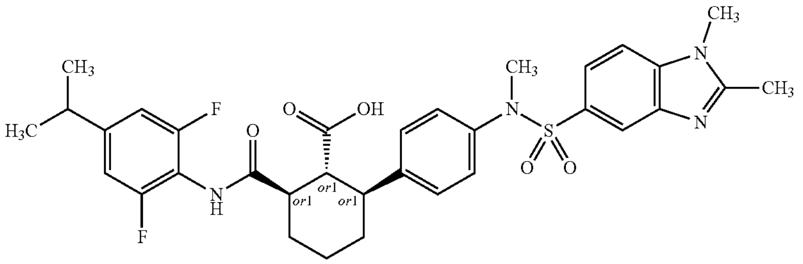 [SMILES: Cc1nc2cc(S(=O)(=O)N(C)c3ccc([C@H]4CCC[C@@H](C(=O)Nc5c(F)cc(C(C)C)cc5F)[C@@H]4C(=O)O)cc3)ccc2n1C] |
| 171 | 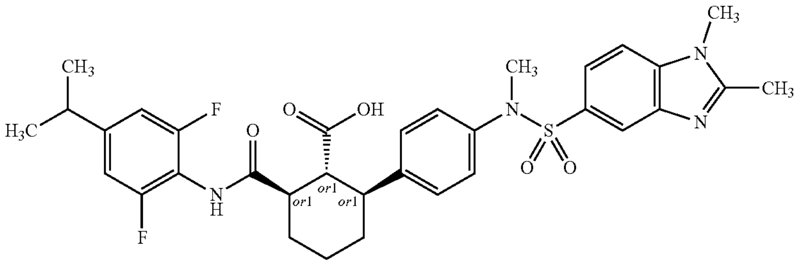 [SMILES: Cc1nc2cc(S(=O)(=O)N(C)c3ccc([C@H]4CCC[C@@H](C(=O)Nc5c(F)cc(C(C)C)cc5F)[C@@H]4C(=O)O)cc3)ccc2n1C] |
| 172 | 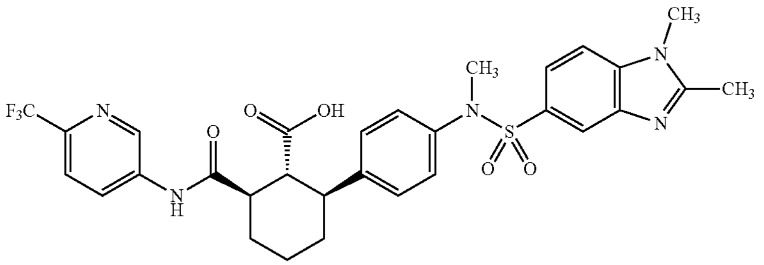 [SMILES: Cc1nc2cc(S(=O)(=O)N(C)c3ccc([C@H]4CCC[C@@H](C(=O)Nc5ccc(C(F)(F)F)nc5)[C@@H]4C(=O)O)cc3)ccc2n1C] |

TABLE 1-continued
| Ex. No. | Structure |
| --- | --- |
| 173 | 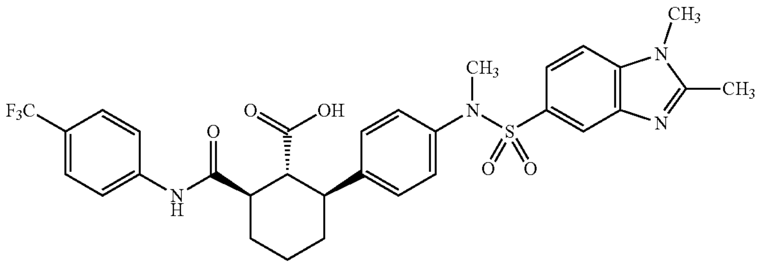 [SMILES: Cc1nc2cc(S(=O)(=O)N(C)c3ccc([C@H]4CCC[C@@H](C(=O)Nc5ccc(C(F)(F)F)cc5)[C@@H]4C(=O)O)cc3)ccc2n1C] |
| 174 | 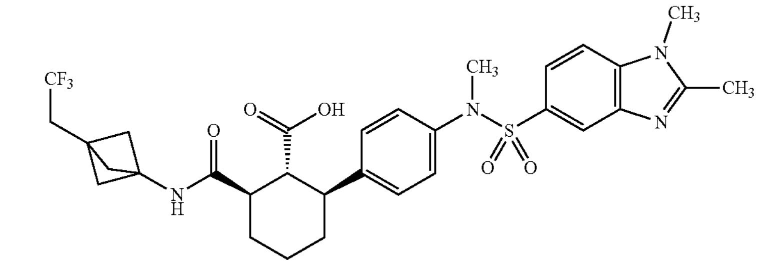 [SMILES: Cc1nc2cc(S(=O)(=O)N(C)c3ccc([C@H]4CCC[C@@H](C(=O)NC56CC(CC(F)(F)F)(C5)C6)[C@@H]4C(=O)O)cc3)ccc2n1C] |
| 175 | 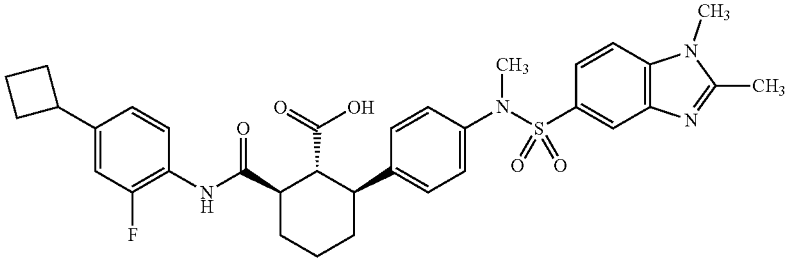 [SMILES: Cc1nc2cc(S(=O)(=O)N(C)c3ccc([C@H]4CCC[C@@H](C(=O)Nc5ccc(C6CCC6)cc5F)[C@@H]4C(=O)O)cc3)ccc2n1C] |
| 176 | 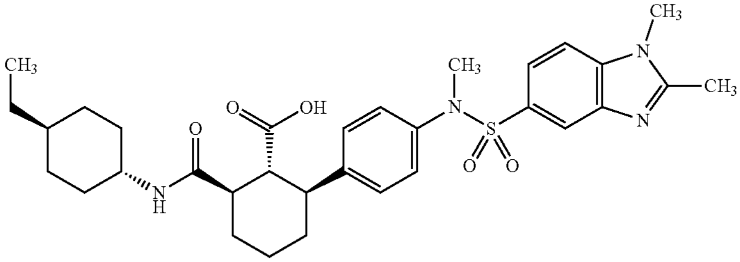 [SMILES: CC[C@H]1CC[C@H](NC(=O)[C@@H]2CCC[C@H](c3ccc(N(C)S(=O)(=O)c4ccc5c(c4)nc(C)n5C)cc3)[C@H]2C(=O)O)CC1] |
| 177 | 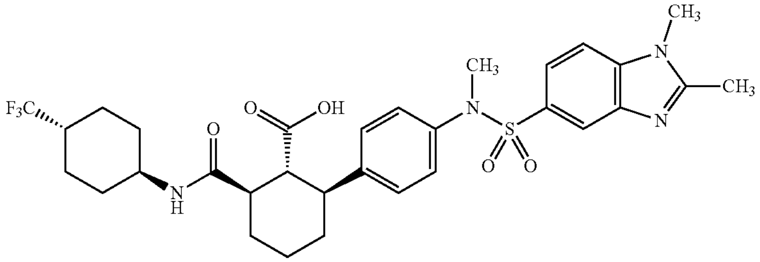 [SMILES: Cc1nc2cc(S(=O)(=O)N(C)c3ccc([C@H]4CCC[C@@H](C(=O)N[C@H]5CC[C@H](C(F)(F)F)CC5)[C@@H]4C(=O)O)cc3)ccc2n1C] |

TABLE 1-continued
| Ex. No. | Structure |
| --- | --- |
| 178 | 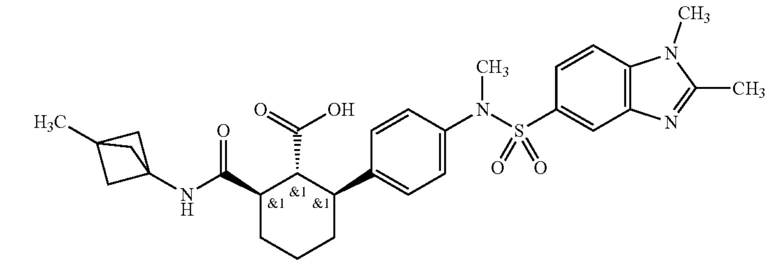 |
| 179 | 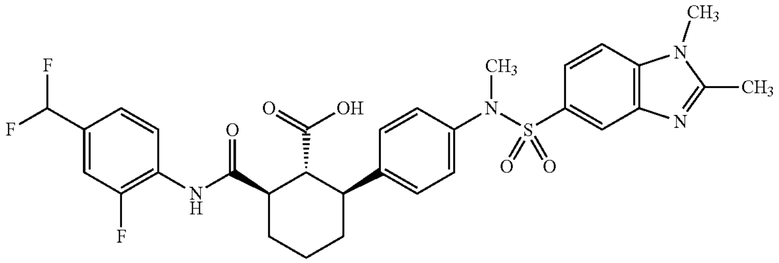 [SMILES: Cc1nc2cc(S(=O)(=O)N(C)c3ccc([C@H]4CCC[C@@H](C(=O)Nc5ccc(C(F)F)cc5F)[C@@H]4C(=O)O)cc3)ccc2n1C] |
| 180 | 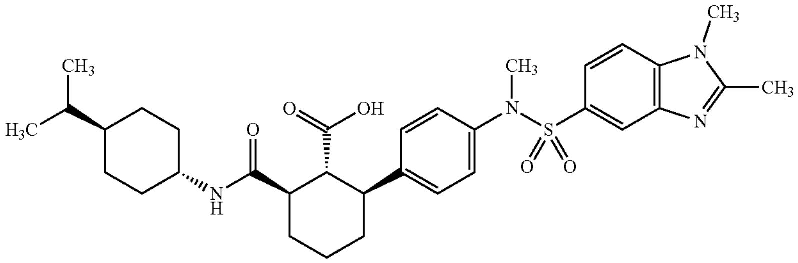 [SMILES: Cc1nc2cc(S(=O)(=O)N(C)c3ccc([C@H]4CCC[C@@H](C(=O)N[C@H]5CC[C@H](C(C)C)CC5)[C@@H]4C(=O)O)cc3)ccc2n1C] |
| 181 | 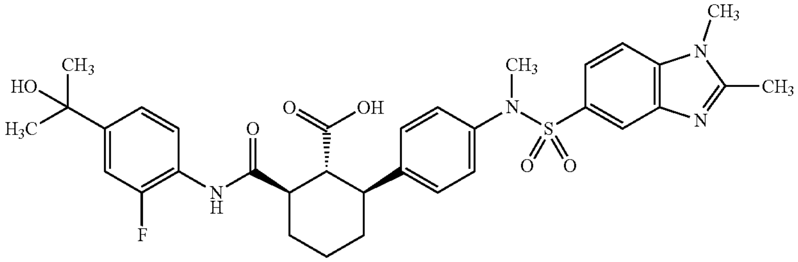 [SMILES: Cc1nc2cc(S(=O)(=O)N(C)c3ccc([C@H]4CCC[C@@H](C(=O)Nc5ccc(C(C)(C)O)cc5F)[C@@H]4C(=O)O)cc3)ccc2n1C] |
| 182 | 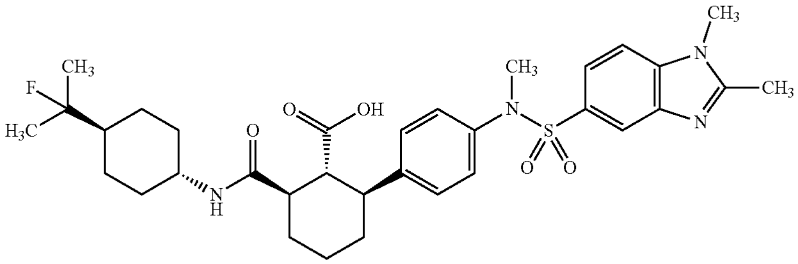 [SMILES: Cc1nc2cc(S(=O)(=O)N(C)c3ccc([C@H]4CCC[C@@H](C(=O)N[C@H]5CC[C@H](C(C)(C)F)CC5)[C@@H]4C(=O)O)cc3)ccc2n1C] |

TABLE 1-continued
| Ex. No. | Structure |
|---|---|
| 183 | 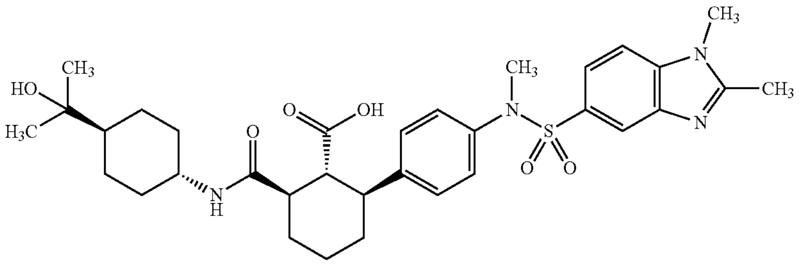 [SMILES: Cc1nc2cc(S(=O)(=O)N(C)c3ccc([C@H]4CCC[C@@H](C(=O)N[C@H]5CC[C@H](C(C)(C)O)CC5)[C@@H]4C(=O)O)cc3)ccc2n1C] |
| 184 | 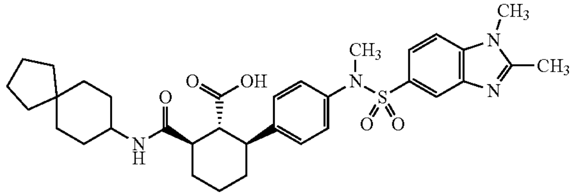 [SMILES: Cc1nc2cc(S(=O)(=O)N(C)c3ccc([C@H]4CCC[C@@H](C(=O)NC5CCC6(CCCC6)CC5)[C@@H]4C(=O)O)cc3)ccc2n1C] |
| 185 | 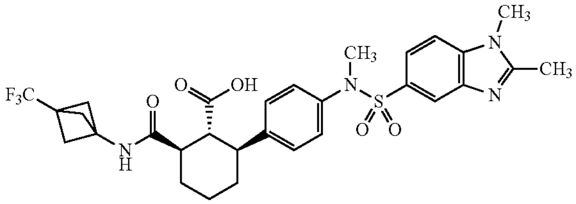 [SMILES: Cc1nc2cc(S(=O)(=O)N(C)c3ccc([C@H]4CCC[C@@H](C(=O)NC56CC(C(F)(F)F)(C5)C6)[C@@H]4C(=O)O)cc3)ccc2n1C] |
| 186 | 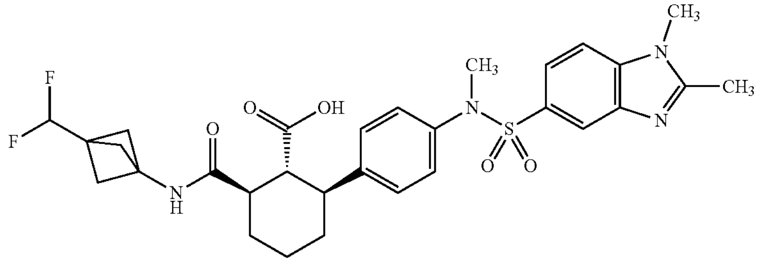 [SMILES: Cc1nc2cc(S(=O)(=O)N(C)c3ccc([C@H]4CCC[C@@H](C(=O)NC56CC(C(F)F)(C5)C6)[C@@H]4C(=O)O)cc3)ccc2n1C] |
| 187 | 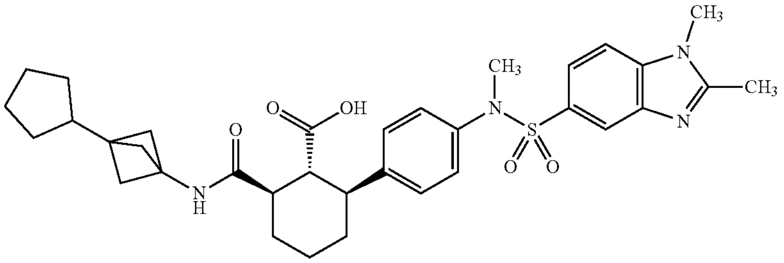 [SMILES: Cc1nc2cc(S(=O)(=O)N(C)c3ccc([C@H]4CCC[C@@H](C(=O)NC56CC(C7CCCC7)(C5)C6)[C@@H]4C(=O)O)cc3)ccc2n1C] |
| 188 | 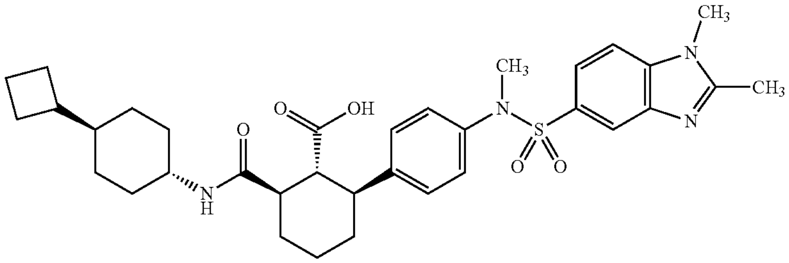 [SMILES: Cc1nc2cc(S(=O)(=O)N(C)c3ccc([C@H]4CCC[C@@H](C(=O)N[C@H]5CC[C@H](C6CCC6)CC5)[C@@H]4C(=O)O)cc3)ccc2n1C] |

TABLE 1-continued
| Ex. No. | Structure |
|---|---|
| 189 | 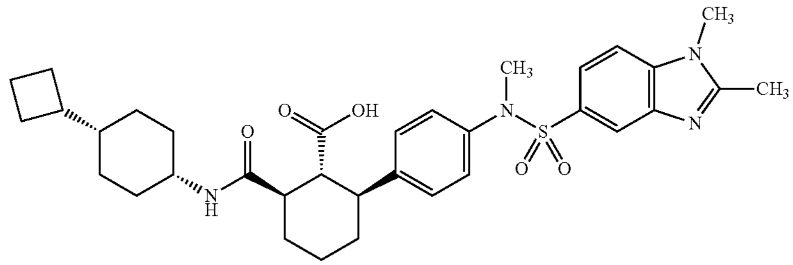 [SMILES: Cc1nc2cc(S(=O)(=O)N(C)c3ccc([C@H]4CCC[C@@H](C(=O)N[C@H]5CC[C@@H](C6CCC6)CC5)[C@@H]4C(=O)O)cc3)ccc2n1C] |
| 190 | 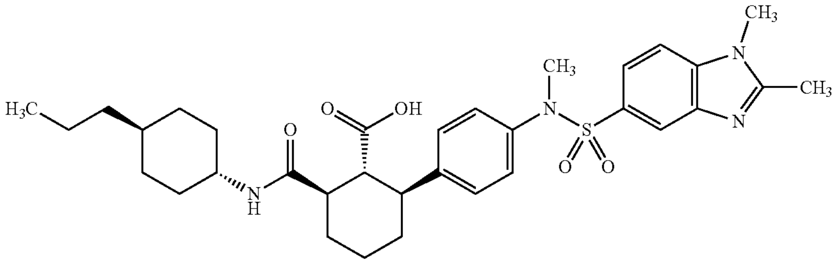 [SMILES: CCC[C@H]1CC[C@H](NC(=O)[C@@H]2CCC[C@H](c3ccc(N(C)S(=O)(=O)c4ccc5c(c4)nc(C)n5C)cc3)[C@H]2C(=O)O)CC1] |
| 191 | 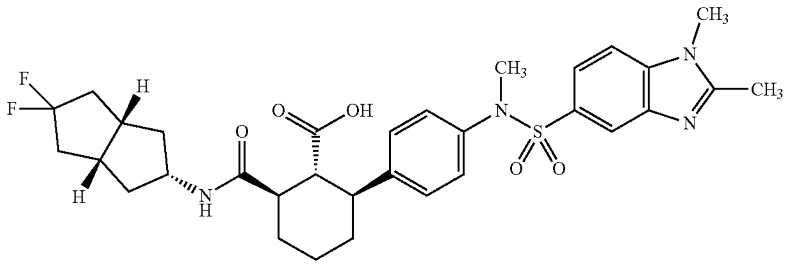 [SMILES: Cc1nc2cc(S(=O)(=O)N(C)c3ccc([C@H]4CCC[C@@H](C(=O)N[C@@H]5C[C@@H]6CC(F)(F)C[C@@H]6C5)[C@@H]4C(=O)O)cc3)ccc2n1C] |
| 192 | 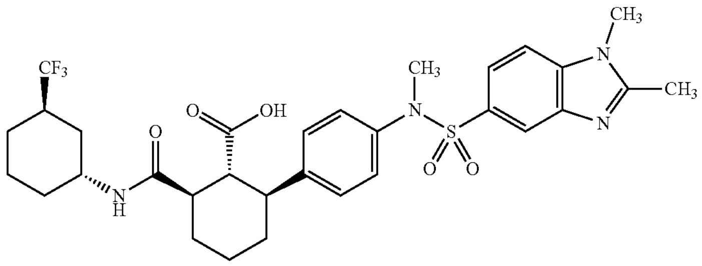 [SMILES: Cc1nc2cc(S(=O)(=O)N(C)c3ccc([C@H]4CCC[C@@H](C(=O)N[C@@H]5CCC[C@@H](C(F)(F)F)C5)[C@@H]4C(=O)O)cc3)ccc2n1C] |
| 193 | 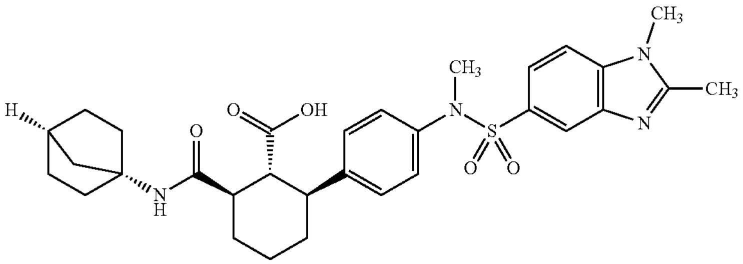 [SMILES: Cc1nc2cc(S(=O)(=O)N(C)c3ccc([C@H]4CCC[C@@H](C(=O)N[C@]56CC[C@H](CC5)C6)[C@@H]4C(=O)O)cc3)ccc2n1C] |

TABLE 1-continued
| Ex. No. | Structure |
|---|---|
| 194 | 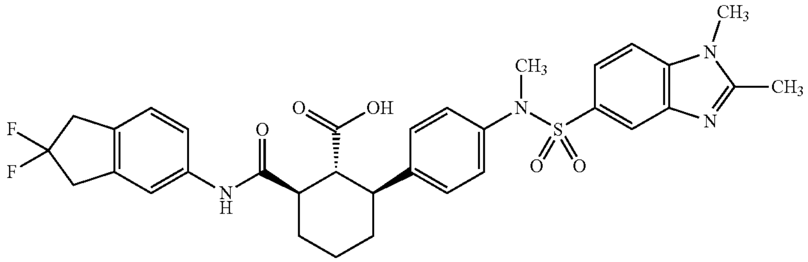 [SMILES: Cc1nc2cc(S(=O)(=O)N(C)c3ccc([C@H]4CCC[C@@H](C(=O)Nc5ccc6c(c5)CC(F)(F)C6)[C@@H]4C(=O)O)cc3)ccc2n1C] |
| 195 | 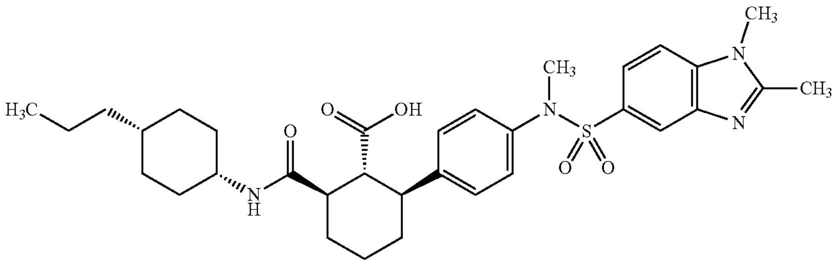 [SMILES: CCC[C@H]1CC[C@@H](NC(=O)[C@@H]2CCC[C@H](c3ccc(N(C)S(=O)(=O)c4ccc5c(c4)nc(C)n5C)cc3)[C@H]2C(=O)O)CC1] |
| 196 | 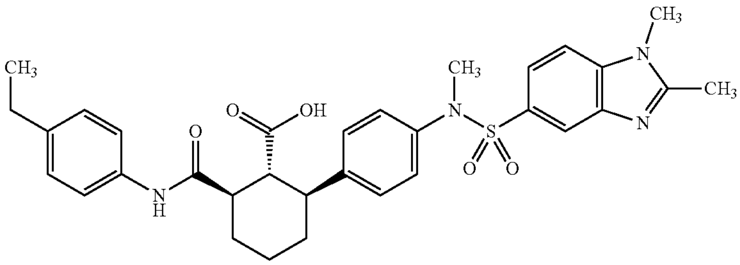 [SMILES: CCc1ccc(NC(=O)[C@@H]2CCC[C@H](c3ccc(N(C)S(=O)(=O)c4ccc5c(c4)nc(C)n5C)cc3)[C@H]2C(=O)O)cc1] |
| 197 | 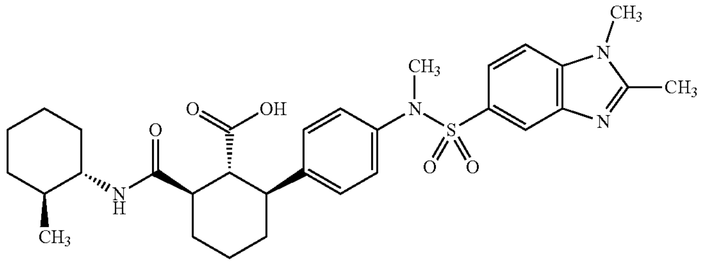 [SMILES: Cc1nc2cc(S(=O)(=O)N(C)c3ccc([C@H]4CCC[C@@H](C(=O)N[C@H]5CCCC[C@@H]5C)[C@@H]4C(=O)O)cc3)ccc2n1C] |
| 198 | 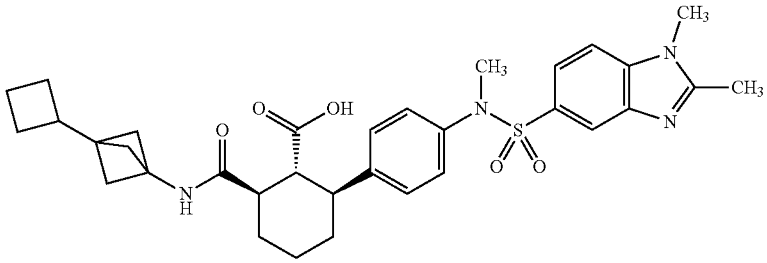 [SMILES: Cc1nc2cc(S(=O)(=O)N(C)c3ccc([C@H]4CCC[C@@H](C(=O)NC56CC(C7CCC7)(C5)C6)[C@@H]4C(=O)O)cc3)ccc2n1C] |

TABLE 1-continued
| Ex. No. | Structure |
| --- | --- |
| 199 | 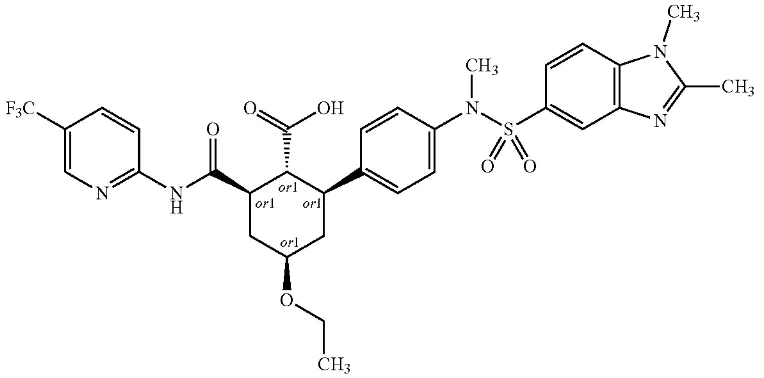 [SMILES: CCO[C@@H]1C[C@H](c2ccc(N(C)S(=O)(=O)c3ccc4c(c3)nc(C)n4C)cc2)[C@@H](C(=O)O)[C@H](C(=O)Nc2ccc(C(F)(F)F)cn2)C1] |
| 200 | 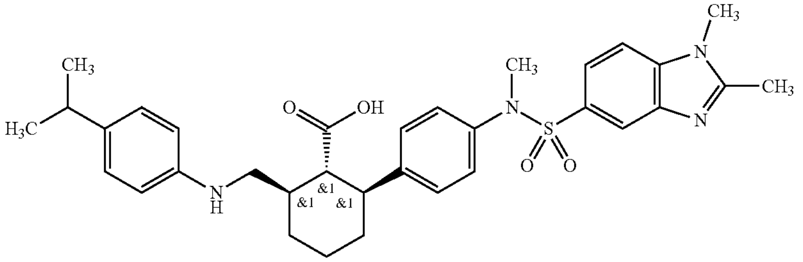 [SMILES: Cc1nc2cc(S(=O)(=O)N(C)c3ccc([C@H]4CCC[C@@H](CNc5ccc(C(C)C)cc5)[C@@H]4C(=O)O)cc3)ccc2n1C] |
| 201 | 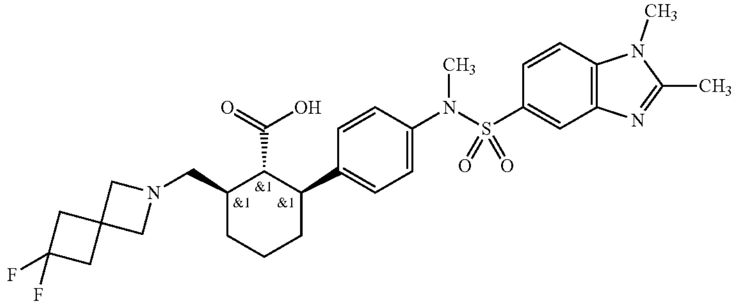 [SMILES: Cc1nc2cc(S(=O)(=O)N(C)c3ccc([C@H]4CCC[C@@H](CN5CC6(C5)CC(F)(F)C6)[C@@H]4C(=O)O)cc3)ccc2n1C] |
| 202 | 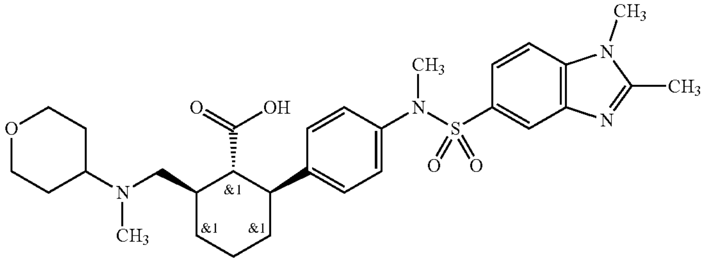 [SMILES: Cc1nc2cc(S(=O)(=O)N(C)c3ccc([C@H]4CCC[C@@H](CN(C)C5CCOCC5)[C@@H]4C(=O)O)cc3)ccc2n1C] |
| 203 | 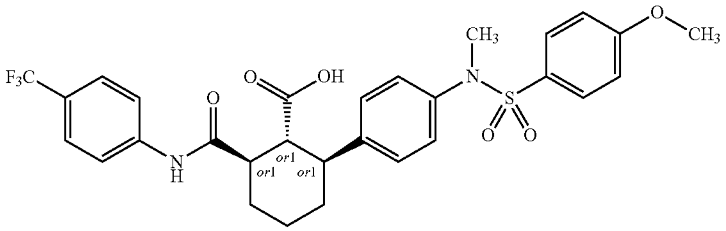 [SMILES: COc1ccc(S(=O)(=O)N(C)c2ccc([C@H]3CCC[C@@H](C(=O)Nc4ccc(C(F)(F)F)cc4)[C@@H]3C(=O)O)cc2)cc1] |

TABLE 1-continued
| Ex. No. | Structure |
|---|---|
| 204 | 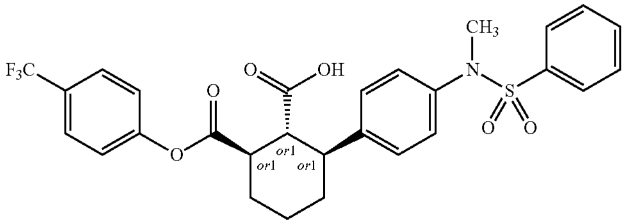 [SMILES: CN(c1ccc([C@H]2CCC[C@@H](C(=O)Oc3ccc(C(F)(F)F)cc3)[C@@H]2C(=O)O)cc1)S(=O)(=O)c1ccccc1] |
| 205 | 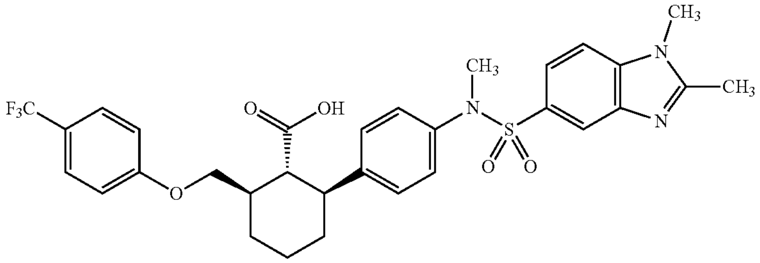 [SMILES: Cc1nc2cc(S(=O)(=O)N(C)c3ccc([C@H]4CCC[C@@H](COc5ccc(C(F)(F)F)cc5)[C@@H]4C(=O)O)cc3)ccc2n1C] |
| 206 | 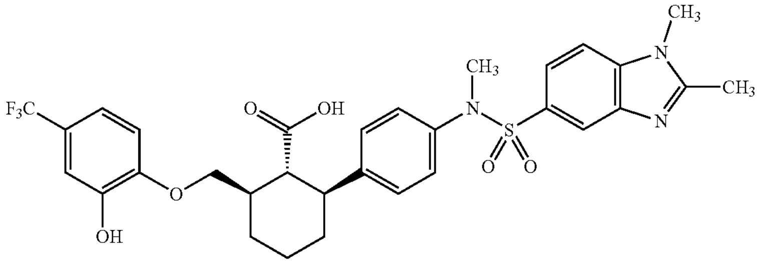 [SMILES: Cc1nc2cc(S(=O)(=O)N(C)c3ccc([C@H]4CCC[C@@H](COc5ccc(C(F)(F)F)cc5O)[C@@H]4C(=O)O)cc3)ccc2n1C] |
| 207 | 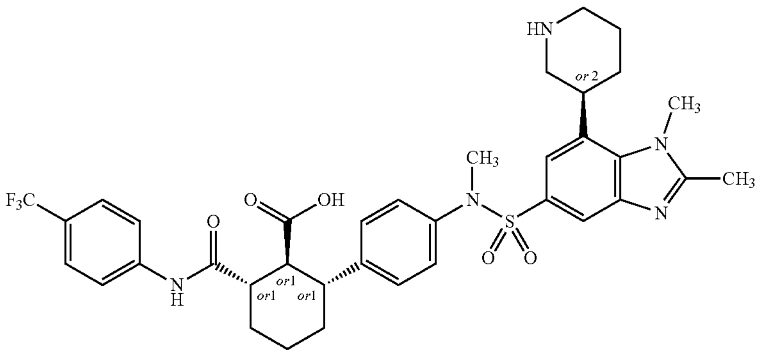 [SMILES: Cc1nc2cc(S(=O)(=O)N(C)c3ccc([C@@H]4CCC[C@H](C(=O)Nc5ccc(C(F)(F)F)cc5)[C@H]4C(=O)O)cc3)cc([C@@H]3CCCNC3)c2n1C] |
| 208 | 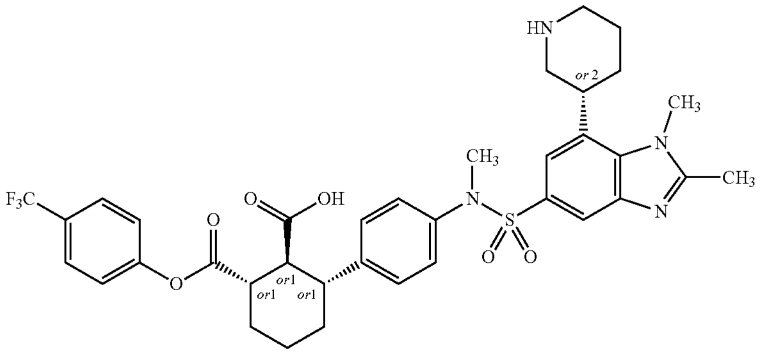 [SMILES: Cc1nc2cc(S(=O)(=O)N(C)c3ccc([C@@H]4CCC[C@H](C(=O)Oc5ccc(C(F)(F)F)cc5)[C@H]4C(=O)O)cc3)cc([C@H]3CCCNC3)c2n1C] |

TABLE 1-continued
| Ex. No. | Structure |
| --- | --- |
| 209 | 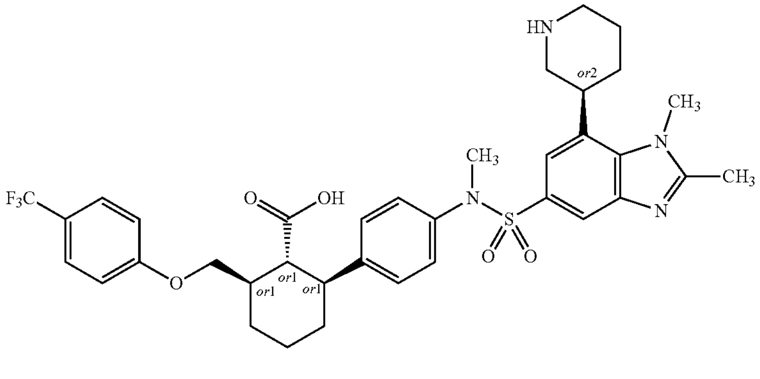 [SMILES: Cc1nc2cc(S(=O)(=O)N(C)c3ccc([C@H]4CCC[C@@H](COc5ccc(C(F)(F)F)cc5)[C@@H]4C(=O)O)cc3)cc([C@@H]3CCCNC3)c2n1C] |
| 210 | 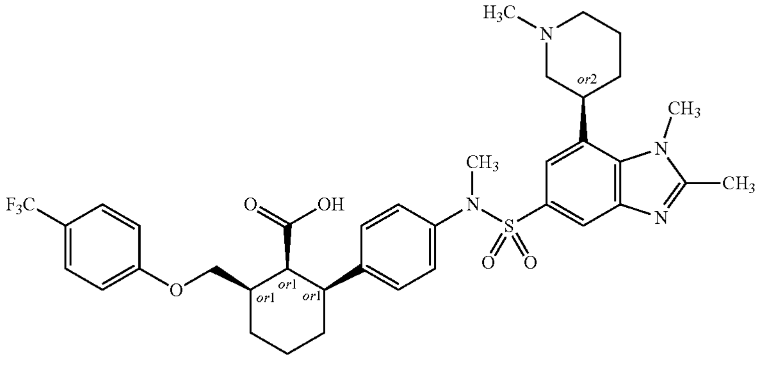 [SMILES: Cc1nc2cc(S(=O)(=O)N(C)c3ccc([C@H]4CCC[C@@H](COc5ccc(C(F)(F)F)cc5)[C@H]4C(=O)O)cc3)cc([C@@H]3CCCN(C)C3)c2n1C] |
| 211 | 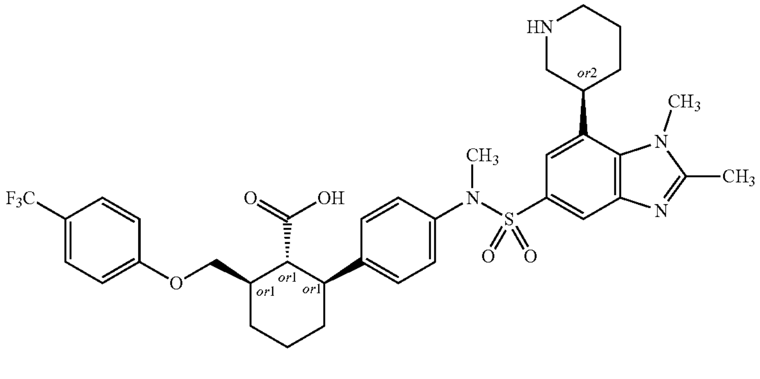 [SMILES: Cc1nc2cc(S(=O)(=O)N(C)c3ccc([C@H]4CCC[C@@H](COc5ccc(C(F)(F)F)cc5)[C@@H]4C(=O)O)cc3)cc([C@@H]3CCCNC3)c2n1C] |
| 212 | 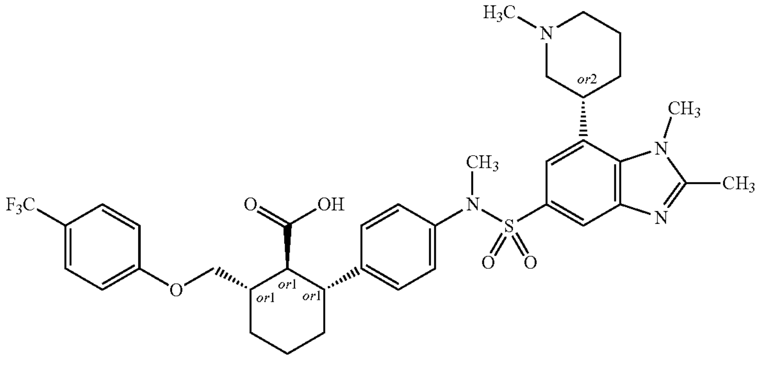 [SMILES: Cc1nc2cc(S(=O)(=O)N(C)c3ccc([C@@H]4CCC[C@H](COc5ccc(C(F)(F)F)cc5)[C@H]4C(=O)O)cc3)cc([C@H]3CCCN(C)C3)c2n1C] |

TABLE 1-continued
| Ex. No. | Structure |
| --- | --- |
| 213 | 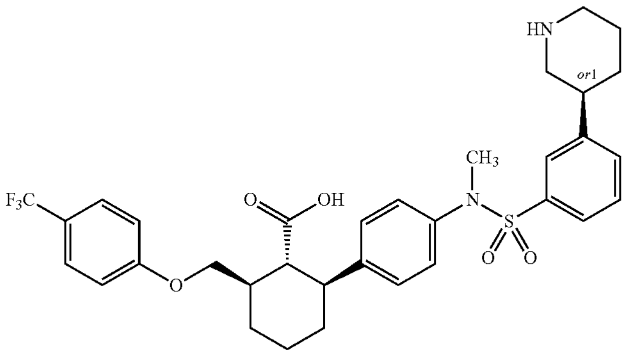 [SMILES: CN(c1ccc([C@H]2CCC[C@@H](COc3ccc(C(F)(F)F)cc3)[C@@H]2C(=O)O)cc1)S(=O)(=O)c1cccc([C@@H]2CCCNC2)c1] |
| 214 | 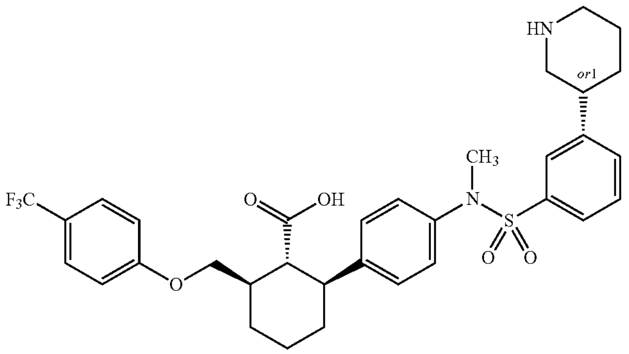 |
| 215 | 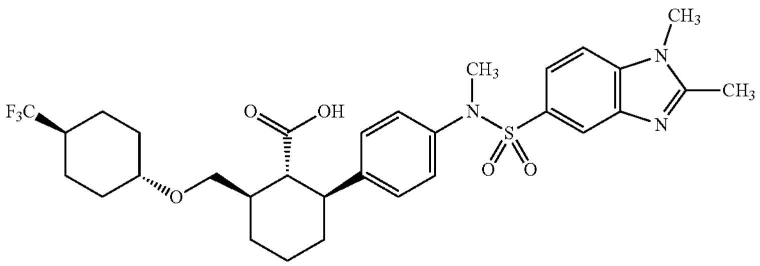 [SMILES: Cc1nc2cc(S(=O)(=O)N(C)c3ccc([C@H]4CCC[C@@H](CO[C@H]5CC[C@H](C(F)(F)F)CC5)[C@@H]4C(=O)O)cc3)ccc2n1C] |
| 216 | 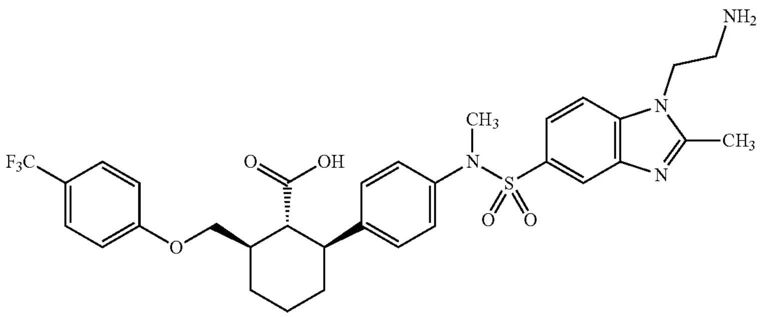 [SMILES: Cc1nc2cc(S(=O)(=O)N(C)c3ccc([C@H]4CCC[C@@H](COc5ccc(C(F)(F)F)cc5)[C@@H]4C(=O)O)cc3)ccc2n1CCN] |

TABLE 1-continued
| Ex. No. | Structure |
| --- | --- |
| 217 | 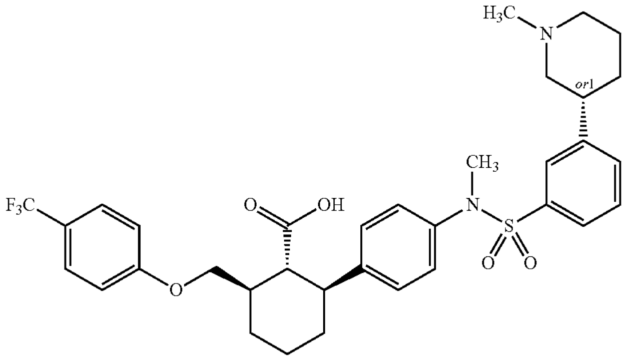 [SMILES: CN1CCC[C@H](c2cccc(S(=O)(=O)N(C)c3ccc([C@H]4CCC[C@@H](COc5ccc(C(F)(F)F)cc5)[C@@H]4C(=O)O)cc3)c2)C1] |
| 218 | 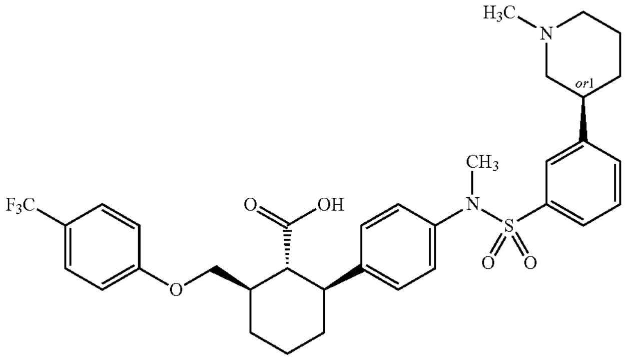 [SMILES: CN1CCC[C@@H](c2cccc(S(=O)(=O)N(C)c3ccc([C@H]4CCC[C@@H](COc5ccc(C(F)(F)F)cc5)[C@@H]4C(=O)O)cc3)c2)C1] |
| 219 | 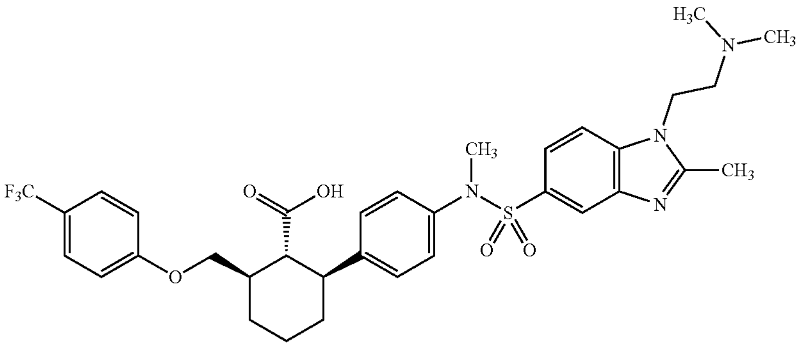 [SMILES: Cc1nc2cc(S(=O)(=O)N(C)c3ccc([C@H]4CCC[C@@H](COc5ccc(C(F)(F)F)cc5)[C@@H]4C(=O)O)cc3)ccc2n1CCN(C)C] |
| 220 | 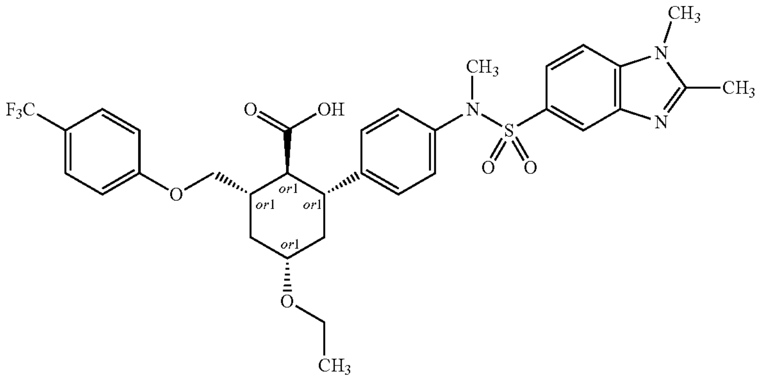 [SMILES: CCO[C@@H]1C[C@H](COc2ccc(C(F)(F)F)cc2)[C@@H](C(=O)O)[C@H](c2ccc(N(C)S(=O)(=O)c3ccc4c(c3)nc(C)n4C)cc2)C1] |

TABLE 1-continued
| Ex. No. | Structure |
|---|---|
| 221 | 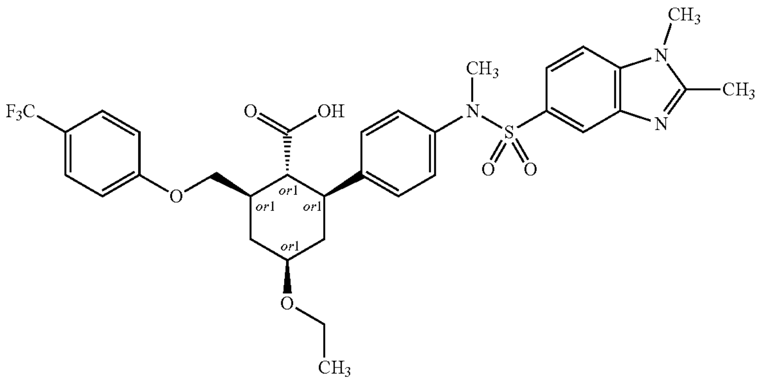 [SMILES: CCO[C@H]1C[C@@H](COc2ccc(C(F)(F)F)cc2)[C@H](C(=O)O)[C@@H](c2ccc(N(C)S(=O)(=O)c3ccc4c(c3)nc(C)n4C)cc2)C1] |
| 222 | 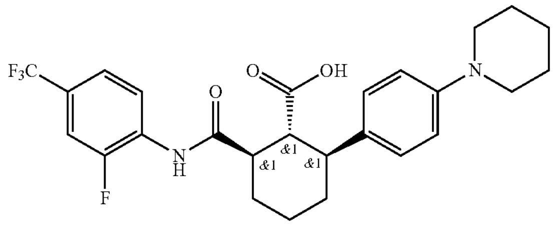 [SMILES: O=C(O)[C@@H]1[C@@H](c2ccc(N3CCCCC3)cc2)CCC[C@H]1C(=O)Nc1ccc(C(F)(F)F)cc1F] |
| 223 | 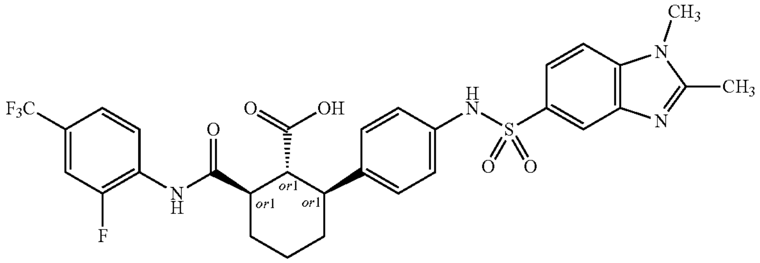 [SMILES: Cc1nc2cc(S(=O)(=O)Nc3ccc([C@H]4CCC[C@@H](C(=O)Nc5ccc(C(F)(F)F)cc5F)[C@@H]4C(=O)O)cc3)ccc2n1C] |
| 224 | 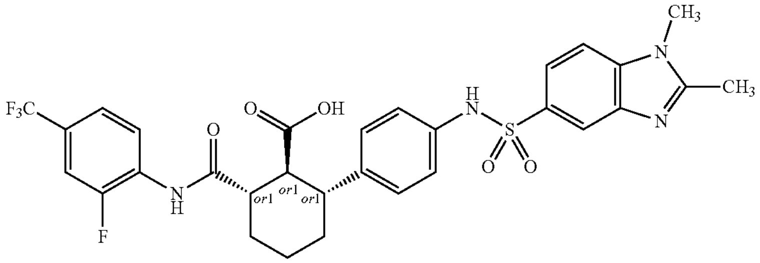 [SMILES: Cc1nc2cc(S(=O)(=O)Nc3ccc([C@@H]4CCC[C@H](C(=O)Nc5ccc(C(F)(F)F)cc5F)[C@H]4C(=O)O)cc3)ccc2n1C] |
| 225 | 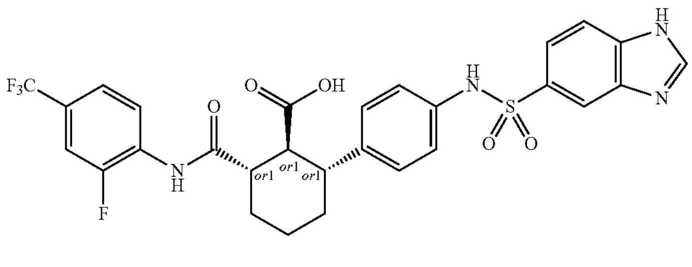 [SMILES: O=C(O)[C@@H]1[C@@H](C(=O)Nc2ccc(C(F)(F)F)cc2F)CCC[C@H]1c1ccc(NS(=O)(=O)c2ccc3[nH]cnc3c2)cc1] |

TABLE 1-continued
| Ex. No. | Structure |
| --- | --- |
| 227 | 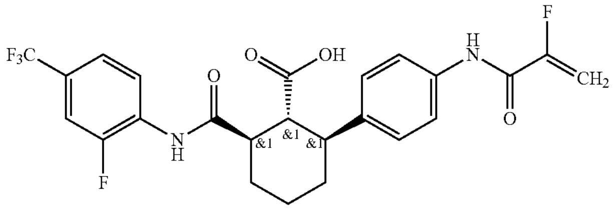 [SMILES: C=C(F)C(=O)Nc1ccc([C@H]2CCC[C@@H](C(=O)Nc3ccc(C(F)(F)F)cc3F)[C@@H]2C(=O)O)cc1] |
| 228 | 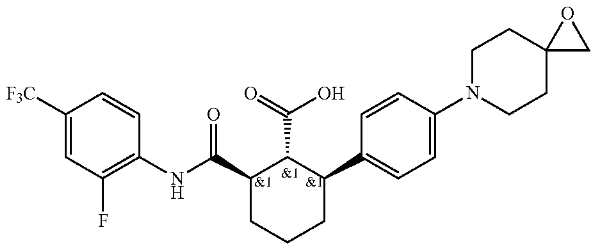 [SMILES: O=C(O)[C@@H]1[C@@H](c2ccc(N3CCC4(CC3)CO4)cc2)CCC[C@H]1C(=O)Nc1ccc(C(F)(F)F)cc1F] |
| 229 | 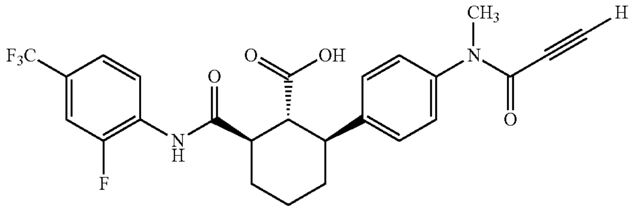 [SMILES: C#CC(=O)N(C)c1ccc([C@H]2CCC[C@@H](C(=O)Nc3ccc(C(F)(F)F)cc3F)[C@@H]2C(=O)O)cc1] |
| 230 | 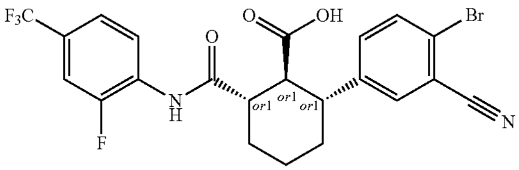 [SMILES: N#Cc1cc([C@@H]2CCC[C@H](C(=O)Nc3ccc(C(F)(F)F)cc3F)[C@H]2C(=O)O)ccc1Br] |
| 231 | 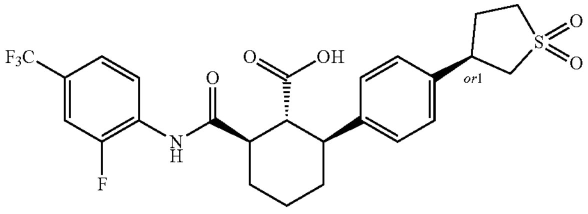 [SMILES: O=C(O)[C@@H]1[C@@H](c2ccc([C@H]3CCS(=O)(=O)C3)cc2)CCC[C@H]1C(=O)Nc1ccc(C(F)(F)F)cc1F] |
| 232 | 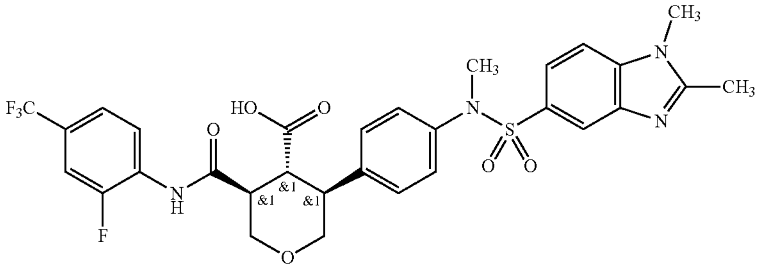 [SMILES: Cc1nc2cc(S(=O)(=O)N(C)c3ccc([C@H]4COC[C@@H](C(=O)Nc5ccc(C(F)(F)F)cc5F)[C@@H]4C(=O)O)cc3)ccc2n1C] |

TABLE 1-continued
| Ex. No. | Structure |
| --- | --- |
| 233 | 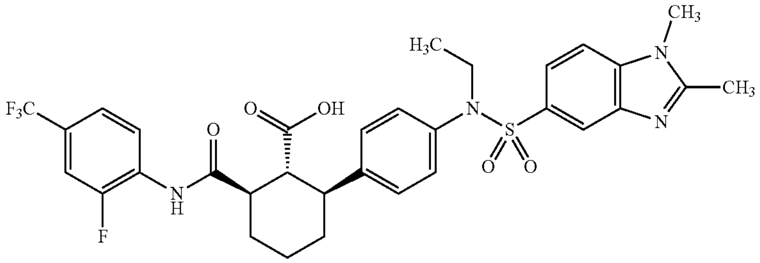 [SMILES: CCN(c1ccc([C@H]2CCC[C@@H](C(=O)Nc3ccc(C(F)(F)F)cc3F)[C@@H]2C(=O)O)cc1)S(=O)(=O)c1ccc2c(c1)nc(C)n2C] |
| 234 | 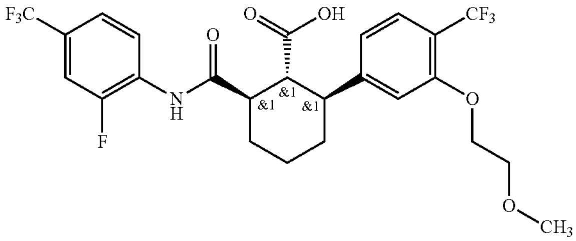 [SMILES: COCCOc1cc([C@H]2CCC[C@@H](C(=O)Nc3ccc(C(F)(F)F)cc3F)[C@@H]2C(=O)O)ccc1C(F)(F)F] |
| 235 | 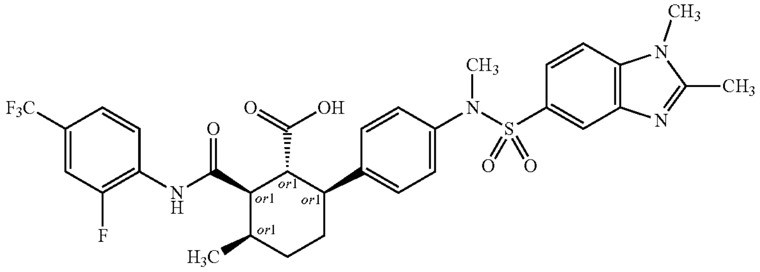 [SMILES: Cc1nc2cc(S(=O)(=O)N(C)c3ccc([C@H]4CC[C@@H](C)[C@@H](C(=O)Nc5ccc(C(F)(F)F)cc5F)[C@@H]4C(=O)O)cc3)ccc2n1C] |
| 236 | 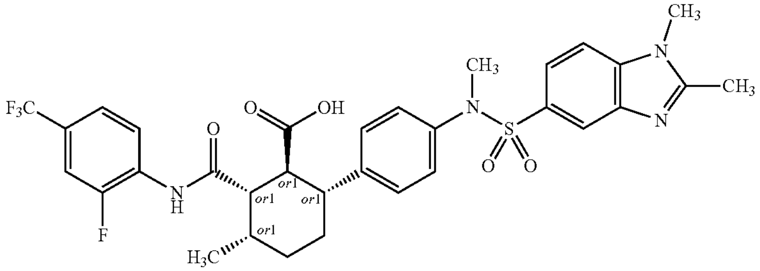 [SMILES: Cc1nc2cc(S(=O)(=O)N(C)c3ccc([C@@H]4CC[C@H](C)[C@H](C(=O)Nc5ccc(C(F)(F)F)cc5F)[C@H]4C(=O)O)cc3)ccc2n1C] |
| 237 | 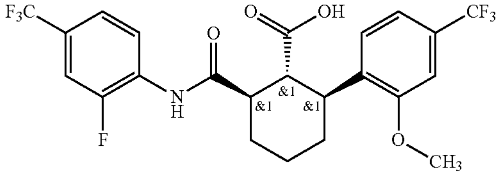 [SMILES: COc1cc(C(F)(F)F)ccc1[C@H]1CCC[C@@H](C(=O)Nc2ccc(C(F)(F)F)cc2F)[C@@H]1C(=O)O] |
| 238 | 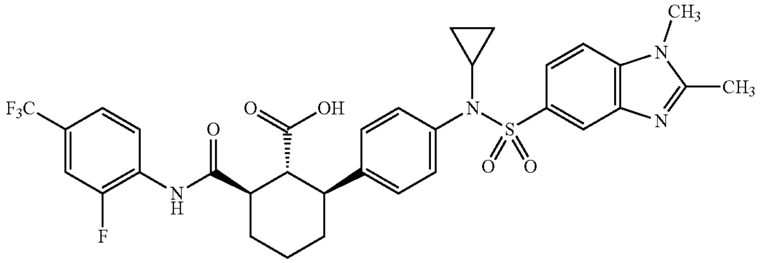 [SMILES: Cc1nc2cc(S(=O)(=O)N(c3ccc([C@H]4CCC[C@@H](C(=O)Nc5ccc(C(F)(F)F)cc5F)[C@@H]4C(=O)O)cc3)C3CC3)ccc2n1C] |

TABLE 1-continued
| Ex. No. | Structure |
|---|---|
| 239 | 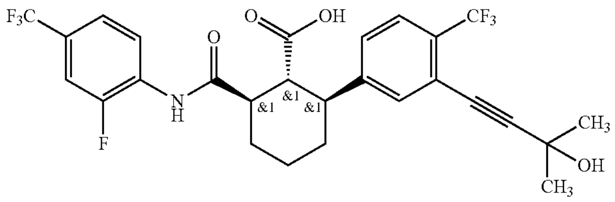 [SMILES: CC(C)(O)C#Cc1cc([C@H]2CCC[C@@H](C(=O)Nc3ccc(C(F)(F)F)cc3F)[C@@H]2C(=O)O)ccc1C(F)(F)F] |
| 240 | 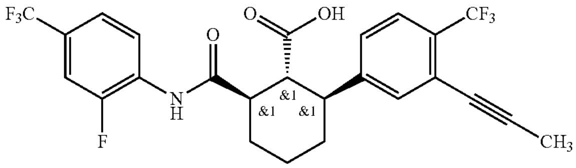 [SMILES: CC#Cc1cc([C@H]2CCC[C@@H](C(=O)Nc3ccc(C(F)(F)F)cc3F)[C@@H]2C(=O)O)ccc1C(F)(F)F] |
| 241 | 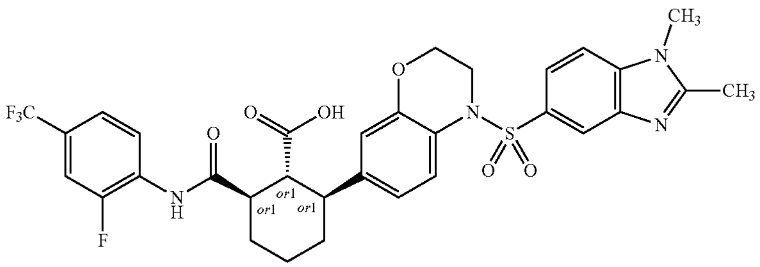 [SMILES: Cc1nc2cc(S(=O)(=O)N3CCOc4cc([C@H]5CCC[C@@H](C(=O)Nc6ccc(C(F)(F)F)cc6F)[C@@H]5C(=O)O)ccc43)ccc2n1C] |
| 242 | 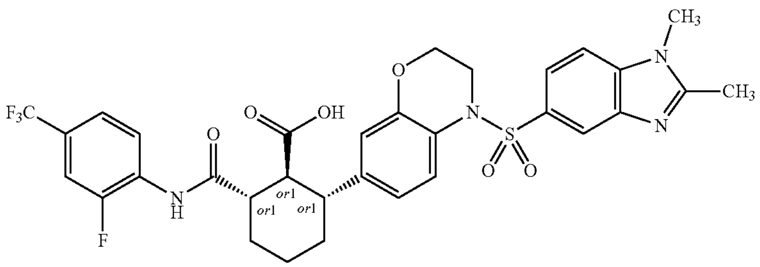 [SMILES: Cc1nc2cc(S(=O)(=O)N3CCOc4cc([C@@H]5CCC[C@H](C(=O)Nc6ccc(C(F)(F)F)cc6F)[C@H]5C(=O)O)ccc43)ccc2n1C] |
| 243 | 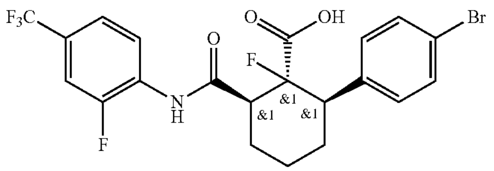 [SMILES: O=C(Nc1ccc(C(F)(F)F)cc1F)[C@@H]1CCC[C@H](c2ccc(Br)cc2)[C@@]1(F)C(=O)O] |
| 244 | 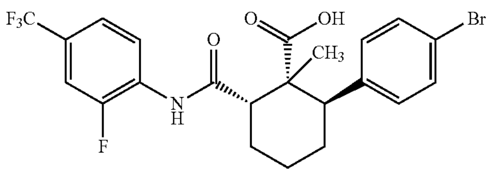 [SMILES: C[C@]1(C(=O)O)[C@@H](C(=O)Nc2ccc(C(F)(F)F)cc2F)CCC[C@@H]1c1ccc(Br)cc1] |
| 245 | 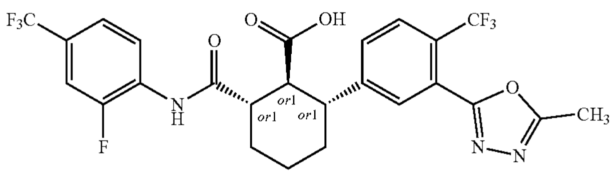 [SMILES: Cc1nnc(-c2cc([C@@H]3CCC[C@H](C(=O)Nc4ccc(C(F)(F)F)cc4F)[C@H]3C(=O)O)ccc2C(F)(F)F)o1] |

TABLE 1-continued
| Ex. No. | Structure |
| --- | --- |
| 246 | 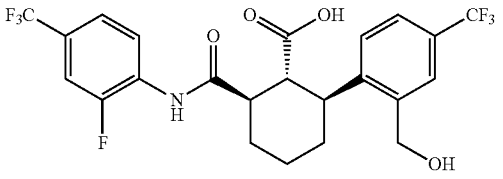 [SMILES: O=C(O)[C@@H]1[C@@H](c2ccc(C(F)(F)F)cc2CO)CCC[C@H]1C(=O)Nc1ccc(C(F)(F)F)cc1F] |
| 246 | 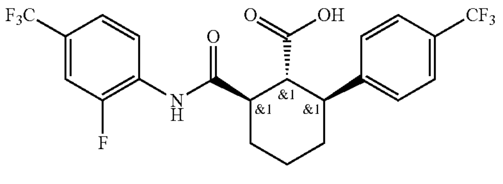 [SMILES: O=C(O)[C@@H]1[C@@H](c2ccc(C(F)(F)F)cc2)CCC[C@H]1C(=O)Nc1ccc(C(F)(F)F)cc1F] |
| 248 | 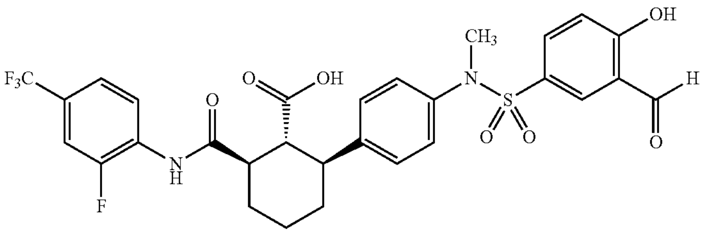 [SMILES: CN(c1ccc([C@H]2CCC[C@@H](C(=O)Nc3ccc(C(F)(F)F)cc3F)[C@@H]2C(=O)O)cc1)S(=O)(=O)c1ccc(O)c(C=O)c1] |
| 249 | 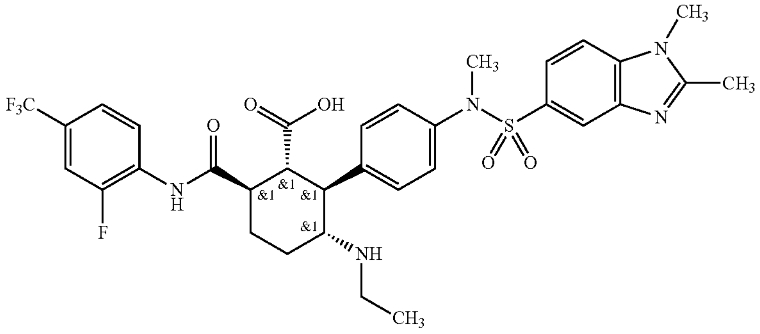 [SMILES: CCN[C@@H]1CC[C@@H](C(=O)Nc2ccc(C(F)(F)F)cc2F)[C@H](C(=O)O)[C@H]1c1ccc(N(C)S(=O)(=O)c2ccc3c(c2)nc(C)n3C)cc1] |
| 250 | 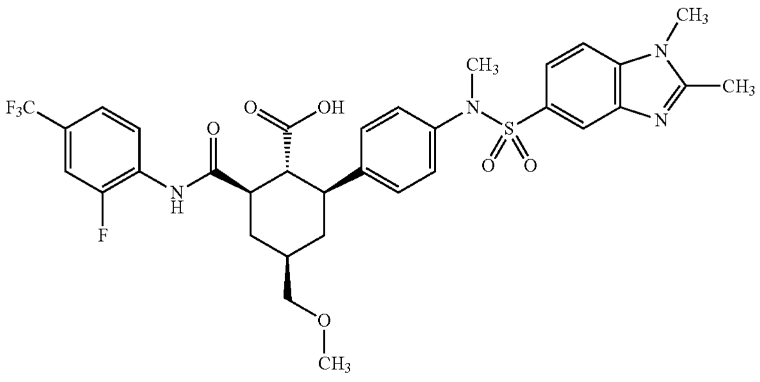 [SMILES: COC[C@@H]1C[C@H](c2ccc(N(C)S(=O)(=O)c3ccc4c(c3)nc(C)n4C)cc2)[C@@H](C(=O)O)[C@H](C(=O)Nc2ccc(C(F)(F)F)cc2F)C1] |

TABLE 1-continued
| Ex. No. | Structure |
|---|---|
| 251 | 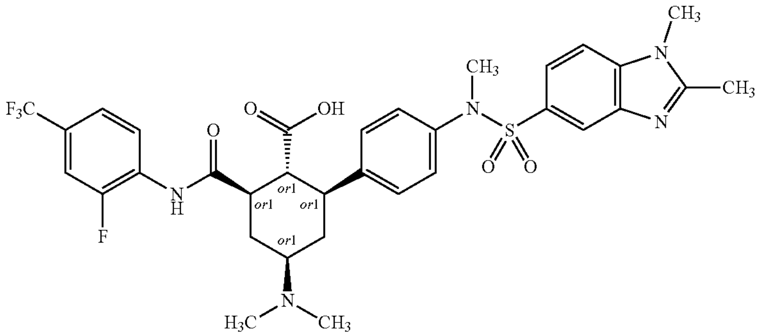 [SMILES: Cc1nc2cc(S(=O)(=O)N(C)c3ccc([C@H]4C[C@@H](N(C)C)C[C@@H](C(=O)Nc5ccc(C(F)(F)F)cc5F)[C@@H]4C(=O)O)cc3)ccc2n1C] |
| 252 | 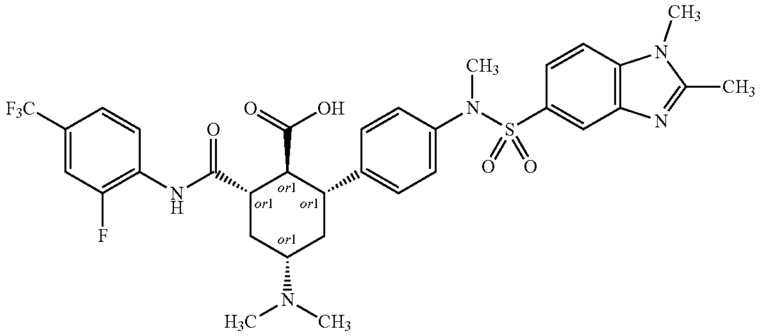 [SMILES: Cc1nc2cc(S(=O)(=O)N(C)c3ccc([C@@H]4C[C@H](N(C)C)C[C@H](C(=O)Nc5ccc(C(F)(F)F)cc5F)[C@H]4C(=O)O)cc3)ccc2n1C] |
| 253 | 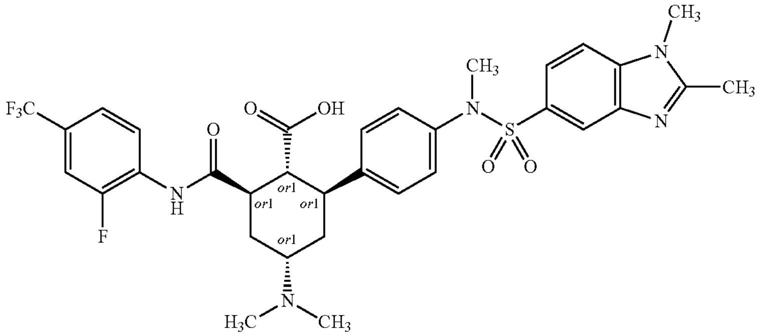 [SMILES: Cc1nc2cc(S(=O)(=O)N(C)c3ccc([C@H]4C[C@H](N(C)C)C[C@@H](C(=O)Nc5ccc(C(F)(F)F)cc5F)[C@@H]4C(=O)O)cc3)ccc2n1C] |
| 254 | 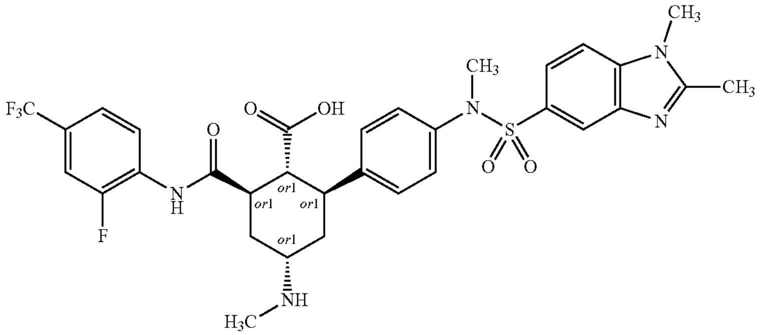 [SMILES: CN[C@H]1C[C@H](c2ccc(N(C)S(=O)(=O)c3ccc4c(c3)nc(C)n4C)cc2)[C@@H](C(=O)O)[C@H](C(=O)Nc2ccc(C(F)(F)F)cc2F)C1] |

TABLE 1-continued
| Ex. No. | Structure |
| --- | --- |
| 255 | 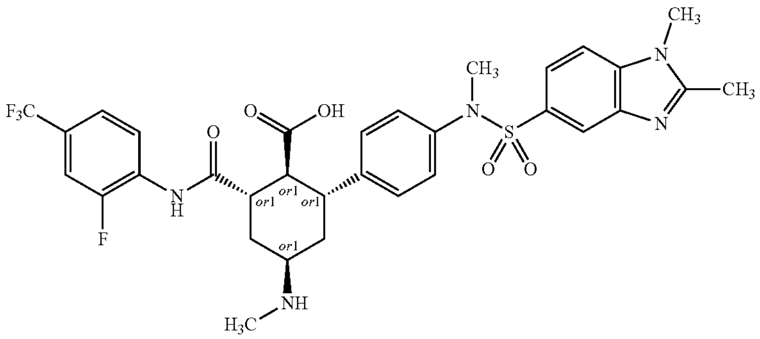 [SMILES: CN[C@H]1C[C@H](C(=O)Nc2ccc(C(F)(F)F)cc2F)[C@@H](C(=O)O)[C@H](c2ccc(N(C)S(=O)(=O)c3ccc4c(c3)nc(C)n4C)cc2)C1] |
| 256 | 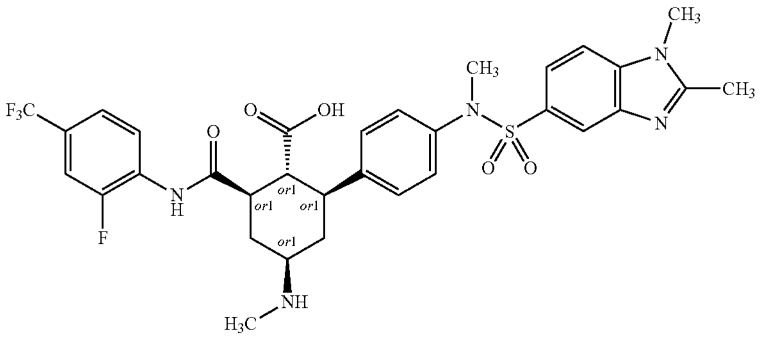 [SMILES: CN[C@@H]1C[C@H](c2ccc(N(C)S(=O)(=O)c3ccc4c(c3)nc(C)n4C)cc2)[C@@H](C(=O)O)[C@H](C(=O)Nc2ccc(C(F)(F)F)cc2F)C1] |
| 257 | 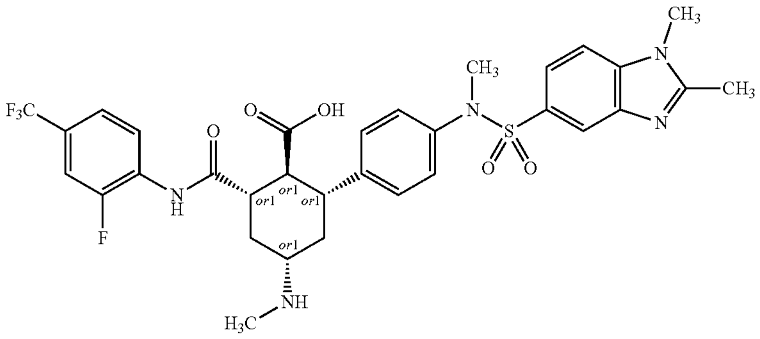 [SMILES: CN[C@@H]1C[C@H](C(=O)Nc2ccc(C(F)(F)F)cc2F)[C@@H](C(=O)O)[C@H](c2ccc(N(C)S(=O)(=O)c3ccc4c(c3)nc(C)n4C)cc2)C1] |
| 258 | 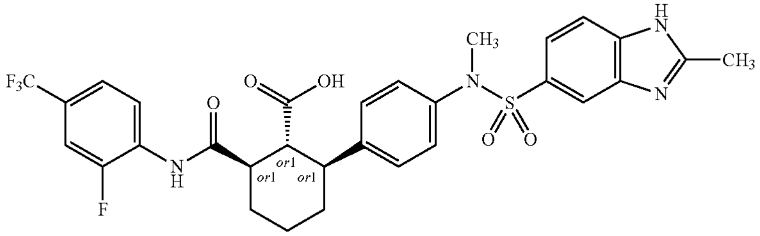 [SMILES: Cc1nc2cc(S(=O)(=O)N(C)c3ccc([C@H]4CCC[C@@H](C(=O)Nc5ccc(C(F)(F)F)cc5F)[C@@H]4C(=O)O)cc3)ccc2[nH]1] ISOMER 1 |

TABLE 1-continued
| Ex. No. | Structure |
|---|---|
| 259 | 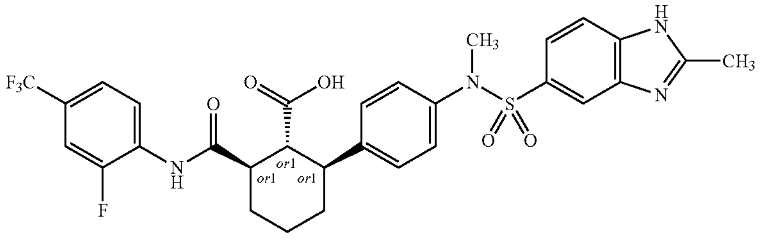 [SMILES: Cc1nc2cc(S(=O)(=O)N(C)c3ccc([C@H]4CCC[C@@H](C(=O)Nc5ccc(C(F)(F)F)cc5F)[C@@H]4C(=O)O)cc3)ccc2[nH]1] ISOMER 2 |
| 260 | 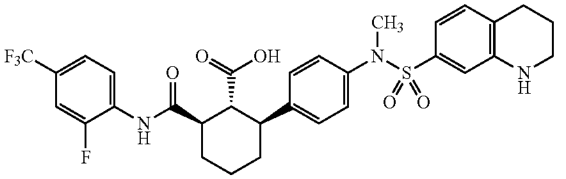 [SMILES: CN(c1ccc([C@H]2CCC[C@@H](C(=O)Nc3ccc(C(F)(F)F)cc3F)[C@@H]2C(=O)O)cc1)S(=O)(=O)c1ccc2c(c1)NCCC2] |
| 261 | 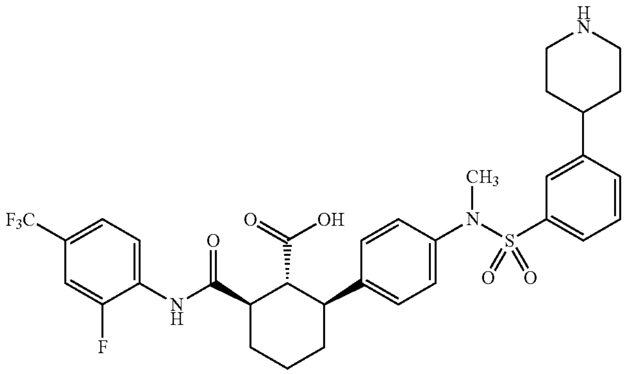 [SMILES: CN(c1ccc([C@H]2CCC[C@@H](C(=O)Nc3ccc(C(F)(F)F)cc3F)[C@@H]2C(=O)O)cc1)S(=O)(=O)c1cccc(C2CCNCC2)c1] |
| 262 | 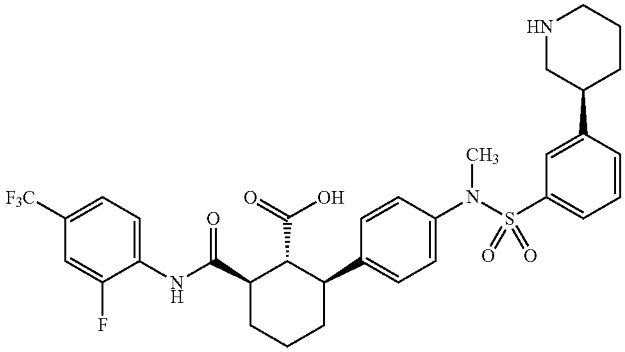 [SMILES: CN(c1ccc([C@H]2CCC[C@@H](C(=O)Nc3ccc(C(F)(F)F)cc3F)[C@@H]2C(=O)O)cc1)S(=O)(=O)c1cccc([C@@H]2CCCNC2)c1] |
| 263 | 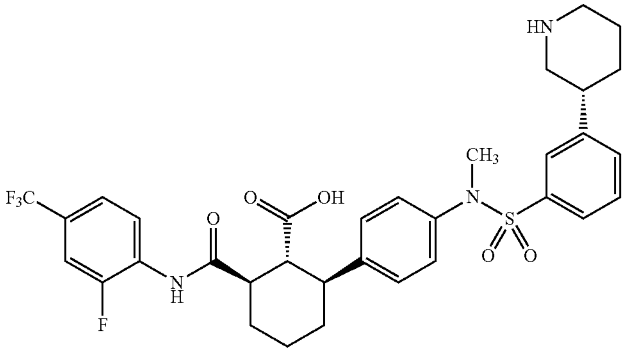 [SMILES: CN(c1ccc([C@H]2CCC[C@@H](C(=O)Nc3ccc(C(F)(F)F)cc3F)[C@@H]2C(=O)O)cc1)S(=O)(=O)c1cccc([C@H]2CCCNC2)c1] |

TABLE 1-continued
| Ex. No. | Structure |
|---|---|
| 264 | 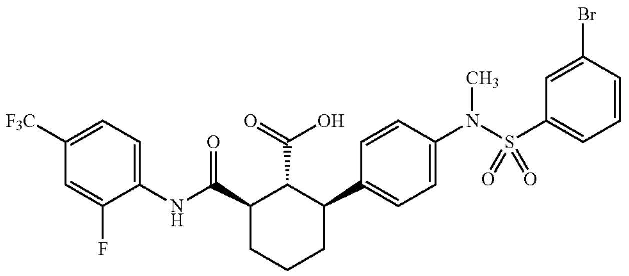 [SMILES: CN(c1ccc([C@H]2CCC[C@@H](C(=O)Nc3ccc(C(F)(F)F)cc3F)[C@@H]2C(=O)O)cc1)S(=O)(=O)c1cccc(Br)c1] |
| 265 | 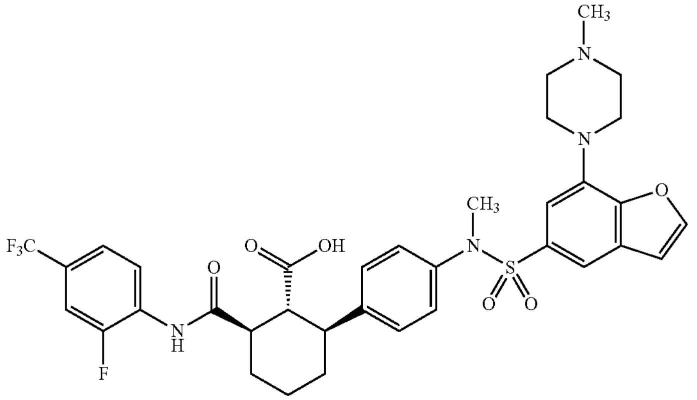 [SMILES: CN1CCN(c2cc(S(=O)(=O)N(C)c3ccc([C@H]4CCC[C@@H](C(=O)Nc5ccc(C(F)(F)F)cc5F)[C@@H]4C(=O)O)cc3)cc3ccoc23)CC1] |
| 266 | 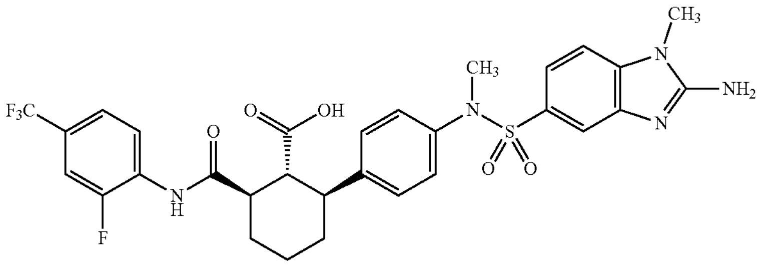 [SMILES: CN(c1ccc([C@H]2CCC[C@@H](C(=O)Nc3ccc(C(F)(F)F)cc3F)[C@@H]2C(=O)O)cc1)S(=O)(=O)c1ccc2c(c1)nc(N)n2C] |
| 267 | 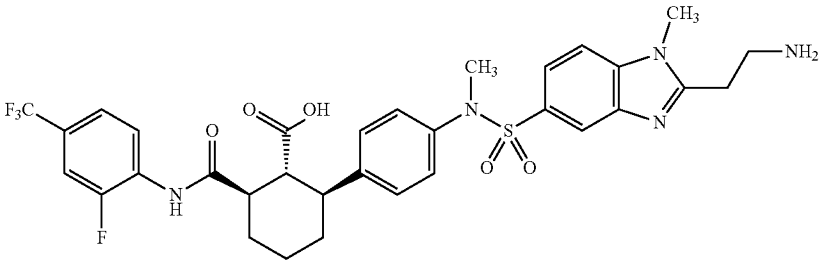 [SMILES: CN(c1ccc([C@H]2CCC[C@@H](C(=O)Nc3ccc(C(F)(F)F)cc3F)[C@@H]2C(=O)O)cc1)S(=O)(=O)c1ccc2c(c1)nc(CCN)n2C] |

TABLE 1-continued
| Ex. No. | Structure |
|---|---|
| 268 | 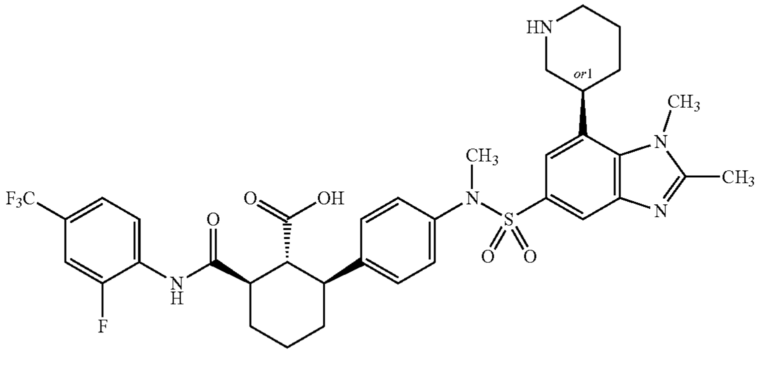 ISOMER 1 |
| 269 | 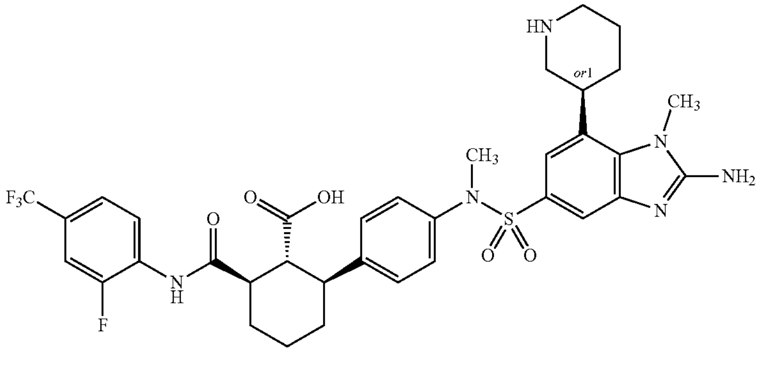 [SMILES: CN(c1ccc([C@H]2CCC[C@@H](C(=O)Nc3ccc(C(F)(F)F)cc3F)[C@@H]2C(=O)O)cc1)S(=O)(=O)c1cc([C@@H]2CCCNC2)c2c(c1)nc(N)n2C] ISOMER 2 |
| 270 | 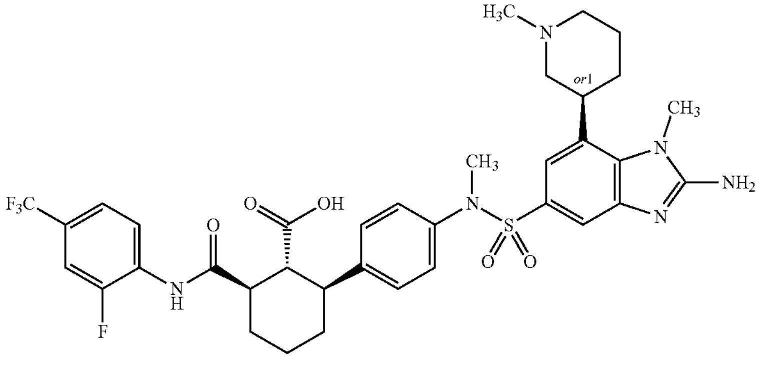 [SMILES: CN1CCC[C@@H](c2cc(S(=O)(=O)N(C)c3ccc([C@H]4CCC[C@@H](C(=O)Nc5ccc(C(F)(F)F)cc5F)[C@@H]4C(=O)O)cc3)cc3nc(N)n(C)c23)C1] ISOMER 1 |

TABLE 1-continued
| Ex. No. | Structure |
| --- | --- |
| 271 | 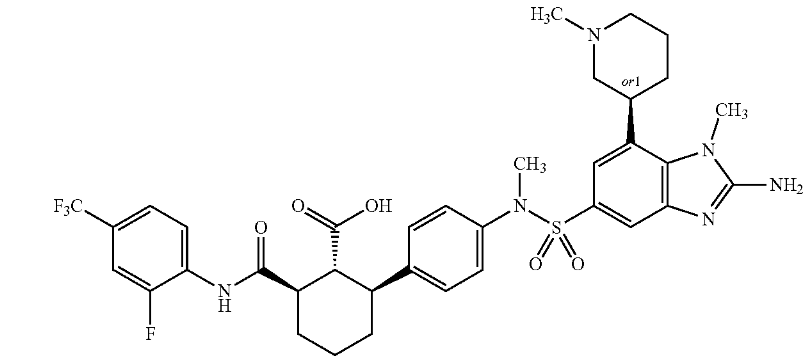 [SMILES: CN1CCC[C@@H](c2cc(S(=O)(=O)N(C)c3ccc([C@H]4CCC[C@@H](C(=O)Nc5ccc(C(F)(F)F)cc5F)[C@@H]4C(=O)O)cc3)cc3nc(N)n(C)c23)C1] ISOMER 2 |
| 272 | 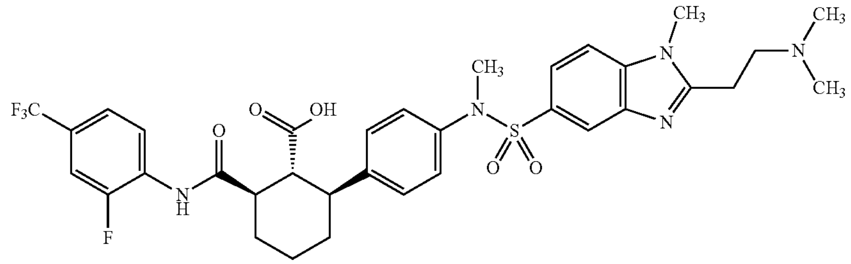 [SMILES: CN(C)CCc1nc2cc(S(=O)(=O)N(C)c3ccc([C@H]4CCC[C@@H](C(=O)Nc5ccc(C(F)(F)F)cc5F)[C@@H]4C(=O)O)cc3)ccc2n1C] |
| 273 | 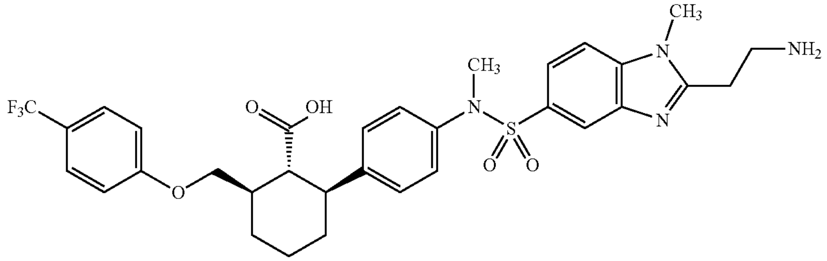 [SMILES: CN(c1ccc([C@H]2CCC[C@@H](COc3ccc(C(F)(F)F)cc3)[C@@H]2C(=O)O)cc1)S(=O)(=O)c1ccc2c(c1)nc(CCN)n2C] |
| 274 | 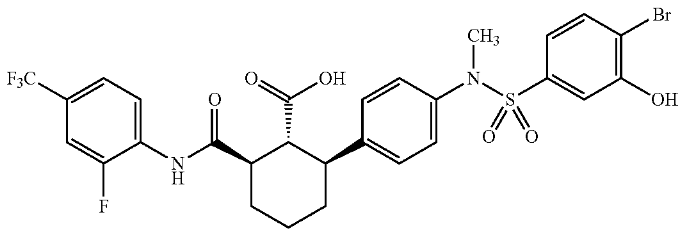 [SMILES: CN(c1ccc([C@H]2CCC[C@@H](C(=O)Nc3ccc(C(F)(F)F)cc3F)[C@@H]2C(=O)O)cc1)S(=O)(=O)c1ccc(Br)c(O)c1] |
| 275 | 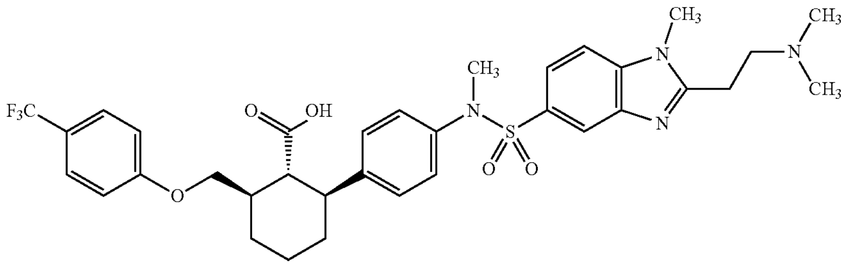 [SMILES: CN(C)CCc1nc2cc(S(=O)(=O)N(C)c3ccc([C@H]4CCC[C@@H](COc5ccc(C(F)(F)F)cc5)[C@@H]4C(=O)O)cc3)ccc2n1C] |

TABLE 1-continued
| Ex. No. | Structure |
|---|---|
| 276 | 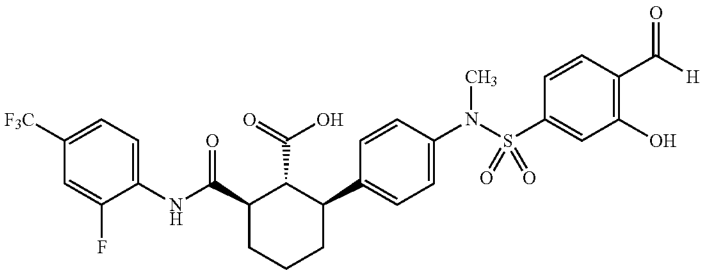 [SMILES: CN(c1ccc([C@H]2CCC[C@@H](C(=O)Nc3ccc(C(F)(F)F)cc3F)[C@@H]2C(=O)O)cc1)S(=O)(=O)c1ccc(C=O)c(O)c1] |
| 277 | 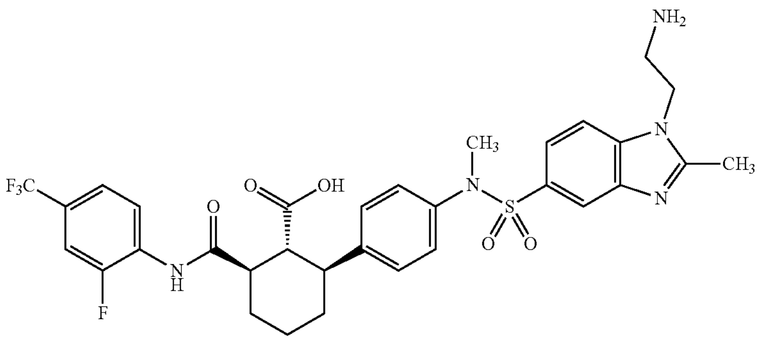 [SMILES: Cc1nc2cc(S(=O)(=O)N(C)c3ccc([C@H]4CCC[C@@H](C(=O)Nc5ccc(C(F)(F)F)cc5F)[C@@H]4C(=O)O)cc3)ccc2n1CCN] |
| 278 | 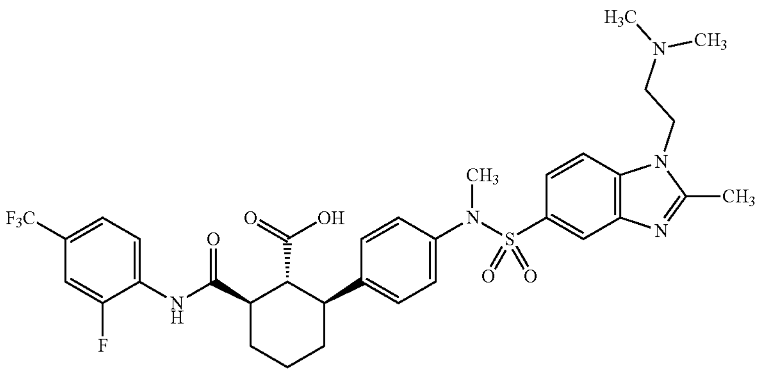 [SMILES: Cc1nc2cc(S(=O)(=O)N(C)c3ccc([C@H]4CCC[C@@H](C(=O)Nc5ccc(C(F)(F)F)cc5F)[C@@H]4C(=O)O)cc3)ccc2n1CCN(C)C] |
| 279 | 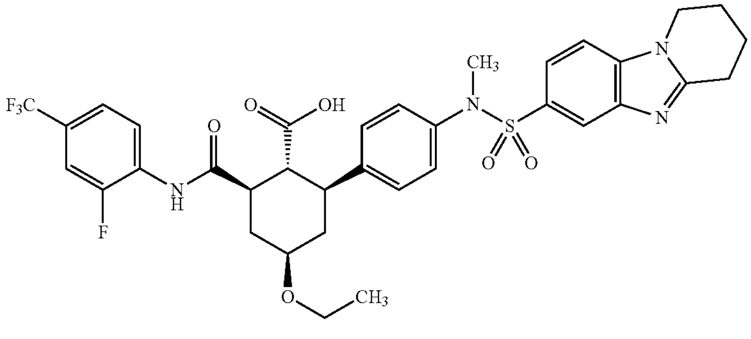 [SMILES: CCO[C@@H]1C[C@H](c2ccc(N(C)S(=O)(=O)c3ccc4c(c3)nc3n4CCCC3)cc2)[C@@H](C(=O)O)[C@H](C(=O)Nc2ccc(C(F)(F)F)cc2F)C1] |

TABLE 1-continued
| Ex. No. | Structure |
|---|---|
| 281 | 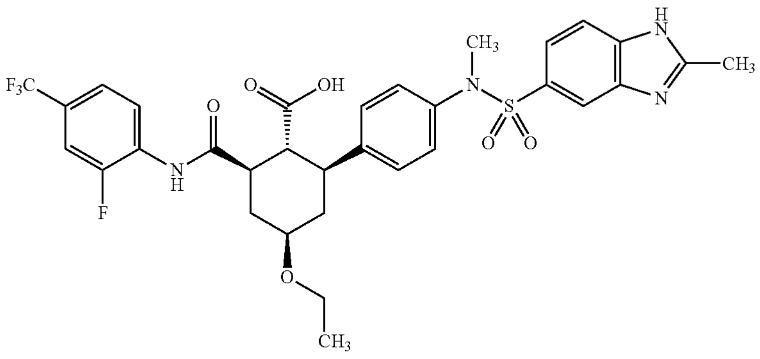 [SMILES: CCO[C@@H]1C[C@H](c2ccc(N(C)S(=O)(=O)c3ccc4[nH]c(C)nc4c3)cc2)[C@@H](C(=O)O)[C@H](C(=O)Nc2ccc(C(F)(F)F)cc2F)C1] |
| 282 | 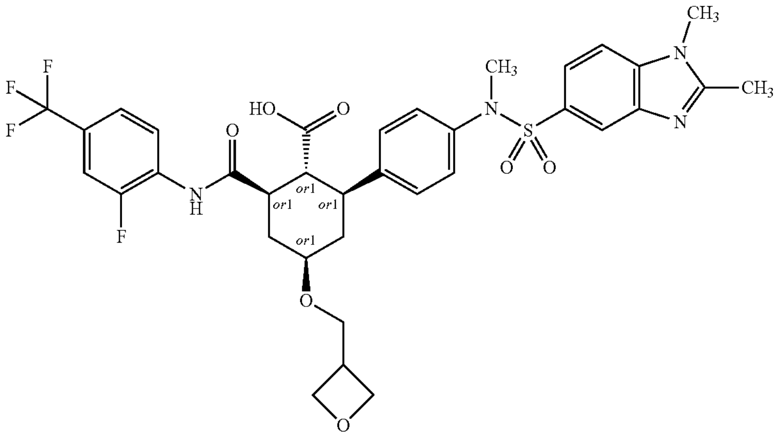 [SMILES: Cc1nc2cc(S(=O)(=O)N(C)c3ccc([C@H]4C[C@@H](OCC5COC5)C[C@@H](C(=O)Nc5ccc(C(F)(F)F)cc5F)[C@@H]4C(=O)O)cc3)ccc2n1C]<br>ISOMER 1 |
| 283 | 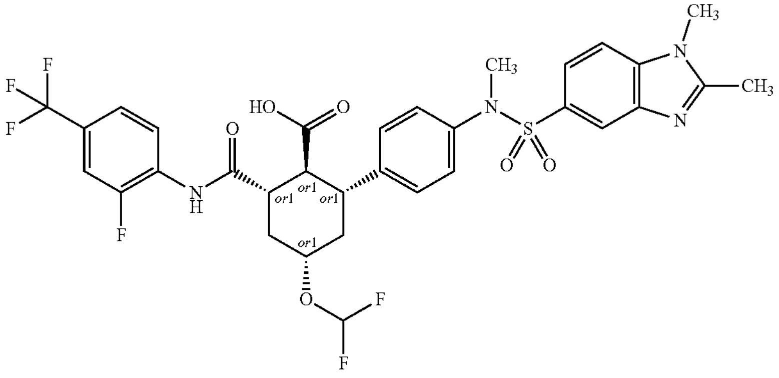 [SMILES: Cc1nc2cc(S(=O)(=O)N(C)c3ccc([C@@H]4C[C@H](OC(F)F)C[C@H](C(=O)Nc5ccc(C(F)(F)F)cc5F)[C@H]4C(=O)O)cc3)ccc2n1C]<br>ISOMER 1 |

TABLE 1-continued
| Ex. No. | Structure |
|---|---|
| 284 | 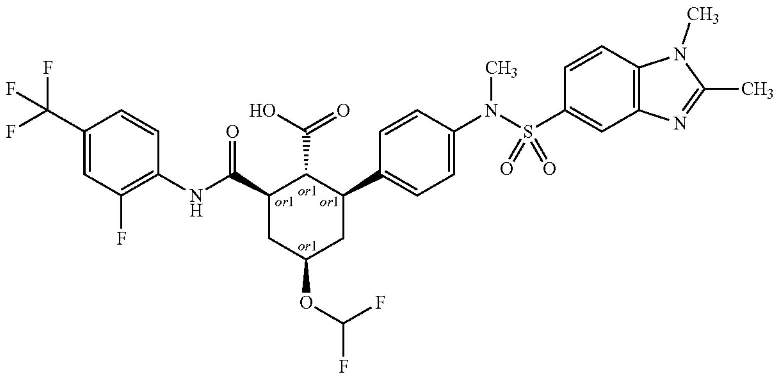 [SMILES: Cc1nc2cc(S(=O)(=O)N(C)c3ccc([C@H]4C[C@@H](OC(F)F)C[C@@H](C(=O)Nc5ccc(C(F)(F)F)cc5F)[C@@H]4C(=O)O)cc3)ccc2n1C] ISOMER 2 |
| 285 | 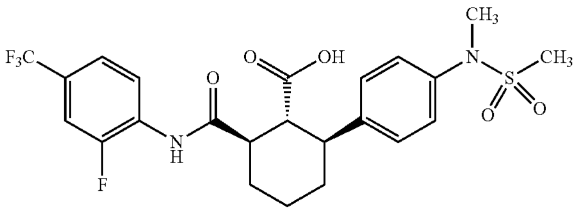 [SMILES: CN(c1ccc([C@H]2CCC[C@@H](C(=O)Nc3ccc(C(F)(F)F)cc3F)[C@@H]2C(=O)O)cc1)S(C)(=O)=O] |
| 286 | 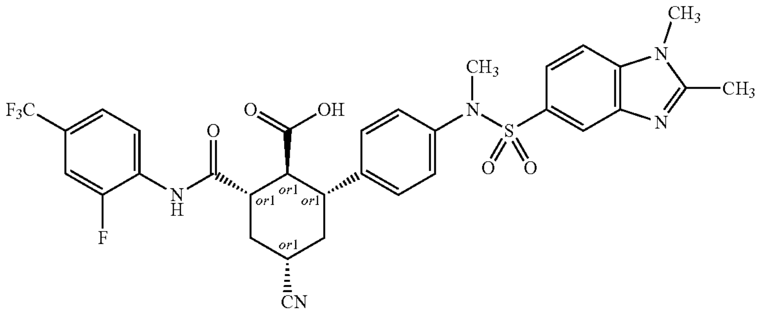 [SMILES: Cc1nc2cc(S(=O)(=O)N(C)c3ccc([C@@H]4C[C@H](C#N)C[C@H](C(=O)Nc5ccc(C(F)(F)F)cc5F)[C@H]4C(=O)O)cc3)ccc2n1C] ISOMER 1 |
| 287 | 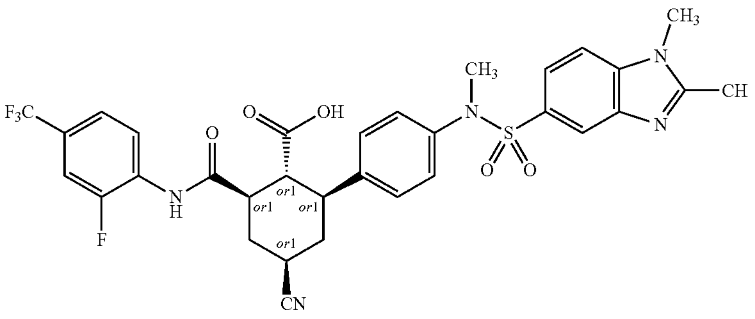 [SMILES: Cc1nc2cc(S(=O)(=O)N(C)c3ccc([C@H]4C[C@@H](C#N)C[C@@H](C(=O)Nc5ccc(C(F)(F)F)cc5F)[C@@H]4C(=O)O)cc3)ccc2n1C] ISOMER 2 |

TABLE 1-continued
| Ex. No. | Structure |
| --- | --- |
| 288 | 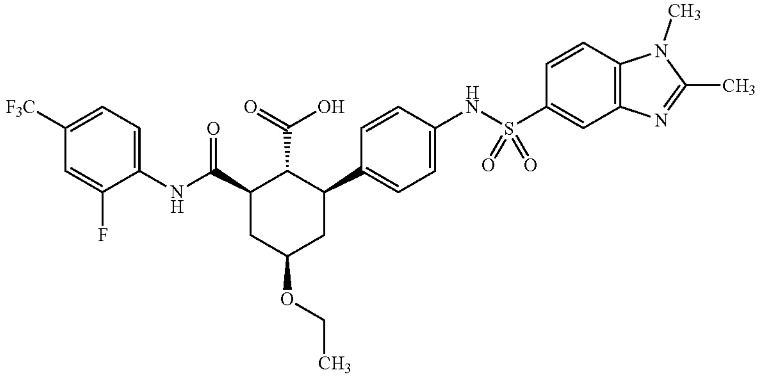 [SMILES: CCO[C@@H]1C[C@H](c2ccc(NS(=O)(=O)c3ccc4c(c3)nc(C)n4C)cc2)[C@@H](C(=O)O)[C@H](C(=O)Nc2ccc(C(F)(F)F)cc2F)C1] |
| 289 | 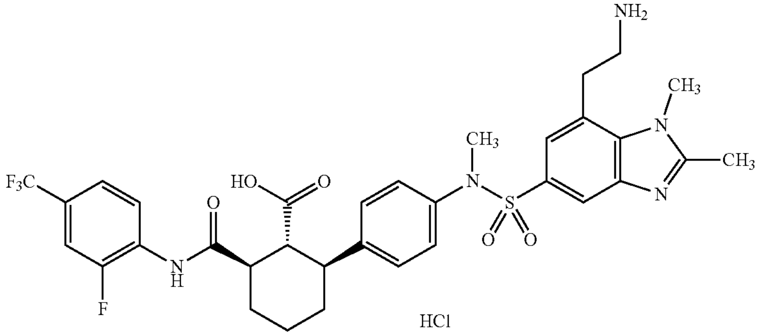 [SMILES: Cc1nc2cc(S(=O)(=O)N(C)c3ccc([C@H]4CCC[C@@H](C(=O)Nc5ccc(C(F)(F)F)cc5F)[C@@H]4C(=O)O)cc3)cc(CCN)c2n1C ; Cl] HCl |
| 290 | 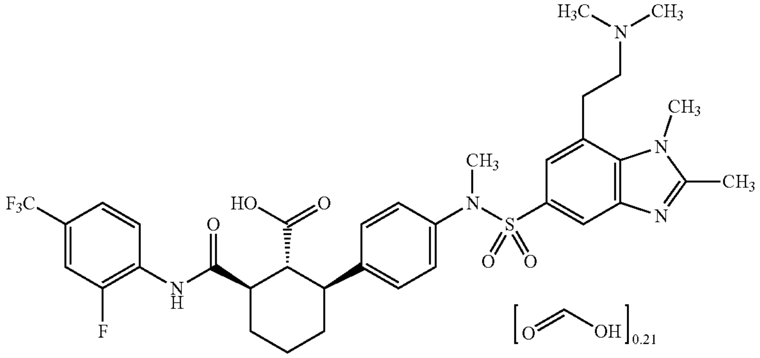 |
| 291 | 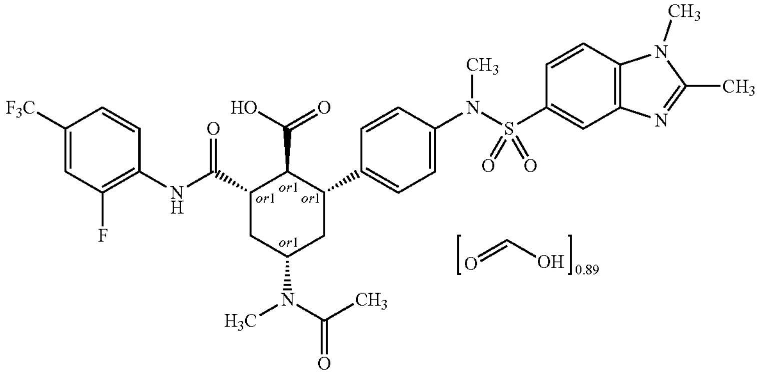 ISOMER 1 |

TABLE 1-continued
| Ex. No. | Structure |
|---|---|
| 292 | 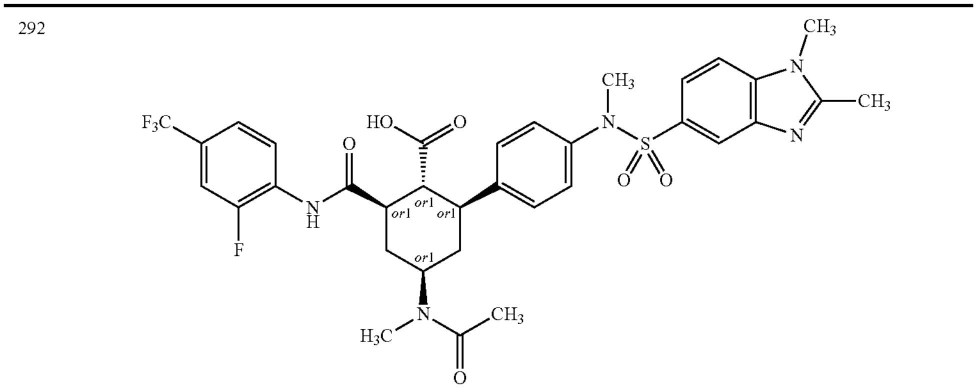<br>ISOMER 2 |
| 293 | 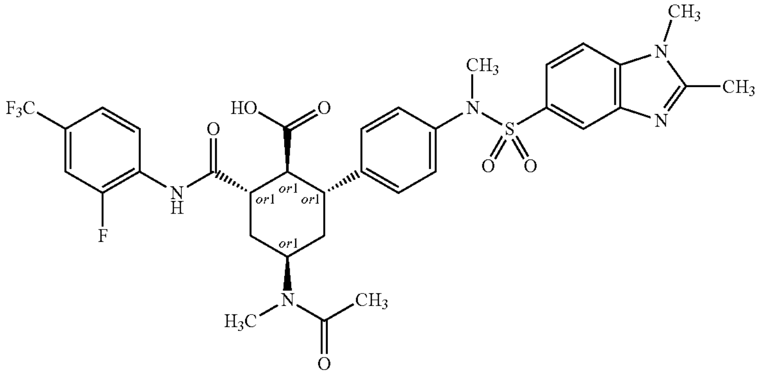 [SMILES: CC(=O)N(C)[C@H]1C[C@H](C(=O)Nc2ccc(C(F)(F)F)cc2F)[C@@H](C(=O)O)[C@H](c2ccc(N(C)S(=O)(=O)c3ccc4c(c3)nc(C)n4C)cc2)C1]<br>ISOMER 1 |
| 294 | 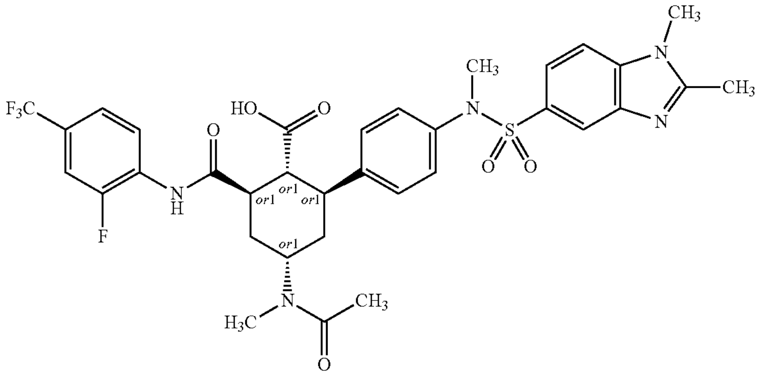 [SMILES: CC(=O)N(C)[C@H]1C[C@H](c2ccc(N(C)S(=O)(=O)c3ccc4c(c3)nc(C)n4C)cc2)[C@@H](C(=O)O)[C@H](C(=O)Nc2ccc(C(F)(F)F)cc2F)C1]<br>ISOMER 2 |
| 295 | 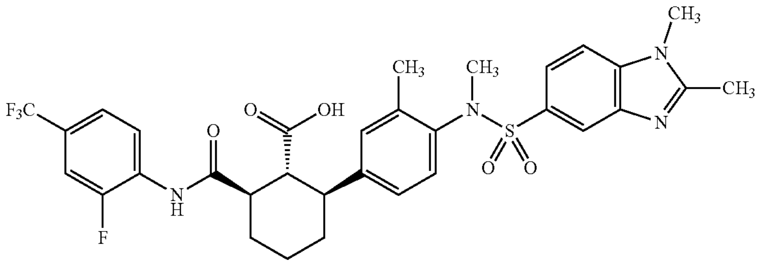 [SMILES: Cc1cc([C@H]2CCC[C@@H](C(=O)Nc3ccc(C(F)(F)F)cc3F)[C@@H]2C(=O)O)ccc1N(C)S(=O)(=O)c1ccc2c(c1)nc(C)n2C] |

TABLE 1-continued
| Ex. No. | Structure |
|---|---|
| 296 | 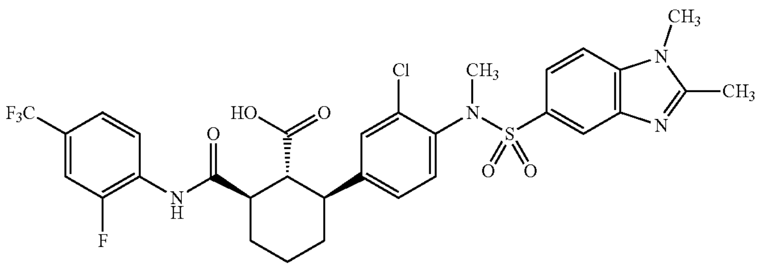 [SMILES: Cc1nc2cc(S(=O)(=O)N(C)c3ccc([C@H]4CCC[C@@H](C(=O)Nc5ccc(C(F)(F)F)cc5F)[C@@H]4C(=O)O)cc3Cl)ccc2n1C] |
| 297 | 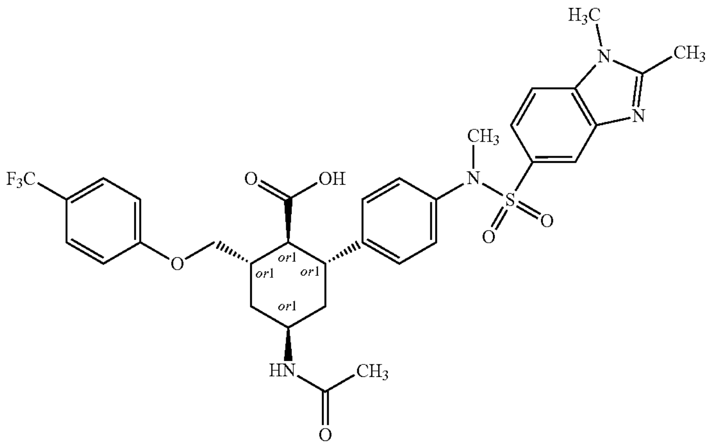 [SMILES: CC(=O)N[C@H]1C[C@H](COc2ccc(C(F)(F)F)cc2)[C@@H](C(=O)O)[C@H](c2ccc(N(C)S(=O)(=O)c3ccc4c(c3)nc(C)n4C)cc2)C1] ISOMER 1 |
| 298 | 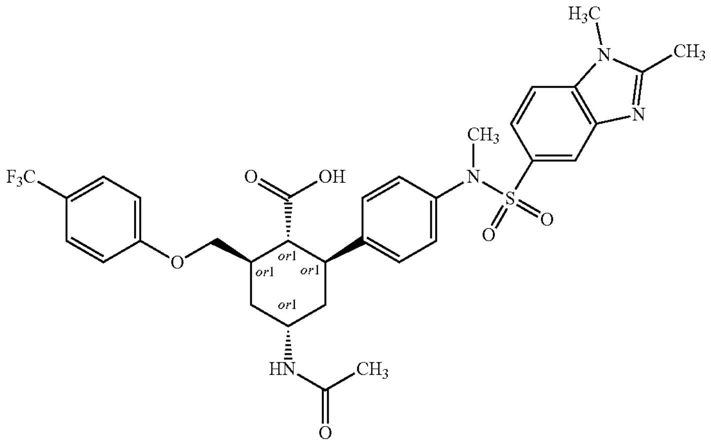 [SMILES: CC(=O)N[C@@H]1C[C@@H](COc2ccc(C(F)(F)F)cc2)[C@H](C(=O)O)[C@@H](c2ccc(N(C)S(=O)(=O)c3ccc4c(c3)nc(C)n4C)cc2)C1] ISOMER 2 |

TABLE 1-continued
| Ex. No. | Structure |
| --- | --- |
| 299 | 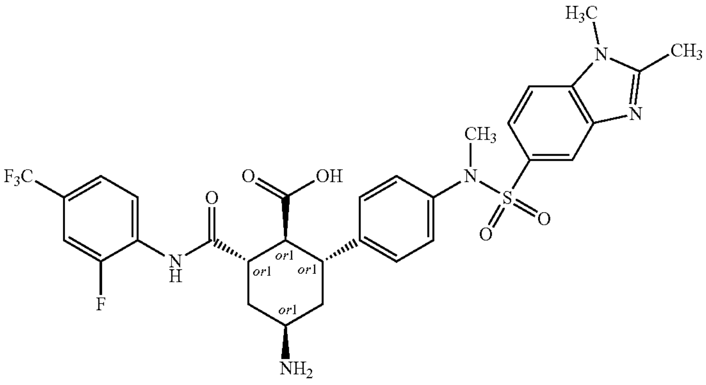 [SMILES: Cc1nc2cc(S(=O)(=O)N(C)c3ccc([C@@H]4C[C@@H](N)C[C@H](C(=O)Nc5ccc(C(F)(F)F)cc5F)[C@H]4C(=O)O)cc3)ccc2n1C] ISOMER 1 |
| 300 | 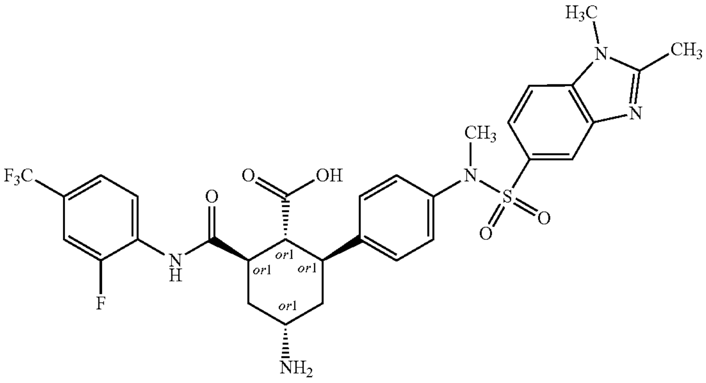 [SMILES: Cc1nc2cc(S(=O)(=O)N(C)c3ccc([C@H]4C[C@H](N)C[C@@H](C(=O)Nc5ccc(C(F)(F)F)cc5F)[C@@H]4C(=O)O)cc3)ccc2n1C] ISOMER 2 |
| 301 | 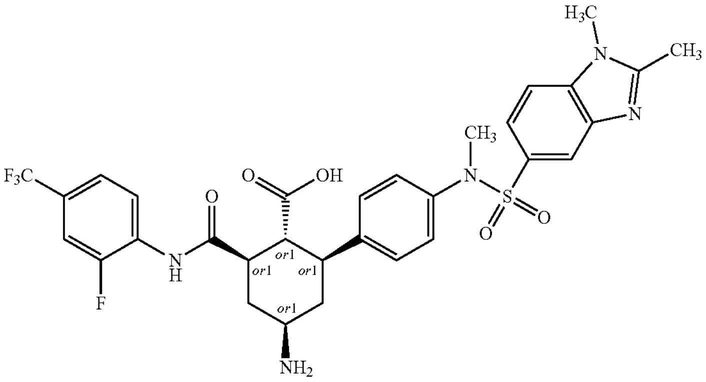 [SMILES: Cc1nc2cc(S(=O)(=O)N(C)c3ccc([C@H]4C[C@@H](N)C[C@@H](C(=O)Nc5ccc(C(F)(F)F)cc5F)[C@@H]4C(=O)O)cc3)ccc2n1C] ISOMER 1 |

TABLE 1-continued
| Ex. No. | Structure |
|---|---|
| 302 | 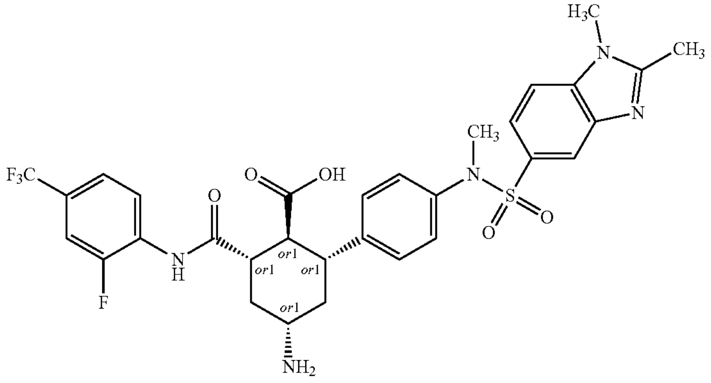 [SMILES: Cc1nc2cc(S(=O)(=O)N(C)c3ccc([C@@H]4C[C@H](N)C[C@H](C(=O)Nc5ccc(C(F)(F)F)cc5F)[C@H]4C(=O)O)cc3)ccc2n1C] ISOMER 2 |
| 303 | 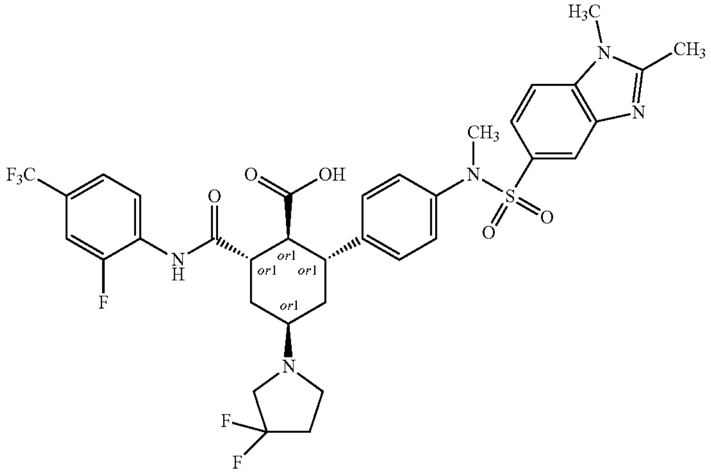 [SMILES: Cc1nc2cc(S(=O)(=O)N(C)c3ccc([C@@H]4C[C@@H](N5CCC(F)(F)C5)C[C@H](C(=O)Nc5ccc(C(F)(F)F)cc5F)[C@H]4C(=O)O)cc3)ccc2n1C] ISOMER 1 |
| 304 | 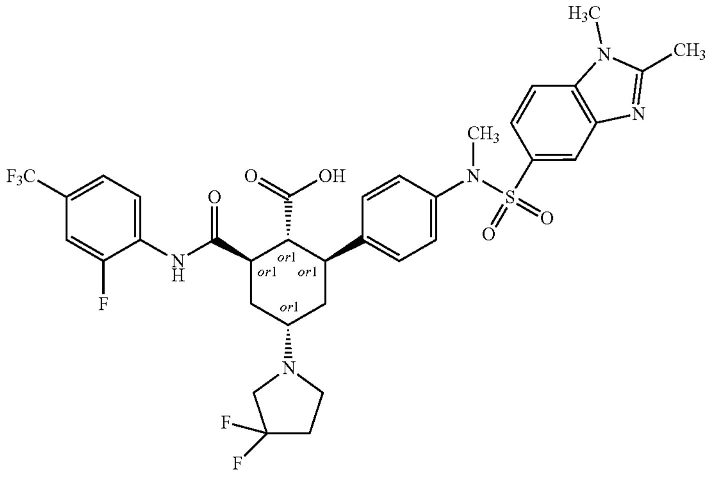 [SMILES: Cc1nc2cc(S(=O)(=O)N(C)c3ccc([C@H]4C[C@H](N5CCC(F)(F)C5)C[C@@H](C(=O)Nc5ccc(C(F)(F)F)cc5F)[C@@H]4C(=O)O)cc3)ccc2n1C] ISOMER 2 |

TABLE 1-continued
| Ex. No. | Structure |
|---|---|
| 305 | 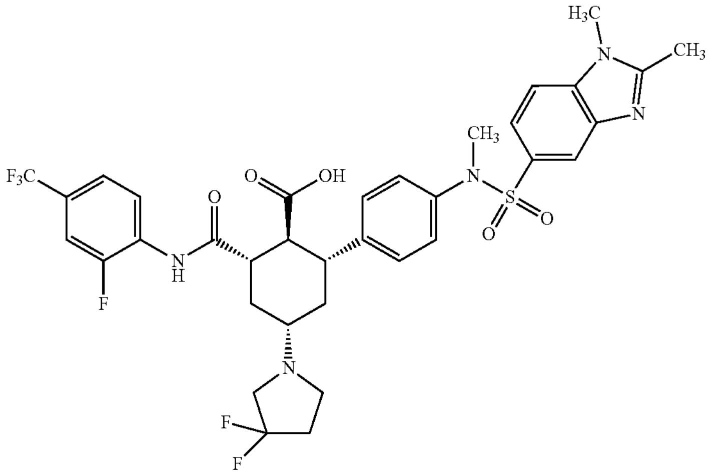 [SMILES: Cc1nc2cc(S(=O)(=O)N(C)c3ccc([C@@H]4C[C@H](N5CCC(F)(F)C5)C[C@H](C(=O)Nc5ccc(C(F)(F)F)cc5F)[C@H]4C(=O)O)cc3)ccc2n1C] |
| 306 | 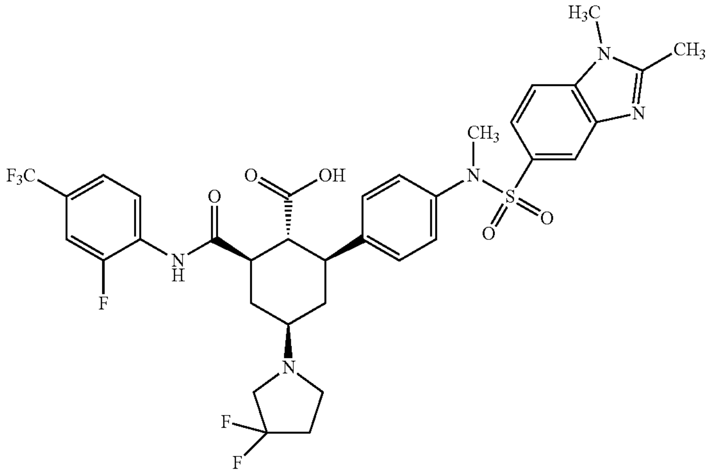 [SMILES: Cc1nc2cc(S(=O)(=O)N(C)c3ccc([C@H]4C[C@@H](N5CCC(F)(F)C5)C[C@@H](C(=O)Nc5ccc(C(F)(F)F)cc5F)[C@@H]4C(=O)O)cc3)ccc2n1C] |
| 307 | 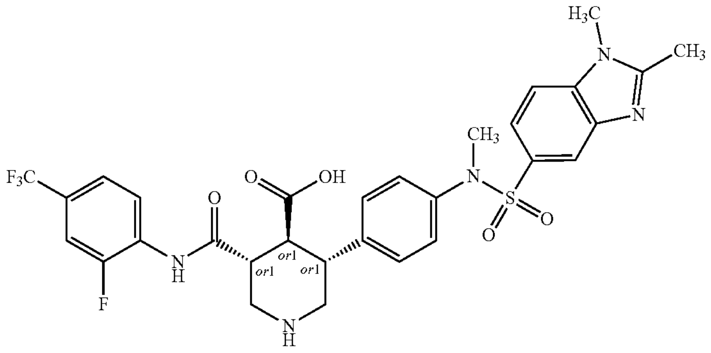 [SMILES: Cc1nc2cc(S(=O)(=O)N(C)c3ccc([C@@H]4CNC[C@H](C(=O)Nc5ccc(C(F)(F)F)cc5F)[C@H]4C(=O)O)cc3)ccc2n1C] ISOMER 1 |

TABLE 1-continued
| Ex. No. | Structure |
| --- | --- |
| 308 | 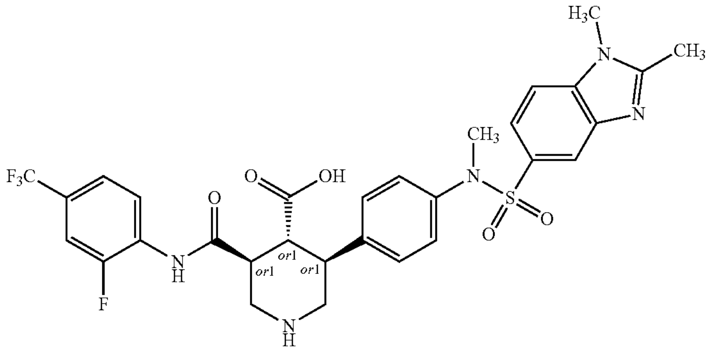 [SMILES: Cc1nc2cc(S(=O)(=O)N(C)c3ccc([C@H]4CNC[C@@H](C(=O)Nc5ccc(C(F)(F)F)cc5F)[C@@H]4C(=O)O)cc3)ccc2n1C] ISOMER 2 |
| 309 | 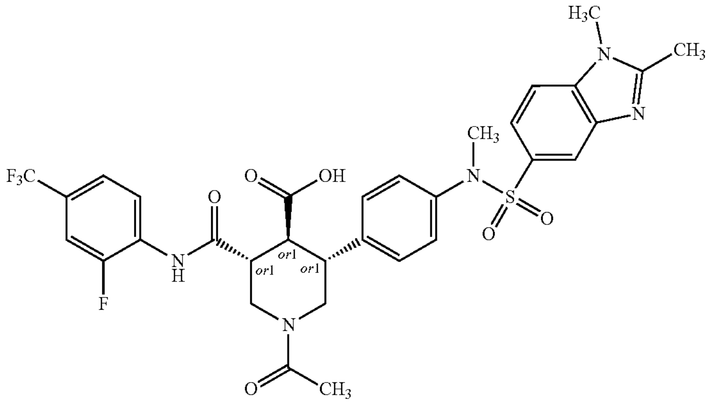 [SMILES: CC(=O)N1C[C@H](C(=O)Nc2ccc(C(F)(F)F)cc2F)[C@@H](C(=O)O)[C@H](c2ccc(N(C)S(=O)(=O)c3ccc4c(c3)nc(C)n4C)cc2)C1] ISOMER 1 |
| 310 | 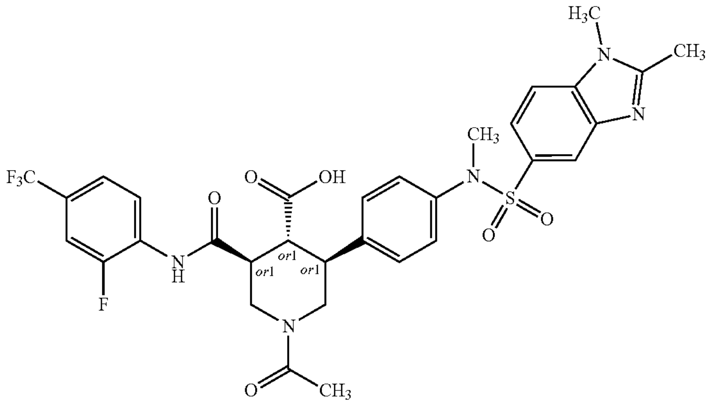 ISOMER 2 |

TABLE 1-continued
| Ex. No. | Structure |
| --- | --- |
| 311 | 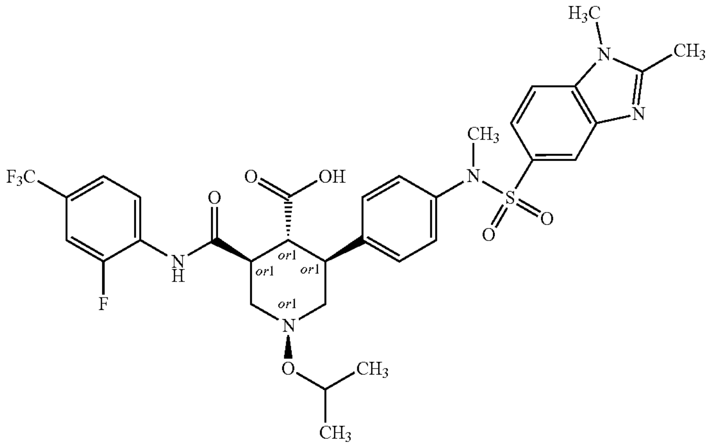 ISOMER 1 |
| 312 | 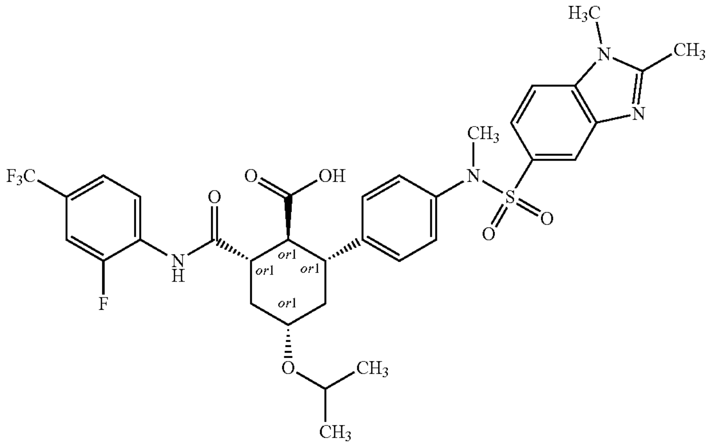 [SMILES: Cc1nc2cc(S(=O)(=O)N(C)c3ccc([C@@H]4C[C@H](OC(C)C)C[C@H](C(=O)Nc5ccc(C(F)(F)F)cc5F)[C@H]4C(=O)O)cc3)ccc2n1C] ISOMER 2 |
| 313 | 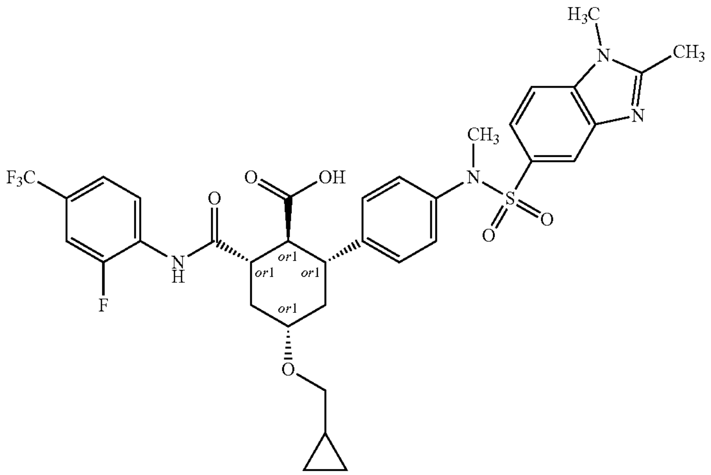 [SMILES: Cc1nc2cc(S(=O)(=O)N(C)c3ccc([C@@H]4C[C@H](OCC5CC5)C[C@H](C(=O)Nc5ccc(C(F)(F)F)cc5F)[C@H]4C(=O)O)cc3)ccc2n1C] ISOMER 1 |

TABLE 1-continued
| Ex. No. | Structure |
| --- | --- |
| 314 | 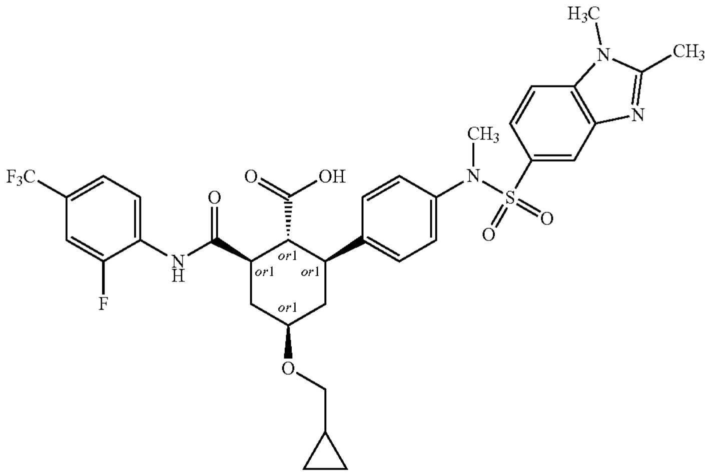 [SMILES: Cc1nc2cc(S(=O)(=O)N(C)c3ccc([C@H]4C[C@@H](OCC5CC5)C[C@@H](C(=O)Nc5ccc(C(F)(F)F)cc5F)[C@@H]4C(=O)O)cc3)ccc2n1C] ISOMER 2 |
| 315 | 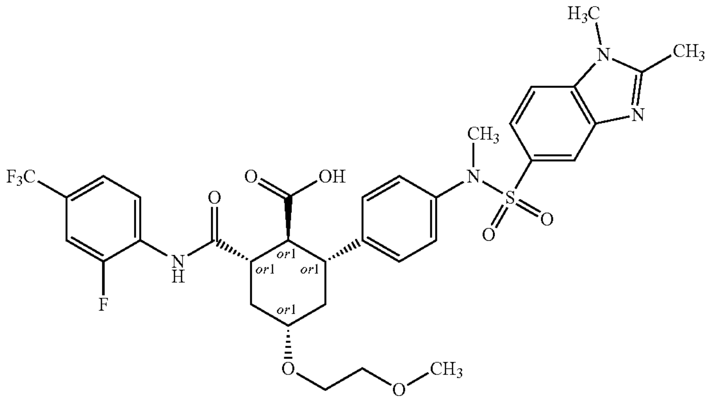 [SMILES: COCCO[C@@H]1C[C@H](C(=O)Nc2ccc(C(F)(F)F)cc2F)[C@@H](C(=O)O)[C@H](c2ccc(N(C)S(=O)(=O)c3ccc4c(c3)nc(C)n4C)cc2)C1] ISOMER 1 |
| 316 | 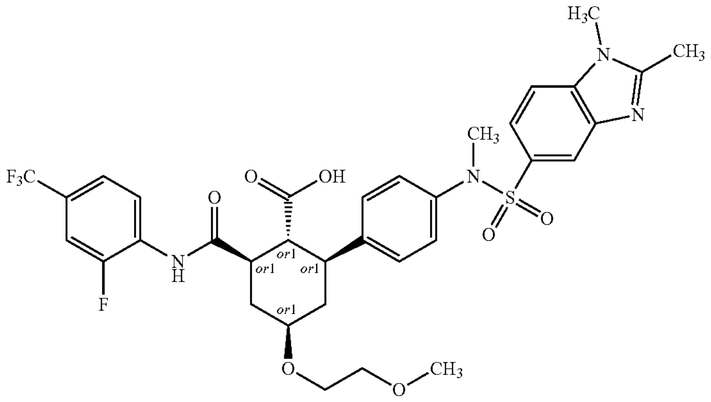 [SMILES: COCCO[C@@H]1C[C@H](c2ccc(N(C)S(=O)(=O)c3ccc4c(c3)nc(C)n4C)cc2)[C@@H](C(=O)O)[C@H](C(=O)Nc2ccc(C(F)(F)F)cc2F)C1] ISOMER 2 |

TABLE 1-continued
| Ex. No. | Structure |
|---|---|
| 317 | 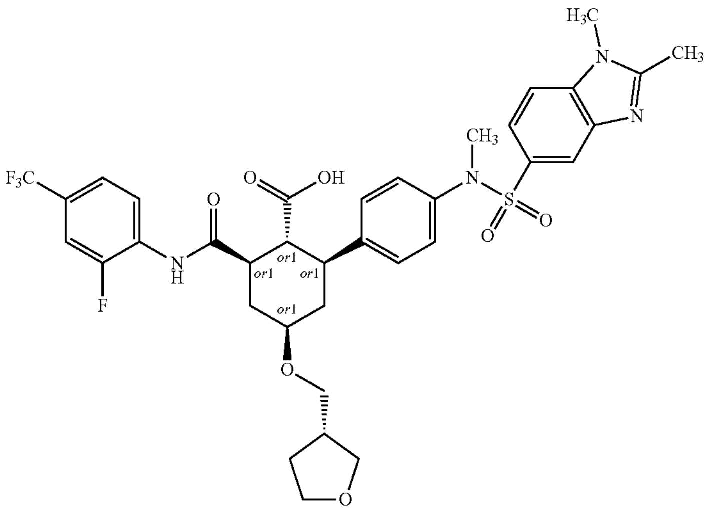 [SMILES: Cc1nc2cc(S(=O)(=O)N(C)c3ccc([C@H]4C[C@@H](OC[C@H]5CCOC5)C[C@@H](C(=O)Nc5ccc(C(F)(F)F)cc5F)[C@@H]4C(=O)O)cc3)ccc2n1C] ISOMER 1 |
| 318 | 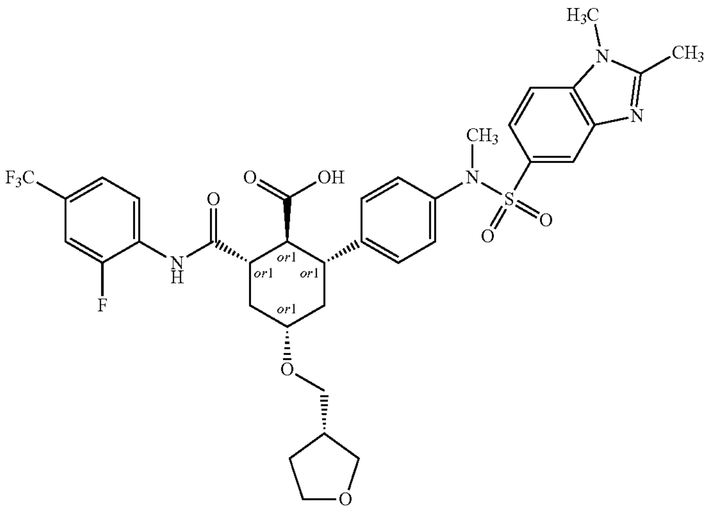 [SMILES: Cc1nc2cc(S(=O)(=O)N(C)c3ccc([C@@H]4C[C@H](OC[C@H]5CCOC5)C[C@H](C(=O)Nc5ccc(C(F)(F)F)cc5F)[C@H]4C(=O)O)cc3)ccc2n1C] ISOMER 2 |

TABLE 1-continued
| Ex. No. | Structure |
| --- | --- |
| 319 | 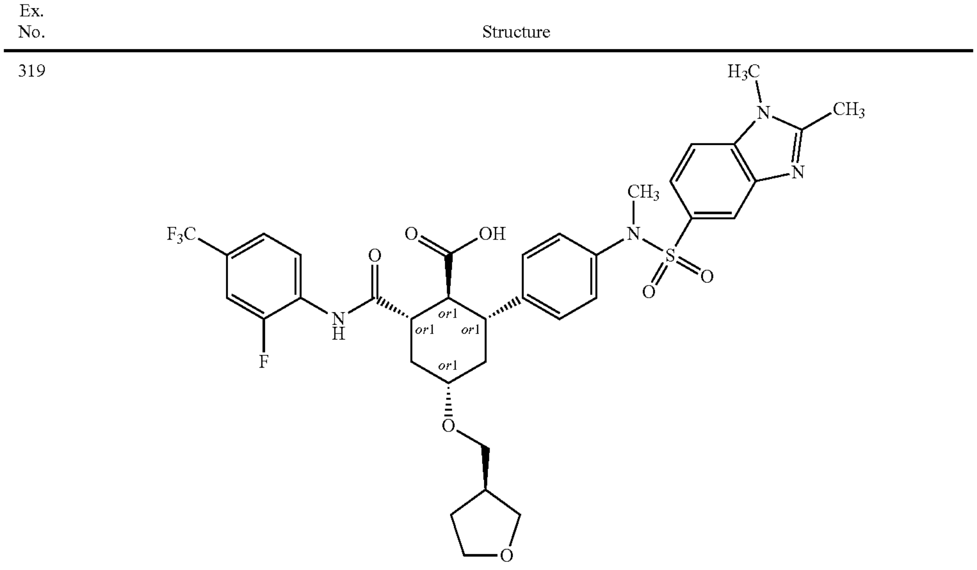 ISOMER 1 |
| 320 | 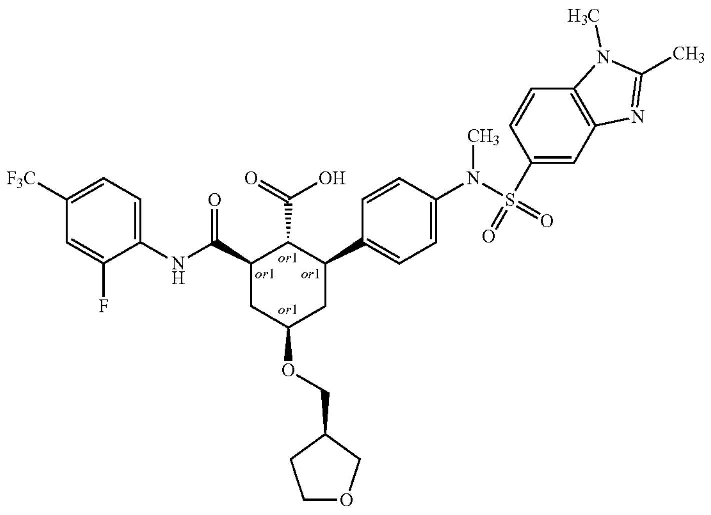 [SMILES: Cc1nc2cc(S(=O)(=O)N(C)c3ccc([C@H]4C[C@@H](OC[C@@H]5CCOC5)C[C@@H](C(=O)Nc5ccc(C(F)(F)F)cc5F)[C@@H]4C(=O)O)cc3)ccc2n1C] ISOMER 2 |
| 321 | 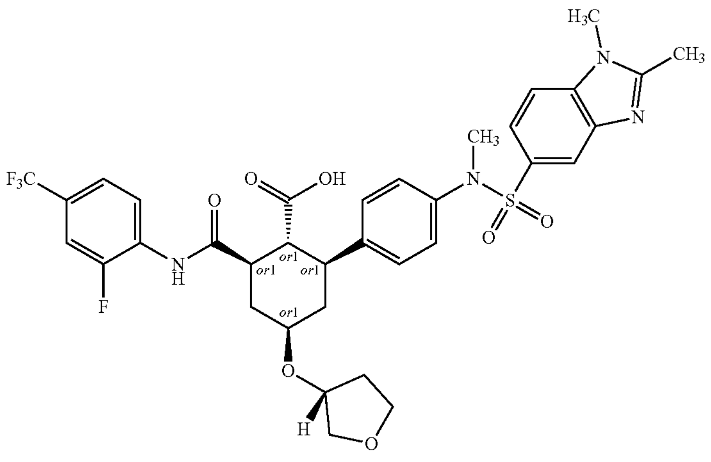 [SMILES: Cc1nc2cc(S(=O)(=O)N(C)c3ccc([C@H]4C[C@@H](O[C@@H]5CCOC5)C[C@@H](C(=O)Nc5ccc(C(F)(F)F)cc5F)[C@@H]4C(=O)O)cc3)ccc2n1C] ISOMER 1 |

TABLE 1-continued
| Ex. No. | Structure |
|---|---|
| 322 | 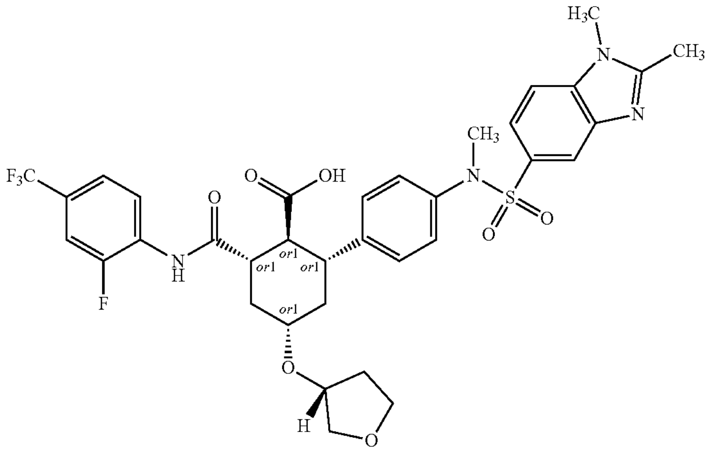 [SMILES: Cc1nc2cc(S(=O)(=O)N(C)c3ccc([C@@H]4C[C@H](O[C@@H]5CCOC5)C[C@H](C(=O)Nc5ccc(C(F)(F)F)cc5F)[C@H]4C(=O)O)cc3)ccc2n1C]<br>ISOMER 2 |
| 323 | 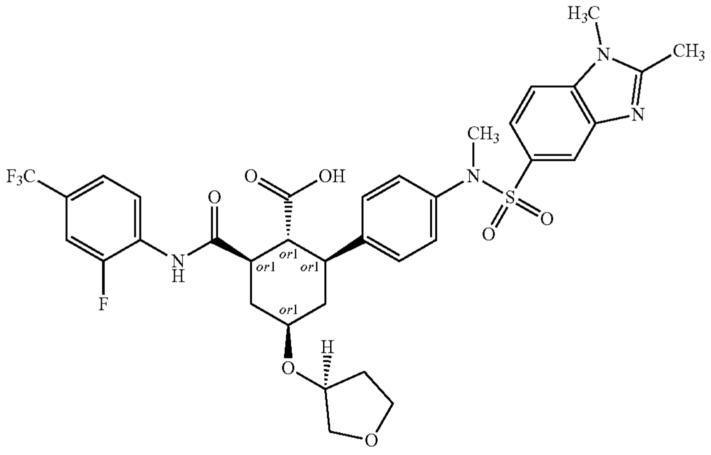 [SMILES: Cc1nc2cc(S(=O)(=O)N(C)c3ccc([C@H]4C[C@@H](O[C@H]5CCOC5)C[C@@H](C(=O)Nc5ccc(C(F)(F)F)cc5F)[C@@H]4C(=O)O)cc3)ccc2n1C]<br>ISOMER 1 |
| 324 | 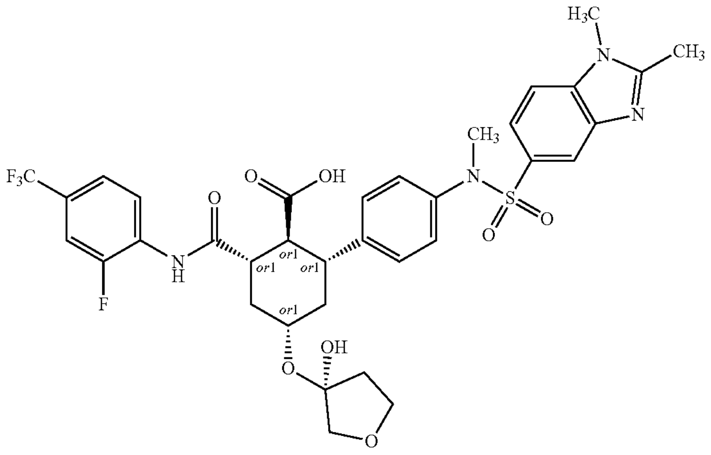 [SMILES: Cc1nc2cc(S(=O)(=O)N(C)c3ccc([C@@H]4C[C@H](O[C@@]5(O)CCOC5)C[C@H](C(=O)Nc5ccc(C(F)(F)F)cc5F)[C@H]4C(=O)O)cc3)ccc2n1C]<br>ISOMER 2 |

TABLE 1-continued
| Ex. No. | Structure |
|---|---|
| 325 | 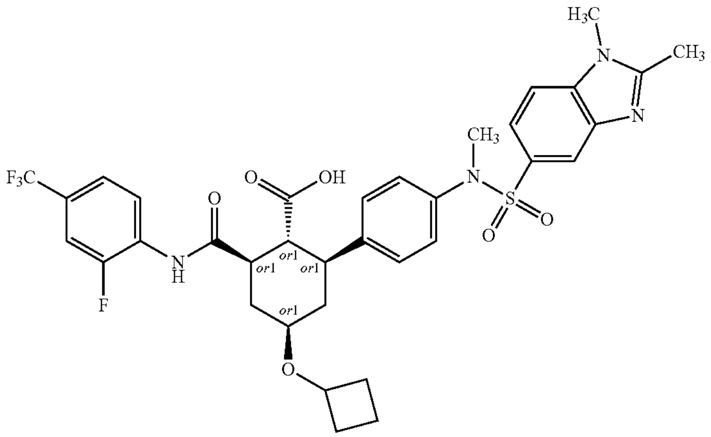 [SMILES: Cc1nc2cc(S(=O)(=O)N(C)c3ccc([C@H]4C[C@@H](OC5CCC5)C[C@@H](C(=O)Nc5ccc(C(F)(F)F)cc5F)[C@@H]4C(=O)O)cc3)ccc2n1C]<br>ISOMER 1 |
| 326 | 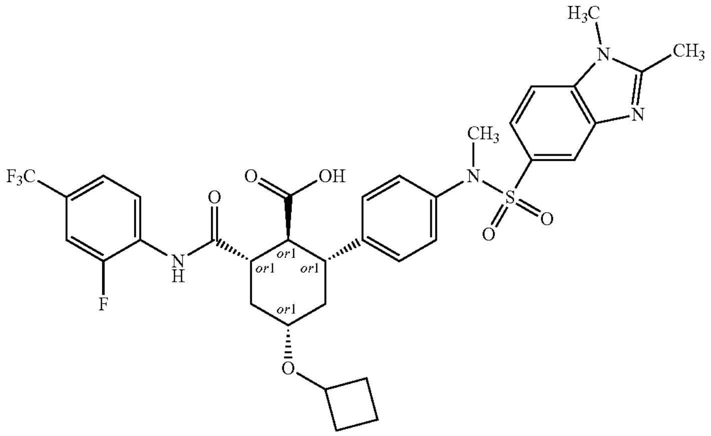 [SMILES: Cc1nc2cc(S(=O)(=O)N(C)c3ccc([C@@H]4C[C@H](OC5CCC5)C[C@H](C(=O)Nc5ccc(C(F)(F)F)cc5F)[C@H]4C(=O)O)cc3)ccc2n1C]<br>ISOMER 2 |
| 327 | 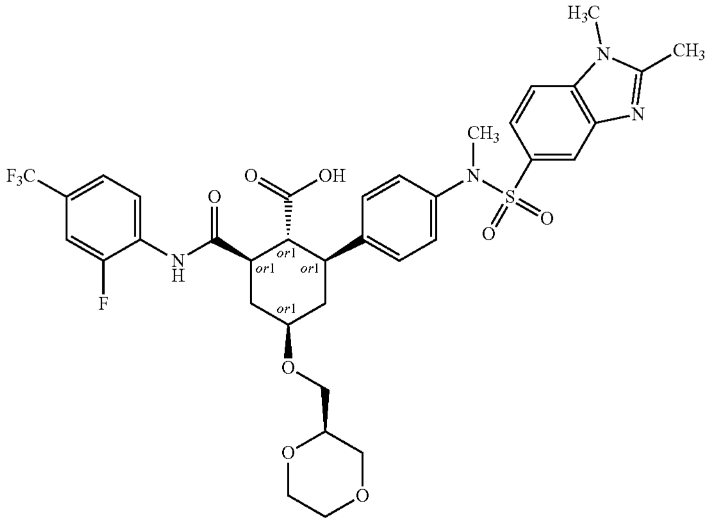 [SMILES: Cc1nc2cc(S(=O)(=O)N(C)c3ccc([C@H]4C[C@@H](OC[C@H]5COCCO5)C[C@@H](C(=O)Nc5ccc(C(F)(F)F)cc5F)[C@@H]4C(=O)O)cc3)ccc2n1C]<br>ISOMER 1 |

TABLE 1-continued
| Ex. No. | Structure |
|---|---|
| 328 | 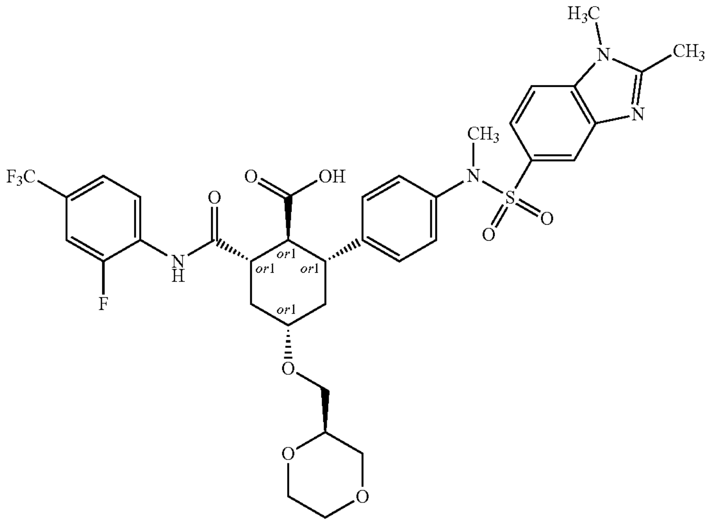 [SMILES: Cc1nc2cc(S(=O)(=O)N(C)c3ccc([C@@H]4C[C@H](OC[C@H]5COCCO5)C[C@H](C(=O)Nc5ccc(C(F)(F)F)cc5F)[C@H]4C(=O)O)cc3)ccc2n1C] ISOMER 2 |
| 329 | 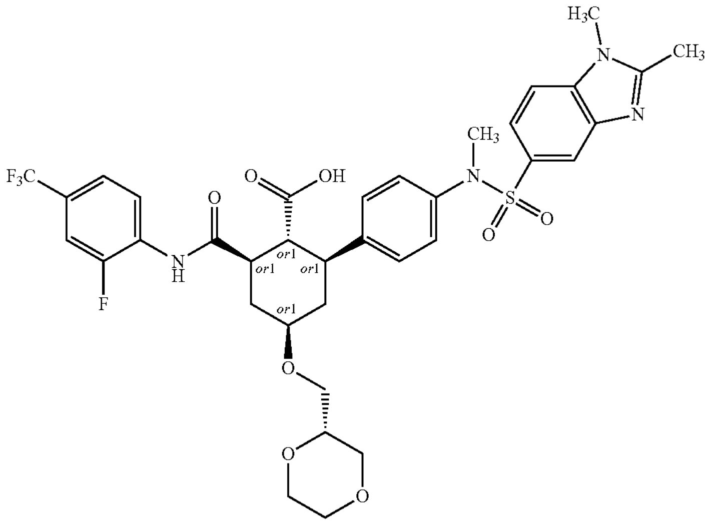 [SMILES: Cc1nc2cc(S(=O)(=O)N(C)c3ccc([C@H]4C[C@@H](OC[C@@H]5COCCO5)C[C@@H](C(=O)Nc5ccc(C(F)(F)F)cc5F)[C@@H]4C(=O)O)cc3)ccc2n1C] ISOMER 1 |
| 330 | 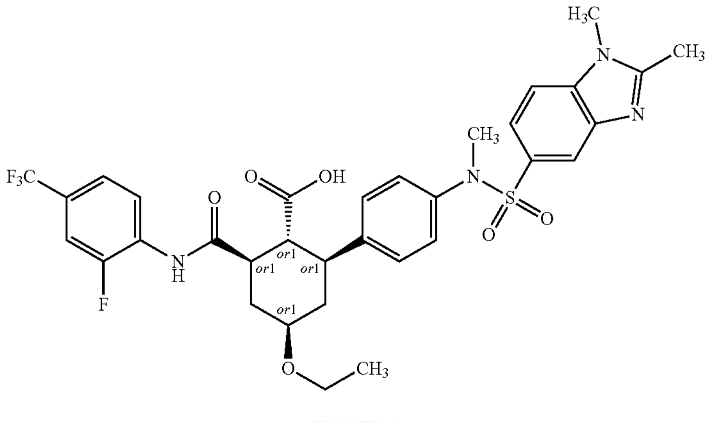 [SMILES: CCO[C@@H]1C[C@H](c2ccc(N(C)S(=O)(=O)c3ccc4c(c3)nc(C)n4C)cc2)[C@@H](C(=O)O)[C@H](C(=O)Nc2ccc(C(F)(F)F)cc2F)C1] ISOMER 1 |

TABLE 1-continued
| Ex. No. | Structure |
|---|---|
| 331 | 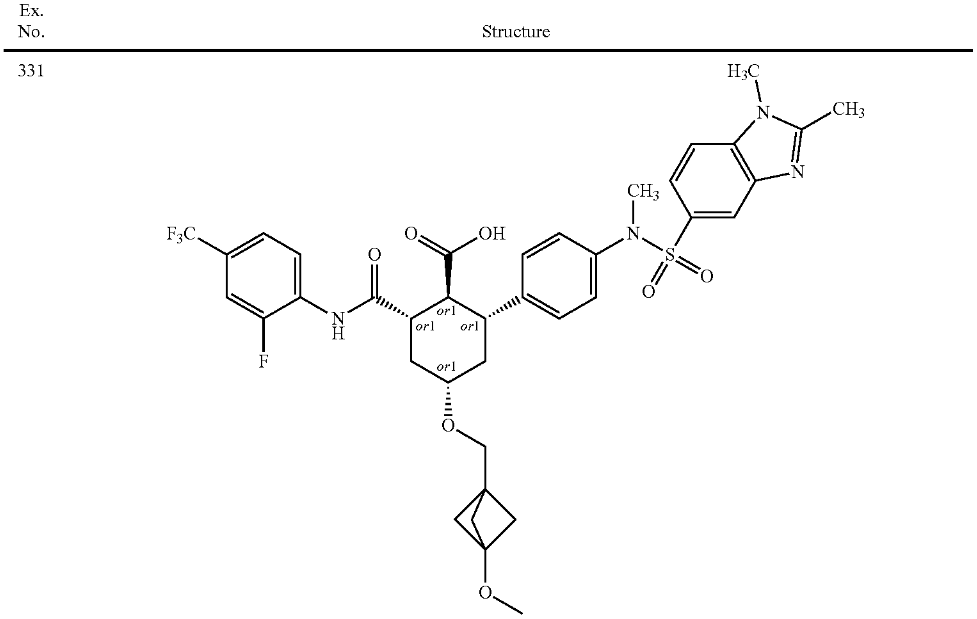<br>ISOMER 1 |
| 332 | 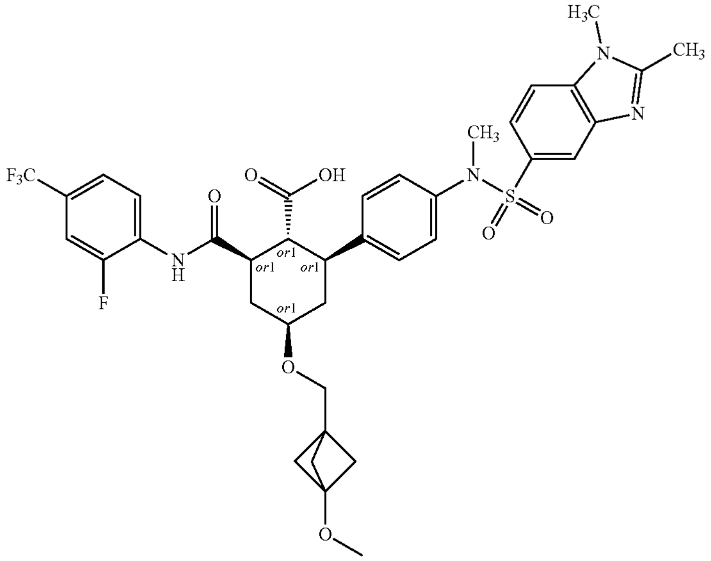 [SMILES: COC12CC(CO[C@@H]3C[C@H](c4ccc(N(C)S(=O)(=O)c5ccc6c(c5)nc(C)n6C)cc4)[C@@H](C(=O)O)[C@H](C(=O)Nc4ccc(C(F)(F)F)cc4F)C3)(C1)C2]<br>ISOMER 2 |
| 333 | 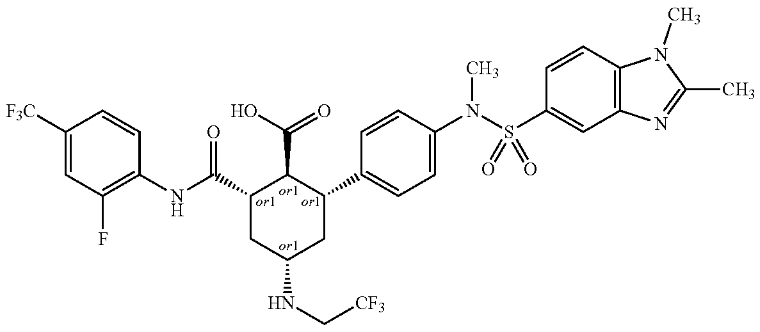 [SMILES: Cc1nc2cc(S(=O)(=O)N(C)c3ccc([C@@H]4C[C@H](NCC(F)(F)F)C[C@H](C(=O)Nc5ccc(C(F)(F)F)cc5F)[C@H]4C(=O)O)cc3)ccc2n1C]<br>ISOMER 1 |

TABLE 1-continued
| Ex. No. | Structure |
|---|---|
| 334 | 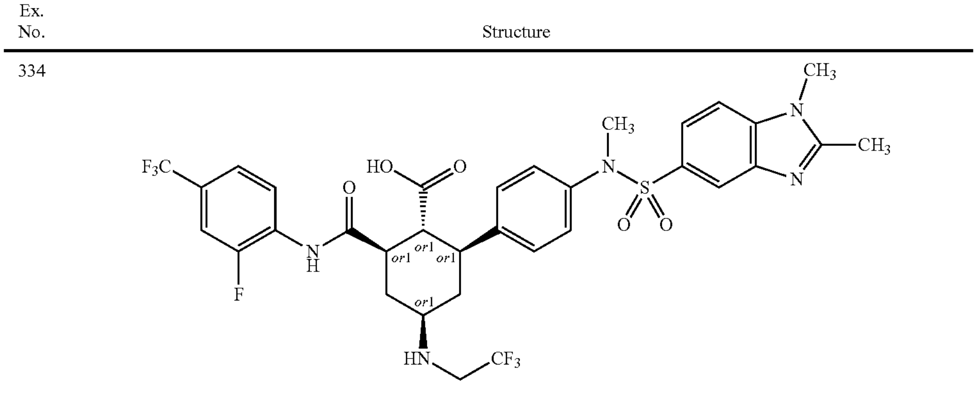 ISOMER 2 |
| 335 | 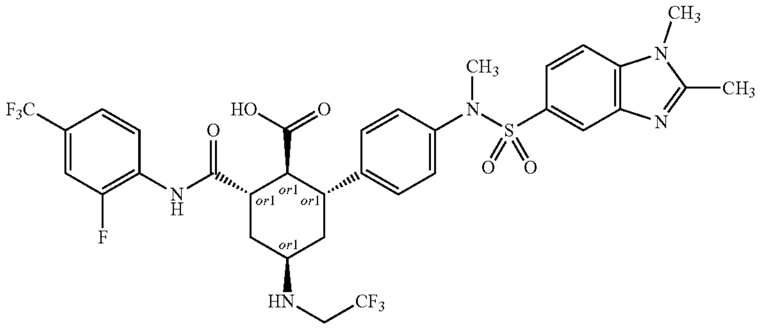 [SMILES: Cc1nc2cc(S(=O)(=O)N(C)c3ccc([C@@H]4C[C@@H](NCC(F)(F)F)C[C@H](C(=O)Nc5ccc(C(F)(F)F)cc5F)[C@H]4C(=O)O)cc3)ccc2n1C] ISOMER 1 |
| 336 | 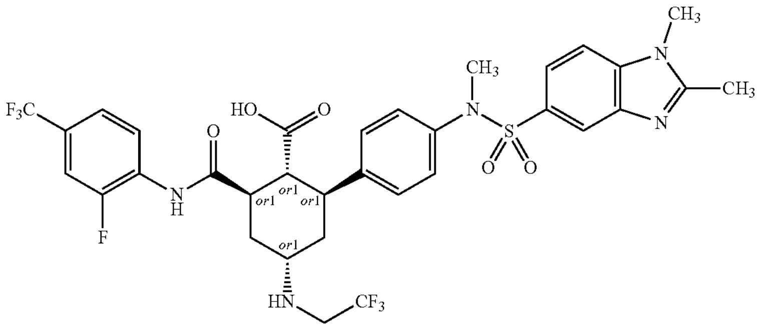 [SMILES: Cc1nc2cc(S(=O)(=O)N(C)c3ccc([C@H]4C[C@H](NCC(F)(F)F)C[C@@H](C(=O)Nc5ccc(C(F)(F)F)cc5F)[C@@H]4C(=O)O)cc3)ccc2n1C] ISOMER 2 |
| 337 | 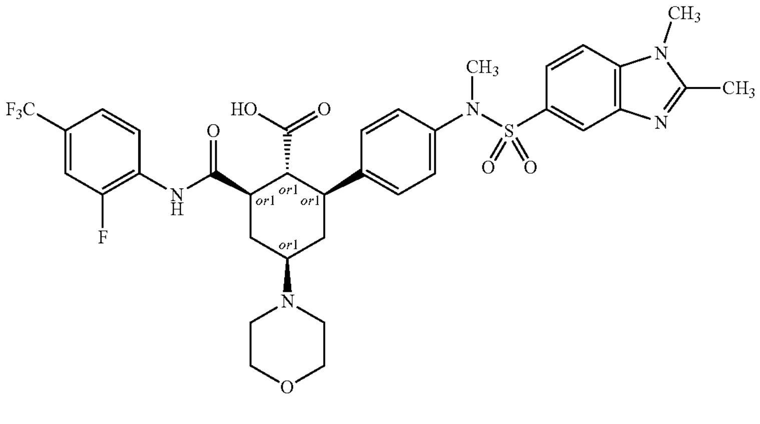 [SMILES: Cc1nc2cc(S(=O)(=O)N(C)c3ccc([C@H]4C[C@@H](N5CCOCC5)C[C@@H](C(=O)Nc5ccc(C(F)(F)F)cc5F)[C@@H]4C(=O)O)cc3)ccc2n1C] ISOMER 1 |

TABLE 1-continued
| Ex. No. | Structure |
| --- | --- |
| 338 | 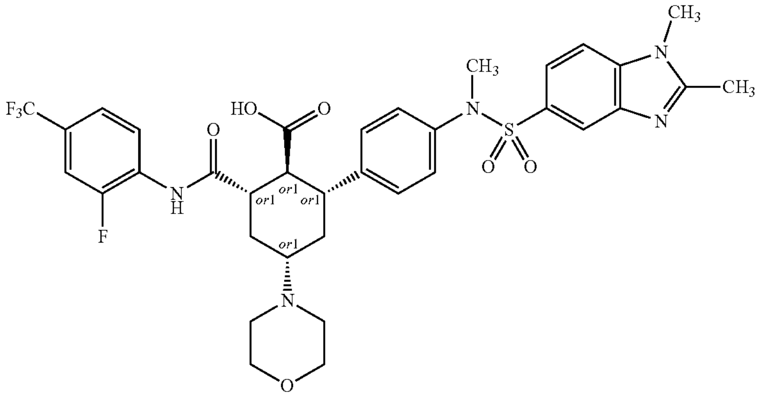 [SMILES: Cc1nc2cc(S(=O)(=O)N(C)c3ccc([C@@H]4C[C@H](N5CCOCC5)C[C@H](C(=O)Nc5ccc(C(F)(F)F)cc5F)[C@H]4C(=O)O)cc3)ccc2n1C]<br>ISOMER 2 |
| 339 | 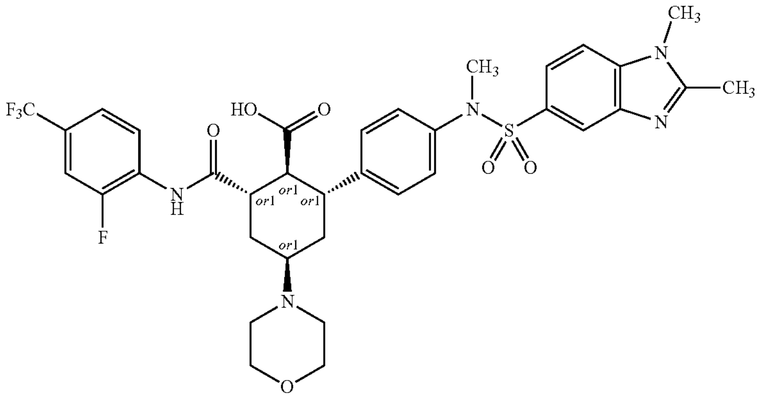 [SMILES: Cc1nc2cc(S(=O)(=O)N(C)c3ccc([C@@H]4C[C@@H](N5CCOCC5)C[C@H](C(=O)Nc5ccc(C(F)(F)F)cc5F)[C@H]4C(=O)O)cc3)ccc2n1C]<br>ISOMER 1 |
| 340 | 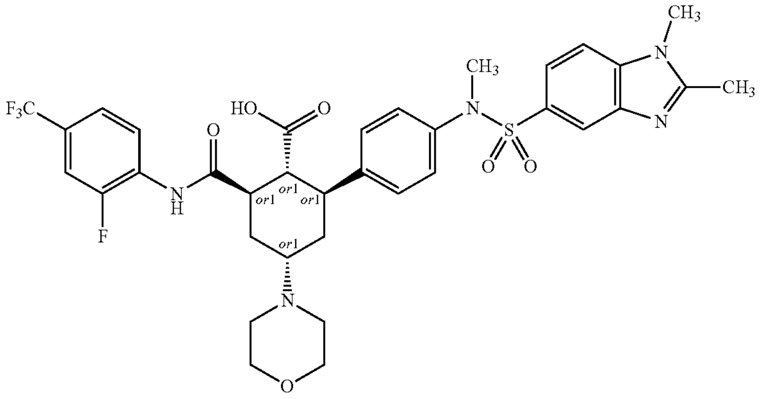 [SMILES: Cc1nc2cc(S(=O)(=O)N(C)c3ccc([C@H]4C[C@H](N5CCOCC5)C[C@@H](C(=O)Nc5ccc(C(F)(F)F)cc5F)[C@@H]4C(=O)O)cc3)ccc2n1C]<br>ISOMER 2 |

TABLE 1-continued
| Ex. No. | Structure |
|---|---|
| 341 | 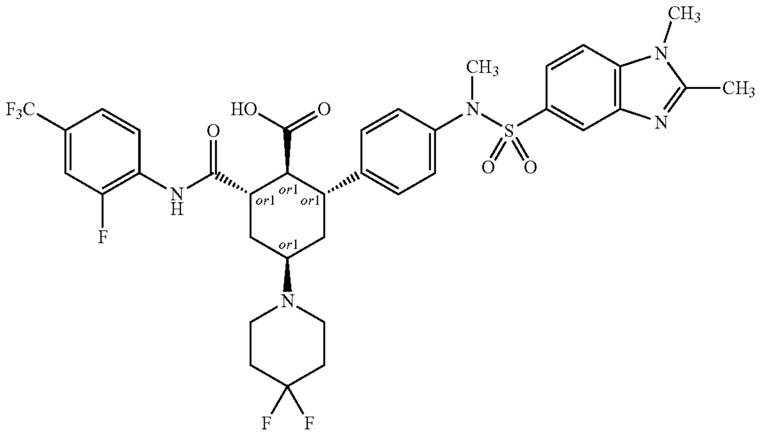 [SMILES: Cc1nc2cc(S(=O)(=O)N(C)c3ccc([C@@H]4C[C@@H](N5CCC(F)(F)CC5)C[C@H](C(=O)Nc5ccc(C(F)(F)F)cc5F)[C@H]4C(=O)O)cc3)ccc2n1C]<br>ISOMER 1 |
| 342 | 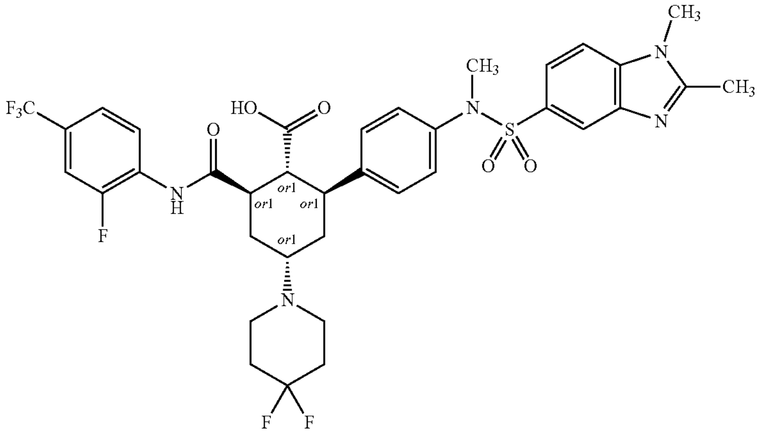 [SMILES: Cc1nc2cc(S(=O)(=O)N(C)c3ccc([C@H]4C[C@H](N5CCC(F)(F)CC5)C[C@@H](C(=O)Nc5ccc(C(F)(F)F)cc5F)[C@@H]4C(=O)O)cc3)ccc2n1C]<br>ISOMER 2 |
| 343 | 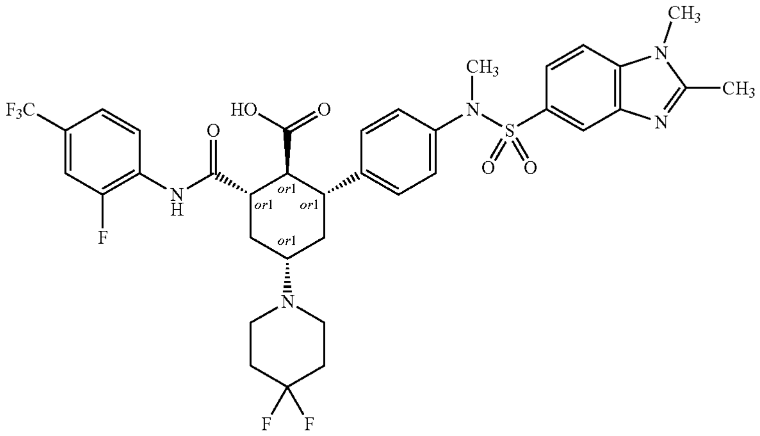 [SMILES: Cc1nc2cc(S(=O)(=O)N(C)c3ccc([C@@H]4C[C@H](N5CCC(F)(F)CC5)C[C@H](C(=O)Nc5ccc(C(F)(F)F)cc5F)[C@H]4C(=O)O)cc3)ccc2n1C]<br>ISOMER 1 |

TABLE 1-continued
| Ex. No. | Structure |
|---|---|
| 344 | 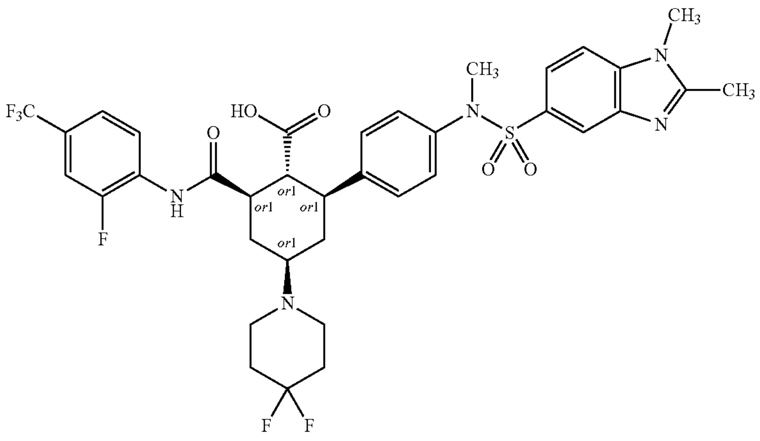 [SMILES: Cc1nc2cc(S(=O)(=O)N(C)c3ccc([C@H]4C[C@@H](N5CCC(F)(F)CC5)C[C@@H](C(=O)Nc5ccc(C(F)(F)F)cc5F)[C@@H]4C(=O)O)cc3)ccc2n1C]<br>ISOMER 2 |
| 345 | 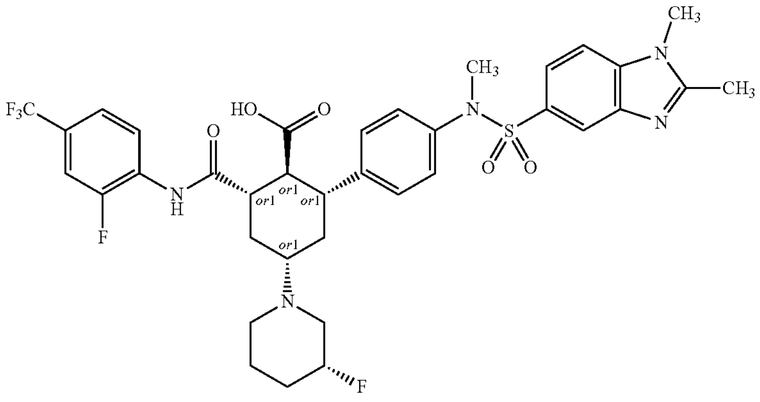 [SMILES: Cc1nc2cc(S(=O)(=O)N(C)c3ccc([C@@H]4C[C@H](N5CCC[C@@H](F)C5)C[C@H](C(=O)Nc5ccc(C(F)(F)F)cc5F)[C@H]4C(=O)O)cc3)ccc2n1C]<br>ISOMER 1 |
| 346 | 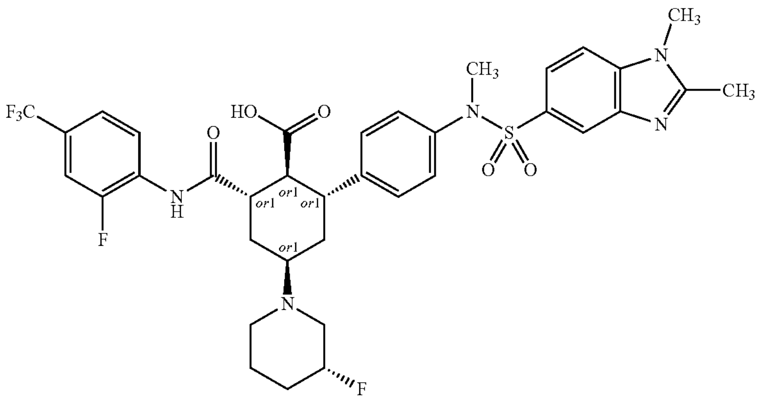 [SMILES: Cc1nc2cc(S(=O)(=O)N(C)c3ccc([C@@H]4C[C@@H](N5CCC[C@@H](F)C5)C[C@H](C(=O)Nc5ccc(C(F)(F)F)cc5F)[C@H]4C(=O)O)cc3)ccc2n1C]<br>ISOMER 1 |

TABLE 1-continued
| Ex. No. | Structure |
|---|---|
| 347 | 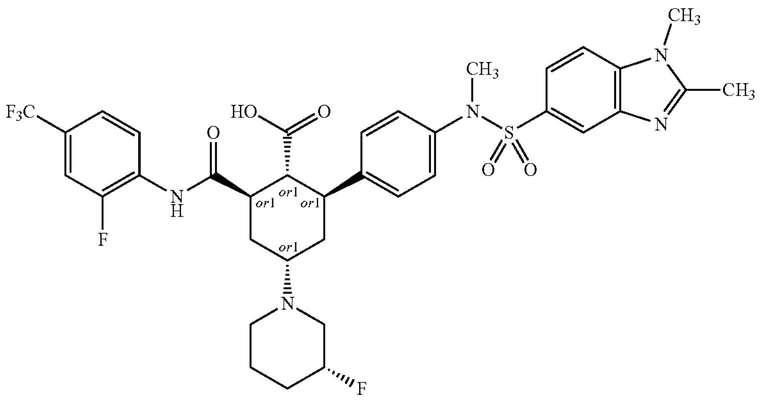 [SMILES: Cc1nc2cc(S(=O)(=O)N(C)c3ccc([C@H]4C[C@H](N5CCC[C@@H](F)C5)C[C@@H](C(=O)Nc5ccc(C(F)(F)F)cc5F)[C@@H]4C(=O)O)cc3)ccc2n1C] ISOMER 2 |
| 348 | 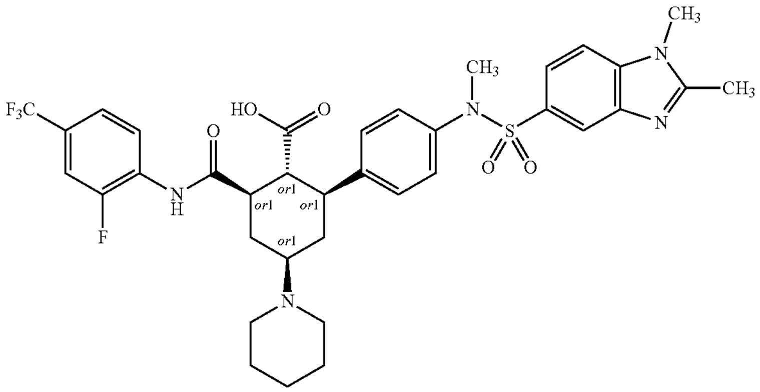 [SMILES: Cc1nc2cc(S(=O)(=O)N(C)c3ccc([C@H]4C[C@@H](N5CCCCC5)C[C@@H](C(=O)Nc5ccc(C(F)(F)F)cc5F)[C@@H]4C(=O)O)cc3)ccc2n1C] ISOMER 2 |
| 349 | 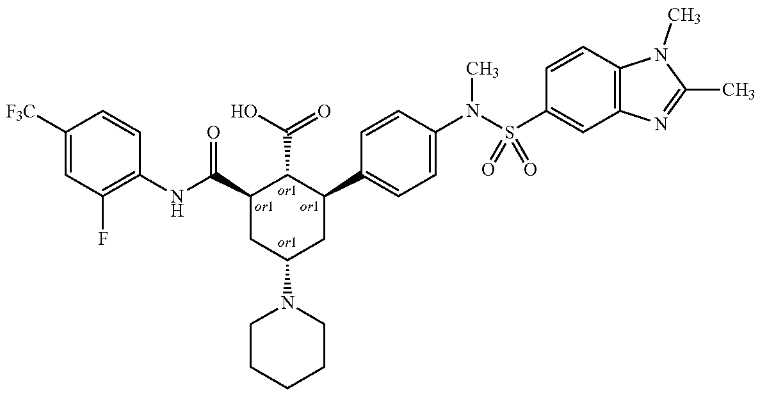 [SMILES: Cc1nc2cc(S(=O)(=O)N(C)c3ccc([C@H]4C[C@H](N5CCCCC5)C[C@@H](C(=O)Nc5ccc(C(F)(F)F)cc5F)[C@@H]4C(=O)O)cc3)ccc2n1C] ISOMER 2 |

TABLE 1-continued
| Ex. No. | Structure |
|---|---|
| 350 | 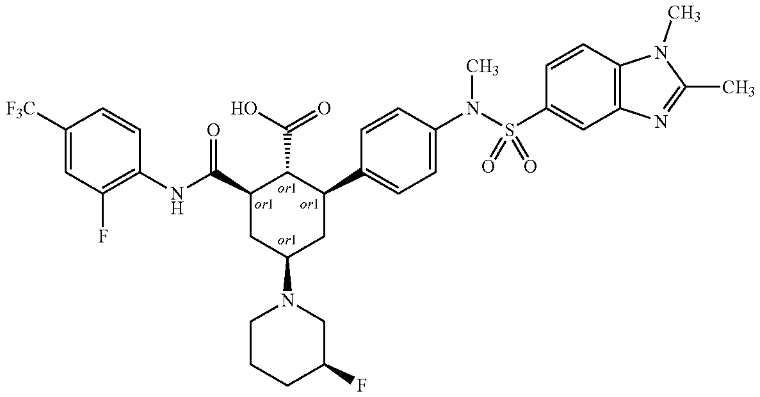 [SMILES: Cc1nc2cc(S(=O)(=O)N(C)c3ccc([C@H]4C[C@@H](N5CCC[C@H](F)C5)C[C@@H](C(=O)Nc5ccc(C(F)(F)F)cc5F)[C@@H]4C(=O)O)cc3)ccc2n1C]<br>ISOMER 2 |
| 351 | 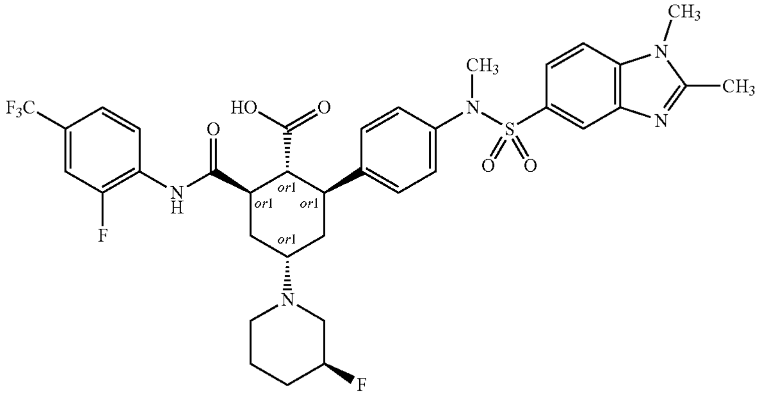 [SMILES: Cc1nc2cc(S(=O)(=O)N(C)c3ccc([C@H]4C[C@H](N5CCC[C@H](F)C5)C[C@@H](C(=O)Nc5ccc(C(F)(F)F)cc5F)[C@@H]4C(=O)O)cc3)ccc2n1C]<br>ISOMER 2 |
| 352 | 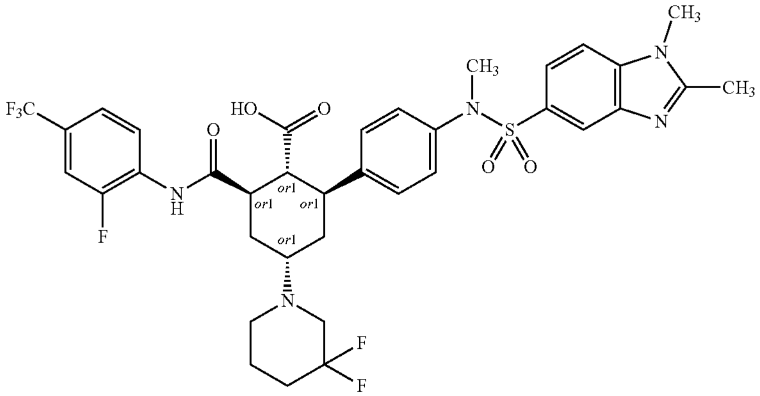 [SMILES: Cc1nc2cc(S(=O)(=O)N(C)c3ccc([C@H]4C[C@H](N5CCCC(F)(F)C5)C[C@@H](C(=O)Nc5ccc(C(F)(F)F)cc5F)[C@@H]4C(=O)O)cc3)ccc2n1C]<br>ISOMER 1 |

TABLE 1-continued
| Ex. No. | Structure |
|---|---|
| 353 | 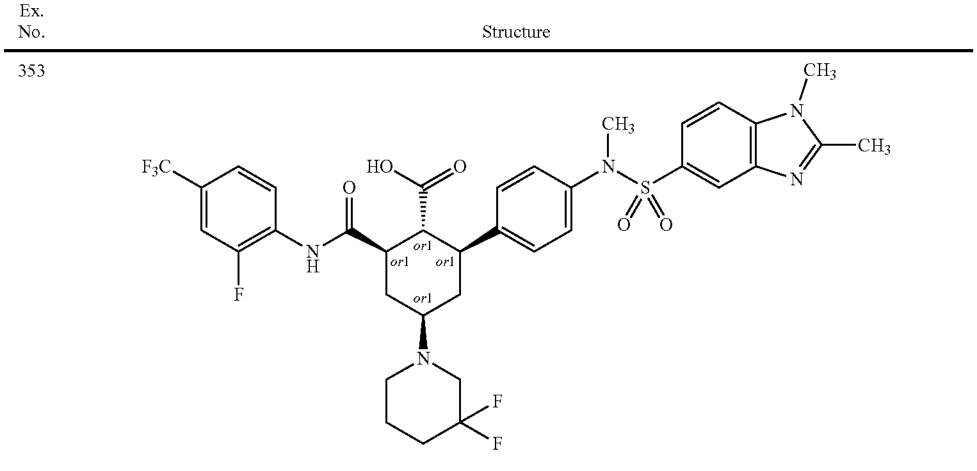 ISOMER 1 |
| 354 | 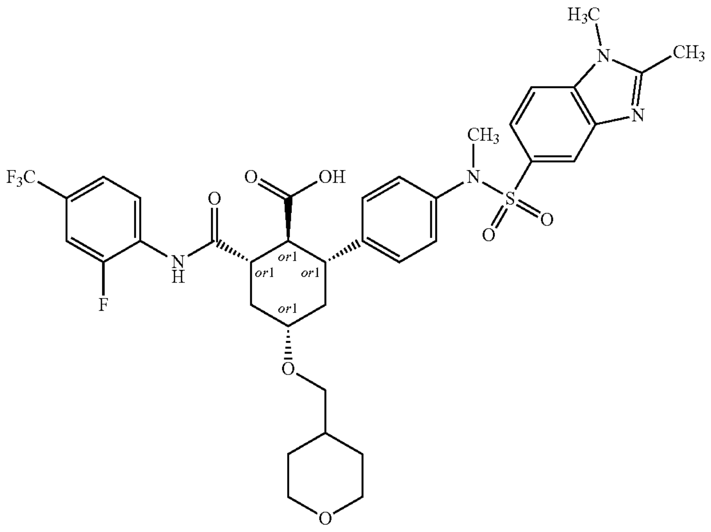 [SMILES: Cc1nc2cc(S(=O)(=O)N(C)c3ccc([C@@H]4C[C@H](OCC5CCOCC5)C[C@H](C(=O)Nc5ccc(C(F)(F)F)cc5F)[C@H]4C(=O)O)cc3)ccc2n1C] ISOMER 1 |
| 355 | 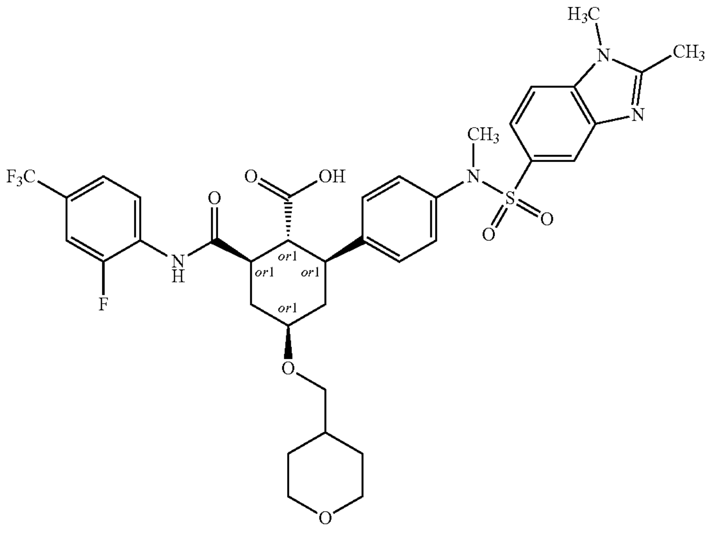 [SMILES: Cc1nc2cc(S(=O)(=O)N(C)c3ccc([C@H]4C[C@@H](OCC5CCOCC5)C[C@@H](C(=O)Nc5ccc(C(F)(F)F)cc5F)[C@@H]4C(=O)O)cc3)ccc2n1C] ISOMER 2 |

TABLE 1-continued
| Ex. No. | Structure |
|---|---|
| 356 | 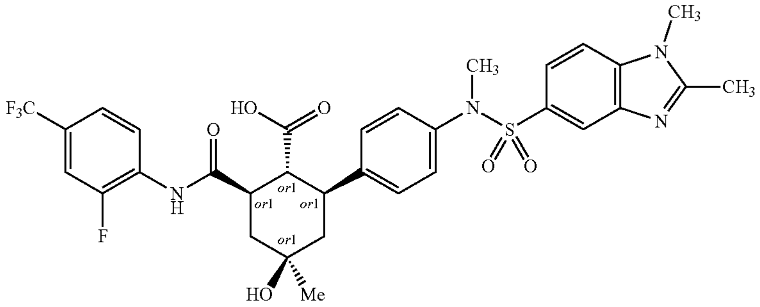 [SMILES: Cc1nc2cc(S(=O)(=O)N(C)c3ccc([C@H]4C[C@@](C)(O)C[C@@H](C(=O)Nc5ccc(C(F)(F)F)cc5F)[C@@H]4C(=O)O)cc3)ccc2n1C] |
| 357 | 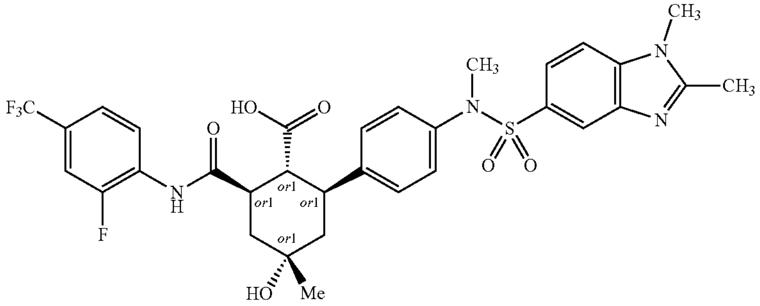 [SMILES: Cc1nc2cc(S(=O)(=O)N(C)c3ccc([C@H]4C[C@](C)(O)C[C@@H](C(=O)Nc5ccc(C(F)(F)F)cc5F)[C@@H]4C(=O)O)cc3)ccc2n1C] |
| 358 | 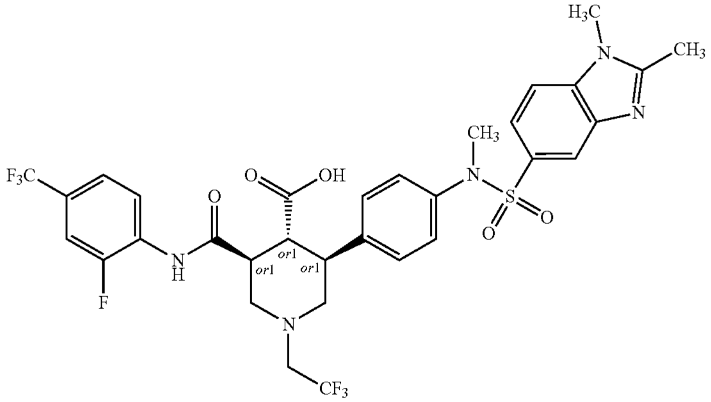 [SMILES: Cc1nc2cc(S(=O)(=O)N(C)c3ccc([C@H]4CN(CC(F)(F)F)C[C@@H](C(=O)Nc5ccc(C(F)(F)F)cc5F)[C@@H]4C(=O)O)cc3)ccc2n1C] ISOMER 1 |
| 359 | 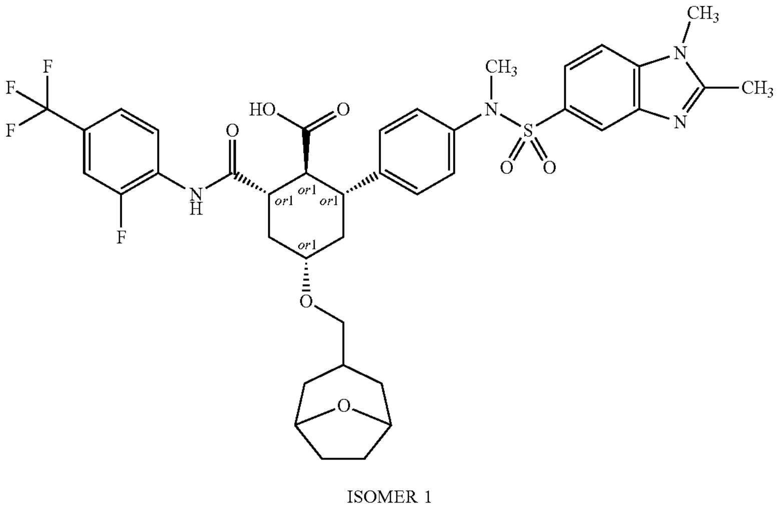 ISOMER 1 |

TABLE 1-continued
| Ex. No. | Structure |
|---|---|
| 360 | 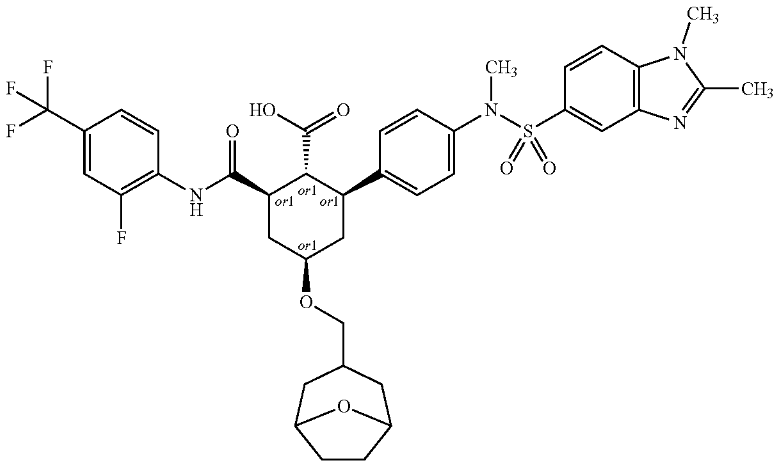 [SMILES: Cc1nc2cc(S(=O)(=O)N(C)c3ccc([C@H]4C[C@@H](OCC5CC6CCC(C5)O6)C[C@@H](C(=O)Nc5ccc(C(F)(F)F)cc5F)[C@@H]4C(=O)O)cc3)ccc2n1C] ISOMER 2 |
| 361 | 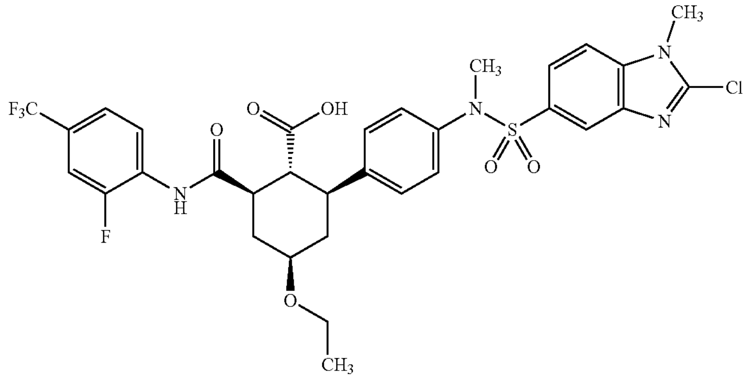 [SMILES: CCO[C@@H]1C[C@H](c2ccc(N(C)S(=O)(=O)c3ccc4c(c3)nc(Cl)n4C)cc2)[C@@H](C(=O)O)[C@H](C(=O)Nc2ccc(C(F)(F)F)cc2F)C1] ISOMER 1 |
| 362 | 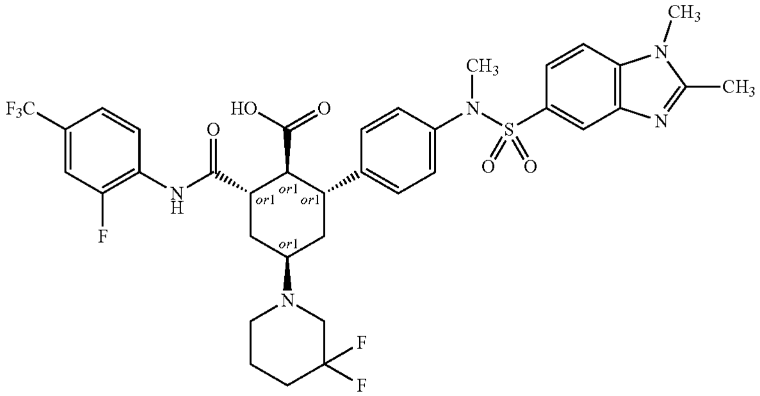 [SMILES: Cc1nc2cc(S(=O)(=O)N(C)c3ccc([C@@H]4C[C@@H](N5CCCC(F)(F)C5)C[C@H](C(=O)Nc5ccc(C(F)(F)F)cc5F)[C@H]4C(=O)O)cc3)ccc2n1C] ISOMER 1 |

TABLE 1-continued
| Ex. No. | Structure |
| --- | --- |
| 363 | 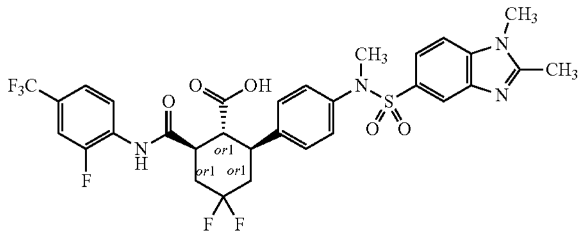 [SMILES: Cc1nc2cc(S(=O)(=O)N(C)c3ccc([C@H]4CC(F)(F)C[C@@H](C(=O)Nc5ccc(C(F)(F)F)cc5F)[C@@H]4C(=O)O)cc3)ccc2n1C] ISOMER 1 |
| 364 | 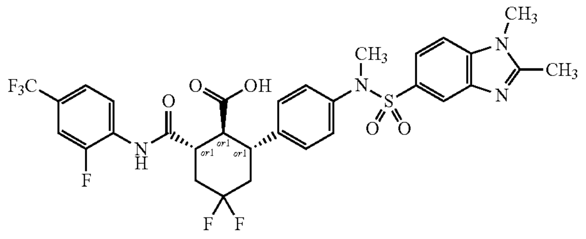 [SMILES: Cc1nc2cc(S(=O)(=O)N(C)c3ccc([C@@H]4CC(F)(F)C[C@H](C(=O)Nc5ccc(C(F)(F)F)cc5F)[C@H]4C(=O)O)cc3)ccc2n1C] ISOMER 2 |
| 365 | 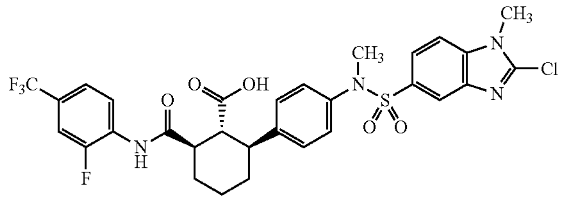 [SMILES: CN(c1ccc([C@H]2CCC[C@@H](C(=O)Nc3ccc(C(F)(F)F)cc3F)[C@@H]2C(=O)O)cc1)S(=O)(=O)c1ccc2c(c1)nc(Cl)n2C] |
| 366 | 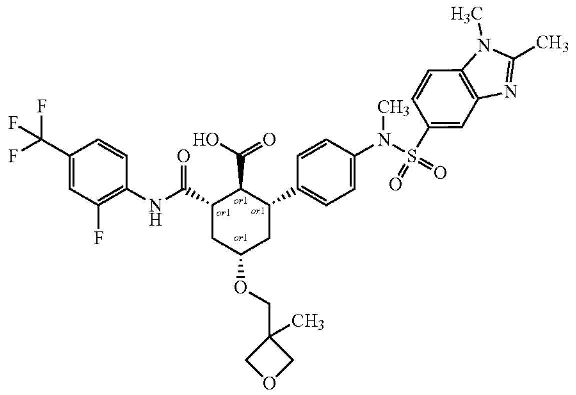 [SMILES: Cc1nc2cc(S(=O)(=O)N(C)c3ccc([C@@H]4C[C@H](OCC5(C)COC5)C[C@H](C(=O)Nc5ccc(C(F)(F)F)cc5F)[C@H]4C(=O)O)cc3)ccc2n1C] ISOMER 3 |

TABLE 1-continued
| Ex. No. | Structure |
|---|---|
| 367 | 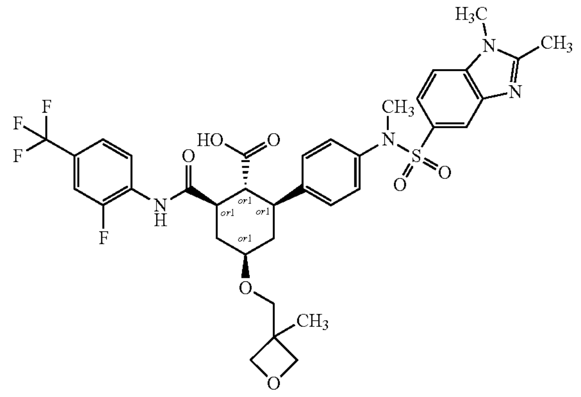 [SMILES: Cc1nc2cc(S(=O)(=O)N(C)c3ccc([C@H]4C[C@@H](OCC5(C)COC5)C[C@@H](C(=O)Nc5ccc(C(F)(F)F)cc5F)[C@@H]4C(=O)O)cc3)ccc2n1C] ISOMER 4 |
| 368 | 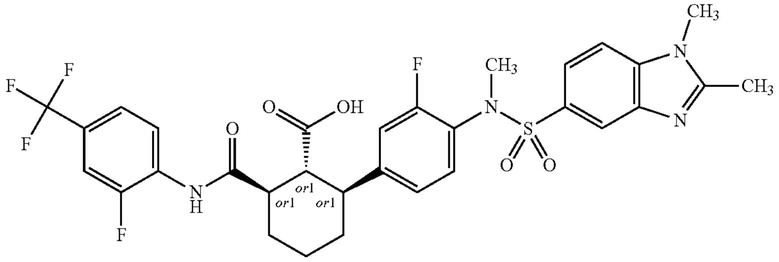 [SMILES: Cc1nc2cc(S(=O)(=O)N(C)c3ccc([C@H]4CCC[C@@H](C(=O)Nc5ccc(C(F)(F)F)cc5F)[C@@H]4C(=O)O)cc3F)ccc2n1C] ISOMER 1 |
| 369 | 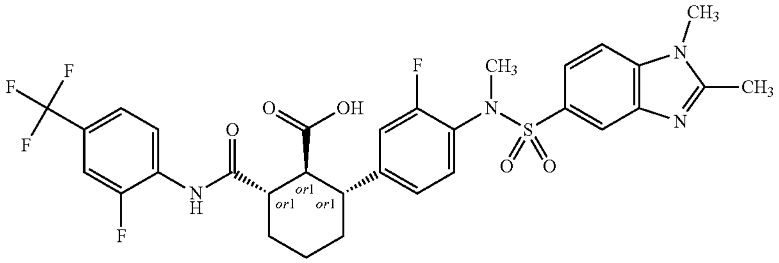 [SMILES: Cc1nc2cc(S(=O)(=O)N(C)c3ccc([C@@H]4CCC[C@H](C(=O)Nc5ccc(C(F)(F)F)cc5F)[C@H]4C(=O)O)cc3F)ccc2n1C] ISOMER 2 |
| 370 | 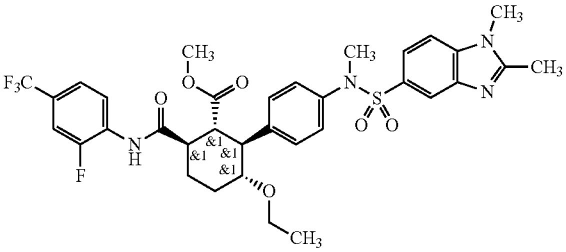 [SMILES: CCO[C@@H]1CC[C@@H](C(=O)Nc2ccc(C(F)(F)F)cc2F)[C@H](C(=O)OC)[C@H]1c1ccc(N(C)S(=O)(=O)c2ccc3c(c2)nc(C)n3C)cc1] |

TABLE 1-continued
| Ex. No. | Structure |
|---|---|
| 371 | 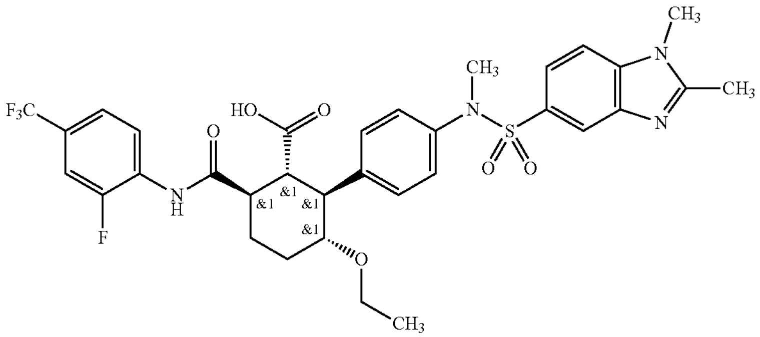 [SMILES: CCO[C@@H]1CC[C@@H](C(=O)Nc2ccc(C(F)(F)F)cc2F)[C@H](C(=O)O)[C@H]1c1ccc(N(C)S(=O)(=O)c2ccc3c(c2)nc(C)n3C)cc1] |
| 372 | 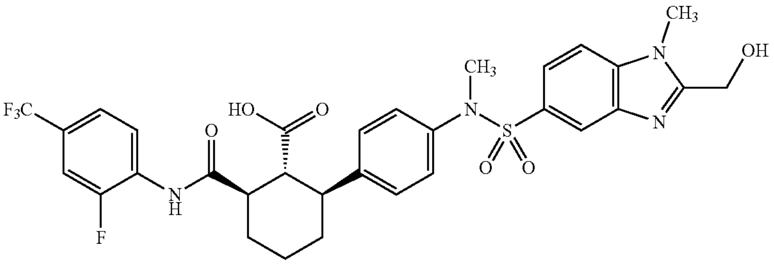 [SMILES: CN(c1ccc([C@H]2CCC[C@@H](C(=O)Nc3ccc(C(F)(F)F)cc3F)[C@@H]2C(=O)O)cc1)S(=O)(=O)c1ccc2c(c1)nc(CO)n2C] |
| 373 | 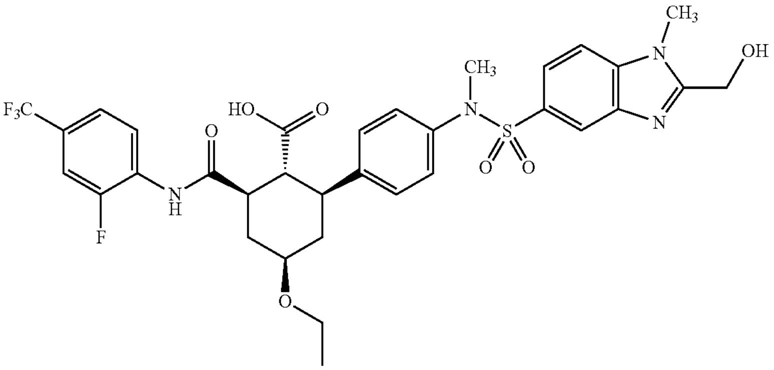 [SMILES: CCO[C@@H]1C[C@H](c2ccc(N(C)S(=O)(=O)c3ccc4c(c3)nc(CO)n4C)cc2)[C@@H](C(=O)O)[C@H](C(=O)Nc2ccc(C(F)(F)F)cc2F)C1] |
| 374 | 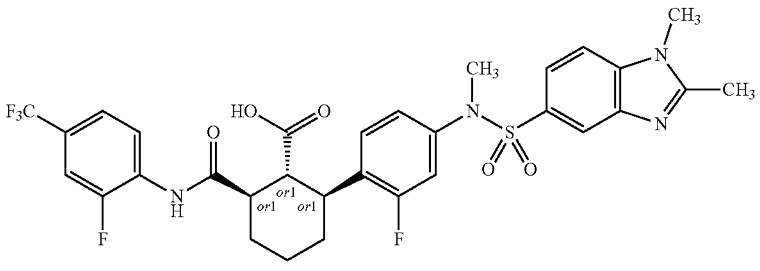 [SMILES: Cc1nc2cc(S(=O)(=O)N(C)c3ccc([C@H]4CCC[C@@H](C(=O)Nc5ccc(C(F)(F)F)cc5F)[C@@H]4C(=O)O)c(F)c3)ccc2n1C] ISOMER 1 |

TABLE 1-continued
| Ex. No. | Structure |
|---|---|
| 375 | 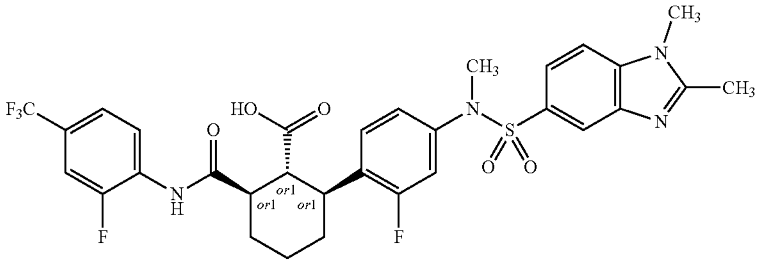 [SMILES: Cc1nc2cc(S(=O)(=O)N(C)c3ccc([C@H]4CCC[C@@H](C(=O)Nc5ccc(C(F)(F)F)cc5F)[C@@H]4C(=O)O)c(F)c3)ccc2n1C] ISOMER 1 |
| 376 | 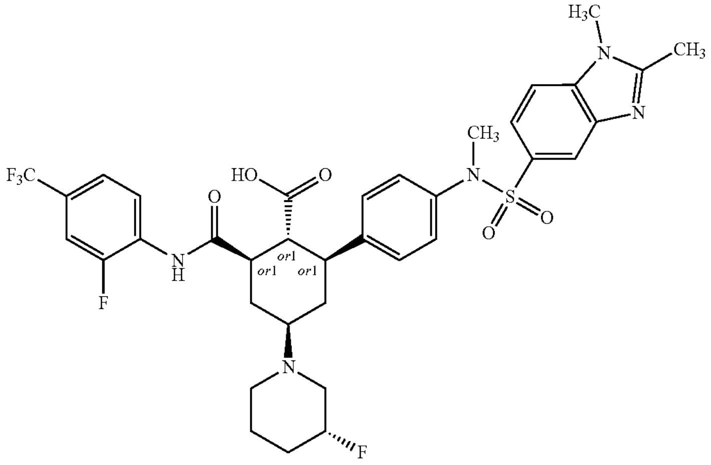 [SMILES: Cc1nc2cc(S(=O)(=O)N(C)c3ccc([C@H]4C[C@@H](N5CCC[C@@H](F)C5)C[C@@H](C(=O)Nc5ccc(C(F)(F)F)cc5F)[C@@H]4C(=O)O)cc3)ccc2n1C] |
| 377 | 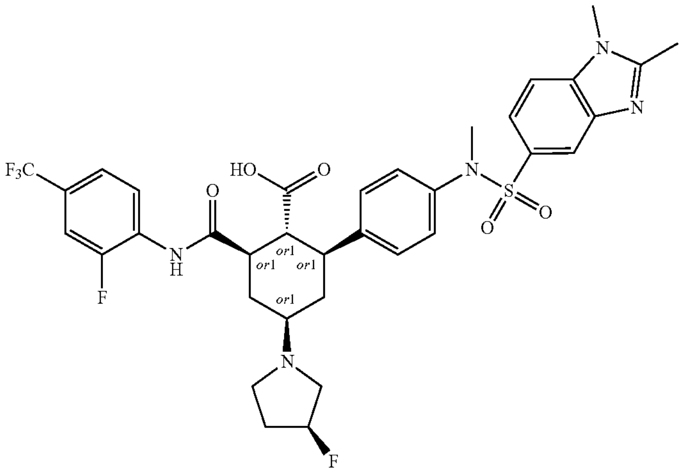 [SMILES: Cc1nc2cc(S(=O)(=O)N(C)c3ccc([C@H]4C[C@@H](N5CC[C@H](F)C5)C[C@@H](C(=O)Nc5ccc(C(F)(F)F)cc5F)[C@@H]4C(=O)O)cc3)ccc2n1C] ISOMER 1 |

TABLE 1-continued
| Ex. No. | Structure |
|---|---|
| 378 | 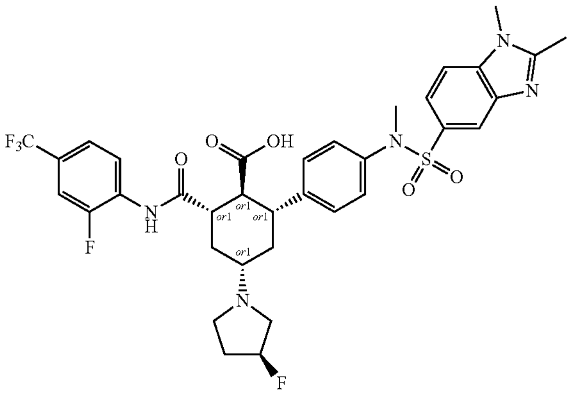 [SMILES: Cc1nc2cc(S(=O)(=O)N(C)c3ccc([C@@H]4C[C@H](N5CC[C@H](F)C5)C[C@H](C(=O)Nc5ccc(C(F)(F)F)cc5F)[C@H]4C(=O)O)cc3)ccc2n1C] ISOMER 2 |
| 379 | 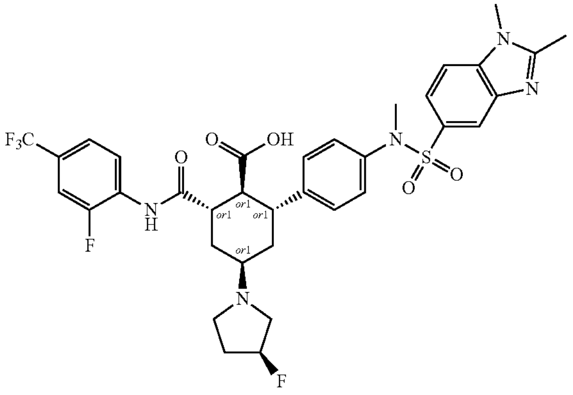 [SMILES: Cc1nc2cc(S(=O)(=O)N(C)c3ccc([C@@H]4C[C@@H](N5CC[C@H](F)C5)C[C@H](C(=O)Nc5ccc(C(F)(F)F)cc5F)[C@H]4C(=O)O)cc3)ccc2n1C] ISOMER 1 |
| 380 | 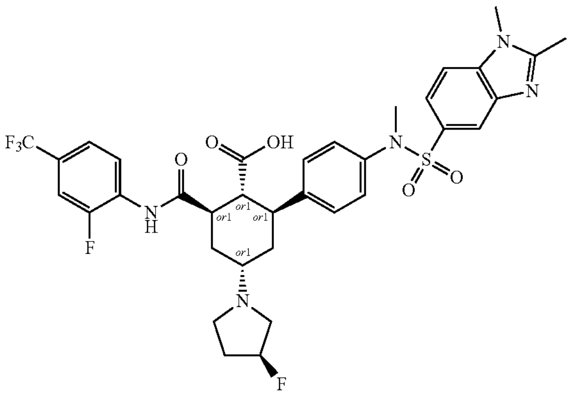 [SMILES: Cc1nc2cc(S(=O)(=O)N(C)c3ccc([C@H]4C[C@H](N5CC[C@H](F)C5)C[C@@H](C(=O)Nc5ccc(C(F)(F)F)cc5F)[C@@H]4C(=O)O)cc3)ccc2n1C] ISOMER 2 |

TABLE 1-continued
| Ex. No. | Structure |
|---|---|
| 381 | 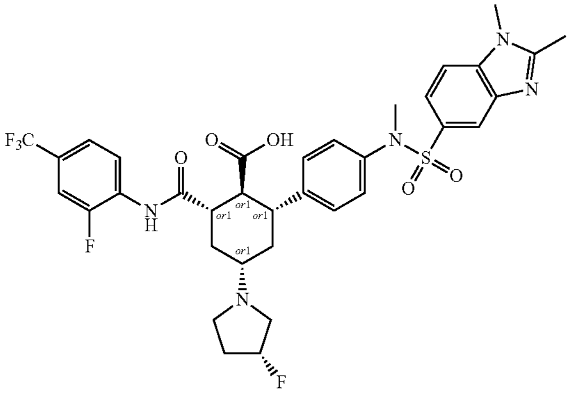 [SMILES: Cc1nc2cc(S(=O)(=O)N(C)c3ccc([C@@H]4C[C@H](N5CC[C@@H](F)C5)C[C@H](C(=O)Nc5ccc(C(F)(F)F)cc5F)[C@H]4C(=O)O)cc3)ccc2n1C] ISOMER 1 |
| 382 | 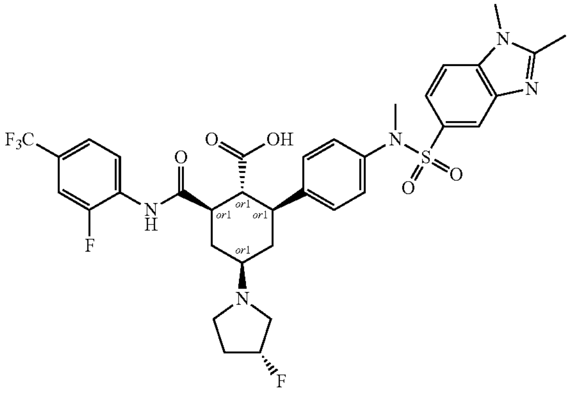 [SMILES: Cc1nc2cc(S(=O)(=O)N(C)c3ccc([C@H]4C[C@@H](N5CC[C@@H](F)C5)C[C@@H](C(=O)Nc5ccc(C(F)(F)F)cc5F)[C@@H]4C(=O)O)cc3)ccc2n1C] ISOMER 2 |
| 383 | 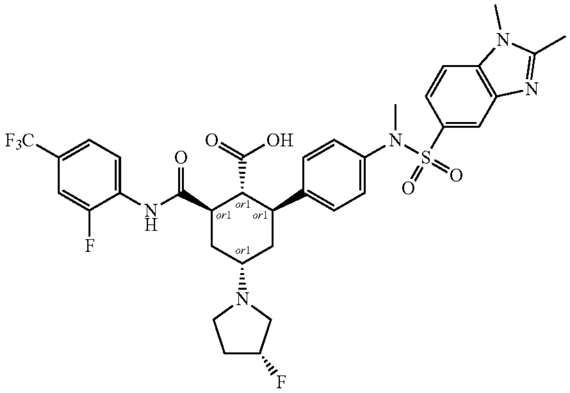 [SMILES: Cc1nc2cc(S(=O)(=O)N(C)c3ccc([C@H]4C[C@H](N5CC[C@@H](F)C5)C[C@@H](C(=O)Nc5ccc(C(F)(F)F)cc5F)[C@@H]4C(=O)O)cc3)ccc2n1C] ISOMER 1 |

TABLE 1-continued
| Ex. No. | Structure |
|---|---|
| 384 | 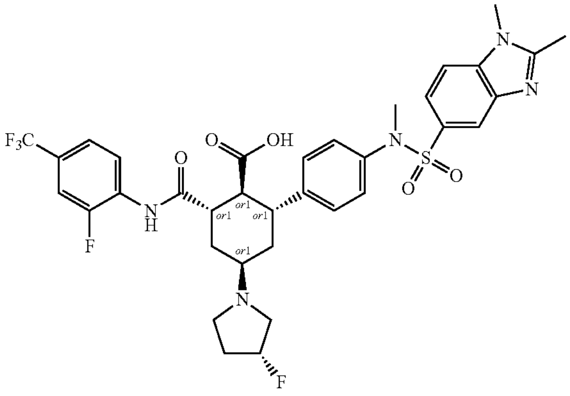 [SMILES: Cc1nc2cc(S(=O)(=O)N(C)c3ccc([C@@H]4C[C@@H](N5CC[C@@H](F)C5)C[C@H](C(=O)Nc5ccc(C(F)(F)F)cc5F)[C@H]4C(=O)O)cc3)ccc2n1C] ISOMER 2 |
| 385 | 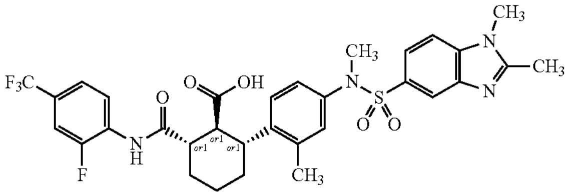 [SMILES: Cc1cc(N(C)S(=O)(=O)c2ccc3c(c2)nc(C)n3C)ccc1[C@@H]1CCC[C@H](C(=O)Nc2ccc(C(F)(F)F)cc2F)[C@H]1C(=O)O] ISOMER 1 |
| 386 | 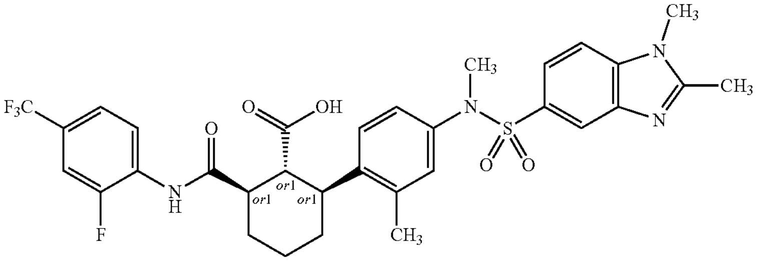 [SMILES: Cc1cc(N(C)S(=O)(=O)c2ccc3c(c2)nc(C)n3C)ccc1[C@H]1CCC[C@@H](C(=O)Nc2ccc(C(F)(F)F)cc2F)[C@@H]1C(=O)O] ISOMER 2 |
| 387 | 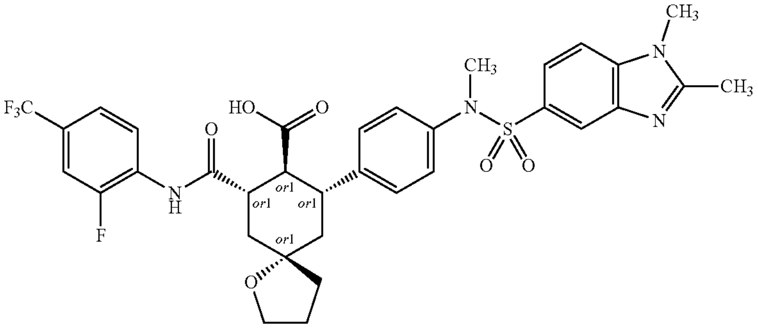 [SMILES: Cc1nc2cc(S(=O)(=O)N(C)c3ccc([C@@H]4C[C@@]5(CCCO5)C[C@H](C(=O)Nc5ccc(C(F)(F)F)cc5F)[C@H]4C(=O)O)cc3)ccc2n1C] ISOMER 1 |

TABLE 1-continued
| Ex. No. | Structure |
|---|---|
| 388 | 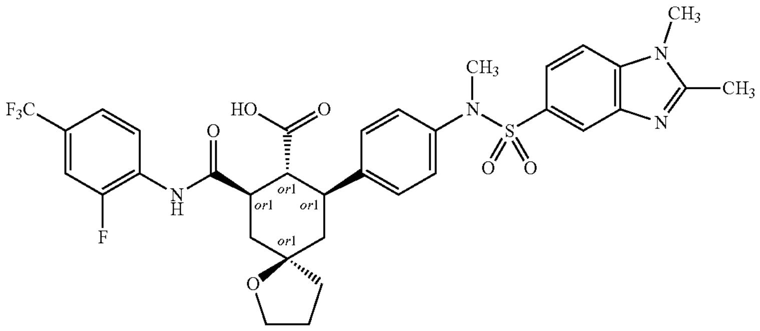 [SMILES: Cc1nc2cc(S(=O)(=O)N(C)c3ccc([C@H]4C[C@]5(CCCO5)C[C@@H](C(=O)Nc5ccc(C(F)(F)F)cc5F)[C@@H]4C(=O)O)cc3)ccc2n1C]<br>ISOMER 2 |
| 389 | 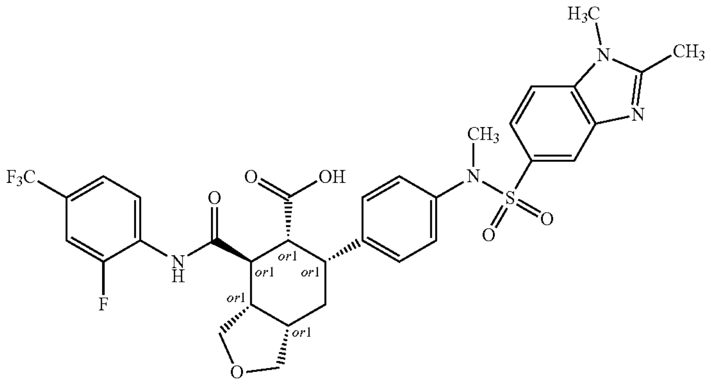 [SMILES: Cc1nc2cc(S(=O)(=O)N(C)c3ccc([C@@H]4C[C@@H]5COC[C@@H]5[C@@H](C(=O)Nc5ccc(C(F)(F)F)cc5F)[C@@H]4C(=O)O)cc3)ccc2n1C]<br>ISOMER 1 |
| 390 | 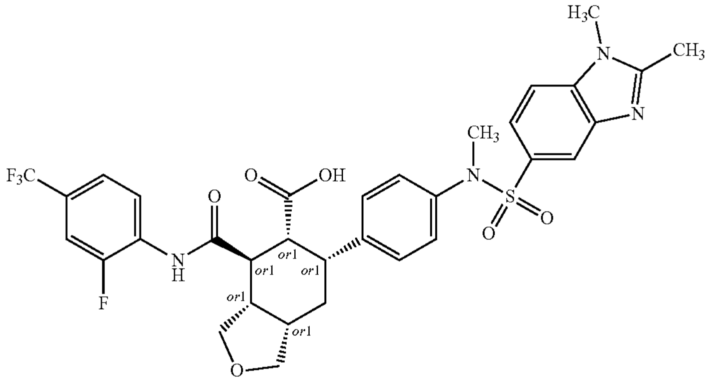 [SMILES: Cc1nc2cc(S(=O)(=O)N(C)c3ccc([C@@H]4C[C@@H]5COC[C@@H]5[C@@H](C(=O)Nc5ccc(C(F)(F)F)cc5F)[C@@H]4C(=O)O)cc3)ccc2n1C]<br>ISOMER 2 |

TABLE 1-continued
| Ex. No. | Structure |
|---|---|
| 391 | 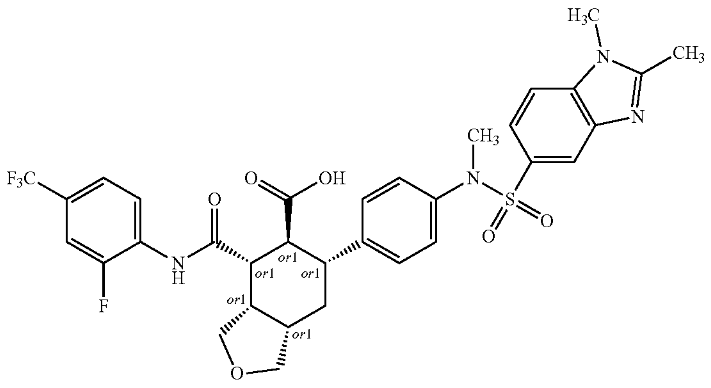 [SMILES: Cc1nc2cc(S(=O)(=O)N(C)c3ccc([C@@H]4C[C@@H]5COC[C@@H]5[C@H](C(=O)Nc5ccc(C(F)(F)F)cc5F)[C@H]4C(=O)O)cc3)ccc2n1C] ISOMER 1 |
| 392 | 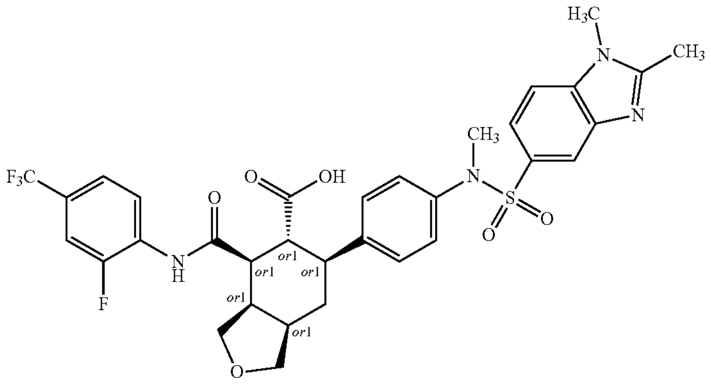 [SMILES: Cc1nc2cc(S(=O)(=O)N(C)c3ccc([C@H]4C[C@H]5COC[C@H]5[C@@H](C(=O)Nc5ccc(C(F)(F)F)cc5F)[C@@H]4C(=O)O)cc3)ccc2n1C] ISOMER 2 |
| 393 | 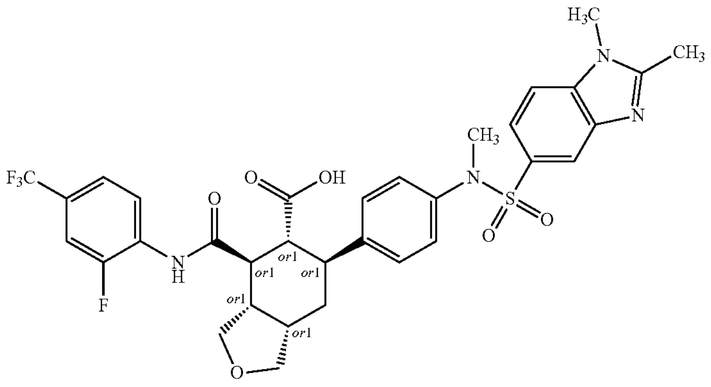 [SMILES: Cc1nc2cc(S(=O)(=O)N(C)c3ccc([C@H]4C[C@@H]5COC[C@@H]5[C@@H](C(=O)Nc5ccc(C(F)(F)F)cc5F)[C@@H]4C(=O)O)cc3)ccc2n1C] ISOMER 1 |

TABLE 1-continued
| Ex. No. | Structure |
|---|---|
| 394 | 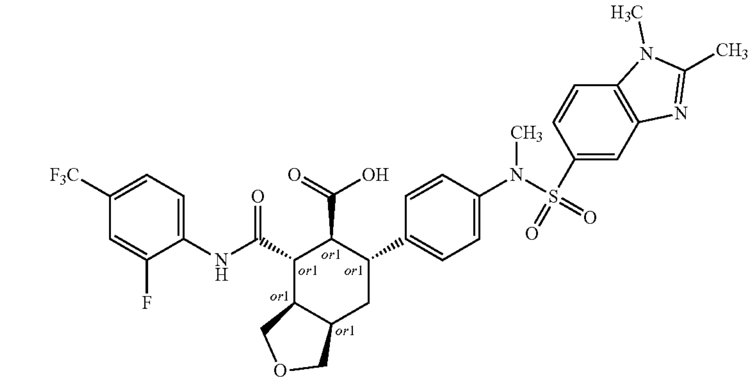 [SMILES: Cc1nc2cc(S(=O)(=O)N(C)c3ccc([C@@H]4C[C@H]5COC[C@H]5[C@H](C(=O)Nc5ccc(C(F)(F)F)cc5F)[C@H]4C(=O)O)cc3)ccc2n1C] ISOMER 2 |
| 395 | 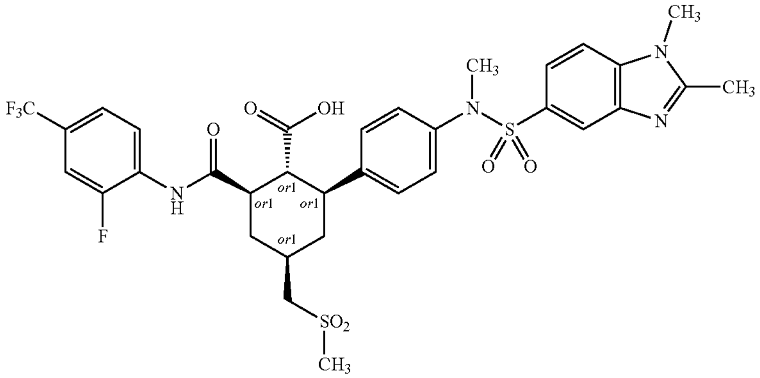 [SMILES: Cc1nc2cc(S(=O)(=O)N(C)c3ccc([C@H]4C[C@@H](CS(C)(=O)=O)C[C@@H](C(=O)Nc5ccc(C(F)(F)F)cc5F)[C@@H]4C(=O)O)cc3)ccc2n1C] |
| 396 | 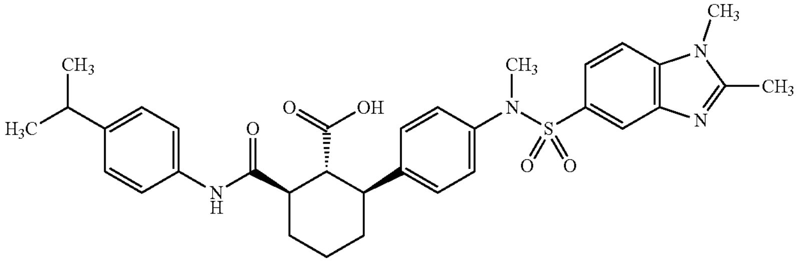 [SMILES: Cc1nc2cc(S(=O)(=O)N(C)c3ccc([C@H]4CCC[C@@H](C(=O)Nc5ccc(C(C)C)cc5)[C@@H]4C(=O)O)cc3)ccc2n1C] |
| 397 | 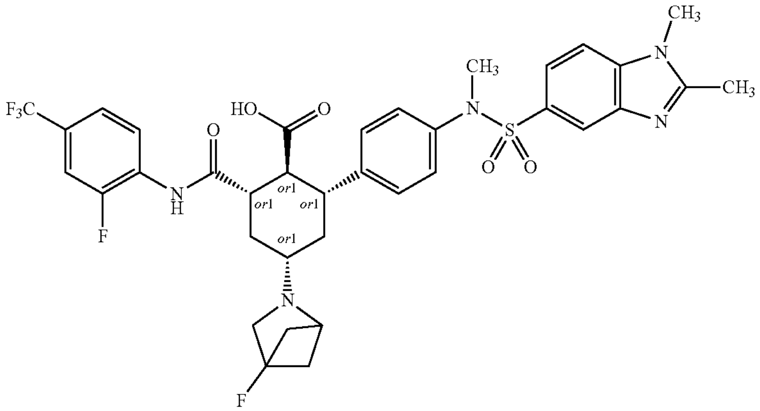 [SMILES: Cc1nc2cc(S(=O)(=O)N(C)c3ccc([C@@H]4C[C@H](N5CC6(F)CC5C6)C[C@H](C(=O)Nc5ccc(C(F)(F)F)cc5F)[C@H]4C(=O)O)cc3)ccc2n1C] |

TABLE 1-continued

| Ex. No. | Structure |
|---|---|
| 398 | 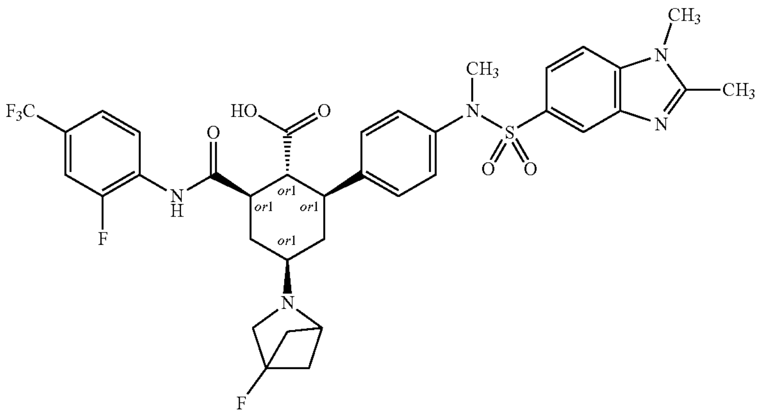 [SMILES: Cc1nc2cc(S(=O)(=O)N(C)c3ccc([C@H]4C[C@@H](N5CC6(F)CC5C6)C[C@@H](C(=O)Nc5ccc(C(F)(F)F)cc5F)[C@@H]4C(=O)O)cc3)ccc2n1C] |
| 399 | 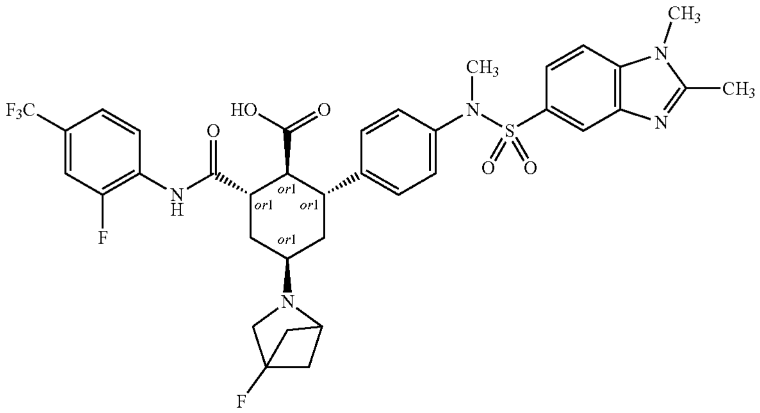 [SMILES: Cc1nc2cc(S(=O)(=O)N(C)c3ccc([C@@H]4C[C@@H](N5CC6(F)CC5C6)C[C@H](C(=O)Nc5ccc(C(F)(F)F)cc5F)[C@H]4C(=O)O)cc3)ccc2n1C] |
| 400 | 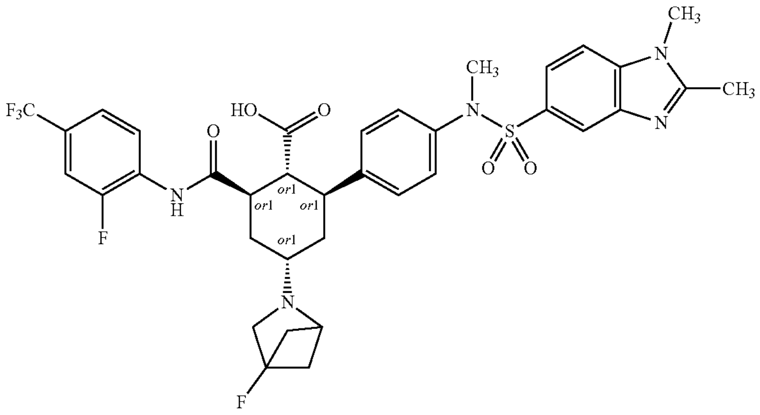 [SMILES: Cc1nc2cc(S(=O)(=O)N(C)c3ccc([C@H]4C[C@H](N5CC6(F)CC5C6)C[C@@H](C(=O)Nc5ccc(C(F)(F)F)cc5F)[C@@H]4C(=O)O)cc3)ccc2n1C] |

In another aspect, the present disclosure provides methods of making a compound or pharmaceutically acceptable salt thereof as disclosed herein and chemical intermediate for making the compound.

In another aspect, the present disclosure provides a pharmaceutical composition comprising a) a compound or pharmaceutically acceptable salt thereof of the invention as disclosed herein and b) a pharmaceutically acceptable excipient. The excipient(s) must be acceptable in the sense of being compatible with the other ingredients of the composition and not deleterious to the recipient thereof.

In another aspect, the present disclosure provides a compound or pharmaceutically acceptable salt thereof of the invention as disclosed herein, for use in therapy.

In another aspect, the present disclosure provides a compound or pharmaceutically acceptable salt thereof of the invention as disclosed herein, for use in the treatment of cancer.

In an embodiment, the cancer is characterised by MSI-H and/or dMMR.

In an embodiment, the cancer is treatable by inhibition of WRN.

In another aspect, the present disclosure provides a method for treating a cancer in a subject in need thereof comprising administering to said subject a therapeutically effective amount of a compound or pharmaceutically acceptable salt thereof of the invention as disclosed herein.

In another aspect, provided is a method for treating a cancer treatable by inhibition of WRN in a patient comprising administering to the patient a therapeutically effective amount of a compound of the present disclosure or a pharmaceutically acceptable salt thereof. In an embodiment, the patient is in recognized need of such treatment. In an embodiment, the compound or a pharmaceutically acceptable salt thereof of the invention as disclosed herein is administered in a pharmaceutical composition.

In another aspect, the present disclosure provides a method of treating a cancer characterized by MSI-H and/or dMMR in a patient comprising administering to the patient, a therapeutically effective amount of a compound of the present invention as disclosed herein, or a pharmaceutically acceptable salt thereof. In an embodiment, the patient is in recognized need of such treatment. In an embodiment, the compound of the present disclosure or a pharmaceutically acceptable salt thereof is administered in a pharmaceutical composition.

In an embodiment, the cancer is characterized by MSI-L or MSI-H according to any method known in the art. For example, a cancer characterized by MSI-L or MSI-H can comprise one or more MSI markers (MSI-L), or preferably two or more MSI markers (MSI-H), in each case selected from the group consisting of BAT25, BAT26, D2S123, D5S346, and D17S250. In an embodiment, the cancer is characterized by dMMR and comprises a mutation that impairs DNA mismatch repair, preferably the cancer comprises a mutation in a MutS homolog and/or a mutation in a MutL homolog. In a subembodiment, the MutS homolog is selected from the group consisting of MSH2, MSH3, and MSH6, and the MutL homolog is selected from the group consisting of MLH1, MLH3, PMS1, and PMS2, preferably a mutation in MLH1, MSH2, and/or PMS2.

In another aspect, the present disclosure provides a pharmaceutical composition comprising a compound of the invention as disclosed herein, or a pharmaceutically acceptable salt thereof, and at least one pharmaceutically acceptable excipient.

In another aspect, the present disclosure provides a compound of the invention as disclosed herein, or a pharmaceutically acceptable salt thereof, for use in the treatment of cancer treatable by inhibition of WRN.

In another aspect, the present disclosure provides a compound of the invention as disclosed herein, or a pharmaceutically acceptable salt thereof, for use in the treatment of cancer characterized by high MSI and/or dMMR in a patient. In an embodiment, the patient is in recognized need of such treatment. In an embodiment, the compound of the present disclosure or a pharmaceutically acceptable salt thereof is administered in a pharmaceutical composition. In an embodiment, the cancer is characterized by MSI-L or MSI-H according to any method known in the art. For example, a cancer characterized by MSI-L or MSI-H can comprise one or more MSI markers (MSI-L), or preferably two or more MSI markers (MSI-H), in each case selected from the group consisting of BAT25, BAT26, D2S123, D5S346, and D17S250. In an embodiment, the cancer is characterized by dMMR and comprises a mutation that impairs DNA mismatch repair, preferably the cancer comprises a mutation in a MutS homolog and/or a mutation in a MutL homolog. In an embodiment, the MutS homolog is selected from the group consisting of MSH2, MSH3, and MSH6, and the MutL homolog is selected from the group consisting of MLH1, MLH3, PMS1, and PMS2, preferably a mutation in MLH1, MSH2, and/or PMS2.

In another aspect, the present disclosure provides a method of treating a cancer in a patient, comprising:

(i) determining if the cancer comprises high MSI and/or dMMR; and (ii) if the cancer comprises high MSI and/or dMMR, then administering to the patient a therapeutically effective amount of a compound of the invention as disclosed herein or a pharmaceutically acceptable salt thereof.

In an embodiment, provided herein is a compound of the present disclosure, or a pharmaceutically acceptable salt thereof, effective for decreasing WRN helicase activity for use in a method of treating an individual with a proliferative disease, the method comprising determining the presence of a low microsatellite instability (MSI-L) or preferably, a high microsatellite instability (MSI-H), or a marker associated with an MSI-L or an MSI-H, in a population of proliferative cells from the individual, determining a likelihood that the individual will respond to a therapy comprising administering to the individual said compound of the present disclosure, or a pharmaceutically acceptable salt thereof, based on the determination of the presence of MSI-L or MSI-H, respectively, or a marker associated with MSI-L or MSI-H, respectively, in the population of proliferative cells, and administering to the individual said compound of the present disclosure, or a pharmaceutically acceptable salt thereof, if the individual is predicted to respond to the therapy. In some embodiments, the determination of the presence of MSI-L or MSI-H in the population of proliferative cells comprises determining the presence of one or more MSI markers (MSI-L), preferably two or more MSI markers (MSI-H), in each case selected from the group consisting of BAT25, BAT26, D2S123, D5S346, and D17S250. In some embodiments, the individual is predicted to respond to the therapy if the amount of cells in the population of proliferative cells determined to have at least one of the MSI markers (MSI-L), or preferably at least two of the MSI markers (MSI-H), respectively is above a pre-determined threshold for the proliferative disease. In some embodiments, the individual is predicted not to respond to the therapy if (a) the amount of cells in the population of proliferative cells determined to have at least one of the MSI markers (MSI-L), or preferably at least two of the MSI markers (MSI-H), respectively, below a pre-determined threshold for the proliferative disease; or (b) the population of proliferative cells is determined to have none of the MSI markers (e.g., is considered microsatellite stable (MSS)).

In an embodiment, according to any of the embodiments described above, the determination of the presence of a marker associated with MSI-H in the population of proliferative cells comprises determining the presence of a mutation that impairs DNA mismatch repair. In some embodiments, the mutation comprises a mutation in a MutS homolog and/or a mutation in a MutL homolog. In some embodiments, the MutS homolog is selected from the group consisting of MSH2, MSH3, and MSH6, and the MutL homolog is selected from the group consisting of MLH1, MLH3, PMS1, and PMS2. In some embodiments, the mutation comprises a mutation in MLH1, MSH2, and/or PMS2.

In some embodiments, according to any of the embodiments described above, the determination of the presence of a marker associated with MSI-H in the population of proliferative cells comprises determining the presence of one or more markers of DNA damage. In some embodiments, the one or more markers of DNA damage are selected from the group consisting of high p21 expression and high γH2AX expression.

In some embodiments, according to any of the embodiments described above, the individual is predicted to respond to the therapy if the amount of cells in the population of proliferative cells determined to have (i) at least one mutation that impairs DNA mismatch repair and/or (ii) at least one marker of DNA damage is above a pre-determined threshold for the proliferative disease. In some embodiments, the at least one mutation that impairs DNA mismatch repair comprises a mutation in MLH1, MSH2, and/or PMS2, and the at least one marker of DNA damage comprises high p21 expression and/or high γH2AX expression.

In some embodiments, according to any of the embodiments described above, the individual is predicted not to respond to the therapy if (a) the amount of cells in the population of proliferative cells determined to have (i) at least one mutation that impairs DNA mismatch repair and/or (ii) at least one marker of DNA damage is below a pre-determined threshold for the proliferative disease; or (b) the population of proliferative cells is determined to have no mutations that impair DNA mismatch repair and no DNA damage markers.

In another aspect, provided herein is an in vitro method for detecting a high microsatellite instability (MSI-H) and the helicase activity of WRN in an individual diagnosed with or thought to have a proliferative disease, the method comprising: (a) contacting a biological sample from the individual with one or more reagents for detecting the presence of an MSI and the helicase activity of WRN; and (b) detecting (i) the presence of an MSI-H; and (ii) the helicase activity of WRN. In some embodiments, the reagent for detecting the presence of an MSI-H in a biological sample comprises a reagent for detecting the presence of two or more MSI markers selected from the group consisting of BAT25, BAT26, D2S123, D5S346, and D17S250.

In another aspect, provided herein is an in vitro method for detecting a marker associated with a high microsatellite instability (MSI-H) and the helicase activity of WRN in an individual diagnosed with or thought to have a proliferative disease, the method comprising: (a) contacting a biological sample from the individual with one or more reagents for detecting the presence of a marker associated with an MSI-H and the helicase activity of WRN helicase; and (b) detecting (i) the presence of the marker associated with an MSI-H; and (ii) the helicase activity of WRN helicase. In some embodiments, the reagent for detecting the presence of a marker associated with an MSI-H in a biological sample comprises a reagent for detecting the presence of (i) one or more mutations that impair DNA mismatch repair and/or (ii) one or more markers of DNA damage. In some embodiments, the one or more mutations that impair DNA mismatch repair comprise a mutation in a MutS homolog and/or a mutation in a MutL homolog. In some embodiments, the MutS homolog is selected from the group consisting of MSH2, MSH3, and MSH6, and the MutL homolog is selected from the group consisting of MLH1, MLH3, PMS1, and PMS2. In some embodiments, the one or more mutations comprise a mutation in MLH1, MSH2, and/or PMS2. In some embodiments, the one or more markers of DNA damage are selected from the group consisting of high p21 expression and high γH2AX expression.

In one approach for this embodiment, the cancer can be characterized by MSI-H according to any method known in the art. For example, a cancer characterized by MSI-H can comprise two or more MSI markers selected from the group consisting of BAT25, BAT26, D2S123, D5S346, and D17S250. In an embodiment, the cancer is characterized by dMMR and comprises a mutation that impairs DNA mismatch repair, preferably the cancer comprises a mutation in a MutS homolog and/or a mutation in a MutL homolog. In an embodiment, the MutS homolog is selected from the group consisting of MSH2, MSH3, and MSH6, and the MutL homolog is selected from the group consisting of MLH1, MLH3, PMS1, and PMS2, preferably a mutation in MLH1, MSH2, and/or PMS2. In an embodiment, the cancer comprises two or more markers of DNA damage.

In an embodiment, the cancer is endometrial cancer, biliary cancer, gastric cancer, pancreatic cancer, small intestine cancer, breast cancer, prostate cancer, bladder cancer, esophageal cancer, sarcoma, retroperitoneal adenocarcinoma, small lung cancer or renal cell cancer. Preferably, the cancer is uterine corpus endometrial carcinoma, stomach adenocarcinoma, colon adenocarcinoma, rectal adenocarcinoma, prostate adenocarcinoma, adrenal cortical carcinoma, oesophageal carcinoma, liver hepatocellular carcinoma, cervical squamous cell carcinoma, head and neck squamous cell carcinoma, lung squamous cell carcinoma, kidney renal clear cell carcinoma, papillary kidney carcinoma, pancreatic cancer, urothelial bladder cancer, ovarian cancer, breast cancer, glioblastoma multiforme, or low grade glioma (see Isidro Cortes-Ciriano et. al. Nature Communication DOI: 10.1038/ncomms15180).

In another aspect, provided herein is a method of identifying WRN helicase inhibitory activity in a test compound of WRN helicase, said method comprising (i) contacting the test compound with isolated WRN enzyme in an assay buffer to form a WRN reaction pre-mixture; (ii) contacting the WRN reaction pre-mixture with a substrate mixture containing 80 uM ATP, 80 nM $dT_{50}$ (single-stranded DNA (ssDNA) containing 50 thymine bases), 200 uM NADH, 4 mM PEP, 10 U/mL lactate dehydrogenase and 20 U/mL pyruvate kinase to form a WRN reaction mixture; and (iii) measuring absorbance (λ=340 nm) of the WRN reaction mixture, wherein said method further comprises performing steps (i)-(iii) with a positive control sample represented by a compound of the present disclosure.

Pharmaceutical Composition

The compounds of Formula (I), or a pharmaceutically acceptable salt thereof, provided herein may be in the form of compositions suitable for administration to a subject. In general, such compositions are pharmaceutical compositions comprising a compound of Formula (I) or a pharmaceutically acceptable salt thereof and one or more pharmaceutically acceptable excipients. The pharmaceutical compositions may be used in the methods disclosed herein; thus, for example, the pharmaceutical compositions can be administered ex vivo or in vivo to a subject in order to practice the therapeutic methods and uses described herein.

The pharmaceutical compositions can be formulated to be compatible with the intended method or route of administration; exemplary routes of administration are set forth herein. Furthermore, the pharmaceutical compositions may be used in combination with other therapeutically active agents or compounds as described herein in order to treat the diseases, disorders and conditions contemplated by the present disclosure.

The pharmaceutical compositions containing the active ingredient (e.g., a compound of Formula (I), a pharmaceutically acceptable salt thereof) may be in a form suitable for oral use, for example, as tablets, capsules, troches, lozenges, aqueous or oily suspensions, dispersible powders or granules, emulsions, hard or soft capsules, or syrups, solutions, microbeads or elixirs. Pharmaceutical compositions intended for oral use may be prepared according to any method known to the art for the manufacture of pharmaceutical compositions, and such compositions may contain one or more agents such as, for example, sweetening agents, flavoring agents, coloring agents and preserving agents in order to provide pharmaceutically elegant and palatable preparations. Tablets and/or capsules contain the active ingredient in admixture with non-toxic pharmaceutically acceptable excipients which are suitable for the manufacture of tablets and/or capsules. These excipients may be, for example, diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc.

The pharmaceutical compositions typically comprise a therapeutically effective amount of a compound of Formula (I), or a pharmaceutically acceptable salt thereof, and one or more pharmaceutically acceptable excipient. Suitable pharmaceutically acceptable excipients include, but are not limited to, antioxidants (e.g., ascorbic acid and sodium bisulfate), preservatives (e.g., benzyl alcohol, methyl parabens, ethyl or n-propyl, p-hydroxybenzoate), emulsifying agents, suspending agents, dispersing agents, solvents, fillers, bulking agents, detergents, buffers, vehicles, diluents, and/or adjuvants. For example, a suitable vehicle may be physiological saline solution or citrate buffered saline, possibly supplemented with other materials common in pharmaceutical compositions for parenteral administration. Neutral buffered saline or saline mixed with serum albumin are further exemplary vehicles. Those skilled in the art will readily recognize a variety of buffers that can be used in the pharmaceutical compositions and dosage forms contemplated herein. Typical buffers include, but are not limited to, pharmaceutically acceptable weak acids, weak bases, or mixtures thereof. As an example, the buffer components can be water soluble materials such as phosphoric acid, tartaric acids, lactic acid, succinic acid, citric acid, acetic acid, ascorbic acid, aspartic acid, glutamic acid, and salts thereof. Acceptable buffering agents include, for example, a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), and N-tris[Hydroxymethyl]methyl-3-aminopropanesulfonic acid (TAPS).

All the compounds and pharmaceutical compositions provided herein can be used in all the methods provided herein. For example, the compounds and pharmaceutical compositions provided herein can be used in all the methods for treatment and/or prevention of all diseases or disorders provided herein. Thus, the compounds and pharmaceutical compositions provided herein are for use as a medicament.

Routes of Administration

Compounds of Formula (I), or a pharmaceutically acceptable salt thereof and compositions containing the same may be administered in any appropriate manner. Suitable routes of administration include oral, parenteral (e.g., intramuscular, intravenous, subcutaneous (e.g., injection or implant), intraperitoneal, intracisternal, intraarticular, intracerebral (intraparenchymal) and intracerebroventricular), sublingual, intraocular, and inhalation. Depot injections, which are generally administered subcutaneously or intramuscularly, may also be utilized to administer the compounds of Formula (I), or a pharmaceutically acceptable salt thereof over a defined period of time. Particular embodiments of the present disclosure contemplate oral administration.

Treatment of Patients Having Tumors Characterized by High Microsatellite Instability In one aspect, provided herein is a method for decreasing proliferation in a proliferative cell having a microsatellite instability (MSI), comprising decreasing the helicase activity of Werner syndrome ATP-dependent helicase (WRN) in the proliferative cell. In some embodiments, decreasing the helicase activity of Werner syndrome ATP-dependent helicase (WRN) in the proliferative cell is achieved by administering a compound of Formula (I) (or any embodiment thereof disclosed herein) or a pharmaceutically acceptable salt thereof. In some embodiments, the proliferative cell is characterized as having MSI low (MSI-L). In some embodiments, the proliferative cell is characterized as having high MSI (MSI-H), used interchangeably with MISH-high. Cells can be characterized as MSI, including MSI-L or MSI-H, or as microsatellite stable (MSS), according to any method known in the art (see, for example, Dudley, Jonathan C., et al., *Clinical Cancer Research,* 22(4): 813-820, 2016.). MSI-H is used to classify tumors as having a high frequency of MSI. A tumor can be classified as MSI, including MSI-low or MSI-high, using polymerase chain reaction (PCR) and/or immunohistochemistry (IHC) assays. As stated in Dudley et al. (supra), a tumor is classified as MSI-H by PCR if (i) there is a shift (usually downward) in the size of at least two microsatellite loci from a reference panel of five microsatellite loci in tumor relative to normal, where the reference panel can be the "Bethesda Panel," also referred to herein as the "NCI-Reference Panel (Bethesda, 1998)", which includes two mononucleotide loci (BAT-25 and BAT-26) and three dinucleotide loci (D2S123, D5S346, and D17S250), or alternatively, the reference panel can be Promega Corporation's MSI Analysis System, which includes five mononucleotide loci (BAT-25, BAT-26, NR-21, NR-24, and MONO-27); or (ii) there is a shift in the size of 30% or more microsatellite loci from a reference panel of more than five microsatellite loci in tumor relative to normal. The MSI-H phenotype is associated with germline defects in the mismatch repair genes MLH1, MSH2, MSH6, and PMS2, and is the primary phenotype observed in tumors from patients with HNPCC/Lynch syndrome. A tumor is classified as MSI-H in IHC test if it shows a loss of protein expression for at least 1 of the above 4 mismatch repair genes. Cells can be similarly classified as MSI-H using the tests described herein for tumors.

In some embodiments, a tumor or cell is classified as MSI-H using PCR to amplify the five microsatellite loci of the "Bethesda Panel" (BAT-25, BAT-26, D2S123, D5S346, and D17S250) from both tumor tissue or cells and normal tissue or cells, wherein the tumor or cell is classified as MSI-H if there is a shift in the size of at least two of the microsatellite loci from the tumor tissue or cells relative to the normal tissue or cells. In some embodiments, the shift in size of the microsatellite loci is a downward shift.

In some embodiments, a tumor or cell is classified as MSI-H using PCR to amplify the five microsatellite loci of Promega Corporation's MSI Analysis System (BAT-25, BAT-26, NR-21, NR-24, and MONO-27) from both tumor tissue or cells and normal tissue or cells, wherein the tumor or cell is classified as MSI-H if there is a shift in the size of at least two of the microsatellite loci from the tumor tissue or cells relative to the normal tissue or cells. In some embodiments, the shift in size of the microsatellite loci is a downward shift.

In some embodiments, a tumor is classified as MSI-H using IHC to determine the expression level of the MMR proteins MLH1, MSH2, MSH6, and/or PMS2 in both tumor tissue and normal tissue, wherein the tumor is classified as MSI-H if there is a loss of protein expression for at least one of the MMR proteins in the tumor tissue relative to the normal tissue. In some embodiments, the loss of protein expression is a decrease of at least 20% (such as a decrease of 30%, 40%, 50%, 60%, 70%, 80%, 90%, 95%, 99%, or more).

In contrast, a tumor is classified as MSI-L by PCR if (i) there is a shift in the size of one microsatellite locus from a reference panel of five microsatellite loci in tumor relative to normal, where the reference panel can be the "Bethesda Panel" or Promega Corporation's MSI Analysis System; or (ii) there is a shift in the size of less than 30% microsatellite loci from a reference panel of more than five microsatellite loci in tumor relative to normal. MSI-L tumors are thought to represent a distinct mutator phenotype with potentially different molecular etiology than MSI-H tumors (Thibodeau, 1998; Wu et al., 1999, Am J Hum Genetics 65:1291-1298). Cells can be similarly classified as MSI-L using the tests described herein for tumors.

Combination Therapy

The present disclosure contemplates the use of compounds of Formula (I), or a pharmaceutically acceptable salt thereof in combination with one or more active therapeutic agents (e.g., chemotherapeutic agents) or other prophylactic or therapeutic modalities (e.g., radiation). In such combination therapy, the various active agents frequently have different, complementary mechanisms of action. Such combination therapy may be especially advantageous by allowing a dose reduction of one or more of the agents, thereby reducing or eliminating the adverse effects associated with one or more of the agents. Furthermore, such combination therapy may have a synergistic therapeutic or prophylactic effect on the underlying disease, disorder, or condition.

As used herein, "combination" is meant to include therapies that can be administered separately, for example, formulated separately for separate administration (e.g., as may be provided in a kit), and therapies that can be administered together in a single formulation (i.e., a "co-formulation").

In certain embodiments, the compounds of Formula (I), or a pharmaceutically acceptable salt thereof are administered or applied sequentially, e.g., where one agent is administered prior to one or more other agents. In other embodiments, the compounds of Formula (I), or a pharmaceutically acceptable salt thereof are administered simultaneously, e.g., where two or more agents are administered at or about the same time; the two or more agents may be present in two or more separate formulations or combined into a single formulation (i.e., a co-formulation). Regardless of whether the two or more agents are administered sequentially or simultaneously, they are considered to be administered in combination for purposes of the present disclosure.

The present disclosure provides methods for treating cancer with a compound of Formula (I), or a pharmaceutically acceptable salt thereof and at least one additional therapeutic or diagnostic agent.

In some embodiments, the compound of Formula (I), or a pharmaceutically acceptable salt thereof is administered in combination with at least one additional therapeutic agent, selected from Temozolomide, Pemetrexed, Pegylated liposomal doxorubicin (Doxil), Eribulin (Halaven), Ixabepilone (Ixempra), Protein-bound paclitaxel (Abraxane), Oxaliplatin, Irinotecan, Venatoclax (bcl2 inhibitor), 5-azacytadine, Anti-CD20 therapeutics, such as Rituxan and obinutuzumab, Hormonal agents (anastrozole, exemestand, letrozole, zoladex, lupon eligard), CDK4/6 inhibitors, Palbociclib, Abemaciclib, CPI (Avelumab, Cemiplimab-rwlc, and Bevacizumab).

In certain embodiments, the present disclosure provides methods for treating cancer comprising administration of a compound of Formula (I), or a pharmaceutically acceptable salt thereof described herein in combination with a signal transduction inhibitor (STI) to achieve additive or synergistic suppression of tumor growth. As used herein, the term "signal transduction inhibitor" refers to an agent that selectively inhibits one or more steps in a signaling pathway. Examples of signal transduction inhibitors (STIs) useful in methods described herein include, but are not limited to: (i) bcr/abl kinase inhibitors (e.g., GLEEVEC); (ii) epidermal growth factor (EGF) receptor inhibitors, including kinase inhibitors and antibodies; (iii) her-2/neu receptor inhibitors (e.g., HERCEPTIN); (iv) inhibitors of Akt family kinases or the Akt pathway (e.g., rapamycin); (v) cell cycle kinase inhibitors (e.g., flavopiridol); and (vi) phosphatidyl inositol kinase inhibitors. Agents involved in immunomodulation can also be used in combination with one or more compounds of Formula (I), or a pharmaceutically acceptable salt thereof described herein for the suppression of tumor growth in cancer patients.

In certain embodiments, the present disclosure provides methods for treating cancer comprising administration of a compound of Formula (I), or a pharmaceutically acceptable salt thereof described herein in combination with a chemotherapeutic agent. Examples of chemotherapeutic agents include, but are not limited to, alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards such as chiorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside (Ara-C); cyclophosphamide; thiotepa; taxoids, e.g., paclitaxel and doxetaxel; chlorambucil; gemcitabine; 6-thioguanine; mercaptopurine; methotrexate; platinum and platinum coordination complexes such as cisplatin and carboplatin; vinblastine; etoposide (VP-16); ifosfamide; mitomycin C; mitoxantrone; vincristine; vinorelbine; navelbine; novantrone; teniposide; daunomycin; aminopterin; xeloda; ibandronate; CPT11; topoisomerase inhibitors; difluoromethylornithine (DMFO); retinoic acid; esperamicins; capecitabine; and pharmaceutically acceptable salts, acids or derivatives of any of the above. In a particular embodiment, compounds of the present disclosure are coadministered with a cytostatic compound selected from the group consisting of cisplatin, doxorubicin, taxol, taxotere and mitomycin C. In a particular embodiment, the cytostatic compound is doxorubicin.

Chemotherapeutic agents also include anti-hormonal agents that act to regulate or inhibit hormonal action on tumors such as anti-estrogens, including for example tamoxifen, raloxifene, aromatase inhibiting 4(5)-imidazoles, 4-hydroxytamoxifen, trioxifene, keoxifene, onapristone, and toremifene; and antiandrogens such as flutamide, nilutamide, bicalutamide, enzalutamide, apalutamide, abiraterone acetate, leuprolide, and goserelin; and pharmaceutically acceptable salts, acids or derivatives of any of the above. In certain embodiments, combination therapy comprises administration of a hormone or related hormonal agent.

The present disclosure also contemplates the use of the compounds of Formula (I), or a pharmaceutically acceptable salt thereof described herein in combination with immune checkpoint inhibitors. The tremendous number of genetic and epigenetic alterations that are characteristic of all cancers provides a diverse set of antigens that the immune system can use to distinguish tumor cells from their normal counterparts. In the case of T cells, the ultimate amplitude (e.g., levels of cytokine production or proliferation) and quality (e.g., the type of immune response generated, such as the pattern of cytokine production) of the response, which is initiated through antigen recognition by the T-cell receptor (TCR), is regulated by a balance between co-stimulatory and inhibitory signals (immune checkpoints). Under normal physiological conditions, immune checkpoints are crucial for the prevention of autoimmunity (i.e., the maintenance of self-tolerance) and also for the protection of tissues from damage when the immune system is responding to pathogenic infection. The expression of immune checkpoint proteins can be dysregulated by tumors as an important immune resistance mechanism. Examples of immune checkpoint inhibitors include but are not limited to CTLA-4, PD-1, PD-L1, BTLA, TIM3, LAG3, OX40, 41BB, VISTA, CD96, TGF3, CD73, CD39, A2AR, A2BR, IDO1, TDO2, Arginase, B7-H3, B7-H4. Cell-based modulators of anti-cancer immunity are also contemplated. Examples of such modulators include but are not limited to chimeric antigen receptor T-cells, tumor infiltrating T-cells, and dendritic-cells.

The present disclosure contemplates the use of compounds of Formula (I), or a pharmaceutically acceptable salt thereof described herein in combination with inhibitors of the aforementioned immune-checkpoint receptors and ligands, for example ipilimumab, abatacept, nivolumab, pembrolizumab, atezolizumab, dostarlimab, and durvalumab.

Additional treatment modalities that may be used in combination with a compound of Formula (I), or a pharmaceutically acceptable salt thereof disclosed herein include radiotherapy, a monoclonal antibody against a tumor antigen, a complex of a monoclonal antibody and toxin, a T-cell adjuvant, bone marrow transplant, or antigen presenting cells (e.g., dendritic cell therapy).

The present disclosure contemplates the use of compounds of Formula (I), or a pharmaceutically acceptable salt thereof described herein for the treatment of glioblastoma either alone or in combination with radiation and/or temozolomide (TMZ), avastin, or lomustine.

Dosing

The compounds of Formula (I), or a pharmaceutically acceptable salt thereof provided herein may be administered to a subject in an amount that is dependent upon, for example, the goal of administration (e.g., the degree of resolution desired); the age, weight, sex, and health and physical condition of the subject to which the formulation is being administered; the route of administration; and the nature of the disease, disorder, condition or symptom thereof. The dosing regimen may also take into consideration the existence, nature, and extent of any adverse effects associated with the agent(s) being administered.

An effective dose (ED) is the dose or amount of an agent that produces a therapeutic response or desired effect in some fraction of the subjects taking it. The "median effective dose" or $ED_{50}$ of an agent is the dose or amount of an agent that produces a therapeutic response or desired effect in 50% of the population to which it is administered. Although the $ED_{50}$ is commonly used as a measure of reasonable expectance of an agent's effect, it is not necessarily the dose that a clinician might deem appropriate taking into consideration all relevant factors. Thus, in some situations the effective amount is more than the calculated $ED_{50}$, in other situations the effective amount is less than the calculated $ED_{50}$, and in still other situations the effective amount is the same as the calculated $ED_{50}$.

EXAMPLES

The following examples and references (intermediates) are put forth so as to provide those of ordinary skill in the art with a complete disclosure and description of how to make and use the present disclosure, and are not intended to limit the scope of what the inventors regard as their disclosure, nor are they intended to represent that the experiments below were performed or that they are all of the experiments that may be performed. It is to be understood that exemplary descriptions written in the present tense were not necessarily performed, but rather that the descriptions can be performed to generate data of a nature described therein. Efforts have been made to ensure accuracy with respect to numbers used (e.g., amounts, temperature, etc.), but some experimental errors and deviations should be accounted for. Some NMR data was processed using computer analysis and may contain artifacts inherent in that process, including reporting of impurity peaks, solvent peaks and miss-integrations. The mass yield of a reaction described herein is the amount of material collected from the reaction but the mmol amount and % yield are adjusted to reflect the purity of the material. For example, if 10 grams of a product (corresponding to 20 mmol if 100% pure) was collected from a reaction but the purity of the product was determined to be 90%, the preparation will be reported as "(10 grams, 18 mmol, 54% yield)". However, when the product is used as a starting material in a subsequent step, for stoichiometry calculation purposes, the product will be considered as 100% pure. For example, the 10 grams product will be described as a starting material of "10 grams, 20 mmol" in a subsequent reaction.

INTERMEDIATES

Intermediate 1: (1R,2S,6R)-2-(4-bromophenyl)-6-((2-fluoro-4-(trifluoromethyl)phenyl)carbamoyl)cyclohexane-1-carboxylic acid

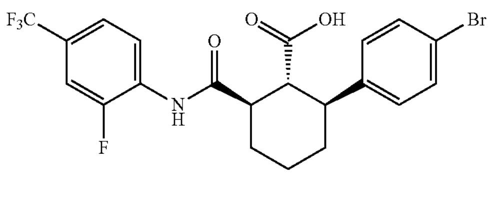 [SMILES: O=C(O)[C@@H]1[C@@H](c2ccc(Br)cc2)CCC[C@H]1C(=O)Nc1ccc(C(F)(F)F)cc1F]

Step 1: (E)-1-bromo-4-(buta-1,3-dien-1-yl)benzene

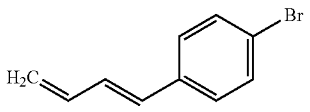

In two separate, equivalent reactions: to a mixture of diethyl allylphosphonate (144 g, 811 mmol) in THF (3000 mL) at 0° C. was added NaH (32.4 g, 811 mmol). After 50 min, 4-bromobenzaldehyde (0.100 kg, 0.540 mol) was added, and the mixtures were allowed to warm to 25° C. for 4 h. The two separate reactions were combined, cooled to 0° C. quenched with aq. $NH_4Cl$ (500 mL), and extracted with EtOAc (500 mL×3). The combined organic layers were washed with brine (500 mL), dried over $Na_2SO_4$, filtered and concentrated. The residue was taken up in petroleum ether (500 mL), and 300 g of silica gel (100-200 mesh silica gel) was added. The resulting mixture was concentrated at 40° C. and to give a dry flowing solid, and was loaded to Biotage using 1,500 g silica gel (self-prepared column chromatography, 100-200 mesh silica gel), eluting with 0-10% ethyl acetate in petroleum ether to give (E)-1-bromo-4-(buta-1,3-dien-1-yl)benzene (90 g, 410 mmol, 38% yield) as a yellow oil. $^1$H NMR (400 MHz, $CDCl_3$) δ 7.43 (d, J=8.4 Hz, 2H), 7.25 (d, J=8.4 Hz, 2H), 6.76 (dd, J=15.6 Hz, 10.4 Hz, 1H), 6.53-6.44 (m, 2H), 5.36 (d, J=17.2 Hz, 1H), 5.21 (d, J=10.0 Hz, 1H).

Step 2: 1:1 mixture of (3aS,4S,7aR)-4-(4-bromophenyl)-3a,4,7,7a-tetrahydroisobenzofuran-1,3-dione and (3aR,4R,7aS)-4-(4-bromophenyl)-3a,4,7,7a-tetrahydroisobenzofuran-1,3-dione

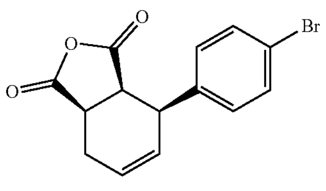

+

-continued

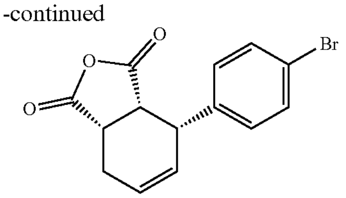

In two separate, equivalent reactions: to a mixture of (E)-1-bromo-4-(buta-1,3-dien-1-yl)benzene (140 g, 670 mmol) in toluene (1400 mL) at 25° C. was added furan-2,5-dione (65.7 g, 0.670 mol). The mixtures were stirred at 120° C. for 12 h. The two reactions were combined, concentrated, triturated with 2:1 n-hexane:ethyl acetate at 20° C. for 30 mins, filtered and washed with n-hexane (200 mL×3) to give a 1:1 mixture of (3aS,4S,7aR)-4-(4-bromophenyl)-3a,4,7,7a-tetrahydroisobenzofuran-1,3-dione and (3aR,4R,7aS)-4-(4-bromophenyl)-3a,4,7,7a-tetrahydroisobenzofuran-1,3-dione (189 g, 599 mmol, 44.5% yield) as a white solid. $^1$H NMR (400 MHz, DMSO-$d_6$) δ 7.52 (d, J=8.4 Hz, 2H), 7.21 (d, J=8.4 Hz, 2H), 6.22 (m, 1H), 6.17-6.15 (m, 1H), 3.83 (d, J=2.0 Hz, 1H), 3.77-3.72 (m, 2H), 2.66-2.60 (m, 1H), 2.50-2.40 (m, 1H).

Step 3: 1:1 mixture of (3aS,4S,7aR)-4-(4-bromophenyl)hexahydroisobenzofuran-1,3-dione and (3aR,4R,7aS)-4-(4-bromophenyl)hexahydroisobenzofuran-1,3-dione

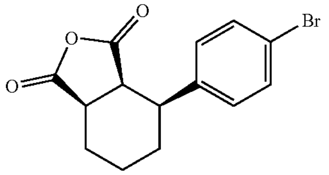

+

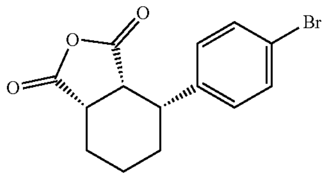

In three separate, equivalent reactions: to a 1:1 mixture of (3aS,4S,7aR)-4-(4-bromophenyl)-3a,4,7,7a-tetrahydroisobenzofuran-1,3-dione and (3aR,4R,7aS)-4-(4-bromophenyl)-3a,4,7,7a-tetrahydroisobenzofuran-1,3-dione (63.0 g, 205 mmol) in THF (1000 mL) at 25° C. under nitrogen was added platinum (8.00 g, 2.05 mmol). The mixtures were placed under hydrogen atmosphere (2 atm). The reactions were degassed via vacuum evacuation, then backfilling with hydrogen (3×). The mixtures were stirred at 25° C. for 40 min under hydrogen. The three reactions were combined, filtered, and the filter cake was washed with THF (1 L×3). The combined filtrates were concentrated, triturated with 5:1 n-hexane:ethyl acetate (500 mL) at 20° C. for 30 mins, filtered, washed with n-hexane (100 mL×3) and dried under reduced pressure at 40° C. to provide a 1:1 mixture of (3aS,4S,7aR)-4-(4-bromophenyl)hexahydroisobenzofuran-1,3-dione and (3aR,4R,7aS)-4-(4-bromophenyl)hexahydroisobenzofuran-1,3-dione (164 g, 477 mmol, 78%) as a white solid. $^1$H NMR (400 MHz, DMSO-$d_6$) δ 7.50 (d, J=8.4 Hz, 2H), 7.25 (d, J=8.4 Hz, 2H), 3.99 (t, J=6.8 Hz, 1H), 3.35-3.29 (m, 1H), 3.16-3.10 (m, 1H), 2.09-2.04 (m, 1H), 1.91-1.86 (m, 1H), 1.81-1.76 (m, 1H), 1.67-1.44 (m, 3H).

Step 4: 1:1 mixture of (3aS,4S,7aR)-2-(4-bromophenyl)-6-(hydroxymethyl)cyclohexane-1-carboxylic acid and (3aR,4R,7aS)-2-(4-bromophenyl)-6-(hydroxymethyl)cyclohexane-1-carboxylic acid

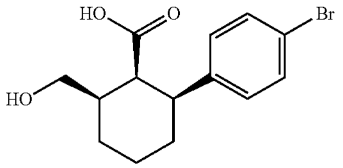

+

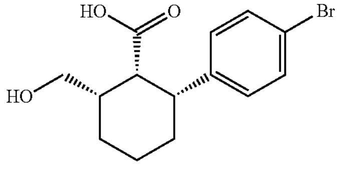

To a 1:1 mixture of (3aS,4S,7aR)-4-(4-bromophenyl)hexahydroisobenzofuran-1,3-dione and (3aR,4R,7aS)-4-(4-bromophenyl)hexahydroisobenzofuran-1,3-dione (164 g, 0.530 mol) in THF (1500 mL) at 0° C. was added $NaBH_4$ (40.1 g, 1.06 mol), in portions. The reaction was stirred for 1 h, quenched with 2 N HCl (1.00 L) to pH<3, then was extracted with EtOAc (300 mL×3). The combined organic layers were washed with brine (500 mL), dried over $Na_2SO_4$, filtered and concentrated to afford a 1:1 mixture of (3aS,4S,7aR)-2-(4-bromophenyl)-6-(hydroxymethyl)cyclohexane-1-carboxylic acid and (3aR,4R,7aS)-2-(4-bromophenyl)-6-(hydroxymethyl)cyclohexane-1-carboxylic acid (135 g, 346 mmol, 65.2% yield) as a white solid, which was used without further purification. $^1H$ NMR (400 MHz, DMSO-$d_6$) δ 11.6 (br.s, 1H), 7.45 (d, J=8.4 Hz, 2H), 7.17 (d, J=8.4 Hz, 2H), 3.34-3.30 (m, 1H), 3.23-3.18 (m, 1H), 2.88 (t, J=4.4 Hz, 1H), 2.85-2.79 (m, 1H), 2.35-2.24 (m, 1H), 1.90-1.75 (m, 2H), 1.56-1.44 (m, 3H), 1.41-1.31 (m, 1H).

Step 5: 1:1 mixture of (3aR,7S,7aS)-7-(4-bromophenyl)hexahydroisobenzofuran-1(3H)-one and (3aS,7R,7aR)-7-(4-bromophenyl)hexahydroisobenzofuran-1(3H)-one

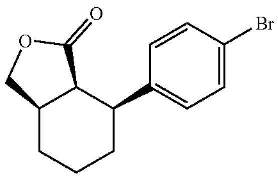

+

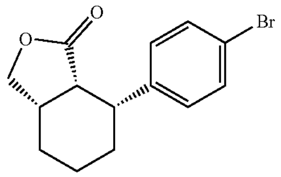

To a 1:1 mixture of (3aS,4S,7aR)-2-(4-bromophenyl)-6-(hydroxymethyl)cyclohexane-1-carboxylic acid and (3aR,4R,7aS)-2-(4-bromophenyl)-6-(hydroxymethyl)cyclohexane-1-carboxylic acid (135 g, 431 mmol) in toluene (1300 mL) at 25° C. was added 4-methylbenzenesulfonic acid (7.42 g, 43.1 mmol). The reaction was stirred at 110° C. for 1 h, cooled to 25° C., diluted with water (300 mL) and extracted with EtOAc (200 mL×3). The combined organic layers were washed with $NaHCO_3$(aq.) (200 mL) and brine (200 mL), dried over $Na_2SO_4$, filtered and concentrated afford a 1:1 mixture of (3aR,7S,7aS)-7-(4-bromophenyl)hexahydroisobenzofuran-1(3H)-one and (3aS,7R,7aR)-7-(4-bromophenyl)hexahydroisobenzofuran-1(3H)-one (118 g, 375 mmol, 87% yield) as a white solid, which was used without further purification. $^1H$ NMR (400 MHz, DMSO-$d_6$) δ 7.45 (d, J=8.4 Hz, 2H), 7.25 (d, J=8.4 Hz, 2H), 4.15 (q, J=4.4 Hz, 1H), 3.84 (d, J=8.4 Hz, 1H), 3.26 (t, J=5.6 Hz, 1H), 3.02-2.98 (m, 1H), 2.61-2.54 (m, 1H), 1.83 (d, J=9.6 Hz, 3H), 1.49-1.34 (m, 2H), 1.12-1.06 (m, 1H).

Step 6: 1:1 mixture of (1R,2S,6R)-2-(4-bromophenyl)-6-(hydroxymethyl)cyclohexane-1-carboxylic acid and (1S,2R,6S)-2-(4-bromophenyl)-6-(hydroxymethyl)cyclohexane-1-carboxylic acid

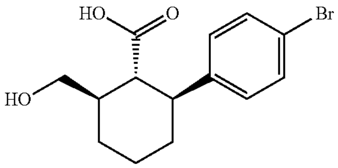

+

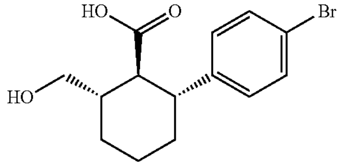

To a 1:1 mixture of (3aR,7S,7aS)-7-(4-bromophenyl)hexahydroisobenzofuran-1(3H)-one and (3aS,7R,7aR)-7-(4-bromophenyl)hexahydroisobenzofuran-1(3H)-one (118 g, 0.400 mol) in methanol (1.18 L) at 25° C. was added KOH (112 g, 2.00 mol). The reaction was stirred at 75° C. for 3 h, cooled to 0° C., quenched with 2 N HCl (1.00 L) to pH<3, and extracted with EtOAc (400 mL×3). The combined organic layers were washed with brine (500 mL), dried over $Na_2SO_4$, filtered and concentrated to afford a 1:1 mixture of (1R,2S,6R)-2-(4-bromophenyl)-6-(hydroxymethyl)cyclohexane-1-carboxylic acid and (1S,2R,6S)-2-(4-bromophenyl)-6-(hydroxymethyl)cyclohexane-1-carboxylic acid (105 g, 287 mmol, 71.9% yield) as a white solid, which was used without further purification. $^1H$ NMR (400 MHz, DMSO-$d_6$) δ 11.8 (s, 1H), 7.46-7.41 (m, 2H), 7.18-7.15 (m, 2H), 4.50 (s, 1H), 3.40-3.36 (m, 1H), 3.20-3.16 (m, 1H), 2.71-2.64 (m, 1H), 2.25 (t, J=10.8 Hz, 1H), 1.94-1.90 (m, 1H), 1.80-1.63 (m, 3H), 1.43-1.37 (m, 2H), 1.12-1.08 (m, 1H).

Step 7: 1:1 mixture of benzyl (1R,2S,6R)-2-(4-bromophenyl)-6-(hydroxymethyl)cyclohexane-1-carboxylate and benzyl (1S,2R,6S)-2-(4-bromophenyl)-6-(hydroxymethyl)cyclohexane-1-carboxylate

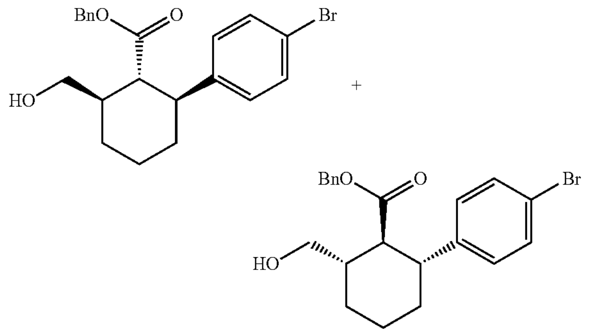

To a 1:1 mixture of (1R,2S,6R)-2-(4-bromophenyl)-6-(hydroxymethyl)cyclohexane-1-carboxylic acid and (1S,2R,6S)-2-(4-bromophenyl)-6-(hydroxymethyl)cyclohexane-1-carboxylic acid (105 g, 335 mmol) in DMF (1050 mL) at 0° C. were added $K_2CO_3$ (139 g, 1.01 mol) and (bromomethyl) benzene (86 g, 0.50 mol). The reaction was stirred at 25° C. for 3 h, diluted with water (500 mL), and extracted with EtOAc (200 mL×3). The combined organic layers were washed with brine (300 mL), dried over $Na_2SO_4$, filtered, concentrated, triturated with 5:1 n-hexane:ethyl acetate (300 mL) at 20° C. for 30 mins, filtered, washed with n-hexane (100 mL×3) and dried under reduced pressure at 40° C. to provide a 1:1 mixture of benzyl (1R,2S,6R)-2-(4-bromophenyl)-6-(hydroxymethyl)cyclohexane-1-carboxylate and benzyl (1S,2R,6S)-2-(4-bromophenyl)-6-(hydroxymethyl)cyclohexane-1-carboxylate (98.0 g, 237 mmol, 70.7% yield) as a white solid. $^1$H NMR (400 MHz, DMSO-$d_6$) δ 7.41 (d, J=8.4 Hz, 2H), 7.25-7.23 (m, 3H), 7.13 (d, J=8.4 Hz, 2H), 6.87-6.85 (m, 2H), 4.87 (d, J=12.4 Hz, 1H), 4.69 (d, J=12.8 Hz, 1H), 4.53 (t, J=4.8 Hz, 1H), 3.30-3.27 (m, 1H), 3.23-3.18 (m, 1H), 2.73-2.67 (m, 1H), 2.43 (t, J=10.8 Hz, 1H), 1.88-1.85 (m, 1H), 1.81-1.70 (m, 3H), 1.52-1.36 (m, 2H), 1.18-1.09 (m, 1H).

Step 8: 1:1 mixture of (1R,2R,3S)-2-((benzyloxy)carbonyl)-3-(4-bromophenyl)cyclohexane-1-carboxylic acid and (1 S,2S,3R)-2-((benzyloxy)carbonyl)-3-(4-bromophenyl)cyclohexane-1-carboxylic acid

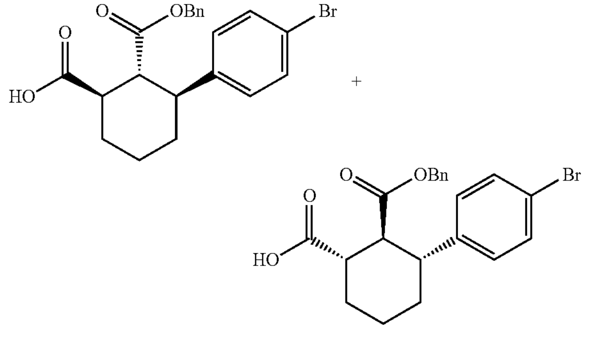

To a 1:1 mixture of benzyl (1R,2S,6R)-2-(4-bromophenyl)-6-(hydroxymethyl)cyclohexane-1-carboxylate and benzyl (1S,2R,6S)-2-(4-bromophenyl)-6-(hydroxymethyl)cyclohexane-1-carboxylate (95 g, 0.24 mol) in acetonitrile (950 mL) and water (30 mL) at 0° C. were added sodium periodate (151 g, 707 mmol) and ruthenium(III) chloride (4.89 g, 23.6 mmol). The reaction was stirred at 25° C. for 3 h, diluted with water (500 mL) and extracted with EtOAc (200 mL×3). The combined organic layers were washed with brine (300 mL), dried over $Na_2SO_4$, filtered, concentrated, triturated with 3:1 n-hexane:ethyl acetate (200 mL) at 20° C. for 30 mins, filtered, washed with n-hexane (50 mL×3) and dried under reduced pressure at 40° C. to provide a 1:1 mixture of (1R,2R,3S)-2-((benzyloxy)carbonyl)-3-(4-bromophenyl)cyclohexane-1-carboxylic acid and (1 S,2S,3R)-2-((benzyloxy)carbonyl)-3-(4-bromophenyl)cyclohexane-1-carboxylic acid (88 g, 0.21 mol, 88% yield) as a yellow solid. $^1$H NMR (400 MHz, DMSO-$d_6$) δ 12.4 (s, 1H), 7.42 (d, J=8.4 Hz, 2H), 7.25-7.23 (m, 3H), 7.17 (d, J=8.4 Hz, 2H), 6.84 (d, J=4.4 Hz, 2H), 4.69 (q, J=12.8 Hz, 2H), 2.77-2.74 (m, 1H), 2.66-2.64 (m, 2H), 2.22-2.10 (m, 1H), 1.78-1.74 (m, 2H), 1.54-1.47 (m, 3H). ES-LCMS m/z 439.0 $[M+Na]^+$.

Step 9: 1:1 mixture of benzyl (1R,2S,6R)-2-(4-bromophenyl)-6-((2-fluoro-4-(trifluoromethyl)phenyl)carbamoyl)cyclohexane-1-carboxylate and benzyl (1S,2R,6S)-2-(4-bromophenyl)-6-((2-fluoro-4-(trifluoromethyl)phenyl)carbamoyl)cyclohexane-1-carboxylate

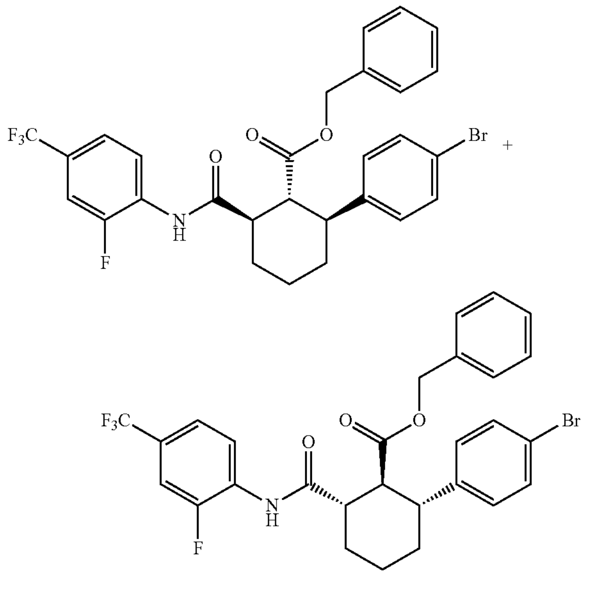

To a 1:1 mixture of (1R,2R,3S)-2-((benzyloxy)carbonyl)-3-(4-bromophenyl)cyclohexane-1-carboxylic acid and (1 S,2S,3R)-2-((benzyloxy)carbonyl)-3-(4-bromophenyl)cyclohexane-1-carboxylic acid (85 g, 0.20 mol) in acetonitrile (850 mL) was added 2-fluoro-4-(trifluoromethyl)aniline (73.0 g, 407 mmol) and 1-methyl-1H-imidazole (33.4 g, 407 mmol). After ~2 min, N-(chloro(dimethylamino)methylene)-N-methylmethanaminium hexafluorophosphate (86 g, 0.31 mol) was added, portion wise. After 12 h at 25° C., the reaction was diluted with water (200 mL) and extracted with EtOAc (200 mL×3). The combined organic layers were washed with brine (200 mL), dried over $Na_2SO_4$, filtered, concentrated, dissolved in EtOAc (500 mL) and combined with of silica gel (300 g, 100-200). The resulting mixture was concentrated at 40° C., loaded onto a silica gel column (300 g, 100-200 mesh silica gel), eluting with 10:1 to 5:1 EtOAc in n-heptane to give a 1:1 mixture of benzyl (1R,2S,6R)-2-(4-bromophenyl)-6-((2-fluoro-4-(trifluoromethyl)phenyl)carbamoyl)cyclohexane-1-carboxylate and benzyl (1S,2R,6S)-2-(4-bromophenyl)-6-((2-fluoro-4-(trifluoromethyl)phenyl)carbamoyl)cyclohexane-1-carboxylate (87 g, 0.15 mol, 73% yield) as a white solid. $^1H$ NMR (400 MHz, CHLOROFORM-d) δ 8.43 (t, J=8.1 Hz, 1H), 7.60-7.52 (m, 1H), 7.41-7.30 (m, 4H), 7.21-7.10 (m, 3H), 7.08-7.00 (m, 2H), 6.87-6.78 (m, 2H), 4.81-4.69 (m, 2H), 3.01-2.92 (m, 1H), 2.86-2.72 (m, 2H), 2.13-2.06 (m, 1H), 2.05-1.98 (m, 1H), 1.99-1.85 (m, 2H), 1.85-1.73 (m, 1H), 1.66-1.53 (m, 2H).

Step 10: benzyl (1S,2R,6S)-2-(4-bromophenyl)-6-((2-fluoro-4-(trifluoromethyl)phenyl)carbamoyl)cyclohexane-1-carboxylate and benzyl (1R,2S,6R)-2-(4-bromophenyl)-6-((2-fluoro-4-(trifluoromethyl)phenyl)carbamoyl)cyclohexane-1-carboxylate

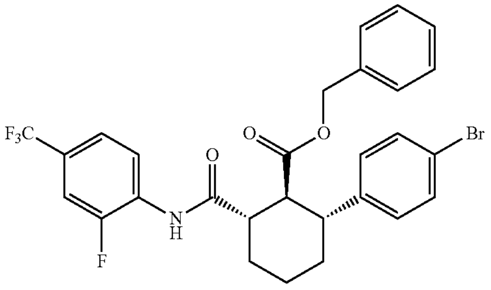

AND

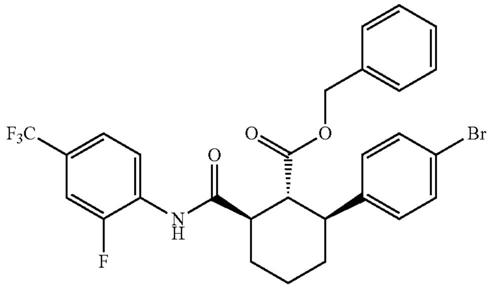

A 1:1 mixture of benzyl (1R,2S,6R)-2-(4-bromophenyl)-6-((2-fluoro-4-(trifluoromethyl)phenyl)carbamoyl)cyclohexane-1-carboxylate and benzyl (1S,2R,6S)-2-(4-bromophenyl)-6-((2-fluoro-4-(trifluoromethyl)phenyl)carbamoyl)cyclohexane-1-carboxylate (35.0 g, 60.5 mmol) was chirally purified by Chiral-Prep-SFC (Column: DAICEL CHIRALPAK AD [250 mm×50 mm, 10 μm]; Mobile Phase A:$CO_2$, Mobile Phase B:MeOH; Flow rate:100 g/min; Gradient: isocratic 40% B; 220 nm) to afford First eluting isomer: Isomer 1: benzyl (1S,2R,6S)-2-(4-bromophenyl)-6-((2-fluoro-4-(trifluoromethyl)phenyl)carbamoyl)cyclohexane-1-carboxylate (15.5 g, 25.1 mmol, 41.5% yield). Analytical Chiral Chromatography: Column: Chiralpak AD-3, 50×4.6 mm I.D., 3 um Mobile phase: A:$CO_2$ B:MeOH (0.1% IPA, v/v) Gradient: 5-50% B over 1.2 min then 50% B for 1 min) Retention Time=1.07 min, as a white solid. $^1H$ NMR (400 MHz, DMSO-$d_6$) δ 10.15 (s, 1H), 8.16 (t, J=8.1 Hz, 1H), 7.72 (dd, J=11.0, 1.5 Hz, 1H), 7.55 (br d, J=8.4 Hz, 1H), 7.45 (d, J=8.4 Hz, 2H), 7.26-7.12 (m, 5H), 6.81 (d, J=6.7 Hz, 2H), 4.77-4.62 (m, 2H), 3.13-3.03 (m, 1H), 2.96 (t, J=11.2 Hz, 1H), 2.74 (td, J=11.6, 3.4 Hz, 1H), 2.07 (br d, J=8.6 Hz, 1H), 1.95-1.84 (m, 1H), 1.82-1.73 (m, 1H), 1.72-1.47 (m, 3H).

Second eluting isomer: Isomer 2: benzyl (1R,2S,6R)-2-(4-bromophenyl)-6-((2-fluoro-4-(trifluoromethyl)phenyl)carbamoyl)cyclohexane-1-carboxylate (15.3 g, 26.2 mmol, 43.4% yield) Analytical Chiral Chromatography: Column: Chiralpak AD-3, 50×4.6 mm I.D., 3 um Mobile phase: A:$CO_2$ B:MeOH (0.1% IPA, v/v) Gradient: 5-50% B over 1.2 min then 50% B for 1 min) Retention Time=1.36 min, as a white solid. Absolute stereochemistry was determined by co-crystal structure of subsequent final compound with WRN protein and then tracing back to the corresponding enantiopure intermediates.

$^1H$ NMR (400 MHz, DMSO-$d_6$) δ 10.15 (s, 1H), 8.16 (t, J=8.1 Hz, 1H), 7.72 (dd, J=10.9, 1.4 Hz, 1H), 7.55 (br d, J=8.4 Hz, 1H), 7.45 (d, J=8.3 Hz, 2H), 7.27-7.09 (m, 5H), 6.81 (d, J=6.7 Hz, 2H), 4.77-4.64 (m, 2H), 3.14-3.03 (m, 1H), 2.96 (t, J=11.1 Hz, 1H), 2.78-2.70 (m, 1H), 2.12-2.02 (m, 1H), 1.93-1.84 (m, 1H), 1.81-1.73 (m, 1H), 1.71-1.45 (m, 3H).

Step 11: (1R,2S,6R)-2-(4-bromophenyl)-6-((2-fluoro-4-(trifluoromethyl)phenyl)carbamoyl)cyclohexane-1-carboxylic acid

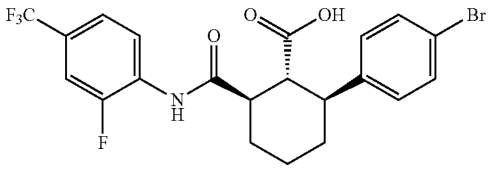 [SMILES: O=C(O)[C@@H]1[C@@H](c2ccc(Br)cc2)CCC[C@H]1C(=O)Nc1ccc(C(F)(F)F)cc1F]

To a mixture of benzyl (1R,2S,6R)-2-(4-bromophenyl)-6-((2-fluoro-4-(trifluoromethyl)phenyl)carbamoyl)cyclohexane-1-carboxylate (0.40 g, 0.69 mmol) in dichloromethane (10 mL) at 0° C. was added $BCl_3$ (1M in DCM, 1.38 mL, 1.38 mmol). After 3 h the reaction was quenched with cold water (2 mL) and concentrated. The resulting residue was subjected to reverse phase purification (70% MeCN in $H_2O$, with 10 mM ammonium bicarbonate modifier) to afford (1R,2S,6R)-2-(4-bromophenyl)-6-((2-fluoro-4-(trifluoromethyl)phenyl)carbamoyl)cyclohexane-1-carboxylic acid (0.27 g, 0.51 mmol, 74% yield) as an off-white solid. $^1H$ NMR (400 MHz, DMSO-$d_6$) δ 11.80 (br s, 1H), 10.13 (s, 1H), 8.21 (t, J=8.0 Hz, 1H), 7.72 (dd, J=10.8, 1.6 Hz, 1H), 7.55 (d, J=8.4 Hz, 1H), 7.46 (d, J=8.4 Hz, 2H), 7.23 (d, J=8.4 Hz, 2H), 2.97-2.95 (m, 1H), 2.78 (t, J=10.8 Hz, 1H), 2.68-2.66 (m, 1H), 2.02-2.00 (m, 1H), 1.90-1.87 (m, 1H), 1.76-1.73 (m, 1H), 1.51-1.48 (m, 3H). ES-LCMS m/z 486.5, 488.5 [M−H]⁻.

Intermediate 2: (1R,2R,6S)-2-((2-fluoro-4-(trifluoromethyl)phenyl)carbamoyl)-6-(4-(4,4,5,5-tetramethyl-1,3,2-dioxaborolan-2-yl)phenyl)cyclohexane-1-carboxylic acid

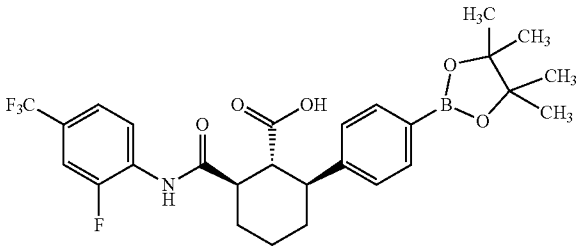 [SMILES: CC1(C)OB(c2ccc([C@H]3CCC[C@@H](C(=O)Nc4ccc(C(F)(F)F)cc4F)[C@@H]3C(=O)O)cc2)OC1(C)C]

A mixture of (1R,2S,6R)-2-(4-bromophenyl)-6-((2-fluoro-4-(trifluoromethyl)phenyl)carbamoyl)cyclohexane-1-carboxylic acid, Intermediate 1 (3.08 g, 6.31 mmol), potassium acetate (2.48 g, 25.2 mmol), $PdCl_2$(dppf)-DCM adduct (0.438 g, 0.536 mmol) and bis(pinacolato)diborane (1.92 g, 7.57 mmol) was flushed with three alternating vacuum and nitrogen purge cycles. 1,4-Dioxane (50 mL) was added, and the reaction was heated at 100° C. After 2.5 h, the mixture was cooled to room temperature, diluted with water and ethyl acetate, and filtered through Celite. The filtrate layers were separated, and the organic layer was washed with brine, concentrated and purified by normal phase silica gel chromatography (ethyl acetate in DCM, 0-20%) to afford (1R,2R,6S)-2-((2-fluoro-4-(trifluoromethyl)phenyl)carbamoyl)-6-(4-(4,4,5,5-tetramethyl-1,3,2-dioxaborolan-2-yl)phenyl)cyclohexane-1-carboxylic acid (1.58 g, 44% yield) as an orange solid. $^{1}$H NMR (400 MHz, CHLOROFORM-d) δ 8.51 (br t, J=8.1 Hz, 1H), 7.79 (d, J=8.3 Hz, 2H), 7.63 (br d, J=3.4 Hz, 1H), 7.42 (br d, J=8.8 Hz, 1H), 7.37 (dd, J=11.0, 1.7 Hz, 1H), 7.27 (d, J=7.8 Hz, 2H), 3.11-3.04 (m, 1H), 2.82 (tt, J=11.5, 3.2 Hz, 2H), 2.15 (br dd, J=13.2, 2.9 Hz, 1H), 2.08-2.02 (m, 1H), 2.01-1.95 (m, 1H), 1.88-1.77 (m, 1H), 1.74-1.59 (m, 2H), 1.37 (s, 12H). ES-LCMS m/z 536.1 $[M+H]^+$.

Intermediate 3: 1:1 mixture of (1R,2S,6S)-2-((4-isopropylphenyl)carbamoyl)-6-(4-(methylamino)phenyl)cyclohexane-1-carboxylic acid and (1 S,2R,6R)-2-((4-isopropylphenyl)carbamoyl)-6-(4-(methylamino)phenyl)cyclohexane-1-carboxylic acid

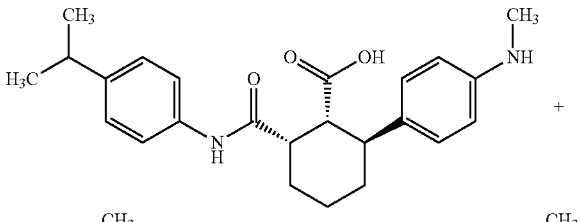

+

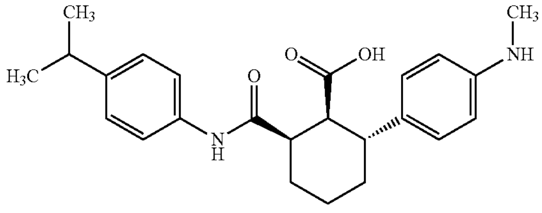

Step 1: 1:1 mixture of (1R,2R,6S)-2-(4-bromophenyl)-6-((4-isopropylphenyl)carbamoyl)cyclohexane-1-carboxylic acid and benzyl (1S,2S,6R)-2-(4-bromophenyl)-6-((4-isopropylphenyl)carbamoyl)cyclohexane-1-carboxylic acid

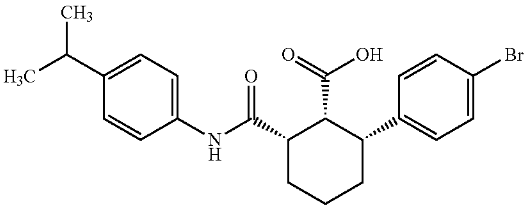

+

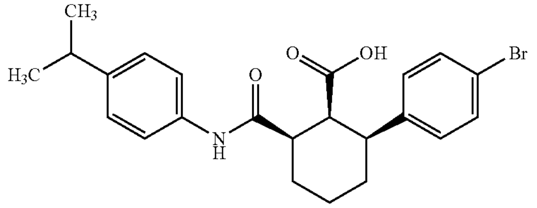

A mixture of 1:1 (3aS,4S,7aR)-4-(4-bromophenyl)hexahydroisobenzofuran-1,3-dione and (3aR,4R,7aS)-4-(4-bromophenyl)hexahydroisobenzofuran-1,3-dione, Intermediate 1 Step 3, (10.0 g, 32.3 mmol) and 4-isopropylaniline (8.75 g, 64.7 mmol) in THF (150 mL) was stirred at 25° C. for 2 h and concentrated. The residue was triturated with ethyl acetate to afford a 1:1 mixture of (1R,2R,6S)-2-(4-bromophenyl)-6-((4-isopropylphenyl)carbamoyl)cyclohexane-1-carboxylic acid and benzyl (1 S,2S,6R)-2-(4-bromophenyl)-6-((4-isopropylphenyl)carbamoyl)cyclohexane-1-carboxylic acid (11.2 g, 25.1 mmol, 78.0% yield) as a white solid. $^{1}$H NMR (400 MHz, DMSO-$d_6$) δ 11.53 (br, 1H), 9.76 (s, 1H), 7.53-7.43 (m, 4H), 7.21 (d, J=8.6 Hz, 2H), 7.14 (d, J=8.6 Hz, 2H), 3.14-3.12 (m, 1H), 2.93-2.73 (m, 3H), 2.43-2.29 (m, 1H), 2.18-2.04 (m, 1H), 1.98-1.95 (m, 1H), 1.70-1.67 (m, 1H), 1.60-1.57 (m, 1H), 1.51-1.43 (m, 1H), 1.17 (d, J=6.8 Hz, 6H). ES-LCMS m/z 442.2 $[M-H]^-$.

Step 2: 1:1 mixture of methyl (1R,2R,6S)-2-(4-bromophenyl)-6-((4-isopropylphenyl)carbamoyl)cyclohexane-1-carboxylate and methyl (1 S,2S,6R)-2-(4-bromophenyl)-6-((4-isopropylphenyl)carbamoyl)cyclohexane-1-carboxylate

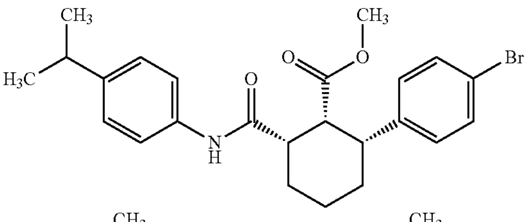

+

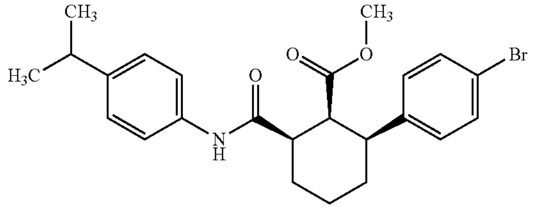

To a 1:1 mixture of (1R,2R,6S)-2-(4-bromophenyl)-6-((4-isopropylphenyl)carbamoyl)cyclohexane-1-carboxylic acid and benzyl (1S,2S,6R)-2-(4-bromophenyl)-6-((4-isopropylphenyl)carbamoyl)cyclohexane-1-carboxylic acid (0.500 g, 1.13 mmol) in DCM (10 mL) and MeOH (1 mL) at 0° C. was added $TMSCHN_2$ (1.1 mL, 2.2 mmol). The reaction was stirred at 22° C. for 16 h and concentrated to afford a 1:1 mixture of methyl (1R,2R,6S)-2-(4-bromophenyl)-6-((4-isopropylphenyl)carbamoyl)cyclohexane-1-carboxylate and methyl (1 S,2S,6R)-2-(4-bromophenyl)-6-((4-isopropylphenyl)carbamoyl)cyclohexane-1-carboxylate (455 mg, 0.993 mmol, 88.0% yield) as a white solid, which was used without purification. $^1$H NMR (400 MHz, DMSO-$d_6$) δ 9.81 (s, 1H), 7.54-7.38 (m, 4H), 7.22-7.08 (m, 4H), 3.25 (s, 3H), 3.12 (t, J=4.5 Hz, 1H), 2.93 (dt, J=13.1, 4.0 Hz, 1H), 2.88-2.77 (m, 2H), 2.40-2.21 (m, 1H), 2.12 (qd, J=13.0, 3.8 Hz, 1H), 2.05-1.93 (m, 1H), 1.76 (dd, J=12.8, 3.7 Hz, 1H), 1.59 (dd, J=13.1, 3.1 Hz, 1H), 1.55-1.41 (m, 1H), 1.17 (d, J=6.9 Hz, 6H).

Step 3: 1:1 mixture of (1R,2S,6S)-2-(4-bromophenyl)-6-((4-isopropylphenyl)carbamoyl)cyclohexane-1-carboxylic acid and (1 S,2R,6R)-2-(4-bromophenyl)-6-((4-isopropylphenyl)carbamoyl)cyclohexane-1-carboxylic acid

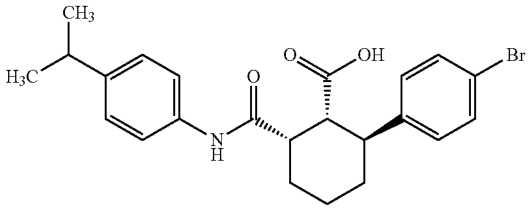

+

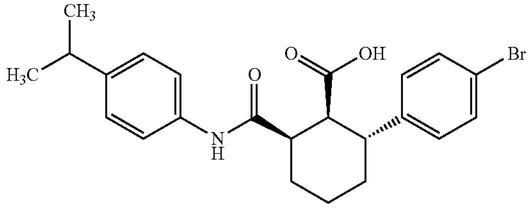

To a 1:1 mixture of methyl (1R,2R,6S)-2-(4-bromophenyl)-6-((4-isopropylphenyl)carbamoyl)cyclohexane-1-carboxylate and methyl (1 S,2S,6R)-2-(4-bromophenyl)-6-((4-isopropylphenyl)carbamoyl)cyclohexane-1-carboxylate (1.03 g, 2.25 mmol) in methanol (20 mL) at 22° C. was added sodium methoxide (30% w/w, 4.05 g, 22.5 mmol) and the resulting reaction mixture was heated at 75° C. for 2 hours and then cooled to room temperature. The mixture was added to HCl (1M, 10 mL, 10 mmol) at 0° C., and then stirred for 30 min at 22° C., quenched with water and extracted with ethyl acetate. The organic layers were washed with brine, dried over anhydrous sodium sulfate, filtered, concentrated, dissolved in DMF (3 mL) and purified over silica (80 g C18 column), eluting with 10-60% acetonitrile in water (0.1% formic acid) to give a 1:1 mixture of (1R,2S,6S)-2-(4-bromophenyl)-6-((4-isopropylphenyl)carbamoyl)cyclohexane-1-carboxylic acid and (1 S,2R,6R)-2-(4-bromophenyl)-6-((4-isopropylphenyl)carbamoyl)cyclohexane-1-carboxylic acid (231 mg, 0.447 mmol, 19.90% yield) as a white solid. $^1$H NMR (400 MHz, DMSO-$d_6$) δ 11.81 (s, 1H), 9.76 (s, 1H), 7.55-7.45 (m, 2H), 7.45-7.36 (m, 2H), 7.29-7.17 (m, 2H), 7.17-7.05 (m, 2H), 3.61 (td, J=12.1, 3.9 Hz, 1H), 3.22 (dq, J=5.0, 2.4 Hz, 1H), 2.92 (dd, J=11.6, 4.9 Hz, 1H), 2.90-2.76 (m, J=6.8 Hz, 1H), 2.00 (t, J=6.1 Hz, 1H), 1.93-1.67 (m, 3H), 1.64-1.46 (m, 1H), 1.46-1.27 (m, 1H), 1.18 (d, J=6.9 Hz, 6H).

Step 4: 1:1 mixture of (1R,2S,6S)-2-((4-isopropylphenyl)carbamoyl)-6-(4-(methylamino)phenyl)cyclohexane-1-carboxylic acid and (1 S,2R,6R)-2-((4-isopropylphenyl)carbamoyl)-6-(4-(methylamino) phenyl)cyclohexane-1-carboxylic acid

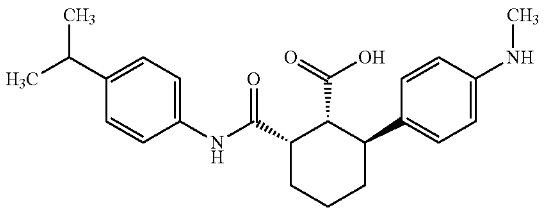

+

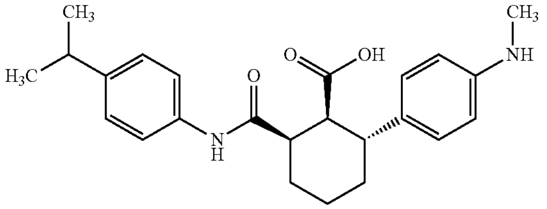

To a 1:1 mixture of (1R,2S,6S)-2-(4-bromophenyl)-6-((4-isopropylphenyl)carbamoyl)cyclohexane-1-carboxylic acid and (1 S,2R,6R)-2-(4-bromophenyl)-6-((4-isopropylphenyl) carbamoyl)cyclohexane-1-carboxylic acid (230 mg, 0.518 mmol), $Cs_2CO_3$ (337 mg, 1.04 mmol) and tBuXPhos Pd G3 (42 mg, 0.053 mmol) was added DMF (3 mL). The reaction was added degassed via vacuum evacuation, then backfilled with nitrogen three times. Methenamines (3.2 mL, 6.4 mmol) was added, and the mixture was heated at 65° C. for 3 h, diluted with water and extracted with ethyl acetate. The organic layers were washed with brine, dried over anhydrous sodium sulfate, filtered, concentrated, dissolved in DMF (3 mL) and purified over silica (80 g C18 column), eluting with 10-60% acetonitrile in water (0.1% formic acid) to give a 1:1 mixture of (1R,2S,6S)-2-((4-isopropylphenyl)carbamoyl)-6-(4-(methylamino)phenyl)cyclohexane-1-carboxylic acid and (1 S,2R,6R)-2-((4-isopropylphenyl)carbamoyl)-6-(4-(methylamino)phenyl)cyclohexane-1-carboxylic acid (82 mg, 0.18 mmol, 34% yield) as a light brown solid. $^1$H NMR (400 MHz, DMSO-$d_6$) δ 11.75 (s, 1H), 9.69 (s, 1H), 8.14 (s, 1H), 7.54-7.42 (m, 2H), 7.20-7.10 (m, 2H), 6.95 (d, J=8.3 Hz, 2H), 6.47-6.38 (m, 2H), 3.41 (td, J=11.7, 3.9 Hz, 1H), 3.10 (q, J=3.6, 2.2 Hz, 1H), 2.94-2.74 (m, 2H), 2.64 (s, 2H), 1.99-1.87 (m, 2H), 1.72 (d, J=13.5 Hz, 2H), 1.50 (d, J=14.1 Hz, 2H), 1.43-1.29 (m, 2H), 1.29-1.08 (m, 9H).

Intermediate 4: 1:1 mixture of (1R,2S,6R)-2-((4-isopropylphenyl)carbamoyl)-6-(4-(methylamino)phenyl)cyclohexane-1-carboxylic acid and (1S,2R,6S)-2-((4-isopropylphenyl)carbamoyl)-6-(4-(methylamino)phenyl)cyclohexane-1-carboxylic acid

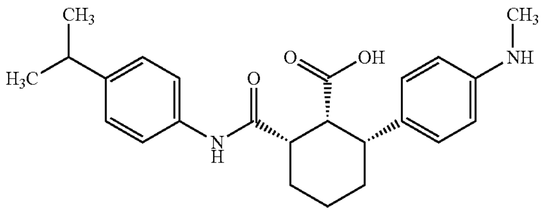

+

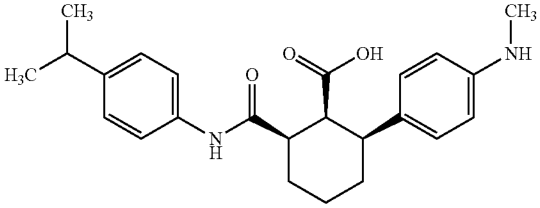

To a 1:1 mixture of (1R,2R,6S)-2-(4-bromophenyl)-6-((4-isopropylphenyl)carbamoyl)cyclohexane-1-carboxylic acid and benzyl (1S,2S,6R)-2-(4-bromophenyl)-6-((4-isopropylphenyl)carbamoyl)cyclohexane-1-carboxylic acid (Intermediate 3 Step 1) (500 mg, 1.13 mmol), $Cs_2CO_3$ (733 mg, 2.25 mmol) and tBuXPhos Pd G3 (89 mg, 0.11 mmol) was added DMF (1 mL). The reaction was added degassed via vacuum evacuation, then backfilled with nitrogen. Methanamine (2M in THF, 6.0 mL, 12 mmol) was added, and the mixture was heated at 60° C. for 3 h, then filtered. The filtrate was concentrated, dissolved in DMF (3 mL) and purified over silica (40 g C18 column), eluting with 5-80% acetonitrile in water (0.1% TFA) to give a 1:1 mixture of (1R,2S,6S)-2-((4-isopropylphenyl)carbamoyl)-6-(4-(methylamino)phenyl)cyclohexane-1-carboxylic acid and (1S,2R,6R)-2-((4-isopropylphenyl)carbamoyl)-6-(4-(methylamino)phenyl)cyclohexane-1-carboxylic acid (0.240 g, 0.578 mmol, 51.4% yield) as a yellow brown solid. $^1H$ NMR (400 MHz, DMSO-$d_6$) δ 11.69-11.24 (br, 1H), 9.76 (s, 1H), 7.57-7.38 (m, 2H), 7.23-7.02 (m, 4H), 6.88-6.84 (m, 2H), 3.10 (t, J=4.6 Hz, 1H), 2.88-2.70 (m, 6H), 2.39-2.35 (m, 1H), 2.19-2.03 (m, 1H), 1.97-1.94 (m, 1H), 1.67-1.63 (m, 1H), 1.57-1.54 (m, 1H), 1.47-1.40 (m, 1H), 1.17 (d, J=6.8 Hz, 6H). ES-LCMS m/z 395.3 $[M+H]^+$.

Intermediate 5: 1:1 mixture of (1R,2R,6S)-2-((4-isopropylphenyl)carbamoyl)-6-(4-(methylamino)phenyl)cyclohexane-1-carboxylic acid and (1S,2S,6R)-2-((4-isopropylphenyl)carbamoyl)-6-(4-(methylamino)phenyl)cyclohexane-1-carboxylic acid

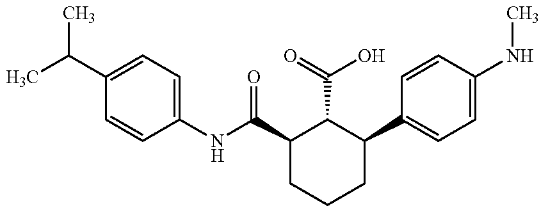

+

-continued

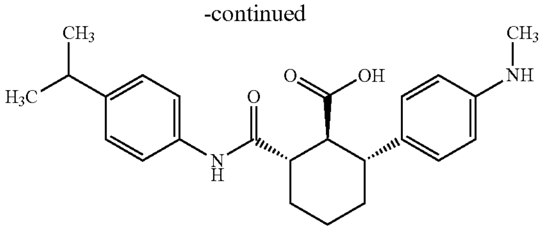

Step 1: 1:1 mixture of benzyl (1R,2S,6R)-2-(4-bromophenyl)-6-((4-isopropylphenyl)carbamoyl)cyclohexane-1-carboxylate and benzyl (1S,2R,6S)-2-(4-bromophenyl)-6-((4-isopropylphenyl)carbamoyl)cyclohexane-1-carboxylate

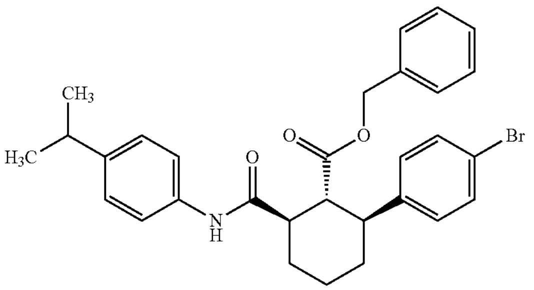

+

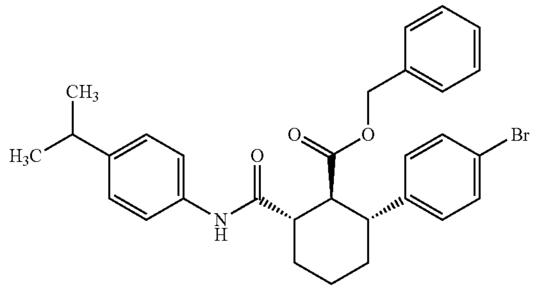

To a 1:1 mixture of (1R,2R,3S)-2-((benzyloxy)carbonyl)-3-(4-bromophenyl)cyclohexane-1-carboxylic acid and (1 S,2S,3R)-2-((benzyloxy)carbonyl)-3-(4-bromophenyl)cyclohexane-1-carboxylic acid (Intermediate 1 Step 8) (1 g, 0.240 mol) in DMF (10 mL) was added HATU (1.09 g, 2.88 mmol), DIEA (1.26 mL, 7.19 mmol) and 4-isopropylaniline (0.389 g, 2.88 mmol). After 12 h at 25° C., the reaction was diluted with water and extracted with EtOAc. The combined organic layers were washed with brine, dried over $Na_2SO_4$, filtered and concentrated to give a 1:1 mixture of benzyl (1R,2S,6R)-2-(4-bromophenyl)-6-((4-isopropylphenyl)carbamoyl)cyclohexane-1-carboxylate and benzyl (1 S,2R,6S)-2-(4-bromophenyl)-6-((4-isopropylphenyl)carbamoyl)cyclohexane-1-carboxylate (1.5 g, 2.3 mmol, 95% yield) as a yellow solid, which was used without further purification. $^1H$ NMR (400 MHz, DMSO-$d_6$) δ 9.92 (s, 1H), 7.96 (s, 1H), 7.46 (ddd, J=10.9, 6.5, 2.2 Hz, 4H), 7.22 (s, 1H), 7.20 (td, J=6.5, 2.9 Hz, 2H), 7.14 (td, J=8.5, 2.4 Hz, 4H), 6.84-6.77 (m, 2H), 4.68 (d, J=3.0 Hz, 2H), 3.01-2.86 (m, 4H), 2.89-2.80 (m, 1H), 2.72 (d, J=16.7 Hz, 6H), 2.69 (s, 1H), 2.01 (dd, J=10.2, 4.8 Hz, 1H), 1.89 (d, J=10.0 Hz, 1H), 1.77 (d, J=12.3 Hz, 1H), 1.64 (dd, J=25.8, 13.1 Hz, 1H), 1.54 (d, J=10.2 Hz, 1H), 1.18 (dd, J=7.0, 2.3 Hz, 7H), 1.15 (s, 1H), 1.13 (d, J=6.9 Hz, 1H).

Step 2: 1:1 mixture of (1R,2S,6R)-2-(4-bromophenyl)-6-((4-isopropylphenyl)carbamoyl)cyclohexane-1-carboxylic acid and (1S,2R,6S)-2-(4-bromophenyl)-6-((4-isopropylphenyl)carbamoyl)cyclohexane-1-carboxylic acid

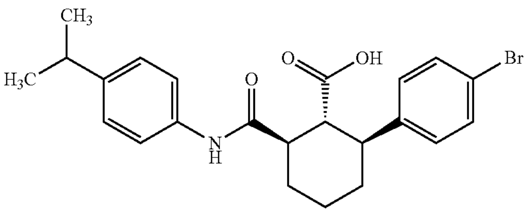

+

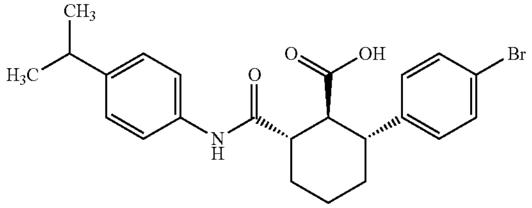

To a 1:1 mixture of benzyl (1R,2S,6R)-2-(4-bromophenyl)-6-((4-isopropylphenyl)carbamoyl)cyclohexane-1-carboxylate and benzyl (1S,2R,6S)-2-(4-bromophenyl)-6-((4-isopropylphenyl)carbamoyl)cyclohexane-1-carboxylate (1.3 g, 2.4 mmol) in dichloromethane (10 mL) at 0° C. was added $BCl_3$ (1M in DCM, 4.86 mL, 4.86 mmol). After 1 h the reaction was quenched with ice and extracted with ethyl acetate. The organic layers were washed with brine, dried over anhydrous sodium sulfate, filtered, concentrated, dissolved in DMF (3 mL) and purified over silica (80 g C18 column), eluting with 5-60% acetonitrile in water (0.1% formic acid) to give 1:1 mixture of (1R,2S,6R)-2-(4-bromophenyl)-6-((4-isopropylphenyl)carbamoyl)cyclohexane-1-carboxylic acid and (1S,2R,6S)-2-(4-bromophenyl)-6-((4-isopropylphenyl)carbamoyl)cyclohexane-1-carboxylic acid (0.480 g, 1.07 mmol, 44.1% yield) as a white solid. $^1H$ NMR (400 MHz, DMSO-$d_6$) δ 11.73 (s, 1H), 9.85 (s, 1H), 7.56-7.38 (m, 4H), 7.22 (d, J=8.8 Hz, 2H), 7.14 (d, J=8.4 Hz, 2H), 2.92-2.63 (m, 4H), 1.94-1.87 (m, 2H), 1.76-1.73 (m, 1H), 1.64-1.38 (m, 2H), 1.17 (d, J=6.8 Hz, 6H). ES-LCMS m/z 444.0 $[M+H]^+$.

Step 3: 1:1 mixture of (1R,2R,6S)-2-((4-isopropylphenyl)carbamoyl)-6-(4-(methylamino)phenyl)cyclohexane-1-carboxylic acid and (1S,2S,6R)-2-((4-isopropylphenyl)carbamoyl)-6-(4-(methylamino)phenyl)cyclohexane-1-carboxylic acid

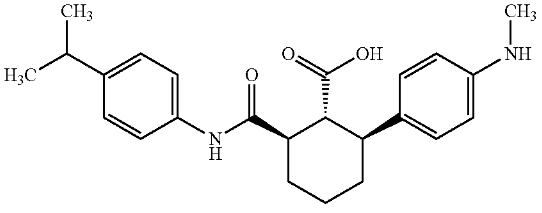

+

-continued

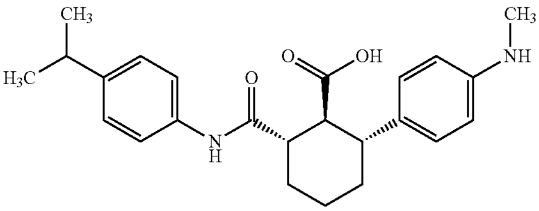

To a degassed solution of a 1:1 mixture of (1R,2S,6R)-2-(4-bromophenyl)-6-((4-isopropylphenyl)carbamoyl)cyclohexane-1-carboxylic acid and (1S,2R,6S)-2-(4-bromophenyl)-6-((4-isopropylphenyl)carbamoyl)cyclohexane-1-carboxylic acid (0.200 g, 0.450 mmol) in DMF (1 mL) were added $Cs_2CO_3$ (0.440 g, 1.35 mmol) and tBuXPhos Pd G3 (54 mg, 0.068 mmol). Methanamine (2M in THF, 2.25 mL, 4.50 mmol) was added, and the mixture was heated at 60° C. for 3 h, then purified over silica (40 g C18 column), eluting with 5-55% acetonitrile in water (0.1% TFA) to give a 1:1 mixture of (1R,2S,6S)-2-((4-isopropylphenyl)carbamoyl)-6-(4-(methylamino)phenyl)cyclohexane-1-carboxylic acid and (1 S,2R,6R)-2-((4-isopropylphenyl)carbamoyl)-6-(4-(methylamino)phenyl)cyclohexane-1-carboxylic acid (0.080 g, 0.20 mmol, 45% yield) as a white solid. $^1H$ NMR (400 MHz, DMSO-$d_6$) δ 11.55 (br, 1H), 9.81 (s, 1H), 7.48 (d, J=8.6 Hz, 2H), 7.13 (d, J=8.6 Hz, 2H), 6.95 (d, J=8.6 Hz, 2H), 6.44 (d, J=8.6 Hz, 2H), 5.40 (br, 1H), 2.85-2.80 (m, 1H), 2.72-2.62 (m, 5H), 2.53-2.52 (m, 1H), 1.92-1.84 (m, 2H), 1.71-1.69 (m, 1H), 1.54-1.50 (m, 3H), 1.17 (d, J=6.8 Hz, 6H). ES-LCMS m/z 395.2 $[M+H]^+$.

Intermediate 6: 1:1 mixture of (1R,2R,6S)-2-((2-fluoro-4-(trifluoromethyl)phenyl)carbamoyl)-6-(4-(methylamino)phenyl)cyclohexane-1-carboxylic acid and (1 S,2S,6R)-2-((2-fluoro-4-trifluoromethyl)phenyl)carbamoyl)-6-(4-(methylamino)phenyl)cyclohexane-1-carboxylicacid

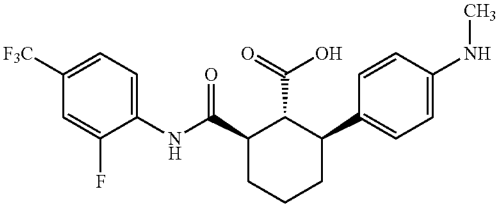

+

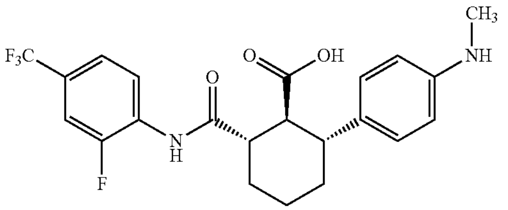

Step 1: 1:1 mixture of (1R,2S,6R)-2-(4-bromophenyl)-6-((2-fluoro-4-(trifluoromethyl)phenyl)carbamoyl)cyclohexane-1-carboxylic acid and (1S,2R,6S)-2-(4-bromophenyl)-6-((2-fluoro-4-(trifluoromethyl)phenyl)carbamoyl)cyclohexane-1-carboxylic acid

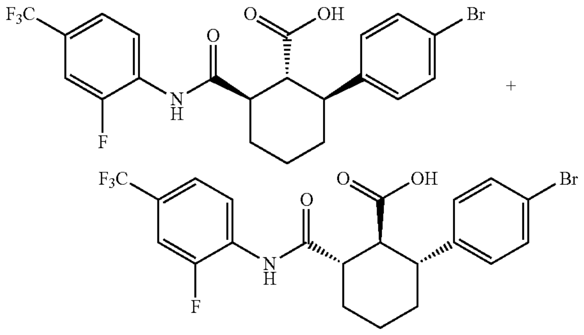

To a 1:1 mixture of benzyl (1R,2S,6R)-2-(4-bromophenyl)-6-((2-fluoro-4-(trifluoromethyl)phenyl)carbamoyl)cyclohexane-1-carboxylate and benzyl (1 S,2R,6S)-2-(4-bromophenyl)-6-((2-fluoro-4-(trifluoromethyl)phenyl)carbamoyl)cyclohexane-1-carboxylate (Intermediate 1 Step 9) (896 mg, 1.55 mmol) in dichloromethane (10 mL) at 0° C. was added $BCl_3$ (1M in DCM, 3.10 mL, 3.10 mmol). After 1 h the reaction was quenched with water and extracted with ethyl acetate. The organic layers were washed with brine, dried over anhydrous sodium sulfate, filtered, concentrated, dissolved in DMF (1.5 mL) and purified over silica (40 g C18 column), eluting with 5-100% acetonitrile in water to give 1:1 mixture of (1R,2S,6R)-2-(4-bromophenyl)-6-((2-fluoro-4-(trifluoromethyl)phenyl)carbamoyl)cyclohexane-1-carboxylic acid and (1S,2R,6S)-2-(4-bromophenyl)-6-((2-fluoro-4-(trifluoromethyl)phenyl)carbamoyl) cyclohexane-1-carboxylic acid (340 mg, 0.689 mmol, 44.5% yield) as a white solid. $^1$H NMR (400 MHz, DMSO-$d_6$) δ 11.76 (s, 1H), 10.09 (s, 1H), 8.20 (t, J=8.0 Hz, 1H), 7.71 (d, J=11.2 Hz, 1H), 7.55 (d, J=8.8 Hz, 1H), 7.47 (d, J=8.4 Hz, 2H), 7.24 (d, J=8.4 Hz, 2H), 2.99 (t, J=11.2 Hz, 1H), 2.76-2.67 (m, 2H), 2.03-2.00 (m, 1H), 1.89-1.88 (m, 1H), 1.77-1.73 (m, 1H), 1.61-1.53 (m, 3H). ES-LCMS m/z 488.1 $[M+H]^+$.

Step 2: 1:1 mixture of (1R,2R,6S)-2-((2-fluoro-4-(trifluoromethyl)phenyl)carbamoyl)-6-(4-(methylamino)phenyl)cyclohexane-1-carboxylic acid and (1S,2S,6R)-2-((2-fluoro-4-(trifluoromethyl)phenyl)carbamoyl)-6-(4-(methylamino)phenyl)cyclohexane-1-carboxylic acid

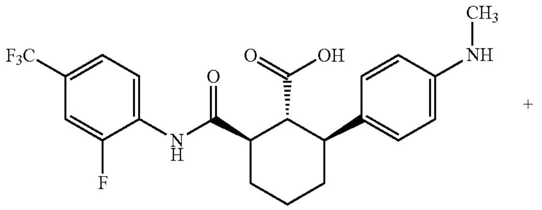

-continued

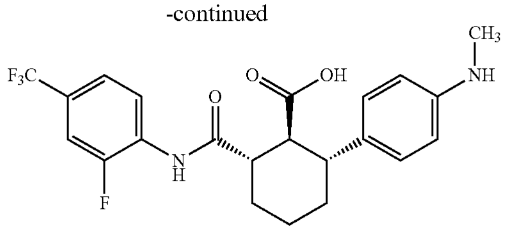

To a degassed solution of a 1:1 mixture of (1R,2S,6R)-2-(4-bromophenyl)-6-((2-fluoro-4-(trifluoromethyl)phenyl)carbamoyl)cyclohexane-1-carboxylic acid and (1 S,2R,6S)-2-(4-bromophenyl)-6-((2-fluoro-4-(trifluoromethyl)phenyl)carbamoyl)cyclohexane-1-carboxylic acid (0.339 g, 0.694 mmol) in DMF (3 mL) were added $Cs_2CO_3$ (679 mg, 2.08 mmol) and t-BuBrettPhos Palladacycle Gen. 3 (119 mg, 0.139 mmol). Methanamine (2M in THF, 2.25 mL, 4.50 mmol) was added, and the mixture was heated at 60° C. for 2 h, quenched with water and extracted with ethyl acetate. The organic layers were washed with brine, dried over anhydrous sodium sulfate, filtered, concentrated, dissolved in DMF (2 mL) and purified over silica (40 g C18 column), eluting with 5-100% acetonitrile in water to give 1:1 mixture of (1R,2R,6S)-2-((2-fluoro-4-(trifluoromethyl)phenyl)carbamoyl)-6-(4-(methylamino)phenyl)cyclohexane-1-carboxylic acid and (1S,2S,6R)-2-((2-fluoro-4-(trifluoromethyl)phenyl)carbamoyl)-6-(4-(methylamino)phenyl)cyclohexane-1-carboxylic acid (0.060 g, 0.14 mmol, 51% yield) as a white solid. $^1$H NMR (400 MHz, DMSO-$d_6$) δ 11.63 (br, 1H), 10.11 (br, 1H), 8.22 (t, J=7.8 Hz, 1H), 7.71-7.68 (m, 1H), 7.54 (d, J=8.4 Hz, 1H), 6.95 (d, J=8.4 Hz, 2H), 6.43 (d, J=8.4 Hz, 2H), 5.39-5.37 (m, 1H), 3.00-2.93 (m, 1H), 2.70-2.67 (m, 2H), 2.64 (d, J=4.0 Hz, 3H), 1.99-1.96 (m, 1H), 1.87-1.84 (m, 1H), 1.73-1.68 (m, 1H), 1.54-1.47 (m, 3H). ES-LCMS m/z 439.1 $[M+H]^+$.

Intermediate 7: (1R,2R,6S)-2-((2-fluoro-4-(trifluoromethyl)phenyl)carbamoyl)-6-(4-(methylamino)phenyl)cyclohexane-1-carboxylic acid

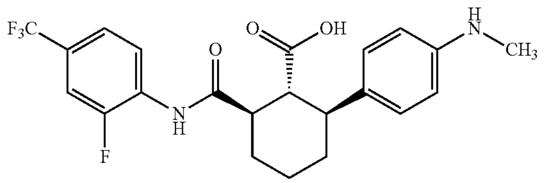 [SMILES: CNc1ccc([C@H]2CCC[C@@H](C(=O)Nc3ccc(C(F)(F)F)cc3F)[C@@H]2C(=O)O)cc1]

To a degassed solution of (1R,2S,6R)-2-(4-bromophenyl)-6-((2-fluoro-4-(trifluoromethyl)phenyl)carbamoyl)cyclohexane-1-carboxylic acid Intermediate 1 (1.50 g, 3.1 mmol) in DMF (30 mL) were added $Cs_2CO_3$ (3.0 g, 9.2 mmol), methanamine (2M in THF, 30.7 mL, 61.4 mmol) and t-BuBrettPhos Palladacycle Gen. 3 (525 mg, 0.614 mmol). The mixture was heated at 60° C. for 2 h, cooled to rt and filtered. The filtrate was concentrated under reduced pressure and the residue was diluted to 100 mL with DMF to give the product as a solution in DMF. Two 9 mL aliquots were removed for subsequent reactions while the remaining 82 mL was concentrated under reduced pressure to yield material that was purified over silica (150 g C18 Gold column), eluting with 30-60% MeCN in water (with 10 nM ammonium bicarbonate and 0.075% ammonium hydroxide)

to give (1R,2R,6S)-2-((2-fluoro-4-(trifluoromethyl)phenyl)carbamoyl)-6-(4-(methylamino)phenyl)cyclohexane-1-carboxylic acid (953 mg, 2.17 mmol, 86% yield) as a tan solid. $^1$H NMR (400 MHz, DMSO-$d_6$) δ 12.82-11.29 (br s, 1H), 10.24 (br s, 1H), 8.21 (t, J=8.1 Hz, 1H), 7.65 (dd, J=10.8, 1.5 Hz, 1H), 7.51 (br d, J=8.3 Hz, 1H), 6.94 (d, J=8.8 Hz, 2H), 6.42 d, J=8.3 Hz, 2H), 5.61-5.14 (m, 1H), 3.06-2.82 (m, 1H), 2.69-2.41 (m, 2H), 2.63 (s, 3H), 1.93 (br d, J=10.3 Hz, 1H), 1.86-1.75 (m, 1H), 1.71-1.61 (m, 1H), 1.55-1.35 (m, 3H). ES-LCMS m/z 439.2 $[M+H]^+$.

Intermediate 7, alternate synthesis: (1R,2R,6S)-2-((2-fluoro-4-(trifluoromethyl)phenyl)carbamoyl)-6-(4-(4,4,5,5-tetramethyl-1,3,2-dioxaborolan-2-yl)phenyl)cyclohexane-1-carboxylic acid

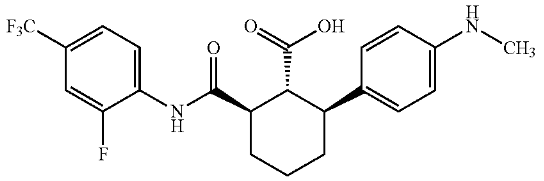 [SMILES: CNc1ccc([C@H]2CCC[C@@H](C(=O)Nc3ccc(C(F)(F)F)cc3F)[C@@H]2C(=O)O)cc1]

Step 1: (1R,2R,3S)-2-((benzyloxy)carbonyl)-3-(4-bromophenyl)cyclohexane-1-carboxylic acid

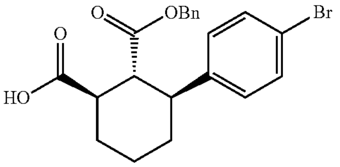 [SMILES: O=C(OCc1ccccc1)[C@@H]1[C@@H](c2ccc(Br)cc2)CCC[C@H]1C(=O)O]

A. Four Reactions (850 g×4) were Conducted in Parallel:

THF (25.5 L) was added to a mixture of (1R)-1-(1-naphthyl)ethanamine (348 g, 2.04 mol) and a 1:1 mixture of (1R,2R,3S)-2-((benzyloxy)carbonyl)-3-(4-bromophenyl)cyclohexane-1-carboxylic acid and (1 S,2S,3R)-2-((benzyloxy)carbonyl)-3-(4-bromophenyl)cyclohexane-1-carboxylic acid Intermediate 1 Step 8 (0.850 kg, 2.04 mol) at 25° C., in one portion. The reaction was heated to 65° C. After 40 min, the mixture was cooled to 60° C. After 2 h, the mixture was further cooled to 50° C., and after 2 h more, the reaction was cooled to 25° C. After 12 h, the four reactions were combined and filtered, and the filter cake was washed with THF (5.00 L). The filter cake was dried under vacuum at 40° C. to give the undesired salt as a white solid (1.50 kg). The mother liquid (~1.70 kg in mother liquid [25.5 L THF]) was used in the next stage directly.

B. Four Reactions (425 g×4) were Conducted in Parallel.

To the mother liquid from step A (~425 g in mother liquid [6.37 L, THF]) was added (1S)-1-(1-naphthyl)ethanamine (174 g, 1.02 mol) at 25° C. in one portion. The mixture was heated to 50° C. for 2 h, then cooled down to 25° C. After 12 h, the four reactions were combined and filtered, and the filter cake was washed with THF (2.00 L). The filter cake was dried under vacuum at 40° C. to give (1R,2R,3S)-2-((benzyloxy)carbonyl)-3-(4-bromophenyl)cyclohexane-1-carboxylic acid, (1S)-1-(1-naphthyl)ethanamine salt (1.50 kg, 3.59 mol, 99.6%) as a white solid. This material was divided and used in four reactions (375 g×4) conducted in parallel.

C. Ethyl acetate (800 mL) was added to the above (1S)-1-(1-naphthyl)ethanamine salt (375 g, 899 mmol) at 25° C. in one portion. The pH of the mixture was adjusted to ~1 with 1 M HCl (899 mL, 899 mmol) at 0~5° C., and the reaction became clear. The four reactions were combined for work up. The organic layer was separated, and the aqueous phase was extracted with EtOAc (3.00 L×3). The combined organic layers were washed with $H_2O$ (2.00 L×3), dried over $Na_2SO_4$, filtered and concentrated under vacuum at 40° C. to give the crude product as a white solid. This material was triturated with MTBE:EtOAc (3:1, 5 L) at 25° C. for 30 mins, filtered, washed with MTBE (500 mL×3) and dried under reduced pressure at 40° C. to give (1R,2R,3S)-2-((benzyloxy)carbonyl)-3-(4-bromophenyl)cyclohexane-1-carboxylic acid (1.19 kg, 2.85 mol, 35.0% yield) as a white solid. $^1$H NMR (400 MHz, DMSO-$d_6$) δ 12.3 (s, 1H), 7.42 (d, J=8.4 Hz, 2H), 7.25-7.23 (m, 3H), 7.17 (d, J=8.4 Hz, 2H), 6.83 (d, J=7.6 Hz, 2H), 4.69 (q, J=12.8 Hz, 2H), 2.77-2.74 (m, 1H), 2.67-2.63 (m, 2H), 2.22-2.10 (m, 1H), 1.78-1.74 (m, 2H), 1.54-1.47 (m, 3H). ES-LCMS m/z 439.2 $[M+Na]^+$.

Step 2: benzyl (1R,2S,6R)-2-(4-bromophenyl)-6-((2-fluoro-4-(trifluoromethyl)phenyl)carbamoyl)cyclohexane-1-carboxylate

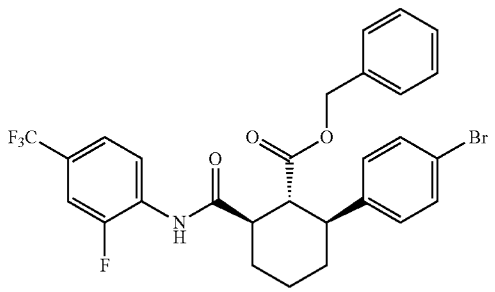 [SMILES: O=C(OCc1ccccc1)[C@@H]1[C@@H](c2ccc(Br)cc2)CCC[C@H]1C(=O)Nc1ccc(C(F)(F)F)cc1F]

Three Reactions (393 g×3) were Conducted in Parallel.

To a mixture of (1R,2R,3S)-2-((benzyloxy)carbonyl)-3-(4-bromophenyl)cyclohexane-1-carboxylic acid (393 g, 942 mmol) in acetonitrile (1.70 L) at 0° C. was added 2-fluoro-4-(trifluoromethyl)aniline (337 g, 1.88 mol) and NMI (155 g, 1.88 mol). After ~2 min, TCFH (396 g, 1.41 mmol) was added portionwise. The reaction was stirred at 25° C. for 12 h. The three reactions were combined, concentrated at 40° C., dissolved in DCM, loaded onto silica gel (100-200 mesh silica gel, self-prepared column chromatography) and eluted with 100:1 to 3:1 EtOAC:petroleum ether to give crude product. This material was triturated with petroleum ether (3.00 L) at 25° C. for 2 h, filtered, washed with petroleum ether (500 mL×3) and dried under reduced pressure at 40° C. to provide benzyl (1R,2S,6R)-2-(4-bromophenyl)-6-((2-fluoro-4-(trifluoromethyl)phenyl)carbamoyl)cyclohexane-1-carboxylate (910 g, 1.57 mol, 55.8% yield) as a white solid. $^1$H NMR (400 MHz, DMSO-$d_6$) δ 10.1 (s, 1H), 8.15 (t, J=8.0 Hz, 1H), 7.70 (d, J=11.2 Hz, 1H), 7.53 (d, J=8.4 Hz, 1H), 7.44 (d, J=8.0 Hz, 2H), 7.21 (d, J=8.0 Hz, 2H), 7.19-7.13 (m, 3H), 6.80 (d, J=6.8 Hz, 2H), 4.68 (q, J=12.4 Hz, 1H), 3.09-3.04 (m, 1H), 2.98-2.92 (m, 1H), 2.75-2.69 (m, 1H), 2.07-2.04 (m, 1H), 1.89-1.87 (m, 1H), 1.77-1.74 (m, 1H), 1.66-1.52 (m, 3H).

Step 3: (1R,2S,6R)-2-(4-bromophenyl)-6-((2-fluoro-4-(trifluoromethyl)phenyl)carbamoyl)cyclohexane-1-carboxylic acid

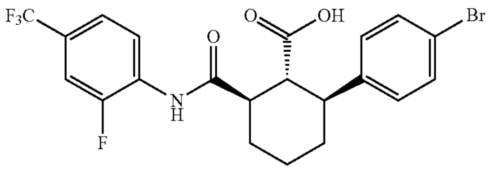 [SMILES: O=C(O)[C@@H]1[C@@H](c2ccc(Br)cc2)CCC[C@H]1C(=O)Nc1ccc(C(F)(F)F)cc1F]

Three reactions (217 g×3) were conducted in parallel.

To a mixture of benzyl (1R,2S,6R)-2-(4-bromophenyl)-6-((2-fluoro-4-(trifluoromethyl)phenyl)carbamoyl)cyclohexane-1-carboxylate (217 g, 375 mmol) in DCM (1.20 L)) at −30° C. was added $BBr_3$ (188 g, 0.750 mol). After 1 h the three reactions were combined, cooled to 0° C., quenched with water (3.00 L) and extracted with EtOAc (2.40 L×3). The combined organic layers were washed with brine (2.00 L), dried over $Na_2SO_4$, filtered and concentrated under reduced pressure at 40° C. to give crude residue. The crude product was triturated with 5:1 PE:EA (4.80 L) at 25° C. for 2 h, filtered, washed with PE (500 mL×3) and dried under reduced pressure at 40° C. to provide (1R,2S,6R)-2-(4-bromophenyl)-6-((2-fluoro-4-(trifluoromethyl)phenyl)carbamoyl)cyclohexane-1-carboxylic acid (0.610 kg, 1.25 mol, 84.9% yield) as a white solid. $^1H$ NMR (400 MHz, DMSO-$d_6$) δ 11.8 (s, 1H), 10.0 (s, 1H), 8.21 (t, J=8.0 Hz, 1H), 7.70 (dd, J=10.8, 1.6 Hz, 1H), 7.53 (d, J=8.4 Hz, 1H), 7.46 (d, J=8.4 Hz, 2H), 7.22 (d, J=8.4 Hz, 2H), 3.03-2.97 (m, 1H), 2.82-2.76 (m, 1H), 2.71-2.65 (m, 1H), 2.02-2.00 (m, 1H), 1.87 (m, 1H), 1.76-1.73 (m, 1H), 1.59-1.47 (m, 3H).

Step 4: (1R,2R,6S)-2-((2-fluoro-4-(trifluoromethyl)phenyl)carbamoyl)-6-(4-(4,4,5,5-tetramethyl-1,3,2-dioxaborolan-2-yl)phenyl)cyclohexane-1-carboxylic acid

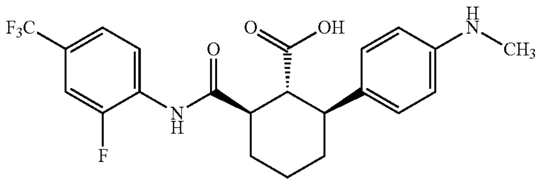 [SMILES: CNc1ccc([C@H]2CCC[C@@H](C(=O)Nc3ccc(C(F)(F)F)cc3F)[C@@H]2C(=O)O)cc1]

Two reactions (100 g x 2) were conducted in parallel.

To a mixture of (1R,2S,6R)-2-(4-bromophenyl)-6-((2-fluoro-4-(trifluoromethyl)phenyl)carbamoyl)cyclohexane-1-carboxylic acid (0.100 kg, 204 mmol) in DMF (600 mL) at 20° C. were added $Cs_2CO_3$ (0.200 kg, 614 mmol), t-BuBrettPhos Palladacycle Gen. 3 (35.0 g, 40.9 mmol) and methanamine (426 g, 4.12 mol). The reaction was heated to 60° C. for 2 h. The two reactions were combined, cooled to 20° C., poured into water (2.40 L) and extracted with MTBE (800 mL×3). The aqueous phase was adjusted to pH=6 with 1 M HCl (1.20 L) and extracted with 2-Me-THF (1.50 L×3). The combined organic layers were washed with brine (1.00 L×3), dried over $Na_2SO_4$, filtered and concentrated under reduced pressure at 30° C. to give crude residue. The crude product was triturated with 1:1 EtOAc: MTBE (600 ml) at 20° C. for 30 min, filtered, washed with PE (500 mL×3) and dried under reduced pressure at 40° C. to give (1R,2R,6S)-2-((2-fluoro-4-(trifluoromethyl)phenyl)carbamoyl)-6-(4-(4,4,5,5-tetramethyl-1,3,2-dioxaborolan-2-yl)phenyl)cyclohexane-1-carboxylic acid (0.120 kg, 273 mmol, 66.8% yield) as a white solid. $^1H$ NMR (400 MHz, DMSO-$d_6$) δ 11.6 (s, 1H), 10.0 (s, 1H), 8.21 (t, J=8.0 Hz, 1H), 7.70 (d, J=9.6 Hz, 1H), 7.54 (d, J=8.8 Hz, 1H), 6.94 (d, J=8.4 Hz, 2H), 6.42 (d, J=8.4 Hz, 2H), 5.42 (s, 1H), 2.99-2.93 (m, 1H), 2.71-2.62 (m, 4H), 2.54-2.50 (m, 1H), 1.98-1.96 (m, 1H), 1.85-1.853 (m, 1H), 1.71-1.68 (m, 1H), 1.51-1.46 (m, 3H).

Intermediate 8: 1:1 mixture of (1R,2R,4R,6S)-4-ethoxy-2-((2-fluoro-4-(trifluoromethyl)phenyl)carbamoyl)-6-(4-(methylamino)phenyl)cyclohexane-1-carboxylic acid and (1 S,2S,4S,6R)-4-ethoxy-2-((2-fluoro-4-(trifluoromethyl)phenyl)carbamoyl)-6-(4-(methylamino)phenyl)cyclohexane-1-carboxylic acid

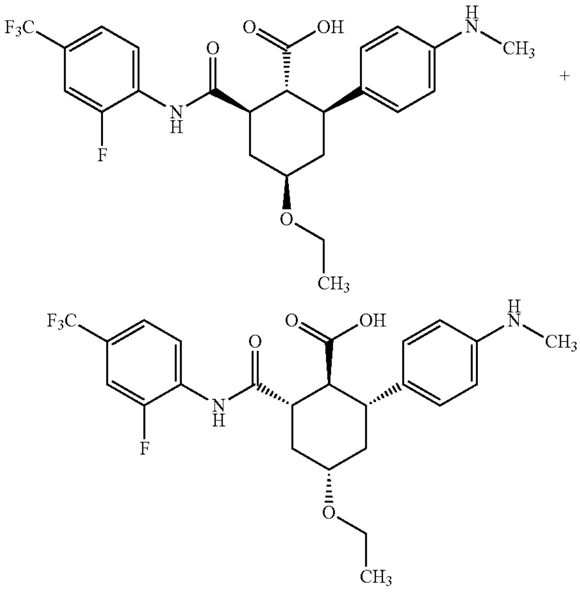

Step 1: (E)-4-(4-bromophenyl)but-3-en-2-one

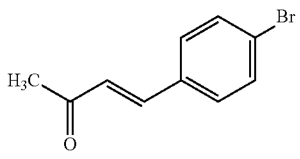

Three reactions were carried out in parallel (1.35 kg×3): To a mixture of 4-bromobenzaldehyde (1.35 kg, 7.30 mol), acetone (5.4 L) and $H_2O$ (10.8 L) was added NaOH (135 g, 3.37 mol), slowly via a dropping funnel at 15-20° C. The reaction mixture was stirred at 15-20° C. for 12 h. The three batches were combined, and the reaction mixture was filtered. The filter cake was washed water (1.00 L) and concentrated in vacuo at 45° C. to give compound (E)-4-(4-bromophenyl)but-3-en-2-one (4.60 kg, 20.0 mol, 89.0% yield) as a white solid. $^1H$ NMR (400 MHz, DMSO-$d_6$) δ

7.68-7.57 (m, 5H), 6.83 (d, J=16 Hz, 1H), 2.33 (s, 3H). ES-LCMS m/z 224.9 $[M+H]^+$.

Step 2: (E)-((4-(4-bromophenyl)buta-1,3-dien-2-yl)oxy)triisopropylsilane

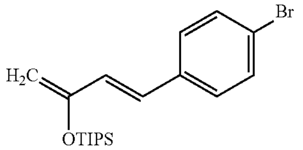

Ten reactions were carried out in parallel (340 g×10): a mixture of (E)-4-(4-bromophenyl)but-3-en-2-one (0.34 kg, 1.51 mol) in 2-methyltetrahydrofuran (2.04 L) was degassed and purged with $N_2$ 3 times. The reaction was cooled to −20° C., and TIPSOTf (451 mL, 1.66 mol) and $Et_3N$ (421 mL, 3.02 mol) were added dropwise. The mixture was stirred at 0° C. for 2 h and the reaction was complete. The reactions were combined, poured to ice water (15.0 L) and partitioned between 2-Me-THF and water. The organic layers were dried over $MgSO_4$ for 12 h, filtered and concentrated below 30° C. in vacuo to give (E)-((4-(4-bromophenyl)buta-1,3-dien-2-yl)oxy)triisopropylsilane (5.75 kg, 14.8 mol, quantitative yield). $^1H$ NMR (400 MHz, DMSO-$d_6$) δ 7.51 (d, J=8.4 Hz, 2H), 7.41 (d, J=8.4 Hz, 2H), 6.83 (d, J=16 Hz, 1H), 6.76 (d, J=17 Hz, 1H), 4.54 (s, 1H), 4.42 (s, 1H), 1.28-1.33 (m, 3H), 1.13-1.08 (m, 18H). ES-LCMS m/z 381.1 $[M+H]^+$.

Step 3: 1:1 mixture of (3aS,4S,7aR)-4-(4-bromophenyl)-6-((triisopropylsilyl)oxy)-3a,4,7,7a-tetrahydroisobenzofuran-1,3-dione and (3aR,4R,7aS)-4-(4-bromophenyl)-6-((triisopropylsilyl)oxy)-3a,4,7,7a-tetrahydroisobenzofuran-1,3-dione

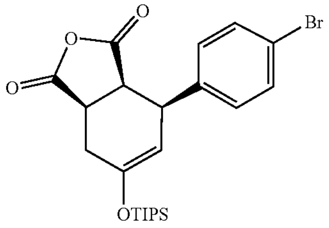

+

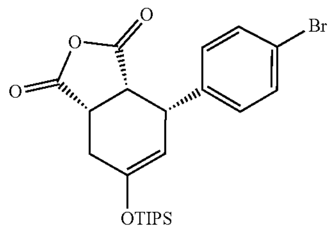

Eighteen reaction were carried in parallel (300 g×18): To a mixture of furan-2,5-dione (390 g, 3.9 mol) in DCM (2.0 L) was added a solution of (E)-((4-(4-bromophenyl)buta-1,3-dien-2-yl)oxy)triisopropylsilane (300 g, 790 mmol) in DCM (1.0 L) slowly over 15 mins at 15° C. Then the mixture was stirred at 25° C. for 3.5 h. The reactions were combined and concentrated in vacuo at 30° C. and triturated with n-heptane (5.00 L). The resulting solid product was collected by filtration and washed with n-heptane (1.00 L). The filtrate was then concentrated in vacuo at 30° C., and then triturated with n-heptane, filtered, and washed with n-heptane to recover additional product. The recovery process was repeated 3 more times and the products were combined to provide a 1:1 mixture of (3aS,4S,7aR)-4-(4-bromophenyl)-6-((triisopropylsilyl)oxy)-3a,4,7,7a-tetrahydroisobenzofuran-1,3-dione and (3aR,4R,7aS)-4-(4-bromophenyl)-6-((triisopropylsilyl)oxy)-3a,4,7,7a-tetrahydroisobenzofuran-1,3-dione (5.60 kg, 8.25 mol, crude) as yellow solid. $^1H$ NMR (400 MHz, DMSO-$d_6$) δ 7.52 (d, J=8.4 Hz, 2H), 7.13 (d, J=8.4 Hz, 2H), 5.07-5.05 (m, 1H), 3.92-3.80 (m, 3H), 2.66-2.53 (m, 2H), 1.08-1.03 (m, 21H).

Step 4: 1:1 mixture of (1S,2S,3R)-4'-bromo-3-(hydroxymethyl)-5-((triisopropylsilyl)oxy)-1,2,3,4-tetrahydro-[1,1'-biphenyl]-2-carboxylic acid and (1R,2R,3S)-4'-bromo-3-(hydroxymethyl)-5-((triisopropylsilyl)oxy)-1,2,3,4-tetrahydro-[1,1'-biphenyl]-2-carboxylic acid

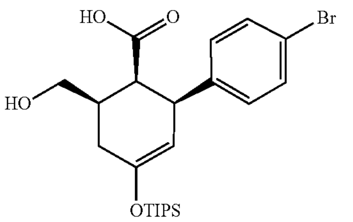

+

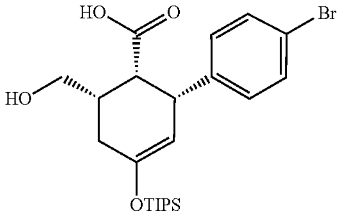

A 1:1 mixture of (3aS,4S,7aR)-4-(4-bromophenyl)-6-((triisopropylsilyl)oxy)-3a,4,7,7a-tetrahydroisobenzofuran-1,3-dione and (3aR,4R,7aS)-4-(4-bromophenyl)-6-((triisopropylsilyl)oxy)-3a,4,7,7a-tetrahydroisobenzofuran-1,3-dione (5.50 kg, 11.5 mol) in THF (36.0 L) was degassed and purged with $N_2$ 3 times. The reaction was cooled to 0° C., and $NaBH_4$ (521 g, 13.8 mol) was added to the mixture, in portions, at 0-3° C. The mixture was stirred at 20° C. for 1 h, and water (962 mL) was added slowly to the reaction at 0-5° C. over 10 min. HCl (1 N) was added to the mixture until pH=7. The reaction was stirred at 5-10° C. for 20 min, and anhydrous $Na_2SO_4$ (1.00 kg) was added. The mixture was filtered and concentrated under reduced pressure to give a 1:1 mixture of (1S,2S,3R)-4'-bromo-3-(hydroxymethyl)-5-((triisopropylsilyl)oxy)-1,2,3,4-tetrahydro-[1,1'-biphenyl]-2-carboxylic acid and (1R,2R,3S)-4'-bromo-3-(hydroxymethyl)-5-((triisopropylsilyl)oxy)-1,2,3,4-tetrahydro-[1,1'-biphenyl]-2-carboxylic acid (3.60 kg, crude) as a white solid, which was used without purification. ES-LCMS m/z 483.2 $[M+H]^+$.

Step 5: 1:1 mixture of (3aR,7S,7aS)-7-(4-bromophenyl)tetrahydroisobenzofuran-1,5(3H,4H)-dione and (3aS,7R,7aR)-7-(4-bromophenyl)tetrahydroisobenzofuran-1,5(3H,4H)-dione

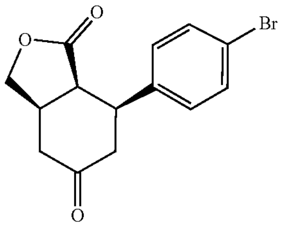

+

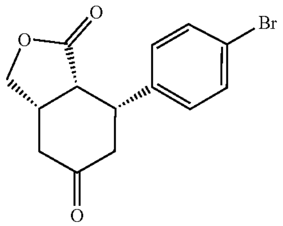

Ten reactions were carried out in parallel (220 g×10): A 1:1 mixture of (1S,2S,3R)-4'-bromo-3-(hydroxymethyl)-5-((triisopropylsilyl)oxy)-1,2,3,4-tetrahydro-[1,1'-biphenyl]-2-carboxylic acid and (1R,2R,3S)-4'-bromo-3-(hydroxymethyl)-5-((triisopropylsilyl)oxy)-1,2,3,4-tetrahydro-[1,1'-biphenyl]-2-carboxylic acid (220 g, 4.55 mol) in toluene (1.32 L) was degassed and purged with $N_2$ 3 times. TsOH (8.70 g, 0.455 mol) was added to the mixture at 20° C., and the reaction was stirred at 110° C. for 12 h. The mixture was poured into $H_2O$ (1.2 L) at 0° C. and the aqueous layer was extracted with ethyl acetate (300 mL×3). The combined organic layers were washed with saturated aqueous sodium bicarbonate solution (150 mL) and brine (150 mL) and dried over sodium sulfate, filtered and concentrated under reduced pressure at 40° C. to provide a crude product.

In a separate reaction, a 1:1 mixture of (1S,2S,3R)-4'-bromo-3-(hydroxymethyl)-5-((triisopropylsilyl)oxy)-1,2,3,4-tetrahydro-[1,1'-biphenyl]-2-carboxylic acid and (1R,2R,3S)-4'-bromo-3-(hydroxymethyl)-5-((triisopropylsilyl)oxy)-1,2,3,4-tetrahydro-[1,1'-biphenyl]-2-carboxylic acid (400 g, 827 mmol) in toluene (2.4 L) was degassed and purged with $N_2$ 3 times. TsOH (15.7 g, 83.0 mmol) was added to the mixture at 20° C., and the reaction was stirred at 110° C. for 13 h. The mixture was poured into $H_2O$ (500 mL) at 0° C. and the aqueous layer was extracted with dichloromethane (500 mL×2). The combined organic layers were washed with saturated aqueous sodium bicarbonate solution (500 mL) and brine (500 mL) and dried over sodium sulfate, filtered and concentrated under reduced pressure to provide a crude product.

The two crude products were combined and triturated with isopropyl ether (700 mL) at 20° C. for 30 min. The mixture was filtered, washed with isopropyl ether (100 mL) and dried under reduced pressure to provide a 1:1 mixture of (3aR,7S,7aS)-7-(4-bromophenyl)tetrahydroisobenzofuran-1,5(3H,4H)-dione and (3aS,7R,7aR)-7-(4-bromophenyl)tetrahydroisobenzofuran-1,5(3H,4H)-dione (550 g, 1.78 mol, 33% yield) as a white solid. $^1H$ NMR (400 MHz, DMSO-$d_6$) δ 7.51-7.49 (m, 2H), 7.29-7.26 (m, 2H), 4.36-4.32 (dd, J=5.6 Hz, J=8.8 Hz, 1H), 3.91-3.88 (dd, J=2.0 Hz, J=9.2 Hz, 1H), 3.69-3.63 (dt, J=4.4 Hz, J=14.0 Hz, 1H), 3.49-3.43 (m, 1H), 3.19-3.11 (m, 1H), 2.73-2.64 (m, 2H), 2.48-2.44 (m, 1H), 2.37-2.30 (m, 1H). ES-LCMS m/z 310.1 [M+H]$^+$.

Step 6: 1:1 mixture of (3aR,5R,7S,7aS)-7-(4-bromophenyl)-5-hydroxyhexahydroisobenzofuran-1(3H)-one and (3aS,5S,7R,7aR)-7-(4-bromophenyl)-5-hydroxyhexahydroisobenzofuran-1(3H)-one

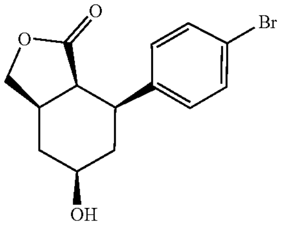

+

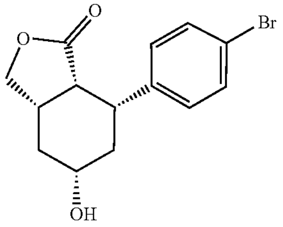

To a 1:1 mixture of (3aR,7S,7aS)-7-(4-bromophenyl)tetrahydroisobenzofuran-1,5(3H,4H)-dione and (3aS,7R,7aR)-7-(4-bromophenyl)tetrahydroisobenzofuran-1,5(3H,4H)-dione (11.0 g, 35.6 mmol), in THF (100 mL) and methanol (100 mL) at 0° C. was added solid sodium borohydride (3.37 g, 89.0 mmol) portion wise over 5 min. The reaction was stirred at rt for 16 h, quenched with water (100 mL) and extracted with EtOAc (500 mL). The EtOAc layer was washed with water (100 mL) and brine (100 mL), dried over sodium sulphate and concentrated to afford a 1:1 mixture of (3aR,5R,7S,7aS)-7-(4-bromophenyl)-5-hydroxyhexahydroisobenzofuran-1(3H)-one and (3aS,5S,7R,7aR)-7-(4-bromophenyl)-5-hydroxyhexahydroisobenzofuran-1(3H)-one (7.00 g, 21.6 mmol, 60.7% yield) as a white solid, which was used without further purification. $^1H$ NMR (400 MHz, DMSO-$d_6$) δ 7.47 (d, J=4 Hz, 2H), 7.24 (d, J=8.4 Hz, 2H), 4.86 (d, J=4.4 Hz, 1H), 4.20-4.16 (m, 1H), 3.86 (d, J=8.4 Hz, 1H), 3.56-3.55 (m, 1H), 3.21-3.18 (m, 1H), 3.11-3.07 (m, 1H), 2.67-2.64 (m, 1H), 1.99-2.02 (m, 2H), 1.39 (q, J=12.8 Hz, 1H), 1.00 (q, J=12.8 Hz, 1H). ES-LCMS m/z 311.1 [M+H]$^+$.

Step 7: 1:1 mixture of (3aR,5R,7S,7aS)-7-(4-bromophenyl)-5-ethoxyhexahydroisobenzofuran-1(3H)-one and (3aS,5S,7R,7aR)-7-(4-bromophenyl)-5-ethoxyhexahydroisobenzofuran-1(3H)-one

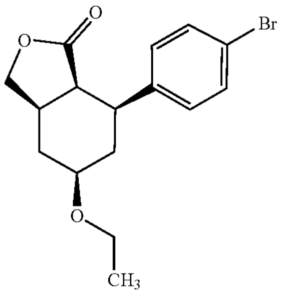

+

-continued

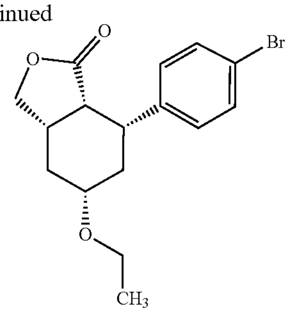

To a 1:1 mixture of (3aR,5R,7S,7aS)-7-(4-bromophenyl)-5-hydroxyhexahydroisobenzofuran-1(3H)-one and (3aS,5S,7R,7aR)-7-(4-bromophenyl)-5-hydroxyhexahydroisobenzofuran-1(3H)-one (5.00 g, 16.1 mmol), in N,N-dimethylformamide (50 mL) at 0° C. was added solid NaH (1.29 g, 32.1 mmol). After 30 min, ethyl iodide (13.0 mL, 161 mmol) was added, and the reaction was stirred at rt for 16 h. The reaction was quenched with 2N HCl (~10 mL) to pH<3 and extracted with EtOAc (100 mL, 3 times). The combined EtOAc layers were washed with water (20 mL) and brine (20 mL), dried over sodium sulphate and concentrated. The resulting residue was taken up in THF (20 mL) and subjected to reverse phase purification (MeCN in $H_2O$, 10 mM ammonium bicarbonate modifier, 0-100% gradient) to afford a 1:1 mixture of (3aR,5R,7S,7aS)-7-(4-bromophenyl)-5-ethoxyhexahydroisobenzofuran-1(3H)-one and (3aS,5S,7R,7aR)-7-(4-bromophenyl)-5-ethoxyhexahydroisobenzofuran-1(3H)-one (1.70 g, 4.56 mmol, 28.4% yield) as a white solid. $^1$H NMR (400 MHz, DMSO-$d_6$) δ 7.51-7.41 (m, 2H), 7.32-7.20 (m, 2H), 4.19 (dd, J=8.8, 4.3 Hz, 1H), 3.95-3.83 (m, 1H), 3.57-3.42 (m, 3H), 3.27-3.07 (m, 2H), 2.75-2.63 (m, 1H), 2.17 (dd, J=12.3, 4.3 Hz, 2H), 1.44-1.21 (m, 2H), 1.14-1.06 (m, 3H). ES-LCMS m/z 341.0 [M+H]$^+$.

Step 8: 1:1 mixture of (1R,2S,4R,6R)-2-(4-bromophenyl)-4-ethoxy-6-(hydroxymethyl)cyclohexane-1-carboxylic acid and (1S,2R,4S,6S)-2-(4-bromophenyl)-4-ethoxy-6-(hydroxymethyl)cyclohexane-1-carboxylic acid

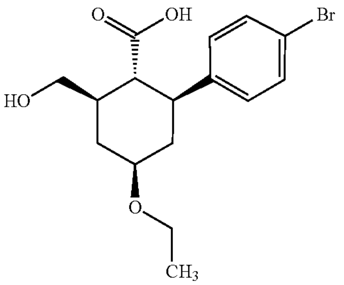

+

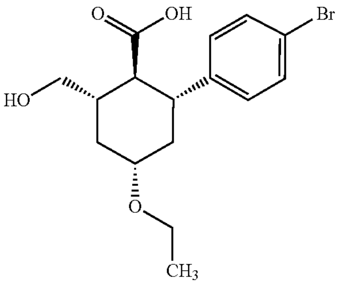

To a 1:1 mixture of (3aR,5R,7S,7aS)-7-(4-bromophenyl)-5-ethoxyhexahydroisobenzofuran-1(3H)-one and (3aS,5S,7R,7aR)-7-(4-bromophenyl)-5-ethoxyhexahydroisobenzofuran-1(3H)-one (2.70 g, 7.96 mmol) in methanol (30 mL) was added KOH (2.23 g, 39.8 mmol), and the reaction mixture was stirred at 75° C. for 16 h. The reaction was quenched with 2N HCl (~15 mL) to pH<3, and solid precipitated out. This solid was filtered, washed with water (5 mL, 4 times), washed with petroleum ether (5 mL, 4 times) and dried to afford a 1:1 mixture of (1R,2S,4R,6R)-2-(4-bromophenyl)-4-ethoxy-6-(hydroxymethyl)cyclohexane-1-carboxylic acid and (1 S,2R,4S,6S)-2-(4-bromophenyl)-4-ethoxy-6-(hydroxymethyl)cyclohexane-1-carboxylic acid (2.40 g, 5.71 mmol, 71.7% yield). $^1$H NMR (400 MHz, DMSO-$d_6$) δ 11.85 (br s, 1H), 7.46-7.42 (m, 2H), 7.22-7.14 (m, 2H), 4.58 (br s, 1H), 3.55-3.38 (m, 4H), 3.23-3.12 (m, 1H), 2.83-2.68 (m, 1H), 2.28-2.17 (m, 2H), 1.98 (d, J=12.5 Hz, 1H), 1.80-1.68 (m, 1H), 1.47-1.24 (m, 1H), 1.15-1.00 (m, 4H). ES-LCMS m/z 357.0 [M+H]$^+$.

Step 9: 1:1 mixture of benzyl (1R,2S,4R,6R)-2-(4-bromophenyl)-4-ethoxy-6-(hydroxymethyl)cyclohexane-1-carboxylate and benzyl (1 S,2R,4S,6S)-2-(4-bromophenyl)-4-ethoxy-6-(hydroxymethyl) cyclohexane-1-carboxylate

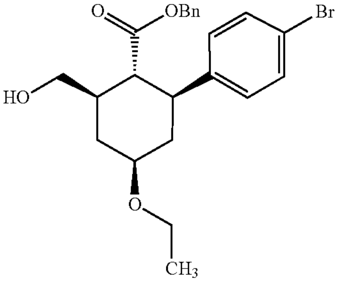

+

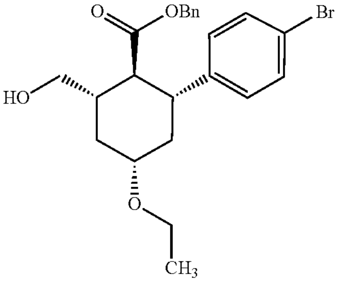

To a 1:1 mixture of (1R,2S,4R,6R)-2-(4-bromophenyl)-4-ethoxy-6-(hydroxymethyl)cyclohexane-1-carboxylic acid and (1 S,2R,4S,6S)-2-(4-bromophenyl)-4-ethoxy-6-(hydroxymethyl)cyclohexane-1-carboxylic acid (2.40 g, 6.72 mmol) and potassium carbonate (2.79 g, 20.2 mmol) in N,N-dimethylformamide (25 mL) at 0° C. was added benzyl bromide (0.799 mL, 6.72 mmol), dropwise over 1 min. After 3 h, ice water (20 mL) was added, and the reaction was extracted with EtOAc (50 mL×3). The combined EtOAc layers were washed with water (10 mL) and brine (20 mL), dried over sodium sulphate and evaporated to afford crude material. The crude material was subjected to normal phase purification (ethyl acetate in petroleum ether, 0-100% gradient, 50 min run) to afford a 1:1 mixture of benzyl (1R,2S,4R,6R)-2-(4-bromophenyl)-4-ethoxy-6-(hydroxymethyl)cyclohexane-1-carboxylate and benzyl (1 S,2R,4S, 6S)-2-(4-bromophenyl)-4-ethoxy-6-(hydroxymethyl) cyclohexane-1-carboxylate (2.30 g, 4.63 mmol, 68.9% yield). $^1$H NMR (400 MHz, DMSO-$d_6$) δ 7.47-7.37 (m, 2H), 7.29-7.22 (m, 3H), 7.19-7.11 (m, 2H), 6.86 (dd, J=7.5, 2.0 Hz, 2H), 4.87 (d, J=12.5 Hz, 1H), 4.70 (d, J=12.5 Hz, 1H), 4.60 (t, J=5.0 Hz, 1H), 3.49-3.41 (m, 3H), 3.35-3.32 (m, 1H), 3.31-3.19 (m, 2H), 2.89-2.74 (m, 1H), 2.42 (t, J=11.0 Hz, 1H), 2.21-1.95 (m, 2H), 1.90-1.77 (m, 1H), 1.42 (q, J=12.0 Hz, 1H), 1.07 (t, J=6.8 Hz, 3H). ES-LCMS m/z showed poor ionization.

Step 10: 1:1 mixture of (1R,2R,3S,5R)-2-((benzyloxy)carbonyl)-3-(4-bromophenyl)-5-ethoxycyclohexane-1-carboxylic acid and (1S,2S,3R,5S)-2-((benzyloxy)carbonyl)-3-(4-bromophenyl)-5-ethoxycyclohexane-1-carboxylic acid

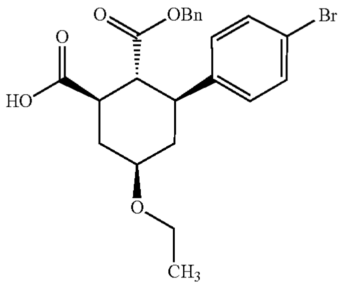

+

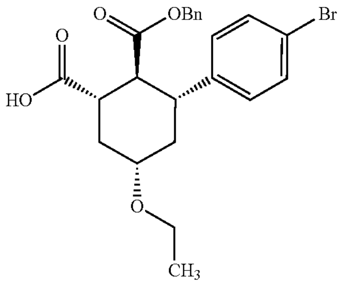

To a 1:1 mixture of benzyl (1R,2S,4R,6R)-2-(4-bromophenyl)-4-ethoxy-6-(hydroxymethyl)cyclohexane-1-carboxylate and benzyl (1 S,2R,4S,6S)-2-(4-bromophenyl)-4-ethoxy-6-(hydroxymethyl)cyclohexane-1-carboxylate (2.30 g, 5.14 mmol) in acetonitrile (10 mL) and water (20 mL) at 0° C. was added sodium periodate (3.30 g, 15.4 mmol) and ruthenium(Ill) chloride (1.07 g, 5.14 mmol). After 1 h, water (100 mL) was added, and the mixture was extracted with EtOAc (500 mL). The EtOAc layer was washed with water (100 mL) and brine (100 mL), dried over sodium sulphate and evaporated concentrated to afford a 1:1 mixture of (1R,2R,3S,5R)-2-((benzyloxy)carbonyl)-3-(4-bromophenyl)-5-ethoxycyclohexane-1-carboxylic acid and (1S,2S,3R,5S)-2-((benzyloxy)carbonyl)-3-(4-bromophenyl)-5-ethoxycyclohexane-1-carboxylic acid (1.60 g, 2.95 mmol, 57.3% yield) as a brown solid. $^1$H NMR (400 MHz, DMSO-$d_6$) δ 12.54 (br s, 1H), 7.53-7.36 (m, 2H), 7.31-7.14 (m, 5H), 6.92-6.79 (m, 2H), 4.81-4.62 (m, 2H), 3.57-3.43 (m, 2H), 3.24-3.05 (m, 1H), 2.96-2.83 (m, 1H), 2.79-2.70 (m, 2H), 2.43-2.18 (m, 1H), 1.99 (dd, J=6.8, 5.8 Hz, 1H), 1.62-1.49 (m, 1H), 1.45-1.30 (m, 1H), 1.08 (t, J=7.0 Hz, 3H). ES-LCMS m/z 461.0 $[M+H]^+$.

Step 11: 1:1 mixture of benzyl (1R,2S,4R,6R)-2-(4-bromophenyl)-4-ethoxy-6-((2-fluoro-4-(trifluoromethyl)phenyl)carbamoyl)cyclohexane-1-carboxylate and benzyl (1 S,2R,4S,6S)-2-(4-bromophenyl)-4-ethoxy-6-((2-fluoro-4-(trifluoromethyl)phenyl)carbamoyl)cyclohexane-1-carboxylate

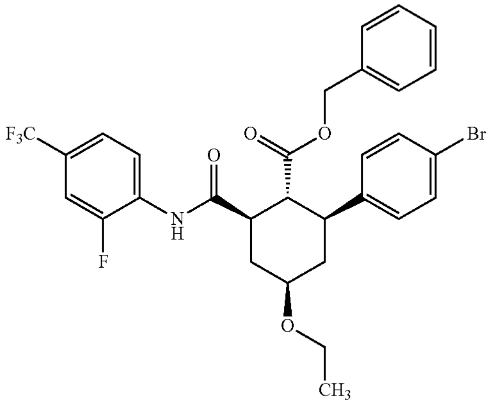

+

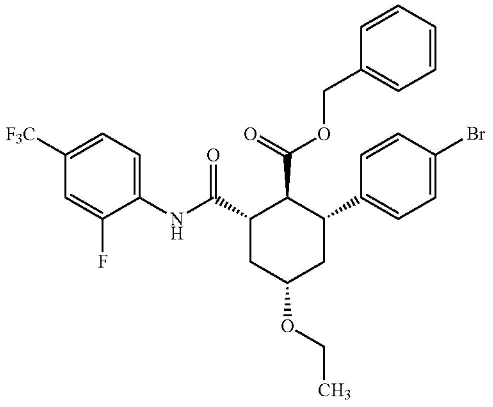

To a 1:1 mixture of (1R,2R,3S,5R)-2-((benzyloxy)carbonyl)-3-(4-bromophenyl)-5-ethoxycyclohexane-1-carboxylic acid and (1S,2S,3R,5S)-2-((benzyloxy)carbonyl)-3-(4-bromophenyl)-5-ethoxycyclohexane-1-carboxylic acid (1.50 g, 3.25 mmol) in acetonitrile (10 mL) was added 1-methyl-1H-imidazole (0.518 mL, 6.50 mmol) and 2-fluoro-4-(trifluoromethyl)aniline (582 mg, 3.25 mmol), sequentially, followed by chloro-N,N,N',N'-tetramethylformamidinium hexafluorophosphate (1.83 g, 6.50 mmol). After 2 h, the mixture was concentrated and subjected to normal phase purification (ethyl acetate in petroleum ether, 0-80% gradient) to afford a 1:1 mixture of benzyl (1R,2S,4R,6R)-2-(4-bromophenyl)-4-ethoxy-6-((2-fluoro-4-(trifluoromethyl) phenyl)carbamoyl)cyclohexane-1-carboxylate and benzyl (1 S,2R,4S,6S)-2-(4-bromophenyl)-4-ethoxy-6-((2-fluoro-4-(trifluoromethyl)phenyl)carbamoyl)cyclohexane-1-carboxylate (1.20 g, 1.79 mmol, 55.1% yield) as a white solid. $^1$H NMR (400 MHz, DMSO-$d_6$) δ 10.17 (s, 1H), 8.17 (t, J=8.0 Hz, 1H), 7.73 (dd, J=11.0, 1.5 Hz, 1H), 7.56 (d, J=9.0 Hz, 1H), 7.46 (d, J=7.7 Hz, 2H), 7.27-7.14 (m, 5H), 6.81 (s, 1H), 6.79 (d, J=1.5 Hz, 1H), 4.74-4.64 (m, 2H), 3.58-3.46 (m, 3H), 3.21-3.05 (m, 1H), 2.96 (t, J=11.3 Hz, 1H), 2.82 (td, J=12.0, 3.0 Hz, 1H), 2.39-2.34 (m, 1H), 2.12-1.97 (m, 1H), 1.69-1.53 (m, 1H), 1.52-1.40 (m, 1H), 1.10 (t, J=7.0 Hz, 3H). ES-LCMS m/z 622.0 $[M+H]^+$.

Step 12: 1:1 mixture of (1R,2S,4R,6R)-2-(4-bromophenyl)-4-ethoxy-6-((2-fluoro-4-(trifluoromethyl)phenyl)carbamoyl)cyclohexane-1-carboxylic acid and (1 S,2R,4S,6S)-2-(4-bromophenyl)-4-ethoxy-6-((2-fluoro-4-(trifluoromethyl)phenyl)carbamoyl)cyclohexane-1-carboxylic acid

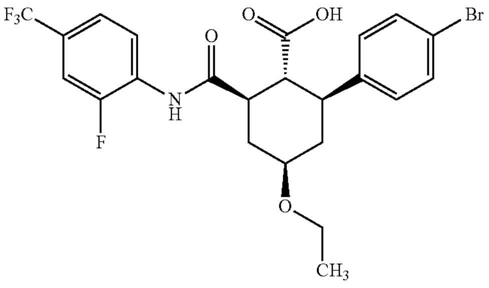

+

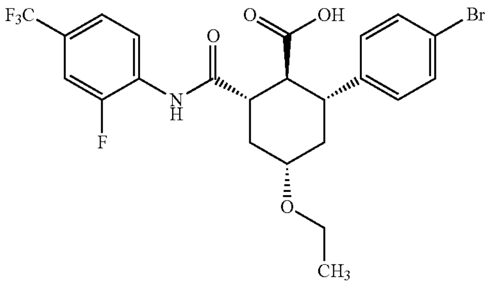

To 1:1 mixture of benzyl (1R,2S,4R,6R)-2-(4-bromophenyl)-4-ethoxy-6-((2-fluoro-4-(trifluoromethyl)phenyl)carbamoyl)cyclohexane-1-carboxylate and benzyl (1 S,2R,4S,6S)-2-(4-bromophenyl)-4-ethoxy-6-((2-fluoro-4-(trifluoromethyl)phenyl)carbamoyl)cyclohexane-1-carboxylate (0.600 g, 0.964 mmol) in DCM (12 mL) at ° C. was added a solution of boron trichloride (1.93 mL, 1.93 mmol, 1M in DCM). After 1 h, ice water (2 mL) was added, and the mixture was concentrated. The resulting residue was taken up in THF (5 mL) and subjected to reverse phase purification (MeCN in $H_2O$, 0.1% ammonium bicarbonate modifier, 0-100% gradient) to afford a 1:1 mixture of (1R,2S,4R,6R)-2-(4-bromophenyl)-4-ethoxy-6-((2-fluoro-4-(trifluoromethyl)phenyl)carbamoyl)cyclohexane-1-carboxylic acid and (1 S,2R,4S,6S)-2-(4-bromophenyl)-4-ethoxy-6-((2-fluoro-4-(trifluoromethyl)phenyl)carbamoyl)cyclohexane-1-carboxylic acid (350 mg, 0.638 mmol, 66.2% yield) as a white solid. $^1H$ NMR (400 MHz, DMSO-$d_6$) δ 10.27 (br s, 1H), 8.23 (t, J=8.0 Hz, 1H), 7.71 (s, 1H), 7.68 (s, 1H), 7.53 (d, J=9.0 Hz, 1H), 7.44 (d, J=8.5 Hz, 2H), 7.23 (d, J=8.0 Hz, 2H), 3.54-3.47 (m, 2H), 3.02-2.95 (m, 1H), 2.84-2.72 (m, 1H), 2.39-2.24 (m, 2H), 2.13-1.91 (m, 2H), 1.56-1.33 (m, 2H), 1.09 (t, J=7.0 Hz, 3H). ES-LCMS m/z 532.0 $[M+H]^+$.

Step 13: 1:1 mixture of (1R,2R,4R,6S)-4-ethoxy-2-((2-fluoro-4-(trifluoromethyl)phenyl)carbamoyl)-6-(4-(methylamino)phenyl)cyclohexane-1-carboxylic acid and (1 S,2S,4S,6R)-4-ethoxy-2-((2-fluoro-4-(trifluoromethyl)phenyl)carbamoyl)-6-(4-(methylamino)phenyl)cyclohexane-1-carboxylic acid

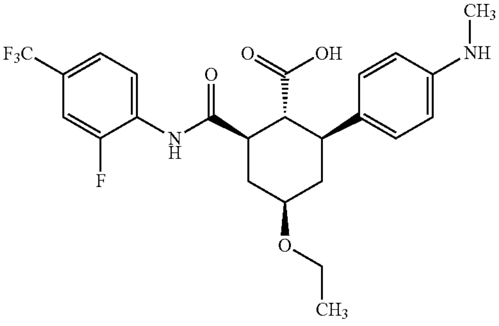

+

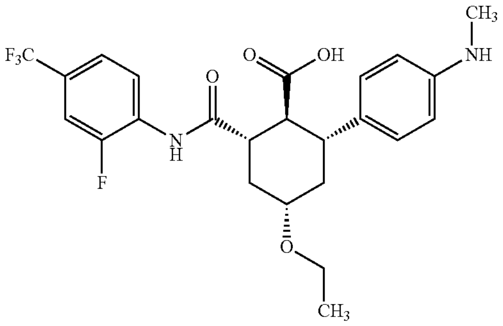

A 1:1 mixture of (1R,2S,4R,6R)-2-(4-bromophenyl)-4-ethoxy-6-((2-fluoro-4-(trifluoromethyl)phenyl)carbamoyl)cyclohexane-1-carboxylic acid and (1 S,2R,4S,6S)-2-(4-bromophenyl)-4-ethoxy-6-((2-fluoro-4-(trifluoromethyl)phenyl)carbamoyl)cyclohexane-1-carboxylic acid (550 mg, 1.03 mmol) and sodium tert-butoxide (298 mg, 3.10 mmol) in 1,4-dioxane (5 mL) was stirred for 5 min. tBuXPhos Pd G3 (82.0 mg, 0.103 mmol) was added, and the mixture was degassed for 5 min. Methanamine (2M in THF, 10.3 mL, 20.7 mmol) was added, and the reaction was heated in a Biotage Initiator (microwave) at 100° C. for 1 h. The mixture was concentrated, and the resulting residue was subjected to reverse phase purification (MeCN in $H_2O$, 10 nM ammonium bicarbonate modifier, 0-100% gradient) to afford a 1:1 mixture of (1R,2R,4R,6S)-4-ethoxy-2-((2-fluoro-4-(trifluoromethyl)phenyl)carbamoyl)-6-(4-(methylamino)phenyl)cyclohexane-1-carboxylic acid and (1 S,2S,4S,6R)-4-ethoxy-2-((2-fluoro-4-(trifluoromethyl)phenyl)carbamoyl)-6-(4-(methylamino)phenyl)cyclohexane-1-carboxylic acid (305 mg, 0.601 mmol, 58.1% yield) as an off-white solid. $^1H$ NMR (400 MHz, DMSO-$d_6$) δ 11.70 (br s, 1H), 10.10 (br s, 1H), 8.21 (t, J=8.0 Hz, 1H), 7.72 (d, J=9.5 Hz, 1H), 7.55 (d, J=8.5 Hz, 1H), 6.99-6.95 (m, 2H), 6.46-6.42 (m, 2H), 5.50-5.36 (m, 1H), 3.54-3.47 (m, 3H), 3.32-3.27 (m, 1H), 3.06-2.98 (m, 1H), 2.71-2.66 (m, 1H), 2.63 (s, 3H), 2.33-2.25 (m, 1H), 2.06-1.94 (m, 1H), 1.51-1.32 (m, 2H), 1.10 (t, J=7.0 Hz, 3H). ES-LCMS m/z 483.2 $[M+H]^+$.

Intermediate 9: (1R,2R,4R,6S)-4-ethoxy-2-((2-fluoro-4-(trifluoromethyl)phenyl)carbamoyl)-6-(4-(methylamino)phenyl)cyclohexane-1-carboxylic acid

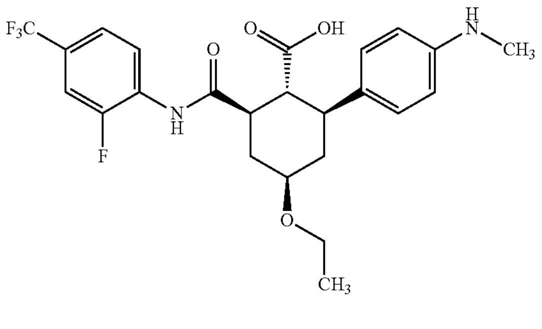 [SMILES: CCO[C@@H]1C[C@H](c2ccc(NC)cc2)[C@@H](C(=O)O)[C@H](C(=O)Nc2ccc(C(F)(F)F)cc2F)C1]

Step 1: (1S,2R,4S,6S)-2-(4-bromophenyl)-4-ethoxy-6-((2-fluoro-4-(trifluoromethyl)phenyl)carbamoyl) cyclohexane-1-carboxylic acid AND (1R,2S,4R,6R)-2-(4-bromophenyl)-4-ethoxy-6-((2-fluoro-4-(trifluoromethyl)phenyl)carbamoyl)cyclohexane-1-carboxylic acid

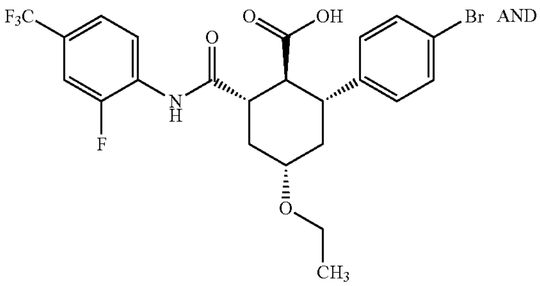

AND

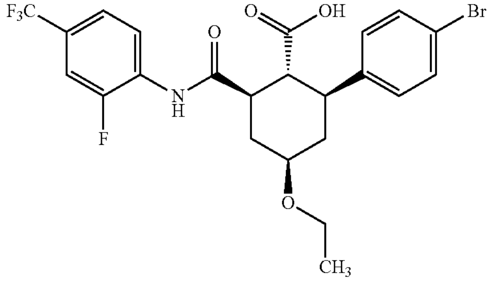

A 1:1 mixture of (1R,2S,4R,6R)-2-(4-bromophenyl)-4-ethoxy-6-((2-fluoro-4-(trifluoromethyl)phenyl)carbamoyl) cyclohexane-1-carboxylic acid and (1 S,2R,4S,6S)-2-(4-bromophenyl)-4-ethoxy-6-((2-fluoro-4-(trifluoromethyl) phenyl)carbamoyl)cyclohexane-1-carboxylic acid (Intermediate 8 Step 12) (4.50 g, 8.45 mmol) was chirally purified by Chiral-Prep-SFC (Column: YMC Cellulose-SA 250×30 mm, 5 μm; Mobile Phase: 75:25 $CO_2$:[MeOH with 0.5% isopropylamine]) to give:

First-eluting isomer (1S,2R,4S,6S)-2-(4-bromophenyl)-4-ethoxy-6-((2-fluoro-4-(trifluoromethyl)phenyl)carbamoyl) cyclohexane-1-carboxylic acid (1.20 g, 2.05 mmol, 24.3% yield). $^1$H NMR (400 MHz, DMSO-$d_6$) δ 10.27 (br s, 1H), 8.29 (t, J=8.3 Hz, 1H), 7.73-7.64 (m, 1H), 7.52 (d, J=8.5 Hz, 1H), 7.41 (d, J=8.5 Hz, 2H), 7.21 (d, J=8.5 Hz, 2H), 3.50-3.47 (m, 2H), 3.09-3.02 (m, 1H), 2.98-2.90 (m, 1H), 2.81-2.71 (m, 1H), 2.52 (br d, J=2.0 Hz, 1H), 2.24 (d, J=12.5 Hz, 1H), 2.04-1.94 (m, 1H), 1.40 (qd, J=12.0, 7.0 Hz, 2H), 1.08 (t, J=7.0 Hz, 3H). ES-LCMS m/z 532.0 $[M+H]^+$.

Second-eluting isomer (1R,2S,4R,6R)-2-(4-bromophenyl)-4-ethoxy-6-((2-fluoro-4-(trifluoromethyl)phenyl)carbamoyl)cyclohexane-1-carboxylic acid (1.60 g, 2.92 mmol, 34.5% yield)$^1$H NMR (400 MHz, DMSO-$d_6$) δ 10.35 (brs, 1H), 8.28 (t, J=8.0 Hz, 1H), 7.68 (dd, J=11.0, 1.5 Hz, 1H), 7.53 (d, J=8.5 Hz, 1H), 7.41 (d, J=8.5 Hz, 2H), 7.21 (d, J=8.5 Hz, 2H), 3.51-3.46 (m, 2H), 3.04 (dt, J=12.6, 6.4 Hz, 1H), 2.98-2.89 (m, 1H), 2.81-2.72 (m, 1H), 2.57-2.53 (m, 1H), 2.25 (d, J=11.5 Hz, 1H), 2.02-1.95 (m, 1H), 1.47-1.34 (m, 2H), 1.09 (t, J=7.0 Hz, 3H). ES-LCMS m/z 532.0 $[M+H]^+$.

Absolute stereochemistry was determined by co-crystal structure of subsequent final compound with WRN protein and then tracing back to the corresponding enantiopure intermediates.

Step 2: (1R,2R,4R,6S)-4-ethoxy-2-((2-fluoro-4-(trifluoromethyl)phenyl)carbamoyl)-6-(4-(methylamino)phenyl)cyclohexane-1-carboxylic acid

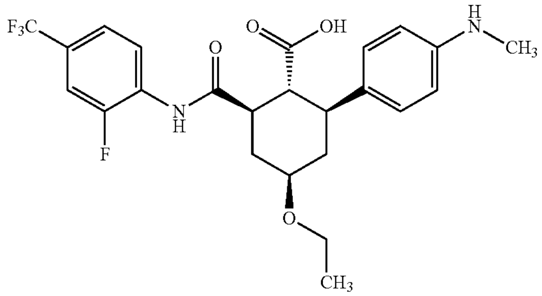 [SMILES: CCO[C@@H]1C[C@H](c2ccc(NC)cc2)[C@@H](C(=O)O)[C@H](C(=O)Nc2ccc(C(F)(F)F)cc2F)C1]

A mixture of (1R,2S,4R,6R)-2-(4-bromophenyl)-4-ethoxy-6-((2-fluoro-4-(trifluoromethyl)phenyl)carbamoyl) cyclohexane-1-carboxylic acid (450 mg, 0.845 mmol) and sodium tert-butoxide (244 mg, 2.54 mmol) in 1,4-dioxane (4.5 mL) was stirred for 5 min. tBuXPhos Pd G3 (67 mg, 0.085 mmol) was added, and the mixture was degassed for 5 min. Methanamine (2M in THF, 8.45 mL, 16.9 mmol) was added, and the reaction was heated in a Biotage Initiator (microwave) at 100° C. for 1 h. The mixture was concentrated, and the resulting residue was subjected to reverse phase purification (MeCN in $H_2O$, 10 nM ammonium bicarbonate modifier, 10-100% gradient) to afford (1R,2R,4R,6S)-4-ethoxy-2-((2-fluoro-4-(trifluoromethyl)phenyl)carbamoyl)-6-(4-(methylamino)phenyl)cyclohexane-1-carboxylic acid (360 mg, 0.709 mmol, 84.0% yield) as an off-white solid. $^1$H NMR (400 MHz, DMSO-$d_6$) δ 10.55 (br s, 1H), 8.29 (t, J=8.0 Hz, 1H), 7.65 (dd, J=11.0, 1.5 Hz, 1H), 7.51 (d, J=8.0 Hz, 1H), 6.94 (d, J=8.5 Hz, 2H), 6.39 (d, J=8.5 Hz, 2H), 5.32 (br s, 1H), 3.47 (qd, J=7.0, 1.5 Hz, 2H), 3.42-3.37 (m, 1H), 2.84 (t, J=10.8 Hz, 1H), 2.69-2.58 (m, 4H), 2.44-2.35 (m, 1H), 2.23 (d, J=12.5 Hz, 1H), 1.92 (d, J=12.0 Hz, 1H), 1.37-1.25 (m, 2H), 1.08 (t, J=7.0 Hz, 3H). ES-LCMS m/z 483.2 $[M+H]^+$.

Intermediate 10: rac-(1R,2S,4S,6R)-2-((2-fluoro-4-(trifluoromethyl)phenyl)carbamoyl)-4-hydroxy-6-(4-(methylamino)phenyl)cyclohexane-1-carboxylic acid

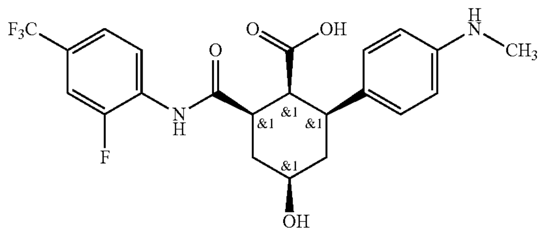 [SMILES: CNc1ccc([C@H]2C[C@@H](O)C[C@@H](C(=O)Nc3ccc(C(F)(F)F)cc3F)[C@H]2C(=O)O)cc1]

Step 1: rac-(1R,2R,6S)-2-(4-bromophenyl)-6-(hydroxymethyl)-4-oxocyclohexane-1-carboxylic acid

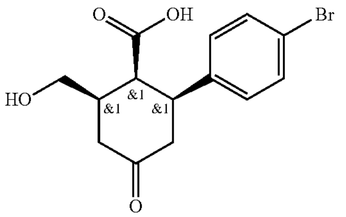 [SMILES: O=C1C[C@@H](CO)[C@@H](C(=O)O)[C@@H](c2ccc(Br)cc2)C1]

To 1:1 mixture of (3aR,7S,7aS)-7-(4-bromophenyl)tetrahydroisobenzofuran-1,5(3H,4H)-dione and (3aS,7R,7aR)-7-(4-bromophenyl)tetrahydroisobenzofuran-1,5(3H,4H)-dione Intermediate 8 Step 5 (9.1 g, 29 mmol) in methanol (100 mL) was added KOH (8.26 g, 147 mmol), and the reaction mixture was stirred at 75° C. for 3 h. The reaction was quenched with 2N HCl (~50 mL) to pH<3, and solid precipitated out. This solid was filtered, washed with water (25 mL, 4 times), washed with petroleum ether (25 mL, 4 times) and dried to afford rac-(1R,2R,6S)-2-(4-bromophenyl)-6-(hydroxymethyl)-4-oxocyclohexane-1-carboxylic acid (9.5 g, 26 mmol, 89% yield). $^1$H NMR (400 MHz, DMSO-$d_6$) δ 12.54-11.83 (m, 1H), 7.51 (d, J=8.5 Hz, 2H), 7.22 (d, J=8.5 Hz, 2H), 3.36-3.25 (m, 5H), 3.01 (t, J=4.0 Hz, 1H), 2.64-2.54 (m, 1H), 2.30-2.21 (m, 3H). ES-LCMS m/z 327.0 $[M+H]^+$.

Step 2: rac-benzyl (1R,2R,6S)-2-(4-bromophenyl)-6-(hydroxymethyl)-4-oxocyclohexane-1-carboxylate

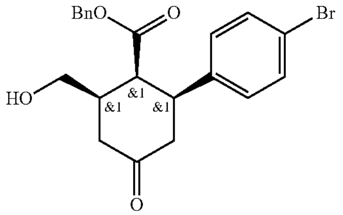 [SMILES: O=C1C[C@@H](CO)[C@@H](C(=O)OCc2ccccc2)[C@@H](c2ccc(Br)cc2)C1]

To a mixture of rac-(1R,2R,6S)-2-(4-bromophenyl)-6-(hydroxymethyl)-4-oxocyclohexane-1-carboxylic acid (9.5 g, 29 mmol) and potassium carbonate (12.0 g, 87.0 mmol) in N,N-dimethylformamide (100 mL) at 0° C. was added benzyl bromide (3.45 mL, 29.0 mmol), dropwise over 1 min. After 3 h, ice water (20 mL) was added, and the reaction was extracted with EtOAc (200 mL×2). The combined EtOAc layers were washed with water (100 mL) and brine (50 mL), dried over sodium sulphate and evaporated to afford crude material. The resulting residue was subjected to normal phase purification (ethyl acetate in petroleum ether, 5-75% gradient) to afford rac-benzyl (1R,2R,6S)-2-(4-bromophenyl)-6-(hydroxymethyl)-4-oxocyclohexane-1-carboxylate (8.70 g, 19.4 mmol, 66.8% yield). $^1$H NMR (400 MHz, DMSO-$d_6$) δ 7.46 (d, J=8.5 Hz, 2H), 7.32-7.12 (m, 5H), 6.98-6.89 (m, 2H), 4.96 (d, J=12.5 Hz, 1H), 4.83-4.71 (m, 2H), 3.49 (dt, J=14.0, 4.3 Hz, 1H), 3.40-3.33 (m, 2H), 3.17 (t, J=4.3 Hz, 1H), 2.74-2.58 (m, 1H), 2.44-2.13 (m, 4H). ES-LCMS m/z 417.0 $[M+H]^+$.

Step 3: rac-(1R,2S,3S)-2-((benzyloxy)carbonyl)-3-(4-bromophenyl)-5-oxocyclohexane-1-carboxylic acid

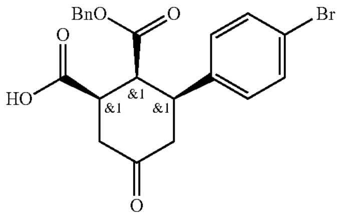 [SMILES: O=C1C[C@H](c2ccc(Br)cc2)[C@H](C(=O)OCc2ccccc2)[C@H](C(=O)O)C1]

To a mixture of rac-benzyl (1R,2R,6S)-2-(4-bromophenyl)-6-(hydroxymethyl)-4-oxocyclohexane-1-carboxylate (10.9 g, 26.1 mmol) in acetonitrile (19.3 mL) and water (4.8 mL) at 0° C. was added sodium periodate (16.8 g, 78.0 mmol) and ruthenium(III) chloride (542 mg, 2.61 mmol). After 2 h, water (100 mL) was added, and the mixture was extracted with EtOAc (500 mL×2). The EtOAc layer was washed with water (50 mL) and brine (50 mL), dried over sodium sulphate, concentrated and subjected to reverse phase purification (MeCN in $H_2O$, 0.1% formic acid modifier, 10-90% gradient) to afford rac-(1R,2S,3S)-2-((benzyloxy)carbonyl)-3-(4-bromophenyl)-5-oxocyclohexane-1-carboxylic acid (6.9 g, 15 mmol, 57% yield). $^1$H NMR (400 MHz, DMSO-$d_6$) δ 12.77 (br s, 1H), 7.57-7.40 (m, 2H), 7.34-7.10 (m, 5H), 6.96-6.84 (m, 2H), 4.89-4.77 (m, 2H), 3.58 (dt, J=14.4, 4.1 Hz, 1H), 3.39 (t, J=4.5 Hz, 1H), 3.34 (br s, 1H), 3.07 (td, J=14.3, 11.0 Hz, 2H), 2.47 (br d, J=5.5 Hz, 1H), 2.36-2.24 (m, 1H). ES-LCMS m/z 429.0 $[M-H]^-$.

Step 4: rac-benzyl (1R,2R,6S)-2-(4-bromophenyl)-6-((2-fluoro-4-(trifluoromethyl)phenyl)carbamoyl)-4-oxocyclohexane-1-carboxylate

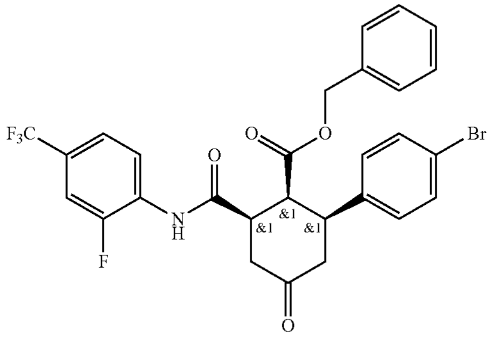 [SMILES: O=C1C[C@H](c2ccc(Br)cc2)[C@H](C(=O)OCc2ccccc2)[C@H](C(=O)Nc2ccc(C(F)(F)F)cc2F)C1]

To a mixture of rac-(1R,2S,3S)-2-((benzyloxy)carbonyl)-3-(4-bromophenyl)-5-oxocyclohexane-1-carboxylic acid (6.9 g, 16 mmol) in acetonitrile (35 mL) was added 1-methyl-1H-imidazole (2.55 mL, 32.0 mmol), 2-fluoro-4-(trifluoromethyl)aniline (2.87 g, 16.0 mmol) and chloro-N,N,N',N'-tetramethylformamidinium hexafluorophosphate (8.98 g, 32.0 mmol). After 16 h, the mixture was concentrated and subjected to normal phase purification (ethyl acetate in petroleum ether, 0-50% gradient) to afford rac-benzyl (1R,2R,6S)-2-(4-bromophenyl)-6-((2-fluoro-4-(trifluoromethyl)phenyl)carbamoyl)-4-oxocyclohexane-1-carboxylate (6.6 g, 11 mmol, 68% yield) as a white solid. $^1$H NMR (400 MHz, DMSO-$d_6$) δ 10.28 (s, 1H), 8.15 (t, J=8.0 Hz, 1H), 7.73 (dd, J=11.0, 2.0 Hz, 1H), 7.58-7.46 (m, 3H), 7.27-7.10 (m, 5H), 6.90-6.83 (m, 2H), 4.94-4.72 (m, 2H), 3.64-3.47 (m, 3H), 3.39-3.32 (m, 1H), 3.11 (t, J=14.3 Hz, 1H), 2.47-2.33 (m, 2H). ES-LCMS m/z 592.0 $[M+H]^+$.

Step 5: rac-(1R,2R,6S)-2-(4-bromophenyl)-6-((2-fluoro-4-(trifluoromethyl)phenyl)carbamoyl)-4-oxocyclohexane-1-carboxylic acid

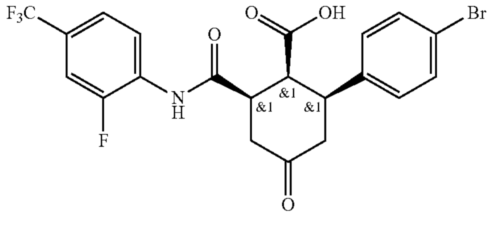 [SMILES: O=C1C[C@H](c2ccc(Br)cc2)[C@H](C(=O)O)[C@H](C(=O)Nc2ccc(C(F)(F)F)cc2F)C1]

To a mixture of rac-benzyl (1R,2R,6S)-2-(4-bromophenyl)-6-((2-fluoro-4-(trifluoromethyl)phenyl)carbamoyl)-4-oxocyclohexane-1-carboxylate (4.00 g, 6.75 mmol) in DCM (40 mL) at 0° C. was added a solution of boron trichloride (13.50 mL, 13.50 mmol, 1M in DCM). After 1 h, water (30 mL) was added, and the mixture was extracted with DCM (50 mL×4). The combined organic layers were washed with water (25 mL×4) and brine (25 mL), dried over sodium sulphate, concentrated and subjected to reverse phase purification (MeCN in $H_2O$, 0.1% formic acid modifier, 10-90% gradient) to afford rac-(1R,2R,6S)-2-(4-bromophenyl)-6-((2-fluoro-4-(trifluoromethyl)phenyl)carbamoyl)-4-oxocyclohexane-1-carboxylic acid (2.5 g, 4.6 mmol, 68% yield). $^1$H NMR (400 MHz, DMSO-$d_6$) δ 12.25 (br s, 1H), 10.24 (s, 1H), 8.22 (t, J=8.3 Hz, 1H), 7.74 (dd, J=11.0, 1.5 Hz, 1H), 7.59-7.50 (m, 3H), 7.24 (d, J=8.5 Hz, 2H), 3.53 (dt, J=13.5, 4.5 Hz, 1H), 3.49-3.41 (m, 2H), 3.18-3.02 (m, 2H), 2.43-2.32 (m, 2H). ES-LCMS m/z 504.0 $[M+H]^+$.

Step 6: rac-(1R,2R,4S,6S)-2-(4-bromophenyl)-6-((2-fluoro-4-(trifluoromethyl)phenyl)carbamoyl)-4-hydroxycyclohexane-1-carboxylic acid

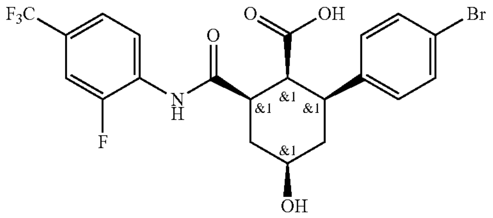 [SMILES: O=C(O)[C@H]1[C@@H](c2ccc(Br)cc2)C[C@@H](O)C[C@H]1C(=O)Nc1ccc(C(F)(F)F)cc1F]

To a mixture of rac-(1R,2R,6S)-2-(4-bromophenyl)-6-((2-fluoro-4-(trifluoromethyl)phenyl)carbamoyl)-4-oxocyclohexane-1-carboxylic acid (0.500 g, 0.996 mmol), in THF (15 mL) and methanol (15 mL) at 0° C. was added solid sodium borohydride (377 mg, 9.96 mmol). The reaction was stirred at rt for 16 h, concentrated and subjected to reverse phase purification (MeCN in $H_2O$ [10 mM ammonium bicarbonate], 10-90% gradient) to afford rac-(1R,2R,4S,6S)-2-(4-bromophenyl)-6-((2-fluoro-4-(trifluoromethyl)phenyl)carbamoyl)-4-hydroxycyclohexane-1-carboxylic acid (0.300 g, 0.563 mmol, 56.5% yield). $^1$H NMR (400 MHz, DMSO-$d_6$) δ 13.58 (br s, 1H), 8.40 (t, J=8.3 Hz, 1H), 7.62 (dd, J=11.3, 1.8 Hz, 1H), 7.51-7.46 (m, 1H), 7.40-7.33 (m, 2H), 7.31-7.22 (m, 2H), 4.67 (br d, J=4.0 Hz, 1H), 3.69-3.51 (m, 1H), 3.17 (d, J=3.0 Hz, 2H), 2.94 (t, J=3.3 Hz, 1H), 2.80-2.62 (m, 2H), 2.02 (br d, J=11.5 Hz, 1H), 1.87 (q, J=11.7 Hz, 1H), 1.69 (br d, J=10.5 Hz, 1H). ES-LCMS m/z 503.9 $[M+H]^+$.

Step 7: rac-(1R,2S,4S,6R)-2-((2-fluoro-4-(trifluoromethyl)phenyl)carbamoyl)-4-hydroxy-6-(4-(methylamino)phenyl)cyclohexane-1-carboxylic acid

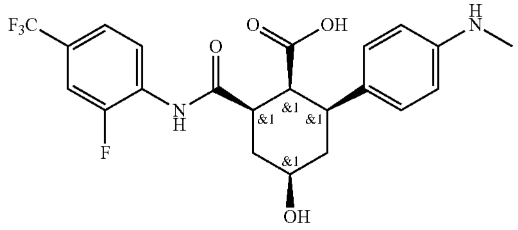 [SMILES: CNc1ccc([C@H]2C[C@@H](O)C[C@@H](C(=O)Nc3ccc(C(F)(F)F)cc3F)[C@H]2C(=O)O)cc1]

A mixture of rac-(1R,2R,4S,6S)-2-(4-bromophenyl)-6-((2-fluoro-4-(trifluoromethyl)phenyl)carbamoyl)-4-hydroxycyclohexane-1-carboxylic acid (0.300 g, 0.595 mmol) and sodium tert-butoxide (172 mg, 1.79 mmol) in 1,4-dioxane (10 mL) was stirred for 5 min. tBuXPhos Pd G3 (47 mg, 0.059 mmol) was added, and the mixture was degassed for 5 min. Methanamine (2M in THF, 5.95 mL, 11.9 mmol) was added, and the reaction was heated in a Biotage Initiator (microwave) at 100° C. for 1.5 h. The mixture was concentrated, and the resulting residue was subjected to reverse phase purification (MeCN in $H_2O$, 10 nM ammonium bicarbonate modifier, 10-80% gradient) to afford rac-(1R,2S,4S,6R)-2-((2-fluoro-4-(trifluoromethyl)phenyl)carbamoyl)-4-hydroxy-6-(4-(methylamino)phenyl)cyclohexane-1-carboxylic acid (0.20 g, 0.41 mmol, 69% yield). $^1$H NMR (400 MHz, DMSO-$d_6$) δ 13.10 (br s, 1H), 8.38 (t, J=8.3 Hz, 1H), 7.62 (dd, J=11.0, 2.0 Hz, 1H), 7.48 (br d, J=8.0 Hz, 1H), 7.05 (d, J=8.5 Hz, 2H), 6.39 (d, J=8.5 Hz, 2H), 5.24 (q, J=5.3 Hz, 1H), 4.59 (br s, 1H), 3.57 (br s, 1H), 3.20-3.08 (m, 1H), 2.91-2.75 (m, 2H), 2.67-2.54 (m, 4H), 2.05-1.82 (m, 2H), 1.61 (br d, J=11.5 Hz, 1H), one proton obscured by solvent. ES-LCMS m/z 455.1 $[M+H]^+$.

Intermediate 11: rac-(1R,2R,4R,6S)-2-((2-fluoro-4-(trifluoromethyl)phenyl)carbamoyl)-4-hydroxy-6-(4-(methylamino)phenyl)cyclohexane-1-carboxylic acid

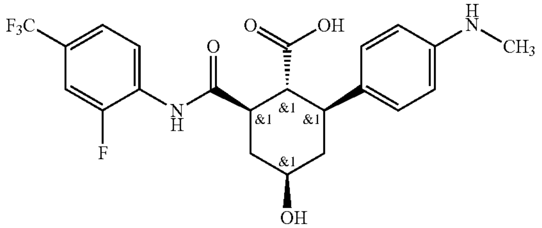 [SMILES: CNc1ccc([C@H]2C[C@@H](O)C[C@@H](C(=O)Nc3ccc(C(F)(F)F)cc3F)[C@@H]2C(=O)O)cc1]

Step 1: rac-(1R,2S,4R,6R)-2-(4-bromophenyl)-4-hydroxy-6-(hydroxymethyl)cyclohexane-1-carboxylic acid

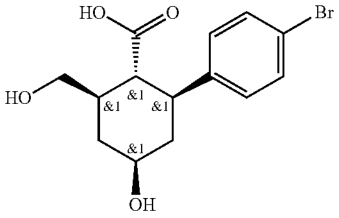 [SMILES: O=C(O)[C@H]1[C@H](CO)C[C@H](O)C[C@@H]1c1ccc(Br)cc1]

To 1:1 mixture of (3aR,5R,7S,7aS)-7-(4-bromophenyl)-5-hydroxyhexahydroisobenzofuran-1(3H)-one and (3aS,5S,7R,7aR)-7-(4-bromophenyl)-5-hydroxyhexahydroisobenzofuran-1(3H)-one Intermediate 8 Step 6 (3.20 g, 10.3 mmol) was added KOH (2.88 g, 51.4 mmol). The reaction was stirred at 75° C. for 3 h, quenched with 2N HCl (~20 mL) to pH<3, concentrated then purified by reverse phase chromatography (MeCN in $H_2O$, 0.1% ammonium bicarbonate modifier, 0-100% gradient) to afford rac-(1R,2S,4R,6R)-2-(4-bromophenyl)-4-hydroxy-6-(hydroxymethyl)cyclohexane-1-carboxylic acid (2.30 g, 6.92 mmol, 67.0% yield) as a white solid. $^1$H NMR (400 MHz, DMSO-$d_6$) δ δ 7.41 (d, J=8.4 Hz, 2H), 7.15 (d, J=8.4 Hz, 2H), 3.58-3.53 (m, 1H), 3.41-3.38 (m, 1H), 3.24-3.21 (m, 1H), 2.78-2.71 (m, 1H), 2.15-2.10 (m, 1H), 2.05 (d, J=12.4 Hz, 1H), 1.83 (d, J=12.0 Hz, 1H), 1.73-1.68 (m, 1H), 1.29 (q, J=12.4 Hz, 1H), 1.05 (q, J=12.4 Hz, 1H), two protons obscured by solvent peak. ES-LCMS m/z 329.0 $[M+H]^+$.

Step 2: rac-benzyl (1R,2S,4R,6R)-2-(4-bromophenyl)-4-hydroxy-6-(hydroxymethyl) cyclohexane-1-carboxylate

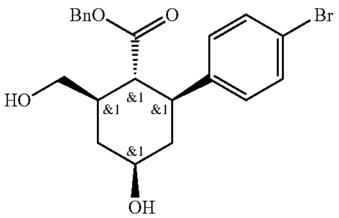 [SMILES: O=C(OCc1ccccc1)[C@H]1[C@H](CO)C[C@H](O)C[C@@H]1c1ccc(Br)cc1]

To a mixture of rac-(1R,2S,4R,6R)-2-(4-bromophenyl)-4-hydroxy-6-(hydroxymethyl)cyclohexane-1-carboxylic acid (2.30 g, 6.99 mmol) and potassium carbonate (2.90 g, 20.9 mmol) in N,N-dimethylformamide (20 mL) at 0° C. was added benzyl bromide (0.83 mL, 7.0 mmol), dropwise over 1 min. The reaction was stirred at rt for 3 h, diluted with ice water (30 mL) and extracted with ethyl acetate (2×50 mL). The combined organic layers were washed with water (20 mL) and brine (20 mL), dried over sodium sulphate, concentrated and purified by reverse phase chromatography (MeCN in $H_2O$, 0.1% ammonium bicarbonate modifier, 0-100% gradient) to afford rac-benzyl (1R,2S,4R,6R)-2-(4-bromophenyl)-4-hydroxy-6-(hydroxymethyl) cyclohexane-1-carboxylate (2.10 g, 4.51 mmol, 65.0% yield) as an off-white solid. $^1$H NMR (400 MHz, DMSO-$d_6$) δ 7.96 (s, 1H), 7.45-7.41 (m, 2H), 7.27-7.22 (m, 3H), 7.16-7.12 (m, 2H), 6.89-6.85 (m, 2H), 4.88 (d, J=12.8 Hz, 1H), 4.74-4.69 (m, 1H), 4.59-4.57 (m, 1H), 3.61 (s, 1H), 3.32-3.20 (m, 1H), 2.90 (s, 2H), 2.79-2.74 (m, 1H), 2.38 (t, J=11.2 Hz, 1H), 2.04-1.09 (m, 4H). ES-LCMS m/z: poor ionization in MS.

Step 3: rac-(1R,2R,3S)-2-((benzyloxy)carbonyl)-3-(4-bromophenyl)-5-oxocyclohexane-1-carboxylic acid

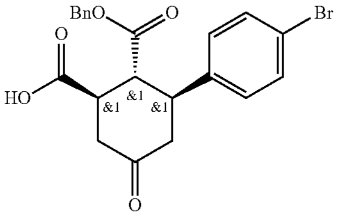 [SMILES: O=C1C[C@H](c2ccc(Br)cc2)[C@@H](C(=O)OCc2ccccc2)[C@H](C(=O)O)C1]

To a mixture of rac-benzyl (1R,2S,4R,6R)-2-(4-bromophenyl)-4-hydroxy-6-(hydroxymethyl) cyclohexane-1-carboxylate (2.10 g, 5.01 mmol) in acetonitrile (31 mL) and water (15 mL) at −20° C. were added sodium periodate (3.21 g, 15.0 mmol) and ruthenium(III) chloride (1.04 g, 5.01 mmol). After 1 h, the reaction was diluted with water (35 mL) and extracted with ethylacetate (4×50 mL). The combined organic layers were washed with water (20 mL) and brine (25 mL), dried over sodium sulphate, concentrated then purified by reverse phase chromatography (MeCN in $H_2O$, 0.1% ammonium bicarbonate modifier, 0-100% gradient) to afford rac-(1R,2R,3S)-2-((benzyloxy)carbonyl)-3-(4-bromophenyl)-5-oxocyclohexane-1-carboxylic acid (1.1 g, 2.4 mmol, 49% yield) as an off-white solid. $^1$H NMR (400 MHz, DMSO-$d_6$) δ 7.48 (d, J=1.6 Hz, 2H), 7.28-7.23 (m, 5H), 6.88 (dd, J=6.6, 4.0 Hz, 2H), 4.77 (d, J=12.4 Hz, 1H), 4.69 (d, J=12.8 Hz, 1H), 3.25 (t, J=11.2 Hz, 1H), 3.16-2.84 (m, 4H), 2.68 (t, J=13.6 Hz, 1H), 2.55-2.53 (m, 1H), 2.26-2.21 (m, 1H). ES-LCMS m/z 429.0 $[M-H]^+$.

Step 4: rac-benzyl (1R,2S,6R)-2-(4-bromophenyl)-6-((2-fluoro-4-(trifluoromethyl)phenyl)carbamoyl)-4-oxocyclohexane-1-carboxylate

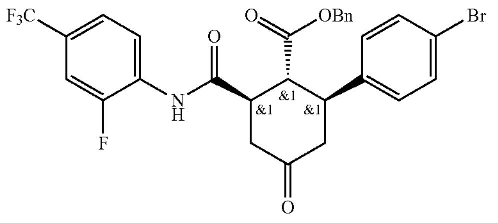 [SMILES: O=C1C[C@H](c2ccc(Br)cc2)[C@@H](C(=O)OCc2ccccc2)[C@H](C(=O)Nc2ccc(C(F)(F)F)cc2F)C1]

To a suspension of rac-(1R,2R,3S)-2-((benzyloxy)carbonyl)-3-(4-bromophenyl)-5-oxocyclohexane-1-carboxylic acid (0.30 g, 0.69 mmol) in acetonitrile (1.5 mL) were added 1-methyl-1H-imidazole (0.111 mL, 1.39 mmol) and 2-fluoro-4-(trifluoromethyl)aniline (125 mg, 0.690 mmol) followed by chloro-N,N,N',N'-tetramethylformamidinium hexafluorophosphate (390 mg, 1.39 mmol). After 2 h, the reaction was concentrated and purified by normal phase chromatography (ethyl acetate in petroleum ether, 0-50% gradient) to afford rac-benzyl (1R,2S,6R)-2-(4-bromophenyl)-6-((2-fluoro-4-(trifluoromethyl)phenyl) carbamoyl)-4-oxocyclohexane-1-carboxylate (0.26 g, 0.40 mmol, 57% yield) as a white solid. $^1$H NMR (400 MHz, DMSO-$d_6$) δ 10.31 (s, 1H), 8.15 (t, J=8.0 Hz, 1H), 7.75 (d, J=2.0 Hz, 1H), 7.57 (d, J=8.4 Hz, 1H), 7.50 (d, J=8.4 Hz, 2H), 7.32 (d, J=8.4 Hz, 2H), 7.23-7.15 (m, 3H), 6.84 (d, J=6.4 Hz, 2H), 4.73 (q, J=12.8 Hz, 2H), 3.54-3.46 (m, 2H), 3.20-3.17 (m, 1H), 3.01 (t, J=13.6 Hz, 1H), 2.83 (t, J=13.2 Hz, 1H), 2.68-2.60 (m, 1H), 2.37-2.33 (m, 1H). ES-LCMS m/z 592.0 $[M-H]^+$.

Step 5: rac-(1R,2S,6R)-2-(4-bromophenyl)-6-((2-fluoro-4-(trifluoromethyl)phenyl)carbamoyl)-4-oxocyclohexane-1-carboxylic acid

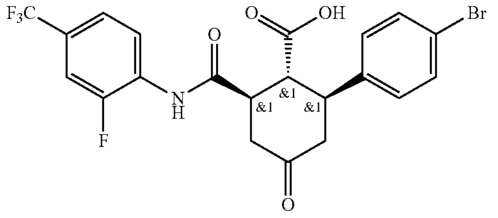 [SMILES: O=C1C[C@H](c2ccc(Br)cc2)[C@@H](C(=O)O)[C@H](C(=O)Nc2ccc(C(F)(F)F)cc2F)C1]

To a mixture of rac-benzyl (1R,2S,6R)-2-(4-bromophenyl)-6-((2-fluoro-4-(trifluoromethyl)phenyl) carbamoyl)-4-oxocyclohexane-1-carboxylate (0.26 g, 0.44 mmol) in dichloromethane (5 mL) at 0° C. was added a solution of boron trichloride (1M in DCM, 0.878 mL, 0.878 mmol), dropwise, over 2 min. After 1 h, the reaction was quenched with ice water (2 mL), concentrated and purified by reverse phase chromatography (MeCN in H2O, 0.1% ammonium bicarbonate modifier, 10-100% gradient) to afford rac-(1R,2S,6R)-2-(4-bromophenyl)-6-((2-fluoro-4-(trifluoromethyl) phenyl)carbamoyl)-4-oxocyclohexane-1-carboxylic acid (0.14 g, 0.26 mmol, 60% yield) as a white solid. $^1$H NMR (400 MHz, DMSO-$d_6$) δ 10.38 (s, 1H), 8.23 (t, J=8.0 Hz, 1H), 7.73 (d, J=9.2 Hz, 1H), 7.57 (d, J=8.4 Hz, 1H), 7.51 (d, J=8.4 Hz, 2H), 7.32 (d, J=8.4 Hz, 2H), 3.42-3.41 (m, 1H), 3.29-3.23 (m, 1H), 3.13 (t, J=4.0, Hz, 1H), 2.92 (t, J=13.6 Hz, 1H), 2.80 (t, J=13.6 Hz, 1H), 2.55-2.52 (m, 1H), 2.46-2.29 (m, 1H). ES-LCMS m/z 499.8 $[M-H]^-$.

Step 6: rac-(1R,2S,4R,6R)-2-(4-bromophenyl)-6-((2-fluoro-4-(trifluoromethyl) phenyl)carbamoyl)-4-hydroxycyclohexane-1-carboxylic acid

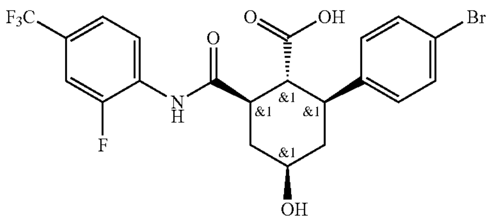 [SMILES: O=C(O)[C@@H]1[C@@H](c2ccc(Br)cc2)C[C@@H](O)C[C@H]1C(=O)Nc1ccc(C(F)(F)F)cc1F]

To a mixture of rac-(1R,2S,6R)-2-(4-bromophenyl)-6-((2-fluoro-4-(trifluoromethyl)phenyl)carbamoyl)-4-oxocyclohexane-1-carboxylic acid (0.14 g, 0.28 mmol) in methanol (2 mL) and tetrahydrofuran (2 mL) at 0° C. was added sodium borohydride (26.4 mg, 0.697 mmol) over 1 min. After 3 h, the reaction was concentrated then purified by reverse phase chromatography (MeCN in H2O, 0.1% ammonium bicarbonate modifier, 0-100% gradient) to afford rac-(1R,2S,4R,6R)-2-(4-bromophenyl)-6-((2-fluoro-4-(trifluoromethyl)phenyl)carbamoyl)-4-hydroxycyclohexane-1-carboxylic acid (70 mg, 0.14 mmol, 49% yield) as a white solid. $^1$H NMR (400 MHz, DMSO-$d_6$) δ 10.19 (s, 1H), 8.21 (t, J=8.0 Hz, 1H), 7.71 (dd, J=11.2, 1.6 Hz, 1H), 7.54 (d, J=8.4 Hz, 1H), 7.46 (d, J=8.4 Hz, 2H), 7.23 (d, J=8.4 Hz, 2H), 4.90 (s, 1H), 3.69-3.33 (m, 1H), 3.08-3.01 (m, 1H), 2.80-2.65 (m, 2H), 2.15 (d, J=12.0 Hz, 1H), 2.09 (d, J=4.8 Hz, 1H), 1.91-1.47 (m, 2H). ES-LCMS m/z 504.0 $[M+H]^+$.

Step 7: rac-(1R,2R,4R,6S)-2-((2-fluoro-4-(trifluoromethyl)phenyl)carbamoyl)-4-hydroxy-6-(4-(methylamino)phenyl)cyclohexane-1-carboxylic acid

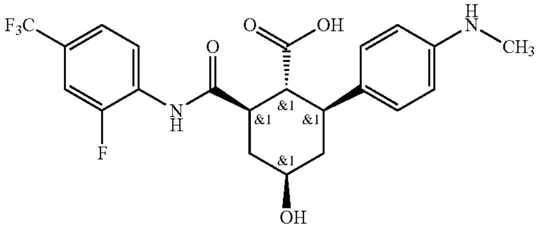 [SMILES: CNc1ccc([C@H]2C[C@@H](O)C[C@@H](C(=O)Nc3ccc(C(F)(F)F)cc3F)[C@@H]2C(=O)O)cc1]

To a mixture of rac-(1R,2S,4R,6R)-2-(4-bromophenyl)-6-((2-fluoro-4-(trifluoromethyl) phenyl)carbamoyl)-4-hydroxycyclohexane-1-carboxylic acid (70.0 mg, 0.140 mmol) and sodium tert-butoxide (40.0 mg, 0.420 mmol) in 1,4-dioxane (2 mL) in a 10 mL microwave vial was added solid tBuXPhos Pd G3 (11.03 mg, 0.0140 mmol) and methanamine (2M in THF, 1.39 mL, 2.78 mmol). The reaction was heated at 100° C. for 1 h in an Anton microwave initiator. The reaction was concentrated then purified by reverse phase chromatography (MeCN in H2O, 0.1% ammonium bicarbonate modifier, 0-100% gradient) to afford rac-(1R,2R,4R,6S)-2-((2-fluoro-4-(trifluoromethyl)phenyl)carbamoyl)-4-hydroxy-6-(4-(methylamino)phenyl)cyclohexane-1-carboxylic acid (35.0 mg, 0.0800 mmol, 54% yield) as a white solid. $^1$H-NMR (400 MHz, DMSO-$d_6$): δ 10.30 (s, 1H), 8.24 (t, J=8.0 Hz, 1H), 7.69 (d, J=10.8 Hz, 1H), 7.54 (d, J=7.6 Hz, 1H), 6.94 (d, J=8.4 Hz, 2H), 6.42 (d, J=8.4 Hz, 2H), 5.40 (s, 1H), 4.77 (d, J=4.0 Hz, 2H), 3.61 (s, 1H), 2.95 (t, J=12.8 Hz, 1H), 2.68-2.58 (m, 5H), 2.11 (d, J=10.0 Hz, 1H), 1.84 (d, J=11.2 Hz, 1H), 1.38 (q, J=12.4 Hz, 1H). ES-LCMS m/z 455.0 $[M+H]^+$.

Intermediate 12: rel-(1R,2R,4R,6S)-2-((2-fluoro-4-(trifluoromethyl)phenyl)carbamoyl)-4-(methoxy-$d_3$)-6-(4-(methylamino)phenyl)cyclohexane-1-carboxylic acid, Isomer 1

ISOMER 1

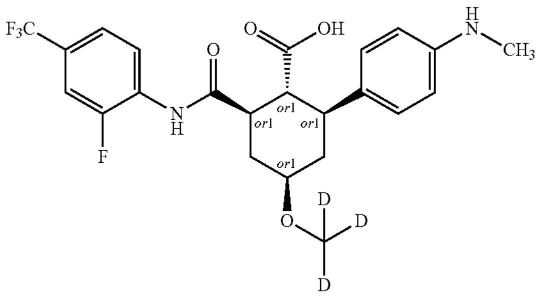

Step 1: rac-benzyl (1R,2S,4R,6R)-2-(4-bromophenyl)-6-((2-fluoro-4-(trifluoromethyl)phenyl)carbamoyl)-4-(methoxy-$d_3$)cyclohexane-1-carboxylate

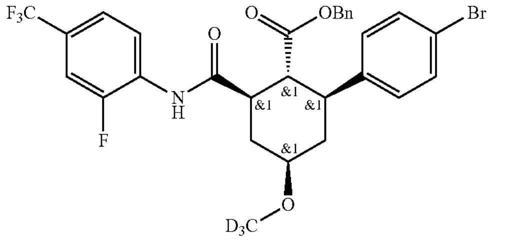 [SMILES: [2H]C([2H])([2H])O[C@@H]1C[C@H](c2ccc(Br)cc2)[C@@H](C(=O)OCc2ccccc2)[C@H](C(=O)Nc2ccc(C(F)(F)F)cc2F)C1]

To a mixture of rac-benzyl (1R,2S,6R)-2-(4-bromophenyl)-6-((2-fluoro-4-(trifluoromethyl)phenyl)carbamoyl)-4-oxocyclohexane-1-carboxylate Intermediate 11 Step 4 (0.500 g, 0.844 mmol) and methan-$d_3$-ol-d (304 mg, 8.44 mmol) in acetonitrile (5 mL) was added triflic acid (0.150 mL, 1.69 mmol) and triethylsilane (1.35 mL, 8.44 mmol) at 0° C. The reaction was stirred at rt overnight, quenched with water (100 mL) and extracted with ethyl acetate (100 mL×3). The organic layers were washed with saturated sodium bicarbonate solution (100 mL) and (brine (100 mL), dried over sodium sulphate, filtered, concentrated and subjected to normal phase purification (ethyl acetate in petroleum ether, 0-20% gradient) to afford rac-benzyl (1R,2S,4R,6R)-2-(4-bromophenyl)-6-((2-fluoro-4-(trifluoromethyl)phenyl)carbamoyl)-4-(methoxy-$d_3$)cyclohexane-1-carboxylate (150 mg, 0.23 mmol, 27% yield) as a white solid.

$^1$HNMR (400 MHz, DMSO-d6): δ 10.19 (s, 1H), 8.17 (t, J=8.0 Hz, 1H), 7.74 (dd, J=10.8, 1.6 Hz, 1H), 7.46 (d, J=8.4 Hz, 1H), 7.46 (d, J=8.4 Hz, 2H), 7.23 (d, J=8.4 Hz, 1H), 7.19-7.14 (m, 4H), 6.79 (d, J=1.6 Hz, 1H), 4.69 (ab q, J=12.8 Hz, 2H), 3.44-3.40 (m, 1H), 3.33-3.10 (m, 1H), 2.97 (t, J=11.2 Hz, 1H), 2.85-2.78 (m, 1H), 2.50-2.41 (m, 1H), 2.34-2.07 (m, 1H), 1.60-1.57 (m, 1H), 1.45-1.42 (m, 1H), δ 1.24-0.83 (m, 1H). ES-LCMS m/z 611.0, 613/0 $[M+H]^+$.

Step 2: rel-(1R,2S,4R,6R)-2-(4-bromophenyl)-6-((2-fluoro-4-(trifluoromethyl)phenyl)carbamoyl)-4-(methoxy-$d_3$)cyclohexane-1-carboxylic acid, Isomer 1

ISOMER 1

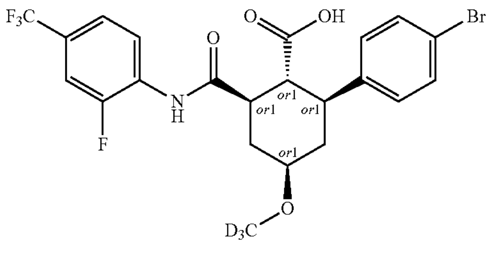

To a mixture of rac-benzyl (1R,2S,4R,6R)-2-(4-bromophenyl)-6-((2-fluoro-4-(trifluoromethyl)phenyl)carbamoyl)-4-(methoxy-$d_3$)cyclohexane-1-carboxylate (0.40 g, 0.65 mmol) in dichloromethane (5 mL) was added boron trichloride (1M in DCM, 1.31 mL, 1.31 mmol) at 0° C. The reaction was stirred at 0° C. for 10 min, then allowed to warm to rt over 1 h. The mixture was quenched with methanol at 0° C., concentrated and subjected to reverse phase purification (MeCN in $H_2O$, 10 mM formic acid modifier, 95-98% gradient) to afford rac-(1R,2S,4R,6R)-2-(4-bromophenyl)-6-((2-fluoro-4-(trifluoromethyl)phenyl)carbamoyl)-4-(methoxy-$d_3$)cyclohexane-1-carboxylic acid (200 mg, 0.37 mmol, 56% yield) as an off white solid. The racemic compound was separated by Chiral-Prep-SFC (Column: Lux Amylose-1 [250×30] mm, 5 μm; CO2: IPA 60:40) to afford rel-(1R,2S,4R,6R)-2-(4-bromophenyl)-6-((2-fluoro-4-(trifluoromethyl)phenyl)carbamoyl)-4-(methoxy-$d_3$)cyclohexane-1-carboxylic acid, Isomer 1 (0.10 g, 0.18 mmol, 48% yield) as a white solid. $^1$H NMR (400 MHz, DMSO-$d_6$): δ 10.20 (s, 1H), 8.23 (t, J=8.0 Hz, 1H), 7.71 (d, J=1.6 Hz, 1H), 7.55 (d, J=8.8 Hz, 1H), 7.47 (d, J=8.4 Hz, 2H), 7.26 (d, J=8.4 Hz, 2H), 3.41-3.36 (m, 1H), 3.18-3.02 (m, 1H), 2.75-2.56 (m, 2H), 2.34-2.33 (m, 1H), 2.07-2.04 (m, 1H), 1.51-1.39 (m, 2H), 1.13-1.11 (m, 1H). ES-LCMS m/z 521.0, 523.0 $[M+H]^+$.

Step 3: rel-(1R,2R,4R,6S)-2-((2-fluoro-4-(trifluoromethyl)phenyl)carbamoyl)-4-(methoxy-d)-6-(4-(methylamino)phenyl)cyclohexane-1-carboxylic acid, Isomer 1

ISOMER 1

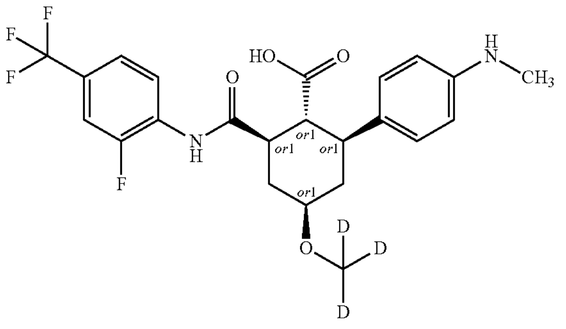

To a mixture of rel-(1R,2S,4R,6R)-2-(4-bromophenyl)-6-((2-fluoro-4-(trifluoromethyl)phenyl)carbamoyl)-4-(methoxy-$d_3$)cyclohexane-1-carboxylic acid, Isomer 1 (0.090 g, 0.17 mmol) in 1,4-dioxane (2 mL) was added solid sodium tert-butoxide (16.6 mg, 0.173 mmol) and tBuXPhos Pd G3 (137 mg, 0.173 mmol) was added in one charge. After degassing for 5 min, methanamine (2M in THF, 0.86 mL, 0.173 mmol) was added, and the reaction vessel was sealed and heated in a Biotage Initiator (microwave) at 100° C. for 1 h. The reaction was stirred at rt for 3 h, concentrated and subjected to reverse phase purification (MeCN in $H_2O$, 0.1% formic acid, 10-55% gradient) to afford rel-(1R,2R,4R,6S)-2-((2-fluoro-4-(trifluoromethyl)phenyl)carbamoyl)-4-(methoxy-$d_3$)-6-(4-(methylamino)phenyl)cyclohexane-1-carboxylic acid, Isomer 1(40 mg, 0.080 mmol, 46% yield) as a white solid. $^1H$ NMR (400 MHz, DMSO-d6): δ 11.73 (br.s, 1H), 10.11 (s, 1H), 8.22 (t, J=8.0 Hz, 1H), 7.73 (dd, J=11.0, 1.6 Hz, 1H), 7.56 (d, J=8.0 Hz, 1H), 6.97 (d, J=8.8 Hz, 2H), 6.44 (d, J=8.8 Hz, 2H), 5.46 (br.s, 1H), 3.39-3.36 (m, 1H), 3.05-3.00 (m, 1H), 2.70-2.61 (m, 5H), 2.34-2.29 (m, 1H), 2.34-2.29 (m, 1H), 1.44-1.35 (m, 2H). ES-LCMS m/z 472.2 $[M+H]^+$.

Intermediate 13 and Intermediate 14: rel-(1R,2R,4R,6S)-2-((2-fluoro-4-(trifluoromethyl)phenyl)carbamoyl)-6-(4-(methylamino)phenyl)-4-phenoxycyclohexane-1-carboxylic acid, Isomer 1 and Isomer 2

ISOMER 1 and ISOMER 2

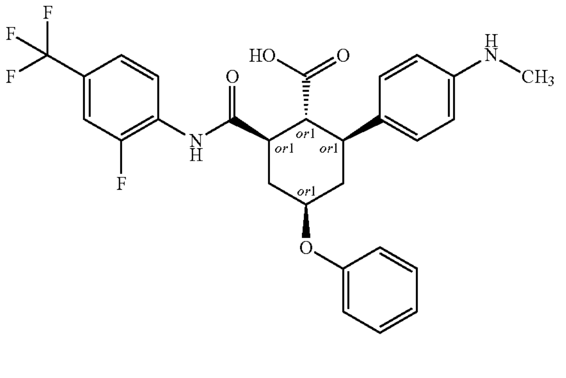

Step 1: rac-(3aR,5R,7S,7aS)-7-(4-bromophenyl)-5-phenoxyhexahydroisobenzofuran-1(3H)-one

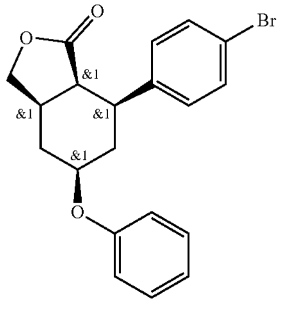 [SMILES: O=C1OC[C@@H]2C[C@H](Oc3ccccc3)C[C@H](c3ccc(Br)cc3)[C@H]12]

To a 1:1 mixture of (3aR,5R,7S,7aS)-7-(4-bromophenyl)-5-hydroxyhexahydroisobenzofuran-1(3H)-one and (3aS,5S,7R,7aR)-7-(4-bromophenyl)-5-hydroxyhexahydroisobenzofuran-1(3H)-one Intermediate 8 Step 6 (2.0 g, 6.4 mmol) in acetonitrile (20 ml) were added 2-(trimethylsilyl)phenyl trifluoromethanesulfonate (2.3 g, 7.7 mmol), potassium fluoride (1.87 g, 32.1 mmol), and 18-crown-6 (4.25 g, 16.1 mmol). After 16 h, the reaction was quenched with water (50 ml) and extracted with ethyl acetate (50 mL×3). The organic layers were washed with brine (50 mL), dried over sodium sulphate, filtered, concentrated and subjected to reverse phase purification (MeCN in $H_2O$, 10 mM formic acid modifier, 95-98% gradient) to afford rac-(3aR,5R,7S,7aS)-7-(4-bromophenyl)-5-phenoxyhexahydroisobenzofuran-1(3H)-one (870 mg, 1.8 mmol, 28% yield) as a white solid. $^1H$ NMR (400 MHz, DMSO-$d_6$) δ 7.49-7.44 (m, 2H), 7.32-7.23 (m, 4H), 7.03-6.96 (m, 2H), 5.01-4.78 (m, 1H), 4.52 (tt, J=11.0, 3.8 Hz, 1H), 4.27-4.15 (m, 1H), 3.91-3.67 (m, 1H), 3.55-3.44 (m, 1H), 2.86 (dt, J=12.0, 6.0 Hz, 1H), 2.39-2.23 (m, 2H), 1.90-1.49 (m, 2H), 1.18 (q, J=12.5 Hz, 1H). ES-LCMS m/z poor ionization.

Step 2: rac-(1R,2S,4R,6R)-2-(4-bromophenyl)-6-(hydroxymethyl)-4-phenoxycyclohexane-1-carboxylic acid

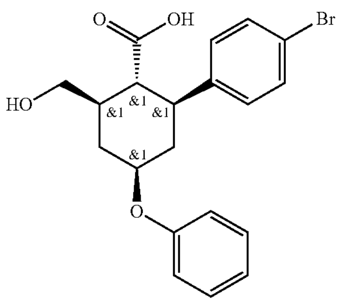 [SMILES: O=C(O)[C@H]1[C@H](CO)C[C@H](Oc2ccccc2)C[C@@H]1c1ccc(Br)cc1]

To a mixture of rac-(3aR,5R,7S,7aS)-7-(4-bromophenyl)-5-phenoxyhexahydroisobenzofuran-1(3H)-one (0.870 g, 2.25 mmol) in methanol (15 mL) was added KOH (0.630 g, 11.3 mmol). The reaction was stirred at 75° C. for 16 h and quenched with 2N HCl (~20 mL) to pH<3. The resulting solid was collected by filtration and washed with water (5 mL×4) and petroleum ether (5 mL×4) to afford rac-(1R,2S,4R,6R)-2-(4-bromophenyl)-6-(hydroxymethyl)-4-phenoxycyclohexane-1-carboxylic acid (0.730 g, 1.44 mmol, 64.0% yield) as an off-white solid. $^1H$ NMR (400 MHz, DMSO-$d_6$) δ 7.43 (d, J=8.5 Hz, 2H), 7.32-7.10 (m, 5H), 6.99-6.94 (m, 2H), 4.62-4.40 (m, 1H), 3.90-3.70 (m, 1H), 3.42 (dd, J=10.5, 3.5 Hz, 2H), 3.06-2.87 (m, 1H), 2.39-2.23 (m, 2H), 2.06 (d, J=11.5 Hz, 1H), 1.96-1.83 (m, 1H), 1.65-1.51 (m, 1H), 1.32-1.22 (m, 1H), 0.84 (dd, J=8.8, 2.3 Hz, 1H). ES-LCMS m/z 405.0 [M−H]≤.

Step 3: rac-benzyl (1R,2S,4R,6R)-2-(4-bromophenyl)-6-(hydroxymethyl)-4-phenoxycyclohexane-1-carboxylate

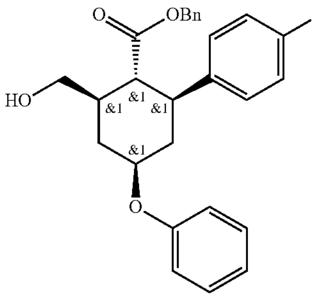

To a mixture of rac-(1R,2S,4R,6R)-2-(4-bromophenyl)-6-(hydroxymethyl)-4-phenoxycyclohexane-1-carboxylic acid (0.730 g, 1.80 mmol) in N,N-dimethylformamide (10 mL) at 0° C. was added potassium carbonate (0.747 g, 5.40 mmol) and benzyl bromide (0.321 mL, 2.70 mmol). The reaction was stirred at rt for 16 h, diluted with water (50 mL) and extracted with ethyl acetate (2×100 mL). The combined organic layers were washed with and brine (50 mL), dried over sodium sulphate, concentrated and purified by normal phase chromatography (EtOAc in petroleum ether, 0-50% gradient) to afford rac-benzyl (1R,2S,4R,6R)-2-(4-bromophenyl)-6-(hydroxymethyl)-4-phenoxycyclohexane-1-carboxylate (0.400 g, 0.686 mmol, 38.1% yield) as a white solid. $^1H$ NMR (400 MHz, DMSO-$d_6$) δ 7.49-7.38 (m, 2H), 7.32-7.13 (m, 7H), 7.03-6.83 (m, 5H), 4.93-4.70 (m, 2H), 4.66 (t, J=5.0 Hz, 1H), 4.63-4.49 (m, 1H), 3.30-3.17 (m, 1H), 3.09-2.94 (m, 1H), 2.71-2.56 (m, 1H), 2.31-1.96 (m, 3H), 1.77-1.60 (m, 1H), 1.44-1.18 (m, 1H). ES-LCMS m/z poor ionization.

Step 4: rac-(1R,2R,3S,5R)-2-((benzyloxy)carbonyl)-3-(4-bromophenyl)-5-phenoxycyclohexane-1-carboxylic acid

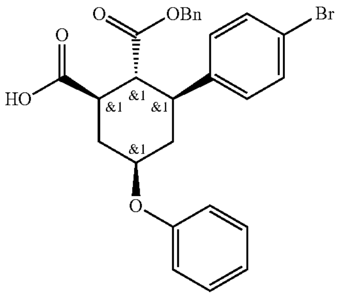 [SMILES: O=C(OCc1ccccc1)[C@@H]1[C@@H](c2ccc(Br)cc2)C[C@@H](Oc2ccccc2)C[C@H]1C(=O)O]

To a mixture of rac-benzyl (1R,2S,4R,6R)-2-(4-bromophenyl)-6-(hydroxymethyl)-4-phenoxycyclohexane-1-carboxylate (0.400 g, 0.807 mmol) in acetonitrile (50 mL) and water (10 mL) at 0° C. were added sodium periodate (518 mg, 2.42 mmol) and ruthenium(III) chloride (16.8 mg, 0.0810 mmol). After 2 h, the reaction was diluted with water (50 mL) and extracted with ethylacetate (3×50 mL). The combined organic layers were washed with and brine (50 mL), dried over sodium sulphate, concentrated then purified by reverse phase chromatography (MeCN in $H_2O$, 10 mM formic acid modifier, 95-98% gradient) to afford rac-(1R,2R,3S,5R)-2-((benzyloxy)carbonyl)-3-(4-bromophenyl)-5-phenoxycyclohexane-1-carboxylic acid (0.290 g, 0.529 mmol, 65.6% yield) as a white solid. $^1H$ NMR (400 MHz, DMSO-$d_6$) δ 12.59 (br s, 1H), 7.44 (d, J=8.5 Hz, 2H), 7.34-7.13 (m, 7H), 7.07-6.81 (m, 5H), 4.81-4.59 (m, 3H), 3.01-2.81 (m, 3H), 2.42 (d, J=11.5 Hz, 1H), 2.07 (d, J=10.5 Hz, 1H), 1.80 (q, J=12.0 Hz, 1H), 1.68-1.53 (m, 1H). ES-LCMS m/z 509.0 [M+H]$^+$.

Step 5: rac-benzyl (1R,2S,4R,6R)-2-(4-bromophenyl)-6-((2-fluoro-4-(trifluoromethyl)phenyl)carbamoyl)-4-phenoxycyclohexane-1-carboxylate

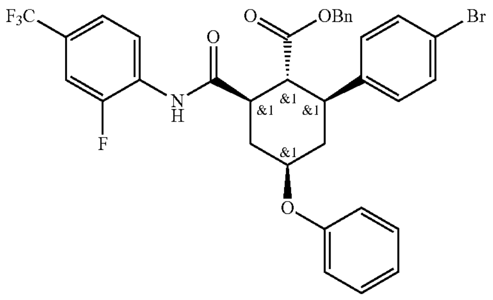 [SMILES: O=C(OCc1ccccc1)[C@@H]1[C@@H](c2ccc(Br)cc2)C[C@@H](Oc2ccccc2)C[C@H]1C(=O)Nc1ccc(C(F)(F)F)cc1F]

To a suspension of rac-(1R,2R,3S,5R)-2-((benzyloxy)carbonyl)-3-(4-bromophenyl)-5-phenoxycyclohexane-1-carboxylic acid (0.290 g, 0.569 mmol) in acetonitrile (0.2 mL) were added 1-methyl-1H-imidazole (0.272 mL, 3.42 mmol) and 2-fluoro-4-(trifluoromethyl)aniline (153 mg, 0.854 mmol) followed by chloro-N,N,N',N'-tetramethylformamidinium hexafluorophosphate (799 mg, 2.85 mmol). After 16 h, the reaction was concentrated and purified by reverse phase chromatography (MeCN in $H_2O$, 10 mM formic acid modified, 95-98% gradient) to afford rac-benzyl (1R,2S,4R,6R)-2-(4-bromophenyl)-6-((2-fluoro-4-(trifluoromethyl)phenyl)carbamoyl)-4-phenoxycyclohexane-1-carboxylate (0.280 g, 0.405 mmol, 71.2% yield) as a white solid. $^1H$ NMR (400 MHz, DMSO-$d_6$) δ 10.21 (s, 1H), 8.17 (t, J=8.0 Hz, 1H), 7.74 (dd, J=11.3, 1.8 Hz, 1H), 7.47 (d, J=8.5 Hz, 2H), 7.31-7.27 (m, 4H), 7.23-7.14 (m, 4H), 7.04 (d, J=7.5 Hz, 2H), 6.93 (t, J=7.3 Hz, 1H), 6.85-6.80 (m, 2H), 4.80-4.65 (m, 2H), 4.63-4.50 (m, 1H), 3.33-3.22 (m, 1H), 3.11-2.98 (m, 2H), 2.47 (br s, 1H), 2.20-2.09 (m, 1H), 1.89 (q, J=11.5 Hz, 1H), 1.71 (q, J=11.7 Hz, 1H). ES-LCMS m/z 670.0 [M+H]$^+$.

Step 6: rel-(1R,2S,4R,6R)-2-(4-bromophenyl)-6-((2-fluoro-4-(trifluoromethyl)phenyl)carbamoyl)-4-phenoxycyclohexane-1-carboxylic acid, Isomer 1 and Isomer 2

ISOMER 1 and ISOMER 2

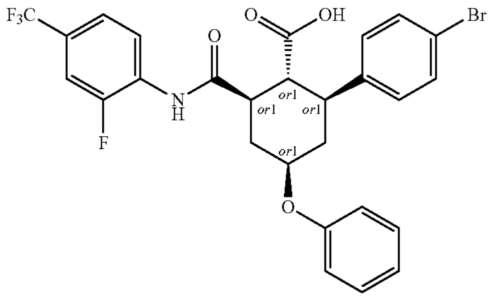

To a mixture of rac-benzyl (1R,2S,4R,6R)-2-(4-bromophenyl)-6-((2-fluoro-4-(trifluoromethyl)phenyl)carbamoyl)-4-(methoxy-$d_3$)cyclohexane-1-carboxylate (0.40 g, 0.65 mmol) in dichloromethane (5 mL) was added boron trichloride (1M in DCM, 1.31 mL, 1.31 mmol) at 0° C. The reaction was stirred at 0° C. for 10 min, then allowed to warm to rt over 1 h. The mixture was quenched with methanol at 0° C., concentrated and subjected to reverse phase purification (MeCN in $H_2O$, 10 mM formic acid modifier, 95-98% gradient) to afford rac-(1R,2S,4R,6R)-2-(4-bromophenyl)-6-((2-fluoro-4-(trifluoromethyl)phenyl)carbamoyl)-4-phenoxycyclohexane-1-carboxylic acid (230 mg, 0.39 mmol, 94% yield) as an off-white solid. $^1$H NMR (400 MHz, DMSO-$d_6$) δ 11.93 (s, 1H), 10.15 (s, 1H), 8.20 (t, J=8.0 Hz, 1H), 7.73 (dd, J=11.0, 2.0 Hz, 1H), 7.55 (d, J=8.0 Hz, 1H), 7.48 (d, J=8.5 Hz, 2H), 7.33-7.24 (m, 4H), 7.06-6.99 (m, 2H), 6.96-6.87 (m, 1H), 4.62-4.47 (m, 1H), 3.25-3.14 (m, 1H), 3.04-2.79 (m, 2H), 2.46-2.36 (m, 1H), 2.13 (br d, J=13.0 Hz, 1H), 1.86-1.59 (m, 2H). ES-LCMS m/z 577.7 $[M-H]^-$.

The racemic compound was separated by Chiral-Prep-SFC (Column: Chiralpak IG [250*30] mm, 5 μm; Mobile Phase: CO2: IPA 60:40) to afford:

The first-eluting isomer rel-(1R,2S,4R,6R)-2-(4-bromophenyl)-6-((2-fluoro-4-(trifluoromethyl)phenyl)carbamoyl)-4-phenoxycyclohexane-1-carboxylic acid, Isomer 1 (110 mg, 0.17 mmol, 43% yield) as a white solid.

AND

The second-eluting isomer rel-(1R,2S,4R,6R)-2-(4-bromophenyl)-6-((2-fluoro-4-(trifluoromethyl)phenyl)carbamoyl)-4-phenoxycyclohexane-1-carboxylic acid, Isomer 2 (110 mg, 0.17 mmol, 43% yield) as a white solid.

Step 7: rel-(1R,2R,4R,6S)-2-((2-fluoro-4-(trifluoromethyl)phenyl)carbamoyl)-6-(4-(methylamino)phenyl)-4-phenoxycyclohexane-1-carboxylic acid, Isomer 1 and Isomer 2

ISOMER 1 and ISOMER 2

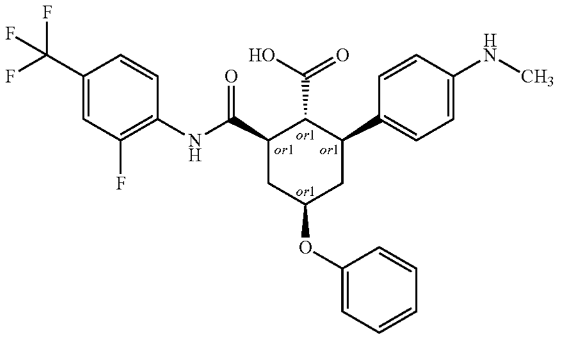

To a mixture of rel-(1R,2S,4R,6R)-2-(4-bromophenyl)-6-((2-fluoro-4-(trifluoromethyl)phenyl)carbamoyl)-4-phenoxycyclohexane-1-carboxylic acid, Isomer 1 (0.0900 g, 0.155 mmol) and sodium tert-butoxide (37.3 mg, 0.388 mmol) in 1,4-dioxane (2 mL) was added tBuXPhos Pd G3 (24.6 mg, 0.0310 mmol). After degassing for 5 min, methanamine (2M in THF, 1.55 mL, 3.10 mmol) was added, and the reaction vessel was sealed and heated in a Biotage Initiator (microwave) at 100° C. for 1 h. The reaction was subjected to reverse phase purification (MeCN in $H_2O$, 10 nM ammonium bicarbonate, 95-98% gradient) to afford rel-(1R,2R,4R,6S)-2-((2-fluoro-4-(trifluoromethyl)phenyl)carbamoyl)-6-(4-(methylamino)phenyl)-4-phenoxycyclohexane-1-carboxylic acid, Isomer 1 (0.070 g, 0.12 mmol, 78% yield) as an off-white solid. $^1$H NMR (400 MHz, DMSO-$d_6$) δ 11.78 (brs, 1H), 10.12 (s, 1H), 8.20 (t, J=8.0 Hz, 1H), 7.72 (dd, J=11.0, 1.5 Hz, 1H), 7.55 (d, J=8.5 Hz, 1H), 7.31-7.25 (m, 2H), 7.05-6.99 (m, 4H), 6.95-6.88 (m, 1H), 6.43 (d, J=9.0 Hz, 2H), 5.47 (br s, 1H), 4.59-4.45 (m, 1H), 3.23-3.09 (m, 1H), 2.84-2.71 (m, 2H), 2.63 (s, 3H), 2.39 (d, J=12.0 Hz, 1H), 2.09 (d, J=12.0 Hz, 1H), 1.77-1.56 (m, 2H). ES-LCMS m/z 531.0 $[M+H]^+$.

In a separate reaction, to a mixture of rel-(1R,2S,4R,6R)-2-(4-bromophenyl)-6-((2-fluoro-4-(trifluoromethyl)phenyl)carbamoyl)-4-phenoxycyclohexane-1-carboxylic acid, Isomer 2 (0.100 g, 0.172 mmol) and sodium tert-butoxide (41.4 mg, 0.431 mmol) in 1,4-dioxane (5 mL) was added tBuXPhos Pd G3 (27.4 mg, 0.0340 mmol). After degassing for 5 min, methanamine (2M in THF, 1.72 mL, 3.45 mmol) was added, and the reaction vessel was sealed and heated in a Biotage Initiator (microwave) at 100° C. for 1 h. The reaction was subjected to reverse phase purification (MeCN in $H_2O$, 10 nM ammonium bicarbonate, 10-100% gradient) to afford rel-(1R,2R,4R,6S)-2-((2-fluoro-4-(trifluoromethyl)phenyl)carbamoyl)-6-(4-(methylamino)phenyl)-4-phenoxycyclohexane-1-carboxylic acid, Isomer 2 (75 mg, 0.13 mmol, 76% yield) as an off-white solid. $^1$H NMR (400 MHz, DMSO-$d_6$) δ 11.84 (brs, 1H), 10.13 (s, 1H), 8.21 (t, J=8.0 Hz, 1H), 7.72 (dd, J=11.0, 1.5 Hz, 1H), 7.55 (d, J=8.5 Hz, 1H), 7.28 (dd, J=8.5, 7.5 Hz, 2H), 7.05-6.98 (m, 4H), 6.95-6.88 (m, 1H), 6.43 (d, J=8.5 Hz, 2H), 5.47 (d, J=4.5 Hz, 1H), 4.66-4.38 (m, 1H), 3.22-3.09 (m, 1H), 2.87-2.69 (m, 2H), 2.63 (d, J=4.0 Hz, 3H), 2.39 (d, J=12.0 Hz, 1H), 2.14-2.01 (m, 1H), 1.80-1.51 (m, 2H). ES-LCMS m/z 531.0 $[M+H]^+$.

Intermediate 15: rac-(3aR,5R,7S,7aS)-7-(4-bromophenyl)-5-(cyclobutylmethoxy)hexahydroisobenzofuran-1(3H)-one

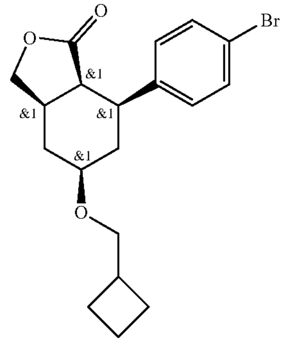 [SMILES: O=C1OC[C@@H]2C[C@H](OCC3CCC3)C[C@H](c3ccc(Br)cc3)[C@H]12]

To a mixture of rac-(3aR,7S,7aS)-7-(4-bromophenyl)tetrahydroisobenzofuran-1,5(3H,4H)-dione Intermediate 8 Step 5 (5.0 g, 16 mmol) and cyclobutylmethanol (3.05 mL, 32.3 mmol) in acetonitrile (50 mL) was added triethylsilane (3.9 mL, 24 mmol) and triflic acid (1.4 mL, 16 mmol). After 16 h the reaction was quenched with ice water (10 mL) and extracted with EtOAc (50 mL×3). The combined EtOAc layers were washed with water (50 mL) and brine (50 mL), dried over sodium sulphate, concentrated and subjected to normal phase purification (ethyl acetate in petroleum ether, 0-100% gradient) to afford rac-(3aR,5R,7S,7aS)-7-(4-bromophenyl)-5-(cyclobutylmethoxy)hexahydroisobenzofuran-1 (3H)-one (1.8 g, 4.4 mmol, 27% yield) as a white solid. $^1H$ NMR (400 MHz, DMSO-$d_6$) δ 7.47 (d, J=8.5 Hz, 2H), 7.28 (d, J=8.5 Hz, 2H), 4.20 (dd, J=8.5, 4.5 Hz, 1H), 3.90 (d, J=9.0 Hz, 1H), 3.52-3.35 (m, 3H), 3.25 (t, J=5.5 Hz, 1H), 3.17-3.06 (m, 1H), 2.76-2.63 (m, 1H), 2.49-2.41 (m, 1H), 2.24-2.13 (m, 2H), 2.01-1.94 (m, 2H), 1.89-1.78 (m, 2H), 1.74-1.65 (m, 2H), 1.39-1.28 (m, 1H), 1.02-0.90 (m, 1H). ES-LCMS m/z 379.0 $[M+H]^+$.

Intermediate 16: rac-methyl (3aR,4S,5S,6R,7aS)-4-((2-fluoro-4-(trifluoromethyl)phenyl)carbamoyl)-6-(4-((N,1,2-trimethyl-1H-benzo[d]imidazole)-5-sulfonamido)phenyl)octahydrobenzofuran-5-carboxylate

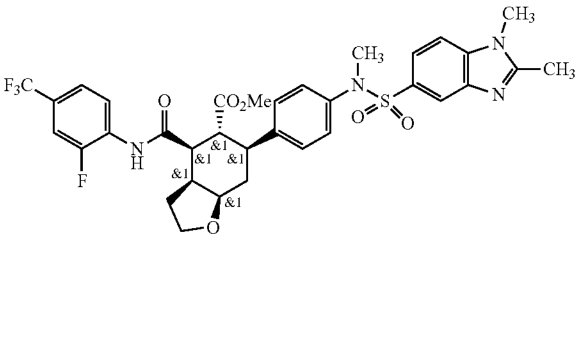 [SMILES: COC(=O)[C@H]1[C@H](C(=O)Nc2ccc(C(F)(F)F)cc2F)[C@@H]2CCO[C@@H]2C[C@@H]1c1ccc(N(C)S(=O)(=O)c2ccc3c(c2)nc(C)n3C)cc1]

Step 1: (E/Z)-2-(4-bromostyryl)furan

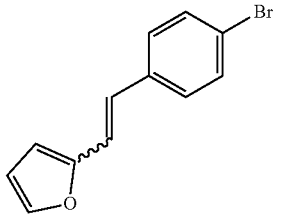 [SMILES: Brc1ccc(C=Cc2ccco2)cc1]

To a mixture of (4-bromobenzyl)triphenylphosphonium bromide (96.0 g, 187 mmol) in tetrahydrofuran (200 mL) at 0° C. was added potassium 2-methylpropan-2-olate (1M, 229 mL, 229 mmol). After 10 min a solution of furan-2-carbaldehyde (20.0 g, 208 mmol) was added dropwise over 5 min. After 4 h, the reaction was quenched with water (100 mL) and extracted with ethyl acetate (3×100 mL). The combined organic layers were washed with brine, dried over anhydrous sodium sulfate filtered, concentrated and subjected to normal phase purification (ethyl acetate in petroleum ether, 0-20% gradient) to afford (E/Z)-2-(4-bromostyryl)furan (33 g, 0.11 mmol, 51% yield) as a yellow oil. $^1H$ NMR (400 MHz, DMSO-$d_6$) δ 7.60 (d, J=1.5 Hz, 1H), 7.56-7.51 (m, 3H), 7.43-7.35 (m, 2H), 6.50-6.47 (m, 1H), 6.46-6.41 (m, 2H). ES-LCMS m/z 249.9 $[M+H]^+$.

Step 2: rac-dimethyl (4R,5S,6R)-6-(4-bromophenyl)-4,5,6,7-tetrahydrobenzofuran-4,5-dicarboxylate

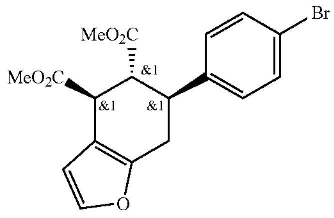 [SMILES: COC(=O)[C@@H]1[C@@H](c2ccc(Br)cc2)Cc2occc2[C@H]1C(=O)OC]

A mixture of (E/Z)-2-(4-bromostyryl)furan (33.0 g, 132 mmol) and dimethyl fumarate (38.2 g, 265 mmol) was stirred at 140° C. for 1 week and subjected to normal phase purification (ethyl acetate petroleum ether, 0-100% gradient) to afford rac-dimethyl (4R,5S,6R)-6-(4-bromophenyl)-4,5,6,7-tetrahydrobenzofuran-4,5-dicarboxylate (8.0 g, 16 mmol, 12% yield) as yellow oil. $^1H$ NMR (400 MHz, DMSO-$d_6$) δ 7.56 (d, J=1.9 Hz, 1H), 7.51 (d, J=8.5 Hz, 2H), 7.32 (d, J=8.5 Hz, 2H), 6.42 (d, J=1.9 Hz, 1H), 3.99-3.92 (m, 1H), 3.67 (s, 3H), 3.27-3.19 (m, 5H), 3.04-2.91 (m, 1H), 2.90-2.79 (m, 1H). NMR interpretation from the major isomer of the diastereomeric mixture. ES-LCMS m/z 393.0 $[M]^+$.

Step 3: rac-dimethyl (4R,5S,6R)-6-(4-(methylamino)phenyl)-4,5,6,7-tetrahydrobenzofuran-4,5-dicarboxylate

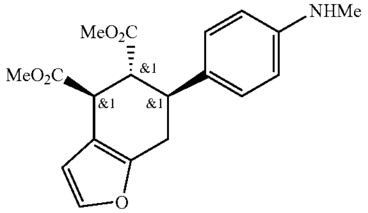 [SMILES: CNc1ccc([C@H]2Cc3occc3[C@@H](C(=O)OC)[C@@H]2C(=O)OC)cc1]

To a mixture of rac-dimethyl (4R,5S,6R)-6-(4-bromophenyl)-4,5,6,7-tetrahydrobenzofuran-4,5-dicarboxylate (8.00 g, 20.3 mmol) and cesium carbonate (19.9 g, 61.0 mmol) in N,N-dimethylformamide (80 mL) (degassed 10 min) was added tBuBrettPhos Pd G3 (0.869 g, 1.02 mmol). After 5 min methanamine (2M in THF, 153 mL, 305 mmol) was added. The reaction was stirred at 60° C. for 16 h, quenched with water (100 mL) and extracted with EtOAc (100 mL×4). The combined EtOAc layers were washed with water (100 mL×2) and brine (100 mL), dried over sodium sulphate, concentrated and subjected to normal phase purification (ethyl acetate in petroleum ether, 0-20% gradient) to afford rac-dimethyl (4R,5S,6R)-6-(4-(methylamino)phenyl)-4,5,6,7-tetrahydrobenzofuran-4,5-dicarboxylate (5.5 g, 14 mmol, 68% yield) as yellow oil.

$^1$H NMR (400 MHz, DMSO-$d_6$) δ 7.54 (d, J=1.8 Hz, 1H), 7.02 (d, J=8.5 Hz, 2H), 6.45 (d, J=8.5 Hz, 2H), 6.39 (d, J=2.0 Hz, 1H), 5.58-5.47 (m, 1H), 3.92 (dd, J=7.8, 2.1 Hz, 1H), 3.66 (s, 3H), 3.25 (s, 3H), 3.06 (dd, J=7.6, 2.8 Hz, 2H), 2.96-2.85 (m, 1H), 2.84-2.73 (m, 1H), 2.65 (d, J=5.1 Hz, 3H). NMR interpretation from the major isomer of the diastereomeric mixture. ES-LCMS m/z 344.2 [M+H]$^+$.

Step 4: rac-dimethyl (3aS,4R,5R,6S,7aR)-6-(4-(methylamino)phenyl)octahydrobenzofuran-4,5-dicarboxylate

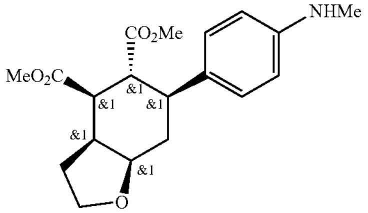 [SMILES: CNc1ccc([C@H]2C[C@H]3OCC[C@H]3[C@@H](C(=O)OC)[C@@H]2C(=O)OC)cc1]

To a mixture of rac-dimethyl (4R,5S,6R)-6-(4-(methylamino)phenyl)-4,5,6,7-tetrahydrobenzofuran-4,5-dicarboxylate (11.5 g, 33.5 mmol) in methanol (200 mL) was added rhodium on carbon (6.89 g, 3.35 mmol), and the reaction was placed under hydrogen atmosphere with a bladder (1 atm). The mixture degassed via vacuum evacuation, then backfilled with hydrogen, and this process was repeated three times. After 16 h the reaction was filtered through Celite, concentrated and subjected to normal phase purification (ethyl acetate in petroleum ether, 0-100% gradient) to afford rac-dimethyl (4R,5R,6S)-6-(4-(methylamino)phenyl)octahydrobenzofuran-4,5-dicarboxylate (0.650 g, 1.60 mmol, 5.00% yield) as a brown oil. $^1$H NMR (400 MHz, DMSO-$d_6$) δ 6.90 (d, J=8.5 Hz, 2H), 6.41 (d, J=8.5 Hz, 2H), 5.45 (br d, J=4.5 Hz, 1H), 4.17 (dt, J=10.6, 6.4 Hz, 1H), 3.97-3.87 (m, 1H), 3.77-3.63 (m, 1H), 3.60-3.54 (m, 2H), 3.33 (s, 3H), 3.23 (dd, J=6.3, 5.3 Hz, 1H), 2.77 (t, J=11.5 Hz, 1H), 2.70-2.57 (m, 4H), 2.46-2.39 (m, 1H), 2.08-2.00 (m, 1H), 1.96-1.84 (m, 1H), 1.67-1.51 (m, 2H), one proton obscured by residual DMSO/$H_2O$ peak. ES-LCMS m/z 348.0 [M+H]$^+$.

Step 5: rac-(3aR,4S,5S,6R,7aS)-5-(methoxycarbonyl)-6-(4-(methylamino)phenyl)octahydrobenzofuran-4-carboxylic acid

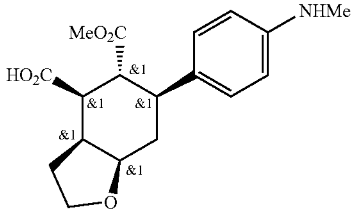 [SMILES: CNc1ccc([C@H]2C[C@H]3OCC[C@H]3[C@@H](C(=O)O)[C@@H]2C(=O)OC)cc1]

To a mixture of rac-dimethyl (4R,5R,6S)-6-(4-(methylamino)phenyl)octahydrobenzofuran-4,5-dicarboxylate (2.50 g, 7.20 mmol) in tetrahydrofuran (55 mL), methanol (55.0 mL) and water (55 mL) at 0° C. was added lithium hydroxide (0.258 g, 10.79 mmol). The reaction was stirred at 60° C. for 16 h, concentrated and subjected to reverse phase purification (MeCN in $H_2O$, 0.1% ammonium bicarbonate modifier, 0-100% gradient) to afford rac-(3aR,4S,5S,6R,7aS)-5-(methoxycarbonyl)-6-(4-(methylamino)phenyl)octahydrobenzofuran-4-carboxylic acid (1.5 g, 4.2 mmol, 59% yield) as an off-white solid. $^1$H NMR (400 MHz, DMSO-$d_6$) δ 6.89-6.81 (m, 2H), 6.40 (m, 2H), 5.39 (br s, 1H), 3.81-3.62 (m, 2H), 3.61-3.47 (m, 1H), 3.19-3.06 (m, 3H), 2.77-2.66 (m, 1H), 2.62 (s, 3H), 2.37-2.25 (m, 1H), 2.21-2.05 (m, 1H), 1.94-1.64 (m, 3H), 1.56-1.45 (m, 1H), two protons obscured by residual DMSO/$H_2O$ peak. ES-LCMS m/z 334.2 [M+H]$^+$.

Step 6: rac-(3aR,4S,5S,6R,7aS)-5-(methoxycarbonyl)-6-(4-((N,1,2-trimethyl-1H-benzo[d]imidazole)-5-sulfonamido)phenyl)octahydrobenzofuran-4-carboxylic acid

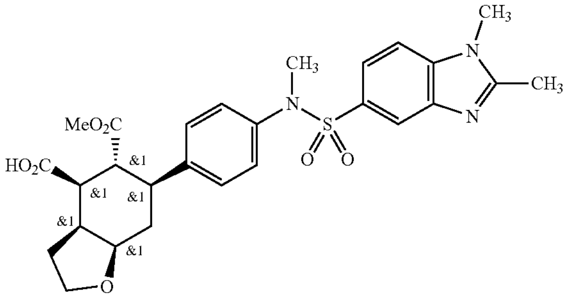 [SMILES: COC(=O)[C@H]1[C@H](C(=O)O)[C@@H]2CCO[C@@H]2C[C@@H]1c1ccc(N(C)S(=O)(=O)c2ccc3c(c2)nc(C)n3C)cc1]

To a suspension of rac-(3aR,4S,5S,6R,7aS)-5-(methoxycarbonyl)-6-(4-(methylamino)phenyl)octahydrobenzofuran-4-carboxylic acid (1.50 g, 4.50 mmol) and 1,2-dimethyl-1H-benzo[d]imidazole-5-sulfonyl chloride (2.64 g, 10.80 mmol) in dichloromethane (20 mL) was added pyridine (1.5 mL, 18.00 mmol). After 1 h the reaction was concentrated and subjected to normal phase purification (MeOH in DCM, 2-25% gradient) to afford rac-(3aR,4S,5S,6R,7aS)-5-(methoxycarbonyl)-6-(4-((N,1,2-trimethyl-1H-benzo[d]imidazole)-5-sulfonamido)phenyl)octahydrobenzofuran-4-carboxylic acid (2.2 g, 3.3 mmol, 72% yield) as an off-white solid. $^1$H NMR (400 MHz, DMSO-$d_6$) δ 8.91-8.89 (m, 3H), 8.54-8.49 (m, 2H), 8.02-7.97 (m, 3H), 7.17 (d, J=8.5 Hz, 1H), 7.01-6.94 (m, 1H), 4.18 (dt, J=10.5, 6.3 Hz, 1H), 3.90 (s, 3H), 3.80-3.69 (m, 1H), 3.16 (s, 3H), 3.15-3.10 (m, 3H), 2.76 (s, 3H), 2.71-2.63 (m, 1H), 2.62-2.54 (m, 1H), 2.47-2.38 (m, 1H), 2.10-2.00 (m, 1H), 1.78-1.54 (m, 2H), one proton obscured by DMSO/$H_2O$ peak. ES-LCMS m/z 542.3 $[M+H]^+$.

Step 7: rac-methyl (3aR,4S,5S,6R,7aS)-4-((2-fluoro-4-(trifluoromethyl)phenyl)carbamoyl)-6-(4-((N,1,2-trimethyl-1H-benzo[d]imidazole)-5-sulfonamido)phenyl)octahydrobenzofuran-5-carboxylate

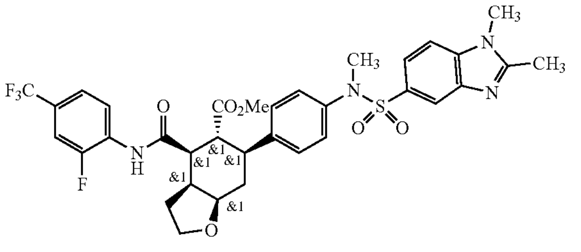 [SMILES: COC(=O)[C@H]1[C@H](C(=O)Nc2ccc(C(F)(F)F)cc2F)[C@@H]2CCO[C@@H]2C[C@@H]1c1ccc(N(C)S(=O)(=O)c2ccc3c(c2)nc(C)n3C)cc1]

To a mixture of rac-(3aR,4S,5S,6R,7aS)-5-(methoxycarbonyl)-6-(4-((N,1,2-trimethyl-1H-benzo[d]imidazole)-5-sulfonamido)phenyl)octahydrobenzofuran-4-carboxylic acid (1.5 g, 2.8 mmol) in acetonitrile (5 mL) at 25° C. were sequentially added TCFH (3.89 g, 13.9 mmol), 2-fluoro-4-(trifluoromethyl)aniline (0.719 mL, 5.54 mmol) and finally NMI (2.21 mL, 27.7 mmol). After 16 h, the reaction was concentrated and subjected to normal phase purification (DCM in MeOH 2-10% gradient) to afford rac-methyl (3aR,4S,5S,6R,7aS)-4-((2-fluoro-4-(trifluoromethyl)phenyl)carbamoyl)-6-(4-((N,1,2-trimethyl-1H-benzo[d]imidazole)-5-sulfonamido)phenyl)octahydrobenzofuran-5-carboxylate (0.25 g, 0.35 mmol, 13% yield) as a white solid. $^1$H NMR (400 MHz, DMSO-$d_6$) δ 10.20 (s, 1H), 8.10 (t, J=8.3 Hz, 1H), 7.77-7.63 (m, 2H), 7.60-7.51 (m, 2H), 7.32 (dd, J=8.3, 1.8 Hz, 1H), 7.19 (d, J=8.5 Hz, 2H), 6.96 (d, J=8.5 Hz, 2H), 4.23-4.13 (m, 1H), 3.99-3.89 (m, 1H), 3.84-3.68 (m, 4H), 3.51 (dd, J=11.8, 5.8 Hz, 2H), 3.17 (s, 3H), 3.12-3.06 (m, 3H), 2.99 (t, J=11.5 Hz, 1H), 2.87-2.72 (m, 2H), 2.57 (s, 3H), 2.17-2.07 (m, 1H), 1.70-1.58 (m, 2H). ES-LCMS m/z 703.2 $[M+H]^+$.

Intermediate 17 and Intermediate 18: rel-(1R,2R,6S)-2-((2-fluoro-4-(trifluoromethyl)phenyl)carbamoyl)-6-(5-(methylamino)pyridin-2-ylcyclohexane-1-carboxylic acid, ISOMER 1 and ISOMER 2

ISOMER 1 and ISOMER 2

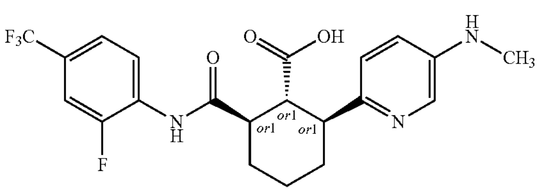

Step 1: 1-(5-bromopyridin-2-yl)but-3-en-1-ol

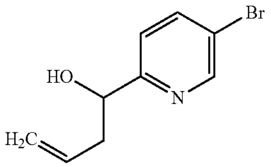

To a mixture of 5-bromopicolinaldehyde (10.0 g, 53.8 mmol) in tetrahydrofuran (150 mL) at −5° C. was added allylmagnesium bromide (1 M in diethyl ether, 53.8 mL, 53.8 mmol), dropwise over a period of 10 mins. The reaction was allowed to warm to rt and stirred for 1 h. The mixture was cooled to 0° C., and additional allylmagnesium bromide (1M in diethyl ether, 10.75 mL, 10.75 mmol) was added over a period of 5 mins. The reaction stirred at rt for 2.5 h, quenched with cold water and concentrated. The resulting residue was washed with 1N HCl (100 mL) and extracted with EtOAc (3×150 mL). The combined organic layers were dried over anhydrous sodium sulfate, filtered and concentrated to afford 1-(5-bromopyridin-2-yl)but-3-en-1-ol (14.1 g, 39.6 mmol, 74.0% yield) as dark brown gum, which was used crude directly in the next step. ES-LCMS m/z 228.2 $[M+H]^+$.

Step 2: 1-(5-bromopyridin-2-yl)but-3-en-1-yl methanesulfonate

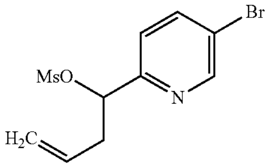 [SMILES: C=CCC(OS(C)(=O)=O)c1ccc(Br)cn1]

To a mixture of 1-(5-bromopyridin-2-yl)but-3-en-1-ol (14.0 g, 39.5 mmol) in dichloromethane (100 mL) at 0° C. was added triethylamine (19.3 mL, 138 mmol) followed by methanesulfonyl chloride (4.61 mL, 59.2 mmol). After 2.5 h, the reaction was quenched with ammonium chloride solution (100 mL) and extracted with EtOAc (2×100 mL). The combined organic layers were dried over anhydrous sodium sulfate, filtered, concentrated and subjected to normal phase chromatography (0-50% EtOAc in petroleum ether) to afford 1-(5-bromopyridin-2-yl)but-3-en-1-yl methanesulfonate (16.8 g, 46.3 mmol, quantitative yield) as a pale brown gum. $^1H$ NMR (400 MHz, DMSO-$d_6$) δ 8.74 (dd, J=2.6, 0.8 Hz, 1H), 8.14 (dd, J=8.4, 2.4 Hz, 1H), 7.50 (d, J=8.4 Hz, 1H), 5.76-5.66 (m, 2H), 5.13-5.06 (m, 1H), 3.16 (s, 3H), 3.11-3.09 (m, 1H), 2.75 (t, J=6.0 Hz, 2H). ES-LCMS m/z 306.0 $[M+H]^+$.

Step 3: (E)-5-bromo-2-(buta-1,3-dien-1-yl)pyridine

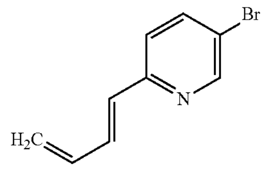

To a mixture of 1-(5-bromopyridin-2-yl)but-3-en-1-yl methanesulfonate (16.0 g, 44.0 mmol) in dichloromethane (100 mL) was added DBU (19.9 mL, 132 mmol). After 2 h additional DBU (5.00 mL, 33.2 mmol) was added, and the reaction was stirred for another 4 h. DBU (10.0 mL, 66.3 mmol) was added again, and the mixture was stirred for 18 h, concentrated and subjected to normal phase chromatography, eluting with 0-20% EtOAc in petroleum ether to afford (E)-5-bromo-2-(buta-1,3-dien-1-yl)pyridine (4.22 g, 17.5 mmol, 40.0% yield) as a pale yellow liquid. $^1H$ NMR (400 MHz, DMSO-$d_6$) δ 8.64 (d, J=2.4 Hz, 1H), 8.01 (dd, J=8.4, 2.4 Hz, 1H), 7.46 (d, J=8.4 Hz, 1H), 7.34-7.27 (m, 1H), 6.72-6.64 (m, 1H), 6.61-6.54 (m, 1H), 5.56-5.51 (m, 1H), 5.36-5.33 (m, 1H). ES-LCMS m/z 210.0 $[M+H]^+$.

Step 4: rac-dimethyl (1R,2R,3R)-3-(5-bromopyridin-2-yl)cyclohex-4-ene-1,2-dicarboxylate with rac-dimethyl (1R,2R,3S)-3-(5-bromopyridin-2-yl)cyclohex-4-ene-1,2-dicarboxylate

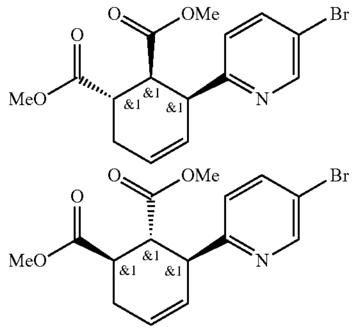

To a mixture of (E)-5-bromo-2-(buta-1,3-dien-1-yl)pyridine (8.50 g, 40.5 mmol) in o-xylene (75 mL) was added dimethyl fumarate (5.83 g, 40.5 mmol). The reaction was heated to 140° C. for 16 h, concentrated and subjected to normal phase chromatography, eluting with 0-30% EtOAc in petroleum ether, to afford rac-dimethyl (1R,2R,3R)-3-(5-bromopyridin-2-yl)cyclohex-4-ene-1,2-dicarboxylate with rac-dimethyl (1R,2R,3S)-3-(5-bromopyridin-2-yl)cyclohex-4-ene-1,2-dicarboxylate (13.0 g, 16.3 mmol, 40.0% yield) as a brown liquid. $^1H$ NMR (400 MHz, DMSO-$d_6$) δ 8.61 (dd, J=5.3, 1.8 Hz, 1H), 7.98 (ddd, J=9.8, 8.3, 2.5 Hz, 1H), 7.22 (dd, J=18.5, 8.0 Hz, 1H), 5.95-5.75 (m, 1H), 5.58 (dd, J=9.8, 1.8 Hz, 1H), 3.81-3.71 (m, 1H), 3.58 (d, J=9.0 Hz, 3H), 3.39 (d, J=5.0 Hz, 3H), 3.17-3.05 (m, 1H), 3.01-2.88 (m, 1H), 2.32-2.21 (m, 1H), 2.17-2.03 (m, 1H). ES-LCMS m/z 354.0 $[M+H]^+$.

Step 5: rac-(1 S,5S,6S)-5-(5-bromopyridin-2-yl)-6-(methoxycarbonyl)cyclohex-3-ene-1-carboxylic acid with rac-(1R,5S,6R)-5-(5-bromopyridin-2-yl)-6-(methoxycarbonyl)cyclohex-3-ene-1-carboxylic acid

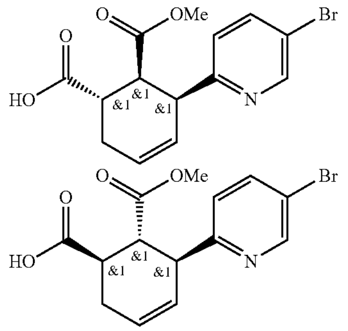

To a mixture of rac dimethyl (1R,2R,3R)-3-(5-bromopyridin-2-cyclohex-4-ene-1,2-dicarboxylate with rac dimethyl (1R,2R,3S)-3-(5-bromopyridin-2-yl)cyclohex-4-ene-1,2-dicarboxylate (13.0 g, 36.8 mmol) in tetrahydrofuran (25 mL), water (25 mL) and methanol (25 mL) was added lithium hydroxide monohydrate (4.64 g, 110 mmol). After 16 h the reaction was concentrated, diluted with cold water (200 mL), acidified with 1.5N HCl and extracted with EtOAc (2×200 mL). The combined organic layers were washed with brine (100 mL), dried over anhydrous sodium sulfate, filtered, concentrated and subjected to SFC achiral purification (Column: YMC EP2; Mobile Phase 85:15 $CO_2$:[0.5% Isopropylamine in MeOH]). The product was diluted with EtOAc (200 mL) and washed with water (150 mL), 0.5N HCl (50 mL) and brine (50 mL). The organic layer was dried over anhydrous sodium sulfate, filtered and concentrated to afford rac-(1S,5S,6S)-5-(5-bromopyridin-2-yl)-6-(methoxycarbonyl)cyclohex-3-ene-1-carboxylic acid with (1R,5S,6R)-5-(5-bromopyridin-2-yl)-6-(methoxycarbonyl)cyclohex-3-ene-1-carboxylic acid (6.0 g, 8.3 mmol, 23% yield) as a colourless gum. $^1H$ NMR (400 MHz, DMSO-$d_6$) δ 12.44 (br s, 1H), 8.67-8.58 (m, 1H), 8.06-7.94 (m, 1H), 7.25-7.11 (m, 1H), 5.99-5.53 (m, 2H), 3.75-3.65 (m, 1H), 3.42-3.35 (m, 3H), 3.09-2.79 (m, 2H), 2.29-2.16 (m, 1H), 2.15-2.03 (m, 1H). ES-LCMS m/z 340.0 $[M+H]^+$.

Step 6: rac-methyl (1R,2S,6R)-2-(5-bromopyridin-2-yl)-6-((2-fluoro-4-(trifluoromethyl)phenylcarbamoyl)cyclohex-3-ene-1-carboxylate

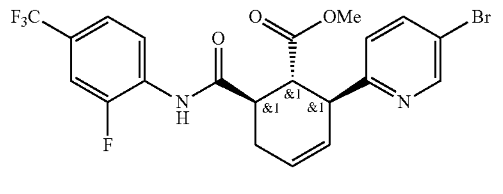 [SMILES: COC(=O)[C@@H]1[C@@H](c2ccc(Br)cn2)C=CC[C@H]1C(=O)Nc1ccc(C(F)(F)F)cc1F]

To a mixture of rac-(1R,5S,6R)-5-(5-bromopyridin-2-yl)-6-(methoxycarbonyl)cyclohex-3-ene-1-carboxylic acid with (1S,5S,6S)-5-(5-bromopyridin-2-yl)-6-(methoxycarbonyl)cyclohex-3-ene-1-carboxylic acid (6.00 g, 8.82 mmol) in acetonitrile (100 mL) and DMF (10 mL) was added 2-fluoro-4-(trifluoromethyl)aniline (1.74 g, 9.70 mmol), NMI (2.11 mL, 26.5 mmol), and N-(chloro(dimethylamino)methylene)-N-methylmethanaminium hexafluorophosphate (V) (2.47 g, 8.82 mmol). After 16 h the reaction was diluted with EtOAc (300 mL), washed with water (100 mL) and brine (100 mL), dried over anhydrous sodium sulfate, filtered, concentrated and subjected to normal phase chromatography, eluting with 0-25% EtOAc in petroleum ether to afford rac-methyl (1R,2S,6R)-2-(5-bromopyridin-2-yl)-6-((2-fluoro-4-(trifluoromethyl)phenylcarbamoyl)cyclohex-3-ene-1-carboxylate (4.60 g, 8.83 mmol, 100% yield) as an off-white solid. $^1$H NMR (400 MHz, DMSO-$d_6$) δ 10.24 (s, 1H), 8.63 (dd, J=0.40, 2.40 Hz, 1H), 8.16 (t, J=8.00 Hz, 1H), 8.00 (dd, J=2.40, 6.20 Hz, 1H), 7.73 (dd, J=2.00, 11.00 Hz, 1H), 7.55 (d, J=8.40 Hz, 1H), 7.27 (dd, J=0.40, 8.40 Hz, 1H), 5.92-5.87 (m, 1H), 5.64-5.61 (m, 1H), 3.76-3.72 (m, 1H), 3.29-3.25 (m, 1H), 3.06 (t, J=11.20 Hz, 1H), 2.55-2.54 (m, 1H), 2.33-2.27 (m, 1H); 3 protons obscured by DMSO-$d_6$/$H_2O$ peaks. ES-LCMS m/z 501.0 [M+H]$^+$.

Step 7: rac-methyl (1R,2S,6R)-2-(5-bromopyridin-2-yl)-6-((2-fluoro-4-(trifluoromethyl)phenyl)carbamoyl)cyclohexane-1-carboxylate

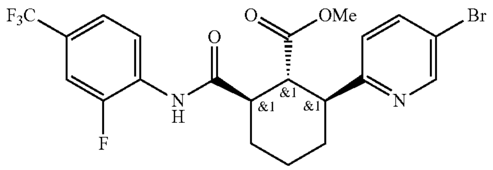 [SMILES: COC(=O)[C@@H]1[C@@H](c2ccc(Br)cn2)CCC[C@H]1C(=O)Nc1ccc(C(F)(F)F)cc1F]

To a mixture of rac-methyl (1R,2S,6R)-2-(5-bromopyridin-2-yl)-6-((2-fluoro-4-(trifluoromethyl)phenyl)carbamoyl)cyclohex-3-ene-1-carboxylate (2.50 g, 4.99 mmol) in DCM (100 mL) was added Crabtree's catalyst (0.80 g, 1.0 mmol). The reaction was stirred under an $H_2$ atmosphere (1 kg bladder pressure) for 16 h, concentrated and subjected to normal phase chromatography, eluting with 0-25% EtOAc in petroleum ether to afford rac-methyl(1R,2S,6R)-2-(5-bromopyridin-2-yl)-6-((2-fluoro-4-(trifluoromethyl)phenyl)carbamoyl)cyclohexane-1-carboxylate (1.7 g, 3.3 mmol, 66% yield) as an off-white solid. $^1$H NMR (400 MHz, DMSO-$d_6$) δ 10.13 (s, 1H), 8.62 (d, J=2.4 Hz, 1H), 8.16 (t, J=8.0 Hz, 1H), 7.96 (dd, J=8.4, 2.4 Hz, 1H), 7.72 (dd, J=11.0, 1.6 Hz, 1H), 7.55 (d, J=8.4 Hz, 1H), 7.28 (d, J=8.4 Hz, 1H), 3.21 (s, 3H), 3.06-3.01 (m, 2H), 2.95-2.88 (m, 1H), 2.05 (d, J=7.6 Hz, 1H), 1.90-1.85 (m, 2H), 1.71-1.63 (m, 1H), 1.56-1.48 (m, 2H). ES-LCMS m/z 503.0 [M+H]$^+$.

Step 8: rel-(1R,2S,6R)-2-(5-bromopyridin-2-yl)-6-((2-fluoro-4-(trifluoromethyl)phenyl)carbamoyl)cyclohexane-1-carboxylic acid, ISOMER 1 and ISOMER 2

ISOMER 1 and ISOMER 2

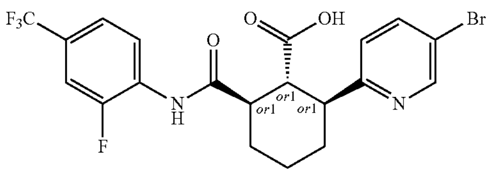

To a mixture of rac-methyl (1R,2S,6R)-2-(4-bromophenyl)-6-((2-fluoro-4-(trifluoromethyl)phenyl)carbamoyl)cyclohexane-1-carboxylate (0.500 g, 0.993 mmol) in acetonitrile (25 mL) was added TMS-I (2.70 mL, 19.87 mmol). The reaction was heated to 90° C. for 16 h, concentrated, diluted with EtOAc (100 mL), washed with 10% sodium thiosulfate solution (25 mL×3) and brine (50 mL), dried over anhydrous sodium sulfate, filtered, concentrated and subjected to reverse phase purification (0-100% MeCN in $H_2O$, with 0.1% formic acid modifier) to afford the racemic compound. This material (200 mg) was purified by ChiralPrep SFC (Column: [R,R] Whelk; Mobile Phase 80:20 $CO_2$: 0.5% Isopropylamine in IPA) to afford:

1$^{st}$ eluting isomer, which was dissolved in water (25 mL) and acidified using 1.5N HCl. The resulting solid was collected by filtration and dried under vacuum to give rel-(1R,2S,6R)-2-(5-bromopyridin-2-yl)-6-((2-fluoro-4-(trifluoromethyl)phenyl)carbamoyl)cyclohexane-1-carboxylic acid, ISOMER 1 (65 mg, 0.13 mmol, 13% yield) as an off-white solid. $^1$H NMR (400 MHz, DMSO-$d_6$) δ 11.83 (s, 1H), 10.11 (s, 1H), 8.61 (d, J=2.4 Hz, 1H), 8.22 (t, J=8.0 Hz, 1H), 7.95 (dd, J=2.4, 8.4 Hz, 1H), 7.71 (dd, J=10.8, 1.6 Hz, 1H), 7.55 (d, J=8.4 Hz, 1H), 7.29 (d, J=8.0 Hz, 1H), 3.03-2.86 (m, 3H), 2.02 (d, J=8.4 Hz, 1H), 1.89-1.82 (m, 2H), 1.65-1.55 (m, 1H), 1.49-1.47 (m, 2H). ES-LCMS m/z 489.0 [M+H]$^+$.

The 2$^{nd}$ eluting isomer was dissolved in water (25 mL) and acidified using 1.5N HCl. The resulting solid was collected by filtration and dried under vacuum to afford rel-(1R,2S,6R)-2-(5-bromopyridin-2-yl)-6-((2-fluoro-4-(trifluoromethyl)phenyl)carbamoyl)cyclohexane-1-carboxylic acid, IOSMER 2 (55 mg, 0.11 mmol, 11% yield) as an off-white solid. $^1$H NMR (400 MHz, DMSO-$d_6$) δ 11.81 (s, 1H), 10.09 (s, 1H), 8.61 (d, J=2.0 Hz, 1H), 8.22 (t, J=8.0 Hz, 1H), 7.95 (dd, J=8.2, 2.4 Hz, 1H), 7.71 (dd, J=11.0, 2.0 Hz, 1H), 7.55 (d, J=8.80 Hz, 1H), 7.30 (d, J=8.0 Hz, 1H), 3.03-2.86 (m, 3H), 2.03 (d, J=8.0 Hz, 1H), 1.89-1.82 (m, 2H), 1.79-1.62 (m, 1H), 1.52-1.45 (m, 2H). ES-LCMS m/z 489.0 [M+H]$^+$.

Step 9: rel-(1R,2R,6S)-2-((2-fluoro-4-(trifluoromethyl)phenyl)carbamoyl)-6-(5-(methylamino)pyridin-2-ylcyclohexane-1-carboxylic acid, ISOMER 1 and ISOMER 2

ISOMER 1 and ISOMER 2

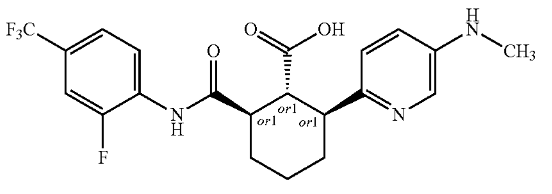

A mixture of rel-(1R,2S,6R)-2-(5-bromopyridin-2-yl)-6-((2-fluoro-4-(trifluoromethyl)phenyl)carbamoyl)cyclohexane-1-carboxylic acid ISOMER 1 (0.070 g, 0.14 mmol) and sodium tert-butoxide (27.5 mg, 0.290 mmol) in dioxane (2.0 mL) was purged with $N_2$ for 2 mins. tBuXPhos Pd G3 (22.7 mg, 0.0300 mmol) and methanamine (2M in THF, 1.43 mL, 2.86 mmol) were added, and the reaction was sealed and heated to 100° C. in a Biotage Initiator for 2 h. The mixture was filtered through a pad of Celite, washing with dioxane (25 mL), and the filtrate was concentrated and subjected to reverse phase purification (0-100% MeCN in $H_2O$, with 0.1% formic acid modifier) to afford rel-(1R,2R,6S)-2-((2-fluoro-4-(trifluoromethyl)phenyl)carbamoyl)-6-(5-(methylamino)pyridin-2-ylcyclohexane-1-carboxylic acid ISOMER 1 (35 mg, 0.080 mmol, 56% yield) as an off-white solid. $^1H$ NMR (400 MHz, DMSO-$d_6$) δ 10.06 (s, 1H), 8.23-8.17 (m, 2H), 7.84 (d, J=2.8 Hz, 1H), 7.70 (d, J=1.6 Hz, 1H), 7.55 (d, J=8.8 Hz, 1H), 6.94 (d, J=8.4 Hz, 1H), 6.78 (dd, J=8.4, 2.8 Hz, 1H), 5.67 (s, 1H), 2.98-2.95 (m, 1H), 2.88 (t, J=11.2 Hz, 1H), 2.74-2.70 (m, 1H), 2.67 (s, 3H), 1.98 (d, J=7.6 Hz, 2H), 1.86 (d, J=5.6 Hz, 2H), 1.74-1.62 (m, 2H), 1.59-1.50 (m, 2H). ES-LCMS m/z 440.2 $[M+H]^+$.

The above procedure was followed on rel-(1R,2S,6R)-2-(5-bromopyridin-2-yl)-6-((2-fluoro-4-(trifluoromethyl)phenyl)carbamoyl)cyclohexane-1-carboxylic acid ISOMER 2 to afford rel-(1R,2R,6S)-2-((2-fluoro-4-(trifluoromethyl) phenyl)carbamoyl)-6-(5-(methylamino)pyridin-2-ylcyclohexane-1-carboxylic acid ISOMER 2 (25 mg, 0.060 mmol, 42% yield) as an off-white solid. $^1H$ NMR (400 MHz, DMSO-$d_6$) δ 10.06 (s, 1H), 8.23-8.18 (m, 2H), 7.84 (d, J=2.8 Hz, 1H), 7.70 (d, J=1.2 Hz, 1H), 7.55 (d, J=8.4 Hz, 1H), 6.94 (d, J=8.4 Hz, 1H), 6.78 (dd, J=8.4, 2.8 Hz, 1H), 5.67 (s, 1H), 2.98-2.95 (m, 1H), 2.87 (t, J=11.2 Hz, 1H), 2.74-2.70 (m, 1H), 2.67 (s, 3H), 1.98 (d, J=8.0 Hz, 1H), 1.86 (d, J=6.0 Hz, 1H), 1.74-1.62 (m, 2H), 1.59-1.50 (m, 2H). ES-LCMS m/z 440.2 $[M+H]^+$.

Intermediate 19: rac-(1R,2S,6R)-2-(3-carbamoyl-4-((N,1,2-trimethyl-1H-benzo[d]imidazole)-5-sulfonamido)phenyl)-6-((2-fluoro-4-(trifluoromethyl)phenyl)carbamoyl)cyclohexane-1-carboxylic acid

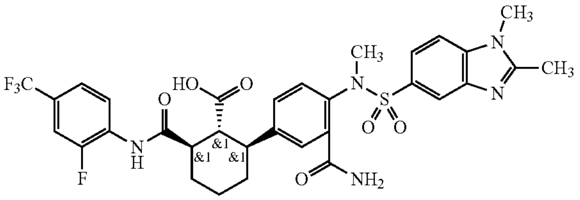 [SMILES: Cc1nc2cc(S(=O)(=O)N(C)c3ccc([C@H]4CCC[C@@H](C(=O)Nc5ccc(C(F)(F)F)cc5F)[C@@H]4C(=O)O)cc3C(N)=O)ccc2n1C]

Step 1: (E)-2-bromo-5-(3-oxoprop-1-en-1-yl)benzonitrile

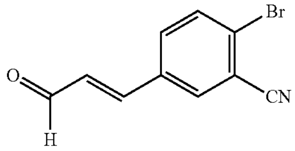 [SMILES: N#Cc1cc(/C=C/C=O)ccc1Br]

To a mixture of 2-bromo-5-formylbenzonitrile (9.50 g, 45.2 mmol) in DMSO (230 mL) was added 2-(triphenyl-$\lambda^5$-phosphaneylidene)acetaldehyde (15.14 g, 49.8 mmol), and the reaction was stirred at 120° C. After 16 h, the reaction was quenched with water (100 ml) and extracted with ethyl acetate (3×100 ml). The combined organic layers were washed with brine, dried over anhydrous sodium sulfate, filtered, concentrated and subjected to normal phase chromatography (0-10% EtOAc in petroleum ether) to give (E)-2-bromo-5-(3-oxoprop-1-en-1-yl)benzonitrile (4.5 g, 14 mmol, 32% yield). $^1H$ NMR (400 MHz, DMSO-$d_6$) δ 9.69 (d, J=7.5 Hz, 1H), 8.40 (s, 1H), 7.99 (s, 2H), 7.72 (d, J=16.0 Hz, 1H), 7.03 (dd, J=16.0, 7.5 Hz, 1H). ES-LCMS m/z did not ionize.

Step 2: (E)-2-bromo-5-(buta-1,3-dien-1-yl)benzonitrile

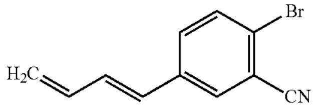

To a mixture of methyltriphenylphosphonium bromide (7.49 g, 21.0 mmol) in THF (45 mL) stirred at 0° C. was added potassium tert-butoxide (1M, 19.06 mL, 19.06 mmol), dropwise, over 5 min. After 10 min a solution of (E)-2-bromo-5-(3-oxoprop-1-en-1-yl)benzonitrile (4.50 g, 19.1 mmol) in THF (45 mL) was added, dropwise, over 5 min. The reaction was warmed to 25° C. for 2 h, quenched with sat. $NH_4Cl$ solution (100 ml) and extracted with ethyl acetate (3×100 ml). The combined organic layers were washed with brine, dried over anhydrous sodium sulfate, filtered, concentrated and subjected to normal phase chromatography (0-10% EtOAc in petroleum ether) to give (E)-2-bromo-5-(buta-1,3-dien-1-yl)benzonitrile (3.13 g, 9.27 mmol, 48.6% yield) as a pale-yellow liquid. $^1$H NMR (400 MHz, DMSO-$d_6$) δ 8.10 (d, J=2.0 Hz, 1H), 7.85-7.81 (m, 1H), 7.76-7.70 (m, 1H), 7.13 (dd, J=15.8, 10.8 Hz, 1H), 6.63 (d, J=16.0 Hz, 1H), 6.58-6.45 (m, 1H), 5.46 (dd, J=17.0, 1.0 Hz, 1H), 5.31 (dd, J=10.0, 1.5 Hz, 1H). ES-LCMS m/z did not ionize.

Step 3: rac-dimethyl (1R,2R,3R)-4'-bromo-3'-cyano-1,2,3,4-tetrahydro-[1,1'-biphenyl]-2,3-dicarboxylate with rac-dimethyl (1R,2R,3S)-4'-bromo-3'-cyano-1,2,3,4-tetrahydro-[1,1'-biphenyl]-2,3-dicarboxylate

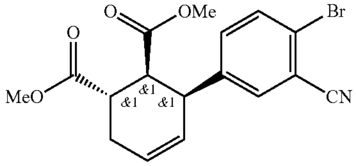

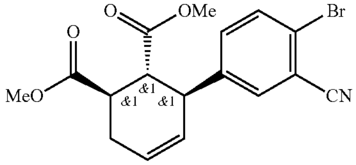

To a mixture of (E)-2-bromo-5-(buta-1,3-dien-1-yl)benzonitrile (3.10 g, 13.2 mmol) in o-xylene (30 mL) was added dimethyl fumarate (1.909 g, 13.24 mmol). The reaction was heated to 140° C. for 8 h, concentrated and subjected to normal phase chromatography, eluting with 30-50% EtOAc in petroleum ether, to afford rac-dimethyl (1R,2R,3R)-4'-bromo-3'-cyano-1,2,3,4-tetrahydro-[1,1'-biphenyl]-2,3-dicarboxylate with rac-dimethyl (1R,2R,3S)-4'-bromo-3'-cyano-1,2,3,4-tetrahydro-[1,1'-biphenyl]-2,3-dicarboxylate (3.10 g, 3.51 mmol, 26.5% yield) as a pale-yellow liquid. $^1$H NMR (400 MHz, DMSO-$d_6$) δ 7.80 (td, J=8.9, 2.8 Hz, 4H), 7.65 (d, J=2.0 Hz, 1H), 7.44 (dd, J=8.3, 2.3 Hz, 1H), 7.36 (dd, J=8.5, 2.0 Hz, 1H), 6.04-5.97 (m, 1H), 5.93-5.85 (m, 1H), 5.74-5.65 (m, 1H), 5.51 (dd, J=10.0, 2.0 Hz, 1H), 3.97 (t, J=5.8 Hz, 1H), 3.72-3.64 (m, 1H), 3.59 (s, 3H), 3.56 (s, 3H), 3.44 (s, 3H), 3.40 (s, 4H), 3.16 (dd, J=12.3, 6.3 Hz, 1H), 2.92 (dd, J=11.0, 5.5 Hz, 1H), 2.86-2.72 (m, 3H), 2.44-2.39 (m, 1H). ES-LCMS m/z did not ionize.

Step 4: rac-dimethyl (1R,2R,3R)-3-(4-bromo-3-cyanophenyl)cyclohexane-1,2-dicarboxylate with rac-dimethyl (1R,2R,3S)-3-(4-bromo-3-cyanophenyl)cyclohexane-1,2-dicarboxylate

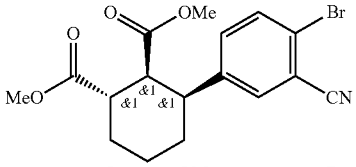

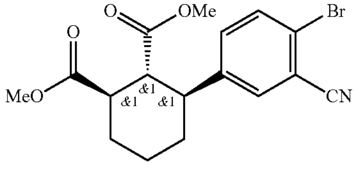

To a mixture of rac-dimethyl (1R,2R,3R)-4'-bromo-3'-cyano-1,2,3,4-tetrahydro-[1,1'-biphenyl]-2,3-dicarboxylate with rac-dimethyl (1R,2R,3S)-4'-bromo-3'-cyano-1,2,3,4-tetrahydro-[1,1'-biphenyl]-2,3-dicarboxylate (5.00 g, 6.61 mmol) in THF (50 mL) was added Pd/C (1.29 g, 0.330 mmol). The reaction was stirred under an $H_2$ atmosphere (2 atm bladder pressure) at 25° C. for 2 h, filtered through Celite and concentrated to afford rac-dimethyl (1R,2R,3R)-3-(4-bromo-3-cyanophenyl)cyclohexane-1,2-dicarboxylate with rac-dimethyl (1R,2R,3S)-3-(4-bromo-3-cyanophenyl)cyclohexane-1,2-dicarboxylate (5.10 g, 6.09 mmol, 92.0% yield) as a pale yellow liquid. $^1$H NMR (400 MHz, DMSO-$d_6$) δ 7.92 (d, J=2.0 Hz, 1H), 7.82-7.75 (m, 3H), 7.54-7.47 (m, 2H), 3.66 (s, 2H), 3.61-3.54 (m, 4H), 3.38 (s, 2H), 3.30-3.27 (m, 1H), 3.25 (s, 3H), 3.13-3.03 (m, 1H), 2.85 (d, J=11.0 Hz, 1H), 2.82-2.70 (m, 2H), 2.45 (br s, 1H), 2.04-2.00 (m, 1H), 1.96-1.88 (m, 1H), 1.85-1.76 (m, 2H), 1.74-1.59 (m, 4H), 1.56-1.42 (m, 3H). ES-LCMS m/z did not ionize.

Step 5: rac-(1R,2R,3R)-3-(4-bromo-3-cyanophenyl)-2-(methoxycarbonyl)cyclohexane-1-carboxylic acid with rac-(1R,2R,3S)-3-(4-bromo-3-cyanophenyl)-2-(methoxycarbonyl)cyclohexane-1-carboxylic acid

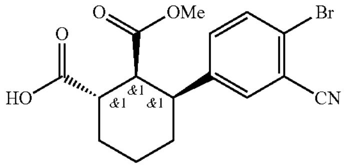

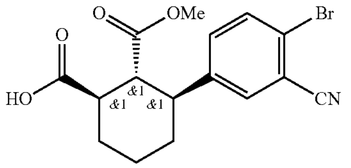

To a mixture of rac-dimethyl (1R,2R,3R)-3-(4-bromo-3-cyanophenyl)cyclohexane-1,2-dicarboxylate with rac-dimethyl (1R,2R,3S)-3-(4-bromo-3-cyanophenyl)cyclohexane-1,2-dicarboxylate (5.00 g, 6.57 mmol) in tetrahydrofuran (20 mL) and methanol (20 mL) was added lithiumhydroxide monohydrate (828 mg, 19.7 mmol) in water (10 mL). After 20 h the reaction was concentrated and subjected to reverse-phase purification, eluting with 80-100% MeCN in water (0.1% formic acid) to afford rac-(1R,2R,3R)-3-(4-bromo-3-cyanophenyl)-2-(methoxycarbonyl)cyclohexane-1-carboxylic acid with rac-(1R,2R,3S)-3-(4-bromo-3-cyanophenyl)-2-(methoxycarbonyl)cyclohexane-1-carboxylic acid (3.70 g, 2.26 mmol, 34.4% yield) as a colourless gum. $^1$H NMR (400 MHz, DMSO-$d_6$) δ 8.37 (s, 1H), 7.88 (d, J=2.5 Hz, 2H), 7.77 (d, J=8.5 Hz, 2H), 7.54-7.43 (m, 3H), 3.37 (s, 1H), 3.30 (d, J=5.0 Hz, 1H), 3.17 (s, 1H), 3.08-2.99 (m, 1H), 2.86-2.60 (m, 5H), 2.01-1.89 (m, 2H), 1.85-1.74 (m, 3H), 1.72-1.54 (m, 5H), 1.50-1.36 (m, 5H). ES-LCMS m/z 365.8 [M+H]$^+$.

Step 6: rac-methyl (1R,2S,3S)-4'-bromo-3'-cyano-3-((2-fluoro-4-(trifluoromethyl)phenyl)carbamoyl)-1,2,3,4-tetrahydro-[1,1'-biphenyl]-2-carboxylate

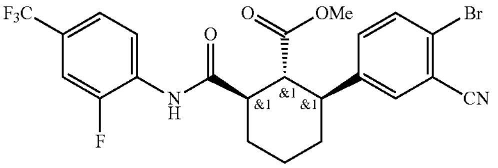 [SMILES: COC(=O)[C@@H]1[C@@H](c2ccc(Br)c(C#N)c2)CCC[C@H]1C(=O)Nc1ccc(C(F)(F)F)cc1F]

To a mixture of rac-(1R,2R,3R)-3-(4-bromo-3-cyanophenyl)-2-(methoxycarbonyl)cyclohexane-1-carboxylic acid with rac-(1R,2R,3S)-3-(4-bromo-3-cyanophenyl)-2-(methoxycarbonyl)cyclohexane-1-carboxylic acid (1.00 g, 1.37 mmol) in acetonitrile (10 mL) was added 2-fluoro-4-(trifluoromethyl)aniline (0.269 g, 1.50 mmol) and NMI (336 mg, 4.10 mmol). After 10 min N-(chloro(dimethylamino)methylene)-N-methylmethanaminium hexafluorophosphate (V) (498 mg, 1.78 mmol) was added, and the reaction was stirred at 25° C. After 16 h the reaction was concentrated and subjected to normal phase chromatography, eluting with 10% EtOAc in petroleum ether to afford rac-methyl (1R,2S,3S)-4'-bromo-3'-cyano-3-((2-fluoro-4-(trifluoromethyl)phenyl)carbamoyl)-1,2,3,4-tetrahydro-[1,1'-biphenyl]-2-carboxylate (0.670 g, 0.854 mmol, 62.5% yield) as a white solid. $^1H$ NMR (400 MHz, DMSO-$d_6$) δ 10.15 (s, 1H), 8.16-8.12 (m, 1H), 7.95 (d, J=2.0 Hz, 1H), 7.80 (d, J=8.5 Hz, 1H), 7.73 (d, J=2.5 Hz, 1H), 7.55 (td, J=5.8, 3.0 Hz, 2H), 3.19 (s, 3H), 3.08-3.00 (m, 2H), 2.79 (td, J=11.1, 4.3 Hz, 1H), 2.05 (d, J=10.5 Hz, 1H), 1.92-1.86 (m, 1H), 1.73 (d, J=9.0 Hz, 1H), 1.58-1.41 (m, 3H). ES-LCMS m/z 525.0 $[M+H]^+$.

Step 7: rac-(1R,2S,6R)-2-(4-bromo-3-cyanophenyl)-6-((2-fluoro-4-(trifluoromethyl)phenyl)carbamoyl)cyclohexane-1-carboxylic acid

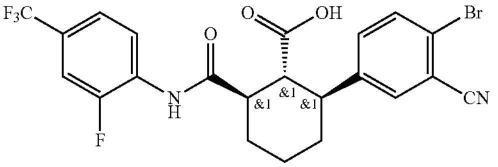 [SMILES: N#Cc1cc([C@H]2CCC[C@@H](C(=O)Nc3ccc(C(F)(F)F)cc3F)[C@@H]2C(=O)O)ccc1Br]

To a mixture of rac-methyl (1R,2S,3S)-4'-bromo-3'-cyano-3-((2-fluoro-4-(trifluoromethyl)phenyl)carbamoyl)-1,2,3,4-tetrahydro-[1,1'-biphenyl]-2-carboxylate (0.480 g, 0.910 mmol) in acetonitrile (2.5 mL) was added TMS-1 (1.28 mL, 9.10 mmol). The reaction was heated to 70° C. for 16 h, concentrated, diluted with THF (10 mL) and subjected to reverse phase purification (90-100% MeCN in $H_2O$, with 0.1% formic acid modifier) to afford rac-(1R,2S,6R)-2-(4-bromo-3-cyanophenyl)-6-((2-fluoro-4-(trifluoromethyl)phenyl)carbamoyl)cyclohexane-1-carboxylic acid (408 mg, 0.793 mmol, 87.0% yield) as an off-white solid. $^1H$ NMR (400 MHz, DMSO-$d_6$) δ 11.89 (s, 1H), 10.12 (s, 1H), 8.20 (t, J=8.0 Hz, 1H), 7.94 (d, J=2.0 Hz, 1H), 7.80 (d, J=8.5 Hz, 1H), 7.71 (dd, J=11.0, 1.5 Hz, 1H), 7.58 (dd, J=8.5, 2.0 Hz, 1H), 7.55 (d, J=8.5 Hz, 1H), 3.05-2.95 (m, 1H), 2.91-2.83 (m, 1H), 2.83-2.73 (m, 1H), 2.06-2.00 (m, 1H), 1.92-1.82 (m, 1H), 1.78-1.71 (m, 1H), 1.66 (d, J=12.0 Hz, 1H), 1.59-1.44 (m, 2H). ES-LCMS m/z 512.8 $[M+H]^+$.

Step 8: rel-(1R,2S,6R)-2-(3-carbamoyl-4-(methylamino)phenyl)-6-((2-fluoro-4-(trifluoromethyl)phenyl)carbamoyl)cyclohexane-1-carboxylic acid

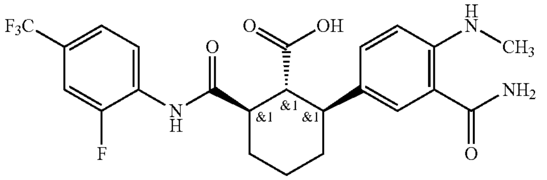 [SMILES: CNc1ccc([C@H]2CCC[C@@H](C(=O)Nc3ccc(C(F)(F)F)cc3F)[C@@H]2C(=O)O)cc1C(N)=O]

To a mixture of rac-(1R,2S,6R)-2-(4-bromo-3-cyanophenyl)-6-((2-fluoro-4-(trifluoromethyl)phenyl)carbamoyl)cyclohexane-1-carboxylic acid (0.200 g, 0.390 mmol) and sodium tert-butoxide (94 mg, 0.97 mmol) in dioxane (2.0 mL) was added tBuXPhos Pd G3 (22.7 mg, 0.0300 mmol). The reaction was degassed for 5 min, and methanamine (3.90 mL, 7.79 mmol) was added. The mixture was heated in a Biotage Initiator to 100° C. for 1 h, dissolved in THF (3 mL) and subjected to reverse phase purification (20-55% MeCN in $H_2O$, with 0.1% formic acid modifier) to afford rel-(1R,2S,6R)-2-(3-carbamoyl-4-(methylamino)phenyl)-6-((2-fluoro-4-(trifluoromethyl)phenyl)carbamoyl)cyclohexane-1-carboxylic acid (0.170 g, 0.224 mmol, 57.4% yield) as an off-white solid. $^1H$ NMR (400 MHz, DMSO-$d_6$) δ 8.37 (t, J=8.3 Hz, 1H), 7.75 (d, J=5.0 Hz, 1H), 7.64 (br d, J=11.5 Hz, 1H), 7.49 (s, 2H), 6.45 (d, J=8.5 Hz, 1H), 2.79-2.66 (m, 4H), 2.65-2.55 (m, 1H), 2.44-2.35 (m, 1H), 1.97-1.61 (m, 3H), 1.53-1.36 (m, 3H). Five protons obscured. ES-LCMS m/z 480.0 $[M+H]^+$.

Step 9: rac-(1R,2S,6R)-2-(3-carbamoyl-4-((N,1,2-trimethyl-1H-benzo[d]imidazole)-5-sulfonamido)phenyl)-6-((2-fluoro-4-(trifluoromethyl)phenyl)carbamoyl)cyclohexane-1-carboxylic acid

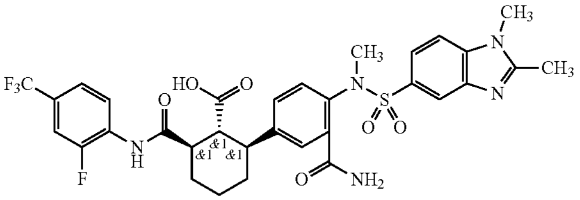 [SMILES: Cc1nc2cc(S(=O)(=O)N(C)c3ccc([C@H]4CCC[C@@H](C(=O)Nc5ccc(C(F)(F)F)cc5F)[C@@H]4C(=O)O)cc3C(N)=O)ccc2n1C]

To a mixture of rel-(1R,2S,6R)-2-(3-carbamoyl-4-(methylamino)phenyl)-6-((2-fluoro-4-(trifluoromethyl)phenyl)carbamoyl)cyclohexane-1-carboxylic acid (0.150 g, 0.312 mmol) and pyridine (0.076 mL, 0.94 mmol) in dichloromethane (3.5 mL) at 0° C. was added 1,2-dimethyl-1H-benzo[d]imidazole-5-sulfonyl chloride (137 mg, 0.561 mmol). The reaction was stirred at rt for 1 h, concentrated and subjected to reverse phase purification (50-75% MeCN in $H_2O$, with 0.1% formic acid modifier) to afford rac-(1R,2S,6R)-2-(3-carbamoyl-4-((N,1,2-trimethyl-1H-benzo[d]imidazole)-5-sulfonamido)phenyl)-6-((2-fluoro-4-(trifluoromethyl)phenyl)carbamoyl)cyclohexane-1-carboxylic acid (0.100 g, 0.132 mmol, 42.4% yield) as an off-white solid. $^1H$ NMR (400 MHz, DMSO-$d_6$) δ 11.99 (s, 1H), 10.11 (s, 1H), 8.22 (t, J=8.00 Hz, 1H), 7.73-7.69 (m, 3H), 7.57-7.40 (m, 5H), 7.21 (dd, J=8.00, 2.00 Hz, 1H), 6.54 (d, J=8.40 Hz, 1H), 3.82 (s, 3H), 3.10 (s, 3H), 3.01-2.85 (m, 1H), 2.82-2.74 (m, 2H), 2.59 (s, 3H), 2.01-1.79 (m, 3H), 1.77-1.52 (m, 3H). ES-LCMS m/z 687.8 $[M+H]^+$.

Intermediate 20: (1R,2S,6R)-2-(3-bromo-4-(methylamino)phenyl)-6-((2-fluoro-4-(trifluoromethyl)phenyl)carbamoyl)cyclohexane-1-carboxylic acid

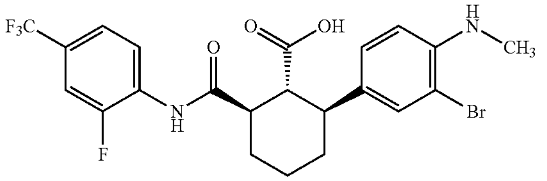 [SMILES: CNc1ccc([C@H]2CCC[C@@H](C(=O)Nc3ccc(C(F)(F)F)cc3F)[C@@H]2C(=O)O)cc1Br]

To a mixture of (1R,2R,6S)-2-((2-fluoro-4-(trifluoromethyl)phenyl)carbamoyl)-6-(4-(methylamino)phenyl)cyclohexane-1-carboxylic acid Intermediate 7, alternate route, Step 3 (0.350 g, 0.798 mmol) in acetonitrile (21 mL) at 0° C. was added N-bromosuccinimide (128 mg, 0.718 mmol) dissolved in acetonitrile (5 mL). After 2 h, the reaction was filtered, concentrated and subjected to reverse phase purification (0-100% MeCN in $H_2O$, with 0.1% formic acid modifier) to afford (1R,2S,6R)-2-(3-bromo-4-(methylamino)phenyl)-6-((2-fluoro-4-(trifluoromethyl)phenyl)carbamoyl)cyclohexane-1-carboxylic acid (0.120 g, 0.222 mmol, 27.8% yield) as a white solid. $^1H$ NMR (400 MHz, DMSO-$d_6$) δ 11.73 (br s, 1H), 10.07 (s, 1H), 8.20 (t, J=8.3 Hz, 1H), 7.71 (dd, J=10.8, 1.8 Hz, 1H), 7.54 (d, J=8.5 Hz, 1H), 7.27 (d, J=2.0 Hz, 1H), 7.07 (dd, J=8.5, 2.0 Hz, 1H), 6.52 (d, J=8.5 Hz, 1H), 5.14 (q, J=4.8 Hz, 1H), 3.17 (d, J=5.0 Hz, 1H), 3.03-2.91 (m, 1H), 2.77-2.70 (m, 3H), 2.60-2.53 (m, 1H), 1.97 (d, J=8.5 Hz, 1H), 1.90-1.80 (m, 1H), 1.76-1.65 (m, 1H), 1.59-1.40 (m, 3H). ES-LCMS m/z 516.8 $[M-H]^+$.

The following compound was synthesized in an analogous manner to the preparation described below (Example 83, second preparation method), using the relevant alkylamine precursor and omitting the debenzylation step:

Intermediate 22: rac-benzyl (1R,2R,6S)-2-(((4-isopropylphenyl)amino)methyl)-6-(4-((N,1,2-trimethyl-1H-benzo[d]imidazole)-5-sulfonamido)phenyl)cyclohexane-1-carboxylate

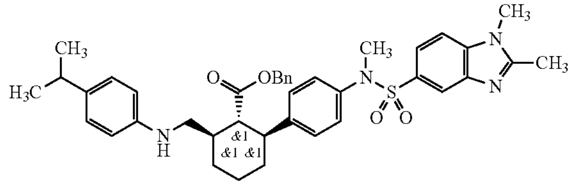 [SMILES: Cc1nc2cc(S(=O)(=O)N(C)c3ccc([C@H]4CCC[C@@H](CNc5ccc(C(C)C)cc5)[C@@H]4C(=O)OCc4ccccc4)cc3)ccc2n1C]

Step 1: rac-benzyl (1R,2S,6R)-2-(4-bromophenyl)-6-formylcyclohexane-1-carboxylate

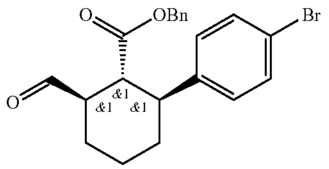 [SMILES: O=C[C@@H]1CCC[C@H](c2ccc(Br)cc2)[C@H]1C(=O)OCc1ccccc1]

To a mixture of rac-benzyl (1R,2S,6R)-2-(4-bromophenyl)-6-(hydroxymethyl)cyclohexane-1-carboxylate Intermediate 1 Step 4 (1.251 g, 3.102 mmol) in dichloromethane (15 ml) at 0° C. was added Dess-Martin Periodinane (1.973 g, 4.653 mmol), slowly. After 2 h the reaction was warmed to rt. After 4 h, the reaction was quenched with sat. aq. $NaHCO_3$ and extracted with dichloromethane (3×10 ml). The combined organic layers were dried over anhydrous $Na_2SO_4$, concentrated and purified via silica gel column chromatography, eluting with 0-10% EtOAc in hexanes to afforded rac-benzyl (1R,2S,6R)-2-(4-bromophenyl)-6-formylcyclohexane-1-carboxylate (0.92 g, 2.3 mmol, 75%) as a white solid. $^1H$ NMR (400 MHz, DMSO-$d_6$) δ (400 MHz, $CDCl_3$) δ 9.71-9.56 (m, 1H), 7.40-7.30 (m, 3H), 7.03 (dq, J=9.1, 2.6 Hz, 2H), 6.97-6.80 (m, 2H), 4.93-4.82 (m, 1H), 4.82-4.72 (m, 1H), 2.99-2.62 (m, 4H), 2.32-2.16 (m, 1H), 2.16-1.99 (m, 2H), 1.99-1.83 (m, 2H), 1.70-1.40 (m, 5H), 1.40-1.18 (m, 2H).

| Int. | Structure/Name | $^1H$ NMR | LCMS |
|---|---|---|---|
| 21 | 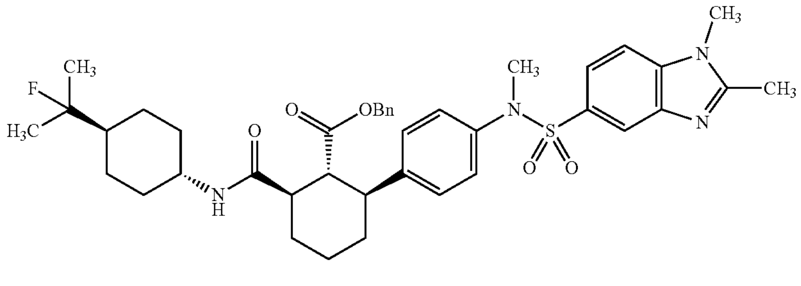 benzyl (1R,2R,6S)-2-(((1r,4R)-4-(2-fluoropropan-2-yl)cyclohexyl)carbamoyl)-6-(4-((N,1,2-trimethyl-1H-benzo[d]imidazole)-5-sulfonamido)phenyl)cyclohexane-1-carboxylate | $^1H$ NMR (400 MHz, DMSO-$d_6$) δ 7.70 (d, J = 8.0 Hz, 1H), 7.60-7.55 (m, 2H), 7.27 (dd, J = 8.5, 1.5 Hz, 1H), 7.25-7.21 (m, 3H), 7.15 (d, J = 8.5 Hz, 2H), 7.02-6.94 (m, 4H), 4.78 (d, J = 12.5 Hz, 1H), 4.57 (d, J = 13.0 Hz, 1H), 3.72 (s, 3H), 3.44-3.35 (m, 2H), 3.06 (s, 3H), 2.86-2.78 (m, 1H), 2.71-2.63 (m, 2H), 2.46-2.39 (m, 2H), 1.88-1.36 (m, 15H), 1.14-0.95 (m, 6H) | ES-LCMS m/z 717.2 [M + H]+. |

Step 2: rac-benzyl (1R,2S,6R)-2-(4-bromophenyl)-6-(((4-isopropylphenyl)amino)methyl)cyclohexane-1-carboxylate

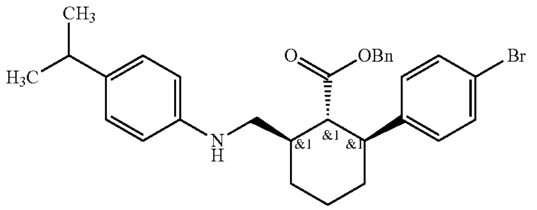 [SMILES: CC(C)c1ccc(NC[C@@H]2CCC[C@H](c3ccc(Br)cc3)[C@H]2C(=O)OCc2ccccc2)cc1]

To a mixture of 4-isopropylaniline (0.342 g, 2.53 mmol) in 1,2-dichloroethane (12 ml) was added rac-benzyl (1R,2S,6R)-2-(4-bromophenyl)-6-formylcyclohexane-1-carboxylate (0.922 g, 2.29 mmol) and glacial acetic acid (0.152 g, 2.53 mmol). After 15 min, sodium triacetoxyborohydride (0.730 g, 3.45 mmol) was added. After 1 h, the reaction was poured into dichloromethane (25 ml), and washed with saturated aqueous $NaHCO_3$ solution (25 ml) and brine (25 ml). The organic layer was dried over anhydrous $MgSO_4$, concentrated and purified via silica gel column chromatography (gradient eluent: 10-50% of EtOAc in hexanes) to give rac-benzyl (1R,2S,6R)-2-(4-bromophenyl)-6-(((4-isopropylphenyl)amino)methyl)cyclohexane-1-carboxylate as a light yellow solid. $^1H$ NMR (400 MHz, DMSO-$d_6$) δ 7.51-7.38 (m, 2H), 7.31-7.09 (m, 5H), 6.96-6.81 (m, 4H), 6.48-6.37 (m, 2H), 5.41 (t, J=5.9 Hz, 1H), 4.86 (d, J=12.5 Hz, 1H), 4.72 (d, J=12.5 Hz, 1H), 3.01-2.85 (m, 1H), 2.85-2.63 (m, 3H), 1.98 (d, J=11.7 Hz, 2H), 1.87-1.66 (m, 2H), 1.62-1.29 (m, 2H), 1.13 (d, J=6.9 Hz, 7H).

Step 3: rac-benzyl (1R,2R,6S)-2-(((4-isopropylphenyl)amino)methyl)-6-(4-(methylamino)phenyl)cyclohexane-1-carboxylate

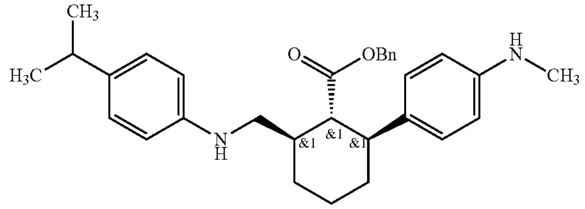 [SMILES: CNc1ccc([C@H]2CCC[C@@H](CNc3ccc(C(C)C)cc3)[C@@H]2C(=O)OCc2ccccc2)cc1]

A mixture of rac-benzyl (1R,2S,6R)-2-(4-bromophenyl)-6-(((4-isopropylphenyl)amino)methyl)cyclohexane-1-carboxylate (63 mg, 0.12 mmol), DMF (1 ml), $Cs_2CO_3$ (79 mg, 0.24 mmol), tBuXPhos Pd G3 (9.6 mg, 0.012 mmol), methylamine (2M in THF, 0.24 ml, 0.48 mmol) was stirred at 80° C. After 18 h, the reaction was diluted with water and extracted with EtOAc (3×10 ml). The organic layers were dried over anhydrous $MgSO_4$, concentrated and purified via silica gel column chromatography (gradient eluent: 10-100% EtOAc in hexanes) to give rac-benzyl (1R,2R,6S)-2-(((4-isopropylphenyl)amino)methyl)-6-(4-(methylamino)phenyl)cyclohexane-1-carboxylate (36 mg, 0.076 mmol, 63%) as an off-white solid. ES-LCMS m/z 471.3 $[M+H]^+$.

Step 4: rac-benzyl (1R,2R,6S)-2-(((4-isopropylphenyl)amino)methyl)-6-(4-((N,1,2-trimethyl-1H-benzo[d]imidazole)-5-sulfonamido)phenyl)cyclohexane-1-carboxylate

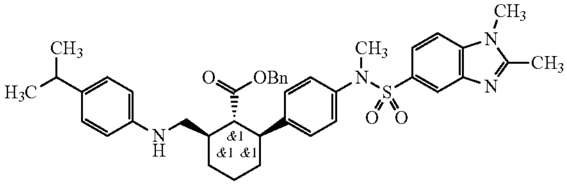 [SMILES: Cc1nc2cc(S(=O)(=O)N(C)c3ccc([C@H]4CCC[C@@H](CNc5ccc(C(C)C)cc5)[C@@H]4C(=O)OCc4ccccc4)cc3)ccc2n1C]

To a mixture of rac-benzyl (1R,2R,6S)-2-(((4-isopropylphenyl)amino)methyl)-6-(4-(methylamino)phenyl)cyclohexane-1-carboxylate (36 mg, 0.076 mmol) and pyridine (0.5 ml) in dichloromethane (0.2 ml) at 0° C. was added 1,2-dimethyl-1H-benzo[d]imidazole-5-sulfonyl chloride (22.5 mg, 0.0920 mmol), and resulting solution was stirred for 2 h at rt. The reaction was concentrated and purified via silica gel column chromatography (gradient eluent: 0-5% MeOH in DCM) to give rac-benzyl (1R,2R,6S)-2-(((4-isopropylphenyl)amino)methyl)-6-(4-((N,1,2-trimethyl-1H-benzo[d]imidazole)-5-sulfonamido)phenyl)cyclohexane-1-carboxylate (29 mg, 0.043 mmol, 56%) as an off-white solid. ES-LCMS m/z 679.3 $[M+H]^+$.

Intermediate 23: benzyl (1R,2R,6S)-2-((4-(trifluoromethyl)phenoxy)methyl)-6-(4-((N,1,2-trimethyl-1H-benzo[d]imidazole)-5-sulfonamido)phenyl)cyclohexane-1-carboxylate

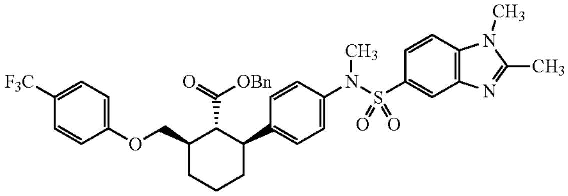 [SMILES: Cc1nc2cc(S(=O)(=O)N(C)c3ccc([C@H]4CCC[C@@H](COc5ccc(C(F)(F)F)cc5)[C@@H]4C(=O)OCc4ccccc4)cc3)ccc2n1C]

Step 1: benzyl (1R,2S,6R)-2-(4-bromophenyl)-6-(hydroxymethyl)cyclohexane-1-carboxylate

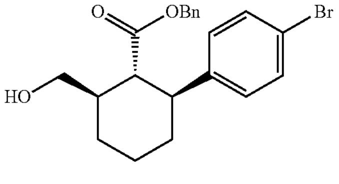 [SMILES: O=C(OCc1ccccc1)[C@H]1[C@H](CO)CCC[C@@H]1c1ccc(Br)cc1]

rac-Benzyl (1R,2S,6R)-2-(4-bromophenyl)-6-(hydroxymethyl)cyclohexane-1-carboxylate Intermediate 1 Step 7 (20.2 g, 50.1 mmol) was purified by chiral chromatography (Column: Chiralpak IA; Mobile Phase 4:4:2 heptane:MTBE:MeCN) to afford the first-eluting isomer benzyl (1R,2S,6R)-2-(4-bromophenyl)-6-(hydroxymethyl)cyclohexane-1-carboxylate (8.2 g, 0.020 mol, 41% yield). $^1H$ NMR (400 MHz, DMSO-$d_6$) δ 7.46-7.39 (m, 2H), 7.29-7.22

(m, 3H), 7.19-7.12 (m, 2H), 6.91-6.85 (m, 2H), 4.93-4.63 (m, 2H), 4.54 (t, J=5.1 Hz, 1H), 3.31-3.27 (m, 1H), 3.25-3.17 (m, 1H), 2.72 (td, J=11.5, 3.4 Hz, 1H), 2.44 (t, J=11.0 Hz, 1H), 1.92-1.68 (m, 4H), 1.56-1.35 (m, 2H), 1.23-1.06 (m, 1H). ES-LCMS m/z 403.1 $[M+1]^+$.

Step 2: benzyl (1R,2S,6R)-2-(4-bromophenyl)-6-((4-(trifluoromethyl)phenoxy)methyl)cyclohexane-1-carboxylate

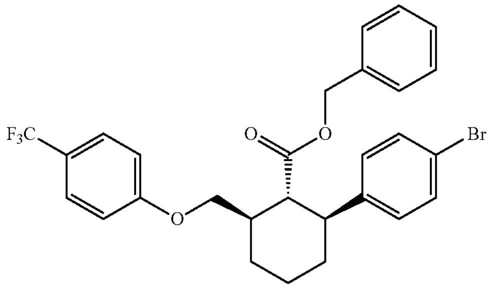 [SMILES: O=C(OCc1ccccc1)[C@H]1[C@H](COc2ccc(C(F)(F)F)cc2)CCC[C@@H]1c1ccc(Br)cc1]

To a mixture of benzyl (1R,2S,6R)-2-(4-bromophenyl)-6-(hydroxymethyl)cyclohexane-1-carboxylate (8.2000 g, 20.331 mmol), 4-(trifluoromethyl)phenol (9.8877 g, 60.994 mmol) and triphenylphosphine (10.665 g, 40.663 mmol) in THF (200 mL) at 0° C. was added DIAD (8.222 g, 7.906 mL, 40.66 mmol), and the reaction was warmed to rt. After stirring over the weekend, the mixture was concentrated and purified by ISCO silica gel column chromatography, eluting with 40-100% EtOAc in heptanes, to provide benzyl (1R,2S,6R)-2-(4-bromophenyl)-6-((4-(trifluoromethyl)phenoxy)methyl)cyclohexane-1-carboxylate (7.60 g, 13.9 mol, 68.3% yield) as a white solid. $^1$H NMR (400 MHz, DMSO-$d_6$) δ 7.62 (d, J=8.3 Hz, 2H), 7.48-7.40 (m, 2H), 7.26-7.14 (m, 5H), 7.03 (d, J=8.3 Hz, 2H), 6.87-6.78 (m, 2H), 4.93-4.63 (m, 2H), 4.04-3.84 (m, 2H), 2.79 (td, J=11.4, 3.2 Hz, 1H), 2.70-2.61 (m, 1H), 2.26-2.10 (m, 1H), 1.98-1.88 (m, 1H), 1.88-1.80 (m, 1H), 1.79-1.70 (m, 1H), 1.61-1.44 (m, 2H), 1.41-1.26 (m, 1H). ES-LCMS m/z 547.1 $[M+1]^+$.

Step 3: benzyl (1R,2S,6R)-2-(4-(methylamino)phenyl)-6-((4-(trifluoromethyl)phenoxy)methyl)cyclohexane-1-carboxylate

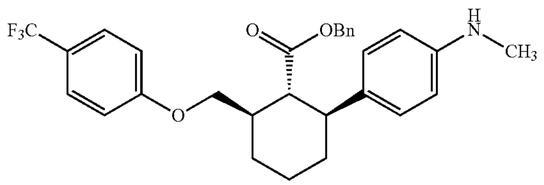 [SMILES: CNc1ccc([C@H]2CCC[C@@H](COc3ccc(C(F)(F)F)cc3)[C@@H]2C(=O)OCc2ccccc2)cc1]

A mixture of benzyl (1R,2S,6R)-2-(4-bromophenyl)-6-((2-fluoro-4-(trifluoromethyl)phenyl)carbamoyl)cyclohexane-1-carboxylate (7.60 g, 13.9 mmol) in DMF (140 ml) was degassed with nitrogen, then treated with $Cs_2CO_3$ (13.00 g, 39.90 mmol), methylamine (2M in THF, 140 ml, 280.0 mmol) and tBuXPhos Pd G3 (2.36 g, 2.76 mmol). The reaction was stirred at 60° C. for 2 h, filtered, diluted with water and extracted with EtOAc (3 x). The organic layers were washed with brine, dried over anhydrous $MgSO_4$, concentrated and purified via silica gel column chromatography, eluting with 50-100% EtOAc in heptanes, to give benzyl (1R,2S,6R)-2-(4-(methylamino)phenyl)-6-((4-(trifluoromethyl)phenoxy)methyl)cyclohexane-1-carboxylate (6.07 g, 0.0122 mol, 87.8% yield) as an off-white solid. $^1$H NMR (400 MHz, DMSO-$d_6$) δ 7.62 (d, J=8.8 Hz, 2H), 7.24-7.13 (m, 3H), 7.02 (d, J=8.8 Hz, 2H), 6.93 (d, J=8.3 Hz, 2H), 6.87-6.81 (m, 2H), 6.44 (d, J=8.8 Hz, 2H), 5.48 (q, J=4.9 Hz, 1H), 4.91-4.66 (m, 2H), 3.96-3.84 (m, 2H), 2.66 (d, J=4.9 Hz, 3H), 2.61 (br dd, J=11.2, 3.4 Hz, 1H), 2.55 (d, J=10.8 Hz, 1H), 2.21-2.08 (m, 1H), 1.95-1.86 (m, 1H), 1.86-1.79 (m, 1H), 1.72 (br d, J=8.3 Hz, 1H), 1.56-1.42 (m, 2H), 1.39-1.20 (m, 1H). ES-LCMS m/z 498.2 $[M+1]^+$.

Step 4: benzyl (1R,2R,6S)-2-((4-(trifluoromethyl)phenoxy)methyl)-6-(4-((N,1,2-trimethyl-1H-benzo[d]imidazole)-5-sulfonamido)phenyl)cyclohexane-1-carboxylate

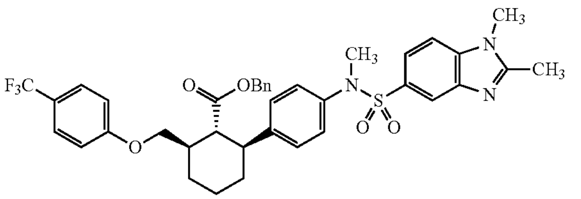 [SMILES: Cc1nc2cc(S(=O)(=O)N(C)c3ccc([C@H]4CCC[C@@H](COc5ccc(C(F)(F)F)cc5)[C@@H]4C(=O)OCc4ccccc4)cc3)ccc2n1C]

To a mixture of benzyl (1R,2S,6R)-2-(4-(methylamino)phenyl)-6-((4-(trifluoromethyl)phenoxy)methyl)cyclohexane-1-carboxylate (1.50 g, 3.01 mmol) and pyridine (0.5 ml) in DMF (30 ml) was added 1,2-dimethyl-1H-benzo[d]imidazole-5-sulfonyl chloride (1.020 g, 4.169 mmol), and the reaction was stirred for 4 h at 23° C. The reaction was diluted with water and extracted with EtOAc (3 x). The organic layers were washed with brine, dried over anhydrous $MgSO_4$, concentrated and purified via silica gel column chromatography, eluting with 0-100% EtOAc in heptanes followed by 20% MeOH in DCM, to give benzyl (1R,2R,6S)-2-((4-(trifluoromethyl)phenoxy)methyl)-6-(4-((N,1,2-trimethyl-1H-benzo[d]imidazole)-5-sulfonamido)phenyl)cyclohexane-1-carboxylate (1.100 g, 1.559 mmol, 51.78%) as an off-white solid. $^1$H NMR (400 MHz, DMSO-$d_6$) δ 7.71-7.47 (m, 4H), 7.32-7.26 (m, 1H), 7.25-7.11 (m, 5H), 7.03-6.90 (m, 6H), 4.89-4.57 (m, 2H), 3.90 (br dd, J=5.1, 3.2 Hz, 2H), 3.73 (s, 3H), 3.08 (s, 3H), 2.83-2.74 (m, 1H), 2.67-2.58 (m, 1H), 2.24-2.09 (m, 1H), 1.97-1.68 (m, 3H), 1.60-1.44 (m, 2H), 1.41-1.26 (m, 1H). One of the methyl peaks is hidden under solvent. ES-LCMS m/z 706.1 $[M+H]^+$.

Intermediate 24: benzyl (1R,2R,6S)-2-((2-(benzyloxy)-4-(trifluoromethyl)phenoxy)methyl)-6-(4-((N,1,2-trimethyl-1H-benzo[d]imidazole)-5-sulfonamido)phenyl)cyclohexane-1-carboxylate

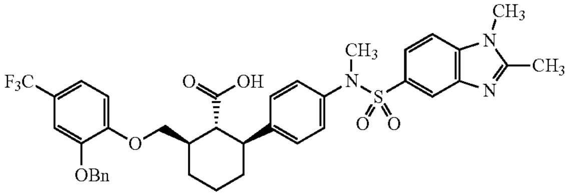 [SMILES: Cc1nc2cc(S(=O)(=O)N(C)c3ccc([C@H]4CCC[C@@H](COc5ccc(C(F)(F)F)cc5OCc5ccccc5)[C@@H]4C(=O)O)cc3)ccc2n1C]

Step 1: benzyl (1R,2S,6R)-2-(4-bromophenyl)-6-(((tert-butyldimethylsilyl)oxy)methyl)cyclohexane-1-carboxylate

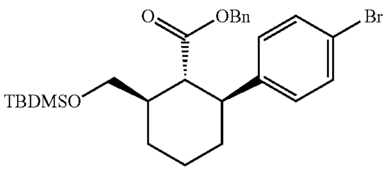 [SMILES: CC(C)(C)[Si](C)(C)OC[C@@H]1CCC[C@H](c2ccc(Br)cc2)[C@H]1C(=O)OCc1ccccc1]

To a mixture of benzyl (1R,2S,6R)-2-(4-bromophenyl)-6-(hydroxymethyl)cyclohexane-1-carboxylate Intermediate 23 Step 1 (3.60 g, 8.93 mmol) in DCM (50 ml) at 0° C. were added DMAP (0.327 g, 2.68 mmol), triethylamine (1.493 mL, 10.71 mmol) and tert-butyldimethylsilyl chloride (2.83 g, 18.7 mmol). After 16 h at 25° C. the reaction was diluted with sat. sodiumbicarbonate (30 ml) and extracted with DCM (3×30 ml). The combined organic layers were washed with water (30 ml) and brine (30 ml), dried over anhydrous sodium sulfate, filtered, concentrated and purified by silica gel column chromatography, eluting with 0-20% EtOAc in petroleum ether, to afford benzyl (1R,2S,6R)-2-(4-bromophenyl)-6-(((tert-butyldimethylsilyl)oxy)methyl)cyclohexane-1-carboxylate (4.0 g, 7.2 mmol, 81% yield). $^1$H NMR (400 MHz, DMSO-$d_6$) 7.42 (d, J=8.5 Hz, 2H), 7.29-7.22 (m, 3H), 7.13 (d, J=8.5 Hz, 2H), 6.89 (dd, J=7.5, 2.0 Hz, 2H), 4.85-4.80 (m, 1H), 4.75-4.68 (m, 1H), 3.46-3.35 (m, 2H), 2.77-2.65 (m, 1H), 2.47-2.41 (m, 1H), 1.89-1.68 (m, 4H), 1.53-1.39 (m, 2H), 1.24-1.11 (m, 1H), 0.84 (s, 8H), 0.87-0.80 (m, 1H), −0.03 (d, J=2.5 Hz, 6H). ES-LCMS m/z 518.8 [M+1]$^+$.

Step 2: benzyl (1R,2S,6R)-2-(((tert-butyldimethylsilyl)oxy)methyl)-6-(4-(methylamino)phenyl)cyclohexane-1-carboxylate

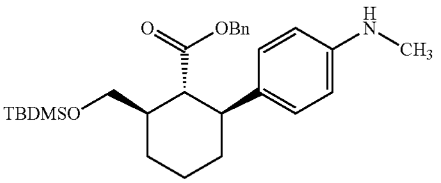 [SMILES: CNc1ccc([C@H]2CCC[C@@H](CO[Si](C)(C)C(C)(C)C)[C@@H]2C(=O)OCc2ccccc2)cc1]

A mixture of benzyl (1R,2S,6R)-2-(4-bromophenyl)-6-(((tert-butyldimethylsilyl)oxy)methyl)cyclohexane-1-carboxylate (4.0 g, 7.7 mmol) and $Cs_2CO_3$ (7.55 g, 23.2 mmol) in DMF (80 ml) was degassed with nitrogen for ten minutes, treated with tBuXPhos Pd G3 (0.200 g, 0.541 mmol), degassed with nitrogen for five minutes, then treated with methylamine (2M in THF, 77.0 ml, 155 mmol). The reaction was stirred at 60° C. for 16 h, diluted with water (100 mL) and extracted with EtOAc (4×50 mL). The organic layers were washed with water (2×50 mL) and brine, dried over sodium sulphate, concentrated and purified via silica gel column chromatography, eluting with 0-20% EtOAc in petroleum ether, to give benzyl (1R,2S,6R)-2-(((tert-butyldimethylsilyl)oxy)methyl)-6-(4-(methylamino)phenyl)cyclohexane-1-carboxylate (3.1 g, 5.4 mmol, 70% yield) as a yellow oil. $^1$H NMR (400 MHz, DMSO-$d_6$) δ 7.28-7.16 (m, 3H), 6.94-6.82 (m, 4H), 6.43 (d, J=8.5 Hz, 2H), 5.46 (d, J=5.5 Hz, 1H), 4.87-4.77 (m, 1H), 4.76-4.67 (m, 1H), 3.47-3.35 (m, 2H), 2.65 (d, J=5.0 Hz, 3H), 2.60-2.54 (m, 1H), 2.36 (t, J=11.0 Hz, 1H), 1.89-1.62 (m, 4H), 1.41 (t, J=11.3 Hz, 2H), 1.22-1.06 (m, 1H), 0.84 (s, 9H), −0.03 (d, J=2.5 Hz, 6H). ES-LCMS m/z 468.2 [M+1]$^+$.

Step 3: benzyl (1R,2S,6R)-2-(((tert-butyldimethylsilyl)oxy)methyl)-6-(4-((N,1,2-trimethyl-1H-benzo[d]imidazole)-5-sulfonamido)phenyl)cyclohexane-1-carboxylate

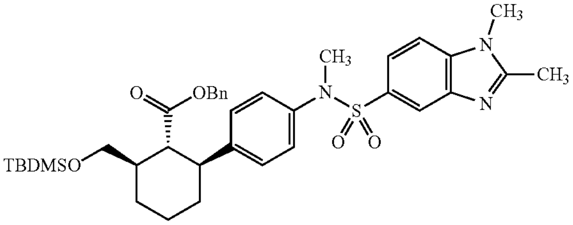 [SMILES: Cc1nc2cc(S(=O)(=O)N(C)c3ccc([C@H]4CCC[C@@H](CO[Si](C)(C)C(C)(C)C)[C@@H]4C(=O)OCc4ccccc4)cc3)ccc2n1C]

To a mixture of benzyl (1R,2S,6R)-2-(((tert-butyldimethylsilyl)oxy)methyl)-6-(4-(methylamino)phenyl)cyclohexane-1-carboxylate (3.1 g, 6.6 mmol) and pyridine (2.68 ml, 33.1 mmol) in DCM (30 ml) at 0° C. was added 1,2-dimethyl-1H-benzo[d]imidazole-5-sulfonyl chloride (2.11 g, 8.62 mmol), and the reaction was quenched with MeOH (10 mL), concentrated and purified via silica gel column chromatography, eluting with 0-5% MeOH in DCM, to give benzyl (1R,2S,6R)-2-(((tert-butyldimethylsilyl)oxy)methyl)-6-(4-((N,1,2-trimethyl-1H-benzo[d]imidazole)-5-sulfonamido)phenyl)cyclohexane-1-carboxylate (3.1 g, 4.1 mmol, 62%) as an off-white solid. $^1$H NMR (400 MHz, DMSO-$d_6$) δ 7.57 (s, 1H), 7.25 (d, J=3.5 Hz, 2H), 7.11 (d, J=8.5 Hz, 2H), 7.05 (dd, J=6.8, 2.8 Hz, 2H), 6.96 (d, J=8.5 Hz, 2H), 4.84 (d, J=12.5 Hz, 1H), 4.68 (d, J=12.5 Hz, 1H), 3.72 (s, 3H), 3.43-3.35 (m, 1H), 3.06 (s, 3H), 2.77-2.65 (m, 1H), 2.46-2.40 (m, 1H), 1.91-1.69 (m, 4H), 1.54-1.36 (m, 2H), 0.82 (s, 9H), −0.05 (d, J=4.0 Hz, 6H). ES-LCMS m/z 676.0 [M+H]$^+$.

Step 4: benzyl (1R,2R,6S)-2-(hydroxymethyl)-6-(4-((N,1,2-trimethyl-1H-benzo[d]imidazole)-5-sulfonamido)phenyl)cyclohexane-1-carboxylate

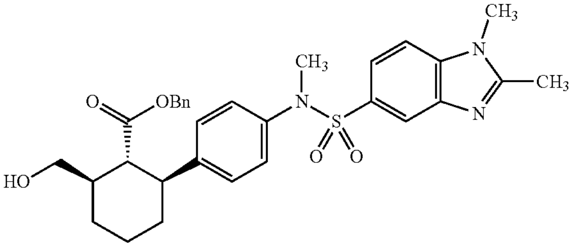 [SMILES: Cc1nc2cc(S(=O)(=O)N(C)c3ccc([C@H]4CCC[C@@H](CO)[C@@H]4C(=O)OCc4ccccc4)cc3)ccc2n1C]

To a mixture of benzyl (1R,2S,6R)-2-(((tert-butyldimethylsilyl)oxy)methyl)-6-(4-((N,1,2-trimethyl-1H-benzo[d]imidazole)-5-sulfonamido)phenyl)cyclohexane-1-carboxylate (3.1 g, 4.6 mmol) in THF (32 mL) and water (8 mL) at 0° C. was added HCl (2N in water, 6.74 mL, 13.5 mmol). After ten min, the reaction was stirred at 25° C. for 1 h, diluted with brine (50 mL) and extracted with EtOAc (4×25 ml). The combined organic layers were washed with water (4×20 mL) and brine (15 mL), dried over sodium sulphate, concentrated and purified via silica gel column chromatography, eluting with 0-5% MeOH in DCM, to give benzyl (1R,2R,6S)-2-(hydroxymethyl)-6-(4-((N,1,2-trimethyl-1H-benzo[d]imidazole)-5-sulfonamido)phenyl)cyclohexane-1-carboxylate (1.100 g, 1.559 mmol, 51.78%) as a brown solid. $^1H$ NMR (400 MHz, DMSO-$d_6$) δ 7.60-7.56 (m, 2H), 7.29-7.22 (m, 4H), 7.12 (d, J=8.5 Hz, 2H), 7.06-7.01 (m, 2H), 6.95 (d, J=8.5 Hz, 2H), 4.82-4.78 (m, 1H), 4.73-4.69 (m, 1H), 4.52 (t, J=5.0 Hz, 1H), 3.72 (s, 3H), 3.30-3.26 (m, 1H), 3.22-3.16 (m, 1H), 3.06 (s, 3H), 2.76-2.66 (m, 1H), 2.51 (br s, 3H), 2.41 (t, J=11.0 Hz, 1H), 1.90-1.67 (m, 4H), 1.56-1.37 (m, 2H), 1.16-1.07 (m, 1H). ES-LCMS m/z 562.0 $[M+H]^+$.

Step 5: benzyl (1R,2R,6S)-2-(((methylsulfonyl)oxy)methyl)-6-(4-((N,1,2-trimethyl-1H-benzo[d]imidazole)-5-sulfonamido)phenyl)cyclohexane-1-carboxylate

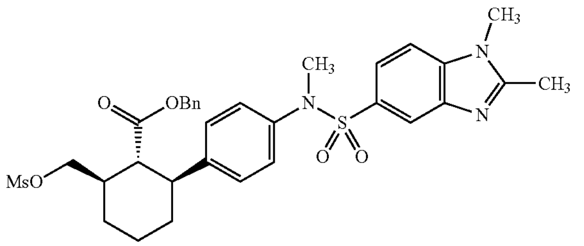 [SMILES: Cc1nc2cc(S(=O)(=O)N(C)c3ccc([C@H]4CCC[C@@H](COS(C)(=O)=O)[C@@H]4C(=O)OCc4ccccc4)cc3)ccc2n1C]

To a mixture of benzyl (1R,2R,6S)-2-(hydroxymethyl)-6-(4-((N,1,2-trimethyl-1H-benzo[d]imidazole)-5-sulfonamido)phenyl)cyclohexane-1-carboxylate (250 mg, 0.445 mmol) in DCM (10 mL) at 0° C. was added TEA (0.186 mL, 1.34 mmol) and mesyl-Cl (0.035 mL, 0.45 mmol). After 1 h at rt, the reaction was diluted with water (100 mL) and extracted with DCM (2×100 ml). The combined organic layers were washed with brine (50 mL), dried over sodium sulphate and concentrated to give benzyl (1R,2R,6S)-2-(((methylsulfonyl)oxy)methyl)-6-(4-((N,1,2-trimethyl-1H-benzo[d]imidazole)-5-sulfonamido)phenyl)cyclohexane-1- carboxylate (0.350 g, 0.536 mmol, 120%), which was used without further purification. ES-LCMS m/z 640.2 $[M+H]^+$.

Step 6: benzyl (1R,2R,6S)-2-((2-(benzyloxy)-4-(trifluoromethyl)phenoxy)methyl)-6-(4-((N,1,2-trimethyl-1H-benzo[d]imidazole)-5-sulfonamido)phenyl)cyclohexane-1-carboxylate

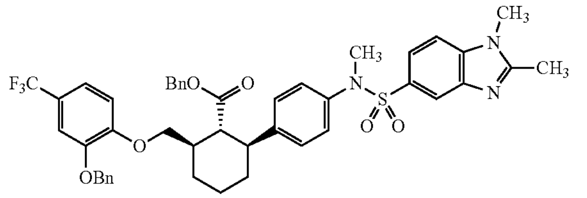 [SMILES: Cc1nc2cc(S(=O)(=O)N(C)c3ccc([C@H]4CCC[C@@H](COc5ccc(C(F)(F)F)cc5OCc5ccccc5)[C@@H]4C(=O)OCc4ccccc4)cc3)ccc2n1C]

To a mixture of benzyl (1R,2R,6S)-2-(((methylsulfonyl)oxy)methyl)-6-(4-((N,1,2-trimethyl-1H-benzo[d]imidazole)-5-sulfonamido)phenyl)cyclohexane-1-carboxylate (350 mg, 0.55 mmol) and 2-(benzyloxy)-4-(trifluoromethyl)phenol (293 mg, 1.09 mmol) in DMF (3.5 mL) was added cesium carbonate (535 mg, 1.64 mmol). The reaction was stirred at 90° C. for 2 h, quenched with water (25 mL) and extracted with EtOAc (25 mL×4). The combined organic layers were washed with water (10 mL×4) and brine (15 mL), dried over sodium sulphate, concentrated and subjected to reverse phase purification (0-55% MeCN in $H_2O$, 0.1% ammonium bicarbonate modifier) to afford (benzyl (1R,2R,6S)-2-((2-(benzyloxy)-4-(trifluoromethyl)phenoxy)methyl)-6-(4-((N,1,2-trimethyl-1H-benzo[d]imidazole)-5-sulfonamido)phenyl)cyclohexane-1-carboxylate (0.200 g, 0.201 mmol, 37.0% yield) as a yellow oil. $^1H$ NMR (400 MHz, DMSO-$d_6$) δ 7.60-7.55 (m, 2H), 7.47 (br d, J=7.5 Hz, 2H), 7.42-7.23 (m, 8H), 7.20-7.02 (m, 5H), 6.97-6.85 (m, 3H), 5.30-5.11 (m, 4H), 4.80 (d, J=12.5 Hz, 1H), 4.65 (d, J=12.5 Hz, 1H), 3.97 (br dd, J=10.0, 4.0 Hz, 1H), 3.82 (br dd, J=10.0, 5.0 Hz, 1H), 3.70 (s, 3H), 3.44-3.36 (m, 1H), 3.07 (s, 3H), 2.81-2.68 (m, 2H), 2.20-2.10 (m, 1H), 1.96-1.71 (m, 3H), 1.55-1.37 (m, 3H). ES-LCMS m/z 812.2 $[M+H]^+$.

The following compounds were synthesized in an analogous manner to the preparation described above (Intermediate 24), using the relevant phenol and sulfonyl chloride:

| Int. | Structure/Name | $^1H$ NMR | LCMS |
| --- | --- | --- | --- |
| 25 | 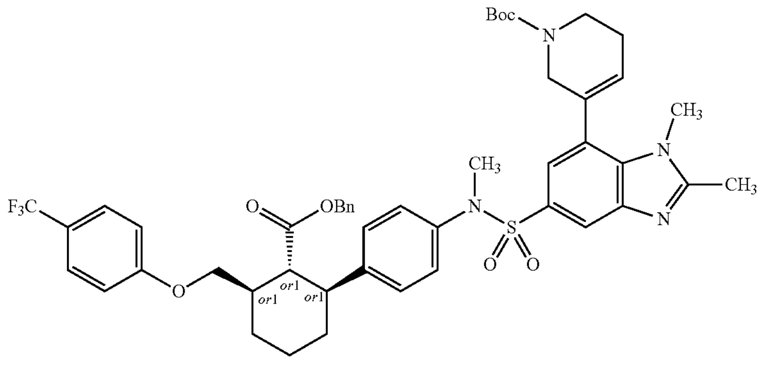 [SMILES: Cc1nc2cc(S(=O)(=O)N(C)c3ccc([C@H]4CCC[C@@H](COc5ccc(C(F)(F)F)cc5)[C@@H]4C(=O)OCc4ccccc4)cc3)cc(C3=CCCN(C(=O)OC(C)(C)C)C3)c2n1C]<br>ISOMER 1<br>rel-tert-butyl 5-(5-(N-(4-((1R,2S,3S)-2-((benzyloxy)carbonyl)-3-((4-(trifluoromethyl)phenoxy)methyl)cyclohexyl)phenyl)-N-methylsulfamoyl)-1,2-dimethyl-1H- | $^1H$ NMR (400 MHz, DMSO-$d_6$) δ 7.64-7.60 (m, 3H), 7.20-7.13 (m, 5H), 7.01 (d, J = 8.4 Hz, 2H), 6.96 (d, J = 8.80 Hz, 2H), 6.90 (d, J = 6.80 Hz, 2H), 6.76 (s, 1H), 5.8 (s, 1H), 4.78 (d, J = 12.40 Hz, 1H), 4.69 (d, J = 12.40 Hz, 1H), 3.94-3.90 (m, 4H), 3.71 (s, 3H), 3.49-3.43 (m, 2H), 3.04 (s, 3H), 2.68-2.66 (m, 1H), 2.59 (s, 3H), 2.33-2.22 (m, 3H), 1.99-1.73 (m, 4H), 1.53-1.48 (m, 3H), 1.42 (s, 9H) | ES-LCMS m/z 887.2 [M + H]+. |

-continued

| Int. | Structure/Name | $^{1}H$ NMR | LCMS |
|---|---|---|---|
| | benzo[d]imidazol-7-yl)-3,6-dihydropyridine-1(2H)-carboxylate, ISOMER 1 | | |
| 26 | 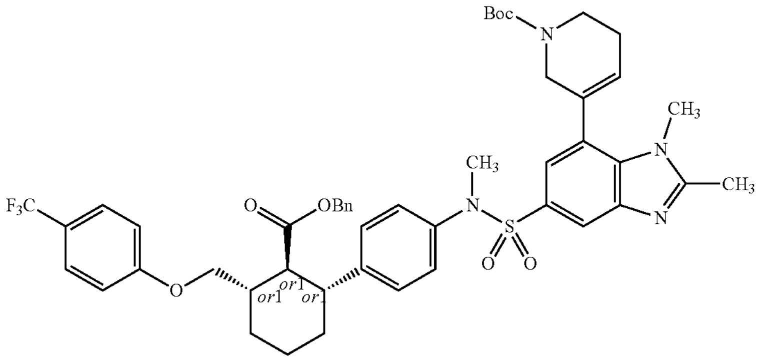 [SMILES: Cc1nc2cc(S(=O)(=O)N(C)c3ccc([C@@H]4CCC[C@H](COc5ccc(C(F)(F)F)cc5)[C@H]4C(=O)OCc4ccccc4)cc3)cc(C3=CCCN(C(=O)OC(C)(C)C)C3)c2n1C] ISOMER 2 rel-tert-butyl 5-(5-(N-(4-((1R,2S,3S)-2-((benzyloxy)carbonyl)-3-((4-(trifluoromethyl)phenoxy)methyl)cyclohexyl)phenyl)-N-methylsulfamoyl)-1,2-dimethyl-1H-benzo[d]imidazol-7-yl)-3,6-dihydropyridine-1(2H)-carboxylate, ISOMER 2 | $^{1}H$ NMR (400 MHz, DMSO-$d_6$) δ 7.64-7.60 (m, 3H), 7.20-7.13 (m, 5H), 7.01 (d, J = 8.4 Hz, 2H), 6.96 (d, J = 8.80 Hz, 2H), 6.90 (d, J = 6.80 Hz, 2H), 6.76 (s, 1H), 5.8 (s, 1H), 4.78 (d, J = 12.40 Hz, 1H), 4.69 (d, J = 12.40 Hz, 1H), 3.94-3.90 (m, 4H), 3.71 (s, 3H), 3.49-3.43 (m, 2H), 3.04 (s, 3H), 2.68-2.66 (m, 1H), 2.59 (s, 3H), 2.33-2.22 (m, 3H), 1.99-1.73 (m, 4H), 1.53-1.48 (m, 3H), 1.42 (s, 9H) | ES-LCMS m/z 887.2 [M + H]+. |

Intermediate 27 and Intermediate 28: rel-(1R,2S,6R)-2-(4-((7-((R)-1-(tert-butoxycarbonyl)piperidin-3-yl)-N,1,2-trimethyl-1H-benzo[d]imidazole)-5-sulfonamido)phenyl)-6-((4-(trifluoromethyl)phenoxy)methyl)cyclohexane-1-carboxylic acid, ISOMER 1 and ISOMER 2

ISOMER 1 and ISOMER 2

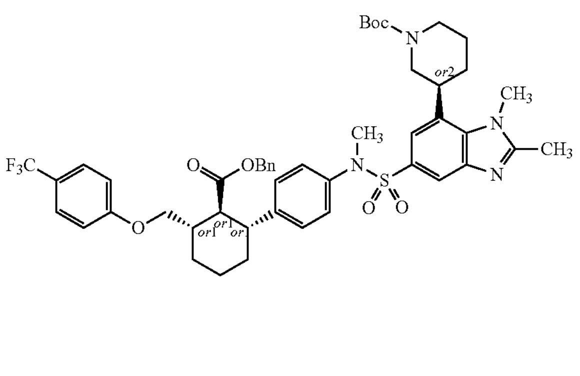

To a mixture of rel-tert-butyl 5-(5-(N-(4-((1R,2S,3S)-2-((benzyloxy)carbonyl)-3-((4-(trifluoromethyl)phenoxy)methyl)cyclohexyl)phenyl)-N-methylsulfamoyl)-1,2-dimethyl-1H-benzo[d]imidazol-7-yl)-3,6-dihydropyridine-1(2H)-carboxylate, ISOMER 2 Intermediate 26 (231 mg, 0.260 mmol) in ethanol (40 mL) under $N_2$ was added palladium hydroxide on carbon (146 mg, 0.210 mmol). The reaction was stirred under $H_2$ atmosphere (1 atm, bladder pressure) for 16 h. The mixture was filtered through Celite, rinsing with MeOH (100 mL). The filtrate was concentrated. For complete double bond reduction, the reaction process was repeated three times. The resulting residue was subjected to prep HPLC purification (0-100% MeCN in $H_2O$, 0.1% ammoinium bicarbonate modifier) to afford the racemic compound. $^{1}H$ NMR (400 MHz, DMSO-$d_6$) b 7.63 (d, J=8.4 Hz, 2H), 7.59 (d, J=0.8 Hz, 1H), 7.19 (d, J=8.8 Hz, 2H), 7.08 (d, J=8.4 Hz, 2H), 6.94 (d, J=8.4 Hz, 2H), 6.86 (E, 1H), 3.99 (S, 3H), 3.95-3.91 (m, 4H), 3.08-3.05 (n, 1° H), 3.01 (s, 3H), 2.78-2.73 (i, 2H), 2.58 (s, 3H), 2.49-2.38 (m, 1H), 2.089-2.03 (m, 1H), 1.94 (brd, J=12.8 Hz, 1H), 1.84-1.70 (m, 2H), 1.70-1.68 (m, 2H), 1.53-1.45 (m, 4H), 1.41 (1, 9H), three protons obscured by solvent peaks.

The racemic compound (115 mg) was purified by Chiral-Prep-SFC (Column: YMC Amylose-SA; Mobile Phase 1:1 CO2: 0.5% Isopropylamine in IPA) to afford the first isomer rel-(1R,2S,6R)-2-(4-((7-((R)-1-(tert-butoxycarbonyl)piperidin-3-yl)-N,1,2-trim ethyl-1H-benzo[d]imidazole)-5-sulfonamido)phenyl)-6-((4-(trifluoromethyl) phenoxy)methyl) cyclohexane-1-carboxylic acid, ISOMER 1 (0.060 g, 0.070 mmol, 52% yield) and the second isomer rel-(1R,2S,6R)-2-(4-((7-((R)-1-(tert-butoxycarbonyl)piperidin-3-yl)-N,12-trimethyl-1H-benzo[d]imidazole)-5-sulfonamido)phenyl)-6-((4-(trifluoromethyl)phenoxy)methyl)cyclohexane-1-carboxylic acid, ISOMER 2(50 mg, 0.06 mmol, 43% yield) as an off white solid.

The following compounds were synthesized in an analogous manner to the preparation described above (Intermediate 27 and Intermediate 28), using the Intermediate 25:

| Int. | Structure/Name | $^1$H NMR | LCMS |
|---|---|---|---|
| 29 | 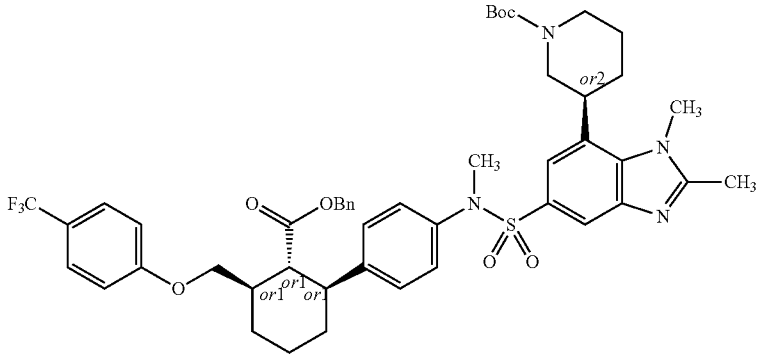 ISOMER 1 rel-(1R,2S,6R)-2-(4-((7-((S)-1-(tert-butoxycarbonyl)piperidin-3-yl)-N,1,2-trimethyl-1H-benzo[d]imidazole)-5-sulfonamido)phenyl)-6-((4-(trifluoromethyl)phenoxy)methyl)cyclohexane-1-carboxylic acid, ISOMER 1 | $^1$H NMR (400 MHz, DMSO-$d_6$) δ 7.64 (d, J = 8.8 Hz, 2H), 7.57 (s, 1H), 7.20 (d, J = 8.4 Hz, 2H), 7.08 (d, J = 8.8 Hz, 2H), 6.95 (d, J = 8.4 Hz, 2H), 6.86 (s, 1H), 4.1 (m, 2H), 3.99 (s, 3H), 3.94 (d, J = 5.2 Hz, 2H), 3.01 (s, 3H), 2.78-2.68 (m, 2H), 2.59 (s, 3H), 2.42-2.39 (m, 1H), 2.15-2.08 (m, 1H), 1.92-1.82 (m, 3H), 1.72-1.64 (m, 2H), 1.54-1.52 (m, 4H), 1.35 (s, 9H), 4 protons obscured by solvent peaks | ES-LCMS m/z 799.2 [M + H]+. |
| 30 | 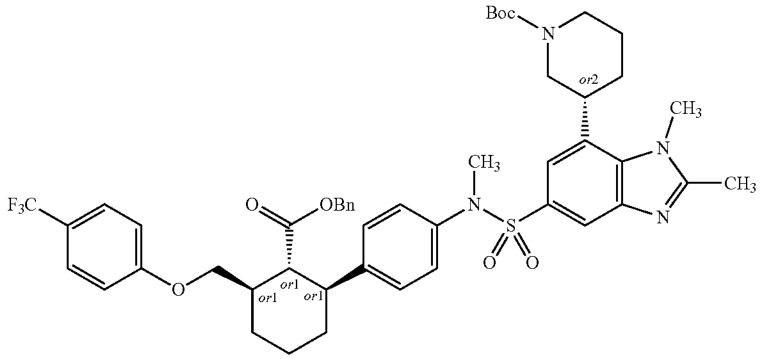 ISOMER 2 rel-(1R,2S,6R)-2-(4-((7-((S)-1-(tert-butoxycarbonyl)piperidin-3-yl)-N,1,2-trimethyl-1H-benzo[d]imidazole)-5-sulfonamido)phenyl)-6-((4-(trifluoromethyl)phenoxy)methyl)cyclohexane-1-carboxylic acid, ISOMER 2 | $^1$H NMR (400 MHz, DMSO-$d_6$) δ 7.64 (d, J = 8.8 Hz, 2H), 7.57 (s, 1H), 7.20 (d, J = 8.4 Hz, 2H), 7.08 (d, J = 8.8 Hz, 2H), 6.95 (d, J = 8.4 Hz, 2H), 6.86 (s, 1H), 4.1 (m, 2H), 3.99 (s, 3H), 3.94 (d, J = 5.2 Hz, 2H), 3.01 (s, 3H), 2.78-2.68 (m, 2H), 2.59 (s, 3H), 2.42-2.39 (m, 1H), 2.15-2.08 (m, 1H), 1.92-1.82 (m, 3H), 1.72-1.64 (m, 2H), 1.54-1.52 (m, 4H), 1.35 (s, 9H), 4 protons obscured by solvent peaks | ES-LCMS m/z 799.2 [M + H]+. |

Intermediate 31: (1R,2S,6R)-2-(4-(methylamino)phenyl)-6-((((1r,4R)-4-(trifluoromethyl)cyclohexyl)oxy)methyl)cyclohexane-1-carboxylic acid

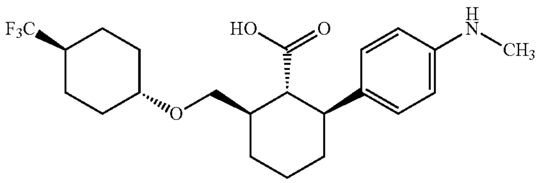 [SMILES: CNc1ccc([C@H]2CCC[C@@H](CO[C@H]3CC[C@H](C(F)(F)F)CC3)[C@@H]2C(=O)O)cc1]

Step 1: 2-benzyl 1-((1r,4R)-4-(trifluoromethyl)cyclohexyl) (1R,2R,3S)-3-(4-bromophenyl)cyclohexane-1,2-dicarboxylate

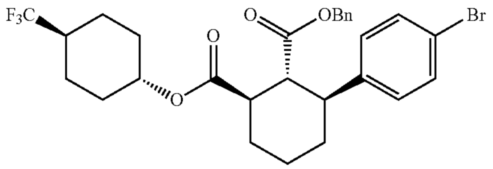 [SMILES: O=C(OCc1ccccc1)[C@@H]1[C@@H](c2ccc(Br)cc2)CCC[C@H]1C(=O)O[C@H]1CC[C@H](C(F)(F)F)CC1]

To a mixture of (1R,2R,3S)-2-((benzyloxy)carbonyl)-3-(4-bromophenyl)cyclohexane-1-carboxylic acid Intermediate 7, alternate route, Step 1 (0.250 g, 0.599 mmol) in dichloromethane (2.5 mL) at 0° C. was added (1r,4r)-4-(trifluoromethyl)cyclohexan-1-ol (302 mg, 1.80 mmol), DMAP (14.6 mg, 0.120 mmol) and DCC (247 mg, 1.20 mmol). The reaction was stirred at room temperature for 5 h, quenched with water (30 mL) and extracted with DCM (3×50 mL). The combined organic layers were washed with brine (50 mL), dried over sodium sulphate, concentrated and subjected to normal phase purification (0-100% ethyl acetate in petroleum ether) to afford 2-benzyl 1-((1r,4R)-4-(trifluoromethyl)cyclohexyl) (1R,2R,3S)-3-(4-bromophenyl)cyclohexane-1,2-dicarboxylate (330 mg, 0.50 mmol, 83% yield) as a colorless liquid. $^{1}H$ NMR (400 MHz, DMSO-$d_6$) δ 7.48-7.37 (m, 2H), 7.29-7.22 (m, 3H), 7.17 (d, J=8.5 Hz, 2H), 6.84 (dd, J=7.0, 2.5 Hz, 2H), 4.74 (t, J=12.0 Hz, 1H), 4.67 (d, J=4.5 Hz, 2H), 2.83-2.75 (m, 1H), 2.73-2.64 (m, 2H), 2.23-2.08 (m, 3H), 1.74-1.46 (m, 8H), 1.39-1.31 (m, 4H). ES-LCMS m/z poor ionization in MS.

Step 2: (1R,2S,6R)-2-(4-bromophenyl)-6-((((1r,4R)-4-(trifluoromethyl)cyclohexyl)oxy)methyl)cyclohexane-1-carboxylic acid

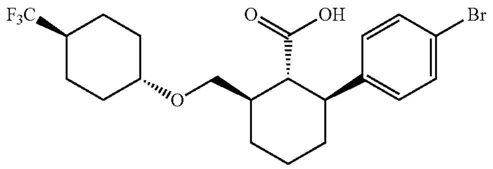 [SMILES: O=C(O)[C@H]1[C@H](CO[C@H]2CC[C@H](C(F)(F)F)CC2)CCC[C@@H]1c1ccc(Br)cc1]

To a mixture of 2-benzyl 1-((1r,4R)-4-(trifluoromethyl) cyclohexyl) (1R,2R,3S)-3-(4-bromophenyl)cyclohexane-1,2-dicarboxylate (0.33 g, 0.58 mmol) in chloroform (5 mL) at 0° C. was added triethylsilane (2.79 mL, 17.4 mmol) and indium bromide (2.06 g, 5.82 mmol). The reaction was stirred at 60° C. for 2 h, diluted with THF, quenched with water (10 mL) and extracted with DCM (3×100 mL). The combined organic layers were washed with brine (50 mL), dried over sodium sulphate, filtered, concentrated and subjected to reverse phase purification (10-100% MeCN in $H_2O$, 0.1% formic acid modifier) to afford (1R,2S,6R)-2-(4-bromophenyl)-6-((((1r,4R)-4-(trifluoromethyl)cyclohexyl)oxy)methyl)cyclohexane-1-carboxylic acid (0.030 g, 0.063 mmol, 11% yield) as a white solid. $^{1}H$ NMR (400 MHz, DMSO-$d_6$) δ 11.80 (br s, 1H), 7.45 (d, J=8.4 Hz, 2H), 7.17 (d, J=8.5 Hz, 2H), 3.32-3.22 (m, 2H), 3.20-3.06 (m, 1H), 2.72-2.63 (m, 1H), 2.32-2.13 (m, 2H), 2.00 (br t, J=11.9 Hz, 2H), 1.92-1.64 (m, 6H), 1.42 (br t, J=10.8 Hz, 2H), 1.34-1.08 (m, 5H).. ES-LCMS m/z 461.0 $[M-H]^-$.

Step 3: (1R,2S,6R)-2-(4-(methylamino)phenyl)-6-((((1r,4R)-4-(trifluoromethyl)cyclohexyl)oxy) methyl)cyclohexane-1-carboxylic acid

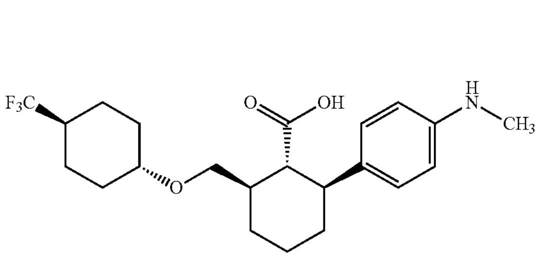 [SMILES: CNc1ccc([C@H]2CCC[C@@H](CO[C@H]3CC[C@H](C(F)(F)F)CC3)[C@@H]2C(=O)O)cc1]

A suspension of (1R,2S,6R)-2-(4-bromophenyl)-6-((((1r, 4R)-4-(trifluoromethyl)cyclohexyl)oxy)methyl)cyclohexane-1-carboxylic acid (0.020 mg, 0.043 mmol) in 1,4-dioxane (0.2 mL) was degassed for 1 h. Sodium tert-butoxide (8.3 mg, 0.086 mmol) was added, and this mixture was degassed for 5 min. tBuXPhos Pd G3 (7.00 mg, 8.63 μmol) was added, followed by methylamine (2 M in THF, 0.216 mL, 0.432 mmol). The reaction vessel was sealed, microwaved at 100° C. for 1 h, concentrated and subjected to reverse phase purification (0-100% MeCN in $H_2O$, 0.1% formic acid modifier) to afford (1R,2S,6R)-2-(4-(methylamino)phenyl)-6-((((1r,4R)-4-(trifluoromethyl)cyclohexyl) oxy)methyl)cyclohexane-1-carboxylic acid (12 mg, 0.020 mmol, 47% yield) as a white solid. ES-LCMS m/z 412.0 $[M-H]^-$.

Intermediate 32: (1R,2S,6R)-2-(4-((1-(2-((tert-butoxycarbonyl)amino)ethyl)-N,2-dimethyl-1H-benzo [d]imidazole)-5-sulfonamido)phenyl)-6-((4-(trifluoromethyl)phenoxy)methyl)cyclohexane-1-carboxylic acid

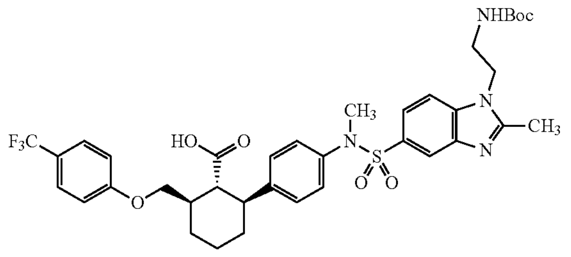 [SMILES: Cc1nc2cc(S(=O)(=O)N(C)c3ccc([C@H]4CCC[C@@H](COc5ccc(C(F)(F)F)cc5)[C@@H]4C(=O)O)cc3)ccc2n1CCNC(=O)OC(C)(C)C]

Step 1: benzyl (1R,2S,6R)-2-(4-((1-(2-((tert-butoxycarbonyl)amino)ethyl)-N,2-dimethyl-1H-benzo[d] imidazole)-5-sulfonamido)phenyl)-6-((4-(trifluoromethyl)phenoxy)methyl)cyclohexane-1-carboxylate

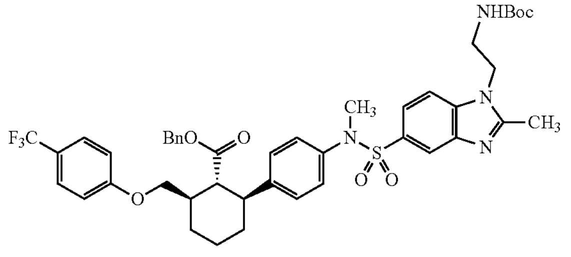 [SMILES: Cc1nc2cc(S(=O)(=O)N(C)c3ccc([C@H]4CCC[C@@H](COc5ccc(C(F)(F)F)cc5)[C@@H]4C(=O)OCc4ccccc4)cc3)ccc2n1CCNC(=O)OC(C)(C)C]

To a mixture of benzyl (1R,2S,6R)-2-(4-(methylamino) phenyl)-6-((4-(trifluoromethyl)phenoxy)methyl)cyclohexane-1-carboxylate Intermediate 23 Step 3 (0.11 g, 0.22 mmol) in dichloromethane (2 mL) was added pyridine (0.090 mL, 1.1 mmol), followed by tert-butyl (2-(5-(chlorosulfonyl)-2-methyl-1H-benzo[d]imidazol-1-yl)ethyl)carbamate (0.16 g, 0.44 mmol) in dichloromethane (2 mL). After 1 h, the reaction was concentrated and subjected to reverse phase purification (10-55% MeCN in $H_2O$, with 0.1% ABC modifier) to afford benzyl (1R,2S,6R)-2-(4-((1-(2-((tert-butoxycarbonyl)amino)ethyl)-N,2-dimethyl-1H-benzo[d]imidazole)-5-sulfonamido)phenyl)-6-((4-(trifluoromethyl)phenoxy)methyl)cyclohexane-1-carboxylate (170 mg, 0.19 mmol, 87% yield)) as an off-white solid. $^{1}H$ NMR (400 MHz, DMSO-$d_6$) δ 7.62-7.35 (m, 4H), 7.30 (dd, J=8.4, 1.6 Hz, 1H), 7.21-7.14 (m, 5H), 7.01-6.93 (m, 6H), 4.81 (d, J=12.4 Hz, 1H), 4.70 (d, J=12.4 Hz, 1H), 4.21 (t, J=5.2 Hz, 2H), 3.91-3.88 (m, 2H), 3.28-3.25 (m, 3H), 3.07 (s, 3H), 2.68 (t, J=1.6 Hz, 1H), 2.64 (t, J=10.8 Hz, 1H), 2.20-2.18 (m, 1H), 1.91-1.85 (m, 1H), 1.83-1.75 (m, 1H), 1.53-1.52 (m, 2H), 1.36-1.32 (m, 1H), 1.24 (s, 9H), four protons obscured by solvent peaks. ES-LCMS m/z 835.2 [M+H]$^+$.

Step 2: (1R,2S,6R)-2-(4-((1-(2-((tert-butoxycarbonyl)amino)ethyl)-N,2-dimethyl-1H-benzo[d]imidazole)-5-sulfonamido)phenyl)-6-((4-(trifluoromethyl)phenoxy)methyl)cyclohexane-1-carboxylic acid

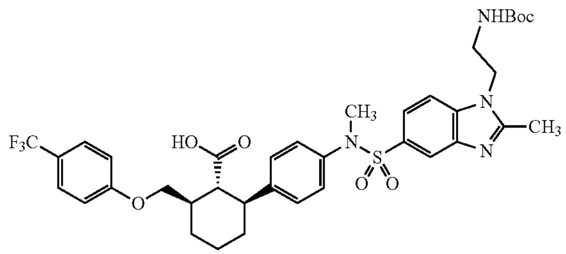 [SMILES: Cc1nc2cc(S(=O)(=O)N(C)c3ccc([C@H]4CCC[C@@H](COc5ccc(C(F)(F)F)cc5)[C@@H]4C(=O)O)cc3)ccc2n1CCNC(=O)OC(C)(C)C]

To a mixture of benzyl (1R,2S,6R)-2-(4-((1-(2-((tert-butoxycarbonyl)amino)ethyl)-N,2-dimethyl-1H-benzo[d]imidazole)-5-sulfonamido)phenyl)-6-((4-(trifluoromethyl)phenoxy)methyl)cyclohexane-1-carboxylate (0.100 g, 0.120 mmol) in methanol (2 mL) was added Pd/C (31.9 mg, 0.300 mmol), and the reaction was stirred under an $H_2$ atmosphere (1 atm, bladder pressure). After16 h, the mixture was filtered through Celite, washing with methanol (150 mL), and concentrated to afford (1R,2S,6R)-2-(4-((1-(2-((tert-butoxycarbonyl)amino)ethyl)-N,2-dimethyl-1H-benzo[d]imidazole)-5-sulfonamido)phenyl)-6-((4-(trifluoromethyl)phenoxy)methyl)cyclohexane-1-carboxylic acid (0.080 g, 0.11 mmol, 88% yield) as a brown oil. $^1$H NMR (400 MHz, DMSO-$d_6$) δ 12.3 (br s, 1H), 7.64-7.60 (m, 3H), 7.51 (s, 1H), 7.29 (d, J=8.8 Hz, 1H), 7.18 (d, J=8.4 Hz, 2H), 7.09 (d, J=8.4 Hz, 2H), 7.01 (t, J=6.0 Hz, 1H), 6.96 (d, J=8.4 Hz, 2H), 4.27-4.25 (m, 2H), 3.97-3.93 (m, 2H), 3.33-3.29 (m, 3H), 3.05 (s, 3H), 2.74-2.72 (m, 2H), 2.56 (s, 3H), 2.08-2.06 (m, 1H), 1.95 (br d, J=13.2 Hz, 1H), 1.83-1.73 (m, 2H), 1.48-1.45 (m, 2H), 1.25 (s, 9H). ES-LCMS m/z 745.2 [M+H]$^+$.

Intermediate 33 and Intermediate 34: rel-benzyl (1R,2R,4R,6S)-4-ethoxy-2-((4-(trifluoromethyl)phenoxy)methyl)-6-(4-((N,1,2-trimethyl-1H-benzo[d]imidazole)-5-sulfonamido)phenyl)cyclohexane-1-carboxylate, ISOMER 1 and ISOMER 2

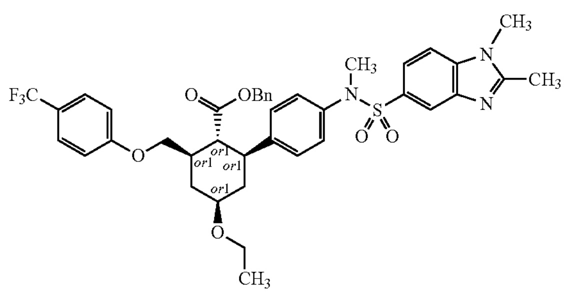

ISOMER 1 and ISOMER 2

Step-1: rac-benzyl (1R,2S,4R,6R)-2-(4-bromophenyl)-4-ethoxy-6-((4-(trifluoromethyl)phenoxy)methyl)cyclohexane-1-carboxylate

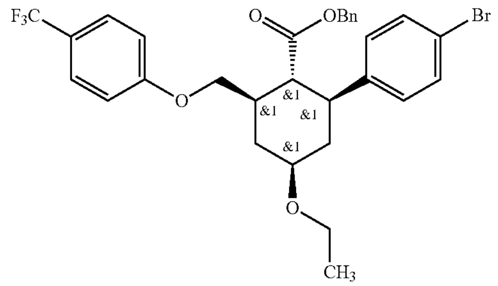 [SMILES: CCO[C@H]1C[C@@H](COc2ccc(C(F)(F)F)cc2)[C@H](C(=O)OCc2ccccc2)[C@@H](c2ccc(Br)cc2)C1]

To a mixture of rac-benzyl (1R,2S,4R,6R)-2-(4-bromophenyl)-4-ethoxy-6-(hydroxymethyl)cyclohexane-1-carboxylate Intermediate 8 Step 9 (1.3 g, 2.9 mmol) in tetrahydrofuran (20 mL) at 0° C. was added 4-(trifluoromethyl)phenol (0.52 g, 3.2 mmol), triphenylphosphane (0.76 g, 2.9 mmol) and diisopropyl diazene-1,2-dicarboxylate (0.59 g, 2.9 mmol). The reaction was stirred at rt for 1 h, then subjected to reverse phase purification (75-85% MeCN in $H_2O$, 0.1% formic acid modifier) to afford rac-benzyl (1R,2S,4R,6R)-2-(4-bromophenyl)-4-ethoxy-6-((4-(trifluoromethyl)phenoxy)methyl)cyclohexane-1-carboxylate (1.2 g, 1.6 mmol, 54% yield) as a white solid. $^1$H NMR (400 MHz, DMSO-$d_6$) δ 7.63 (d, J=8.8 Hz, 2H), 7.45 (d, J=8.4 Hz, 2H), 7.26-7.16 (m, 5H), 7.04 (d, J=8.4 Hz, 2H), 6.81 (d, J=8.4 Hz, 2H), 4.85 (d, J=12.8 Hz, 1H), 4.69 (d, J=12.4 Hz, 1H), 3.99-3.93 (m, 2H), 3.55-3.46 (m, 3H), 2.91-2.83 (m, 1H), 2.64 (t, J=11.2 Hz, 1H), 2.33-2.18 (m, 2H), 2.05 (d, J=12.4 Hz, 1H), 1.48 (q, J=11.2 Hz, 1H), 1.26 (q, J=12.4 Hz, 1H), 1.09 (t, J=7.20 Hz, 3H). ES-LCMS m/z: poor ionization.

Step-2: rac-benzyl (1R,2S,4R,6R)-4-ethoxy-2-(4-(methylamino)phenyl)-6-((4-(trifluoromethyl)phenoxy)methyl)cyclohexane-1-carboxylate

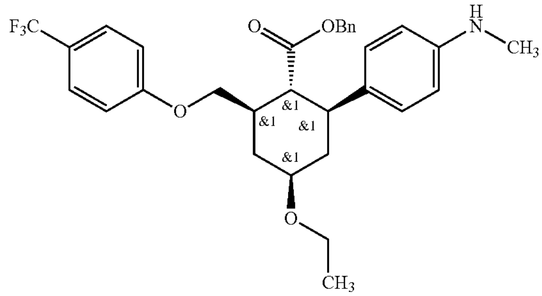 [SMILES: CCO[C@H]1C[C@@H](COc2ccc(C(F)(F)F)cc2)[C@H](C(=O)OCc2ccccc2)[C@@H](c2ccc(NC)cc2)C1]

To a mixture of rac-benzyl (1R,2S,4R,6R)-2-(4-bromophenyl)-4-ethoxy-6-((4-(trifluoromethyl)phenoxy)methyl)cyclohexane-1-carboxylate (450 mg, 0.76 mmol) and sodium 2-methylpropan-2-olate (0.110 g, 1.14 mmol) in dioxane (2 mL) was added tBuXPhos Pd G3 (121 mg, 0.150 mmol), and the reaction was degassed for 5 min. Methanamine (2M in THF, 7.61 mL, 15.2 mmol) was added, and the mixture was microwaved at 100° C. After 1 h, the reaction was concentrated and subjected to reverse phase purification (75-85% MeCN in $H_2O$, with 0.1% formic acid modifier) to afford rac-benzyl (1R,2S,4R,6R)-4-ethoxy-2-(4-(methylamino)phenyl)-6-((4-(trifluoromethyl)phenoxy)methyl)cyclohexane-1-carboxylate (220 mg, 0.29 mmol, 37% yield) as white solid. $^1$H NMR (400 MHz, DMSO-$d_6$) δ 7.63 (d, J=6.40 Hz, 2H), 7.18-7.16 (m, 3H), 7.03 (d, J=7.20 Hz, 2H), 6.94 (d, J=7.60 Hz, 2H), 6.83 (d, J=6.40 Hz, 2H), 6.45 (d, J=7.20 Hz, 2H), 5.5 (s, 1H), 4.85 (d, J=12.00 Hz, 1H), 4.70 (d, J=13.20 Hz, 1H), 3.92 (m, 2H), 3.49-3.47 (m, 3H), 2.7 (m, 1H), 2.66 (s, 3H), 2.3-2.2 (m, 2H), 1.9 (m, 2H), 1.44-1.41 (m, 1H), 1.24-1.16 (m, 1H), 1.12 (t, J=6.80 Hz, 3H). ES-LCMS m/z 542.2 $[M+H]^+$.

Step-3: rel-benzyl (1R,2R,4R,6S)-4-ethoxy-2-((4-(trifluoromethyl)phenoxy)methyl)-6-(4-((N,1,2-trimethyl-1H-benzo[d]imidazole)-5-sulfonamido)phenyl)cyclohexane-1-carboxylate, ISOMER 1 and ISOMER 2

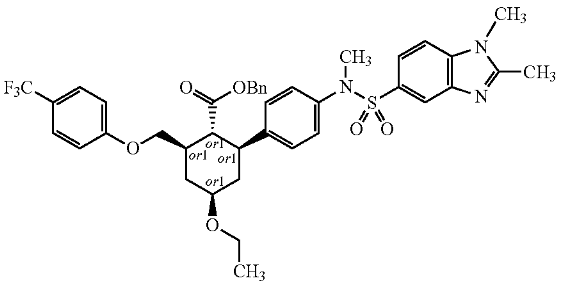

ISOMER 1 and ISOMER 2

To a mixture of rac-benzyl (1R,2S,4R,6R)-4-ethoxy-2-(4-(methylamino)phenyl)-6-((4-(trifluoromethyl)phenoxy)methyl)cyclohexane-1-carboxylate (0.220 g, 0.416 mmol) in dichloromethane (2 mL) and pyridine (0.10 mL, 1.22 mmol) at 0° C. was added 1,2-dimethyl-1H-benzo[d]imidazole-5-sulfonyl chloride (119 mg, 0.490 mmol), portion wise. The reaction was stirred at rt for 45 min, concentrated and subjected to reverse phase purification (75-85% MeCN in $H_2O$, with 0.1% formic acid modifier) to afford rac-benzyl (1R,2R,4R,6S)-4-ethoxy-2-((4-(trifluoromethyl)phenoxy)methyl)-6-(4-((N,1,2-trimethyl-1H-benzo[d]imidazole)-5-sulfonamido)phenyl)cyclohexane-1-carboxylate (250 mg, 0.33 mmol, 81% yield) as white solid.

$^1$H NMR (400 MHz, DMSO-$d_6$) δ 7.63-7.58 (m, 4H), 7.28 (dd, J=8.4, 2.0 Hz, 1H), 7.22-7.14 (m, 5H), 7.02-6.97 (m, 4H), 6.93 (d, J=8.4 Hz, 2H), 4.81 (d, J=12.4 Hz, 1H), 4.70 (d, J=12.4 Hz, 1H), 3.95-3.90 (m, 2H), 3.73 (s, 3H), 3.55-3.46 (m, 3H), 3.08 (s, 3H), 2.86-2.80 (m, 1H), 2.62 (t, J=11.2 Hz, 1H), 2.34-2.17 (m, 2H), 2.06 (d, J=13.20 Hz, 1H), 1.48 (q, J=11.6 Hz, 1H), 1.29 (q, J=11.6 Hz, 1H), 1.09 (t, J=6.8 Hz, 3H), three protons obscured by solvent peaks. ES-LCMS m/z 542.2 $[M+H]^+$.

The racemic compound (300 mg) was purified by Chiral-Prep-SFC (Column: YMC Amylose-SA; Mobile Phase 55:45 $CO_2$: 0.5% Isopropylamine in IPA) to afford:

rel-benzyl (1R,2R,4R,6S)-4-ethoxy-2-((4-(trifluoromethyl)phenoxy)methyl)-6-(4-((N,1,2-trimethyl-1H-benzo[d]imidazole)-5-sulfonamido)phenyl)cyclohexane-1-carboxylate ISOMER 1 (120 mg, 0.15 mmol, 38% yield) as white solid and rel-benzyl(1R,2R,4R,6S)-4-ethoxy-2-((4-(trifluoromethyl)phenoxy)methyl)-6-(4-((N,1,2-trimethyl-1H-benzo[d]imidazole)-5-sulfonamido)phenyl)cyclohexane-1-carboxylate ISOMER 2 (120 mg, 0.16 mmol, 39% yield) as white solid.

Intermediate 35: rac-(1R,2S,6R)-2-(4-aminophenyl)-6-((2-fluoro-4-(trifluoromethyl)phenyl)carbamoyl)cyclohexane-1-carboxylic acid

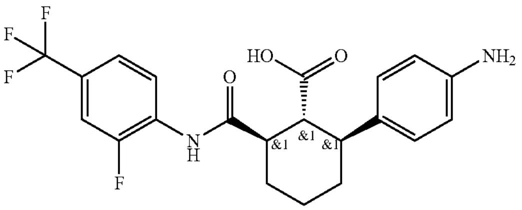 [SMILES: Nc1ccc([C@H]2CCC[C@@H](C(=O)Nc3ccc(C(F)(F)F)cc3F)[C@@H]2C(=O)O)cc1]

Step 1: rac-(1R,2S,6R)-2-(4-((tert-butoxycarbonyl)amino)phenyl)-6-((2-fluoro-4-(trifluoromethyl)phenyl)carbamoyl)cyclohexane-1-carboxylic acid

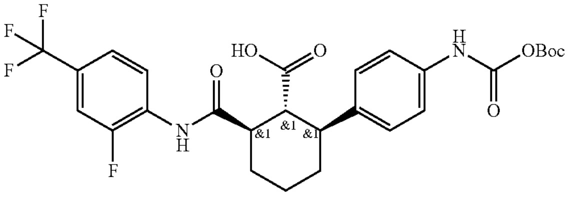

To mixture of rac-(1R,2S,6R)-2-(4-bromophenyl)-6-((2-fluoro-4-(trifluoromethyl)phenyl)carbamoyl)cyclohexane-1-carboxylic acid Intermediate 6 Step 1 (0.030 g, 0.61 mmol), tert-butyl carbamate (0.360 g, 3.07 mmol) and sodium tert-butoxide (148 mg, 1.54 mmol) in degassed dioxane (6 mL) was added tBuXPhos Pd G3 (98 mg, 0.12 mmol). The reaction was microwaved at 100° C. for 1 h, filtered through Celite, concentrated and subjected to reverse phase purification (0-100% MeCN in $H_2O$, 0.1% ammonium bicarbonate modifier) to afford rac-(1R,2S,6R)-2-(4-((tert-butoxycarbonyl)amino)phenyl)-6-((2-fluoro-4-(trifluoromethyl)phenyl)carbamoyl)cyclohexane-1-carboxylic acid (250 mg, 0.34 mmol, 56% yield) as a white solid. $^1$H NMR (400 MHz, DMSO-$d_6$) δ 11.24 (s, 1H), 10.15 (br s, 1H), 9.21 (s, 1H), 8.21 (t, J=8.3 Hz, 1H), 7.69 (dd, J=11.0, 1.5 Hz, 1H), 7.53 (d, J=8.5 Hz, 1H), 7.31 (d, J=8.5 Hz, 2H), 7.10 (d, J=8.5 Hz, 2H), 2.95 (t, J=9.0 Hz, 1H), 2.76-2.62 (m, 2H), 2.03-1.81 (m, 2H), 1.75-1.66 (m, 1H), 1.54-1.44 (m, 12H). ES-LCMS m/z 523.3 $[M-H]^-$.

Step 2: rac-(1R,2S,6R)-2-(4-aminophenyl)-6-((2-fluoro-4-(trifluoromethyl)phenyl)carbamoyl)cyclohexane-1-carboxylic acid

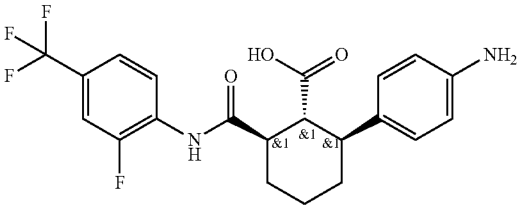 [SMILES: Nc1ccc([C@H]2CCC[C@@H](C(=O)Nc3ccc(C(F)(F)F)cc3F)[C@@H]2C(=O)O)cc1]

To a mixture of rac-(1R,2S,6R)-2-(4-((tert-butoxycarbonyl)amino)phenyl)-6-((2-fluoro-4-(trifluoromethyl)phenyl) carbamoyl)cyclohexane-1-carboxylic acid (0.25 g, 0.48 mmol) in 1,2-dichloroethane (6 mL) at 0° C. was added TFA (0.734 mL, 9.53 mmol), dropwise. The reaction was stirred at rt for 16 h, concentrated and subjected to reverse phase purification (0-100% MeCN in $H_2O$, 0.1% ammonium bicarbonate modifier) to afford rac-(1R,2S,6R)-2-(4-aminophenyl)-6-((2-fluoro-4-(trifluoromethyl)phenyl)carbamoyl) cyclohexane-1-carboxylic acid (0.130 g, 0.295 mmol, 62.0% yield) as a white solid. $^1$H NMR (400 MHz, DMSO-$d_6$) δ 10.08 (bs, 1H), 8.20 (t, J=8.0 Hz, 1H), 7.70 (dd, J=11.0, 1.5 Hz, 1H), 7.54 (d, J=9.0 Hz, 1H), 6.86 (d, J=8.0 Hz, 2H), 6.44 (d, J=8.0 Hz, 2H), 4.83 (br s, 2H), 2.94 (t, J=9.8 Hz, 1H), 2.71-2.59 (m, 2H), 2.01-1.64 (m, 3H), 1.56-1.43 (m, 3H) one proton obscured by solvent peaks. ES-LCMS m/z 423.0 $[M-H]^-$.

Intermediate 36: (1R,2R,6S)-2-((2-fluoro-4-(trifluoromethyl)phenyl)carbamoyl)-6-(4-hydroxyphenyl) cyclohexane-1-carboxylic acid

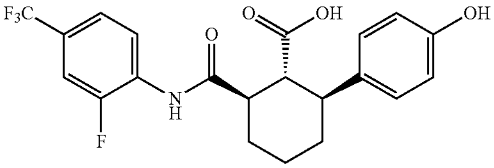 [SMILES: O=C(O)[C@@H]1[C@@H](c2ccc(O)cc2)CCC[C@H]1C(=O)Nc1ccc(C(F)(F)F)cc1F]

A mixture of (1R,2S,6R)-2-(4-bromophenyl)-6-((2-fluoro-4-(trifluoromethyl)phenyl)carbamoyl)cyclohexane-1-carboxylic acid Intermediate 1 (1.000 g, 2.048 mmol), RockPhos Pd G3 (0.172 g, 0.205 mmol), (E)-benzaldehyde oxime (0.372 g, 3.07 mmol) and $Cs_2CO_3$ (2.00 g, 6.14 mmol) in NMP (10 mL) was heated at 80° C. over the weekend, filtered and purified by reverse phase silica gel chromatography (35-80% acetonitrile in water, 0.1% formic acid) to afford (1R,2R,6S)-2-((2-fluoro-4-(trifluoromethyl) phenyl)carbamoyl)-6-(4-hydroxyphenyl)cyclohexane-1-carboxylic acid (217 mg, 0.510 mmol, 24.1% yield) as a white solid. $^1$H NMR (400 MHz, DMSO-$d_6$) δ=11.68 (s, 1H), 10.07 (s, 1H), 9.15 (s, 1H), 8.21 (t, J=8.1 Hz, 1H), 7.72 (dd, J=1.7, 11.0 Hz, 1H), 7.55 (br d, J=8.8 Hz, 1H), 7.02 (d, J=8.3 Hz, 2H), 6.65 (d, J=8.8 Hz, 2H), 3.03-2.93 (m, 1H), 2.75-2.67 (m, 1H), 2.63-2.54 (m, 1H), 1.99 (br d, J=8.8 Hz, 1H), 1.89-1.83 (m, 1H), 1.77-1.69 (m, 1H), 1.59-1.44 (m, 3H). ES-LCMS m/z 426.2 $[M+H]^+$.

Intermediate 37: rac-(1R,2R,6S)-2-((2-fluoro-4-(trifluoromethyl)phenyl)carbamoyl)-6-(4-(4-oxopiperidin-1-yl)phenyl)cyclohexane-1-carboxylic acid

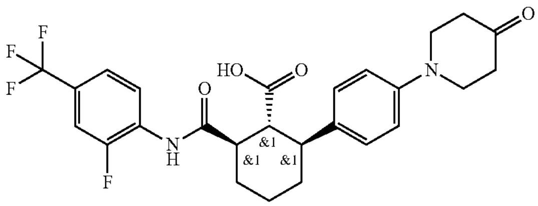 [SMILES: O=C1CCN(c2ccc([C@H]3CCC[C@@H](C(=O)Nc4ccc(C(F)(F)F)cc4F)[C@@H]3C(=O)O)cc2)CC1]

Step 1: rac-(1R,2S,6R)-2-(4-(1,4-dioxa-8-azaspiro [4.5]decan-8-yl)phenyl)-6-((2-fluoro-4-(trifluoromethyl)phenyl)carbamoyl)cyclohexane-1-carboxylic acid

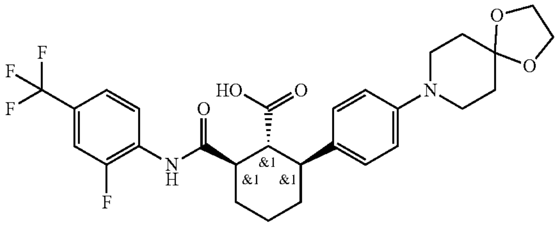 [SMILES: O=C(O)[C@@H]1[C@@H](c2ccc(N3CCC4(CC3)OCCO4)cc2)CCC[C@H]1C(=O)Nc1ccc(C(F)(F)F)cc1F]

To a mixture of rac-(1R,2S,6R)-2-(4-bromophenyl)-6-((2-fluoro-4-(trifluoromethyl)phenyl)carbamoyl)cyclohexane-1-carboxylic acid Intermediate 6 Step 1 (0.20 g, 0.41 mmol) and 1,4-dioxa-8-azaspiro[4.5]decane (293 mg, 2.05 mmol) in degassed dioxane (4 mL) was added sodium 2-methylpropan-2-olate (98 mg, 1.024 mmol). The reaction was degassed for 10 min, and tBuXPhos Pd G3 (65 mg, 0.082 mmol) was added. The mixture was heated at 100° C. for 1 h, concentrated and subjected to reverse phase purification (95-100% MeCN in $H_2O$, 0.1% ammonium bicarbonate modifier) to afford rac-(1R,2S,6R)-2-(4-(1,4-dioxa-8-azaspiro[4.5]decan-8-yl)phenyl)-6-((2-fluoro-4-(trifluoromethyl)phenyl)carbamoyl)cyclohexane-1-carboxylic acid (110 mg, 0.18 mmol, 43% yield) as a white solid. $^1$H NMR (400 MHz, DMSO-$d_6$) δ 10.11 (br s, 1H), 8.32-8.15 (m, 1H), 7.69 (br d, J=10.5 Hz, 1H), 7.53 (br d, J=8.5 Hz, 1H), 7.24 (br s, 1H), 7.06 (br d, J=8.0 Hz, 2H), 6.83 (br d, J=8.5 Hz, 2H), 3.24-3.17 (m, 4H), 3.04-2.88 (m, 1H), 2.76-2.63 (m, 3H), 1.97 (br d, J=7.5 Hz, 1H), 1.84 (br s, 1H), 1.75-1.62 (m, 6H), 1.58-1.35 (m, 5H). ES-LCMS m/z 551.2 $[M+H]^+$.

Step 2: rac-(1R,2R,6S)-2-((2-fluoro-4-(trifluoromethyl)phenyl)carbamoyl)-6-(4-(4-oxopiperidin-1-yl) phenyl)cyclohexane-1-carboxylic acid

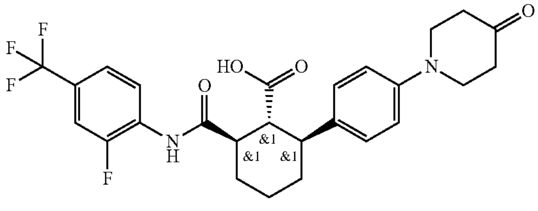 [SMILES: O=C1CCN(c2ccc([C@H]3CCC[C@@H](C(=O)Nc4ccc(C(F)(F)F)cc4F)[C@@H]3C(=O)O)cc2)CC1]

To a mixture of rac-(1R,2S,6R)-2-(4-(1,4-dioxa-8-azaspiro[4.5]decan-8-yl)phenyl)-6-((2-fluoro-4-(trifluoromethyl)phenyl)carbamoyl)cyclohexane-1-carboxylic acid (110 mg, 0.20 mmol) in acetone (4 mL) and water (2 mL) was added p-toluenesulfonic acid (38.0 mg, 0.200 mmol). The reaction was microwaved at 100° C. for 2 h, concentrated and subjected to reverse phase purification (95-100% MeCN in $H_2O$, 0.1% ammonium bicarbonate modifier) to afford rac-(1R,2R,6S)-2-((2-fluoro-4-(trifluoromethyl)phenyl)carbamoyl)-6-(4-(4-oxopiperidin-1-yl)phenyl)cyclohexane-1-carboxylic acid (0.070 g, 0.10 mmol, 51% yield) as an off-white solid. $^1$H NMR (400 MHz, DMSO-$d_6$) δ 11.91 (br s, 1H), 10.17 (br s, 1H), 8.22 (t, J=7.3 Hz, 1H), 7.67 (d, J=10.5 Hz, 1H), 7.52 (d, J=8.5 Hz, 1H), 7.10 (d, J=7.5 Hz, 2H), 6.90 (d, J=7.5 Hz, 2H), 3.52 (t, J=5.5 Hz, 4H), 3.01-2.84 (m, 1H), 2.77-2.60 (m, 2H), 2.40 (t, J=6.0 Hz, 4H), 2.02-1.90 (m, 1H), 1.83 (br s, 1H), 1.68 (br s, 1H), 1.48 (br d, J=5.0 Hz, 3H). ES-LCMS m/z 505.2 [M−H]$^-$.

Intermediate 38: rac-(1R,2S,6R)-2-(3-bromo-4-(trifluoromethyl)phenyl)-6-((2-fluoro-4-(trifluoromethyl)phenyl)carbamoyl)cyclohexane-1-carboxylic acid

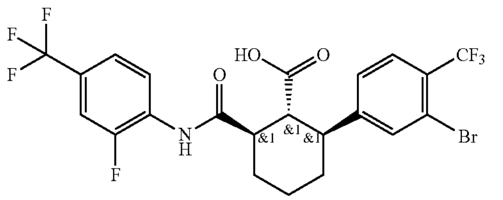 [SMILES: O=C(O)[C@@H]1[C@@H](c2ccc(C(F)(F)F)c(Br)c2)CCC[C@H]1C(=O)Nc1ccc(C(F)(F)F)cc1F]

Step 1: (E)-3-(3-bromo-4-(trifluoromethyl)phenyl)acrylaldehyde

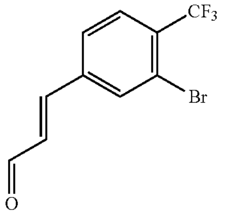 [SMILES: O=C/C=C/c1ccc(C(F)(F)F)c(Br)c1]

To a mixture of 3-bromo-4-(trifluoromethyl)benzaldehyde (19 g, 75 mmol) in DMSO (350 mL) was added 2-(triphenyl-15-phosphaneylidene)acetaldehyde (23 g, 75 mmol). The reaction was stirred at 120° C. for 3 h, quenched with ice cold water (400 mL) and extracted with EtOAc (300 mL×3). The combined EtOAc layers were washed with cold brine (300 mL), dried over sodium sulphate, concentrated and subjected to normal phase purification (5-10% ethyl acetate in petroleum ether) to afford (E)-3-(3-bromo-4-(trifluoromethyl)phenyl)acrylaldehyde (16.8 g, 57.1 mmol, 76.0% yield) as a pale yellow solid. $^1$H NMR (400 MHz, DMSO-$d_6$) δ 9.73-9.71 (m, 1H), 8.32 (s, 1H), 7.97-7.91 (m, 2H), 7.79 (d, J=16 Hz, 1H), 7.08 (dd, J=16.0, 7.6 Hz, 1H). ES-LCMS m/z 278.0, 280.0 [M−H]$^-$ Step 2: (E)-2-bromo-4-(buta-1,3-dien-1-yl)-1-(trifluoromethyl)benzene

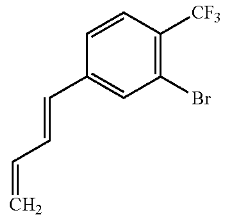

To a suspension of methyltriphenylphosphonium bromide (32.1 g, 90.0 mmol) in tetrahydrofuran (250 mL) at 0° C. was added potassium 2-methylpropan-2-olate (59.8 mL, 59.8 mmol, 1M in THF), dropwise over 10 min. After 10 min, a solution of (E)-3-(3-bromo-4-(trifluoromethyl)phenyl)acrylaldehyde (16.7 g, 59.8 mmol) in tetrahydrofuran (20 mL) was added, and the reaction was stirred at rt. for 2 h, quenched with ice cold water (150 mL) and extracted with EtOAc (200 mL×3). The combined EtOAc layers were washed with brine (150 mL), dried over sodium sulphate, concentrated and subjected to normal phase purification (0-5% ethyl acetate in petroleum ether) to afford (E)-2-bromo-4-(buta-1,3-dien-1-yl)-1-(trifluoromethyl)benzene (7.0 g, 24 mmol, 40% yield) as a pale yellow oil. $^1$H NMR (400 MHz, DMSO-$d_6$) δ 8.02 (s, 1H), 7.78 (d, J=8.4 Hz, 1H), 7.68 (d, J=8.0 Hz, 1H), 7.19 (dd, J=15.8, 10.8 Hz, 1H), 6.69 (d, J=16.0 Hz, 1H), 6.61-6.51 (m, 1H), 5.52 (d, J=17.2 Hz, 1H), 5.35 (d, J=10.0 Hz, 1H). ES-LCMS m/z poor ionization.

Step 3: rac-(3aR,4R,7aS)-4-(3-bromo-4-(trifluoromethyl)phenyl)-3a,4,7,7a-tetrahydroisobenzofuran-1,3-dione

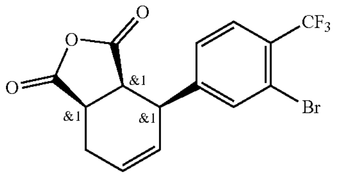 [SMILES: O=C1OC(=O)[C@@H]2CC=C[C@H](c3ccc(C(F)(F)F)c(Br)c3)[C@H]12]

To a mixture of (E)-2-bromo-4-(buta-1,3-dien-1-yl)-1-(trifluoromethyl)benzene (7.0 g, 25 mmol) in toluene (70 mL) was added furan-2,5-dione (2.5 g, 25 mmol). The reaction was heated for 16 h at 120° C., concentrated and triturated with n-hexane (50 mL) to obtain rac-(3aR,4R,7aS)-4-(3-bromo-4-(trifluoromethyl)phenyl)-3a,4,7,7a-tetrahydroisobenzofuran-1,3-dione (6.9 g, 18 mmol, 72% yield) as a brown solid. $^1$H NMR (400 MHz, DMSO-$d_6$) δ 7.85-7.80 (m, 2H), 7.54 (d, J=8.0 Hz, 1H), 6.37-6.33 (m, 1H), 6.23-6.17 (m, 1H), 4.98-4.93 (m, 1H), 3.86 (dd, J=9.2, 6.8 Hz, 1H), 3.77-3.72 (m, 1H), 2.66 (ddd, J=16.1, 6.8, 2.0 Hz, 1H), 2.40-2.34 (m, 1H). ES-LCMS m/z 373, 375 [M+H]$^-$.

Step 4: rac-(1R,2S,3S)-3-(3-bromo-4-(trifluoromethyl)phenyl)cyclohexane-1,2-dicarboxylic acid

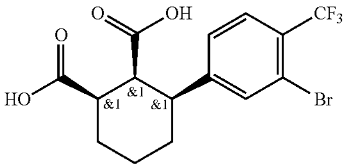 [SMILES: O=C(O)[C@H]1[C@@H](c2ccc(C(F)(F)F)c(Br)c2)CCC[C@H]1C(=O)O]

To a mixture of rac-(3aR,4R,7aS)-4-(3-bromo-4-(trifluoromethyl)phenyl)-3a,4,7,7a-tetrahydroisobenzofuran-1,3-dione (6.85 g, 18.3 mmol) in tetrahydrofuran (80 mL) was added platinum on carbon (7.12 g, 1.83 mmol), under nitrogen at 25° C. The reaction was degassed via vacuum evacuation, then backfilling with hydrogen. The mixture was stirred at 25° C. for 16 h under hydrogen (1 atm), diluted with ethyl acetate (100 mL), filtered through Celite pad (washing with ethyl acetate [200 mL]), concentrated and triturated with n-hexane (100 mL) to afford rac-(1R,2S,3S)-3-(3-bromo-4-(trifluoromethyl)phenyl)cyclohexane-1,2-dicarboxylic acid (4.4 g, 9.46 mmol, 52% yield) as a light brown solid. $^1$H NMR (400 MHz, DMSO-$d_6$) δ 12.11 (br s, 2H), 7.77 (d, J=8.4 Hz, 1H), 7.73 (s, 1H), 7.44 (d, J=8.0 Hz, 1H), 3.20 (t, J=4.4 Hz, 1H), 3.07-3.07 (m, 1H), 2.70-2.66 (m, 1H), 2.10-1.90 (m, 3H), 1.82-1.73 (m, 2H), 1.64 (d, J=12.8 Hz, 1H). ES-LCMS m/z 393.0, 395.0 $[M-H]^-$.

Step 5: rac-(3aR,4R,7aS)-4-(3-bromo-4-(trifluoromethyl)phenyl)hexahydroisobenzofuran-1,3-dione

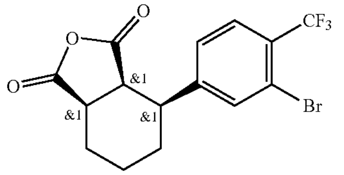 [SMILES: O=C1OC(=O)[C@@H]2CCC[C@H](c3ccc(C(F)(F)F)c(Br)c3)[C@H]12]

To a suspension of rac-(1R,2S,3S)-3-(3-bromo-4-(trifluoromethyl)phenyl)cyclohexane-1,2-dicarboxylic acid (4.4 g, 11 mmol) in dichloromethane (50 mL) at 0° C. was added trifluoroacetic anhydride (1.89 mL, 13.36 mmol). The reaction was stirred at rt. for 2 h, concentrated and triturated with n-hexane (50 mL×2) to afford rac-(3aR,4R,7aS)-4-(3-bromo-4-(trifluoromethyl)phenyl)hexahydroisobenzofuran-1,3-dione (3.9 g, 9.3 mmol, 84% yield) as a light brown semi-solid. $^1$H NMR (400 MHz, DMSO-$d_6$) δ 7.82 (s, 1H), 7.81 (d, J=8.0 Hz, 1H), 7.52 (d, J=8.0 Hz, 1H), 4.11 (t, J=6.8 Hz, 1H), 3.37-3.26 (m, 2H), 2.13-2.05 (m, 1H), 1.98-1.90 (m, 1H), 1.86-1.77 (m, 1H), 1.72-1.61 (m, 1H), 1.59-1.46 (m, 2H). ES-LCMS m/z 375.0, 377.0 $[M-H]^-$.

Step 6: rac-(1R,2R,6S)-2-(3-bromo-4-(trifluoromethyl)phenyl)-6-(hydroxymethyl)cyclohexane-1-carboxylic acid

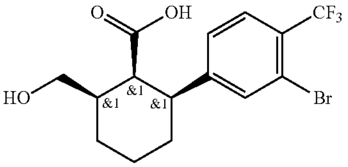 [SMILES: O=C(O)[C@@H]1[C@H](CO)CCC[C@@H]1c1ccc(C(F)(F)F)c(Br)c1]

To a mixture of rac-(3aR,4R,7aS)-4-(3-bromo-4-(trifluoromethyl)phenyl)hexahydroisobenzofuran-1,3-dione (3.9 g, 10 mmol) in tetrahydrofuran (80 mL) was added sodium borohydride (0.782 g, 20.7 mmol). The reaction was stirred at rt for 3 h and quenched with 1.5 N HCl (~20 mL) to adjust to pH<4. The mixture was extracted with ethyl acetate (100 mL×3). The combined organic layers were washed with brine (150 mL), dried over anhydrous sodium sulfate, filtered and concentrated to afford rac-(1R,2R,6S)-2-(3-bromo-4-(trifluoromethyl)phenyl)-6-(hydroxymethyl)cyclohexane-1-carboxylic acid (2.8 g, 5.9 mmol, 57% yield) as a white solid. $^1$H NMR (400 MHz, DMSO-$d_6$) δ 11.82 (br s, 1H), 7.77 (d, J=8.4 Hz, 1H), 7.72 (s, 1H), 7.44 (d, J=8.0 Hz, 1H), 3.34 (dd, J=10.4, 6.8 Hz, 1H), 3.23 (dd, J=10.4, 7.6 Hz, 1H), 3.03-2.94 (m, 2H), 2.36-2.24 (m, 1H), 1.92-1.82 (m, 2H), 1.61 (d, J=12.8 Hz, 2H), 1.55-1.46 (m, 1H), 1.45-1.37 (m, 1H), one proton obscured by solvent peaks. ES-LCMS m/z 378.8, 380.8 $[M-H]^-$.

Step 7: rac-(3aR,7S,7aS)-7-(3-bromo-4-(trifluoromethyl)phenyl)hexahydroisobenzofuran-1(3H)-one

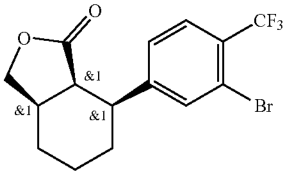 [SMILES: O=C1OC[C@@H]2CCC[C@H](c3ccc(C(F)(F)F)c(Br)c3)[C@H]12]

To a mixture of rac-(1R,2R,6S)-2-(3-bromo-4-(trifluoromethyl)phenyl)-6-(hydroxymethyl)cyclohexane-1-carboxylic acid (2.8 g, 7.4 mmol) in toluene (30 mL) was added p-TSOH (0.140 g, 0.735 mmol). The reaction was stirred at 110° C. for 16 h, diluted with aq 10% $NaHCO_3$ solution and extracted with ethyl acetate (25 mL×2). The combined organic layers were washed with brine (40 mL), dried over sodium sulfate, filtered, concentrated and triturated with petroleum ether (30 mL) to afford rac-(3aR,7S,7aS)-7-(3-bromo-4-(trifluoromethyl)phenyl)hexahydroisobenzofuran-1(3H)-one (2.5 g, 5.6 mmol, 76% yield). $^1$HNMR not recorded. ES-LCMS m/z: poor ionization.

Step 8: rac-(1R,2R,3S)-2-((benzyloxy)carbonyl)-3-(3-bromo-4-(trifluoromethyl)phenyl)cyclohexane-1-carboxylic acid

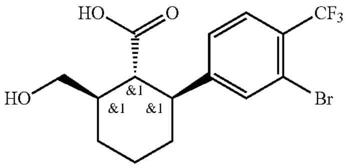 [SMILES: O=C(O)[C@H]1[C@H](CO)CCC[C@@H]1c1ccc(C(F)(F)F)c(Br)c1]

To a mixture of rac-(3aR,7S,7aS)-7-(3-bromo-4-(trifluoromethyl)phenyl)hexahydroisobenzofuran-1(3H)-one (2.5 g, 6.9 mmol) in methanol (30 mL) was added KOH (1.93 g, 34.4 mmol). The reaction was stirred at 75° C. for 3 h and quenched with 1.5 N HCl (~25 mL) to pH<4. The mixture was extracted with ethyl acetate (50 mL×3). The combined organic layers were washed with brine (50 mL), dried over anhydrous sodium sulfate, filtered, concentrated and triturated with petroleum ether (30 mL) to afford rac-(1R,2R,3S)-2-((benzyloxy)carbonyl)-3-(3-bromo-4-(trifluoromethyl)phenyl)cyclohexane-1-carboxylic acid (2.5 g, 5.6 mmol, 81% yield) as an off-white solid. $^1$H NMR (400 MHz, DMSO-$d_6$) δ 11.92 (br s, 1H), 7.78-7.74 (m, 2H), 7.45 (d, J=8.0 Hz, 1H), 4.54 (m, 1H), 3.39 (d, J=10.8 Hz, 1H), 3.22 (d, J=9.2 Hz, 1H), 2.83-2.77 (m, 1H), 2.36 (t, J=11.2 Hz, 1H), 1.94-1.91 (m, 1H), 1.83-1.79 (m, 1H), 1.76-1.63 (m, 2H), 1.54-1.34 (m, 2H), 1.18-1.12 (m, 1H). ES-LCMS m/z 381.0 $[M]^-$, 379.0 $[M-2H]^-$.

Step 9: rac-benzyl (1R,2S,6R)-2-(3-bromo-4-(trifluoromethyl)phenyl)-6-(hydroxymethyl)cyclohexane-1-carboxylate

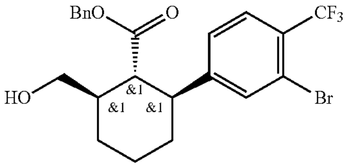 [SMILES: O=C(OCc1ccccc1)[C@H]1[C@H](CO)CCC[C@@H]1c1ccc(C(F)(F)F)c(Br)c1]

To a mixture of rac-(1R,2R,3S)-2-((benzyloxy)carbonyl)-3-(3-bromo-4-(trifluoromethyl)phenyl)cyclohexane-1-carboxylic acid (2.5 g, 6.6 mmol) in DMF (30 mL)) at 0° C. were added potassium carbonate (2.72 g, 19.7 mmol) and benzyl bromide (1.17 mL, 9.84 mmol). The reaction was stirred at rt for 3 h, diluted with water (50 mL) and extracted with ethyl acetate (50 mL×3). The combined organic layers were washed with brine, dried over anhydrous sodium sulfate, filtered, concentrated and subjected to normal phase purification (20-50% ethyl acetate in petroleum ether) to afford rac-benzyl (1R,2S,6R)-2-(3-bromo-4-(trifluoromethyl)phenyl)-6-(hydroxymethyl)cyclohexane-1-carboxylate (2.3 g, 4.5 mmol, 69% yield) a pale yellow oil. $^1$H NMR (400 MHz, DMSO-$d_6$) δ 7.75 (s, 1H), 7.67 (d, J=8.0 Hz, 1H), 7.38 (d, J=8.0 Hz, 1H), 7.27-7.18 (m, 3H), 6.89 (dd, J=7.8, 1.6 Hz, 2H), 4.88 (d, J=12.4 Hz, 1H), 4.71 (d, J=12.4 Hz, 1H), 4.58 (t, J=5.2 Hz, 1H), 3.36-3.21 (m, 2H), 2.89-2.81 (m, 1H), 2.56 (t, J=11.2 Hz, 1H), 1.88-1.72 (m, 4H), 1.56-1.39 (m, 2H), 1.21-1.13 (m, 1H). ES-LCMS m/z poor ionization.

Step 10: rac-(1R,2R,3S)-2-((benzyloxy)carbonyl)-3-(3-bromo-4-(trifluoromethyl)phenyl)cyclohexane-1-carboxylic acid

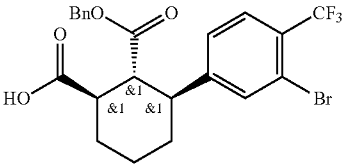 [SMILES: O=C(OCc1ccccc1)[C@@H]1[C@@H](c2ccc(C(F)(F)F)c(Br)c2)CCC[C@H]1C(=O)O]

To a mixture of rac-benzyl (1R,2S,6R)-2-(3-bromo-4-(trifluoromethyl)phenyl)-6-(hydroxymethyl)cyclohexane-1-carboxylate (2.3 g, 4.9 mmol) in acetonitrile (20 mL) and water (5 mL) at 0° C. were added sodium periodate (3.13 g, 14.6 mmol) and ruthenium(III) chloride (0.101 g, 0.488 mmol). The reaction was stirred at rt. for 2 h, diluted with water (20 mL) and extracted with ethyl acetate (30 mL×3). The combined organic layers were washed with brine (50 mL), dried over anhydrous sodium sulfate, filtered, concentrated and triturated with n-hexane (30 mL×2) to afford rac-(1R,2R,3S)-2-((benzyloxy)carbonyl)-3-(3-bromo-4-(trifluoromethyl)phenyl)cyclohexane-1-carboxylic acid (2.0 g, 3.7 mmol, 76% yield) as a grey solid. $^1$H NMR (400 MHz, DMSO-$d_6$) δ 12.43 (m, 1H), 7.84 (s, 1H), 7.67 (d, J=8.4 Hz, 1H), 7.41 (d, J=8.0 Hz, 1H), 7.26-7.19 (m, 3H), 6.85 (dd, J=9.2, 1.6 Hz, 2H), 4.71 (dd, J=15.6, 12.4 Hz, 2H), 2.93 (t, J=11.6 Hz, 1H), 2.83-2.76 (m, 1H), 2.69-2.62 (m, 1H), 2.08-2.03 (m, 1H), 1.87-1.82 (m, 1H), 1.74-1.62 (m, 2H), 1.56-1.46 (m, 2H). ES-LCMS m/z 482.8, 484.8 $[M-H]^-$.

Step 11: rac-benzyl (1R,2S,6R)-2-(3-bromo-4-(trifluoromethyl)phenyl)-6-((2-fluoro-4-(trifluoromethyl)phenyl)carbamoyl)cyclohexane-1-carboxylate

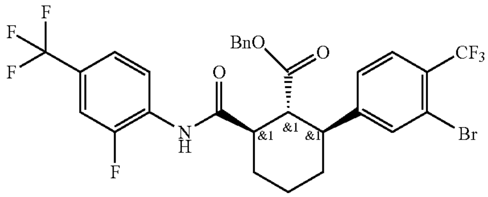 [SMILES: O=C(OCc1ccccc1)[C@@H]1[C@@H](c2ccc(C(F)(F)F)c(Br)c2)CCC[C@H]1C(=O)Nc1ccc(C(F)(F)F)cc1F]

To a mixture of rac-(1R,2R,3S)-2-((benzyloxy)carbonyl)-3-(3-bromo-4-(trifluoromethyl)phenyl)cyclohexane-1-carboxylic acid (2.0 g, 4.1 mmol) in acetonitrile (8 mL) were added 1-methyl-1H-imidazole (0.657 mL, 8.24 mmol) followed by 2-fluoro-4-(trifluoromethyl)aniline (0.738 g, 4.12 mmol) and N-(chloro(dimethylamino)methylene)-N-methylmethanaminium hexafluorophosphate(V) (2.31 g, 8.24 mmol). The reaction was stirred at rt. for 16 h, diluted with water (20 mL) and extracted with EtOAc (25 mL×3). The combined EtOAc layers were washed with brine (30 mL), dried over sodium sulphate, concentrated and subjected to normal phase purification (20-70% ethyl acetate in petroleum ether) to afford rac-benzyl (1R,2S,6R)-2-(3-bromo-4-(trifluoromethyl)phenyl)-6-((2-fluoro-4-(trifluoromethyl)phenyl)carbamoyl)cyclohexane-1-carboxylate (1.8 g, 2.6 mmol, 62% yield) as an off-white solid. $^1$H NMR (400 MHz, DMSO-$d_6$) δ 10.20 (s, 1H), 8.17 (t, J=8.0 Hz, 1H), 7.89 (s, 1H), 7.75-7.68 (m, 2H), 7.56 (d, J=8.4 Hz, 1H), 7.46 (d, J=8.0 Hz, 1H), 7.22-7.11 (m, 3H), 6.82 (d, J=7.2 Hz, 2H), 4.70 (dd, J=18.4, 12.4 Hz, 2H), 3.14-3.06 (m, 2H), 2.89-2.82 (m, 1H), 2.08 (d, J=10.0 Hz, 1H), 1.91-1.88 (m, 1H), 1.79-1.63 (m, 2H), 1.62-1.47 (m, 2H). ES-LCMS m/z 645.8, 647.8 $[M+H]^+$.

Step 12: rac-(1R,2S,6R)-2-(3-bromo-4-(trifluoromethyl)phenyl)-6-((2-fluoro-4-(trifluoromethyl)phenyl)carbamoyl)cyclohexane-1-carboxylic acid

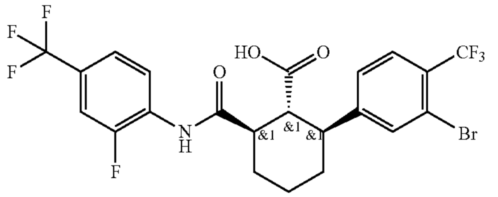 [SMILES: O=C(O)[C@@H]1[C@@H](c2ccc(C(F)(F)F)c(Br)c2)CCC[C@H]1C(=O)Nc1ccc(C(F)(F)F)cc1F]

To a mixture of rac-benzyl (1R,2S,6R)-2-(3-bromo-4-(trifluoromethyl)phenyl)-6-((2-fluoro-4-(trifluoromethyl)phenyl)carbamoyl)cyclohexane-1-carboxylate (1.7 g, 2.6 mmol) in dichloromethane (3 mL) at 0° C. was added boron trichloride (5.26 mL, 5.26 mmol, 1M in DCM). After 1 h, the reaction was concentrated and subjected to reverse phase purification (45-75% MeCN in $H_2O$, 0.1% ammonium bicarbonate modifier) to afford rac-(1R,2S,6R)-2-(3-bromo-4-(trifluoromethyl)phenyl)-6-((2-fluoro-4-(trifluoromethyl)phenyl)carbamoyl)cyclohexane-1-carboxylic acid (850 mg, 1.5 mmol, 56% yield) as a white solid. $^1H$ NMR (400 MHz, DMSO-$d_6$) δ 11.92 (br s, 1H), 10.14 (s, 1H), 8.21 (t, J=8.0 Hz, 1H), 7.84 (s, 1H), 7.77 (d, J=8.4 Hz, 1H), 7.73 (dd, J=11.0, 1.6 Hz, 1H), 7.56 (d, J=9.6 Hz, 1H), 7.52 (d, J=8.4 Hz, 1H), 3.04-2.98 (m, 1H), 2.90 (t, J=10.4 Hz, 1H), 2.82 (dt, J=11.4, 3.6 Hz, 1H), 2.03 (d, J=9.6 Hz, 1H), 1.89 (d, J=12.0 Hz, 1H), 1.79-1.76 (m, 1H), 1.70-1.43 (m, 3H). ES-LCMS m/z 553.8, 556.0 $[M-H]^-$.

Intermediate 39: rac-(1R,2R,3R,6S)-2-((2-fluoro-4-(trifluoromethyl)phenyl)carbamoyl)-3-methyl-6-(4-(methylamino)phenyl)cyclohexane-1-carboxylic acid

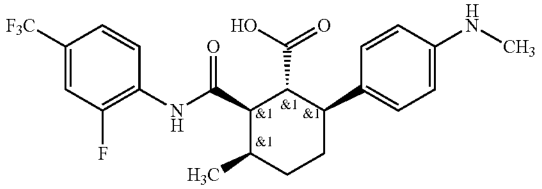 [SMILES: CNc1ccc([C@H]2CC[C@@H](C)[C@@H](C(=O)Nc3ccc(C(F)(F)F)cc3F)[C@@H]2C(=O)O)cc1]

Step 1: 1-bromo-4-((1E)-penta-1,3-dien-1-yl)benzene

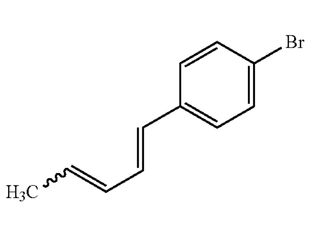

To a mixture of ethyltriphenylphosphonium bromide (66.0 g, 178 mmol) in tetrahydrofuran (250 mL) at 0° C. was added potassium tert-butoxide (1M in THF, 178 mL, 178 mmol), dropwise over 10 min, followed by (E)-3-(4-bromophenyl)acrylaldehyde (25.0 g, 118 mmol) in tetrahydrofuran (250 mL). The reaction was stirred at rt. for 2 h, diluted with water (250 mL) and extracted with EtOAc (100 mL×3). The combined EtOAc layers were washed with water (100 mL×3) and brine (200 mL), dried over sodium sulphate, concentrated and subjected to normal phase purification (0-2% ethyl acetate in petroleum ether) to afford 1-bromo-4-((1E)-penta-1,3-dien-1-yl)benzene (25.5 g, 107 mmol, 91.0% yield) as a white solid. $^1H$ NMR (400 MHz, DMSO-$d_6$) δ 7.52-7.46 (m, 5H), 7.41-7.34 (m, 1H), 7.27-7.17 (m, 1H), 6.89 (dd, J=16.0, 10.5 Hz, 1H), 6.53 (d, J=15.5 Hz, 1H), 6.43 (d, J=16.0 Hz, 1H), 6.27-6.11 (m, 2H), 5.89 (dd, J=15.3, 6.8 Hz, 1H), 5.68-5.56 (m, 1H), 1.84 (dd, J=7.3, 1.8 Hz, 3H), 1.78 (d, J=7.0 Hz, 2H). ES-LCMS m/z poor ionization in MS.

Step 2: rac-dimethyl (1S,2R,3R,4R)-4'-bromo-4-methyl-1,2,3,4-tetrahydro-[1,1'-biphenyl]-2,3-dicarboxylate

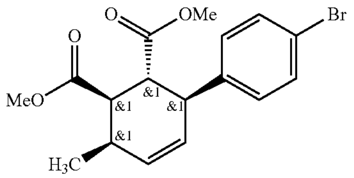 [SMILES: COC(=O)[C@H]1[C@H](C(=O)OC)[C@@H](c2ccc(Br)cc2)C=C[C@H]1C]

A mixture of 1-bromo-4-((1E)-penta-1,3-dien-1-yl)benzene (20 g, 90 mmol) and dimethyl fumarate (12.92 g, 90.00 mmol) in p-xylene (20 mL) was stirred at 140° C. for 72 h, concentrated and subjected to normal phase purification (0-2% ethyl acetate in petroleum ether) to afford rac-dimethyl (1S,2R,3R,4R)-4'-bromo-4-methyl-1,2,3,4-tetrahydro-[1,1'-biphenyl]-2,3-dicarboxylate (7.0 g, 15 mmol, 16% yield) as an off-white solid. $^1H$ NMR (400 MHz, DMSO-$d_6$) δ 7.54-7.47 (m, 4H), 7.09-6.98 (m, 4H), 5.82-5.76 (m, 1H), 5.71-5.65 (m, 1H), 3.92-3.87 (m, 1H), 3.62 (s, 2H), 3.56 (s, 3H), 3.45 (s, 3H), 3.23-3.07 (m, 2H), 2.78-2.60 (m, 2H), 2.35-2.24 (m, 2H), 1.13 (d, J=6.5 Hz, 3H), 0.92 (d, J=7.0 Hz, 2H). ES-LCMS m/z 335.0 $[M-31]^+$.

Step 3: rac-dimethyl (1R,2R,3S,6R)-3-(4-bromophenyl)-6-methylcyclohexane-1,2-dicarboxylate

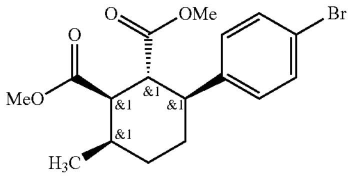 [SMILES: COC(=O)[C@H]1[C@H](C(=O)OC)[C@@H](c2ccc(Br)cc2)CC[C@H]1C]

To a mixture of rac-dimethyl (1 S,2R,3R,4R)-4'-bromo-4-methyl-1,2,3,4-tetrahydro-[1,1-biphenyl]-2,3-dicarboxylate (7 g, 20 mmol) in tetrahydrofuran (30 mL) was added platinum on carbon (5.21 g, 1.33 mmol) under nitrogen. The reaction was placed under hydrogen atmosphere with a bladder (2 atm) and degassed via vacuum evacuation, then backfilling with hydrogen, three times. The mixture was stirred for 16 h, filtered through a Celite pad, concentrated and subjected to normal phase purification (10-20% ethyl acetate in petroleum ether) to afford rac-dimethyl (1R,2R, 3S,6R)-3-(4-bromophenyl)-6-methylcyclohexane-1,2-dicarboxylate (7.0 g, 17 mmol, 90% yield) as an off-white solid. $^1H$ NMR (400 MHz, DMSO-$d_6$) δ 7.48-7.44 (m, 3H), 7.23-7.17 (m, 3H), 3.59 (d, J=5.0 Hz, 5H), 3.40 (s, 2H), 3.19-3.17 (m, 1H), 3.00-2.92 (m, 1H), 2.89-2.80 (m, 1H), 2.58 (d, J=11.5 Hz, 2H), 2.40 (dd, J=6.8, 2.8 Hz, 1H), 1.90-1.74 (m, 3H), 1.58-1.47 (m, 2H), 0.93 (dd, J=6.8, 2.8 Hz, 5H). ES-LCMS m/z poor ionization in MS.

Step 4: rac-(1R,2R,3S,6R)-3-(4-bromophenyl)-2-(methoxycarbonyl)-6-methylcyclohexane-1-carboxylic acid

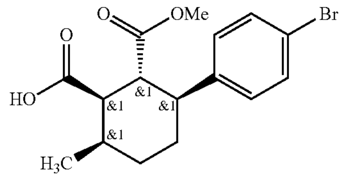 [SMILES: COC(=O)[C@H]1[C@H](C(=O)O)[C@H](C)CC[C@@H]1c1ccc(Br)cc1]

To a mixture of rac-dimethyl (1R,2R,3S,6R)-3-(4-bromophenyl)-6-methylcyclohexane-1,2-dicarboxylate (3.60 g, 9.75 mmol) in tetrahydrofuran (10 mL), methanol (10 mL) and water (10 mL) was then added lithium hydroxide (0.350 g, 14.6 mmol). The reaction was stirred at 60° C. for 16 h, concentrated and subjected to reverse phase purification (0-100% MeCN in $H_2O$, 0.1% ammonium bicarbonate modifier) to afford rac-(1R,2R,3S,6R)-3-(4-bromophenyl)-2-(methoxycarbonyl)-6-methylcyclohexane-1-carboxylic acid (2.2 g, 5.8 mmol, 60% yield) as a white solid. $^1H$ NMR (400 MHz, DMSO-$d_6$) δ 7.44 (d, J=8.5 Hz, 3H), 7.16 (d, J=8.5 Hz, 3H), 3.37 (s, 3H), 2.76-2.62 (m, 4H), 2.45-2.36 (m, 2H), 1.79-1.59 (m, 4H), 1.51-1.43 (m, 2H), 1.26 (m, 1H), 0.91 (d, J=7.0 Hz, 4H). ES-LCMS m/z 355.0 $[M-H]^-$.

Step 5: rac-methyl (1R,2R,3R,6S)-6-(4-bromophenyl)-2-((2-fluoro-4-(trifluoromethyl)phenyl)carbamoyl)-3-methylcyclohexane-1-carboxylate

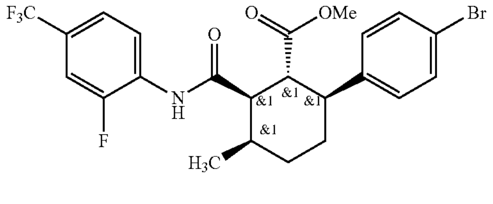 [SMILES: COC(=O)[C@H]1[C@H](C(=O)Nc2ccc(C(F)(F)F)cc2F)[C@H](C)CC[C@@H]1c1ccc(Br)cc1]

To a mixture of rac-(1R,2R,3S,6R)-3-(4-bromophenyl)-2-(methoxycarbonyl)-6-methylcyclohexane-1-carboxylic acid (3.30 g, 9.29 mmol) in acetonitrile (16 mL) were sequentially added 1-methylimidazole (1.48 mL, 18.6 mmol), 2-fluoro-4-(trifluoromethyl)aniline (1.66 g, 9.29 mmol) and TCFH (5.21 g, 18.6 mmol). The reaction was stirred for 16 h. diluted with water (50 mL) and extracted with EtOAc (30 mL×3). The combined EtOAc layers were washed with water (30 mL×3) and brine (20 mL), dried over sodium sulphate, concentrated and subjected to normal phase purification (7-20% ethyl acetate in petroleum ether) to afford rac-methyl (1R,2R,3R,6S)-6-(4-bromophenyl)-2-((2-fluoro-4-(trifluoromethyl)phenyl)carbamoyl)-3-methylcyclohexane-1-carboxylate (1.3 g, 2.4 mmol, 26% yield) as an off-white solid. $^1H$ NMR (400 MHz, DMSO-$d_6$) δ 10.13 (s, 1H), 8.11 (t, J=8.0 Hz, 1H), 7.71 (dd, J=11.0, 2.0 Hz, 1H), 7.53 (br d, J=8.5 Hz, 1H), 7.47 (d, J=8.5 Hz, 2H), 7.23 (d, J=8.5 Hz, 2H), 3.28-3.16 (m, 1H), 3.13 (s, 3H), 2.95 (t, J=11.5 Hz, 1H), 2.69-2.53 (m, 2H), 1.86-1.66 (m, 3H), 1.60-1.50 (m, 1H), 0.97 (d, J=7.0 Hz, 3H). ES-LCMS m/z 513.8 $[M-H]^+$.

Step 6: rac-(1R,2R,3R,6S)-6-(4-bromophenyl)-2-((2-fluoro-4-(trifluoromethyl)phenyl)carbamoyl)-3-methylcyclohexane-1-carboxylic acid

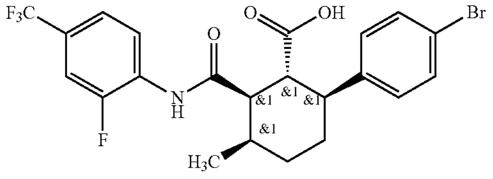 [SMILES: C[C@@H]1CC[C@H](c2ccc(Br)cc2)[C@@H](C(=O)O)[C@@H]1C(=O)Nc1ccc(C(F)(F)F)cc1F]

To a mixture of rac-methyl (1R,2R,3R,6S)-6-(4-bromophenyl)-2-((2-fluoro-4-(trifluoromethyl)phenyl)carbamoyl)-3-methylcyclohexane-1-carboxylate (1.30 g, 2.52 mmol) in 1,2-dichloroethane (10 mL) was added trimethyltin hydroxide (2.28 g, 12.6 mmol), and the reaction was stirred at 80° C. After 16 h, additional trimethyltin hydroxide (0.46 g, 2.52 mmol) was added. After another 16 h, the reaction was quenched with 2 N HCl (1 mL), and solvent was evaporated to obtain crude material. The resulting residue was subjected to normal phase purification (15-30% ethyl acetate in petroleum ether) to afford rac-(1R,2R,3R, 6S)-6-(4-bromophenyl)-2-((2-fluoro-4-(trifluoromethyl) phenyl)carbamoyl)-3-methylcyclohexane-1-carboxylic acid (0.700 g, 1.38 mmol, 55.0% yield) as a white solid. $^1H$ NMR (400 MHz, DMSO-$d_6$) δ 11.61 (s, 1H), 10.10 (s, 1H), 8.17 (t, J=8.0 Hz, 1H), 7.71 (dd, J=11.0, 2.0 Hz, 1H), 7.54 (d, J=8.0 Hz, 1H), 7.45 (d, J=8.5 Hz, 2H), 7.25 (d, J=8.5 Hz, 2H), 3.18 (dd, J=11.3, 4.3 Hz, 1H), 2.90 (t, J=11.5 Hz, 1H), 2.64-2.53 (m, 2H), 1.82-1.65 (m, 3H), 1.58-1.48 (m, 1H), 0.97 (d, J=7.5 Hz, 3H). ES-LCMS m/z 500.0 $[M-H]^-$.

Step 7: rac-(1R,2R,3R,6S)-6-(4-bromophenyl)-2-((2-fluoro-4-(trifluoromethyl)phenyl)carbamoyl)-3-methylcyclohexane-1-carboxylic acid

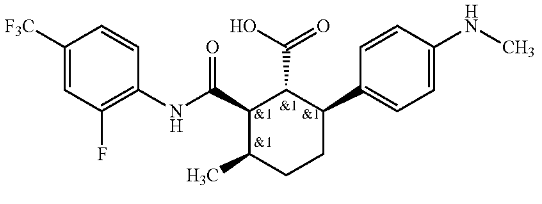 [SMILES: CNc1ccc([C@H]2CC[C@@H](C)[C@@H](C(=O)Nc3ccc(C(F)(F)F)cc3F)[C@@H]2C(=O)O)cc1]

To a mixture of rac-(1R,2R,3R,6S)-6-(4-bromophenyl)-2-((2-fluoro-4-(trifluoromethyl)phenyl)carbamoyl)-3-methylcyclohexane-1-carboxylic acid (0.600 g, 1.20 mmol) and sodium tert-butoxide (344 mg, 3.58 mmol) in dioxane (1.2 mL) was added tBuXPhos Pd G3 (95 mg, 0.120 mmol). The reaction was degassed for 5 min, and methanamine (2M in THF, 11.94 mL, 23.89 mmol) was added. The mixture was microwaved at 100° C. for 1 h, filtered through a Celite pad, concentrated and subjected to reverse phase purification (10-55% MeCN in $H_2O$, 0.1% ammonium bicarbonate modifier) to afford rac-(1R,2R,3R,6S)-6-(4-bromophenyl)-2-((2-fluoro-4-(trifluoromethyl)phenyl)carbamoyl)-3-methylcyclohexane-1-carboxylic acid (350 mg, 0.74 mmol, 62% yield) as an off-white solid. $^1$H NMR (400 MHz, DMSO-$d_6$) δ 10.19 (br s, 1H), 8.17 (t, J=8.0 Hz, 1H), 7.70 (dd, J=11.0, 1.5 Hz, 1H), 7.53 (d, J=8.5 Hz, 1H), 6.95 (d, J=8.5 Hz, 2H), 6.42 (d, J=8.5 Hz, 2H), 5.39 (d, J=5.0 Hz, 1H), 3.11 (dd, J=11.5, 4.0 Hz, 1H), 2.81 (t, J=11.5 Hz, 1H), 2.63 (d, J=3.5 Hz, 3H), 2.42 (br dd, J=8.3, 3.3 Hz, 2H), 1.81-1.60 (m, 3H), 1.52-1.40 (m, 1H), 0.95 (d, J=7.0 Hz, 3H). ES-LCMS m/z 453.0 $[M+H]^+$.

The following compound was synthesized in an analogous manner to the preparation described above (Intermediate 38):

Step 1: 7-bromo-2H-benzo[b][1,4]oxazin-3(4H)-one

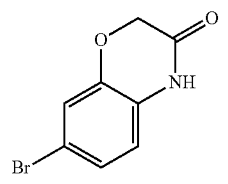

To a mixture of 2-amino-5-bromophenol (50.0 g, 266 mmol) in DMF (500 mL) at 0° C. were added potassium carbonate (74.0 g, 532 mmol) followed by 2-chloroacetyl chloride (30.0 mL, 372 mmol), dropwise. The reaction was stirred at 80° C. for 16 h, then poured into ice cold water (300 mL). The resulting solid was collected by filtration to afford 7-bromo-2H-benzo[b][1,4]oxazin-3(4H)-one (43.0 g, 188 mmol, 71% yield) as a pale yellow solid. $^1$H NMR (400 MHz, DMSO-$d_6$) δ 10.78 (s, 1H), 7.17 (d, J=2.0 Hz, 1H), 7.13 (dd, J=8.4, 2.0 Hz, 1H), 6.84 (d, J=8.4 Hz, 1H), 4.60 (s, 2H). ES-LCMS m/z 227.8 $[M+H]^+$.

| Int. | Structure/Name | $^1$H NMR | LCMS |
|---|---|---|---|
| 40 | 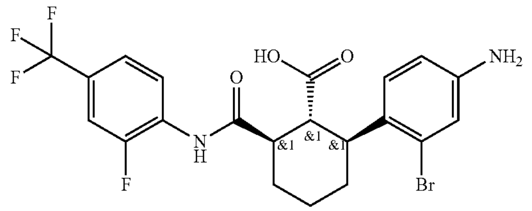 [SMILES: Nc1ccc([C@H]2CCC[C@@H](C(=O)Nc3ccc(C(F)(F)F)cc3F)[C@@H]2C(=O)O)c(Br)c1] rac-(1R,2S,6R)-2-(2-bromo-4-(trifluoromethyl)phenyl)-6-((2-fluoro-4-(trifluoromethyl)phenyl)carbamoyl)cyclohexane-1-carboxylic acid | $^1$H NMR (400 MHz, DMSO-$d_6$) δ 8.35 (t, J = 8.00 Hz, 1H), 7.82 (s, 1H), 7.74-7.71 (m, 1H), 7.64-7.62 (m, 1H), 7.48-7.45 (m, 2H), 3.54 (m, 1H), 2.95 (m, 2H), 2.06 (m, 1H), 1.97-1.93 (m, 2H), 1.64 (m, 2H), 1.44-1.42 (m, 1H) ppm | ES-LCMS m/z 553.8 $[M-2]^-$. |

Intermediate 41: rac-(1R,2S,6R)-2-(3,4-dihydro-2H-benzo[b][1,4]oxazin-7-yl)-6-((2-fluoro-4-(trifluoromethyl)phenyl)carbamoyl)cyclohexane-1-carboxylic acid

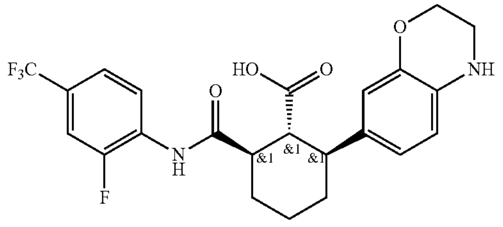 [SMILES: O=C(O)[C@@H]1[C@@H](c2ccc3c(c2)OCCN3)CCC[C@H]1C(=O)Nc1ccc(C(F)(F)F)cc1F]

Step 2: 7-bromo-3,4-dihydro-2H-benzo[b][1,4]oxazine

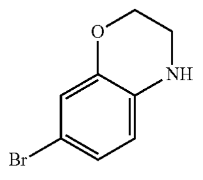

To a mixture of 7-bromo-2H-benzo[b][1,4]oxazin-3(4H)-one (43.0 g, 189 mmol) in tetrahydrofuran (450 mL) at 0° C. was added borane-tetrahydrofuran complex (1M in THF, 377 mL, 377 mmol), dropwise over 20 min. The reaction was stirred at 60° C. After 16 h, the mixture was cooled to 0° C. and methanol (150 mL) added slowly, followed by conc. hydrochloric acid (50 mL). The reaction was again stirred for 2 h at 60° C., cooled to rt and concentrated. The vessel containing the residue was cooled to 0° C., and basified with 10% aq. sodium hydroxide solution to pH=8-9, maintaining temperature at 0° C. The mixture was extracted with ethyl acetate (2×200 mL). The combined organic layers were washed with brine, dried over anhydrous sodium sulphate, filtered and concentrated to afford 7-bromo-3,4-dihydro-2H-benzo[b][1,4]oxazine (54.0 g, 202 mmol, 107% yield) as a brown liquid. $^1H$ NMR (400 MHz, DMSO-$d_6$) δ 6.81-6.78 (m, 2H), 6.52-6.49 (m, 1H), 5.96 (s, 1H), 4.11 (t, J=4.4 Hz, 2H), 3.28-3.25 (m, 2H). ES-LCMS m/z 213.8 $[M-H]^-$ Step 3: tert-butyl 7-bromo-2,3-dihydro-4H-benzo[b 1,4]oxazine-4-carboxylate

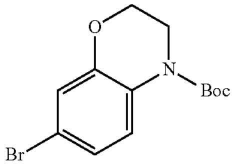 [SMILES: CC(C)(C)OC(=O)N1CCOc2cc(Br)ccc21]

A mixture of 7-bromo-3,4-dihydro-2H-benzo[b][1,4] oxazine (53.0 g, 248 mmol) and BOC-anhydride (287 ml, 124 mmol) was stirred at 100° C. for 16 h. The reaction was poured into ice cold water (300 mL) and extracted with ethyl acetate (3×250 mL). The combined organic layers were washed with brine (300 mL), dried over anhydrous sodium sulphate, filtered, concentrated and subjected to normal phase purification (0-100% ethyl acetate in petroleum ether). The resulting impure material was subjected to reverse phase purification (0-100% MeCN in $H_2O$, 0.1% ammonium bicarbonate modifier) to afford tert-butyl 7-bromo-2,3-dihydro-4H-benzo[b][1,4]oxazine-4-carboxylate (80.0 g, 234 mmol, 95.0% yield) as an off-white solid. $^1H$ NMR (400 MHz, DMSO-$d_6$) δ 7.72 (d, J=8.4 Hz, 1H), 7.07-7.03 (m, 2H), 4.23 (dd, J=5.0, 4.0 Hz, 2H), 3.79 (t, J=4.4 Hz, 2H), 1.46 (s, 9H). ES-LCMS m/z 216.0 $[M-99]^+$ Step 4: tert-butyl (E)-7-(3,3-diethoxyprop-1-en-1-yl)-2,3-dihydro-4H-benzo[b][1,4]oxazine-4-carboxylate

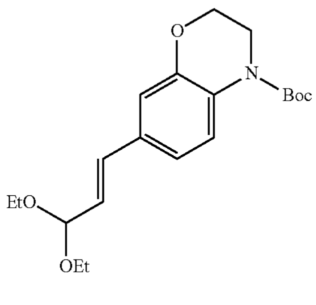 [SMILES: CCOC(/C=C/c1ccc2c(c1)OCCN2C(=O)OC(C)(C)C)OCC]

A mixture of tert-butyl 7-bromo-2,3-dihydro-4H-benzo [b][1,4]oxazine-4-carboxylate (50.0 g, 159 mmol), potassium carbonate (28.6 g, 207 mmol), potassium chloride (11.9 g, 159 mmol), tetrabutyl ammonium acetate (115 g, 318 mmol) and 3,3-diethoxyprop-1-ene (36.4 mL, 239 mmol) in DMF (500 mL) was degassed with nitrogen for 10 min. $Pd(OAc)_2$ (3.57 g, 15.9 mmol) was added, and the reaction was stirred at 90° C. After 16 h, the mixture was diluted with ethyl acetate (200 mL) and filtered over Celite bed. Cold water (500 mL) was added to the filtrate, the layers were separated and the aqueous layer was extracted with ethyl acetate (3×300 mL). The combined ethyl acetate layers were washed with brine (300 mL), dried over anhydrous sodium sulphate, filtered and concentrated to afford tert-butyl (E)-7-(3,3-diethoxyprop-1-en-1-yl)-2,3-dihydro-4H-benzo[b][1,4]oxazine-4-carboxylate (110 g, 100 mmol, 63% yield) as black gum. $^1H$ NMR (400 MHz, DMSO-$d_6$) δ 7.74 (t, J=6.8 Hz, 1H), 7.08-6.97 (m, 3H), 6.56 (d, J=16.0 Hz, 1H), 6.15 (dd, J=16.2, 5.2 Hz, 1H), 4.24-4.19 (m, 2H), 3.78 (t, J=4.8 Hz, 2H), 3.60 (q, J=6.8 Hz, 2H), 3.47 (q, J=6.8 Hz, 2H), 1.49 (s, 9H), 1.14 (t, J=7.20 Hz, 6H). ES-LCMS m/z 290.0 $[M-73]^+$.

Step 5: tert-butyl (E)-7-(3-oxoprop-1-en-1-yl)-2,3-dihydro-4H-benzo[b][1,4]oxazine-4-carboxylate

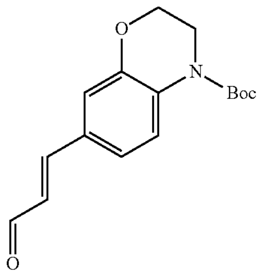 [SMILES: CC(C)(C)OC(=O)N1CCOc2cc(/C=C/C=O)ccc21]

To a mixture of tert-butyl (E)-7-(3,3-diethoxyprop-1-en-1-yl)-2,3-dihydro-4H-benzo[b][1,4]oxazine-4-carboxylate (0.020 kg, 55 mmol) in acetonitrile (100 mL) and water (100 mL) was added amberlyst 15 wet (8.6 g, 27 mmol). The reaction was stirred at 50° C. for 2 h, filtered through Celite (washing with ethyl acetate) and concentrated to ~50% volume to remove acetonitrile. The remaining material was diluted with ethyl acetate (200 mL). The layers were separated, and the aqueous layer was extracted with ethyl acetate (3×200 mL). The combined ethyl acetate layers were washed with brine (300 mL), dried over anhydrous sodium sulphate, filtered, concentrated and subjected to normal phase purification (0-100% ethyl acetate in petroleum ether) to afford tert-butyl (E)-7-(3-oxoprop-1-en-1-yl)-2,3-dihydro-4H-benzo[b][1,4]oxazine-4-carboxylate (5.0 g, 17 mmol, 31% yield) as a pale yellow solid. $^1H$ NMR (400 MHz, DMSO-$d_6$) δ 9.63 (d, J=8.0 Hz, 1H), 7.91 (d, J=8.8 Hz, 1H), 7.62 (d, J=16.0 Hz, 1H), 7.29-7.26 (m, 2H), 6.77 (dd, J=15.8, 8.0 Hz, 1H), 4.25 (t, J=4.8 Hz, 2H), 3.83 (t, J=4.4 Hz, 2H), 1.51 (s, 9H). ES-LCMS m/z 290.0 $[M+H]^+$ Step 6: tert-butyl (E)-7-(buta-1,3-dien-1-yl)-2,3-dihydro-4H-benzo[b][1,4]oxazine-4-carboxylate

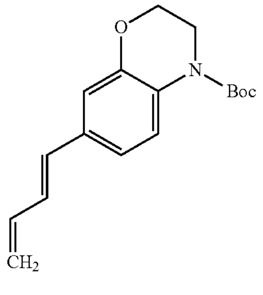 [SMILES: C=C/C=C/c1ccc2c(c1)OCCN2C(=O)OC(C)(C)C]

To a mixture of methyltriphenylphosphonium bromide (56.8 g, 159 mmol) in tetrahydrofuran (230 mL) at 0° C. was added potassium tert-butoxide (1M in THF, 159 mL, 159 mmol), dropwise over 20 min. After 10 min, a solution of tert-butyl (E)-7-(3-oxoprop-1-en-1-yl)-2,3-dihydro-4H-benzo[b][1,4]oxazine-4-carboxylate (23.0 g, 79.0 mmol) in THF (50 mL) was added, dropwise over 10 min. The reaction was slowly warmed to rt, stirred for 2 h, diluted water (300 mL) and extracted with ethyl acetate (3×300 mL). The combined ethyl acetate layers were washed with brine (300 mL), dried over anhydrous sodium sulphate, filtered, concentrated and subjected to normal phase purification (0-100% ethyl acetate in petroleum ether) to afford tert-butyl (E)-7-(buta-1,3-dien-1-yl)-2,3-dihydro-4H-benzo[b][1,4]oxazine-4-carboxylate (19.0 g, 65.0 mmol, 82.0% yield) as an off-white solid. $^1$H NMR (400 MHz, DMSO-$d_6$) δ 7.74 (d, J=8.4 Hz, 1H), 7.01 (dd, J=8.8, 2.0 Hz, 1H), 6.97 (d, J=2.0 Hz, 1H), 6.83 (dd, J=15.6, 10.4 Hz, 1H), 6.55-6.45 (m, 2H), 535 (d, J=16.0 Hz, 1H). 5.16 (d, J=9.6 Hz, 1H), 4.21 (t, J=4.8 Hz, 2H), 3.79 (t, J=4.4 Hz, 2H), 1.49 (s, 9H). ES-LCMS m/z 188.2 $[M-99]^+$.

Step 7: rac-dimethyl (1R,2R,3S)-3-(4-(tert-butoxycarbonyl)-3,4-dihydro-2H-benzo[b][1,4]oxazin-7-yl)cyclohex-4-ene-1,2-dicarboxylate

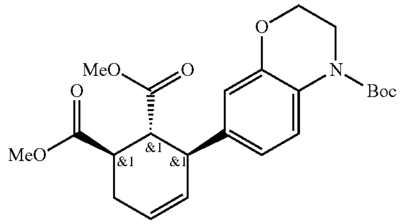 [SMILES: COC(=O)[C@@H]1[C@@H](c2ccc3c(c2)OCCN3C(=O)OC(C)(C)C)C=CC[C@H]1C(=O)OC]

To a mixture of tert-butyl (E)-7-(buta-1,3-dien-1-yl)-2,3-dihydro-4H-benzo[b][1,4]oxazine-4-carboxylate (19 g, 66 mmol) in p-xylene (200 mL) was added dimethyl fumarate (9.53 g, 66.0 mmol). The reaction mixture was stirred at 140° C. overnight, concentrated and subjected to normal phase purification (0-100% ethyl acetate in petroleum ether) to afford rac-dimethyl (1R,2R,3S)-3-(4-(tert-butoxycarbonyl)-3,4-dihydro-2H-benzo[b][1,4]oxazin-7-yl)cyclohex-4-ene-1,2-dicarboxylate (22 g, 51 mmol, 77% yield) as an off-white solid. $^1$H NMR (400 MHz, DMSO-$d_6$) 7.68 (d, J=8.00 Hz, 1H), 6.63-6.53 (m, 2H), 5.86-5.81 (m, 1H), 5.56-5.52 (m, 1H), 4.20-4.18 (m, 2H), 3.84-372 (m, 2H), 3.59 (s, 3H), 3.42 (s, 3H), 2.94-2.88 (m, 1H), 2.64 (t, J=10.80 Hz, 1H), 2.48-2.36 (m, 2H), 1.48 (s, 9H), one proton obscured by solvent peaks. ES-LCMS m/z 449.8 $[M+H_2O]^+$.

Step 8: rac-dimethyl (1R,2R,3S)-3-(4-(tert-butoxycarbonyl)-3,4-dihydro-2H-benzo[b][1,4]oxazin-7-yl)cyclohexane-1,2-dicarboxylate

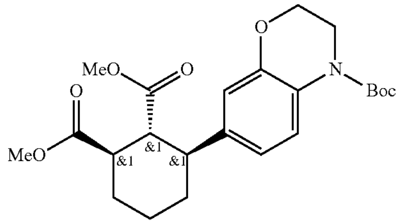 [SMILES: COC(=O)[C@@H]1[C@@H](c2ccc3c(c2)OCCN3C(=O)OC(C)(C)C)CCC[C@H]1C(=O)OC]

A mixture of rac-dimethyl (1R,2R,3S)-3-(4-(tert-butoxycarbonyl)-3,4-dihydro-2H-benzo[b][1,4]oxazin-7-yl)cyclohex-4-ene-1,2-dicarboxylate (22 g, 51 mmol) in ethyl acetate (250 mL) was purged with nitrogen for 1 min. Palladium on carbon (5.4 g, 5.1 mmol) was added, and the reaction was stirred under hydrogen gas (bladder pressure) at 25° C. After 16 h, the mixture was filtered through Celite, washing with methanol (100 mL) and ethyl acetate (300 mL). The filtrate was concentrated to afford rac-dimethyl (1R,2R,3S)-3-(4-(tert-butoxycarbonyl)-3,4-dihydro-2H-benzo[b][1,4]oxazin-7-yl)cyclohexane-1,2-dicarboxylate (19 g, 41 mmol, 80% yield) as an off-white solid. $^1$H NMR (400 MHz, DMSO-$d_6$) δ 7.65 (s, 1H), 6.71-6.66 (m, 2H), 4.18 (t, J=3.6 Hz, 2H), 3.77-3.74 (m, 2H), 3.57 (s, 3H), 3.33 (s, 3H), 3.22-3.15 (m, 1H), 2.68-2.59 (m, 2H), 2.00-1.92 (m, 1H), 1.82-1.53 (m, 3H), 1.48 (s, 9H), two protons obscured by solvent peaks. ES-LCMS m/z 346.2 $[M-87]^+$.

Step 9: rac-(1R,2R,3S)-3-(4-(tert-butoxycarbonyl)-3,4-dihydro-2H-benzo[b][1,4]oxazin-7-yl)-2-(methoxycarbonyl)cyclohexane-1-carboxylic acid

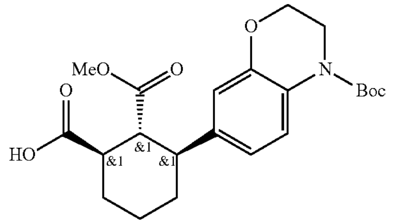 [SMILES: COC(=O)[C@@H]1[C@@H](c2ccc3c(c2)OCCN3C(=O)OC(C)(C)C)CCC[C@H]1C(=O)O]

To a mixture of rac-dimethyl (1R,2R,3S)-3-(4-(tert-butoxycarbonyl)-3,4-dihydro-2H-benzo[b][1,4]oxazin-7-yl)cyclohexane-1,2-dicarboxylate (8.5 g, 19 mmol) in tetrahydrofuran (30 mL) and methanol (30 mL) was added lithium hydroxide monohydrate (1.4 g, 59 mmol) in water (30 mL). After 16 h, the reaction was concentrated and subjected to reverse phase purification (0-100% MeCN in $H_2O$, 0.1% ammonium bicarbonate modifier) to afford rac-(1R,2R,3S)-3-(4-(tert-butoxycarbonyl)-3,4-dihydro-2H-benzo[b][1,4]oxazin-7-yl)-2-(methoxycarbonyl)cyclohexane-1-carboxylic acid (6.6 g, 16 mmol, 79% yield) as an off-white solid. $^1$H NMR (400 MHz, DMSO-$d_6$) δ 7.60 (d, J=7.6 Hz, 1H), 6.69-6.57 (m, 2H), 4.17 (t, J=4.8 Hz, 2H), 3.80-3.70 (m, 2H), 3.18 (s, 3H), 2.49-2.42 (m, 1H), 2.18-2.09 (m, 1H), 2.01-1.92 (m, 1H), 1.75 (d, J=11.6 Hz, 1H), 1.64 (d, J=11.2 Hz, 1H), 1.48 (s, 9H), 1.48-1.19 (n, 3H), two protons obscured by solvent peaks. ES-LCMS m/z 418.2 $[M-H]^-$.

Step 10: rac-tert-butyl 7-((1R,2S,3S)-3-((2-fluoro-4-(trifluoromethyl)phenyl)carbamoyl)-2-(methoxycarbonyl)cyclohexyl)-2,3-dihydro-4H-benzo[b][1,4]oxazine-4-carboxylate

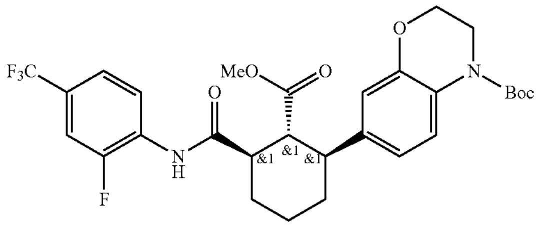 [SMILES: COC(=O)[C@@H]1[C@@H](c2ccc3c(c2)OCCN3C(=O)OC(C)(C)C)CCC[C@H]1C(=O)Nc1ccc(C(F)(F)F)cc1F]

To a mixture of rac-(1R,2R,3S)-3-(4-(tert-butoxycarbonyl)-3,4-dihydro-2H-benzo[b][1,4]oxazin-7-yl)-2-(methoxycarbonyl)cyclohexane-1-carboxylic acid (0.750 g, 1.79 mmol) in DMF (10 mL) were added 2-fluoro-4-(trifluoromethyl)aniline (320 mg, 1.79 mmol) followed by N-(chloro(dimethylamino)methylene)-N-methylmethanaminium hexafluorophosphate(V) (1003 mg, 3.580 mmol) and 1-methyl-1H-imidazole (0.57 mL, 7.2 mmol). After 16 h, the reaction was added to ice cold water (50 mL) and stirred for 10 mins. The layers were separated, and the aqueous layer was extracted with ethyl acetate (3×50 mL). The combined ethyl acetate layers were washed with brine (25 mL), dried over anhydrous sodium sulphate, filtered, concentrated and subjected to reverse phase purification (30-100% MeCN in $H_2O$, 0.1% ammonium bicarbonate modifier). The partially pure material was further purified by Achiral-Prep-SFC (Column: YMC EP-2 250×30 mm, 5 μm; 90:10 $CO_2$:methanol) to afford rac-tert-butyl 7-((1R,2S,3S)-3-((2-fluoro-4-(trifluoromethyl)phenyl)carbamoyl)-2-(methoxycarbonyl)cyclohexyl)-2,3-dihydro-4H-benzo[b][1,4]oxazine-4-carboxylate (180 mg, 0.30 mmol, 17% yield) as an off-white solid. $^1$H NMR (400 MHz, DMSO-$d_6$) δ 8.17 (t, J=8.0 Hz, 1H), 7.68 (d, J=7.2 Hz, 1H), 7.53-7.47 (m, 2H), 6.75-6.72 (m, 2H), 4.22 (t, J=4.4 Hz, 2H), 3.88-3.81 (m, 2H), 3.35 (s, 3H), 3.02-2.96 (m, 1H), 2.91 (t, J=11.2 Hz, 1H), 2.78-2.69 (m, 1H), 2.13-2.11 (m, 1H), 2.01-2.00 (m, 1H), 1.91-1.88 (m, 1H), 1.71-1.62 (m, 3H), 0.55 (s, 9H). ES-LCMS m/z 579.0 $[M-H]^-$.

Step 11: rac-(1R,2S,6R)-2-(3,4-dihydro-2H-benzo[b][1,4]oxazin-7-yl)-6-((2-fluoro-4-(trifluoromethyl)phenyl)carbamoyl)cyclohexane-1-carboxylic acid

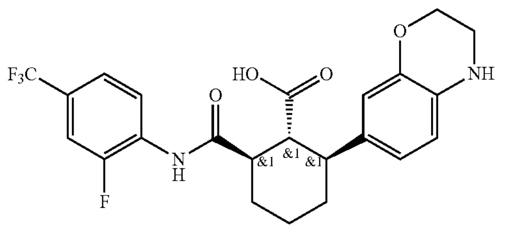 [SMILES: O=C(O)[C@@H]1[C@@H](c2ccc3c(c2)OCCN3)CCC[C@H]1C(=O)Nc1ccc(C(F)(F)F)cc1F]

To a mixture of rac-tert-butyl 7-((1R,2S,3S)-3-((2-fluoro-4-(trifluoromethyl)phenyl)carbamoyl)-2-(methoxycarbonyl)cyclohexyl)-2,3-dihydro-4H-benzo[b][1,4]oxazine-4-carboxylate (160 mg, 0.28 mmol) in dichloromethane (15 mL) at 0° C. was added boron tribromide (1M in dichloromethane, 1.65 mL, 1.65 mmol). The reaction was stirred at rt for 1 h, quenched with ice water (10 mL), concentrated and subjected to reverse phase purification (0-100% MeCN in $H_2O$, 0.1% ammonium bicarbonate modifier) to afford rac-(1R,2S,6R)-2-(3,4-dihydro-2H-benzo[b][1,4]oxazin-7-yl)-6-((2-fluoro-4-(trifluoromethyl)phenyl)carbamoyl)cyclohexane-1-carboxylic acid (55 mg, 0.10 mmol, 39% yield) as an off-white solid. $^1$H NMR (400 MHz, DMSO-$d_6$) δ 8.23 (t, J=8.0 Hz, 1H), 7.51-7.46 (m, 2H), 6.64-6.61 (m, 2H), 6.56 (d, J=8.0 Hz, 1H), 4.19-4.17 (m, 2H), 3.30-2.93 (m, 1H), 2.83 (t, J=11.2 Hz, 1H), 2.69-2.63 (m, 1H), 2.11-2.07 (m, 1H), 1.99-1.97 (m, 1H), 1.87-1.84 (m, 1H), 1.72-1.54 (m, 3H), five protons obscured by solvent peaks. ES-LCMS m/z 465.0 $[M-H]^-$.

Intermediate 42: rac-methyl (1R,2R,6R)-6-(4-bromophenyl)-2-fluoro-2-((4-(trifluoromethyl)phenyl)carbamoyl)cyclohexane-1-carboxylate with rac-methyl (1R,2S,6R)-2-(4-bromophenyl)-1-fluoro-6-((4-(trifluoromethyl)phenyl)carbamoyl)cyclohexane-1-carboxylate

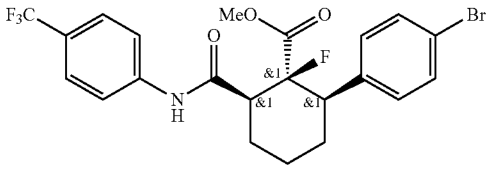

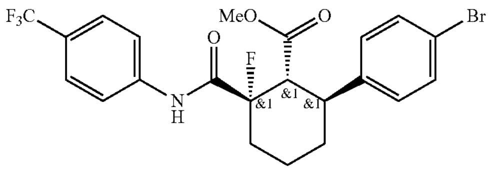

Step-1: dimethyl 2-fluorofumarate

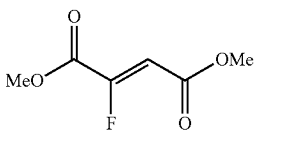 [SMILES: COC(=O)/C=C(\F)C(=O)OC]

To a mixture of dimethyl but-2-ynedioate (0.050 kg, 350 mmol) in in DMF (750 mL), acetonitrile (750 mL) and water (25 mL) was added potassium fluoride (40.9 g, 704 mmol). The reaction was heated to 80° C. for 6 h, diluted with EtOAc (1000 mL), washed with water (2×750 mL) and brine (500 mL), dried over anhydrous sodium sulfate, filtered, concentrated and subjected to normal phase chromatography, eluting with 0-10% of EtOAc in petroleum ether, to afford dimethyl 2-fluorofumarate (11 g, 67 mmol, 19% yield) as an off-white gummy solid. $^1$H NMR (400 MHz, DMSO-$d_6$) δ 6.37 (d, J=28.8 Hz, 1H), 3.91 (s, 3H), 3.82 (s, 3H). ES-GCMS m/z 162.0 $[M+H]^+$.

Step 2: rac-dimethyl (1R,2R,3R)-4'-bromo-3-fluoro-1,2,3,4-tetrahydro-[1,1'-biphenyl]-2,3-dicarboxylate with rac-dimethyl (1R,2S,3S)-4'-bromo-2-fluoro-1,2,3,4-tetrahydro-[1,1'-biphenyl]-2,3-dicarboxylate

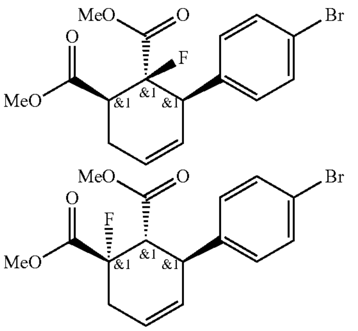

A mixture of (E)-1-bromo-4-(buta-1,3-dien-1-yl)benzene Intermediate 1 Step 1 (5.000 g, 23.91 mmol) and dimethyl 2-fluorofumarate (4.65 g, 28.7 mmol) was heated to 145° C. for 48 h and subjected to reverse phase purification (0-100% MeCN in $H_2O$, with 0.1% formic acid modifier) to afford rac-dimethyl (1R,2R,3R)-4'-bromo-3-fluoro-1,2,3,4-tetrahydro-[1,1'-biphenyl]-2,3-dicarboxylate with rac-dimethyl (1R,2S,3S)-4'-bromo-2-fluoro-1,2,3,4-tetrahydro-[1,1'-biphenyl]-2,3-dicarboxylate (2.0 g, 2.6 mmol, 11% yield) as an off-white gummy solid mixture of regioisomers. $^1$H NMR (400 MHz, CHLOROFORM-d) δ 7.47-7.42 (m, 2H), 7.07-7.00 (m, 2H), 6.11-5.95 (m, 1H), 5.70-5.55 (m, 1H), 3.94-3.84 (m, 1H), 3.68 (s, 3H), 3.44 (s, 3H), 3.28-3.11 (m, 1H), 2.66-2.57 (m, 1H), 2.53-2.42 (m, 1H). ES-UPLC m/z 393.0 $[M+Na]^+$.

Step 3: rac-dimethyl (1R,2R,3R)-3-(4-bromophenyl)-1-fluorocyclohexane-1,2-dicarboxylate with rac-dimethyl (1R,2R,6S)-6-(4-bromophenyl)-1-fluorocyclohexane-1,2-dicarboxylate

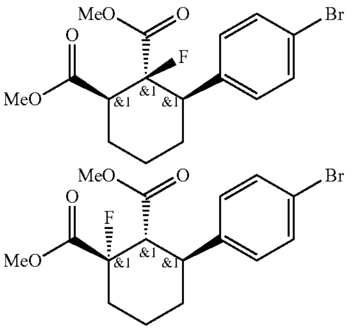

To a mixture of rac-dimethyl (1R,2R,3R)-4'-bromo-3-fluoro-1,2,3,4-tetrahydro-[1,1'-biphenyl]-2,3-dicarboxylate with rac-dimethyl (1R,2S,3S)-4'-bromo-2-fluoro-1,2,3,4-tetrahydro-[1,1'-biphenyl]-2,3-dicarboxylate (1.1 g, 3.0 mmol) in dichloromethane (100 mL) was added Crabtree's catalyst (0.36 g, 0.45 mmol). The reaction was stirred under an $H_2$ atmosphere (1 kg bladder pressure) for 16 h, diluted with DCM (50 mL), washed with water (50 mL) and brine (50 mL), dried over anhydrous sodium sulfate, filtered, and concentrated to afford rac-dimethyl (1R,2R,3R)-3-(4-bromophenyl)-1-fluorocyclohexane-1,2-dicarboxylate with rac-dimethyl (1R,2R,6S)-6-(4-bromophenyl)-1-fluorocyclohexane-1,2-dicarboxylate (1.3 g, 1.52 mmol, 51% yield)) as an orange gum mixture of regiosiomers. $^1$H NMR (400 MHz, CHLOROFORM-d) δ 7.44-7.38 (m, 2H), 7.23-7.17 (m, 1H), 7.15-7.07 (m, 1H), 3.73 (s, 3H), 3.72-3.69 (m, 1H), 3.68 (s, 3H), 3.04-2.88 (m, 1H), 2.57-2.44 (m, 1H), 2.41-2.27 (m, 1H), 2.24-2.13 (m, 1H), 2.10-1.87 (m, 3H). ES-LCMS m/z 352.8$[M+H-F]^+$.

Step 4: rac-(1R,2R,3R)-3-(4-bromophenyl)-1-fluoro-2-(methoxycarbonyl)cyclohexane-1-carboxylic acid with rac-(1R,2R,3S)-3-(4-bromophenyl)-2-fluoro-2-(methoxycarbonyl)cyclohexane-1-carboxylic acid

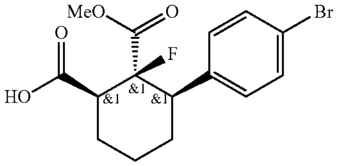

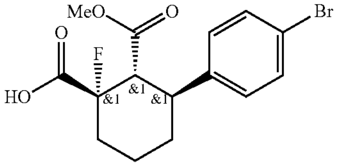

To a mixture of rac-dimethyl (1R,2R,3R)-3-(4-bromophenyl)-1-fluorocyclohexane-1,2-dicarboxylate with rac-dimethyl (1R,2R,6S)-6-(4-bromophenyl)-1-fluorocyclohexane-1,2-dicarboxylate (1.3 g, 3.5 mmol) in tetrahydrofuran (25 mL) and water (25 mL) was added lithiumhydroxide monohydrate (0.440 g, 10.4 mmol). The reaction was stirred for 2 h, acidified with 10% citric acid solution and extracted with EtOAc (2×50 mL). The combined organic layers were washed with brine (50 mL), dried over anhydrous sodium sulfate, filtered and concentrated to afford rac-(1R,2R,3R)-3-(4-bromophenyl)-1-fluoro-2-(methoxycarbonyl)cyclohexane-1-carboxylic acid with rac-(1R,2R,3S)-3-(4-bromophenyl)-2-fluoro-2-(methoxycarbonyl)cyclohexane-1-carboxylic acid (1.2 g, 1.07 mmol, 31% yield) as a colourless gum mixture of regioisomers. $^1$H NMR (400 MHz, DMSO-$d_6$) δ 12.71 (br s, 1H), 7.54-7.43 (m, 2H), 7.29-7.07 (m, 2H), 3.44 (s, 3H), 3.25-3.01 (m, 1H), 2.40-2.20 (m, 1H), 1.93-1.73 (m, 3H), 1.71-1.43 (m, 3H). ES-LCMS m/z 356.8$[M+H]^+$.

Step 5: rac-methyl (1R,2R,6R)-6-(4-bromophenyl)-2-fluoro-2-((4-(trifluoromethyl)phenyl)carbamoyl)cyclohexane-1-carboxylate with rac-methyl (1R,2S,6R)-2-(4-bromophenyl)-1-fluoro-6-((4-(trifluoromethyl)phenyl)carbamoyl)cyclohexane-1-carboxylate

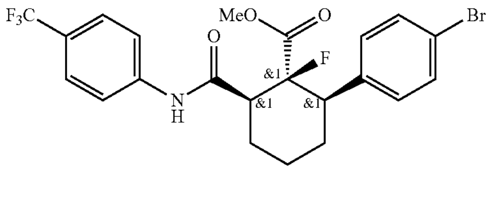

-continued

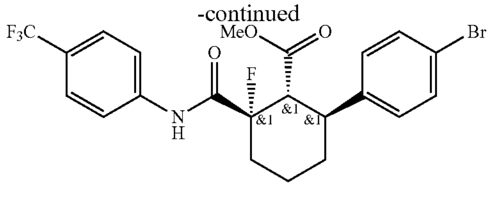

To a mixture of rac-(1R,2R,3R)-3-(4-bromophenyl)-1-fluoro-2-(methoxycarbonyl)cyclohexane-1-carboxylic acid with rac-(1R,2R,3S)-3-(4-bromophenyl)-2-fluoro-2-(methoxycarbonyl)cyclohexane-1-carboxylic acid (1.2 g, 3.3 mmol) in acetonitrile (25 mL) under at 0° C. was added 4-(trifluoromethyl)aniline (0.59 g, 3.67 mmol) and 1-methyl-1H-imidazole (0.82 g, 10.02 mmol). After 10 min N-(chloro(dimethylamino)methylene)-N-methylmethanaminium hexafluorophosphate(V) (1.22 g, 4.34 mmol) was added, and the reaction mixture was stirred at rt. After 16 h, the reaction was quenched with water (25 mL) and diluted with EtOAc (50 mL). The organic layer was separated, washed with brine (30 mL), dried over anhydrous sodium sulfate, filtered, concentrated and subjected to normal phase chromatography, eluting with 0-50% EtOAc in petroleum ether, to afford rac-methyl (1R,2R,6R)-6-(4-bromophenyl)-2-fluoro-2-((4-(trifluoromethyl)phenyl)carbamoyl)cyclohexane-1-carboxylate with rac-methyl (1R,2S,6R)-2-(4-bromophenyl)-1-fluoro-6-((4-(trifluoromethyl)phenyl)carbamoyl)cyclohexane-1-carboxylate (150 mg, 0.090 mmol, 3.0% yield) as a yellow gum mixture of regioisomers. $^1$H NMR (400 MHz, DMSO-$d_6$) δ 7.78-7.63 (m, 4H), 7.54-7.48 (m, 2H), 7.24-7.16 (m, 2H), 3.37-3.35 (m, 2H), 2.68 (s, 3H), 2.00-1.89 (m, 4H), 1.69-1.59 (m, 2H). ES-LCMS m/z 501.8 $[M+H]^+$.

Intermediate 43: rac-(1R,2R,6S)-2-((2-fluoro-4-(trifluoromethyl)phenyl)carbamoyl)-6-(2-formyl-4-(trifluoromethyl)phenyl)cyclohexane-1-carboxylic acid

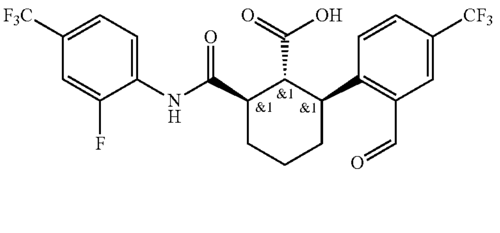 [SMILES: O=Cc1cc(C(F)(F)F)ccc1[C@H]1CCC[C@@H](C(=O)Nc2ccc(C(F)(F)F)cc2F)[C@@H]1C(=O)O]

Step 1: rac-(1R,2R,6S)-2-((2-fluoro-4-(trifluoromethyl)phenyl)carbamoyl)-6-(4-(trifluoromethyl)-2-vinylphenyl)cyclohexane-1-carboxylic acid

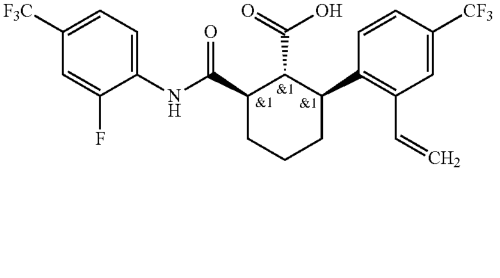 [SMILES: C=Cc1cc(C(F)(F)F)ccc1[C@H]1CCC[C@@H](C(=O)Nc2ccc(C(F)(F)F)cc2F)[C@@H]1C(=O)O]

To a mixture of (1R,2S,6R)-2-(2-bromo-4-(trifluoromethyl)phenyl)-6-((2-fluoro-4-(trifluoromethyl)phenyl)carbamoyl)cyclohexane-1-carboxylic acid Intermediate 40 (150 mg, 0.27 mmol) and trifluoro(vinyl)-14-borane, potassium salt (72 mg, 0.54 mmol) in dioxane (2.4 mL) and water (0.6 mL) was added potassium carbonate (112 mg, 0.810 mmol). The reaction was degassed for 10 min and cooled to 0° C. $PdCl_2$(dppf)-$CH_2Cl_2$ adduct (22.0 mg, 0.0270 mmol) was added, and the mixture was stirred at 100° C. After 16 h, the reaction was concentrated and subjected to reverse phase purification (10-100% MeCN in $H_2O$, 0.1% ammonium bicarbonate modifier) to afford rac-(1R,2R,6S)-2-((2-fluoro-4-(trifluoromethyl)phenyl)carbamoyl)-6-(4-(trifluoromethyl)-2-vinylphenyl)cyclohexane-1-carboxylic acid (0.010 g, 0.17 mmol, 63% yield) as a yellow solid. $^1$H NMR (400 MHz, DMSO-$d_6$) δ 10.11 (br s, 1H), 8.21 (t, J=7.8 Hz, 1H), 7.87-7.39 (m, 6H), 7.10 (dd, J=16.8, 11.3 Hz, 1H), 5.76 (d, J=18.0 Hz, 1H), 5.46 (d, J=11.5 Hz, 1H), 3.19 (d, J=2.0 Hz, 1H), 3.08-2.92 (m, 2H), 2.03 (d, J=9.0 Hz, 1H), 1.91-1.83 (m, 1H), 1.71-1.49 (m, 4H). ES-LCMS m/z 502.0 $[M-H]^-$.

Step 2: rac-(1R,2R,6S)-2-((2-fluoro-4-(trifluoromethyl)phenyl)carbamoyl)-6-(2-formyl-4-(trifluoromethyl)phenyl)cyclohexane-1-carboxylic acid

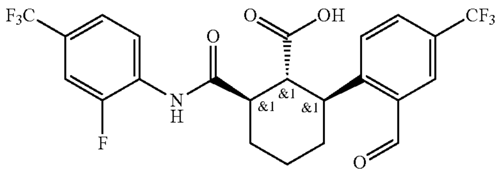 [SMILES: O=Cc1cc(C(F)(F)F)ccc1[C@H]1CCC[C@@H](C(=O)Nc2ccc(C(F)(F)F)cc2F)[C@@H]1C(=O)O]

To a mixture of rac-(1R,2R,6S)-2-((2-fluoro-4-(trifluoromethyl)phenyl)carbamoyl)-6-(4-(trifluoromethyl)-2-vinylphenyl)cyclohexane-1-carboxylic acid (0.090 g, 0.18 mmol) and 2,6 lutidine (38 mg, 0.36 mmol) in 1,4-dioxane (5.4 mL) was added osmium tetroxide (5.6 μl, 0.018 mmol) followed by sodium periodate (190 mg, 0.89 mmol) dissolved in water (2 mL). After 30 min, the reaction was concentrated and subjected to reverse phase purification (10-100% MeCN in $H_2O$, 0.1% ammonium bicarbonate modifier) to afford rac-(1R,2R,6S)-2-((2-fluoro-4-(trifluoromethyl)phenyl)carbamoyl)-6-(2-formyl-4-(trifluoromethyl)phenyl)cyclohexane-1-carboxylic acid (73 mg, 0.14 mmol, 77% yield) as a brown solid. $^1$H NMR (400 MHz, DMSO-$d_6$) δ 11.91 (br s, 1H), 10.39 (s, 1H), 10.14 (s, 1H), 8.20 (t, J=8.3 Hz, 1H), 8.08 (s, 1H), 8.04-7.93 (m, 2H), 7.71 (dd, J=11.0, 1.5 Hz, 1H), 7.55 (br d, J=8.5 Hz, 1H), 4.15-3.93 (m, 1H), 3.11-2.93 (m, 2H), 2.09-1.52 (m, 6H). ES-LCMS m/z 504.0 $[M-H]^-$.

Intermediate 44: rac-(3aR,7S,7aS)-7-(4-bromophenyl)-5-(methoxymethyl)hexahydroisobenzofuran-1(3H)-one

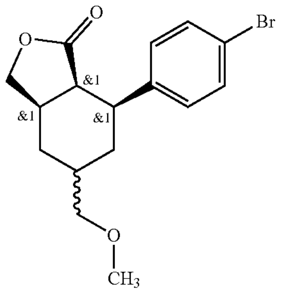 [SMILES: COCC1C[C@H]2COC(=O)[C@H]2[C@@H](c2ccc(Br)cc2)C1]

Step 1: rac-(3aR,7S,7aS)-7-(4-bromophenyl)-5-(methoxymethylene)hexahydroisobenzofuran-1(3H)-one

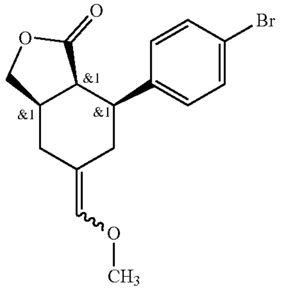 [SMILES: COC=C1C[C@H]2COC(=O)[C@H]2[C@@H](c2ccc(Br)cc2)C1]

To a mixture of (methoxymethyl)triphenylphosphonium chloride (6.65 g, 19.4 mmol) in tetrahydrofuran (100 mL) at 0° C. was added potassium 2-methylpropan-2-olate (16.17 mL, 16.17 mmol, 1M in THF). After 1 h, rac-(3aR,7S,7aS)-7-(4-bromophenyl)tetrahydroisobenzofuran-1,5(3H,4H)-dione Intermediate 8 Step 5 (5.0 g, 16.17 mmol) was added portionwise. The reaction was stirred at rt for 14 h, diluted with water (15 mL), concentrated and subjected to reverse phase purification (0-100% MeCN in $H_2O$, 0.1% ammonium bicarbonate modifier) to afford rac-(3aR,7S,7aS)-7-(4-bromophenyl)-5-(methoxymethylene)hexahydroisobenzofuran-1(3H)-one (2.0 g, 5.0 mmol, 31% yield) as an off-white solid. (E/Z mixture). $^1H$ NMR (400 MHz, DMSO-$d_6$) δ 7.46 (d, J=8.5 Hz, 2H), 7.28 (dd, J=8.5, 6.0 Hz, 2H), 6.09-5.96 (m, 1H), 4.19 (td, J=9.0, 4.5 Hz, 1H), 3.96-3.85 (m, 1H), 3.51 (s, 3H), 3.00 (ddt, J=17.4, 13.1, 4.3 Hz, 1H), 2.85 (dd, J=14.0, 6.0 Hz, 1H), 2.77-2.61 (m, 1H), 2.39-2.21 (m, 1H), 2.19-2.06 (m, 1H), 1.74 (dd, J=13.5, 10.5 Hz, 1H), 1.48 (t, J=13.3 Hz, 1H). ES-LCMS m/z poor ionization.

Step 2: rac-(3aR,7S,7aS)-7-(4-bromophenyl)-5-(methoxymethyl)hexahydroisobenzofuran-1(3H)-one

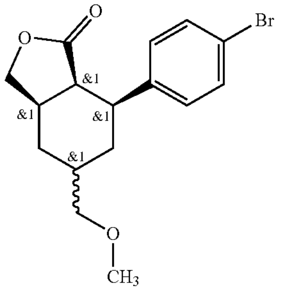 [SMILES: COCC1C[C@H]2COC(=O)[C@H]2[C@@H](c2ccc(Br)cc2)C1]

To a mixture of rac-(3aR,7S,7aS)-7-(4-bromophenyl)-5-(methoxymethylene)hexahydroisobenzofuran-1(3H)-one (2.00 g, 5.93 mmol) in tetrahydrofuran (50 mL) was added platinum on carbon 10% (0.814 g, 0.415 mmol), under nitrogen. The reaction was placed under a hydrogen atmosphere with a bladder (1 atm). The reaction was degassed via vacuum evacuation, then backfilling with hydrogen, and this process was repeated three times. The mixture was stirred at rt for 16 h, filtered through a Celite pad, concentrated and subjected to reverse phase purification (50-70% MeCN in $H_2O$, 0.1% ammonium bicarbonate modifier) to afford rac-(3aR,7S,7aS)-7-(4-bromophenyl)-5-(methoxymethyl)hexahydroisobenzofuran-1(3H)-one (1.5 g, 4.0 mmol, 67% yield) as an off-white solid. $^1H$ NMR (400 MHz, DMSO-$d_6$) δ 7.45 (d, J=8.5 Hz, 2H), 7.28-7.23 (m, 2H), 4.20-4.15 (m, 1H), 3.89-3.81 (m, 1H), 3.41 (t, J=8.0 Hz, 1H), 3.28-3.19 (m, 5H), 3.13-3.04 (m, 1H), 2.68-2.58 (m, 1H), 1.94-1.66 (m, 3H), 1.33-1.17 (m, 1H), 0.85 (q, J=12.5 Hz, 1H). ES-LCMS m/z 339.0 $[M+H]^+$.

Intermediate 45: rac-(1R,2R,6S)-2-((2-fluoro-4-(trifluoromethyl)phenyl)carbamoyl)-4-(methoxymethyl)-6-(4-(methylamino)phenyl)cyclohexane-1-carboxylic acid

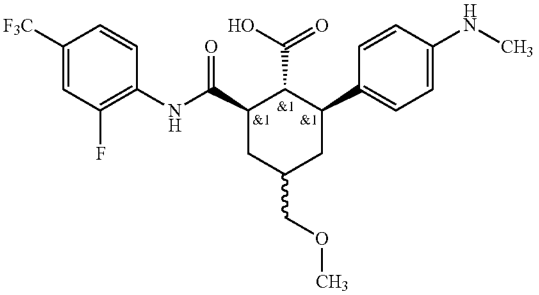 [SMILES: CNc1ccc([C@H]2CC(COC)C[C@@H](C(=O)Nc3ccc(C(F)(F)F)cc3F)[C@@H]2C(=O)O)cc1]

Step 1: rac-(1R,2S,6R)-2-(4-bromophenyl)-6-(hydroxymethyl)-4-(methoxymethyl)cyclohexane-1-carboxylic acid

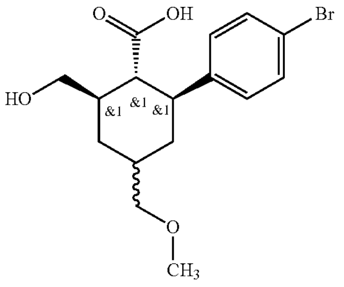 [SMILES: COCC1C[C@@H](CO)[C@H](C(=O)O)[C@@H](c2ccc(Br)cc2)C1]

To a mixture of rac-(3aR,7S,7aS)-7-(4-bromophenyl)-5-(methoxymethyl)hexahydroisobenzofuran-1(3H)-one Intermediate 44 (1.50 g, 4.42 mmol) in methanol (15 mL) was added KOH (1.24 g, 22.1 mmol), and the reaction mixture was stirred at 65° C. for 16 h. The reaction was concentrated, quenched with 2N HCl to pH<3, and solid precipitated out. This solid was filtered, washed with water (5 mL, 4 times), washed with petroleum ether (10 mL, 4 times) and dried to afford rac-(1R,2S,6R)-2-(4-bromophenyl)-6-(hydroxymethyl)-4-(methoxymethyl)cyclohexane-1-carboxylic acid (1.38 g, 3.32 mmol, 75% yield) as an off-white solid which was used without further purification. $^1$H NMR (400 MHz, DMSO-$d_6$) δ 12.04-11.62 (m, 1H), 7.44 (d, J=8.5 Hz, 2H), 7.17 (d, J=8.4 Hz, 2H), 4.54 (br dd, J=4.7, 2.9 Hz, 1H), 3.50-3.35 (m, 2H), 3.30-3.13 (m, 5H), 2.90-2.64 (m, 1H), 2.31-2.17 (m, 1H), 2.03-1.87 (m, 1H), 1.85-1.54 (m, 3H), 1.16 (q, J=12.5 Hz, 1H), 0.95-0.78 (m, 1H). ES-LCMS m/z 357.0 [M−H]$^-$.

Step 2: rac-benzyl (1R,2S,6R)-2-(4-bromophenyl)-6-(hydroxymethyl)-4-(methoxymethyl)cyclohexane-1-carboxylate

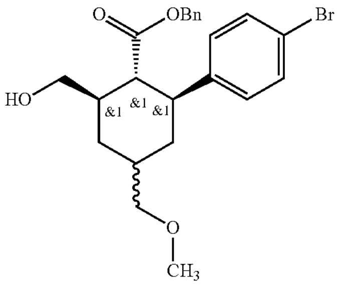 [SMILES: COCC1C[C@@H](CO)[C@H](C(=O)OCc2ccccc2)[C@@H](c2ccc(Br)cc2)C1]

To a mixture of rac-(1R,2S,6R)-2-(4-bromophenyl)-6-(hydroxymethyl)-4-(methoxymethyl)cyclohexane-1-carboxylic acid (1.38 g, 3.86 mmol) and potassium carbonate (1.60 g, 11.6 mmol) in DMF (15 mL) at 0° C. was added benzyl bromide (0.551 mL, 4.64 mmol), dropwise over 1 min. After 14 h at rt, water (50 mL) was added, and the reaction was extracted with EtOAc (50 mL×4). The combined EtOAc layers were washed with water (20 mL×4) and brine (20 mL), dried over sodium sulfate and evaporated to afford crude material. The resulting crude material was subjected to normal phase purification (ethyl acetate in petroleum ether, 40-60% gradient, 50 min run) to afford rac-benzyl (1R,2S,6R)-2-(4-bromophenyl)-6-(hydroxymethyl)-4-(methoxymethyl)cyclohexane-1-carboxylate (1.68 g, 3.67 mmol, 95% yield). $^1$H NMR (400 MHz, DMSO-$d_6$) δ 7.51-7.39 (m, 2H), 7.34-7.20 (m, 3H), 7.19-7.11 (m, 2H), 6.93-6.80 (m, 2H), 4.94-4.84 (m, 1H), 4.77-4.64 (m, 1H), 4.63-4.48 (m, 1H), 3.45 (d, J=7.6 Hz, 1H), 3.32-3.15 (m, 6H), 2.90-2.70 (m, 1H), 2.47-2.35 (m, 1H), 1.95-1.61 (m, 4H), 1.28-1.20 (m, 1H), 1.02-0.84 (m, 1H). ES-LCMS m/z showed poor ionization.

Step 3: rac-(1R,2R,3S)-2-((benzyloxy)carbonyl)-3-(4-bromophenyl)-5-(methoxymethyl)cyclohexane-1-carboxylic acid

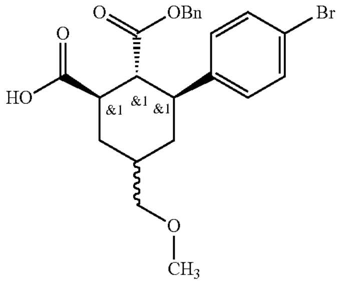 [SMILES: COCC1C[C@H](c2ccc(Br)cc2)[C@@H](C(=O)OCc2ccccc2)[C@H](C(=O)O)C1]

To a mixture of rac-benzyl (1R,2S,4R,6R)-2-(4-bromophenyl)-6-(hydroxymethyl)-4-(methoxymethyl)cyclohexane-1-carboxylate (1.67 g, 3.73 mmol) in MeCN (25 mL) and water (12 mL) at 0° C. was added sodium periodate (1.60 g, 7.47 mmol) and ruthenium(III) chloride (0.054 g, 0.26 mmol). After 30 min, water (50 mL) was added, and the mixture was extracted with EtOAc (50 mL×3). The EtOAc layer was washed with water (30 mL×2) and brine (30 mL), dried over sodium sulfate and concentrated. The residue was triturated (with sonication) in pet ether (25 mL) twice to afford rac-(1R,2R,3S)-2-((benzyloxy)carbonyl)-3-(4-bromophenyl)-5-(methoxymethyl)cyclohexane-1-carboxylic acid (1.44 g, 3.08 mmol, 83% yield) as a light brown solid, which was used without further purification. $^1$H NMR (400 MHz, DMSO-$d_6$) δ 12.45 (br s, 1H), 7.44 (d, J=8.5 Hz, 2H), 7.32-7.15 (m, 5H), 6.89-6.77 (m, 2H), 4.79-4.63 (m, 2H), 3.54-3.41 (m, 1H), 3.28-3.14 (m, 4H), 2.84-2.70 (m, 3H), 2.12-2.02 (m, 1H), 1.97-1.77 (m, 1H), 1.76-1.63 (m, 1H), 1.44-1.17 (m, 2H). ES-LCMS m/z 458.8 [M−H]$^-$.

Step 4: rac-benzyl (1R,2S,6R)-2-(4-bromophenyl)-6-((2-fluoro-4-(trifluoromethyl)phenyl)carbamoyl)-4-(methoxymethyl)cyclohexane-1-carboxylate

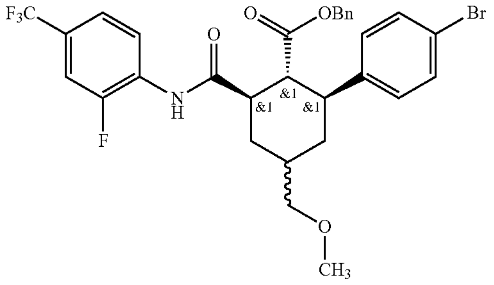 [SMILES: COCC1C[C@H](c2ccc(Br)cc2)[C@@H](C(=O)OCc2ccccc2)[C@H](C(=O)Nc2ccc(C(F)(F)F)cc2F)C1]

To a mixture of rac-(1R,2R,3S)-2-((benzyloxy)carbonyl)-3-(4-bromophenyl)-5-(methoxymethyl)cyclohexane-1-carboxylic acid (0.70 g, 1.5 mmol) in MeCN (14 mL) was added 2-fluoro-4-(trifluoromethyl)aniline (326 mg, 1.82 mmol) (with sonication) and 1-methyl-1H-imidazole (747 mg, 9.10 mmol), sequentially, followed after 15 min by chloro-N,N,N',N'-tetramethylformamidinium hexafluorophosphate (2.13 g, 7.59 mmol). After 16 h, the mixture was concentrated and subjected to reverse phase purification (MeCN in water with 0.1% formic acid, 50-80% gradient) to afford a rac-benzyl (1R,2S,6R)-2-(4-bromophenyl)-6-((2-fluoro-4-(trifluoromethyl)phenyl)carbamoyl)-4-(methoxymethyl)cyclohexane-1-carboxylatebenzyl (0.950 g, 1.46 mmol, 96% yield) as a white solid. $^{1}H$ NMR (400 MHz, DMSO-$d_6$) δ 11.86 (br s, 1H), 10.15 (s, 1H), 8.20 (t, J=8.0 Hz, 1H), 7.73 (br d, J=11.0 Hz, 1H), 7.56 (br d, J=8.6 Hz, 1H), 7.51-7.44 (m, 2H), 7.23 (d, J=8.4 Hz, 2H), 3.60-3.48 (m, 1H), 3.29-3.13 (m, 4H), 3.11-2.99 (m, 1H), 2.88-2.71 (m, 2H), 2.24-2.03 (m, 1H), 1.96-1.83 (m, 1H), 1.75 (br d, J=8.6 Hz, 1H), 1.43-1.22 (m, 1H). ES-LCMS m/z 622.0 $[M+H]^+$.

Step 5: rac-(1R,2S,6R)-2-(4-bromophenyl)-6-((2-fluoro-4-(trifluoromethyl)phenyl)carbamoyl)-4-(methoxymethyl)cyclohexane-1-carboxylic acid

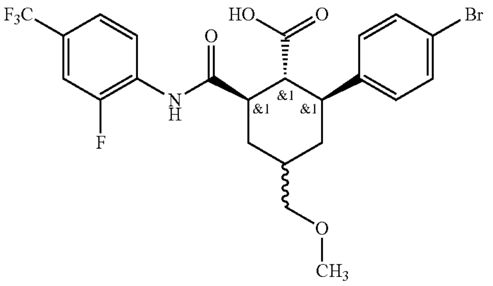 [SMILES: COCC1C[C@H](c2ccc(Br)cc2)[C@@H](C(=O)O)[C@H](C(=O)Nc2ccc(C(F)(F)F)cc2F)C1]

To a mixture of rac-benzyl (1R,2S,6R)-2-(4-bromophenyl)-6-((2-fluoro-4-(trifluoromethyl)phenyl)carbamoyl)-4-(methoxymethyl)cyclohexane-1-carboxylatebenzyl (0.900 g, 1.45 mmol) in DCM (10 mL) at −10° C. was added boron trichloride (5.78 mL, 5.78 mmol, 1M in DCM). After 45 min, 10% aq sodium bicarbonate (5 mL) was added, and the mixture was concentrated. The resulting residue was taken up in THF (3 mL) and water (5 mL) and subjected to reverse phase purification (MeCN in $H_2O$, 0.1% formic acid, 80-100% gradient) to afford rac-(1R,2S,6R)-2-(4-bromophenyl)-6-((2-fluoro-4-(trifluoromethyl)phenyl)carbamoyl)-4-(methoxymethyl)cyclohexane-1-carboxylic acid (0.750 g, 1.31 mmol, 91% yield) as a white solid. $^{1}H$ NMR (400 MHz, DMSO-$d_6$) δ 11.86 (br s, 1H), 10.15 (s, 1H), 8.20 (t, J=8.0 Hz, 1H), 7.73 (br d, J=11.0 Hz, 1H), 7.56 (br d, J=8.6 Hz, 1H), 7.51-7.44 (m, 2H), 7.23 (d, J=8.4 Hz, 2H), 3.60-3.48 (m, 1H), 3.29-3.13 (m, 4H), 3.11-2.99 (m, 1H), 2.88-2.71 (m, 2H), 2.24-2.03 (m, 1H), 1.96-1.83 (m, 1H), 1.75 (br d, J=8.6 Hz, 1H), 1.44-1.21 (m, 1H). ES-LCMS m/z 532.0 $[M-H]^-$.

Step 6: rac-(1R,2R,6S)-2-((2-fluoro-4-(trifluoromethyl)phenyl)carbamoyl)-4-(methoxymethyl)-6-(4-(methylamino)phenyl)cyclohexane-1-carboxylic acid

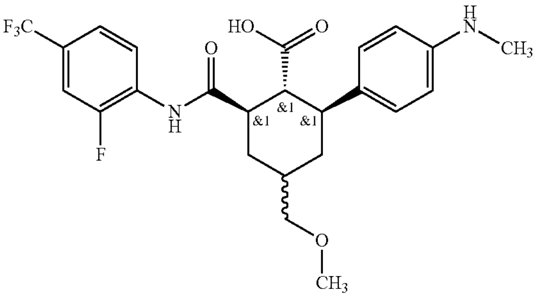 [SMILES: CNc1ccc([C@H]2CC(COC)C[C@@H](C(=O)Nc3ccc(C(F)(F)F)cc3F)[C@@H]2C(=O)O)cc1]

A mixture of rac-(1R,2S,6R)-2-(4-bromophenyl)-6-((2-fluoro-4-(trifluoromethyl)phenyl)carbamoyl)-4-(methoxymethyl)cyclohexane-1-carboxylic acid (350 mg, 0.657 mmol) and sodium tert-butoxide (190 mg, 1.97 mmol) in dioxane (10 mL) was degassed for 5 min. tBuXPhos Pd G3 (52 mg, 0.066 mmol) was added, and the mixture was degassed for 5 min. Methanamine (2M in THF, 6.57 mL, 13.2 mmol) was added, and the reaction was heated at 100° C. for 1 h. The mixture was filtered through Celite, concentrated, and the resulting residue was subjected to reverse phase purification (MeCN in $H_2O$, 0.1% formic acid, 30-60% gradient) to afford rac-(1R,2R,6S)-2-((2-fluoro-4-(trifluoromethyl)phenyl)carbamoyl)-4-(methoxymethyl)-6-(4-(methylamino)phenyl)cyclohexane-1-carboxylic acid (350 mg, 0.522 mmol, 79% yield) as a yellow solid. $^{1}H$ NMR (400 MHz, DMSO-$d_6$) δ 10.10 (s, 1H), 8.19 (t, J=8.3 Hz, 1H), 7.71 (d, J=10.5 Hz, 1H), 7.54 (d, J=9.0 Hz, 1H), 6.94 (d, J=8.5 Hz, 2H), 6.42 (d, J=8.5 Hz, 2H), 5.43 (d, J=2.0 Hz, 1H), 3.25-3.19 (m, 4H), 3.07-2.94 (m, 1H), 2.72-2.57 (m, 6H), 2.20-1.98 (m, 1H), 1.93-1.65 (m, 3H), 1.34-1.16 (m, 2H). ES-LCMS m/z 483.2 $[M+H]^+$.

Intermediate 46 and Intermediate 47: rac-benzyl (1R,2R,4R,6S)-4-(dimethylamino)-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylate and rac-benzyl (1R,2R,4S,6S)-4-(dimethylamino)-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylate

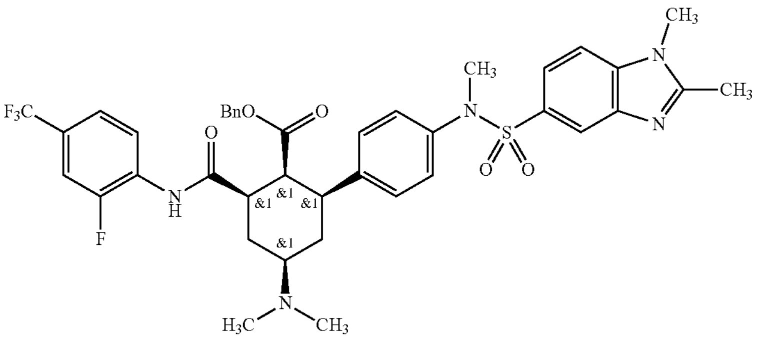

AND

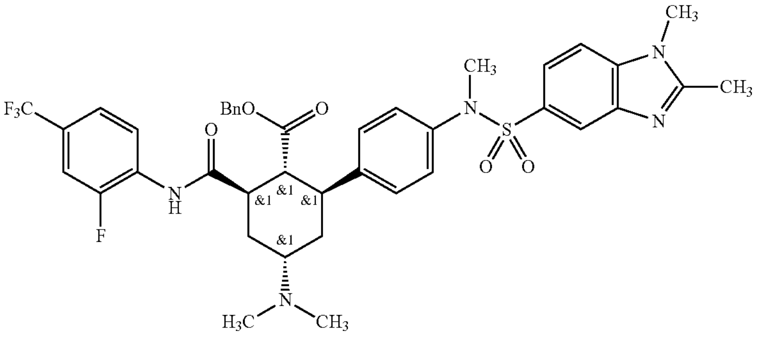

Step 1: rac-benzyl (1R,2R,6S)-2-((2-fluoro-4-(trifluoromethyl)phenyl)carbamoyl)-6-(4-(methylamino)phenyl)-4-oxocyclohexane-1-carboxylate

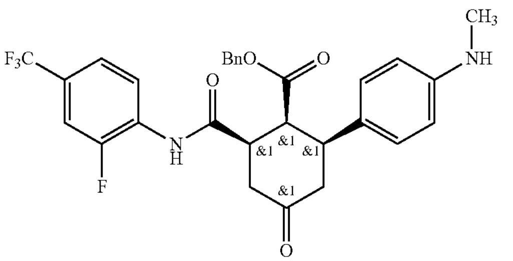 [SMILES: CNc1ccc([C@H]2CC(=O)C[C@@H](C(=O)Nc3ccc(C(F)(F)F)cc3F)[C@H]2C(=O)OCc2ccccc2)cc1]

To a mixture of rac-benzyl (1R,2S,6R)-2-(4-bromophenyl)-6-((2-fluoro-4-(trifluoromethyl)phenyl)carbamoyl)-4-oxocyclohexane-1-carboxylate Intermediate 11 Step 4 (1.05 g, 1.77 mmol) and sodium 2-methylpropan-2-olate (0.256 g, 2.66 mmol) in dioxane (30 mL) was added tBuXPhos Pd G3 (282 mg, 0.354 mmol), and the reaction was degassed for 5 min. Methanamine (2M in THF, 17.7 mL, 35.4 mmol) was added, and the mixture was microwaved at 100° C. After 1 h, the reaction was concentrated and subjected to normal phase purification (50-100% EtOAc in per ether) to afford rac-benzyl (1R,2R,6S)-2-((2-fluoro-4-(trifluoromethyl)phenyl)carbamoyl)-6-(4-(methylamino)phenyl)-4-oxocyclohexane-1-carboxylate (0.180 g, 0.265 mmol, 15.0% yield) as a brown solid. $^1$H NMR (400 MHz, DMSO-$d_6$) δ 10.26 (s, 1H), 8.15 (t, J=8.0 Hz, 1H), 7.73 (dd, J=11.0, 2.0 Hz, 1H), 7.56 (d, J=8.5 Hz, 1H), 7.21-7.06 (m, 3H), 7.04 (d, J=8.5 Hz, 2H), 6.87-6.79 (m, 2H), 6.48 (d, J=8.5 Hz, 2H), 5.61 (q, J=5.0 Hz, 1H), 4.73 (d, J=1.5 Hz, 2H), 3.46-3.35 (m, 2H), 3.03-2.93 (m, 2H), 2.87-2.73 (m, 1H), 2.67 (d, J=5.0 Hz, 3H), 2.58 (d, J=1.5 Hz, 1H), 2.31-2.22 (m, 1H). ES-LCMS m/z 541.3 $[M-H]^-$.

Step 2: rac-benzyl (1R,2R,6S)-2-((2-fluoro-4-(trifluoromethyl)phenyl)carbamoyl)-4-oxo-6-(4-((N,1,2-trimethyl-1H-benzo[d]imidazole)-5-sulfonamido)phenyl)cyclohexane-1-carboxylate

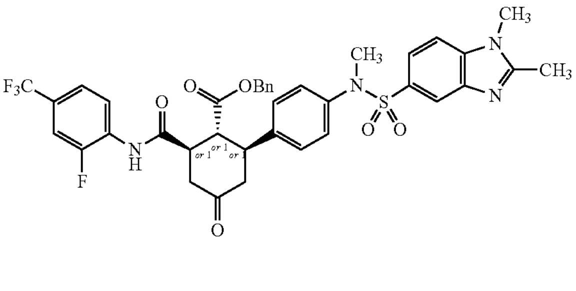 [SMILES: Cc1nc2cc(S(=O)(=O)N(C)c3ccc([C@H]4CC(=O)C[C@@H](C(=O)Nc5ccc(C(F)(F)F)cc5F)[C@@H]4C(=O)OCc4ccccc4)cc3)ccc2n1C]

To a mixture of rac-benzyl (1R,2R,6S)-2-((2-fluoro-4-(trifluoromethyl)phenyl)carbamoyl)-6-(4-(methylamino)phenyl)-4-oxocyclohexane-1-carboxylate (203 mg, 0.374 mmol) in dichloromethane (10 mL) and pyridine (0.091 mL, 1.1 mmol) at 0° C. was added 1,2-dimethyl-1H-benzo[d]imidazole-5-sulfonyl chloride (110 mg, 0.450 mmol), portion wise. The reaction was stirred at rt for 45 min, concentrated and subjected to reverse phase purification (0-90% MeCN in $H_2O$, with 0.1% formic acid modifier) to afford rac-benzyl (1R,2R,6S)-2-((2-fluoro-4-(trifluoromethyl)phenyl)carbamoyl)-4-oxo-6-(4-((N,1,2-trimethyl-1H-benzo[d]imidazole)-5-sulfonamido)phenyl)cyclohexane-1-carboxylate (145 mg, 0.155 mmol, 41.4% yield) as an off-white solid. $^1$H NMR (400 MHz, DMSO-$d_6$) δ 10.29 (s, 1H), 8.14 (t, J=8.0 Hz, 1H), 7.74 (dd, J=10.8, 1.8 Hz, 1H), 7.63-7.53 (m, 3H), 7.32-7.26 (m, 3H), 7.19-7.10 (m, 3H), 7.04 (d, J=8.5 Hz, 2H), 6.99-6.93 (m, 2H), 4.84 (d, J=13.0 Hz, 1H), 4.62 (d, J=13.0 Hz, 1H), 3.74 (s, 3H), 3.52-3.41 (m, 2H), 3.24-3.13 (m, 1H), 3.08 (s, 3H), 3.07-2.96 (m, 1H), 2.90-2.74 (m, 1H), 2.60 (d, J=14.0 Hz, 1H), 2.53 (s, 3H), 2.37 (d, J=4.0 Hz, 1H). ES-LCMS m/z 751.0 [M+H]$^+$.

Step 3: rac-benzyl (1R,2R,4R,6S)-4-(dimethylamino)-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylate and rac-benzyl (1R,2R,4S,6S)-4-(dimethylamino)-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylate

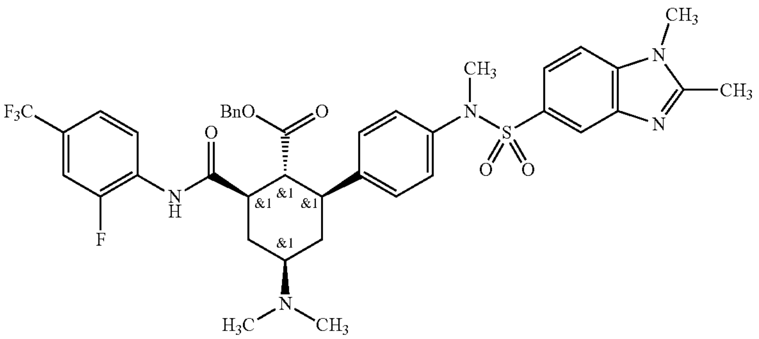

AND

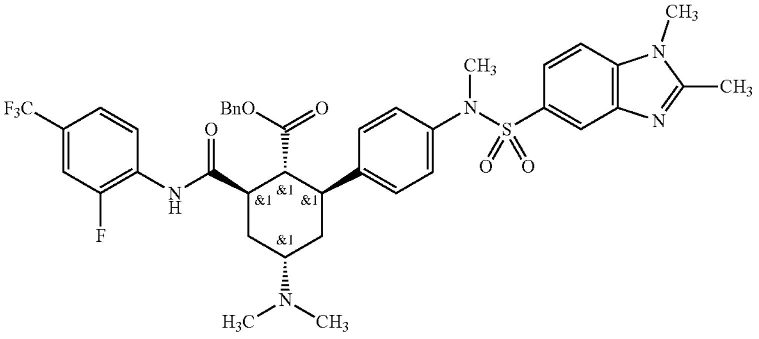

To a mixture of rac-benzyl (1R,2R,6S)-2-((2-fluoro-4-(trifluoromethyl)phenyl)carbamoyl)-4-oxo-6-(4-((N,1,2-trimethyl-1H-benzo[d]imidazole)-5-sulfonamido)phenyl)cyclohexane-1-carboxylate (0.3 g, 0.4 mmol) and dimethylamine (2M in THF, 1.8 mL, 3.6 mmol) in 1,2-dichloroethane (8 mL) was added acetic acid (0.02 mL, 0.40 mmol). After 5 h, sodium triacetoxyhydroborate (0.76 g, 3.6 mmol) was added. After 16 h, the reaction was quenched with water (0.5 mL), concentrated and subjected to Prep HPLC purification (0-100% MeCN in $H_2O$, 0.1% ammonium bicarbonate modifier) to afford:

The first-eluting diastereomer Intermediate 46: rac-benzyl (1R,2R,4R,6S)-4-(dimethylamino)-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylate (0.18 g, 0.22 mmol, 55% yield) as a white solid. $^1$H NMR (400 MHz, DMSO-$d_6$) δ10.18 (s, 1H), 8.17 (t, J=8.0 Hz, 1H), 7.72 (d, J=10.8 Hz, 1H), 7.61-7.59 (m, 2H), 7.55 (d, J=8.4 Hz, 1H), 7.31 (dd, J=8.6, 1.6 Hz, 1H), 7.24 (d, J=8.4 Hz, 2H), 7.16-7.10 (m, 3H), 7.00 (d, J=8.4 Hz, 2H), 6.94 (d, J=6.8 Hz, 2H), 4.81 (d, J=12.8 Hz, 1H), 4.59 (d, J=12.8 Hz, 1H), 3.74 (s, 3H), 3.17 (d, J=3.2 Hz, 1H), 3.11 (m, 1H), 3.07 (s, 3H), 2.93 (t, J=11.2 Hz, 1H), 2.68 (t, J=2.0 Hz, 1H), 2.21 (s, 6H), 2.14 (d, J=9.6 Hz, 1H), 1.83 (d, J=12.4 Hz, 1H), 1.65 (q, J=12.4 Hz, 1H), 1.52 (q, J=12.0 Hz, 1H), 3 protons obscured by solvent peaks. ES-LCMS m/z 780.2 [M+H]$^+$.

And the second-eluting diastereomer Intermediate 47: rac-benzyl (1R,2R,4S,6S)-4-(dimethylamino)-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylate (62 mg, 0.070 mmol, 18% yield) as a white solid. $^1$H NMR (400 MHz, DMSO-$d_6$) δ10.16 (s, 1H), 8.00 (t, J=8.4 Hz, 1H), 7.68 (d, J=8.8 Hz, 1H), 7.61-7.58 (m, 2H), 7.53 (m, 1H), 7.30 (dd, J=8.4, 1.6 Hz, 1H), 7.20-7.07 (m, 5H), 6.99 (d, J=8.4 Hz, 2H), 6.93 (d, J=7.2 Hz, 2H), 4.83 (d, J=12.8 Hz, 1H), 4.64 (d, J=12.8 Hz, 1H), 3.73 (s, 3H), 3.18-3.13 (m, 2H), 3.07 (s, 3H), 3.00 (t, J=11.2 Hz, 1H), 2.33 (s, 6H), 2.25 (s, 3H), 2.14 (m, 1H), 1.97 (br d, J=14.0 Hz, 1H), 1.81-1.69 (m, 2H), 1 proton obscured by solvent peaks. ES-LCMS m/z 780.2 [M+H]$^+$.

Intermediate 48 and Intermediate 49: rel-benzyl (1R,2R,4R,6S)-4-(dimethylamino)-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylate acid ISOMER 1 and ISOMER 2

ISOMER 1 and ISOMER 2

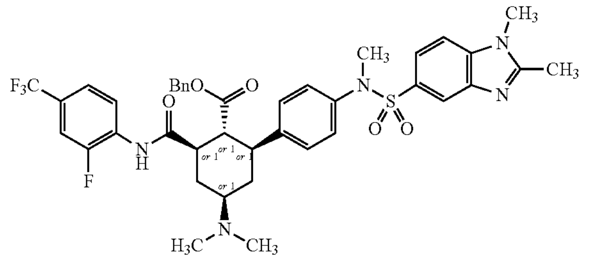

Racemic compound rac-benzyl (1R,2R,4R,6S)-4-(dimethylamino)-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylate Intermediate 46 (300 mg) was purified by Chiral-Prep-SFC (Column: YMC Cellulose-SC; 60:40 $CO_2$: 0.5% isopropylamine in methanol) to afford: The first-eluting isomer Intermediate 48 rel-benzyl (1R,2R,4R,6S)-4-(dimethylamino)-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylate acid ISOMER 1 (81 mg, 0.10 mmol, 45% yield).

And the second-eluting isomer Intermediate 49 rel-benzyl (1R,2R,4R,6S)-4-(dimethylamino)-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylate acid ISOMER 2 (50 mg, 0.06 mmol, 28% yield).

The following compounds were synthesized in an analogous manner to the preparation described above (Intermediate 48 and Intermediate 49), using the appropriate alkylamines and Chiral purifications.

| Int. | Structure/Name | $^1$H NMR | LCMS |
|---|---|---|---|
| 50 | 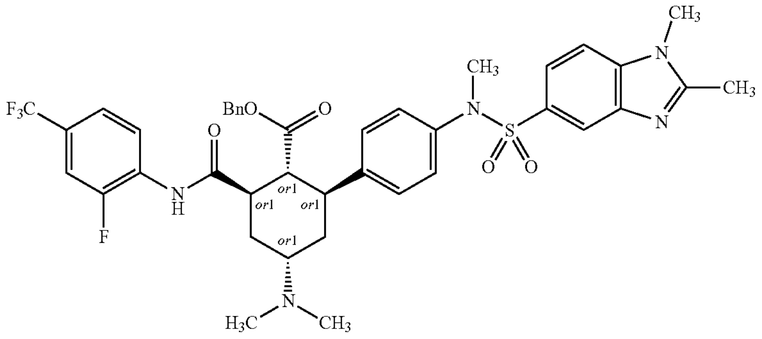 [SMILES: Cc1nc2cc(S(=O)(=O)N(C)c3ccc([C@H]4C[C@H](N(C)C)C[C@@H](C(=O)Nc5ccc(C(F)(F)F)cc5F)[C@@H]4C(=O)OCc4ccccc4)cc3)ccc2n1C]<br>ISOMER 2<br>rel-benzyl (1R,2R,4S,6S)-4-(dimethylamino)-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylate | $^1$H NMR (400 MHZ, DMSO-$d_6$) δ 10.16 (s, 1H), 8.00 (t, J = 8.4 Hz, 1H), 7.68 (d, J = 8.8 Hz, 1H), 7.61-7.58 (m, 2H), 7.53 (m, 1H), 7.30 (dd, J = 8.4, 1.6 Hz, 1H), 7.20-7.07 (m, 5H), 6.99 (d, J = 8.4 Hz, 2H), 6.93 (d, J = 7.2 Hz, 2H), 4.83 (d, J = 12.8 Hz, 1H), 4.64 (d, J = 12.8 Hz, 1H), 3.73 (s, 3H), 3.18-3.13 (m, 2H), 3.07 (s, 3H), 3.00 (t, J = 11.2 Hz, 1H), 2.33 (s, 6H), 2.25 (s, 3H), 2.14 (m, 1H), 1.97 (br d, J = 14.0 Hz, 1H), 1.81-1.69 (m, 2H), 1 proton obscured by solvent peaks | ES-LCMS m/z 780.2 $[M + H]^+$. |
| 51 | 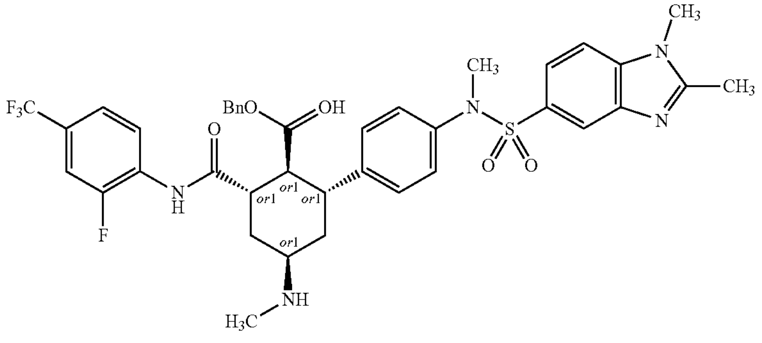 [SMILES: CN[C@H]1C[C@H](C(=O)Nc2ccc(C(F)(F)F)cc2F)[C@@H](C(=O)OCc2ccccc2)[C@H](c2ccc(N(C)S(=O)(=O)c3ccc4c(c3)nc(C)n4C)cc2)C1]<br>ISOMER 1<br>rel-benzyl benzyl (1R,2R,4S,6S)-2-((2-fluoro-4-(trifluoromethyl)phenyl)carbamoyl)-4-(methylamino)-6-(4-((N,1,2-trimethyl-1H-benzo[d]imidazole)-5-sulfonamido)phenyl)cyclohexane-1-carboxylate ISOMER 1 | $^1$H NMR (400 MHZ, DMSO-$d_6$) δ 10.08 (s, 1H), 8.07 (t, J = 8.0 Hz, 1H), 7.72 (dd, J = 10.8, 1.6 Hz, 1H), 7.61-7.59 (m, 2H), 7.54 (d, J = 8.4 Hz, 1H), 7.30 (dd, J = 8.6, 1.6 Hz, 1H), 7.19-7.10 (m, 5H), 7.00-6.93 (m, 4H), 4.80 (d, J = 12.8 Hz, 1H), 4.59 (d, J = 12.8 Hz, 1H), 3.74 (s, 3H), 3.42-3.37 (m, 1H), 3.27-3.19 (m, 1H), 3.07 (s, 3H), 2.94 (t, J = 11.6 Hz, 1H), 2.89 (m, 1H), 2.33 (s, 3H), 2.05 (d, J = 13.2 Hz, 1H), 1.80-1.72 (m, 3H), 3 protons obscured by solvent peaks | ES-LCMS m/z 766.0 $[M + H]^+$. |

-continued

| Int. | Structure/Name | $^1H$ NMR | LCMS |
|---|---|---|---|
| 52 | 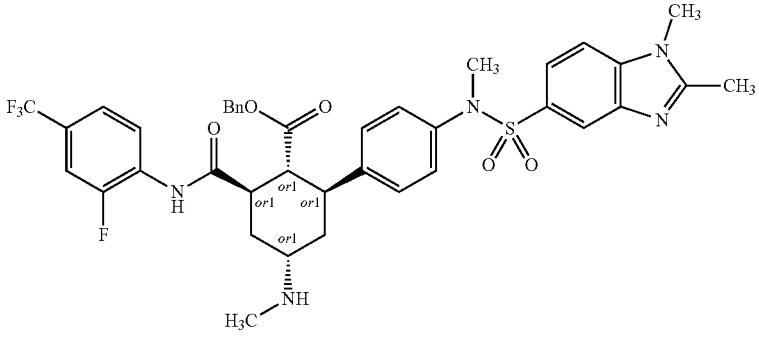 [SMILES: CN[C@H]1C[C@H](c2ccc(N(C)S(=O)(=O)c3ccc4c(c3)nc(C)n4C)cc2)[C@@H](C(=O)OCc2ccccc2)[C@H](C(=O)Nc2ccc(C(F)(F)F)cc2F)C1] ISOMER 2 rel-benzyl benzyl (1R,2R,4S,6S)-2-((2-fluoro-4-(trifluoromethyl)phenyl)carbamoyl)-4-(methylamino)-6-(4-((N,1,2-trimethyl-1H-benzo[d]imidazole)-5-sulfonamido)phenyl)cyclohexane-1-carboxylate ISOMER 2 | $^1H$ NMR (400 MHZ, DMSO-$d_6$) δ 10.08 (s, 1H), 8.07 (t, J = 8.0 Hz, 1H), 7.72 (dd, J = 10.8, 1.6 Hz, 1H), 7.61-7.59 (m, 2H), 7.54 (d, J = 8.4 Hz, 1H), 7.30 (dd, J = 8.6, 1.6 Hz, 1H), 7.19-7.10 (m, 5H), 7.00-6.93 (m, 4H), 4.80 (d, J = 12.8 Hz, 1H), 4.59 (d, J = 12.8 Hz, 1H), 3.74 (s, 3H), 3.42-3.37 (m, 1H), 3.27-3.19 (m, 1H), 3.07 (s, 3H), 2.94 (t, J = 11.6 Hz, 1H), 2.89 (m, 1H), 2.33 (s, 3H), 2.05 (d, J = 13.2 Hz, 1H), 1.80-1.72 (m, 3H), 3 protons obscured by solvent peaks | ES-LCMS m/z 766.0 $[M + H]^+$. |
| 53 | 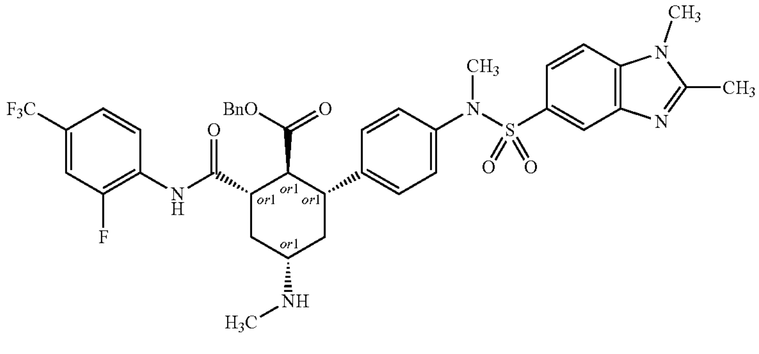 [SMILES: CN[C@@H]1C[C@H](C(=O)Nc2ccc(C(F)(F)F)cc2F)[C@@H](C(=O)OCc2ccccc2)[C@H](c2ccc(N(C)S(=O)(=O)c3ccc4c(c3)nc(C)n4C)cc2)C1] ISOMER 1 rel-benzyl benzyl (1R,2R,4R,6S)-2-((2-fluoro-4-(trifluoromethyl)phenyl)carbamoyl)-4-(methylamino)-6-(4-((N,1,2-trimethyl-1H-benzo[d]imidazole)-5-sulfonamido)phenyl)cyclohexane-1-carboxylate ISOMER 1 | $^1H$ NMR (400 MHZ, DMSO-$d_6$) δ 10.15 (s, 1H), 8.15 (t, J = 8.0 Hz, 1H), 7.72 (dd, J = 11.2, 1.6 Hz, 1H), 7.62-7.54 (m, 3H), 7.31 (dd, J = 8.4, 2.0 Hz, 1H), 07.21-7.01 (m, 5H), 6.97 (d, J = 15.6 Hz, 2H), 6.93 (d, J = 1.6 Hz, 2H), 4.81 (d, J = 12.8 Hz, 1H), 4.60 (d, J = 12.8 Hz, 1H), 3.76 (s, 3H), 3.13-3.10 (m 1H), 3.05 (s, 3H), 2.94-2.88 (m, 1H), 2.92 (t, J = 11.2 Hz, 1H), 2.83-2.80 (m, 1H), 2.56-2.55 (m, 1H), 2.52 (s, 3H), 2.33 (s, 3H), 2.32-2.27 (m, 1H), 2.09 (d, J = 4.4 Hz, 1H), 1.41-1.27 (m, 1H), 1.24-1.03 (m, 1H) | ES-LCMS m/z 766.2 $[M + H]^+$. |
| 54 | 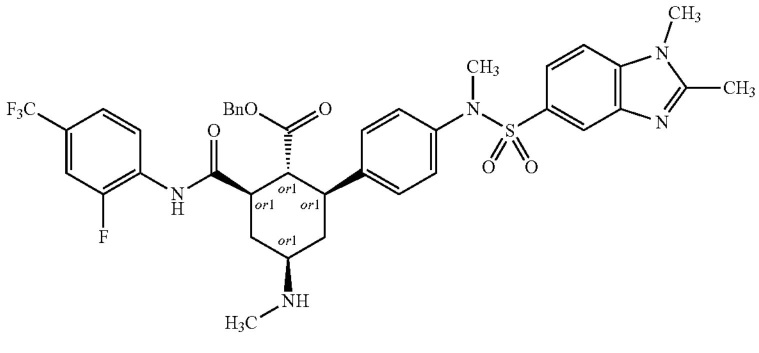 [SMILES: CN[C@@H]1C[C@H](c2ccc(N(C)S(=O)(=O)c3ccc4c(c3)nc(C)n4C)cc2)[C@@H](C(=O)OCc2ccccc2)[C@H](C(=O)Nc2ccc(C(F)(F)F)cc2F)C1] ISOMER 2 rel-benzyl benzyl (1R,2R,4R,6S)-2-((2-fluoro-4-(trifluoromethyl)phenyl)carbamoyl)-4-(methylamino)-6-(4-((N,1,2-trimethyl-1H-benzo[d]imidazole)-5-sulfonamido)phenyl)cyclohexane-1-carboxylate ISOMER 2 | $^1H$ NMR (400 MHZ, DMSO-$d_6$) δ 10.15 (s, 1H), 8.15 (t, J = 8.0 Hz, 1H), 7.72 (dd, J = 11.2, 1.6 Hz, 1H), 7.62-7.54 (m, 3H), 7.31 (dd, J = 8.4, 2.0 Hz, 1H), 07.21-7.01 (m, 5H), 6.97 (d, J = 15.6 Hz, 2H), 6.93 (d, J = 1.6 Hz, 2H), 4.81 (d, J = 12.8 Hz, 1H), 4.60 (d, J = 12.8 Hz, 1H), 3.76 (s, 3H), 3.13-3.10 (m 1H), 3.05 (s, 3H), 2.94-2.88 (m, 1H), 2.92 (t, J = 11.2 Hz, 1H), 2.83-2.80 (m, 1H), 2.56-2.55 (m, 1H), 2.52 (s, 3H), 2.33 (s, 3H), 2.32-2.27 (m, 1H), 2.09 (d, J = 4.4 Hz, 1H), 1.41-1.27 (m, 1H), 1.24-1.03 (m, 1H) | ES-LCMS m/z 766.2 $[M + H]^+$. |

Intermediate 55: rac-methyl (1R,2S,3R,6R)-3-(ethylamino)-6-((4-isopropylphenyl)carbamoyl)-2-(4-((N,1,2-trimethyl-1H-benzo[d]imidazole)-5-sulfonamido)phenyl)cyclohexane-1-carboxylate

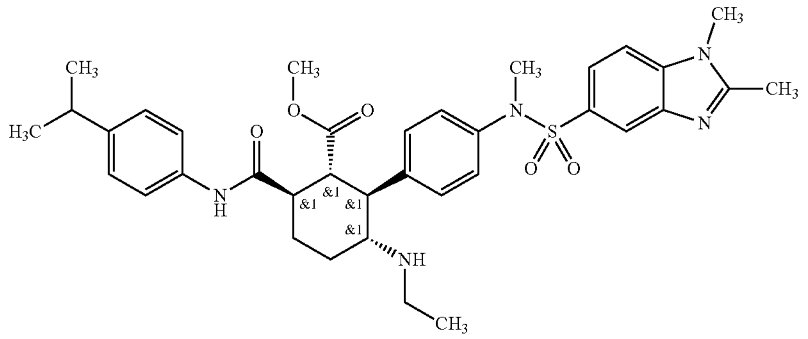 [SMILES: CCN[C@@H]1CC[C@@H](C(=O)Nc2ccc(C(C)C)cc2)[C@H](C(=O)OC)[C@H]1c1ccc(N(C)S(=O)(=O)c2ccc3c(c2)nc(C)n3C)cc1]

Step 1: dimethyl (1-methoxyallyl)phosphonate

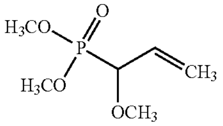

To 3,3-dimethoxyprop-1-ene (15.00 g, 147.0 mmol) at 0° C. was added trichlorophosphane (5.78 ml, 66.1 mmol). The reaction was stirred at rt, and after 15 min trimethyl phosphite (13.9 ml, 117 mmol) was added. After 1 hr, the mixture was concentrated and subjected to normal phase chromatography, eluting with 0-100% EtOAc in petroleum ether to afford dimethyl (1-methoxyallyl)phosphonate (21.5 g, 107 mmol, 73.0% yield) as a pale yellow oil. $^1$H NMR (400 MHz, DMSO-$d_6$ δ 5.81-5.72 (m, 1H), 5.45-5.35 (m, 2H), 4.26-4.20 (m, 1H), 3.69 (d, J=2.4 Hz, 3H), 3.66 (d, J=2.4 Hz, 3H), 3.33 (d, J=0.8 Hz, 3H). ES-LCMS m/z 181.2 $[M+H]^+$.

Step 2: tert-butyl (4-formylphenyl)(methyl)carbamate

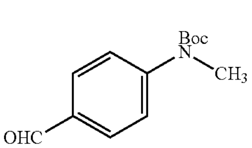 [SMILES: CN(C(=O)OC(C)(C)C)c1ccc(C=O)cc1]

To a mixture of 4-bromobenzaldehyde (0.020 kg, 0.011 mol), cesium carbonate (52.8 g, 162 mmol) and tert-butyl methylcarbamate (17.0 g, 0.130 mol) in dioxane (150 ml) were added (9,9-dimethyl-9H-xanthene-4,5-diyl)bis(diphenylphosphane) (6.25 g, 10.8 mmol) and $Pd_2(dba)_3$ (3.76 g, 4.11 mmol). The reaction was purged with nitrogen for 10 min, heated to 100° C. for 16 h, filtered through Celite (washing with EtOAc [200 mL]), concentrated and subjected to normal phase chromatography, eluting with 5% EtOAc in petroleum ether to afford tert-butyl (4-formylphenyl)(methyl)carbamate (12.5 g, 44.0 mmol, 54.0% yield)) as a yellow oil. $^1$H NMR (400 MHz, DMSO-$d_6$) δ 9.95 (s, 1H), 7.89-7.82 (m, 2H), 7.55-7.52 (m, 2H), 3.26 (s, 3H), 1.43 (s, 9H). ES-LCMS m/z 180.0 $[MH-tBu]^+$.

Step 3: tert-butyl (4-(2-methoxybuta-1,3-dien-1-yl)phenyl)(methyl)carbamate

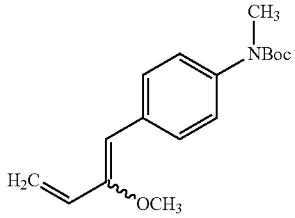 [SMILES: C=CC(=Cc1ccc(N(C)C(=O)OC(C)(C)C)cc1)OC]

To a mixture of dimethyl (1-methoxyallyl)phosphonate (7.66 g, 42.5 mmol) in tetrahydrofuran (100 mL) at 0° C. was added sodium hydride (1.79 g, 44.6 mmol). The reaction was stirred at rt for 1 h, and tert-butyl (4-formylphenyl)(methyl)carbamate (5.000 g, 21.25 mmol) in THF (30 mL) was added, dropwise. After 16 h the mixture was cooled to 0° C., quenched with ice and extracted with EtOAc (150 mL). The organic layer was washed with water (25 mL), dried over anhydrous sodium sulfate, filtered, concentrated and subjected to normal phase chromatography, eluting with 15% of EtOAc in petroleum ether to afford tert-butyl (4-(2-methoxybuta-1,3-dien-1-yl)phenyl)(methyl)carbamate (1.88 g, 6.3 mmol, 30% yield) as yellow oil. $^1$H NMR (400 MHz, DMSO-$d_6$) δ 7.26-7.22 (m, 2H), 7.17 (d, J=8.4 Hz, 2H), 6.56 (dd, J=17.0, 11.2 Hz, 1H), 5.94 (s, 1H), 5.66 (dd, J=16.8, 2.0 Hz, 1H), 5.27 (dt, J=11.07, 2.0 Hz, 1H), 3.70 (s, 3H), 3.18 (d, J=2.4 Hz, 3H), 1.39 (s, 9H). ES-LCMS m/z 234.0 $[MH-tBu]^+$.

Step 4: rac-dimethyl (1R,2S,3S)-4'-((tert-butoxycarbonyl)(methyl)amino)-6-methoxy-1,2,3,4-tetrahydro-[1,1'-biphenyl]-2,3-dicarboxylate

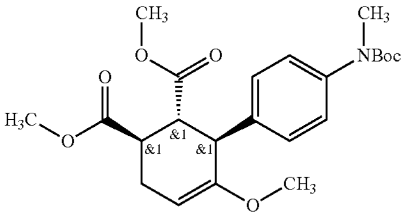 [SMILES: COC(=O)[C@@H]1[C@@H](c2ccc(N(C)C(=O)OC(C)(C)C)cc2)C(OC)=CC[C@H]1C(=O)OC]

To a mixture of tert-butyl (4-(2-methoxybuta-1,3-dien-1-yl)phenyl)(methyl)carbamate (6.80 g, 23.5 mmol) in o-xylene (50 mL) was added dimethyl fumarate (4.06 g, 28.2 mmol). The reaction was heated to 140° C. for 16 h, concentrated and subjected to normal phase chromatography, eluting with 40% of EtOAc in petroleum ether to afford rac-dimethyl (1R,2S,3S)-4'-((tert-butoxycarbonyl)(methyl)amino)-6-methoxy-1,2,3,4-tetrahydro-[1,1'-biphenyl]-2,3-dicarboxylate (4 g, 8 mmol, 40% yield) as yellow oil. $^1$H NMR (400 MHz, DMSO-$d_6$) δ 7.20-7.10 (m, 2H), 7.02 (dd, J=8.4, 1.6 Hz, 2H), 4.96-4.91 (m, 1H), 3.55 (m, 3H), 3.43 (s, 3H), 3.23 (s, 3H), 3.16 (s, 3H), 2.86 (m, 1H), 2.77-2.74 (m, 1H), 2.58-2.53 (m, 1H), 2.49-2.43 (m, 1H), 2.18-2.15 (m, 1H), 1.38 (s, 9H). ES-LCMS m/z 456.2 [M+Na]$^+$.

Step 5: rac-dimethyl (1R,2R,3S)-3-(4-(methylamino)phenyl)-4-oxocyclohexane-1,2-dicarboxylate hydrochloride

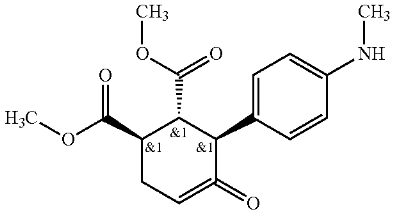

To a mixture of rac-dimethyl (1R,2S,3S)-4'-((tert-butoxycarbonyl)(methyl)amino)-6-methoxy-1,2,3,4-tetrahydro-[1,1'-biphenyl]-2,3-dicarboxylate (4.00 g, 3.32 mmol) in acetonitrile (40 mL) was added HCl (32% in $H_2O$, 0.950 mL, 9.97 mmol). After 2 h, the resulting precipitated solid was collected by filtration, washed with MeCN (5 mL) and dried under vaccum to afford rac-dimethyl (1R,2R,3S)-3-(4-(methylamino)phenyl)-4-oxocyclohexane-1,2-dicarboxylate hydrochloride (900 mg, 2.48 mmol, 75.0% yield) as off-white solid. $^1$H NMR (400 MHz, DMSO-$d_6$) δ 7.23-7.17 (m, 4H), 3.99 (d, J=11.6 Hz, 1H), 3.61 (s, 3H), 3.28-3.26 (m, 2H), 3.25 (s, 3H), 3.24 (m, 1H), 2.82 (s, 3H), 2.79 (td, J=14.2, 6.0 Hz, 1H), 2.39-2.34 (m, 1H), 2.29-2.25 (m, 1H), 2.08-2.04 (m, 1H). ES-LCMS m/z 320.0 [M+H]$^+$.

Step 6: rac-dimethyl (1R,2R,3S)-4-oxo-3-(4-((N,1,2-trimethyl-1H-benzo[d]imidazole)-5-sulfonamido)phenyl)cyclohexane-1,2-dicarboxylate

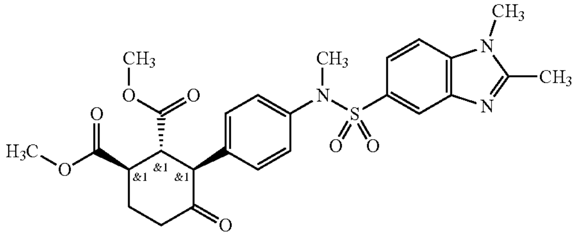

To a mixture of rac-dimethyl (1R,2R,3S)-3-(4-(methylamino)phenyl)-4-oxocyclohexane-1,2-dicarboxylate (1.20 g, 3.76 mmol) in dichloromethane (20 mL) at 0° C. was added 1,2-dimethyl-1H-benzo[d]imidazole-5-sulfonyl chloride (1.01 g, 4.13 mmol). After 20 min, the reaction was concentrated and subjected to reverse phase purification (50-70% MeCN in $H_2O$, with 0.1% formic acid modifier) to afford rac-dimethyl (1R,2R,3S)-4-oxo-3-(4-((N,1,2-trimethyl-1H-benzo[d]imidazole)-5-sulfonamido)phenyl)cyclohexane-1,2-dicarboxylate (0.90 g, 1.6 mmol, 43% yield) as a brown gum. $^1$H NMR (400 MHz, DMSO-$d_6$) δ 7.65 (d, J=8.8 Hz, 1H), 7.58 (d, J=1.6 Hz, 1H), 7.29 (dd, J=8.4, 1.6 Hz, 1H), 7.05 (m, 2H), 6.98-6.96 (m, 2H), 3.93 (dd, J=9.0, 2.8 Hz, 1H), 3.78 (s, 3H), 3.62 (s, 3H), 3.28 (dt, J=9.8, 1.6 Hz, 2H), 3.10 (s, 3H), 2.78 (td, J=14.4, 6.0 Hz, 1H), 2.56 (s, 3H), 2.39-2.33 (m, 1H), 2.29-2.26 (m, 1H), 2.09-2.02 (m, 1H). ES-LCMS m/z 528.2 [M+H]$^+$.

Step 7: rac-dimethyl (1R,2R,3S,4R)-4-((4-methoxybenzyl)amino)-3-(4-((N,1,2-trimethyl-1H-benzo[d]imidazole)-5-sulfonamido)phenyl)cyclohexane-1,2-dicarboxylate

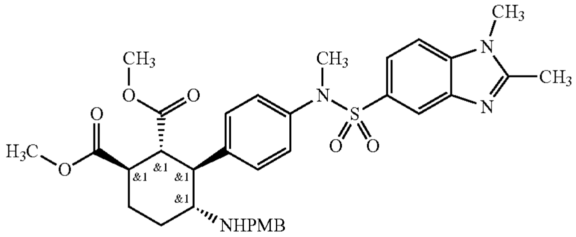

To a mixture of rac-dimethyl (1R,2R,3S)-4-oxo-3-(4-((N,1,2-trimethyl-1H-benzo[d]imidazole)-5-sulfonamido)phenyl)cyclohexane-1,2-dicarboxylate (0.900 g, 1.71 mmol) and (4-methoxyphenyl)methanamine (257 mg, 1.88 mmol) in 1,2-dichloroethane (20 mL) was added AcOH (0.100 mL, 1.71 mmol). After 16 h, sodium cyanotrihydroborate (214 mg, 3.41 mmol) was added. After 1 h, the reaction was concentrated and subjected to reverse phase purification (10-40% MeCN in $H_2O$, with 0.1% formic acid modifier) to afford rac-dimethyl (1R,2R,3S,4R)-4-((4-methoxybenzyl)amino)-3-(4-((N,1,2-trimethyl-1H-benzo[d]imidazole)-5-sulfonamido)phenyl)cyclohexane-1,2-dicarboxylate (460 mg, 0.70 mmol, 41% yield) as the major isomer as an off-white solid. $^1$H NMR (400 MHz, DMSO-$d_6$) δ 7.62 (d, J=1.6 Hz, 1H), 7.60-7.48 (m, 1H), 7.27-7.23 (m, 2H), 7.17-7.09 (m, 2H), 6.99 (d, J=8.8 Hz, 2H), 6.89 (d, J=8.8 Hz, 1H), 6.87-6.77 (m, 2H), 3.74 (s, 3H), 3.69 (s, 3H), 3.56 (s, 3H), 3.37-3.34 (m, 2H), 3.27 (s, 3H), 3.17 (s, 3H), 2.81-2.75 (m, 1H), 2.73-2.68 (m, 2H), 2.57-2.54 (m, 1H), 2.53 (s, 3H), 2.18-2.05 (m, 2H), 1.58-1.36 (m, 2H). ES-LCMS m/z 649.2 $[M+H]^+$.

Step 8: rac-(1R,2R,3S,4R)-4-((4-methoxybenzyl) amino)-2-(methoxycarbonyl)-3-(4-((N,1,2-trimethyl-1H-benzo[d]imidazole)-5-sulfonamido)phenyl)cyclohexane-1-carboxylic acid

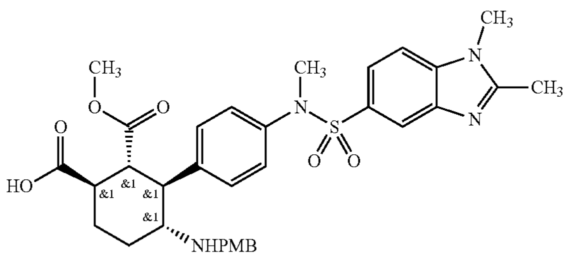

To a mixture of rac-dimethyl (1R,2R,3S,4R)-4-((4-methoxybenzyl)amino)-3-(4-((N,1,2-trimethyl-1H-benzo[d]imidazole)-5-sulfonamido)phenyl)cyclohexane-1,2-dicarboxylate (260 mg, 0.40 mmol) in 1,2-dichloroethane (8 mL) was added trimethyl tin hydroxide (729 mg, 4.01 mmol). The reaction was heated to 90° C. for 16 h, concentrated and subjected to reverse phase purification (0-80% MeCN in $H_2O$, with 0.1% formic acid modifier) to afford rac-(1R,2R,3S,4R)-4-((4-methoxybenzyl)amino)-2-(methoxycarbonyl)-3-(4-((N,1,2-trimethyl-1H-benzo[d]imidazole)-5-sulfonamido)phenyl)cyclohexane-1-carboxylic acid (183 mg, 0.169 mmol, 42.0% yield) as an off-white solid. $^1H$ NMR (400 MHz, DMSO-$d_6$) δ 7.62 (m, 1H), 7.52-7.50 (m, 1H), 7.23 (dd, J=8.6, 2.0 Hz, 1H), 7.09 (d, J=8.0 Hz, 2H), 6.98 (d, J=8.4 Hz, 2H), 6.97-6.90 (m, 2H), 6.77-6.73 (m, 2H), 3.75 (s, 3H), 3.68 (s, 3H), 3.18 (s, 3H), 3.16-3.11 (m, 2H), 3.07 (s, 3H), 2.72-2.67 (m, 2H), 2.57 (m, 2H), 2.55 (s, 3H), 2.17-2.13 (m, 1H), 2.07-2.02 (m, 1H), 1.56-1.46 (m, 1H), 1.33-1.24 (m, 1H). ES-LCMS m/z 635.2 $[M+H]^+$.

Step 9: rac-methyl (1R,2S,3R,6R)-6-((4-isopropylphenyl)carbamoyl)-3-((4-methoxybenzyl)amino)-2-(4-((N,1,2-trimethyl-1H-benzo[d]imidazole)-5-sulfonamido)phenyl)cyclohexane-1-carboxylate

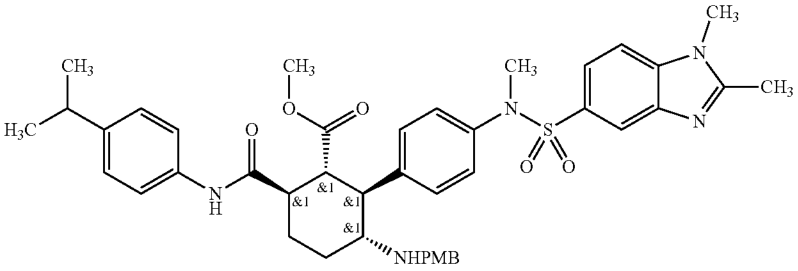

To a mixture of rac-(1R,2R,3S,4R)-4-((4-methoxybenzyl) amino)-2-(methoxycarbonyl)-3-(4-((N,1,2-trimethyl-1H-benzo[d]imidazole)-5-sulfonamido)phenyl)cyclohexane-1-carboxylic acid (180 mg, 0.28 mmol), 4-isopropylaniline (0.050 mL, 0.34 mmol) and 1-methyl-1H-imidazole (0.070 mL, 0.85 mmol) in acetonitrile (2 mL) at 0° C. was added N-(chloro(dimethylamino)methylene)-N-methylmethanaminium hexafluorophosphate(V) (120 mg, 0.43 mmol). The reaction was stirred at rt for 16 h, and the resulting precipitated solid was collected by filtration, washing with ACN (5 mL), and dried under vacuum to afford rac-methyl (1R,2S,3R,6R)-6-((4-isopropylphenyl)carbamoyl)-3-((4-methoxybenzyl)amino)-2-(4-((N,1,2-trimethyl-1H-benzo[d]imidazole)-5-sulfonamido)phenyl)cyclohexane-1-carboxylate (85 mg, 0.09 mmol, 33% yield) as an off-white solid. $^1H$ NMR (400 MHz, DMSO-$d_6$) δ 9.93 (s, 1H), 7.64 (d, J=1.6 Hz, 1H), 7.52 (d, J=8.4 Hz, 1H), 7.43 (d, J=8.4 Hz, 2H), 7.38-7.29 (m, 3H), 7.28-7.10 (m, 6H), 6.93 (d, J=8.4 Hz, 2H), 3.80-3.75 (m, 2H), 3.74 (s, 6H), 3.60-3.49 (m, 2H), 3.16 (s, 3H), 3.12 (s, 3H), 3.03-3.01 (m, 2H), 2.84-2.74 (m, 2H), 2.54 (s, 3H), 2.09-2.07 (m, 1H), 1.69-1.66 (m, 2H), 1.16 (d, J=6.8 Hz, 6H). ES-LCMS m/z 752.2 $[M+H]^+$.

Step 10: rac-methyl (1R,2S,3R,6R)-3-(ethylamino)-6-((4-isopropylphenyl)carbamoyl)-2-(4-((N,1,2-trimethyl-1H-benzo[d]imidazole)-5-sulfonamido)phenyl) cyclohexane-1-carboxylate

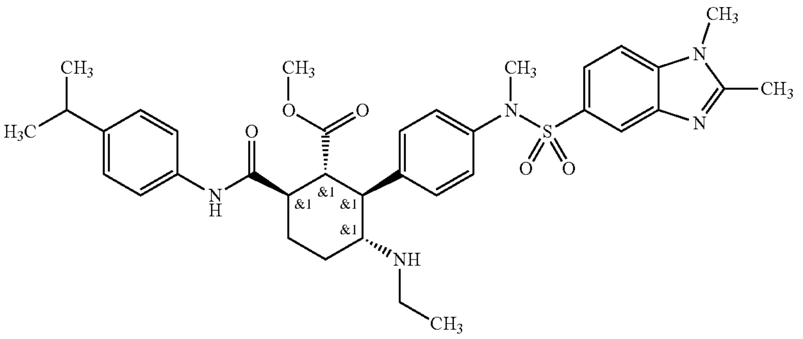 [SMILES: CCN[C@@H]1CC[C@@H](C(=O)Nc2ccc(C(C)C)cc2)[C@H](C(=O)OC)[C@H]1c1ccc(N(C)S(=O)(=O)c2ccc3c(c2)nc(C)n3C)cc1]

To a mixture of rac-methyl (1R,2S,3R,6R)-6-((4-isopropylphenyl)carbamoyl)-3-((4-methoxybenzyl)amino)-2-(4-((N,1,2-trimethyl-1H-benzo[d]imidazole)-5-sulfonamido) phenyl)cyclohexane-1-carboxylate (50 mg, 0.07 mmol) in ethanol (6 mL) under $N_2$ was added palladium on carbon (70.8 mg, 0.0700 mmol). The reaction was stirred under $H_2$ atmosphere (1 kg bladder pressure) for 16 h, filtered through Celite (washing with ethanol [20 mL]), concentrated and subjected to reverse phase purification (0-90% MeCN in $H_2O$, with 0.1% formic acid modifier) to afford rac-methyl (1R,2S,3R,6R)-3-(ethylamino)-6-((4-isopropylphenyl)carbamoyl)-2-(4-((N,1,2-trimethyl-1H-benzo[d]imidazole)-5-sulfonamido)phenyl)cyclohexane-1-carboxylate (22 mg, 0.030 mmol, 50% yield) as an off-white solid. $^1$H NMR (400 MHz, DMSO-$d_6$) δ 9.89 (s, 1H), 7.62 (d, J=8.4 Hz, 1H), 7.57 (d, J=1.6 Hz, 1H), 7.44 (d, J=8.4 Hz, 2H), 7.27 (d, J=1.6 Hz, 1H), 7.15-7.13 (m, 4H), 7.01 (d, J=8.4 Hz, 2H), 3.78 (s, 3H), 3.18 (s, 3H), 3.10 (s, 3H), 2.92 (t, J=11.2 Hz, 1H), 2.84 (t, J=7.2 Hz, 1H), 2.77-2.67 (m, 3H), 2.56 (s, 3H), 2.32-2.20 (m, 2H), 2.03 (d, J=2.8 Hz, 1H), 1.76-1.64 (m, 1H), 1.17 (d, J=6.8 Hz, 6H), 0.82 (t, J=6.4 Hz, 3H), two protons obscured by solvent peaks. ES-LCMS m/z 660.2 [M+H]$^+$.

Intermediate 56: (1R,2R,6S)-2-((2-fluoro-4-(trifluoromethyl)phenyl)carbamoyl)-6-(4-((3-hydroxy-N-methyl-4-vinylphenyl)sulfonamido)phenyl)cyclohexane-1-carboxylic acid

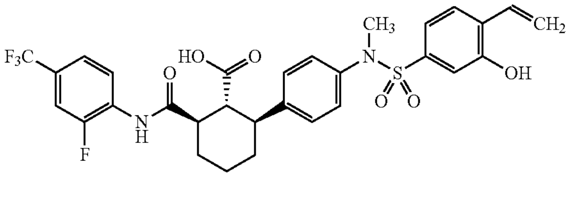 [SMILES: C=Cc1ccc(S(=O)(=O)N(C)c2ccc([C@H]3CCC[C@@H](C(=O)Nc4ccc(C(F)(F)F)cc4F)[C@@H]3C(=O)O)cc2)cc1O]

To a mixture of (1R,2S,6R)-2-(4-((4-bromo-3-hydroxy-N-methylphenyl)sulfonamido)phenyl)-6-((2-fluoro-4-(trifluoromethyl)phenyl)carbamoyl)cyclohexane-1-carboxylic acid Example 274 (0.080 mg, 0.12 mmol) in 1,4-dioxane (5 mL) was added tripotassium phosphate (76 mg, 0.36 mmol) and water (11 μl, 0.59 mmol), followed by S—PHOS (3.90 mg, 9.50 μmol) and 4,4,5,5-tetramethyl-2-vinyl-1,3,2-dioxaborolane (37 mg, 0.24 mmol). The reaction was degassed for 15 min, and palladium(II) acetate (1.07 mg, 4.75 μmol) was added. The mixture was stirred at 80° C. for 16 h, concentrated and subjected to reverse phase purification (0-100% MeCN in $H_2O$, 0.1% ammonium bicarbonate modifier). The fractions containing the desired product were combined, freeze dried and lyophilized to afford (1R,2R,6S)-2-((2-fluoro-4-(trifluoromethyl)phenyl)carbamoyl)-6-(4-((3-hydroxy-N-methyl-4-vinylphenyl)sulfonamido)phenyl)cyclohexane-1-carboxylic acid (46 mg, 0.073 mmol, 62% yield) as a white solid. $^1$H NMR (400 MHz, DMSO-$d_6$) δ 10.04 (s, 1H), 8.26 (t, J=7.6 Hz, 1H), 7.71 (dd, J=10.2, 3.6 Hz, 1H), 7.55-7.53 (m, 3H), 7.22-6.69 (m, 10H), 5.92 (d, J=18.4 Hz, 1H), 5.36 (d, J=12.0 Hz, 1H), 3.04 (t, J=14.8 Hz, 3H), 1.98-1.51 (m, 6H). ES-LCMS m/z 619.0 [M−H]$^-$.

Intermediate 57 and Intermediate 58: rel-(1R,2R,4R,6S)-4-cyano-2-((2-fluoro-4-(trifluoromethyl)phenyl)carbamoyl)-6-(4-(methylamino)phenyl)cyclohexane-1-carboxylic acid ISOMER 1 and rel-(1R,2R,4R,6S)-4-cyano-2-((2-fluoro-4-(trifluoromethyl)phenyl)carbamoyl)-6-(4-(methylamino)phenyl)cyclohexane-1-carboxylic acid ISOMER2

ISOMER 1 and ISOMER 2

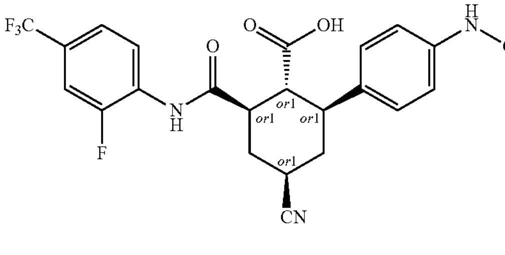

Step 1: rac-(3aR,7S,7aS)-7-(4-bromophenyl)-1-oxooctahydroisobenzofuran-5-carbonitrile

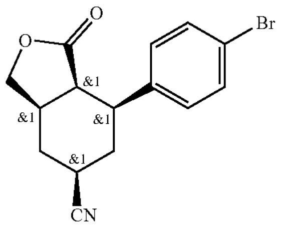 [SMILES: N#C[C@H]1C[C@H]2COC(=O)[C@H]2[C@@H](c2ccc(Br)cc2)C1]

To a mixture of rac-(3aR,7S,7aS)-7-(4-bromophenyl)tetrahydroisobenzofuran-1,5(3H,4H)-dione, Intermediate 8, Step 5 (3.00 g, 9.70 mmol) and 1-((isocyanomethyl)sulfonyl)-4-methylbenzene (2.84 g, 14.6 mmol) in 1,2-dimethoxyethane (15 mL) at −78° C. was added tert-butanol (15 mL) and potassium tert-butoxide (29.1 mL, 29.1 mmol). The reaction was warmed to rt, stirred for 16 h, quenched with ice water (20 mL), acidified with 0.1 N HCl and extracted with ethyl acetate (3×50 mL). The organic layers were washed with brine (50 mL), dried over sodium sulphate, concentrated and subjected to reverse phase purification (0-100% MeCN in $H_2O$, 0.1% formic acid modifier) to afford rac-(3aR,7S,7aS)-7-(4-bromophenyl)-1-oxooctahydroisobenzofuran-5-carbonitrile (1.05 g, 2.48 mmol, 26.0% yield) as a yellow solid. $^1$H NMR (400 MHz, DMSO-$d_6$) δ 7.53-7.44 (m, 2H), 7.25-7.15 (m, 2H), 4.80-4.59 (m, 1H), 3.29-3.15 (m, 1H), 3.04-2.88 (m, 1H), 2.77 (td, J=11.9, 3.3 Hz, 1H), 2.40-2.28 (m, 1H), 2.24-2.06 (m, 1H), 2.03-1.91 (m, 1H), 1.88-1.72 (m, 2H), 1.55-1.39 (m, 1H). ES-LCMS m/z poor ionization.

Step 2: rac-(1R,2S,4R,6R)-2-(4-bromophenyl)-4-cyano-6-((2-fluoro-4-(trifluoromethyl)phenyl)carbamoyl)cyclohexane-1-carboxylic acid

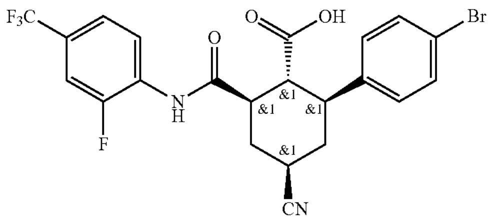

In an analogous manner to the preparation described above (Intermediate 8, Steps 8 through 12) using rac-(3aR,7S,7aS)-7-(4-bromophenyl)-1-oxooctahydroisobenzofuran-5-carbonitrile in place of Intermediate 8, Step 7, rac-(1R,2S,4R,6R)-2-(4-bromophenyl)-4-cyano-6-((2-fluoro-4-(trifluoromethyl)phenyl)carbamoyl)cyclohexane-1-carboxylic acid (130 mg, 0.25 mmol, 58% yield) was obtained as white solid. $^1$H NMR (400 MHz, DMSO-$d_6$) δ 10.27 (br s, 1H), 8.23 (t, J=8.0 Hz, 1H), 7.71 (s, 1H), 7.68 (s, 1H), 7.53 (d, J=9.0 Hz, 1H), 7.44 (d, J=8.5 Hz, 2H), 7.23 (d, J=8.0 Hz, 2H), 3.54-3.47 (m, 2H), 3.02-2.95 (m, 1H), 2.84-2.72 (m, 1H), 2.39-2.24 (m, 2H), 2.13-1.91 (m, 2H), 1.56-1.33 (m, 2H), 1.09 (t, J=7.0 Hz, 3H). ES-LCMS m/z 532.0 $[M+H]^+$.

Step 3: rel-(1R,2S,4R,6R)-2-(4-bromophenyl)-4-cyano-6-((2-fluoro-4-(trifluoromethyl)phenyl)carbamoyl)cyclohexane-1-carboxylic acid ISOMER 1 and rel-(1R,2S,4R,6R)-2-(4-bromophenyl)-4-cyano-6-((2-fluoro-4-(trifluoromethyl)phenyl)carbamoyl)cyclohexane-1-carboxylic acid ISOMER 2

ISOMER 1 and ISOMER 2

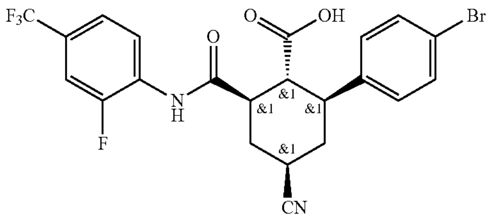 [SMILES: N#C[C@@H]1C[C@H](c2ccc(Br)cc2)[C@@H](C(=O)O)[C@H](C(=O)Nc2ccc(C(F)(F)F)cc2F)C1]

rac-(1R,2S,4R,6R)-2-(4-Bromophenyl)-4-cyano-6-((2-fluoro-4-(trifluoromethyl)phenyl)carbamoyl)cyclohexane-1-carboxylic acid was separated by Chiral-Prep-SFC (Column: YMC Amylose SA 250×20 mm, 5 µm; Mobile Phase: $CO_2$: IPA 65:35) to afford:

First-eluting peak rel-(1R,2S,4R,6R)-2-(4-bromophenyl)-4-cyano-6-((2-fluoro-4-(trifluoromethyl)phenyl)carbamoyl)cyclohexane-1-carboxylic acid ISOMER 1 (0.060 g, 0.12 mmol, 46% yield) as white solid. $^1$H NMR (400 MHz, DMSO-$d_6$) δ 10.28 (br s, 1H), 8.22 (t, J=8.0 Hz, 1H), 7.70 (dd, J=11.3, 1.8 Hz, 1H), 7.54 (d, J=9.0 Hz, 1H), 7.46 (d, J=8.0 Hz, 2H), 7.24 (d, J=8.5 Hz, 2H), 3.06-2.92 (m, 2H), 2.84-2.72 (m, 2H), 2.37-2.25 (m, 1H), 2.05-1.77 (m, 3H). ES-LCMS m/z 511.0 $[M-H]^-$.

Second-eluting peak rel-(1R,2S,4R,6R)-2-(4-bromophenyl)-4-cyano-6-((2-fluoro-4-(trifluoromethyl)phenyl)carbamoyl)cyclohexane-1-carboxylic acid ISOMER 2 (38 mg, 0.070 mmol, 28% yield) as white solid. $^1$H NMR (400 MHz, DMSO-$d_6$) δ 10.27 (br s, 1H), 8.22 (t, J=8.0 Hz, 1H), 7.78-7.67 (m, 1H), 7.54 (d, J=8.5 Hz, 1H), 7.47 (d, J=8.5 Hz, 2H), 7.24 (d, J=8.5 Hz, 2H), 3.09-2.95 (m, 2H), 2.84-2.72 (m, 2H), 2.37-2.25 (m, 1H), 2.05-1.77 (m, 3H). ES-LCMS m/z 511.0 $[M-H]^-$.

Step 4: rel-(1R,2R,4R,6S)-4-cyano-2-((2-fluoro-4-(trifluoromethyl)phenyl)carbamoyl)-6-(4-(methylamino)phenyl)cyclohexane-1-carboxylic acid ISOMER 1 and rel-(1R,2R,4R,6S)-4-cyano-2-((2-fluoro-4-(trifluoromethyl)phenyl)carbamoyl)-6-(4-(methylamino)phenyl)cyclohexane-1-carboxylic acid ISOMER 2

ISOMER 1 and ISOMER 2

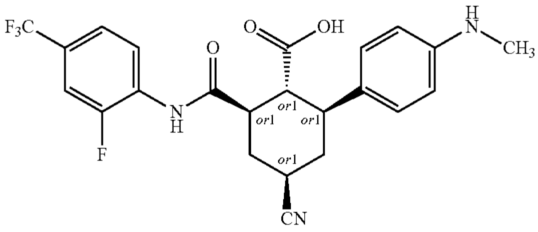

To a mixture of rel-(1R,2S,4R,6R)-2-(4-bromophenyl)-4-cyano-6-((2-fluoro-4-(trifluoromethyl)phenyl)carbamoyl) cyclohexane-1-carboxylic acid ISOMER 2 (38 mg, 0.074 mmol) in dioxane (1 mL) was added sodium tert-butoxide (21.3 mg, 0.222 mmol). After degassing for 5 min, tBuX-Phos Pd G3 (5.88 mg, 7.40 μmol) was added, followed by methanamine (2M in THF, 0.740 mL, 1.48 mmol). The reaction was heated at 100° C. for 1 h, concentrated and subjected to reverse-phase purification (0-100% MeCN in water, formic acid additive) to afford rel-(1R,2R,4R,6S)-4-cyano-2-((2-fluoro-4-(trifluoromethyl)phenyl)carbamoyl)-6-(4-(methylamino)phenyl)cyclohexane-1-carboxylic acid ISOMER 1 (25 mg, 0.044 mmol, 60% yield) as a white solid. $^1$H NMR (400 MHz, DMSO-$d_6$) δ 10.13 (s, 1H), 8.19 (t, J=8.0 Hz, 1H), 7.73 (dd, J=11.0, 2.0 Hz, 1H), 7.56 (d, J=8.5 Hz, 1H), 6.97 (d, J=8.5 Hz, 2H), 6.44 (d, J=8.5 Hz, 2H), 5.49 (d, J=3.5 Hz, 1H), 3.08-2.94 (m, 2H), 2.74 (t, J=11.3 Hz, 1H), 2.66-2.58 (m, 4H), 2.34-2.27 (m, 1H), 2.02-1.95 (m, 1H), 1.85 (dq, J=19.5, 12.5 Hz, 2H). ES-LCMS m/z 462.2 $[M-H]^-$. Concurrently, to a mixture of rel-(1R,2S,4R,6R)-2-(4-bromophenyl)-4-cyano-6-((2-fluoro-4-(trifluoromethyl)phenyl)carbamoyl)cyclohexane-1-carboxylic acid ISOMER 1 (0.060 g, 0.12 mmol) in dioxane (1.5 mL) was added sodium tert-butoxide (33.7 mg, 0.351 mmol). After degassing for 5 min, tBuXPhos Pd G3 (9.3 mg, 0.012 mmol) was added, followed by methanamine (2M in THF, 1.17 mL, 2.34 mmol). The reaction was heated at 100° C. for 1 h, concentrated and subjected to reverse-phase purification (0-100% MeCN in water, formic acid additive) to afford rel-(1R,2R,4R,6S)-4-cyano-2-((2-fluoro-4-(trifluoromethyl)phenyl)carbamoyl)-6-(4-(methylamino) phenyl)cyclohexane-1-carboxylic acid ISOMER 2 (28 mg, 0.055 mmol, 47% yield) was obtained as white solid. $^1$H NMR (400 MHz, DMSO-$d_6$) δ 11.83 (br s, 1H), 10.13 (s, 1H), 8.19 (t, J=8.0 Hz, 1H), 7.73 (dd, J=11.0, 2.0 Hz, 1H), 7.56 (d, J=9.0 Hz, 1H), 6.97 (d, J=8.5 Hz, 2H), 6.44 (d, J=8.5 Hz, 2H), 5.55-5.42 (m, 1H), 3.06-2.94 (m, 2H), 2.74 (t, J=11.3 Hz, 1H), 2.63 (br s, 3H), 2.34-2.25 (m, 1H), 2.03-1.76 (m, 3H). ES-LCMS m/z 462.2 $[M-H]^-$.

Intermediate 59: (1R,2S,4R,6R)-2-(4-aminophenyl)-4-ethoxy-6-((2-fluoro-4-(trifluoromethyl)phenyl) carbamoyl)cyclohexane-1-carboxylic acid

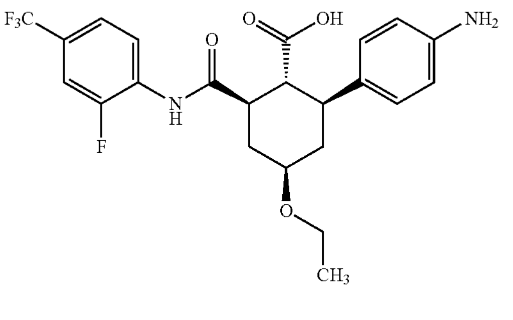 [SMILES: CCO[C@@H]1C[C@H](c2ccc(N)cc2)[C@@H](C(=O)O)[C@H](C(=O)Nc2ccc(C(F)(F)F)cc2F)C1]

Step 1: (1R,2S,4R,6R)-2-(4-((tert-butoxycarbonyl) amino)phenyl)-4-ethoxy-6-((2-fluoro-4-(trifluoromethyl)phenyl)carbamoyl)cyclohexane-1-carboxylic acid

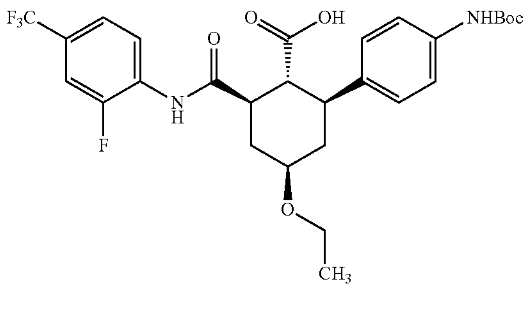 [SMILES: CCO[C@@H]1C[C@H](c2ccc(NC(=O)OC(C)(C)C)cc2)[C@@H](C(=O)O)[C@H](C(=O)Nc2ccc(C(F)(F)F)cc2F)C1]

To a mixture of (1R,2S,4R,6R)-2-(4-bromophenyl)-4-ethoxy-6-((2-fluoro-4-(trifluoromethyl)phenyl)carbamoyl) cyclohexane-1-carboxylic acid Intermediate 9 Step 1 second-eluting compound (0.100 g, 0.188 mmol)) and sodium tert-butoxide (54.2 mg, 0.564 mmol) in dioxane (1 mL) was added tBuXPhos Pd G3 (15 mg, 0.019 mmol) was added, and the mixture was degassed for 5 min. tert-Butyl carbamate (66.0 mg, 0.564 mmol) was added, and the reaction was microwaved at 100° C. for 1 h. The mixture was concentrated, and the resulting residue was subjected to normal phase purification (0-10% MeOH in DCM) to afford (1R, 2S,4R,6R)-2-(4-((tert-butoxycarbonyl)amino)phenyl)-4-ethoxy-6-((2-fluoro-4-(trifluoromethyl)phenyl)carbamoyl) cyclohexane-1-carboxylic acid (0.060 g, 0.10 mmol, 56% yield) as an off-white solid. $^1$H NMR (400 MHz, DMSO-$d_6$) δ 10.13 (s, 1H), 9.23 (s, 1H), 8.21 (t, J=8.3 Hz, 1H), 7.71 (dd, J=11.0, 1.5 Hz, 1H), 7.54 (d, J=8.0 Hz, 1H), 7.33 (d, J=8.5 Hz, 2H), 7.12 (d, J=8.5 Hz, 2H), 3.57-3.41 (m, 3H), 3.10-2.95 (m, 1H), 2.75-2.63 (m, 2H), 2.37-2.25 (m, 1H), 2.01 (d, J=12.5 Hz, 1H), 1.56-1.33 (m, 12H), 1.09 (t, J=7.0 Hz, 3H).ES-LCMS m/z 567.2 $[M-H]^-$.

Step 2: (1R,2S,4R,6R)-2-(4-aminophenyl)-4-ethoxy-6-((2-fluoro-4-(trifluoromethyl)phenyl)carbamoyl) cyclohexane-1-carboxylic acid

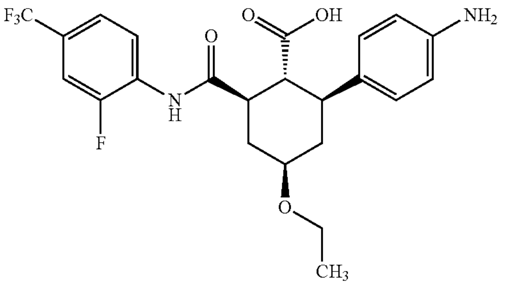 [SMILES: CCO[C@@H]1C[C@H](c2ccc(N)cc2)[C@@H](C(=O)O)[C@H](C(=O)Nc2ccc(C(F)(F)F)cc2F)C1]

To a mixture of (1R,2S,4R,6R)-2-(4-((tert-butoxycarbonyl)amino)phenyl)-4-ethoxy-6-((2-fluoro-4-(trifluoromethyl)phenyl)carbamoyl)cyclohexane-1-carboxylic acid (60.0 mg, 0.106 mmol) in DCM (5 mL) at 0° C. was added 4 M HCl in dioxane (0.264 mL, 1.06 mmol), dropwise. The reaction was stirred at rt for 16 h, concentrated, diluted with water (10 mL), basified with sat. aq. sodium bicarbonate and extracted with EtOAc (4×10 mL). The combined organics were washed with water (2×10 mL) and brine (10 mL), dried over sodium sulphate, concentrated and subjected to normal phase purification (0-100% EtOAC in pet ether) to afford (1R,2S,4R,6R)-2-(4-aminophenyl)-4-ethoxy-6-((2-fluoro-4-(trifluoromethyl)phenyl)carbamoyl)cyclohexane-1-carboxylic acid (35 mg, 0.067 mmol, 64% yield) as an off-white solid. $^1$H NMR (400 MHz, DMSO-$d_6$) δ 11.77 (br s, 1H), 10.17 (s, 1H), 8.21 (t, J=8.0 Hz, 1H), 7.70 (d, J=11.0 Hz, 1H), 7.54 (d, J=8.5 Hz, 1H), 6.88 (d, J=8.5 Hz, 2H), 6.44 (d, J=8.5 Hz, 2H), 4.83 (s, 1H), 3.57 (s, 2H), 3.49 (q, J=7.0 Hz, 2H), 2.96 (d, J=10.0 Hz, 1H), 2.58 (d, J=9.5 Hz, 2H), 2.26 (d, J=11.5 Hz, 1H), 2.01-1.92 (m, 1H), 1.45-1.30 (m, 2H), 1.09 (t, J=7.0 Hz, 3H). ES-LCMS m/z 469.2 [M+H]$^+$.

Intermediate 60: (1R,2S,6R)-2-(4-((7-(2-((tert-butoxycarbonyl)amino)ethyl)-N,1,2-trimethyl-1H-benzo[d]imidazole)-5-sulfonamido)phenyl)-6-((2-fluoro-4-(trifluoromethyl)phenyl)carbamoyl)cyclohexane-1-carboxylic acid

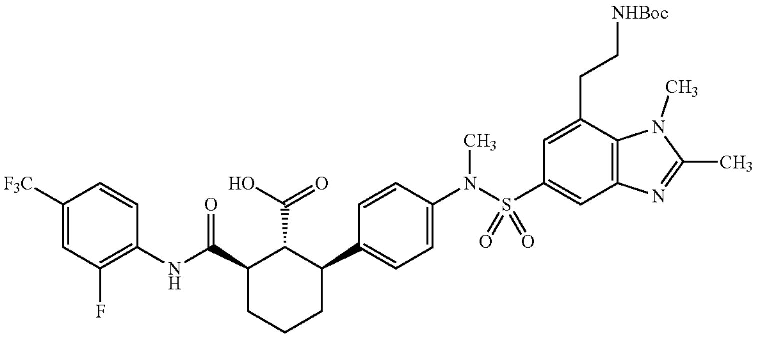 [SMILES: Cc1nc2cc(S(=O)(=O)N(C)c3ccc([C@H]4CCC[C@@H](C(=O)Nc5ccc(C(F)(F)F)cc5F)[C@@H]4C(=O)O)cc3)cc(CCNC(=O)OC(C)(C)C)c2n1C]

Step 1: 4-bromo-2-chloro-N-methyl-6-nitroaniline

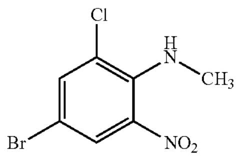

To a mixture of 4-bromo-2-chloro-6-nitroaniline (49.5 g, 197 mmol) in toluene (300 mL) at 0° C. was added sodium hydroxide (79 g, 2.0 mol) in water (300 mL), dimethyl sulfate (22.6 mL, 236 mmol) followed by tetrabutylammonium hydrogen sulfate (4.01 g, 11.8 mmol). The reaction mixture was stirred at rt for 2 h, diluted with EtOAc (1 L) and washed with water (3×200 mL). The organic layer was dried over sodium sulfate, concentrated, dissolved in DCM (40 mL), adsorbed on silica gel 60-120 mesh (620 g) and purified through a silica column (330 g), eluting with 15% EtOAc in pet ether to afford partially pure product 4-bromo-2-chloro-N-methyl-6-nitroaniline (82 g, 0.26 mmol, quantitative yield) as a yellow solid. $^1$H NMR (400 MHz, DMSO-$d_6$) δ 8.13 (d, J=2.5 Hz, 1H), 7.94 (d, J=2.0 Hz, 1H), 7.41 (br s, 2H). ES-LCMS m/z 265.0 [M+H]$^+$.

Step 2: 4-bromo-6-chloro-N1-methylbenzene-1,2-diamine

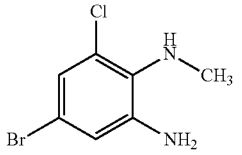

In two parallel reactions, to a mixture of 4-bromo-2-chloro-N-methyl-6-nitroaniline (41.0 g, 154 mmol) in ethanol (410 mL) was added anhydrous tin(II) chloride (43.9 g, 232 mmol). After 16 h, the reactions were combined, concentrated, diluted with EtOAc (1 L) and neutralized with 10% KOH solution. The resulting solid was filtered off, washing with EtOAc (800 mL). The organic layer was separated, washed with brine (550 mL), dried over sodium sulfate, concentrated, dissolved in DCM (100 mL) and purified over silica, eluting with 12% EtOAc in pet ether. This crude material was subjected to further normal phase purification (0-100% EtOAC in pet ether) to afford 4-bromo-6-chloro-N1-methylbenzene-1,2-diamine (22 g, 53 mmol, 30% yield) as a dark brown solid. $^1$H NMR (400 MHz, DMSO-$d_6$) δ 6.74 (d, J=2.0 Hz, 1H), 6.70 (d, J=2.0 Hz, 1H), 5.33 (br s, 1H), 2.71 (d, J=5.0 Hz, 3H). ES-LCMS m/z 237.1 [M+H]$^+$.

Step 3: 5-bromo-7-chloro-1,2-dimethyl-1H-benzo[d]imidazole

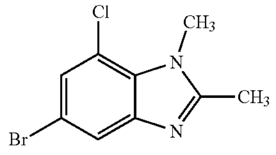

To a mixture of 4-bromo-6-chloro-N1-methylbenzene-1,2-diamine (22 g, 93 mmol) in DMF (180 mL) at 25° C. was added 1,1,1-trimethoxyethane (0.100 L, 747 mmol). The reaction was stirred at 100° C. for an hour. Acetic acid (10.7 mL, 187 mmol), and heating was continued for 16 h. The mixture was poured slowly into 10% sodium bicarbonate solution (100 mL) at 0° C., and the precipitated solid was filtered, washed with water (100 mL), dried under vacuum and triturated with MTBE (20 mL) to obtain product as a pale-yellow solid. The filtrate was concentrated completely under reduced pressure, dissolved in DCM (5 mL), adsorbed on silica gel (60 g) and purified through silica (100 g), eluting with 10% MeOH in DCM to afford additional 5-bromo-7-chloro-1,2-dimethyl-1H-benzo[d]imidazole. Product (14 g, 48 mmol, 52% yield) was combined as a pale yellow solid. $^1$H NMR (400 MHz, DMSO-$d_6$) δ 7.70 (d, J=1.5 Hz, 1H), 7.39 (d, J=1.5 Hz, 1H), 3.33 (s, 3H), 2.53 (s, 3H). ES-LCMS m/z 261.0 [M+H]$^+$.

Step 4: 7-chloro-5-((4-methoxybenzyl)thio)-1,2-dimethyl-1H-benzo[d]imidazole

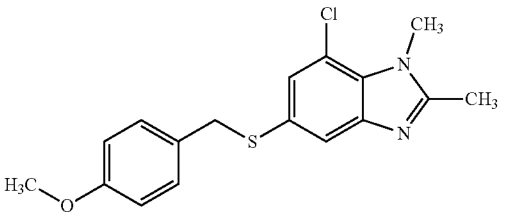

A mixture of 5-bromo-7-chloro-1,2-dimethyl-1H-benzo[d]imidazole (8.0 g, 31 mmol) and DIPEA (10.8 mL, 61.6 mmol) in dioxane (30 mL) was stirred under nitrogen and degassed for 10 min. (4-Methoxyphenyl)methanethiol (6.48 mL, 46.2 mmol) was added, followed by Xantphos (1.78 g, 3.08 mmol) and $Pd_2(dba)_3$ (2.258 g, 2.466 mmol) in one charge. The reaction was stirred at 100° C. for 16 h, filtered through Celite, washing with EtOAc (100 mL), concentrated, dissolved in DCM (10 mL), adsorbed on silica gel (40 g) and purified through silica (100 g), eluting with EtOAc to afford product. This material was triturated with MTBE (20 mL) to give 7-chloro-5-((4-methoxybenzyl)thio)-1,2-dimethyl-1H-benzo[d]imidazole (9.0 g, 23 mmol, 75% yield) as a pale-yellow solid. $^1$H NMR (400 MHz, DMSO-$d_6$) δ 7.44 (d, J=1.5 Hz, 1H), 7.22-7.18 (m, 2H), 7.15 (d, J=1.5 Hz, 1H), 6.82 (d, J=9.0 Hz, 2H), 4.16 (s, 2H), 3.94 (s, 3H), 3.70 (s, 3H), 2.53-2.51 (m, 3H). ES-LCMS m/z 333.0 [M+H]$^+$.

Step 5: tert-butyl (2-(5-((4-methoxybenzyl)thio)-1,2-dimethyl-1H-benzo[d]imidazol-7-yl)ethyl)carbamate

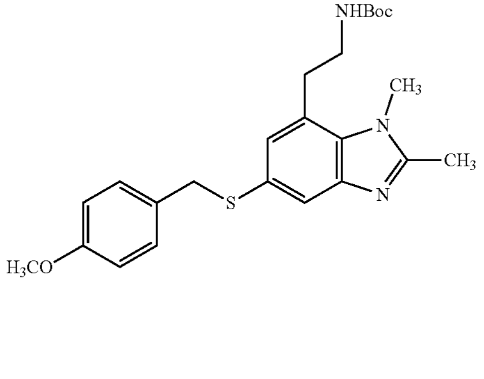 [SMILES: COc1ccc(CSc2cc(CCNC(=O)OC(C)(C)C)c3c(c2)nc(C)n3C)cc1]

A mixture of 7-chloro-5-((4-methoxybenzyl)thio)-1,2-dimethyl-1H-benzo[d]imidazole (1.0 g, 3.0 mmol), tert-butyl (2-(trifluoro-14-boraneyl)ethyl)carbamate, potassium salt (1.51 g, 6.01 mmol), $Cs_2CO_3$ (2.45 g, 7.51 mmol) and XPhos (0.29 g, 0.60 mmol) in tetrahydrofuran (10 mL) and water (2 mL) was purged with nitrogen for 3 mins. XPhos Pd G3 (0.26 g, 0.30 mmol) was added, and the reaction was purged with nitrogen for 3 mins. The mixture was heated to 100° C. for 16 h, concentrated and subjected to reverse phase purification (MeCN/H2O, 0.1% ABC modifier, 0 to 100% gradient) to afford tert-butyl (2-(5-((4-methoxybenzyl)thio)-1,2-dimethyl-1H-benzo[d]imidazol-7-yl)ethyl)carbamate (0.25 g, 0.50 mmol, 17% yield) as white solid. $^1$H NMR (400 MHz, DMSO-$d_6$) δ 7.35-7.29 (m, 1H), 7.22-7.12 (m, 2H), 7.04 (t, J=5.5 Hz, 1H), 6.89 (d, J=1.5 Hz, 1H), 6.84-6.75 (m, 2H), 4.06 (s, 2H), 3.89 (s, 3H), 3.70 (s, 3H), 3.17-3.13 (m, 2H), 3.08-3.02 (m, 2H), 2.48 (s, 3H), 1.37 (s, 9H). ES-LCMS m/z 442.2 [M+H]$^+$.

Step 6: tert-butyl (2-(5-(chlorosulfonyl)-1,2-dimethyl-1H-benzo[d]imidazol-7-yl)ethyl)carbamate

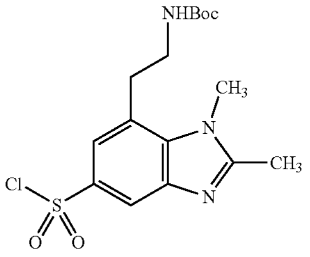 [SMILES: Cc1nc2cc(S(=O)(=O)Cl)cc(CCNC(=O)OC(C)(C)C)c2n1C]

To a mixture of tert-butyl (2-(5-((4-methoxybenzyl)thio)-1,2-dimethyl-1H-benzo[d]imidazol-7-yl)ethyl)carbamate (0.25 g, 0.57 mmol) in acetic acid (2.5 mL) and water (0.25 mL) at 0° C. was added NCS (300 mg, 2.27 mmol). The reaction was stirred at RT for 1 h, diluted with EtOAc (50 mL), washed with water (15 mL) and brine (15 mL), dried over sodium sulfate, filtered and concentrated to afford tert-butyl (2-(5-(chlorosulfonyl)-1,2-dimethyl-1H-benzo[d]imidazol-7-yl)ethyl)carbamate (350 mg, 0.40 mmol, 70% yield) as a colorless oil. $^1$H NMR (400 MHz, DMSO-$d_6$) δ 7.75 (d, J=1.6 Hz, 1H), 7.56 (d, J=1.5 Hz, 1H), 3.80 (s, 3H), 3.19-3.17 (m, 4H), 1.38 (s, 9H), three protons obscured by solvent peaks. ES-LCMS m/z 388.2 [M+H]$^+$.

Step 7: (1R,2S,6R)-2-(4-((7-(2-((tert-butoxycarbonyl)amino)ethyl)-N,1,2-trimethyl-1H-benzo[d]imidazole)-5-sulfonamido)phenyl)-6-((2-fluoro-4-(trifluoromethyl)phenyl)carbamoyl)cyclohexane-1-carboxylic acid

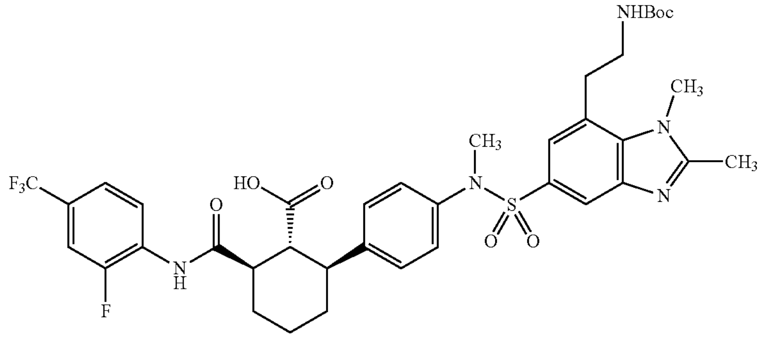 [SMILES: Cc1nc2cc(S(=O)(=O)N(C)c3ccc([C@H]4CCC[C@@H](C(=O)Nc5ccc(C(F)(F)F)cc5F)[C@@H]4C(=O)O)cc3)cc(CCNC(=O)OC(C)(C)C)c2n1C]

To a mixture of (1R,2R,6S)-2-((2-fluoro-4-(trifluoromethyl)phenyl)carbamoyl)-6-(4-(methylamino)phenyl)cyclohexane-1-carboxylic acid (0.25 g, 0.57 mmol) in dichloromethane (2.5 mL) at 0° C. was added pyridine (0.180 mL, 2.28 mmol) followed by tert-butyl (2-(5-(chlorosulfonyl)-1,2-dimethyl-1H-benzo[d]imidazol-7-yl)ethyl)carbamate (0.33 g, 0.86 mmol) in dichloromethane (2.5 mL). The reaction was stirred at RT for 1 h, concentrated and subjected to reverse phase purification (0-100% MeCN in $H_2O$, 0.1% formic acid modifier) to afford (1R,2S,6R)-2-(4-((7-(2-((tert-butoxycarbonyl)amino)ethyl)-N,1,2-trimethyl-1H-benzo[d]imidazole)-5-sulfonamido)phenyl)-6-((2-fluoro-4-(trifluoromethyl)phenyl)carbamoyl)cyclohexane-1-carboxylic acid (0.25 g, 0.25 mmol, 43% yield) as a white solid. $^1$H NMR (400 MHz, DMSO-$d_6$) δ 12.16 (br s, 1H), 10.26-9.82 (m, 1H), 8.23 (t, J=8.0 Hz, 1H), 7.71 (d, J=11.0 Hz, 1H), 7.53 (d, J=8.0 Hz, 1H), 7.31 (d, J=1.0 Hz, 1H), 7.18 (d, J=8.5 Hz, 2H), 6.94 (d, J=8.0 Hz, 3H), 3.96 (s, 3H), 3.17-3.06 (m, 5H), 3.02 (s, 3H), 2.78 (t, J=10.8 Hz, 1H), 2.72-2.65 (m, 1H), 2.55 (s, 3H), 2.05-1.98 (m, 1H), 1.92-1.84 (m, 1H), 1.81-1.72 (m, 1H), 1.68-1.44 (m, 3H), 1.34 (s, 9H). ES-LCMS m/z 790.2 $[M+H]^+$.

Intermediate 61: rel-benzyl (1R,2R,4R,6S)-2-((2-fluoro-4-(trifluoromethyl)phenyl)carbamoyl)-4-(N-methylacetamido)-6-(4-((N,1,2-trimethyl-1H-benzo[d]imidazole)-5-sulfonamido)phenyl)cyclohexane-1-carboxylate ISOMER 1

ISOMER 1

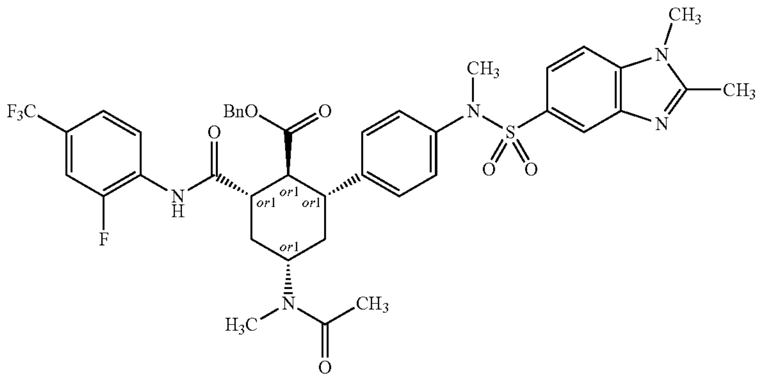

To rel-benzyl (1R,2R,4R,6S)-2-((2-fluoro-4-(trifluoromethyl)phenyl)carbamoyl)-4-(methylamino)-6-(4-((N,1,2-trimethyl-1H-benzo[d]imidazole)-5-sulfonamido)phenyl) cyclohexane-1-carboxylate, ISOMER 1, Intermediate 53 (102 mg, 0.133 mmol) at 0° C. was added acetic anhydride (0.800 mL, 8.48 mmol). The reaction was stirred at rt for 3 h and directly subjected to reverse phase purification (0-100% MeCN in H2O, 0.1% ABC modifier) to afford rel-benzyl (1R,2R,4R,6S)-2-((2-fluoro-4-(trifluoromethyl) phenyl)carbamoyl)-4-(N-methylacetamido)-6-(4-((N,1,2-trimethyl-1H-benzo[d]imidazole)-5-sulfonamido)phenyl) cyclohexane-1-carboxylate ISOMER 1 (89 mg, 0.11 mmol, 81% yield) as an off-white solid. $^1H$ NMR (400 MHz, DMSO-$d_6$) δ 10.26 (s, 1H), 8.21-8.05 (m, 1H), 7.78-7.66 (m, 1H), 7.63-7.47 (m, 3H), 7.32-7.21 (m, 3H), 7.18-7.07 (m, 3H), 7.03-6.89 (m, 4H), 4.79 (d, J=13.0 Hz, 1H), 4.62-4.53 (m, 2H), 3.91-3.89 (m, 1H), 3.73 (s, 3H), 3.28-3.15 (m, 1H), 3.06 (d, J=2.0 Hz, 3H), 3.00 (d, J=10.5 Hz, 1H), 2.85 (s, 3H), 2.13-2.08 (m, 1H), 1.98 (s, 3H), 1.92-1.58 (m, 3H), three protons obscured by solvent peaks. ES-LCMS m/z 265.0 [M+H]$^+$.

The following compounds were synthesized in an analogous manner to the preparation described above (Intermediate 61), using the appropriate amine precursors.

| Int. | Structure/Name | $^1H$ NMR | LCMS |
|---|---|---|---|
| 62 | 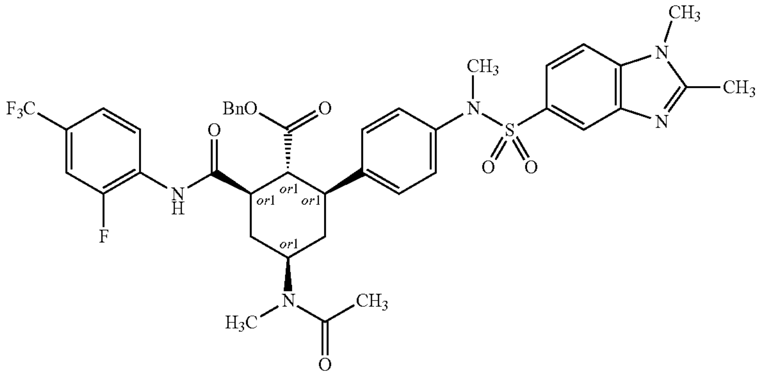 [SMILES: CC(=O)N(C)[C@@H]1C[C@H](c2ccc(N(C)S(=O)(=O)c3ccc4c(c3)nc(C)n4C)cc2)[C@@H](C(=O)OCc2ccccc2)[C@H](C(=O)Nc2ccc(C(F)(F)F)cc2F)C1] ISOMER 2<br>rel-benzyl (1R,2R,4R,6S)-2-((2-fluoro-4-(trifluoromethyl)phenyl)carbamoyl)-4-(N-methylacetamido)-6-(4-((N,1,2-trimethyl-1H-benzo[d]imidazole)-5-sulfonamido)phenyl)cyclohexane-1-carboxylate ISOMER 2 | $^1H$ NMR (400 MHZ, DMSO-$d_6$) δ 10.27 (s, 1H), 8.21-8.09 (m, 1H), 7.78-7.65 (m, 1H), 7.63-7.50 (m, 3H), 7.31-7.22 (m, 3H), 7.18-7.09 (m, 3H), 7.04-6.90 (m, 4H), 4.81 (d, J = 13.0 Hz, 1H), 4.63-4.56 (m, 2H), 3.92-3.88 (m, 1H), 3.75 (s, 3H), 3.24-3.21 (m, 1H), 3.07 (d, J = 2.0 Hz, 3H), 3.01 (d, J = 11.0 Hz, 1H), 2.87 (s, 3H), 2.13-2.08 (m, 1H), 1.99 (s, 3H), 1.92-1.86 (m, 2H), 1.81-1.57 (m, 1H), three protons obscured by solvent peaks | ES-LCMS m/z 808.2 [M + H]$^+$. |
| 63 | 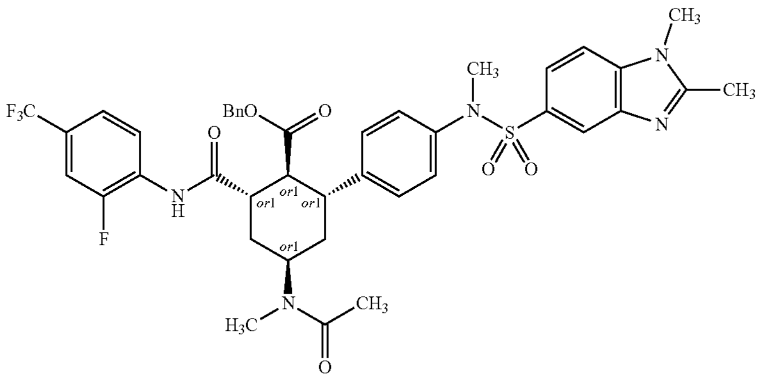 [SMILES: CC(=O)N(C)[C@H]1C[C@H](C(=O)Nc2ccc(C(F)(F)F)cc2F)[C@@H](C(=O)OCc2ccccc2)[C@H](c2ccc(N(C)S(=O)(=O)c3ccc4c(c3)nc(C)n4C)cc2)C1] ISOMER 1<br>rel-benzyl (1R,2R,4S,6S)-2-((2-fluoro-4-(trifluoromethyl)phenyl)carbamoyl)-4-(N-methylacetamido)-6-(4-((N,1,2-trimethyl-1H-benzo[d]imidazole)-5-sulfonamido)phenyl)cyclohexane-1-carboxylate ISOMER 1 | $^1H$ NMR (400 MHZ, DMSO-$d_6$) δ 10.24 (s, 1H), 8.10 (t, J = 8.0 Hz, 1H), 7.72 (dd, J = 11.0, 1.5 Hz, 1H), 7.63-7.49 (m, 3H), 7.31-7.20 (m, 3H), 7.17-7.05 (m, 3H), 7.02-6.91 (m, 4H), 4.83 (d, J = 12.5 Hz, 1H), 4.65 (d, J = 13.0 Hz, 2H), 3.73 (s, 3H), 3.18-3.13 (m, 3H), 3.06 (s, 3H), 2.52 (s, 3H), 2.22 (s, 3H), 2.17-2.07 (m, 2H), 2.05 (s, 3H), 1.92-1.90 (m, 2H) | ES-LCMS m/z 808.2 [M + H]$^+$. |

-continued

| Int. | Structure/Name | $^1H$ NMR | LCMS |
|---|---|---|---|
| 64 | 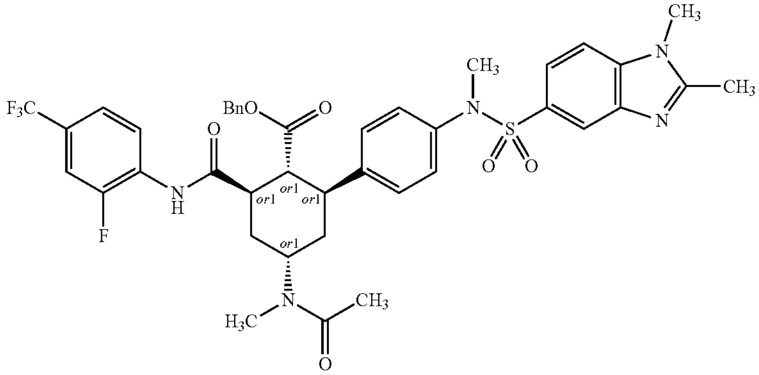 [SMILES: CC(=O)N(C)[C@H]1C[C@H](c2ccc(N(C)S(=O)(=O)c3ccc4c(c3)nc(C)n4C)cc2)[C@@H](C(=O)OCc2ccccc2)[C@H](C(=O)Nc2ccc(C(F)(F)F)cc2F)C1] ISOMER 2 rel-benzyl (1R,2R,4S,6S)-2-((2-fluoro-4-(trifluoromethyl)phenyl)carbamoyl)-4-(N-methylacetamido)-6-(4-((N,1,2-trimethyl-1H-benzo[d]imidazole)-5-sulfonamido)phenyl)cyclohexane-1-carboxylate ISOMER 2 | $^1H$ NMR (400 MHZ, DMSO-$d_6$) δ 10.24 (s, 1H), 8.10 (t, J = 8.0 Hz, 1H), 7.72 (dd, J = 11.0, 1.5 Hz, 1H), 7.63-7.49 (m, 3H), 7.31-7.20 (m, 3H), 7.17-7.05 (m, 3H), 7.02-6.91 (m, 4H), 4.83 (d, J = 12.5 Hz, 1H), 4.65 (d, J = 13.0 Hz, 2H), 3.73 (s, 3H), 3.18-3.13 (m, 3H), 3.06 (s, 3H), 2.52 (s, 3H), 2.22 (s, 3H), 2.17-2.07 (m, 2H), 2.05 (s, 3H), 1.92-1.90 (m, 2H) | ES-LCMS m/z 808.2 $[M + H]^+$. |

Intermediate 65: (1R,2S,6R)-2-(3-chloro-4-(methylamino)phenyl)-6-((2-fluoro-4-(trifluoromethyl)phenyl)carbamoyl)cyclohexane-1-carboxylic acid

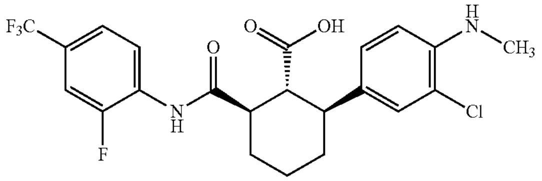 [SMILES: CNc1ccc([C@H]2CCC[C@@H](C(=O)Nc3ccc(C(F)(F)F)cc3F)[C@@H]2C(=O)O)cc1Cl]

To a mixture of (1R,2R,6S)-2-((2-fluoro-4-(trifluoromethyl)phenyl) carbamoyl)-6-(4-(methylamino)phenyl)cyclohexane-1-carboxylic acid Intermediate 7, alternate route, Step 3 (0.25 g, 0.57 mmol) in acetonitrile (5 mL) was added NCS (76 mg, 0.57 mmol) dissolved in acetonitrile (1 mL). The reaction was heated to 60° C. for 3 h, concentrated and subjected to reverse phase purification (MeCN in $H_2O$, 0.1% formic acid modifier, 0 to 100% gradient) to afford (1R,2S,6R)-2-(3-chloro-4-(methylamino)phenyl)-6-((2-fluoro-4-(trifluoromethyl)phenyl)carbamoyl)cyclohexane-1-carboxylic acid (0.25 g, 0.51 mmol, 90% yield) as white solid. $^1H$ NMR (400 MHz, DMSO-$d_6$) δ 11.8 (s, 1H), 10.09 (s, 1H), 8.21 (t, J=8.4 Hz, 1H), 7.72 (dd, J=11.2, 1.6 Hz, 1H), 7.55 (d, J=8.4 Hz, 1H), 7.12 (d, J=2.0 Hz, 1H), 7.03 (dd, J=8.2, 2.0 Hz, 1H), 6.55 (d, J=8.4 Hz, 1H), 5.31 (q, J=5.0 Hz, 1H), 2.97 (t, J=9.6 Hz, 1H), 2.72 (d, J=7.2 Hz, 3H), 2.68-2.64 (m, 1H), 2.55-2.53 (m, 1H), 1.99-1.98 (m, 1H), 1.97-0.186 (m, 1H), 1.73-1.70 (m, 1H), 1.53-1.45 (m, 3H). ES-LCMS m/z 516.8 $[M-H]^-$.

Intermediate 66 and Intermediate 67: rel-(1R,2R,4S,6S)-4-amino-2-((4-(trifluoromethyl)phenoxy)methyl)-6-(4-((N,1,2-trimethyl-1H-benzo[d]imidazole)-5-sulfonamido)phenyl)cyclohexane-1-carboxylic acid ISOMER 1 and rel-(1R,2R,4S,6S)-4-amino-2-((4-(trifluoromethyl)phenoxy)methyl)-6-(4-((N,1,2-trimethyl-1H-benzo[d]imidazole)-5-sulfonamido)phenyl)cyclohexane-1-carboxylic acid ISOMER 2

ISOMER 1

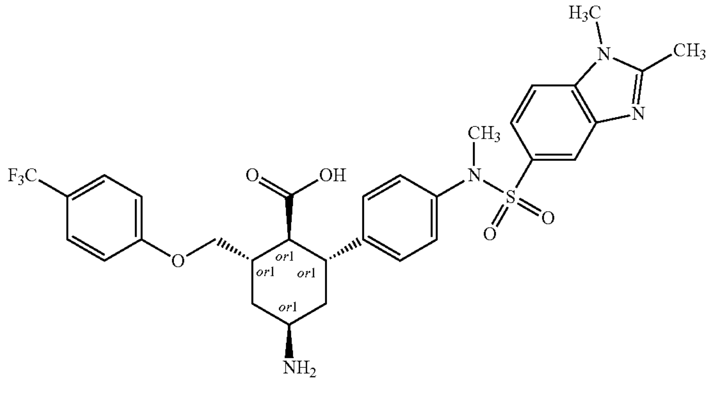

AND

-continued

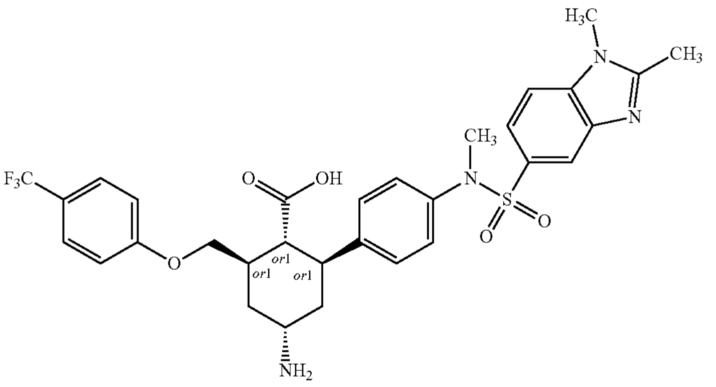

ISOMER 2

Step 1: rac-benzyl (1R,2S,4R,6R)-2-(4-bromophenyl)-4-hydroxy-6-((tosyloxy)methyl)cyclohexane-1-carboxylate

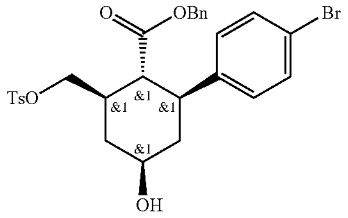 [SMILES: Cc1ccc(S(=O)(=O)OC[C@@H]2C[C@H](O)C[C@H](c3ccc(Br)cc3)[C@H]2C(=O)OCc2ccccc2)cc1]

To a mixture of rac-benzyl (1R,2S,4R,6R)-2-(4-bromophenyl)-4-hydroxy-6-(hydroxymethyl)cyclohexane-1-carboxylate, Intermediate 11, Step 2 (3.00 g, 7.15 mmol) and triethylamine (1.99 mL, 14.3 mmol) in dichloromethane (30 mL) at 0° C. was added tosyl-Cl (1.77 g, 9.30 mmol) and N,N-dimethylpyridin-4-amine (0.170 g, 1.43 mmol). The reaction was stirred at rt for 3 h, quenched with 10% sodium bicarbonate solution (50 mL) and extracted with DCM (150 mL). The combined organics were washed with brine (50 mL), dried over anhydrous sodium sulfate, filtered, concentrated and subjected to normal phase chromatography (40-50% EtOAc in petroleum ether) to afford rac-benzyl (1R,2S,4R,6R)-2-(4-bromophenyl)-4-hydroxy-6-((tosyloxy)methyl)cyclohexane-1-carboxylate (2.0 g, 3.3 mmol, 46% yield) as white solid. $^1$H NMR (400 MHz, DMSO-$d_6$) δ 7.74 (d, J=8.0 Hz, 2H), 7.50-7.39 (m, 4H), 7.29-7.19 (m, 3H), 7.13 (d, J=8.5 Hz, 2H), 6.81 (dd, J=7.8, 1.8 Hz, 2H), 4.82 (dd, J=8.5, 4.0 Hz, 2H), 4.57 (d, J=12.5 Hz, 1H), 3.87 (qd, J=10.0, 5.0 Hz, 2H), 3.65-3.52 (m, 1H), 2.83-2.72 (m, 1H), 2.41 (s, 3H), 2.15-2.03 (m, 1H), 1.84 (dt, J=8.8, 3.9 Hz, 2H), 1.47-1.34 (m, 1H), 1.21-1.07 (m, 1H). ES-LCMS m/z 595.0 [M+Na]$^+$.

Step 2: rac-benzyl (1R,2S,4R,6R)-2-(4-bromophenyl)-4-hydroxy-6-((4-(trifluoromethyl)phenoxy)methyl)cyclohexane-1-carboxylate

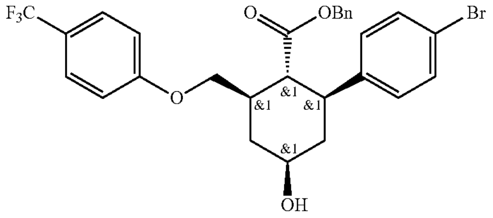 [SMILES: O=C(OCc1ccccc1)[C@H]1[C@H](COc2ccc(C(F)(F)F)cc2)C[C@H](O)C[C@@H]1c1ccc(Br)cc1]

To a mixture of rac-benzyl (1R,2S,4R,6R)-2-(4-bromophenyl)-4-hydroxy-6-((tosyloxy)methyl)cyclohexane-1-carboxylate (2.00 g, 3.49 mmol) in N,N-dimethylformamide (30 mL) was added 4-(trifluoromethyl)phenol (0.74 g, 4.5 mmol) and $K_2CO_3$ (1.11 g, 8.02 mmol). The reaction was heated to 80° C. for 16 h, concentrated, diluted with EtOAc (100 mL), washed with water (25 mL) and brine (25 mL), dried over anhydrous sodium sulfate, filtered, concentrated and subjected to reverse phase purification (0-100% MeCN in $H_2O$ with 0.1% formic acid modifier) to afford rac-benzyl (1R,2S,4R,6R)-2-(4-bromophenyl)-4-hydroxy-6-((4-(trifluoromethyl)phenoxy)methyl)cyclohexane-1-carboxylate (1.5 g, 2.2 mmol, 63% yield) as an off-white solid. $^1$H NMR (400 MHz, DMSO-$d_6$) δ 7.63 (d, J=8.5 Hz, 2H), 7.45 (d, J=8.5 Hz, 2H), 7.32-7.10 (m, 5H), 7.04 (d, J=8.5 Hz, 2H), 6.84-6.75 (m, 2H), 4.91-4.77 (m, 1H), 4.69 (d, J=12.5 Hz, 1H), 4.02-3.87 (m, 2H), 3.75-3.62 (m, 1H), 2.90-2.78 (m, 1H), 2.60 (t, J=11.3 Hz, 1H), 2.29-2.22 (m, 1H), 2.05 (d, J=13.0 Hz, 1H), 1.90 (d, J=12.0 Hz, 1H), 1.48 (d, J=11.0 Hz, 1H), 1.29 (d, J=11.5 Hz, 1H). ES-LCMS m/z 545.0 [M−OH]$^+$.

Step 3: rac-benzyl (1R,2S,6R)-2-(4-bromophenyl)-4-oxo-6-((4-(trifluoromethyl)phenoxy)methyl)cyclohexane-1-carboxylate

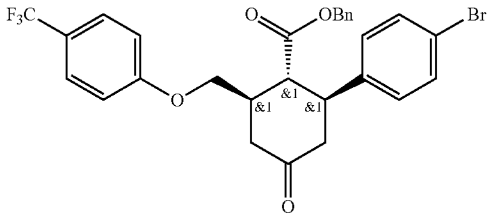 [SMILES: O=C1C[C@@H](COc2ccc(C(F)(F)F)cc2)[C@H](C(=O)OCc2ccccc2)[C@@H](c2ccc(Br)cc2)C1]

To a mixture of rac-benzyl (1R,2S,4R,6R)-2-(4-bromophenyl)-4-hydroxy-6-((4-(trifluoromethyl)phenoxy)methyl)cyclohexane-1-carboxylate (1.50 g, 2.66 mmol) in acetonitrile (10 mL) and water (5 mL) was added sodium periodate (1.71 g, 7.99 mmol) followed by ruthenium(III) chloride (0.110 g, 0.532 mmol). After 1 h the reaction was quenched with water (50 mL) and filtered through Celite, washing with EtOAc (200 mL). The organic layer was separated, washed with brine (50 mL), dried over anhydrous sodium sulfate, filtered, concentrated and subjected to normal phase chromatography (0-20% EtOAc in petroleum ether) to afford rac-benzyl (1R,2S,6R)-2-(4-bromophenyl)-4-oxo-6-((4-(trifluoromethyl)phenoxy)methyl)cyclohexane-1-carboxylate (0.86 g, 1.4 mmol, 52% yield) as an off-white solid. $^1$H NMR (400 MHz, DMSO-$d_6$) δ 7.64 (d, J=8.5 Hz, 1H), 7.69-7.55 (m, 1H), 7.48 (d, J=8.5 Hz, 3H), 7.30-7.13 (m, 4H), 7.05 (d, J=8.5 Hz, 2H), 6.88-6.77 (m, 2H), 5.04-4.81 (m, 1H), 4.77-4.65 (m, 1H), 4.00 (d, J=4.0 Hz, 2H), 3.28-3.16 (m, 2H), 2.86 (t, J=13.5 Hz, 1H), 2.62 (d, J=8.0 Hz, 2H), 2.36-2.25 (m, 2H). ES-LCMS m/z 560.6 [M−H]$^-$.

Step 4: rac-benzyl (1R,2R,6S)-2-((2-fluoro-4-(trifluoromethyl)phenyl)carbamoyl)-6-(4-(methylamino)phenyl)-4-oxocyclohexane-1-carboxylate

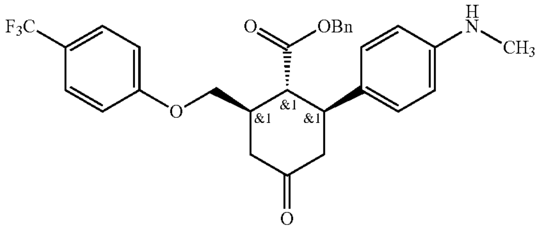 [SMILES: CNc1ccc([C@H]2CC(=O)C[C@@H](COc3ccc(C(F)(F)F)cc3)[C@@H]2C(=O)OCc2ccccc2)cc1]

To a mixture of rac-benzyl (1R,2S,6R)-2-(4-bromophenyl)-6-((2-fluoro-4-(trifluoromethyl)phenyl)carbamoyl)-4-oxocyclohexane-1-carboxylate (0.85 g, 1.4 mmol) and sodium 2-methylpropan-2-olate (0.21 g, 2.2 mmol) in dioxane (6 mL) was added tBuXPhos Pd G3 (0.23 g, 0.29 mmol). The reaction was degassed for 5 mins, methanamine (2M solution in THF, 12.9 mL, 25.8 mmol) was added, and the reaction vessel was sealed and heated in Biotage Initiator at 100° C. for 30 mins. The mixture was diluted with EtOAc (200 mL), washed with water (100 mL) and brine (50 mL), dried over anhydrous sodium sulfate, filtered, concentrated and subjected to normal phase chromatography (0-20% EtOAc in petroleum ether) to afford rac-benzyl (1R,2R,6S)-2-((2-fluoro-4-(trifluoromethyl)phenyl)carbamoyl)-6-(4-(methylamino)phenyl)-4-oxocyclohexane-1-carboxylate (0.50 g, 0.79 mmol, 55% yield) as an off-white solid. $^1$H NMR (400 MHz, DMSO-$d_6$) δ 7.63 (d, J=9.0 Hz, 2H), 7.23-7.11 (m, 3H), 7.07-6.95 (m, 4H), 6.88-6.81 (m, 2H), 6.46 (d, J=8.5 Hz, 2H), 5.59 (d, J=5.0 Hz, 1H), 4.89-4.81 (m, 1H), 4.76-4.67 (m, 1H), 3.97 (d, J=4.5 Hz, 2H), 3.14-2.96 (m, 2H), 2.82 (br t, J=13.5 Hz, 1H), 2.66 (d, J=5.0 Hz, 3H), 2.59 (br d, J=10.5 Hz, 2H), 2.47-2.42 (m, 1H), 2.30-2.17 (m, 1H). ES-LCMS m/z 512.0 [M+H]$^+$.

Step 5: rac-benzyl (1R,2R,6S)-4-oxo-2-((4-(trifluoromethyl)phenoxy)methyl)-6-(4-((N,1,2-trimethyl-1H-benzo[d]imidazole)-5-sulfonamido)phenyl)cyclohexane-1-carboxylate

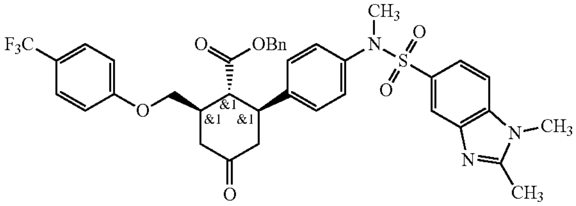 [SMILES: Cc1nc2cc(S(=O)(=O)N(C)c3ccc([C@H]4CC(=O)C[C@@H](COc5ccc(C(F)(F)F)cc5)[C@@H]4C(=O)OCc4ccccc4)cc3)ccc2n1C]

To a mixture of rac-benzyl (1R,2S,6R)-2-(4-(methylamino)phenyl)-4-oxo-6-((4-(trifluoromethyl)phenoxy)methyl)cyclohexane-1-carboxylate (0.50 g, 0.98 mmol) and pyridine (0.24 mL, 2.93 mmol) in dichloromethane (6 mL) at 0° C. was added 1,2-dimethyl-1H-benzo[d]imidazole-5-sulfonyl chloride (0.26 g, 1.1 mmol), portionwise. The reaction was stirred at rt for 30 mins, concentrated and subjected to reverse phase purification (0-100% MeCN in $H_2O$ with 0.1% formic acid modifier) to afford rac-benzyl (1R,2R,6S)-4-oxo-2-((4-(trifluoromethyl)phenoxy)methyl)-6-(4-((N,1,2-trimethyl-1H-benzo[d]imidazole)-5-sulfonamido)phenyl)cyclohexane-1-carboxylate (0.55 g, 0.76 mmol, 78% yield) as an off-white solid. $^1$H NMR (400 MHz, DMSO-$d_6$) δ 7.66-7.53 (m, 4H), 7.31-7.10 (m, 6H), 7.06-6.99 (m, 4H), 6.98-6.90 (m, 2H), 4.87-4.78 (m, 1H), 4.75-4.67 (m, 1H), 3.97 (br d, J=3.5 Hz, 2H), 3.72 (s, 3H), 3.21 (d, J=9.5 Hz, 2H), 3.08 (s, 3H), 2.86 (s, 1H), 2.65-2.56 (m, 2H), 2.52 (s, 3H), 2.31-2.25 (m, 2H). ES-LCMS m/z 720.0 [M+H]$^+$.

Step 6: rac-benzyl (1R,2R,4R,6S)-4-((4-methoxybenzyl)amino)-2-((4-(trifluoromethyl)phenoxy)methyl)-6-(4-((N,1,2-trimethyl-1H-benzo[d]imidazole)-5-sulfonamido)phenyl)cyclohexane-1-carboxylate and rac-benzyl (1R,2R,4R,6S)-4-((4-methoxybenzyl)amino)-2-((4-(trifluoromethyl)phenoxy)methyl)-6-(4-((N,1,2-trimethyl-1H-benzo[d]imidazole)-5-sulfonamido)phenyl)cyclohexane-1-carboxylate

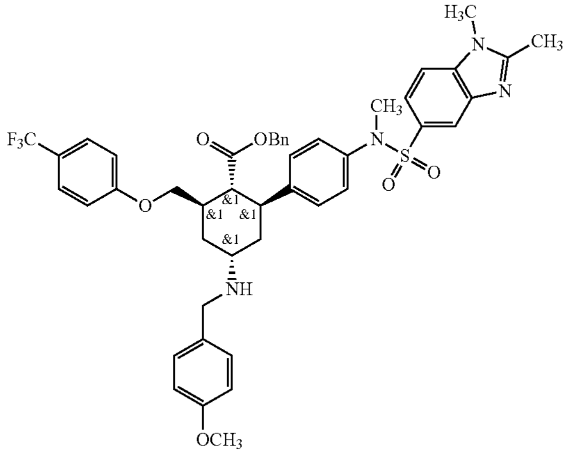

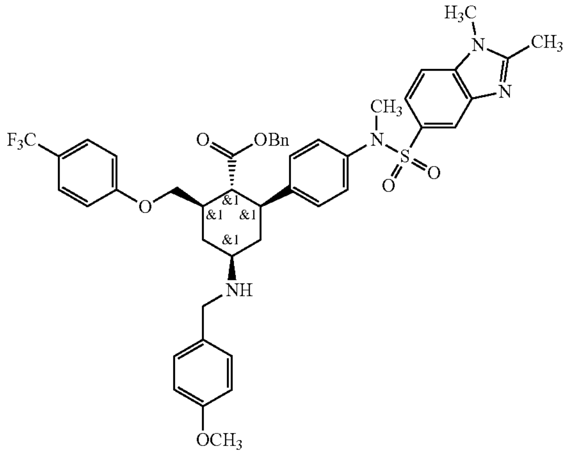

To a mixture of rac-benzyl (1R,2R,6S)-4-oxo-2-((4-(trifluoromethyl)phenoxy)methyl)-6-(4-((N,1,2-trimethyl-1H-benzo[d]imidazole)-5-sulfonamido)phenyl)cyclohexane-1-carboxylate (0.70 g, 0.97 mmol) and (4-methoxyphenyl)methanamine (0.250 mL, 1.95 mmol) in 1,2-dichloroethane (10 mL) was added acetic acid (0.060 mL, 0.97 mmol). After 5 h, sodium triacetoxyhydroborate (0.82 g, 3.9 mmol) was added. After 16 h the reaction was diluted with EtOAc (200 mL), washed with water (50 mL) and brine (20 mL), dried over anhydrous sodium sulfate, filtered, concentrated and subjected to normal phase chromatography (0-10% MeOH in DCM) to afford a mixture of rac-benzyl (1R,2R,4R,6S)-4-((4-methoxybenzyl)amino)-2-((4-(trifluoromethyl)phenoxy)methyl)-6-(4-((N,1,2-trimethyl-1H-benzo[d]imidazole)-5-sulfonamido)phenyl)cyclohexane-1-carboxylate and rac-benzyl (1R,2R,4R,6S)-4-((4-methoxybenzyl)amino)-2-((4-(trifluoromethyl)phenoxy)methyl)-6-(4-((N,1,2-trimethyl-1H-benzo[d]imidazole)-5-sulfonamido)phenyl)cyclohexane-1-carboxylate (0.70 g, 0.81 mmol, 83% yield) as a yellow solid. The diastereomeric mixture (600 mg) was purified by Prep-SFC (Column: YMC Hilic; Mobile Phase A:$CO_2$, Mobile Phase B: 0.5% Isopropylamine in IPA; Gradient: 35% B) to afford:

First-eluting compound rac-benzyl (1R,2R,4S,6S)-4-((4-methoxybenzyl)amino)-2-((4-(trifluoromethyl)phenoxy)methyl)-6-(4-((N,1,2-trimethyl-1H-benzo[d]imidazole)-5-sulfonamido)phenyl)cyclohexane-1-carboxylate (0.45 g, 0.50 mmol, 70% yield) as an off white solid. $^1H$ NMR (400 MHz, DMSO-$d_6$) δ 7.63-7.53 (m, 4H), 7.30-7.17 (m, 4H), 7.15-7.11 (m, 4H), 7.02-6.88 (m, 6H), 6.85 (d, J=8.5 Hz, 2H), 4.83-4.75 (m, 1H), 4.72-4.65 (m, 1H), 3.87 (dd, J=4.5, 2.0 Hz, 2H), 3.71 (s, 6H), 3.62 (s, 2H), 3.34-3.31 (m, 1H), 3.06 (s, 3H), 2.98-2.96 (m, 1H), 2.61 (d, J=11.0 Hz, 2H), 2.54 (s, 3H), 1.97-1.88 (m, 1H), 1.78 (d, J=12.5 Hz, 1H), 1.70-1.59 (m, 1H), 1.51-1.39 (m, 1H). ES-LCMS m/z 841.3 $[M+H]^+$.

And second-eluting compound rac-benzyl (1R,2R,4R,6S)-4-((4-methoxybenzyl)amino)-2-((4-(trifluoromethyl)phenoxy)methyl)-6-(4-((N,1,2-trimethyl-1H-benzo[d]imidazole)-5-sulfonamido)phenyl)cyclohexane-1-carboxylate (0.10 mg, 0.11 mmol, 15% yield) as an off-white solid. $^1H$ NMR (400 MHz, DMSO-$d_6$) δ 7.67-7.51 (m, 4H), 7.34-7.13 (m, 8H), 7.04-6.96 (m, 4H), 6.96-6.83 (m, 4H), 4.85-4.78 (m, 1H), 4.73-4.67 (m, 1H), 3.93 (d, J=5.0 Hz, 2H), 3.73 (s, 8H), 3.34-3.32 (m, 1H), 3.08 (s, 3H), 2.84-2.81 (m, 1H), 2.62 (d, J=12.0 Hz, 1H), 2.53 (s, 3H), 2.28-2.18 (m, 3H), 2.11-1.96 (m, 2H). ES-LCMS m/z 841.2 $[M+H]^+$.

Step-7: rel-benzyl (1R,2R,4S,6S)-4-((4-methoxybenzyl)amino)-2-((4-(trifluoromethyl)phenoxy)methyl)-6-(4-((N,1,2-trimethyl-1H-benzo[d]imidazole)-5-sulfonamido)phenyl)cyclohexane-1-carboxylate ISOMER 1 and ISOMER 2

ISOMER 1

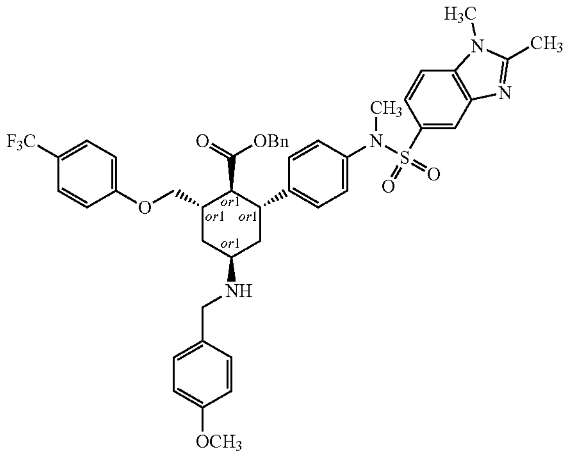

-continued

ISOMER 2

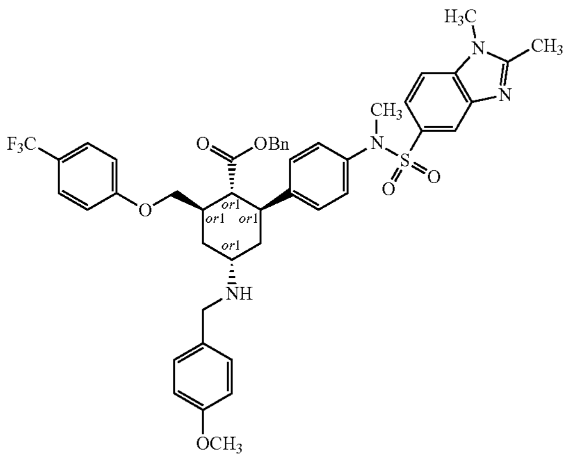

Racemic compound rac-benzyl (1R,2R,4S,6S)-4-((4-methoxybenzyl)amino)-2-((4-(trifluoromethyl)phenoxy)methyl)-6-(4-((N,1,2-trimethyl-1H-benzo[d]imidazole)-5-sulfonamido)phenyl)cyclohexane-1-carboxylate (450 mg) was purified by Chiral-Prep-SFC (Column: Chiralpak IG; Mobile Phase A:$CO_2$, Mobile Phase B: 0.5% Isopropylamine in IPA; Gradient: 40% B) to afford:

First-eluting isomer rel-benzyl (1R,2R,4S,6S)-4-((4-methoxybenzyl)amino)-2-((4-(trifluoromethyl)phenoxy)methyl)-6-(4-((N,1,2-trimethyl-1H-benzo[d]imidazole)-5- sulfonamido)phenyl)cyclohexane-1-carboxylate ISOMER 1 (0.14 g, 0.16 mmol, 31% yield) as white solid. $^1$H NMR (400 MHz, DMSO-$d_6$) δ 7.64-7.54 (m, 4H), 7.30-7.07 (m, 8H), 7.03-6.89 (m, 6H), 6.86 (d, J=9.0 Hz, 2H), 4.84-4.76 (m, 1H), 4.74-4.66 (m, 1H), 3.91-3.83 (m, 2H), 3.72 (s, 6H), 3.63 (s, 2H), 3.07 (s, 3H), 2.98 (s, 1H), 2.62 (d, J=11.0 Hz, 2H), 2.13-2.08 (m, 1H), 1.94 (d, J=13.0 Hz, 1H), 1.79 (d, J=13.0 Hz, 1H), 1.70-1.58 (m, 1H), 1.50-1.39 (m, 1H). ES-LCMS m/z 841.2 $[M+H]^+$.

And second-eluting isomer rel-benzyl (1R,2R,4S,6S)-4-((4-methoxybenzyl)amino)-2-((4-(trifluoromethyl)phenoxy)methyl)-6-(4-((N,1,2-trimethyl-1H-benzo[d]imidazole)-5-sulfonamido)phenyl)cyclohexane-1-carboxylate (110 mg, 0.115 mmol, 22.0% yield) as white solid. $^1$H NMR (400 MHz, DMSO-$d_6$) δ 7.65-7.54 (m, 4H), 7.33-7.06 (m, 8H), 7.03-6.90 (m, 6H), 6.86 (d, J=8.5 Hz, 2H), 4.84-4.78 (m, 1H), 4.73-4.68 (m, 1H), 3.91-3.84 (m, 2H), 3.75-3.71 (m, 6H), 3.63 (s, 2H), 3.08 (s, 3H), 2.99 (s, 1H), 2.63 (d, J=11.0 Hz, 2H), 2.16-2.08 (m, 1H), 1.94 (d, J=13.0 Hz, 1H), 1.82-1.72 (m, 1H), 1.66 (td, J=13.1, 2.3 Hz, 1H), 1.52-1.41 (m, 1H). ES-LCMS m/z 841.2 $[M+H]^+$.

Step 8: rel-(1R,2R,4S,6S)-4-amino-2-((4-(trifluoromethyl)phenoxy)methyl)-6-(4-((N,1,2-trimethyl-1H-benzo[d]imidazole)-5-sulfonamido)phenyl)cyclohexane-1-carboxylic acid ISOMER 1 and rel-(1R,2R,4S,6S)-4-amino-2-((4-(trifluoromethyl)phenoxy)methyl)-6-(4-((N,1,2-trimethyl-1H-benzo[d]imidazole)-5-sulfonamido)phenyl)cyclohexane-1-carboxylic acid ISOMER 2

ISOMER 1

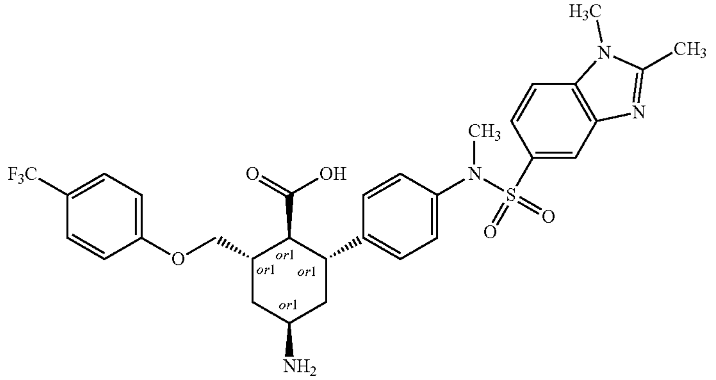

AND

ISOMER 2

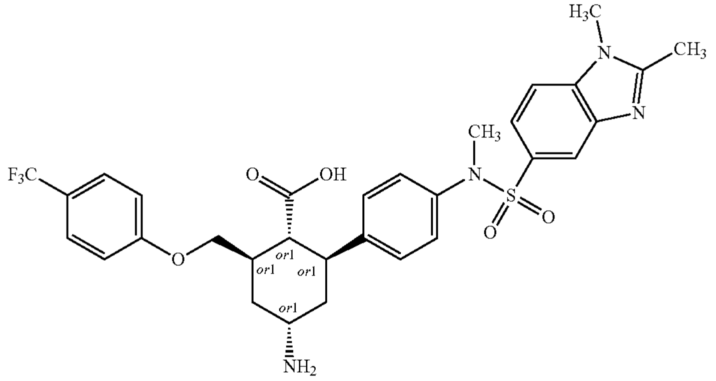

To a mixture of rel-benzyl (1R,2R,4S,6S)-4-((4-methoxybenzyl)amino)-2-((4-(trifluoromethyl)phenoxy)methyl)-6-(4-((N,1,2-trimethyl-1H-benzo[d]imidazole)-5-sulfonamido)phenyl)cyclohexane-1-carboxylate ISOMER 1 (0.14 g, 0.17 mmol) in acetic acid (4 mL, 69.9 mmol) under $N_2$ was added Pd—C(177 mg, 0.17 mmol). The reaction was stirred under $H_2$ atmosphere (1 atm, bladder pressure) for 20 h, filtered through the Celite bed, washing with 10% MeOH in DCM (50 mL). The filtrate was concentrated and subjected to reverse phase purification (0 to 100% MeCN in $H_2O$, 0.1% formic acid modifier) to afford rel-(1R,2R,4S,6S)-4-amino-2-((4-(trifluoromethyl)phenoxy)methyl)-6-(4-((N,1,2-trimethyl-1H-benzo[d]imidazole)-5-sulfonamido)phenyl)cyclohexane-1-carboxylic acid ISOMER 1 (60 mg, 0.08 mmol, 50% yield) as a white solid. $^1H$ NMR (400 MHz, DMSO-$d_6$) δ 7.65-7.62 (m, 3H), 7.51 (d, J=1.5 Hz, 1H), 7.27 (dd, J=8.5, 2.0 Hz, 1H), 7.17 (d, J=8.5 Hz, 2H), 7.09 (d, J=8.0 Hz, 2H), 6.95 (d, J=8.5 Hz, 2H), 3.93 (d, J=6.0 Hz, 2H), 3.79 (s, 3H), 3.05 (s, 4H), 2.57 (s, 3H), 2.54-2.52 (m, 1H), 2.41 (d, J=11.0 Hz, 1H), 1.84-1.78 (m, 1H), 1.74-1.68 (m, 1H), 1.67-1.62 (m, 1H), 1.61-1.55 (m, 1H). ES-LCMS m/z 631.2 $[M+H]^+$.

The above procedure was followed for rel-benzyl (1R,2R,4S,6S)-4-((4-methoxybenzyl)amino)-2-((4-(trifluoromethyl)phenoxy)methyl)-6-(4-((N,1,2-trimethyl-1H-benzo[d]imidazole)-5-sulfonamido)phenyl)cyclohexane-1-carboxylate ISOMER 2 to afford rel-(1R,2R,4S,6S)-4-amino-2-((4-(trifluoromethyl)phenoxy)methyl)-6-(4-((N,1,2-trimethyl-1H-benzo[d]imidazole)-5-sulfonamido)phenyl)cyclohexane-1-carboxylic acid ISOMER 2 (45 mg, 0.060 mmol, 45% yield) as white solid. $^1H$ NMR (400 MHz, DMSO-$d_6$) δ 7.65-7.62 (m, 3H), 7.51 (d, J=1.5 Hz, 1H), 7.27 (dd, J=8.5, 1.5 Hz, 1H), 7.17 (d, J=8.5 Hz, 2H), 7.09 (d, J=8.5 Hz, 2H), 6.96 (d, J=8.5 Hz, 2H), 3.93 (d, J=5.0 Hz, 2H), 3.79 (s, 3H), 3.06 (s, 4H), 2.57 (s, 4H), 2.42 (d, J=11.0 Hz, 2H), 1.82 (br d, J=12.0 Hz, 1H), 1.72 (br dd, J=13.3, 2.8 Hz, 1H), 1.68-1.52 (m, 2H). ES-LCMS m/z 631.2 $[M+H]^+$.

Intermediate 68 and Intermediate 69: rel-benzyl (1R,2R,4S,6S)-2-((2-fluoro-4-(trifluoromethyl)phenyl)carbamoyl)-4-((4-methoxybenzyl)amino)-6-(4-((N,1,2-trimethyl-1H-benzo[d]imidazole)-5-sulfonamido)phenyl)cyclohexane-1-carboxylate ISOMER 1 and rel-benzyl (1R,2R,4S,6S)-2-((2-fluoro-4-(trifluoromethyl)phenyl)carbamoyl)-4-((4-methoxybenzyl)amino)-6-(4-((N,1,2-trimethyl-1H-benzo[d]imidazole)-5-sulfonamido)phenyl)cyclohexane-1-carboxylate ISOMER 2

ISOMER 1

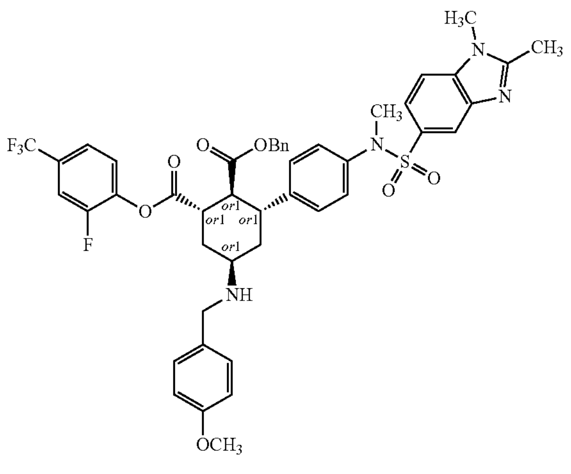

-continued

ISOMER 2

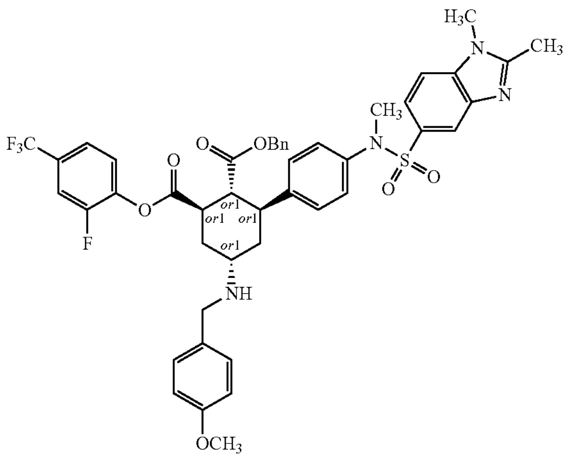

Step 1: rac-benzyl (1R,2R,4S,6S)-2-((2-fluoro-4-(trifluoromethyl)phenyl)carbamoyl)-4-((4-methoxybenzyl)amino)-6-(4-((N,1,2-trimethyl-1H-benzo[d]imidazole)-5-sulfonamido)phenyl)cyclohexane-1-carboxylate and rac-benzyl (1R,2R,4R,6S)-2-((2-fluoro-4-(trifluoromethyl)phenyl)carbamoyl)-4-((4-methoxybenzyl)amino)-6-(4-((N,1,2-trimethyl-1H-benzo[d]imidazole)-5-sulfonamido)phenyl)cyclohexane-1-carboxylate

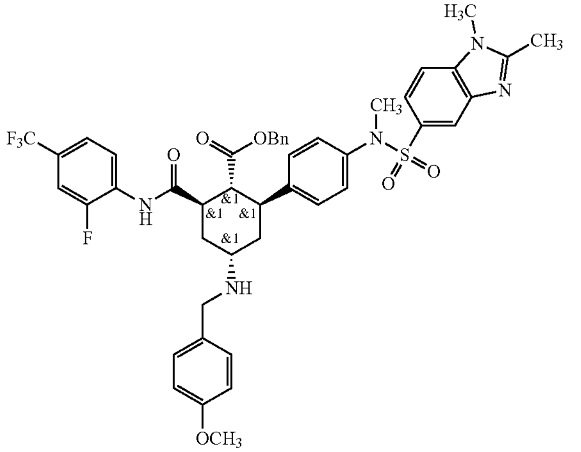

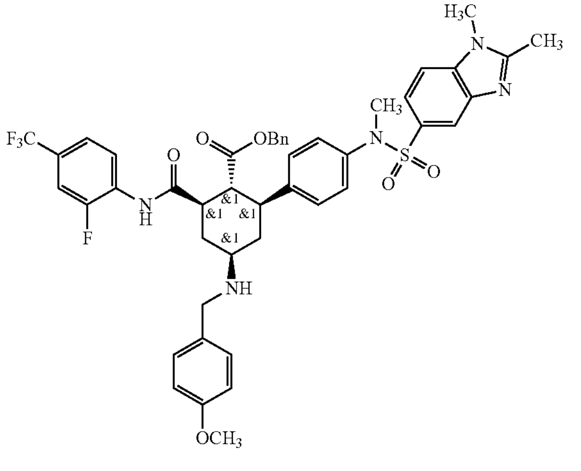

To a mixture of rac-benzyl (1R,2R,6S)-2-((2-fluoro-4-(trifluoromethyl)phenyl)carbamoyl)-4-oxo-6-(4-((N,1,2-trimethyl-1H-benzo[d]imidazole)-5-sulfonamido)phenyl) cyclohexane-1-carboxylate (Intermediate 46 and Intermediate 47, Step 2) (0.6 g, 0.8 mmol) and (4-methoxy-phenyl)methanamine (0.21 mL, 1.6 mmol) in 1,2-dichloro-ethane (20 mL) was added acetic acid (0.05 mL, 0.8 mmol). After 5 h, sodium triacetoxyhydroborate (0.68 g, 3.2 mmol) was added. After 16 h, the reaction was diluted with water (150 mL) and extracted with ethyl acetate (3×100 mL). The combined organic layers were washed with brine (100 mL), dried over anhydrous sodium sulfate, filtered, concentrated and purified by Achiral-Prep-SFC (Column: YMC Hilic; Mobile Phase A:$CO_2$, Mobile Phase B: 0.5% Isopropylamine in IPA; Gradient: 30% B) to afford:

the first-eluting compound rac-benzyl (1R,2R,4S,6S)-2-((2-fluoro-4-(trifluoromethyl)phenyl)carbamoyl)-4-((4-methoxybenzyl)amino)-6-(4-((N,1,2-trimethyl-1H-benzo[d]imidazole)-5-sulfonamido)phenyl)cyclohexane-1-carboxylate (0.31 g, 0.31 mmol, 35% yield) as an off-white solid. $^1H$ NMR (400 MHz, DMSO-$d_6$) δ10.08 (s, 1H), 8.10 (t, J=8.4 Hz, 1H), 7.72 (dd, J=11.2, 1.6 Hz, 1H), 7.61-7.59 (m, 2H), 7.54 (d, J=8.4 Hz, 1H), 7.33-7.28 (m, 3H), 7.17-7.10 (m, 5H), 6.99-6.89 (m, 6H), 4.81 (d, J=12.8 Hz, 1H), 4.60 (d, J=12.8 Hz, 1H), 3.73 (s, 6H), 3.71-3.68 (m, 2H), 3.50 (td, J=13.4, 3.6 Hz, 1H), 3.07 (s, 3H), 3.03 (m, 1H), 2.95 (t, J=11.6 Hz, 1H), 2.53 (s, 3H), 2.49-2.45 (m, 1H), 2.04-2.02 (m, 2H), 1.81-1.73 (m, 3H). ES-LCMS m/z 872.0 $[M+H]^+$.

And the second-eluting compound rac-benzyl (1R,2R,4R,6S)-2-((2-fluoro-4-(trifluoromethyl)phenyl)carbamoyl)-4-((4-methoxybenzyl)amino)-6-(4-((N,1,2-trimethyl-1H-benzo[d]imidazole)-5-sulfonamido)phenyl)cyclohexane-1-carboxylate (0.38 g, 0.35 mmol, 39% yield) as an off-white solid. $^1H$ NMR (400 MHz, DMSO-$d_6$) δ 10.08 (s, 1H), 8.15 (t, J=8.4 Hz, 1H), 7.72 (dd, J=10.8, 1.6 Hz, 1H), 7.62-7.54 (m, 2H), 7.55 (d, J=9.6 Hz, 1H), 7.31 (dd, J=8.6, 2.0 Hz, 1H), 7.26-721 (m, 2H), 7.20-7.10 (m, 5H), 7.00 (d, J=8.4 Hz, 2H), 6.95-6.87 (m, 4H), 4.80 (d, J=12.8 Hz, 1H), 4.59 (d, J=12.8 Hz, 1H), 3.78 (s, 3H), 3.75 (s, 3H), 3.69 (s, 2H), 3.14-3.11 (m, 1H), 3.07 (s, 3H), 2.92 (t, J=11.2 Hz, 1H), 2.89-2.76 (m, 1H), 2.53 (s, 3H), 2.51-2.49 (m, 1H), 2.34-2.27 (m, 1H), 2.08-2.04 (m, 1H), 1.48 (q, J=12.0 Hz, 1H), 1.37 (q, J=12.0 Hz, 1H). ES-LCMS m/z 872.0 $[M+H]^+$.

Step 2: rel-benzyl (1R,2R,4S,6S)-2-((2-fluoro-4-(trifluoromethyl)phenyl)carbamoyl)-4-((4-methoxy-benzyl)amino)-6-(4-((N,1,2-trimethyl-1H-benzo[d]imidazole)-5-sulfonamido)phenyl)cyclohexane-1-carboxylate ISOMER 1 and rel-benzyl (1R,2R,4S,6S)-2-((2-fluoro-4-(trifluoromethyl)phenyl)carbamoyl)-4-((4-methoxybenzyl)amino)-6-(4-((N,1,2-trimethyl-1H-benzo[d]imidazole)-5-sulfonamido)phenyl)cyclohexane-1-carboxylate ISOMER 2

ISOMER 1

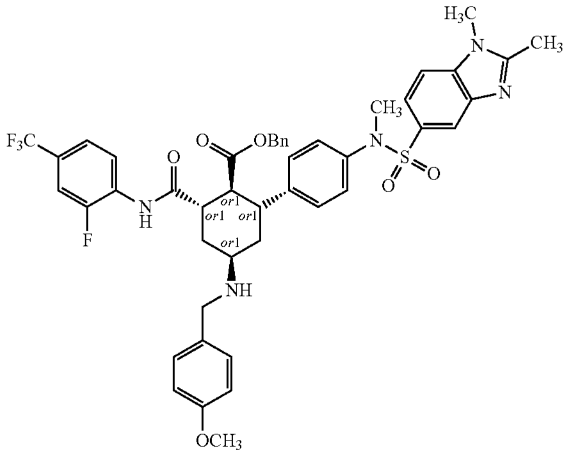

ISOMER 2

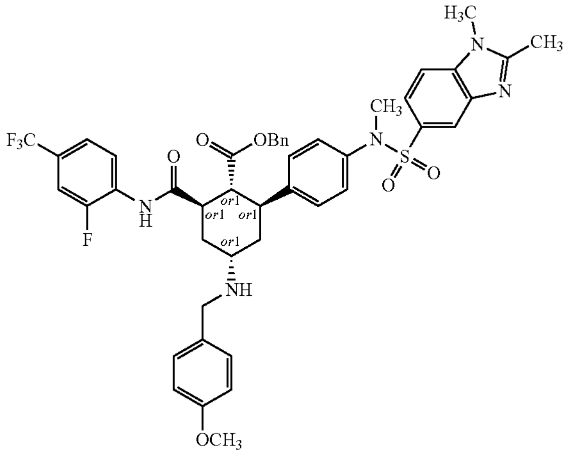

Racemic compound rac-benzyl (1R,2R,4S,6S)-2-((2-fluoro-4-(trifluoromethyl)phenyl)carbamoyl)-4-((4-methoxybenzyl)amino)-6-(4-((N,1,2-trimethyl-1H-benzo[d]imidazole)-5-sulfonamido)phenyl)cyclohexane-1-carboxylate (310 mg) was purified by Chiral-Prep-SFC (Column: YMC Amylose-SA; Mobile Phase A:$CO_2$, Mobile Phase B: 0.5% isopropylamine in IPA; Gradient: 45% B) to afford: the first-eluting isomer rel-benzyl (1R,2R,4S,6S)-2-((2-fluoro-4-(trifluoromethyl)phenyl)carbamoyl)-4-((4-methoxybenzyl)amino)-6-(4-((N,1,2-trimethyl-1H-benzo[d]imidazole)-5-sulfonamido)phenyl)cyclohexane-1-carboxylate ISOMER 1 (0.13 g, 0.12 mmol, 35% yield) as an off-white solid. $^1H$ NMR (400 MHz, DMSO-$d_6$) δ 10.08 (s, 1H), 8.10 (t, J=8.3 Hz, 1H), 7.72 (dd, J=11.3, 1.8 Hz, 1H), 7.63-7.47 (m, 3H), 7.35-7.25 (m, 3H), 7.21-7.08 (m, 5H), 7.01-6.85 (m, 6H), 4.81 (d, J=12.5 Hz, 1H), 4.60 (d, J=12.5

Hz, 1H), 3.74 (s, 6H), 3.70 (s, 2H), 3.55-3.42 (m, 1H), 3.30-3.23 (m, 1H), 3.07 (s, 3H), 3.03 (br s, 1H), 2.95 (t, J=11.3 Hz, 1H), 2.10-1.99 (m, 2H), 1.89-1.63 (m, 3H). 3 protons obscured by solvent peaks. ES-LCMS m/z 872.2 $[M+H]^+$.

And the second-eluting isomer rel-benzyl (1R,2R,4S,6S)-2-((2-fluoro-4-(trifluoromethyl)phenyl)carbamoyl)-4-((4-methoxybenzyl)amino)-6-(4-((N,1,2-trimethyl-1H-benzo[d]imidazole)-5-sulfonamido)phenyl)cyclohexane-1-carboxylate ISOMER 2 (93 mg, 0.080 mmol, 23% yield) as an off-white solid. $^1$H NMR (400 MHz, DMSO-$d_6$) δ 10.07 (s, 1H), 8.09 (t, J=8.0 Hz, 1H), 7.71 (dd, J=11.0, 2.0 Hz, 1H), 7.61-7.54 (m, 2H), 7.53 (s, 1H), 7.36-7.23 (m, 3H), 7.20-7.06 (m, 5H), 7.01-6.84 (m, 6H), 4.80 (d, J=12.5 Hz, 1H), 4.59 (d, J=12.5 Hz, 1H), 3.73 (s, 6H), 3.69 (s, 2H), 3.54-3.43 (m, 1H), 3.28 (d, J=3.0 Hz, 1H), 3.06 (s, 3H), 3.02 (s, 1H), 2.94 (t, J=11.3 Hz, 1H), 2.10-1.99 (m, 2H), 1.86-1.64 (m, 3H). 3 protons obscured by solvent peaks. ES-LCMS m/z 872.2 $[M+H]^+$.

Intermediate 70 and Intermediate 71: rel-benzyl (1R,2R,4R,6S)-2-((2-fluoro-4-(trifluoromethyl)phenyl)carbamoyl)-4-((4-methoxybenzyl)amino)-6-(4-((N,1,2-trimethyl-1H-benzo[d]imidazole)-5-sulfonamido)phenyl)cyclohexane-1-carboxylate ISOMER 1 and rel-benzyl (1R,2R,4R,6S)-2-((2-fluoro-4-(trifluoromethyl)phenyl)carbamoyl)-4-((4-methoxybenzyl)amino)-6-(4-((N,1,2-trimethyl-1H-benzo[d]imidazole)-5-sulfonamido)phenyl)cyclohexane-1-carboxylate ISOMER 2

ISOMER 1

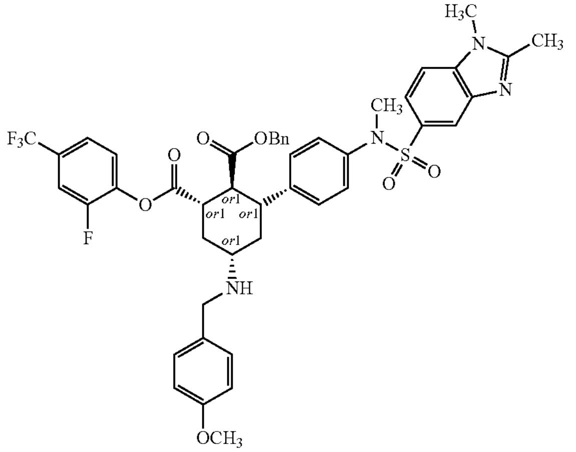

ISOMER 2

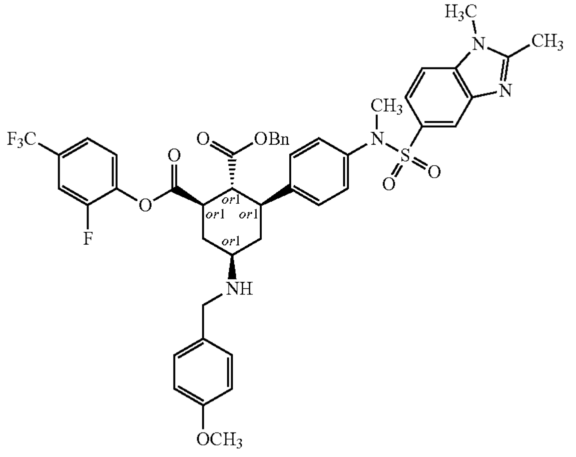

Racemic compound rac-benzyl (1R,2R,4R,6S)-2-((2-fluoro-4-(trifluoromethyl)phenyl)carbamoyl)-4-((4-methoxybenzyl)amino)-6-(4-((N,1,2-trimethyl-1H-benzo[d]imidazole)-5-sulfonamido)phenyl)cyclohexane-1-carboxylate Intermediate 68 and Intermediate 69, Step 1 (380 mg) was purified by Chiral-Prep-SFC (Column: YMC Amylose-SA; Mobile Phase A:$CO_2$, Mobile Phase B: 0.5% isopropylamine in IPA; Gradient: 50% B) to afford: the first-eluting isomer rel-benzyl (1R,2R,4R,6S)-2-((2-fluoro-4-(trifluoromethyl)phenyl)carbamoyl)-4-((4-methoxybenzyl)amino)-6-(4-((N,1,2-trimethyl-1H-benzo[d]imidazole)-5-sulfonamido)phenyl)cyclohexane-1-carboxylate ISOMER 1 (0.17 g, 0.19 mmol, 43% yield) as an off-white solid. $^1$H NMR (400 MHz, DMSO-$d_6$) δ 10.17 (s, 1H), 8.15 (t, J=8.3 Hz, 1H), 7.73 (dd, J=11.0, 1.5 Hz, 1H), 7.65-7.50 (m, 3H), 7.35-7.07 (m, 8H), 7.03-6.83 (m, 6H), 4.80 (d, J=13.0 Hz, 1H), 4.59 (d, J=12.5 Hz, 1H), 3.74 (s, 3H), 3.72 (s, 3H), 3.69 (s, 2H), 3.11 (s, 1H), 3.08 (s, 3H), 2.92 (t, J=11.3 Hz, 1H), 2.76 (td, J=12.0, 3.0 Hz, 1H), 2.28 (d, J=12.0 Hz, 1H), 2.05 (d, J=9.5 Hz, 2H), 1.54-1.30 (m, 2H), 3 protons obscured by solvent peaks. ES-LCMS m/z 872.2 $[M+H]^+$.

and the second-eluting isomer rel-benzyl (1R,2R,4R,6S)-2-((2-fluoro-4-(trifluoromethyl)phenyl)carbamoyl)-4-((4-methoxybenzyl)amino)-6-(4-((N,1,2-trimethyl-1H-benzo[d]imidazole)-5-sulfonamido)phenyl)cyclohexane-1-carboxylate ISOMER 2 (0.19 g, 0.19 mmol, 44% yield) as an off-white solid. $^1$H NMR (400 MHz, DMSO-$d_6$) δ 8.15 (t, J=8.3 Hz, 1H), 7.76-7.67 (m, 1H), 7.65-7.48 (m, 2H), 7.34-7.26 (m, 1H), 7.18-7.08 (m, 4H), 7.26-7.08 (m, 4H), 7.00 (d, J=8.5 Hz, 2H), 6.95-6.91 (m, 2H), 6.89-6.83 (m, 2H), 4.80 (d, J=12.5 Hz, 1H), 4.59 (d, J=13.0 Hz, 1H), 3.75 (s, 3H), 3.73 (s, 3H), 3.68 (s, 2H), 3.11 (s, 1H), 3.08 (s, 3H), 2.91 (t, J=11.0 Hz, 1H), 2.81-2.70 (m, 1H), 2.30-2.23 (m, 1H), 2.08-2.00 (m, 2H), 1.55-1.31 (m, 2H), 3 protons obscured by solvent peaks. ES-LCMS m/z 872.2 $[M+H]^+$.

Intermediate 72 and Intermediate 73: rel-benzyl (1R,2R,4S,6S)-4-(3,3-difluoropyrrolidin-1-yl)-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylate ISOMER 1 and rel-benzyl (1R,2R,4S,6S)-4-(3,3-difluoropyrrolidin-1-yl)-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylate ISOMER 2

ISOMER 1

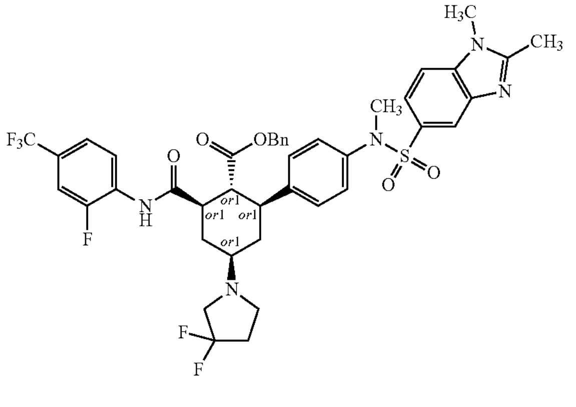

-continued

ISOMER 2

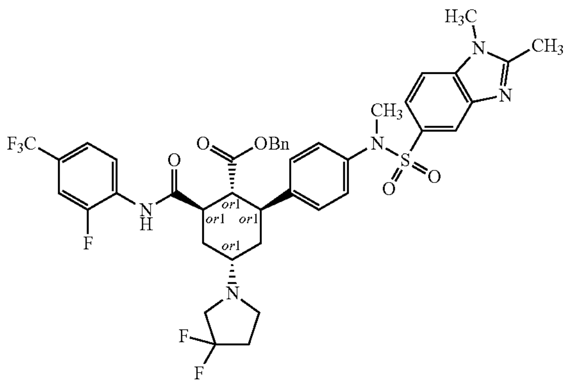

Step 1: rac-benzyl (1R,2R,4R,6S)-4-(3,3-difluoropyrrolidin-1-yl)-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylate and rac-benzyl (1R,2R,4S,6S)-4-(3,3-difluoropyrrolidin-1-yl)-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylate

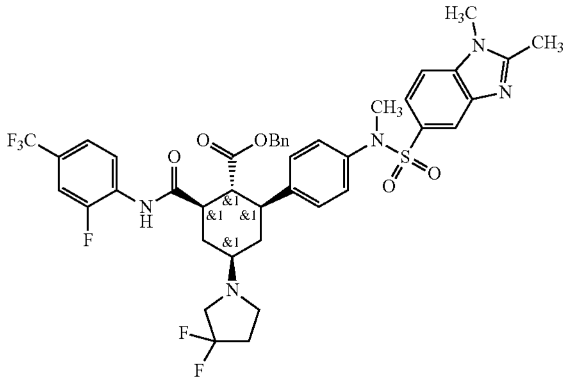

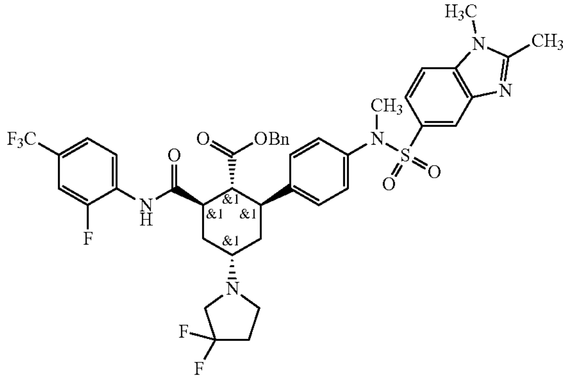

Two reactions were run in parallel: A suspension of rac-benzyl (1R,2R,6S)-2-((2-fluoro-4-(trifluoromethyl)phenyl)carbamoyl)-4-oxo-6-(4-((N,1,2-trimethyl-1H-benzo[d]imidazole)-5-sulfonamido)phenyl)cyclohexane-1-carboxylate (Intermediate 46 and Intermediate 47, Step 2) (200 mg, 0.27 mmol; 100 mg, 0.13 mmol) and 3,3-difluoropyrrolidine (86 mg, 0.80 mmol; 43 mg, 0.40 mmol) in MeOH (0.5 mL; 0.5 mL), THF (0.5 mL; 0.5 mL) and DMA (0.5 mL; 0.5 mL) was heated to 80° C. After 2 h, sodium cyanoborohydride (25 mg, 0.40 mmol; 13 mg, 0.20 mmol) was added, and the reactions were stirred for 2 h at rt, combined, quenched with water, diluted with MeOH (1 mL) and THF (2 mL), then purified by reverse-phase chromatography (Column: Grace C18 100 g), eluting with 0-100% MeCN in aq. 0.1% ammonium carbonate to afford: the first-eluting compound rac-benzyl (1R,2R,4R,6S)-4-(3,3-difluoropyrrolidin-1-yl)-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylate (150 mg, 0.16 mmol, 59% yield) as a brown solid.

$^1$H NMR (400 MHz, DMSO-$d_6$) δ 10.16 (s, 1H), 8.16 (t, J=8.3 Hz, 1H), 7.72 (dd, J=11.0, 2.0 Hz, 1H), 7.64-7.44 (m, 3H), 7.36-7.14 (m, 3H), 7.19-7.05 (m, 3H), 7.03-6.88 (m, 4H), 4.80 (d, J=12.5 Hz, 1H), 4.58 (d, J=12.5 Hz, 1H), 3.74 (s, 3H), 3.20-3.09 (m, 2H), 3.07 (s, 3H), 3.03-2.86 (m, 3H), 2.87-2.69 (m, 3H), 2.52 (s, 3H), 2.29-2.11 (m, 3H), 1.97 (d, J=12.0 Hz, 1H), 1.61 (q, J=12.2 Hz, 1H), 1.50-1.39 (m, 1H). ES-LCMS m/z 842.2 $[M+H]^+$. Relative stereochemistry was determined by co-crystal structure of subsequent final compound with WRN protein and then tracing back to the corresponding intermediates.

And the second-eluting compound rac-benzyl (1R,2R,4S,6S)-4-(3,3-difluoropyrrolidin-1-yl)-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylate (110 mg, 0.13 mmol, 47% yield) as an off-white solid. $^1$H NMR (400 MHz, DMSO-$d_6$) δ 10.21 (s, 1H), 8.03 (t, J=7.8 Hz, 1H), 7.70 (dd, J=10.8, 1.3 Hz, 1H), 7.62-7.56 (m, 2H), 7.54 (d, J=9.0 Hz, 1H), 7.31 (dd, J=8.5, 1.5 Hz, 1H), 7.21 (d, J=8.5 Hz, 2H), 7.15-7.04 (m, 3H), 7.00 (d, J=9.0 Hz, 2H), 6.91 (d, J=7.0 Hz, 2H), 4.83 (d, J=13.0 Hz, 1H), 4.62 (d, J=13.0 Hz, 1H), 3.74 (s, 3H), 3.40-3.38 (m, 2H), 3.07 (s, 3H), 2.94-2.83 (m, 3H), 2.76-2.67 (m, 3H), 2.55 (s, 3H), 2.42-2.28 (m, 2H), 2.13-2.01 (m, 1H), 1.92-1.71 (m, 3H). ES-LCMS m/z 842.2 $[M+H]^+$.

Step 2: rel-benzyl (1R,2R,4S,6S)-2-((2-fluoro-4-(trifluoromethyl)phenyl)carbamoyl)-4-((4-methoxybenzyl)amino)-6-(4-((N,1,2-trimethyl-1H-benzo[d]imidazole)-5-sulfonamido)phenyl)cyclohexane-1-carboxylate ISOMER 1 and rel-benzyl (1R,2R,4S,6S)-2-((2-fluoro-4-(trifluoromethyl)phenyl)carbamoyl)-4-((4-methoxybenzyl)amino)-6-(4-((N,1,2-trimethyl-1H-benzo[d]imidazole)-5-sulfonamido)phenyl)cyclohexane-1-carboxylate ISOMER 2

ISOMER 1

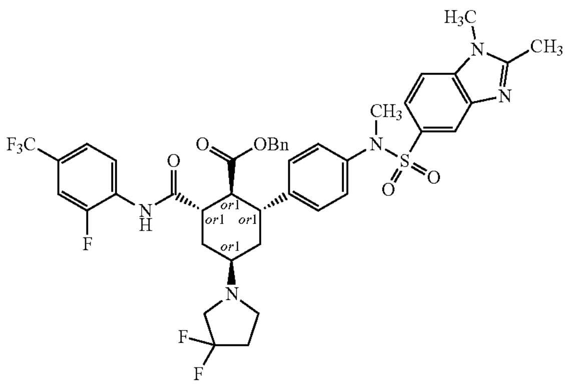

-continued

ISOMER 2

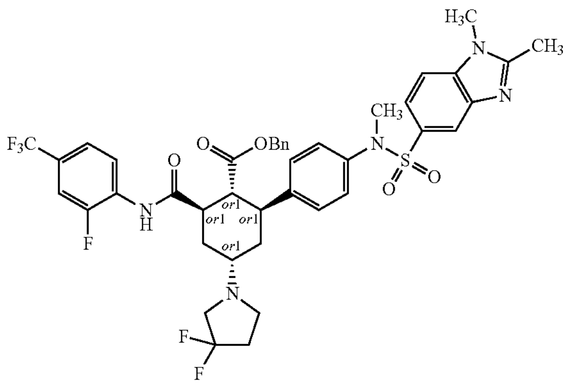

Racemic compound rac-benzyl (1R,2R,4S,6S)-4-(3,3-difluoropyrrolidin-1-yl)-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylate (110 mg) was purified by Chiral-Prep-SFC (Column: YMC Amylose-SA; Mobile Phase A:$CO_2$, Mobile Phase B: 0.5% isopropylamine in IPA; Gradient: 35% B) to afford: the first-eluting isomer rel-benzyl (1R,2R,4S,6S)-4-(3,3-difluoropyrrolidin-1-yl)-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylate ISOMER 1 (48 mg, 0.060 mmol, 41% yield) as an off-white solid. $^1$H NMR (400 MHz, DMSO-$d_6$) δ 10.21 (s, 1H), 8.03 (t, J=8.0 Hz, 1H), 7.71 (dd, J=11.0, 1.5 Hz, 1H), 7.63-7.56 (m, 2H), 7.55 (d, J=8.5 Hz, 1H), 7.31 (dd, J=8.5, 2.0 Hz, 1H), 7.22 (d, J=9.0 Hz, 2H), 7.16-7.03 (m, 3H), 7.00 (d, J=9.0 Hz, 2H), 6.93-6.89 (m, 2H), 4.83 (d, J=13.0 Hz, 1H), 4.62 (d, J=12.5 Hz, 1H), 3.74 (s, 3H), 3.45-3.34 (m, 2H), 3.23-3.09 (m, 2H), 3.07 (s, 3H), 3.03-2.92 (m, 2H), 2.90-2.71 (m, 2H), 2.57 (s, 3H), 2.41-2.29 (m, 2H), 2.12-2.03 (m, 1H), 1.91-1.73 (m, 3H). ES-LCMS m/z 842.2 [M+H]$^+$.

And the second-eluting isomer rel-benzyl (1R,2R,4S,6S)-4-(3,3-difluoropyrrolidin-1-yl)-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylate ISOMER 2 (44 mg, 0.050 mmol, 36% yield) as an off-white solid. $^1$H NMR (400 MHz, DMSO-$d_6$) δ 10.21 (s, 1H), 8.03 (t, J=8.0 Hz, 1H), 7.71 (dd, J=11.3, 1.8 Hz, 1H), 7.62-7.49 (m, 3H), 7.31 (dd, J=8.5, 1.5 Hz, 1H), 7.22 (d, J=8.5 Hz, 2H), 7.16-7.04 (m, 3H), 7.00 (d, J=8.5 Hz, 2H), 6.94-6.88 (m, 2H), 4.83 (d, J=13.0 Hz, 1H), 4.62 (d, J=12.5 Hz, 1H), 3.74 (s, 3H), 3.46-3.37 (m, 2H), 3.22-3.10 (m, 2H), 3.07 (s, 3H), 3.05-2.95 (m, 2H), 2.93-2.84 (m, 1H), 2.75 (d, J=8.0 Hz, 1H), 2.54 (s, 3H), 2.43-2.29 (m, 2H), 2.13-2.01 (m, 1H), 1.93-1.70 (m, 3H). ES-LCMS m/z 842.2 [M+H]$^+$.

Intermediate 74 and Intermediate 75: benzyl (1 S,2S,4S,6R)-4-(3,3-difluoropyrrolidin-1-yl)-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylate and benzyl (1R,2R,4R,6S)-4-(3,3-difluoropyrrolidin-1-yl)-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylate

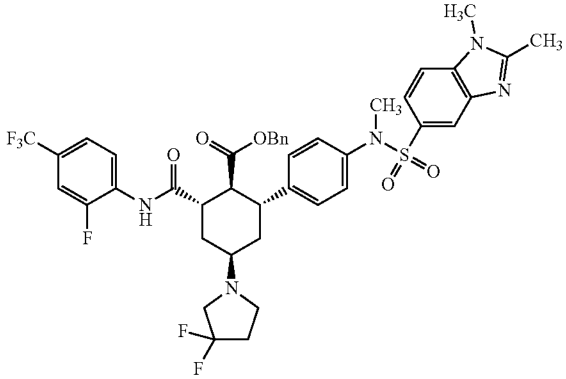

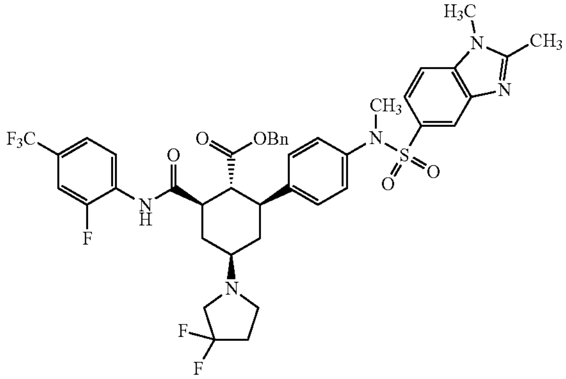

Racemic compound rac-benzyl (1R,2R,4R,6S)-4-(3,3-difluoropyrrolidin-1-yl)-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylate from Intermediate 72 and Intermediate 73, Step 1, the first-eluting compound (150 mg) was purified by Chiral-Prep-SFC (Column: YMC Cellulose-SC; Mobile Phase A:$CO_2$, Mobile Phase B: 0.5% isopropylamine in IPA; Gradient: 50% B) to afford:

Intermediate 74: the first-eluting isomer benzyl (1S,2S,4S,6R)-4-(3,3-difluoropyrrolidin-1-yl)-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylate (75 mg, 0.090 mmol, 48% yield) as an off-white solid. $^1$H NMR (400 MHz, DMSO-$d_6$) δ 10.17 (s, 1H), 8.17 (t, J=8.0 Hz, 1H), 7.73 (dd, J=11.0, 1.5 Hz, 1H), 7.62-7.51 (m, 3H), 7.32-7.26 (m, 1H), 7.24 (d, J=8.5 Hz, 2H), 7.18-7.08 (m, 3H), 7.00 (d, J=8.5 Hz, 2H), 6.97-6.90 (m, 2H), 4.81 (d, J=13.0 Hz, 1H), 4.59 (d, J=12.5 Hz, 1H), 3.77-3.76 (m, 1H), 3.75 (s, 3H), 3.19-3.07 (m, 1H), 3.07 (s, 3H), 3.02-2.72 (m, 6H), 2.30-2.11 (m, 3H), 2.01-1.89 (m, 1H), 1.71-1.37 (m, 2H), 3 protons obscured by solvent peaks. ES-LCMS m/z 842.2 $[M+H]^+$ and Intermediate 75: the second-eluting isomer benzyl (1R,2R,4R,6S)-4-(3,3-difluoropyrrolidin-1-yl)-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylate (66 mg, 0.080 mmol, 42% yield) as an off-white solid. $^1$H NMR (400 MHz, DMSO-$d_6$) δ 10.17 (s, 1H), 8.17 (t, J=8.3 Hz, 1H), 7.73 (dd, J=11.0, 1.5 Hz, 1H), 7.64-7.49 (m, 3H), 7.31 (dd, J=8.5, 2.0 Hz, 1H), 7.24 (d, J=8.5 Hz, 2H), 7.18-7.07 (m, 3H), 7.00 (d, J=8.5 Hz, 2H), 6.96-6.90 (m, 2H), 4.81 (d, J=13.0 Hz, 1H), 4.59 (d, J=13.0 Hz, 1H), 3.75 (s, 3H), 3.84-3.66 (m, 1H), 3.20-3.11 (m, 1H), 3.07 (s, 3H), 3.03-2.75 (m, 6H), 2.53 (s, 3H), 2.31-2.09 (m, 3H), 1.97 (d, J=12.0 Hz, 1H), 1.68-1.37 (m, 2H). ES-LCMS m/z 842.2 $[M+H]^+$ Absolute stereochemistry was determined by co-crystal structure of subsequent final compound with WRN protein and then tracing back to the corresponding enantiopure intermediates.

Intermediate 76 and Intermediate 77: rel-methyl (3R,4S,5R)-3-((2-fluoro-4-(trifluoromethyl)phenyl)carbamoyl)-5-(4-((N,1,2-trimethyl-1H-benzo[d]imidazole)-5-sulfonamido)phenyl)piperidine-4-carboxylate ISOMER 1 and rel-methyl (3R,4S,5R)-3-((2-fluoro-4-(trifluoromethyl)phenyl)carbamoyl)-5-(4-((N,1,2-trimethyl-1H-benzo[d]imidazole)-5-sulfonamido)phenyl)piperidine-4-carboxylate ISOMER 2

ISOMER 1

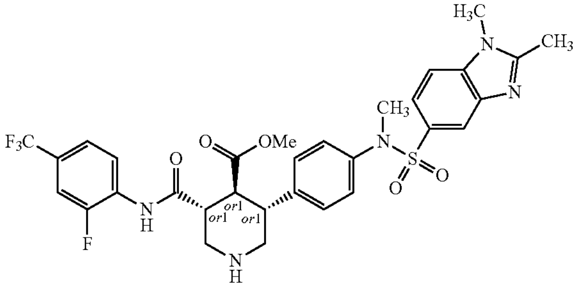

-continued

ISOMER 2

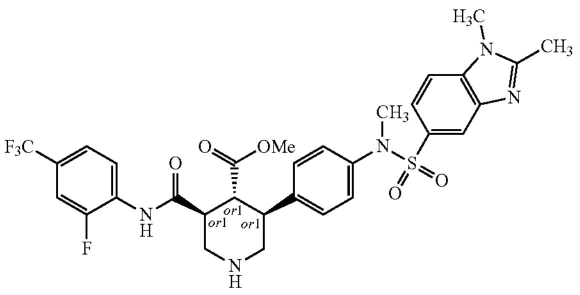

Step 1: dimethyl 5-(4-((tert-butoxycarbonyl)(methyl)amino)phenyl)pyridine-3,4-dicarboxylate

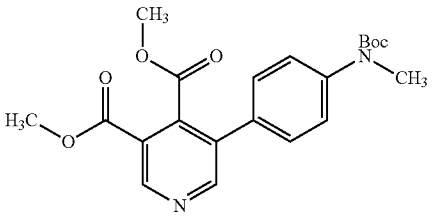

To a mixture of dimethyl 5-(4-(methylamino)phenyl)pyridine-3,4-dicarboxylate (5.50 g, 16.3 mmol) in dichloromethane (50 mL) was added $Et_3N$ (6.83 mL, 49.0 mmol), DMAP (0.40 g, 3.3 mmol) and Boc-anhydride (5.69 mL, 24.5 mmol). After 16 h the reaction was concentrated and subjected to normal phase chromatography (20% EtOAc in petroleum ether) to afford dimethyl 5-(4-((tert-butoxycarbonyl)(methyl)amino)phenyl)pyridine-3,4-dicarboxylate (6.0 g, 15 mmol, 91% yield) as an off white solid. $^1$H NMR (400 MHz, DMSO-$d_6$) δ 9.13 (s, 1H), 8.93 (s, 1H), 7.46-7.37 (m, 4H), 3.90 (s, 3H), 3.70 (s, 3H), 3.24 (s, 3H), 1.42 (s, 9H). ES-LCMS m/z 401.2 $[M+H]^+$.

Step 2: dimethyl 5-(4-((tert-butoxycarbonyl)(methyl)amino)phenyl)piperidine-3,4-dicarboxylate

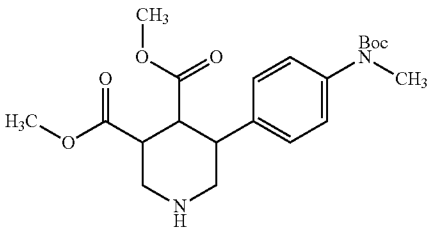

To a mixture of dimethyl 5-(4-((tert-butoxycarbonyl)(methyl)amino)phenyl)pyridine-3,4-dicarboxylate (6.0 g, 15 mmol) in acetic acid (30 mL) was added Pd—C(10%) (2.39 g, 2.25 mmol) and platinum(IV) oxide (0.51 g, 2.3 mmol). The reaction was stirred under hydrogen atmosphere (bladder pressure) at rt for 16 h, filtered through Celite (washing with methanol [30 mL]), concentrated and dissolved in acetic acid (20 mL). Pd—C(10%) (0.48 g) and platinum(IV) oxide (0.1 g) were added, and the resulting mixture was stirred under $H_2$ atmosphere (bladder pressure) for 16 h, filtered through Celite (washing with methanol [30 mL]) and concentrated to afford the crude product dimethyl 5-(4-((tert-butoxycarbonyl)(methyl)amino)phenyl)piperidine-3,4-dicarboxylate (5.6 g, 13 mmol, 85% yield) as a colorless oil. $^1$H NMR (400 MHz, DMSO-$d_6$) δ 7.22-7.14 (m, 2H), 7.08 (d, J=8.5 Hz, 2H), 3.57 (s, 3H), 3.24 (s, 3H), 3.15 (s, 3H), 3.09-2.97 (m, 3H), 2.93 (dt, J=11.8, 4.6 Hz, 2H), 2.79 (dd, J=12.5, 3.5 Hz, 1H), 2.63-2.53 (m, 1H), 1.38 (s, 9H). ES-LCMS m/z 407.2 $[M+H]^+$.

Step 3: 1-benzyl 3,4-dimethyl 5-(4-((tert-butoxycarbonyl)(methyl)amino)phenyl)piperidine-1,3,4-tricarboxylate

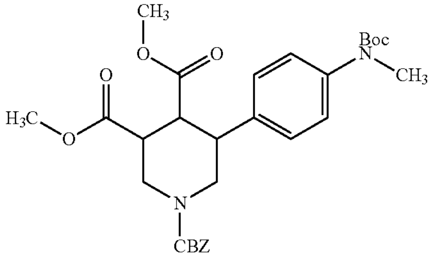

To a mixture of dimethyl 5-(4-((tert-butoxycarbonyl)(methyl)amino)phenyl)piperidine-3,4-dicarboxylate (5.6 g, 14 mmol) in tetrahydrofuran (30 mL) and water (30 mL) was added benzyl (2,5-dioxopyrrolidin-1-yl)carbonate (4.12 g, 16.5 mmol) and sodium bicarbonate (4.63 g, 55.1 mmol). The reaction was stirred at rt for 2 h, diluted with water (15 mL) and extracted with ethyl acetate (30×3 mL). The combined organic layers were washed with brine (10 mL), dried over sodium sulfate, concentrated and subjected to reverse phase purification (0-100% MeCN in $H_2O$, 0.1% formic acid modifier) to afford 1-benzyl 3,4-dimethyl 5-(4-((tert-butoxycarbonyl)(methyl)amino)phenyl)piperidine-1,3,4-tricarboxylate (5.9 g, 10 mmol, 75% yield) as a pale-yellow oil. $^1$H NMR (400 MHz, DMSO-$d_6$) δ 7.51-7.38 (m, 4H), 7.23 (d, J=8.5 Hz, 2H), 7.18-7.05 (m, 3H), 5.13 (d, J=2.0 Hz, 2H), 4.36-4.21 (m, 1H), 4.07-3.93 (m, 1H), 3.63 (s, 3H), 3.59-3.46 (m, 2H), 3.29 (s, 3H), 3.23-3.19 (m, 2H), 3.17 (s, 4H), 1.43-1.37 (m, 9H). ES-LCMS m/z 563.2 $[M+Na]^+$.

Step 4: rac-(3R,4S,5R)-1-((benzyloxy)carbonyl)-5-(4-((tert-butoxycarbonyl)(methyl)amino)phenyl)-4-(methoxycarbonyl)piperidine-3-carboxylic acid

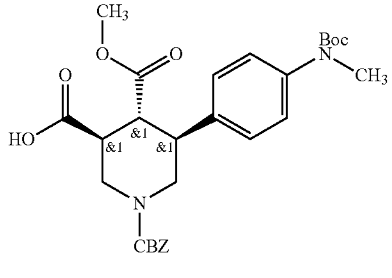

To a mixture of 1-benzyl 3,4-dimethyl 5-(4-((tert-butoxycarbonyl)(methyl)amino)phenyl)piperidine-1,3,4-tricarboxylate (1.9 g, 3.5 mmol) in methanol (15 mL) was added sodium methoxide (25% wt in methanol, 1.62 mL, 7.03 mmol). The reaction was heated to 50° C. for 2 h, concentrated and subjected to reverse phase purification (0-100% MeCN in $H_2O$, with 0.1% ABC modifier) to afford rac-(3R,4S,5R)-1-((benzyloxy)carbonyl)-5-(4-((tert-butoxycarbonyl)(methyl)amino)phenyl)-4-(methoxycarbonyl)piperidine-3-carboxylic acid (1.25 g, 2.12 mmol, 60.0% yield) as an off-white solid. $^1$H NMR (400 MHz, DMSO-$d_6$) δ 7.41-7.28 (m, 4H), 7.17-7.01 (m, 5H), 5.11 (s, 2H), 4.34 (dd, J=13.3, 4.3 Hz, 1H), 3.97-3.84 (m, 1H), 3.17 (s, 6H), 2.78-2.67 (m, 2H), 2.60 (d, J=4.0 Hz, 1H), 2.37-2.20 (m, 2H), 1.38 (s, 9H). ES-LCMS m/z 525.2 $[M-H]^-$.

Step 5: rac-1-benzyl 4-methyl (3R,4S,5R)-3-(4-((tert-butoxycarbonyl)(methyl)amino)phenyl)-5-((2-fluoro-4-(trifluoromethyl)phenyl)carbamoyl)piperidine-1,4-dicarboxylate

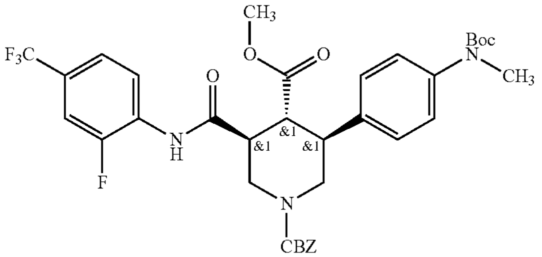

To a mixture of rac-(3R,4S,5R)-1-((benzyloxy)carbonyl)-5-(4-((tert-butoxycarbonyl)(methyl)amino)phenyl)-4-(methoxycarbonyl)piperidine-3-carboxylic acid (1.25 g, 2.37 mmol) in acetonitrile (8 mL) was added N-(chloro(dimethylamino)methylene)-N-methylmethanaminium hexafluorophosphate(V) (1.33 g, 4.75 mmol) and 1-methylimidazole (0.378 mL, 4.75 mmol) followed by 2-fluoro-4-(trifluoromethyl)aniline (0.425 g, 2.37 mmol). After 2 hr, the reaction was concentrated and subjected to reverse phase purification (0-100% MeCN in $H_2O$, with 0.1% formic acid modifier) to afford rac-1-benzyl 4-methyl (3R,4S,5R)-3-(4-((tert-butoxycarbonyl)(methyl)amino)phenyl)-5-((2-fluoro-4-(trifluoromethyl)phenyl)carbamoyl)piperidine-1,4-dicarboxylate (0.950 g, 1.37 mmol, 58.0% yield) as an off-white solid. $^1$H NMR (400 MHz, DMSO-$d_6$) δ 8.12-8.04 (m, 1H), 7.74 (dd, J=11.0, 1.5 Hz, 1H), 7.56 (d, J=9.0 Hz, 2H), 7.35-7.29 (m, 3H), 7.28-7.14 (m, 5H), 5.13 (s, 2H), 4.35 (d, J=2.0 Hz, 1H), 4.03-3.97 (m, 1H), 3.56-3.44 (m, 1H), 3.30-3.28 (m, 2H), 3.23 (s, 3H), 3.17 (s, 3H), 3.08-2.97 (m, 1H), 2.82 (td, J=11.0, 4.0 Hz, 1H), 1.37 (s, 9H). ES-LCMS m/z 686.2 $[M-H]^-$.

Step 6: rac-1-benzyl 4-methyl (3R,4S,5R)-3-((2-fluoro-4-(trifluoromethyl)phenyl)carbamoyl)-5-(4-(methylamino)phenyl)piperidine-1,4-dicarboxylate

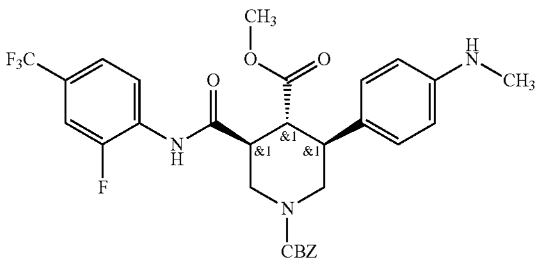

To a mixture of rac-1-benzyl 4-methyl (3R,4S,5R)-3-(4-((tert-butoxycarbonyl)(methyl)amino)phenyl)-5-((2-fluoro-4-(trifluoromethyl)phenyl)carbamoyl)piperidine-1,4-dicarboxylate (0.950 g, 1.38 mmol) in methanol (6 mL) at 25° C. was added HCl in dioxane (0.41 mL, 1.7 mmol). After 1 h, the reaction was concentrated to afford the crude compound rac-1-benzyl 4-methyl (3R,4S,5R)-3-((2-fluoro-4-(trifluoromethyl)phenyl)carbamoyl)-5-(4-(methylamino)phenyl)piperidine-1,4-dicarboxylate (0.900 g, 1.34 mmol, 97.0% yield) as a pale brown solid. $^1$H NMR (400 MHz, DMSO-$d_6$) δ 10.43 (s, 1H), 8.15-8.05 (m, 1H), 7.78-7.69 (m, 1H), 7.57 (d, J=7.5 Hz, 1H), 7.43-7.29 (m, 8H), 7.21 (br s, 3H), 5.13 (s, 2H), 4.35 (br s, 1H), 3.98 (d, J=10.5 Hz, 1H), 3.57 (s, 3H), 3.54-3.45 (m, 1H), 3.26 (s, 3H), 3.23-3.06 (m, 3H), 2.88 (br d, J=4.0 Hz, 1H), 2.85-2.80 (m, 3H). ES-LCMS m/z 588.2 [M+H]$^+$.

Step 7: rac-1-benzyl 4-methyl (3R,4S,5R)-3-((2-fluoro-4-(trifluoromethyl)phenyl)carbamoyl)-5-(4-((N,1,2-trimethyl-1H-benzo[d]imidazole)-5-sulfonamido)phenyl)piperidine-1,4-dicarboxylate

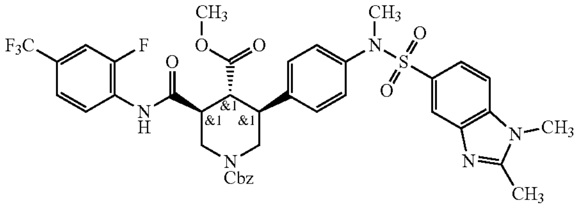 [SMILES: COC(=O)[C@@H]1[C@@H](c2ccc(N(C)S(=O)(=O)c3ccc4c(c3)nc(C)n4C)cc2)CN(C(=O)OCc2ccccc2)C[C@H]1C(=O)Nc1ccc(C(F)(F)F)cc1F]

To a mixture of rac-1-benzyl 4-methyl (3R,4S,5R)-3-((2-fluoro-4-(trifluoromethyl)phenyl)carbamoyl)-5-(4-(methylamino)phenyl)piperidine-1,4-dicarboxylate (0.900 g, 1.34 mmol) in DCM (5 mL) was added pyridine (0.248 mL, 3.06 mmol) and 1,2-dimethyl-1H-benzo[d]imidazole-5-sulfonyl chloride (0.450 g, 1.84 mmol). After 1 h the reaction was concentrated and subjected to reverse phase purification (0-100% MeCN in $H_2O$, with 0.1% formic acid modifier) to afford rac-1-benzyl 4-methyl (3R,4S,5R)-3-((2-fluoro-4-(trifluoromethyl)phenyl)carbamoyl)-5-(4-((N,1,2-trimethyl-1H-benzo[d]imidazole)-5-sulfonamido)phenyl)piperidine-1,4-dicarboxylate (1.5 g, 1.7 mmol) as a pale green solid. $^1$H NMR (400 MHz, DMSO-$d_6$) δ 10.45 (s, 1H), 8.11 (t, J=7.8 Hz, 1H), 7.77 (d, J=11.0 Hz, 1H), 7.66 (d, J=8.5 Hz, 1H), 7.60-7.53 (m, 2H), 7.42-7.22 (m, 7H), 7.15 (d, J=8.5 Hz, 1H), 7.08-6.93 (m, 2H), 5.18-5.08 (m, 2H), 4.39 (d, J=9.5 Hz, 1H), 4.25-4.03 (m, 1H), 4.05-3.95 (m, 1H), 3.77 (s, 3H), 3.35-3.31 (m, 1H), 3.17 (s, 4H), 3.09 (s, 4H), 2.83-2.78 (m, 1H), 2.57 (s, 3H). ES-LCMS m/z 796.0 [M+H]$^+$.

Step-8: rel-methyl (3R,4S,5R)-3-((2-fluoro-4-(trifluoromethyl)phenyl)carbamoyl)-5-(4-((N,1,2-trimethyl-1H-benzo[d]imidazole)-5-sulfonamido)phenyl) piperidine-4-carboxylate ISOMER 1 and rel-methyl (3R,4S,5R)-3-((2-fluoro-4-(trifluoromethyl)phenyl) carbamoyl)-5-(4-((N,1,2-trimethyl-1H-benzo[d]imidazole)-5-sulfonamido)phenyl)piperidine-4-carboxylate ISOMER 2

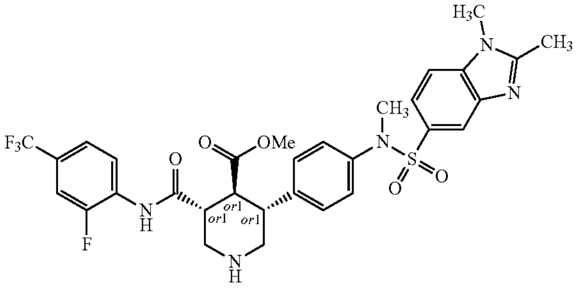

ISOMER 1

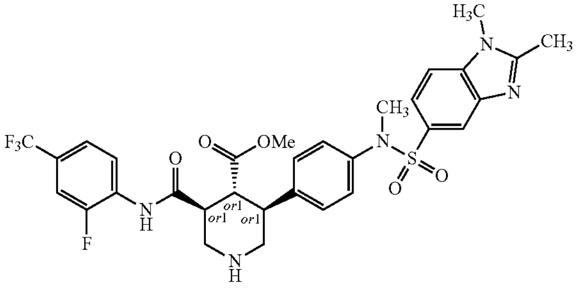

ISOMER 2

To a mixture of rac-1-benzyl 4-methyl (3R,4S,5R)-3-((2-fluoro-4-(trifluoromethyl)phenyl)carbamoyl)-5-(4-((N,1,2-trimethyl-1H-benzo[d]imidazole)-5-sulfonamido)phenyl) piperidine-1,4-dicarboxylate (0.50 g, 0.63 mmol) in methanol (5 mL) was added acetic acid (0.1 mL) and Pd—C(10%) (0.33 g, 0.31 mmol). The reaction was stirred under $H_2$ atmosphere (Bladder pressure) at rt for 16 h, filtered through Celite (washing with methanol [5 mL]), concentrated and subjected to reverse phase purification (0-100% MeCN in $H_2O$, 0.1% ABC modifier) to afford rac-methyl (3R,4S,5R)-3-((2-fluoro-4-(trifluoromethyl)phenyl)carbamoyl)-5-(4-((N,1,2-trimethyl-1H-benzo[d]imidazole)-5-sulfonamido)phenyl)piperidine-4-carboxylate (0.32 g, 0.46 mmol, 73% yield) as white solid. A portion of the racemic compound (153 mg) was purified by Chiral-Prep-SFC (Column: Chiralpak IG (250*20) mm; Mobile Phase A:$CO_2$, Mobile Phase B: 0.5% isopropylamine in IPA; Gradient: 45% B) to afford: the first-eluting isomer rel-methyl (3R,4S,5R)-3-((2-fluoro-4-(trifluoromethyl)phenyl)carbamoyl)-5-(4-((N,1,2-trimethyl-1H-benzo[d]imidazole)-5-sulfonamido)phenyl)piperidine-4-carboxylate ISOMER 1 (0.12 g, 0.17 mmol, 34% yield) as an off-white solid. $^1$H NMR (400 MHz, DMSO-$d_6$) δ 10.20 (s, 1H), 8.10 (t, J=8.0 Hz, 1H), 7.72 (d, J=11.0 Hz, 1H), 7.65 (d, J=8.5 Hz, 1H), 7.59-7.50 (m, 2H), 7.31-7.24 (m, 1H), 7.16 (d, J=8.5 Hz, 2H), 7.02-6.93 (m, 2H), 3.79 (s, 3H), 3.27 (s, 4H), 3.08 (s, 4H), 3.05-3.00 (m, 2H), 2.90 (br d, J=8.5 Hz, 1H), 2.79-2.62 (m, 2H), 2.56 (s, 3H). ES-LCMS m/z 662.1 [M+H]$^+$.

And the second-eluting isomer rel-methyl (3R,4S,5R)-3-((2-fluoro-4-(trifluoromethyl)phenyl)carbamoyl)-5-(4-((N,1,2-trimethyl-1H-benzo[d]imidazole)-5-sulfonamido)phenyl)piperidine-4-carboxylate ISOMER 2 (0.10 g, 0.15 mmol, 30% yield) as an off-white solid. $^1$H NMR (400 MHz, DMSO-$d_6$) δ 10.21 (s, 1H), 8.10 (t, J=8.0 Hz, 1H), 7.73 (dd, J=11.0, 1.5 Hz, 1H), 7.65 (d, J=8.5 Hz, 1H), 7.57-7.52 (m, 2H), 7.28 (dd, J=8.5, 1.5 Hz, 1H), 7.17 (d, J=8.5 Hz, 2H), 6.98 (d, J=8.5 Hz, 2H), 3.78 (s, 3H), 3.27 (s, 4H), 3.17 (d, J=4.5 Hz, 1H), 3.09 (s, 3H), 3.05-3.00 (m, 2H), 2.97-2.89 (m, 1H), 2.76-2.65 (m, 2H), 2.56 (s, 3H). ES-LCMS m/z 662.2 $[M+H]^+$.

Intermediate 78: rel-methyl (3R,4S,5R)-1-acetyl-3-((2-fluoro-4-(trifluoromethyl)phenyl)carbamoyl)-5-(4-((N,1,2-trimethyl-1H-benzo[d]imidazole)-5-sulfonamido)phenyl)piperidine-4-carboxylate ISOMER 1

ISOMER 1

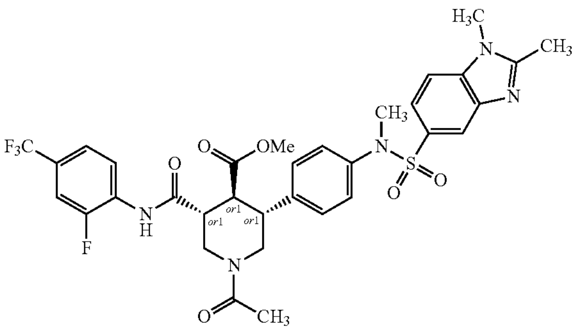

A mixture of rel-methyl (3R,4S,5R)-3-((2-fluoro-4-(trifluoromethyl)phenyl)carbamoyl)-5-(4-((N,1,2-trimethyl-1H-benzo[d]imidazole)-5-sulfonamido)phenyl)piperidine-4-carboxylate ISOMER 1 Intermediate 76 (50 mg, 0.08 mmol) in acetic anhydride (0.50 mL, 5.3 mmol) was stirred at rt for 2 h, quenched with water (1 mL), concentrated and subjected to reverse phase purification (0-100% MeCN in $H_2O$, 0.1% ABC modifier) to afford rel-methyl (3R,4S,5R)-1-acetyl-3-((2-fluoro-4-(trifluoromethyl)phenyl)carbamoyl)-5-(4-((N,1,2-trimethyl-1H-benzo[d]imidazole)-5-sulfonamido)phenyl)piperidine-4-carboxylate ISOMER 1 (0.040 g, 0.020 mmol, 18% yield) as an off-white solid. $^1$H NMR (400 MHz, DMSO-$d_6$) δ 8.18-8.13 (m, 1H), 7.79-7.70 (m, 1H), 7.65 (dd, J=8.5, 2.0 Hz, 1H), 7.60-7.52 (m, 2H), 7.34-7.17 (m, 3H), 7.11-7.01 (m, 2H), 4.40-4.31 (m, 1H), 4.14-3.98 (m, 1H), 3.80 (s, 3H), 3.29 (s, 3H), 3.24-3.16 (m, 3H), 3.07 (s, 3H), 2.96-2.70 (m, 2H), 2.55 (s, 3H), 2.17-2.05 (m, 3H). ES-LCMS m/z 702.0 $[M-H]^-$.

The following compound was synthesized in an analogous manner to the preparation described above (Intermediate 78), using the appropriate amine precursor:

| Int. | Structure/Name | $^1$H NMR | LCMS |
|---|---|---|---|
| 79 | 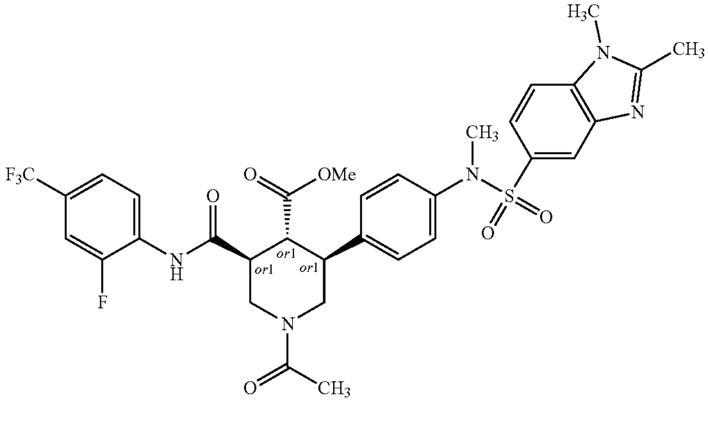 [SMILES: COC(=O)[C@@H]1[C@@H](c2ccc(N(C)S(=O)(=O)c3ccc4c(c3)nc(C)n4C)cc2)CN(C(C)=O)C[C@H]1C(=O)Nc1ccc(C(F)(F)F)cc1F] ISOMER 2 rel-methyl (3R,4S,5R)-1-acetyl-3-((2-fluoro-4-(trifluoromethyl)phenyl)carbamoyl)-5-(4-((N,1,2-trimethyl-1H-benzo[d]imidazole)-5-sulfonamido)phenyl)piperidine-4-carboxylate ISOMER 2 | $^1$H NMR (400 MHZ, DMSO-$d_6$) δ 10.44-10.34 (m, 1H), 8.20-8.02 (m, 1H), 7.76 (br dd, J = 9.5, 6.5 Hz, 1H), 7.67-7.62 (m, 1H), 7.60-7.56 (m, 2H), 7.33-7.23 (m, 3H), 7.03 (dd, J = 8.5, 6.0 Hz, 2H), 4.80-4.71 (m, 1H), 4.40-4.09 (m, 1H), 3.78 (d, J = 2.0 Hz, 3H), 3.29 (s, 3H), 3.24-3.16 (m, 2H), 3.10 (s, 3H), 3.03-2.75 (m, 3H), 2.56 (s, 3H), 2.18-2.08 (m, 3H) | ES-LCMS m/z 704.2 $[M + H]^+$. |

Intermediate 80 and Intermediate 81: rel-(1R,2S,4R,6R)-2-(4-bromophenyl)-6-((2-fluoro-4-(trifluoromethyl)phenyl)carbamoyl)-4-isopropoxycyclohexane-1-carboxylic acid ISOMER 1 and rel-(1R,2S,4R,6R)-2-(4-bromophenyl)-6-((2-fluoro-4-(trifluoromethyl)phenyl)carbamoyl)-4-isopropoxycyclohexane-1-carboxylic acid ISOMER 2

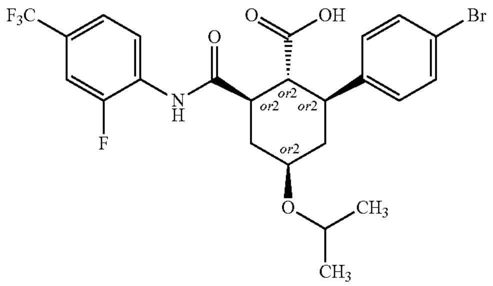

ISOMER 1

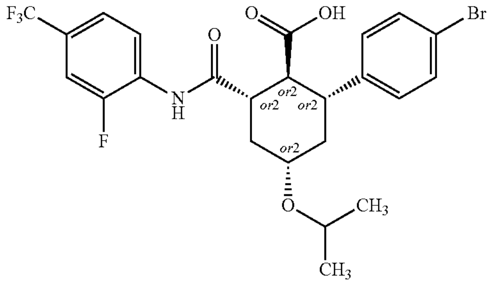

ISOMER 2

Step 1: rac-(3aR,5R,7S,7aS)-7-(4-bromophenyl)-5-isopropoxyhexahydroisobenzofuran-1(3H)-one

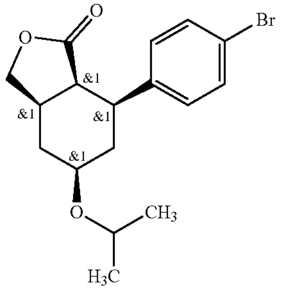 [SMILES: CC(C)O[C@H]1C[C@H]2COC(=O)[C@H]2[C@@H](c2ccc(Br)cc2)C1]

To a mixture of rac-(3aR,7S,7aS)-7-(4-bromophenyl)tetrahydroisobenzofuran-1,5(3H,4H)-dione Intermediate 8, Step 5 (2.50 g, 8.09 mmol) and propan-2-ol (4.86 g, 81.0 mmol) in acetonitrile (25 mL) at 0° C. was added chlorodimethylsilane (4.50 mL, 40.4 mmol). The reaction was stirred at room temperature for 16 h and diluted with water (20 mL). Acetonitrile was evaporated, and the remaining material was extracted with ethyl acetate (50 mL×3). The combined organic layers were washed with brine (50 mL), dried over anhydrous sodium sulfate, filtered, concentrated and subjected to normal phase purification (ethyl acetate in petroleum ether, 0-50% gradient) to afford rac-(3aR,5R,7S,7aS)-7-(4-bromophenyl)-5-isopropoxyhexahydroisobenzofuran-1(3H)-one (1.30 g, 3.35 mmol, 41.0% yield) as a white solid. $^{1}$H NMR (400 MHz, DMSO-$d_6$) δ 7.49-7.43 (m, 2H), 7.26 (d, J=8.5 Hz, 2H), 4.19 (dd, J=8.8, 4.3 Hz, 1H), 3.88 (d, J=8.5 Hz, 1H), 3.75 (quin, J=6.0 Hz, 1H), 3.48 (tt, J=11.0, 3.8 Hz, 1H), 3.26-3.20 (m, 1H), 3.17-3.09 (m, 1H), 2.69 (dq, J=10.6, 6.0 Hz, 1H), 2.15-2.05 (m, 2H), 1.41-1.28 (m, 1H), 1.08 (dd, J=6.0, 1.5 Hz, 6H), 1.01-0.87 (m, 1H). ES-LCMS m/z 355.0 [M+1]$^+$.

Step 2: rac-(1R,2S,4R,6R)-2-(4-bromophenyl)-6-(hydroxymethyl)-4-isopropoxycyclohexane-1-carboxylic acid

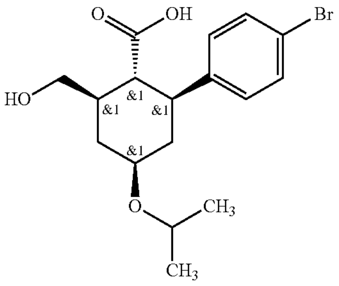 [SMILES: CC(C)O[C@H]1C[C@@H](CO)[C@H](C(=O)O)[C@@H](c2ccc(Br)cc2)C1]

To a mixture of rac-(3aR,5R,7S,7aS)-7-(4-bromophenyl)-5-isopropoxyhexahydroisobenzofuran-1(3H)-one (1.30 g, 3.68 mmol) in methanol (20 mL) was added potassium hydroxide (1.032 g, 18.40 mmol). The reaction was stirred at ° C. for 2 h, and the methanol was evaporated. The reaction was quenched with water (10 ml), acidified with 1.5 N HCl and extracted with ethyl acetate (3×50 ml). The organic layers were washed with brine (50 mL), dried over sodium sulphate and evaporated to afford crude rac-(1R,2S,4R,6R)-2-(4-bromophenyl)-6-(hydroxymethyl)-4-isopropoxycyclohexane-1-carboxylic acid (1.30 g, 3.22 mmol, 88.0% yield) as a brown solid. $^{1}$H NMR (400 MHz, DMSO-$d_6$) δ 11.84 (br s, 1H), 7.44 (d, J=8.5 Hz, 2H), 7.18 (d, J=8.5 Hz, 2H), 4.56 (br s, 1H), 3.70 (dt, J=12.0, 6.0 Hz, 1H), 3.53-3.44 (m, 1H), 3.38 (dd, J=10.8, 3.8 Hz, 1H), 3.20 (dd, J=10.5, 7.0 Hz, 1H), 2.85-2.72 (m, 1H), 2.46 (dd, J=3.5, 1.5 Hz, 1H), 2.21 (t, J=11.3 Hz, 1H), 2.13 (d, J=12.0 Hz, 1H), 1.95-1.87 (m, 1H), 1.76 (ddt, J=19.5, 7.4, 3.3 Hz, 1H), 1.41-1.28 (m, 1H), 1.05 (dd, J=10.0, 6.0 Hz, 6H). ES-LCMS m/z 371.0 [M+1]$^+$.

Step 3: rac-benzyl (1R,2S,4R,6R)-2-(4-bromophenyl)-6-(hydroxymethyl)-4-isopropoxycyclohexane-1-carboxylate

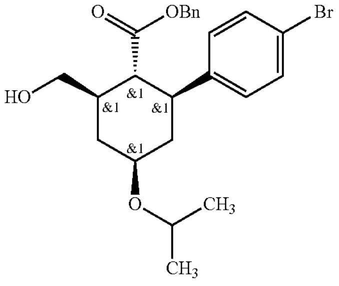 [SMILES: CC(C)O[C@H]1C[C@@H](CO)[C@H](C(=O)OCc2ccccc2)[C@@H](c2ccc(Br)cc2)C1]

To a mixture of rac-(1R,2S,4R,6R)-2-(4-bromophenyl)-6-(hydroxymethyl)-4-isopropoxycyclohexane-1-carboxylic acid (1.30 g, 3.50 mmol) in DMF (15 mL) at 0° C. were added potassium carbonate (1.452 g, 10.50 mmol) and benzyl bromide (0.500 mL, 4.20 mmol). The reaction was stirred at rt for 3 h, quenched with water (50 ml) and extracted with ethyl acetate (2×100 mL). The organic layers were washed with brine (50 mL), dried over sodium sulphate, and subjected to column chromatography, eluting with 0-100% ethyl acetate in pet ether to afford rac-benzyl (1R,2S,4R,6R)-2-(4-bromophenyl)-6-(hydroxymethyl)-4-isopropoxycyclohexane-1-carboxylate (1.30 g, 2.54 mmol, 72.0% yield) as a white solid. $^1$H NMR (400 MHz, DMSO-$d_6$) δ 7.95 (s, 1H), 7.42 (d, J=8.5 Hz, 2H), 7.27-7.22 (m, 3H), 7.16 (d, J=8.5 Hz, 2H), 6.86 (dd, J=7.3, 2.3 Hz, 2H), 4.87 (d, J=12.5 Hz, 1H), 4.69 (d, J=13.0 Hz, 1H), 4.59 (t, J=4.8 Hz, 1H), 3.70 (dt, J=12.0, 6.0 Hz, 1H), 3.51 (tt, J=10.9, 3.9 Hz, 1H), 3.31-3.28 (m, 1H), 3.26-3.19 (m, 1H), 2.85-2.77 (m, 1H), 2.40 (t, J=11.3 Hz, 1H), 2.13-2.04 (m, 1H), 1.96-1.89 (m, 1H), 1.88-1.78 (m, 1H), 1.48-1.35 (m, 1H), 1.05 (dd, J=9.5, 6.0 Hz, 6H). ES-LCMS m/z No ionization.

Step 4: rac-(1R,2R,3S,5R)-2-((benzyloxy)carbonyl)-3-(4-bromophenyl)-5-isopropoxycyclohexane-1-carboxylic acid

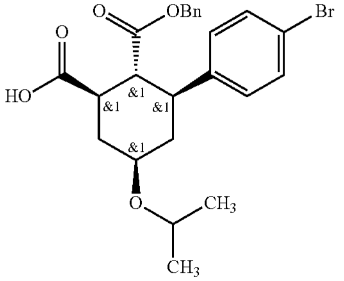 [SMILES: CC(C)O[C@@H]1C[C@H](c2ccc(Br)cc2)[C@@H](C(=O)OCc2ccccc2)[C@H](C(=O)O)C1]

To a mixture of rac-benzyl (1R,2S,4R,6R)-2-(4-bromophenyl)-6-(hydroxymethyl)-4-isopropoxycyclohexane-1-carboxylate (2.40 g, 5.20 mmol) in acetonitrile (20 mL) and water (10 mL) at 0° C. were added sodium periodate (3.34 g, 15.6 mmol) and ruthenium(III) chloride (0.108 g, 0.520 mmol). The reaction was stirred at rt for 2 h, diluted with water (20 mL) and extracted with ethyl acetate (50 mL×3). The combined organic layers were washed with brine (30 mL), dried over anhydrous sodium sulfate, filtered and concentrated to afford crude rac-(1R,2R,3S,5R)-2-((benzyloxy)carbonyl)-3-(4-bromophenyl)-5-isopropoxycyclohexane-1-carboxylic acid (2.40 g, 4.49 mmol, 86.0% yield) as a brown solid. $^1$H NMR (400 MHz, DMSO-$d_6$) δ 12.49 (br s, 1H), 7.43 (d, J=8.5 Hz, 2H), 7.27-7.23 (m, 3H), 7.19 (d, J=8.5 Hz, 2H), 6.84 (dd, J=7.3, 2.3 Hz, 2H), 4.76-4.63 (m, 2H), 3.71 (dt, J=12.4, 6.1 Hz, 1H), 3.64-3.52 (m, 1H), 2.83-2.73 (m, 3H), 2.29-2.20 (m, 1H), 1.96-1.86 (m, 1H), 1.62-1.48 (m, 1H), 1.45-1.31 (m, 1H), 1.05 (dd, J=10.0, 6.0 Hz, 6H). ES-LCMS m/z 475.0 [M+1]$^+$.

Step 5: rac-benzyl (1R,2S,4R,6R)-2-(4-bromophenyl)-6-((2-fluoro-4-(trifluoromethyl)phenyl)carbamoyl)-4-isopropoxycyclohexane-1-carboxylate

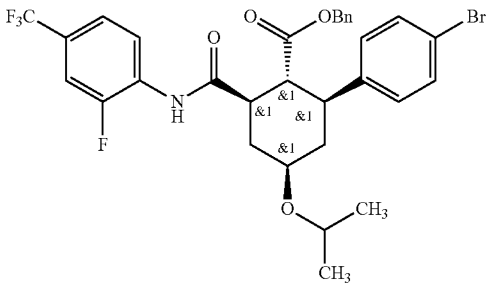 [SMILES: CC(C)O[C@@H]1C[C@H](c2ccc(Br)cc2)[C@@H](C(=O)OCc2ccccc2)[C@H](C(=O)Nc2ccc(C(F)(F)F)cc2F)C1]

To a mixture of rac-(1R,2R,3S,5R)-2-((benzyloxy)carbonyl)-3-(4-bromophenyl)-5-isopropoxycyclohexane-1-carboxylic acid (2.30 g, 4.84 mmol) in acetonitrile (2 mL) was added 2-fluoro-4-(trifluoromethyl)aniline (0.953 g, 5.32 mmol), N-(chloro(dimethylamino)methylene)-N-methylmethanaminium hexafluorophosphate(V) (2.72 g, 9.68 mmol) and 1-methyl-1H-imidazole (0.771 mL, 9.68 mmol). After 16 h the reaction was subjected to reverse phase purification (0-100% MeCN in $H_2O$, 0.1% formic acid modifier) to afford rac-benzyl (1R,2S,4R,6R)-2-(4-bromophenyl)-6-((2-fluoro-4-(trifluoromethyl)phenyl)carbamoyl)-4-isopropoxycyclohexane-1-carboxylate (1.9 g, 2.9 mmol, 60% yield) as an off-white solid. $^1$H NMR (400 MHz, DMSO-$d_6$) δ 10.14 (s, 1H), 8.15 (t, J=8.3 Hz, 1H), 7.72 (dd, J=11.0, 2.0 Hz, 1H), 7.55 (d, J=9.0 Hz, 1H), 7.45 (d, J=8.5 Hz, 2H), 7.24 (d, J=8.5 Hz, 2H), 7.21-7.13 (m, 3H), 6.82-6.78 (m, 2H), 4.75-4.62 (m, 2H), 3.75 (dt, J=12.4, 6.1 Hz, 1H), 3.65-3.54 (m, 1H), 3.18-3.08 (m, 1H), 2.96-2.90 (m, 1H), 2.83 (td, J=12.0, 3.5 Hz, 1H), 2.35-2.26 (m, 1H), 1.98 (d, J=12.0 Hz, 1H), 1.67-1.54 (m, 1H), 1.49-1.38 (m, 1H), 1.08 (t, J=6.5 Hz, 6H). ES-LCMS m/z 636.0 [M+1]$^+$.

Step 6: rel-(1R,2S,4R,6R)-2-(4-bromophenyl)-6-((2-fluoro-4-(trifluoromethyl)phenyl)carbamoyl)-4-isopropoxycyclohexane-1-carboxylic acid ISOMER 1 and rel-(1R,2S,4R,6R)-2-(4-bromophenyl)-6-((2-fluoro-4-(trifluoromethyl)phenyl)carbamoyl)-4-isopropoxycyclohexane-1-carboxylic acid ISOMER 2

ISOMER 1

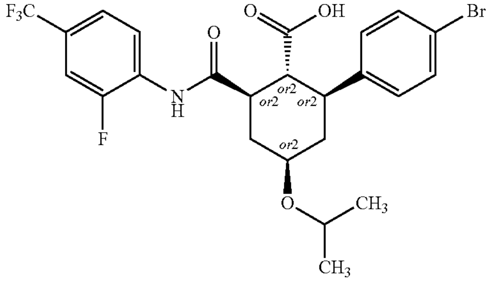

-continued

ISOMER 2

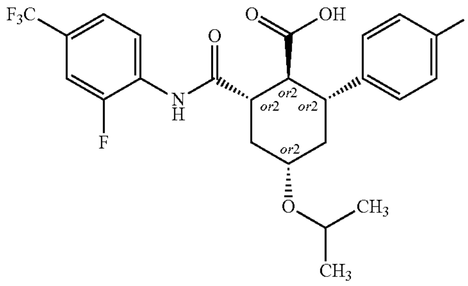

To a mixture of rac-benzyl (1R,2S,4R,6R)-2-(4-bromophenyl)-6-((2-fluoro-4-(trifluoromethyl)phenyl)carbamoyl)-4-isopropoxycyclohexane-1-carboxylate (0.800 g, 1.26 mmol) in DMSO (8 mL) at 0° C. was added aluminum trichloride (0.670 mg, 5.03 mmol). The reaction was stirred at rt for 3 h, diluted with water (10 mL), concentrated and subjected to normal phase purification (ethyl acetate in petroleum ether, 10-80% gradient) to afford rac-(1R,2S,4R,6R)-2-(4-bromophenyl)-6-((2-fluoro-4-(trifluoromethyl)phenyl)carbamoyl)-4-isopropoxycyclohexane-1-carboxylic acid (0.480 g, 0.828 mmol, 66.0% yield) as a white solid. The racemic compound was separated by Chiral-Prep-SFC (Column: Chiralpak-IA; Mobile Phase: $CO_2$: 0.5% isopropylamine in IPA (60:40)%,) to afford:

the first-eluting peak rel-(1R,2S,4R,6R)-2-(4-bromophenyl)-6-((2-fluoro-4-(trifluoromethyl)phenyl)carbamoyl)-4-isopropoxycyclohexane-1-carboxylic acid ISOMER 1 (0.480 g, 0.832 mmol, 39.0% yield) as a white solid. $^1H$ NMR (400 MHz, DMSO-$d_6$) δ 11.84 (br s, 1H), 10.11 (s, 1H), 8.20 (t, J=8.3 Hz, 1H), 7.72 (dd, J=11.0, 2.0 Hz, 1H), 7.55 (d, J=8.5 Hz, 1H), 7.46 (d, J=8.5 Hz, 2H), 7.25 (d, J=8.5 Hz, 2H), 3.74 (quin, J=6.1 Hz, 1H), 3.61-3.50 (m, 1H), 3.10-2.99 (m, 1H), 2.85-2.70 (m, 2H), 2.25 (d, J=12.0 Hz, 1H), 1.96 (d, J=12.0 Hz, 1H), 1.61-1.33 (m, 2H), 1.12-0.97 (m, 6H). ES-LCMS m/z 546.0 $[M+1]^+$. and the second-eluting peak rel-(1R,2S,4R,6R)-2-(4-bromophenyl)-6-((2-fluoro-4-(trifluoromethyl)phenyl)carbamoyl)-4-isopropoxycyclohexane-1-carboxylic acid ISOMER 2 (500 mg, 0.895 mmol, 42% yield) as a white solid. $^1H$ NMR (400 MHz, DMSO-$d_6$) δ 11.83 (br s, 1H), 10.10 (s, 1H), 8.20 (t, J=8.0 Hz, 1H), 7.72 (dd, J=11.0, 1.5 Hz, 1H), 7.55 (dd, J=8.5, 1.0 Hz, 1H), 7.46 (d, J=8.0 Hz, 2H), 7.25 (d, J=8.5 Hz, 2H), 3.82-3.69 (m, 1H), 3.62-3.50 (m, 1H), 3.11-2.98 (m, 1H), 2.84-2.71 (m, 2H), 2.25 (d, J=12.0 Hz, 1H), 1.96 (d, J=12.5 Hz, 1H), 1.60-1.34 (m, 2H), 1.13-1.00 (m, 6H). ES-LCMS m/z 548.0 $[M+1]^+$.

The following compounds were synthesized in an analogous manner to the preparation described above (Intermediate 4), using the appropriate bromoaryl precursor, and using sodium tert-butoxide as base:

| Int. | Structure/Name | $^1H$ NMR | LCMS |
|---|---|---|---|
| 82 | 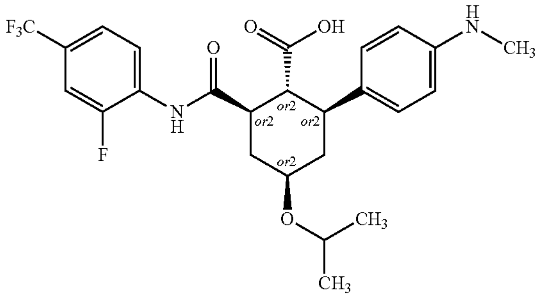 [SMILES: CNc1ccc([C@H]2C[C@@H](OC(C)C)C[C@@H](C(=O)Nc3ccc(C(F)(F)F)cc3F)[C@@H]2C(=O)O)cc1] ISOMER 1 rel-(1R,2R,4R,6S)-2-((2-fluoro-4-(trifluoromethyl)phenyl)carbamoyl)-4-isopropoxy-6-(4-(methylamino)phenyl)cyclohexane-1-carboxylic acid ISOMER 1 | $^1H$ NMR (400 MHz, DMSO-$d_6$) δ 11.69 (br s, 1H), 10.11 (br s, 1H), 8.21 (t, J = 8.3 Hz, 1H), 7.71 (dd, J = 11.3, 1.8 Hz, 1H), 7.59-7.46 (m, 1H), 6.96 (d, J = 8.5 Hz, 2H), 6.42 (d, J = 8.5 Hz, 2H), 5.42 (d, J = 4.0 Hz, 1H), 3.73 (dt, J = 12.1, 6.2 Hz, 1H), 3.60-3.43 (m, 1H), 3.00 (t, J = 9.8 Hz, 1H), 2.71-2.56 (m, 5H), 2.21 (d, J = 12.0 Hz, 1H), 1.92 (d, J = 11.5 Hz, 1H), 1.50-1.31 (m, 2H), 1.07 (t, J= 5.8 Hz, 6H) | ES-LCMS m/z 495.2 $[M-H]^-$. |
| 83 | 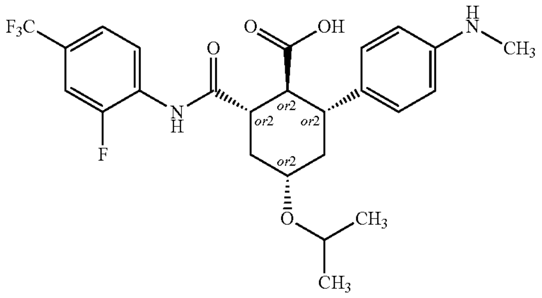 [SMILES: CNc1ccc([C@@H]2C[C@H](OC(C)C)C[C@H](C(=O)Nc3ccc(C(F)(F)F)cc3F)[C@H]2C(=O)O)cc1] ISOMER 2 rel-(1R,2R,4R,6S)-2-((2-fluoro-4-(trifluoromethyl)phenyl)carbamoyl)-4-isopropoxy-6-(4-(methylamino)phenyl)cyclohexane-1-carboxylic acid ISOMER 2 | $^1H$ NMR (400 MHz, DMSO-$d_6$) δ 11.67 (br s, 1H), 10.06 (s, 1H), 8.20 (t, J = 8.3 Hz, 1H), 7.71 (dd, J = 11.0, 1.5 Hz, 1H), 7.54 (d, J = 9.5 Hz, 1H), 6.96 (d, J = 8.5 Hz, 2H), 6.43 (d, J = 8.5 Hz, 2H), 5.42 (br s, 1H), 3.73 (quin, J = 6.0 Hz, 1H), 3.56-3.46 (m, 1H), 3.09-2.95 (m, 1H), 2.65-2.58 (m, 5H), 2.21 (d, J = 11.5 Hz, 1H), 1.92 (d, J = 13.0 Hz, 1H), 1.51-1.30 (m, 2H), 1.07 (t, J = 5.8 Hz, 6H) | ES-LCMS m/z 495.2 $[M-H]^-$. |

The following compound was synthesized in an analogous manner to the preparation described above (intermediate 80 and Intermediate 81, Step 4), using the appropriate alcohol:

| Int. | Structure/Name | $^1H$ NMR | LCMS |
|---|---|---|---|
| 84 | 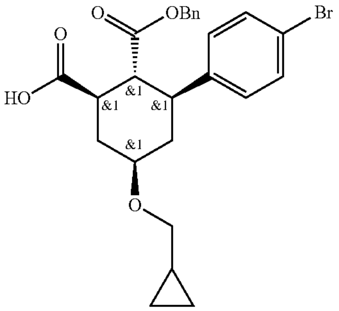 [SMILES: O=C(OCc1ccccc1)[C@@H]1[C@@H](c2ccc(Br)cc2)C[C@@H](OCC2CC2)C[C@H]1C(=O)O] rac-(1R,2R,3S,5R)-2-((benzyloxy)carbonyl)-3-(4-bromophenyl)-5-(cyclopropylmethoxy)cyclohexane-1-carboxylic acid | $^1H$ NMR (400 MHz, DMSO-$d_6$) δ 12.50 (br s, 1H), 7.45-7.40 (m, 2H), 7.26-7.23 (m, 3H), 7.21-7.17 (m, 2H), 6.83 (dd, J = 7.3, 2.3 Hz, 2H), 4.72-4.68 (m, 2H), 3.53 (ddd, J = 15.0, 10.8, 4.3 Hz, 1H), 3.29-3.24 (m, 2H), 2.79-2.70 (m, 3H), 2.37-2.28 (m, 1H), 2.04-1.93 (m, 1H), 1.63-1.48 (m, 1H), 1.46-1.31 (m, 1H), 1.02-0.89 (m, 1H), 0.47-0.37 (m, 2H), 0.18-0.07 (m, 2H) | ES-LCMS m/z 485.2 $[M - H]^-$. |

Intermediate 85: rac-(1R,2R,4R,6S)-4-(cyclopropylmethoxy)-2-((2-fluoro-4-(trifluoromethyl)phenyl)carbamoyl)-6-(4-(methylamino)phenyl)cyclohexane-1-carboxylic

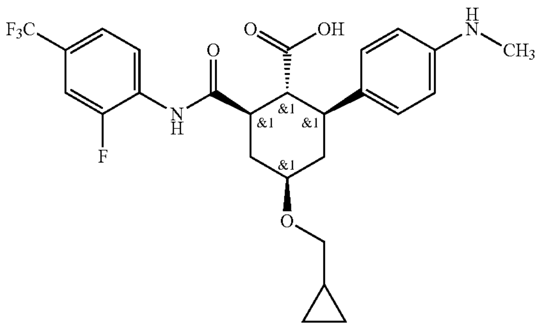 [SMILES: CNc1ccc([C@H]2C[C@@H](OCC3CC3)C[C@@H](C(=O)Nc3ccc(C(F)(F)F)cc3F)[C@@H]2C(=O)O)cc1]

Step 1: rac-benzyl (1R,2S,4R,6R)-2-(4-bromophenyl)-6-(chlorocarbonyl)-4-(cyclopropylmethoxy)cyclohexane-1-carboxylate

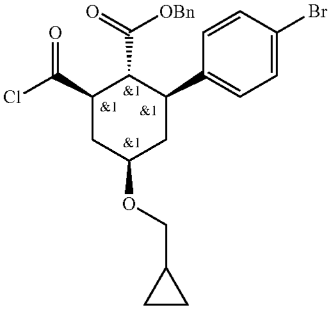 [SMILES: O=C(OCc1ccccc1)[C@@H]1[C@@H](c2ccc(Br)cc2)C[C@@H](OCC2CC2)C[C@H]1C(=O)Cl]

To a mixture of rac-(1R,2R,3S,5R)-2-((benzyloxy)carbonyl)-3-(4-bromophenyl)-5-(cyclopropylmethoxy)cyclohexane-1-carboxylic acid Intermediate 84 (1.60 g, 3.28 mmol) in DCM (20 mL) at 0° C. was added thionyl chloride (1.198 mL, 16.41 mmol), dropwise. The reaction was stirred at rt for 16 h and concentrated to give crude rac-benzyl (1R,2S,4R,6R)-2-(4-bromophenyl)-6-(chlorocarbonyl)-4-(cyclopropylmethoxy)cyclohexane-1-carboxylate (1.60 g, 1.96 mmol, 60.0% yield) as a yellow oil. $^1$HNMR not reported. ES-LCMS m/z 501.3 $[M+1]^+$. (Small aliquot was quenched with MeOH, methyl ester mass reported)

Step 2: rac-benzyl (1R,2S,4R,6R)-2-(4-bromophenyl)-4-(cyclopropylmethoxy)-6-((2-fluoro-4-(trifluoromethyl)phenyl)carbamoyl)cyclohexane-1-carboxylate

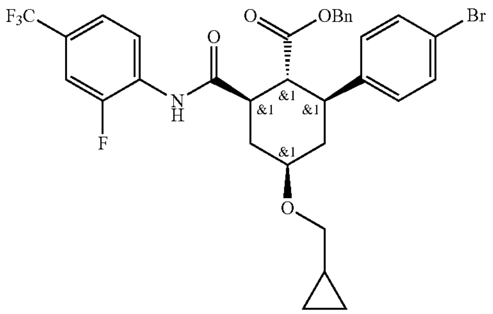 [SMILES: O=C(OCc1ccccc1)[C@@H]1[C@@H](c2ccc(Br)cc2)C[C@@H](OCC2CC2)C[C@H]1C(=O)Nc1ccc(C(F)(F)F)cc1F]

To a mixture of rac-benzyl (1R,2S,4R,6R)-2-(4-bromophenyl)-6-(chlorocarbonyl)-4-(cyclopropylmethoxy)cyclohexane-1-carboxylate (1.60 g, 3.16 mmol) in DCM (15 mL) at 0° C. was added pyridine (6.4 mL, 79 mmol) and 2-fluoro-4-(trifluoromethyl)aniline (0.493 mL, 3.80 mmol). The reaction was stirred at rt for 2 h, concentrated and subjected to reverse phase purification (0-100% MeCN in $H_2O$, 10 mM ammonium bicarbonate modifier) to afford rac-benzyl (1R,2S,4R,6R)-2-(4-bromophenyl)-4-(cyclopropylmethoxy)-6-((2-fluoro-4-(trifluoromethyl)phenyl)carbamoyl)cyclohexane-1-carboxylate (1.40 g, 1.94 mmol, 61.0% yield) as an off-white solid. $^1$H NMR (400 MHz, DMSO-$d_6$) δ 10.16 (s, 1H), 8.16 (t, J=8.0 Hz, 1H), 7.73 (dd, J=11.0, 2.0 Hz, 1H), 7.55 (d, J=8.5 Hz, 1H), 7.45 (d, J=8.5 Hz, 2H), 7.24 (d, J=8.5 Hz, 2H), 7.21-7.13 (m, 3H), 6.82-6.77 (m, 2H), 4.76-4.62 (m, 2H), 3.61-3.48 (m, 1H), 3.30 (d, J=7.0 Hz, 2H), 3.17-3.08 (m, 1H), 2.95 (t, J=11.3 Hz, 1H), 2.80 (td, J=12.1, 2.8 Hz, 1H), 2.36 (d, J=12.0 Hz, 1H), 2.09-2.02 (m, 1H), 1.66-1.55 (m, 1H), 1.45 (q, J=12.0 Hz, 1H), 1.02-0.92 (m, 1H), 0.47-0.40 (m, 2H), 0.18-0.11 (m, 2H). ES-LCMS m/z 648.2 $[M+1]^+$.

Step 3: rac-(1R,2S,4R,6R)-2-(4-bromophenyl)-4-(cyclopropylmethoxy)-6-((2-fluoro-4-(trifluoromethyl)phenyl)carbamoyl)cyclohexane-1-carboxylic acid

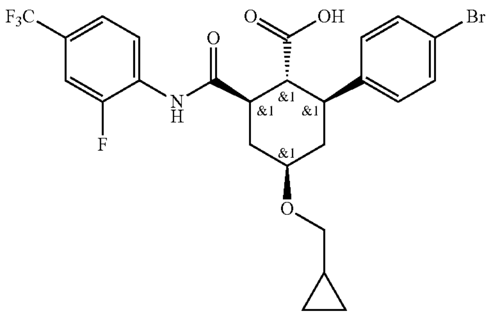 [SMILES: O=C(O)[C@@H]1[C@@H](c2ccc(Br)cc2)C[C@@H](OCC2CC2)C[C@H]1C(=O)Nc1ccc(C(F)(F)F)cc1F]

To a mixture of benzyl (1R,2S,4R,6R)-2-(4-bromophenyl)-4-(cyclopropylmethoxy)-6-((2-fluoro-4-(trifluoromethyl)phenyl)carbamoyl)cyclohexane-1-carboxylate (0.500 g, 0.771 mmol) in DMSO (10 mL) was added aluminum trichloride (206 mg, 1.54 mmol). After 2 h the reaction was diluted with water (5 mL), concentrated and subjected to normal phase purification (ethyl acetate in petroleum ether, 10-80% gradient) to afford rac-(1R,2S,4R,6R)-2-(4-bromophenyl)-4-(cyclopropylmethoxy)-6-((2-fluoro-4-(trifluoromethyl)phenyl)carbamoyl)cyclohexane-1-carboxylic acid (0.260 g, 0.419 mmol, 54.0% yield) as a white solid. $^1$H NMR (400 MHz, DMSO-$d_6$) δ 11.87 (s, 1H), 10.12 (br s, 1H), 8.20 (t, J=8.3 Hz, 1H), 7.72 (dd, J=11.0, 1.5 Hz, 1H), 7.55 (d, J=10.0 Hz, 1H), 7.47 (d, J=8.5 Hz, 2H), 7.25 (d, J=8.5 Hz, 2H), 3.57-3.46 (m, 1H), 3.29 (d, J=7.0 Hz, 2H), 3.10-3.00 (m, 2H), 2.80-2.74 (m, 2H), 2.30 (br s, 1H), 2.08-2.00 (m, 1H), 1.46-1.37 (m, 1H), 1.03-0.94 (m, 1H), 0.49-0.39 (m, 2H), 0.22-0.09 (m, 2H). ES-LCMS m/z 556.0 $[M-1]^-$.

Step 4: rac-(1R,2R,4R,6S)-4-(cyclopropylmethoxy)-2-((2-fluoro-4-(trifluoromethyl)phenyl)carbamoyl)-6-(4-(methylamino)phenyl)cyclohexane-1-carboxylic acid

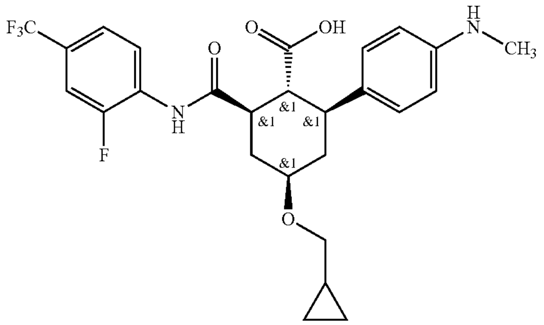 [SMILES: CNc1ccc([C@H]2C[C@@H](OCC3CC3)C[C@@H](C(=O)Nc3ccc(C(F)(F)F)cc3F)[C@@H]2C(=O)O)cc1]

To a mixture of rac-(1R,2S,4R,6R)-2-(4-bromophenyl)-4-(cyclopropylmethoxy)-6-((2-fluoro-4-(trifluoromethyl)phenyl)carbamoyl)cyclohexane-1-carboxylic acid (0.850 g, 1.52 mmol) and sodium tert-butoxide (439 mg, 4.57 mmol) in dioxane (8 mL) was added tBuXPhos Pd G3 (121 mg, 0.152 mmol). After degassing for 5 min and methanamine (2M in THF, 15.2 mL, 30.4 mmol) was added. The reaction was stirred at 100° C. for 1 h, concentrated and subjected to reverse phase purification (10-100% MeCN in $H_2O$, 10 mM ammonium bicarbonate modifier) to afford rac-(1R,2R,4R,6S)-4-(cyclopropylmethoxy)-2-((2-fluoro-4-(trifluoromethyl)phenyl)carbamoyl)-6-(4-(methylamino)phenyl)cyclohexane-1-carboxylic acid (0.450 g, 0.752 mmol, 49.0% yield) as an off-white solid. $^1$H NMR (400 MHz, DMSO-$d_6$) δ 10.10 (br s, 1H), 8.20 (t, J=8.0 Hz, 1H), 7.75-7.67 (m, 1H), 7.54 (d, J=8.5 Hz, 1H), 6.96 (d, J=8.5 Hz, 2H), 6.43 (d, J=8.5 Hz, 2H), 5.42 (br s, 1H), 3.52-3.45 (m, 1H), 3.29 (d, J=6.5 Hz, 2H), 3.06-2.94 (m, 1H), 2.68-2.57 (m, 5H), 2.30-2.22 (m, 1H), 1.99 (d, J=13.0 Hz, 1H), 1.93-1.85 (m, 1H), 1.50-1.32 (m, 2H), 1.02-0.91 (m, 1H), 0.47-0.40 (m, 2H), 0.17-0.11 (m, 2H). ES-LCMS m/z 507.0 $[M-H]^-$.

The following compound was synthesized in an analogous manner to the preparation described above (Intermediate 8, Step 10), using the relevant alkyl tosylate as the alkylating agent:

| Int. | Structure/Name | $^1$H NMR | LCMS |
|---|---|---|---|
| 86 | 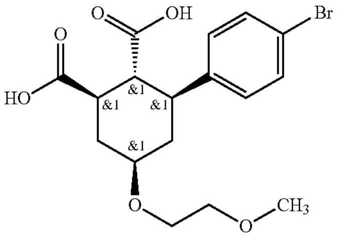 [SMILES: COCCO[C@@H]1C[C@H](c2ccc(Br)cc2)[C@@H](C(=O)O)[C@H](C(=O)O)C1]<br>rac-(1R,2R,3S,5R)-2-((benzyloxy)carbonyl)-3-(4-bromophenyl)-5-(2-methoxyethoxy)cyclohexane-1-carboxylic acid | $^1$H NMR (400 MHz, DMSO-$d_6$) δ 12.57 (br s, 1H), 7.43 (d, J = 8.5 Hz, 2H), 7.28-7.23 (m, 3H), 7.19 (d, J = 8.5 Hz, 2H), 6.83 (dd, J = 7.0, 2.5 Hz, 2H), 4.74-4.65 (m, 2H), 3.58-3.52 (m, 3H), 3.42-3.38 (m, 2H), 3.22 (s, 3H), 2.79-2.69 (m, 3H), 2.38-2.30 (m, 1H), 1.99 (dd, J = 10.8, 1.8 Hz, 1H), 1.61-1.49 (m, 1H), 1.45-1.32 (m, 1H) | ES-LCMS m/z no ionization |

The following compound was synthesized in an analogous manner to the preparation described above (Intermediate 85), using Intermediate 86 as the starting acid:

| Int | Structure/Name | $^1$H NMR | LCMS |
|---|---|---|---|
| 87 | 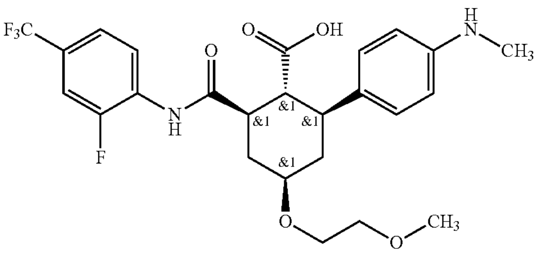 [SMILES: CNc1ccc([C@H]2C[C@@H](OCCOC)C[C@@H](C(=O)Nc3ccc(C(F)(F)F)cc3F)[C@@H]2C(=O)O)cc1]<br>rac-(1R,2R,3R,5S)-2-((2-fluoro-4-(trifluoromethyl)phenyl)carbamoyl)-4-(2-methoxyethoxy)-6-(4-(methylamino)phenyl)cyclohexane-1-carboxylic acid | $^1$H NMR (400 MHz, DMSO-$d_6$) δ 11.72 (br s, 1H), 10.08 (s, 1H), 8.20 (t, J = 8.0 Hz, 1H), 7.71 (dd, J = 11.0, 2.0 Hz, 1H), 7.54 (d, J = 8.5 Hz, 1H), 6.96 (d, J = 9.0 Hz, 2H), 6.43 (d, J = 8.5 Hz, 2H), 5.43 (s, 1H), 3.59-3.55 (m, 2H), 3.53-3.44 (m, 1H), 3.42 (dd, J = 5.5, 4.0 Hz, 2H), 3.23 (s, 3H), 3.05-2.97 (m, 1H), 2.71-2.58 (m, 5H), 2.28 (d, J = 11.5 Hz, 1H), 2.00 (d, J = 12.5 Hz, 1H), 1.52-1.32 (m, 2H) | ES-LCMS m/z 511.2 [M − H]$^-$. |

The following compound was synthesized in an analogous manner to the preparation described above (Intermediate 85, Step 2), using the appropriate starting alcohol:

| Int. | Structure/Name | $^1$H NMR | LCMS |
|---|---|---|---|
| 88 | 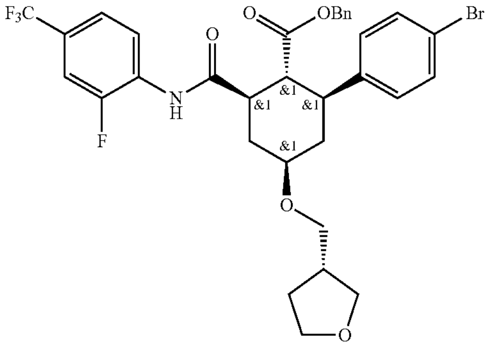 [SMILES: O=C(OCc1ccccc1)[C@@H]1[C@@H](c2ccc(Br)cc2)C[C@@H](OC[C@H]2CCOC2)C[C@H]1C(=O)Nc1ccc(C(F)(F)F)cc1F]<br>benzyl (1RS,2SR,4RS,6RS)-2-(4-bromophenyl)-6-((2-fluoro-4-(trifluoromethyl)phenyl)carbamoyl)-4-(((S)-tetrahydrofuran-3-yl)methoxy)cyclohexane-1-carboxylate | $^1$H NMR (400 MHz, DMSO-$d_6$) δ 10.16 (s, 1H), 8.16 (t, J = 8.0 Hz, 1H), 7.72 (dd, J = 11.0, 2.0 Hz, 1H), 7.55 (br d, J = 9.0 Hz, 1H), 7.45 (d, J = 8.5 Hz, 2H), 7.24 (d, J = 8.5 Hz, 2H), 7.21-7.12 (m, 3H), 6.82-6.77 (m, 2H), 4.75-4.63 (m, 2H), 3.71-3.63 (m, 2H), 3.62-3.48 (m, 2H), 3.47-3.33 (m, 4H), 3.18-3.08 (m, 1H), 2.95 (t, J = 11.3 Hz, 1H), 2.81 (td, J = 12.0, 3.0 Hz, 1H), 2.42-2.35 (m, 1H), 2.11-2.02 (m, 1H), 1.96-1.83 (m, 1H), 1.68-1.55 (m, 1H), 1.54-1.43 (m, 2H) | ES-LCMS m/z 676.0 [M − H]$^-$. |

Intermediate 89 and Intermediate 90: (1R*,2S*,4R*,6R*)-2-(4-bromophenyl)-6-((2-fluoro-4-(trifluoromethyl)phenyl)carbamoyl)-4-(((S)-tetrahydrofuran-3-yl)methoxy)cyclohexane-1-carboxylic acid ISOMER 1 and (1R*,2S*,4R*,6R*)-2-(4-bromophenyl)-6-((2-fluoro-4-(trifluoromethyl)phenyl)carbamoyl)-4-(((S)-tetrahydrofuran-3-yl)methoxy)cyclohexane-1-carboxylic acid ISOMER 2

ISOMER 1

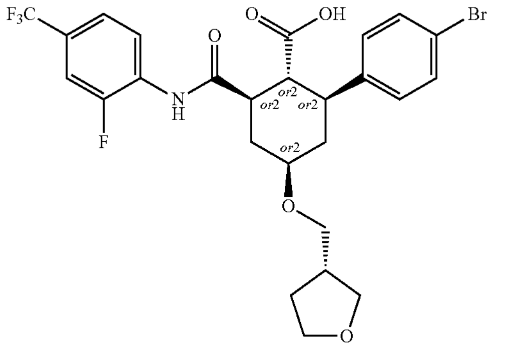

ISOMER 2

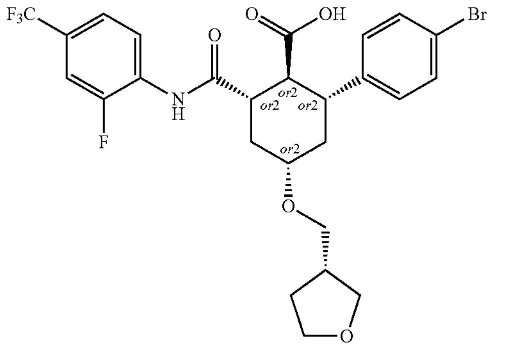

To a mixture of benzyl (1RS,2SR,4RS,6RS)-2-(4-bromophenyl)-6-((2-fluoro-4-(trifluoromethyl)phenyl)carbamoyl)-4-(((S)-tetrahydrofuran-3-yl)methoxy)cyclohexane-1-carboxylate Intermediate 88 (1.60 g, 2.36 mmol) in DMSO (20 mL) at 0° C. was added aluminum trichloride (1.26 g, 9.43 mmol). The reaction was stirred at rt for 16 h, concentrated and subjected to normal phase purification (ethyl acetate in petroleum ether, 0-100% gradient) to afford (1RS,2SR,4RS,6RS)-2-(4-bromophenyl)-6-((2-fluoro-4-(trifluoromethyl)phenyl)carbamoyl)-4-(((S)-tetrahydrofuran-3-yl)methoxy)cyclohexane-1-carboxylic acid (0.550 g, 0.888 mmol, 38.0% yield) as a white solid. This racemic compound was separated by Chiral-Prep-SFC (Column: Chiralpak IG (250*20) mm, 5 μm; Mobile Phase: $CO_2$: 0.5% isopropylamine in IPA (80:20)) to afford:

the first-eluting peak (1R*,2S*,4R*,6R*)-2-(4-bromophenyl)-6-((2-fluoro-4-(trifluoromethyl)phenyl)carbamoyl)-4-(((S)-tetrahydrofuran-3-yl)methoxy)cyclohexane-1-carboxylic acid ISOMER 1 (0.170 mg, 0.286 mmol, 31.0% yield) as a white solid. $^1$H NMR (400 MHz, DMSO-$d_6$) δ 10.37 (br s, 1H), 8.26 (t, J=8.3 Hz, 1H), 7.69 (d, J=11.0 Hz, 1H), 7.53 (d, J=8.5 Hz, 1H), 7.43 (d, J=8.5 Hz, 2H), 7.23 (d, J=8.5 Hz, 2H), 3.70-3.63 (m, 2H), 3.61-3.54 (m, 1H), 3.49-3.36 (m, 4H), 3.10 (dt, J=12.6, 6.4 Hz, 1H), 2.99-2.90 (m, 2H), 2.81-2.73 (m, 1H), 2.42-2.36 (m, 1H), 2.30 (d, J=10.0 Hz, 1H), 2.01 (d, J=12.0 Hz, 1H), 1.93-1.85 (m, 1H), 1.54-1.38 (m, 3H). ES-LCMS m/z 586.0 [M−1]$^-$.

and the second-eluting peak (1R*,2S*,4R*,6R*)-2-(4-bromophenyl)-6-((2-fluoro-4-(trifluoromethyl)phenyl)carbamoyl)-4-(((S)-tetrahydrofuran-3-yl)methoxy)cyclohexane-1-carboxylic acid ISOMER 2 (171 mg, 0.285 mmol, 30.0% yield) as a white solid. $^1$H NMR (400 MHz, DMSO-$d_6$) δ 10.36 (br s, 1H), 8.26 (t, J=8.3 Hz, 1H), 7.69 (d, J=11.0 Hz, 1H), 7.53 (d, J=8.5 Hz, 1H), 7.43 (d, J=8.5 Hz, 2H), 7.23 (d, J=8.5 Hz, 2H), 3.70-3.63 (m, 2H), 3.61-3.54 (m, 1H), 3.49-3.36 (m, 4H), 3.09 (dt, J=12.6, 6.4 Hz, 1H), 2.99-2.90 (m, 2H), 2.81-2.73 (m, 1H), 2.42-2.36 (m, 1H), 2.29 (d, J=10.0 Hz, 1H), 2.01 (d, J=12.0 Hz, 1H), 1.93-1.85 (m, 1H), 1.54-1.38 (m, 3H). ES-LCMS m/z 586.0 [M−1]$^-$.

Intermediate 91: (1R*,2S*,4R*,6R*)-2-((2-fluoro-4-(trifluoromethyl)phenyl)carbamoyl)-6-(4-(methylamino)phenyl)-4-(((S)-tetrahydrofuran-3-yl)methoxy)cyclohexane-1-carboxylic acid ISOMER 1

ISOMER 1

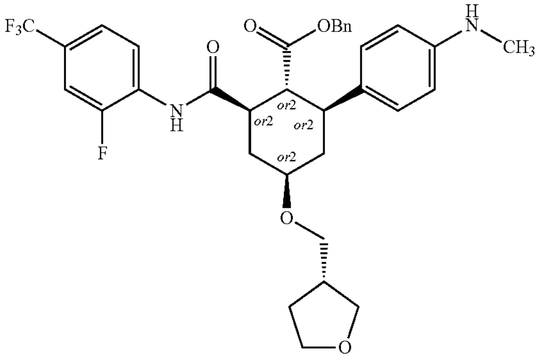

A suspension of (1R*,2S*,4R*,6R*)-2-(4-bromophenyl)-6-((2-fluoro-4-(trifluoromethyl)phenyl)carbamoyl)-4-(((S)-tetrahydrofuran-3-yl)methoxy)cyclohexane-1-carboxylic acid ISOMER 1 Intermediate 89 (0.170 g, 0.289 mmol) in dioxane (2 mL) was degassed for 1 h. Sodium tert-butoxide (83 mg, 0.87 mmol) was added, and the reaction was degassed for 5 min. tBuXPhos Pd G3 (23 mg, 0.029 mmol) and methanamine (2M in THF, 2.89 mL, 5.78 mmol) were added. The reaction heated to 100° C. for 1 h, concentrated subjected to reverse phase purification (10-100% MeCN in $H_2O$, formic acid modifier) to afford (1R*,2S*,4R*,6R*)-2-((2-fluoro-4-(trifluoromethyl)phenyl)carbamoyl)-6-(4-(methylamino)phenyl)-4-(((S)-tetrahydrofuran-3-yl)methoxy)cyclohexane-1-carboxylic acid ISOMER 1 (0.70 mg, 0.13 mmol, 44% yield) was as a white solid. HH NMR (400 MHz, DMSO-$d_6$) δ 11.71 (br s, 1H), 10.08 (s, 1H), 8.20 (t, J=8.3 Hz, 1H), 7.72 (dd, J=11.0, 1.5 Hz, 1H), 7.55 (d, J=9.5 Hz, 1H), 6.96 (d, J=8.5 Hz, 2H), 6.43 (d, J=8.5 Hz, 2H), 5.44 (q, J=4.7 Hz, 1H), 3.70-3.64 (i, 2H), 3.61-3.55 (m, 2H), 3.49-3.38 (m, 5H), 3.05-2.97 (m, 12H), 2.63 (d, J=5.0 Hz, 5H), 2.06-1.96 (m, 1H), 1.94-1.83 (m, 1H), 1.56-1.35 (i, 3H). ES-LCMS m/z 537.2 [M−H]$^-$.

The following compound was synthesized in an analogous manner to the preparation described above (Intermediate 91), using the appropriate arylbromide:

| Int | Structure/Name | $^1$H NMR | LCMS |
| --- | --- | --- | --- |
| 92 | 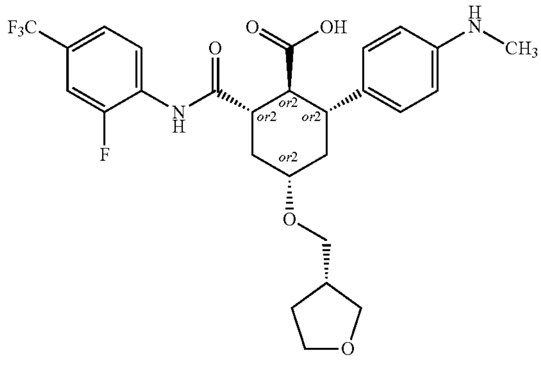 [SMILES: CNc1ccc([C@@H]2C[C@H](OC[C@H]3CCOC3)C[C@H](C(=O)Nc3ccc(C(F)(F)F)cc3F)[C@H]2C(=O)O)cc1] ISOMER 2 (1R*,2S*,4R*,6R*)-2-((2-fluoro-4-(trifluoromethyl)phenyl)carbamoyl)-6-(4-(methylamino)phenyl)-4-(((S)-tetrahydrofuran-3-yl)methoxy)cyclohexane-1-carboxylic acid ISOMER 2 | $^1$H NMR (400 MHz, DMSO-$d_6$) δ 11.70 (br s, 1H), 10.08 (s, 1H), 8.20 (t, J = 8.0 Hz, 1H), 7.72 (dd, J = 10.8, 1.8 Hz, 1H), 7.55 (d, J = 9.0 Hz, 1H), 6.96 (d, J = 8.5 Hz, 2H), 6.43 (d, J = 8.5 Hz, 2H), 5.44 (br s, 1H), 3.71-3.64 (m, 2H), 3.62-3.55 (m, 1H), 3.50-3.37 (m, 4H), 3.05-2.97 (m, 1H), 2.70-2.60 (m, 5H), 2.42-2.25 (m, 2H), 2.00 (d, J = 11.5 Hz, 1H), 1.93-1.83 (m, 1H), 1.54-1.32 (m, 3H) | ES-LCMS m/z 537.2 [M − H]$^-$. |

Intermediate 93 and Intermediate 94: rel-(1R,2S,4R,6R)-2-(4-bromophenyl)-6-((2-fluoro-4-(trifluoromethyl)phenyl)carbamoyl)-4-((tetrahydro-2H-pyran-4-yl)methoxy)cyclohexane-1-carboxylic acid ISOMER 1 and rel-(1R,2S,4R,6R)-2-(4-bromophenyl)-6-((2-fluoro-4-(trifluoromethyl)phenyl)carbamoyl)-4-((tetrahydro-2H-pyran-4-yl)methoxy)cyclohexane-1-carboxylic acid ISOMER 2

ISOMER 1

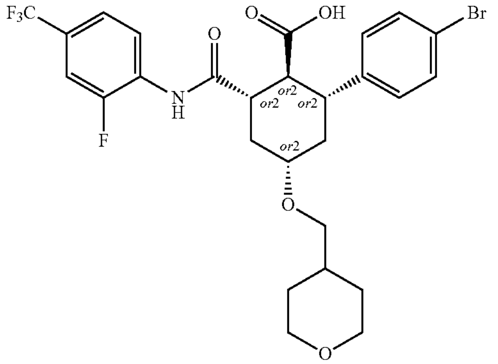

ISOMER 2

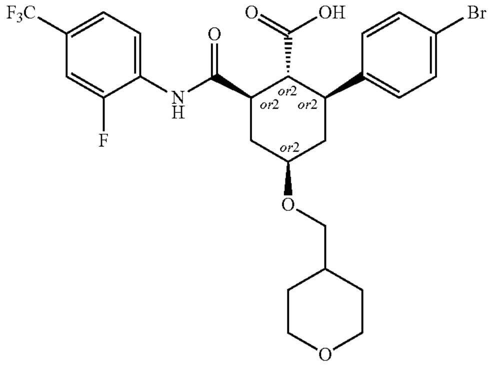

Step 1: rac-benzyl (1R,2S,4R,6R)-2-(4-bromophenyl)-6-((2-fluoro-4-(trifluoromethyl)phenyl)carbamoyl)-4-((tetrahydro-2H-pyran-4-yl)methoxy)cyclohexane-1-carboxylate

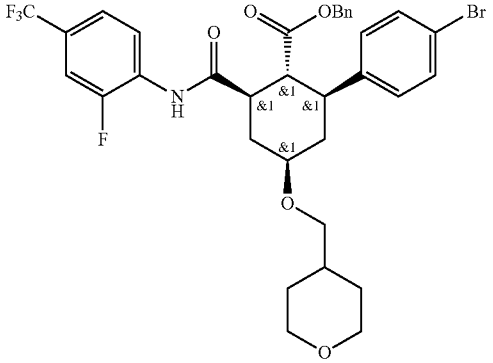 [SMILES: O=C(OCc1ccccc1)[C@@H]1[C@@H](c2ccc(Br)cc2)C[C@@H](OCC2CCOCC2)C[C@H]1C(=O)Nc1ccc(C(F)(F)F)cc1F]

To a mixture of rac-benzyl (1R,2S,6R)-2-(4-bromophenyl)-6-((2-fluoro-4-(trifluoromethyl)phenyl)carbamoyl)-4-oxocyclohexane-1-carboxylate Intermediate 10, Step 4 (1.50 g, 2.53 mmol) in acetonitrile (15 mL) at 0° C. was added chlorodimethylsilane (2.40 g, 25.3 mmol) followed by (tetrahydro-2H-pyran-4-yl)methanol (0.441 g, 3.80 mmol), dropwise. The reaction was stirred at rt for 16 h, quenched with water (3 ml), concentrated and subjected to normal phase purification (20% ethyl acetate in petroleum ether) to afford rac-benzyl (1R,2S,4R,6R)-2-(4-bromophenyl)-6-((2-fluoro-4-(trifluoromethyl)phenyl)carbamoyl)-4-((tetrahydro-2H-pyran-4-yl)methoxy)cyclohexane-1-carboxylate (750 mg, 0.95 mmol, 37% yield) as an off-white solid. $^1$H NMR (400 MHz, DMSO-$d_6$) δ 10.17 (s, 1H), 8.16 (t, J=8.0 Hz, 1H), 7.73 (dd, J=11.0, 2.0 Hz, 1H), 7.55 (br d, J=8.0 Hz, 1H), 7.46 (d, J=8.5 Hz, 2H), 7.29-7.10 (m, 5H), 6.82-6.75 (m, 2H), 4.74-4.62 (m, 2H), 3.83-3.77 (m, 2H), 3.55-3.42 (m, 1H), 3.26-3.24 (m, 3H), 3.16-3.05 (m, 1H), 2.96 (t, J=11.3 Hz, 1H), 2.87-2.73 (m, 1H), 2.42-2.33 (m, 1H), 2.06 (d, J=12.5 Hz, 1H), 1.75-1.67 (m, 1H), 1.46 (d, J=11.5 Hz, 1H), 1.53-1.40 (m, 4H), 1.12-1.05 (m, 2H). ES-LCMS m/z 692.2 [M+H]$^+$.

Step 2: rel-(1R,2S,4R,6R)-2-(4-bromophenyl)-6-((2-fluoro-4-(trifluoromethyl)phenyl)carbamoyl)-4-((tetrahydro-2H-pyran-4-yl)methoxy)cyclohexane-1-carboxylic acid ISOMER 1 and rel-(1R,2S,4R,6R)-2-(4-bromophenyl)-6-((2-fluoro-4-(trifluoromethyl)phenyl)carbamoyl)-4-((tetrahydro-2H-pyran-4-yl)methoxy)cyclohexane-1-carboxylic acid ISOMER 2

ISOMER 1

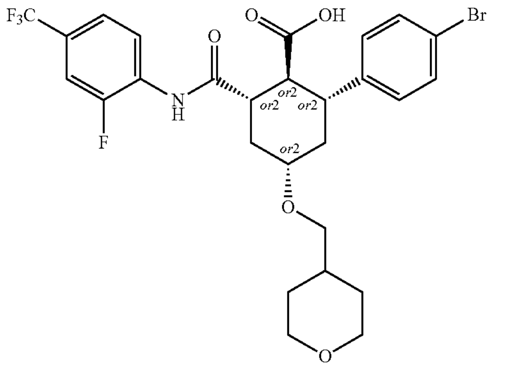

ISOMER 2

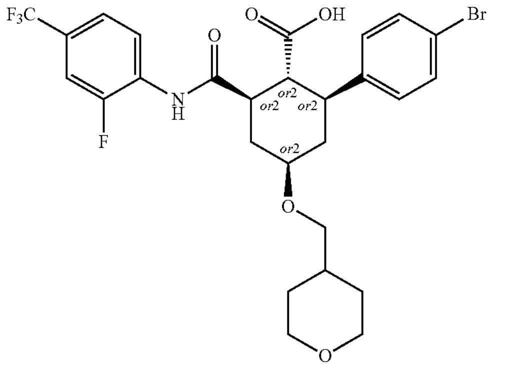

To a mixture of rac-benzyl (1R,2S,4R,6R)-2-(4-bromophenyl)-6-((2-fluoro-4-(trifluoromethyl)phenyl)carbamoyl)-4-((tetrahydro-2H-pyran-4-yl)methoxy)cyclohexane-1-carboxylate (0.750 g, 1.08 mmol) in DCM (8 mL) at 0° C. was added trichloroborane (1.624 mL, 1.624 mmol). The reaction was stirred at rt for 1 h, quenched with ice water, concentrated and subjected to reverse phase purification (10-100% MeCN in $H_2O$, 0.1% ammonium carbonate modifier) to afford rac-(1R,2S,4R,6R)-2-(4-bromophenyl)-6-((2-fluoro-4-(trifluoromethyl)phenyl)carbamoyl)-4-((tetrahydro-2H-pyran-4-yl)methoxy)cyclohexane-1-carboxylic acid (410 mg, 0.66 mmol, 61% yield) as a white solid. This racemic compound (620 mg) was purified by Chiral-Prep-SFC (Column: Chiralpak IA (250*30) mm; Mobile Phase A:$CO_2$, Mobile Phase B: IPA; Gradient: 35% B) to afford: the first-eluting isomer rel-(1R,2S,4R,6R)-2-(4-bromophenyl)-6-((2-fluoro-4-(trifluoromethyl)phenyl)carbamoyl)-4-((tetrahydro-2H-pyran-4-yl)methoxy)cyclohexane-1-carboxylic acid ISOMER 1 (270 mg, 0.35 mmol, 34% yield) as an off-white solid. $^1$H NMR (400 MHz, DMSO-$d_6$) δ 10.12 (s, 1H), 8.21 (t, J=8.3 Hz, 1H), 7.73 (dd, J=11.0, 2.0 Hz, 1H), 7.55 (d, J=9.0 Hz, 1H), 7.47 (d, J=8.5 Hz, 2H), 7.26 (d, J=8.5 Hz, 2H), 3.82 (dt, J=9.3, 2.4 Hz, 2H), 3.53-3.42 (m, 1H), 3.30-3.23 (m, 4H), 3.09-2.96 (m, 1H), 2.82-2.73 (m, 2H), 2.38-2.28 (m, 1H), 2.05 (d, J=12.0 Hz, 1H), 1.80-1.66 (m, 1H), 1.58-1.34 (m, 4H), 1.24-1.08 (m, 2H). ES-LCMS m/z 602.1 $[M+H]^+$.

and the second-eluting isomer rel-(1R,2S,4R,6R)-2-(4-bromophenyl)-6-((2-fluoro-4-(trifluoromethyl)phenyl)carbamoyl)-4-((tetrahydro-2H-pyran-4-yl)methoxy)cyclohexane-1-carboxylic acid ISOMER 2 (230 mg, 0.35 mmol, 34% yield) as an off-white solid. $^1$H NMR (400 MHz, DMSO-$d_6$) δ 10.15 (s, 1H), 8.21 (t, J=8.0 Hz, 1H), 7.74-7.68 (m, 1H), 7.54 (d, J=8.5 Hz, 1H), 7.46 (d, J=8.5 Hz, 2H), 7.25 (d, J=8.0 Hz, 2H), 3.81 (dd, J=11.0, 3.0 Hz, 2H), 3.50-3.42 (m, 1H), 3.30-3.20 (m, 4H), 3.08-2.97 (m, 1H), 2.79-2.71 (m, 2H), 2.36-2.26 (m, 1H), 2.04 (d, J=11.5 Hz, 1H), 1.77-1.66 (m, 1H), 1.59-1.37 (m, 4H), 1.17 (qd, J=12.2, 4.5 Hz, 2H). ES-LCMS m/z 600.0 $[M-H]^-$.

The following compound was synthesized in an analogous manner to the preparation described above (Intermediate 91), using the appropriate arylbromide:

| Int. | Structure/Name | $^1$H NMR | LCMS |
|---|---|---|---|
| 95 | 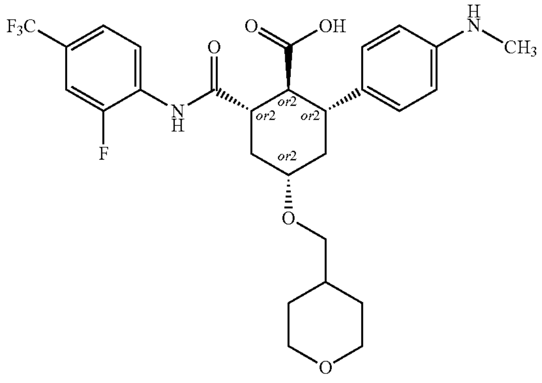 [SMILES: CNc1ccc([C@@H]2C[C@H](OCC3CCOCC3)C[C@H](C(=O)Nc3ccc(C(F)(F)F)cc3F)[C@H]2C(=O)O)cc1] ISOMER 1 rel-(1R,2R,4R,6S)-2-((2-fluoro-4-(trifluoromethyl)phenyl)carbamoyl)-6-(4-(methylamino)phenyl)-4-((tetrahydro-2H-pyran-4-yl)methoxy)cyclohexane-1-carboxylic acid ISOMER 1 | $^1$H NMR (400 MHz, DMSO-$d_6$) δ 11.72 (s, 1H), 10.14 (s, 1H), 8.20 (t, J = 8.3 Hz, 1H), 7.70 (d, J= 11.5 Hz, 1H), 7.54 ( d, J= 9.0 Hz, 1H), 6.95 (d, J = 8.5 Hz, 2H), 6.42 (d, J = 8.5 Hz, 2H), 5.46-5.37 (m, 1H), 3.85-3.76 (m, 2H), 3.48-3.37 (m, 1H), 3.28-3.21 (m, 4H), 3.03-2.98 (m, 1H), 2.62 (s, 3H), 2.59-2.56 (m, 2H), 2.30-2.23 (m, 1H), 2.03-1.95 (m, 1H), 1.75-1.67 (m, 1H), 1.58-1.50 (m, 2H), 1.46-1.32 (m, 2H), 1.26-1.07 (m, 2H) | ES-LCMS m/z 553.2 $[M + H]^+$. |

-continued

| Int. | Structure/Name | $^1$H NMR | LCMS |
|---|---|---|---|
| 96 | 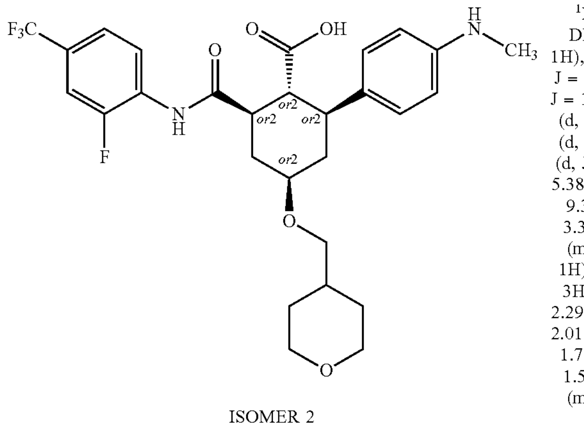 ISOMER 2 rel-(1R,2R,4R,6S)-2-((2-fluoro-4-(trifluoromethyl)phenyl)carbamoyl)-6-(4-(methylamino)phenyl)-4-((tetrahydro-2H-pyran-4-yl)methoxy)cyclohexane-1-carboxylic acid ISOMER 2 | $^1$H NMR (400 MHz, DMSO-$d_6$) δ 11.72 (s, 1H), 10.09 (s, 1H), 8.21 (t, J = 8.0 Hz, 1H), 7.72 (dd, J = 11.0, 2.0 Hz, 1H), 7.55 (d, J = 8.5 Hz, 1H), 6.97 (d, J = 8.5 Hz, 2H), 6.44 (d, J = 8.5 Hz, 2H), 5.46-5.38 (m, 1H), 3.82 (dt, J = 9.3, 2.4 Hz, 2H), 3.49-3.38 (m, 1H), 3.28-3.21 (m, 4H), 3.07-2.94 (m, 1H), 2.64 (d, J = 4.0 Hz, 3H), 2.62-2.53 (m, 2H), 2.29 ( d, J = 11.0 Hz, 1H), 2.01 ( d, J = 12.5 Hz, 1H), 1.76-1.66 (m, 1H), 1.59-1.52 (m, 2H), 1.48-1.36 (m, 2H), 1.23-1.09 (m, 2H) | ES-LCMS m/z 553.2 [M + H]$^+$. |

Intermediate 97: rel-(1R,2R,6S)-2-((2-fluoro-4-(trifluoromethyl)phenyl)carbamoyl)-4-oxo-6-(4-((N,1,2-trimethyl-1H-benzo[d]imidazole)-5-sulfonamido)phenyl)cyclohexane-1-carboxylic acid

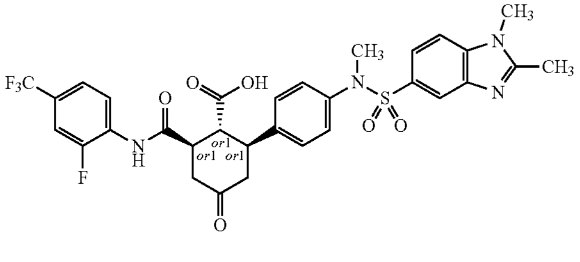 [SMILES: Cc1nc2cc(S(=O)(=O)N(C)c3ccc([C@H]4CC(=O)C[C@@H](C(=O)Nc5ccc(C(F)(F)F)cc5F)[C@@H]4C(=O)O)cc3)ccc2n1C]

To a mixture of rac-benzyl (1R,2R,6S)-2-((2-fluoro-4-(trifluoromethyl)phenyl)carbamoyl)-4-oxo-6-(4-((N,1,2-trimethyl-1H-benzo[d]imidazole)-5-sulfonamido)phenyl)cyclohexane-1-carboxylate Intermediate 46 and Intermediate 47, Step 2, (0.500 g, 0.666 mmol) in DCM (4 mL) 0° C. was added trichloroborane (0.999 mL, 0.999 mmol). The reaction was stirred at rt for 6 h, quenched with water (10 mL) and concentrated. Additional trichloroborane (0.999 mL, 0.999 mmol) was added. After 1 h, the reaction was quenched with ice water (15 mL), concentrated and subjected to reverse phase purification (0-100% MeCN in $H_2O$, with 0.1% ammonium bicarbonate modifier) to afford rel-(1R,2R,6S)-2-((2-fluoro-4-(trifluoromethyl)phenyl)carbamoyl)-4-oxo-6-(4-((N,1,2-trimethyl-1H-benzo[d]imidazole)-5-sulfonamido)phenyl)cyclohexane-1-carboxylic acid (0.350 g, 0.488 mmol, 73.3% yield) as an off-white solid. $^1$H NMR (400 MHz, DMSO-$d_6$) δ 10.69 (br s, 1H), 8.27 (t, J=8.3 Hz, 1H), 7.71 (dd, J=11.0, 2.0 Hz, 1H), 7.63 (d, J=8.5 Hz, 1H), 7.60-7.52 (m, 2H), 7.30-7.21 (m, 2H), 6.98 (d, J=8.5 Hz, 2H), 4.09 (d, J=2.0 Hz, 1H), 3.77 (s, 3H), 3.23-3.11 (m, 3H), 3.06 (s, 3H), 2.87 (t, J=13.5 Hz, 1H), 2.76 (t, J=13.8 Hz, 1H), 2.56 (s, 2H), 2.54 (s, 3H), 2.35-2.25 (in, 1H). ES-LCMS m/z 661.0 [M+H]$^+$.

The following compound was synthesized in an analogous manner to the preparation described above (Intermediate 80 and Intermediate 81, Step 5), using the appropriate alcohol:

| Int | Structure/Name | $^1$H NMR | LCMS |
|---|---|---|---|
| 98 | 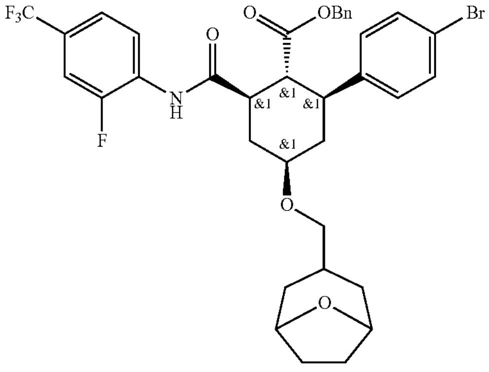 [SMILES: O=C(OCc1ccccc1)[C@@H]1[C@@H](c2ccc(Br)cc2)C[C@@H](OCC2CC3CCC(C2)O3)C[C@H]1C(=O)Nc1ccc(C(F)(F)F)cc1F]<br>rac-benzyl (1R,2S,4R,6R)-4-((8-oxabicyclo[3.2.1]octan-3-yl)methoxy)-2-(4-bromophenyl)-6-((2-fluoro-4-(trifluoromethyl)phenyl)carbamoyl)cyclohexane-1-carboxylate | $^1$H NMR (400 MHz, DMSO-$d_6$) δ 10.15 (s, 1H), 8.15 (t, J = 8.0 Hz, 1H), 7.73 (dd, J = 11.0, 1.5 Hz, 1H), 7.55 (d, J = 8.5 Hz, 1H), 7.45 (d, J = 8.5 Hz, 2H), 7.24 (d, J = 8.5 Hz, 2H), 7.20-7.13 (m, 3H), 6.83-6.76 (m, 2H), 4.73-4.63 (m, 2H), 4.25 (br s, 2H), 3.52-3.42 (m, 1H), 3.25 (dd, J = 6.5, 1.0 Hz, 2H), 3.15-3.07 (m, 1H), 2.95 (t, J = 11.3 Hz, 1H), 2.80 (td, J = 12.1, 2.8 Hz, 1H), 2.36 (d, J = 12.5 Hz, 1H), 2.04 (d, J = 12.5 Hz, 1H), 2.00-1.89 (m, 1H), 1.80-1.74 (m, 2H), 1.69-1.62 (m, 2H), 1.62-1.52 (m, 1H), 1.49-1.37 (m, 3H), 1.32-1.22 (m, 2H) | ES-LCMS m/z 716.2 $[M - H]^-$. |

The following compound was synthesized in an analogous manner to the preparation methods described herein using Intermediate 98.

| Int. | Structure/Name | $^1$H NMR | LCMS |
|---|---|---|---|
| 99 | 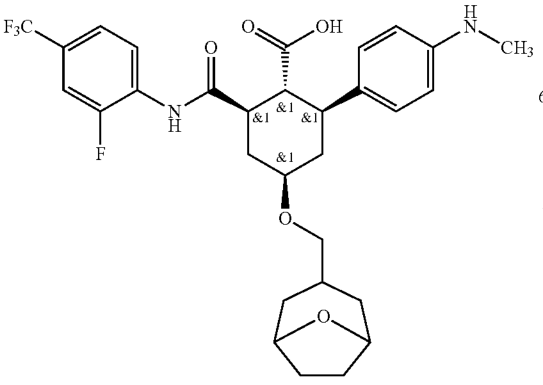<br>rac-(1R,2R,4R,6S)-4-((8-oxabicyclo[3.2.1]octan-3-yl)methoxy)-2-((2-fluoro-4-(trifluoromethyl)phenyl) carbamoyl)-6-(4-(methylamino)phenyl)cyclohexane-1-carboxylic acid | $^1$H NMR (400 MHz, DMSO-$d_6$) δ 10.73 (br s, 1H), 8.32 (t, J = 8.0 Hz, 1H), 7.65 (dd, J = 11.0, 1.5 Hz, 1H), 7.51 (d, J = 9.0 Hz, 1H), 6.93 (d, J = 8.5 Hz, 2H), 6.38 (d, J=8.5 Hz, 2H), 5.29 (d, J = 4.5 Hz, 1H), 4.25 (br s, 2H), 3.42-3.37 (m, 1H), 3.22 (dd, J = 6.3, 1.3 Hz, 2H), 2.85-2.72 (m, 1H), 2.65-2.57 (m, 4H), 2.21 (d, J = 12.0 Hz, 1H), 1.99-1.85 (m, 2H), 1.80-1.72 (m, 2H), 1.70-1.63 (m, 2H), 1.43 (d, J = 13.0 Hz, 2H), 1.34-1.20 (m, 4H). | ES-LCMS m/z 579.2 $[M + 1]^+$. |

Intermediate 100: 2-chloro-1-methyl-1H-benzo[d]imidazole-5-sulfonyl chloride

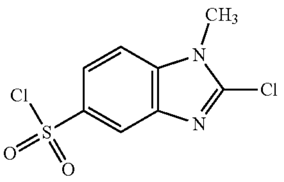

Step 1: 5-((4-methoxybenzyl)thio)-1-methyl-1H-benzo[d]imidazole

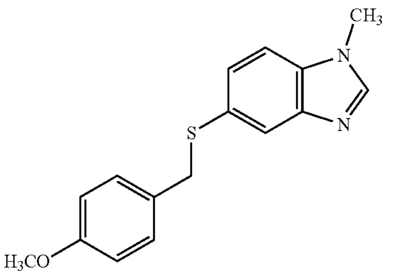 [SMILES: COc1ccc(CSc2ccc3c(c2)ncn3C)cc1]

A mixture of 5-bromo-1-methyl-1H-benzo[d]imidazole (1.000 g, 4.738 mmol) and N-ethyl-N-isopropylpropan-2-amine (612.4 mg, 4.738 mmol) in dioxane (12 mL) was degassed for 10 min, followed by the addition of (9,9-dimethyl-9H-xanthene-4,5-diyl)bis(diphenylphosphane) (2.742 g, 4.738 mmol), $Pd_2(dba)_3$ (4.339 g, 4.738 mmol) and (4-methoxyphenyl)methanethiol (730.7 mg, 4.738 mmol). The reaction was stirred at 100° C. for 16 h in a sealed tube and filtered through Celite bed, washing with EtOAc (20 mL). The filtrate was concentrated and subjected to normal phase purification (eluting with ethyl acetate in petroleum ether, 0-100% gradient) to afford 5-((4-methoxybenzyl)thio)-1-methyl-1H-benzo[d]imidazole (0.290 g, 623 μmol, 13.0% yield) as a pale-yellow solid. $^1H$ NMR (400 MHz, DMSO-$d_6$) δ 8.16 (s, 1H), 7.61 (d, J=1.0 Hz, 1H), 7.50 (d, J=8.5 Hz, 1H), 7.25 (dd, J=8.5, 1.5 Hz, 1H), 7.22-7.17 (m, 2H), 6.85-6.76 (m, 2H), 4.14 (s, 2H), 3.81 (s, 3H), 3.70 (s, 3H). ES-LCMS m/z 285.1 $[M+1]^+$.

Step 2: 2-chloro-5-((4-methoxybenzyl)thio)-1-methyl-1H-benzo[d]imidazole

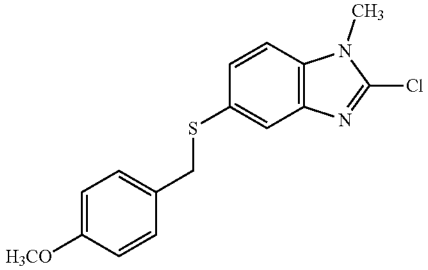 [SMILES: COc1ccc(CSc2ccc3c(c2)nc(Cl)n3C)cc1]

To a mixture of 5-((4-methoxybenzyl)thio)-1-methyl-1H-benzo[d]imidazole (250.0 mg, 879.1 μmol) in THF (4 mL) at −5° C. was add lithium bis(trimethylsilyl)amide (1M in THF, 1.05 mL, 1.05 mmol). After 10 min 1-chloropyrrolidine-2,5-dione (129.1 mg, 967.0 μmol) was added. After 2 h the reaction was concentrated under vacuum, taken up in EtOAc, washed with brine (50 mL), dried over sodium sulphate, concentrated and subjected to reverse phase purification (MeCN in $H_2O$, 0.1% formic acid modifier, 0-100% gradient) to afford 2-chloro-5-((4-methoxybenzyl)thio)-1-methyl-1H-benzo[d]imidazole (60.0 mg, 187 μmol, 21.0% yield) as a red solid. $^1H$ NMR (400 MHz, DMSO-$d_6$) δ 7.57-7.50 (m, 2H), 7.28 (dd, J=8.5, 2.0 Hz, 1H), 7.23-7.18 (m, 2H), 6.85-6.79 (m, 2H), 4.16 (s, 2H), 3.76 (s, 3H), 3.70 (s, 3H). ES-LCMS m/z 319.0 $[M+1]^+$.

Step 3: 2-chloro-1-methyl-1H-benzo[d]imidazole-5-sulfonyl chloride

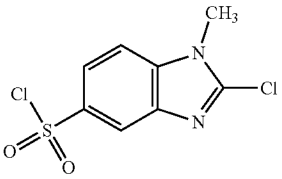

To a mixture of 2-chloro-5-((4-methoxybenzyl)thio)-1-methyl-1H-benzo[d]imidazole (40.00 mg, 125.5 μmol) in acetic acid (0.5 mL) was added N-chlorosuccinimide (67.01 mg, 501.9 μmol). After 1 h the reaction was diluted with water (10 mL) and extracted with ethyl acetate (3×15 mL). The combined organic layers were washed with brine (20 mL), dried over anhydrous sodium sulfate, filtered and concentrated under vacuum to afford crude 2-chloro-1-methyl-1H-benzo[d]imidazole-5-sulfonyl chloride (60 mg, 0.18 mmol, quantitative yield) as a brown gummy solid. $^1$HNMR not recorded. ES-LCMS m/z 265.0 $[M+1]^+$.

Intermediate 101 and Intermediate 102: rel-(1R,2S,6R)-2-(4-bromophenyl)-4,4-difluoro-6-((2-fluoro-4-(trifluoromethyl)phenyl)carbamoyl)cyclohexane-1-carboxylic acid ISOMER 1 and rel-(1R,2S,6R)-2-(4-bromophenyl)-4,4-difluoro-6-((2-fluoro-4-(trifluoromethyl)phenyl)carbamoyl)cyclohexane-1-carboxylic acid ISOMER 2

ISOMER 1

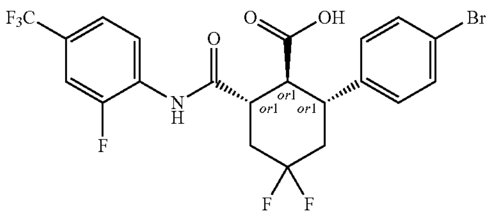

ISOMER 2

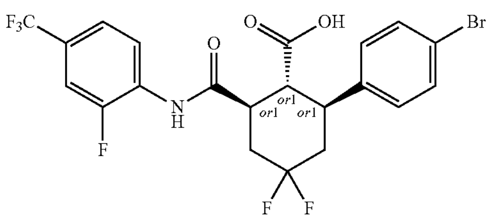

Step 1: rac-(3aR,7S,7aS)-7-(4-bromophenyl)-5,5-difluorohexahydroisobenzofuran-1(3H)-one

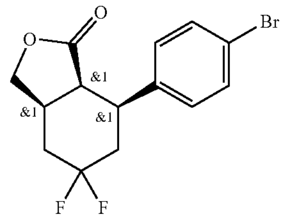 [SMILES: O=C1OC[C@@H]2CC(F)(F)C[C@H](c3ccc(Br)cc3)[C@H]12]

To a mixture of rac-(3aR,7S,7aS)-7-(4-bromophenyl)tetrahydroisobenzofuran-1,5(3H,4H)-dione Intermediate 8, Step 5 (2.000 g, 6.469 mmol) in DCM (20 mL) at 0° C. was added diethylaminosulfur trifluoride (2.086 g, 12.94 mmol), dropwise. The reaction was stirred at rt for 2 h, concentrated and subjected to normal phase purification (ethyl acetate in petroleum ether, 0-20% gradient) to afford rac-(3aR,7S,7aS)-7-(4-bromophenyl)-5,5-difluorohexahydroisobenzofuran-1(3H)-one (1.70 g, 5.13 mmol, 79.0% yield) as an off-white solid. $^1$H NMR (400 MHz, DMSO-$d_6$) δ 7.49 (d, J=8.5 Hz, 2H), 7.30 (d, J=8.5 Hz, 2H), 4.25 (ddd, J=8.9, 4.4, 2.8 Hz, 1H), 3.97 (d, J=9.0 Hz, 1H), 3.45-3.33 (m, 3H), 2.87 (dq, J=10.5, 6.0 Hz, 1H), 2.42-2.31 (m, 1H), 2.22-2.04 (m, 1H), 1.77-1.56 (m, 1H). ES-LCMS m/z No ionization.

Step 2: rac-(1R,2S,6R)-2-(4-bromophenyl)-4,4-difluoro-6-(hydroxymethyl)cyclohexane-1-carboxylic acid

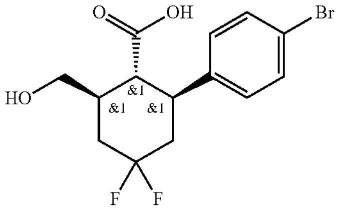 [SMILES: O=C(O)[C@H]1[C@H](CO)CC(F)(F)C[C@@H]1c1ccc(Br)cc1]

To a mixture of rac-(3aR,7S,7aS)-7-(4-bromophenyl)-5,5-difluorohexahydroisobenzofuran-1(3H)-one (2.400 g, 7.247 mmol) in methanol (25 mL) was added potassium hydroxide (2.033 g, 36.236 mmol). The reaction was stirred at 75° C. for 2 h, concentrated, acidified with 0.1 N HCl and extracted with ethyl acetate (3×50 ml). The organic layers were washed with brine (50 mL), dried over sodium sulphate and concentrated to give crude rac-(1R,2S,6R)-2-(4-bromophenyl)-4,4-difluoro-6-(hydroxymethyl)cyclohexane-1-carboxylic acid (2.20 g, 5.90 mmol, 82.0% yield) as an off-white solid. $^1$H NMR (400 MHz, DMSO-$d_6$) δ 12.10 (br s, 1H), 7.51-7.47 (m, 2H), 7.26 (d, J=8.5 Hz, 2H), 4.76 (br s, 1H), 3.52-3.20 (m, 4H), 3.03-2.87 (m, 1H), 2.31-2.19 (m, 1H), 2.14-2.03 (m, 1H), 1.97 (dd, J=7.0, 3.5 Hz, 1H), 1.90-1.73 (m, 1H). ES-LCMS m/z 349.0 $[M-1]^-$.

Step 3: rac-benzyl (1R,2S,6R)-2-(4-bromophenyl)-4,4-difluoro-6-(hydroxymethyl)cyclohexane-1-carboxylate

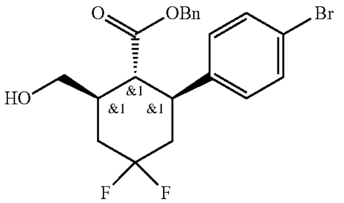 [SMILES: O=C(OCc1ccccc1)[C@H]1[C@H](CO)CC(F)(F)C[C@@H]1c1ccc(Br)cc1]

To a mixture of rac-(1R,2S,6R)-2-(4-bromophenyl)-4,4-difluoro-6-(hydroxymethyl)cyclohexane-1-carboxylic acid (2.200 g, 6.301 mmol) in DMF (20 mL) at 0° C. was added potassium carbonate (2.612 g, 18.90 mmol) followed by benzyl bromide (1.293 g, 7.561 mmol) dropwise. The reaction was stirred at rt for 2 h, quenched with cold water (10 ml) and extracted with ethyl acetate (3×50 mL). The organic phases were combined and washed with brine (20 ml), dried over anhydrous $Na_2SO_4$, concentrated, dissolved in DCM (10 mL) and purified over silica, eluting with 5-100% EtOAc in petroleum ether to afford rac-benzyl (1R,2S,6R)-2-(4-bromophenyl)-4,4-difluoro-6-(hydroxymethyl)cyclohexane-1-carboxylate (2.20 g, 4.50 mmol, 72.0% yield) as an off-white solid. $^1$H NMR (400 MHz, DMSO-$d_6$) δ 7.49-7.43 (m, 2H), 7.30-7.16 (m, 6H), 6.87 (dd, J=7.3, 2.3 Hz, 2H), 4.90 (d, J=12.5 Hz, 1H), 4.83-4.77 (m, 1H), 4.73 (d, J=13.0 Hz, 1H), 3.37 (dd, J=10.0, 4.5 Hz, 1H), 3.31-3.22 (m, 1H), 2.98 (td, J=12.0, 3.5 Hz, 1H), 2.69 (t, J=11.3 Hz, 1H), 2.35-2.16 (m, 2H), 2.16-2.01 (m, 2H). ES-LCMS m/z No ionization.

Step 4: rac-(1R,2R,3S)-2-((benzyloxy)carbonyl)-3-(4-bromophenyl)-5,5-difluorocyclohexane-1-carboxylic acid

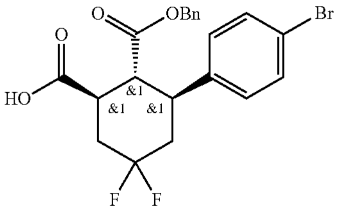 [SMILES: O=C(OCc1ccccc1)[C@@H]1[C@@H](c2ccc(Br)cc2)CC(F)(F)C[C@H]1C(=O)O]

To a mixture of rac-benzyl (1R,2S,6R)-2-(4-bromophenyl)-4,4-difluoro-6-(hydroxymethyl)cyclohexane-1-carboxylate (2.000 g, 4.553 mmol) in acetonitrile (20 mL) and water (10 mL) at 0° C. was added sodium metaperiodate (2.921 g, 13.66 mmol) and ruthenium trichloride (94.43 mg, 455.3 μmol). The reaction was stirred at rt for 1 h, diluted with water (50 mL) and extracted with EtOAc (100 mL×3). The combined EtOAc layers were washed with water (50 mL×3) and brine (100 mL), dried over sodium sulphate, concentrated, dissolved in THF (5 mL) and purified by reverse phase chromatography, eluting with 10-55% MeCN in water (0.1% of formic acid) to afford rac-(1R,2R,3S)-2-((benzyloxy)carbonyl)-3-(4-bromophenyl)-5,5-difluorocyclohexane-1-carboxylic acid (1.10 g, 2.10 mmol, 46.0% yield) as an off-white solid. $^1$H NMR (400 MHz, DMSO-$d_6$) δ 12.90 (br s, 1H), 7.50-7.46 (m, 2H), 7.29-7.23 (m, 5H), 6.90-6.81 (m, 2H), 4.81-4.67 (m, 2H), 3.02 (d, J=11.0 Hz, 1H), 2.98-2.82 (m, 2H), 2.44-2.35 (m, 1H), 2.31-2.03 (m, 3H). ES-LCMS m/z 451.0 $[M-1]^-$.

Step 5: rac-benzyl (1R,2S,6R)-2-(4-bromophenyl)-6-(chlorocarbonyl)-4,4-difluorocyclohexane-1-carboxylate

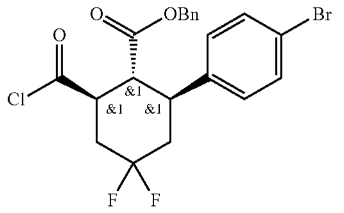 [SMILES: O=C(OCc1ccccc1)[C@@H]1[C@@H](c2ccc(Br)cc2)CC(F)(F)C[C@H]1C(=O)Cl]

To a mixture of rac-(1R,2R,3S)-2-((benzyloxy)carbonyl)-3-(4-bromophenyl)-5,5-difluorocyclohexane-1-carboxylic acid (1.100 g, 2.427 mmol) in DCM (10 mL) at 0° C. was added thionyl chloride (2.887 g, 24.27 mmol), dropwise. The reaction was stirred at 30° C. for 16 h and concentrated to afford crude rac-benzyl (1R,2S,6R)-2-(4-bromophenyl)-6-(chlorocarbonyl)-4,4-difluorocyclohexane-1-carboxylate (1.2000 g, 2.0 mmol, 84% yield) as a black oil. $^1$HNMR was not recorded. ES-LCMS m/z 377.0 $[M+1]^+$ (aliquot was quenched with MeOH, methyl ester minus benzyl mass reported).

Step 6: rac-benzyl (1R,2S,6R)-2-(4-bromophenyl)-4,4-difluoro-6-((2-fluoro-4-(trifluoromethyl)phenyl)carbamoyl)cyclohexane-1-carboxylate

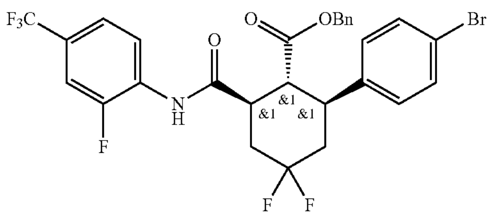 [SMILES: O=C(OCc1ccccc1)[C@@H]1[C@@H](c2ccc(Br)cc2)CC(F)(F)C[C@H]1C(=O)Nc1ccc(C(F)(F)F)cc1F]

To a mixture of rac-benzyl (1R,2S,6R)-2-(4-bromophenyl)-6-(chlorocarbonyl)-4,4-difluorocyclohexane-1-carboxylate (1.20 g, 2.54 mmol) in DCM (10 mL) at 0° C. was added pyridine (1.01 g, 12.7 mmol) and 2-fluoro-4-(trifluoromethyl)aniline (501 mg, 2.80 mmol), dropwise. The reaction was stirred at rt for 16 h, concentrated, dissolved in THF (5 mL) and purified by reverse phase chromatography, eluting with 10-55% MeCN in water (10 mM ammonium bicarbonate), to afford rac-benzyl (1R,2S,6R)-2-(4-bromophenyl)-4,4-difluoro-6-((2-fluoro-4-(trifluoromethyl)phenyl)carbamoyl)cyclohexane-1-carboxylate (0.500 g, 0.800 mmol, 31.0% yield) as an off-white solid. $^1$H NMR (400 MHz, DMSO-$d_6$) δ 10.40 (s, 1H), 8.09 (t, J=8.0 Hz, 1H), 7.73 (dd, J=11.0, 2.0 Hz, 1H), 7.59-7.53 (m, 1H), 7.49 (d, J=8.5 Hz, 2H), 7.31 (d, J=8.5 Hz, 2H), 7.21-7.12 (m, 3H), 6.83-6.78 (m, 2H), 4.78-4.65 (m, 2H), 3.44-3.34 (m, 1H), 3.20 (t, J=11.5 Hz, 1H), 3.00 (td, J=12.4, 3.3 Hz, 1H), 2.48-2.37 (m, 2H), 2.27-2.09 (m, 2H). ES-LCMS m/z 612.0 $[M-1]^-$.

Step 7: rel-(1R,2S,6R)-2-(4-bromophenyl)-4,4-difluoro-6-((2-fluoro-4-(trifluoromethyl)phenyl)carbamoyl)cyclohexane-1-carboxylic acid ISOMER 1 and rel-(1R,2S,6R)-2-(4-bromophenyl)-4,4-difluoro-6-((2-fluoro-4-(trifluoromethyl)phenyl)carbamoyl)cyclohexane-1-carboxylic acid ISOMER 2

ISOMER 1

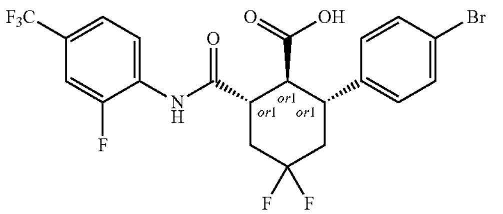

ISOMER 2

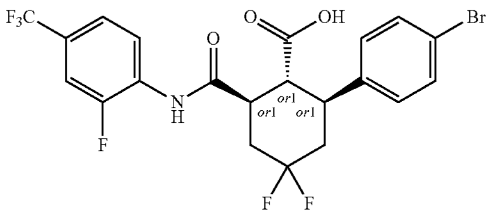

To a mixture of rac-benzyl (1R,2S,6R)-2-(4-bromophenyl)-4,4-difluoro-6-((2-fluoro-4-(trifluoromethyl)phenyl)carbamoyl)cyclohexane-1-carboxylate (450.0 mg, 732.5 μmol) in DCM (5 mL) at 0° C. was added boron trichloride (1 M, 1.46 mL, 1.46 mmol), dropwise. The reaction was stirred at 35° C. for 1 h, concentrated, dissolved in THF (5 mL) and purified via reverse phase chromatography, eluting with 10-55% MeCN in water (10 mM ammonium bicarbonate), to afford rac-(1R,2S,6R)-2-(4-bromophenyl)-4,4-difluoro-6-((2-fluoro-4-(trifluoromethyl)phenyl)carbamoyl)cyclohexane-1-carboxylic acid (0.300 g, 572 μmol, 78.0% yield) as an off-white solid The racemic compound was separated by Chiral-Prep-SFC (Column: Chiralpak IG 250×20 mm, 5 μm; Mobile Phase $CO_2$: IPA 65:35) to afford:

First-eluting peak rel-(1R,2S,6R)-2-(4-bromophenyl)-4,4-difluoro-6-((2-fluoro-4-(trifluoromethyl)phenyl)carbamoyl)cyclohexane-1-carboxylic acid ISOMER 1 (0.110 g, 210 μmol, 37.0% yield) as a white solid. $^1$H NMR (400 MHz, DMSO-$d_6$) δ 12.08 (br s, 1H), 10.38 (br s, 1H), 8.16 (t, J=8.3 Hz, 1H), 7.72 (dd, J=10.8, 1.8 Hz, 1H), 7.56 (d, J=8.5 Hz, 1H), 7.50 (d, J=8.5 Hz, 2H), 7.32 (d, J=8.5 Hz, 2H), 3.26 (d, J=6.0 Hz, 1H), 3.02-2.92 (m, 2H), 2.46-2.35 (m, 2H), 2.26-2.05 (m, 2H). ES-LCMS m/z 524.0 $[M-1]^-$.

Second-eluting peak rel-(1R,2S,6R)-2-(4-bromophenyl)-4,4-difluoro-6-((2-fluoro-4-(trifluoromethyl)phenyl)carbamoyl)cyclohexane-1-carboxylic acid ISOMER 2 (0.120 g, 210 μmol, 36.0% yield) as a white solid. $^1$H NMR (400 MHz, DMSO-$d_6$) δ 12.09 (br s, 1H), 10.37 (br s, 1H), 8.16 (t, J=8.0 Hz, 1H), 7.72 (dd, J=10.8, 1.8 Hz, 1H), 7.56 (d, J=9.0 Hz, 1H), 7.50 (d, J=8.5 Hz, 2H), 7.32 (d, J=8.5 Hz, 2H), 3.28-3.22 (in, 1H), 3.01-2.93 (m, 2H), 2.45-2.34 (m, 2H), 2.23-2.03 (in, 2H). ES-LCMS m/z 522.0 $[M-2]^-$.

The following compounds were synthesized in an analogous manner to the preparation described above (Intermediate 91), using the appropriate arylbromide:

| Int. | Structure/Name | $^1$H NMR | LCMS |
|---|---|---|---|
| 103 | 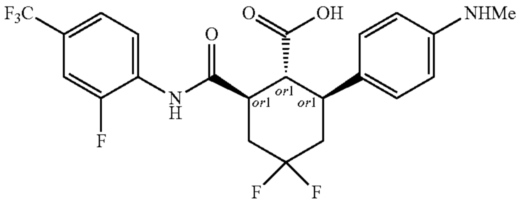 [SMILES: CNc1ccc([C@H]2CC(F)(F)C[C@@H](C(=O)Nc3ccc(C(F)(F)F)cc3F)[C@@H]2C(=O)O)cc1] ISOMER 1 rel-(1R,2R,6S)-4,4-difluoro-2-((2-fluoro-4-(trifluoromethyl)phenyl)carbamoyl)-6-(4-(methylamino)phenyl)cyclohexane-1-carboxylic acid ISOMER 1 | $^1$H NMR (400 MHz, DMSO-$d_6$) δ 12.16 (br s, 1H), 10.34 (br s, 1H), 8.16 (t, J = 8.0 Hz, 1H), 7.71 (dd, J = 11.0, 1.5 Hz, 1H), 7.58-7.53 (m, 1H), 7.01 (d, J = 9.0 Hz, 2H), 6.44 (d, J = 8.5 Hz, 2H), 5.49 (d, J = 5.0 Hz, 1H), 3.23 (br s, 1H), 2.87-2.79 (m, 2H), 2.64 (s, 3H), 2.38-2.24 (m, 2H), 2.16-1.94 (m, 2H) | ES-LCMS m/z 473.2 $[M-H]^-$. |
| 104 | 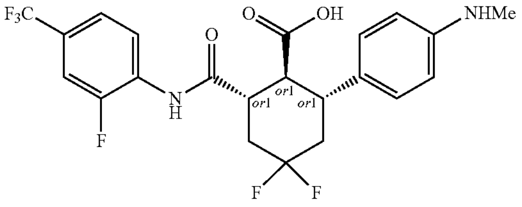 [SMILES: CNc1ccc([C@@H]2CC(F)(F)C[C@H](C(=O)Nc3ccc(C(F)(F)F)cc3F)[C@H]2C(=O)O)cc1] ISOMER 2 rel-(1R,2R,6S)-4,4-difluoro-2-((2-fluoro-4-(trifluoromethyl)phenyl)carbamoyl)-6-(4-(methylamino)phenyl)cyclohexane-1-carboxylic acid ISOMER 2 | $^1$H NMR (400 MHz, METHANOL-$d_4$) δ 8.20 (t, J = 8.0 Hz, 1H), 7.52-7.42 (m, 2H), 7.10-7.04 (m, 2H), 6.59 (d, J= 8.5 Hz, 2H), 3.27-3.20 (m, 1H), 3.10-3.00 (m, 1H), 2.97-2.86 (m, 1H), 2.74 (s, 3H), 2.47-2.34 (m, 1H), 2.30-2.05 (m, 3H) | ES-LCMS m/z 472.6 $[M-H]^-$. |

The following compound was synthesized in an analogous manner to the preparation described above (Intermediate 8, Step 11), using the relevant alkyl tosylate as the alkylating agent:

| Int. | Structure/Name | $^1$H NMR | LCMS |
|---|---|---|---|
| 105 | 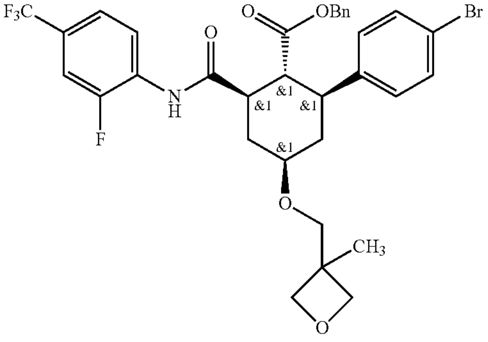 [SMILES: CC1(CO[C@@H]2C[C@H](c3ccc(Br)cc3)[C@@H](C(=O)OCc3ccccc3)[C@H](C(=O)Nc3ccc(C(F)(F)F)cc3F)C2)COC1] rac-benzyl (1R,2S,4R,6R)-2-(4-bromophenyl)-6-((2-fluoro-4-(trifluoromethyl)phenyl)carbamoyl)-4-((3-methyloxetan-3-yl)methoxy)cyclohexane-1-carboxylate | $^1$H NMR (400 MHz, DMSO-$d_6$) δ 10.18 (s, 1H), 8.16 (t, J= 8.3 Hz, 1H), 7.73 (dd, J = 10.8, 1.8 Hz, 1H), 7.55 (d, J= 8.0 Hz, 1H), 7.45 (d, J = 8.5 Hz, 2H), 7.28-7.24 (m, 2H), 7.21-7.14 (m, 3H), 6.82-6.76 (m, 2H), 4.76-4.64 (m, 2H), 4.33 (d, J = 6.0 Hz, 2H), 4.18 (d, J = 5.5 Hz, 2H), 3.54 (d, J = 4.5 Hz, 3H), 3.19-3.08 (m, 1H), 2.97 (t, J = 11.3 Hz, 1H), 2.83 (td, J= 12.0, 3.0 Hz, 1H), 2.45-2.38 (m, 1H), 2.10 (d, J = 12.0 Hz, 1H), 1.73-1.59 (m, 1H), 1.56-1.44 (m, 1H), 1.21 (s, 3H) | ES-LCMS m/z 676.2 $[M-H]^-$. |

Intermediate 106: rac-(1R,2R,4R,6S)-2-((2-fluoro-4-(trifluoromethyl)phenyl)carbamoyl)-6-(4-(methylamino)phenyl)-4-((3-methyloxetan-3-yl)methoxy)cyclohexane-1-carboxylic acid

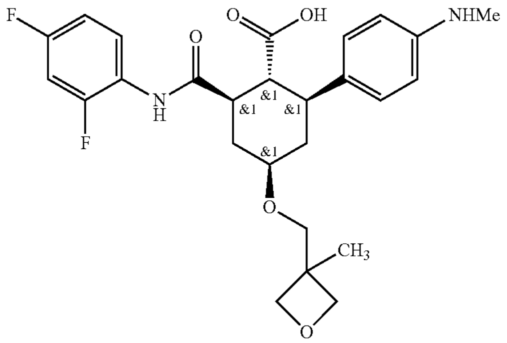 [SMILES: CNc1ccc([C@H]2C[C@@H](OCC3(C)COC3)C[C@@H](C(=O)Nc3ccc(F)cc3F)[C@@H]2C(=O)O)cc1]

Step 1: rac-(1R,2S,4R,6R)-2-(4-bromophenyl)-4-(3-chloro-2-(hydroxymethyl)-2-methylpropoxy)-6-((2-fluoro-4-(trifluoromethyl)phenyl)carbamoyl)cyclohexane-1-carboxylic acid

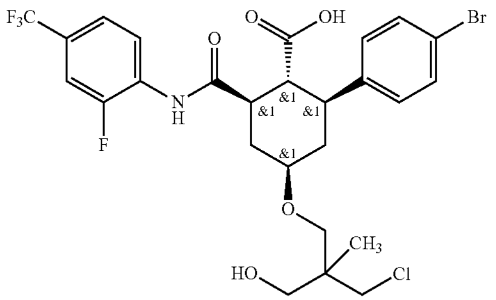 [SMILES: CC(CO)(CCl)CO[C@@H]1C[C@H](c2ccc(Br)cc2)[C@@H](C(=O)O)[C@H](C(=O)Nc2ccc(C(F)(F)F)cc2F)C1]

To a mixture of rac-benzyl (1R,2S,4R,6R)-2-(4-bromophenyl)-6-((2-fluoro-4-(trifluoromethyl)phenyl)carbamoyl)-4-((3-methyloxetan-3-yl)methoxy)cyclohexane-1-carboxylate (810.0 mg, 1.194 mmol) in dichloromethane (14 mL) at −78° C. was added boron trichloride (1 M, 0.575 mL, 575 μmol). After 1 h the reaction was concentrated and subjected to reverse phase purification (MeCN in $H_2O$, 0.1% ammonium bicarbonate modifier, 0-100% gradient) to afford rac-(1R,2S,4R,6R)-2-(4-bromophenyl)-4-(3-chloro-2-(hydroxymethyl)-2-methylpropoxy)-6-((2-fluoro-4-(trifluoromethyl)phenyl)carbamoyl)cyclohexane-1-carboxylic acid (0.400 g, 0.560 mmol, 47.0% yield) as a white solid. $^1H$ NMR (400 MHz, DMSO-$d_6$) δ 11.86 (s, 1H), 10.12 (s, 1H), 8.21 (t, J=8.3 Hz, 1H), 7.72 (dd, J=11.0, 1.5 Hz, 1H), 7.55 (d, J=9.0 Hz, 1H), 7.47 (d, J=8.5 Hz, 2H), 7.26 (d, J=8.5 Hz, 2H), 4.64 (t, J=5.3 Hz, 1H), 3.52 (s, 3H), 3.35-3.32 (m, 1H), 3.27 (d, J=5.0 Hz, 3H), 3.07-3.00 (m, 1H), 2.82-2.75 (m, 2H), 2.35 (br s, 1H), 2.04 (d, J=12.0 Hz, 1H), 1.62-1.48 (m, 1H), 1.46-1.37 (m, 1H), 0.87 (s, 3H). ES-LCMS m/z 622.0 $[M-1]^-$.

Step 2: rac-(1R,2S,4R,6R)-2-(4-bromophenyl)-6-((2-fluoro-4-(trifluoromethyl)phenyl)carbamoyl)-4-((3-methyloxetan-3-yl)methoxy)cyclohexane-1-carboxylic acid

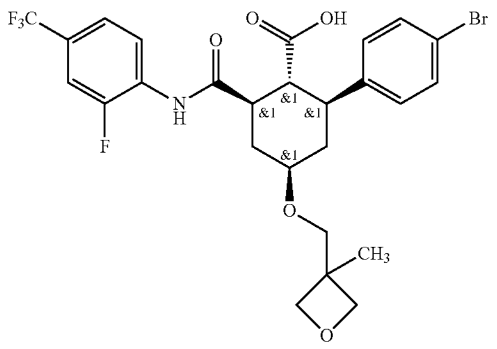

To a mixture of rac-(1R,2S,4R,6R)-2-(4-bromophenyl)-4-(3-chloro-2-(hydroxymethyl)-2-methylpropoxy)-6-((2-fluoro-4-(trifluoromethyl)phenyl)carbamoyl)cyclohexane-1-carboxylic acid (400.0 mg, 640.2 μmol) in DMSO (4 mL) at 0° C. was added sodium hydride (51.21 mg, 60% wt, 1.280 mmol), slowly. The reaction was stirred at RT for 2 h, quenched with ice water (30 mL) and extracted with EtOAc (50 mL×3). The combined organics were washed with brine (20 mL), dried over sodium sulphate, concentrated and subjected to reverse phase purification (MeCN in $H_2O$, 0.1% ammonium bicarbonate modifier, 0-100% gradient) to afford rac-(1R,2S,4R,6R)-2-(4-bromophenyl)-6-((2-fluoro-4-(trifluoromethyl)phenyl)carbamoyl)-4-((3-methyloxetan-3-yl)methoxy)cyclohexane-1-carboxylic acid (0.32 g, 0.47 mmol, 74% yield) as a white solid. $^1H$ NMR (400 MHz, DMSO-$d_6$) δ 11.87 (br s, 1H), 10.12 (s, 1H), 8.21 (t, J=8.0 Hz, 1H), 7.72 (dd, J=11.0, 2.0 Hz, 1H), 7.55 (d, J=8.5 Hz, 1H), 7.47 (d, J=8.5 Hz, 3H), 7.27 (d, J=8.5 Hz, 2H), 4.33 (d, J=5.5 Hz, 2H), 4.18 (d, J=6.0 Hz, 2H), 3.54 (d, J=4.5 Hz, 2H), 3.12-3.01 (m, 1H), 2.79 (dd, J=7.8, 2.8 Hz, 2H), 2.37 (d, J=12.0 Hz, 1H), 2.13-2.09 (m, 1H), 1.62-1.43 (m, 2H), 1.21 (s, 3H). ES-LCMS m/z 587.5 $[M-H]^-$.

Step 3: rac-(1R,2R,4R,6S)-2-((2-fluoro-4-(trifluoromethyl)phenyl)carbamoyl)-6-(4-(methylamino)phenyl)-4-((3-methyloxetan-3-yl)methoxy)cyclohexane-1-carboxylic acid

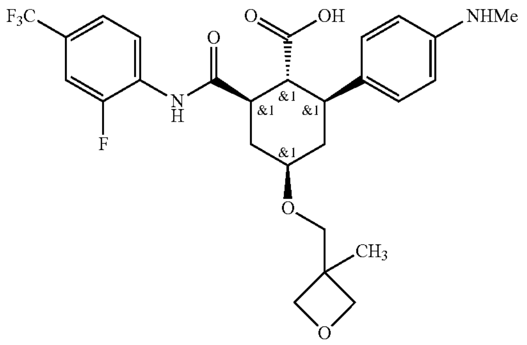 [SMILES: CNc1ccc([C@H]2C[C@@H](OCC3(C)COC3)C[C@@H](C(=O)Nc3ccc(C(F)(F)F)cc3F)[C@@H]2C(=O)O)cc1]

To a mixture of rac-(1R,2S,4R,6R)-2-(4-bromophenyl)-6-((2-fluoro-4-(trifluoromethyl)phenyl)carbamoyl)-4-((3- methyloxetan-3-yl)methoxy)cyclohexane-1-carboxylic acid (300.0 mg, 509.9 μmol) in dioxane (3 mL) was added sodium 2-methylpropan-2-olate (122.5 mg, 1.275 mmol) and tBuXPhos Pd G3 (40.50 mg, 50.99 μmol). The reaction was degassed for 5 min, and methylamine (2 M, 5.099 mL, 10.20 mmol) was added dropwise. The mixture was stirred at 100° C. for 1 h, evaporated and purified via reverse phase chromatography (10-100% MeCN in water, 0.1% formic acid) to afford rac-(1R,2R,4R,6S)-2-((2-fluoro-4-(trifluoromethyl)phenyl)carbamoyl)-6-(4-(methylamino)phenyl)-4-((3-methyloxetan-3-yl)methoxy)cyclohexane-1-carboxylic acid (0.17 g, 0.27 mmol, 52% yield) as a white solid. $^1$H NMR (400 MHz, DMSO-$d_6$) δ 11.76 (br s, 1H), 10.08 (s, 1H), 8.24-8.17 (m, 1H), 7.71 (dd, J=11.0, 1.5 Hz, 1H), 7.55 (d, J=8.0 Hz, 1H), 7.01-6.94 (m, 2H), 6.43 (d, J=8.5 Hz, 2H), 5.43 (br s, 1H), 4.33 (d, J=5.5 Hz, 2H), 4.18 (d, J=5.5 Hz, 2H), 3.53 (d, J=3.5 Hz, 3H), 3.02 (d, J=9.5 Hz, 1H), 2.66-2.57 (m, 5H), 2.33 (dt, J=3.6, 1.9 Hz, 1H), 2.07-1.99 (m, 1H), 1.57-1.39 (m, 2H), 1.21 (s, 3H). ES-LCMS m/z 537.2 $[M-H]^-$.

Intermediate 107: rac-(1R,2S,6R)-2-(4-bromo-3-fluorophenyl)-6-((2-fluoro-4-(trifluoromethyl)phenyl)carbamoyl)cyclohexane-1-carboxylic acid

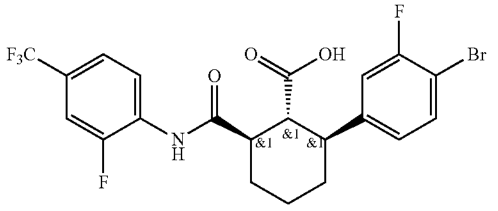 [SMILES: O=C(O)[C@@H]1[C@@H](c2ccc(Br)c(F)c2)CCC[C@H]1C(=O)Nc1ccc(C(F)(F)F)cc1F]

Step 1: (E)-3-(4-bromo-3-fluorophenyl)acrylaldehyde

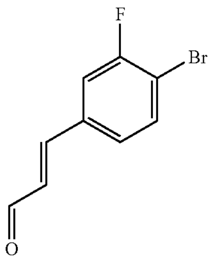 [SMILES: O=C/C=C/c1ccc(Br)c(F)c1]

A mixture of 4-bromo-3-fluorobenzaldehyde (10.00 g, 49.26 mmol) and 2-(triphenyl-15-phosphaneylidene)acetaldehyde (17.99 g, 59.11 mmol) in DMSO (100 mL) was heated to 110° C. for 16 h, diluted with water (100 mL) and extracted with EtOAc (250 mL). The organic layer was washed with brine (10 mL), dried over sodium sulfate, concentrated and subjected to normal phase chromatography, eluting with 10% EtOAc in petroleum ether to afford (E)-3-(4-bromo-3-fluorophenyl)acrylaldehyde (9.50 g, 41.5 mmol, 84.0% yield) as an off-white solid. $^1$H NMR (400 MHz, DMSO-$d_6$) δ 9.68 (d, J=7.5 Hz, 1H), 7.89-7.78 (m, 2H), 7.72 (d, J=16.0 Hz, 1H), 7.54 (dd, J=8.0, 2.0 Hz, 1H), 6.97 (dd, J=16.0, 7.5 Hz, 1H). ES-LCMS m/z [M+H]*. No ionization for desired mass.

Step 2: (E)-1-bromo-4-(buta-1,3-dien-1-yl)-2-fluorobenzene

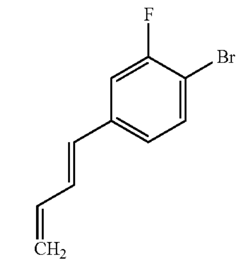

To a mixture of methyltriphenylphosphonium bromide (17.78 g, 49.71 mmol) in THF (100 mL) at −10° C. was added 2-methylpropan-2-olate potassium (1 M, 49.771 mL, 49.77 mmol), dropwise. After 30 min (E)-3-(4-bromo-3-fluorophenyl)acrylaldehyde (9.500 g, 41.48 mmol) in THF (100 mL) was added. The reaction was stirred at RT for 16 h, quenched with ice and extracted with EtOAc (200 mL). The organic layer was washed with water (50 mL) and brine (50 mL), dried over sodium sulfate, concentrated and subjected to normal phase chromatography, eluting with petroleum ether to afford (E)-1-bromo-4-(buta-1,3-dien-1-yl)-2-fluorobenzene (9.00 g, 39.6 mmol, 96.0% yield) as a colorless oil. $^1$H NMR (400 MHz, DMSO-$d_6$) δ 7.67-7.59 (m, 1H), 7.54 (dd, J=10.8, 1.8 Hz, 1H), 7.26 (dd, J=8.5, 2.0 Hz, 1H), 7.03 (dd, J=15.5, 10.5 Hz, 1H), 6.67-6.43 (m, 2H), 5.46-5.39 (m, 1H), 5.29-5.22 (m, 1H). ES-LCMS m/z $[M+H]^+$. No ionization for desired mass.

Step 3: rac-dimethyl (1R,3S)-4'-bromo-3'-fluoro-1,2,3,4-tetrahydro-[1,1'-biphenyl]-2,3-dicarboxylate

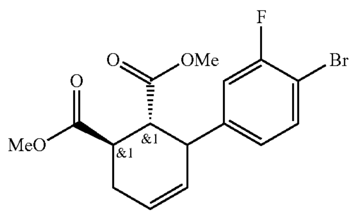 [SMILES: COC(=O)[C@@H]1C(c2ccc(Br)c(F)c2)C=CC[C@H]1C(=O)OC]

A mixture of (E)-1-bromo-4-(buta-1,3-dien-1-yl)-2-fluorobenzene (7.000 g, 30.83 mmol) and dimethyl fumarate (6.665 g, 46.24 mmol) was heated to 110° C. for 16 h and subjected to reverse phase purification (0-100% MeCN in $H_2O$, 0.1% formic acid modifier) to afford rac-dimethyl (1R,3S)-4'-bromo-3'-fluoro-1,2,3,4-tetrahydro-[1,1'-biphenyl]-2,3-dicarboxylate (8.4 g, 21 mmol, 70% yield) as a colorless oil. $^1$H NMR (400 MHz, DMSO-$d_6$) δ7.63 (t, J=8.0 Hz, 2H), 7.18 (dd, J=10.0, 2.0 Hz, 1H), 7.06 (dd, J=10.0, 2.0 Hz, 1H), 6.95 (dd, J=8.5, 2.0 Hz, 1H), 6.89 (dd, J=8.0, 2.0 Hz, 1H), 6.02-5.94 (m, 1H), 5.89-5.83 (m, 1H), 5.76-5.71 (m, 1H), 5.53 (dd, J=10.0, 1.5 Hz, 1H), 3.95-3.89 (m, 1H), 3.64-3.63 (m, 1H), 3.60 (s, 3H), 3.54 (s, 3H), 3.46 (s, 3H), 3.41 (s, 3H), 3.14 (dd, J=12.3, 6.3 Hz, 1H), 2.93 (td, J=11.4, 5.8 Hz, 1H), 2.80-2.66 (m, 2H), 2.59-2.55 (m, 1H), 2.43-2.37 (m, 1H), 2.37-2.28 (m, 1H), 2.15-2.04 (m, 1H). ES-LCMS m/z $[M+H]^+$. No ionization for desired mass.

Step 4: rac-dimethyl (1R,3S)-3-(4-bromo-3-fluorophenyl)cyclohexane-1,2-dicarboxylate

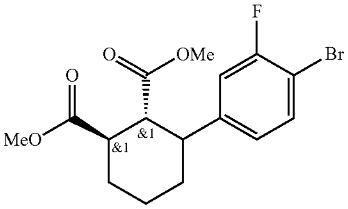 [SMILES: COC(=O)[C@@H]1C(c2ccc(Br)c(F)c2)CCC[C@H]1C(=O)OC]

To a mixture of rac-dimethyl (1R,3S)-4'-bromo-3'-fluoro-1,2,3,4-tetrahydro-[1,1'-biphenyl]-2,3-dicarboxylate (2.000 g, 5.388 mmol) in methanol (20 mL) under $N_2$ was added platinum (2.102 g, 10% wt, 1.078 mmol). The reaction was stirred at RT under hydrogen atmosphere (bladder pressure) for 8 h, filtered through Celite bed (washing with methanol [400 mL]), concentrated and subjected to reverse phase purification (0-100% MeCN in $H_2O$, 0.1% formic acid modifier) to afford rac-dimethyl (1R,3S)-3-(4-bromo-3-fluorophenyl)cyclohexane-1,2-dicarboxylate (1.4 g, 3.2 mmol, 58% yield) as a pale yellow gum. $^1$H NMR (400 MHz, DMSO-$d_6$) δ 7.63-7.57 (m, 1H), 7.37-7.14 (m, 2H), 7.11-6.91 (m, 3H), 3.65 (s, 3H), 3.57 (s, 3H), 3.37 (d, J=8.5 Hz, 3H), 3.31-3.30 (m, 2H), 3.26-3.19 (m, 3H), 3.02 (dt, J=7.3, 3.4 Hz, 1H), 2.84-2.61 (m, 3H), 2.02-1.89 (m, 3H), 1.85-1.70 (m, 2H), 1.73-1.62 (m, 4H), 1.53-1.48 (m, 3H). ES-LCMS m/z [M+H]$^+$. No ionization for desired mass.

Step 5: rac-(1R,2R,3S)-3-(4-bromo-3-fluorophenyl)-2-(methoxycarbonyl)cyclohexane-1-carboxylic acid

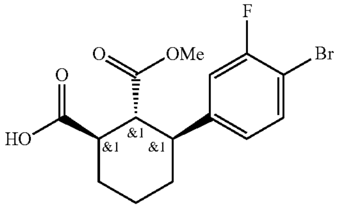 [SMILES: COC(=O)[C@@H]1[C@@H](c2ccc(Br)c(F)c2)CCC[C@H]1C(=O)O]

To a mixture of rac-dimethyl (1R,3S)-3-(4-bromo-3-fluorophenyl)cyclohexane-1,2-dicarboxylate (3.450 g, 9.244 mmol) in methanol (20 mL) was added sodium methoxide (3.5 mL, 25% wt, 9.2 mmol). The reaction was stirred at 50° C. for 4 h, acidified with 1.5 N HCl and subjected to reverse-phase chromatography (0-100% MeCN in $H_2O$, 0.1% formic acid modifier) to afford rac-(1R,2R,3S)-3-(4-bromo-3-fluorophenyl)-2-(methoxycarbonyl)cyclohexane-1-carboxylic acid (1.5 g, 2.9 mmol, 31% yield) as white solid. $^1$H NMR (400 MHz, DMSO-$d_6$) δ 7.60-7.52 (m, 1H), 7.36-7.19 (m, 1H), 6.99-6.97 (m, 1H), 3.21 (s, 3H), 3.19-3.17 (m, 1H), 2.64-2.59 (m, 2H), 2.03-2.01 (m, 1H), 1.82-1.79 (m, 1H), 1.71-1.68 (m, 1H), 1.56-1.46 (m, 1H), 1.41-1.38 (m, 2H). ES-LCMS m/z 357.0 [M−H]$^-$.

Step 6: rac-methyl (1R,2S,6R)-2-(4-bromo-3-fluorophenyl)-6-(chlorocarbonyl)cyclohexane-1-carboxylate

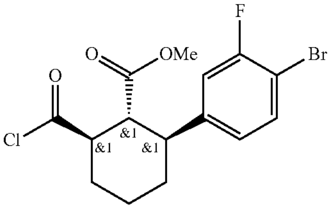 [SMILES: COC(=O)[C@@H]1[C@@H](c2ccc(Br)c(F)c2)CCC[C@H]1C(=O)Cl]

To a mixture of rac-(1R,2R,3S)-3-(4-bromo-3-fluorophenyl)-2-(methoxycarbonyl)cyclohexane-1-carboxylic acid (1.500 g, 4.176 mmol) in DCM (15 mL) at 0° C. was added thionyl chloride (1.524 mL, 20.88 mmol). The reaction was stirred at RT for 2 h and concentrated to afford crude rac-methyl (1R,2S,6R)-2-(4-bromo-3-fluorophenyl)-6-(chlorocarbonyl)cyclohexane-1-carboxylate (1.5 g, 2.8 mmol, 67% yield) as an off-white solid, which was used without further purification. ES-LCMS m/z 375.0 [M−H]$^-$.

Step 7: rac-methyl (1R,2S,6R)-2-(4-bromo-3-fluorophenyl)-6-((2-fluoro-4-(trifluoromethyl)phenyl)carbamoyl)cyclohexane-1-carboxylate

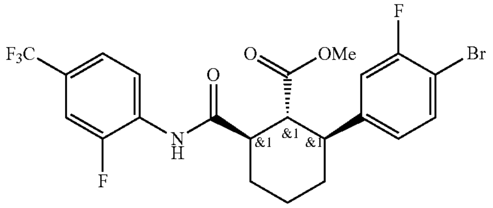

To a solution of rac-methyl (1R,2S,6R)-2-(4-bromo-3-fluorophenyl)-6-(chlorocarbonyl)cyclohexane-1-carboxylate (1.400 g, 3.707 mmol) in DCM (14 mL) at 0° C. was added 2-fluoro-4-(trifluoromethyl)aniline (796.9 mg, 4.449 mmol) and pyridine (2.933 g, 37.07 mmol). The reaction was stirred at RT for 1 h, quenched with water (30 mL) and extracted with ethyl acetate (200 mL). The organic layer was washed with brine (50 mL), dried over sodium sulphate, concentrated and subjected to reverse phase purification (0-100% MeCN in $H_2O$, 0.1% ABC modifier) to afford rac-methyl (1R,2S,6R)-2-(4-bromo-3-fluorophenyl)-6-((2-fluoro-4-(trifluoromethyl)phenyl)carbamoyl)cyclohexane-1-carboxylate (0.200 g, 380 μmol, 10.0% yield) as a white solid. $^1$H NMR (400 MHz, DMSO-$d_6$) δ 10.13 (s, 1H), 8.14 (t, J=8.0 Hz, 1H), 7.72 (dd, J=11.0, 2.0 Hz, 1H), 7.63-7.49 (m, 2H), 7.35 (dd, J=10.3, 1.8 Hz, 1H), 7.04 (dd, J=8.0, 2.0 Hz, 1H), 3.21 (s, 3H), 3.06-2.95 (m, 1H), 2.93-2.86 (m, 1H), 2.75 (td, J=11.6, 3.3 Hz, 1H), 2.09-1.98 (m, 1H), 1.89 (dd, J=9.3, 2.8 Hz, 1H), 1.79-1.76 (m, 1H), 1.70-1.67 (m, 1H), 1.57-1.52 (m, 2H). ES-LCMS m/z 518.0 [M−H]$^-$.

Step 8: rac-(1R,2S,6R)-2-(4-bromo-3-fluorophenyl)-6-((2-fluoro-4-(trifluoromethyl)phenyl)carbamoyl) cyclohexane-1-carboxylic acid

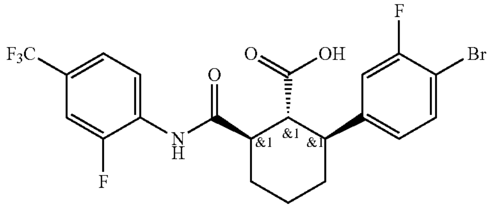 [SMILES: O=C(O)[C@@H]1[C@@H](c2ccc(Br)c(F)c2)CCC[C@H]1C(=O)Nc1ccc(C(F)(F)F)cc1F]

To a mixture of rac-methyl (1R,2S,6R)-2-(4-bromo-3-fluorophenyl)-6-((2-fluoro-4-(trifluoromethyl)phenyl)carbamoyl)cyclohexane-1-carboxylate (200.0 mg, 384.4 μmol) in DCM (2 mL) at 0° C. was added $BBr_3$ (192.6 mg, 768.8 μmol). The reaction was stirred at RT for 8 h, concentrated and subjected to reverse phase purification (0-100% MeCN in $H_2O$, 0.1% ABC modifier) to afford rac-(1R,2S,6R)-2-(4-bromo-3-fluorophenyl)-6-((2-fluoro-4-(trifluoromethyl) phenyl)carbamoyl)cyclohexane-1-carboxylic acid (0.100 g, 194 μmol, 51.0% yield) as a white solid. $^1$H NMR (400 MHz, DMSO-$d_6$) δ 11.85 (s, 1H), 8.20 (t, J=8.0 Hz, 1H), 7.72 (dd, J=11.0, 2.0 Hz, 1H), 7.63-7.52 (m, 2H), 7.35 (dd, J=10.5, 2.0 Hz, 1H), 7.08 (dd, J=8.5, 2.0 Hz, 1H), 3.05-2.95 (m, 1H), 2.86-2.79 (m, 1H), 2.77-2.70 (m, 1H), 2.02 (d, J=9.0 Hz, 1H), 1.91-1.85 (m, 1H), 1.79-1.72 (m, 1H), 1.66-1.46 (m, 3H). ES-LCMS m/z 504.0 $[M-H]^-$.

The following compound was synthesized in an analogous manner to the preparation described above (Intermediate 91), using the appropriate arylbromide:

| Int. | Structure/Name | $^1$H NMR | LCMS |
|---|---|---|---|
| 108 | 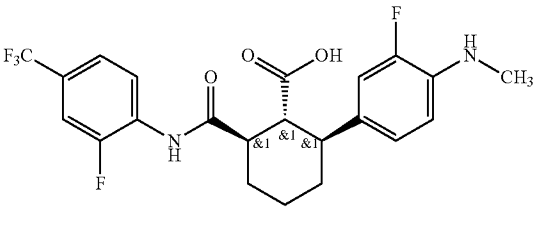 [SMILES: CNc1ccc([C@H]2CCC[C@@H](C(=O)Nc3ccc(C(F)(F)F)cc3F)[C@@H]2C(=O)O)cc1F] rac-(1R,2S,6R)-2-(3-fluoro-4-(methylamino)phenyl)-6-((2-fluoro-4-(trifluoromethyl)phenyl)carbamoyl)cyclohexane-1-carboxylic acid | $^1$H NMR (400 MHz, DMSO-$d_6$) δ 10.06 (s, 1H), 8.19 (t, J = 8.0 Hz, 1H), 7.70 (dd, J = 11.0, 1.5 Hz, 1H), 7.54 (d, J = 9.0 Hz, 1H), 6.90 (dd, J = 13.3, 1.8 Hz, 1H), 6.83 (dd, J = 8.0, 1.5 Hz, 1H), 6.52 (t, J = 9.0 Hz, 1H), 5.31 (dd, J = 5.0, 1.5 Hz, 1H), 3.01-2.89 (m, 1H), 2.67 (d, J = 5.0 Hz, 3H), 2.55-2.53(m, 2H), 2.02-1.90 (m, 1H), 1.88-1.78 (m, 1H), 1.76-1.64 (m, 1H), 1.52-1.49 (m, 3H) | ES-LCMS m/z 455.0 $[M-H]^-$. |

Intermediate 109: rac-methyl (1R,2S,3R,6R)-6-(chlorocarbonyl)-3-ethoxy-2-(4-((N,1,2-trimethyl-1H-benzo[d]imidazole)-5-sulfonamido)phenyl)cyclohexane-1-carboxylate

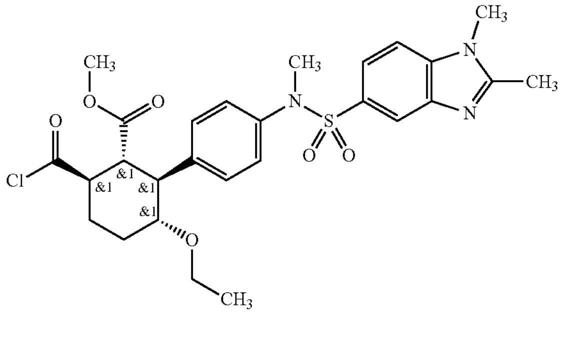 [SMILES: CCO[C@@H]1CC[C@@H](C(=O)Cl)[C@H](C(=O)OC)[C@H]1c1ccc(N(C)S(=O)(=O)c2ccc3c(c2)nc(C)n3C)cc1]

Step 1: rac-dimethyl (1R,2R,3S,4R)-4-ethoxy-3-(4-((N,1,2-trimethyl-1H-benzo[d]imidazole)-5-sulfonamido)phenyl)cyclohexane-1,2-dicarboxylate

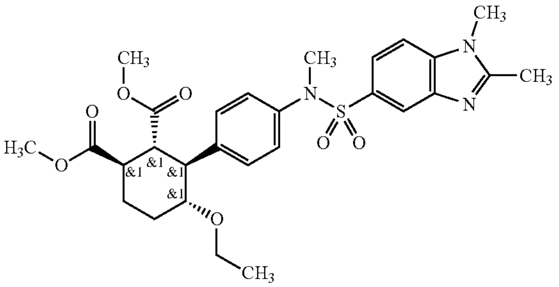

To a mixture of rac-dimethyl (1R,2R,3S)-4-oxo-3-(4-((N,1,2-trimethyl-1H-benzo[d]imidazole)-5-sulfonamido)phenyl)cyclohexane-1,2-dicarboxylate Intermediate 55, Step 6 (2.00 g, 3.79 mmol) in acetonitrile (20 mL) at 0° C. was added ethanol (873 mg, 19.0 mmol) and chlorodimethylsilane (3.59 g, 37.9 mmol). The reaction was stirred at 60° C. for 16 h, quenched with 10% sodium bicarbonate solution (100 mL) and extracted with 10% methanol in DCM (500 mL). The organic layer was washed with brine (50 mL), dried over sodium sulphate, concentrated and purified by reverse-phase chromatography, eluting with 0-100% acetonitrile in water (0.1% formic acid) to afford rac-dimethyl (1R,2R,3S,4R)-4-ethoxy-3-(4-((N,1,2-trimethyl-1H-benzo[d]imidazole)-5-sulfonamido)phenyl)cyclohexane-1,2-dicarboxylate (0.55 g, 0.98 mmol, 26%). $^1$H NMR (400 MHz, DMSO-$d_6$) δ 7.60 (d, J=8.5 Hz, 1H), 7.55 (d, J=1.5 Hz, 1H), 7.24 (dd, J=8.5, 1.5 Hz, 1H), 7.14 (d, J=8.5 Hz, 2H), 6.94 (d, J=8.5 Hz, 2H), 3.77 (s, 3H), 3.57 (s, 3H), 3.50 (td, J=10.5, 4.5 Hz, 1H), 3.24 (s, 3H), 3.09 (s, 3H), 2.93 (dq, J=9.5, 7.0 Hz, 1H), 2.83 (d, J=11.5 Hz, 1H), 2.73-2.64 (m, 1H), 2.55 (s, 3H), 2.45 (dt, J=3.6, 1.9 Hz, 2H), 2.18-2.10 (m, 1H), 2.06-1.98 (m, 1H), 1.69-1.54 (m, 1H), 1.44-1.31 (m, 1H), 0.77 (t, J=7.0 Hz, 3H). ES-LCMS m/z 558.0 [M+H]$^+$.

Step 2: rac-(1R,2R,3S,4R)-4-ethoxy-2-(methoxycarbonyl)-3-(4-((N,1,2-trimethyl-1H-benzo[d]imidazole)-5-sulfonamido)phenyl)cyclohexane-1-carboxylic acid

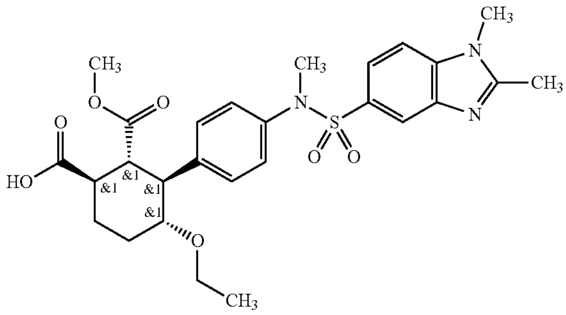 [SMILES: CCO[C@@H]1CC[C@@H](C(=O)O)[C@H](C(=O)OC)[C@H]1c1ccc(N(C)S(=O)(=O)c2ccc3c(c2)nc(C)n3C)cc1]

In two separate reactions, to a mixture of rac-dimethyl (1R,2R,3S,4R)-4-ethoxy-3-(4-((N,1,2-trimethyl-1H-benzo[d]imidazole)-5-sulfonamido)phenyl)cyclohexane-1,2-dicarboxylate (0.450 g, 807 μmol and 0.100 g, 179 μmol) in THF (2.5 mL and 0.5 mL), water (2.5 mL and 0.5 mL) and methanol (1.25 mL and 0.25 mL) at 0° C. was added LiOH (19.3 mg, 807 μmol and 4.30 mg, 179 μmol). The reactions were stirred at rt for 2 h, combined, concentrated and acidified with 1.5N HCl. The resulting solid was collected by filtration and dried under vacuum to afford rac-(1R,2R,3S,4R)-4-ethoxy-2-(methoxycarbonyl)-3-(4-((N,1,2-trimethyl-1H-benzo[d]imidazole)-5-sulfonamido)phenyl)cyclohexane-1-carboxylic acid (0.55 g, 1.0 mmol) as a white solid. $^1$H NMR (400 MHz, DMSO-$d_6$) δ 7.82 (d, J=8.5 Hz, 1H), 7.74 (s, 1H), 7.37 (dd, J=8.5, 1.5 Hz, 1H), 7.22 (d, J=8.5 Hz, 2H), 6.96 (d, J=8.5 Hz, 2H), 3.87 (s, 3H), 3.48-3.39 (m, 3H), 3.23 (s, 3H), 3.13 (s, 3H), 2.97 (dd, J=9.5, 7.0 Hz, 1H), 2.85 (dd, J=12.0, 2.0 Hz, 1H), 2.70 (s, 3H), 2.61 (td, J=11.8, 4.0 Hz, 1H), 2.02 (dd, J=13.8, 2.8 Hz, 1H), 1.83-1.51 (m, 3H), 0.96 (t, J=6.8 Hz, 3H). ES-LCMS m/z 544.2 [M+H]$^+$.

Step 3: rac-methyl (1R,2S,3R,6R)-6-(chlorocarbonyl)-3-ethoxy-2-(4-((N,1,2-trimethyl-1H-benzo[d]imidazole)-5-sulfonamido)phenyl)cyclohexane-1-carboxylate

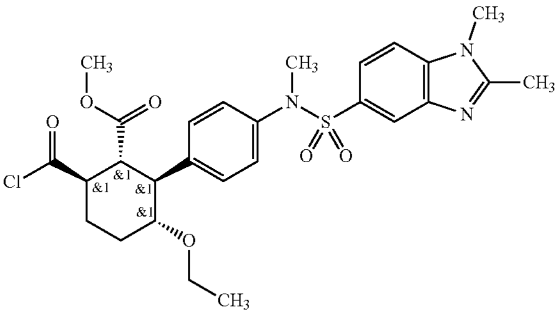 [SMILES: CCO[C@@H]1CC[C@@H](C(=O)Cl)[C@H](C(=O)OC)[C@H]1c1ccc(N(C)S(=O)(=O)c2ccc3c(c2)nc(C)n3C)cc1]

To a mixture of rac-(1R,2R,3S,4R)-4-ethoxy-2-(methoxycarbonyl)-3-(4-((N,1,2-trimethyl-1H-benzo[d]imidazole)-5-sulfonamido)phenyl)cyclohexane-1-carboxylic acid (0.450 g, 828 μmol) in DCM (5 mL) at 0° C. was added thionyl chloride (302 μL, 4.14 mmol). The reaction was stirred at RT for 2 h and concentrated to afford crude rac-methyl (1R,2S,3R,6R)-6-(chlorocarbonyl)-3-ethoxy-2-(4-((N,1,2-trimethyl-1H-benzo[d]imidazole)-5-sulfonamido)phenyl)cyclohexane-1-carboxylate (0.450 g, 765 μmol, 92.0%) as an off-white solid. ES-LCMS m/z 557.7 [M+H]$^+$, quenched with methanol and observed methyl ester mass.

Intermediate 110: 2-(hydroxymethyl)-1-methyl-1H-benzo[d]imidazole-5-sulfonyl chloride

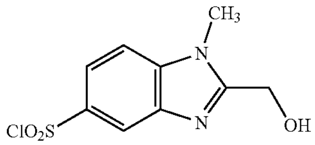

Step-1: methyl 5-bromo-1-methyl-1H-benzo[d]imidazole-2-carboxylate

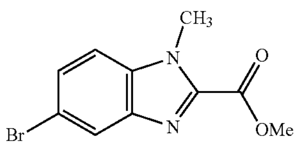

To a solution of 4-bromo-N1-methylbenzene-1,2-diamine (4.000 g, 19.89 mmol), in 1,2-dichloroethane (40 mL), stirred under nitrogen at rt was added methyl 2,2-dichloro-2-methoxyacetate (5.162 g, 29.84 mmol). The reaction was stirred at 80° C. for 16 h, concentrated and subjected to reverse phase purification (MeCN in $H_2O$, 0.1% formic acid modifier, 40-60% gradient) to afford methyl 5-bromo-1-methyl-1H-benzo[d]imidazole-2-carboxylate (2.1 g, 7.6 mmol, 38% yield) as a syrupy liquid. $^1$H NMR (400 MHz, DMSO-$d_6$) δ 7.99 (d, J=2.0 Hz, 1H), 7.73 (d, J=8.5 Hz, 1H), 7.60-7.55 (m, 1H), 4.08 (s, 3H), 3.93 (s, 3H). ES-LCMS m/z 271.0 $[M+1]^+$.

Step-2: (5-bromo-1-methyl-1H-benzo[d]imidazol-2-yl)methanol

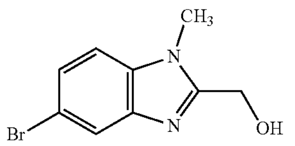

To a mixture of methyl 5-bromo-1-methyl-1H-benzo[d]imidazole-2-carboxylate (1.000 g, 3.716 mmol) in THF (10 mL) at 0° C. was added DIBAL-H (1M in THF, 7.43 mL, 7.43 mmol). The reaction mixture was allowed to stir at rt for 16 h, quenched with 10% sodium potassium tartrate (10 mL) and stirred for 1 h. The reaction was concentrated, subjected to reverse phase purification (MeCN in $H_2O$, 0.1% formic acid modifier, 40-60% gradient) to afford (5-bromo-1-methyl-1H-benzo[d]imidazol-2-yl)methanol (0.41 g, 1.5 mmol, 41% yield) as an orange-red solid. $^1$H NMR (300 MHz, DMSO-$d_6$) δ 7.77 (d, J=1.8 Hz, 1H), 7.53 (d, J=8.6 Hz, 1H), 7.38 (dd, J=8.6, 1.8 Hz, 1H), 5.63 (t, J=5.7 Hz, 1H), 4.71 (d, J=6.1 Hz, 2H), 3.33 (s, 3H). ES-LCMS m/z 242.9 $[M+1]^+$.

Step-3: 5-bromo-2-(((tert-butyldimethylsilyl)oxy)methyl)-1-methyl-1H-benzo[d]imidazole

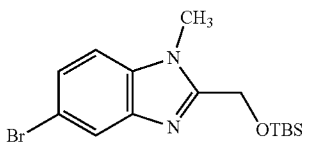 [SMILES: Cn1c(CO[Si](C)(C)C(C)(C)C)nc2cc(Br)ccc21]

To a mixture of (5-bromo-1-methyl-1H-benzo[d]imidazol-2-yl)methanol (460.0 mg, 1.908 mmol) in DCM (5 mL) at 0° C. was added imidazole (194.8 mg, 2.862 mmol) and TBDMS-Cl (575.2 mg, 3.816 mmol). The reaction was stirred at rt for 16 h, quenched with water and extracted with ethyl acetate (2×100 mL). The ethyl acetate layer was washed with brine (50 mL), dried over anhydrous sodium sulfate, filtered concentrated and subjected to normal phase purification (ethyl acetate in petroleum ether, 10-50% gradient) to afford 5-bromo-2-(((tert-butyldimethylsilyl)oxy)methyl)-1-methyl-1H-benzo[d]imidazole (0.350 g, 961 μmol, 50.0% yield) as an off-white solid. $^1$H NMR (400 MHz, DMSO-$d_6$) δ 7.81 (d, J=2.0 Hz, 1H), 7.55 (d, J=9.0 Hz, 1H), 7.43-7.37 (m, 1H), 4.92 (s, 2H), 3.82 (s, 3H), 0.86 (s, 9H), 0.06 (s, 6H). ES-LCMS m/z 355.0 $[M+1]^+$.

Step-4: 2-(((tert-butyldimethylsilyl)oxy)methyl)-5-((4-methoxybenzyl)thio)-1-methyl-1H-benzo[d]imidazole

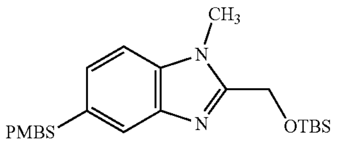

To a mixture of 5-bromo-2-(((tert-butyldimethylsilyl)oxy)methyl)-1-methyl-1H-benzo[d]imidazole (200.0 mg, 562.8 μmol) in dioxane (2 mL) was added DIPEA (363.7 mg, 2.814 mmol). The reaction was purged with nitrogen for 10 minutes, and (4-methoxyphenyl)methanethiol (434.0 mg, 2.814 mmol), $Pd_2(dba)_3$ (103.1 mg, 112.6 μmol) and Xantphos (32.57 mg, 56.28 μmol) were added. The mixture was heated to 100° C. for 16 h, filtered through Celite and washed with ethyl acetate (50 mL). The ethyl acetate layer was washed with water (60 mL), dried over anhydrous sodium sulfate, filtered, concentrated and subjected to normal phase purification (ethyl acetate in petroleum ether, 10-50% gradient) to afford 2-(((tert-butyldimethylsilyl)oxy)methyl)-5-((4-methoxybenzyl)thio)-1-methyl-1H-benzo[d]imidazole (0.15 g, 0.31 mmol, 55% yield) as an off-white solid. $^1$H NMR (400 MHz, DMSO-$d_6$) δ 7.57 (d, J=1.0 Hz, 1H), 7.48 (d, J=8.0 Hz, 1H), 7.24 (dd, J=8.3, 1.8 Hz, 1H), 7.18 (d, J=8.5 Hz, 2H), 6.81 (d, J=9.0 Hz, 2H), 4.90 (s, 2H), 4.13 (s, 2H), 3.80 (s, 3H), 3.70 (s, 3H), 0.86 (s, 9H), 0.06 (s, 6H). ES-LCMS m/z 429.1 $[M+H]^+$.

Step-5: 2-(hydroxymethyl)-1-methyl-1H-benzo[d]imidazole-5-sulfonyl chloride

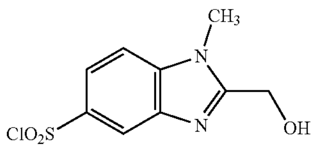 [SMILES: Cn1c(CO)nc2cc(S(=O)(=O)Cl)ccc21]

To a mixture of 2-(((tert-butyldimethylsilyl)oxy)methyl)-5-((4-methoxybenzyl)thio)-1-methyl-1H-benzo[d]imidazole (100.0 mg, 233.3 μmol) in acetic acid (1 mL) and water (0.2 mL) at 0° C. was added NCS (124.6 mg, 933.1 μmol), portion wise. The reaction was stirred at rt for 16 h, concentrated under high vacuum to remove acetic acid and water, and triturated with EtOAc (10 mL) to afford crude 2-(hydroxymethyl)-1-methyl-1H-benzo[d]imidazole-5-sulfonyl chloride (0.050 g, 0.15 mmol, 66% yield) as a yellow solid, which was used without further purification. $^1$HNMR not recorded. ES-LCMS m/z 261.0 $[M+H]^+$.

The following compounds were synthesized in an analogous manner to the preparation described above (Intermediate 107), using the appropriate p-bromobenzaldehyde, followed by chiral separation of the final product.

| Int. | Structure/Name | $^1$H NMR | LCMS |
|---|---|---|---|
| 111 | 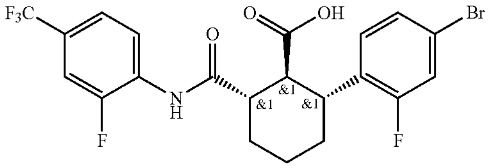 [SMILES: O=C(O)[C@@H]1[C@@H](C(=O)Nc2ccc(C(F)(F)F)cc2F)CCC[C@H]1c1ccc(Br)cc1F] ISOMER 1 rel-(1R,2S,6R)-2-(4-bromo-2-fluorophenyl)-6-((2-fluoro-4-(trifluoromethyl)phenyl)carbamoyl)cyclohexane-1-carboxylic acid ISOMER 1 | $^1$H NMR (400 MHz, DMSO-$d_6$) δ 10.23 (br s, 1H), 8.28 (t, J = 8.3 Hz, 1H), 7.67 (dd, J = 11.0, 1.5 Hz, 1H), 7.55-7.50 (m, 1H), 7.41-7.34 (m, 2H), 7.33-7.29 (m, 1H), 3.06 (dt, J = 12.9, 6.3 Hz, 1H), 3.02-2.88 (m, 2H), 2.78-2.70 (m, 1H), 1.96 (d, J = 10.0 Hz, 1H), 1.84 (d, J = 5.5 Hz, 1H), 1.74-1.66 (m, 1H), 1.60-1.42 (m, 3H) | ES-LCMS m/z 504.0 $[M - H]^-$. |
| 112 | 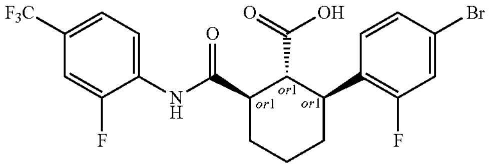 [SMILES: O=C(O)[C@@H]1[C@@H](c2ccc(Br)cc2F)CCC[C@H]1C(=O)Nc1ccc(C(F)(F)F)cc1F] ISOMER 2 rel-(1R,2S,6R)-2-(4-bromo-2-fluorophenyl)-6-((2-fluoro-4-(trifluoromethyl)phenyl) carbamoyl)cyclohexane-1-carboxylic acid ISOMER 2 | $^1$H NMR (400 MHz, DMSO-$d_6$) δ 10.36 (br s, 1H), 8.28 (t, J = 8.0 Hz, 1H), 7.68 (dd, J = 11.0, 2.0 Hz, 1H), 7.52 (d, J = 8.5 Hz, 1H), 7.41-7.29 (m, 3H), 3.08-3.02 (m, 1H), 2.99-2.86 (m, 2H), 2.76-2.70 (m, 1H), 1.97 (d, J = 9.5 Hz, 1H), 1.87-1.80 (m, 1H), 1.70 (d, J = 10.0 Hz, 1H), 1.56-1.45 (m, 3H) | ES-LCMS m/z 504.0 $[M - H]^-$. |

The following compounds were synthesized in an analogous manner to the preparation described above (intermediate 91), using the appropriate arylbromide:

| Int. | Structure/Name | $^1$H NMR | LCMS |
|---|---|---|---|
| 113 | 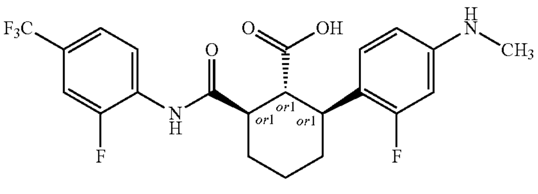 [SMILES: CNc1ccc([C@H]2CCC[C@@H](C(=O)Nc3ccc(C(F)(F)F)cc3F)[C@@H]2C(=O)O)c(F)c1] ISOMER 1 rel-(1R,2S,6R)-2-(2-fluoro-4-(methylamino)phenyl)-6-((2-fluoro-4-(trifluoromethyl)phenyl)carbamoyl)cyclohexane-1-carboxylic acid ISOMER 1 | $^1$H NMR (400 MHz, DMSO-$d_6$) δ 10.17 (br s, 1H), 8.22 (t, J = 8.0 Hz, 1H), 7.70 (dd, J = 11.3, 1.8 Hz, 1H), 7.57-7.50 (m, 1H), 7.02 (t, J = 8.5 Hz, 1H), 6.28 (dd, J = 8.3, 2.3 Hz, 1H), 6.17 (dd, J = 13.8, 2.3 Hz, 1H), 5.73 (d, J = 4.5 Hz, 1H), 2.94 (br s, 1H), 2.86-2.73 (m, 2H), 2.63 (d, J = 5.0 Hz, 3H), 2.05-1.93 (m, 1H), 1.84 (br s, 1H), 1.68 (d, J = 11.0 Hz, 1H), 1.57-1.41 (m, 3H) | ES-LCMS m/z 455.0 $[M - H]^-$. |
| 114 | 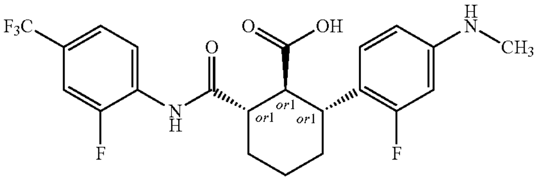 [SMILES: CNc1ccc([C@@H]2CCC[C@H](C(=O)Nc3ccc(C(F)(F)F)cc3F)[C@H]2C(=O)O)c(F)c1] ISOMER 2 rel-(1R,2S,6R)-2-(2-fluoro-4-(methylamino)phenyl)-6-((2-fluoro-4-(trifluoromethyl)phenyl)carbamoyl)cyclohexane-1-carboxylic acid ISOMER 2 | $^1$H NMR (400 MHz, DMSO-$d_6$) δ 11.71 (s, 1H), 10.06 (s, 1H), 8.20 (t, J = 8.3 Hz, 1H), 7.71 (dd, J = 11.0, 2.0 Hz, 1H), 7.54 (d, J = 8.0 Hz, 1H), 7.02 (t, J = 8.5 Hz, 1H), 6.29 (dd, J = 8.5, 2.5 Hz, 1H), 6.18 (dd, J = 13.5, 2.5 Hz, 1H), 5.76 (d, J = 5.0 Hz, 1H), 2.96 (d, J = 9.0 Hz, 1H), 2.87-2.77 (m, 2H), 2.63 (d, J = 5.0 Hz, 3H), 2.03-1.94 (m, 1H), 1.84 (dd, J = 4.3, 3.3 Hz, 1H), 1.73-1.65 (m, 1H), 1.55-1.43 (m, 3H) | ES-LCMS m/z 455.2 $[M - H]^-$. |

The following compounds were synthesized in an analogous manner to the preparation described above (intermediates 68-71), using the appropriate amine precursor, and substituting sodium cyanoborohydride as the reducing agent:

| Int. | Structure/Name | $^1$H NMR | LCMS |
|---|---|---|---|
| 115 | 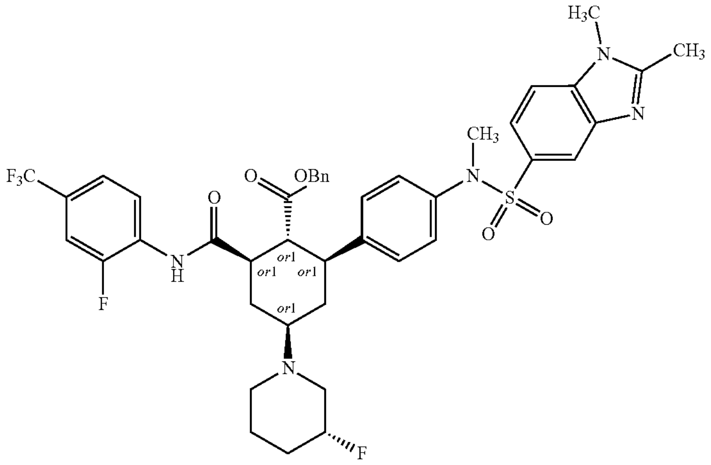 [SMILES: Cc1nc2cc(S(=O)(=O)N(C)c3ccc([C@H]4C[C@@H](N5CCC[C@@H](F)C5)C[C@@H](C(=O)Nc5ccc(C(F)(F)F)cc5F)[C@@H]4C(=O)OCc4ccccc4)cc3)ccc2n1C] ISOMER 2 rel-benzyl (1R*,2R*,4R*,6S*)-2-((2-fluoro-4-(trifluoromethyl)phenyl)carbamoyl)-4-((R)-3-fluoropiperidin-1-yl)-6-(4-((N, 1,2-trimethyl-1H-benzo[d]imidazole)-5-sulfonamido)phenyl)cyclohexane-1-carboxylate ISOMER 2 | $^1$H NMR (400 MHz, DMSO-$d_6$) δ 10.15 (s, 1H), 8.15 (t, J = 8.3 Hz, 1H), 7.74-7.69 (m, 1H), 7.63-7.57 (m, 2H), 7.56-7.52 (m, 1H), 7.30 (dd, J = 8.5, 1.5 Hz, 1H), 7.23 (d, J = 9.0 Hz, 2H), 7.18-7.10 (m, 3H), 6.99 (d, J = 8.5 Hz, 2H), 6.93 (dd, J = 7.8, 1.8 Hz, 2H), 4.79 (d, J = 12.5 Hz, 1H), 4.66-4.45 (m, 3H), 3.74 (s, 3H), 3.45-3.37 (m, 1H), 3.26-3.18 (m, 1H), 3.15-3.03 (m, 4H), 2.93 (t, J = 11.3 Hz, 2H), 2.46-2.36 (m, 3H), 2.15-2.07 (m, 1H), 1.88-1.62 (m, 5H), 1.52-1.35 (m, 3H), 0.85 (td, J = 7.3, 4.0 Hz, 1H) | ES-LCMS m/z 838.2 [M + H]$^+$. |
| 116 | 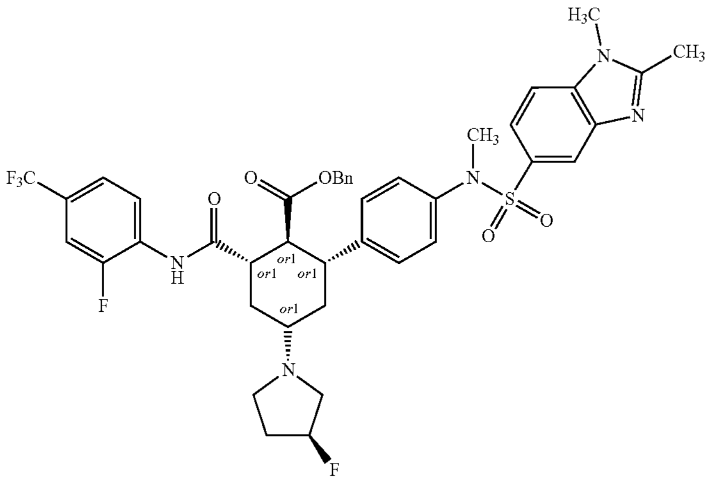 ISOMER 1 rel-benzyl (1R*,2R*,4R*,6S*)-2-((2-fluoro-4-(trifluoromethyl)phenyl)carbamoyl)-4-((S)-3-fluoropyrrolidin-1-yl)-6-(4-((N, 1,2-trimethyl-1H-benzo[d]imidazole)-5-sulfonamido)phenyl)cyclohexane-1-carboxylate ISOMER 1 | $^1$H NMR (400 MHz, DMSO-$d_6$) δ 10.16 (br s, 1H), 8.16 (t, J = 8.0 Hz, 1H), 7.76-7.69 (m, 1H), 7.62-7.58 (m, 2H), 7.54 (d, J = 7.5 Hz, 1H), 7.30 (dd, J = 8.5, 2.0 Hz, 1H), 7.23 (d, J = 8.5 Hz, 2H), 7.17-7.09 (m, 3H), 6.99 (d, J = 8.5 Hz, 2H), 6.94 (d, J = 6.0 Hz, 2H), 5.24-5.09 (m, 1H), 4.80 (d, J= 12.5 Hz, 1H), 4.58 (d, J = 12.5 Hz, 1H), 3.74 (s, 3H), 3.21-3.11 (m, 2H), 3.07 (s, 3H), 2.98-2.90 (m, 1H), 2.86-2.78 (m, 2H), 2.47-2.40 (m, 4H), 2.31-2.25 (m, 1H), 2.13-1.93 (m, 3H), 1.92-1.74 (m, 2H), 1.68-1.56 (m, 1H), 1.53-1.41 (m, 1H) | ES-LCMS m/z 824.3 [M + H]$^+$. |

-continued

| Int. | Structure/Name | $^1$H NMR | LCMS |
|---|---|---|---|
| 117 | 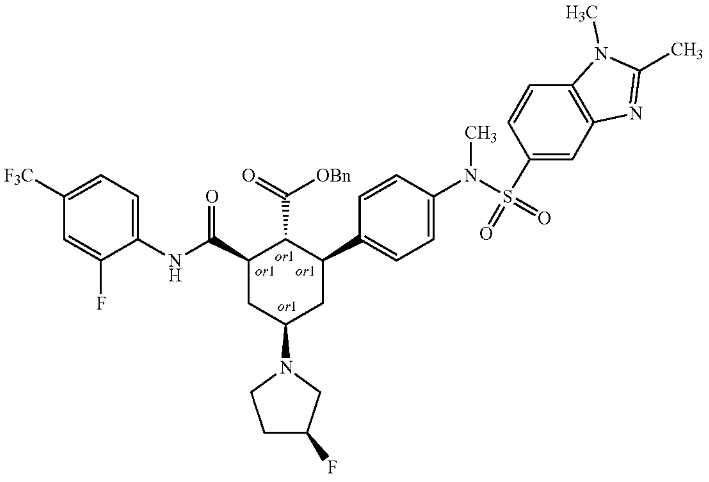 [SMILES: Cc1nc2cc(S(=O)(=O)N(C)c3ccc([C@H]4C[C@@H](N5CC[C@H](F)C5)C[C@@H](C(=O)Nc5ccc(C(F)(F)F)cc5F)[C@@H]4C(=O)OCc4ccccc4)cc3)ccc2n1C] ISOMER 2 rel-benzyl (1R*,2R*,4R*,6S*)-2-((2-fluoro-4-(trifluoromethyl)phenyl)carbamoyl)-4-((S)-3-fluoropyrrolidin-1-yl)-6-(4-((N, 1,2-trimethyl-1H-benzo[d]imidazole)-5-sulfonamido)phenyl)cyclohexane-1-carboxylate ISOMER 2 | $^1$H NMR (400 MHz, DMSO-d$_6$) δ 10.16 (s, 1H), 8.16 (t, J = 8.3 Hz, 1H), 7.72 (dd, J = 11.0, 1.5 Hz, 1H), 7.63-7.57 (m, 2H), 7.54 (d, J = 8.0 Hz, 1H), 7.30 (dd, J = 8.5, 2.0 Hz, 1H), 7.23 (d, J = 8.5 Hz, 2H), 7.18-7.09 (m, 3H), 6.99 (d, J= 8.5 Hz, 2H), 6.94 (d, J= 6.5 Hz, 2H), 5.26-5.08 (m, 1H), 4.80 (d, J= 12.5 Hz, 1H), 4.58 (d, J = 12.5 Hz, 1H), 3.74 (s, 3H), 3.44-3.33 (m, 2H), 3.15-3.03 (m, 4H), 3.00-2.74 (m, 5H), 2.73-2.68 (m, 1H), 2.46-2.38 (m, 2H), 2.31-2.24 (m, 1H), 2.15-1.94 (m, 2H), 1.92-1.75 (m, 1H), 1.70-1.55 (m, 1H), 1.47 (q, J = 11.7 Hz, 1H) | ES-LCMS m/z 824.3 [M + H]$^+$. |
| 118 | 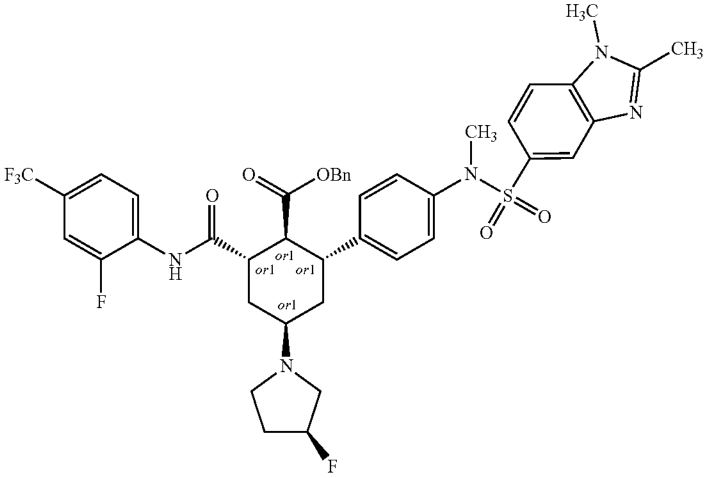 [SMILES: Cc1nc2cc(S(=O)(=O)N(C)c3ccc([C@@H]4C[C@@H](N5CC[C@H](F)C5)C[C@H](C(=O)Nc5ccc(C(F)(F)F)cc5F)[C@H]4C(=O)OCc4ccccc4)cc3)ccc2n1C] ISOMER 1 rel-benzyl (1R*,2R*,4S*,6S*)-2-((2-fluoro-4-(trifluoromethyl)phenyl)carbamoyl)-4-((S)-3-fluoropyrrolidin-1-yl)-6-(4-((N, 1,2-trimethyl-1H-benzo[d]imidazole)-5-sulfonamido)phenyl)cyclohexane-1-carboxylate ISOMER 1 | $^1$H NMR (400 MHz, DMSO-d$_6$) δ 10.19 (s, 1H), 8.03 (t, J = 8.0 Hz, 1H), 7.69 (dd, J = 11.0, 2.0 Hz, 1H), 7.63-7.57 (m, 2H), 7.53 (d, J = 8.5 Hz, 1H), 7.30 (dd, J = 8.5, 1.5 Hz, 1H), 7.19 (d, J = 8.5 Hz, 2H), 7.15-7.05 (m, 3H), 6.99 (d, J= 8.5 Hz, 2H), 6.91 (d, J= 7.0 Hz, 2H), 5.37-5.17 (m, 1H), 4.83 (d, J= 12.5 Hz, 1H), 4.61 (d, J = 13.0 Hz, 1H), 3.77-3.70 (m, 3H), 3.50-3.40 (m, 1H), 3.33 (s, 3H), 3.24-3.14 (m, 1H), 3.07 (s, 3H), 3.04-2.95 (m, 2H), 2.90-2.75 (m, 2H), 2.58-2.53 (m, 1H), 2.37 (d, J = 6.0 Hz, 1H), 2.28-2.13 (m, 1H), 2.12-2.02 (m, 2H), 1.94-1.70 (m, 3H) | ES-LCMS m/z 824.3 [M + H]$^+$. |

-continued

| Int. | Structure/Name | $^1$H NMR | LCMS |
|---|---|---|---|
| 119 | 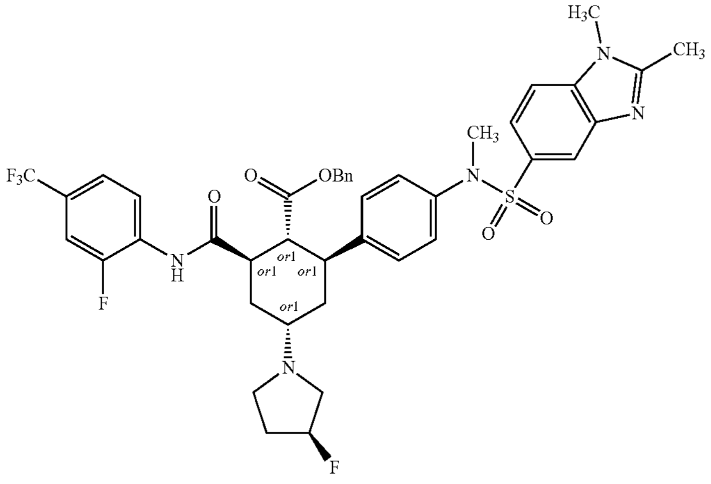 [SMILES: Cc1nc2cc(S(=O)(=O)N(C)c3ccc([C@H]4C[C@H](N5CC[C@H](F)C5)C[C@@H](C(=O)Nc5ccc(C(F)(F)F)cc5F)[C@@H]4C(=O)OCc4ccccc4)cc3)ccc2n1C] ISOMER 2 rel-benzyl (1R*,2R*,4S*,6S*)-2-((2-fluoro-4-(trifluoromethyl)phenyl)carbamoyl)-4-((S)-3-fluoropyrrolidin-1-yl)-6-(4-((N, 1,2-trimethyl-1H-benzo[d]imidazole)-5-sulfonamido)phenyl)cyclohexane-1-carboxylate ISOMER 2 | $^1$H NMR (400 MHz, DMSO-$d_6$) δ 10.21 (s, 1H), 7.98 (t, J = 8.0 Hz, 1H), 7.72-7.66 (m, 1H), 7.62-7.57 (m, 2H), 7.53 (d, J = 7.5 Hz, 1H), 7.34-7.28 (m, 1H), 7.20 (d, J= 8.5 Hz, 2H), 7.16-7.05 (m, 3H), 6.99 (d, J= 8.5 Hz, 2H), 6.91 (d, J= 7.0 Hz, 2H), 5.38-5.21 (m, 1H), 4.82 (d, J= 12.5 Hz, 1H), 4.62 (d, J = 13.0 Hz, 1H), 3.73 (s, 3H), 3.44-3.35 (m, 1H), 3.29 (br s, 1H), 3.25-3.15 (m, 1H), 3.07 (s, 3H), 3.04-2.97 (m, 1H), 2.87-2.80 (m, 1H), 2.79-2.71 (m, 1H), 2.64-2.57 (m, 1H), 2.52 (br s, 3H), 2.48-2.42 (m, 2H), 2.24-2.06 (m, 2H), 1.90-1.73 (m, 3H) | ES-LCMS m/z 824.3 [M + H]$^+$. |
| 120 | 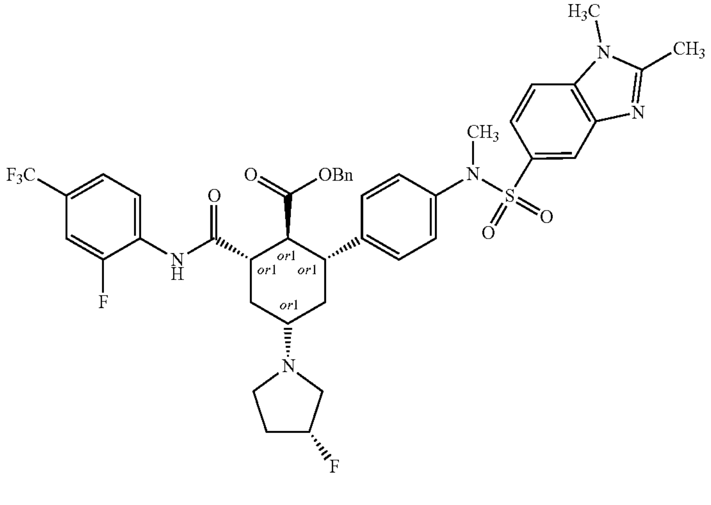 ISOMER 1 rel-benzyl (1R*,2R*,4R*,6S*)-2-((2-fluoro-4-(trifluoromethyl)phenyl)carbamoyl)-4-((R)-3-fluoropyrrolidin-1-yl)-6-(4-((N, 1,2-trimethyl-1H-benzo[d]imidazole)-5-sulfonamido)phenyl)cyclohexane-1-carboxylate ISOMER 1 | $^1$H NMR (400 MHz, DMSO-$d_6$) δ 10.15 (s, 1H), 8.16 (t, J = 8.0 Hz, 1H), 7.71 (dd, J = 11.0, 1.5 Hz, 1H), 7.62-7.57 (m, 2H), 7.54 (d, J = 8.5 Hz, 1H), 7.33-7.28 (m, 1H), 7.23 (d, J = 9.0 Hz, 2H), 7.17-7.09 (m, 3H), 6.99 (d, J = 8.5 Hz, 2H), 6.94 (dd, J = 7.8, 1.8 Hz, 2H), 5.27-5.06 (m, 1H), 4.80 (d, J = 13.0 Hz, 1H), 4.58 (d, J = 13.0 Hz, 1H), 3.74 (s, 3H), 3.12-3.03 (m, 4H), 2.99-2.91 (m, 1H), 2.88-2.75 (m, 3H), 2.74-2.64 (m, 1H), 2.52 (s, 3H), 2.47-2.39 (m, 2H), 2.28 (d, J = 12.0 Hz, 1H), 2.14-1.94 (m, 2H), 1.93-1.75 (m, 1H), 1.62 (q, J= 12.0 Hz, 1H), 1.53-1.41 (m, 1H) | ES-LCMS m/z 824.3 [M + H]$^+$. |

-continued

| Int. | Structure/Name | $^1$H NMR | LCMS |
| --- | --- | --- | --- |
| 121 | 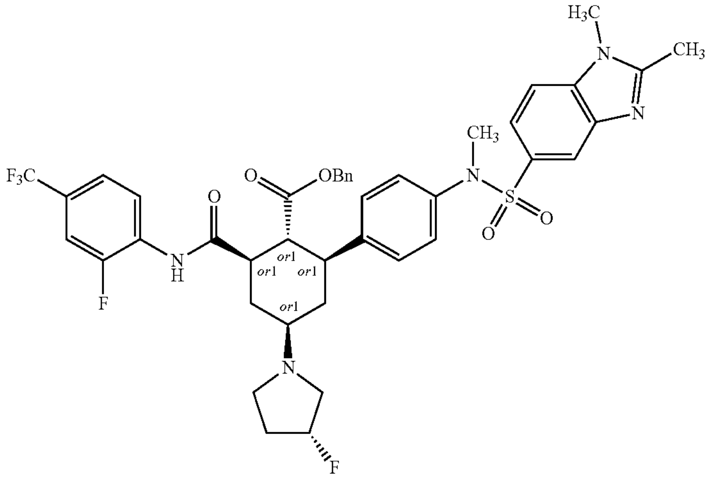 [SMILES: Cc1nc2cc(S(=O)(=O)N(C)c3ccc([C@H]4C[C@@H](N5CC[C@@H](F)C5)C[C@@H](C(=O)Nc5ccc(C(F)(F)F)cc5F)[C@@H]4C(=O)OCc4ccccc4)cc3)ccc2n1C] ISOMER 2<br>rel-benzyl (1R*,2R*,4R*,6S*)-2-((2-fluoro-4-(trifluoromethyl)phenyl)carbamoyl)-4-((R)-3-fluoropyrrolidin-1-yl)-6-(4-((N, 1,2-trimethyl-1H-benzo[d]imidazole)-5-sulfonamido)phenyl)cyclohexane-1-carboxylate<br>ISOMER 2 | $^1$H NMR (400 MHz, DMSO-$d_6$) δ 10.15 (s, 1H), 8.16 (t, J = 8.3 Hz, 1H), 7.71 (dd, J = 11.0, 1.5 Hz, 1H), 7.62-7.58 (m, 2H), 7.55 (d, J = 9.0 Hz, 1H), 7.33-7.29 (m, 1H), 7.23 (d, J = 8.5 Hz, 2H), 7.17-7.10 (m, 3H), 6.99 (d, J = 8.5 Hz, 2H), 6.94 (dd, J = 8.0, 1.5 Hz, 2H), 5.25-5.09 (m, 1H), 4.80 (d, J = 13.0 Hz, 1H), 4.58 (d, J = 13.0 Hz, 1H), 3.74 (s, 3H), 3.15-3.04 (m, 4H), 2.98-2.90 (m, 2H), 2.88-2.76 (m, 3H), 2.46-2.40 (m, 2H), 2.28 (d, J = 11.5 Hz, 1H), 2.15-1.94 (m, 3H), 1.92-1.75 (m, 2H), 1.68-1.56 (m, 1H), 1.48 (q, J = 11.8 Hz, 2H) | ES-LCMS m/z 824.3 $[M + H]^+$. |
| 122 | 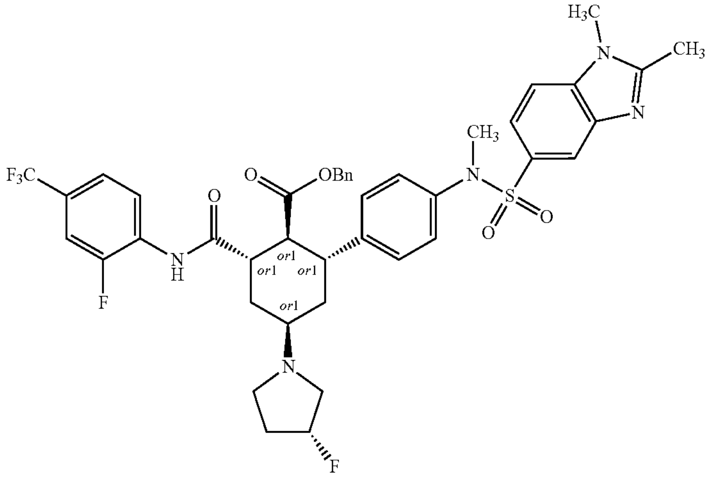 [SMILES: Cc1nc2cc(S(=O)(=O)N(C)c3ccc([C@@H]4C[C@@H](N5CC[C@@H](F)C5)C[C@H](C(=O)Nc5ccc(C(F)(F)F)cc5F)[C@H]4C(=O)OCc4ccccc4)cc3)ccc2n1C] ISOMER 1<br>rel-benzyl (1R*,2R*,4S*,6S*)-2-((2-fluoro-4-(trifluoromethyl)phenyl)carbamoyl)-4-((R)-3-fluoropyrrolidin-1-yl)-6-(4-((N, 1,2-trimethyl-1H-benzo[d]imidazole)-5-sulfonamido)phenyl)cyclohexane-1-carboxylate<br>ISOMER 1 | $^1$H NMR (400 MHz, DMSO-$d_6$) δ 10.20 (s, 1H), 7.98 (t, J = 8.3 Hz, 1H), 7.68 (d, J = 10.0 Hz, 1H), 7.62-7.57 (m, 2H), 7.53 (d, J = 9.0 Hz, 1H), 7.31 (dd, J = 9.0, 1.5 Hz, 1H), 7.20 (d, J = 8.5 Hz, 2H), 7.16-7.05 (m, 3H), 6.99 (d, J = 8.5 Hz, 2H), 6.91 (d, J = 7.0 Hz, 2H), 5.36-5.21 (m, 1H), 4.82 (d, J = 12.5 Hz, 1H), 4.62 (d, J = 13.0 Hz, 1H), 3.73 (s, 4H), 3.47-3.35 (m, 2H), 3.24-3.15 (m, 1H), 3.07 (s, 3H), 3.04-2.97 (m, 1H), 2.87-2.81 (m, 1H), 2.79-2.72 (m, 1H), 2.64-2.57 (m, 2H), 2.46-2.40 (m, 1H), 2.27-2.19 (m, 1H), 2.18-2.00 (m, 3H), 1.92-1.73 (m, 3H) | ES-LCMS m/z 824.3 $[M + H]^+$. |

-continued

| Int. | Structure/Name | $^1$H NMR | LCMS |
|---|---|---|---|
| 123 | 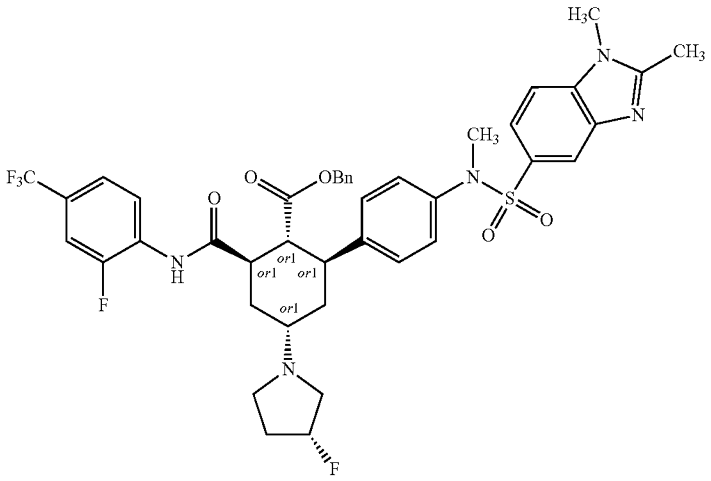 [SMILES: Cc1nc2cc(S(=O)(=O)N(C)c3ccc([C@H]4C[C@H](N5CC[C@@H](F)C5)C[C@@H](C(=O)Nc5ccc(C(F)(F)F)cc5F)[C@@H]4C(=O)OCc4ccccc4)cc3)ccc2n1C] ISOMER 2 rel-benzyl (1R*,2R*,4S*,6S*)-2-((2-fluoro-4-(trifluoromethyl)phenyl) carbamoyl)-4-((R)-3-fluoropyrrolidin-1-yl)-6-(4-((N, 1,2-trimethyl-1H-benzo[d]imidazole)-5-sulfonamido)phenyl)cyclohexane-1-carboxylate ISOMER 2 | $^1$H NMR (400 MHz, DMSO-d$_6$) δ 10.18 (s, 1H), 8.06-7.99 (m, 1H), 7.68 (d, J = 11.0 Hz, 1H), 7.62-7.57 (m, 2H), 7.53 (d, J = 9.0 Hz, 1H), 7.30 (dd, J = 9.0, 1.5 Hz, 1H), 7.18 (d, J = 8.5 Hz, 2H), 7.14-7.04 (m, 3H), 6.99 (d, J = 8.5 Hz, 2H), 6.91 (d, J = 7.0 Hz, 2H), 5.35-5.18 (m, 1H), 4.83 (d, J = 13.0 Hz, 1H), 4.61 (d, J = 13.0 Hz, 1H), 3.73 (s, 3H), 3.44 (t, J = 10.8 Hz, 1H), 3.37-3.32 (m, 1H), 3.26 (br s, 1H), 3.18 (td, J = 11.5, 4.0 Hz, 1H), 3.07 (s, 3H), 3.03-2.95 (m, 2H), 2.89-2.75 (m, 2H), 2.57-2.54 (m, 1H), 2.45 (br s, 1H), 2.37 (d, J = 7.0 Hz, 1H), 2.28-2.02 (m, 3H), 1.92-1.71 (m, 3H) | ES-LCMS m/z 824.3 [M + H]$^+$. |

The following compound was synthesized in an analogous manner to the preparation methods described herein using tert-butyl (3-bromo-4-formylphenyl)(methyl) carbamate.

| Int. | Structure/Name | $^1$H NMR | LCMS |
|---|---|---|---|
| 124 | 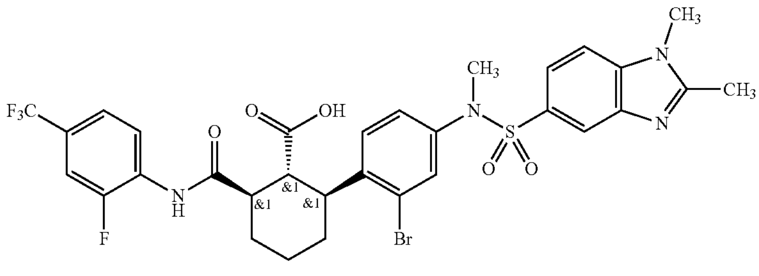 rac-(1R,2S,6R)-2-(2-bromo-4-((N,1,2-trimethyl-1H-benzo[d]imidazole)-5-sulfonamido)phenyl)-6-((2-fluoro-4-(trifluoromethyl)phenyl)carbamoyl)cyclohexane-1-carboxylic acid | $^1$H NMR (400 MHz, DMSO-d$_6$) δ 12.03 (br s, 1H), 10.11 (s, 1H), 8.23 (t, J = 8.3 Hz, 1H), 7.72 (dd, J = 10.8, 1.8 Hz, 1H), 7.69-7.61 (m, 2H), 7.56 (d, J = 8.0 Hz, 1H), 7.49 (d, J = 8.5 Hz, 1H), 7.31-7.28 (m, 1H), 7.22 (dd, J = 8.5, 2.0 Hz, 1H), 7.09-7.01 (m, 1H), 3.78 (d, J = 1.0 Hz, 3H), 3.28-3.21 (m, 1H), 3.08 (s, 3H), 2.98-2.88 (m, 1H), 2.57 (s, 3H), 2.44 (br s, 1H), 2.01 (d, J = 9.5 Hz, 1H), 1.94-1.82 (m, 1H), 1.73-1.66 (m, 1H), 1.62-1.35 (m, 3H). | ES-LCMS m/z 524.0 [M − H]$^-$ |

Intermediate 125: rac-(5R,7R,8R,9S)-7-((2-fluoro-4-(trifluoromethyl)phenyl)carbamoyl)-9-(4-(methylamino)phenyl)-1-oxaspiro[4.5]decane-8-carboxylic acid

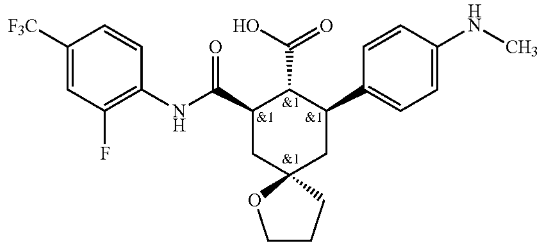 [SMILES: CNc1ccc([C@H]2C[C@]3(CCCO3)C[C@@H](C(=O)Nc3ccc(C(F)(F)F)cc3F)[C@@H]2C(=O)O)cc1]

Step 1: rac-(1R,2S,4R,6R)-4-allyl-2-(4-bromophenyl)-6-((2-fluoro-4-(trifluoromethyl)phenyl)carbamoyl)-4-hydroxycyclohexane-1-carboxylic acid

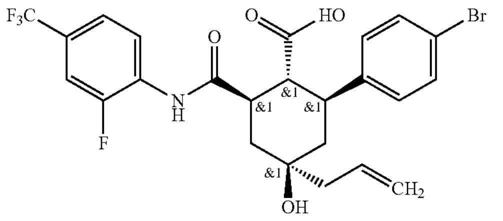 [SMILES: C=CC[C@@]1(O)C[C@H](c2ccc(Br)cc2)[C@@H](C(=O)O)[C@H](C(=O)Nc2ccc(C(F)(F)F)cc2F)C1]

To a mixture of rac-(1R,2S,6R)-2-(4-bromophenyl)-6-((2-fluoro-4-(trifluoromethyl)phenyl)carbamoyl)-4-oxocyclohexane-1-carboxylic acid Intermediate 10, Step 5 (2.000 g, 3.982 mmol) in THF (20 mL) at 0° C. was added allylmagnesium bromide (9.96 mL, 1 M, 9.96 mmol). The reaction was warmed to RT for 16 h, quenched with saturated ammonium chloride solution (8 mL), concentrated and purified by reverse phase purification (MeCN in $H_2O$, 0.1% Ammonium bicarbonate modifier, 0-100%) to afford rac-(1R,2S,4R,6R)-4-allyl-2-(4-bromophenyl)-6-((2-fluoro-4-(trifluoromethyl)phenyl)carbamoyl)-4-hydroxycyclohexane-1-carboxylic acid (0.470 g, 0.760 mmol, 19.0% yield) as an off-white solid. $^1H$ NMR (400 MHz, DMSO-$d_6$) δ 10.16 (br s, 1H), 8.11 (br s, 1H), 7.68 (d, J=10.5 Hz, 1H), 7.53 (d, J=8.5 Hz, 1H), 7.43 (d, J=7.5 Hz, 2H), 7.18 (d, J=8.0 Hz, 2H), 5.96-5.82 (m, 1H), 5.08-4.97 (m, 2H), 4.48 (br s, 1H), 4.08 (d, J=6.0 Hz, 1H), 3.22-3.09 (m, 2H), 2.74-2.62 (m, 1H), 2.47-2.37 (m, 1H), 2.18 (d, J=7.5 Hz, 2H), 1.82 (d, J=12.0 Hz, 1H), 1.65-1.49 (m, 2H). ES-LCMS m/z 542.0 $[M-1]^-$.

Step 2: rac-(1R,2S,4R,6R)-2-(4-bromophenyl)-6-((2-fluoro-4-(trifluoromethyl)phenyl)carbamoyl)-4-hydroxy-4-(3-hydroxypropyl)cyclohexane-1-carboxylic acid

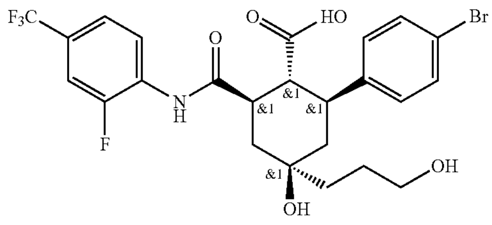 [SMILES: O=C(O)[C@@H]1[C@@H](c2ccc(Br)cc2)C[C@](O)(CCCO)C[C@H]1C(=O)Nc1ccc(C(F)(F)F)cc1F]

To a mixture of rac-(1R,2S,4R,6R)-4-allyl-2-(4-bromophenyl)-6-((2-fluoro-4-(trifluoromethyl)phenyl)carbamoyl)-4-hydroxycyclohexane-1-carboxylic acid (500.0 mg, 918.5 μmol) in THF (10 mL) at 0° C. was added $BH_3$-DMS (1.837 mL, 1 M, 1.837 mmol), slowly. After 2 h at RT, the reaction was cooled to 0° C., and sodium perborate tetrahydrate (424.0 mg, 2.756 mmol) in water (2.5 mL) was added. The mixture was stirred at RT for 16 h, diluted with water (10 mL), acidified with 1.5 N HCL, and was extracted with EtOAc (10 mL×2). The combined EtOAc layers were washed with brine (10 mL), dried over sodium sulphate, concentrated and subjected to reverse phase purification (MeCN in $H_2O$, 0.1% formic acid modifier, 0-100%) to give rac-(1R,2S,4R,6R)-2-(4-bromophenyl)-6-((2-fluoro-4-(trifluoromethyl)phenyl)carbamoyl)-4-hydroxy-4-(3-hydroxypropyl)cyclohexane-1-carboxylic acid (0.25 g, 0.35 mmol, 38% yield) as an off-white solid. $^1H$ NMR (400 MHz, DMSO-$d_6$) δ 11.88 (s, 1H), 10.08 (br s, 1H), 8.09 (t, J=8.0 Hz, 1H), 7.69 (dd, J=11.0, 1.5 Hz, 1H), 7.54 (d, J=8.5 Hz, 1H), 7.45 (d, J=8.5 Hz, 2H), 7.21 (d, J=8.5 Hz, 2H), 4.46-4.28 (m, 2H), 3.36 (br s, 2H), 3.15 (td, J=11.4, 5.3 Hz, 2H), 2.72 (t, J=11.3 Hz, 1H), 2.48-2.38 (m, 1H), 1.85 (dd, J=13.5, 2.5 Hz, 1H), 1.58-1.37 (m, 6H). ES-LCMS m/z 562.0 $[M+1]^+$.

Step 3: rac-(1R,2S,4R,6R)-2-(4-bromophenyl)-6-((2-fluoro-4-(trifluoromethyl)phenyl)carbamoyl)-4-hydroxy-4-(3-oxopropyl)cyclohexane-1-carboxylic acid

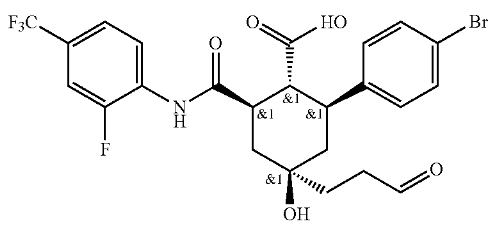 [SMILES: O=CCC[C@@]1(O)C[C@H](c2ccc(Br)cc2)[C@@H](C(=O)O)[C@H](C(=O)Nc2ccc(C(F)(F)F)cc2F)C1]

To a mixture of rac-(1R,2S,4R,6R)-2-(4-bromophenyl)-6-((2-fluoro-4-(trifluoromethyl)phenyl)carbamoyl)-4-hydroxy-4-(3-hydroxypropyl)cyclohexane-1-carboxylic acid (175.0 mg, 311.2 μmol) in DCM (4 mL) at 0° C. was added Dess-Martin periodinane (198.0 mg, 466.8 μmol). The reaction was stirred at 25° C. for 1 h, concentrated and subjected to reverse phase purification (MeCN in $H_2O$, 0.1% formic acid modifier, 0-100%) to afford rac-(1R,2S,4R,6R)-2-(4-bromophenyl)-6-((2-fluoro-4-(trifluoromethyl)phenyl)carbamoyl)-4-hydroxy-4-(3-oxopropyl)cyclohexane-1-carboxylic acid (0.080 g, 0.15 mmol, 46%) as a white solid. $^{1}$H NMR (400 MHz, DMSO-$d_6$) δ 11.90 (br s, 1H), 9.94 (s, 1H), 8.04 (t, J=8.3 Hz, 1H), 7.71 (dd, J=11.0, 1.5 Hz, 1H), 7.55 (d, J=8.5 Hz, 1H), 7.50-7.42 (m, 2H), 7.25-7.17 (m, 2H), 5.79 (d, J=5.0 Hz, 1H), 5.40 (d, J=4.5 Hz, 1H), 3.06 (td, J=12.1, 3.3 Hz, 1H), 2.80 (d, J=11.0 Hz, 1H), 2.11-1.99 (m, 2H), 1.95-1.80 (m, 3H), 1.78-1.57 (m, 4H). ES-LCMS m/z 559.9 $[M-1]^-$.

Step 4: rac-(5R,7S,8R,9R)-7-(4-bromophenyl)-9-((2-fluoro-4-(trifluoromethyl)phenyl)carbamoyl)-1-oxaspiro[4.5]decane-8-carboxylic acid

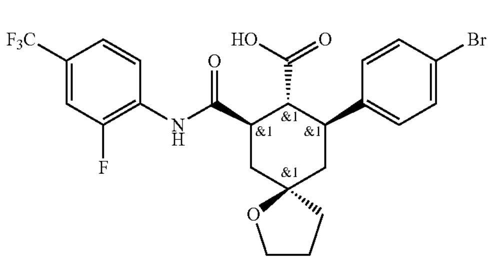 [SMILES: O=C(O)[C@@H]1[C@@H](c2ccc(Br)cc2)C[C@]2(CCCO2)C[C@H]1C(=O)Nc1ccc(C(F)(F)F)cc1F]

To a mixture of rac-(1R,2S,4R,6R)-2-(4-bromophenyl)-6-((2-fluoro-4-(trifluoromethyl)phenyl)carbamoyl)-4-hydroxy-4-(3-oxopropyl)cyclohexane-1-carboxylic acid (110.0 mg, 196.3 μmol) in acetonitrile (2.5 mL) was added chlorodimethylsilane (92.86 mg, 981.6 μmol). The reaction was stirred at 25° C. for 16 h and subjected to reverse phase purification (MeCN in $H_2O$, 0.1% formic acid modifier, 0-100%) to afford rac-(5R,7S,8R,9R)-7-(4-bromophenyl)-9-((2-fluoro-4-(trifluoromethyl)phenyl)carbamoyl)-1-oxaspiro[4.5]decane-8-carboxylic acid (519 mg, 0.720 mmol, 41.0% yield) as a white solid. $^{1}$H NMR (400 MHz, DMSO-$d_6$) δ 11.85 (br s, 1H), 10.18 (br s, 1H), 8.04 (t, J=7.8 Hz, 1H), 7.69 (dd, J=10.8, 1.8 Hz, 1H), 7.54 (d, J=8.5 Hz, 1H), 7.48-7.43 (m, 2H), 7.22 (d, J=8.5 Hz, 2H), 3.88-3.74 (m, 2H), 3.05 (td, J=12.1, 3.3 Hz, 1H), 2.85-2.74 (m, 1H), 1.96-1.80 (m, 4H), 1.76-1.59 (m, 5H). ES-LCMS m/z 541.9 $[M-1]^-$.

Step 5: rac-(5R,7R,8R,9S)-7-((2-fluoro-4-(trifluoromethyl)phenyl)carbamoyl)-9-(4-(methylamino)phenyl)-1-oxaspiro[4.5]decane-8-carboxylic acid

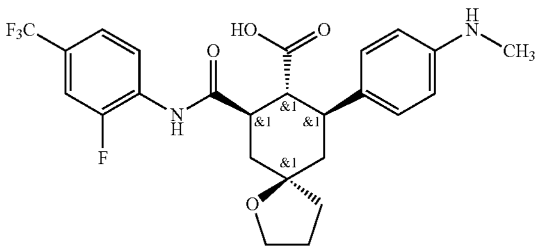 [SMILES: CNc1ccc([C@H]2C[C@]3(CCCO3)C[C@@H](C(=O)Nc3ccc(C(F)(F)F)cc3F)[C@@H]2C(=O)O)cc1]

A mixture of rac-(5R,7S,8R,9R)-7-(4-bromophenyl)-9-((2-fluoro-4-(trifluoromethyl)phenyl)carbamoyl)-1-oxaspiro[4.5]decane-8-carboxylic acid (40.00 mg, 73.48 μmol) and sodium tert-butoxide (14.12 mg, 147.0 μmol) in dioxane (0.400 mL) was degassed for 5 min followed by the addition of tBuXPhos-Pd-G3 (5.84 mg, 7.35 μmol) and degassing for 5 min more. Methylamine (2 M in THF, 734.8 μL, 1.470 mmol) was added, and the reaction vessel was sealed and heated at 100° C. in Biotage Initiator for 1 h. The mixture was filtered through syringe filter, concentrated and subjected to reverse phase purification (MeCN in $H_2O$, 0.1% ammonium bicarbonate modifier, 0-100% gradient) to afford rac-(5R,7R,8R,9S)-7-((2-fluoro-4-(trifluoromethyl)phenyl)carbamoyl)-9-(4-(methylamino)phenyl)-1-oxaspiro[4.5]decane-8-carboxylic acid (27 mg, 46 μmol, 63% yield) as a white solid. $^{1}$H NMR (400 MHz, DMSO-$d_6$) δ 11.66 (br s, 1H), 10.12 (s, 1H), 8.05 (t, J=8.0 Hz, 1H), 7.69 (dd, J=10.8, 1.8 Hz, 1H), 7.54 (d, J=8.5 Hz, 1H), 6.93 (d, J=8.5 Hz, 2H), 6.42 (d, J=8.5 Hz, 2H), 5.46-5.38 (m, 1H), 3.80 (dq, J=14.4, 7.5 Hz, 3H), 3.23 (dd, J=11.8, 2.8 Hz, 1H), 2.92 (td, J=12.0, 4.0 Hz, 1H), 2.63 (bd, J=4.5 Hz, 3H), 1.93-1.81 (m, 3H), 1.75-1.58 (m, 5H). ES-LCMS m/z 493.1 $[M-1]^-$ Intermediate 126, Intermediate 127 and Intermediate 128: rac-methyl (3aS,4R,5R,6R,7aS)-4-((2-fluoro-4-(trifluoromethyl)phenyl)carbamoyl)-6-(4-((N,1,2-trimethyl-1H-benzo[d]imidazole)-5-sulfonamido)phenyl)octahydroisobenzofuran-5-carboxylate, rac-methyl (3aR,4R,5R,6S,7aR)-4-((2-fluoro-4-(trifluoromethyl)phenyl)carbamoyl)-6-(4-((N,1,2-trimethyl-1H-benzo[d]imidazole)-5-sulfonamido)phenyl)octahydroisobenzofuran-5-carboxylate and rac-methyl (3aR,4R,5S,6S,7aR)-4-((2-fluoro-4-(trifluoromethyl)phenyl)carbamoyl)-6-(4-((N,1,2-trimethyl-1H-benzo[d]imidazole)-5-sulfonamido)phenyl)octahydroisobenzofuran-5-carboxylate

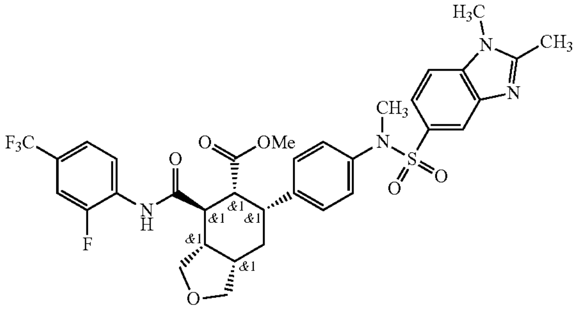

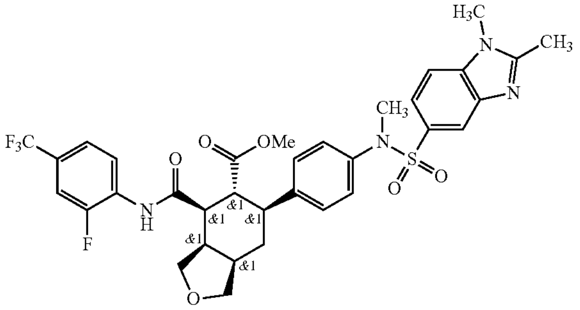

-continued

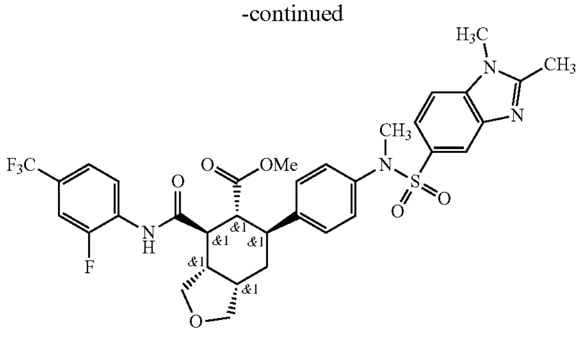

Step 1: (E)-3-(4-bromophenyl)prop-2-en-1-ol

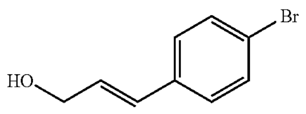 [SMILES: OC/C=C/c1ccc(Br)cc1]

To a mixture of methyl (E)-3-(4-bromophenyl)acrylate (10.00 g, 41.48 mmol) in THF (100 mL) at −78° C. was added, dropwise, diisobutylaluminum hydride (1 M in THF, 124.4 mL, 124.4 mmol). The reaction was stirred at RT for 2 h, quenched with saturated ammonium chloride solution, stirred for 6 h, filtered through Celite and extracted with ethyl acetate (3×100 mL). The combined organic layers were concentrated to afford (E)-3-(4-bromophenyl)prop-2-en-1-ol (8.5 g, 39 mmol, 95% yield) as an off-white solid. $^1$H NMR (400 MHz, DMSO-$d_6$) δ 7.53-7.47 (m, 2H), 7.42-7.35 (m, 2H), 6.57-6.50 (m, 1H), 6.46-6.38 (m, 1H), 4.89 (t, J=5.5 Hz, 1H), 4.10 (td, J=5.3, 1.5 Hz, 2H). ES-GCMS m/z 212.0 [M].

Step 2: (E)-1-bromo-4-(3-(prop-2-yn-1-yloxy) prop-1-en-1-yl) benzene

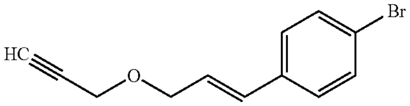

To a mixture of (E)-3-(4-bromophenyl)prop-2-en-1-ol (8.500 g, 39.89 mmol) in DMF (80 mL) at 0° C. was added sodium hydride (3.191 g, 60% Wt, 79.79 mmol). After 10 min, 3-bromoprop-1-yne (8.898 g, 80% Wt, 59.84 mmol) was added. After 5 h, the reaction was quenched with cold water (100 mL) and extracted with ethyl acetate (3×100 mL). The combined organic layers were concentrated and subjected to normal phase purification (ethyl acetate in petroleum ether, 0-20% gradient) to afford (E)-1-bromo-4-(3-(prop-2-yn-1-yloxy)prop-1-en-1-yl)benzene (8.0 g, 31 mmol, 77% yield) as a yellow syrupy liquid. $^1$H NMR (400 MHz, DMSO-$d_6$) δ 7.54-7.50 (m, 2H), 7.44-7.41 (m, 2H), 6.64-6.57 (m, 1H), 6.45-6.36 (m, 1H), 4.18 (d, J=2.5 Hz, 2H), 4.14 (dd, J=5.5, 1.5 Hz, 2H), 3.48-3.45 (m, 1H). ES-GCMS m/z 250.0 [M].

Step 3: (E)-3-(4-bromostyryl)-2,5-dihydrofuran

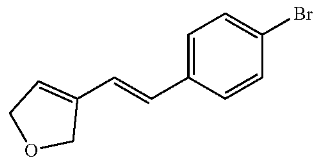 [SMILES: Brc1ccc(/C=C/C2=CCOC2)cc1]

To a mixture of (E)-1-bromo-4-(3-(prop-2-yn-1-yloxy) prop-1-en-1-yl)benzene (8.000 g, 31.86 mmol) in DCM (240 mL) was added Grubbs Catalyst 2nd Generation (4.057 g, 4.779 mmol). After 16 h, the reaction was concentrated and subjected to normal phase purification (ethyl acetate in petroleum ether, 0-20% gradient) to afford (E)-3-(4-bromostyryl)-2,5-dihydrofuran (4.7 g, 18 mmol, 55% yield) as an off-white solid. $^1$H NMR (400 MHz, DMSO-$d_6$) δ7.58-7.51 (m, 2H), 7.48-7.42 (m, 2H), 7.14 (d, J=16.5 Hz, 1H), 6.37 (d, J=16.5 Hz, 1H), 6.14 (t, J=2.0 Hz, 1H), 4.83-4.59 (m, 4H). ES-GCMS m/z 250.0 [M].

Step 4: dimethyl 6-(4-bromophenyl)-1,3,3a,4,5,6-hexahydroisobenzofuran-4,5-dicarboxylate

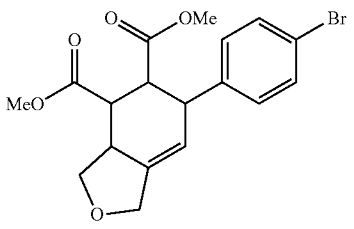 [SMILES: COC(=O)C1C2COCC2=CC(c2ccc(Br)cc2)C1C(=O)OC]

To a mixture of (E)-3-(4-bromostyryl)-2,5-dihydrofuran (4.700 g, 18.72 mmol) in o-xylene (75 mL) was added dimethyl fumarate (8.093 g, 56.15 mmol). The reaction was heated to 120° C. for 16 h, concentrated and subjected to normal phase purification (ethyl acetate in petroleum ether, 0-50% gradient) to afford dimethyl 6-(4-bromophenyl)-1,3,3a,4,5,6-hexahydroisobenzofuran-4,5-dicarboxylate (5.0 g, 12 mmol, 66% yield) as a brown gum. $^1$H NMR (400 MHz, DMSO-$d_6$) δ 7.55-7.45 (m, 2H), 7.17-7.03 (m, 2H), 5.68-5.54 (m, 1H), 4.42-4.22 (m, 2H), 4.12 (t, J=7.8 Hz, 1H), 4.01-3.95 (m, 1H), 3.90 (t, J=7.8 Hz, 1H), 3.64-3.55 (m, 2H), 3.51-3.42 (m, 3H), 3.54-3.41 (m, 1H), 3.29-3.24 (m, 1H), 3.05-2.95 (m, 1H), 2.80-2.73 (m, 1H) (Mixture of isomers). ES-LCMS m/z 397.0 $[M+H]^+$.

Step 5: dimethyl 6-(4-((tert-butoxycarbonyl)(methyl)amino)phenyl)-1,3,3a,4,5,6-hexahydroisobenzofuran-4,5-dicarboxylate

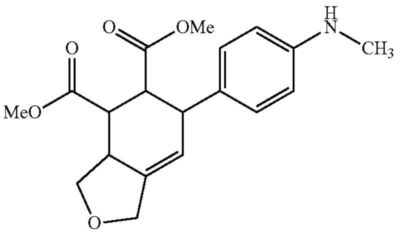 [SMILES: CNc1ccc(C2C=C3COCC3C(C(=O)OC)C2C(=O)OC)cc1]

A mixture of dimethyl 6-(4-bromophenyl)-1,3,3a,4,5,6-hexahydroisobenzofuran-4,5-dicarboxylate (5.000 g, 12.65 mmol) and cesium carbonate (12.37 g, 37.95 mmol) in DMF (100 mL) was degassed with nitrogen for 10 min. tBuBrett-Phos Pd G3 (540.4 mg, 632.5 μmol) was added, followed by methylamine (2 M in THF, 94.88 mL, 189.8 mmol). The reaction was stirred at 60° C. for 16 h, filtered through Celite, diluted with water (150 mL) and extracted with ethyl acetate (3×150 mL). The combined organic layers were concentrated and subjected to normal phase purification (ethyl acetate in petroleum ether, 0-30% gradient) to afford dimethyl 6-(4-(methylamino)phenyl)-1,3,3a,4,5,6-hexahydroisobenzofuran-4,5-dicarboxylate (4.0 g, 11 mmol, 89% yield) as a syrupy liquid. $^1$H NMR (400 MHz, DMSO-$d_6$) δ 6.99-6.75 (m, 2H), 6.54-6.40 (m, 2H), 5.60-5.53 (m, 1H), 4.41-4.23 (m, 2H), 4.14-3.99 (m, 1H), 3.95-3.77 (m, 1H), 3.65-3.49 (m, 4H), 3.46-3.33 (m, 2H), 3.30-3.24 (m, 1H), 3.21-3.05 (m, 1H), 2.90-2.76 (m, 1H), 2.69-2.60 (m, 3H), 2.48-2.42 (m, 1H), 2.38 (dd, J=10.8, 3.8 Hz, 1H). (Mixture of isomers). ES-LCMS m/z 346.1 $[M+H]^+$.

Step 6: dimethyl 6-(4-((tert-butoxycarbonyl)(methyl)amino)phenyl)-1,3,3a,4,5,6-hexahydroisobenzofuran-4,5-dicarboxylate

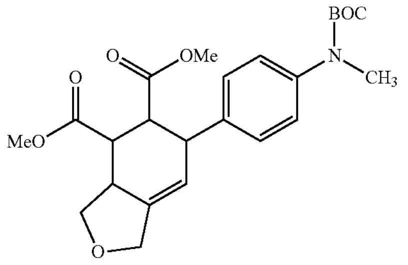 [SMILES: COC(=O)C1C2COCC2=CC(c2ccc(N(C)C(=O)OC(C)(C)C)cc2)C1C(=O)OC]

To a mixture of dimethyl 6-(4-(methylamino)phenyl)-1,3,3a,4,5,6-hexahydroisobenzofuran-4,5-dicarboxylate (4.000 g, 11.58 mmol) in THF (40 mL) and water (40 mL) was added sodium bicarbonate (2.919 g, 34.74 mmol) and di-tert-butyl dicarbonate (7.583 g, 34.74 mmol), dropwise. After 16 h, water (100 mL) was added, and the mixture was extracted with EtOAc (3×100 mL). The combined organic layers were concentrated and subjected to normal phase purification (ethyl acetate in petroleum ether, 0-45% gradient) to afford dimethyl 6-(4-((tert-butoxycarbonyl)(methyl)amino)phenyl)-1,3,3a,4,5,6-hexahydroisobenzofuran-4,5-dicarboxylate (4.8 g, 11 mmol, 91% yield) as a syrupy liquid. $^1$H NMR (400 MHz, DMSO-$d_6$) δ 7.28-7.21 (m, 2H), 7.20-7.02 (m, 2H), 5.65-5.55 (m, 1H), 4.44-4.25 (m, 3H), 4.16-4.05 (m, 1H), 3.69-3.55 (m, 4H), 3.53-3.46 (m, 1H), 3.38-3.33 (m, 2H), 3.29-3.23 (m, 1H), 3.20-3.12 (m, 3H), 2.89-2.75 (m, 1H), 2.41 (dd, J=11.0, 3.5 Hz, 1H), 1.48-1.30 (m, 9H). (Mixture of isomers). ES-LCMS m/z 390.1 $[M-tBu+H]^+$.

Step 7: dimethyl 6-(4-((tert-butoxycarbonyl)(methyl)amino)phenyl)octahydroisobenzofuran-4,5-dicarboxylate

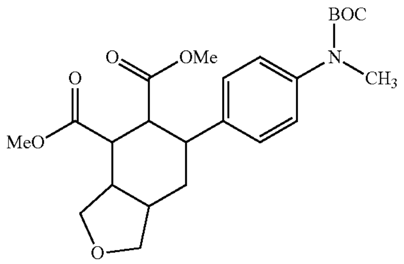 [SMILES: COC(=O)C1C(c2ccc(N(C)C(=O)OC(C)(C)C)cc2)CC2COCC2C1C(=O)OC]

To a mixture of dimethyl 6-(4-((tert-butoxycarbonyl)(methyl)amino)phenyl)-1,3,3a,4,5,6-hexahydroisobenzofuran-4,5-dicarboxylate (5.000 g, 11.22 mmol) in THF (50 mL) was added dihydroxypalladium (1.576 g, 20% Wt, 2.245 mmol) under nitrogen. The reaction was hydrogenated under an $H_2$ bladder for 16 h, filtered through Celite (rinsing with DCM [100 mL]) and concentrated to afford dimethyl 6-(4-((tert-butoxycarbonyl)(methyl)amino)phenyl)octahydroisobenzofuran-4,5-dicarboxylate (5.0 g, 10 mmol, 91% yield) as a syrupy liquid. (Mixture of isomers). $^1$H NMR (400 MHz, DMSO-$d_6$) δ 7.23-7.12 (m, 4H), 3.94-3.83 (m, 1H), 3.77 (dd, J=8.5, 5.5 Hz, 1H), 3.70-3.63 (m, 1H), 3.58 (d, J=2.5 Hz, 3H), 3.45-3.33 (m, 3H), 3.22-3.08 (m, 5H), 3.04-2.91 (m, 2H), 2.44-2.34 (m, 1H), 1.84-1.59 (m, 2H), 1.55-1.43 (m, 1H), 1.40-1.34 (m, 9H). ES-LCMS m/z 392.0 $[M-tert-butyl+H]^+$.

Step 8: dimethyl 6-(4-(methylamino)phenyl)octahydroisobenzofuran-4,5-dicarboxylate

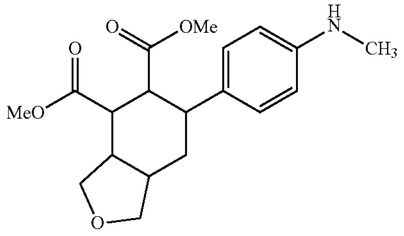 [SMILES: CNc1ccc(C2CC3COCC3C(C(=O)OC)C2C(=O)OC)cc1]

To a mixture of dimethyl 6-(4-((tert-butoxycarbonyl)(methyl)amino)phenyl)octahydroisobenzofuran-4,5-dicarboxylate (7.500 g, 16.76 mmol) in dioxane (80 mL) was added HCl in dioxane (41.90 mL, 4 M, 167.6 mmol). After 16 h the reaction was quenched with water (100 mL) and extracted with DCM (3×100 mL). The combined organic layers were concentrated and subjected to normal phase purification (ethyl acetate in petroleum ether, 0-80% gradient) to afford dimethyl 6-(4-(methylamino)phenyl)octahydroisobenzofuran-4,5-dicarboxylate (6.2 g, 17 mmol, 100% yield) as a syrupy liquid. $^1$H NMR (400 MHz, DMSO-$d_6$) δ6.98-6.84 (m, 2H), 6.48-6.37 (m, 2H), 5.43 (quin, J=4.6 Hz, 1H), 4.03 (q, J=7.0 Hz, 1H), 3.91-3.73 (m, 2H), 3.64-3.49 (m, 4H), 3.43-3.34 (m, 2H), 3.15-3.00 (m, 3H), 2.98-2.85 (m, 1H), 2.65-2.59 (m, 3H), 2.43-2.31 (m, 1H), 1.81-1.54 (m, 2H), 1.43 (q, J=12.7 Hz, 1H). (Mixture of isomers). ES-LCMS m/z 348.1 $[M+H]^+$.

Step 9: 5-(methoxycarbonyl)-6-(4-(methylamino)phenyl)octahydroisobenzofuran-4-carboxylic acid

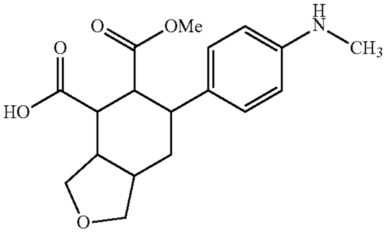 [SMILES: CNc1ccc(C2CC3COCC3C(C(=O)O)C2C(=O)OC)cc1]

To a mixture of dimethyl 6-(4-(methylamino)phenyl)octahydroisobenzofuran-4,5-dicarboxylate (6.200 g, 17.85 mmol) in THF (60 mL) and water (60 mL) was added lithium hydroxide monohydrate (1.123 g, 26.77 mmol). After 16 h, the reaction was concentrated and subjected to reverse phase purification (MeCN in $H_2O$, 0.1% ammonium bicarbonate modifier, 0-100% gradient) to afford 5-(methoxycarbonyl)-6-(4-(methylamino)phenyl)octahydroisobenzofuran-4-carboxylic acid (6.0 g, 14 mmol, 80% yield) as a syrupy liquid. $^1$H NMR (400 MHz, DMSO-$d_6$) δ 6.99-6.81 (m, 2H), 6.45-6.37 (m, 2H), 5.42-5.21 (m, 1H), 3.93-3.67 (m, 2H), 3.62-3.48 (m, 1H), 3.33-3.21 (m, 1H), 3.20-3.08 (m, 3H), 2.97-2.85 (m, 1H), 2.78-2.68 (m, 1H), 2.63 (dd, J=5.0, 2.5 Hz, 3H), 2.59-2.54 (m, 1H), 2.49-2.44 (m, 1H), 2.41-2.20 (m, 1H), 1.91 (q, J=12.7 Hz, 1H), 1.59-1.45 (m, 1H), 1.37-1.23 (m, 1H). (Mixture of isomers). ES-LCMS m/z 334.1 $[M+H]^+$.

Step 10: 5-(methoxycarbonyl)-6-(4-((N,1,2-trimethyl-1H-benzo[d]imidazole)-5-sulfonamido)phenyl)octahydroisobenzofuran-4-carboxylic acid

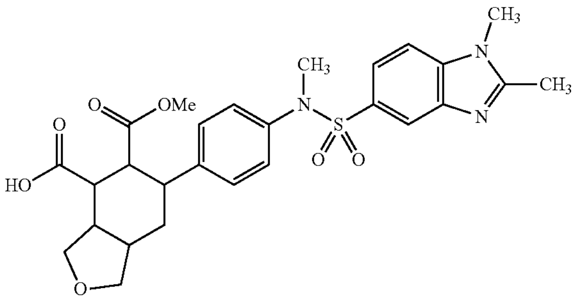

To a mixture of 5-(methoxycarbonyl)-6-(4-(methylamino)phenyl)octahydroisobenzofuran-4-carboxylic acid (6.000 g, 18.00 mmol) in DCM (100 mL) was added 1,2-dimethyl-1H-benzo[d]imidazole-5-sulfonyl chloride (4.844 g, 19.80 mmol) and pyridine (7.118 g, 89.99 mmol). After 16 h the reaction was concentrated and subjected to normal phase purification (methanol in dichloromethane, 0-5% gradient) to afford 5-(methoxycarbonyl)-6-(4-((N,1,2-trimethyl-1H-benzo[d]imidazole)-5-sulfonamido)phenyl)octahydroisobenzofuran-4-carboxylic acid (4.2 g, 7.1 mmol, 39% yield) as a white solid. $^1$H NMR (400 MHz, DMSO-$d_6$) δ 12.49 (br s, 1H), 7.70-7.53 (m, 2H), 7.28 (ddd, J=8.5, 5.3, 1.8 Hz, 1H), 7.20 (d, J=8.5 Hz, 1H), 7.10 (d, J=8.5 Hz, 1H), 7.02-6.88 (m, 2H), 3.94-3.84 (m, 1H), 3.78 (s, 3H), 3.68-3.54 (m, 1H), 3.48-3.34 (m, 3H), 3.19-3.10 (m, 1H), 3.07 (s, 3H), 3.01-2.78 (m, 1H), 2.71-2.59 (m, 1H), 2.56 (s, 3H), 2.46-2.31 (m, 2H), 1.82-1.60 (m, 2H), 1.51-1.34 (m, 1H), 0.90-0.78 (m, 1H). (Mixture of isomers). ES-LCMS m/z 542.2 $[M+H]^+$.

Step 11: methyl 4-(chlorocarbonyl)-6-(4-((N,1,2-trimethyl-1H-benzo[d]imidazole)-5-sulfonamido)phenyl)octahydroisobenzofuran-5-carboxylate

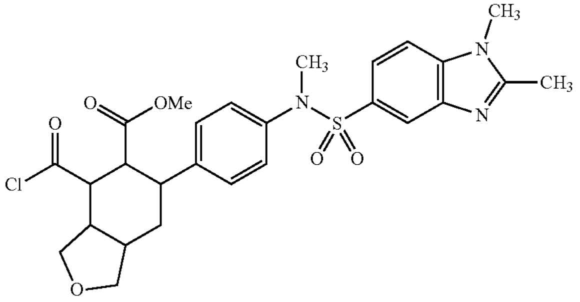

To a mixture of 5-(methoxycarbonyl)-6-(4-((N,1,2-trimethyl-1H-benzo[d]imidazole)-5-sulfonamido)phenyl)octahydroisobenzofuran-4-carboxylic acid (4.200 g, 7.755 mmol) in DCM (50 mL) at 0° C. was added thionyl chloride (9.225 g, 77.55 mmol). The reaction was stirred at RT for 3 h. and concentrated to afford crude methyl 4-(chlorocarbonyl)-6-(4-((N,1,2-trimethyl-1H-benzo[d]imidazole)-5-sulfonamido)phenyl)octahydroisobenzofuran-5-carboxylate (4.2 g, 6.1 mmol, 78% yield) as syrupy liquid. $^1$HNMR not recorded. ES-UPLC m/z 556.3 $[M+methylester]^+$.

Step 12: rac-methyl (3aS,4R,5R,6R,7aS)-4-((2-fluoro-4-(trifluoromethyl)phenyl)carbamoyl)-6-(4-((N,1,2-trimethyl-1H-benzo[d]imidazole)-5-sulfonamido)phenyl)octahydroisobenzofuran-5-carboxylate, rac-methyl (3aR,4R,5R,6S,7aR)-4-((2-fluoro-4-(trifluoromethyl)phenyl)carbamoyl)-6-(4-((N,1,2-trimethyl-1H-benzo[d]imidazole)-5-sulfonamido)phenyl)octahydroisobenzofuran-5-carboxylate and rac-methyl (3aR,4R,5S,6S,7aR)-4-((2-fluoro-4-(trifluoromethyl)phenyl)carbamoyl)-6-(4-((N,1,2-trimethyl-1H-benzo[d]imidazole)-5-sulfonamido)phenyl)octahydroisobenzofuran-5-carboxylate

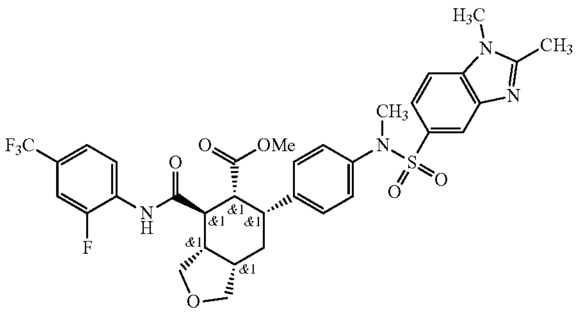

-continued

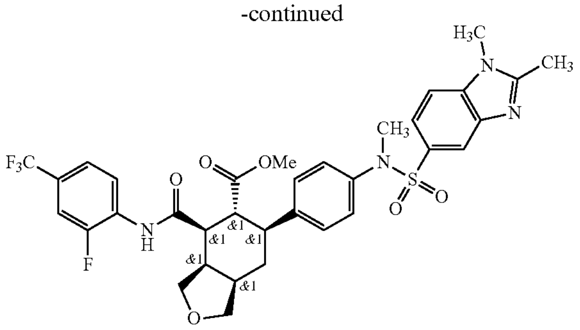

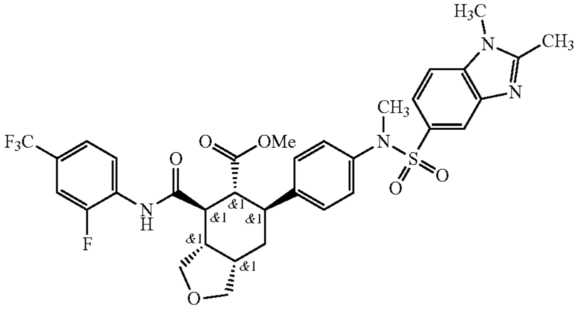

To a mixture of methyl 4-(chlorocarbonyl)-6-(4-((N,1,2-trimethyl-1H-benzo[d]imidazole)-5-sulfonamido)phenyl) octahydroisobenzofuran-5-carboxylate (4.200 g, 7.499 mmol) in DCM (50 mL) was added pyridine (2.966 g, 37.50 mmol) and 2-fluoro-4-(trifluoromethyl)aniline (1.478 g, 8.249 mmol). After 16 h the reaction was concentrated and subjected to reverse phase purification (MeCN in $H_2O$, 0.1% ammonium bicarbonate modifier, 0-100% gradient) to afford methyl 4-((2-fluoro-4-(trifluoromethyl)phenyl)carbamoyl)-6-(4-((N,1,2-trimethyl-1H-benzo[d]imidazole)-5-sulfonamido)phenyl)octahydroisobenzofuran-5-carboxylate (3.1 g, 3.4 mmol, 45% yield) as a white solid. $^1$H NMR (400 MHz, DMSO-$d_6$) δ 12.56 (br s, 1H), 10.28-10.08 (m, 1H), 8.21-8.04 (m, 1H), 7.75 (dd, J=11.0, 2.0 Hz, 1H), 7.69-7.52 (m, 3H), 7.36-7.26 (m, 1H), 7.24-7.14 (m, 2H), 7.05-6.92 (m, 2H), 3.97-3.72 (m, 6H), 3.70-3.54 (m, 1H), 3.46-3.37 (m, 2H), 3.29-3.17 (m, 2H), 3.14-2.96 (m, 5H), 2.65-2.54 (m, 3H), 2.48-2.31 (m, 1H), 1.87-1.78 (m, 1H), 1.74-1.60 (m, 1H). ES-LCMS m/z 703.2 $[M+H]^+$.

The isomers were separated by achiral-Prep-SFC (Column: YMC Hilic (250×20) mm, 5 μm; Mobile Phase: $CO_2$: 0.5% IPAm in IPA (65:35) %;) to afford 3 isomers (relative stereochemistry was determined by 2D NMR structure elucidation).

Isomer 1: rac-methyl (3aS,4R,5R,6R,7aS)-4-((2-fluoro-4-(trifluoromethyl)phenyl)carbamoyl)-6-(4-((N,1,2-trimethyl-1H-benzo[d]imidazole)-5-sulfonamido)phenyl)octahydroisobenzofuran-5-carboxylate (0.73 g, 0.98 mmol, 27% yield) as a white solid. $^1$H NMR (400 MHz, DMSO-$d_6$) δ 10.21 (s, 1H), 8.15 (t, J=8.0 Hz, 1H), 7.74 (dd, J=11.0, 1.5 Hz, 1H), 7.63 (d, J=8.5 Hz, 1H), 7.59 (d, J=1.5 Hz, 1H), 7.55 (d, J=8.0 Hz, 1H), 7.28 (dd, J=8.5, 2.0 Hz, 1H), 7.16 (d, J=8.5 Hz, 2H), 6.97 (d, J=8.5 Hz, 2H), 3.91-3.71 (m, 6H), 3.45-3.34 (m, 3H), 3.28-3.19 (m, 1H), 3.08 (s, 3H), 3.08 (s, 3H), 2.55 (s, 3H), 2.47-2.37 (m, 2H), 1.86-1.77 (m, 1H), 1.74-1.61 (m, 1H). ES-LCMS m/z 703.2 $[M+H]^+$.

Isomer 2: rac-methyl (3aR,4R,5R,6S,7aR)-4-((2-fluoro-4-(trifluoromethyl)phenyl)carbamoyl)-6-(4-((N,1,2-trimethyl-1H-benzo[d]imidazole)-5-sulfonamido)phenyl)octahydroisobenzofuran-5-carboxylate (0.15 g, 0.21 mmol, 5.9% yield) as a white solid. $^1$H NMR (400 MHz, DMSO-$d_6$) δ 10.24 (s, 1H), 8.06 (t, J=8.3 Hz, 1H), 7.73 (dd, J=11.0, 1.5 Hz, 1H), 7.66 (d, J=8.5 Hz, 1H), 7.58-7.52 (m, 2H), 7.31 (dd, J=8.5, 1.5 Hz, 1H), 7.20 (d, J=8.5 Hz, 2H), 6.97 (d, J=8.5 Hz, 2H), 3.92-3.83 (m, 1H), 3.81-3.73 (m, 4H), 3.64-3.50 (m, 3H), 3.19 (s, 3H), 3.09 (s, 3H), 2.99 (t, J=11.5 Hz, 1H), 2.92-2.81 (m, 1H), 2.74-2.65 (m, 1H), 2.56 (s, 3H), 2.44-2.36 (m, 1H), 1.74-1.63 (m, 2H). ES-LCMS m/z 703.0 $[M+H]^+$.

Isomer 3: rac-methyl (3aR,4R,5S,6S,7aR)-4-((2-fluoro-4-(trifluoromethyl)phenyl)carbamoyl)-6-(4-((N,1,2-trimethyl-1H-benzo[d]imidazole)-5-sulfonamido)phenyl)octahydroisobenzofuran-5-carboxylate (0.14 g, 0.18 mmol, 4.9% yield) as a white solid. $^1$H NMR (400 MHz, DMSO-$d_6$) δ 10.14 (s, 1H), 8.10 (t, J=8.0 Hz, 1H), 7.73 (dd, J=11.0, 1.5 Hz, 1H), 7.63 (d, J=8.5 Hz, 1H), 7.58-7.52 (m, 2H), 7.28 (dd, J=8.5, 1.5 Hz, 1H), 7.17 (d, J=8.5 Hz, 2H), 7.00 (d, J=8.5 Hz, 2H), 4.12 (dd, J=10.5, 8.5 Hz, 1H), 3.81-3.71 (m, 5H), 3.67-3.57 (m, 2H), 3.35 (d, J=5.0 Hz, 1H), 3.23 (s, 3H), 3.08 (s, 3H), 3.03-2.94 (m, 1H), 2.80-2.70 (m, 1H), 2.55 (s, 3H), 2.39-2.28 (m, 2H), 1.63 (d, J=6.0 Hz, 1H). ES-LCMS m/z 703.0 $[M+H]^+$.

Intermediate 129 and Intermediate 130: rel-methyl (3aR,4S,5S,6S,7aR)-4-((2-fluoro-4-(trifluoromethyl)phenyl)carbamoyl)-6-(4-((N,1,2-trimethyl-1H-benzo[d]imidazole)-5-sulfonamido)phenyl)octahydroisobenzofuran-5-carboxylate ISOMER 1 and rel-methyl (3aR,4S,5S,6S,7aR)-4-((2-fluoro-4-(trifluoromethyl)phenyl)carbamoyl)-6-(4-((N,1,2-trimethyl-1H-benzo[d]imidazole)-5-sulfonamido)phenyl) octahydroisobenzofuran-5-carboxylate ISOMER 2

ISOMER 1

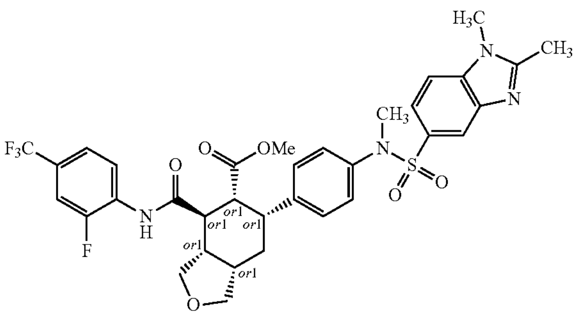

ISOMER 2

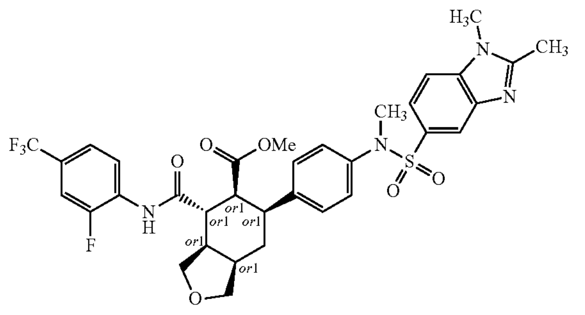

rac-Methyl (3aS,4R,5R,6R,7aS)-4-((2-fluoro-4-(trifluoromethyl)phenyl)carbamoyl)-6-(4-((N,1,2-trimethyl-1H-benzo[d]imidazole)-5-sulfonamido)phenyl)octahydroisobenzofuran-5-carboxylate Intermediate 126 (0.73 g, 0.98 mmol) was separated by Chiral-Prep-SFC (Column:

Chiralcel OD-H (250×20) mm, 5 μm; Mobile Phase: $CO_2$: 0.5% IPAm in IPA 60:40) to afford First-eluting peak rel-methyl (3aR,4S,5S,6S,7aR)-4-((2-fluoro-4-(trifluoromethyl)phenyl)carbamoyl)-6-(4-((N,1,2-trimethyl-1H-benzo[d]imidazole)-5-sulfonamido)phenyl)octahydroisobenzofuran-5-carboxylate ISOMER 1 (0.25 g, 0.36 mmol, 34% yield) as a white solid. $^1$H NMR (400 MHz, DMSO-$d_6$) δ 10.21 (s, 1H), 8.15 (t, J=8.3 Hz, 1H), 7.74 (dd, J=11.0, 1.5 Hz, 1H), 7.63 (d, J=8.5 Hz, 1H), 7.59 (d, J=1.5 Hz, 1H), 7.55 (d, J=9.0 Hz, 1H), 7.28 (dd, J=8.5, 1.5 Hz, 1H), 7.16 (d, J=9.0 Hz, 2H), 6.97 (d, J=8.5 Hz, 2H), 3.93-3.68 (m, 6H), 3.45-3.36 (m, 2H), 3.28-3.14 (m, 2H), 3.08 (s, 3H), 3.08 (s, 3H), 2.55 (s, 3H), 2.46-2.36 (m, 2H), 1.87-1.76 (m, 1H), 1.75-1.59 (m, 1H). ES-LCMS m/z 703.2 [M+H]$^+$, and Second-eluting peak rel-methyl (3aR,4S,5S,6S,7aR)-4-((2-fluoro-4-(trifluoromethyl)phenyl)carbamoyl)-6-(4-((N,1,2-trimethyl-1H-benzo[d]imidazole)-5-sulfonamido)phenyl) octahydroisobenzofuran-5-carboxylate ISOMER 2 (0.28 g, 0.40 mmol, 38% yield) as a white solid. $^1$H NMR (400 MHz, DMSO-$d_6$) δ 10.21 (br s, 1H), 8.15 (t, J=8.0 Hz, 1H), 7.74 (d, J=9.5 Hz, 1H), 7.66-7.52 (m, 3H), 7.28 (dd, J=8.5, 1.5 Hz, 1H), 7.16 (d, J=8.0 Hz, 2H), 6.97 (d, J=8.5 Hz, 2H), 3.91-3.83 (m, 1H), 3.81-3.70 (m, 5H), 3.47-3.36 (m, 2H), 3.28-3.14 (m, 2H), 3.08 (s, 3H), 3.08 (s, 3H), 2.55 (s, 3H), 2.47-2.37 (m, 2H), 1.87-1.77 (m, 1H), 1.67 (q, J=12.3 Hz, 1H). ES-LCMS m/z 703.2 [M+H]$^+$.

Intermediate 131 and Intermediate 132: rel-methyl (3aR,4R,5R,6S,7aR)-4-((2-fluoro-4-(trifluoromethyl)phenyl)carbamoyl)-6-(4-((N,1,2-trimethyl-1H-benzo[d]imidazole)-5-sulfonamido)phenyl)octahydroisobenzofuran-5-carboxylate ISOMER 1 and rel-methyl (3aR,4R,5R,6S,7aR)-4-((2-fluoro-4-(trifluoromethyl)phenyl)carbamoyl)-6-(4-((N,1,2-trimethyl-1H-benzo[d]imidazole)-5-sulfonamido)phenyl) octahydroisobenzofuran-5-carboxylate ISOMER 2

ISOMER 1

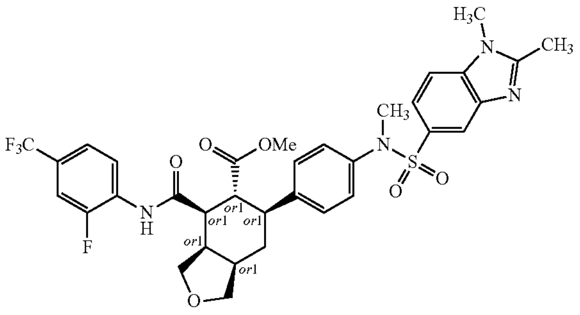

ISOMER 2

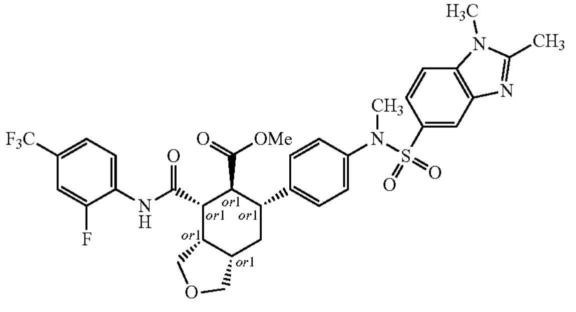

rac-Methyl (3aR,4R,5R,6S,7aR)-4-((2-fluoro-4-(trifluoromethyl)phenyl)carbamoyl)-6-(4-((N,1,2-trimethyl-1H-benzo[d]imidazole)-5-sulfonamido)phenyl)octahydroisobenzofuran-5-carboxylate Intermediate 127 (0.15 g, 0.21 mmol) was separated by Chiral-Prep-SFC (Column: YMC Cellulose-SZ (250×20) mm, 5 μm; Mobile Phase: $CO_2$: 0.5% IPAm in IPA 60:40) to afford First-eluting peak rel-methyl (3aR,4R,5R,6S,7aR)-4-((2-fluoro-4-(trifluoromethyl)phenyl)carbamoyl)-6-(4-((N,1,2-trimethyl-1H-benzo[d]imidazole)-5-sulfonamido)phenyl)octahydroisobenzofuran-5-carboxylate ISOMER 1 (0.040 g, 57 μmol, 33% yield) of pure product was isolated as a white solid. $^1$H NMR (400 MHz, DMSO-$d_6$) δ 10.23 (s, 1H), 8.06 (t, J=8.0 Hz, 1H), 7.73 (dd, J=11.0, 2.0 Hz, 1H), 7.66 (d, J=8.5 Hz, 1H), 7.58-7.52 (m, 2H), 7.31 (dd, J=8.5, 2.0 Hz, 1H), 7.20 (d, J=8.5 Hz, 2H), 6.97 (d, J=8.5 Hz, 2H), 3.86 (dd, J=11.0, 8.5 Hz, 1H), 3.81-3.74 (m, 4H), 3.63-3.51 (m, 3H), 3.19 (s, 3H), 3.09 (s, 3H), 2.99 (t, J=11.5 Hz, 1H), 2.93-2.82 (m, 1H), 2.76-2.69 (m, 1H), 2.56 (s, 3H), 2.44-2.36 (m, 1H), 1.72-1.63 (m, 2H). ES-LCMS m/z 703.2 [M+H]$^+$, and Second-eluting peak rel-methyl (3aR,4R,5R,6S,7aR)-4-((2-fluoro-4-(trifluoromethyl)phenyl)carbamoyl)-6-(4-((N,1,2-trimethyl-1H-benzo[d]imidazole)-5-sulfonamido)phenyl)octahydroisobenzofuran-5-carboxylate ISOMER 2 (0.042 g, 0.060 mmol, 35% yield) as a white solid. $^1$H NMR (400 MHz, DMSO-$d_6$) δ 10.23 (s, 1H), 8.06 (t, J=8.0 Hz, 1H), 7.73 (dd, J=11.0, 1.5 Hz, 1H), 7.66 (d, J=8.5 Hz, 1H), 7.58-7.52 (m, 2H), 7.31 (dd, J=8.5, 2.0 Hz, 1H), 7.20 (d, J=8.5 Hz, 2H), 6.97 (d, J=8.5 Hz, 2H), 3.86 (dd, J=11.0, 8.5 Hz, 1H), 3.81-3.72 (m, 4H), 3.63-3.50 (m, 3H), 3.19 (s, 3H), 3.09 (s, 3H), 2.99 (t, J=11.5 Hz, 1H), 2.91-2.83 (m, 1H), 2.76-2.68 (m, 1H), 2.56 (s, 3H), 2.41-2.35 (m, 1H), 1.72-1.64 (m, 2H). ES-LCMS m/z 703.2 [M+H]$^+$.

Intermediate 133 and Intermediate 134: rel-methyl (3aR,4S,5S,6R,7aR)-4-((2-fluoro-4-(trifluoromethyl)phenyl)carbamoyl)-6-(4-((N,1,2-trimethyl-1H-benzo[d]imidazole)-5-sulfonamido)phenyl)octahydroisobenzofuran-5-carboxylate ISOMER 1 and rel-methyl (3aR,4S,5S,6R,7aR)-4-((2-fluoro-4-(trifluoromethyl)phenyl)carbamoyl)-6-(4-((N,1,2-trimethyl-1H-benzo[d]imidazole)-5-sulfonamido)phenyl) octahydroisobenzofuran-5-carboxylate ISOMER 2

ISOMER 1

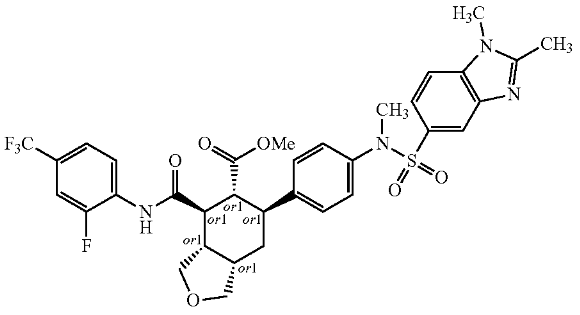

-continued

ISOMER 2

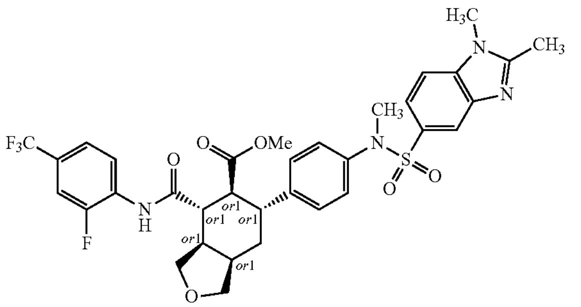

rac-Methyl (3aR,4S,5S,6R,7aR)-4-((2-fluoro-4-(trifluoromethyl)phenyl)carbamoyl)-6-(4-((N,1,2-trimethyl-1H-benzo[d]imidazole)-5-sulfonamido)phenyl)octahydroisobenzofuran-5-carboxylate Intermediate 128 (0.14 g, 0.18 mmol) was separated by Chiral-Prep-SFC (Column: YMC Cellulose-SZ (250×20) mm, 5 μm; Mobile Phase: $CO_2$: 0.5% IPAm in IPA 55:45) to afford First-eluting peak rel-methyl (3aR,4S,5S,6R,7aR)-4-((2-fluoro-4-(trifluoromethyl)phenyl)carbamoyl)-6-(4-((N,1,2-trimethyl-1H-benzo[d]imidazole)-5-sulfonamido)phenyl)octahydroisobenzofuran-5-carboxylate ISOMER 1 (0.040 g, 55 μmol, 29% yield) of pure product was isolated as a white solid. $^1$H NMR (400 MHz, DMSO-$d_6$) δ 10.14 (s, 1H), 8.10 (t, J=8.0 Hz, 1H), 7.73 (dd, J=11.0, 1.5 Hz, 1H), 7.63 (d, J=8.5 Hz, 1H), 7.58-7.52 (m, 2H), 7.28 (dd, J=8.5, 2.0 Hz, 1H), 7.17 (d, J=8.5 Hz, 2H), 7.00 (d, J=8.5 Hz, 2H), 4.12 (dd, J=10.5, 8.5 Hz, 1H), 3.81-3.72 (m, 5H), 3.68-3.55 (m, 2H), 3.38-3.33 (m, 1H), 3.23 (s, 3H), 3.08 (s, 3H), 3.02-2.95 (m, 1H), 2.74 (tt, J=9.8, 5.2 Hz, 1H), 2.55 (s, 3H), 2.40-2.33 (m, 2H), 1.63 (br d, J=7.0 Hz, 1H). ES-LCMS m/z 703.2 $[M+H]^+$, and Second-eluting peak rel-methyl (3aR,4S,5S,6R,7aR)-4-((2-fluoro-4-(trifluoromethyl)phenyl)carbamoyl)-6-(4-((N,1,2-trimethyl-1H-benzo[d]imidazole)-5-sulfonamido)phenyl)octahydroisobenzofuran-5-carboxylate ISOMER 2 (0.040 g, 0.053 mmol, 29% yield) as a white solid. $^1$H NMR (400 MHz, DMSO-$d_6$) δ 10.14 (s, 1H), 8.10 (t, J=8.0 Hz, 1H), 7.73 (dd, J=11.0, 1.5 Hz, 1H), 7.63 (d, J=8.5 Hz, 1H), 7.58-7.52 (m, 2H), 7.28 (dd, J=8.5, 2.0 Hz, 1H), 7.17 (d, J=8.5 Hz, 2H), 7.00 (d, J=8.5 Hz, 2H), 4.12 (dd, J=10.5, 8.5 Hz, 1H), 3.82-3.72 (m, 5H), 3.67-3.56 (m, 2H), 3.38-3.33 (m, 1H), 3.23 (s, 3H), 3.08 (s, 3H), 3.02-2.95 (m, 1H), 2.80-2.70 (m, 1H), 2.55 (s, 3H), 2.42-2.34 (m, 2H), 1.63 (d, J=7.5 Hz, 1H). ES-LCMS m/z 703.2 $[M+H]^+$.

Intermediate 135: rac-benzyl (1R,2R,6S,E)-2-((2-fluoro-4-(trifluoromethyl)phenyl)carbamoyl)-4-((methylsulfonyl)methylene)-6-(4-((N,1,2-trimethyl-1H-benzo[d]imidazole)-5-sulfonamido)phenyl)cyclohexane-1-carboxylate

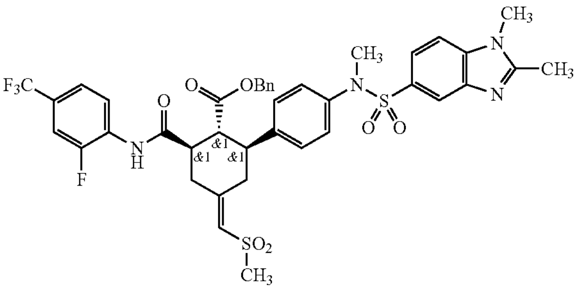 [SMILES: Cc1nc2cc(S(=O)(=O)N(C)c3ccc([C@H]4C/C(=C\S(C)(=O)=O)C[C@@H](C(=O)Nc5ccc(C(F)(F)F)cc5F)[C@@H]4C(=O)OCc4ccccc4)cc3)ccc2n1C]

To a mixture of diethyl ((methylsulfonyl)methyl)phosphonate (1.227 g, 5.328 mmol) in DMF (10 mL) at 0° C. was added NaH (266.4 mg, 60% Wt, 6.660 mmol). After 30 min, rac-benzyl (1R,2R,6S)-2-((2-fluoro-4-(trifluoromethyl)phenyl)carbamoyl)-4-oxo-6-(4-((N,1,2-trimethyl-1H-benzo[d]imidazole)-5-sulfonamido)phenyl)cyclohexane-1-carboxylate Intermediate 46 and Intermediate 47, Step 2 (1.000 g, 1.332 mmol) was added, and the reaction was stirred at room temperature for 5 h, quenched with 1.5 N HCl (20 mL), concentrated and subjected to reverse phase purification (MeCN in $H_2O$, 0.1% formic acid modifier, 0-100% gradient) to afford rac-benzyl (1R,2R,6S,E)-2-((2-fluoro-4-(trifluoromethyl)phenyl)carbamoyl)-4-((methylsulfonyl)methylene)-6-(4-((N,1,2-trimethyl-1H-benzo[d]imidazole)-5-sulfonamido)phenyl)cyclohexane-1-carboxylate (0.33 g, 0.32 mmol, 24% yield) as a white solid.

$^1$H NMR (400 MHz, DMSO-$d_6$) δ 10.36 (s, 1H), 8.12 (t, J=8.3 Hz, 1H), 7.74 (dd, J=11.0, 2.0 Hz, 1H), 7.66-7.51 (m, 4H), 7.32 (dd, J=8.5, 2.0 Hz, 1H), 7.24 (d, J=8.5 Hz, 2H), 7.19-7.10 (m, 3H), 7.03 (d, J=8.5 Hz, 2H), 6.99-6.94 (m, 2H), 5.92 (s, 1H), 4.85 (d, J=12.5 Hz, 1H), 4.61 (d, J=13.0 Hz, 1H), 4.05-3.88 (m, 4H), 3.73 (s, 3H), 3.26 (dd, J=11.8, 10.3 Hz, 2H), 3.12-3.07 (m, 3H), 3.04-2.94 (m, 4H), 2.47 (d, J=2.0 Hz, 2H). ES-LCMS m/z 827.2 $[M+H]^+$.

The following compound was synthesized in an analogous manner to the preparation described above (Intermediate 7, alternate synthesis), using the appropriate aniline precursor:

| Int. | Structure/Name | $^1$H NMR | LCMS |
| --- | --- | --- | --- |
| 136 | 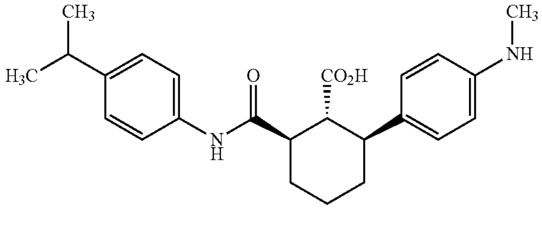 [SMILES: CNc1ccc([C@H]2CCC[C@@H](C(=O)Nc3ccc(C(C)C)cc3)[C@@H]2C(=O)O)cc1] (1R,2R,6S)-2-((4-isopropylphenyl)carbamoyl)-6-(4-(methylamino)phenyl)cyclohexane-1-carboxylic acid | $^1$H NMR (400 MHz, DMSO-ES-$d_6$) δ 11.57 (br s, 1H), 9.81 (s, 1H), 7.47 (d, J = 8.5 Hz, 2H), 7.12 (d, J = 8.5 Hz, 2H), 6.94 (d, J = 8.5 Hz, 2H), 6.43 (d, J = 8.5 Hz, 2H), 5.39 (d, J = 3.5 Hz, 1H), 2.81 (dt, J = 13.6, 6.9 Hz, 1H), 2.71-2.61 (m, 5H), 2.54 (br s, 1H), 1.96-1.81 (m, 2H), 1.69 (d, J = 9.0 Hz, 1H), 1.56-1.42 (m, 3H), 1.16 (d, J = 6.5 Hz, 6H) | LCMS m/z 395.2 $[M + H]^+$. |

Intermediate 137: rac-(3R,4S,5R)-3-((2-fluoro-4-(trifluoromethyl)phenyl)carbamoyl)-5-(4-(methylamino)phenyl)tetrahydro-2H-pyran-4-carboxylic acid

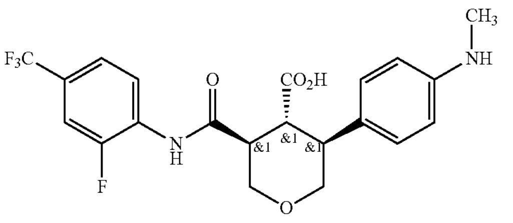 [SMILES: CNc1ccc([C@H]2COC[C@@H](C(=O)Nc3ccc(C(F)(F)F)cc3F)[C@@H]2C(=O)O)cc1]

Step 1: dimethyl 2-(2-(benzyloxy)ethylidene)malonate

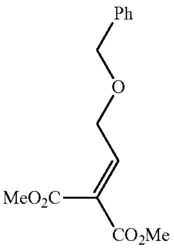 [SMILES: COC(=O)C(=CCOCc1ccccc1)C(=O)OC]

To a mixture of dimethyl malonate (22.0 g, 166 mmol) in DCM (250 mL) at 0° C. was added titanium(IV) chloride (31.6 g, 166 mmol). After 30 min, 2-(benzyloxy)acetaldehyde (25.0 g, 166 mmol) was added, followed by pyridine (26.3 g, 333 mmol), dropwise over 15 min. The reaction was brought to rt for 16 h, quenched with water (100 mL) and extracted with DCM (3×100 mL). The organic layers were washed with brine (100 mL), dried over sodium sulphate, concentrated and subjected to normal phase purification, eluting with 10-50% EtOAc in pet ether to afford dimethyl 2-(2-(benzyloxy)ethylidene)malonate (30.0 g, 0.110 mol, 65.0% yield) as a yellow liquid. $^1H$ NMR (400 MHz, DMSO-$d_6$) δ 6.56-6.50 (m, 5H), 6.24-6.19 (m, 1H), 3.68 (s, 2H), 3.50 (d, J=5.0 Hz, 2H), 2.91 (s, 3H), 2.81 (s, 3H). ES-LCMS m/z 265.1 [M+1]+

Step 2: dimethyl 2-(1-(benzyloxy)-3-(4-bromophenyl)-4-oxo-4-(piperidin-1-yl)butan-2-yl)malonate

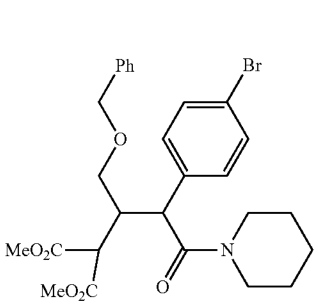 [SMILES: COC(=O)C(C(=O)OC)C(COCc1ccccc1)C(C(=O)N1CCCCC1)c1ccc(Br)cc1]

To a mixture of 2-(4-bromophenyl)-1-(piperidin-1-yl)ethan-1-one (18.0 g, 63.8 mmol) in THF (360 mL) at 0° C. was added lithium bis(trimethylsilyl)amide (1 M in THF, 76.5 mL, 76.547 mmol), drop wise. After 1 h, the reaction was cooled to −78° C., and dimethyl 2-(2-(benzyloxy)ethylidene)malonate (20.2 g, 76.5 mmol) in THF (75 mL) was added drop wise. After 2.5 h, the reaction was quenched by the addition of $NH_4Cl$ (100 mL), and the mixture was extracted with ethyl acetate (3×100 mL). The combined organics were dried over sodium sulphate, concentrated and subjected to reverse phase purification, eluting with 0-100% MeCN in $H_2O$, 0.1% formic acid modifier, to afford dimethyl 2-(1-(benzyloxy)-3-(4-bromophenyl)-4-oxo-4-(piperidin-1-yl)butan-2-yl)malonate (25 g, 34 mmol, 54% yield) as a yellow liquid. $^1H$ NMR (400 MHz, DMSO-$d_6$) δ 7.56-7.46 (m, 2H), 7.39-7.22 (m, 7H), 4.41-4.24 (m, 2H), 3.67-3.62 (m, 2H), 3.59 (d, J=4.5 Hz, 2H), 3.56-3.47 (m, 3H), 3.42 (s, 2H), 3.32 (s, 3H), 3.19-3.08 (m, 1H), 3.06-2.93 (m, 1H), 1.59-1.38 (m, 3H), 1.33-1.18 (m, 2H), 1.02-0.85 (m, 1H), one proton obscured by solvent peak. ES-LCMS m/z 548.2 $[M+1]^+$ Step 3: 3-((benzyloxy)methyl)-2-(4-bromophenyl)-5-hydroxy-4-(hydroxymethyl)-1-(piperidin-1-yl)pentan-1-one

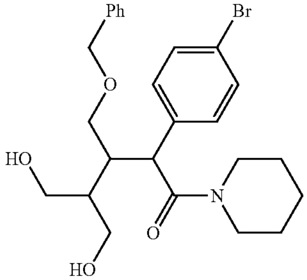 [SMILES: O=C(C(c1ccc(Br)cc1)C(COCc1ccccc1)C(CO)CO)N1CCCCC1]

To a mixture of dimethyl 2-(1-(benzyloxy)-3-(4-bromophenyl)-4-oxo-4-(piperidin-1-yl)butan-2-yl)malonate (25.0 g, 45.7 mmol) in THF (500 mL) at 0° C. was added lithium borohydride (10.0 g, 457 mmol) portion wise. After 16 h at 25° C., the reaction was quenched with saturated ammonium chloride (200 mL) at 0° C., warmed to rt and extracted with ethyl acetate (3×100 mL). The organic layers were dried over sodium sulfate, concentrated and subjected to reverse phase purification, eluting with 0-100% MeCN in $H_2O$, 0.1% formic acid modifier, to afford 3-((benzyloxy)methyl)-2-(4-bromophenyl)-5-hydroxy-4-(hydroxymethyl)-1-(piperidin-1-yl)pentan-1-one (14 g, 22 mmol, 48% yield) as an off-white solid. $^1H$ NMR (400 MHz, DMSO-$d_6$) δ 7.51-7.45 (m, 2H), 7.38-7.32 (m, 2H), 7.38-7.23 (m, 4H), 7.20-7.11 (m, 1H), 4.43-4.36 (m, 1H), 4.33-4.28 (m, 1H), 4.12-4.07 (m, 3H), 3.60-3.55 (m, 1H), 3.56-3.48 (m, 3H), 3.44-3.37 (m, 3H), 3.01 (dd, J=10.0, 5.5 Hz, 1H), 2.71-2.64 (m, 1H), 2.56 (ddd, J=10.9, 5.6, 2.5 Hz, 1H), 1.80 (td, J=6.3, 2.5 Hz, 1H), 1.59-1.18 (m, 6H), 1.12-0.91 (m, 1H). ES-LCMS m/z 492.3 [M+1]+

Step 4: 4-((benzyloxy)methyl)-3-(4-bromophenyl)-5-(hydroxymethyl)tetrahydro-2H-pyran-2-one

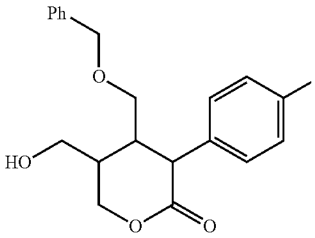

To a mixture of 3-((benzyloxy)methyl)-2-(4-bromophenyl)-5-hydroxy-4-(hydroxymethyl)-1-(piperidin-1-yl)pentan-1-one (13.5 g, 27.5 mmol) in toluene (135 mL) and DCM (45 mL) was added methanesulfonic acid (4.87 g, 50.6 mmol). The reaction was stirred at 28° C. for 16 h, quenched with saturated $NaHCO_3$ (100 mL) and extracted with EtOAc (3×100 mL). The combined organics were washed with brine (100 mL) dried over sodium sulfate, concentrated and subjected to reverse phase purification, eluting with 50-85% MeCN in $H_2O$, 0.1% formic acid modifier, to afford 4-((benzyloxy)methyl)-3-(4-bromophenyl)-5-(hydroxymethyl)tetrahydro-2H-pyran-2-one (8.6 g, 16 mmol, 58% yield) as a yellow liquid. $^1$H NMR (400 MHz, DMSO-$d_6$) δ 7.53-7.46 (m, 2H), 7.40-7.21 (m, 5H), 7.20-7.12 (m, 2H), 4.90 (t, J=5.3 Hz, 1H), 4.45-4.37 (m, 3H), 4.09 (q, J=5.5 Hz, 1H), 3.43-3.37 (m, 2H), 2.21-2.11 (m, 1H), 2.00-1.87 (m, 1H), 1.61-1.50 (m, 1H), 1.44-1.31 (m, 1H). ES-LCMS m/z 407.0 $[M+1]^+$ Step 5: 3-((benzyloxy)methyl)-2-(4-bromophenyl)-4-(hydroxymethyl)pentane-1,5-diol

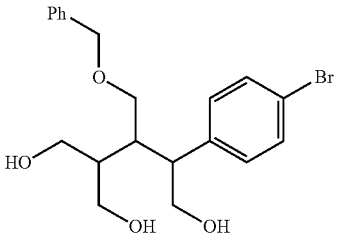 [SMILES: OCC(CO)C(COCc1ccccc1)C(CO)c1ccc(Br)cc1]

To a mixture of 4-((benzyloxy)methyl)-3-(4-bromophenyl)-5-(hydroxymethyl)tetrahydro-2H-pyran-2-one (8.50 g, 21.0 mmol) in THF (160 mL) at −78° C. was added diisobutylaluminum hydride (1M in THF, 83.9 mL, 83.9 mmol). After 16 h at rt, the reaction was quenched with aq ammonium chloride (50 mL), filtered through Celite and extracted with ethyl acetate (5×100 mL). The combined organics were washed with brine (250 mL) concentrated and subjected to reverse phase purification, eluting with 0-100% MeCN in $H_2O$, 0.1% formic acid modifier, to afford 3-((benzyloxy)methyl)-2-(4-bromophenyl)-4-(hydroxymethyl)pentane-1,5-diol (6.6 g, 9.7 mmol, 46% yield) as a colorless gum. $^1$H NMR (400 MHz, DMSO-$d_6$) δ 7.48-7.39 (m, 2H), 7.38-7.09 (m, 7H), 4.55-4.29 (m, 3H), 4.38-4.26 (m, 1H), 4.22-4.13 (m, 1H), 3.67 (d, J=4.5 Hz, 1H), 3.60-3.43 (m, 3H), 3.08-2.90 (m, 1H), 2.88-2.79 (m, 1H), 2.26-2.13 (m, 1H), 1.95-1.82 (m, 1H), 1.68-1.28 (m, 2H). ES-LCMS m/z 409.1 $[M+1]^+$ Step 6: (4-((benzyloxy)methyl)-5-(4-bromophenyl)tetrahydro-2H-pyran-3-yl)methanol

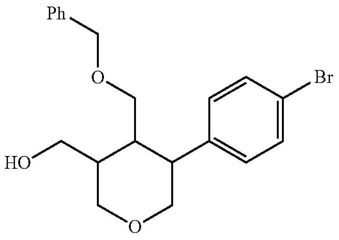 [SMILES: OCC1COCC(c2ccc(Br)cc2)C1COCc1ccccc1]

To a mixture of 3-((benzyloxy)methyl)-2-(4-bromophenyl)-4-(hydroxymethyl)pentane-1,5-diol (6.60 g, 16.1 mmol) in THF (198 mL) at 0° C. was added sodium hydride (60% in mineral oil, 1.94 g, 48.4 mmol). After 30 min 1-((4-methylphenyl)sulfonyl)-1H-imidazole (3.94 g, 17.7 mmol) was added, and the reaction was stirred at 25° C. After 16 h, the reaction was quenched with ice water (100 mL) and extracted with EtOAc (4×50 mL). The combined organics were washed with water (2×50 mL) and brine (50 mL), dried over sodium sulfate, concentrated and subjected to reverse phase purification, eluting with 45-100% MeCN in $H_2O$, 0.1% formic acid modifier, to afford (4-((benzyloxy)methyl)-5-(4-bromophenyl)tetrahydro-2H-pyran-3-yl)methanol (2.5 g, 5.1 mmol, 32% yield) as a yellow oil. $^1$H NMR (400 MHz, DMSO-$d_6$) δ 7.52-7.41 (m, 2H), 7.39-7.10 (m, 7H), 4.51-4.41 (m, 1H), 4.38-4.22 (m, 2H), 4.14-3.89 (m, 2H), 3.73-3.54 (m, 2H), 3.50-3.32 (m, 4H), 3.09-2.99 (m, 1H), 2.92-2.75 (m, 1H), 1.93-1.83 (m, 1H). ES-LCMS m/z 393.0 $[M+1]^+$ Step 7: 4-((benzyloxy)methyl)-5-(4-bromophenyl)tetrahydro-2H-pyran-3-carboxylic acid

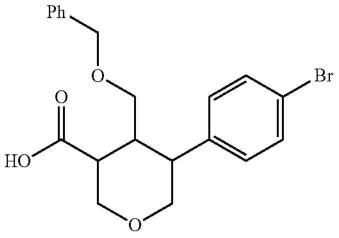 [SMILES: O=C(O)C1COCC(c2ccc(Br)cc2)C1COCc1ccccc1]

To a mixture of (4-((benzyloxy)methyl)-5-(4-bromophenyl)tetrahydro-2H-pyran-3-yl)methanol (1.00 g, 2.56 mmol) in acetone (30 mL) at 0° C. was added Jones reagent (2 M aq., 3.19 mL, 6.39 mmol). After 3 h at rt, the reaction was concentrated, diluted with water (10 mL) and extracted with EtOAc (4×20 mL). The combined EtOAc layers were washed with water (2×20 mL) and brine (20 mL) dried over sodium sulfate, concentrated and subjected to reverse phase purification, eluting with 10-100% MeCN in $H_2O$, 0.1% formic acid modifier, to afford 4-((benzyloxy)methyl)-5-(4-bromophenyl)tetrahydro-2H-pyran-3-carboxylic acid (510 mg, 1.0 mmol, 40% yield) as a yellow oil. $^1$H NMR (400 MHz, DMSO-$d_6$) δ 12.44 (br s, 1H), 7.51-7.44 (m, 2H), 7.38-7.19 (m, 7H), 4.48-4.39 (m, 1H), 4.37-4.16 (m, 2H), 4.11-4.01 (m, 1H), 3.81-3.69 (m, 2H), 3.55-3.41 (m, 1H), 3.29-3.21 (m, 1H), 3.09-3.01 (m, 1H), 2.92-2.78 (m, 1H), 2.77-2.64 (m, 1H). ES-LCMS m/z 407.0 [M+1]$^+$ Step 8: 4-((benzyloxy)methyl)-5-(4-bromophenyl)-N-(2-fluoro-4-(trifluoromethyl)phenyl)tetrahydro-2H-pyran-3-carboxamide

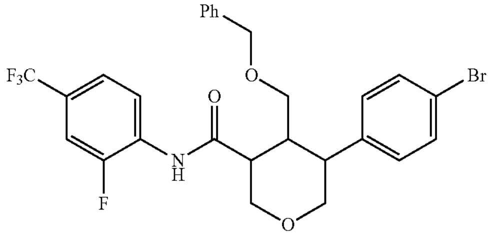 [SMILES: O=C(Nc1ccc(C(F)(F)F)cc1F)C1COCC(c2ccc(Br)cc2)C1COCc1ccccc1]

To a mixture of 4-((benzyloxy)methyl)-5-(4-bromophenyl)tetrahydro-2H-pyran-3-carboxylic acid (620 mg, 1.53 mmol) in acetonitrile (2 mL) at 0° C. was added 1-methylimidazole (628 mg, 7.65 mmol) followed by 2-fluoro-4-(trifluoromethyl)aniline (274 mg, 1.53 mmol) and N,N,N',N'-tetramethylchloroformamidinium hexafluorophosphate (1.07 g, 3.82 mmol). After 16 h at rt, the reaction was concentrated and triturated with water (10 mL) to obtain 4-((benzyloxy)methyl)-5-(4-bromophenyl)-N-(2-fluoro-4-(trifluoromethyl)phenyl)tetrahydro-2H-pyran-3-carboxamide (150 mg, 0.21 mmol, 14% yield) as a yellow solid. $^1$H NMR (400 MHz, DMSO-$d_6$) δ 10.14 (s, 1H), 8.22-8.15 (m, 1H), 7.38-7.30 (m, 4H), 7.20-7.16 (m, 3H), 7.11 (s, 4H), 4.30-4.28 (m, 1H), 4.26 (s, 1H), 4.06-3.95 (m, 2H), 3.87-3.70 (m, 4H), 3.42 (dt, J=11.5, 5.8 Hz, 1H), 3.02-2.92 (m, 2H). ES-LCMS m/z 568.1 [M+1]$^+$ Step 9: 5-(4-bromophenyl)-N-(2-fluoro-4-(trifluoromethyl)phenyl)-4-(hydroxymethyl)tetrahydro-2H-pyran-3-carboxamide

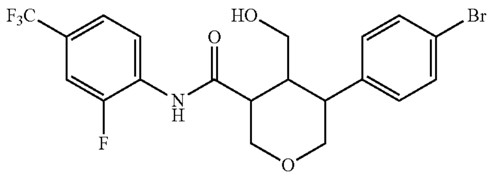 [SMILES: O=C(Nc1ccc(C(F)(F)F)cc1F)C1COCC(c2ccc(Br)cc2)C1CO]

To a mixture of 4-((benzyloxy)methyl)-5-(4-bromophenyl)-N-(2-fluoro-4-(trifluoromethyl)phenyl)tetrahydro-2H-pyran-3-carboxamide (150 mg, 265 μmol) in DCM (5 mL) at 0° C. was added boron trichloride (1M in DCM, 0.794 mL, 794 μmol). After 2 h at rt, the reaction was quenched with ice water (10 mL), concentrated and subjected to reverse phase purification, eluting with 10-100% MeCN in $H_2O$, 0.1% formic acid modifier, to afford 5-(4-bromophenyl)-N-(2-fluoro-4-(trifluoromethyl)phenyl)-4-(hydroxymethyl)tetrahydro-2H-pyran-3-carboxamide (65 mg, 96 μmol, 36% yield) as a yellow oil. $^1$H NMR (300 MHz, DMSO-$d_6$) δ 10.15-10.09 (m, 1H), 8.24-8.16 (m, 1H), 7.76-7.67 (m, 1H), 7.40-7.32 (m, 2H), 7.30-7.23 (m, 3H), 4.64-4.55 (m, 1H), 4.51-4.41 (m, 1H), 4.15-4.01 (m, 3H), 3.84-3.73 (m, 2H), 3.43-3.36 (m, 1H), 3.09 (dd, J=8.1, 4.8 Hz, 2H). ES-LCMS m/z 476.1 [M+1]$^+$ Step 10: rac-(3R,4S,5R)-3-(4-bromophenyl)-5-((2-fluoro-4-(trifluoromethyl)phenyl)carbamoyl)tetrahydro-2H-pyran-4-carboxylic acid

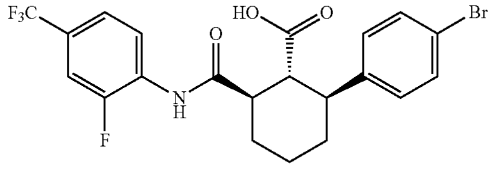 [SMILES: O=C(O)[C@@H]1[C@@H](c2ccc(Br)cc2)CCC[C@H]1C(=O)Nc1ccc(C(F)(F)F)cc1F]

To a mixture of 5-(4-bromophenyl)-N-(2-fluoro-4-(trifluoromethyl)phenyl)-4-(hydroxymethyl)tetrahydro-2H-pyran-3-carboxamide (130 mg, 273 μmol) in acetone (5 mL) at 0° C. was added Jones reagent (2M aq., 341 μL, 682 μmol). After 3 h at rt., the reaction was quenched with ice water (2 mL), concentrated and purified by reverse phase purification, eluting with 55-85% MeCN in $H_2O$, 0.1% formic acid modifier, followed by another purification by prep HPLC (Column: X-SELECT CSH-C18 20-80% MeCN in $H_2O$, 0.1% TFA modifier) to afford rac-(3R,4S,5R)-3-(4-bromophenyl)-5-((2-fluoro-4-(trifluoromethyl)phenyl)carbamoyl)tetrahydro-2H-pyran-4-carboxylic acid (20 mg, 40 μmol, 15% yield) as a yellow oil. $^1$H NMR (400 MHz, DMSO-$d_6$) δ 12.11 (br s, 1H), 10.32 (s, 1H), 8.17 (t, J=8.0 Hz, 1H), 7.73 (dd, J=11.0, 2.0 Hz, 1H), 7.56 (d, J=8.0 Hz, 1H), 7.50 (d, J=8.5 Hz, 2H), 7.31 (d, J=8.5 Hz, 2H), 4.16 (dd, J=11.0, 4.5 Hz, 1H), 3.79 (dd, J=11.0, 4.5 Hz, 1H), 3.54 (t, J=11.0 Hz, 1H), 3.47 (t, J=11.3 Hz, 1H), 3.29-3.23 (m, 1H), 3.15 (t, J=11.3 Hz, 1H), 2.96 (td, J=11.5, 4.5 Hz, 1H). ES-LCMS m/z 490.0 [M+1]$^+$ Step 11: rac-(3R,4S,5R)-3-((2-fluoro-4-(trifluoromethyl)phenyl)carbamoyl)-5-(4-(methylamino)phenyl)tetrahydro-2H-pyran-4-carboxylic acid

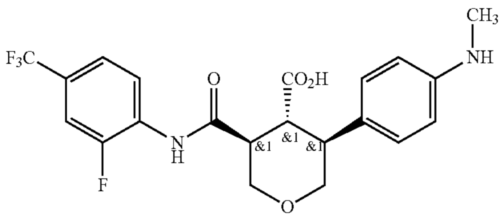 [SMILES: CNc1ccc([C@H]2COC[C@@H](C(=O)Nc3ccc(C(F)(F)F)cc3F)[C@@H]2C(=O)O)cc1]

To a mixture of rac-(3R,4S,5R)-3-(4-bromophenyl)-5-((2-fluoro-4-(trifluoromethyl)phenyl)carbamoyl)tetrahydro-2H-pyran-4-carboxylic acid (14.0 mg, 28.6 μmol) in dioxane (2 mL) was added sodium 2-methylpropan-2-olate (4.12 mg, 42.8 μmol) and tBuXPhos Pd G3 (2.27 mg, 2.86 μmol). The reaction was degassed for 5 min, and methylamine (2M in THF, 0.286 mL, 571 μmol) was added drop wise. The mixture was heated at 100° C. in a Biotage Initiator for 1 h, concentrated and subjected to reverse phase purification eluting with 0-100% MeCN in $H_2O$, 0.1% ammonium bicarbonate modifier, to afford rac-(3R,4S,5R)-3-((2-fluoro-4-(trifluoromethyl)phenyl)carbamoyl)-5-(4-(methylamino)phenyl)tetrahydro-2H-pyran-4-carboxylic acid (9.0 mg, 20 μmol, 70% yield) as an off-white solid. $^1$H NMR (400 MHz, DMSO-$d_6$) δ 11.98 (s, 1H), 10.39-10.27 (m, 1H), 8.17 (t, J=8.0 Hz, 1H), 7.72 (d, J=10.5 Hz, 1H), 7.56 (d, J=8.5 Hz, 1H), 7.00 (d, J=8.5 Hz, 2H), 6.45 (d, J=8.5 Hz, 2H), 5.51 (d, J=4.5 Hz, 1H), 4.12 (dd, J=10.8, 3.8 Hz, 1H), 3.72 (dd, J=11.5, 4.5 Hz, 1H), 3.48 (t, J=11.3 Hz, 1H), 3.39-3.35 (m, 1H), 3.24 (dd, J=11.3, 3.8 Hz, 1H), 3.03 (t, J=11.3 Hz, 1H), 2.78 (td, J=11.5, 4.5 Hz, 1H), 2.64 (d, J=4.0 Hz, 3H). ES-LCMS m/z 441.2 $[M+1]^+$ Example 1

(1R,2S,6R)-2-(4-(1H-indazol-4-yl)phenyl)-6-((2-fluoro-4-(trifluoromethyl)phenyl)carbamoyl)cyclohexane-1-carboxylic acid

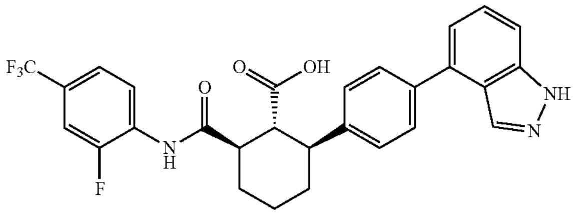 [SMILES: O=C(O)[C@@H]1[C@@H](c2ccc(-c3cccc4[nH]ncc34)cc2)CCC[C@H]1C(=O)Nc1ccc(C(F)(F)F)cc1F]

To a vial containing (1H-indazol-4-yl)boronic acid (32.4 mg, 0.200 mmol) a solution of APhos Pd G3 (3.18 mg, 5.00 μmol), DPPF Pd G3 (4.62 mg, 5.00 μmol) and (1R,2S,6R)-2-(4-bromophenyl)-6-((2-fluoro-4-(trifluoromethyl)phenyl)carbamoyl)cyclohexane-1-carboxylic acid, Intermediate 1 (48.8 mg, 100 μmol) in dioxane (0.800 mL) was added, followed by aqueous potassium carbonate (2 M, 0.200 mL, 0.400 mmol). The reaction was capped and heated to 80° C. for 15 h. MeOH (1 mL) was added, and the reaction was filtered, using additional MeOH to rinse. The effluent was concentrated under a stream of nitrogen. The residue was taken up in 1:1 DMSO:MeOH (1.5 mL), filtered and subjected to reverse phase purification (MeCN in 10 mM ammonium bicarbonate in $H_2O$ adjusted to pH 10 with ammonia, 15-100% gradient) to afford (1R,2S,6R)-2-(4-(1H-indazol-4-yl)phenyl)-6-((2-fluoro-4-trifluoromethyl)phenyl)carbamoyl)cyclohexane-1-carboxylic acid (25.6 mg, 46.8 μmol, 24.6% yield). $^1H$ NMR (600 MHz, DMSO-$d_6$) δ 13.22 (br s, 1H), 10.13 (br s, 1H), 8.23 (br t, J=8.2 Hz, 1H), 8.16 (s, 1H), 7.73 (br dd, J=1.8, 10.9 Hz, 1H), 7.68 (d, J=8.0 Hz, 2H), 7.56 (br d, J=8.4 Hz, 1H), 7.53 (d, J=8.4 Hz, 1H), 7.43 (td, J=3.5, 8.3 Hz, 3H), 7.23 (d, J=6.5 Hz, 1H), 3.09-3.02 (m, 1H), 2.89 (br t, J=11.1 Hz, 1H), 2.81 (dt, J=3.3, 11.6 Hz, 1H), 2.07-2.03 (m, 1H), 1.94-1.90 (m, 1H), 1.87-1.82 (m, 1H), 1.70-1.53 (m, 3H). ES-LCMS m/z 526.3 $[M+H]^+$.

The following compounds were synthesized in an analogous manner to the preparation described above in Example 1, using the relevant boronic acid or ester precursors from commercial sources or the Intermediate synthesis section. Compounds were purified using reverse phase chromatography (MeCN/$H_2O$, basic or acidic modifiers).

| Ex | Structure/Name | $^1H$ NMR | LCMS |
|---|---|---|---|
| 2 | 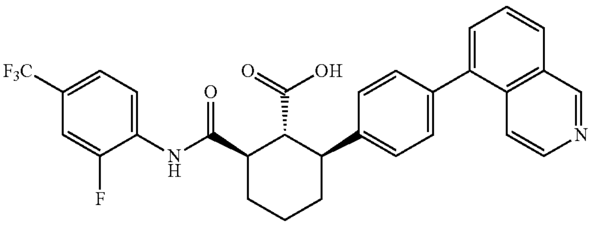 [SMILES: O=C(O)[C@@H]1[C@@H](c2ccc(-c3cccc4cnccc34)cc2)CCC[C@H]1C(=O)Nc1ccc(C(F)(F)F)cc1F] (1R,2R,6S)-2-((2-fluoro-4-(trifluoromethyl)phenyl)carbamoyl)-6-(4-(isoquinolin-5-yl)phenyl)cyclohexane-1-carboxylic acid | $^1H$ NMR (600 MHz, DMSO-$d_6$) δ 11.87 (br s, 1H), 10.13 (br s, 1H), 9.40 (br d, J = 0.7 Hz, 1H), 8.51 (d, J = 6.2 Hz, 1H), 8.26-8.22 (m, 1H), 8.16 (br d, J = 7.6 Hz, 1H), 7.80-7.70 (m, 3H), 7.66 (br d, J = 5.8 Hz, 1H), 7.57 (br d, J = 8.7 Hz, 1H), 7.50-7.41 (m, 4H), 3.10-3.04 (m, 1H), 2.95-2.89 (m, 1H), 2.84 (dt, J = 3.1, 11.7 Hz, 1H), 2.06 (br d, J = 9.1 Hz, 1H), 1.93 (br dd, J = 3.5, 6.4 Hz, 1H), 1.90-1.84 (m, 1H), 1.73-1.65 (m, 1H), 1.62-1.55 (m, 2H). | ES-LCMS m/z 537.3 $[M + H]^+$. |
| 3 | 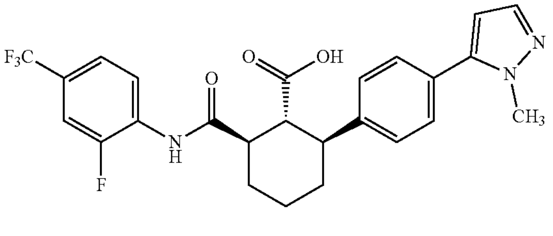 [SMILES: Cn1nccc1-c1ccc([C@H]2CCC[C@@H](C(=O)Nc3ccc(C(F)(F)F)cc3F)[C@@H]2C(=O)O)cc1] (1R,2R,6S)-2-((2-fluoro-4-(trifluoromethyl)phenyl)carbamoyl)-6-(4-(1-methyl-1H-pyrazol-5-yl)phenyl)cyclohexane-1-carboxylic acid | $^1H$ NMR (600 MHz, DMSO-$d_6$) δ 11.84-11.81 (m, 1H), 10.12 (br s, 1H), 8.24-8.20 (m, 1H), 7.74-7.71 (m, 1H), 7.56 (br d, J = 8.7 Hz, 1H), 7.47-7.44 (m, 3H), 7.39 (br d, J = 8.4 Hz, 2H), 6.38 (d, J = 1.8 Hz, 1H), 3.85 (s, 3H), 3.06-3.00 (m, 1H), 2.90-2.84 (m, 1H), 2.78 (dt, J = 3.5, 11.5 Hz, 1H), 2.06-2.00 (m, 1H), 1.92-1.88 (m, 1H), 1.83-1.78 (m, 1H), 1.67-1.60 (m, 1H), 1.59-1.49 (m, 2H). | ES-LCMS m/z 490.4 $[M + H]^+$. |

-continued

| Ex | Structure/Name | $^1$H NMR | LCMS |
|---|---|---|---|
| 4 | 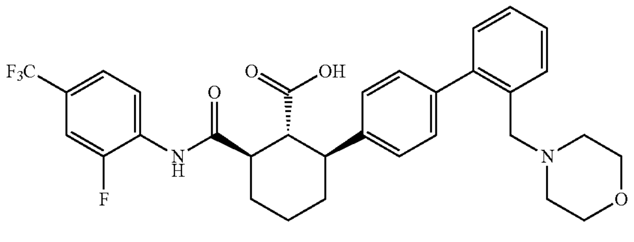 [SMILES: O=C(O)[C@@H]1[C@@H](c2ccc(-c3ccccc3CN3CCOCC3)cc2)CCC[C@H]1C(=O)Nc1ccc(C(F)(F)F)cc1F] (1R,2R,6S)-2-((2-fluoro-4-(trifluoromethyl)phenyl)carbamoyl)-6-(2'-(morpholinomethyl)-[1,1'-biphenyl]-4-yl)cyclohexane-1-carboxylic acid | $^1$H NMR (600 MHz, DMSO-$d_6$) δ 11.85-11.80 (m, 1H), 10.11 (br s, 1H), 8.24-8.21 (m, 1H), 7.72 (br dd, J = 1.8, 10.9 Hz, 1H), 7.56 (br d, J = 8.0 Hz, 1H), 7.49 (dd, J= 1.6, 7.4 Hz, 1H), 7.40-7.28 (m, 6H), 7.23 (dd, J = 1.8, 7.3 Hz, 1H), 3.52 (br t, J = 4.5 Hz, 2H), 3.34 (s, 6H), 3.06-3.01 (m, 1H), 2.86 (br t, J = 11.1 Hz, 1H), 2.77 (dt, J = 3.3, 11.8 Hz, 1H), 2.50 (br s, 4H), 2.06-2.00 (m, 1H), 1.91 (td, J = 2.8, 6.0 Hz, 1H), 1.85-1.80 (m, 1H), 1.69-1.60 (m, 1H), 1.59-1.50 (m, 2H). | ES LCMS m/z 585.4 $[M + H]^+$. |
| 5 | 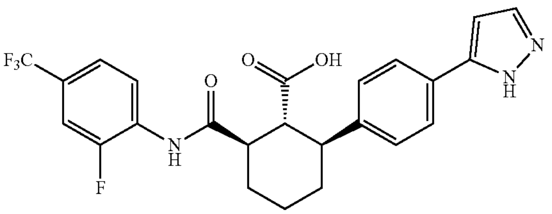 [SMILES: O=C(O)[C@@H]1[C@@H](c2ccc(-c3ccn[nH]3)cc2)CCC[C@H]1C(=O)Nc1ccc(C(F)(F)F)cc1F] (1R,2S,6R)-2-(4-(1H-pyrazol-5-yl)phenyl)-6-((2-fluoro-4-(trifluoromethyl)phenyl)carbamoyl)cyclohexane-1-carboxylic acid | $^1$H NMR (600 MHz, DMSO-$d_6$) δ 12.83-12.80 (m, 1H), 11.80-11.76 (m, 1H), 10.11 (br s, 1H), 8.24-8.20 (m, 1H), 7.74-7.67 (m, 3H), 7.55 (br d, J = 9.1 Hz, 2H), 7.29 (br s, 2H), 6.66 (br s, 1H), 3.04-2.99 (m, 1H), 2.85-2.80 (m, 1H), 2.72 (dt, J = 2.9, 11.8 Hz, 1H), 2.05-2.00 (m, 1H), 1.90 (td, J = 3.1, 6.2 Hz, 1H), 1.81-1.76 (m, 1H), 1.64-1.59 (m, 1H), 1.57-1.50 (m, 2H). | ES LCMS m/z 476.4 $[M + H]^+$. |
| 6 | 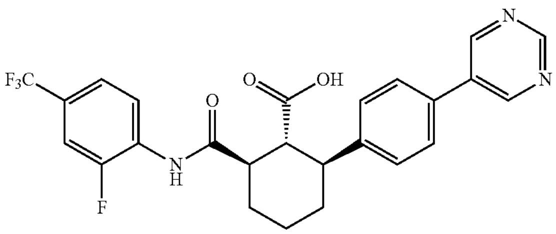 [SMILES: O=C(O)[C@@H]1[C@@H](c2ccc(-c3cncnc3)cc2)CCC[C@H]1C(=O)Nc1ccc(C(F)(F)F)cc1F] (1R,2R,6S)-2-((2-fluoro-4-(trifluoromethyl)phenyl)carbamoyl)-6-(4-(pyrimidin-5-yl)phenyl)cyclohexane-1-carboxylic acid | $^1$H NMR (600 MHz, DMSO-$d_6$) δ 11.82 (br s, 1H), 10.12 (s, 1H), 9.18 (s, 1H), 9.14 (s, 2H), 8.22 (br t, J = 8.0 Hz, 1H), 7.75 (d, J = 8.0 Hz, 2H), 7.72 (dd, J = 1.6, 11.1 Hz, 1H), 7.56 (br d, J = 8.7 Hz, 1H), 7.44 (d, J = 8.0 Hz, 2H), 3.04 (dt, J = 3.1, 11.2 Hz, 1H), 2.89 (t, J = 11.1 Hz, 1H), 2.80 (dt, J = 3.1, 11.7 Hz, 1H), 2.04 (br d, J = 10.5 Hz, 1H), 1.94-1.88 (m, 1H), 1.82-1.77 (m, 1H), 1.69-1.61 (m, 1H), 1.61-1.51 (m, 2H). | ES-LCMS m/z 488.3 $[M + H]^+$. |
| 7 | 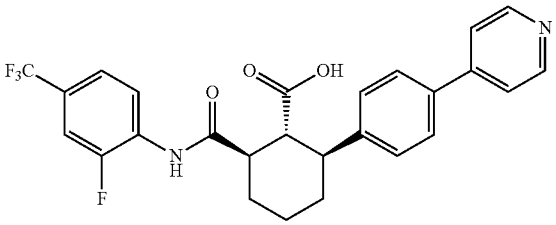 [SMILES: O=C(O)[C@@H]1[C@@H](c2ccc(-c3ccncc3)cc2)CCC[C@H]1C(=O)Nc1ccc(C(F)(F)F)cc1F] (1R,2R,6S)-2-((2-fluoro-4-(trifluoromethyl)phenyl)carbamoyl)-6-(4-(pyridin-4-yl)phenyl)cyclohexane-1-carboxylic acid | $^1$H NMR (600 MHz, DMSO-$d_6$) δ 11.81 (br s, 1H), 10.12 (s, 1H), 8.64-8.60 (m, 2H), 8.22 (br t, J = 8.2 Hz, 1H), 7.74 (d, J = 8.4 Hz, 2H), 7.72-7.67 (m, 3H), 7.56 (br d, J = 8.7 Hz, 1H), 7.42 (d, J = 8.0 Hz, 2H), 3.04 (dt, J = 3.3, 11.3 Hz, 1H), 2.88 (t, J = 11.1 Hz, 1H), 2.79 (dt, J = 3.3, 11.8 Hz, 1H), 2.04 (br d, J = 10.2 Hz, 1H), 1.92-1.88 (m, 1H), 1.82-1.78 (m, 1H), 1.68-1.61 (m, 1H), 1.59-1.52 (m, 2H). | ES-LCMS m/z 487.3 $[M + H]^+$. |

-continued

| Ex | Structure/Name | $^{1}$H NMR | LCMS |
|---|---|---|---|
| 8 | 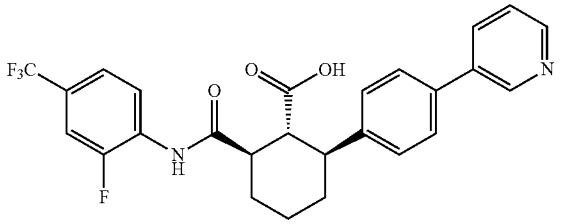 [SMILES: O=C(O)[C@@H]1[C@@H](c2ccc(-c3cccnc3)cc2)CCC[C@H]1C(=O)Nc1ccc(C(F)(F)F)cc1F]<br>(1R,2R,6S)-2-((2-fluoro-4-(trifluoromethyl)phenyl)carbamoyl)-6-(4-(pyridin-3-yl)phenyl)cyclohexane-1-carboxylic acid | $^{1}$H NMR (600 MHz, DMSO-$d_6$) δ 11.81 (br s, 1H), 10.12 (br s, 1H), 8.89 (d, J = 2.2 Hz, 1H), 8.56 (dd, J = 1.8, 4.7 Hz, 1H), 8.22 (br t, J= 8.0 Hz, 1H), 8.09-8.05 (m, 1H), 7.72 (dd, J = 1.6, 11.1 Hz, 1H), 7.66 (d, J = 8.4 Hz, 2H), 7.56 (br d, J = 8.7 Hz, 1H), 7.50-7.46 (m, 1H), 7.40 (d, J = 8.4 Hz, 2H), 3.04 (dt, J = 3.3, 11.3 Hz, 1H), 2.88 (t, J = 11.3 Hz, 1H), 2.78 (dt, J = 3.5, 11.7 Hz, 1H), 2.04 (br d, J = 9.8 Hz, 1H), 1.93-1.88 (m, 1H), 1.83-1.78 (m, 1H), 1.68-1.50 (m, 3H). | ES-LCMS m/z 487.4 [M + H]$^+$. |
| 9 | 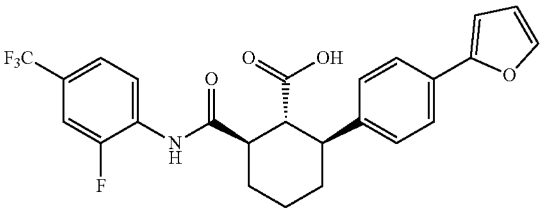 [SMILES: O=C(O)[C@@H]1[C@@H](c2ccc(-c3ccco3)cc2)CCC[C@H]1C(=O)Nc1ccc(C(F)(F)F)cc1F]<br>(1R,2R,6S)-2-((2-fluoro-4-(trifluoromethyl)phenyl)carbamoyl)-6-(4-(furan-2-yl)phenyl)cyclohexane-1-carboxylic acid | $^{1}$H NMR (600 MHz, DMSO-$d_6$) δ 11.78 (br s, 1H), 10.11 (s, 1H), 8.21 (br t, J = 8.0 Hz, 1H), 7.75-7.70 (m, 2H), 7.61 (d, J = 8.4 Hz, 2H), 7.55 (br d, J = 9.1 Hz, 1H), 7.31 (d, J = 8.4 Hz, 2H), 6.90-6.88 (m, 1H), 6.58 (dd, J = 1.8, 3.3 Hz, 1H), 3.02 (dt, J = 3.5, 11.4 Hz, 1H), 2.83 (t, J = 11.1 Hz, 1H), 2.72 (dt, J = 3.5, 11.7 Hz, 1H), 2.05-2.01 (m, 1H), 1.91-1.87 (m, 1H), 1.80-1.75 (m, 1H), 1.65-1.53 (m, 3H). | ES-LCMS m/z 474.2 [M + H]$^+$. |
| 10 | 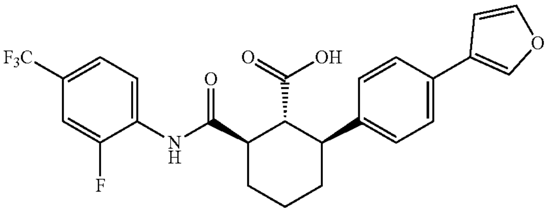 [SMILES: O=C(O)[C@@H]1[C@@H](c2ccc(-c3ccoc3)cc2)CCC[C@H]1C(=O)Nc1ccc(C(F)(F)F)cc1F]<br>(1R,2R,6S)-2-((2-fluoro-4-(trifluoromethyl)phenyl)carbamoyl)-6-(4-(furan-3-yl)phenyl) cyclohexane-1-carboxylic acid | $^{1}$H NMR (600 MHz, DMSO-$d_6$) δ 11.80-11.71 (m, 1H), 10.11 (br s, 1H), 8.21 (br t, J = 8.2 Hz, 1H), 8.14 (s, 1H), 7.74-7.71 (m, 2H), 7.55 (br d, J = 8.4 Hz, 1H), 7.51 (d, J = 8.4 Hz, 2H), 7.27 (d, J = 8.4 Hz, 2H), 6.94-6.93 (m, 1H), 3.04-2.99 (m, 1H), 2.82 (br t, J = 11.3 Hz, 1H), 2.71 (dt, J = 3.1, 11.7 Hz, 1H), 2.02 (br d, J = 9.8 Hz, 1H), 1.91-1.87 (m, 1H), 1.80-1.75 (m, 1H), 1.64-1.49 (m, 3H). | ES-LCMS m/z 474.2 [M + H]$^+$. |
| 11 | 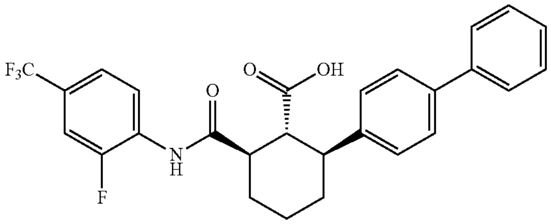 [SMILES: O=C(O)[C@@H]1[C@@H](c2ccc(-c3ccccc3)cc2)CCC[C@H]1C(=O)Nc1ccc(C(F)(F)F)cc1F]<br>(1R,2S,6R)-2-([1,1'-biphenyl]-4-yl)-6-((2-fluoro-4-(trifluoromethyl)phenyl)carbamoyl)cyclohexane-1-carboxylic acid | $^{1}$H NMR (600 MHz, DMSO-$d_6$) δ 11.83-11.75 (m, 1H), 10.12 (br s, 1H), 8.22 (br t, J = 8.2 Hz, 1H), 7.72 (dd, J = 1.5, 10.9 Hz, 1H), 7.66-7.63 (m, 2H), 7.58 (d, J = 8.0 Hz, 2H), 7.56 (br d, J = 8.4 Hz, 1H), 7.46 (t, J = 7.8 Hz, 2H), 7.38-7.33 (m, 3H), 3.03 (dt, J = 3.3, 11.3 Hz, 1H), 2.86 (t, J = 11.1 Hz, 1H), 2.76 (dt, J = 3.5, 11.7 Hz, 1H), 2.03 (br d, J = 9.8 Hz, 1H), 1.92-1.88 (m, 1H), 1.82-1.78 (m, 1H), 1.66-1.53 (m, 3H). | ES-LCMS m/z 484.2 [M + H]$^+$ |
| 12 | 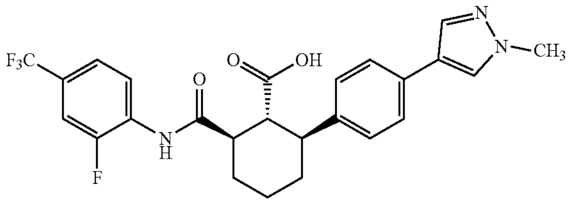 [SMILES: Cn1cc(-c2ccc([C@H]3CCC[C@@H](C(=O)Nc4ccc(C(F)(F)F)cc4F)[C@@H]3C(=O)O)cc2)cn1]<br>(1R,2R,6S)-2-((2-fluoro-4-(trifluoromethyl)phenyl)carbamoyl)-6-(4-(1-methyl-1H-pyrazol-4-yl)phenyl)cyclohexane-1-carboxylic acid | $^{1}$H NMR (700 MHz, DMSO-$d_6$) δ 11.75 (br d, J = 5.2 Hz, 1H), 10.09 (s, 1H), 8.23-8.19 (m, 1H), 8.08 (s, 1H), 7.81 (s, 1H), 7.72 (br d, J = 11.2 Hz, 1H), 7.55 (br d, J = 9.0 Hz, 1H), 7.45 (br d, J = 8.2 Hz, 2H), 7.23 (br d, J = 8.2 Hz, 2H), 3.85 (s, 3H), 3.01 (dt, J = 3.2, 11.3 Hz, 1H), 2.84-2.79 (m, 1H), 2.68 (dt, J = 3.7, 11.7 Hz, 1H), 2.04-1.99 (m, 1H), 1.89 (br dd, J = 3.0, 9.5 Hz, 1H), 1.79-1.74 (m, 1H), 1.63-1.48 (m, 3H). | ES-LCMS m/z 490.1 [M + H]$^+$. |

-continued

| Ex | Structure/Name | $^1$H NMR | LCMS |
|---|---|---|---|
| 13 | 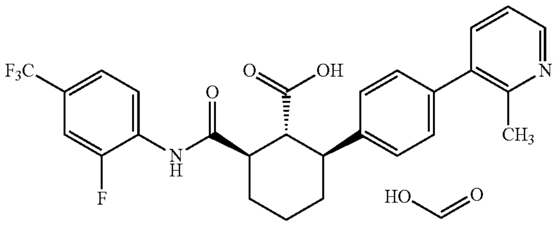 (1R,2R,6S)-2-((2-fluoro-4-(trifluoromethyl)phenyl)carbamoyl)-6-(4-(2-methylpyridin-3-yl)phenyl)cyclohexane-1-carboxylic acid, formic acid salt | $^1$H NMR (700 MHz, DMSO-$d_6$) δ 11.83 (s, 1H), 10.11 (s, 1H), 8.45 (br dd, J = 1.5, 4.9 Hz, 1H), 8.25-8.20 (m, 1H), 7.75-7.71 (m, 1H), 7.59 (br dd, J = 1.5, 7.5 Hz, 1H), 7.56 (br d, J = 8.2 Hz, 1H), 7.36 (br d, J = 8.2 Hz, 2H), 7.32 (br d, J = 8.2 Hz, 2H), 7.29 (br dd, J = 4.9, 7.5 Hz, 1H), 3.07-3.00 (m, 1H), 2.90-2.84 (m, 1H), 2.81-2.75 (m, 1H), 2.43 (s, 3H), 2.07-2.02 (m, 1H), 1.91 (br dd, J = 2.6, 8.2 Hz, 1H), 1.85-1.80 (m, 1H), 1.70-1.53 (m, 3H). | ES-LCMS m/z 501.1 $[M + H]^+$. |
| 14 | 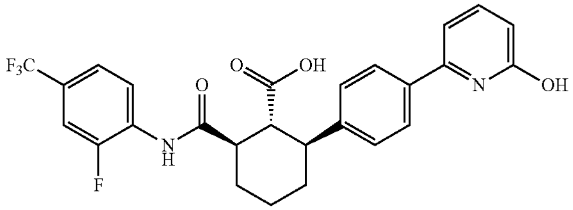 [SMILES: O=C(O)[C@@H]1[C@@H](c2ccc(-c3cccc(O)n3)cc2)CCC[C@H]1C(=O)Nc1ccc(C(F)(F)F)cc1F] (1R,2R,6S)-2-((2-fluoro-4-(trifluoromethyl)phenyl)carbamoyl)-6-(4-(6-hydroxypyridin-2-yl)phenyl)cyclohexane-1-carboxylic acid | $^1$H NMR (600 MHz, DMSO-$d_6$) δ 11.81-11.74 (m, 1H), 10.12 (br s, 1H), 10.10 (br s, 1H), 8.22 (dt, J = 4.2, 8.1 Hz, 1H), 7.72 (br d, J= 10.9 Hz, 2H), 7.56 (br d, J = 8.4 Hz, 2H), 7.52 (br s, 1H), 7.37 (d, J = 8.4 Hz, 1H), 7.30-7.24 (m, 2H), 7.21-7.16 (m, 1H), 3.02 (td, J = 7.5, 10.8 Hz, 1H), 2.87 (br t, J= 11.1 Hz, 1H), 2.80-2.75 (m, 1H), 2.05-2.00 (m, 1H), 1.90 (br dd, J = 2.4, 7.8 Hz, 1H), 1.81-1.74 (m, 1H), 1.66-1.51 (m, 3H). | ES-LCMS m/z 503.1 $[M + H]^+$. |
| 15 | 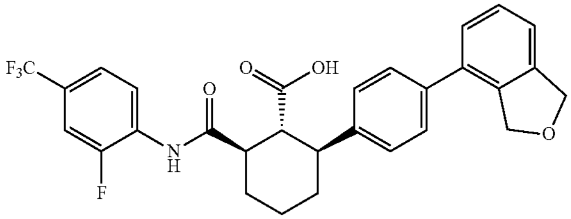 [SMILES: O=C(O)[C@@H]1[C@@H](c2ccc(-c3cccc4c3COC4)cc2)CCC[C@H]1C(=O)Nc1ccc(C(F)(F)F)cc1F] (1R,2S,6R)-2-(4-(1,3-dihydroisobenzofuran-4-yl)phenyl)-6-((2-fluoro-4-(trifluoromethyl)phenyl)carbamoyl)cyclohexane-1-carboxylic acid | $^1$H NMR (600 MHz, DMSO-$d_6$) δ 11.81 (br s, 1H), 10.11 (s, 1H), 8.22 (t, J = 8.2 Hz, 1H), 7.72 (dd, J = 1.5, 10.9 Hz, 1H), 7.56 (br d, J = 8.4 Hz, 1H), 7.43-7.33 (m, 6H), 7.31 (d, J = 7.3 Hz, 1H), 5.17-5.10 (m, 2H), 5.07 (s, 2H), 3.03 (dt, J = 3.3, 11.3 Hz, 1H), 2.86 (t, J = 11.3 Hz, 1H), 2.77 (dt, J = 3.5, 11.7 Hz, 1H), 2.06-2.01 (m, 1H), 1.93-1.88 (m, 1H), 1.84-1.78 (m, 1H), 1.66-1.52 (m, 3H) | ES-LCMS m/z 528.1 $[M + H]^+$. |
| 16 | 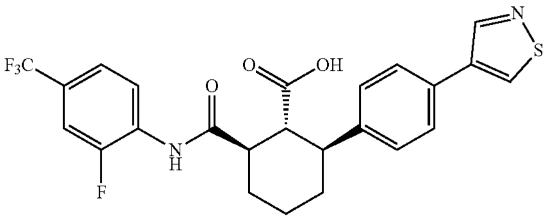 [SMILES: O=C(O)[C@@H]1[C@@H](c2ccc(-c3cnsc3)cc2)CCC[C@H]1C(=O)Nc1ccc(C(F)(F)F)cc1F] (1R,2R,6S)-2-((2-fluoro-4-(trifluoromethyl)phenyl)carbamoyl)-6-(4-(isothiazol-4-yl)phenyl)cyclohexane-1-carboxylic acid | $^1$H NMR (600 MHz, DMSO-$d_6$) δ 11.81-11.77 (m, 1H), 10.11 (br s, 1H), 9.32 (s, 1H), 9.03 (s, 1H), 8.24-8.20 (m, 1H), 7.74-7.68 (m, 3H), 7.56 (br d, J = 8.4 Hz, 1H), 7.35 (br d, J = 8.4 Hz, 2H), 2.89-2.84 (m, 1H), 2.75 (dt, J = 3.3, 11.6 Hz, 1H), 2.64-2.61 (m, 1H), 2.06-2.01 (m, 1H), 1.93-1.88 (m, 1H), 1.82-1.76 (m, 1H), 1.68-1.51 (m, 3H). | ES-LCMS m/z 493.1 $[M + H]^+$ |

-continued

| Ex | Structure/Name | $^1$H NMR | LCMS |
|---|---|---|---|
| 17 | 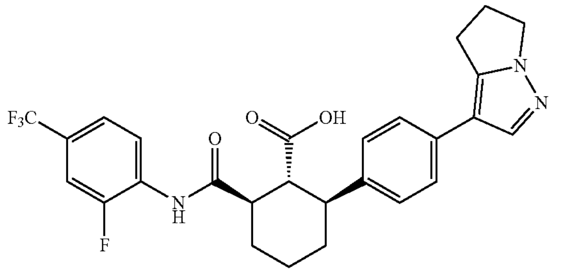 [SMILES: O=C(O)[C@@H]1[C@@H](c2ccc(-c3cnn4c3CCC4)cc2)CCC[C@H]1C(=O)Nc1ccc(C(F)(F)F)cc1F]<br>(1R,2S,6R)-2-(4-(5,6-dihydro-4H-pyrrolo[1,2-b]pyrazol-3-yl)phenyl)-6-((2-fluoro-4-(trifluoromethyl)phenyl)carbamoyl)cyclohexane-1-carboxylic acid | $^1$H NMR (600 MHz, DMSO-$d_6$) δ 11.77-11.72 (m, 1H), 10.09 (br s, 1H), 8.24-8.19 (m, 1H), 7.83 (s, 1H), 7.72 (br dd, J= 1.6, 11.1 Hz, 1H), 7.55 (br d, J = 8.7 Hz, 1H), 7.40 (br d, J = 8.4 Hz, 2H), 7.24 (br d, J = 8.4 Hz, 2H), 4.11-4.06 (m, 2H), 3.04-2.98 (m, 1H), 2.84-2.78 (m, 1H), 2.69 (dt, J = 3.3, 11.6 Hz, 1H), 2.64-2.58 (m, 2H), 2.54-2.52 (m, 1H), 2.41-2.38 (m, 1H), 2.02 (br d, J = 10.2 Hz, 1H), 1.89 (br dd, J = 3.1, 6.0 Hz, 1H), 1.79-1.75 (m, 1H), 1.63-1.51 (m, 3H). | ES-LCMS m/z 516.1 $[M + H]^+$. |
| 18 | 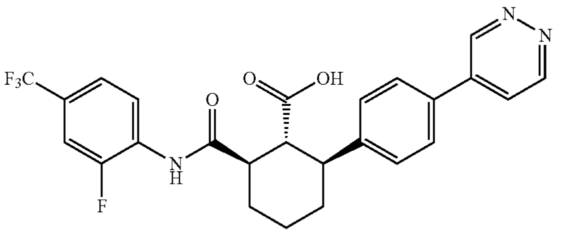 [SMILES: O=C(O)[C@@H]1[C@@H](c2ccc(-c3ccnnc3)cc2)CCC[C@H]1C(=O)Nc1ccc(C(F)(F)F)cc1F]<br>(1R,2R,6S)-2-((2-fluoro-4-(trifluoromethyl)phenyl)carbamoyl)-6-(4-(pyridazin-4-yl)phenyl)cyclohexane-1-carboxylic acid | $^1$H NMR (600 MHz, DMSO-$d_6$) δ 11.86-11.80 (m, 1H), 10.12 (br s, 1H), 9.64 (br dd, J = 1.1, 2.5 Hz, 1H), 9.26 (br dd, J = 1.1, 5.4 Hz, 1H), 8.24-8.20 (m, 1H), 8.01 (br dd, J = 2.5, 5.8 Hz, 1H), 7.87 (br d, J = 8.4 Hz, 2H), 7.72 (br dd, J = 1.5, 10.9 Hz, 1H), 7.56 (br d, J = 9.1 Hz, 1H), 7.48 (br d, J = 8.4 Hz, 2H), 3.04 (dt, J = 3.1, 11.2 Hz, 1H), 2.90 (br t, J = 11.3 Hz, 1H), 2.85-2.78 (m, 1H), 2.06-2.00 (m, 1H), 1.93-1.87 (m, 1H), 1.83-1.75 (m, 1H), 1.69-1.51 (m, 3H). | ES-LCMS m/z 488.1 $[M + H]^+$. |
| 19 | 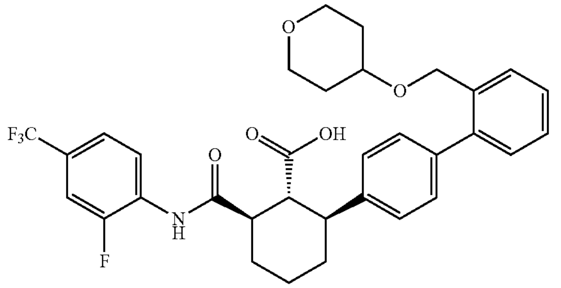 [SMILES: O=C(O)[C@@H]1[C@@H](c2ccc(-c3ccccc3COC3CCOCC3)cc2)CCC[C@H]1C(=O)Nc1ccc(C(F)(F)F)cc1F]<br>(1R,2R,6S)-2-((2-fluoro-4-(trifluoromethyl)phenyl)carbamoyl)-6-(2'-(((tetrahydro-2H-pyran-4-yl)oxy)methyl)-[1,1'-biphenyl]-4-yl) cyclohexane-1-carboxylic acid | $^1$H NMR (600 MHz, DMSO-$d_6$) δ 11.81 (br s, 1H), 10.11 (s, 1H), 8.22 (br t, J = 8.0 Hz, 1H), 7.73 (br dd, J = 1.6, 11.1 Hz, 1H), 7.56 (br d, J = 8.4 Hz, 1H), 7.52-7.49 (m, 1H), 7.39-7.35 (m, 2H), 7.35-7.28 (m, 4H), 7.27-7.24 (m, 1H), 4.38 (d, J = 1.1 Hz, 2H), 3.75 (td, J = 4.4, 11.3 Hz, 2H), 3.43 (ddd, J = 4.2, 8.9, 13.1 Hz, 2H), 3.31-3.30 (m, 1H), 3.04 (dt, J = 3.3, 11.3 Hz, 1H), 2.87 (br t, J= 11.1 Hz, 1H), 2.77 (dt, J = 3.1, 11.7 Hz, 1H), 2.06-2.01 (m, 1H), 1.91 (td, J = 2.7, 5.9 Hz, 1H), 1.85-1.79 (m, 1H), 1.74 (td, J = 4.3, 12.8 Hz, 2H), 1.68-1.51 (m, 3H), 1.36 (dtd, J = 4.2, 9.3, 13.2 Hz, 2H). | ES-LCMS m/z 600.0 $[M + H]^+$ |
| 20 | 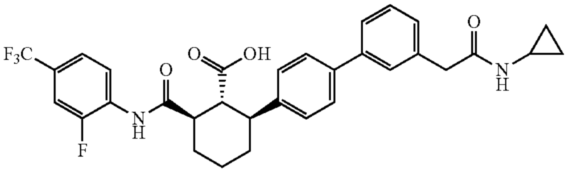 [SMILES: O=C(Cc1cccc(-c2ccc([C@H]3CCC[C@@H](C(=O)Nc4ccc(C(F)(F)F)cc4F)[C@@H]3C(=O)O)cc2)c1)NC1CC1]<br>(1R,2S,6R)-2-(3'-(2-(cyclopropylamino)-2-oxoethyl)-[1,1'-biphenyl]-4-yl)-6-((2-fluoro-4-(trifluoromethyl)phenyl)carbamoyl)cyclohexane-1-carboxylic acid | $^1$H NMR (600 MHz, DMSO-$d_6$) δ 12.55 (br s, 1H), 11.83-11.76 (m, 1H), 10.12 (br d, J = 1.1 Hz, 1H), 8.70-8.66 (m, 1H), 8.25-8.20 (m, 1H), 8.18-8.13 (m, 1H), 7.80-7.75 (m, 1H), 7.74-7.70 (m, 1H), 7.58-7.47 (m, 3H), 7.40-7.34 (m, 2H), 7.21 (br d, J = 7.7 Hz, 1H), 3.51 (s, 2H), 3.06-3.00 (m, 1H), 2.90-2.82 (m, 1H), 2.76 (dt, J = 3.5, 11.6 Hz, 1H), 2.61 (ddd, J = 3.9, 7.4, 11.1 Hz, 1H), 2.06-2.01 (m, 1H), 1.93-1.85 (m, 1H), 1.83-1.76 (m, 1H), 1.68-1.48 (m, 3H), 0.61 (dt, J = 5.0, 7.1 Hz, 2H), 0.40 (br dd, J = 2.4, 4.2 Hz, 2H). | ES-LCMS m/z 583.0 $[M + H]^+$. |

-continued

| Ex | Structure/Name | $^1$H NMR | LCMS |
|---|---|---|---|
| 21 | 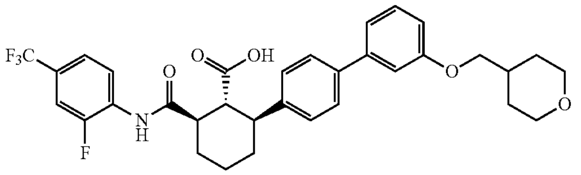 [SMILES: O=C(O)[C@@H]1[C@@H](c2ccc(-c3cccc(OCC4CCOCC4)c3)cc2)CCC[C@H]1C(=O)Nc1ccc(C(F)(F)F)cc1F] (1R,2R,6S)-2-((2-fluoro-4-(trifluoromethyl)phenyl)carbamoyl)-6-(3'-(((tetrahydro-2H-pyran-4-yl)oxy)methyl)-[1,1'-biphenyl]-4-yl) cyclohexane-1-carboxylic acid | $^1$H NMR (600 MHz, DMSO-$d_6$) δ 11.84-11.79 (m, 1H), 10.13 (br s, 1H), 8.22 (br t, J = 8.3 Hz, 1H), 7.72 (br dd, J = 1.8, 11.0 Hz, 1H), 7.61-7.52 (m, 5H), 7.43 (t, J = 7.5 Hz, 1H), 7.36 (d, J = 8.4 Hz, 2H), 7.32 (br d, J = 7.3 Hz, 1H), 4.59 (s, 2H), 3.83 (td, J = 4.3, 11.6 Hz, 2H), 3.61 (ddd, J = 4.0, 8.9, 13.1 Hz, 2H), 3.06-3.00 (m, 1H), 2.86 (br t, J = 11.2 Hz, 1H), 2.76 (dt, J = 3.1, 11.6 Hz, 1H), 2.06-2.01 (m, 1H), 1.94-1.86 (m, 2H), 1.83-1.76 (m, 1H), 1.67-1.53 (m, 3H), 1.53-1.44 (m, 4H) | ES-LCMS m/z 600.0 $[M + H]^+$ |
| 22 | 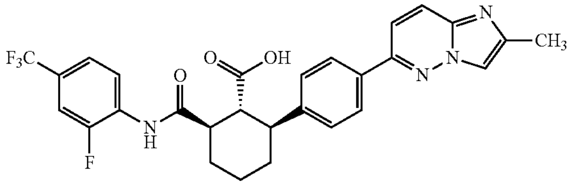 [SMILES: Cc1cn2nc(-c3ccc([C@H]4CCC[C@@H](C(=O)Nc5ccc(C(F)(F)F)cc5F)[C@@H]4C(=O)O)cc3)ccc2n1] (1R,2R,6S)-2-((2-fluoro-4-(trifluoromethyl)phenyl)carbamoyl)-6-(4-(2-methylimidazo[1,2-b]pyridazin-6-yl)phenyl)cyclohexane-1-carboxylic acid | $^1$H NMR (600 MHz, DMSO-$d_6$) δ 11.86-11.80 (m, 1H), 10.14 (br s, 1H), 8.22 (br t, J = 8.1 Hz, 1H), 8.09 (s, 1H), 8.06 (d, J = 9.5 Hz, 1H), 7.96 (d, J = 8.4 Hz, 2H), 7.72 (d, J = 9.5 Hz, 2H), 7.56 (br d, J = 8.4 Hz, 1H), 7.44 (d, J = 8.4 Hz, 2H), 3.04 (dt, J = 3.7, 11.2 Hz, 1H), 2.89 (br t, J = 11.2 Hz, 1H), 2.80 (dt, J = 3.3, 11.7 Hz, 1H), 2.41 (s, 3H), 2.07-2.02 (m, 1H), 1.94-1.88 (m, 1H), 1.81 (br dd, J = 2.9, 12.8 Hz, 1H), 1.69-1.48 (m, 3H). | ES-LCMS m/z 541.0 $[M + H]^+$ |
| 23 | 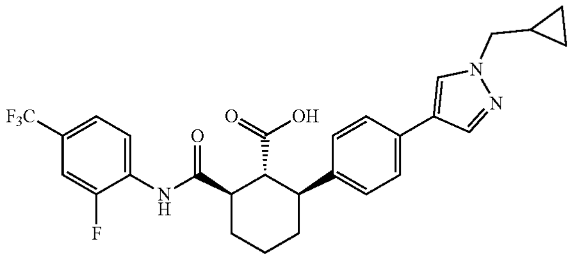 [SMILES: O=C(O)[C@@H]1[C@@H](c2ccc(-c3cnn(CC4CC4)c3)cc2)CCC[C@H]1C(=O)Nc1ccc(C(F)(F)F)cc1F] (1R,2S,6R)-2-(4-(1-(cyclopropylmethyl)-1H-pyrazol-4-yl)phenyl)-6-((2-fluoro-4-(trifluoromethyl)phenyl)carbamoyl)cyclohexane-1-carboxylic acid | $^1$H NMR (600 MHz, DMSO-$d_6$) δ 11.75 (br s, 1H), 10.10 (s, 1H), 8.21 (br t, J = 8.1 Hz, 1H), 8.15 (s, 1H), 7.82 (d, J = 0.7 Hz, 1H), 7.72 (dd, J = 1.8, 11.0 Hz, 1H), 7.56 (br d, J = 8.8 Hz, 1H), 7.47 (d, J = 8.4 Hz, 2H), 7.23 (d, J = 8.4 Hz, 2H), 3.97 (d, J = 7.0 Hz, 2H), 3.01 (dt, J = 3.5, 11.3 Hz, 1H), 2.82 (t, J = 11.2 Hz, 1H), 2.69 (dt, J = 3.3, 11.7 Hz, 1H), 2.05-1.99 (m, 1H), 1.89 (td, J = 2.8, 6.1 Hz, 1H), 1.80-1.75 (m, 1H), 1.65-1.49 (m, 3H), 1.29-1.23 (m, 1H), 0.57-0.51 (m, 2H), 0.41-0.36 (m, 2H). | ES-LCMS m/z 530.1 $[M + H]^+$. |
| 24 | 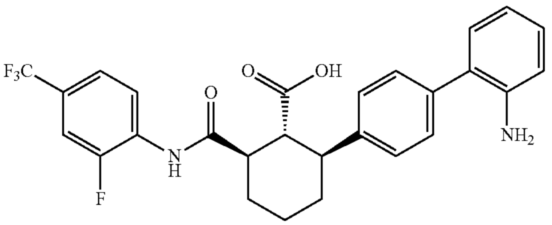 [SMILES: Nc1ccccc1-c1ccc([C@H]2CCC[C@@H](C(=O)Nc3ccc(C(F)(F)F)cc3F)[C@@H]2C(=O)O)cc1] (1R,2S,6R)-2-(2'-amino-[1,1'-biphenyl]-4-yl)-6-((2-fluoro-4-(trifluoromethyl)phenyl)carbamoyl)cyclohexane-1-carboxylic acid | $^1$H NMR (600 MHz, DMSO-$d_6$) δ 11.86-11.74 (m, 1H), 10.12 (s, 1H), 8.22 (br t, J = 8.1 Hz, 1H), 7.73 (dd, J = 1.8, 11.0 Hz, 1H), 7.56 (br d, J = 8.1 Hz, 1H), 7.34 (s, 4H), 7.06-7.02 (m, 1H), 6.98 (dd, J = 1.7, 7.5 Hz, 1H), 6.76 (dd, J = 1.1, 8.1 Hz, 1H), 6.64 (dt, J = 1.3, 7.4 Hz, 1H), 4.69 (br s, 2H), 3.03 (dt, J = 3.5, 11.3 Hz, 1H), 2.86 (t, J = 11.2 Hz, 1H), 2.76 (dt, J = 3.3, 11.7 Hz, 1H), 2.06-2.01 (m, 1H), 1.91 (td, J= 2.7, 6.0 Hz, 1H), 1.85-1.79 (m, 1H), 1.67-1.50 (m, 3H). | ES-LCMS m/z 501.1 $[M + H]^+$. |

-continued

| Ex | Structure/Name | $^1$H NMR | LCMS |
|---|---|---|---|
| 25 | 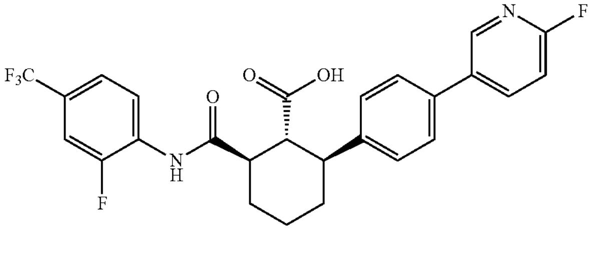 [SMILES: O=C(O)[C@@H]1[C@@H](c2ccc(-c3ccc(F)nc3)cc2)CCC[C@H]1C(=O)Nc1ccc(C(F)(F)F)cc1F] (1R,2R,6S)-2-((2-fluoro-4-(trifluoromethyl)phenyl)carbamoyl)-6-(4-(6-fluoropyridin-3-yl)phenyl)cyclohexane-1-carboxylic acid | $^1$H NMR (600 MHz, DMSO-$d_6$) δ 11.84-11.75 (m, 1H), 10.12 (s, 1H), 8.54 (d, J = 2.57 Hz, 1H), 8.28 (td, J = 8.16, 2.75 Hz, 1H), 8.25-8.19 (m, 1H), 7.76-7.70 (m, 1H), 7.65 (d, J = 8.44 Hz, 2H), 7.58-7.53 (m, 1H), 7.40 (d, J = 8.07 Hz, 2H), 7.27 (dd, J = 8.44, 2.93 Hz, 1H), 3.07-3.00 (m, 1H), 2.88 (t, J = 11.19 Hz, 1H), 2.77 (td, J = 11.65, 3.48 Hz, 1H), 2.06-2.01 (m, 1H), 1.94-1.86 (m, 1H), 1.79 (br dd, J = 12.65, 2.38 Hz, 1H), 1.67-1.50 (m, 3H). | ES-LCMS m/z 505.2 $[M + H]^+$. |
| 26 | 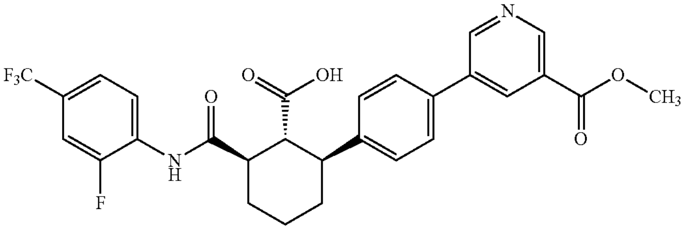 [SMILES: COC(=O)c1cncc(-c2ccc([C@H]3CCC[C@@H](C(=O)Nc4ccc(C(F)(F)F)cc4F)[C@@H]3C(=O)O)cc2)c1] (1R,2R,6S)-2-((2-fluoro-4-(trifluoromethyl)phenyl)carbamoyl)-6-(4-(5-(methoxycarbonyl)pyridin-3-yl)phenyl)cyclohexane-1-carboxylic acid | $^1$H NMR (600 MHz, DMSO-$d_6$) δ 11.75-11.90 (m, 1H), 10.07-10.19 (m, 1H), 9.15 (d, J = 2.20 Hz, 1H), 9.06 (d, J = 1.83 Hz, 1H), 8.47 (t, J = 2.02 Hz, 1H), 8.22 (t, J = 8.07 Hz, 1H), 7.70 (s, 1 H), 7.68-7.78 (m, 2H), 7.56 (br d, J = 8.07 Hz, 1H), 7.44 (d, J = 8.07 Hz, 2H), 3.89-3.99 (m, 3H), 3.00-3.08 (m, 1H), 2.89 (t, J = 11.19 Hz, 1H), 2.73 (br dd, J = 12.47, 5.50 Hz, 1H), 2.00-2.09 (m, 1H), 1.95 (s, 1H), 1.75-1.83 (m, 1H), 1.49-1.69 (m, 3H). | ES-LCMS m/z 545.2 $[M + H]^+$. |
| 27 | 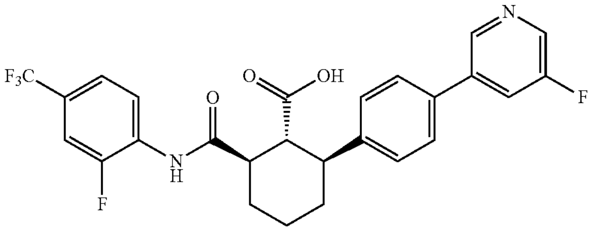 [SMILES: O=C(O)[C@@H]1[C@@H](c2ccc(-c3cncc(F)c3)cc2)CCC[C@H]1C(=O)Nc1ccc(C(F)(F)F)cc1F] (1R,2R,6S)-2-((2-fluoro-4-(trifluoromethyl)phenyl)carbamoyl)-6-(4-(5-fluoropyridin-3-yl)phenyl)cyclohexane-1-carboxylic acid | $^1$H NMR (600 MHz, DMSO-$d_6$) δ 11.74-11.92 (m, 1H), 10.07-10.15 (m, 1H), 8.80 (t, J = 1.64 Hz, 1H), 8.56 (d, J = 2.54 Hz, 1H), 8.17-8.25 (m, 1H), 8.03-8.09 (m, 1H), 7.70-7.77 (m, 3H), 7.53-7.60 (m, 1H), 7.39-7.46 (m, 2H), 3.03 (td, J = 11.08, 3.27 Hz, 1H), 2.89 (t, J = 11.26 Hz, 1H), 2.79 (td, J = 11.72, 3.09 Hz, 1H), 2.01-2.08 (m, 1H), 1.87-1.93 (m, 1H), 1.76-1.83 (m, 1H), 1.50-1.68 (m, 3H). | ES-LCMS m/z 505.3 $[M + H]^+$. |

Example 28

(1R,2R,6S)-2-((2-fluoro-4-(trifluoromethyl)phenyl)carbamoyl)-6-(4-(4-hydroxy-3-methylisothiazol-5-yl)phenyl)cyclohexane-1-carboxylic acid

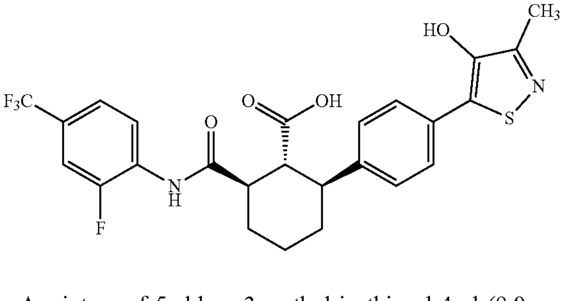

A mixture of 5-chloro-3-methyl isothiazol-4-ol (9.0 mg, 0.061 mmol), (1R,2R,6S)-2-((2-fluoro-4-(trifluoromethyl)phenyl)carbamoyl)-6-(4-(4,4,5,5-tetramethyl-1,3,2-dioxaborolan-2-yl)phenyl)cyclohexane-1-carboxylic acid Intermediate 2 (27 mg, 0.050 mmol), APhos Pd G3 (1.60 mg, 2.52 mmol), DPPF Pd G3 (2.33 mg, 2.52 mmol), 1,4-dioxane (0.40 mL) and 2M aqueous $K_2CO_3$ (0.10 mL, 0.20 mmol) was heated at 85° C. for 16 hours. Solvent was removed under a stream of nitrogen, DMSO (1 mL) was added and the mixture was stirred vigorously for 15 minutes. The mixture was filtered though a 0.45 um cartridge, and the filtrate was subjected to reverse phase purification (35-100% MeCN in $H_2O$, with 0.1% formic acid modifier) to afford (1R,2R,6S)-2-((2-fluoro-4-(trifluoromethyl)phenyl)carbamoyl)-6-(4-(4-hydroxy-3-methyl isothiazol-5-yl)phenyl)cyclohexane-1-carboxylic acid (3.9 mg, 14% yield). H NMR (700 MHz, DMSO-$d_6$) δ 11.85-11.76 (m, 1H), 10.11 (brd, J=14.2 Hz, 1H), 9.46-9.38 (m, 1H), 8.24-8.19 (5, 1H), 7.72 (br d, J=10.8 Hz, 1H), 7.61 (br d, J=8.2 Hz, 1H), 7.55 (brd, J=8.6 Hz, 1H), 7.36 (brd, J=8.2 Hz, 1H), 7.29-7.23 (m, 12H), 7.21-7.17 (m, 1H), 3.05-2.98 (m, 1H), 2.87-2.81 (m, 1H), 2.74 (td, J=11.7, 3.7 Hz, 1H), 2.05-1.99 (m, 1H), 1.92-0.86 (8, 1H), 1.80-1.74 (m, 1H), 1.64-1.49 (m, 3H). Note: methyl peak hidden under solvent. ES-LMS m/z 523.3 $[M+H]^+$.

The following compounds were synthesized in an analogous manner to the preparation described above (Example 28) using Intermediate 2 and the appropriate heteroaryl halide. Compounds were purified using one of two options: (1) normal phase chromatography ([3:1 EtOAc:EtOH]/heptane); (2) reverse phase chromatography (MeCN/$H_2O$, basic or acidic modifiers).

| Ex | Structure/Name | $^1$H NMR | LCMS |
|---|---|---|---|
| 29 | 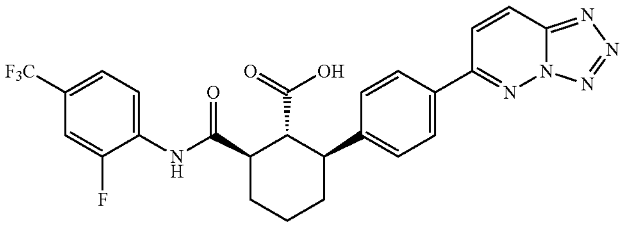 [SMILES: O=C(O)[C@@H]1[C@@H](c2ccc(-c3ccc4nnnn4n3)cc2)CCC[C@H]1C(=O)Nc1ccc(C(F)(F)F)cc1F] (1R,2R,6S)-2-((2-fluoro-4-(trifluoromethyl)phenyl)carbamoyl)-6-(4-(tetrazolo[1,5-b]pyridazin-6-yl)phenyl) cyclohexane-1-carboxylic acid | $^1$H NMR (600 MHz, DMSO-$d_6$) δ 11.96-11.83 (m, 1H), 10.14 (br s, 1H), 8.87 (d, J = 9.4 Hz, 1H), 8.45 (d, J = 9.8 Hz, 1H), 8.22 (br t, J = 8.0 Hz, 1H), 8.15 (d, J = 8.4 Hz, 2H), 7.72 (dd, J = 1.5, 10.9 Hz, 1H), 7.62-7.52 (m, 3H), 3.08-3.01 (m, 1H), 2.92 (br t, J = 11.1 Hz, 1H), 2.88-2.81 (m, 1H), 2.09-2.03 (m, 1H), 1.94-1.89 (m, 1H), 1.82 (br d, J = 10.2 Hz, 1H), 1.72-1.63 (m, 1H), 1.61-1.51 (m, 2H). | ES-LCMS m/z 529.2 $[M + H]^+$. |
| 30 | 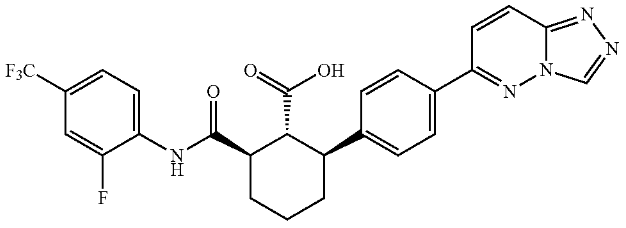 [SMILES: O=C(O)[C@@H]1[C@@H](c2ccc(-c3ccc4nncn4n3)cc2)CCC[C@H]1C(=O)Nc1ccc(C(F)(F)F)cc1F] (1R,2S,6R)-2-(4-([1,2,4]triazolo[4,3-b]pyridazin-6-yl)phenyl)-6-((2-fluoro-4-(trifluoromethyl)phenyl)carbamoyl)cyclohexane-1-carboxylic acid | $^1$H NMR (600 MHz, DMSO-$d_6$) δ 11.93-11.80 (m, 1H), 10.13 (br s, 1H), 9.69 (s, 1H), 8.45 (d, J = 9.8 Hz, 1H), 8.21 (br t, J = 8.4 Hz, 1H), 8.03 (d, J = 8.4 Hz, 2H), 7.96 (d, J = 9.8 Hz, 1H), 7.72 (br dd, J = 1.6, 10.7 Hz, 1H), 7.58-7.54 (m, 1H), 7.49 (br d, J = 8.4 Hz, 2H), 3.07-3.01 (m, 1H), 2.90 (br t, J = 11.1 Hz, 1H), 2.82 (dt, J = 3.1, 11.7 Hz, 1H), 2.07-2.02 (m, 1H), 1.94-1.89 (m, 1H), 1.81 (br dd, J= 2.5, 13.1 Hz, 1H), 1.73-1.48 (m, 3H). | ES-LCMS m/z 528.3 $[M + H]^+$. |
| 31 | 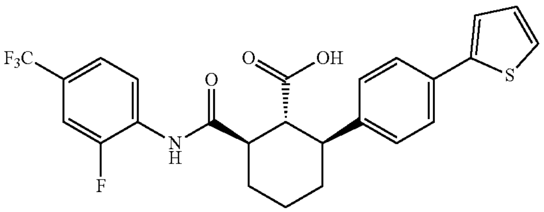 (1R,2R,6S)-2-((2-fluoro-4-(trifluoromethyl)phenyl)carbamoyl)-6-(4-(thiophen-2-yl)phenyl)cyclohexane-1-carboxylic acid | $^1$H NMR (700 MHz, DMSO-$d_6$) δ 11.83-11.79 (m, 1H), 10.11 (s, 1H), 8.23-8.20 (m, 1H), 7.72 (br dd, J = 1.9, 11.0 Hz, 1H), 7.58-7.54 (m, 3H), 7.52 (br dd, J = 1.1, 4.9 Hz, 1H), 7.47 (br dd, J= 1.1, 3.7 Hz, 1H), 7.30 (br d, J = 8.6 Hz, 2H), 7.13 (br dd, J = 3.9, 5.2 Hz, 1H), 3.05-2.99 (m, 1H), 2.86-2.80 (m, 1H), 2.75-2.70 (m, 1H), 2.03 (br d, J = 9.9 Hz, 1H), 1.92-1.87 (m, 1H), 1.80-1.75 (m, 1H), 1.65-1.50 (m, 3H). | ES-LCMS m/z 492.2 $[M + H]^+$. |
| 32 | 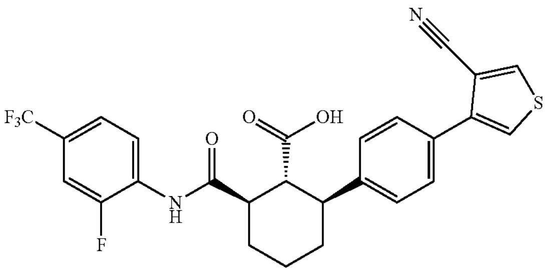 [SMILES: N#Cc1cscc1-c1ccc([C@H]2CCC[C@@H](C(=O)Nc3ccc(C(F)(F)F)cc3F)[C@@H]2C(=O)O)cc1] (1R,2S,6R)-2-(4-(4-cyanothiophen-3-yl)phenyl)-6-((2-fluoro-4-(trifluoromethyl)phenyl)carbamoyl)cyclohexane-1-carboxylic acid | $^1$H NMR (600 MHz, DMSO-$d_6$) δ 11.83 (br s, 1H), 10.11 (br s, 1H), 8.70 (d, J = 3.3 Hz, 1H), 8.22 (br t, J = 8.0 Hz, 1H), 7.92 (d, J = 3.3 Hz, 1H), 7.74-7.70 (m, 1H), 7.60-7.53 (m, 3H), 7.40 (d, J= 8.4 Hz, 2H), 3.06-3.00 (m, 1H), 2.88 (br t, J = 11.3 Hz, 1H), 2.78 (td, J= 11.8, 3.3 Hz, 1H), 2.06-2.02 (m, 1H), 1.90 (br dd, J = 9.3, 2.7 Hz, 1H), 1.83-1.78 (m, 1H), 1.66-1.52 (m, 3H). | ES-LCMS m/z 517.3 $[M + H]^+$. |

-continued

| Ex | Structure/Name | $^1$H NMR | LCMS |
|---|---|---|---|
| 33 | 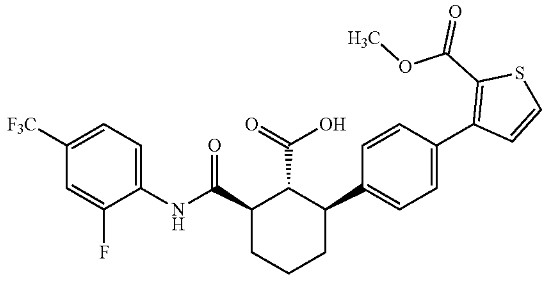 [SMILES: COC(=O)c1sccc1-c1ccc([C@H]2CCC[C@@H](C(=O)Nc3ccc(C(F)(F)F)cc3F)[C@@H]2C(=O)O)cc1] (1R,2R,6S)-2-((2-fluoro-4-(trifluoromethyl)phenyl)carbamoyl)-6-(4-(2-(methoxycarbonyl)thiophen-3-yl)phenyl)cyclohexane-1-carboxylic acid | $^1$H NMR (600 MHz, DMSO-$d_6$) δ 11.83 (br s, 1H), 10.11 (s, 1H), 8.24-8.20 (m, 1H), 7.92 (d, J = 5.1 Hz, 1H), 7.72 (br d, J = 10.5 Hz, 1H), 7.56 (br d, J = 8.7 Hz, 1H), 7.40 (br d, J = 8.0 Hz, 2H), 7.30 (br d, J = 8.0 Hz, 2H), 7.23 (d, J = 5.1 Hz, 1H), 3.71 (s, 3H), 3.05-3.01 (m, 1H), 2.87 (br t, J = 11.1 Hz, 1H), 2.77 (td, J = 11.7, 3.1 Hz, 1H), 2.05-2.01 (m, 1H), 1.93-1.88 (m, 1H), 1.84-1.79 (m, 1H), 1.64-1.53 (m, 3H). | ES-LCMS m/z 550.1 $[M + H]^+$. |
| 34 | 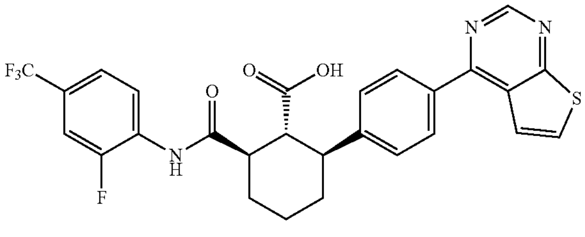 [SMILES: O=C(O)[C@@H]1[C@@H](c2ccc(-c3ncnc4sccc34)cc2)CCC[C@H]1C(=O)Nc1ccc(C(F)(F)F)cc1F] (1R,2R,6S)-2-((2-fluoro-4-(trifluoromethyl)phenyl)carbamoyl)-6-(4-(thieno[2,3-d]pyrimidin-4-yl)phenyl)cyclohexane-1-carboxylic acid | $^1$H NMR (600 MHz, DMSO-$d_6$) δ 11.86 (br s, 1H), 10.13 (s, 1H), 9.15 (s, 1H), 8.22 (br t, J = 8.2 Hz, 1H), 8.05 (d, J = 6.2 Hz, 1H), 7.97 (d, J = 8.4 Hz, 2H), 7.76-7.70 (m, 2H), 7.56 (br d, J = 8.7 Hz, 1H), 7.52 (d, J = 8.4 Hz, 2H), 3.09-3.03 (m, 1H), 2.92 (br t, J = 11.3 Hz, 1H), 2.85 (td, J = 11.7, 3.1 Hz, 1H), 2.08-2.04 (m, 1H), 1.93 (dt, J = 6.4, 3.0 Hz, 1H), 1.89-1.83 (m, 1H), 1.72-1.65 (m, 1H), 1.62-1.54 (m, 2H). | ES-LCMS m/z 544.2 $[M + H]^+$. |
| 35 | 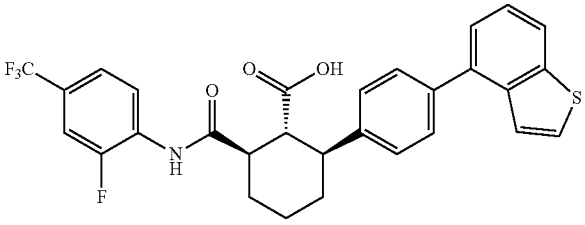 [SMILES: O=C(O)[C@@H]1[C@@H](c2ccc(-c3cccc4sccc34)cc2)CCC[C@H]1C(=O)Nc1ccc(C(F)(F)F)cc1F] (1R,2S,6R)-2-(4-(benzo[b]thiophen-4-yl)phenyl)-6-((2-fluoro-4-(trifluoromethyl)phenyl)carbamoyl) cyclohexane-1-carboxylic acid | $^1$H NMR (600 MHz, DMSO-$d_6$) δ 11.84 (br s, 1H), 10.12 (s, 1H), 8.25-8.21 (m, 1H), 8.02 (br d, J = 8.0 Hz, 1H), 7.81 (d, J = 5.8 Hz, 1H), 7.73 (br dd, J= 11.3, 1.5 Hz, 1H), 7.56 (br d, J = 8.4 Hz, 1H), 7.51 (br d, J = 8.0 Hz, 2H), 7.48-7.41 (m, 4H), 7.37 (br d, J = 6.5 Hz, 1H), 3.08-3.03 (m, 1H), 2.90 (br t, J = 11.1 Hz, 1H), 2.83-2.78 (m, 1H), 2.07-2.03 (m, 1H), 1.94-1.91 (m, 1H), 1.88-1.83 (m, 1H), 1.70-1.65 (m, 1H), 1.61-1.54 (m, 2H). | ES-LCMS m/z 542.2 $[M + H]^+$. |
| 36 | 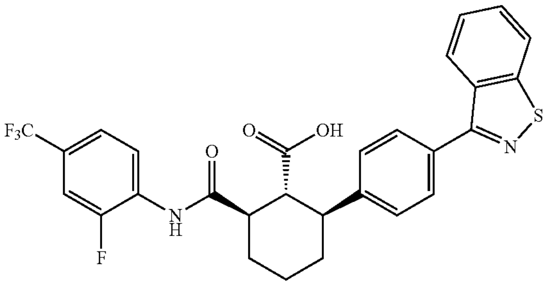 [SMILES: O=C(O)[C@@H]1[C@@H](c2ccc(-c3nsc4ccccc34)cc2)CCC[C@H]1C(=O)Nc1ccc(C(F)(F)F)cc1F] (1R,2S,6R)-2-(4-(benzo[d]isothiazol-3-yl)phenyl)-6-((2-fluoro-4-(trifluoromethyl)phenyl)carbamoyl)cyclohe xane-1-carboxylic acid | $^1$H NMR (600 MHz, DMSO-$d_6$) δ 11.85 (br s, 1H), 10.13 (s, 1H), 8.30 (d, J = 8.4 Hz, 1H), 8.25-8.20 (m, 2H), 7.83 (d, J = 8.0 Hz, 1H), 7.73 (br dd, J = 10.9, 1.8 Hz, 1H), 7.70-7.66 (m, 1H), 7.61-7.47 (m, 4H), 7.43-7.37 (m, 1H), 3.06 (td, J = 11.1, 3.3 Hz, 1H), 2.92 (br t, J = 11.1 Hz, 1H), 2.87-2.80 (m, 1H), 2.08-2.03 (m, 1H), 1.93 (dt, J= 6.0, 2.8 Hz, 1H), 1.89-1.84 (m, 1H), 1.72-1.65 (m, 1H), 1.61-1.52 (m, 2H). | ES-LCMS m/z 543.2 $[M + H]^+$. |

-continued

| Ex | Structure/Name | $^1$H NMR | LCMS |
|---|---|---|---|
| 37 | 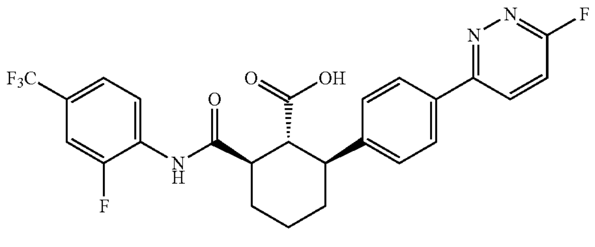 [SMILES: O=C(O)[C@@H]1[C@@H](c2ccc(-c3ccc(F)nn3)cc2)CCC[C@H]1C(=O)Nc1ccc(C(F)(F)F)cc1F] (1R,2R,6S)-2-((2-fluoro-4-(trifluoromethyl)phenyl)carbamoyl)-6-(4-(4,4,5,5-tetramethyl-1,3,2-dioxaborolan-2-yl)phenyl)cyclohexane-1-carboxylic acid | $^1$H NMR (600 MHz, DMSO-$d_6$) δ 11.88-11.79 (m, 1H), 10.12 (s, 1H), 8.47 (br dd, J = 9.3, 7.4 Hz, 1H), 8.22 (br t, J = 8.0 Hz, 1H), 8.04 (d, J = 8.4 Hz, 2H), 7.79 (br dd, J = 9.3, 1.3 Hz, 1H), 7.72 (br dd, J= 11.1, 1.6 Hz, 1H), 7.56 (br d, J = 9.1 Hz, 1H), 7.46 (d, J = 8.4 Hz, 2H), 3.04 (td, J = 11.2, 3.1 Hz, 1H), 2.89 (br t, J = 11.1 Hz, 1H), 2.81 (td, J= 11.6, 3.3 Hz, 1H), 2.07-2.02 (m, 1H), 1.94-1.88 (m, 1H), 1.84-1.78 (m, 1H), 1.70-1.62 (m, 1H), 1.60-1.51 (m, 2H). | ES-LCMS m/z 506.3 [M + H]$^+$. |
| 38 | 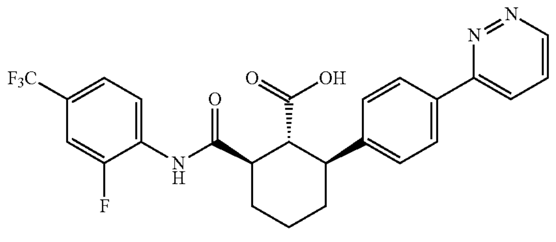 [SMILES: O=C(O)[C@@H]1[C@@H](c2ccc(-c3cccnn3)cc2)CCC[C@H]1C(=O)Nc1ccc(C(F)(F)F)cc1F] (1R,2R,6S)-2-((2-fluoro-4-(trifluoromethyl)phenyl)carbamoyl)-6-(4-(pyridazin-3-yl)phenyl)cyclohexane-1-carboxylic acid | $^1$H NMR (400 MHz, DMSO-$d_6$) δ 11.82 (br s, 1H), 10.12 (s, 1H), 9.20 (dd, J = 4.9, 1.5 Hz, 1H), 8.25-8.19 (m, 2H), 8.08 (d, J = 8.3 Hz, 2H), 7.80-7.75 (m, 1H), 7.73 (dd, J = 11.0, 1.7 Hz, 1H), 7.56 (br d, J = 8.3 Hz, 1H), 7.46 (d, J = 8.8 Hz, 2H), 3.09-3.01 (m, 1H), 2.93-2.87 (m, 1H), 2.85-2.77 (m, 1H), 2.05 (br d, J = 9.3 Hz, 1H), 1.92 (br dd, J = 5.9, 2.4 Hz, 1H), 1.87-1.79 (m, 1H), 1.73-1.52 (m, 3H). | ES-LCMS m/z 488.2 [M + H]$^+$. |
| 39 | 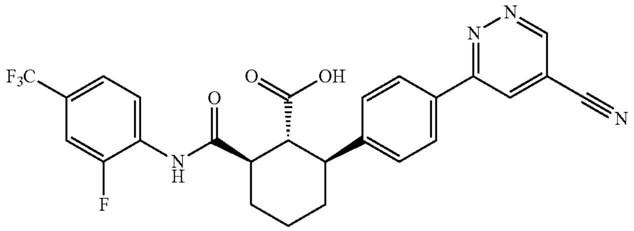 [SMILES: N#Cc1cnnc(-c2ccc([C@H]3CCC[C@@H](C(=O)Nc4ccc(C(F)(F)F)cc4F)[C@@H]3C(=O)O)cc2)c1] (1R,2R,6S)-2-(4-(5-cyanopyridazin-3-yl)phenyl)-6-((2-fluoro-4-(trifluoromethyl)phenyl)carbamoyl)cyclohexane-1-carboxylic acid | $^1$H NMR (600 MHz, DMSO-$d_6$) δ 11.85 (br s, 1H), 10.13 (s, 1H), 9.59 (d, J = 1.8 Hz, 1H), 8.83 (d, J = 1.8 Hz, 1H), 8.22 (br t, J = 8.3 Hz, 1H), 8.15 (d, J = 8.1 Hz, 2H), 7.73 (dd, J = 11.0, 1.8 Hz, 1H), 7.56 (br d, J = 7.7 Hz, 1H), 7.50 (d, J = 8.4 Hz, 2H), 3.05 (td, J = 11.0, 3.3 Hz, 1H), 2.91 (t, J = 11.0 Hz, 1H), 2.82 (td, J = 11.7, 3.3 Hz, 1H), 2.07-2.03 (m, 1H), 1.91 (dt, J = 9.2, 2.8 Hz, 1H), 1.84-1.80 (m, 1H), 1.70-1.64 (m, 1H), 1.62-1.54 (m, 2H). | ES-LCMS m/z 513.3 [M + H]$^+$. |
| 40 | 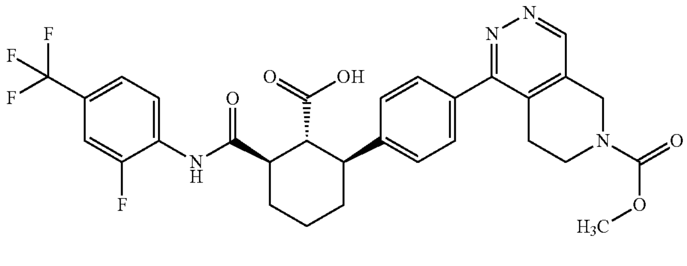 [SMILES: COC(=O)N1CCc2c(cnnc2-c2ccc([C@H]3CCC[C@@H](C(=O)Nc4ccc(C(F)(F)F)cc4F)[C@@H]3C(=O)O)cc2)C1] (1R,2R,6S)-2-((2-fluoro-4-(trifluoromethyl)phenyl) carbamoyl)-6-(4-(6-(methoxycarbonyl)-5,6,7,8-tetrahydropyrido[3,4-d]pyridazin-1-yl)phenyl)cyclohexane-1-carboxylic acid | $^1$H NMR (600 MHz, DMSO-$d_6$) δ 10.13 (s, 1H), 9.06 (br s, 1H), 8.25-8.18 (m, 2H), 7.74-7.71 (m, 1H), 7.56 (br d, J = 8.1 Hz, 2H), 7.42 (br d, J = 8.4 Hz, 2H), 4.68 (br s, 2H), 3.68 (s, 3H), 3.59-3.55 (m, 2H), 3.06-3.03 (m, 1H), 2.91-2.87 (m, 1H), 2.83-2.76 (m, 3H), 2.06-2.02 (m, 1H), 1.94-1.90 (m, 1H), 1.85-1.81 (m, 1H), 1.66 (br d, J = 12.5 Hz, 1H), 1.60-1.54 (m, 2H). | ES-LCMS m/z 601.3 [M + H]$^+$. |

-continued

| Ex | Structure/Name | $^{1}$H NMR | LCMS |
|---|---|---|---|
| 41 | 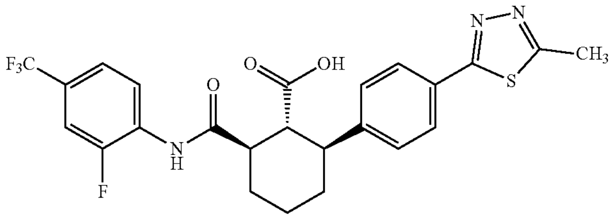 [SMILES: Cc1nnc(-c2ccc([C@H]3CCC[C@@H](C(=O)Nc4ccc(C(F)(F)F)cc4F)[C@@H]3C(=O)O)cc2)s1] (1R,2R,6S)-2-((2-fluoro-4-(trifluoromethyl)phenyl)carbamoyl)-6-(4-(5-methyl-1,3,4-thiadiazol-2-yl)phenyl)cyclohexane-1-carboxylic acid | $^{1}$H NMR (600 MHz, DMSO-$d_6$) δ 10.13 (br s, 1H), 8.24-8.19 (m, 1H), 7.85 (br d, J = 8.4 Hz, 2H), 7.72 (br dd, J = 11.2, 1.7 Hz, 1H), 7.56 (br d, J = 8.4 Hz, 1H), 7.45 (br d, J = 8.1 Hz, 2H), 3.06-3.01 (m, 1H), 2.89-2.85 (m, 1H), 2.82-2.71 (m, 4H), 2.06-2.02 (m, 1H), 1.92-1.88 (m, 1H), 1.82-1.78 (m, 1H), 1.66-1.61 (m, 1H), 1.59-1.52 (m, 2H). | ES-LCMS m/z 508.2 $[M + H]^+$. |
| 42 | 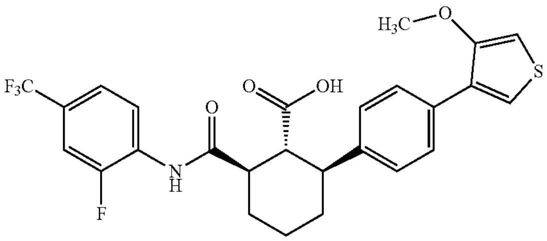 [SMILES: COc1cscc1-c1ccc([C@H]2CCC[C@@H](C(=O)Nc3ccc(C(F)(F)F)cc3F)[C@@H]2C(=O)O)cc1] (1R,2R,6S)-2-((2-fluoro-4-(trifluoromethyl)phenyl)carbamoyl)-6-(4-(4-methoxythiophen-3-yl)phenyl) cyclohexane-1-carboxylic acid | $^{1}$H NMR (600 MHz, DMSO-$d_6$) δ 11.79 (s, 1H), 10.11 (s, 1H), 8.23-8.20 (m, 1H), 7.72 (br dd, J = 10.8, 1.7 Hz, 1H), 7.59 (d, J = 3.3 Hz, 1H), 7.57-7.51 (m, 3H), 7.27 (br d, J = 8.4 Hz, 2H), 6.71 (d, J = 3.3 Hz, 1H), 3.83 (s, 3H), 3.02 (td, J = 11.2, 3.3 Hz, 1H), 2.84 (br t, J = 11.2 Hz, 1H), 2.72 (br dd, J = 11.6, 8.3 Hz, 1H), 2.04-2.01 (m, 1H), 1.91-1.88 (m, 1H), 1.80-1.76 (m, 1H), 1.62-1.53 (m, 3H). | ES-LCMS m/z 522.3 $[M + H]^+$ |
| 43 | 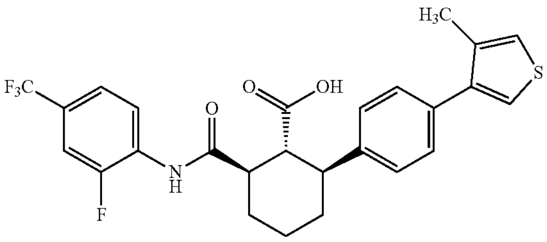 [SMILES: Cc1cscc1-c1ccc([C@H]2CCC[C@@H](C(=O)Nc3ccc(C(F)(F)F)cc3F)[C@@H]2C(=O)O)cc1] (1R,2R,6S)-2-((2-fluoro-4-(trifluoromethyl)phenyl)carbamoyl)-6-(4-(4-methylthiophen-3-yl)phenyl)cyclohexane-1-carboxylic acid | $^{1}$H NMR (600 MHz, DMSO-$d_6$) δ 11.81 (br s, 1H), 10.11 (s, 1H), 8.22 (br t, J = 8.1 Hz, 1H), 7.72 (dd, J = 11.0, 1.8 Hz, 1H), 7.56 (br d, J = 8.1 Hz, 1H), 7.44 (d, J = 3.3 Hz, 1H), 7.36-7.33 (m, 2H), 7.33-7.29 (m, 2H), 7.26 (br dd, J= 3.1, 0.9 Hz, 1H), 3.05-3.00 (m, 1H), 2.86 (br t, J = 11.2 Hz, 1H), 2.75 (td, J= 11.6, 3.3 Hz, 1H), 2.24 (s, 3H), 2.05-2.01 (m, 1H), 1.90 (dt, J = 5.8, 2.8 Hz, 1H), 1.80 (br dd, J = 12.7, 2.8 Hz, 1H), 1.63-1.53 (m, 3H). | ES-LCMS m/z 506.3 $[M + H]^+$ |
| 44 | 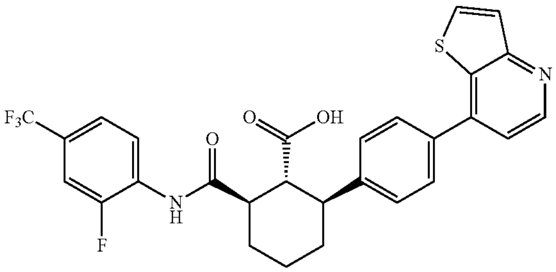 [SMILES: O=C(O)[C@@H]1[C@@H](c2ccc(-c3ccnc4ccsc34)cc2)CCC[C@H]1C(=O)Nc1ccc(C(F)(F)F)cc1F] (1R,2R,6S)-2-((2-fluoro-4-(trifluoromethyl)phenyl) carbamoyl)-6-(4-(thieno[3,2-b]pyridin-7-yl)phenyl)cyclohexane-1-carboxylic acid | $^{1}$H NMR (600 MHz, DMSO-$d_6$) δ 11.88 (br s, 1H), 10.13 (s, 1H), 8.74 (d, J= 4.8 Hz, 1H), 8.25-8.19 (m, 2H), 7.78 (d, J = 8.1 Hz, 2H), 7.73 (br dd, J = 11.0, 1.8 Hz, 1H), 7.66 (d, J = 5.5 Hz, 1H), 7.56 (br d, J = 8.8 Hz, 1H), 7.52 (d, J = 8.1 Hz, 2H), 7.49 (d, J = 4.8 Hz, 1H), 3.08-3.03 (m, 1H), 2.92 (br t, J = 11.2 Hz, 1H), 2.84 (td, J= 11.7, 3.3 Hz, 1H), 2.07-2.03 (m, 1H), 1.94-1.90 (m, 1H), 1.87-1.82 (m, 1H), 1.69-1.64 (m, 1H), 1.62-1.54 (m, 2H). | ES-LCMS m/z 543.2 $[M + H]^+$. |

-continued

| Ex | Structure/Name | $^1$H NMR | LCMS |
|---|---|---|---|
| 45 | 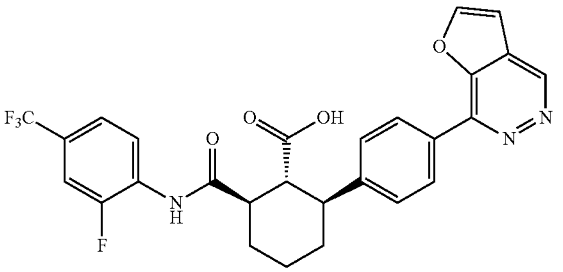 [SMILES: O=C(O)[C@@H]1[C@@H](c2ccc(-c3nncc4ccoc34)cc2)CCC[C@H]1C(=O)Nc1ccc(C(F)(F)F)cc1F] (1R,2R,6S)-2-((2-fluoro-4-(trifluoromethyl)phenyl)carbamoyl)-6-(4-(furo[2,3-d]pyridazin-7-yl)phenyl)cyclohexane-1-carboxylic acid | $^1$H NMR (700 MHz, DMSO-$d_6$) δ 10.13 (s, 1H), 9.63 (s, 1H), 8.48 (br d, J = 2.2 Hz, 1H), 8.29 (br d, J = 8.2 Hz, 2H), 8.25-8.20 (m, 1H), 7.73 (br d, J = 9.5 Hz, 1H), 7.62-7.51 (m, 3H), 7.30 (br d, J = 2.2 Hz, 1H), 3.09-3.04 (m, 1H), 2.95-2.90 (m, 1H), 2.84 (td, J = 11.4, 3.4 Hz, 1H), 2.08-2.04 (m, 1H), 1.93 (dt, J = 8.8, 3.3 Hz, 1H), 1.88-1.83 (m, 1H), 1.73-1.68 (m, 1H), 1.62-1.55 (m, 2H). | ES-LCMS m/z 528.2 $[M + H]^+$. |
| 46 | 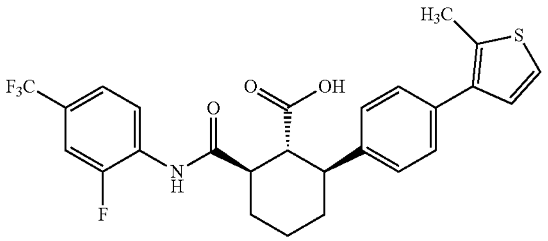 [SMILES: Cc1sccc1-c1ccc([C@H]2CCC[C@@H](C(=O)Nc3ccc(C(F)(F)F)cc3F)[C@@H]2C(=O)O)cc1] (1R,2R,6S)-2-((2-fluoro-4-(trifluoromethyl)phenyl)carbamoyl)-6-(4-(2-methylthiophen-3-yl)phenyl)cyclohexane-1-carboxylic acid | $^1$H NMR (700 MHz, DMSO-$d_6$) δ 11.80 (br s, 1H), 10.11 (s, 1H), 8.23-8.20 (m, 1H), 7.72 (br d, J = 9.5 Hz, 1H), 7.56 (br d, J = 8.6 Hz, 1H), 7.38-7.29 (m, 5H), 7.11 (d, J = 5.2 Hz, 1H), 3.03 (td, J = 11.4, 3.4 Hz, 1H), 2.85 (br t, J= 11.2 Hz, 1H), 2.75 (td, J = 11.6, 3.4 Hz, 1H), 2.47 (s, 3H), 2.03 (br d, J = 9.5 Hz, 1H), 1.91-1.88 (m, 1H), 1.82-1.79 (m, 1H), 1.63-1.54 (m, 3H). | ES-LCMS m/z 504.2 $[M - H]^-$. |
| 47 | 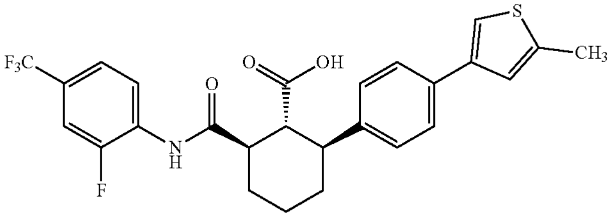 [SMILES: Cc1cc(-c2ccc([C@H]3CCC[C@@H](C(=O)Nc4ccc(C(F)(F)F)cc4F)[C@@H]3C(=O)O)cc2)cs1] (1R,2R,6S)-2-((2-fluoro-4-(trifluoromethyl)phenyl)carbamoyl)-6-(4-(5-methylthiophen-3-yl)phenyl)cyclohexane-1-carboxylic acid | $^1$H NMR (700 MHz, DMSO-$d_6$) δ 10.10 (br s, 1H), 8.23-8.18 (m, 1H), 7.72 (br d, J = 11.6 Hz, 1H), 7.60-7.50 (m, 4H), 7.27 (br d, J = 8.2 Hz, 2H), 7.22 (br s, 1H), 3.04-2.99 (m, 1H), 2.84-2.81 (m, 1H), 2.71 (td, J= 11.7, 3.2 Hz, 1H), 2.02 (br d, J = 9.5 Hz, 1H), 1.89 (br dd, J = 8.8, 2.8 Hz, 1H), 1.78 (br d, J = 14.6 Hz, 1H), 1.63-1.53 (m, 3H). Methyl group obscured by solvent peak. | ES-LCMS m/z 504.3 $[M - H]^-$. |
| 48 | 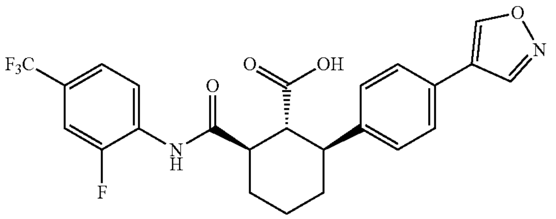 [SMILES: O=C(O)[C@@H]1[C@@H](c2ccc(-c3cnoc3)cc2)CCC[C@H]1C(=O)Nc1ccc(C(F)(F)F)cc1F] (1R,2R,6S)-2-((2-fluoro-4-(trifluoromethyl)phenyl)carbamoyl)-6-(4-(isoxazol-4-yl)phenyl)cyclohexane-1-carboxylic acid | $^1$H NMR (400 MHz, CHLOROFORM-d) o 8.64 (s, 1H), 8.52 (s, 1H), 8.46 (br t, J = 8.1 Hz, 1H), 7.60 (br d, J = 2.4 Hz, 1H), 7.38 (br d, J = 8.3 Hz, 3H), 7.35-7.31 (m, 1H), 7.24 (d, J = 8.3 Hz, 2H), 3.04-2.95 (m, 1H), 2.84-2.74 (m, 2H), 2.16-2.08 (m, 1H), 2.03 (br dd, J= 9.3, 2.9 Hz, 1H), 1.95 (br d, J = 10.3 Hz, 1H), 1.84-1.72 (m, 1H), 1.68-1.53 (m, 2H). | ES-LCMS m/z 475.2 $[M - H]^-$. |

-continued

| Ex | Structure/Name | $^1$H NMR | LCMS |
|---|---|---|---|
| 49 | 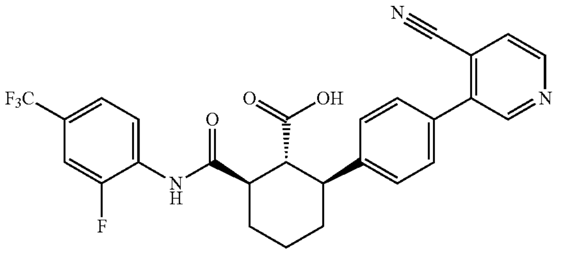 [SMILES: N#Cc1ccncc1-c1ccc([C@H]2CCC[C@@H](C(=O)Nc3ccc(C(F)(F)F)cc3F)[C@@H]2C(=O)O)cc1] (1R,2R,6S)-2-(4-(4-cyanopyridin-3-yl)phenyl)-6-((2-fluoro-4-(trifluoromethyl)phenyl)carbamoyl)cyclohexane-1-carboxylic acid | $^1$H NMR (700 MHz, DMSO-$d_6$) δ 10.13 (br s, 1H), 8.91 (s, 1H), 8.81 (d, J = 4.7 Hz, 1H), 8.24-8.20 (m, 1H), 7.97 (d, J= 5.2 Hz, 1H), 7.72 (br dd, J = 10.8, 1.7 Hz, 1H), 7.62 (br d, J = 8.2 Hz, 2H), 7.56 (br d, J = 8.2 Hz, 1H), 7.49 (br d, J = 8.2 Hz, 2H), 3.04 (td, J = 11.3, 3.2 Hz, 1H), 2.94-2.90 (m, 1H), 2.83 (td, J = 11.8, 3.4 Hz, 1H), 2.04 (br d, J = 10.3 Hz, 1H), 1.93-1.89 (m, 1H), 1.85-1.81 (m, 1H), 1.67-1.62 (m, 1H), 1.59-1.52 (m, 2H). | ES-LCMS m/z 510.2 $[M + H]^+$. |
| 50 | 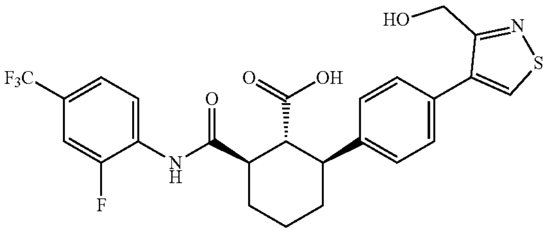 [SMILES: O=C(O)[C@@H]1[C@@H](c2ccc(-c3csnc3CO)cc2)CCC[C@H]1C(=O)Nc1ccc(C(F)(F)F)cc1F] (1R,2R,6S)-2-((2-fluoro-4-(trifluoromethyl)phenyl)carbamoyl)-6-(4-(3-(hydroxymethyl)isothiazol-4-yl)phenyl)cyclohexane-1-carboxylic acid | $^1$H NMR (700 MHz, DMSO-$d_6$) δ 10.12 (s, 1H), 9.04 (s, 1H), 8.23-8.20 (m, 1H), 7.74-7.70 (m, 1H), 7.63-7.51 (m, 3H), 7.35 (br d, J = 8.2 Hz, 2H), 5.48-5.44 (m, 1H), 4.55 (br d, J = 5.6 Hz, 2H), 3.06-3.01 (m, 1H), 2.89-2.85 (m, 1H), 2.77 (td, J = 11.6, 3.4 Hz, 1H), 2.05-2.01 (m, 1H), 1.90 (br dd, J = 9.2, 2.4 Hz, 1H), 1.82-1.78 (m, 1H), 1.64-1.53 (m, 3H). | ES-LCMS m/z 523.4 $[M + H]^+$ |
| 51 | 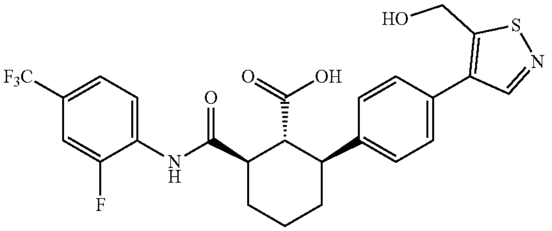 [SMILES: O=C(O)[C@@H]1[C@@H](c2ccc(-c3cnsc3CO)cc2)CCC[C@H]1C(=O)Nc1ccc(C(F)(F)F)cc1F] (1R,2R,6S)-2-((2-fluoro-4-(trifluoromethyl)phenyl)carbamoyl)-6-(4-(5-(hydroxymethyl)isothiazol-4-yl)phenyl) cyclohexane-1-carboxylic acid | $^1$H NMR (700 MHz, DMSO-$d_6$) δ 10.11 (s, 1H), 8.68 (s, 1H), 8.23-8.20 (m, 1H), 7.72 (br dd, J = 10.5, 1.9 Hz, 1H), 7.56 (br d, J = 7.3 Hz, 1H), 7.43 (br d, J = 8.2 Hz, 2H), 7.36 (br d, J = 8.2 Hz, 2H), 6.13-6.09 (m, 1H), 4.90 (br d, J = 5.2 Hz, 2H), 3.05-3.00 (m, 1H), 2.88-2.84 (m, 1H), 2.76 (td, J = 12.0, 3.4 Hz, 1H), 2.03 (br d, J = 12.9 Hz, 1H), 1.92-1.87 (m, 1H), 1.80 (br d, J = 13.8 Hz, 1H), 1.64-1.53 (m, 3H). | ES-LCMS m/z 523.3 $[M + H]^+$ |
| 52 | 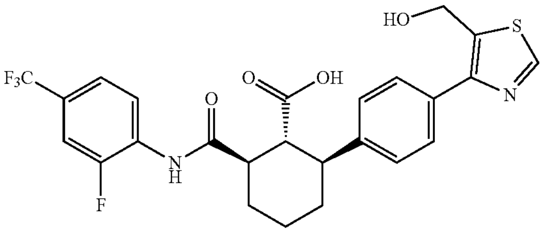 [SMILES: O=C(O)[C@@H]1[C@@H](c2ccc(-c3ncsc3CO)cc2)CCC[C@H]1C(=O)Nc1ccc(C(F)(F)F)cc1F] (1R,2R,6S)-2-((2-fluoro-4-(trifluoromethyl)phenyl)carbamoyl)-6-(4-(5-(hydroxymethyl)thiazol-4-yl)phenyl)cyclohexane-1-carboxylic acid | $^1$H NMR (700 MHz, DMSO-$d_6$) δ 10.11 (br s, 1H), 9.04 (s, 1H), 8.23-8.20 (m, 1H), 7.72 (br d, J = 9.5 Hz, 1H), 7.59 (br s, 2H), 7.55 (br d, J = 9.5 Hz, 1H), 7.36 (br d, J = 8.2 Hz, 2H), 5.87-5.84 (m, 1H), 4.78 (br d, J = 5.2 Hz, 2H), 3.06-3.01 (m, 1H), 2.88-2.84 (m, 1H), 2.78-2.74 (m, 1H), 2.06-2.02 (m, 1H), 1.93-1.89 (m, 1H), 1.83-1.79 (m, 1H), 1.66-1.62 (m, 1H), 1.59-1.52 (m, 2H). | ES-LCMS m/z 523.3 $[M + H]^+$. |

-continued

| Ex | Structure/Name | $^1H$ NMR | LCMS |
|---|---|---|---|
| 53 | 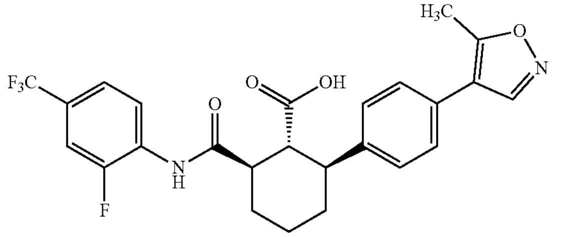 [SMILES: Cc1oncc1-c1ccc([C@H]2CCC[C@@H](C(=O)Nc3ccc(C(F)(F)F)cc3F)[C@@H]2C(=O)O)cc1] (1R,2R,6S)-2-((2-fluoro-4-(trifluoromethyl)phenyl)carbamoyl)-6-(4-(5-methylisoxazol-4-yl)phenyl)cyclohexane-1-carboxylic acid | $^1H$ NMR (700 MHz, DMSO-$d_6$) δ 10.11 (s, 1H), 8.85 (br s, 1H), 8.23-8.20 (m, 1H), 7.72 (br d, J = 10.8 Hz, 1H), 7.55 (br d, J = 8.6 Hz, 1H), 7.45 (br d, J = 8.2 Hz, 2H), 7.35 (br d, J = 8.2 Hz, 2H), 3.04-3.00 (m, 1H), 2.87-2.84 (m, 1H), 2.77-2.73 (m, 1H), 2.04-2.01 (m, 1H), 1.90 (br d, J = 9.5 Hz, 1H), 1.79-1.76 (m, 1H), 1.62-1.53 (m, 3H). Methyl group obscured by solvent peak. | ES-LCMS m/z 489.2 $[M - H]^-$. |

Example 54

(1R,2S,6R)-2-(4-(2-cyanopyrimidin-5-yl)phenyl)-6-((2-fluoro-4-(trifluoromethyl)phenyl)carbamoyl)cyclohexane-1-carboxylic acid

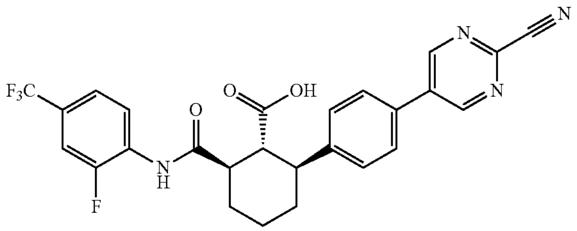

To a mixture of (1R,2R,6S)-2-((2-fluoro-4-(trifluoromethyl)phenyl)carbamoyl)-6-(4-(4,4,5,5-tetramethyl-1,3,2-dioxaborolan-2-yl)phenyl)cyclohexane-1-carboxylic acid Intermediate 2 (0.10 g, 0.19 mmol) and 5-chloropyrimidine-2-carbonitrile (26.1 mg, 0.19 mmol) in 1,4-dioxane (1 mL) and water (0.3 mL) was added sodium carbonate (39.6 mg, 0.370 mmol). The reaction was degassed for 10 minutes, and $PdCl_2$(dppf) (14 mg, 0.019 mmol) was added. The mixture was stirred at 80° C. for 3 h, concentrated and subjected to reverse phase purification (60% MeCN in $H_2O$, with 10 mM ammonium bicarbonate modifier) to afford (1R,2S,6R)-2-(4-(2-cyanopyrimidin-5-yl)phenyl)-6-((2-fluoro-4-(trifluoromethyl)phenyl)carbamoyl)cyclohexane-1-carboxylic acid (37 mg, 0.070 mmol, 39% yield) as a light brown solid. $^1H$ NMR (400 MHz, DMSO-$d_6$) δ 10.25 (s, 1H), 9.38 (s, 2H), 8.24 (dd, J=8.0 Hz, 1H), 7.84 (d, J=8.4 Hz, 2H), 7.70 (d, J=10.0 Hz, 1H), 7.54 (d, J=8.0 Hz, 1H), 7.47 (d, J=8.4 Hz, 2H), 2.98-2.96 (m, 1H), 2.83-2.81 (m, 2H), 2.03-2.01 (m, 1H), 1.89-1.87 (m, 1H), 1.78-1.75 (m, 1H), 1.62-1.53 (m, 3H). ES-LCMS m/z 511.0 $[M-H]^-$ The following compound was synthesized in an analogous manner to the preparation described above (Example 54) using Intermediate 2 and the appropriate heteroaryl halide.

| Ex | Structure/Name | $^1H$ NMR | LCMS |
|---|---|---|---|
| 55 | 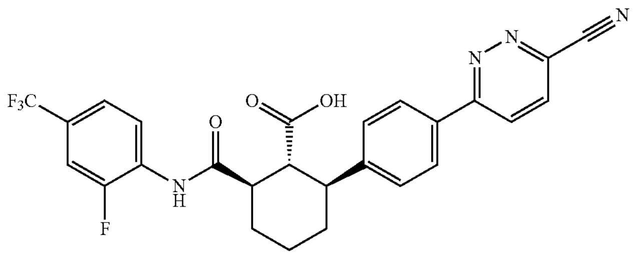 [SMILES: N#Cc1ccc(-c2ccc([C@H]3CCC[C@@H](C(=O)Nc4ccc(C(F)(F)F)cc4F)[C@@H]3C(=O)O)cc2)nn1] (1R,2S,6R)-2-(4-(6-cyanopyridazin-3-yl)phenyl)-6-((2-fluoro-4-(trifluoromethyl)phenyl)carbamoyl)cyclohexane-1-carboxylic acid | $^1H$ NMR (400 MHz, DMSO-$d_6$) δ 10.17 (s, 1H), 8.52 (d, J = 8.8 Hz, 1H), 8.43 (d, J = 9.2 Hz, 1H), 8.25-8.17 (m, 3H), 7.72 (d, J = 11.20 Hz, 1H), 7.56-7.50 (m, 3H), 3.28-3.01 (m, 1H), 2.92-2.80 (m, 2H), 2.05-2.03 (m, 1H), 1.20-1.91 (m, 1H), 1.82-1.80 (m, 1H), 1.68-1.65 (m, 3H). | ES-LCMS m/z 513.0 $[M + H]^+$ |

Example 56

(1R,2S,6R)—2-(4-(3,4-dihydro-2H-pyran-5-yl)phenyl)-6-((2-fluoro-4-(trifluoromethyl)phenyl)carbamoyl)cyclohexane-1-carboxylic acid

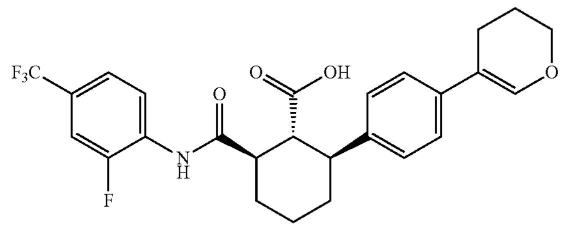

To a mixture of (1R,2S,6R)-2-(4-bromophenyl)-6-((2-fluoro-4-(trifluoromethyl)phenyl)carbamoyl)cyclohexane-1-carboxylic acid, Intermediate 1 (0.20 g, 0.41 mmol) and 2-(3,4-dihydro-2H-pyran-5-yl)-4,4,5,5-tetramethyl-1,3,2-dioxaborolane (0.10 g, 0.49 mmol) in 1,4-dioxane (3.5 mL) and water (1.0 mL) was added $Na_2CO_3$ (87 mg, 0.82 mmol). The reaction was degassed with nitrogen for 5 min, then $PdCl_2$(dppf)-$CH_2Cl_2$ complex (33 mg, 0.040 mmol) was added. The mixture was stirred at 80° C. for 2 h, concentrated and subjected to reverse phase purification (40-70% MeCN in $H_2O$, with 10 mM ammonium bicarbonate modifier) to afford (1R,2S,6R)-2-(4-(3,4-dihydro-2H-pyran-5-yl)phenyl)-6-((2-fluoro-4-(trifluoromethyl)phenyl)carbamoyl)cyclohexane-1-carboxylic acid (0.11 g, 0.14 mmol, 34% yield) as an off-white solid. $^1$H NMR (400 MHz, DMSO-$d_6$) δ 10.10 (s, 1H), 8.21 (dd, J=8.4, 8.4 Hz, 1H), 7.71 (dd, J=11.0, 1.6 Hz, 1H), 7.55 (d, J=8.0 Hz, 1H), 7.23 (d, J=8.4 Hz, 2H), 7.15 (d, J=8.4 Hz, 2H), 7.03 (s, 1H), 3.95 (t, J=5.2 Hz, 1H), 3.02-2.97 (m, 1H), 2.78 (t, J=10.8 Hz, 1H), 2.68-2.63 (m, 2H), 2.34-2.31 (m, 4H), 1.99-1.73 (m, 5H), 1.58-1.51 (m, 3H). ES-LCMS m/z 490.0 $[M-H]^-$.

The following compounds were synthesized in an analogous manner to the preparation described above (Example 56) using Intermediate 1 and the appropriate boronate.

| Ex | Structure/Name | $^1$H NMR | LCMS |
|---|---|---|---|
| 57 | 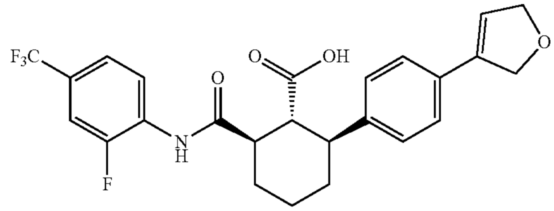 [SMILES: O=C(O)[C@@H]1[C@@H](c2ccc(C3=CCOC3)cc2)CCC[C@H]1C(=O)Nc1ccc(C(F)(F)F)cc1F]<br>(1R,2S,6R)-2-(4-(2,5-dihydrofuran-3-yl)phenyl)-6-((2-fluoro-4-(trifluoromethyl)phenyl)carbamoyl) cyclohexane-1-carboxylic acid | $^1$H NMR (400 MHz, DMSO-$d_6$) δ 10.16 (br s, 1H), 8.21 (t, J = 8.0 Hz, 1H), 7.69 (dd, J = 10.8, 1.8 Hz, 1H), 7.53 (br d, J = 8.0 Hz, 1H), 7.34-7.30 (m, 2H), 7.27-7.21 (m, 2H), 6.41 (t, J = 1.8 Hz, 1H), 4.91-4.84 (m, 2H), 4.71 (br t, J = 3.8 Hz, 2H), 3.05-2.92 (m, 1H), 2.83-2.66 (m, 2H), 2.04-1.71 (m, 3H), 1.63-1.44 (m, 3H). | ES-LCMS m/z 476.0 $[M-H]^-$. |
| 58 | 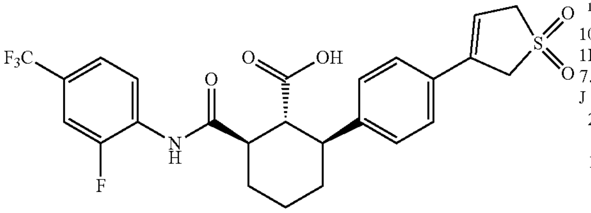<br>(1R,2S,6R)-2-(4-(1,1-dioxido-2,5-dihydrothiophen-3-yl)phenyl)-6-((2-fluoro-4-(trifluoromethyl)phenyl)carbamoyl) cyclohexane-1-carboxylic acid | $^1$H NMR (400 MHz, DMSO-$d_6$) δ 10.18 (br s, 1H), 8.21 (t, J = 8.0 Hz, 1H), 7.70 (dd, J = 10.8, 1.8 Hz, 1H), 7.53 (br d, J = 8.5 Hz, 1H), 7.43 (d, J = 8.0 Hz, 2H), 7.28 (d, J = 8.5 Hz, 2H), 6.55 (br s, 1H), 4.28 (s, 2H), 4.11-4.02 (m, 2H), 3.03-2.91 (m, 1H), 2.83-2.64 (m, 2H), 2.03-1.67 (m, 3H), 1.63-1.42 (m, 3H). | ES-LCMS m/z 476.0 $[M-H]^-$. |

Example 59

1:1 Mixture of (1R,2R,6S)-2-((2-fluoro-4-(trifluoromethyl)phenyl)carbamoyl)-6-(4-((S)-oxepan-4-yl)phenyl)cyclohexane-1-carboxylic acid AND (1R,2R,6S)-2-((2-fluoro-4-(trifluoromethyl)phenyl)carbamoyl)-6-(4-((R)-oxepan-4-yl)phenyl)cyclohexane-1-carboxylic acid

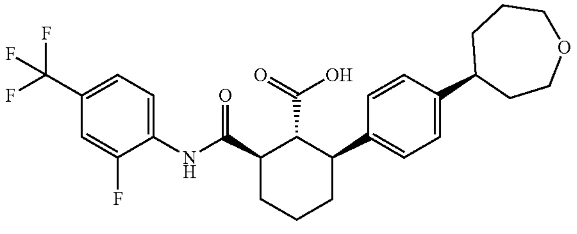

+

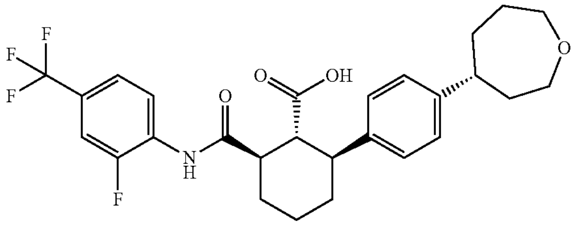

To a mixture of (1R,2S,6R)-2-(4-bromophenyl)-6-((2-fluoro-4-(trifluoromethyl)phenyl)carbamoyl)cyclohexane-1-carboxylic acid, Intermediate 1 (49 mg, 0.10 mmol), 4-bromooxepane (36 mg, 0.20 mmol), (4,4'-dtbbpy)$NiCl_Z$ (2.0 mg, 5.0 μmol), $[Ir(dtbbpy)(ppy)_2]PF_6$ (0.90 mg, 1.0 μmol), Aminosupersilane (0.060 g, 0.15 mmol), and $Na_2CO_3$(32 mg, 0.30 mmol) was added THF (0.5 mL). The mixture was placed in a Lumidox reactor (blue LED, 315 mW per well, 7.6 W total radiant power) on a tumble stirrer with the cooling set to 5° C. (internal temperature ~23° C.) and irradiated for 18 h. Then reaction was concentrated via blowdown (40° C., $N_2$), and the residue was subjected to reverse phase purification (MeCN in $H_2O$, 0.1% formic acid modifier, 40-100% gradient) to afford 1:1 mixture of (1R,2R,6S)-2-((2-fluoro-4-(trifluoromethyl)phenyl)carbamoyl)-6-(4-((S)-oxepan-4-yl)phenyl)cyclohexane-1-carboxylic acid AND (1R,2R,6S)-2-((2-fluoro-4-(trifluoromethyl)phenyl)carbamoyl)-6-(4-((R)-oxepan-4-yl)phenyl)cyclohexane-1-carboxylic acid (9.5 mg, 19 μmol, 10% yield). $^1H$ NMR (600 MHz, DMSO-$d_6$) δ 11.62-11.84 (m, 1H), 10.06-10.11 (m, 1H), 8.17-8.23 (m, 1H), 7.71 (br d, J=11.00 Hz, 1H), 7.55 (d, J=8.44 Hz, 1H), 7.13 (s, 4H), 3.75 (dt, J=12.20, 3.99 Hz, 2H), 3.55-3.66 (m, 2H), 2.95-3.02 (m, 1H), 2.77-2.82 (m, 1H), 2.69-2.76 (m, 1H), 2.62-2.69 (m, 1H), 1.97-2.03 (m, 1H), 1.84-1.88 (m, 1H), 1.70-1.83 (m, 7H), 1.48-1.58 (m, 3H). ES-LCMS m/z 508.3 $[M+H]^+$.

The following compounds were synthesized in an analogous manner to the preparation described above (Example 59) using the relevant alkyl bromide precursors. Compounds were purified using reverse phase chromatography (MeCN/$H_2O$, basic or acidic modifiers).

| Ex | Structure/Name | $^1H$ NMR | LCMS |
|---|---|---|---|
| 60 | 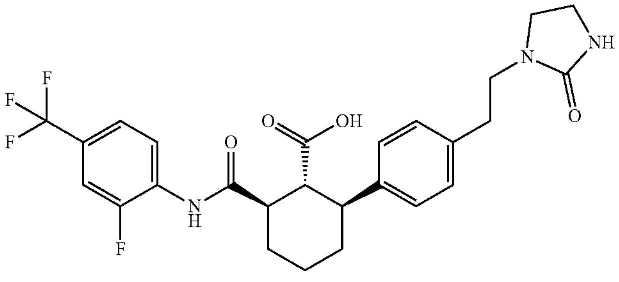 [SMILES: O=C(O)[C@@H]1[C@@H](c2ccc(CCN3CCNC3=O)cc2)CCC[C@H]1C(=O)Nc1ccc(C(F)(F)F)cc1F] (1R,2R,6S)-2-((2-fluoro-4-(trifluoromethyl)phenyl)carbamoyl)-6-(4-(2-(2-oxoimidazolidin-1-yl)ethyl)phenyl)cyclohexane-1-carboxylic acid | $^1H$ NMR (600 MHz, DMSO-$d_6$) δ 11.60-11.82 (m, 1H), 10.06-10.13 (m, 1H), 8.18-8.24 (m, 1H), 7.70-7.73 (m, 1H), 7.53-7.58 (m, 1H), 7.16-7.19 (m, 2H), 7.13-7.15 (m, 2H), 6.26 (s, 1H), 3.23-3.29 (m, 4H), 3.15-3.21 (m, 2H), 2.96-3.03 (m, 1H), 2.75-2.82 (m, 1H), 2.65-2.72 (m, 3H), 1.99-2.04 (m, 1H), 1.83-1.90 (m, 1H), 1.72-1.78 (m, 1H), 1.49-1.61 (m, 3H). | ES-LCMS m/z 522.4 $[M + H]^+$. |

-continued

| Ex | Structure/Name | $^1$H NMR | LCMS |
| --- | --- | --- | --- |
| 61 | 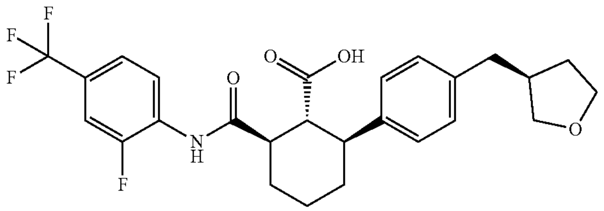 [SMILES: O=C(O)[C@@H]1[C@@H](c2ccc(C[C@H]3CCOC3)cc2)CCC[C@H]1C(=O)Nc1ccc(C(F)(F)F)cc1F] 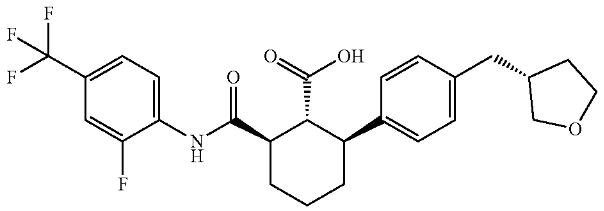 [SMILES: O=C(O)[C@@H]1[C@@H](c2ccc(C[C@@H]3CCOC3)cc2)CCC[C@H]1C(=O)Nc1ccc(C(F)(F)F)cc1F] 1:1 Mixture of (1R,2R,6S)-2-((2-fluoro-4-(trifluoromethyl)phenyl)carbamoyl)-6-(4-(((S)-tetrahydrofuran-3-yl)methyl)phenyl)cyclohexane-1-carboxylic acid AND (1R,2R,6S)-2-((2-fluoro-4-(trifluoromethyl)phenyl)carbamoyl)-6-(4-(((R)-tetrahydrofuran-3-yl)methyl)phenyl) cyclohexane-1-carboxylic acid | $^1$H NMR (600 MHz, DMSO-$d_6$) δ 10.16-10.34 (m, 1H), 8.21-8.29 (m, 1H), 7.67-7.73 (m, 1H), 7.52-7.57 (m, 1H), 7.15-7.28 (m, 4H), 2.91-2.99 (m, 1H), 2.67-2.77 (m, 2H), 1.96-2.03 (m, 3H), 1.83-1.90 (m, 1H), 1.70-1.77 (m, 1H), 1.50-1.63 (m, 10H). | ES-LCMS m/z 511.4 $[M + NH_4]^+$. |
| 62 | 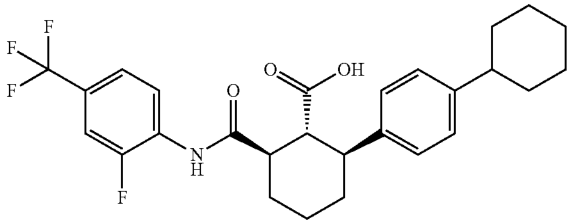 [SMILES: O=C(O)[C@@H]1[C@@H](c2ccc(C3CCCCC3)cc2)CCC[C@H]1C(=O)Nc1ccc(C(F)(F)F)cc1F] (1R,2S,6R)-2-(4-cyclohexylphenyl)-6-((2-fluoro-4-(trifluoromethyl)phenyl)carbamoyl) cyclohexane-1-carboxylic acid | $^1$H NMR (600 MHz, DMSO-$d_6$) δ 10.06-10.11 (m, 1H), 8.20 (t, J = 8.17 Hz, 1H), 7.67-7.73 (m, 1H), 7.51-7.57 (m, 1H), 7.08-7.17 (m, 4H), 2.94-3.02 (m, 1H), 2.78 (t, J = 11.26 Hz, 1H), 2.63-2.70 (m, 1H), 2.41-2.46 (m, 1H), 1.96-2.02 (m, 1H), 1.82-1.89 (m, 1H), 1.67-1.79 (m, 6H), 1.46-1.57 (m, 3H), 1.31-1.41 (m, 4H), 1.18-1.26 (m, 1H). | ES-LCMS m/z 490.3 $[M - H]^-$. |
| 63 | 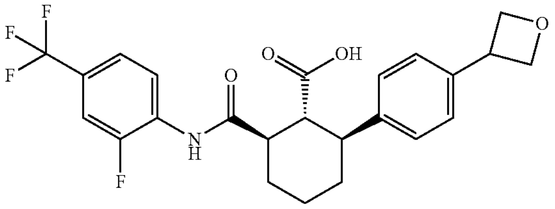 [SMILES: O=C(O)[C@@H]1[C@@H](c2ccc(C3COC3)cc2)CCC[C@H]1C(=O)Nc1ccc(C(F)(F)F)cc1F] (1R,2R,6S)-2-((2-fluoro-4-(trifluoromethyl)phenyl) carbamoyl)-6-(4-(oxetan-3-yl)phenyl)cyclohexane-1-carboxylic acid | $^1$H NMR (700 MHz, DMSO-$d_6$) δ 10.07-10.14 (m, 1H), 8.17-8.24 (m, 1H), 7.71 (dd, J = 10.97, 1.51 Hz, 1H), 7.55 (d, J = 8.60 Hz, 1H), 7.31 (d, J = 7.74 Hz, 2H), 7.25 (d, J = 8.17 Hz, 2H), 4.92 (dd, J = 8.17, 6.02 Hz, 2H), 4.60 (dd, J = 11.40, 6.24 Hz, 2H), 4.21 (s, 1H), 2.96-3.04 (m, 1H), 2.79-2.84 (m, 1H), 2.70 (td, J = 11.62, 3.44 Hz, 1H), 1.98-2.03 (m, 1H), 1.97-1.97 (m, 1H), 1.84-1.92 (m, 1H), 1.72-1.78 (m, 1H), 1.48-1.61 (m, 2H). | ES-LCMS m/z 466.3 $[M + H]^+$. |

-continued

| Ex | Structure/Name | $^1$H NMR | LCMS |
|---|---|---|---|
| 64 | 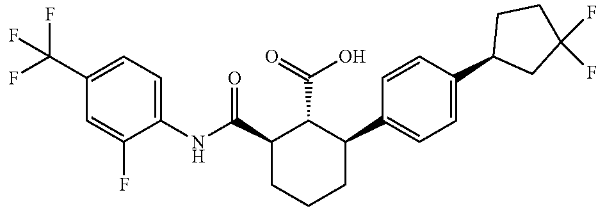 [SMILES: O=C(O)[C@@H]1[C@@H](c2ccc([C@H]3CCC(F)(F)C3)cc2)CCC[C@H]1C(=O)Nc1ccc(C(F)(F)F)cc1F]<br>+<br>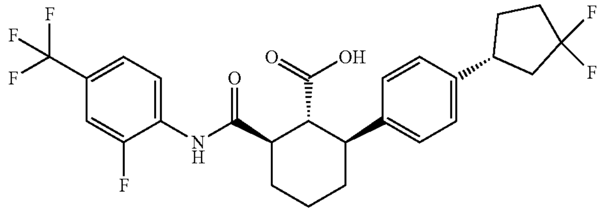 [SMILES: O=C(O)[C@@H]1[C@@H](c2ccc([C@@H]3CCC(F)(F)C3)cc2)CCC[C@H]1C(=O)Nc1ccc(C(F)(F)F)cc1F]<br>1:1 Mixture of (1R,2S,6R)-2-(4-((S)-3,3-difluorocyclopentyl)phenyl)-6-((2-fluoro-4-(trifluoromethyl)phenyl)carbamoyl) cyclohexane-1-carboxylic acid AND (1R,2S,6R)-2-(4-((R)-3,3-difluorocyclopentyl)phenyl)-6-((2-fluoro-4-(trifluoromethyl)phenyl)carbamoyl) cyclohexane-1-carboxylic acid | $^1$H NMR (700 MHz, DMSO-$d_6$) δ 10.08-10.13 (m, 1H), 8.19-8.23 (m, 1H), 7.69-7.74 (m, 1H), 7.55 (d, J = 8.60 Hz, 1H), 7.17-7.24 (m, 4H), 3.30 (br d, J = 3.44 Hz, 1H), 2.95-3.03 (m, 1H), 2.77-2.83 (m, 1H), 2.65-2.73 (m, 1H), 2.25-2.34 (m, 1H), 2.10-2.20 (m, 3H), 1.99-2.04 (m, 1H), 1.85-1.90 (m, 1H), 1.71-1.82 (m, 3H), 1.49-1.58 (m, 3H). | ES-LCMS m/z 514.3 $[M + H]^+$. |
| 65 | 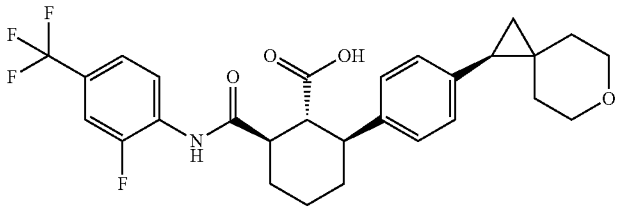 [SMILES: O=C(O)[C@@H]1[C@@H](c2ccc([C@H]3CC34CCOCC4)cc2)CCC[C@H]1C(=O)Nc1ccc(C(F)(F)F)cc1F]<br>+<br>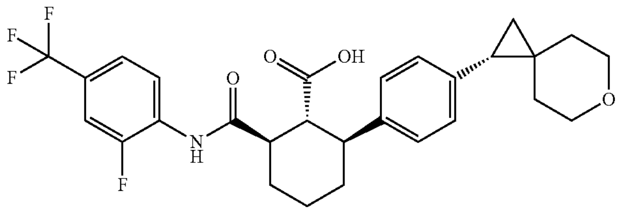 [SMILES: O=C(O)[C@@H]1[C@@H](c2ccc([C@@H]3CC34CCOCC4)cc2)CCC[C@H]1C(=O)Nc1ccc(C(F)(F)F)cc1F]<br>1:1 Mixture of (1R,2S,6R)-2-(4-((S)-6-oxaspiro[2.5]octan-1-yl)phenyl)-6-((2-fluoro-4-(trifluoromethyl)phenyl)carbamoyl)cyclohexane-1-carboxylic acid AND (1R,2S,6R)-2-(4-((R)-6-oxaspiro[2.5]octan-1-yl)phenyl)-6-((2-fluoro-4-(trifluoromethyl)phenyl)carbamoyl)cyclohexane-1-carboxylic acid | $^1$H NMR (700 MHz, DMSO-$d_6$) δ 10.04-10.14 (m, 1H), 8.16-8.24 (m, 1H), 7.68-7.74 (m, 1H), 7.51-7.56 (m, 1H), 7.12-7.14 (m, 2H), 7.09-7.11 (m, 2H), 3.66-3.72 (m, 1H), 3.59-3.63 (m, 1H), 3.38-3.43 (m, 2H), 2.95-3.01 (m, 1H), 2.72-2.77 (m, 1H), 2.62-2.68 (m, 1H), 1.98-2.02 (m, 1H), 1.90-1.96 (m, 1H), 1.81-1.87 (m, 1H), 1.71-1.77 (m, 1H), 1.42-1.55 (m, 5H), 1.06-1.16 (m, 2H), 0.94-0.98 (m, 1H), 0.76-0.81 (m, 1H). | ES-LCMS m/z 518.2 $[M - H]^-$. |

-continued

| Ex | Structure/Name | $^1H$ NMR | LCMS |
|---|---|---|---|
| 66 | 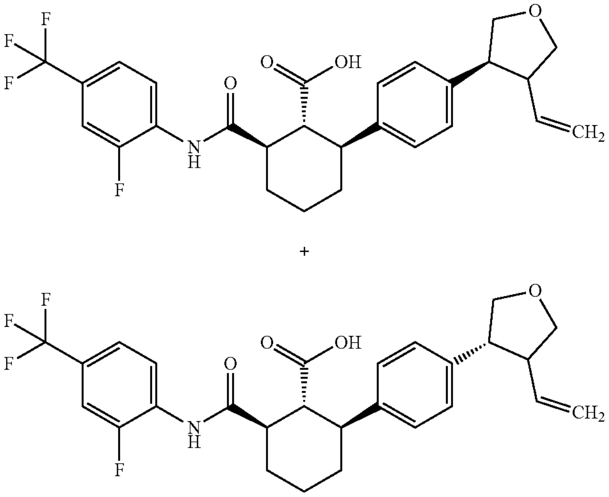 1:1 Mixture of (1R,2R,6S)-2-((2-fluoro-4-(trifluoromethyl)phenyl)carbamoyl)-6-(4-((3S)-4-vinyltetrahydrofuran-3-yl)phenyl)cyclohexane-1-carboxylic acid AND (1R,2R,6S)-2-((2-fluoro-4-(trifluoromethyl)phenyl)carbamoyl)-6-(4-((3R)-4-vinyltetrahydrofuran-3-yl)phenyl)cyclohexane-1-carboxylic acid | $^1H$ NMR (700 MHz, DMSO-$d_6$) δ 10.06-10.13 (m, 1H), 8.21 (t, J = 8.39 Hz, 1H), 7.71 (dd, J = 10.76, 1.72 Hz, 1H), 7.52-7.58 (m, 1H), 7.17-7.22 (m, 4H), 5.71-5.79 (m, 1H), 5.00-5.04 (m, 1H), 4.95-4.99 (m, 1H), 4.09-4.14 (m, 1H), 4.04-4.09 (m, 1H), 3.60-3.65 (m, 1H), 3.54-3.58 (m, 1H), 3.11-3.18 (m, 1H), 2.91-3.01 (m, 2H), 2.79 (t, J = 11.19 Hz, 1H), 2.64-2.71 (m, 1H), 1.97-2.03 (m, 1H), 1.83-1.91 (m, 1H), 1.70-1.78 (m, 1H), 1.46-1.59 (m, 3H). | ES-LCMS m/z 506.3 $[M + H]^+$. |

-continued

| Ex | Structure/Name | $^1H$ NMR | LCMS |
|---|---|---|---|
| 67 | 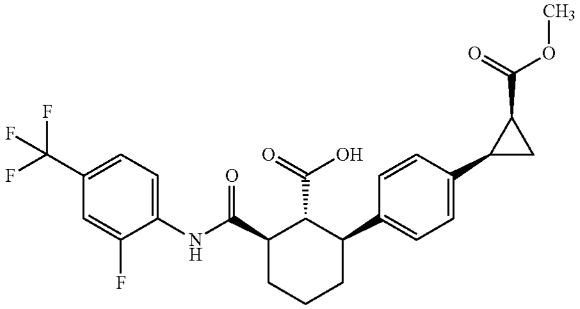 [SMILES: COC(=O)[C@H]1C[C@H]1c1ccc([C@H]2CCC[C@@H](C(=O)Nc3ccc(C(F)(F)F)cc3F)[C@@H]2C(=O)O)cc1] + 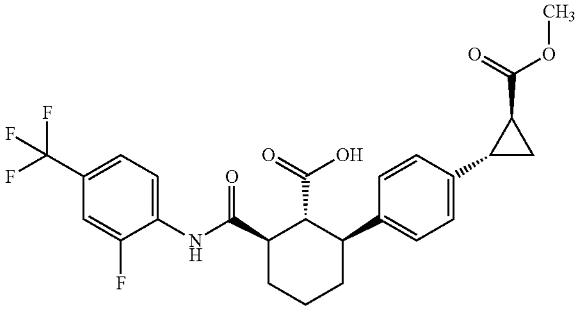 [SMILES: COC(=O)[C@H]1C[C@@H]1c1ccc([C@H]2CCC[C@@H](C(=O)Nc3ccc(C(F)(F)F)cc3F)[C@@H]2C(=O)O)cc1] 1:1 Mixture of (1R,2R,6S)-2-((2-fluoro-4-(trifluoromethyl)phenyl)carbamoyl)-6-(4-((1R,2S)-2-(methoxycarbonyl)cyclopropyl)phenyl) cyclohexane-1-carboxylic acid AND (1R,2R,6S)-2-((2-fluoro-4-(trifluoromethyl)phenyl)carbamoyl)-6-(4-((1S,2S)-2-(methoxycarbonyl)cyclopropyl)phenyl) cyclohex ane-1-carboxylic acid | $^1H$ NMR (400 MHz, METHANOL-$d_4$) δ 8.21 (t, J = 8.07 Hz, 1H), 7.37-7.55 (m, 2H), 7.11-7.25 (m, 2H), 7.05 (d, J = 8.31 Hz, 2H), 3.59-3.80 (m, 3H), 2.86-3.04 (m, 2H), 2.78 (td, J = 11.13, 3.18 Hz, 1H), 2.37-2.49 (m, 1H), 2.10 (br d, J = 10.76 Hz, 1H), 1.93-2.03 (m, 1H), 1.79-1.93 (m, 2H), 1.57-1.73 (m, 3H), 1.45-1.56 (m, 1H), 1.24-1.45 (m, 1H). One exchangeable H not observed. | ES-LCMS m/z 508.2 $[M + H]^+$. |
| 68 | 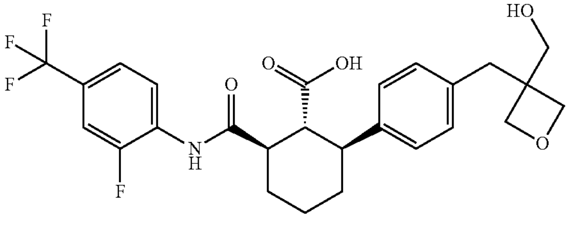 [SMILES: O=C(O)[C@@H]1[C@@H](c2ccc(CC3(CO)COC3)cc2)CCC[C@H]1C(=O)Nc1ccc(C(F)(F)F)cc1F] (1R,2R,6S)-2-((2-fluoro-4-(trifluoromethyl)phenyl)carbamoyl)-6-(4-((3-(hydroxymethyl)oxetan-3-yl)methyl)phenyl) cyclohexane-1-carboxylic acid | $^1H$ NMR (400 MHz, METHANOL-$d_4$) δ 8.22 (t, J = 7.82 Hz, 1H), 7.42-7.51 (m, 2H), 7.17-7.25 (m, 2H), 7.08-7.17 (m, 2H), 4.57 (d, J = 5.38 Hz, 2H), 4.35-4.44 (m, 2H), 3.62 (s, 2H), 2.87-3.04 (m, 4H), 2.80 (td, J = 11.25, 3.42 Hz, 1H), 2.05-2.15 (m, 1H), 1.93-2.05 (m, 1H), 1.82-1.92 (m, 1H), 1.53-1.74 (m, 3H). Two exchangeable Hs not observed. | ES-LCMS m/z 508.2 $[M - H]^-$. |
| 69 | 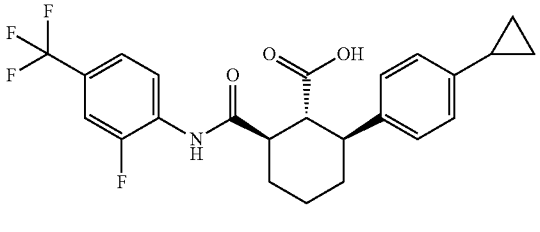 [SMILES: O=C(O)[C@@H]1[C@@H](c2ccc(C3CC3)cc2)CCC[C@H]1C(=O)Nc1ccc(C(F)(F)F)cc1F] (1R,2S,6R)-2-(4-cyclopropylphenyl)-6-((2-fluoro-4-(trifluoromethyl)phenyl)carbamoyl) cyclohexane-1-carboxylic acid | $^1H$ NMR (400 MHz, METHANOL-$d_4$) δ 8.21 (t, J = 8.07 Hz, 1H), 7.41-7.51 (m, 2H), 7.06-7.16 (m, 2H), 6.98 (d, J = 8.31 Hz, 2H), 2.85-3.02 (m, 2H), 2.76 (td, J = 11.13, 3.18 Hz, 1H), 2.04-2.12 (m, 1H), 1.93-2.04 (m, 1H), 1.77-1.90 (m, 2H), 1.55-1.73 (m, 3H), 0.84-0.97 (m, 2H), 0.56-0.68 (m, 2H). One exchangeable H not observed. | ES-LCMS m/z 448.2 $[M - H]^-$. |

Example 70

Mixture of formic acid salts of (1R,2S,6R)-2-(4-((1R,6R,7R)-3-azabicyclo[4.1.0]heptan-7-yl)phenyl)-6-((2-fluoro-4-(trifluoromethyl)phenyl)carbamoyl)cyclohexane-1-carboxylic acid AND (1R,2S,6R)-2-(4-((1R,6R,7S)-3-azabicyclo[4.1.0]heptan-7-yl)phenyl)-6-((2-fluoro-4-(trifluoromethyl)phenyl)carbamoyl)cyclohexane-1-carboxylic acid AND (1R,2S,6R)-2-(4-((1S,6S,7S)-3-azabicyclo[4.1.0]heptan-7-yl)phenyl)-6-((2-fluoro-4-(trifluoromethyl)phenyl)carbamoyl)cyclohexane-1-carboxylic acid AND (1R,2S,6R)-2-(4-((1S,6S,7R)-3-azabicyclo[4.1.0]heptan-7-yl)phenyl)-6-((2-fluoro-4-(trifluoromethyl)phenyl)carbamoyl)cyclohexane-1-carboxylic acid

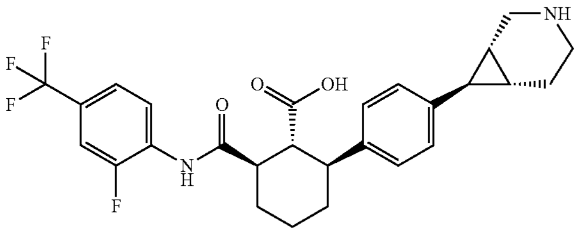

+

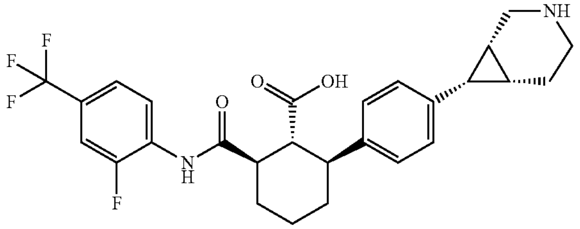

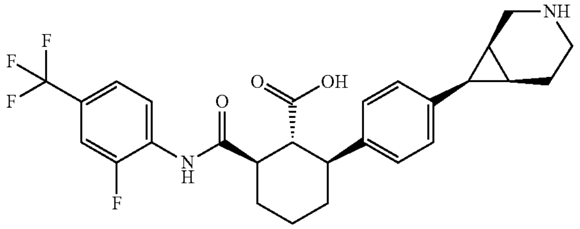

+

-continued

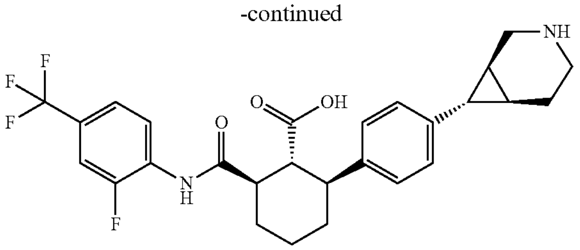

To a mixture of (1R,2S,6R)-2-(4-bromophenyl)-6-((2-fluoro-4-(trifluoromethyl)phenyl)carbamoyl)cyclohexane-1-carboxylic acid Intermediate 1 (73 mg, 0.15 mmol), rac-4-tert-butyl (1S,6S,7R)-7-bromo-3-azabicyclo[4.1.0]heptane-3-carboxylate (83 mg, 0.30 mmol), (4,4'-dtbbpy)$NiCl_2$ (3.0 mg, 7.5 μmol), $[Ir(dtbbpy)(ppy)_2]PF_6$ (1.4 mg, 1.5 μmol), Aminosupersilane (0.090 g, 0.23 mmol), and $Na_2CO_3$ (48 mg, 0.45 mmol) was added THF (0.75 mL). The reaction was placed in a Lumidox reactor (blue LED, 315 mW per well, 7.6 W total radiant power) on a tumble stirrer with the cooling set to 5° C. (internal temperature ~23° C.) and irradiated for 18 h, then concentrated via blowdown (40° C., $N_2$). The crude material was dissolved in DCM (0.5 mL) and treated with TFA (0.5 mL). The resulting reaction mixture was heated to 30° C. for 1 h, then concentrated via blowdown (40° C., $N_2$), and the residue was subjected to reverse phase purification (MeCN/$H_2O$, 0.1% formic acid modifier, 15-100% gradient) to afford a mixture of formic acid salts of (1R,2S,6R)-2-(4-((1R,6R,7R)-3-azabicyclo[4.1.0]heptan-7-yl)phenyl)-6-((2-fluoro-4-(trifluoromethyl)phenyl)carbamoyl)cyclohexane-1-carboxylic acid, (1R,2S,6R)-2-(4-((1R,6R,7S)-3-azabicyclo[4.1.0]heptan-7-yl)phenyl)-6-((2-fluoro-4-(trifluoromethyl)phenyl)carbamoyl)cyclohexane-1-carboxylic acid, (1R,2S,6R)-2-(4-((1S,6S,7S)-3-azabicyclo[4.1.0]heptan-7-yl)phenyl)-6-((2-fluoro-4-(trifluoromethyl)phenyl)carbamoyl)cyclohexane-1-carboxylic acid and (1R,2S,6R)-2-(4-((1S,6S,7R)-3-azabicyclo[4.1.0]heptan-7-yl)phenyl)-6-((2-fluoro-4-(trifluoromethyl)phenyl)carbamoyl)cyclohexane-1-carboxylic acid (6.5 mg, 11 μmol, 7% yield). The proton NMR is complicated due to the mixture of 4 diastereomers. ES-LCMS m/z 505.4 $[M+H]^+$.

The following compound was synthesized in an analogous manner to the preparation described above (Example 70) using the relevant alkyl bromide precursors. The compound was purified using reverse phase chromatography (MeCN/$H_2O$, basic modifiers).

| Ex | Structure/Name | $^1H$ NMR | LCMS |
|---|---|---|---|
| 71 | 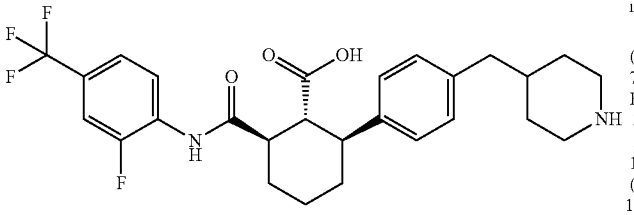 (1R,2R,6S)-2-((2-fluoro-4-(trifluoromethyl)phenyl)carbamoyl)-6-(4-(piperidin-4-ylmethyl)phenyl)cyclohexane-1-carboxylic acid | $^1H$ NMR (700 MHz, DMSO-$d_6$) δ 10.06-10.10 (m, 1H), 8.17-8.21 (m, 1H), 7.70-7.73 (m, 1H), 7.53-7.56 (m, 1H), 7.17 (br d, J = 7.31 Hz, 2H), 7.06-7.09 (m, 2H), 3.20-3.24 (m, 2H), 2.97-3.02 (m, 1H), 2.75-2.84 (m, 3H), 2.65-2.70 (m, 1H), 1.98-2.04 (m, 1H), 1.85-1.90 (m, 1H), 1.67-1.79 (m, 4H), 1.48-1.56 (m, 3H), 1.24-1.32 (m, 2H). 3 Hs obscured by solvent peak | ES-LCMS m/z 507.4 $[M + H]^+$. |

Example 72 rac-(1R,2S,6S)-2-((4-isopropylphenyl)carbamoyl)-6-(4-((N,1,2-trimethyl-1H-benzo[d]imidazole)-5-sulfonamido)phenyl)cyclohexane-1-carboxylic acid

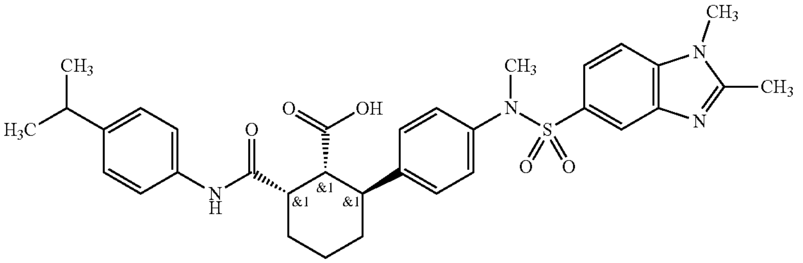 [SMILES: Cc1nc2cc(S(=O)(=O)N(C)c3ccc([C@H]4CCC[C@H](C(=O)Nc5ccc(C(C)C)cc5)[C@@H]4C(=O)O)cc3)ccc2n1C]

To a 1:1 mixture of (1R,2S,6S)-2-((4-isopropylphenyl)carbamoyl)-6-(4-(methylamino)phenyl)cyclohexane-1-carboxylic acid and (1 S,2R,6R)-2-((4-isopropylphenyl)carbamoyl)-6-(4-(methylamino)phenyl)cyclohexane-1-carboxylic acid Intermediate 3 (0.080 g, 0.20 mmol) in DCM (2 mL) at 0° C. were added pyridine (0.050 mL, 0.62 mmol) and 1,2-dimethyl-1H-benzo[d]imidazole-5-sulfonyl chloride (0.050 g, 0.20 mmol). After 1 h, the reaction was diluted with water and extracted with DCM. The organic layers were washed with brine, dried over anhydrous sodium sulfate, filtered, concentrated, dissolved in DMF (2 mL) and purified over silica (40 g C18 column), eluting with 10-50% acetonitrile in water (0.1% formic acid) to give rac-(1R,2S,6S)-2-((4-isopropylphenyl)carbamoyl)-6-(4-((N,1,2-trimethyl-1H-benzo[d]imidazole)-5-sulfonamido)phenyl)cyclohexane-1-carboxylic acid (25 mg, 0.040 mmol, 20% yield) as a white solid. $^{1}H$ NMR (400 MHz, DMSO-$d_6$) δ 11.88 (br, 1H), 9.85 (br, 1H), 7.74-7.58 (m, 2H), 7.54-7.40 (m, 2H), 7.24 (dd, J=8.4, 1.8 Hz, 1H), 7.19 (d, J=8.4 Hz, 2H), 7.14 (d, J=8.4 Hz, 2H), 6.96-6.88 (m, 2H), 3.79 (s, 3H), 3.67-3.54 (m, 1H), 3.23-3.17 (m, 1H), 3.07 (s, 3H), 2.94-2.73 (m, 2H), 2.57 (s, 3H), 2.09-1.93 (m, 1H), 1.91-1.82 (m, 1H), 1.81-1.66 (m, 2H), 1.58-1.47 (m, 1H), 1.43-1.29 (m, 1H), 1.18 (d, J=6.8 Hz, 6H). ES-LCMS m/z 603.3 $[M+H]^+$.

Example 73 and Example 74 rel-(1R,2S,6S)-2-((4-isopropylphenyl)carbamoyl)-6-(4-((N,1,2-trimethyl-1H-benzo[d]imidazole)-5-sulfonamido)phenyl)cyclohexane-1-carboxylic acid ISOMER 1 AND ISOMER 2

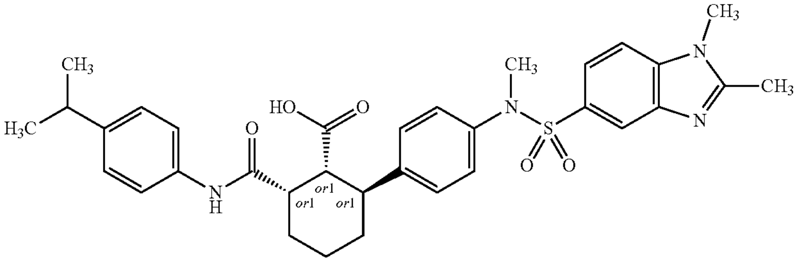

ISOMER 1 and ISOMER 2

Rac-(1R,2S,6S)-2-((4-isopropylphenyl)carbamoyl)-6-(4-((N,1,2-trimethyl-1H-benzo[d]imidazole)-5-sulfonamido)phenyl)cyclohexane-1-carboxylic acid (50 mg, 0.083 mmol) was chirally purified (Column: Lux Cell-4 [4.6 mm×150 mm, 5 micron]; Mobile Phase: 1:1 heptane:EtOH) to give: Example 73, first eluting isomer: rel-(1R,2S,6S)-2-((4-isopropylphenyl)carbamoyl)-6-(4-((N,1,2-trimethyl-1H-benzo[d]imidazole)-5-sulfonamido)phenyl)cyclohexane-1-carboxylic acid ISOMER 1 (19.0 mg, 0.0315 mmol, 38.0%). $^{1}H$ NMR (400 MHz, METHANOL-d) δ 7.68-7.52 (m, 2H), 7.50-7.36 (m, 3H), 7.19 (t, J=8.8 Hz, 4H), 6.95 (d, J=8.3 Hz, 2H), 3.83 (s, 3H), 3.76-3.65 (m, 1H), 3.24 (br s, 1H), 3.14 (s, 3H), 2.95 (br dd, J=11.5, 4.2 Hz, 1H), 2.88 (quin, J=7.0 Hz, 1H), 2.63 (s, 3H), 2.22-2.00 (m, 2H), 1.97-1.79 (m, 2H), 1.67 (br d, J=13.7 Hz, 1H), 1.60-1.41 (m, 1H), 1.24 (d, J=6.8 Hz, 6H). One exchangeable H not observed. ES-LCMS m/z 603.2 [M+H]$^+$. Example 74, second eluting isomer: rel-(1R,2S,6S)-2-((4-isopropylphenyl)carbamoyl)-6-(4-((N,1,2-trimethyl-1H-benzo[d]imidazole)-5-sulfonamido)phenyl)cyclohexane-1-carboxylic acid ISOMER 2 (18.2 mg, 0.0302 mmol, 36.4%). $^1$H NMR (400 MHz, METHANOL-d) δ 7.62-7.53 (m, 2H), 7.47-7.39 (m, 3H), 7.19 (t, J=8.8 Hz, 4H), 6.95 (d, J=8.3 Hz, 2H), 3.83 (s, 3H), 3.70 (td, J=11.9, 3.7 Hz, 1H), 3.27-3.22 (m, 1H), 3.14 (s, 3H), 2.95 (dd, J=11.5, 4.6 Hz, 1H), 2.88 (quin, J=6.8 Hz, 1H), 2.63 (s, 3H), 2.20-2.00 (m, 2H), 1.95-1.78 (m, 2H), 1.71-1.61 (m, 1H), 1.51 (qd, J=13.0, 3.7 Hz, 1H), 1.24 (d, J=6.8 Hz, 6H). One exchangeable H not observed. ES-LCMS m/z 603.2 [M+H]$^+$.

Example 75 rac-(1R,2S,6R)-2-((4-isopropylphenyl)carbamoyl)-6-(4-((N,1,2-trimethyl-1H-benzo[d]imidazole)-5-sulfonamido)phenyl)cyclohexane-1-carboxylic acid

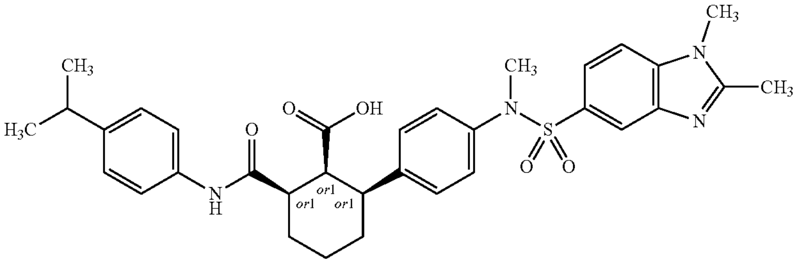 [SMILES: Cc1nc2cc(S(=O)(=O)N(C)c3ccc([C@H]4CCC[C@@H](C(=O)Nc5ccc(C(C)C)cc5)[C@H]4C(=O)O)cc3)ccc2n1C]

To a 1:1 mixture of (1R,2S,6R)-2-((4-isopropylphenyl)carbamoyl)-6-(4-(methylamino)phenyl)cyclohexane-1-carboxylic acid and (1S,2R,6S)-2-((4-isopropylphenyl)carbamoyl)-6-(4-(methylamino)phenyl)cyclohexane-1-carboxylic acid Intermediate 4 (0.120 g, 0.304 mmol) in DCM (2 mL) at 0° C. were added pyridine (0.073 mL, 0.62 mmol) and 1,2-dimethyl-1H-benzo[d]imidazole-5-sulfonyl chloride (89 mg, 0.37 mmol). After 1 h, the reaction was diluted with water and extracted with EtOAc. The organic layers were washed with brine, dried over anhydrous sodium sulfate, filtered, concentrated, dissolved in DMF (3 mL) and purified over silica (25 g C18 column), eluting with 5-80% acetonitrile in water (0.1% TFA) to give rac-(1R,2S,6R)-2-((4-isopropylphenyl)carbamoyl)-6-(4-((N,1,2-trimethyl-1H-benzo[d]imidazole)-5-sulfonamido)phenyl)cyclohexane-1-carboxylic acid (103 mg, 0.168 mmol, 55.3% yield) as a white solid. $^1$H NMR (400 MHz, DMSO-$d_6$) δ 9.77 (s, 1H), 7.74 (d, J=8.4 Hz, 1H), 7.62 (s, 1H), 7.51-7.43 (m, 2H), 7.32-7.30 (m, 1H), 7.22-7.10 (m, 4H), 7.03-6.96 (m, 2H), 3.83 (s, 3H), 3.15-3.13 (m, 1H), 3.09 (s, 3H), 2.90 (d, J=13.2 Hz, 1H), 2.87-2.74 (m, 2H), 2.65 (s, 3H), 2.42-2.29 (m, 1H), 2.16-2.06 (m, 1H), 1.97 (d, J=12.8 Hz, 1H), 1.69 (d, J=12.8 Hz, 1H), 1.59 (d, J=12.4 Hz, 1H), 1.47 (d, J=13.6 Hz, 1H), 1.18 (d, J=6.8 Hz, 6H). ES-LCMS m/z 603.4 [M+H]$^+$.

Example 76 and Example 77 rel-(1R,2S,6R)-2-((4-isopropylphenyl)carbamoyl)-6-(4-((N,1,2-trimethyl-1H-benzo[d]imidazole)-5-sulfonamido)phenyl)cyclohexane-1-carboxylic acid. ISOMER 1 AND ISOMER 2

ISOMER 1 AND ISOMER 2

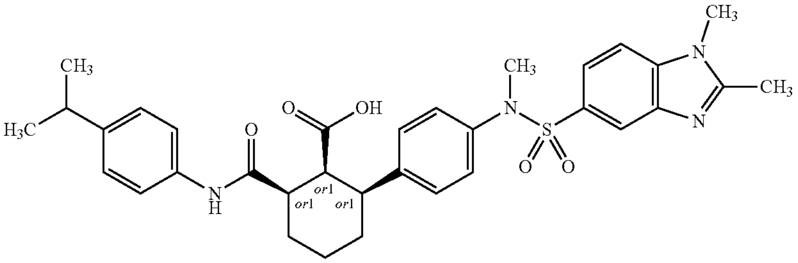

Rac-(1R,2S,6R)-2-((4-isopropylphenyl)carbamoyl)-6-(4-((N,1,2-trimethyl-1H-benzo[d]imidazole)-5-sulfonamido)phenyl)cyclohexane-1-carboxylic acid (50 mg, 0.083 mmol) was chirally purified (Column: Chiralpak OJ-H [20 mm×150 mm, 5 micron]; Mobile Phase: 65:35 $CO_2$:MeOH) to give: Example 76, the first-eluting isomer: rel-(1R,2S,6R)-2-((4-isopropylphenyl)carbamoyl)-6-(4-((N,1,2-trimethyl-1H-benzo[d]imidazole)-5-sulfonamido)phenyl)cyclohexane-1-carboxylic acid, ISOMER 1 (17 mg, 0.028 mmol, 34%). $^1$H NMR (400 MHz, METHANOL-d) δ 7.59 (d, J=8.8 Hz, 1H), 7.49-7.37 (m, 4H), 7.19 (dd, J=11.5, 8.6 Hz, 4H), 6.97 (d, J=8.8 Hz, 2H), 3.84 (s, 3H), 3.26 (t, J=4.4 Hz, 1H), 3.14 (s, 3H), 3.01 (dt, J=13.1, 4.0 Hz, 1H), 2.92-2.82 (m, 2H), 2.65 (s, 3H), 2.55-2.24 (m, 2H), 2.14-2.04 (m, 1H), 1.82 (br dd, J=13.0, 3.2 Hz, 1H), 1.69 (br dd, J=12.7, 2.4 Hz, 1H), 1.64-1.49 (m, 1H), 1.24 (d, J=6.8 Hz, 6H). One exchangeable H not observed. ES-LCMS m/z 603.2 $[M+H]^+$.

Example 77, the second-eluting isomer: rel-(1R,2S,6R)-2-((4-isopropylphenyl)carbamoyl)-6-(4-((N,1,2-trimethyl-1H-benzo[d]imidazole)-5-sulfonamido)phenyl)cyclohexane-1-carboxylic acid, ISOMER 2 (16 mg, 0.027 mmol, 32%). $^1$H NMR (400 MHz, METHANOL-d) δ 7.59 (d, J=9.3 Hz, 1H), 7.49-7.41 (m, 4H), 7.24-7.15 (m, 4H), 6.97 (d, J=8.3 Hz, 2H), 3.84 (s, 3H), 3.26 (br s, 1H), 3.14 (s, 3H), 3.06-2.96 (m, 1H), 2.94-2.82 (m, 2H), 2.65 (s, 3H), 2.54-2.25 (m, 2H), 2.14-2.05 (m, 1H), 1.88-1.78 (m, 1H), 1.68 (br d, J=10.8 Hz, 1H), 1.64-1.49 (m, 1H), 1.24 (d, J=6.8 Hz, 6H). One exchangeable H not observed. ES-LCMS m/z 603.2 $[M+H]^+$.

Example 78 rac-(1R,2R,6S)-2-((4-isopropylphenyl)carbamoyl)-6-(4-((N,1,2-trimethyl-1H-benzo[d]imidazole)-5-sulfonamido)phenyl)cyclohexane-1-carboxylic acid

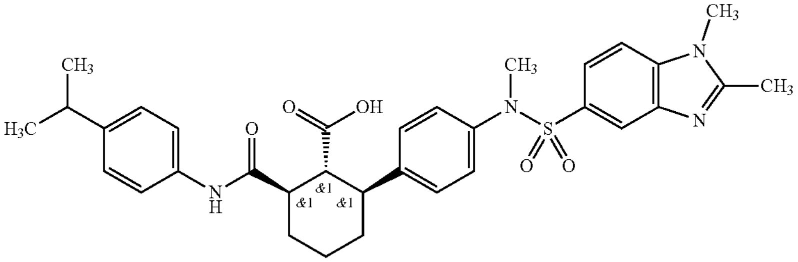

To a 1:1 mixture of (1R,2S,6S)-2-((4-isopropylphenyl)carbamoyl)-6-(4-(methylamino)phenyl)cyclohexane-1-carboxylic acid and (1S,2R,6R)-2-((4-isopropylphenyl)carbamoyl)-6-(4-(methylamino)phenyl)cyclohexane-1-carboxylic acid Intermediate 5 (0.0600 g, 0.152 mmol) in DCM (1 mL) at 0° C. were added pyridine (0.037 mL, 0.46 mmol) and 1,2-dimethyl-1H-benzo[d]imidazole-5-sulfonyl chloride (40.9 mg, 0.167 mmol). After 1 h, the reaction was diluted with water and extracted with DCM. The organic layers were washed with brine, dried over anhydrous sodium sulfate, filtered and concentrated to give rac-(1R,2R,6S)-2-((4-isopropylphenyl)carbamoyl)-6-(4-((N,1,2-trimethyl-1H-benzo[d]imidazole)-5-sulfonamido)phenyl)cyclohexane-1-carboxylic acid (103 mg, 0.168 mmol, 55.3% yield) as an off white solid. $^1$H NMR (400 MHz, DMSO-$d_6$) δ 11.99 (s, 1H), 9.86 (s, 1H), 7.63 (d, J=8.4 Hz, 1H), 7.52-7.48 (m, 3H), 7.26-7.13 (m, 5H), 6.97 (d, J=8.4 Hz, 2H), 3.79 (s, 3H), 3.06 (s, 3H), 2.85-2.67 (m, 4H), 2.57 (s, 3H), 1.93-1.84 (m, 2H), 1.74-1.70 (m, 1H), 1.54-1.48 (m, 3H), 1.17 (d, J=6.8 Hz, 6H). ES-LCMS m/z 603.2 $[M+H]^+$.

Example 79 and Example 80 rel-(1R,2R,6S)-2-((4-isopropylphenyl)carbamoyl)-6-(4-((N,1,2-trimethyl-1H-benzo[d]imidazole)-5-sulfonamido)phenyl)cyclohexane-1-carboxylic acid, ISOMER 1 AND ISOMER 2

ISOMER 1 AND ISOMER 2

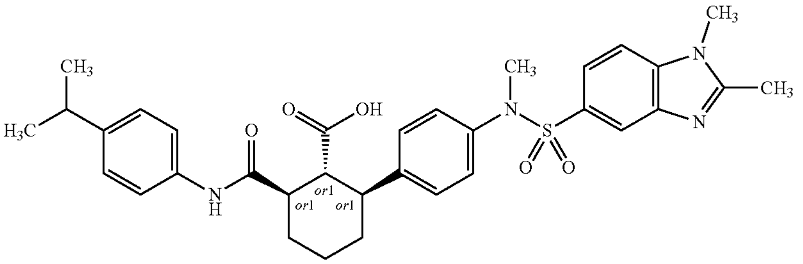 [SMILES: Cc1nc2cc(S(=O)(=O)N(C)c3ccc([C@H]4CCC[C@@H](C(=O)Nc5ccc(C(C)C)cc5)[C@@H]4C(=O)O)cc3)ccc2n1C]

Rac-(1R,2R,6S)-2-((4-isopropylphenyl)carbamoyl)-6-(4-((N,1,2-trimethyl-1H-benzo[d]imidazole)-5-sulfonamido)phenyl)cyclohexane-1-carboxylic acid (11 mg, 0.018 mmol) was chirally purified (Column: Chiralpak OJ-H [20 mm×150 mm, 5 micron]; Mobile Phase: 75:25 $CO_2$:MeOH) to give: Example 79, the first-eluting isomer: rel-(1R,2R,6S)-2-((4-isopropylphenyl)carbamoyl)-6-(4-((N,1,2-trimethyl-1H-benzo[d]imidazole)-5-sulfonamido)phenyl)cyclohexane-1-carboxylic acid, ISOMER 1 (4 mg, 0.007 mmol). $^1H$ NMR (400 MHz, METHANOL-$d_4$) δ 7.58 (d, J=8.8 Hz, 1H), 7.53 (s, 1H), 7.47-7.38 (m, 3H), 7.22-7.16 (m, 4H), 6.98 (d, J=8.8 Hz, 2H), 3.84 (s, 3H), 3.14 (s, 3H), 2.97-2.73 (m, 4H), 2.64 (s, 3H), 2.15-1.96 (m, 2H), 1.92-1.85 (m, 1H), 1.79-1.57 (m, 3H), 1.24 (d, J=6.8 Hz, 6H). One exchangeable H not observed. ES-LCMS m/z 603.2 $[M+H]^+$. AND Example 80, the second-eluting isomer: rel-(1R,2R,6S)-2-((4-isopropylphenyl)carbamoyl)-6-(4-((N,1,2-trimethyl-1H-benzo[d]imidazole)-5-sulfonamido)phenyl)cyclohexane-1-carboxylic acid, ISOMER 2 (4 mg, 0.007 mmol). $^1H$ NMR (400 MHz, METHANOL-$d_4$) δ 7.59 (d, J=8.3 Hz, 1H), 7.53 (s, 1H), 7.47-7.37 (m, 3H), 7.23-7.16 (m, 4H), 6.98 (d, J=8.8 Hz, 2H), 3.84 (s, 3H), 3.14 (s, 3H), 2.98-2.75 (m, 4H), 2.64 (s, 3H), 2.16-1.98 (m, 2H), 1.94-1.84 (m, 1H), 1.77-1.56 (m, 3H), 1.24 (d, J=6.8 Hz, 6H). One exchangeable H not observed. ES-LCMS m/z 603.2 $[M+H]^+$.

Example 81 rac-(1R,2R,6S)-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylic acid

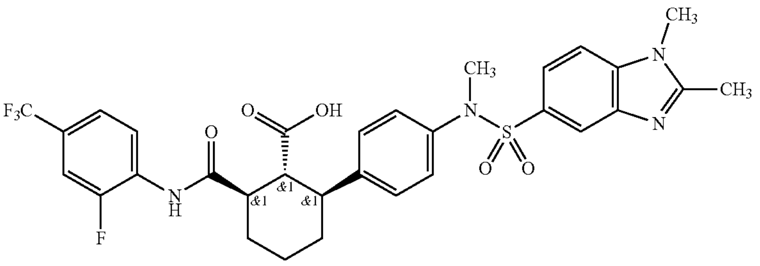 [SMILES: Cc1nc2cc(S(=O)(=O)N(C)c3ccc([C@H]4CCC[C@@H](C(=O)Nc5ccc(C(F)(F)F)cc5F)[C@@H]4C(=O)O)cc3)ccc2n1C]

To a 1:1 mixture of (1R,2R,6S)-2-((2-fluoro-4-(trifluoromethyl)phenyl)carbamoyl)-6-(4-(methylamino)phenyl)cyclohexane-1-carboxylic acid and (1S,2S,6R)-2-((2-fluoro-4-(trifluoromethyl)phenyl)carbamoyl)-6-(4-(methylamino)phenyl)cyclohexane-1-carboxylic acid Intermediate 6 (0.0550 g, 0.125 mmol) in DCM (2 mL) at 0° C. were added pyridine (0.030 mL, 0.38 mmol) and 1,2-dimethyl-1H-benzo[d]imidazole-5-sulfonyl chloride (30.7 mg, 0.125 mmol). After 1 h, the reaction was diluted with water and extracted with EtOAc. The organic layers were washed with brine, dried over anhydrous sodium sulfate, concentrated, dissolved in DMF (2 mL) and purified over silica (40 g C18 column), eluting with 5-100% acetonitrile in water to give rac-(1R,2R,6S)-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylic acid (0.030 g, 0.045 mmol, 36.0% yield) as a white solid. $^1H$ NMR (400 MHz, DMSO-$d_6$) δ 12.03 (br, 1H), 10.09 (s, 1H), 8.22 (t, J=8.0 Hz, 1H), 7.72 (d, J=10.4 Hz, 1H), 7.63 (d, J=8.4 Hz, 1H), 7.56 (d, J=9.2 Hz, 1H), 7.57-7.51 (m, 1H), 7.25 (dd, J=6.8, 1.6 Hz, 1H), 7.18-7.17 (m, 2H), 6.97 (d, J=8.4 Hz, 2H), 3.79 (s, 3H), 3.06 (s, 3H), 3.04-3.00 (m, 1H), 2.82-2.67 (m, 2H), 2.57 (s, 3H), 2.04-2.00 (m, 1H), 1.90-1.85 (m, 1H), 1.76-1.74 (m, 1H), 1.70-1.51 (m, 3H). ES-LCMS m/z 647.3 $[M+H]^+$.

The following compounds were synthesized in an analogous manner to the preparation described above (Example 81) using the relevant sulfonyl chloride precursors. Compounds were purified using reverse phase chromatography (MeCN/$H_2O$, basic or acidic modifiers)

| Ex | Structure/Name | $^1H$ NMR | LCMS |
|---|---|---|---|
| 82 | 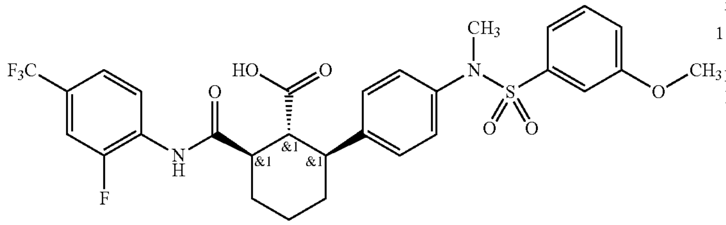 rac-(1R,2R,6S)-2-((2-fluoro-4-(trifluoromethyl)phenyl)carbamoyl)-6-(4-((3-methoxy-N-methylphenyl)sulfonamido)phenyl) cyclohexane-1-carboxylic acid | $^1H$ NMR (400 MHz, DMSO-$d_6$) δ 11.40 (br s, 1H), 10.10 (s, 1H), 8.22 (t, J = 8.0 Hz, 1H), 7.71 (dd, J = 11.0, 2.0 Hz, 1H), 7.55 (d, J = 8.4 Hz, 1H), 7.48 (t, J = 8.0 Hz, 1H), 7.27-7.24 (m, 3H), 7.05-7.00 (m, 3H), 6.86-6.85 (m, 1H), 3.70 (s, 3H), 3.10 (s, 3H), 3.01-2.80 (m, 1H), 2.77-2.67 (m, 2H), 2.02-2.00 (m, 1H), 1.88-1.74 (m, 1H), 1.72-1.58 (m, 1H), 1.55-1.48 (m, 3H). | ES-LCMS m/z 607.1 $[M-H]^-$. |

Example 83 and Example 84

(1R,2R,6S)-2-((2-fluoro-4-(trifluoromethyl)phenyl) carbamoyl)-6-(4-((N,1,2-trimethyl-1H-benzo[d]imidazole)-5-sulfonamido)phenyl)cyclohexane-1-carboxylic acid AND (1S,2S,6R)-2-((2-fluoro-4-(trifluoromethyl)phenyl)carbamoyl)-6-(4-((N,1,2-trimethyl-1H-benzo[d]imidazole)-5-sulfonamido) phenyl)cyclohexane-1-carboxylic acid

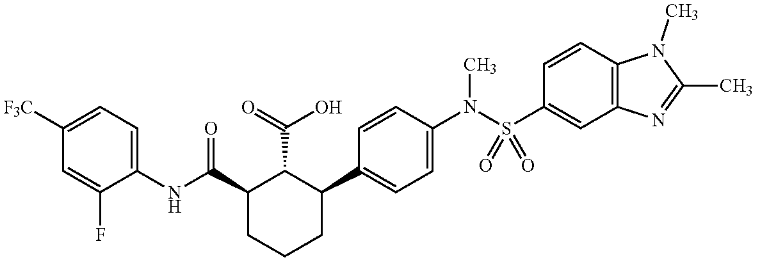

AND

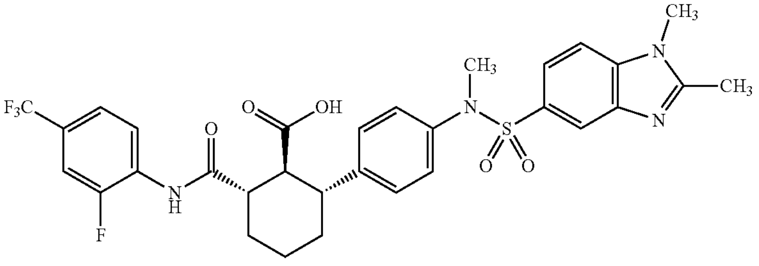

Rac-(1R,2R,6S)-2-((2-fluoro-4-(trifluoromethyl)phenyl) carbamoyl)-6-(4-((N,1,2-trimethyl-1H-benzo[d]imidazole)-5-sulfonamido)phenyl)cyclohexane-1-carboxylic acid (Example 81) (0.030 g, 0.046 mmol) was chirally purified (Column: CHIRALPAK IE [2 mm×25 mm, 5 micron]; Mobile Phase: 81:19 hexane [0.2% formic acid]:[1:1 EtOH: DCM]) to give: Example 83, the first-eluting isomer: (1R, 2R,6S)-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylic acid (9.0 mg, 0.014 mmol, 30% yield). $^1H$ NMR (700 MHz, DMSO-$d_6$) δ 12.06 (br s, 1H), 10.10 (s, 1H), 8.22 (t, J=8.1 Hz, 1H), 7.71 (d, J=10.9 Hz, 1H), 7.62 (d, J=8.5 Hz, 1H), 7.55 (d, J=8.6 Hz, 1H), 7.50 (s, 1H), 7.24 (dd, J=8.5, 1.5 Hz, 1H), 7.19 (d, J=8.4 Hz, 2H), 6.96 (d, J=8.4 Hz, 2H), 3.78 (s, 3H), 3.05 (s, 3H), 3.00 (td, J=11.4, 3.2 Hz, 1H), 2.78 (t, J=11.6 Hz, 1H), 2.67 (td, J=11.8, 3.2 Hz, 1H), 2.56 (s, 3H), 2.05-1.97 (m, 1H), 1.91-1.84 (m, 1H), 1.79-1.72 (m, 1H), 1.65-1.57 (m, 1H), 1.53-1.51 (m, 1H), 1.53-1.50 (m, 1H). ES-LCMS m/z 647.2 $[M+H]^+$. Absolute stereochemistry was assigned by co-crystallization with WRN protein.

Example 84, the second-eluting isomer: (1S,2S,6R)-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylic acid (8.9 mg, 0.014 mmol, 30% yield). $^1H$ NMR (700 MHz, DMF-$d_7$) δ 12.06 (br s, 1H), 10.11 (s, 1H), 8.22 (t, J=8.1 Hz, 1H), 7.71 (d, J=10.9 Hz, 1H), 7.62 (d, J=8.5 Hz, 1H), 7.55 (d, J=8.5 Hz, 1H), 7.51-7.49 (m, 1H), 7.24 (dd, J=8.5, 1.5 Hz, 1H), 7.19 (d, J=8.5 Hz, 2H), 6.96 (d, J=8.4 Hz, 2H), 3.78 (s, 3H), 3.05 (s, 3H), 3.00 (td, J=11.2, 3.1 Hz, 1H), 2.78 (t, J=11.2 Hz, 1H), 2.67 (td, J=11.8, 3.3 Hz, 1H), 2.56 (s, 3H), 2.05-1.99 (m, 1H), 1.91-1.85 (m, 1H), 1.78-1.72 (m, 1H), 1.66-1.57 (m, 1H), 1.56-1.51 (m, 1H), 1.52-1.44 (m, 1H). ES-LCMS m/z 647.2 $[M+H]^+$.

Example 83, Second Preparation Method (1R,2R,6S)-2-((2-fluoro-4-(trifluoromethyl)phenyl) carbamoyl)-6-(4-((N,1,2-trimethyl-1H-benzo[d]imidazole)-5-sulfonamido)phenyl)cyclohexane-1-carboxylic acid

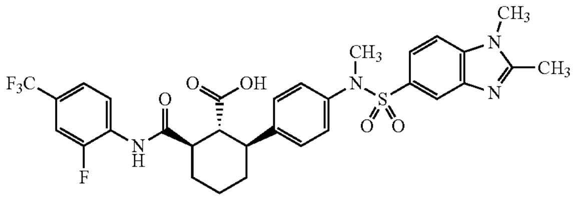 [SMILES: Cc1nc2cc(S(=O)(=O)N(C)c3ccc([C@H]4CCC[C@@H](C(=O)Nc5ccc(C(F)(F)F)cc5F)[C@@H]4C(=O)O)cc3)ccc2n1C]

To a mixture of (1R,2R,6S)-2-((2-fluoro-4-(trifluoromethyl)phenyl)carbamoyl)-6-(4-(methylamino)phenyl)cyclohexane-1-carboxylic acid (Intermediate 7) (0.180 kg, 411 mmol) in MeCN (1.08 L) at 0° C. was added TEA (62.3 g, 616 mmol) and 1,2-dimethyl-1H-benzo[d]imidazole-5-sulfonyl chloride (151 g, 616 mmol). The reaction was stirred at 25° C. for 1 h. Water (7.2 L) was added into the mixture slowly at rt. After 1 h, the reaction was filtered, and the resulting solid was washed with water (900 ml) to give a residue (200 g, 309 mmol) as a light blue solid. This residue was triturated with MeCN (1.00 L) at 25° C. for 2 h and filtered. The filter cake was washed with MeCN (100 mL) to give a residue (195 g, 301 mmol) which was dissolved in 5:1 DCM:MeOH (MeOH [650 mL] and DCM [3250 mL]) at 45° C. for 40 min (until the mixture became clear). 21× Palladium Removal Silica Gel was added (30% by weight of crude material) to the mixture, then the mixture was refluxed for 12 hrs. The mixture was filtered while hot, then the filter cake was washed with DCM (1.3 L). The filtrate was concentrated under reduced pressure at 35° C. for 2 h to give a residue (177 g, 274 mmol). This residue was dissolved in 5:1 DCM:MeOH (MeOH [590 mL] and DCM [2950 mL]) at 45° C. for 40 min (until the mixture became clear). 22× Palladium Removal Silica Gel was added (30% by weight of crude material) to the mixture, then the mixture was refluxed for 12 h. The mixture was filtered while hot, then the filter cake was washed with DCM (1.2 L). The filtrate was concentrated under reduced pressure at 35° C. for 2 h to give a residue which was further concentrated under reduced pressure (−0.1 MPa) at 35° C. for 4 h, to remove DCM and MeOH, to give (1R,2R,6S)-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylic acid (168 g, 260 mmol, 63.2% yield) as a white solid. $^1H$ NMR (400 MHz, DMSO-$d_6$) δ 10.1 (s, 1H), 8.21 (t, J=8.0 Hz, 1H), 7.70-7.73 (m, 2H), 7.60 (d, J=1.2 Hz, 12H), 7.55 (d, J=8.4 Hz, 1H), 7.29 (dd, J=8.4, 1.6 Hz, 1H), 7.20 (d, J=8.8 Hz, 2H), 6.96 (d, J=8.4 Hz, 2H), 3.82 (s, 3H), 3.07 (m, 3H), 2.97-3.03 (i n, H), 2.75-2.80 (m, 1H), 2.67-2.70 (m, 1H), 2.63 (d, 3H), 2.01-2.03 (m, 12H), 1.88-1.89 (m, 1H), 1.74-1.77 (n, 1H), 1.50-1.61 (nm, 3H). ES-L (MS m/z 647.3 $[M+H]^-$.

The following compounds were synthesized in an analogous manner to the preparation described above (Example 81) using the relevant sulfonyl chloride precursors. Compounds were purified using reverse phase chromatography (MeCN/$H_2O$, basic or acidic modifiers) followed by separation on a Chiral column.

| Ex | Structure/Name | $^1H$ NMR | LCMS |
| --- | --- | --- | --- |
| 85 | 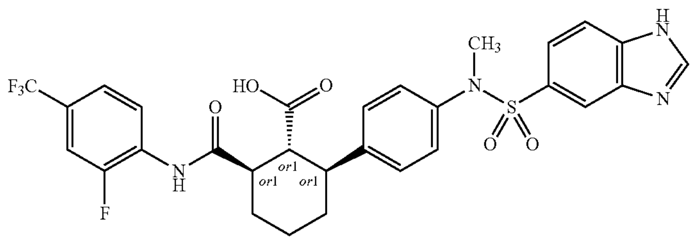 [SMILES: CN(c1ccc([C@H]2CCC[C@@H](C(=O)Nc3ccc(C(F)(F)F)cc3F)[C@@H]2C(=O)O)cc1)S(=O)(=O)c1ccc2[nH]cnc2c1] ISOMER 1 rel-(1R,2R,6S)-2-((2-fluoro-4-(trifluoromethyl)phenyl) carbamoyl)-6-(4-(N-methyl-1H-benzo[d]imidazole-5-sulfonamido)phenyl)cyclohexane-1-carboxylic acid, ISOMER 1 | $^1H$ NMR (400 MHz, DMSO-$d_6$) δ 12.10 (s, 1H), 10.08 (s, 1H), 8.43 (s, 1H), 8.25 (t, J = 8.4 Hz, 1H), 7.73-7.67 (m, 2H), 7.55 (d, J = 8.4 Hz, 2H), 7.24-7.22 (m, 1H), 7.20-7.18 (m, 2H), 6.97 (d, J = 8.4 Hz, 2H), 3.07 (s, 3H), 3.02-2.96 (m, 1H), 2.77-2.65 (m, 3H), 2.02-2.00 (m, 1H), 2.00-1.89 (m, 1H), 1.77-1.74 (m, 1H), 1.62-1.51 (m, 3H). | ES-LCMS m/z 619.0 $[M + H]^+$. |

-continued

| Ex | Structure/Name | $^1H$ NMR | LCMS |
|---|---|---|---|
| 86 | 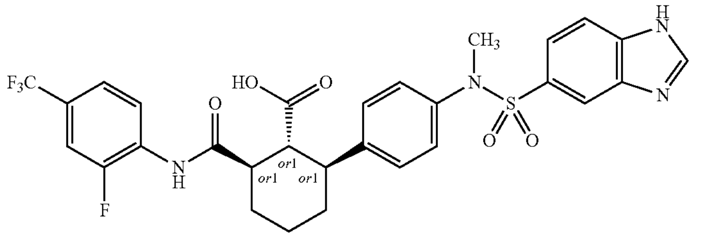 [SMILES: CN(c1ccc([C@H]2CCC[C@@H](C(=O)Nc3ccc(C(F)(F)F)cc3F)[C@@H]2C(=O)O)cc1)S(=O)(=O)c1ccc2[nH]cnc2c1] ISOMER 2 rel-(1R,2R,6S)-2-((2-fluoro-4-(trifluoromethyl)phenyl)carbamoyl)-6-(4-(N-methyl-1H-benzo[d]imidazole-5-sulfonamido)phenyl)cyclohexane-1-carboxylic acid, ISOMER 2 | $^1H$ NMR (400 MHz, DMSO-$d_6$) δ 12.10 (s, 1H), 10.08 (s, 1H), 8.43 (s, 1H), 8.25 (t, J = 8.4 Hz, 1H), 7.73-7.67 (m, 2H), 7.55 (d, J = 8.4 Hz, 2H), 7.24-7.22 (m, 1H), 7.20-7.18 (m, 2H), 6.97 (d, J = 8.4 Hz, 2H), 3.07 (s, 3H), 3.02-2.96 (m, 1H), 2.77-2.65 (m, 3H), 2.02-2.00 (m, 1H), 2.00-1.89 (m, 1H), 1.77-1.74 (m, 1H), 1.62-1.51 (m, 3H). | ES-LCMS m/z 619.0 $[M + H]^+$. |
| 87 | 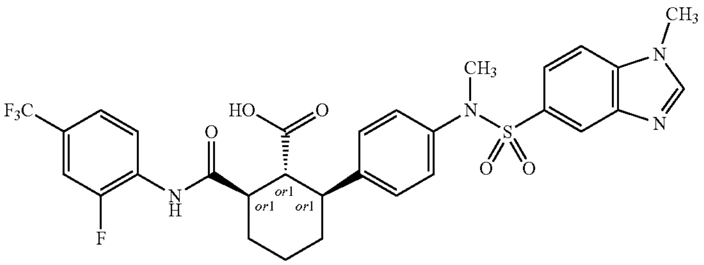 [SMILES: CN(c1ccc([C@H]2CCC[C@@H](C(=O)Nc3ccc(C(F)(F)F)cc3F)[C@@H]2C(=O)O)cc1)S(=O)(=O)c1ccc2c(c1)ncn2C] ISOMER 1 rel-(1R,2S,6R)-2-(4-((N,1-dimethyl-1H-benzo[d]imidazole)-5-sulfonamido)phenyl)-6-((2-fluoro-4-(trifluoromethyl)phenyl)carbamoyl) cyclohexane-1-carboxylic acid, ISOMER 1 | $^1H$ NMR (400 MHz, DMSO-$d_6$) δ 11.90 (br s, 1H), 10.12 (s, 1H), 8.44 (s, 1H), 8.23 (t, J = 8.00 Hz, 1H), 7.73-7.71 (m, 3H), 7.56 (d, J = 8.80 Hz, 1H), 7.28 (dd, J = 8.80, 1.60 Hz, 1H), 7.21 (d, J = 8.80 Hz, 2H), 6.99 (d, J = 8.80 Hz, 2H), 3.90 (s, 3H), 3.08 (s, 3H), 3.03-2.98 (m, 1H), 2.78 (t, J = 10.80 Hz, 1H), 2.71-2.65 (m, 1H), 2.08-1.75 (m, 3H), 1.62-1.51 (m, 3H). | ES-LCMS m/z 633.2 $[M + H]^+$. |
| 88 | 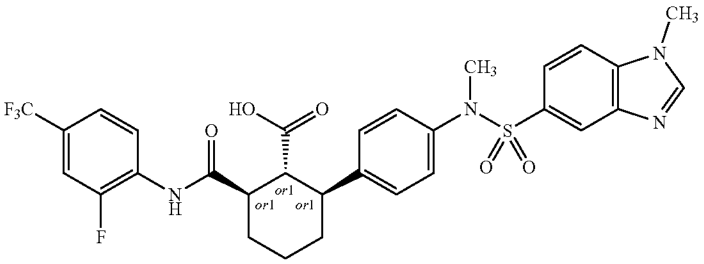 [SMILES: CN(c1ccc([C@H]2CCC[C@@H](C(=O)Nc3ccc(C(F)(F)F)cc3F)[C@@H]2C(=O)O)cc1)S(=O)(=O)c1ccc2c(c1)ncn2C] ISOMER 2 rel-(1R,2S,6R)-2-(4-((N,1-dimethyl-1H-benzo[d]imidazole)-5-sulfonamido)phenyl)-6-((2-fluoro-4-(trifluoromethyl)phenyl) carbamoyl) cyclohexane-1-carboxylic acid, ISOMER 2 | $^1H$ NMR (400 MHz, DMSO-$d_6$) δ 11.90 (br s, 1H), 10.12 (s, 1H), 8.44 (s, 1H), 8.23 (t, J = 8.00 Hz, 1H), 7.73-7.71 (m, 3H), 7.56 (d, J = 8.80 Hz, 1H), 7.28 (dd, J = 8.80, 1.60 Hz, 1H), 7.21 (d, J = 8.80 Hz, 2H), 6.99 (d, J = 8.80 Hz, 2H), 3.90 (s, 3H), 3.08 (s, 3H), 3.03-2.98 (m, 1H), 2.78 (t, J = 10.80 Hz, 1H), 2.71-2.65 (m, 1H), 2.08-1.75 (m, 3H), 1.62-1.51 (m, 3H). | ES-LCMS m/z 633.2 $[M + H]^+$. |

-continued

| Ex | Structure/Name | $^1$H NMR | LCMS |
|---|---|---|---|
| 89 | 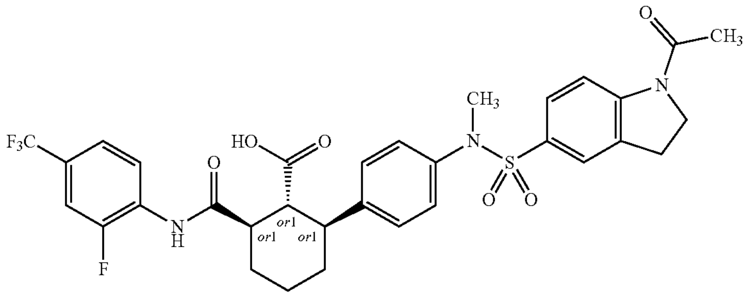 [SMILES: CC(=O)N1CCc2cc(S(=O)(=O)N(C)c3ccc([C@H]4CCC[C@@H](C(=O)Nc5ccc(C(F)(F)F)cc5F)[C@@H]4C(=O)O)cc3)ccc21] ISOMER 1 rel-(1R,2S,6R)-2-(4-((1-acetyl-N-methylindoline)-5-sulfonamido)phenyl)-6-((2-fluoro-4-(trifluoromethyl)phenyl)carbamoyl) cyclohexane-1-carboxylic acid, ISOMER 1 | $^1$H NMR (400 MHz, DMSO-$d_6$) δ 11.80 (br s, 1H), 10.12 (s, 1H), 8.22 (t, J = 8.0 Hz, 1H), 8.10 (d, J = 8.4 Hz, 1H), 7.72 (dd, J = 11.0, 1.6 Hz, 1H), 7.55 (d, J = 8.8 Hz, 1H), 7.27-7.21 (m, 4H), 6.99 (d, J = 8.4 Hz, 2H), 4.16 (t, J = 8.4 Hz, 2H), 3.13 (t ,J = 8.8 Hz, 2H), 3.07 (s, 3H), 3.04-2.99 (m, 1H), 2.86 (t, J = 11.6 Hz,1H), 2.75-2.66 (m, 1H), 2.33 (s, 3H), 2.33-2.02 (m, 3H), 1.89-1.60 (m, 3H). | ES-LCMS m/z 662.2 $[M + H]^+$. |
| 90 | 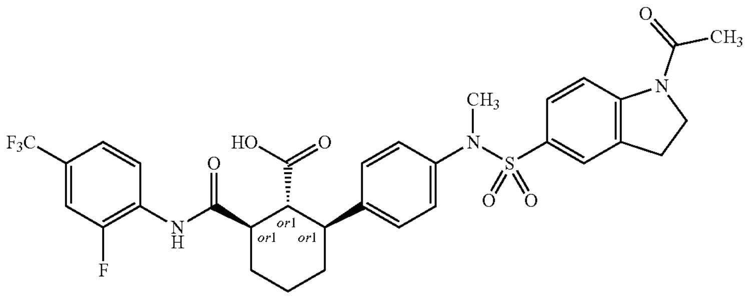 [SMILES: CC(=O)N1CCc2cc(S(=O)(=O)N(C)c3ccc([C@H]4CCC[C@@H](C(=O)Nc5ccc(C(F)(F)F)cc5F)[C@@H]4C(=O)O)cc3)ccc21] ISOMER 2 rel-(1R,2S,6R)-2-(4-((1-acetyl-N-methylindoline)-5-sulfonamido)phenyl)-6-((2-fluoro-4-(trifluoromethyl)phenyl)carbamoyl) cyclohexane-1-carboxylic acid, ISOMER 2 | $^1$H NMR (400 MHz, DMSO-$d_6$) δ 11.80 (br s, 1H), 10.12 (s, 1H), 8.22 (t, J = 8.0 Hz, 1H), 8.10 (d, J = 8.4 Hz, 1H), 7.72 (dd, J = 11.0, 1.6 Hz, 1H), 7.55 (d, J = 8.8 Hz, 1H), 7.27-7.21 (m, 4H), 6.99 (d, J = 8.4 Hz, 2H), 4.16 (t, J = 8.4 Hz, 2H), 3.13 (t, J = 8.8 Hz, 2H),3.07 (s, 3H), 3.04-2.99 (m, 1H), 2.86 (t, J = 11.6 Hz,1H), 2.75-2.66 (m, 1H), 2.33 (s,3H), 2.33-2.02 (m, 3H), 1.89-1.60 (m, 3H). | ES-LCMS m/z 662.2 $[M + H]^+$ |
| 91 | 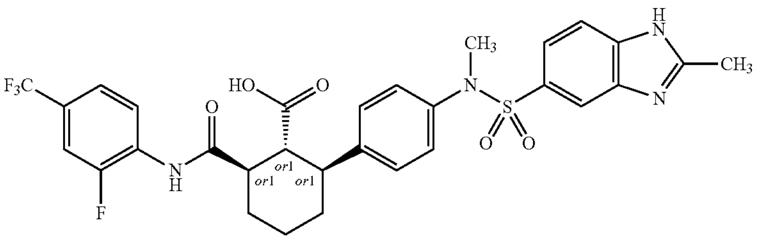 [SMILES: Cc1nc2cc(S(=O)(=O)N(C)c3ccc([C@H]4CCC[C@@H](C(=O)Nc5ccc(C(F)(F)F)cc5F)[C@@H]4C(=O)O)cc3)ccc2[nH]1] ISOMER 1 rel-(1R,2S,6R)-2-(4-((N,2-dimethyl-1H-benzo[d]imidazole)-5-sulfonamido)phenyl)-6-((2-fluoro-4-(trifluoromethyl)phenyl)carbamoyl) cyclohexane-1-carboxylic acid, ISOMER 1 | $^1$H NMR (400 MHz, DMSO-$d_6$) δ 12.50 (br s, 1H), 10.09 (s, 1H), 8.24 (t, J = 8.00 Hz, 1H), 7.77 (d, J = 8.00 Hz, 1H), 7.72 (dd, J = 7.80, 5.20 Hz, 1H), 7.59-7.55 (m, 3H), 7.21-7.16 (m, 3H), 6.97 (d, J = 8.80 Hz, 2H), 3.07 (s, 3H), 3.03-2.98 (m, 1H), 2.78 (t, J = 11.20 Hz, 1H), 2.71-2.65 (m, 1H), 2.57 (s, 3H), 2.04-0.75 (m, 3H), 1.62-1.51 (m, 3H). | ES-LCMS m/z 633.0 $[M + H]^+$. |

-continued

| Ex | Structure/Name | $^1$H NMR | LCMS |
|---|---|---|---|
| 92 | 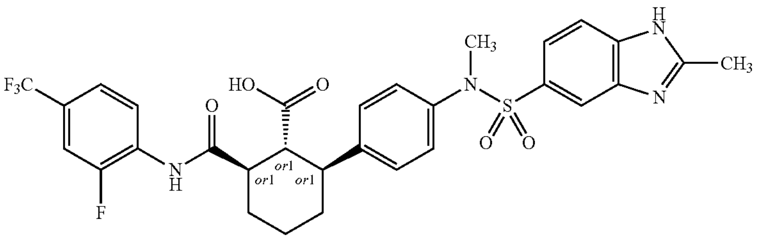 [SMILES: Cc1nc2cc(S(=O)(=O)N(C)c3ccc([C@H]4CCC[C@@H](C(=O)Nc5ccc(C(F)(F)F)cc5F)[C@@H]4C(=O)O)cc3)ccc2[nH]1] ISOMER 2 rel-(1R,2S,6R)-2-(4-((N,2-dimethyl-1H-benzo[d]imidazole)-5-sulfonamido)phenyl)-6-((2-fluoro-4-(trifluoromethyl)phenyl)carbamoyl) cyclohexane-1-carboxylic acid, ISOMER 2 | $^1$H NMR (400 MHz, DMSO-$d_6$) δ 12.50 (br s, 1H), 10.09 (s, 1H), 8.24 (t, J = 8.00 Hz, 1H), 7.77 (d, J = 8.00 Hz, 1H), 7.72 (dd, J = 7.80, 5.20 Hz, 1H), 7.59-7.55 (m, 3H), 7.21-7.16 (m, 3H), 6.97 (d, J = 8.80 Hz, 2H), 3.07 (s, 3H), 3.03-2.98 (m, 1H), 2.78 (t, J = 11.20 Hz, 1H), 2.71-2.65 (m, 1H), 2.57 (s, 3H), 2.04-0.75 (m, 3H), 1.62-1.51 (m, 3H). | ES-LCMS m/z 633.0 [M + H]$^+$. |

Example 93

(1R,2R,6S)-2-((2-fluoro-4-(trifluoromethyl)phenyl) carbamoyl)-6-(4-(N-methyl benzofuran-5-sulfonamido)phenyl)cyclohexane-1-carboxylic acid

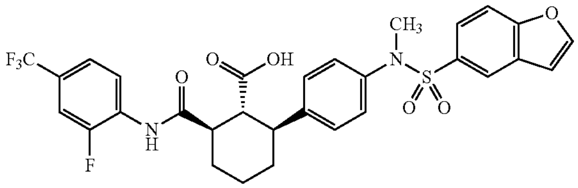 [SMILES: CN(c1ccc([C@H]2CCC[C@@H](C(=O)Nc3ccc(C(F)(F)F)cc3F)[C@@H]2C(=O)O)cc1)S(=O)(=O)c1ccc2occc2c1]

To a mixture of (1R,2R,6S)-2-((2-fluoro-4-(trifluoromethyl)phenyl) carbamoyl)-6-(4-(methylamino)phenyl)cyclohexane-1-carboxylic acid Intermediate 7 (35 mg, 0.080 mmol) in DMF (1 mL) was added pyridine (0.129 mL, 1.60 mmol), followed by benzofuran-5-sulfonyl chloride (25.9 mg, 0.120 mmol). After 16 h, the reaction was filtered, concentrated and purified over silica (Phenomenex Gemini 018 column), eluting with 50-90% acetonitrile (0.1% formic acid) in water (0.1% formic acid) to give (1R,2R,6S)-2-((2-fluoro-4-(trifluoromethyl)phenyl) carbamoyl)-6-(4-(N-methylbenzofuran-5-sulfonamido)phenyl)cyclohexane-1-carboxylic acid (6.6 mg, 11 μmol, 13% yield) as a white solid. H NMR (400 MHz, DMSO-$d_6$) δ 11.87 (brs, 1H), 10.12 (s, 1H), 8.22 (t, J=8.1 Hz, 1H), 8.18 (d, J=2.4 Hz, 1H), 7.80 (d, J=2.0 Hz, 1H), 7.77-7.69 (m, 2H), 7.56 (br d, J=8.8 Hz, 1H), 7.31 (dd, J=8.3, 2.0 Hz, 1H), 7.21 (d, J=8.3 Hz, 2H), 7.09 (dd, J=2.4, 1.0 Hz, 1H), 6.98 (d, J=8.8 Hz, 2H), 3.10 (P, 3H), 3.06-2.95 (i, 1H), 2.83-2.62 (i, 2H), 2.06-1.97 (m, 1H), 1.88 (br d, J=3.4 Hz, 1H), 1.81-1.70 (m, 1H), 1.66-1.40 (m, 3H). ES-LCMS m/z 619.3 [M+H]$^+$. The following compounds were synthesized in an analogous manner to the preparation described above (Example 93) using the relevant sulfonyl chloride precursors. Compounds were purified using reverse phase chromatography (MeCN/$H_2O$, basic or acidic modifiers).

| Ex | Structure/Name | $^1$H NMR | LCMS |
|---|---|---|---|
| 94 | 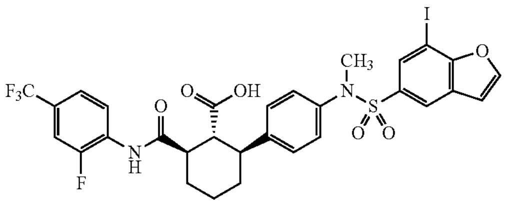 [SMILES: CN(c1ccc([C@H]2CCC[C@@H](C(=O)Nc3ccc(C(F)(F)F)cc3F)[C@@H]2C(=O)O)cc1)S(=O)(=O)c1cc(I)c2occc2c1] (1R,2R,6S)-2-((2-fluoro-4-(trifluoromethyl)phenyl)carbamoyl)-6-(4-((7-iodo-N-methylbenzofuran)-5-sulfonamido)phenyl)cyclohexane-1-carboxylic acid | $^1$H NMR (400 MHz, DMSO-$d_6$) δ 11.83 (br s, 1H), 10.11 (s, 1H), 8.27 (d, J = 2.0 Hz, 1H), 8.22 (t, J = 8.1 Hz, 1H), 7.78-7.69 (m, 2H), 7.64 (d, J = 2.0 Hz, 1H), 7.55 (br d, J = 8.3 Hz, 1H), 7.29-7.19 (m, 3H), 7.02 (d, J = 8.3 Hz, 2H), 3.11 (s, 3H), 3.05-2.95 (m, 1H), 2.86-2.67 (m, 2H), 2.02 (br d, J = 7.8 Hz, 1H), 1.89 (br d, J = 3.4 Hz, 1H), 1.82-1.72 (m, 1H), 1.66-1.41 (m, 3H). | ES-LCMS m/z 745.1 [M + H]$^+$. |

-continued

| Ex | Structure/Name | $^1$H NMR | LCMS |
| --- | --- | --- | --- |
| 95 | 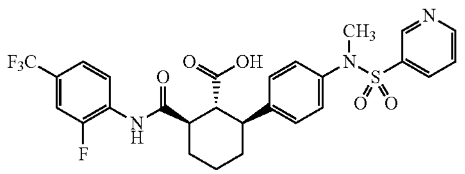 [SMILES: CN(c1ccc([C@H]2CCC[C@@H](C(=O)Nc3ccc(C(F)(F)F)cc3F)[C@@H]2C(=O)O)cc1)S(=O)(=O)c1cccnc1] (1R,2R,6S)-2-((2-fluoro-4-(trifluoromethyl)phenyl) carbamoyl)-6-(4-(N-methylpyridine-3-sulfonamido)phenyl)cyclohexane-1-carboxylic acid | $^1$H NMR (400 MHz, DMSO-$d_6$) δ 11.82 (br s, 1H), 10.10 (s, 1H), 8.87 (dd, J = 4.9, 1.5 Hz, 1H), 8.75-8.59 (m, 1H), 8.21 (t, J = 8.3 Hz, 1H), 7.84-7.67 (m, 2H), 7.65-7.51 (m, 2H), 7.25 (d, J = 8.8 Hz, 2H), 7.03 (d, J = 8.8 Hz, 2H), 3.16 (s, 3H), 3.08-2.96 (m, 1H), 2.87-2.64 (m, 2H), 2.01 (br d, J = 1.5 Hz, 1H), 1.88 (br d, J = 6.4 Hz, 1H), 1.76 (br d, J = 12.2 Hz, 1H), 1.66-1.42 (m, 3H). | ES-LCMS m/z 580.2 [M + H]$^+$. |
| 96 | 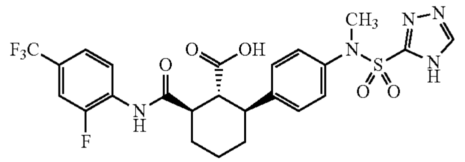 [SMILES: CN(c1ccc([C@H]2CCC[C@@H](C(=O)Nc3ccc(C(F)(F)F)cc3F)[C@@H]2C(=O)O)cc1)S(=O)(=O)c1nnc[nH]1] (1R,2R,6S)-2-((2-fluoro-4-(trifluoromethyl)phenyl)carbamoyl)-6-(4-(N-methyl-4H-1,2,4-triazole-3-sulfonamido)phenyl)cyclohexane-1-carboxylic acid | $^1$H NMR (400 MHz, DMSO-$d_6$) δ 15.23-14.55 (m, 1H), 12.08-11.41 (m, 1H), 10.09 (s, 1H), 8.86 (s, 1H), 8.21 (t, J = 8.3 Hz, 1H), 7.72 (dd, J = 11.0, 1.7 Hz, 1H), 7.55 (br d, J = 8.3 Hz, 1H), 7.30-7.22 (m, 2H), 7.20-7.14 (m, 2H), 3.32 (s, 3H), 3.08-2.93 (m, 1H), 2.88-2.78 (m, 1H), 2.76-2.67 (m, 1H), 2.00 (br d, J = 8.3 Hz, 1H), 1.94-1.82 (m, 1H), 1.81-1.66 (m, 1H), 1.63-1.44 (m, 3H). | ES-LCMS m/z 570.1 [M + H]$^+$ |
| 97 | 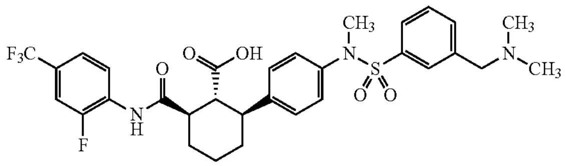 [SMILES: CN(C)Cc1cccc(S(=O)(=O)N(C)c2ccc([C@H]3CCC[C@@H](C(=O)Nc4ccc(C(F)(F)F)cc4F)[C@@H]3C(=O)O)cc2)c1] (1R,2R,6S)-2-((2-fluoro-4-(trifluoromethyl)phenyl)carbamoyl)-6-(4-(methylamino)phenyl)cyclohexane-1-carboxylic acid | $^1$H NMR (400 MHz, DMSO-$d_6$) δ 10.06 (s, 1H), 8.21 (t, J = 8.1 Hz, 1H), 8.16 (s, 1H), 7.72 (dd, J = 10.8, 2.0 Hz, 1H), 7.65-7.58 (m, 1H), 7.57-7.51 (m, 2H), 7.46-7.36 (m, 1H), 7.24 (s, 1H), 7.19 (d, J = 8.3 Hz, 2H), 6.96 (d, J = 8.8 Hz, 2H), 3.60-3.37 (m, 2H), 3.10 (s, 3H), 3.04-2.88 (m, 1H), 2.79-2.61 (m, 2H), 2.13 (s, 6H), 2.00 (br s, 1H), 1.91-1.82 (m, 1H), 1.79-1.68 (m, 1H), 1.65-1.41 (m, 3H). | ES-LCMS m/z 636.3 [M + H]$^+$. |
| 98 | 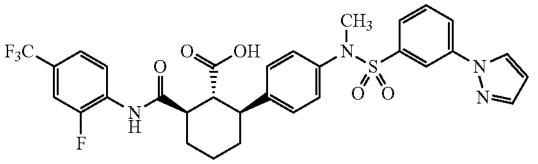 [SMILES: CN(c1ccc([C@H]2CCC[C@@H](C(=O)Nc3ccc(C(F)(F)F)cc3F)[C@@H]2C(=O)O)cc1)S(=O)(=O)c1cccc(-n2cccn2)c1] (1R,2R,6S)-2-((2-fluoro-4-(trifluoromethyl)phenyl)carbamoyl)-6-(4-((N-methyl-4-(1H-pyrazol-1-yl)phenyl)sulfonamido)phenyl)cyclohexane-1-carboxylic acid | $^1$H NMR (600 MHz, DMSO-$d_6$) δ 12.01-11.62 (m, 1H), 10.12 (s, 1H), 8.64 (d, J = 2.5 Hz, 1H), 8.22 (t, J = 8.2 Hz, 1H), 8.02 (d, J = 8.7 Hz, 2H), 7.85 (d, J = 1.1 Hz, 1H), 7.72 (d, J = 10.9 Hz, 1H), 7.56 (d, J = 8.7 Hz, 1H), 7.51 (d, J = 8.7 Hz, 2H), 7.24 (d, J = 8.4 Hz, 2H), 7.03 (d, J = 8.4 Hz, 2H), 6.64 (t, J = 2.0 Hz, 1H), 3.13 (s, 3H), 3.05-2.97 (m, 1H), 2.82-2.75 (m, 1H), 2.73-2.65 (m, 1H), 2.06-1.98 (m, 1H), 1.93-1.85 (m, 1H), 1.80-1.72 (m, 1H), 1.67-1.48 (m, 3H). | ES-LCMS m/z 645.3 [M + H]$^+$. |
| 99 | 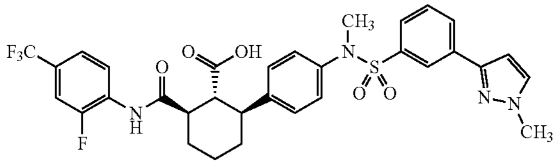 [SMILES: CN(c1ccc([C@H]2CCC[C@@H](C(=O)Nc3ccc(C(F)(F)F)cc3F)[C@@H]2C(=O)O)cc1)S(=O)(=O)c1cccc(-c2ccn(C)n2)c1] (1R,2R,6S)-2-((2-fluoro-4-(trifluoromethyl)phenyl)carbamoyl)-6-(4-((N-methyl-4-(1-methyl-1H-pyrazol-3-yl)phenyl)sulfonamido)phenyl)cyclohexane-1-carboxylic acid | $^1$H NMR (600 MHz, DMSO-$d_6$) δ 11.95-11.74 (m, 1H), 10.12 (s, 1H), 8.22 (t, J = 8.2 Hz, 1H), 7.93 (d, J = 8.4 Hz, 2H), 7.81 (d, J = 2.2 Hz, 1H), 7.72 (d, J = 10.9 Hz, 1H), 7.56 (d, J = 8.7 Hz, 1H), 7.41 (d, J = 8.4 Hz, 2H), 7.23 (d, J = 8.4 Hz, 2H), 7.01 (d, J = 8.4 Hz, 2H), 6.82 (d, J = 2.2 Hz, 1H), 3.92 (s, 3H), 3.11 (s, 3H), 3.05-2.97 (m, 1H), 2.81-2.75 (m, 1H), 2.74-2.66 (m, 1H), 2.05-1.99 (m, 1H), 1.92-1.85 (m, 1H), 1.81-1.73 (m, 1H), 1.66-1.46 (m, 3H). | ES LCMS m/z 659.4 [M + H]$^+$. |

-continued

| Ex | Structure/Name | $^1$H NMR | LCMS |
|---|---|---|---|
| 100 | 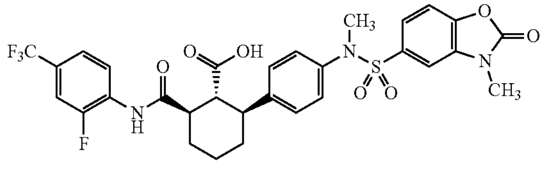 [SMILES: CN(c1ccc([C@H]2CCC[C@@H](C(=O)Nc3ccc(C(F)(F)F)cc3F)[C@@H]2C(=O)O)cc1)S(=O)(=O)c1ccc2oc(=O)n(C)c2c1] (1R,2S,6R)-2-(4-((N,3-dimethyl-2-oxo-2,3-dihydrobenzo[d]oxazole)-5-sulfonamido) phenyl)-6-((2-fluoro-4-(trifluoromethyl)phenyl)carbamoyl) cyclohexane-1-carboxylic acid | $^1$H NMR (600 MHz, DMSO-$d_6$) δ 11.99-11.70 (m, 1H), 10.13 (br s, 1H), 8.22 (t, J = 8.0 Hz, 1H), 7.72 (d, J = 10.9 Hz, 1H), 7.55 (d, J = 8.4 Hz, 1H), 7.45 (d, J = 1.5 Hz, 1H), 7.37 (d, J = 8.0 Hz, 1H), 7.26 (dd, J = 8.4, 1.5 Hz, 1H), 7.23 (d, J = 8.4 Hz, 2H), 7.01 (d, J = 8.4 Hz, 2H), 3.38 (s, 3H), 3.11 (s, 3H), 3.04-2.95 (m, 1H), 2.82-2.74 (m, 1H), 2.73-2.65 (m, 1H), 2.02 (br d, J = 9.1 Hz, 1H), 1.88 (br dd, J = 5.8, 2.5 Hz, 1H), 1.81-1.71 (m, 1H), 1.64-1.46 (m, 3H) | ES LCMS m/z 650.3 $[M + H]^+$. |
| 101 | 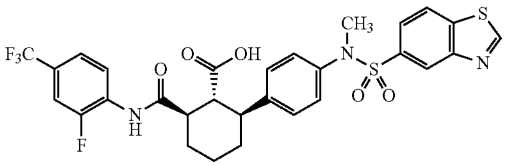 [SMILES: CN(c1ccc([C@H]2CCC[C@@H](C(=O)Nc3ccc(C(F)(F)F)cc3F)[C@@H]2C(=O)O)cc1)S(=O)(=O)c1ccc2scnc2c1] (1R,2R,6S)-2-((2-fluoro-4-(trifluoromethyl)phenyl)carbamoyl)-6-(4-(N-methylbenzo[d]thiazole-5-sulfonamido)phenyl)cyclohexane-1-carboxylic acid | $^1$H NMR (600 MHz, DMSO-$d_6$) δ 12.00-11.67 (m, 1H), 10.12 (br s, 1H), 9.60 (s, 1H), 8.33 (d, J = 8.7 Hz, 1H), 8.25-8.18 (m, 2H), 7.72 (br d, J = 10.9 Hz, 1H), 7.56 (br d, J = 8.7 Hz, 1H), 7.37 (dd, J = 8.5, 1.6 Hz, 1H), 7.23 (d, J = 8.7 Hz, 2H), 7.04 (d, J = 8.4 Hz, 2H), 3.15 (s, 3H), 3.05-2.95 (m, 1H), 2.83-2.75 (m, 1H), 2.74-2.66 (m, 1H), 2.05-1.98 (m, 1H), 1.92-1.85 (m, 1H), 1.80-1.73 (m, 1H), 1.61-1.49 (m, 3H). | ES-LCMS m/z 636.3 $[M + H]^+$. |
| 102 | 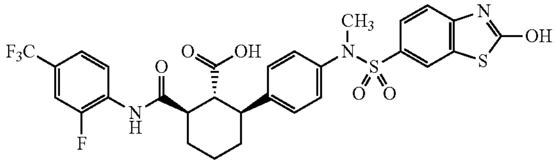 [SMILES: CN(c1ccc([C@H]2CCC[C@@H](C(=O)Nc3ccc(C(F)(F)F)cc3F)[C@@H]2C(=O)O)cc1)S(=O)(=O)c1ccc2nc(O)sc2c1] (1R,2R,6S)-2-((2-fluoro-4-(trifluoromethyl)phenyl)carbamoyl)-6-(4-((2-hydroxy-N-methylbenzo[d]thiazole)-6-sulfonamido)phenyl)cyclohexane-1-carboxylic acid | $^1$H NMR (600 MHz, DMSO-$d_6$) δ 12.59-12.17 (m, 1H), 10.12 (s, 1H), 8.21 (t, J = 8.2 Hz, 1H), 7.80 (d, J = 1.5 Hz, 1H), 7.74-7.69 (m, 1H), 7.55 (d, J = 8.7 Hz, 1H), 7.24-7.14 (m, 4H), 7.01 (d, J = 8.4 Hz, 2H), 3.10 (s, 3H), 3.00 (td, J = 11.2, 3.5 Hz, 1H), 2.82-2.74 (m, 1H), 2.72-2.63 (m, 1H), 2.03 (br d, J = 8.7 Hz, 1H), 1.93-1.83 (m, 1H), 1.79-1.72 (m, 1H), 1.62-1.47 (m, 3H). NOTE: OH is buried under solvent. | ES-LCMS m/z 652.3 $[M + H]^+$. |
| 103 | 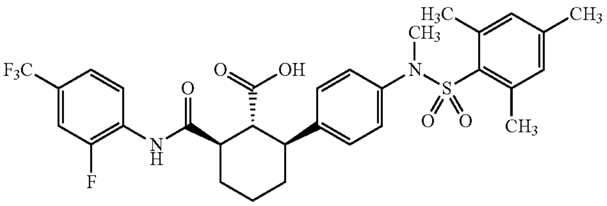 [SMILES: Cc1cc(C)c(S(=O)(=O)N(C)c2ccc([C@H]3CCC[C@@H](C(=O)Nc4ccc(C(F)(F)F)cc4F)[C@@H]3C(=O)O)cc2)c(C)c1] (1R,2R,6S)-2-((2-fluoro-4-(trifluoromethyl)phenyl)carbamoyl)-6-(4-((N,2,4,6-tetramethylphenyl)sulfonamido)phenyl) cyclohexane-1-carboxylic acid | $^1$H NMR (400 MHz, DMSO-$d_6$) δ 11.82 (br d, J = 1.5 Hz, 1H), 10.11 (s, 1H), 8.21 (t, J = 8.1 Hz, 1H), 7.71 (dd, J = 11.0, 1.7 Hz, 1H), 7.55 (br d, J = 8.3 Hz, 1H), 7.23 (d, J = 8.8 Hz, 2H), 7.12-6.96 (m, 4H), 3.12 (s, 3H), 3.05-2.91 (m, 1H), 2.86-2.62 (m, 2H), 2.32 (s, 6H), 2.28 (s, 3H), 2.00 (br d, J = 9.8 Hz, 1H), 1.87 (br d, J = 6.8 Hz, 1H), 1.77-1.63 (m, 1H), 1.61-1.38 (m, 3H). | ES-LCMS m/z 621.2 $[M + H]^+$ |
| 104 | 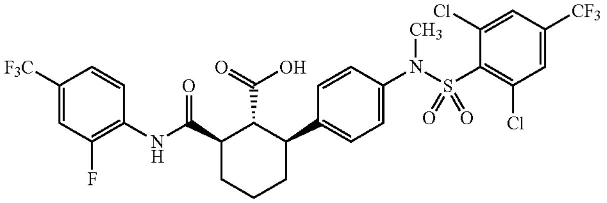 [SMILES: CN(c1ccc([C@H]2CCC[C@@H](C(=O)Nc3ccc(C(F)(F)F)cc3F)[C@@H]2C(=O)O)cc1)S(=O)(=O)c1c(Cl)cc(C(F)(F)F)cc1Cl] (1R,2S,6R)-2-(4-((2,6-dichloro-N-methyl-4-(trifluoromethyl)phenyl) sulfonamido) phenyl)-6-((2-fluoro-4-(trifluoromethyl)phenyl)carbamoyl) cyclohexane-1-carboxylic acid | $^1$H NMR (400 MHz, DMSO-$d_6$) δ 12.00-11.16 (m, 1H), 10.11 (br s, 1H), 8.21 (br t, J = 8.1 Hz, 1H), 8.08 (s, 2H), 7.71 (br d, J = 9.8 Hz, 1H), 7.55 (br d, J = 8.3 Hz, 1H), 7.29-7.23 (m, 2H), 7.22-7.15 (m, 2H), 3.39 (s, 3H), 3.07-2.93 (m, 1H), 2.83-2.64 (m, 2H), 2.00 (br d, J = 9.3 Hz, 1H), 1.86 (br d, J = 5.9 Hz, 1H), 1.77-1.65 (m, 1H), 1.62-1.44 (m, 3H). | ES-LCMS m/z 713.1 $[M - H]^-$. |

-continued

| Ex | Structure/Name | $^1$H NMR | LCMS |
|---|---|---|---|
| 105 | 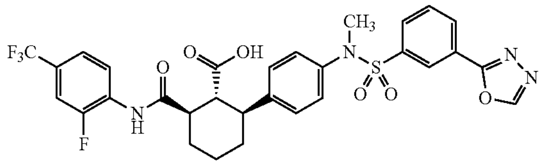 [SMILES: CN(c1ccc([C@H]2CCC[C@@H](C(=O)Nc3ccc(C(F)(F)F)cc3F)[C@@H]2C(=O)O)cc1)S(=O)(=O)c1cccc(-c2nnco2)c1] (1R,2R,6S)-2-((2-fluoro-4-(trifluoromethyl)phenyl)carbamoyl)-6-(4-((N-methyl-3-(1,3,4-oxadiazol-2-yl)phenyl)sulfonamido)phenyl)cyclohexane-1-carboxylic acid | $^1$H NMR (600 MHz, DMSO-$d_6$) δ 11.82 (br s, 1H), 10.11 (s, 1H), 9.40 (s, 1H), 8.34 (d, J = 7.6 Hz, 1H), 8.21 (t, J = 8.2 Hz, 1H), 8.04 (s, 1H), 7.77 (t, J = 7.8 Hz, 1H), 7.72 (br d, J = 10.9 Hz, 1H), 7.55 (t, J = 8.7 Hz, 2H), 7.24 (d, J = 8.4 Hz, 2H), 7.04 (d, J = 8.4 Hz, 2H), 3.16 (s, 3H), 3.01 (td, J = 11.2, 3.5 Hz, 1H), 2.83-2.76 (m, 1H), 2.74-2.67 (m, 1H), 2.02 (br d, J = 9.1 Hz, 1H), 1.90-1.84 (m, 1H), 1.73 (br d, J = 12.0 Hz, 1H), 1.62-1.46 (m, 3H). | ES-LCMS m/z 647.3 [M + H]$^+$. |
| 106 | 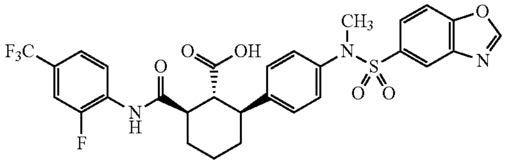 [SMILES: CN(c1ccc([C@H]2CCC[C@@H](C(=O)Nc3ccc(C(F)(F)F)cc3F)[C@@H]2C(=O)O)cc1)S(=O)(=O)c1ccc2ocnc2c1] (1R,2R,6S)-2-((2-fluoro-4-(trifluoromethyl)phenyl)carbamoyl)-6-(4-(N-methylbenzo[d]oxazole-5-sulfonamido)phenyl)cyclohexane-1-carboxylic acid | $^1$H NMR (600 MHz, DMSO-$d_6$) δ 11.97 -11.74 (m, 1H), 10.11 (s, 1H), 8.98 (s, 1H), 8.22 (t, J = 8.0 Hz, 1H), 7.98 (d, J = 1.5 Hz, 1H), 7.92 (d, J = 8.7 Hz, 1H), 7.72 (d, J = 10.9 Hz, 1H), 7.56 (d, J = 8.7 Hz, 1H), 7.39 (dd, J = 8.7, 1.8 Hz, 1H), 7.22 (d, J = 8.4 Hz, 2H), 7.01 (d, J = 8.4 Hz, 2H), 3.13 (s, 3H), 3.04-2.97 (m, 1H), 2.83-2.75 (m, 1H), 2.70 (td, J = 11.5, 3.5 Hz, 1H), 2.02 (br d, J = 9.1 Hz, 1H), 1.91-1.84 (m, 1H), 1.79-1.70 (m, 1H), 1.64-1.45 (m, 3H). | ES-LCMS m/z 620.3 [M + H]$^+$. |
| 107 | 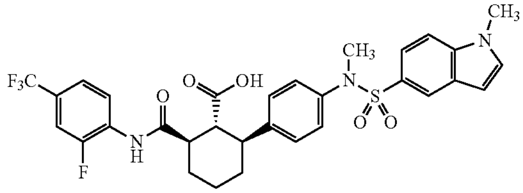 [SMILES: CN(c1ccc([C@H]2CCC[C@@H](C(=O)Nc3ccc(C(F)(F)F)cc3F)[C@@H]2C(=O)O)cc1)S(=O)(=O)c1ccc2c(ccn2C)c1] (1R,2S,6R)-2-(4-((N, 1-dimethyl-1H-indole)-5-sulfonamido)phenyl)-6-((2-fluoro-4-(trifluoromethyl)phenyl)carbamoyl) cyclohexane-1-carboxylic acid | $^1$H NMR (400 MHz, DMSO-$d_6$) δ 11.84 (br s, 1H), 10.11 (s, 1H), 8.22 (t, J = 8.1 Hz, 1H), 7.79-7.68 (m, 2H), 7.55 (d, J = 8.8 Hz, 2H), 7.52 (d, J = 2.9 Hz, 1H), 7.19 (d, J = 8.3 Hz, 2H), 7.13 (dd, J = 8.8, 2.0 Hz, 1H), 6.98 (d, J = 8.3 Hz, 2H), 6.64-6.58 (m, 1H), 3.85 (s, 3H), 3.06 (s, 3H), 3.01 (br d, J = 2.4 Hz, 1H), 2.83-2.65 (m, 2H), 2.02 (br d, J = 8.3 Hz, 1H), 1.93-1.81 (m, 1H), 1.80-1.72 (m, 1H), 1.61-1.52 (m, 3H). | ES-LCMS m/z 632.2 [M + H]$^+$. |
| 108 | 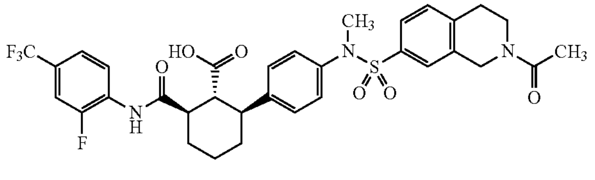 (1R,2R,6S)-2-((2-fluoro-4-(trifluoromethyl)phenyl)carbamoyl)-6-(4-((N-methyl-2-(2,2,2-trifluoroacetyl)-1,2,3,4-tetrahydroisoquinoline)-7-sulfonamido)phenyl)cyclohexane-1-carboxylic acid | $^1$H NMR (400 MHz, DMSO-$d_6$) δ 11.81 (br s, 1H), 10.10 (br s, 1H), 8.22 (t, J = 8.1 Hz, 1H), 7.72 (dd, J = 11.2, 2.0 Hz, 1H), 7.55 (br d, J = 8.3 Hz, 1H), 7.52-7.43 (m, 1H), 7.40-7.31 (m, 1H), 7.28-7.20 (m, 2H), 7.16 (dd, J = 7.8, 2.0 Hz, 1H), 7.06-6.96 (m, 2H), 4.89-4.68 (m, 2H), 3.93-3.77 (m, 2H), 3.15-3.08 (m, 3H), 3.06-2.95 (m, 3H), 2.88-2.64 (m, 2H), 2.03 (br d, J = 7.8 Hz, 1H), 1.89 (br d, J = 3.4 Hz, 1H), 1.83-1.72 (m, 1H), 1.69-1.46 (m, 3H). | ES-LCMS m/z 730.2 [M + H]$^+$ |
| 109 | 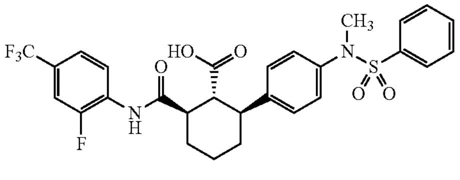 [SMILES: CN(c1ccc([C@H]2CCC[C@@H](C(=O)Nc3ccc(C(F)(F)F)cc3F)[C@@H]2C(=O)O)cc1)S(=O)(=O)c1ccccc1] (1R,2R,6S)-2-((2-fluoro-4-(trifluoromethyl)phenyl)carbamoyl)-6-(4-(N-methylphenylsulfonamido)phenyl) cyclohexane-1-carboxylic acid | $^1$H NMR (400 MHz, DMSO-$d_6$) δ 11.82 (br s, 1H), 10.11 (s, 1H), 8.22 (t, J = 8.1 Hz, 1H), 7.78-7.64 (m, 2H), 7.60-7.52 (m, 2H), 7.47-7.39 (m, 2H), 7.22 (d, J = 8.8 Hz, 2H), 6.99 (d, J = 8.8 Hz, 2H), 3.10 (s, 2H), 3.05-2.94 (m, 1H), 2.82-2.73 (m, 1H), 2.73-2.62 (m, 1H), 2.09-1.99 (m, 1H), 1.93-1.84 (m, 1H), 1.81-1.72 (m, 1H), 1.68-1.45 (m, 3H). | ES-LCMS m/z 579.3 [M + H]$^+$ |

-continued

| Ex | Structure/Name | ¹H NMR | LCMS |
|---|---|---|---|
| 110 | 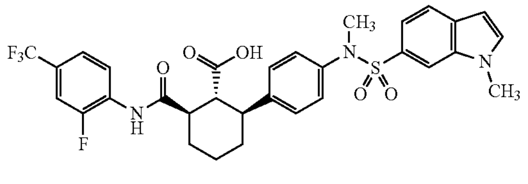 [SMILES: CN(c1ccc([C@H]2CCC[C@@H](C(=O)Nc3ccc(C(F)(F)F)cc3F)[C@@H]2C(=O)O)cc1)S(=O)(=O)c1ccc2ccn(C)c2c1] (1R,2S,6R)-2-(4-((N,1-dimethyl-1H-indole)-6-sulfonamido)phenyl)-6-((2-fluoro-4-(trifluoromethyl)phenyl) carbamoyl)cyclohexane-1-carboxylic acid | 1H NMR (400 MHz, DMSO-$d_6$) δ 11.83 (s, 1H), 10.10 (s, 1H), 8.22 (t, J = 8.1 Hz, 1H), 7.72 (dd, J = 11.0, 1.7 Hz, 1H), 7.66 (d, J = 8.8 Hz, 1H), 7.62 (d, J = 2.9 Hz, 1H), 7.59-7.51 (m, 2H), 7.21 (d, J = 8.8 Hz, 2H), 7.05 (dd, J = 8.3, 1.5 Hz, 1H), 6.98 (d, J = 8.3 Hz, 2H), 6.58 (dd, J = 2.9, 1.0 Hz, 1H), 3.80 (s, 3H), 3.08 (s, 3H), 3.05-2.96 (m, 1H), 2.85-2.75 (m, 1H), 2.74-2.65 (m, 1H), 2.09-1.98 (m, 1H), 1.89 (br d, J = 3.4 Hz, 1H), 1.81-1.70 (m, 1H), 1.67-1.46 (m, 3H) | ES-LCMS m/z 632.4 $[M + H]^+$. |
| 111 | 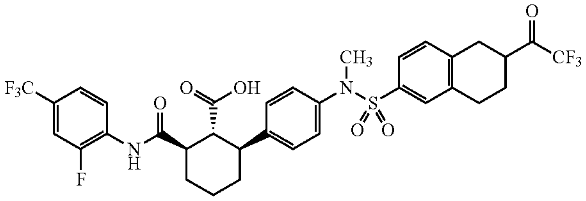 [SMILES: CN(c1ccc([C@H]2CCC[C@@H](C(=O)Nc3ccc(C(F)(F)F)cc3F)[C@@H]2C(=O)O)cc1)S(=O)(=O)c1ccc2c(c1)CCC(C(=O)C(F)(F)F)C2] (1R,2R,6S)-2-((2-fluoro-4-(trifluoromethyl)phenyl)carbamoyl)-6-(4-((N-methyl-2-(2,2,2-trifluoroacetyl)-1,2,3,4-tetrahydroisoquinoline)-6-sulfonamido)phenyl)cyclohexane-1-carboxylic acid | ¹H NMR (400 MHz, DMSO-$d_6$) δ 8.22 (t, J = 8.3 Hz, 1H), 7.72 (dd, J = 11.0, 1.7 Hz, 1H), 7.55 (br d, J = 8.3 Hz, 1H), 7.52-7.43 (m, 1H), 7.42-7.31 (m, 1H), 7.28-7.19 (m, 2H), 7.16 (dd, J = 8.1, 1.7 Hz, 1H), 7.06-6.96 (m, 2H), 4.87-4.73 (m, 2H), 3.92-3.76 (m, 2H), 3.11 (d, J = 4.9 Hz, 3H), 3.05-2.95 (m, 3H), 2.88-2.75 (m, 1H), 2.74-2.64 (m, 1H), 2.03 (br d, J = 8.3 Hz, 1H), 1.89 (br d, J = 3.4 Hz, 1H), 1.84-1.71 (m, 1H), 1.69-1.44 (m, 3H). | ES-LCMS m/z 730.4 $[M + H]^+$. |
| 112 | 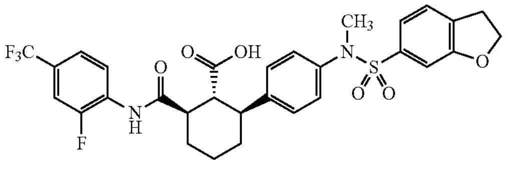 [SMILES: CN(c1ccc([C@H]2CCC[C@@H](C(=O)Nc3ccc(C(F)(F)F)cc3F)[C@@H]2C(=O)O)cc1)S(=O)(=O)c1ccc2c(c1)OCC2] (1R,2R,6S)-2-((2-fluoro-4-(trifluoromethyl)phenyl)carbamoyl)-6-(4-((N-methyl-2,3-dihydrobenzofuran)-6-sulfonamido)phenyl)cyclohexane-1-carboxylic acid | ¹H NMR (400 MHz, DMSO-$d_6$) δ 11.83 (br d, J = 1.0 Hz, 1H), 10.11 (s, 1H), 8.22 (t, J = 8.1 Hz, 1H), 7.72 (dd, J = 11.0, 1.7 Hz, 1H), 7.55 (br d, J = 8.3 Hz, 1H), 7.40-7.32 (m, 1H), 7.23 (d, J = 8.3 Hz, 2H), 7.03 (d, J = 8.8 Hz, 2H), 6.91-6.79 (m, 2H), 4.62 (t, J = 8.8 Hz, 2H), 3.27 (br t, J = 8.6 Hz, 2H), 3.09 (s, 3H), 3.05-2.93 (m, 1H), 2.84-2.66 (m, 2H), 2.02 (br d, J = 8.8 Hz, 1H), 1.93-1.84 (m, 1H), 1.80-1.71 (m, 1H), 1.66-1.43 (m, 3H). | ES-LCMS m/z 621.2 $[M + H]^+$. |
| 113 | 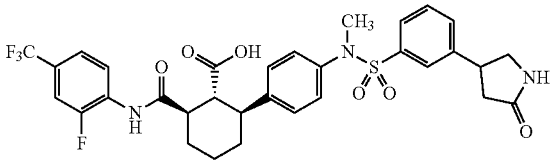 [SMILES: CN(c1ccc([C@H]2CCC[C@@H](C(=O)Nc3ccc(C(F)(F)F)cc3F)[C@@H]2C(=O)O)cc1)S(=O)(=O)c1cccc(C2CNC(=O)C2)c1] (1R,2R,6S)-2-((2-fluoro-4-(trifluoromethyl)phenyl)carbamoyl)-6-(4-((N-methyl-3-(5-oxopyrrolidin-3-yl)phenyl)sulfonamido)phenyl)cyclohexane-1-carboxylic acid | ¹H NMR (400 MHz, DMSO-$d_6$) δ 12.52-11.45 (m, 1H), 10.10 (s, 1H), 8.22 (t, J = 8.1 Hz, 1H), 7.78-7.69 (m, 2H), 7.65 (br d, J = 7.3 Hz, 1H), 7.59-7.50 (m, 2H), 7.42-7.33 (m, 1H), 7.27-7.19 (m, 3H), 6.97 (dd, J = 8.6, 3.7 Hz, 2H), 3.75-3.55 (m, 2H), 3.17-3.10 (m, 1H), 3.08 (s, 3H), 3.05-2.95 (m, 1H), 2.85-2.76 (m, 1H), 2.75-2.65 (m, 1H), 2.57-2.47 (m, 1H), 2.18 (dd, J = 16.4, 8.6 Hz, 1H), 2.02 (br d, J = 8.3 Hz, 1H), 1.92-1.85 (m, 1H), 1.81-1.72 (m, 1H), 1.64-1.46 (m, 3H). | ES-LCMS m/z 662.5 $[M + H]^+$. |
| 114 | 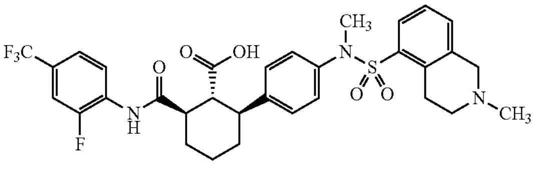 [SMILES: CN1CCc2c(cccc2S(=O)(=O)N(C)c2ccc([C@H]3CCC[C@@H](C(=O)Nc4ccc(C(F)(F)F)cc4F)[C@@H]3C(=O)O)cc2)C1] (1R,2S,6R)-2-(4-((N,2-dimethyl-1,2,3,4-tetrahydroisoquinoline)-5-sulfonamido)phenyl)-6-((2-fluoro-4-(trifluoromethyl)phenyl)carbamoyl) cyclohexane-1-carboxylic acid | ¹H NMR (400 MHz, DMSO-$d_6$) δ 10.00 (s, 1H), 8.20 (t, J = 8.1 Hz, 1H), 7.74-7.68 (m, 2H), 7.55 (br d, J = 8.8 Hz, 1H), 7.45-7.36 (m, 2H), 7.22 (d, J = 8.8 Hz, 2H), 7.11 (s, 1H), 7.02 (d, J = 8.8 Hz, 2H), 3.81-3.72 (m, 1H), 3.63-3.54 (m, 1H), 3.16 (s, 3H), 3.02-2.93 (m, 1H), 2.90-2.76 (m, 2H), 2.73-2.58 (m, 2H), 2.29 (br s, 3H), 2.03-1.97 (m, 1H), 1.94-1.80 (m, 2H), 1.75 (br d, J = 8.8 Hz, 1H), 1.60-1.44 (m, 3H) | ES-LCMS m/z 648.3 $[M + H]^+$. |

-continued

| Ex | Structure/Name | $^1$H NMR | LCMS |
|---|---|---|---|
| 115 | 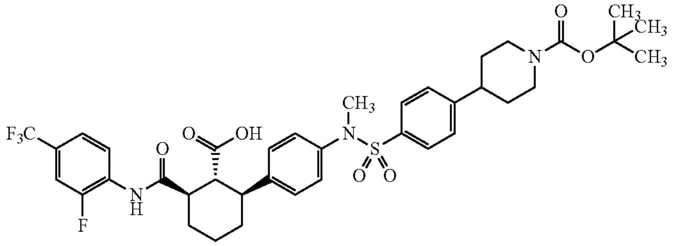 [SMILES: CN(c1ccc([C@H]2CCC[C@@H](C(=O)Nc3ccc(C(F)(F)F)cc3F)[C@@H]2C(=O)O)cc1)S(=O)(=O)c1ccc(C2CCN(C(=O)OC(C)(C)C)CC2)cc1] (1R,2S,6R)-2-(4-((3-(1-(tert-butoxycarbonyl)piperidin-4-yl)-N-methylphenyl)sulfonamido)phenyl)-6-((2-fluoro-4-(trifluoromethyl)phenyl)carbamoyl) cyclohexane-1-carboxylic acid | $^1$H NMR (400 MHz, DMSO-$d_6$) δ 11.81 (br d, J = 1.0 Hz, 1H), 8.59-8.57 (m, 1H), 8.26-8.15 (m, 1H), 7.84-7.76 (m, 1H), 7.71 (br d, J = 11.2 Hz, 1H), 7.63-7.57 (m, 1H), 7.56-7.47 (m, 2H), 7.40-7.38 (m, 1H), 7.22 (br d, J = 7.8 Hz, 2H), 6.95 (br d, J = 8.8 Hz, 2H), 4.13-3.99 (m, 2H), 3.06 (s, 3H), 3.04-2.95 (m, 1H), 2.84-2.65 (m, 6H), 2.07-1.97 (m, 1H), 1.94-1.83 (m, 1H), 1.80-1.64 (m, 3H), 1.61-1.46 (m, 3H), 1.41 (s, 9H). | ES-LCMS m/z 762.2 [M + H]$^+$ |
| 116 | 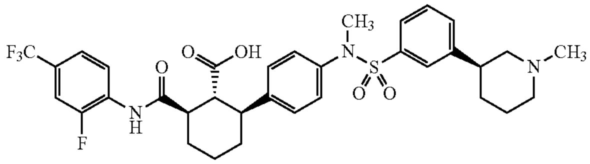 [SMILES: CN1CCC[C@@H](c2cccc(S(=O)(=O)N(C)c3ccc([C@H]4CCC[C@@H](C(=O)Nc5ccc(C(F)(F)F)cc5F)[C@@H]4C(=O)O)cc3)c2)C1] (1R,2R,6S)-2-((2-fluoro-4-(trifluoromethyl)phenyl)carbamoyl)-6-(4-((N-methyl-3-((S)-1-methylpiperidin-3-yl)phenyl)sulfonamido)phenyl)cyclohexane-1-carboxylic acid | $^1$H NMR (400 MHz, METHANOL-$d_4$) δ 8.20 (t, J = 8.1 Hz, 1H), 7.74-7.70 (m, 1H), 7.66-7.61 (m, 2H), 7.56-7.52 (m, 1H), 7.51-7.47 (m, 1H), 7.28 (d, J = 8.3 Hz, 2H), 7.02-6.97 (m, 2H), 3.14 (s, 3H), 3.12-3.01 (m, 4H), 2.96-2.85 (m, 5H), 2.84-2.69 (m, 2H), 2.21-2.12 (m, 2H), 2.08-1.84 (m, 5H), 1.78-1.65 (m, 4H). One exchangeable H not observed | ES-LCMS m/z 676.3 [M + H]$^+$. |
| 117 | 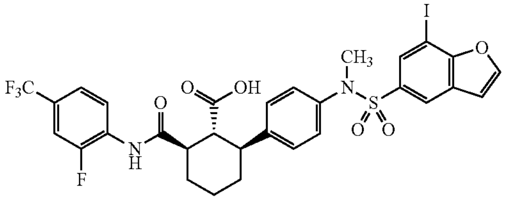 [SMILES: CN(c1ccc([C@H]2CCC[C@@H](C(=O)Nc3ccc(C(F)(F)F)cc3F)[C@@H]2C(=O)O)cc1)S(=O)(=O)c1cc(I)c2occc2c1] (1R,2R,6S)-2-((2-fluoro-4-(trifluoromethyl)phenyl)carbamoyl)-6-(4-((7-iodo-N-methylbenzofuran)-5-sulfonamido)phenyl)cyclohexane-1-carboxylic acid | $^1$H NMR (400 MHz, METHANOL-$d_4$) δ 8.24 (t, J = 8.1 Hz, 1H), 8.01 (d, J = 2.4 Hz, 1H), 7.77-7.69 (m, 2H), 7.53-7.44 (m, 2H), 7.26-7.20 (m, 2H), 7.13-7.10 (m, 1H), 7.03-6.98 (m, 2H), 4.89 (br s, 3H), 3.06-2.99 (m, 1H), 2.94 (t, J = 11.0 Hz, 1H), 2.89-2.81 (m, 1H), 2.16-2.10 (m, 1H), 2.01 (br d, J = 3.4 Hz, 1H), 1.92 (br d, J = 9.3 Hz, 1H), 1.74-1.62 (m, 3H). One exchangeable H not observed | ES-LCMS m/z 745.0 [M + H]$^+$ |
| 118 | 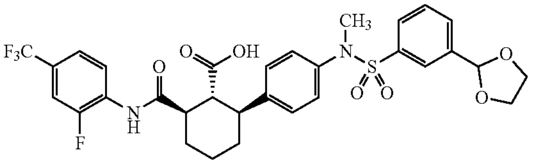 [SMILES: CN(c1ccc([C@H]2CCC[C@@H](C(=O)Nc3ccc(C(F)(F)F)cc3F)[C@@H]2C(=O)O)cc1)S(=O)(=O)c1cccc(C2OCCO2)c1] (1R,2S,6R)-2-(4-((3-(1,3-dioxolan-2-yl)-N-methylphenyl)sulfonamido)phenyl)-6-((2-fluoro-4-(trifluoromethyl)phenyl)carbamoyl) cyclohexane-1-carboxylic acid | $^1$H NMR (400 MHz, METHANOL-$d_4$) δ 8.24 (t, J = 8.1 Hz, 1H), 7.77-7.72 (m, 1H), 7.60 (t, J = 1.7 Hz, 1H), 7.57-7.51 (m, 2H), 7.50-7.44 (m, 3H), 7.26-7.21 (m, 2H), 7.04-6.99 (m, 2H), 5.80 (s, 1H), 4.12-4.01 (m, 4H), 3.35-3.22 (m, 3H), 3.06-2.98 (m, 1H), 2.92 (t, J = 10.8 Hz, 1H), 2.89-2.80 (m, 1H), 2.17-2.11 (m, 1H), 2.04-1.99 (m, 1H), 1.93-1.87 (m, 1H), 1.78-1.61 (m, 3H). One exchangeable H not observed | ES-LCMS m/z 651.2 [M + H]$^+$. |

-continued

| Ex | Structure/Name | $^1$H NMR | LCMS |
|---|---|---|---|
| 119 | 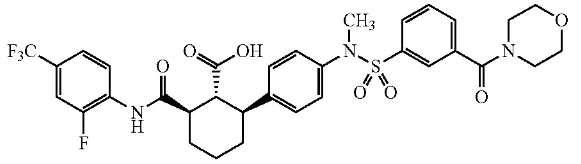 [SMILES: CN(c1ccc([C@H]2CCC[C@@H](C(=O)Nc3ccc(C(F)(F)F)cc3F)[C@@H]2C(=O)O)cc1)S(=O)(=O)c1cccc(C(=O)N2CCOCC2)c1] (1R,2R,6S)-2-((2-fluoro-4-(trifluoromethyl)phenyl) carbamoyl)-6-(4-((N-methyl-3-(morpholine-4-carbonyl)phenyl) sulfonamido)phenyl) cyclo hexane-1-carboxylic acid | $^1$H NMR (400 MHz, METHANOL-$d_4$) δ 8.25 (t, J = 7.8 Hz, 1H), 7.74-7.69 (m, 1H), 7.68-7.64 (m, 1H), 7.64-7.58 (m, 1H), 7.56-7.45 (m, 3H), 7.27-7.20 (m, 2H), 7.08-7.00 (m, 2H), 3.75 (br s, 3H), 3.63 (br s, 2H), 3.33 (quin, J = 1.7 Hz, 3H), 3.20 (s, 3H), 3.06-2.98 (m, 1H), 2.94-2.79 (m, 2H), 2.17-2.10 (m, 1H), 2.03-1.99 (m, 1H), 1.95-1.88 (m, 1H), 1.77-1.62 (m, 3H). One exchangeable H not observed | ES-LCMS m/z 692.2 $[M + H]^+$ |
| 120 | 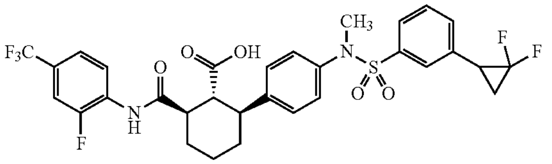 [SMILES: CN(c1ccc([C@H]2CCC[C@@H](C(=O)Nc3ccc(C(F)(F)F)cc3F)[C@@H]2C(=O)O)cc1)S(=O)(=O)c1cccc(C2CC2(F)F)c1] (1R,2S,6R)-2-(4-((3-(2,2-difluorocyclopropyl)-N-methylphenyl)sulfonamido)phenyl)-6-((2-fluoro-4-(trifluoromethyl)phenyl)carbamoyl) cyclohexane-1-carboxylic acid | $^1$H NMR (400 MHz, METHANOL-$d_4$) δ 8.24 (t, J = 8.1 Hz, 1H), 7.58-7.55 (m, 1H), 7.52-7.45 (m, 3H), 7.43-7.39 (m, 1H), 7.32 (s, 1H), 7.26-7.22 (m, 2H), 7.02-6.99 (m, 2H), 3.14 (s, 3H), 3.05-2.98 (m, 1H), 2.96-2.89 (m, 2H), 2.88-2.84 (m, 1H), 2.15-2.11 (m, 1H), 2.02-1.88 (m, 3H), 1.72-1.63 (m, 4H). One exchangeable H not observed | ES-LCMS m/z 655.2 $[M + H]^+$. |
| 121 | 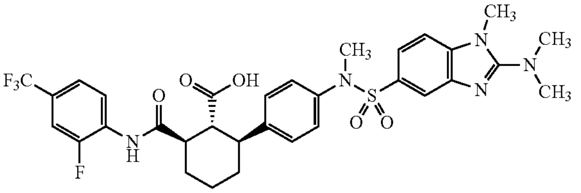 [SMILES: CN(C)c1nc2cc(S(=O)(=O)N(C)c3ccc([C@H]4CCC[C@@H](C(=O)Nc5ccc(C(F)(F)F)cc5F)[C@@H]4C(=O)O)cc3)ccc2n1C] (1R,2S,6R)-2-(4-((2-(dimethylamino)-N, 1-dimethyl-1H-benzo[d]imidazole)-5-sulfonamido)phenyl)-6-((2-fluoro-4-(trifluoromethyl)phenyl) carbamoyl) cyclohexane-1-carboxylic acid | $^1$H NMR (400 MHz, DMSO-$d_6$) δ 12.40 (br s, 1H), 10.12 (s, 1H), 8.19 (dd, J = 8.4, 8.2 Hz, 1H), 7.72 (dd, J = 10.8, 1.6 Hz, 1H), 7.56 (d, J = 8.4 Hz, 1H), 7.43 (d, J = 8.4 Hz, 1H), 7.21-7.15 (m, 4H), 6.99 (d, J = 8.8 Hz, 2H), 3.68 (s, 3H), 3.05 (s, 3H), 3.02-2.96 (m, 6H), 2.75 (t, J = 10.8 Hz, 1H), 2.70-2.64 (m, 2H), 2.12-2.09 (m, 1H), 2.03-2.01 (m, 1H), 1.91-1.57 (m, 4H). | ES-LCMS m/z 676.1 $[M + H]^+$ |
| 122 | 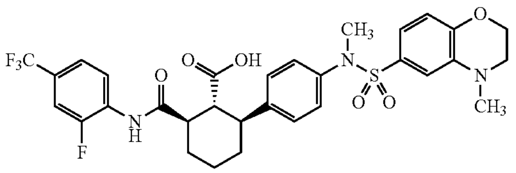 [SMILES: CN1CCOc2ccc(S(=O)(=O)N(C)c3ccc([C@H]4CCC[C@@H](C(=O)Nc5ccc(C(F)(F)F)cc5F)[C@@H]4C(=O)O)cc3)cc21] (1R,2S,6R)-2-(4-((N,4-dimethyl-3,4-dihydro-2H-benzo[b][1,4]oxazine)-6-sulfonamido)phenyl)-6-((2-fluoro-4-cyclohe(trifluoromethyl)phenyl)carbamoyl) xane-1-carboxylic acid | $^1$H NMR (400 MHz, DMSO-$d_6$) δ 10.17 (s, 1H), 8.23 (dd, J = 8.0, 8.0 Hz, 1H), 7.71 (dd, J = 11.0, 1.6 Hz, 1H), 7.55 (d, J = 8.0 Hz, 1H), 7.23 (d, J = 8.4 Hz, 2H), 7.03 (d, J = 8.4 Hz, 2H), 6.79 (d, J = 8.4 Hz, 1H), 6.72 (dd, J = 8.0, 2.0 Hz, 1H), 6.47 (d, J = 2.0 Hz, 1H), 4.30 (t, J = 4.4 Hz, 2H), 3.27 (t, J = 4.4 Hz, 2H), 3.04 (s, 3H), 2.98-2.96 (m, 1H), 2.74-2.71 (m, 5H), 2.09-2.02 (m, 1H), 2.00-1.98 (m, 1H), 1.73-1.71 (m, 1H), 1.53-1.51 (m, 3H). | ES-LCMS m/z 650.2 $[M + H]^+$. |
| 123 | 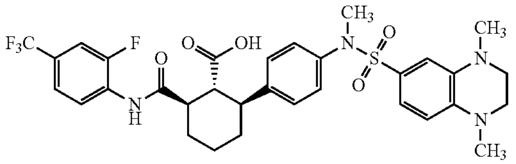 [SMILES: CN1CCN(C)c2cc(S(=O)(=O)N(C)c3ccc([C@H]4CCC[C@@H](C(=O)Nc5ccc(C(F)(F)F)cc5F)[C@@H]4C(=O)O)cc3)ccc21] (1R,2R,6S)-2-((2-fluoro-4-(trifluoromethyl)phenyl)carbamoyl)-6-(4-((N,1,4-trimethyl-1,2,3,4-tetrahydroquinoxaline)-6-sulfonamido)phenyl)cyclohexane-1-carboxylic acid | $^1$H NMR (400 MHz, DMSO-$d_6$) δ 10.16 (s, 1H), 8.23 (t, J = 8.0 Hz, 1H), 7.72 (dd, J = 11,2, 1.6 Hz, 1H), 7.55 (d, J = 8.4 Hz, 1H), 7.22 (d, J = 8.4 Hz, 2H), 7.03 (d, J = 8.4 Hz, 2H), 6.79 (dd, J = 8.4, 2.0 Hz, 1H), 6.46 (d, J = 8.4 Hz, 1H), 6.15 (d, J = 2.4 Hz, 1H), 3.42 (t, J = 5.6 Hz, 2H), 3.21 (t, J = 4.8 Hz, 2H), 2.99 (s, 3H), 2.99-2.92 (m, 1H), 2.89 (s, 3H). | ES-LCMS m/z 663.2 $[M + H]^+$. |

-continued

| Ex | Structure/Name | $^1$H NMR | LCMS |
|---|---|---|---|
| 124 | 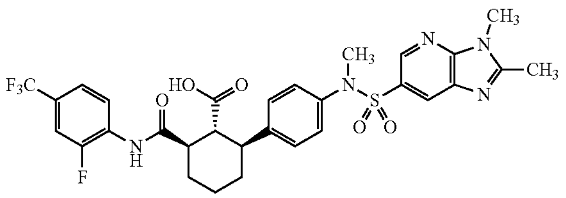 [SMILES: Cc1nc2cc(S(=O)(=O)N(C)c3ccc([C@H]4CCC[C@@H](C(=O)Nc5ccc(C(F)(F)F)cc5F)[C@@H]4C(=O)O)cc3)cnc2n1C] (1R,2R,6S)-2-((2-fluoro-4-(trifluoromethyl)phenyl)carbamoyl)-6-(4-((N,2,3-trimethyl-3H-imidazo[4,5-b]pyridine)-6-sulfonamido)phenyl)cyclohexane-1-carboxylic acid | $^1$H NMR (400 MHz, DMSO-$d_6$) δ 11.56 (br s, 1H), 10.13 (s, 1H), 8.34 (d, J = 2.0 Hz, 1H), 8.22 (t, J = 8.0 Hz, 1H), 7.89 (d, J = 2.0 Hz, 1H), 7.72 (dd, J = 11.0, 1.6 Hz, 1H), 7.55 (d, J = 8.8 Hz, 1H), 7.23 (d, J = 8.4 Hz, 2H), 7.01 (d, J = 8.8 Hz, 2H), 3.81 (s, 3H), 3.12 (s, 3H), 3.02-2.96 (m, 1H), 2.78 (t, J = 10.4 Hz, 1H), 2.73-2.67 (m, 1H), 2.64 (s, 3H), 2.02 (d, J = 8.8 Hz, 1H), 1.93-1.85 (m, 1H), 1.78-1.74 (m, 1H), 1.62-1.48 (m, 3H). | ES-LCMS m/z 648.2 [M + H]$^+$. |
| 125 | 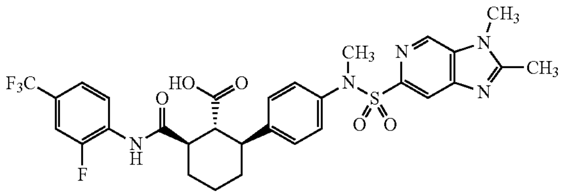 [SMILES: Cc1nc2cc(S(=O)(=O)N(C)c3ccc([C@H]4CCC[C@@H](C(=O)Nc5ccc(C(F)(F)F)cc5F)[C@@H]4C(=O)O)cc3)ncc2n1C] (1R,2R,6S)-2-((2-fluoro-4-(trifluoromethyl)phenyl)carbamoyl)-6-(4-((N,2,3-trimethyl-3H-imidazo[4,5-c]pyridine)-6-sulfonamido)phenyl)cyclohexane-1-carboxylic acid | $^1$H NMR (400 MHz, DMSO-$d_6$) δ 10.19 (br s, 1H), 9.05 (s, 1H), 8.21 (t, J = 8.0 Hz, 1H), 7.84 (s, 1H), 7.69 (dd, J = 11.0, 1.5 Hz, 1H), 7.53 (d, J = 8.5 Hz, 1H), 7.16 (d, J = 8.5 Hz, 2H), 7.05 (d, J = 8.5 Hz, 2H), 3.91 (s, 3H), 3.32 (br s, 3H), 2.98-2.86 (m, 1H), 2.74-2.65 (m, 2H), 2.62 (s, 3H), 1.99-1.66 (m, 3H), 1.56-1.41 (m, 3H). | ES-LCMS m/z 647.8 [M + H]$^+$. |
| 126 | 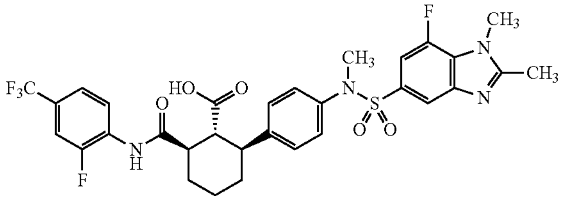 [SMILES: Cc1nc2cc(S(=O)(=O)N(C)c3ccc([C@H]4CCC[C@@H](C(=O)Nc5ccc(C(F)(F)F)cc5F)[C@@H]4C(=O)O)cc3)cc(F)c2n1C] (1R,2R,6S)-2-((2-fluoro-4-(trifluoromethyl)phenyl)carbamoyl)-6-(4-((7-fluoro-N, 1,2-trimethyl-1H-benzo[d]imidazole)-5-sulfonamido)phenyl)cyclohexane-1-carboxylic acid | $^1$H NMR (400 MHz, DMSO-$d_6$) δ 11.88 (br s, 1H), 10.11 (s, 1H), 8.21 (t, J = 8.0 Hz, 1H), 7.71 (dd, J = 11.0, 1.5 Hz, 1H), 7.54 (d, J = 8.5 Hz, 1H), 7.40 (d, J = 1.5 Hz, 1H), 7.21 (d, J = 8.5 Hz, 2H), 7.08-6.92 (m, 3H), 3.91 (s, 3H), 3.09 (s, 3H), 3.04-2.93 (m, 1H), 2.82-2.64 (m, 2H), 2.56 (s, 3H), 2.05-1.70 (m, 3H), 1.66-1.45 (m, 3H). | ES-LCMS m/z 665.2 [M + H]$^+$ |
| 127 | 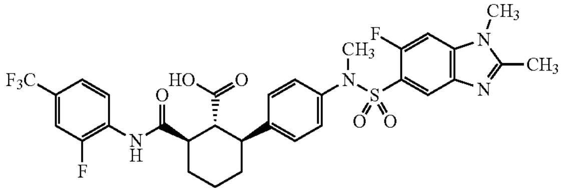 [SMILES: Cc1nc2cc(S(=O)(=O)N(C)c3ccc([C@H]4CCC[C@@H](C(=O)Nc5ccc(C(F)(F)F)cc5F)[C@@H]4C(=O)O)cc3)c(F)cc2n1C] (1R,2R,6S)-2-((2-fluoro-4-(trifluoromethyl)phenyl)carbamoyl)-6-(4-((6-fluoro-N,1,2-trimethyl-1H-benzo[d]imidazole)-5-sulfonamido)phenyl)cyclohexane-1-carboxylic acid | $^1$H NMR (400 MHz, DMSO-$d_6$) δ 11.62 (br s, 1H), 10.08 (s, 1H), 8.20 (t, J = 8.0 Hz, 1H), 7.75-7.51 (m, 4H), 7.19 (d, J = 8.5 Hz, 2H), 7.06 (d, J = 8.5 Hz, 2H), 3.75 (s, 3H), 3.20 (d, J = 2.0 Hz, 3H), 3.03-2.92 (m, 1H), 2.81-2.73 (m, 1H), 2.72-2.62 (m, 1H), 2.54 (s, 3H), 2.04-1.94 (m, 1H), 1.89-1.69 (m, 2H), 1.60-1.43 (m, 3H). | ES-LCMS m/z 664.8 [M + H]$^+$. |

-continued

| Ex | Structure/Name | $^1$H NMR | LCMS |
|---|---|---|---|
| 128 | 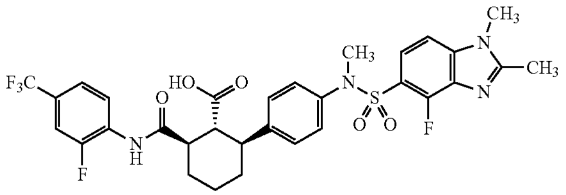 [SMILES: Cc1nc2c(F)c(S(=O)(=O)N(C)c3ccc([C@H]4CCC[C@@H](C(=O)Nc5ccc(C(F)(F)F)cc5F)[C@@H]4C(=O)O)cc3)ccc2n1C] (1R,2R,6S)-2-((2-fluoro-4-(trifluoromethyl)phenyl)carbamoyl)-6-(4-((4-fluoro-N,1,2-trimethyl-1H-benzo[d]imidazole)-5-sulfonamido)phenyl)cyclohexane-1-carboxylic acid | $^1$H NMR (400 MHz, DMSO-$d_6$) δ 11.76 (br s, 1H), 10.09 (s, 1H), 8.20 (t, J = 8.3 Hz, 1H), 7.71 (dd, J = 11.0, 2.0 Hz, 1H), 7.54 (br d, J = 8.0 Hz, 1H), 7.41 (d, J = 8.5 Hz, 1H), 7.27-7.17 (m, 3H), 7.04 (d, J = 8.5 Hz, 2H), 3.77 (s, 2H), 3.84-3.68 (m, 1H), 3.20 (d, J = 1.5 Hz, 3H), 3.04-2.92 (m, 1H), 2.80-2.72 (m, 1H), 2.71-2.62 (m, 1H), 2.58 (s, 3H), 2.02-1.70 (m, 3H), 1.58-1.37 (m, 3H). | ES-LCMS m/z 662.8 $[M - H]^-$. |
| 129 | 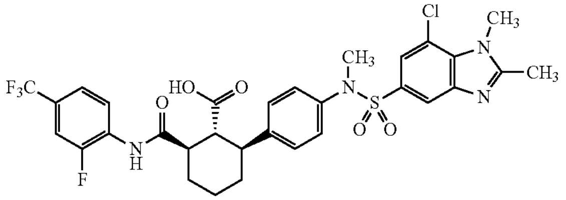 [SMILES: Cc1nc2cc(S(=O)(=O)N(C)c3ccc([C@H]4CCC[C@@H](C(=O)Nc5ccc(C(F)(F)F)cc5F)[C@@H]4C(=O)O)cc3)cc(Cl)c2n1C] (1R,2S,6R)-2-(4-((7-chloro-N,1,2-trimethyl-1H-benzo[d]imidazole)-5-sulfonamido)phenyl)-6-((2-fluoro-4-(trifluoromethyl)phenyl) carbamoyl) cyclohexane-1-carboxylic acid | $^1$H NMR (400 MHz, DMSO-$d_6$) δ 11.92 (s, 1H), 10.10 (s, 1H), 8.22 (t, J = 8.0 Hz, 1H), 7.72 (dd, J = 10.8, 1.6 Hz, 1H), 7.55 (d, J = 8.4 Hz, 1H), 7.49 (d, J = 1.6 Hz, 1H), 7.24-7.19 (m, 3H), 7.01 (d, J = 8.4 Hz, 2H), 4.03 (s, 3H), 3.09 (s, 3H), 3.02-2.98 (m, 1H), 2.80 (t, J = 10.8 Hz, 1H), 2.73-2.61 (m, 1H), 2.58 (s, 3H), 2.05-2.00 (m, 1H), 1.89 (d, J = 3.2 Hz, 1H), 1.77-1.74 (m, 1H), 1.61-1.51 (m, 3H). | ES-LCMS m/z 680.8 $[M + H]^+$. |
| 130 | 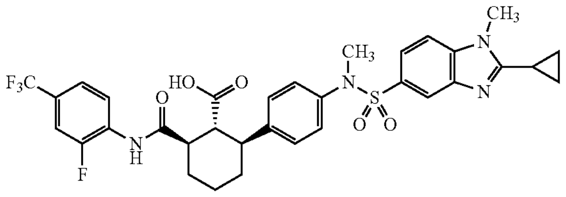 [SMILES: CN(c1ccc([C@H]2CCC[C@@H](C(=O)Nc3ccc(C(F)(F)F)cc3F)[C@@H]2C(=O)O)cc1)S(=O)(=O)c1ccc2c(c1)nc(C1CC1)n2C] (1R,2S,6R)-2-(4-((2-cyclopropyl-N,1-dimethyl-1H-benzo[d]imidazole)-5-sulfonamido)phenyl)-6-((2-fluoro-4-(trifluoromethyl)phenyl)carbamoyl) cyclohexane-1-carboxylic acid | $^1$H NMR (400 MHz, DMSO-$d_6$) δ 12.00 (br s, 1H), 10.10 (s, 1H), 8.21 (t, J = 8.0 Hz, 1H), 7.73 (dd, J = 11.2. 1.6 Hz, 1H), 7.61 (d, J = 2.8 Hz, 1H), 7.56 (d, J = 8.4 Hz, 1H), 7.43 (d, J = 1.6 Hz, 1H), 7.23-7.18 (m, 3H), 6.99 (d, J = 8.4 Hz, 1H), 3.9 (s, 3H), 3.48-3.42 (m, 1H), 3.05 (s, 3H), 3.0 (m, 1H), 2.76 (t, J = 10.8 Hz, 1H), 2.67-2.55 (m, 1H), 2.33-2.28 (m, 1H), 2.03-2.0 (m, 1H), 1.91-1.88 (m, 1H), 1.75 (m, 1H), 1.65-1.51 (m, 3H), 1.10-1.03 (m, 4H). | ES-LCMS m/z 673.0 $[M + H]^+$. |
| 131 | 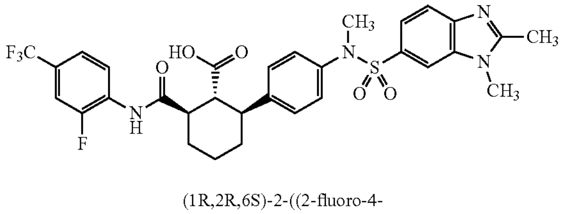 (1R,2R,6S)-2-((2-fluoro-4-(trifluoromethyl)phenyl)carbamoyl)-6-(4-((N,1,2-trimethyl-1H-benzo[d]imidazole)-6-sulfonamido)phenyl)cyclohexane-1-carboxylic acid | $^1$H NMR (400 MHz, DMSO-$d_6$) δ 11.80 (s, 1H), 10.10 (s, 1H), 8.22 (t, J = 8.4 Hz, 1H), 7.73 (d, J = 9.6 Hz, 1H), 7.62-7.54 (m, 3H), 7.21-7.15 (m, 3H), 6.96 (d, J = 8.4 Hz, 2H), 3.73 (s, 3H), 3.08 (s, 3H), 3.03-2.97 (m, 1H), 2.78 (t, J = 10.8 Hz, 1H), 2.71-2.67 (m, 1H), 2.58 (s, 3H), 2.08-2.03 (m, 1H), 1.91-1.88 (m, 1H), 1.76-1.73 (m, 1H), 1.59-1.49 (m, 3H). | ES-LCMS m/z 647.2 $[M + H]^+$. |

-continued

| Ex | Structure/Name | $^1$H NMR | LCMS |
|---|---|---|---|
| 132 | 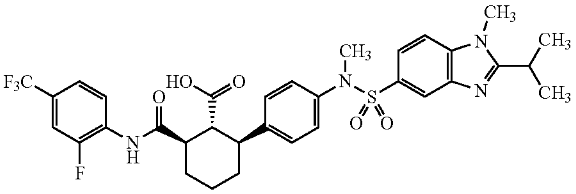 [SMILES: CC(C)c1nc2cc(S(=O)(=O)N(C)c3ccc([C@H]4CCC[C@@H](C(=O)Nc5ccc(C(F)(F)F)cc5F)[C@@H]4C(=O)O)cc3)ccc2n1C] (1R,2R,6S)-2-((2-fluoro-4-(trifluoromethyl)phenyl)carbamoyl)-6-(4-((2-isopropyl-N, 1-dimethyl-1H-benzo[d]imidazole)-5-sulfonamido)phenyl)cyclohexane-1-carboxylic acid | $^1$H NMR (400 MHz, DMSO-$d_6$) δ 12.19 (br s, 1H), 10.09 (s, 1H), 8.21 (t, J = 8.4 Hz, 1H), 7.73 (dd, J = 10.8, 1.6 Hz, 1H), 7.65 (d, J = 8.4 Hz, 1H), 7.56 (d, J = 9.2 Hz, 1H), 7.51 (d, J = 1.2 Hz, 1H), 7.25 (dd, J = 8.6, 2.0 Hz, 1H), 7.20 (d, J = 8.8 Hz, 2H), 7.01 (d, J = 8.8 Hz, 2H), 3.83 (s, 3H), 3.07 (s, 3H), 3.01 (t, J = 8.8 Hz, 1H), 2.77 (t, J = 10.8 Hz, 1H), 2.77-2.64 (m, 1H), 2.02 (d, J = 10.8 Hz, 1H), 1.90 (d, J = 6.4 Hz, 1H), 1.78 (d, J = 13.2 Hz, 1H), 1.66-1.49 (m, 3H), 1.32 (d, J = 6.8 Hz, 3H), 1.30 (d, J = 6.8 Hz, 3H), one proton was merged with residual DMSO/$H_2O$ peaks | ES-LCMS m/z 675.2 $[M + H]^+$. |
| 133 | 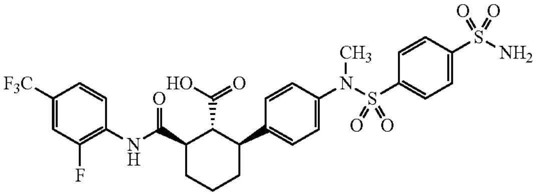 [SMILES: CN(c1ccc([C@H]2CCC[C@@H](C(=O)Nc3ccc(C(F)(F)F)cc3F)[C@@H]2C(=O)O)cc1)S(=O)(=O)c1ccc(S(N)(=O)=O)cc1] (1R,2R,6S)-2-((2-fluoro-4-(trifluoromethyl)phenyl)carbamoyl)-6-(4-((N-methyl-4-sulfamoylphenyl)sulfonamido)phenyl) cyclohexane-1-carboxylic acid | $^1$H NMR (400 MHz, DMSO-$d_6$) δ 10.19 (br s, 1H), 8.23 (br t, J = 8.3 Hz, 1H), 7.97 (d, J = 8.5 Hz, 2H), 7.75-7.51 (m, 4H), 7.23 (d, J = 8.5 Hz, 2H), 7.01 (d, J = 8.5 Hz, 2H), 3.14 (s, 3H), 3.03-2.92 (m, 1H), 2.78-2.68 (m, 1H), 2.06-1.97 (m, 1H), 1.87 (br d, J = 3.0 Hz, 1H), 1.74 (br d, J = 8.5 Hz, 1H), 1.65-1.43 (m, 3H), four protons were not observed | ES-LCMS m/z 656.0 $[M - H]^-$. |
| 134 | 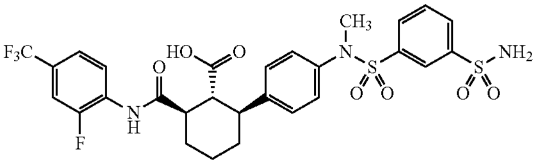 [SMILES: CN(c1ccc([C@H]2CCC[C@@H](C(=O)Nc3ccc(C(F)(F)F)cc3F)[C@@H]2C(=O)O)cc1)S(=O)(=O)c1cccc(S(N)(=O)=O)c1] (1R,2R,6S)-2-((2-fluoro-4-(trifluoromethyl)phenyl)carbamoyl)-6-(4-((N-methyl-3-sulfamoylphenyl)sulfonamido)phenyl) cyclohexane-1-carboxylic acid | 1H NMR (400 MHz, DMSO-$d_6$) δ 10.13 (br s, 1H), 8.23 (t, J = 8.0 Hz, 1H), 8.14-8.05 (m, 1H), 7.98 (s, 1H), 7.78-7.67 (m, 2H), 7.59-7.47 (m, 2H), 7.22 (d, J = 8.5 Hz, 2H), 6.98 (d, J = 8.5 Hz, 2H), 3.13 (s, 3H), 3.05-2.92 (m, 1H), 2.77-2.63 (m, 2H), 1.99 (br d, J = 9.0 Hz, 1H), 1.90-1.70 (m, 2H), 1.62-1.45 (m, 3H), three protons were not observed | ES-LCMS m/z 656.0 $[M - H]^-$. |
| 135 | 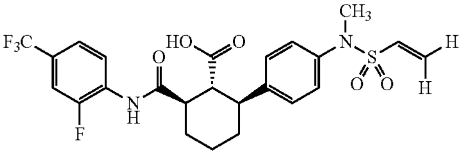 [SMILES: C=CS(=O)(=O)N(C)c1ccc([C@H]2CCC[C@@H](C(=O)Nc3ccc(C(F)(F)F)cc3F)[C@@H]2C(=O)O)cc1] (1R,2R,6S)-2-((2-fluoro-4-(trifluoromethyl)phenyl)carbamoyl)-6-(4-(N-methylvinylsulfonamido)phenyl) cyclohexane-1-carboxylic acid | $^1$H NMR (400 MHz, DMSO-$d_6$) δ 11.69 (br s, 1H), 10.15 (s, 1H), 8.22 (t, J = 8.4 Hz, 1H), 7.72 (d, J = 11.2 Hz, 1H), 7.55 (d, J = 8.4 Hz, 1H), 7.29-7.22 (m, 4H), 6.82 (dd, J = 16.4, 10.0 Hz, 1H), 6.14 (d, J = 10.0 Hz, 1H), 6.03 (d, J = 16.4 Hz, 1H), 3.15 (s, 3H), 3.01-2.98 (m, 1H), 2.80-2.72 (m, 2H), 2.02-2.00 (m, 1H), 1.89-1.87 (m, 1H), 1.75 (d, J = 9.20 Hz, 1H), 1.74-1.48 (m, 3H). | ES-LCMS m/z 527.2 $[M - H]^-$. |
| 136 | 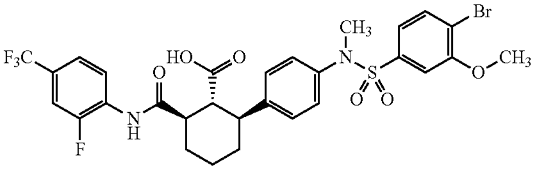 [SMILES: COc1cc(S(=O)(=O)N(C)c2ccc([C@H]3CCC[C@@H](C(=O)Nc4ccc(C(F)(F)F)cc4F)[C@@H]3C(=O)O)cc2)ccc1Br] (1R,2S,6R)-2-(4-((4-bromo-3-methoxy-N-methylphenyl)sulfonamido)phenyl)-6-((2-fluoro-4-(trifluoromethyl)phenyl)carbamoyl) cyclohexane-1-carboxylic acid | $^1$H NMR (400 MHz, DMSO-$d_6$) δ 10.24 (s, 1H), 8.24 (t, J = 8.4 Hz, 1H), 7.80 (d, J = 8.0 Hz, 1H), 7.71 (dd, J = 10.8, 1.6 Hz, 1H), 7.55 (d, J = 7.6 Hz, 1H), 7.25 (d, J = 8.4 Hz, 2H), 7.04 (d, J = 8.4 Hz, 2H), 6.98 (dd, J = 8.0, 1.2 Hz, 1H), 6.82 (d, J = 2.0 Hz, 1H), 3.74 (s, 3H), 3.10 (s, 3H), 2.96 (s, 1H), 2.77-2.67 (m, 1H), 2.01 (d, J = 9.2 Hz, 1H), 1.87 (d, J = 3.2 Hz, 1H), 1.72 (d, J = 10.8 Hz, 1H), 1.57-1.50 (m, 3H). | ES-LCMS m/z 685.0 $[M - H]^-$. |

Example 137 and Example 138

(1S,2S,4S,6R)-4-ethoxy-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylic acid AND (1R,2R,4R,6S)-4-ethoxy-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylic acid

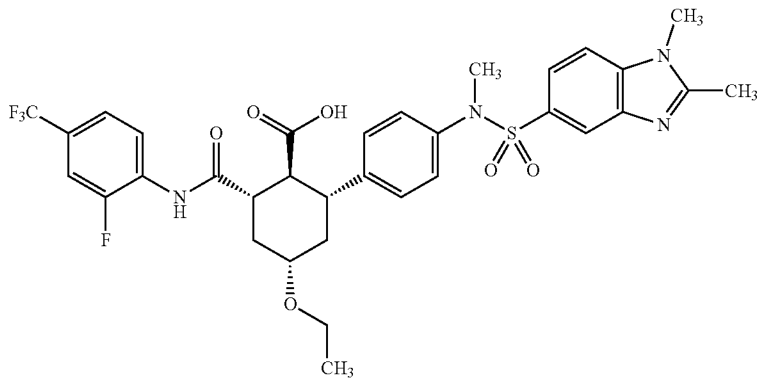

AND

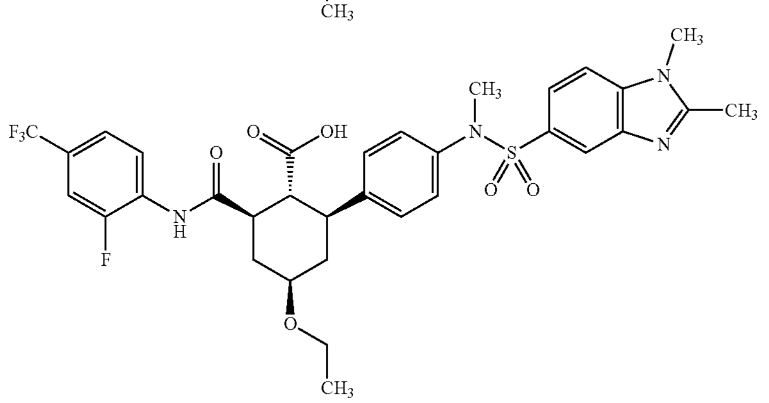

To a 1:1 mixture of (1R,2R,4R,6S)-4-ethoxy-2-((2-fluoro-4-(trifluoromethyl)phenyl)carbamoyl)-6-(4-(methylamino)phenyl)cyclohexane-1-carboxylic acid and (1 S,2S,4S,6R)-4-ethoxy-2-((2-fluoro-4-(trifluoromethyl)phenyl)carbamoyl)-6-(4-(methylamino)phenyl)cyclohexane-1-carboxylic acid (Intermediate 8) (0.290 g, 0.601 mmol) and pyridine (0.146 mL, 1.80 mmol) in dichloromethane (3 mL) at 0° C. was added 1,2-dimethyl-1H-benzo[d]imidazole-5-sulfonyl chloride (294 mg, 1.20 mmol). After 1 h, the reaction was quenched with MeOH (2 mL), concentrated and subjected to reverse phase purification (MeCN in $H_2O$, 10 mM ammonium bicarbonate modifier, 10-100% gradient) to afford a 1:1 mixture of (1R,2R,4R,6S)-4-ethoxy-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylic acid and (1S,2S,4S,6R)-4-ethoxy-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylic acid (0.300 g, 0.426 mmol, 70.8% yield). This material was chirally purified (Column: YMC Amylose SA, 250×20 mm, 5 μm; Mobile Phase: 1:1 $CO_2$:IPA) to give:

Example 137, the first-eluting isomer: (1S,2S,4S,6R)-4-ethoxy-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylic acid (9.0 mg, 0.014 mmol, 30% yield). $^1$H NMR (400 MHz, DMSO-$d_6$) δ 12.13 (br s, 1H), 10.12 (s, 1H), 8.22 (t, J=8.3 Hz, 1H), 7.77-7.68 (m, 1H), 7.62 (d, J=8.5 Hz, 1H), 7.56 (d, J=8.5 Hz, 1H), 7.48 (d, J=1.5 Hz, 1H), 7.32-7.14 (m, 3H), 6.96 (d, J=9.0 Hz, 2H), 3.78 (s, 3H), 3.60-3.42 (m, 3H), 3.05 (s, 3H), 2.79-2.64 (m, 2H), 2.56 (s, 3H), 2.33 (dt, J=3.6, 1.9 Hz, 2H), 2.05 (d, J=12.0 Hz, 1H), 1.56 (d, J=11.0 Hz, 1H), 1.51-1.34 (m, 1H), 1.10 (t, J=7.0 Hz, 3H). ES-LCMS m/z 691.2 $[M+H]^+$.

Example 138, the second-eluting isomer: (1R,2R,4R,6S)-4-ethoxy-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylic acid (0.13 g, 0.19 mmol, 43% yield). $^1$H NMR (400 MHz, DMSO-$d_6$) δ 12.13 (br s, 1H), 10.12 (s, 1H), 8.22 (t, J=8.3 Hz, 1H), 7.77-7.68 (m, 1H), 7.62 (d, J=8.5 Hz, 1H), 7.56 (d, J=8.5 Hz, 1H), 7.48 (d, J=1.5 Hz, 1H), 7.32-7.14 (m, 3H), 6.96 (d, J=9.0 Hz, 2H), 3.78 (s, 3H), 3.60-3.42 (m, 3H), 3.05 (s, 3H), 2.79-2.64 (m, 2H), 2.56 (s, 3H), 2.33 (dt, J=3.6, 1.9 Hz, 2H), 2.05 (d, J=12.0 Hz, 1H), 1.56 (d, J=11.0 Hz, 1H), 1.51-1.34 (m, 1H), 1.10 (t, J=7.0 Hz, 3H). ES-LCMS m/z 691.2 $[M+H]^+$. Absolute stereochemistry was assigned by co-crystallization with WRN protein.

Example 139

(1R,2S,4R,6R)-2-(4-((2-(dimethylamino)-N,1-dimethyl-1H-benzo[d]imidazole)-5-sulfonamido)phenyl)-4-ethoxy-6-((2-fluoro-4-(trifluoromethyl)phenyl)carbamoyl)cyclohexane-1-carboxylic acid

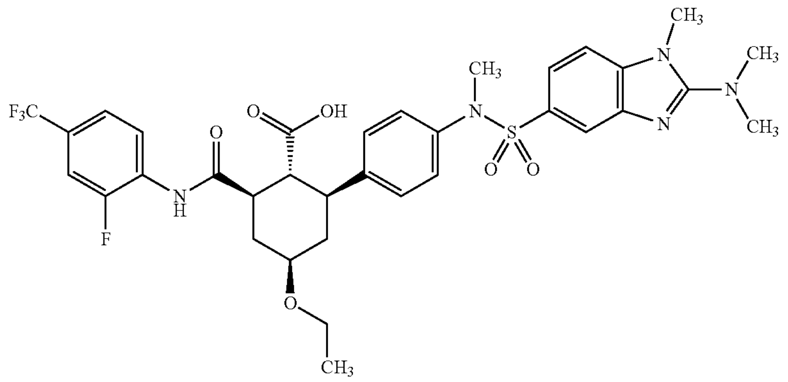 [SMILES: CCO[C@@H]1C[C@H](c2ccc(N(C)S(=O)(=O)c3ccc4c(c3)nc(N(C)C)n4C)cc2)[C@@H](C(=O)O)[C@H](C(=O)Nc2ccc(C(F)(F)F)cc2F)C1]

To a mixture of (1R,2R,4R,6S)-4-ethoxy-2-((2-fluoro-4-(trifluoromethyl)phenyl)carbamoyl)-6-(4-(methylamino)phenyl)cyclohexane-1-carboxylic acid Intermediate 9 (0.0500 g, 0.104 mmol) and pyridine (0.025 mL, 0.31 mmol) in dichloromethane (1 mL) at 0° C. was added 2-(dimethylamino)-1-methyl-1H-benzo[d]imidazole-5-sulfonyl chloride (42.6 mg, 0.155 mmol). After 1 h, the reaction was concentrated and subjected to reverse phase purification (MeCN in $H_2O$, 10 mM ammonium bicarbonate modifier, 95-98% gradient) to give (1R,2S,4R,6R)-2-(4-((2-(dimethylamino)-N,1-dimethyl-1H-benzo[d]imidazole)-5-sulfonamido)phenyl)-4-ethoxy-6-((2-fluoro-4-(trifluoromethyl)phenyl)carbamoyl)cyclohexane-1-carboxylic acid (45 mg, 0.62 mmol, 60% yield) as an off-white solid. $^1H$ NMR (400 MHz, DMSO-$d_6$) δ 12.43 (s, 1H), 10.14 (s, 1H), 8.20 (t, J=8.0 Hz, 1H), 7.76-7.72 (m, 1H), 7.56 (d, J=7.6 Hz, 1H), 7.44 (d, J=8.4 Hz, 1H), 7.23-7.12 (m, 4H), 6.99 (d, J=8.4 Hz, 2H), 3.68 (s, 3H), 3.55-3.48 (m, 3H), 3.06-2.96 (m, 4H), 2.98 (s, 6H), 2.75-2.68 (m, 2H), 2.07 (d, J=11.2 Hz, 1H), 1.60 (q, J=10.8 Hz, 1H), 1.45 (q, J=11.6 Hz, 1H), 1.11 (t, J=6.80 Hz, 3H), one proton was merged with residual DMSO-$d_6$/$H_2O$ peak. ES-LCMS m/z 720.5 $[M+H]^+$.

The following compounds were synthesized in an analogous manner to the preparation described above (Example 139) using the relevant sulfonyl chloride precursors. Compounds were purified using reverse phase chromatography (MeCN/$H_2O$, basic or acidic modifiers).

| Ex | Structure/Name | $^1H$ NMR | LCMS |
|---|---|---|---|
| 140 | 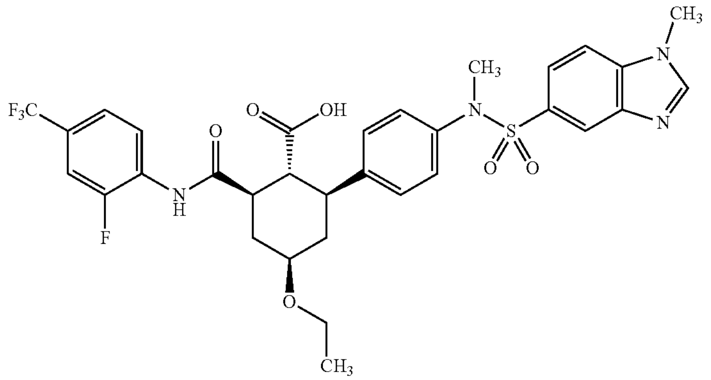 [SMILES: CCO[C@@H]1C[C@H](c2ccc(N(C)S(=O)(=O)c3ccc4c(c3)ncn4C)cc2)[C@@H](C(=O)O)[C@H](C(=O)Nc2ccc(C(F)(F)F)cc2F)C1] (1R,2S,4R,6R)-2-(4-((N,1-dimethyl-1H-benzo[d]imidazole)-5-sulfonamido)phenyl)-4-ethoxy-6-((2-fluoro-4-(trifluoromethyl)phenyl)carbamoyl)cyclohexane-1-carboxylic acid | $^1H$ NMR (400 MHz, DMSO-$d_6$) δ 11.93 (br s, 1H), 10.15 (s, 1H), 8.44 (s, 1H), 8.23 (t, J = 8.0 Hz, 1H), 7.75-7.71 (m, 3H), 7.56 (d, J = 8.4 Hz, 1H), 7.29-7.22 (m, 3H), 7.00 (d, J = 8.4 Hz, 2H), 3.90 (s, 3H), 3.58-3.48 (m, 3H), 3.09 (s, 3H), 3.08-3.03 (m, 1H), 2.77-2.71 (m, 2H), 2.38-2.32 (m, 1H), 2.08-2.04 (m, 1H), 1.54 (q, J = 12.0 Hz, 1H), 1.43 (q, J = 12.0 Hz, 1H), 1.13 (t, J = 7.2 Hz, 3H). | ES-LCMS m/z 677.2 $[M + H]^+$. |

-continued

| Ex | Structure/Name | $^1H$ NMR | LCMS |
| --- | --- | --- | --- |
| 141 | 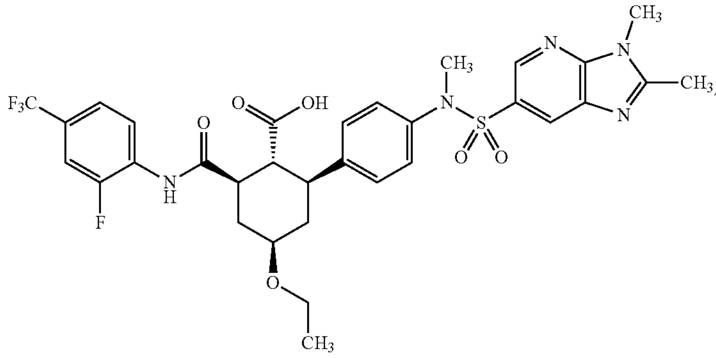 (1R,2R,4R,6S)-4-ethoxy-2-((2-fluoro-4-(trifluoromethyl)phenyl)carbamoyl)-6-(4-((N,2,3-trimethyl-3H-imidazo[4,5-b]pyridine)-6-sulfonamido)phenyl)cyclohexane-1-carboxylic acid | $^1H$ NMR (400 MHz, DMSO-$d_6$) δ 11.96 (s, 1H), 10.14 (s, 1H), 8.34 (d, J = 2.0 Hz, 1H), 8.23 (t, J = 8.0 Hz, 1H), 7.88 (d, J = 2.0 Hz, 1H), 7.73 (dd, J = 10.8, 1.6 Hz, 1H), 7.56 (d, J = 8.0 Hz, 1H), 7.25 (d, J = 8.4 Hz, 2H), 7.02 (d, J = 8.4 Hz, 2H), 3.81 (s, 3H), 3.55-3.48 (m, 3H), 3.12 (s, 3H), 3.08-3.03 (m, 1H), 2.80-2.73 (m, 2H), 2.64 (s, 3H), 2.34-2.31 (m, 1H), 2.06 (d, J = 11.6 Hz, 1H), 1.54 (q, J = 11.2 Hz, 1H), 1.43 (q, J = 12.0 Hz, 1H), 1.11 (t, J = 6.8 Hz, 3H). | ES-LCMS m/z 692.0 $[M + H]^+$. |

Example 142 and Example 143 rel-(1R,2R,4S,6S)-2-((2-fluoro-4-(trifluoromethyl)phenyl)carbamoyl)-4-hydroxy-6-(4-((N,1,2-trimethyl-1H-benzo[d]imidazole)-5-sulfonamido)phenyl)cyclohexane-1-carboxylic acid, ISOMER 1 AND ISOMER 2

ISOMER 1 and ISOMER 2

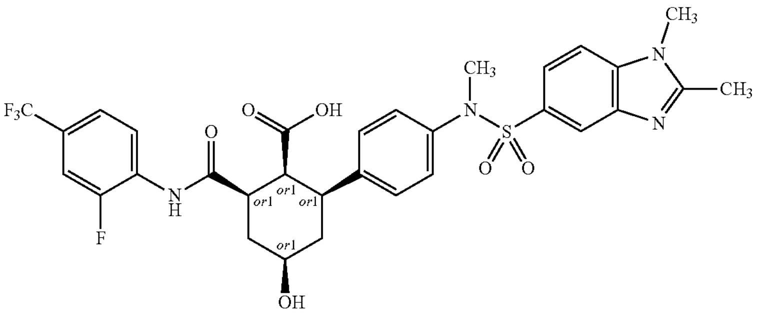

To a mixture of rac-(1R,2S,4S,6R)-2-((2-fluoro-4-(trifluoromethyl)phenyl)carbamoyl)-4-hydroxy-6-(4-(methylamino)phenyl)cyclohexane-1-carboxylic acid Intermediate 10 (0.200 g, 0.440 mmol) and pyridine (0.107 mL, 1.32 mmol) in dichloromethane (5 mL) at 0° C. was added 1,2-dimethyl-1H-benzo[d]imidazole-5-sulfonyl chloride (162 mg, 0.660 mmol). After 1 h, the reaction was concentrated and subjected to reverse phase purification (MeCN in $H_2O$, 10 mM ammonium bicarbonate modifier, 10-75% gradient) to afford rac-(1R,2R,4S,6S)-2-((2-fluoro-4-(trifluoromethyl)phenyl)carbamoyl)-4-hydroxy-6-(4-((N,1,2-trimethyl-1H-benzo[d]imidazole)-5-sulfonamido)phenyl)cyclohexane-1-carboxylic acid (0.200 g, 0.280 mmol, 63.6% yield). This material was chirally purified (Column: YMC Cellulose-SC, 250×30 mm, 5 μm; Mobile Phase: 60:40 $CO_2$:[1:1 ACN:IPA]) to give:

Example 142, the first-eluting isomer: rel-(1R,2R,4S,6S)-2-((2-fluoro-4-(trifluoromethyl)phenyl)carbamoyl)-4-hydroxy-6-(4-((N,1,2-trimethyl-1H-benzo[d]imidazole)-5-sulfonamido)phenyl)cyclohexane-1-carboxylic acid, ISOMER 1 (65 mg, 0.090 mmol, 32% yield). $^1H$ NMR (400 MHz, DMSO-$d_6$) δ 11.73 (br s, 1H), 10.16 (br s, 1H), 8.22 (t, J=8.3 Hz, 1H), 7.72 (dd, J=11.0, 1.5 Hz, 1H), 7.63 (d, J=8.5 Hz, 1H), 7.54 (br d, J=8.5 Hz, 1H), 7.49 (d, J=1.5 Hz, 1H), 7.24 (dd, J=8.5, 2.0 Hz, 1H), 7.17 (d, J=8.5 Hz, 2H), 6.99 (d, J=9.0 Hz, 2H), 4.82 (d, J=4.5 Hz, 1H), 3.77 (s, 3H), 3.71-3.58 (m, 1H), 3.15-3.10 (m, 1H), 3.06 (s, 3H), 3.04-3.00 (m, 1H), 2.98-2.90 (m, 1H), 2.56 (s, 3H), 2.36-2.26 (m, 1H), 2.08-1.97 (m, 1H), 1.93-1.71 (m, 2H). ES-LCMS m/z 663.2 $[M+H]^+$.

Example 143, the second-eluting isomer: rel-(1R,2R,4S,6S)-2-((2-fluoro-4-(trifluoromethyl)phenyl)carbamoyl)-4-hydroxy-6-(4-((N,1,2-trimethyl-1H-benzo[d]imidazole)-5-sulfonamido)phenyl)cyclohexane-1-carboxylic acid, ISOMER 2 (0.060 g, 0.087 mmol, 29% yield). $^1H$ NMR (400 MHz, DMSO-$d_6$) δ 11.73 (br s, 1H), 10.16 (br s, 1H), 8.22 (t, J=8.3 Hz, 1H), 7.72 (dd, J=11.0, 1.5 Hz, 1H), 7.63 (d, J=8.5 Hz, 1H), 7.54 (br d, J=8.5 Hz, 1H), 7.49 (d, J=1.5 Hz, 1H), 7.24 (dd, J=8.5, 2.0 Hz, 1H), 7.17 (d, J=8.5 Hz, 2H), 6.99 (d, J=9.0 Hz, 2H), 4.82 (d, J=4.5 Hz, 1H), 3.77 (s, 3H), 3.71-3.58 (m, 1H), 3.15-3.10 (m, 1H), 3.06 (s, 3H), 3.04-3.00 (m, 1H), 2.98-2.90 (m, 1H), 2.56 (s, 3H), 2.36-2.26 (m, 1H), 2.08-1.97 (m, 1H), 1.93-1.71 (m, 2H). ES-LCMS m/z 663.2 [M+H]$^+$.

Example 144 and Example 145 rel-(1R,2R,4R,6S)-2-((2-fluoro-4-(trifluoromethyl)phenyl) carbamoyl)-4-hydroxy-6-(4-((N,1,2-trimethyl-1H-benzo[d]imidazole)-5-sulfonamido)phenyl) cyclohexane-1-carboxylic acid, ISOMER 1 AND ISOMER 2

ISOMER 1 and ISOMER 2

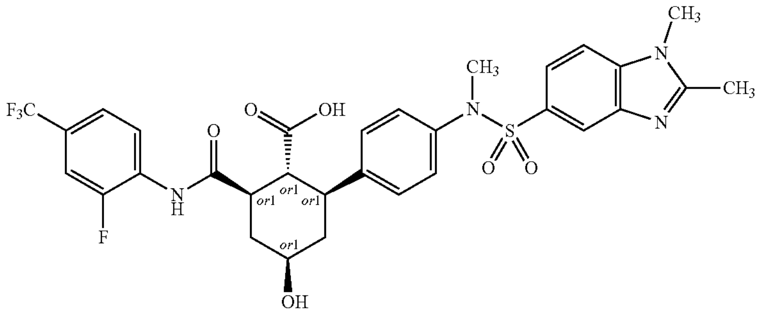

To a mixture of rac-(1R,2R,4R,6S)-2-((2-fluoro-4-(trifluoromethyl)phenyl)carbamoyl)-4-hydroxy-6-(4-(methylamino)phenyl)cyclohexane-1-carboxylic acid Intermediate 11 (35 g, 0.077 mmol) and pyridine (0.019 mL, 0.23 mmol) in dichloromethane (1 mL) at 0° C. was added 1,2-dimethyl-1H-benzo[d]imidazole-5-sulfonyl chloride (37.7 mg, 0.154 mmol). After 1 h, the reaction was quenched with MeOH (1 mL), concentrated and subjected to reverse phase purification (MeCN in $H_2O$, 0.1% ammonium bicarbonate modifier, 0-100% gradient) to afford rac-(1R,2R,4R,6S)-2-((2-fluoro-4-(trifluoromethyl)phenyl)carbamoyl)-4-hydroxy-6-(4-((N,1,2-trimethyl-1H-benzo[d]imidazole)-5-sulfonamido)phenyl)cyclohexane-1-carboxylic acid (35 mg, 0.050 mmol, 65% yield). This material was chirally purified (Column: Chiralpack ID, 250×20 mm, 5 μm; Mobile Phase: 60:40 $CO_2$:[1:1 ACN:IPA]) to give:

Example 144, the first-eluting isomer: rel-(1R,2R,4R,6S)-2-((2-fluoro-4-(trifluoromethyl)phenyl)carbamoyl)-4-hydroxy-6-(4-((N,1,2-trimethyl-1H-benzo[d]imidazole)-5-sulfonamido)phenyl)cyclohexane-1-carboxylic acid, ISOMER 1 (14 mg, 0.021 mmol, 10% yield). $^1$H NMR (400 MHz, DMSO-$d_6$) δ 10.15 (s, 1H), 8.22 (t, J=8.3 Hz, 1H), 7.72 (dd, J=11.0, 1.5 Hz, 1H), 7.63 (d, J=8.5 Hz, 1H), 7.55 (d, J=8.5 Hz, 1H), 7.50 (d, J=1.5 Hz, 1H), 7.28-7.16 (m, 3H), 6.96 (d, J=8.5 Hz, 2H), 4.90 (br s, 1H), 3.78 (s, 3H), 3.73-3.58 (m, 1H), 3.11-3.01 (m, 4H), 2.77-2.64 (m, 2H), 2.56 (s, 3H), 2.16 (d, J=11.5 Hz, 1H), 1.91 (d, J=12.0 Hz, 1H), 1.60-1.37 (m, 2H). ES-LCMS m/z 663.8 [M+H]$^+$.

Example 145, the second-eluting isomer: rel-(1R,2R,4R,6S)-2-((2-fluoro-4-(trifluoromethyl)phenyl)carbamoyl)-4-hydroxy-6-(4-((N,1,2-trimethyl-1H-benzo[d]imidazole)-5-sulfonamido)phenyl)cyclohexane-1-carboxylic acid, ISOMER 2 (12 mg, 0.017 mmol, 33% yield). $^1$H NMR (400 MHz, DMSO-$d_6$) δ 10.15 (s, 1H), 8.22 (t, J=8.3 Hz, 1H), 7.72 (dd, J=11.0, 1.5 Hz, 1H), 7.63 (d, J=8.5 Hz, 1H), 7.55 (d, J=8.5 Hz, 1H), 7.50 (d, J=1.5 Hz, 1H), 7.28-7.16 (m, 3H), 6.96 (d, J=8.5 Hz, 2H), 4.90 (br s, 1H), 3.78 (s, 3H), 3.73-3.58 (m, 1H), 3.11-3.01 (m, 4H), 2.77-2.64 (m, 2H), 2.56 (s, 3H), 2.16 (d, J=11.5 Hz, 1H), 1.91 (d, J=12.0 Hz, 1H), 1.60-1.37 (m, 2H). ES-LCMS m/z 663.2 [M+H]$^+$.

The following compound was synthesized in an analogous manner to the preparation described above (Example 137 and Example 138) using the relevant alkyl halide precursor and Chiral chromatographic resolution. Compound was purified using reverse phase chromatography (MeCN/$H_2O$, basic or acidic modifiers).

| Ex | Structure/Name | $^1$H NMR | LCMS |
|---|---|---|---|
| 146 | 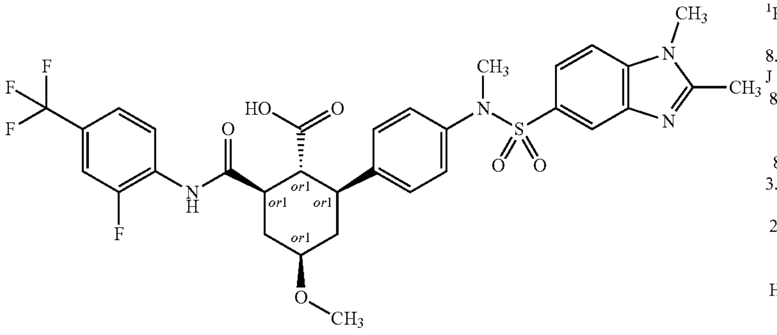 ISOMER 1 rel-(1R,2R,4R,6S)-2-((2-fluoro-4-(trifluoromethyl)phenyl)carbamoyl)-4-methoxy-6-(4-((N,1,2-trimethyl-1H-benzo[d]imidazole)-5-sulfonamido)phenyl)cyclohexane-1-carboxylic acid, Isomer 1 | $^1$H NMR (400 MHz, DMSO-$d_6$) δ 12.10 (br s, 1H), 10.14 (s, 1H), 8.23 (t, J = 8.3 Hz, 1H), 7.72 (dd, J = 11.0, 1.5 Hz, 1H), 7.62 (d, J = 8.5 Hz, 1H), 7.55 (d, J = 8.5 Hz, 1H), 7.49 (d, J = 1.5 Hz, 1H), 7.33-7.13 (m, 3H), 6.97 (d, J = 8.5 Hz, 2H), 3.44-3.34 (m, 1H), 3.32 (s, 3H), 3.29 (s, 3H), 3.05 (s, 3H), 2.86-2.66 (m, 2H), 2.60-2.52 (m, 3H), 2.46-2.23 (m, 1H), 2.21-1.95 (m, 2H), 1.53 (q, J= 11.0 Hz, 1H), 1.41 (q, J = 12.0 Hz, 1H), one proton obscured by solvent peak. | ES-LCMS m/z 677.2 [M + H]$^+$. |

Example 147 rel-(1R,2R,4R,6S)-2-((2-fluoro-4-(trifluoromethyl)phenyl)carbamoyl)-4-(methoxy-d)-6-(4-((N,1,2-trimethyl-1H-benzo[d]imidazole)-5-sulfonamido)phenyl)cyclohexane-1-carboxylic acid, ISOMER 1

ISOMER 1

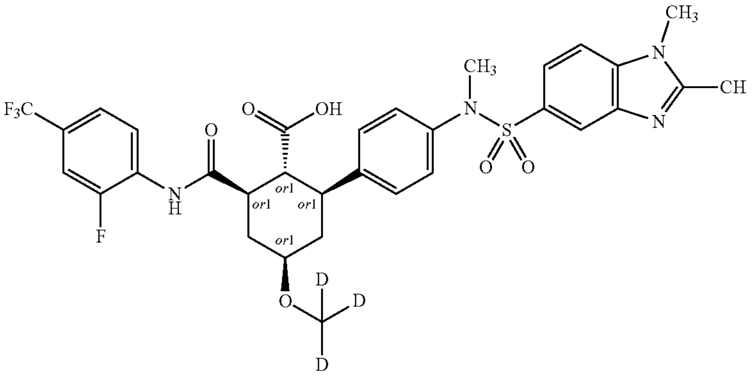

To a mixture of rel-(1R,2R,4R,6S)-2-((2-fluoro-4-(trifluoromethyl)phenyl)carbamoyl)-4-(methoxy-$d_3$)-6-(4-(methylamino)phenyl)cyclohexane-1-carboxylic acid, Isomer 1 Intermediate 12 (25 g, 0.053 mmol) and 1,2-dimethyl-1H-benzo[d]imidazole-5-sulfonyl chloride (19.5 mg, 0.0800 mmol) in dichloromethane (2 mL) at was added pyridine (0.019 mL, 0.23 mmol), dropwise over 1 min. The reaction was stirred at 0° C. for 10 min, then at rt for 1 h. The mixture was concentrated and subjected to reverse phase purification (MeCN in $H_2O$, 10 mM ammonium bicarbonate modifier, 95-98% gradient) to afford rel-(1R,2R,4R,6S)-2-((2-fluoro-4-(trifluoromethyl)phenyl)carbamoyl)-4-(methoxy-$d_3$)-6-(4-((N, 1,2-trim ethyl-1H-benzo[d]imidazole)-5-sulfonamido)phenyl)cyclohexane-1-carboxylic acid, ISOMER 1 (15 mg, 0.021 mmol, 40% yield). H NMR (400 MHz, DMSO-$d_6$) 12.16 (s, 1H), 10.15 (s, 1H), 8.24 (t, J=8.00 Hz, 1H), 7.74 (dd, J=1.60, 11.00 Hz, 1H), 7.64 (d, J=8.80 Hz, 1H), 7.57 (d, J=8.00 Hz, 1H), 7.50 (d, J=1.60 Hz, 1H), 7.24-7.24 (m, 3H), 6.97 (d, J=8.80 Hz, 2H), 3.79 (s, 3H), 3.37 (d, J=7.60 Hz, 1H), 3.06 (s, 4H), 2.76 (d, J=9.20 Hz, 2H), 2.57 (s, 3H), 2.08 (d, J=13.20 Hz, 1H), 1.54 (d, J=11.60 Hz, 1H), 1.41 (d, J=12.40 Hz, 14H), 1.37 (s, 1H). ES-LCMS m/z 680.0 [M+H]$^+$.

The following compound was synthesized in an analogous manner to the preparation described above (Example 137 and Example 138) using the relevant alkyl halide precursor and Chiral chromatographic resolution. Compound was purified using reverse phase chromatography (MeCN/$H_2O$, basic or acidic modifiers).

| Ex | Structure/Name | $^1$H NMR | LCMS |
|---|---|---|---|
| 148 | 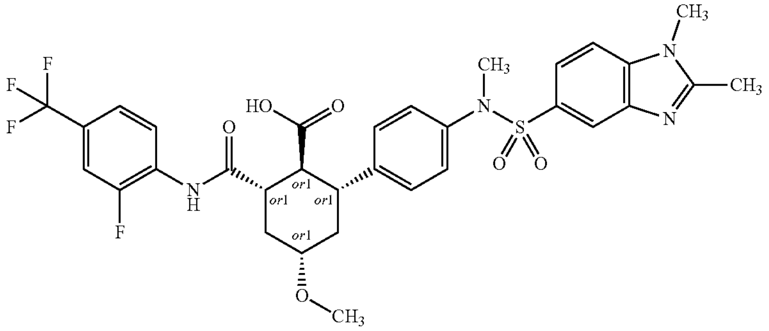 ISOMER 2 rel-(1R,2R,4R,6S)-2-((2-fluoro-4-(trifluoromethyl)phenyl)carbamoyl)-4-methoxy-6-(4-((N,1,2-trimethyl-1H-benzo[d]imidazole)-5-sulfonamido)phenyl)cyclohexane-1-carboxylic acid, Isomer 2 | $^1$H NMR (400 MHz, DMSO-$d_6$) δ 12.10 (br s, 1H), 10.14 (s, 1H), 8.23 (t, J = 8.3 Hz, 1H), 7.72 (dd, J = 11.0, 1.5 Hz, 1H), 7.62 (d, J = 8.5 Hz, 1H), 7.55 (d, J = 8.5 Hz, 1H), 7.49 (d, J = 1.5 Hz, 1H), 7.33-7.13 (m, 3H), 6.97 (d, J = 8.5 Hz, 2H), 3.44-3.34 (m, 1H), 3.32 (s, 3H), 3.29 (s, 3H), 3.05 (s, 3H), 2.86-2.66 (m, 2H), 2.60-2.52 (m, 3H), 2.46-2.23 (m, 1H), 2.21-1.95 (m, 2H), 1.53 (q, J = 11.0 Hz, 1H), 1.41 (q, J = 12.0 Hz, 1H), one proton obscured by solvent peak. | ES-LCMS m/z 677.2 [M + H]$^+$. |

The following compound was synthesized in an analogous manner to the preparation described above (Example 147) using the relevant deuterated intermediate precursor. Compound was purified using reverse phase chromatography (MeCN/$H_2O$, basic or acidic modifiers).

| Ex | Structure/Name | $^1$H NMR | LCMS |
|---|---|---|---|
| 149 | 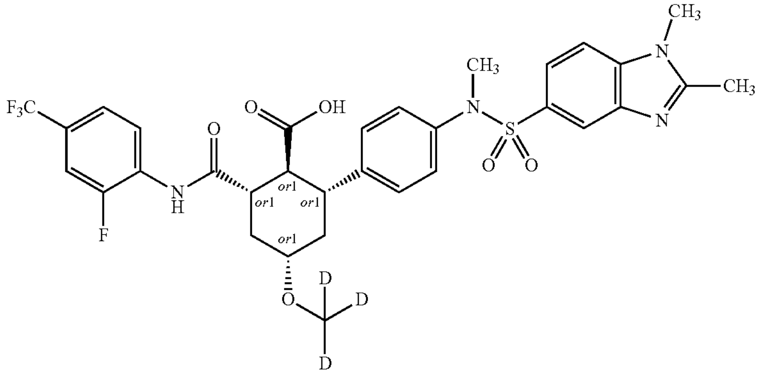 ISOMER 2 rel-(1R,2R,4R,6S)-2-((2-fluoro-4-(trifluoromethyl)phenyl)carbamoyl)-4-methoxy-6-(4-((N,1,2-trimethyl-1H-benzo[d]imidazole)-5-sulfonamido)phenyl)cyclohexane-1-carboxylic acid, Isomer 2 | $^1$H NMR (400 MHz, DMSO-$d_6$) δ 12.16 (s, 1H), 10.15 (s, 1H), 8.24 (t, J = 8.0 Hz, 1H), 7.74 (dd, J = 11.0, 1.6 Hz, 1H), 7.64 (d, J = 8.8 Hz, 1H), 7.57 (d, J = 8.8 Hz, 1H), 7.50 (d, J = 1.2 Hz, 1H), 7.27-7.22 (m, 3H), 6.97 (d, J = 8.4 Hz, 2H), 3.83 (s, 3H), 3.43-3.35 (m, 2H), 3.13 (s, 3H), 2.68 (t, J = 1.6 Hz, 2H), 2.58 (s, 3H), 2.34-2.33 (m, 1H), 2.10-2.07 (m, 1H), 1.56-1.52 (m, 1H), 1.43-1.40 (m, 1H). | ES-LCMS m/z 680.2 [M + H]$^+$. |

The following compounds were synthesized in an analogous manner to the preparation described above (Example 137 and Example 138) using the relevant alkyl halide precursors and Chiral chromatographic resolution. Compounds was purified using reverse phase chromatography (MeCN/$H_2O$, basic or acidic modifiers).

| Ex | Structure/Name | $^1$H NMR | LCMS |
|---|---|---|---|
| 150 | 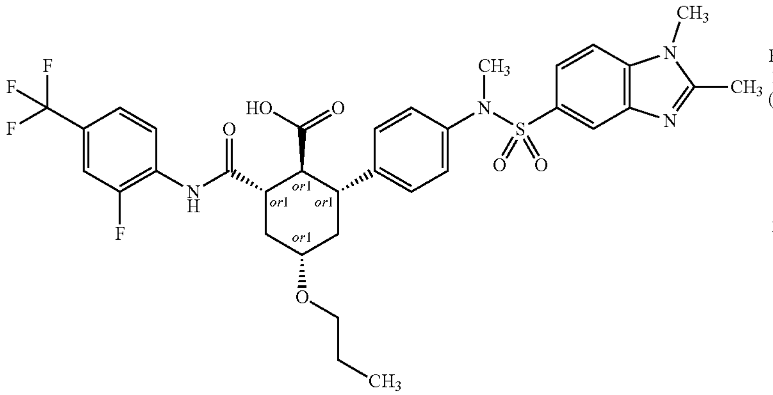 ISOMER 1 rel-(1R,2R,4R,6S)-2-((2-fluoro-4-(trifluoromethyl)phenyl)carbamoyl)-4-propoxy-6-(4-((N,1,2-trimethyl-1H-benzo[d]imidazole)-5-sulfonamido)phenyl)cyclohexane-1-carboxylic acid, ISOMER 1 | $^1$H NMR (400 MHz, DMSO-$d_6$) δ 10.14 (br s, 1H), 8.23 (t, J = 8.3 Hz, 1H), 7.73 (dd, J = 11.0, 2.0 Hz, 1H), 7.63 (d, J = 8.5 Hz, 1H), 7.55 (d, J = 8.5 Hz, 1H), 7.49 (d, J = 1.5 Hz, 1H), 7.35-7.11 (m, 3H), 6.96 (d, J = 8.5 Hz, 2H), 3.78 (s, 2H), 3.52-3.45 (m, 1H), 3.42 (t, J = 6.5 Hz, 2H), 3.12-2.91 (m, 4H), 2.80-2.71 (m, 2H), 2.58-2.55 (m, 2H), 2.33 (dt, J = 3.8, 1.6 Hz, 2H), 2.05 (br d, J = 12.0 Hz, 1H), 1.60-1.36 (m, 4H), 0.86 (t, J = 7.5 Hz, 3H), two protons were obscured by solvent peaks. | ES-LCMS m/z 705.0 [M + H]$^+$. |
| 151 | 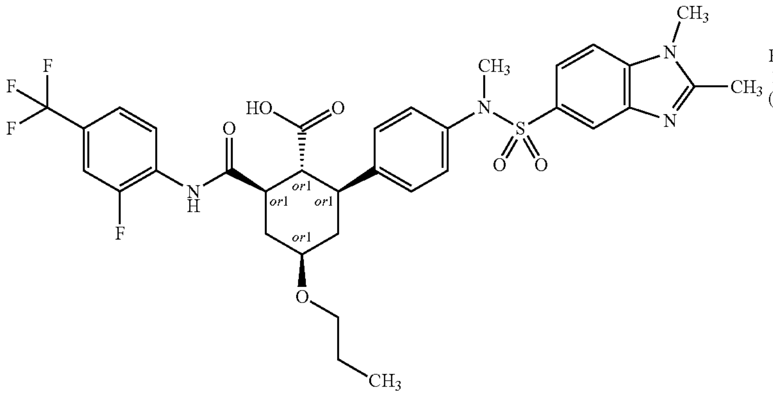 ISOMER 2 rel-(1R,2R,4R,6S)-2-((2-fluoro-4-(trifluoromethyl)phenyl)carbamoyl)-4-propoxy-6-(4-((N,1,2-trimethyl-1H-benzo[d]imidazole)-5-sulfonamido)phenyl)cyclohexane-1-carboxylic acid, ISOMER 2 | $^1$H NMR (400 MHz, DMSO-$d_6$) δ 10.14 (br s, 1H), 8.23 (t, J = 8.3 Hz, 1H), 7.73 (dd, J = 11.0, 2.0 Hz, 1H), 7.63 (d, J = 8.5 Hz, 1H), 7.55 (d, J = 8.5 Hz, 1H), 7.49 (d, J = 1.5 Hz, 1H), 7.35-7.11 (m, 3H), 6.96 (d, J = 8.5 Hz, 2H), 3.78 (s, 2H), 3.52-3.45 (m, 1H), 3.42 (t, J = 6.5 Hz, 2H), 3.12-2.91 (m, 4H), 2.80-2.71 (m, 2H), 2.58-2.55 (m, 2H), 2.33 (dt, J= 3.8, 1.6 Hz, 2H), 2.05 (br d, J = 12.0 Hz, 1H), 1.60-1.36 (m, 4H), 0.86 (t, J = 7.5 Hz, 3H), two protons were obscured by solvent peaks. | ES-LCMS m/z 705.0 [M + H]$^+$. |

Example 152 rel-(1R,2R,4R,6S)-2-((2-fluoro-4-(trifluoromethyl) phenyl)carbamoyl)-4-phenoxy-6-(4-((N,1,2-trimethyl-1H-benzo[d]imidazole)-5-sulfonamido)phenyl) cyclohexane-1-carboxylic acid, ISOMER 1

ISOMER 1

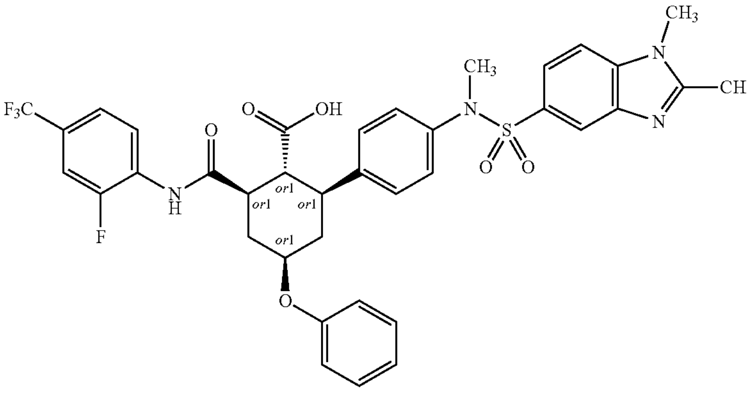

To a mixture of rel-(1R,2R,4R,6S)-2-((2-fluoro-4-(trifluoromethyl)phenyl)carbamoyl)-6-(4-(methylamino)phenyl)-4-phenoxycyclohexane-1-carboxylic acid, ISOMER 2 Intermediate 14 (75 mg, 0.14 mmol) in dichloromethane (5 mL) at 0° C. was added pyridine (0.034 mL, 0.42 mmol) and 1,2-dimethyl-1H-benzo[d]imidazole-5-sulfonyl chloride (69.2 mg, 0.283 mmol). The reaction was stirred for 1 h, then at rt for 1 h. The mixture was quenched with MeOH (2 mL), concentrated and subjected to reverse phase purification (MeCN in $H_2O$, 10 mM ammonium bicarbonate modifier, 10-100% gradient) to afford rel-(1R,2R,4R,6S)-2-((2-fluoro-4-(trifluoromethyl)phenyl)carbamoyl)-4-phenoxy-6-(4-((N,1,2-trimethyl-1H-benzo[d]imidazole)-5-sulfonamido)phenyl)cyclohexane-1-carboxylic acid, ISOMER 1 (98 mg, 0.13 mmol, 92% yield). $^1$H NMR (400 MHz, DMSO-$d_6$) δ 12.20 (br s, 1H), 10.17 (s, 1H), 8.22 (t, J=8.0 Hz, 1H), 7.73 (dd, J=11.0, 1.5 Hz, 1H), 7.62 (d, J=8.5 Hz, 1H), 7.55 (d, J=8.5 Hz, 1H), 7.48 (d, J=1.5 Hz, 1H), 7.36-7.20 (m, 5H), 7.08-6.87 (m, 5H), 4.70-4.45 (m, 1H), 3.77 (s, 3H), 3.25-3.13 (m, 1H), 3.05 (s, 3H), 3.02-2.91 (m, 1H), 2.90-2.80 (m, 1H), 2.56 (s, 3H), 2.45 (d, J=2.0 Hz, 1H), 2.14 (d, J=12.5 Hz, 1H), 1.91-1.77 (m, 1H), 1.73-1.60 (m, 1H). ES-LCMS m/z 737.0 [M−H]$^-$.

The following compounds were synthesized in an analogous manner to the preparation described above (Example 152) using Intermediate 13 (Example 153) or Intermediate 15 (Example 154 and Example 155) in the sequence, as appropriate. Compounds were purified using reverse phase chromatography (MeCN/$H_2O$, basic or acidic modifiers).

| Ex | Structure/Name | $^1$H NMR | LCMS |
|---|---|---|---|
| 153 | 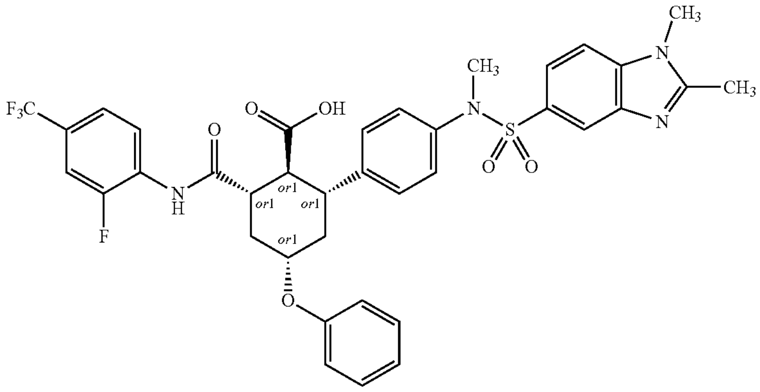 ISOMER 2 rel-(1R,2R,4R,6S)-2-((2-fluoro-4-(trifluoromethyl)phenyl)carbamoyl)-4-phenoxy-6-(4-((N,1,2-trimethyl-1H-benzo[d]imidazole)-5-sulfonamido)phenyl)cyclohexane-1- | $^1$H NMR (400 MHz, DMSO-$d_6$) δ 12.21 (s, 1H), 10.16 (s, 1H), 8.23 (t, J = 8.00 Hz, 1H), 7.74 (dd, J = 1.20, 11.00 Hz, 1H), 7.63 (d, J = 8.80 Hz, 1H), 7.56 (d, J = 8.80 Hz, 1H), 7.49 (d, J = 1.20 Hz, 1H), 7.32-7.23 (m, 5H), 7.04 (d, J = 8.00 Hz, 2H), 6.99-6.92 (m, 3H), 4.57-4.55 (m, 1H), 3.78 (s, 3H), 3.34-3.24 (m, 1H), 3.18 (s, 3H), 2.97-2.93 (m, 1H), 2.86 (t, J = 11.20 Hz, 1H),2.57 (s, 3H), 2.50-2.43 (m, 1H), 2.33-2.14 (m, 1H), 1.85-1.83 (m, 1H), 1.70-1.67 (m, 1H) | ES-LCMS m/z 739.0 [M + H]$^+$. |

-continued

| Ex | Structure/Name | $^1$H NMR | LCMS |
|---|---|---|---|
| | carboxylic acid, ISOMER 2 | | |
| 154 | 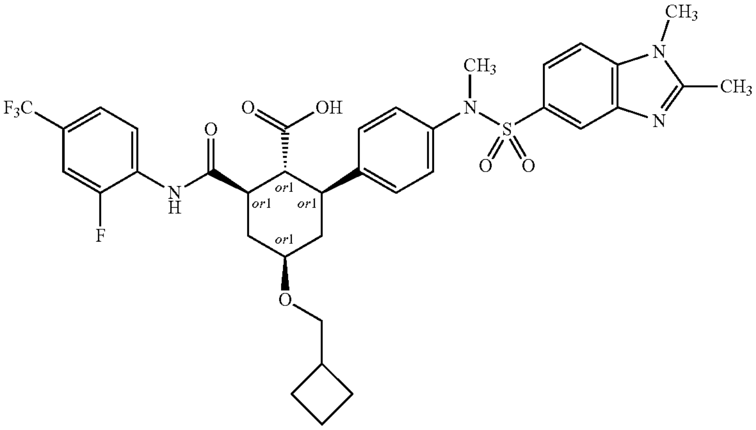 ISOMER 1 rel-(1R,2R,4R,6S)-4-(cyclobutylmethoxy)-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylic acid, ISOMER 1 | $^1$H NMR (400 MHz, DMSO-$d_6$) δ 12.14 (br s, 1H), 10.13 (s, 1H), 8.23 (t, J = 8.0 Hz, 1H), 7.78-7.68 (m, 1H), 7.63 (d, J = 8.5 Hz, 1H), 7.56 (br d, J = 8.5 Hz, 1H), 7.48 (d, J = 1.5 Hz, 1H), 7.34-7.12 (m, 3H), 6.96 (d, J = 8.5 Hz, 2H), 3.78 (s, 3H), 3.54-3.36 (m, 3H), 3.10-2.98 (m, 4H), 2.80-2.70 (m, 2H), 2.60-2.52 (m, 3H), 2.48-2.42 (m, 1H), 2.39-2.28 (m, 1H), 2.08-1.91 (m, 3H), 1.88-1.75 (m, 2H), 1.72-1.60 (m, 2H), 1.56 (br d, J = 11.5 Hz, 1H), 1.42 (q, J = 11.7 Hz, 1H) | ES-LCMS m/z 731.2 [M + H]$^+$. |
| 155 | 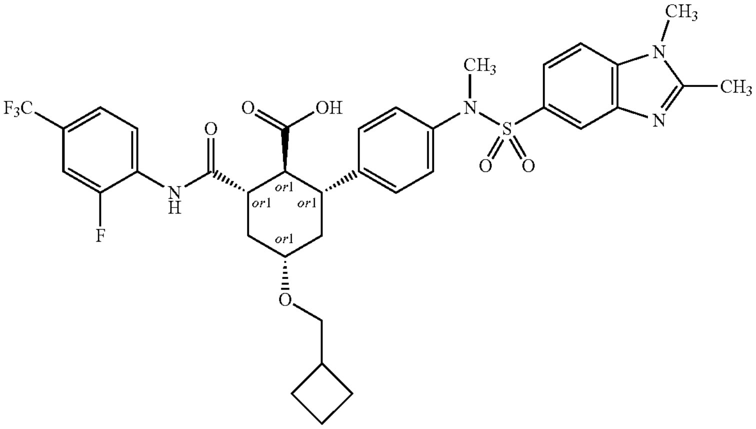 ISOMER 2 rel-(1R,2R,4R,6S)-4-(cyclobutylmethoxy)-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylic acid, ISOMER 2 | $^1$H NMR (400 MHz, DMSO-$d_6$) δ 12.14 (br s, 1H), 10.13 (s, 1H), 8.23 (t, J = 8.0 Hz, 1H), 7.78-7.68 (m, 1H), 7.63 (d, J = 8.5 Hz, 1H), 7.56 (br d, J = 8.5 Hz, 1H), 7.48 (d, J = 1.5 Hz, 1H), 7.34-7.12 (m, 3H), 6.96 (d, J = 8.5 Hz, 2H), 3.78 (s, 3H), 3.54-3.36 (m, 3H), 3.10-2.98 (m, 4H), 2.80-2.70 (m, 2H), 2.60-2.52 (m, 3H), 2.48-2.42 (m, 1H), 2.39-2.28 (m, 1H), 2.08-1.91 (m, 3H), 1.88-1.75 (m, 2H), 1.72-1.60 (m, 2H), 1.56 (br d, J = 11.5 Hz, 1H), 1.42 (q, J = 11.7 Hz, 1H) | ES-LCMS m/z 731.2 [M + H]$^+$. |

The following compound was synthesized in an analogous manner to the preparation described above (Example 139) using the relevant arylamine precursor.

| Ex | Structure/Name | $^1H$ NMR | LCMS |
|---|---|---|---|
| 156 | 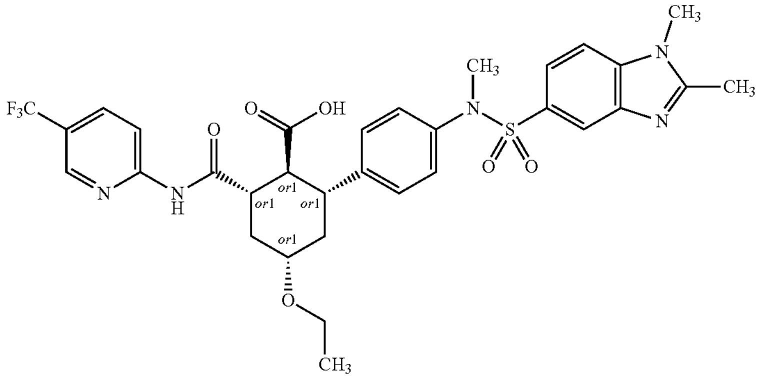 ISOMER 2 rel-(1R,2R,4R,6S)-4-ethoxy-2-((5-(trifluoromethyl)pyridin-2-yl)carbamoyl)-6-(4-((N,1,2-trimethyl-1H-benzo[d]imidazole)-5-sulfonamido)phenyl)cyclohexane-1-carboxylic acid, ISOMER 2 | $^1H$ NMR (400 MHz, DMSO-$d_6$) δ 12.12 (s, 1H), 11.02 (s, 1H), 8.72 (m, 1H), 8.25 (d, J = 8.80 Hz, 1H), 8.17 (dd, J = 2.40, 8.80 Hz, 1H), 7.64 (s, 1H), 7.24 (m, 3H), 6.96 (d, J = 4.00 Hz, 1H), 3.82 (s, 3H), 3.4-3.46 (m, 4H), 3.03 (m, 4H), 2.67 (m, 2H), 2.60 (m, 4H), 2.04 (d, J = 11.60 Hz, 1H), 1.58-1.55 (m, 1H), 1.42 (q, J = 12.40 Hz, 1H), 1.11 (t, J = −6.80 Hz, 3H) | ES-LCMS m/z 674.0 $[M + H]^+$. |

Example 157 and Example 158 rel-(3aR,4S,5S,6R,7aS)-4-((2-fluoro-4-(trifluoromethyl)phenyl)carbamoyl)-6-(4-((N,1,2-trimethyl-1H-benzo[d]imidazole)-5-sulfonamido)phenyl)octahydrobenzofuran-5-carboxylic acid, ISOMER 1 AND ISOMER 2

ISOMER 1 and ISOMER 2

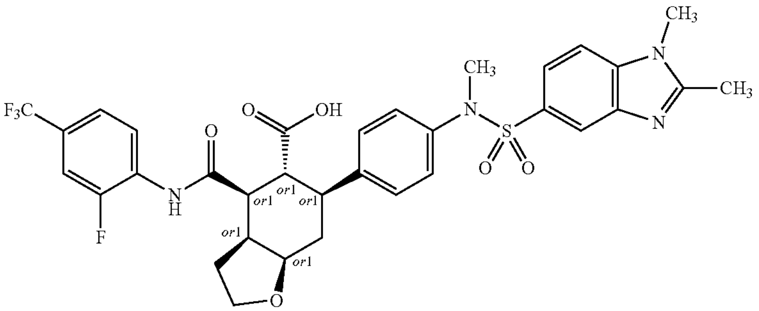

To a mixture of rac-methyl (3aR,4S,5S,6R,7aS)-4-((2-fluoro-4-(trifluoromethyl)phenyl)carbamoyl)-6-(4-((N,1,2-trimethyl-1H-benzo[d]imidazole)-5-sulfonamido)phenyl) octahydrobenzofuran-5-carboxylate Intermediate 16 (250 mg, 0.36 mmol) in dichloromethane (10 mL) at 0° C. was added tribromoborane (1M in DCM, 3.6 mL, 3.6 mmol). After 2 h the reaction was quenched with ice water (1 mL), concentrated and subjected to reverse phase purification (MeCN in $H_2O$, 0.1% ammonium bicarbonate modifier, 0-100% gradient) to afford rac-(3aR,4S,5S,6R,7aS)-4-((2-fluoro-4-(trifluoromethyl)phenyl)carbamoyl)-6-(4-((N,1,2-trimethyl-1H-benzo[d]imidazole)-5-sulfonamido)phenyl) octahydrobenzofuran-5-carboxylic (125 mg, 0.143 mmol, 40.0% yield) as an off-white solid. This material was chirally purified (Column: YMC Amylose-SA, 250×20 mm, 5 μm; Mobile Phase: 1:1 $CO_2$:IPA) to give:

Example 157, the second-eluting isomer: rel-(3aR,4S,5S,6R,7aS)-4-((2-fluoro-4-(trifluoromethyl)phenyl)carbamoyl)-6-(4-((N,1,2-trimethyl-1H-benzo[d]imidazole)-5-sulfonamido)phenyl)octahydrobenzofuran-5-carboxylic acid, ISOMER 1 (39 mg, 0.056 mmol, 24% yield). $^1H$ NMR (400 MHz, DMSO-$d_6$) δ 12.15 (br s, 1H), 10.18 (s, 1H), 8.19 (t, J=8.1 Hz, 1H), 7.74 (dd, J=11.0, 1.6 Hz, 1H), 7.63 (d, J=8.4 Hz, 1H), 7.57 (br d, J=8.4 Hz, 1H), 7.46 (d, J=1.5 Hz, 1H), 7.31-7.18 (m, 3H), 6.96 (d, J=8.6 Hz, 2H), 4.24-4.11 (m, 1H), 3.95 (br t, J=8.0 Hz, 1H), 3.80-3.68 (m, 4H), 3.49 (dd, J=11.4, 5.4 Hz, 1H), 3.06 (s, 3H), 2.96 (t, J=11.4 Hz, 1H), 2.76 (td, J=12.4, 6.6 Hz, 1H), 2.69-2.62 (m, 1H), 2.57 (s, 3H), 2.23-2.09 (m, 1H), 1.82-1.45 (m, 3H). ES-LCMS m/z 687.0 $[M-H]^-$.

Example 158, the first-eluting isomer: rel-(3aR,4S,5S,6R,7aS)-4-((2-fluoro-4-(trifluoromethyl)phenyl)carbamoyl)-6-(4-((N,1,2-trimethyl-1H-benzo[d]imidazole)-5-sulfonamido)phenyl)octahydrobenzofuran-5-carboxylic acid, ISOMER 2 (37 mg, 0.050 mmol, 23% yield). $^1H$ NMR (400

MHz, DMSO-$d_6$) δ 12.15 (br s, 1H), 10.19 (s, 1H), 8.19 (t, J=8.1 Hz, 1H), 7.74 (dd, J=11.0, 1.5 Hz, 1H), 7.63 (d, J=8.5 Hz, 1H), 7.57 (br d, J=7.4 Hz, 1H), 7.46 (d, J=1.4 Hz, 1H), 7.31-7.18 (m, 3H), 6.96 (d, J=8.5 Hz, 2H), 4.17 (dt, J=10.1, 6.2 Hz, 1H), 4.02-3.87 (m, 1H), 3.79-3.70 (m, 4H), 3.49 (dd, J=11.5, 5.4 Hz, 1H), 3.06 (s, 3H), 2.96 (t, J=11.5 Hz, 1H), 2.83-2.71 (m, 1H), 2.69-2.62 (m, 1H), 2.57 (s, 3H), 2.25-2.10 (m, 1H), 1.83-1.57 (m, 3H). LCMS m/z 687.1 $[M-H]^-$.

The following compound was synthesized in an analogous manner to the preparation described above (Example 137 and Example 138) using the relevant alkyl halide precursor and Chiral chromatographic resolution.

| Ex | Structure/Name | $^1$H NMR | LCMS |
|---|---|---|---|
| 159 | 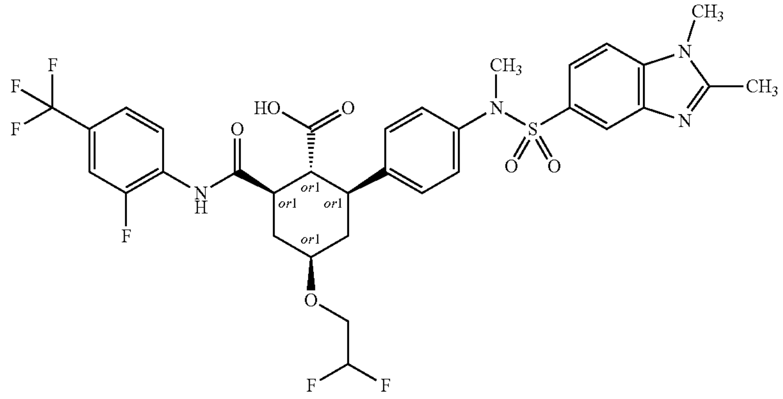 ISOMER 2 rel-(1R,2R,4R,6S)-4-(2,2-difluoroethoxy)-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylic acid, Isomer 2 | $^1$H NMR (400 MHz, DMSO-$d_6$) δ 10.23 (br s, 1H), 8.24 (t, J = 8.0 Hz, 1H), 7.75-7.71 (m, 1H), 7.63 (d, J = 8.5 Hz, 1H), 7.56 (d, J = 9.0 Hz, 1H), 7.50 (d, J = 1.5 Hz, 1H), 7.26-7.20 (m, 3H), 6.96 (d, J = 8.5 Hz, 2H), 6.27-5.96 (m, 1H), 3.80-3.71 (m, 5H), 3.67-3.58 (m, 1H), 3.05 (s, 3H), 3.03-2.98 (m, 1H), 2.78-2.71 (m, 2H), 2.56 (s, 3H), 2.38-2.33 (m, 1H), 2.08 (d, J = 11.0 Hz, 1H), 1.64-1.43 (m, 2H) | ES-LCMS m/z 727.2 $[M + H]^+$. |

Example 160 rel-(1R,2R,6S)-2-((2-fluoro-4-(trifluoromethyl)phenyl)carbamoyl)-6-(5-((N,1,2-trimethyl-1H-benzo[d]imidazole)-5-sulfonamido)pyridin-2-yl)cyclohexane-1-carboxylic acid, ISOMER 2

ISOMER 2

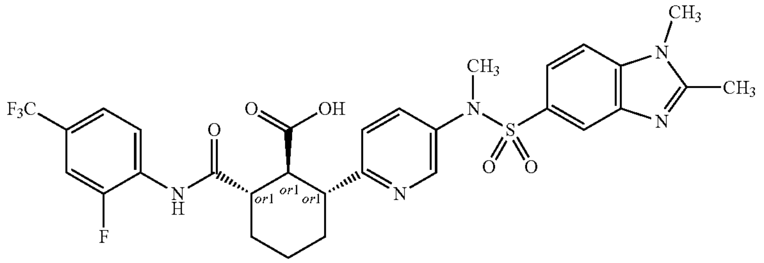

To a mixture of rel-(1R,2R,6S)-2-((2-fluoro-4-(trifluoromethyl)phenyl)carbamoyl)-6-(5-(methylamino)pyridin-2-yl)cyclohexane-1-carboxylic acid ISOMER 2 Intermediate 18 (25 mg, 0.057 mmol) and pyridine (0.023 mL, 0.28 mmol) in dichloromethane (5 mL) at 0° C. was added 1,2-dimethyl-1H-benzo[d]imidazole-5-sulfonyl chloride (16.7 mg, 0.0680 mmol). The reaction was stirred at rt for 16 h, concentrated and subjected to reverse phase purification (0-100% MeCN in $H_2O$, with 0.1% Formic acid modifier) to afford rel-(1R,2R,6S)-2-((2-fluoro-4-(trifluoromethyl)phenyl)carbamoyl)-6-(5-((N,1,2-trimethyl-1H-benzo[d]imidazole)-5-sulfonamido)pyridin-2-yl)cyclohexane-1-carboxylic acid ISOMER 2 (25 mg, 0.038 mmol, 67% yield) as an off-white solid. $^1$H NMR (400 MHz, DMSO-$d_6$) δ 12.05 (br s, 1H), 10.12 (s, 1H), 8.26-8.22 (m, 2H), 7.74 (d, J=1.6 Hz, 1H), 7.65 (d, J=8.4 Hz, 1H), 7.58-7.54 (m, 2H), 7.35 (dd, J=8.4, 2.8 Hz, 1H), 7.25-7.20 (m, 2H), 3.79 (s, 3H), 3.10 (s, 3H), 2.98-2.93 (m, 3H), 2.52 (s, 3H), 2.03 (d, J=7.2 Hz, 1H), 1.88-1.76 (m, 2H), 1.68-1.65 (m, 1H), 1.52-1.47 (m, 2H). ES-LCMS m/z 646.2 [M−H]$^-$.

The following compound was synthesized in an analogous manner to the preparation described above (Example 160) using Intermediate 17:

| Ex | Structure/Name | $^1$H NMR | LCMS |
|---|---|---|---|
| 161 | 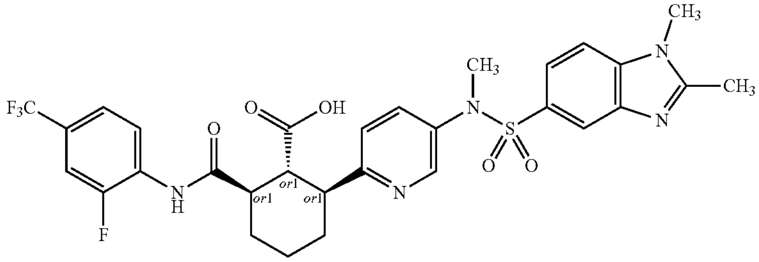 [SMILES: Cc1nc2cc(S(=O)(=O)N(C)c3ccc([C@H]4CCC[C@@H](C(=O)Nc5ccc(C(F)(F)F)cc5F)[C@@H]4C(=O)O)nc3)ccc2n1C] ISOMER 1 rel-(1R,2R,6S)-2-((2-fluoro-4-(trifluoromethyl)phenyl)carbamoyl)-6-(5-((N,1,2-trimethyl-1H-benzo[d]imidazole)-5-sulfonamido)pyridin-2-yl)cyclohexane-1-carboxylic acid, ISOMER 1 | $^1$H NMR (400 MHz, DMSO-$d_6$) δ 12.05 (br s, 1H), 10.12 (s, 1H), 8.26-8.22 (m, 2H), 7.74 (d, J = 1.6 Hz, 1H), 7.65 (d, J = 8.4 Hz, 1H), 7.58-7.54 (m, 2H), 7.35 (dd, J = 8.4, 2.4 Hz, 1H), 7.25-7.20 (m, 2H), 3.79 (s, 3H), 3.10 (s, 3H), 2.98-2.92 (m, 3H), 2.03 (d, J = 6.8 Hz, 1H), 1.90-1.78 (m, 2H), 1.89-1.78 (m, 1H), 1.68-1.62 (m, 1H), 1.55-1.47 (m, 2H). | ES-LCMS m/z 646.0 [M − H]$^-$. |

Example 162 and Example 163 rel-(1R,2S,6R)-2-(3-cyano-4-((N,1,2-trimethyl-1H-benzo[d]imidazole)-5-sulfonamido)phenyl)-6-((2-fluoro-4-(trifluoromethyl)phenyl)carbamoyl)cyclohexane-1-carboxylic acid, ISOMER 1 AND ISOMER 2

ISOMER 1 and ISOMER 2

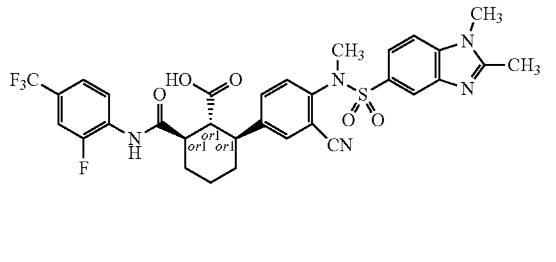

To a mixture of rac-(1R,2S,6R)-2-(3-carbamoyl-4-((N,1,2-trimethyl-1H-benzo[d]imidazole)-5-sulfonamido)phenyl)-6-((2-fluoro-4-(trifluoromethyl)phenyl)carbamoyl)cyclohexane-1-carboxylic acid Intermediate 19 (0.050 g, 0.072 mmol) in acetonitrile (2 mL) and water (1 mL) at 20° C. was added palladium(II) chloride (12.9 mg, 0.0700 mmol). The reaction was stirred at 70° C. for 1 h, concentrated under reduced pressure and subjected to reverse phase purification (0-100% MeCN in $H_2O$, 0.1% ammonium bicarbonate modifier) to afford rac-(1R,2S,6R)-2-(3-cyano-4-((N,1,2-trimethyl-1H-benzo[d]imidazole)-5-sulfonamido)phenyl)-6-((2-fluoro-4-(trifluoromethyl)phenyl)carbamoyl)cyclohexane-1-carboxylic acid (38 mg, 0.056 mmol, 77% yield) as an off-white solid. The racemic compound was separated by Chiral Prep SFC (Column: YMC Cellulose-SZ 250×30 mm, 5 μm; 75:25 $CO_2$: Methanol) to afford: Example 162, the first-eluting peak: rel-(1R,2S,6R)-2-(3-cyano-4-((N,1,2-trimethyl-1H-benzo[d]imidazole)-5-sulfonamido)phenyl)-6-((2-fluoro-4-(trifluoromethyl)phenyl)carbamoyl)cyclohexane-1-carboxylic acid ISOMER 1 (8.1 mg, 0.012 mmol, 23% yield) as a white solid. $^1$H NMR (400 MHz, DMSO-$d_6$) δ 12.12 (br s, 1H), 10.13 (s, 1H), 8.22 (t, J=8.3 Hz, 1H), 7.86 (d, J=2.0 Hz, 1H), 7.76-7.70 (m, 3H), 7.58-7.51 (m, 2H), 7.38 (dd, J=8.5, 1.5 Hz, 1H), 6.86 (d, J=8.5 Hz, 1H), 3.81 (s, 3H), 3.09 (s, 3H), 3.04-2.95 (m, 1H), 2.90-2.74 (i, 2H), 2.59 (7, 3H), 2.02 (br dd, J=7.3, 2.3 Hz, 1H), 1.91-1.84 (m, 1H), 1.80-1.72 (m, 1H), 1.68-1.47 (n, 3H). ES-LCMS m/z 671.8 [M+H]7.

Example 163, the second-eluting peak: rel-(1R,2S,6R)-2-(3-cyano-4-((N,1,2-trimethyl-1H-benzo[d]imidazole)-5-sulfonamido)phenyl)-6-((2-fluoro-4-(trifluoromethyl)phenyl)carbamoyl)cyclohexane-1-carboxyl c acid ISOMER 2 (9.35 mg, 0.0140 mmol, 27.0% yield) as a white solid. $^1$H NMR (400 MHz, DMSO-$d_6$) b 12.10 (br s, 1H), 10.13 (s, 1H), 8.21 (t, J=8.3 Hz, 1H), 7.86 (d, J=2.0 Hz, 1H), 7.76-7.70 (m, 3H), 7.58-7.51 (m, 2H), 7.38 (dd, J=8.5, 1.5 Hz, 1H), 6.85 (d, J=8.5 Hz, 1H), 3.81 (z, 3H), 3.09 (s, 3H), 3.04-2.95 (m, 1H), 2.90-2.74 (m, 2H), 2.59 ((, 3H), 2.02 (br dd, J=7.3, 2.3 Hz, 1H), 1.91-1.84 (m, 1H), 1.80-1.72 (m, 1H), 1.68-1.47 (3, 3H). ES-LCMS m/z 671.8 [M+H]$^+$.

The following compounds were synthesized in an analogous manner to the preparation described above (intermediate 19), substituting 5-bromopyrazine-2-carbaldehyde for 2-bromo-5-formylbenzonitrile and utilizing appropriate chiral chromatographic resolution.

| Ex | Structure/Name | $^1$H NMR | LCMS |
|---|---|---|---|
| 164 | 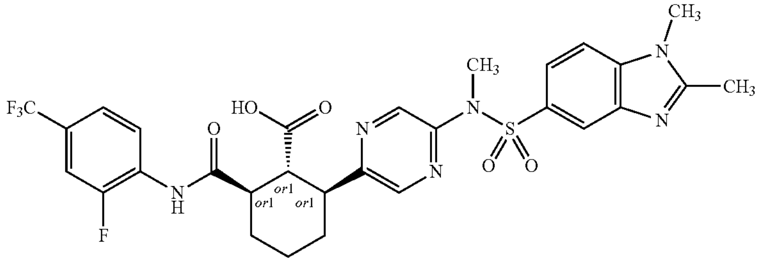 [SMILES: Cc1nc2cc(S(=O)(=O)N(C)c3cnc([C@H]4CCC[C@@H](C(=O)Nc5ccc(C(F)(F)F)cc5F)[C@@H]4C(=O)O)cn3)ccc2n1C] ISOMER 1 rel-(1R,2R,6S)-2-((2-fluoro-4-(trifluoromethyl)phenyl)carbamoyl)-6-(5-((N,1,2-trimethyl-1H-benzo[d]imidazole)-5-sulfonamido)pyrazin-2-yl)cyclohexane-1-carboxylic acid, Isomer 1 | $^1$H NMR (400 MHz, DMSO-$d_6$) δ 12.11 (br s, 1H), 10.18 (br s, 1H), 8.80 (d, J = 1.5 Hz, 1H), 8.28-8.21 (m, 2H), 7.72 (dd, J = 11.3, 1.8 Hz, 1H), 7.66-7.61 (m, 2H), 7.55 (d, J = 9.0 Hz, 1H), 7.28 (dd, J = 8.5, 1.5 Hz, 1H), 3.77 (s, 3H), 3.12 (s, 3H), 3.08-2.89 (m, 3H), 2.56 (s, 3H), 2.06 (d, J = 7.5 Hz, 1H), 1.96-1.88 (m, 1H), 1.86-1.66 (m, 2H), 1.59-1.42 (m, 2H) | ES-LCMS m/z 648.8 [M + H]$^+$. |
| 165 | 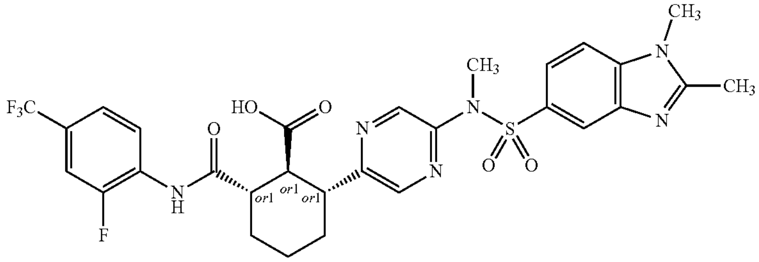 [SMILES: Cc1nc2cc(S(=O)(=O)N(C)c3cnc([C@@H]4CCC[C@H](C(=O)Nc5ccc(C(F)(F)F)cc5F)[C@H]4C(=O)O)cn3)ccc2n1C] ISOMER 2 rel-(1R,2R,6S)-2-((2-fluoro-4-(trifluoromethyl)phenyl)carbamoyl)-6-(5-((N,1,2-trimethyl-1H-benzo[d]imidazole)-5-sulfonamido)pyrazin-2-yl)cyclohexane-1-carboxylic acid, Isomer 2 | $^1$H NMR (400 MHz, DMSO-$d_6$) δ 12.13 (br s, 1H), 10.18 (br s, 1H), 8.81 (d, J = 1.0 Hz, 1H), 8.28-8.21 (m, 2H), 7.72 (br d, J = 11.0 Hz, 1H), 7.66-7.61 (m, 2H), 7.55 (br d, J = 9.0 Hz, 1H), 7.28 (dd, J = 8.5, 2.0 Hz, 1H), 3.77 (s, 3H), 3.12 (s, 3H), 3.07-2.92 (m, 3H), 2.56 (s, 3H), 2.05 (br d, J = 6.0 Hz, 1H), 1.90 (br d, J = 3.5 Hz, 1H), 1.84-1.67 (m, 2H), 1.58-1.43 (m, 2H) | ES-LCMS m/z 648.8 [M + H]$^+$. |

Example 166

(1R,2S,6R)-2-(3-bromo-4-((N,1,2-trimethyl-1H-benzo[d]imidazole)-5-sulfonamido)phenyl)-6-((2-fluoro-4-(trifluoromethyl)phenyl)carbamoyl)cyclohexane-1-carboxylic acid

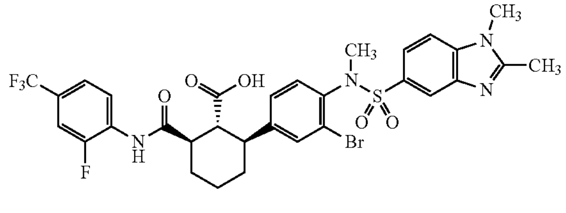 [SMILES: Cc1nc2cc(S(=O)(=O)N(C)c3ccc([C@H]4CCC[C@@H](C(=O)Nc5ccc(C(F)(F)F)cc5F)[C@@H]4C(=O)O)cc3Br)ccc2n1C]

To a mixture of (1R,2S,6R)-2-(3-bromo-4-(methylamino)phenyl)-6-((2-fluoro-4-(trifluoromethyl)phenyl)carbamoyl)cyclohexane-1-carboxylic acid Intermediate 20 (0.120 g, 0.232 mmol) and pyridine (55.0 mg, 0.696 mmol) in dichloromethane (1.2 mL) at 0° C. was added 1,2-dimethyl-1H-benzo[d]imidazole-5-sulfonyl chloride (227 mg, 0.928 mmol). The reaction was stirred at rt for 1 h, concentrated and subjected to reverse phase purification (0-100% MeCN in $H_2O$, with 0.1% formic acid modifier) to afford (1R,2S,6R)-2-(3-bromo-4-((N,1,2-trimethyl-1H-benzo[d]imidazole)-5-sulfonamido)phenyl)-6-((2-fluoro-4-(trifluoromethyl)phenyl)carbamoyl)cyclohexane-1-carboxylic acid (97 mg, 0.13 mmol, 55% yield) as an off-white solid. $^1$H NMR (400 MHz, DMSO-$d_6$) δ 10.11 (s, 1H), 8.21 (t, J=8.40 Hz, 1H), 7.85 (s, 1H), 7.75-7.71 (m, 2H), 7.63 (d, J=2.00 Hz, 1H), 7.55 (d, J=8.40 Hz, 2H), 7.25 (dd, J=1.60, 8.20 Hz, 1H), 6.83 (d, J=8.40 Hz, 1H), 3.82 (d, J=3.60 Hz, 3H), 3.04 (t, J=14.40 Hz, 3H), 2.97 (t, J=3.60 Hz, 1H), 2.85 (dd, J=10.80, 24.40 Hz, 1H), 2.76-2.67 (m, 1H), 2.60 (d, J=2.80 Hz, 3H), 2.01 (d, J=9.60 Hz, 1H), 1.87 (d, J=8.80 Hz, 1H), 1.77 (d, J=12.40 Hz, 1H), 1.61-1.48 (m, 3H). ES-LCMS m/z 724.8 [M−H]$^-$.

Example 167

(1R,2R,6S)—2-((2-fluoro-4-(trifluoromethyl)phenyl)carbamoyl)-6-(3-(3-hydroxy-3-methylbut-1-yn-1-yl)-4-((N,1,2-trimethyl-1H-benzo[d]imidazole)-5-sulfonamido)phenyl)cyclohexane-1-carboxylic acid

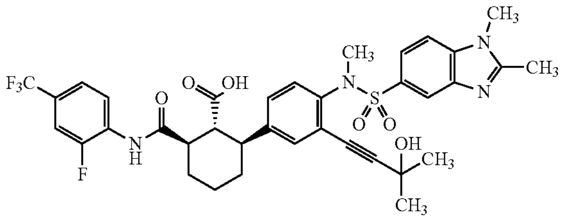 [SMILES: Cc1nc2cc(S(=O)(=O)N(C)c3ccc([C@H]4CCC[C@@H](C(=O)Nc5ccc(C(F)(F)F)cc5F)[C@@H]4C(=O)O)cc3C#CC(C)(C)O)ccc2n1C]

To a mixture of (1R,2S,6R)-2-(3-bromo-4-((N,1,2-trimethyl-1H-benzo[d]imidazole)-5-sulfonamido)phenyl)-6-((2-fluoro-4-(trifluoromethyl)phenyl)carbamoyl)cyclohexane-1-carboxylic acid Example 166 (0.080 g, 0.11 mmol), cesium carbonate (93 mg, 0.29 mmol) and XPhos (1.58 mg, 3.31 μmol) in dioxane (6.0 mL) (degassed for 30 min) was added $Pd(CH_3CN)_2Cl_2$ (0.286 mg, 1.10 μmol), followed by a solution of 2-methylbut-3-yn-2-ol (23.2 mg, 0.276 mmol) in dioxane (2.00 mL). The reaction was stirred at 90° C. for 16 h, filtered through Celite, concentrated and subjected to reverse phase purification (0-100% MeCN in $H_2O$, 10 nM ammonium bicarbonate) to afford (1R,2R,6S)-2-((2-fluoro-4-(trifluoromethyl)phenyl)carbamoyl)-6-(3-(3-hydroxy-3-methylbut-1-yn-1-yl)-4-((N,1,2-trimethyl-1H-benzo[d]imidazole)-5-sulfonamido)phenyl)cyclohexane-1-carboxylic acid (13 mg, 0.018 mmol, 16% yield) as a white solid. $^1H$ NMR (400 MHz, DMSO-$d_6$) δ 12.00 (s, 1H), 10.12 (s, 1H), 8.22 (t, J=8.00 Hz, 1H), 7.83 (d, J=1.60 Hz, 1H), 7.73-7.67 (m, 2H), 7.56 (d, J=8.40 Hz, 1H), 7.49 (dd, J=1.60, 8.40 Hz, 1H), 7.29-7.25 (m, 2H), 7.07 (d, J=8.40 Hz, 1H), 5.33 (s, 1H), 3.80 (s, 3H), 3.14 (s, 3H), 2.98 (t, J=11.20 Hz, 1H), 2.83-2.74 (m, 1H), 2.72-2.67 (m, 1H), 2.59 (s, 3H), 2.01 (d, J=10.00 Hz, 1H), 1.88 (d, J=8.00 Hz, 1H), 1.76 (d, J=9.20 Hz, 1H), 1.64-1.54 (m, 3H), 1.24 (d, J=2.00 Hz, 6H). ES-LCMS m/z 729.2 $[M-H]^-$.

The following compounds were synthesized in an analogous manner to the preparation described above (Example 83 and Example 84) using the relevant arylamine precursors. Compounds were purified using reverse phase chromatography (MeCN/$H_2O$, basic or acidic modifiers) and resolution on a Chiral column.

| Ex | Structure/Name | $^1H$ NMR | LCMS |
|---|---|---|---|
| 168 | 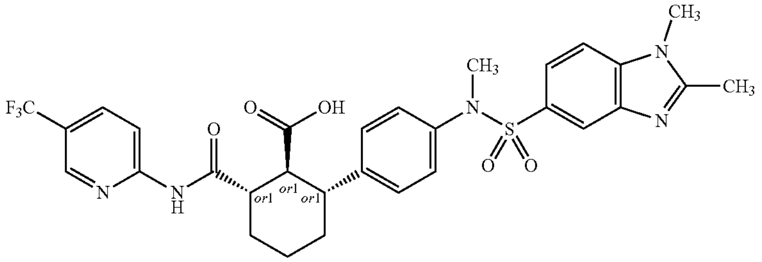 [SMILES: Cc1nc2cc(S(=O)(=O)N(C)c3ccc([C@@H]4CCC[C@H](C(=O)Nc5ccc(C(F)(F)F)cn5)[C@H]4C(=O)O)cc3)ccc2n1C] ISOMER 1<br>rel-(1R,2R,6S)-2-((5-(trifluoromethyl)pyridin-2-yl)carbamoyl)-6-(4-((N,1,2-trimethyl-1H-benzo[d]imidazole)-5-sulfonamido)phenyl)cyclohexane-1-carboxylic acid, ISOMER 1 | $^1H$ NMR (400 MHz, DMSO-$d_6$) δ 12.00 (br, s, 1H), 11.00 (s, 1H), 8.71 (d, J = 1.60 Hz, 1H), 8.26 (d, J = 9.20 Hz, 1H), 8.16 (d, J = 6.80 Hz, 1H), 7.63 (d, J = 8.40 Hz, 1H), 7.52 (d, J = 1.20 Hz, 1H), 7.25 (d, J = 6.80 Hz, 1H), 7.20 (d, J = 8.40 Hz, 2H), 6.96 (d, J = 8.80 Hz, 2H), 3.79 (s, 3H), 3.06 (s, 3H), 2.97-2.82 (m, 1H), 2.80-2.70 (m, 1H), 2.69-2.62 (m, 1H), 2.57 (s, 3H), 2.04-1.50 (m, 6H) | ES-LCMS m/z 630.0 [M + H]+. |
| 169 | 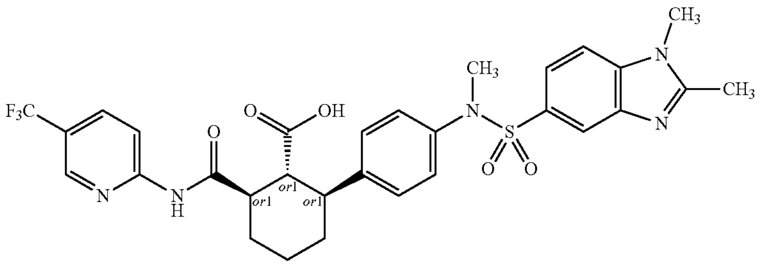 [SMILES: Cc1nc2cc(S(=O)(=O)N(C)c3ccc([C@H]4CCC[C@@H](C(=O)Nc5ccc(C(F)(F)F)cn5)[C@@H]4C(=O)O)cc3)ccc2n1C] ISOMER 2<br>rel-(1R,2R,6S)-2-((5-(trifluoromethyl)pyridin-2-yl)carbamoyl)-6-(4-((N,1,2-trimethyl-1H-benzo[d]imidazole)-5-sulfonamido)phenyl)cyclohexane-1-carboxylic acid, ISOMER 2 | $^1H$ NMR (400 MHz, DMSO-$d_6$) δ 12.00 (br, s, 1H), 11.00 (s, 1H), 8.71 (d, J = 1.60 Hz, 1H), 8.26 (d, J = 9.20 Hz, 1H), 8.16 (d, J = 6.80 Hz, 1H), 7.63 (d, J = 8.40 Hz, 1H), 7.52 (d, J = 1.20 Hz, 1H), 7.25 (d, J = 6.80 Hz, 1H), 7.20 (d, J = 8.40 Hz, 2H), 6.96 (d, J = 8.80 Hz, 2H), 3.79 (s, 3H), 3.06 (s, 3H), 2.97-2.82 (m, 1H), 2.80-2.70 (m, 1H), 2.69-2.62 (m, 1H), 2.57 (s, 3H), 2.04-1.50 (m, 6H) | ES-LCMS m/z 630.2 [M + H]+. |

-continued

| Ex | Structure/Name | $^1$H NMR | LCMS |
|---|---|---|---|
| 170 | 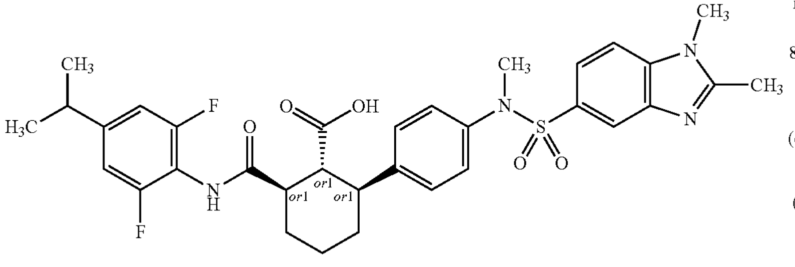<br>ISOMER 1<br>rel-(1R,2R,6S)-2-((2,6-difluoro-4-isopropylphenyl)carbamoyl)-6-(4-((N,1,2-trimethyl-1H-benzo[d]imidazole)-5-sulfonamido)phenyl)cyclohexane-1-carboxylic acid, ISOMER 1 | $^1$H NMR (400 MHz, DMSO-$d_6$) δ 9.60 (br s, 1H), 7.63 (d, J = 8.5 Hz, 1H), 7.49 (d, J = 1.0 Hz, 1H), 7.24 (dd, J = 8.8, 1.8 Hz, 1H), 7.18 (d, J = 8.5 Hz, 2H), 7.01 (d, J = 9.0 Hz, 2H), 6.95 (d, J = 8.5 Hz, 2H), 3.78 (s, 3H), 3.05 (s, 3H), 2.94-2.87 (m, 1H), 2.79 (br s, 1H), 2.69-2.62 (m, 1H), 2.57 (s, 3H), 2.02 (d, J = 9.5 Hz, 1H), 1.92-1.83 (m, 1H), 1.74 (d, J = 10.5 Hz, 1H), 1.65-1.45 (m, 4H), 1.18 (d, J = 7.0 Hz, 6H). | ES-LCMS m/z 639.2 [M + H]+. |
| 171 | 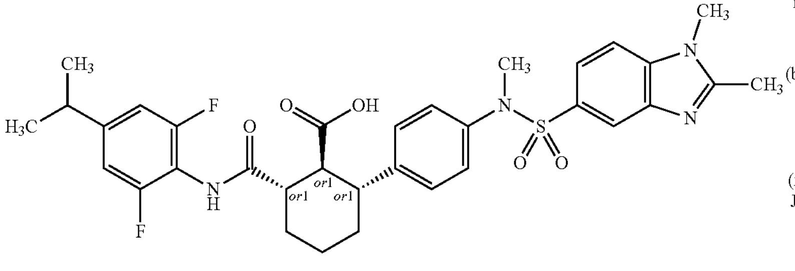<br>ISOMER 2<br>rel-(1R,2R,6S)-2-((2,6-difluoro-4-isopropylphenyl)carbamoyl)-6-(4-((N,1,2-trimethyl-1H-benzo[d]imidazole)-5-sulfonamido)phenyl)cyclohexane-1-carboxylic acid, ISOMER 2 | $^1$H NMR (400 MHz, DMSO-$d_6$) δ 9.72 (br s, 1H), 7.63 (d, J = 8.5 Hz, 1H), 7.51 (s, 1H), 7.25 (br d, J = 8.5 Hz, 1H), 7.18 (d, J = 8.0 Hz, 2H), 7.00 (d, J = 8.5 Hz, 2H), 6.94 (d, J = 8.0 Hz, 2H), 3.78 (s, 3H), 3.05 (s, 3H), 2.94-2.86 (m, 1H), 2.79-2.67 (m, 3H), 2.57 (s, 3H), 2.03 (br d, J = 8.0 Hz, 1H), 1.88 (br s, 1H), 1.78-1.68 (m, 1H), 1.63-1.42 (m, 3H), 1.18 (d, J = 7.0 Hz, 6H). | ES-LCMS m/z 639.0 [M + H]+. |

The following compounds were synthesized in an analogous manner to the preparation described above (Example 83, second preparation method) using the relevant arylamine or alkylamine precursors. Compounds were purified using reverse phase chromatography (MeCN/$H_2O$, basic or acidic modifiers).

| Ex | Structure/Name | $^1$H NMR | LCMS |
|---|---|---|---|
| 172 | 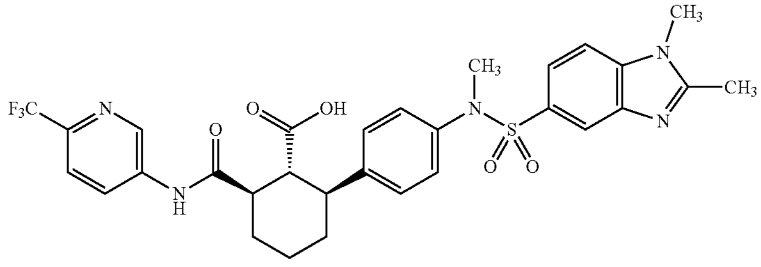 [SMILES: Cc1nc2cc(S(=O)(=O)N(C)c3ccc([C@H]4CCC[C@@H](C(=O)Nc5ccc(C(F)(F)F)nc5)[C@@H]4C(=O)O)cc3)ccc2n1C]<br>(1R,2R,6S)-2-((6-(trifluoromethyl)pyridin-3-yl)carbamoyl)-6-(4-((N,1,2-trimethyl-1H-benzo[d]imidazole)-5-sulfonamido)phenyl)cyclohexane-1-carboxylic acid | $^1$H NMR (400 MHz, DMSO-$d_6$) δ 10.73 (br s, 1H), 8.86 (d, J = 2.5 Hz, 1H), 8.31 (dd, J = 8.5, 2.0 Hz, 1H), 7.84 (d, J = 8.5 Hz, 1H), 7.62 (d, J = 8.5 Hz, 1H), 7.53 (d, J = 1.0 Hz, 1H), 7.27-7.14 (m, 3H), 6.98-6.91 (m, 2H), 3.77 (s, 3H), 3.05 (s, 3H), 2.84-2.69 (m, 3H), 2.56 (s, 3H), 2.03-1.72 (m, 3H), 1.62-1.43 (m, 3H) | ES-LCMS m/z 627.8 [M + H]+. |

-continued

| Ex | Structure/Name | $^1$H NMR | LCMS |
|---|---|---|---|
| 173 | 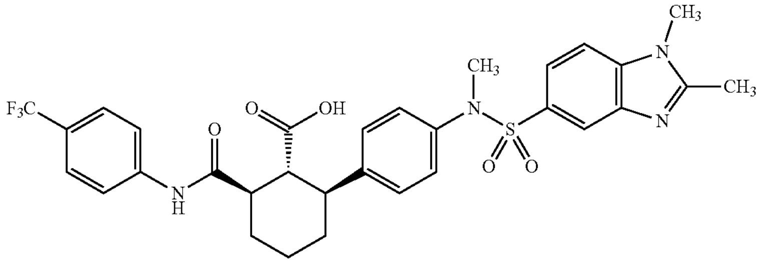 [SMILES: Cc1nc2cc(S(=O)(=O)N(C)c3ccc([C@H]4CCC[C@@H](C(=O)Nc5ccc(C(F)(F)F)cc5)[C@@H]4C(=O)O)cc3)ccc2n1C] (1R,2R,6S)-2-((4-(trifluoromethyl)phenyl)carbamoyl)-6-(4-((N,1,2-trimethyl-1H-benzo[d]imidazole)-5-sulfonamido)phenyl)cyclohexane-1-carboxylic acid | $^1$H NMR (400 MHz, DMSO-$d_6$) δ 10.43 (s, 1H), 7.81 (d, J = 8.4 Hz, 2H), 7.66-7.62 (m, 3H), 7.53 (d, J = 1.6 Hz, 1H), 7.25 (dd, J = 8.4, 1.6 Hz, 1H), 7.21 (d, J = 8.4 Hz, 2H), 6.96 (d, J = 8.4 Hz, 2H), 3.78 (s, 3H), 3.06 (s, 3H), 2.76-2.68 (m, 3H), 2.57 (s, 3H), 2.00-1.98 (m, 1H), 1.90-1.88 (m, 1H), 1.76-1.74 (m, 1H), 1.61-1.51 (m, 3H) | ES-LCMS m/z 629.0 [M + H]+. |
| 174 | 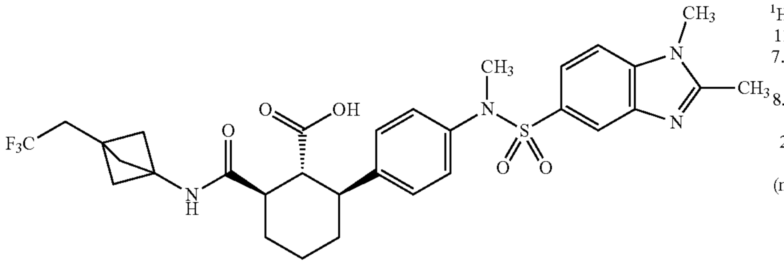 (1R,2R,6S)-2-((3-(2,2,2-trifluoroethyl)bicyclo[1.1.1]pentan-1-yl)carbamoyl)-6-(4-((N,1,2-trimethyl-1H-benzo[d]imidazole)-5-sulfonamido)phenyl)cyclohexane-1-carboxylic acid | $^1$H NMR (400 MHz, DMSO-$d_6$) δ 11.50 (br s, 1H), 8.41 (br s, 1H), 7.62 (d, J = 8.5 Hz, 1H), 7.53 (d, J = 1.0 Hz, 1H), 7.22 (dd, J = 8.5, 1.5 Hz, 1H), 7.13 (d, J = 8.5 Hz, 2H), 6.93 (d, J = 8.5 Hz, 2H), 3.78 (s, 3H), 3.04 (s, 3H), 2.61-2.55 (m, 6H), 2.43-2.34 (m, 1H), 1.94 (s, 7H), 1.81 (br s, 2H), 1.68 (br d, J = 11.0 Hz, 1H), 1.50-1.31 (m, 3H) | ES-LCMS m/z 634.1 [M + H]+. |
| 175 | 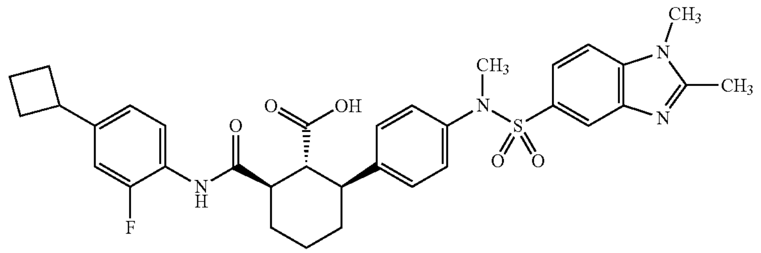 [SMILES: Cc1nc2cc(S(=O)(=O)N(C)c3ccc([C@H]4CCC[C@@H](C(=O)Nc5ccc(C6CCC6)cc5F)[C@@H]4C(=O)O)cc3)ccc2n1C] (1R,2R,6S)-2-((4-cyclobutyl-2-fluorophenyl)carbamoyl)-6-(4-((N,1,2-trimethyl-1H-benzo[d]imidazole)-5-sulfonamido)phenyl) cyclohexane-1-carboxylic acid | $^1$H NMR (400 MHz, METHANOL-$d_4$) δ 7.68 (t, J = 8.5 Hz, 1H), 7.60-7.50 (m, 2H), 7.40 (dd, J = 8.5, 1.5 Hz, 1H), 7.17 (d, J = 8.5 Hz, 2H), 7.05-6.92 (m, 4H), 3.83 (s, 3H), 3.59-3.47 (m, 1H), 3.12 (s, 3H), 2.94-2.74 (m, 3H), 2.63 (s, 3H), 2.39-2.28 (m, 2H), 2.17-1.96 (m, 5H), 1.91-1.80 (m, 2H), 1.75-1.55 (m, 3H), two exchangeable protons not observed | ES-LCMS m/z 633.0 [M + H]+. |
| 176 | 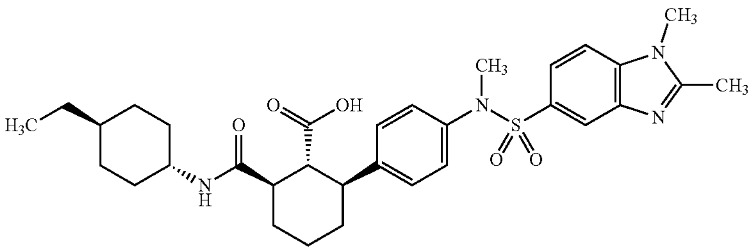 [SMILES: CC[C@H]1CC[C@H](NC(=O)[C@@H]2CCC[C@H](c3ccc(N(C)S(=O)(=O)c4ccc5c(c4)nc(C)n5C)cc3)[C@H]2C(=O)O)CC1] (1R,2R,6S)-2-(((1r,4R)-4-ethylcyclohexyl)carbamoyl)-6-(4-((N, 1,2-trimethyl-1H-benzo[d]imidazole)-5-sulfonamido)phenyl)cyclohexane-1-carboxylic acid | $^1$H NMR (400 MHz, DMSO-$d_6$) δ 11.90 (br s, 1H), 7.69-7.63 (m, 2H), 7.53 (s, 1H), 7.25 (d, J = 8.40 Hz, 1H), 7.15 (d, J = 8.40 Hz, 2H), 6.93 (d, J = 8.40 Hz, 2H), 3.79 (s, 3H), 3.43-3.38 (m, 1H), 3.05 (s, 3H), 2.68-2.63 (m, 2H), 2.61 (s, 3H), 2.47-2.41 (m, 1H), 1.81-1.68 (m, 7H), 1.42 (s, 3H), 1.22-1.01 (m, 5H), 0.93-0.82 (m, 5H) | ES-LCMS m/z 595.0 [M + H]+. |

-continued

| Ex | Structure/Name | $^1H$ NMR | LCMS |
|---|---|---|---|
| 177 | 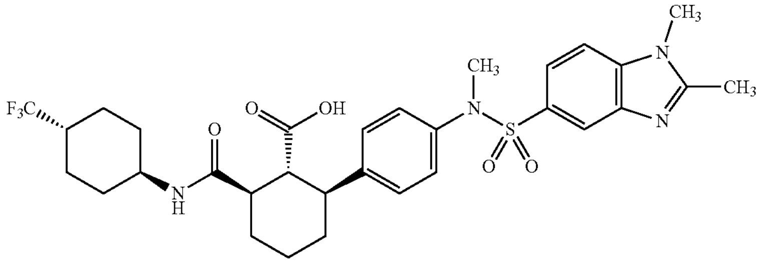 [SMILES: Cc1nc2cc(S(=O)(=O)N(C)c3ccc([C@H]4CCC[C@@H](C(=O)N[C@H]5CC[C@H](C(F)(F)F)CC5)[C@@H]4C(=O)O)cc3)ccc2n1C] (1R,2R,6S)-2-(((1r,4R)-4-(trifluoromethyl)cyclohexyl)carbamoyl)-6-(4-((N,1,2-trimethyl-1H-benzo[d]imidazole)-5-sulfonamido)phenyl)cyclohexane-1-carboxylic acid | $^1H$ NMR (400 MHz, DMSO-$d_6$) δ 7.77 (d, J = 7.6 Hz, 1H), 7.63 (d, J = 8.4 Hz, 1H), 7.51 (d, J = 1.6 Hz, 1H), 7.24 (dd, J = 8.4, 1.6 Hz, 1H), 7.15 (d, J = 8.8 Hz, 2H), 6.95 (d, J = 8.4 Hz, 2H), 3.79 (s, 3H), 3.48-3.44 (m, 1H), 3.05 (s, 3H), 2.68-2.61 (m, 2H), 2.57 (s, 3H), 2.46-2.41 (m, 2H), 1.87-1.79 (m, 6H), 1.73-1.70 (m, 1H), 1.54-1.45 (m, 3H), 1.28-1.15 (m, 4H) | ES-LCMS m/z 635.2 [M + H]+. |

The following compound was synthesized in an analogous manner to the preparation described above (Example 81), using the relevant alkylamine precursor.

| Ex | Structure/Name | $^1H$ NMR | LCMS |
|---|---|---|---|
| 178 | 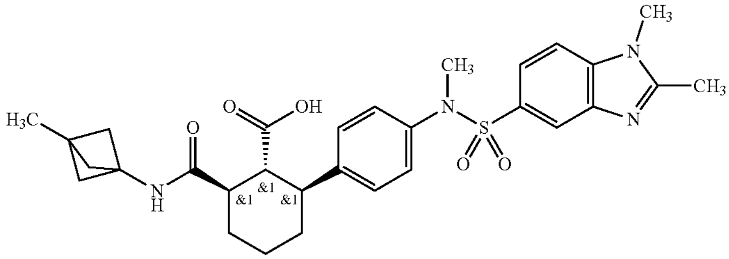 rac-(1R,2R,6S)-2-((3-methylbicyclo[1.1.1]pentan-1-yl)carbamoyl)-6-(4-((N,1,2-trimethyl-1H-benzo[d]imidazole)-5-sulfonamido)phenyl)cyclohexane-1-carboxylic acid | $^1H$ NMR (400 MHz, METHANOL-$d_4$) δ 7.47 (d, J = 8.8 Hz, 1H), 7.41 (d, J = 1.5 Hz, 1H), 7.30 (dd, J = 8.3, 1.5 Hz, 1H), 7.04 (s, 1H), 7.03-7.01 (m, 1H), 6.84 (d, J = 7.5 Hz, 2H), 3.73 (s, 3H), 3.23-3.23 (m, 1H), 3.03 (br d, J = 1.5 Hz, 1H), 3.02 (s, 3H), 2.68-2.54 (m, 2H), 2.53 (s, 3H), 2.44-2.35 (m, 1H), 1.84-1.81 (m, 1H), 1.79 (s, 6H), 1.72 (br d, J = 11.7 Hz, 1H), 1.56-1.38 (m, 3H), 1.10 (s, 3H) | ES-LCMS m/z 565.3 [M + H]$^+$. |

The following compounds were synthesized in an analogous manner to the preparation described above (Example 83, second preparation method) using the relevant arylamine or alkylamine precursors. Compounds were purified using reverse phase chromatography (MeCN/$H_2O$, basic or acidic modifiers).

| Ex | Structure/Name | $^1H$ NMR | LCMS |
|---|---|---|---|
| 179 | 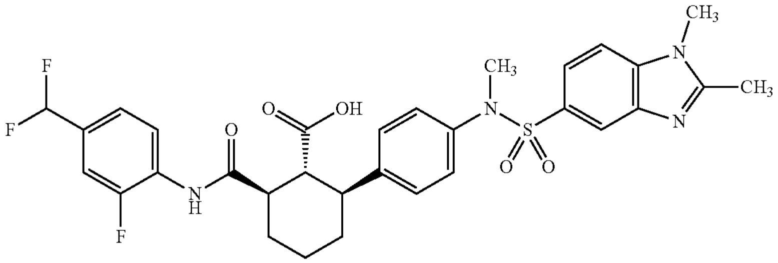 [SMILES: Cc1nc2cc(S(=O)(=O)N(C)c3ccc([C@H]4CCC[C@@H](C(=O)Nc5ccc(C(F)F)cc5F)[C@@H]4C(=O)O)cc3)ccc2n1C] (1R,2R,6S)-2-((4-(difluoromethyl)-2-fluorophenyl) carbamoyl)-6-(4-((N,1,2-trimethyl-1H-benzo[d]imidazole)-5-sulfonamido)phenyl)cyclohexane-1-carboxylic acid | $^1H$ NMR (400 MHz, DMSO-$d_6$) δ 9.96 (s, 1H), 8.07 (t, J = 8.0 Hz, 1H), 7.62 (d, J = 8.5 Hz, 1H), 7.54-7.44 (m, 2H), 7.37 (d, J = 8.0 Hz, 1H), 7.28-7.11 (m, 3H), 7.03-6.82 (m, 3H), 3.78 (s, 3H), 3.05 (s, 3H), 3.01-2.88 (m, 1H), 2.81-2.73 (m, 1H), 2.71-2.62 (m, 1H), 2.56 (s, 3H), 2.07-1.44 (m, 6H) | ES-LCMS m/z 628.8 [M + H]$^+$. |

-continued

| Ex | Structure/Name | $^1$H NMR | LCMS |
|---|---|---|---|
| 180 | 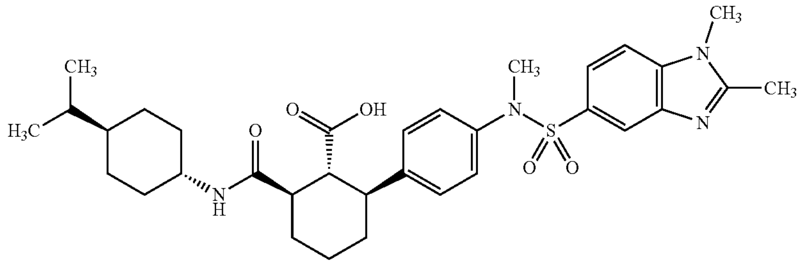 [SMILES: Cc1nc2cc(S(=O)(=O)N(C)c3ccc([C@H]4CCC[C@@H](C(=O)N[C@H]5CC[C@H](C(C)C)CC5)[C@@H]4C(=O)O)cc3)ccc2n1C] (1R,2R,6S)-2-(((1r,4R)-4-isopropylcyclohexyl)carbamoyl)-6-(4-((N,1,2-trimethyl-1H-benzo[d]imidazole)-5-sulfonamido)phenyl)cyclohexane-1-carboxylic acid | $^1$H NMR (400 MHz, DMSO-$d_6$) δ 11.85 (s, 1H), 7.64-7.58 (m, 2H), 7.50 (d, J = 1.5 Hz, 1H), 7.24 (dd, J = 8.5, 2.0 Hz, 1H), 7.14 (d, J = 8.5 Hz, 2H), 6.94 (d, J = 8.5 Hz, 2H), 3.78 (s, 3H), 3.47-3.34 (m, 1H), 3.04 (s, 3H), 2.72-2.61 (m, 2H), 2.57 (s, 3H), 2.46-2.36 (m, 2H), 1.85-1.62 (m, 7H), 1.58-1.34 (m, 5H), 1.14-0.98 (m, 3H), 0.83 (d, J = 6.5 Hz, 6H) | ES-LCMS m/z 609.0 $[M + H]^+$. |
| 181 | 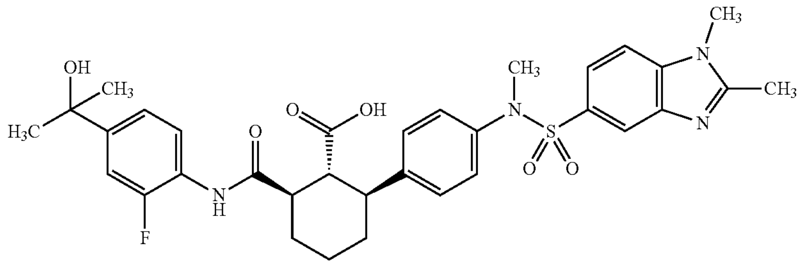 [SMILES: Cc1nc2cc(S(=O)(=O)N(C)c3ccc([C@H]4CCC[C@@H](C(=O)Nc5ccc(C(C)(C)O)cc5F)[C@@H]4C(=O)O)cc3)ccc2n1C] (1R,2R,6S)-2-((2-fluoro-4-(2-hydroxypropan-2-yl)phenyl)carbamoyl)-6-(4-((N,1,2-trimethyl-1H-benzo[d]imidazole)-5-sulfonamido)phenyl)cyclohexane-1-carboxylic acid | $^1$H NMR (400 MHz, METHANOL-$d_4$) δ 8.18 (s, 1 H), 7.74 (t, J = 8.31 Hz, 1 H), 7.59 (d, J = 8.31 Hz, 1 H), 7.51 (d, J = 1.47 Hz, 1 H), 7.42-7.45 (m, 1 H), 7.15-7.31 (m, 4 H), 6.98 (d, J = 7.09 Hz, 2 H), 3.85 (s, 3 H), 3.14 (s, 3 H), 2.78-2.98 (m, 3 H), 2.63-2.68 (m, 3 H), 2.12 (br d, J = 11.74 Hz, 1 H), 1.96-2.06 (m, 1 H), 1.85-1.94 (m, 1 H), 1.61-1.77 (m, 3 H), 1.53 (s, 6 H) | ES-LCMS m/z 637.3 $[M + H]^+$. |
| 182 | 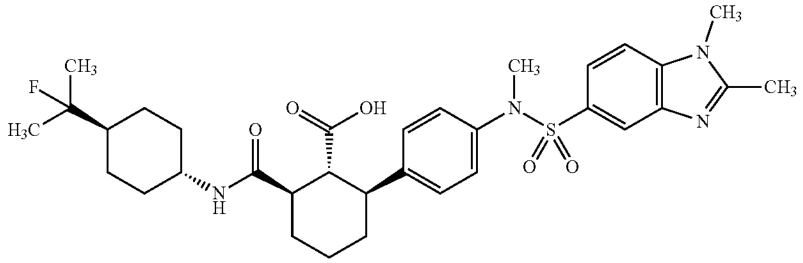 (1R,2R,6S)-2-(((1r,4R)-4-(2-fluoropropan-2-yl)cyclohexyl)carbamoyl)-6-(4-((N, 1,2-trimethyl-1H-benzo[d]imidazole)-5-sulfonamido)phenyl)cyclohexane-1-carboxylic acid | $^1$H NMR (400 MHz, DMSO-$d_6$) δ 11.60 (br s, 1H), 7.67-7.62 (m, 2H), 7.50 (s, 1H), 7.24 (d, J = 8.5 Hz, 1H), 7.14 (d, J = 8.0 Hz, 2H), 6.94 (d, J = 8.0 Hz, 2H), 3.78 (s, 3H), 3.04 (s, 4H), 2.63 (br t, J = 10.5 Hz, 2H), 2.56 (s, 3H), 2.43 (br s, 1H), 1.86-1.75 (m, 7H), 1.58-1.36 (m, 4H), 1.30-1.19 (m, 6H), 1.16-1.09 (m, 4H) | ES-LCMS m/z 672.2 $[M + H]^+$. |

Example 183

(1R,2R,6S)-2-(((1r,4R)-4-(2-hydroxypropan-2-yl)cyclohexyl)carbamoyl)-6-(4-((N,1,2-trimethyl-1H-benzo[d]imidazole)-5-sulfonamido)phenyl)cyclohexane-1-carboxylic acid

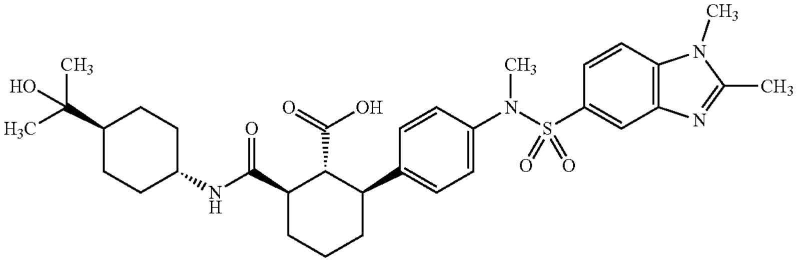 [SMILES: Cc1nc2cc(S(=O)(=O)N(C)c3ccc([C@H]4CCC[C@@H](C(=O)N[C@H]5CC[C@H](C(C)(C)O)CC5)[C@@H]4C(=O)O)cc3)ccc2n1C]

To a mixture of benzyl (1R,2R,6S)-2-(((1r,4R)-4-(2-fluoropropan-2-yl)cyclohexyl)carbamoyl)-6-(4-((N,1,2-trimethyl-1H-benzo[d]imidazole)-5-sulfonamido)phenyl)cyclohexane-1-carboxylate Intermediate 21 (85 mg, 0.12 mmol) in dichloromethane (2 mL) at 0° C. was added boron trichloride (1M in DCM, 0.24 mL, 0.24 mmol). After 1 h, the reaction was quenched with ice cold water (1 mL), concentrated and subjected to reverse phase purification (MeCN in $H_2O$, 0.1% ammonium bicarbonate modifier, 0-100% gradient) to afford (1R,2R,6S)-2-(((1r,4R)-4-(2-hydroxypropan-2-yl)cyclohexyl)carbamoyl)-6-(4-((N,1,2-trimethyl-1H-benzo[d]imidazole)-5-sulfonamido)phenyl) cyclohexane-1-carboxylic acid (8.5 mg, 0.013 mmol, 11% yield) as a white solid. $^1H$ NMR (400 MHz, DMSO-$d_6$) δ 11.85 (br s, 1H), 7.66-7.58 (m, 2H), 7.50 (d, J=1.5 Hz, 1H), 7.23 (dd, J=8.5, 1.5 Hz, 1H), 7.14 (d, J=8.5 Hz, 2H), 6.94 (d, J=8.5 Hz, 2H), 4.00 (s, 1H), 3.78 (s, 3H), 3.04 (s, 3H), 2.73-2.63 (m, 2H), 2.57 (s, 3H), 2.46-2.36 (m, 2H), 1.86-1.68 (m, 7H), 1.56-1.38 (m, 3H), 1.16-0.95 (m, 11H). ES-LCMS m/z 623.2 $[M-H]^-$.

The following compounds were synthesized in an analogous manner to the preparation described above (Example 83, second preparation method) using the relevant arylamine or alkylamine precursors. Compounds were purified using reverse phase chromatography (MeCN/$H_2O$, basic or acidic modifiers).

| Ex | Structure/Name | $^1H$ NMR | LCMS |
|---|---|---|---|
| 184 | 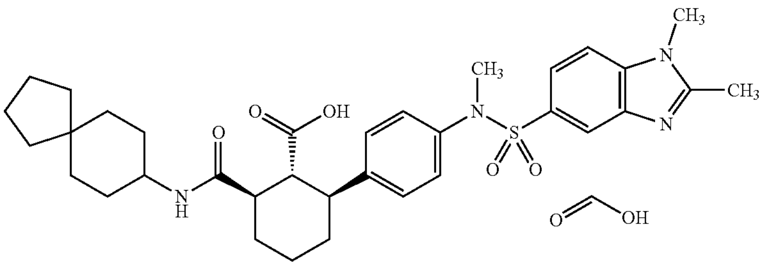 (1R,2R,6S)-2-(spiro[4.5]decan-8-ylcarbamoyl)-6-(4-((N,1,2-trimethyl-1H-benzo[d]imidazole)-5-sulfonamido)phenyl)cyclohexane-1-carboxylic acid, formic acid salt | $^1H$ NMR (600 MHz, DMSO-$d_6$) δ 7.67 (d, J = 8.44 Hz, 1 H), 7.62 (d, J = 8.07 Hz, 1 H), 7.53 (d, J = 1.47 Hz, 1 H), 7.26 (dd, J = 8.62, 1.65 Hz, 1 H), 7.17-7.13 (m, 2 H), 6.96-6.93 (m, 2 H), 3.79 (s, 3 H), 3.05 (s, 3 H), 2.68-2.55 (m, 5 H), 2.48-2.40 (m, 1 H), 1.83-1.76 (m, 2 H), 1.73-1.65 (m, 1 H), 1.58-1.50 (m, 7 H), 1.46-1.35 (m, 6 H), 1.31 (t, J = 7.15 Hz, 2 H), 1.28-1.18 (m, 5 H) | ES-LCMS m/z 621.5 $[M + H]^+$. |

-continued

| Ex | Structure/Name | $^1$H NMR | LCMS |
|---|---|---|---|
| 185 | 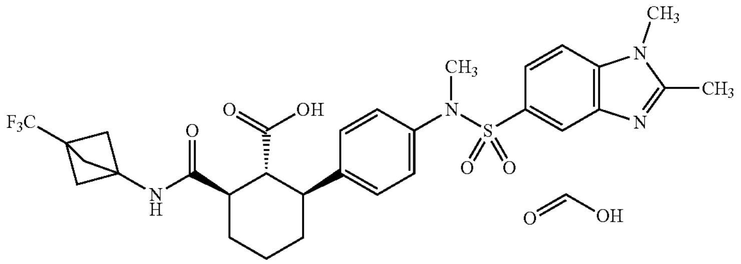 (1R,2R,6S)-2-((3-(trifluoromethyl)bicyclo[1.1.1]pentan-1-yl)carbamoyl)-6-(4-((N,1,2-trimethyl-1H-benzo[d]imidazole)-5-sulfonamido)phenyl)cyclohexane-1-carboxylic acid, formic acid salt | $^1$H NMR (600 MHz, DMSO-d$_6$) δ 8.62 (s, 1 H), 7.68 (d, J = 8.44 Hz, 1 H), 7.58 (d, J = 1.10 Hz, 1 H), 7.25 (dd, J = 8.44, 1.47 Hz, 1 H), 7.17-7.12 (m, 2 H), 6.96-6.94 (m, 2 H), 3.80 (s, 3 H), 3.06 (s, 3 H), 2.65-2.61 (m, 2 H), 2.60 (s, 3 H), 2.47-2.37 (m, 1 H), 2.17 (s, 6 H), 1.86-1.78 (m, 2 H), 1.76-1.64 (m, 1 H), 1.47-1.37 (m, 2 H), 1.23 (s, 1 H) | ES-LCMS m/z 619.3 [M + H]$^+$. |
| 186 | 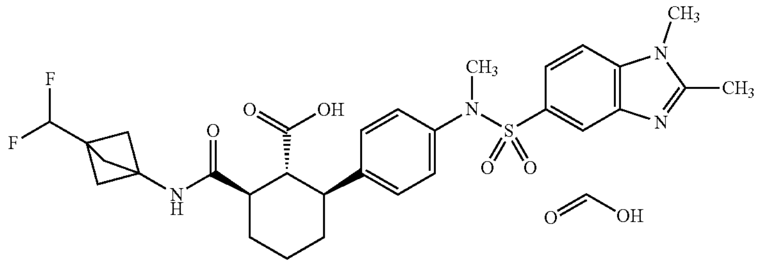 (1R,2R,6S)-2-((3-(difluoromethyl)bicyclo[1.1.1]pentan-1-yl)carbamoyl)-6-(4-((N,1,2-trimethyl-1H-benzo[d]imidazole)-5-sulfonamido)phenyl)cyclohexane-1-carboxylic acid, formic acid salt | $^1$H NMR (600 MHz, DMSO-d$_6$) δ 8.49 (s, 1 H), 7.69 (d, J = 8.80 Hz, 1 H), 7.61-7.59 (m, 1 H), 7.26 (dd, J = 8.44, 1.83 Hz, 1 H), 7.17-7.12 (m, 2 H), 6.96-6.93 (m, 2 H), 3.81 (s, 3 H), 3.06 (s, 3 H), 2.65-2.59 (m, 5 H), 2.54 (s, 1 H), 2.47-2.35 (m, 1 H), 2.00 (s, 6 H), 1.86-1.77 (m, 2 H), 1.76-1.64 (m, 1 H), 1.47-1.36 (m, 2 H), 1.23 (s, 1 H) | ES-LCMS m/z 601.4 [M + H]$^+$. |
| 187 | 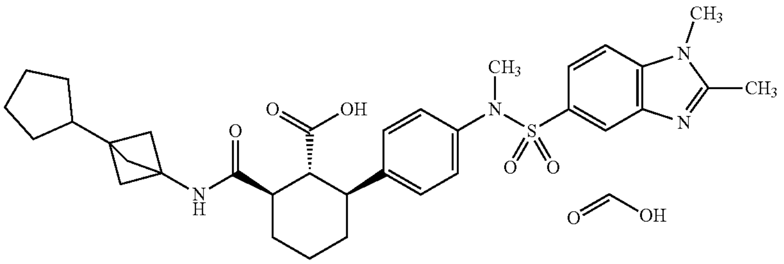 (1R,2R,6S)-2-((3-cyclopentylbicyclo[1.1.1]pentan-1-yl)carbamoyl)-6-(4-((N,1,2-trimethyl-1H-benzo[d]imidazole)-5-sulfonamido)phenyl)cyclohexane-1-carboxylic acid, formic acid salt | $^1$H NMR (600 MHz, DMSO-d$_6$) δ 8.24 (s, 1 H), 7.68 (d, J = 8.44 Hz, 1 H), 7.57 (d, J = 1.47 Hz, 1 H), 7.25 (dd, J = 8.62, 1.65 Hz, 1 H), 7.13 (d, J = 7.91 Hz, 2 H), 6.94 (d, J = 7.99 Hz, 2 H), 3.80 (s, 3 H), 3.05 (s, 3 H), 2.63-2.58 (m, 5 H), 2.40 (br s, 1 H), 1.98-1.93 (m, 1 H), 1.80 (br d, J = 6.60 Hz, 2 H), 1.71 (s, 6 H), 1.57-1.44 (m, 7 H), 1.40 (br t, J = 10.64 Hz, 2 H), 1.24-1.15 (m, 3 H) | ES-LCMS m/z 619.4 [M + H]$^+$. |

-continued

| Ex | Structure/Name | $^1$H NMR | LCMS |
|---|---|---|---|
| 188 | 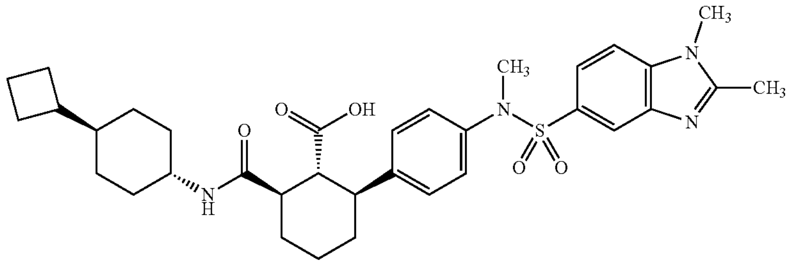 [SMILES: Cc1nc2cc(S(=O)(=O)N(C)c3ccc([C@H]4CCC[C@@H](C(=O)N[C@H]5CC[C@H](C6CCC6)CC5)[C@@H]4C(=O)O)cc3)ccc2n1C] (1R,2R,6S)-2-(((1r,4R)-4-cyclobutylcyclohexyl)carbamoyl)-6-(4-((N,1,2-trimethyl-1H-benzo[d]imidazole)-5-sulfonamido)phenyl)cyclohexane-1-carboxylic acid | $^1$H NMR (400 MHz, DMSO-$d_6$) δ 11.97 (br s, 1H), 7.62 (d, J = 8.5 Hz, 2H), 7.50 (d, J = 1.5 Hz, 1H), 7.23 (dd, J = 8.5, 2.0 Hz, 1H), 7.14 (d, J = 8.5 Hz, 2H), 6.94 (d, J = 8.5 Hz, 2H), 3.78 (s, 3H), 3.39 (br dd, J = 8.0, 4.0 Hz, 1H), 3.04 (s, 3H), 2.70-2.54 (m, 6H), 1.99-1.87 (m, 3H), 1.85-1.55 (m, 11H), 1.47-1.36 (m, 2H), 1.15-0.94 (m, 3H), 0.84-0.66 (m, 2H) | ES-LCMS m/z 621.2 $[M + H]^+$. |
| 189 | 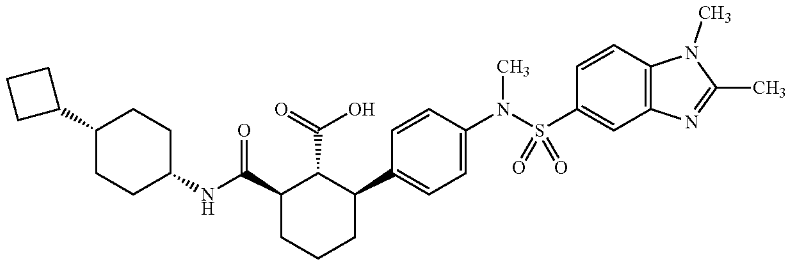 [SMILES: Cc1nc2cc(S(=O)(=O)N(C)c3ccc([C@H]4CCC[C@@H](C(=O)N[C@H]5CC[C@@H](C6CCC6)CC5)[C@@H]4C(=O)O)cc3)ccc2n1C] (1R,2R,6S)-2-(((1s,4S)-4-cyclobutylcyclohexyl)carbamoyl)-6-(4-((N,1,2-trimethyl-1H-benzo[d]imidazole)-5-sulfonamido)phenyl)cyclohexane-1-carboxylic acid | $^1$H NMR (400 MHz, DMSO-$d_6$) δ 7.63 (d, J = 8.5 Hz, 1H), 7.57 (d, J = 7.0 Hz, 1H), 7.47 (d, J = 1.5 Hz, 1H), 7.24 (dd, J= 8.5, 1.5 Hz, 1H), 7.14 (d, J = 8.5 Hz, 2H), 6.94 (d, J = 8.5 Hz, 2H), 3.78 (s, 3H), 3.69 (s, 1H), 3.04 (s, 3H), 2.70-2.60 (m, 3H), 2.56 (s, 3H), 2.19-2.07 (m, 1H), 1.99-1.89 (m, 2H), 1.85-1.76 (m, 3H), 1.74-1.65 (m, 2H), 1.63-1.53 (m, 3H), 1.49-1.42 (m, 3H), 1.40-1.33 (m, 4H), 1.27-1.14 (m, 4H) | ES-LCMS m/z 621.2 $[M + H]^+$. |

-continued

| Ex | Structure/Name | $^1$H NMR | LCMS |
|---|---|---|---|
| 190 | 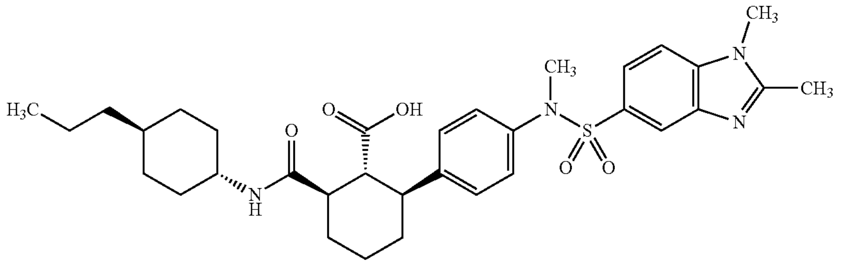 [SMILES: CCC[C@H]1CC[C@H](NC(=O)[C@@H]2CCC[C@H](c3ccc(N(C)S(=O)(=O)c4ccc5c(c4)nc(C)n5C)cc3)[C@H]2C(=O)O)CC1] (1R,2R,6S)-2-(((1s,4R)-4-propylcyclohexyl)carbamoyl)-6-(4-((N,1,2-trimethyl-1H-benzo[d]imidazole)-5-sulfonamido)phenyl)cyclohexane-1-carboxylic acid | $^1$H NMR (400 MHz, DMSO-$d_6$) δ 7.63 (d, J = 8.40 Hz, 2H), 7.51 (d, J = 1.60 Hz, 1H), 7.24 (dd, J = 8.40, 1.60 Hz, 1H), 7.15 (d, J = 8.40 Hz, 2H), 6.95 (d, J = 8.40 Hz, 2H), 3.79 (s, 3H), 3.43-3.39 (m, 1H), 3.05 (s, 3H), 2.69-2.62 (m, 2H), 2.61 (s, 3H), 2.50-2.42 (m, 1H), 1.82-1.70 (m, 7H), 1.51-1.41 (m, 3H), 1.31-1.25 (m, 2H), 1.15-1.07 (m, 5H), 0.93-0.83 (m, 5H) | ES-LCMS m/z 609.2 $[M + H]^+$. |
| 191 | 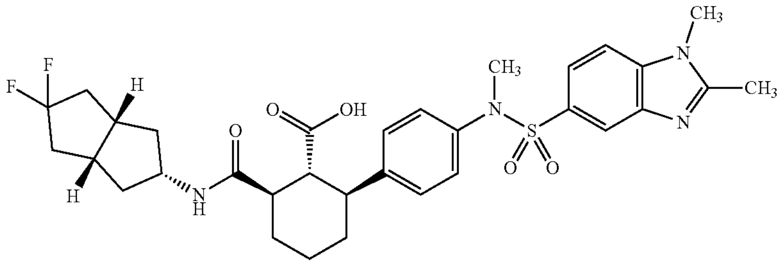 [SMILES: Cc1nc2cc(S(=O)(=O)N(C)c3ccc([C@H]4CCC[C@@H](C(=O)N[C@@H]5C[C@@H]6CC(F)(F)C[C@@H]6C5)[C@@H]4C(=O)O)cc3)ccc2n1C] (1R,2R,6S)-2-(((2s,3aR,6aS)-5,5-difluorooctahydropentalen-2-yl)carbamoyl)-6-(4-((N,1,2-trimethyl-1H-benzo[d]imidazole)-5-sulfonamido)phenyl)cyclohexane-1-carboxylic acid | $^1$H NMR (600 MHz, DMSO-$d_6$) δ 7.75 (d, J = 7.34 Hz, 1 H), 7.63 (d, J = 8.44 Hz, 1 H), 7.49 (d, J = 1.83 Hz, 1 H), 7.24 (dd, J = 8.44, 1.83 Hz, 1 H), 7.14 (m, J = 8.80 Hz, 2 H), 6.94 (m, J = 8.80 Hz, 2 H), 4.16-4.09 (m, 1 H), 3.78 (s, 3 H), 3.04 (s, 3 H), 2.68-2.58 (m, 4 H), 2.56 (s, 3 H), 2.48-2.43 (m, 1 H), 2.30-2.18 (m, 2 H), 1.84-1.75 (m, 4 H), 1.73-1.67 (m, 1 H), 1.65-1.55 (m, 4 H), 1.52 (br d, J = 12.47 Hz, 1 H), 1.48-1.39 (m, 2 H), 1.23 (s, 1 H) | ES-LCMS m/z 629.4 $[M + H]^+$. |

-continued

| Ex | Structure/Name | $^1$H NMR | LCMS |
|---|---|---|---|
| 192 | 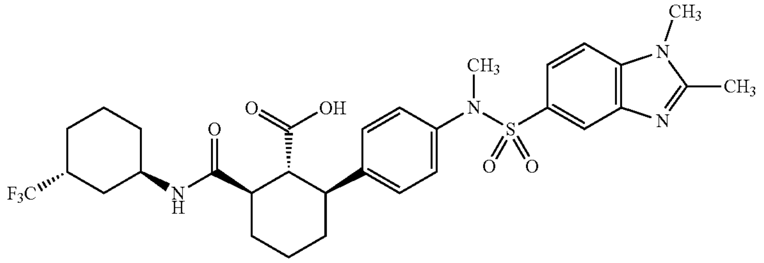 [SMILES: Cc1nc2cc(S(=O)(=O)N(C)c3ccc([C@H]4CCC[C@@H](C(=O)N[C@@H]5CCC[C@@H](C(F)(F)F)C5)[C@@H]4C(=O)O)cc3)ccc2n1C] (1R,2R,6S)-2-(((1R,3R)-3-(trifluoromethyl)cyclohexyl)carbamoyl)-6-(4-((N,1,2-trimethyl-1H-benzo[d]imidazole)-5-sulfonamido)phenyl)cyclohexane-1-carboxylic acid | $^1$H NMR (600 MHz, DMSO-$d_6$) δ 7.78-7.72 (m, 2H), 7.61 (br d, J = 8.8 Hz, 1H), 7.32 (td, J = 1.5, 8.4 Hz, 1H), 7.16 (d, J = 8.4 Hz, 2H), 6.96 (dd, J = 1.1, 8.4 Hz, 2H), 4.04-4.00 (m, 1H), 3.99-3.95 (m, 1H), 3.83 (s, 3H), 3.08 (d, J = 1.1 Hz, 3H), 2.66-2.64 (m, 3H), 1.86-1.69 (m, 6H), 1.62-1.50 (m, 4H), 1.49-1.37 (m, 4H), three protons obscured by solvent peak | ES-LCMS m/z 635.4 [M + H]$^+$. |
| 193 | 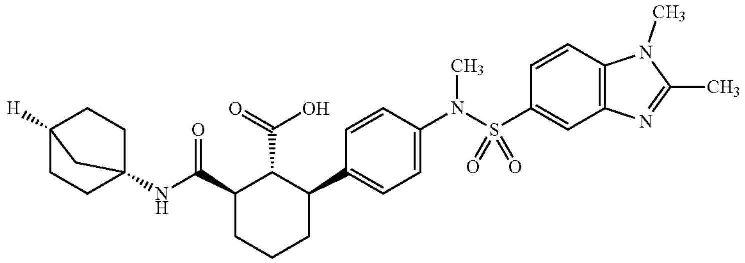 [SMILES: Cc1nc2cc(S(=O)(=O)N(C)c3ccc([C@H]4CCC[C@@H](C(=O)N[C@]56CC[C@H](CC5)C6)[C@@H]4C(=O)O)cc3)ccc2n1C] (1R,2R,6S)-2-(((1r,4R)-bicyclo[2.2.1]heptan-1-yl) carbamoyl)-6-(4-((N,1,2-trimethyl-1H-benzo[d]imidazole)-5-sulfonamido)phenyl)cyclohexane-1-carboxylic acid | $^1$H NMR (600 MHz, DMSO-$d_6$) δ 7.85 (s, 1 H), 7.74 (d, J = 8.44 Hz, 1 H), 7.64 (s, 1 H), 7.30 (dd, J = 8.62, 1.65 Hz, 1 H), 7.17-7.13 (m, 2 H), 7.00 (s, 1 H), 6.96-6.94 (m, 2 H), 3.83 (s, 3 H), 3.07 (s, 3 H), 2.65 (s, 2 H), 2.64-2.61 (m, 2 H), 2.57 (s, 1 H), 2.06-2.03 (m, 1 H), 1.80 (br d, J = 11.37 Hz, 2 H), 1.66-1.58 (m, 4 H), 1.56-1.46 (m, 5 H), 1.42 (br d, J = 11.37 Hz, 2 H), 1.33-1.19 (m, 3 H) | ES-LCMS m/z 579.4 [M + H]$^+$. |

-continued

| Ex | Structure/Name | $^1H$ NMR | LCMS |
|---|---|---|---|
| 194 | 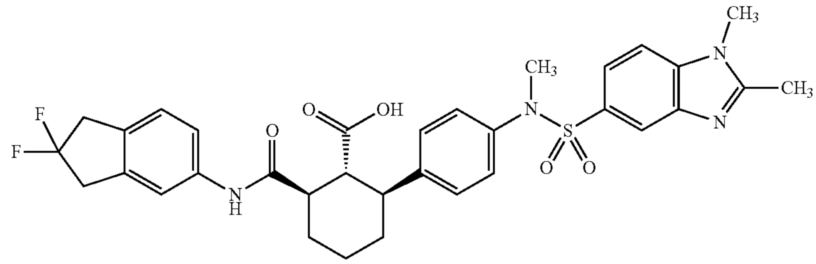 [SMILES: Cc1nc2cc(S(=O)(=O)N(C)c3ccc([C@H]4CCC[C@@H](C(=O)Nc5ccc6c(c5)CC(F)(F)C6)[C@@H]4C(=O)O)cc3)ccc2n1C] (1R,2R,6S)-2-((2,2-difluoro-2,3-dihydro-1H-inden-5-yl)carbamoyl)-6-(4-((N,1,2-trimethyl-1H-benzo[d]imidazole)-5-sulfonamido)phenyl)cyclohexane-1-carboxylic acid | $^1H$ NMR (400 MHz, DMSO-$d_6$) δ 11.85 (br s, 1H), 9.97 (s, 1H), 7.64 (s, 1H), 7.62 (s, 1H), 7.51 (d, J = 1.60 Hz, 1H), 7.37 (dd, J = 8.0, 1.60 Hz, 1H), 7.25 (dd, J = 8.4, 1.60 Hz, 1H), 7.22-7.15 (m, 3H), 6.97 (d, J = 8.8 Hz, 2H), 3.79 (s, 3H), 3.48-3.36 (m, 4H), 3.06 (s, 3H), 2.80-2.62 (m, 3H), 2.57 (s, 3H), 2.01-1.92 (m, 1H), 1.91-1.84 (m, 1H), 1.80-1.72 (m, 1H), 1.67-1.46 (m, 3H) | ES-LCMS m/z 637.2 $[M + H]^+$. |
| 195 | 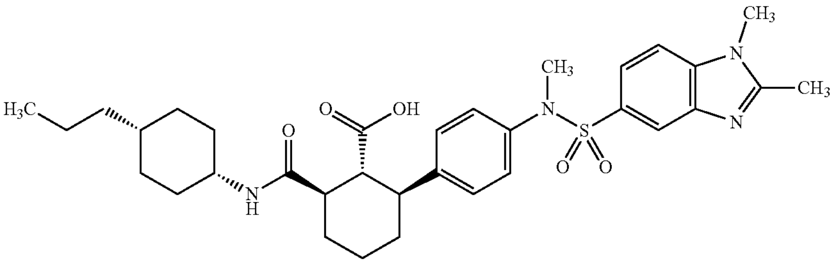 [SMILES: CCC[C@H]1CC[C@@H](NC(=O)[C@@H]2CCC[C@H](c3ccc(N(C)S(=O)(=O)c4ccc5c(c4)nc(C)n5C)cc3)[C@H]2C(=O)O)CC1] (1R,2R,6S)-2-(((1r,4R)-4-propylcyclohexyl)carbamoyl)-6-(4-((N,1,2-trimethyl-1H-benzo[d]imidazole)-5-sulfonamido)phenyl)cyclohexane-1-carboxylic acid | $^1H$ NMR (400 MHz, DMSO-$d_6$) δ 12.00 (br s, 1H), 7.63 (d, J = 8.4 Hz, 1H), 7.58 (d, J = 7.6 Hz, 1H), 7.48 (d, J = 1.2 Hz, 1H), 7.25 (dd, J = 8.4, 1.6 Hz, 1H), 7.15 (d, J = 8.4 Hz, 2H), 6.95 (d, J = 8.4 Hz, 2H), 3.79 (s, 3H), 3.33 (s, 1H), 3.05 (s, 3H), 2.67-2.53 (m, 5H), 1.80 (d, J = 8.8 Hz, 2H), 1.51-1.42 (m, 1H), 1.32-1.26 (m, 9H), 1.23-1.19 (m, 7H), 0.87 (t, J = 7.2 Hz, 3H), one proton obscured by solvent peak | ES-LCMS m/z 609.2 $[M + H]^+$. |
| 196 | 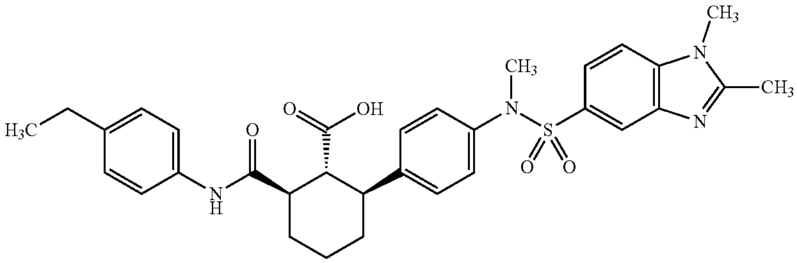 [SMILES: CCc1ccc(NC(=O)[C@@H]2CCC[C@H](c3ccc(N(C)S(=O)(=O)c4ccc5c(c4)nc(C)n5C)cc3)[C@H]2C(=O)O)cc1] (1R,2R,6S)-2-((4-ethylphenyl)carbamoyl)-6-(4-((N,1,2-trimethyl-1H-benzo[d]imidazole)-5-sulfonamido)phenyl)cyclohexane-1-carboxylic acid | $^1H$ NMR (400 MHz, DMSO-$d_6$) δ 9.88 (s, 1H), 7.62 (d, J = 8.5 Hz, 1H), 7.56-7.42 (m, 3H), 7.28-7.15 (m, 3H), 7.10 (d, J = 8.5 Hz, 2H), 6.95 (d, J = 8.5 Hz, 2H), 3.78 (s, 3H), 3.05 (s, 3H), 2.81-2.69 (m, 3H), 2.56 (s, 4H), 2.00-1.68 (m, 4H), 1.66-1.40 (m, 3H), 1.14 (t, J = 7.5 Hz, 3H) | ES-LCMS m/z 587.2 $[M - H]^-$. |

-continued

| Ex | Structure/Name | $^1$H NMR | LCMS |
|---|---|---|---|
| 197 | 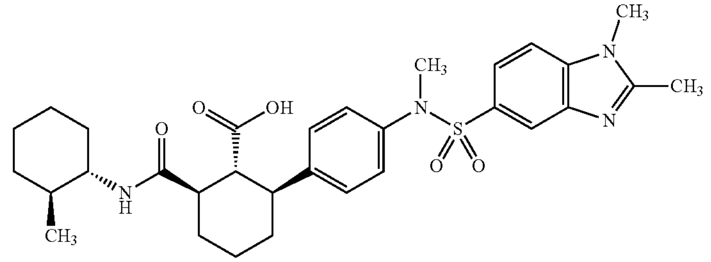 [SMILES: Cc1nc2cc(S(=O)(=O)N(C)c3ccc([C@H]4CCC[C@@H](C(=O)N[C@H]5CCCC[C@@H]5C)[C@@H]4C(=O)O)cc3)ccc2n1C] (1R,2R,6S)-2-(((1S,2S)-2-methylcyclohexyl)carbamoyl)-6-(4-((N,1,2-trimethyl-1H-benzo[d]imidazole)-5-sulfonamido)phenyl)cyclohexane-1-carboxylic acid | $^1$H NMR (400 MHz, DMSO-$d_6$) δ 7.63 (d, J = 8.80 Hz, 1H), 7.58 (d, J = 8.80 Hz, 1H), 7.50 (d, J = 1.60 Hz, 1H), 7.25 (dd, J = 1.60, 8.40 Hz, 1H), 7.15 (d, J = 8.40 Hz, 2H), 6.95 (d, J = 8.40 Hz, 2H), 3.79 (s, 3H), 3.22 (t, J= 12.40 Hz, 1H), 3.05 (s, 3H), 2.68-2.64 (m, 3H), 2.60 (s, 4H), 1.83 (d, J = 9.60 Hz, 2H), 1.66-1.45 (m, 8H), 1.26-0.99 (m, 5H), 0.80 (d, J = 6.40 Hz, 3H) | ES-LCMS m/z 581.4 [M + H]$^+$. |
| 198 | 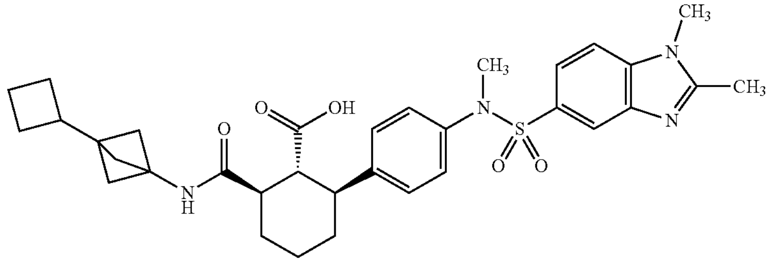 [SMILES: Cc1nc2cc(S(=O)(=O)N(C)c3ccc([C@H]4CCC[C@@H](C(=O)NC56CC(C7CCC7)(C5)C6)[C@@H]4C(=O)O)cc3)ccc2n1C] (1R,2R,6S)-2-((3-cyclobutylbicyclo[1.1.1]pentan-1-yl)carbamoyl)-6-(4-((N,1,2-trimethyl-1H-benzo[d]imidazole)-5-sulfonamido)phenyl)cyclohexane-1-carboxylic acid | $^1$H NMR (600 MHz, DMSO-$d_6$) δ 11.81 (br s, 1H), 8.26 (s, 1H), 7.62 (d, J = 8.5 Hz, 1H), 7.52 (d, J = 1.5 Hz, 1H), 7.21 (dd, J = 8.5, 1.5 Hz, 1H), 7.13 (d, J = 8.5 Hz, 2H), 6.94 (d, J = 8.5 Hz, 2H), 3.78 (s, 3H), 3.04 (s, 3H), 2.62 (d, J = 9.0 Hz, 2H), 2.57 (s, 3H), 2.45-2.36 (m, 3H), 1.97-1.86 (m, 3H), 1.84-1.77 (m, 4H), 1.74-1.57 (m, 6H), 1.52-1.34 (m, 4H) | ES-LCMS m/z 603.2 [M − H]$^-$. |

The following compound was synthesized in an analogous manner to the preparation described above (Example 139) using the relevant arylamine precursor.

| Ex | Structure/Name | $^1$H NMR | LCMS |
|---|---|---|---|
| 199 | 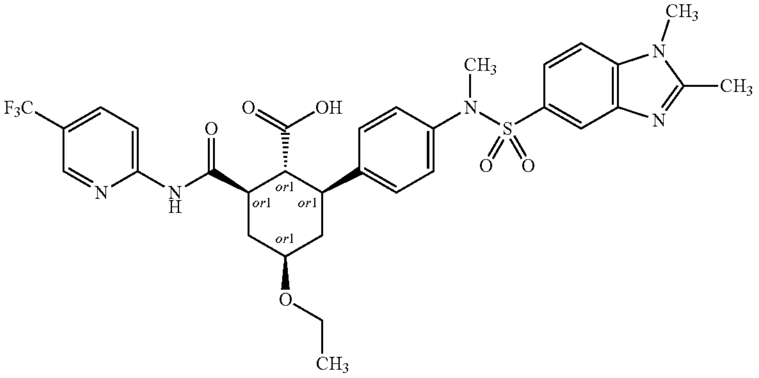 [SMILES: CCO[C@@H]1C[C@H](c2ccc(N(C)S(=O)(=O)c3ccc4c(c3)nc(C)n4C)cc2)[C@@H](C(=O)O)[C@H](C(=O)Nc2ccc(C(F)(F)F)cn2)C1] ISOMER 1 rel-(1R,2R,4R,6S)-4-ethoxy-2-((5-(trifluoromethyl)pyridin-2-yl)carbamoyl)-6-(4-((N,1,2-trimethyl-1H-benzo[d]imidazole)-5-sulfonamido)phenyl)cyclohexane-1-carboxylic acid, ISOMER 1 | $^1$H NMR (400 MHz, DMSO-$d_6$) δ 12.22 (br s, 1H), 11.02 (s, 1H), 8.78-8.62 (m, 1H), 8.30-8.09 (m, 2H), 7.62 (d, J = 8.5 Hz, 1H), 7.49 (d, J = 1.5 Hz, 1H), 7.29-7.16 (m, 3H), 6.96 (d, J = 8.5 Hz, 2H), 3.78 (s, 3H), 3.54-3.47 (m, 3H), 3.06-2.97 (m, 4H), 2.79-2.72 (m, 2H), 2.56 (s, 3H), 2.38-2.33 (m, 1H), 2.03 (d, J = 12.0 Hz, 1H), 1.61-1.51 (m, 1H), 1.46-1.36 (m, 1H), 1.10 (t, J = 7.0 Hz, 3H) | ES-LCMS m/z 674.0 $[M + H]^+$. |

Example 200 rac-(1R,2R,6S)-2-(((4-isopropylphenyl) amino) methyl)-6-(4-((N,1,2-trimethyl-1H-benzo[d]imidazole)-5-sulfonamido)phenyl)cyclohexane-1-carboxylic acid

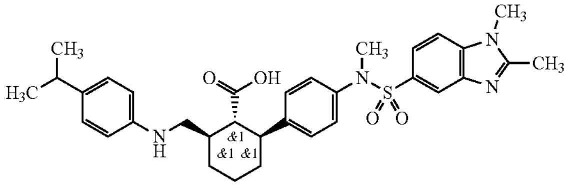 [SMILES: Cc1nc2cc(S(=O)(=O)N(C)c3ccc([C@H]4CCC[C@@H](CNc5ccc(C(C)C)cc5)[C@@H]4C(=O)O)cc3)ccc2n1C]

A mixture of rac-benzyl (1R,2R,6S)-2-(((4-isopropylphenyl)amino)methyl)-6-(4-((N,1,2-trimethyl-1H-benzo[d]imidazole)-5-sulfonamido)phenyl)cyclohexane-1-carboxylate Intermediate 22 (29 mg, 0.043 mmol) in EtOAc (0.5 ml) and MeOH (0.5 ml) was flushed with nitrogen, and 10% wt. Pd/C (0.5 mg) was added, followed by further flushing with hydrogen. The reaction was stirred under a hydrogen balloon (1 atm) for 5 h at 55° C., filtered and washed with EtOAc (33×5 ml). The filtrate was concentrated and purified via silica gel column chromatography, eluting with 0-10% MeOH in DCM, to give rac-(1R,2R,6S)-2-(((4-isopropylphenyl)amino)methyl)-6-(4-((N,1,2-trimethyl-1H-benzo[d]imidazole)-5-sulfonamido)phenyl)cyclohexane-1-carboxylic acid (19 mg, 0.032 mmol, 75%) as an off-white solid. $^1$H NMR (400 MHz, DMSO-$d_6$) δ 12.22 (s, 1H), 7.64 (d, J=8.5 Hz, 1H), 7.53 (d, J=1.7 Hz, 1H), 7.25 (dd, J=8.5, 1.7 Hz, 1H), 7.21-7.13 (m, 2H), 6.99-6.89 (m, 4H), 6.52-6.44 (m, 2H), 5.43 (s, 1H), 3.79 (s, 3H), 3.30 (s, 2H), 3.06 (s, 3H), 3.02 (s, 1H), 2.81-2.64 (m, 2H), 2.58 (s, 3H), 2.31 (d, J=12.5 Hz, 1H), 2.02 (d, J=12.7 Hz, 1H), 1.89 (d, J=10.8 Hz, 1H), 1.80 (d, J=12.5 Hz, 1H), 1.72 (d, J=12.4 Hz, 1H), 1.46 (dd, J=24.5, 11.9 Hz, 1H), 1.37 (d, J=12.9 Hz, 1H), 1.13 (d, J=6.9 Hz, 6H), 1.08 (s, 1H). ES-LCMS m/z 589.3 $[M+H]^+$.

The following compounds were synthesized in an analogous manner to the preparation described above (Example 200) using the relevant arylamine precursors. Compounds were purified using reverse phase chromatography (MeCN/$H_2O$, basic or acidic modifiers).

| Ex | Structure/Name | $^1$H NMR | LCMS |
|---|---|---|---|
| 201 | 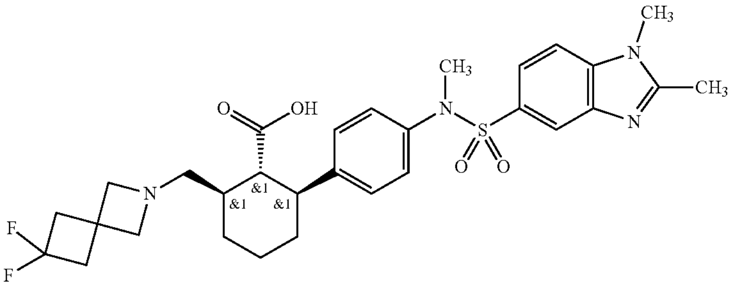 [SMILES: Cc1nc2cc(S(=O)(=O)N(C)c3ccc([C@H]4CCC[C@@H](CN5CC6(C5)CC(F)(F)C6)[C@@H]4C(=O)O)cc3)ccc2n1C] rac-(1R,2R,6S)-2-((6,6-difluoro-2-azaspiro[3.3]heptan-2-yl)methyl)-6-(4-((N,1,2-trimethyl-1H-benzo[d]imidazole)-5-sulfonamido)phenyl)cyclohexane-1-carboxylic acid | $^1$H NMR (400 MHz, DMSO-$d_6$) δ 7.64 (d, J = 7.83 Hz, 1H), 7.51 (d, J = 1.47 Hz, 1H), 7.28-7.24 (m, 1H), 7.13 (d, J = 8.80 Hz, 2H), 6.94 (d, J = 8.31 Hz, 2H), 3.79 (s, 3H), 3.17-3.09 (m, 5H), 3.05 (s, 3H), 2.67 (t, J = 12.72 Hz, 4H), 2.58 (s, 3H), 2.35-2.10 (m, 4H), 1.98-1.88 (m, 1 H), 1.81-1.65 (m, 2 H), 1.60-1.31 (m, 3 H), 1.05-0.92 (m, 1 H) | ES-LCMS m/z 587.2 $[M + H]^+$. |

-continued

| Ex | Structure/Name | $^1$H NMR | LCMS |
|---|---|---|---|
| 202 | 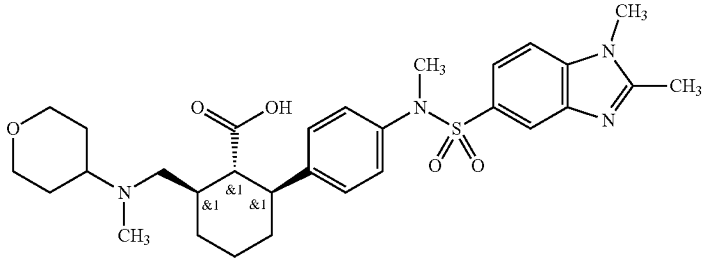 [SMILES: Cc1nc2cc(S(=O)(=O)N(C)c3ccc([C@H]4CCC[C@@H](CN(C)C5CCOCC5)[C@@H]4C(=O)O)cc3)ccc2n1C] rac-(1R,2R,6S)-2-((methyl(tetrahydro-2H-pyran-4-yl)amino)methyl)-6-(4-((N,1,2-trimethyl-1H-benzo[d]imidazole)-5-sulfonamido)phenyl)cyclohexane-1-carboxylic acid | $^1$H NMR (400 MHz, DMSO-$d_6$) δ 12.24-11.82 (m, 1H), 7.64 (d, J = 8.31 Hz, 1H), 7.52 (d, J = 1.47 Hz, 1 H), 7.25 (dd, J = 8.56, 1.71 Hz, 1H), 7.13 (m, J = 8.31 Hz, 2H), 6.93 (d, J = 8.31 Hz, 2H), 3.87 (br dd, J = 11.25, 2.93 Hz, 2H), 3.79 (s, 3 H), 3.24 (tdd, J = 11.62, 11.62, 6.11, 1.96 Hz, 2 H), 3.05 (s, 3 H), 2.72-2.61 (m, 1 H), 2.57 (s, 3 H), 2.48-2.41 (m, 1 H), 2.29-2.22 (m, 2 H), 2.17-2.08 (m, 4H), 2.05-1.95 (m, 1H), 1.81-1.67 (m, 3H), 1.58 (br dd, J = 19.56, 13.21 Hz, 2H), 1.51-1.28 (m, 4 H), 1.02-0.87 (m, 1H) | ES-LCMS m/z 569.2 [M + H]$^+$. |

Example 205

(1R,2R,6S)-2-((4-(trifluoromethyl)phenoxy)methyl)-6-(4-((N,1,2-trimethyl-1H-benzo[d]imidazole)-5-sulfonamido)phenyl)cyclohexane-1-carboxylic acid

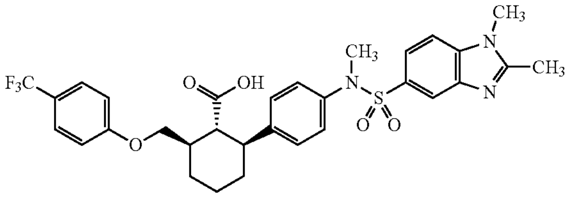 [SMILES: Cc1nc2cc(S(=O)(=O)N(C)c3ccc([C@H]4CCC[C@@H](COc5ccc(C(F)(F)F)cc5)[C@@H]4C(=O)O)cc3)ccc2n1C]

A mixture of benzyl (1R,2R,6S)-2-((4-(trifluoromethyl)phenoxy)methyl)-6-(4-((N,1,2-trimethyl-1H-benzo[d]imidazole)-5-sulfonamido)phenyl)cyclohexane-1-carboxylate Intermediate 23 (1.1000 g, 1.5585 mmol) and 10% wt. Pd/C (100.00 mg, 93.967 μmol) in THF (25 ml) was stirred under a hydrogen balloon (1 atm) for 20 h at 23° C., filtered concentrated and purified via silica gel column chromatography, eluting with 10-20% MeOH in DCM, to give (1R,2R,6S)-2-((4-(trifluoromethyl)phenoxy)methyl)-6-(4-((N,1,2-trimethyl-1H-benzo[d]imidazole)-5-sulfonamido)phenyl)cyclohexane-1-carboxylic acid (704 mg, 1.14 mmol, 73.4%) as an off-white solid. $^1$H NMR (400 MHz, DMSO-$d_6$) δ 12.19 (br s, 1H), 7.64 (br d, J=7.8 Hz, 3H), 7.49 (s, 1H), 7.27 (br d, J=8.3 Hz, 1H), 7.17 (br d, J=7.8 Hz, 2H), 7.10 (br d, J=8.3 Hz, 2H), 6.97 (br d, J=7.8 Hz, 2H), 3.95 (br d, J=4.4 Hz, 2H), 3.79 (s, 3H), 3.06 (s, 3H), 2.74 (br s, 1H), 2.57 (s, 3H), 2.12 (br d, J=5.9 Hz, 1H), 2.00-1.68 (m, 4H), 1.61-1.33 (m, 3H). ES-LCMS m/z 616.1 [M+H]$^+$.

Example 206

(1R,2R,6S)-2-((2-hydroxy-4-(trifluoromethyl)phenoxy)methyl)-6-(4-((N,1,2-trimethyl-1H-benzo[d]imidazole)-5-sulfonamido)phenyl)cyclohexane-1-carboxylic acid

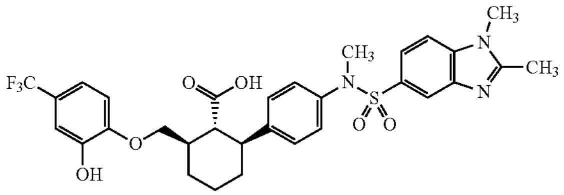 [SMILES: Cc1nc2cc(S(=O)(=O)N(C)c3ccc([C@H]4CCC[C@@H](COc5ccc(C(F)(F)F)cc5O)[C@@H]4C(=O)O)cc3)ccc2n1C]

To a mixture of benzyl (1R,2R,6S)-2-((2-(benzyloxy)-4-(trifluoromethyl)phenoxy)methyl)-6-(4-((N,1,2-trimethyl-1H-benzo[d]imidazole)-5-sulfonamido)phenyl)cyclohexane-1-carboxylate Intermediate 24 (0.160 g, 0.197 mmol) and 1,2,3,4,5-pentamethylbenzene (175 mg, 1.18 mmol) in dichloromethane (3.2 mL) at 0° C. was added boron trichloride (0.591 mL, 0.591 mmol), dropwise over 5 min. After 2 h, the reaction was quenched with ice. The organic layer was concentrated and subjected to reverse phase purification (0-100% MeCN in $H_2O$, 0.1% ammonium bicarbonate modifier) to afford (1R,2R,6S)-2-((2-hydroxy-4-(trifluoromethyl)phenoxy)methyl)-6-(4-((N,1,2-trimethyl-1H-benzo[d]imidazole)-5-sulfonamido)phenyl)cyclohexane-1-carboxylic acid (0.030 g, 0.046 mmol, 23% yield) as an off-white solid. $^1$H NMR (400 MHz, DMSO-$d_6$) δ 12.22 (br s, 1H), 9.43 (br s, 1H), 7.63 (d, J=8.5 Hz, 1H), 7.49 (d, J=1.5 Hz, 1H), 7.26 (dd, J=8.5, 1.5 Hz, 1H), 7.18 (d, J=8.5 Hz, 2H), 7.12-7.01 (m, 3H), 6.96 (d, J=8.5 Hz, 2H), 3.97-3.84 (m, 2H), 3.78 (s, 3H), 3.05 (s, 3H), 2.79-2.71 (m, 1H), 2.64-2.59 (m, 1H), 2.57 (s, 3H), 2.13-2.04 (m, 1H), 2.00 (br d, J=10.0 Hz, 1H), 1.88-1.72 (m, 2H), 1.58-1.40 (m, 3H). ES-LCMS m/z 632.0 [M+H]$^+$.

Example 207 rel-(1R,2R,6S)-2-((4-(trifluoromethyl)phenoxy)methyl)-6-(4-((N,1,2-trimethyl-7-((R)-piperidin-3-yl)-1H-benzo[d]imidazole)-5-sulfonamido)phenyl)cyclohexane-1-carboxylic acid, hydrochloride ISOMER 1

ISOMER 1

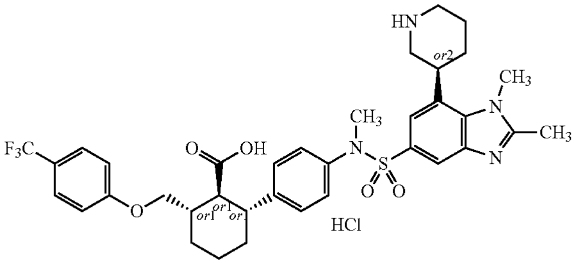

To a mixture of rel-(1R,2S,6R)-2-(4-((7-((R)-1-(tert-butoxycarbonyl)piperidin-3-yl)-N,1,2-trimethyl-1H-benzo[d]imidazole)-5-sulfonamido)phenyl)-6-((4-(trifluoromethyl)phenoxy)methyl)cyclohexane-1-carboxylic acid, ISOMER 1 Intermediate 27 (0.060 g, 0.070 mmol) in dioxane (2 mL) at 0° C. was added HCl (4M HCl in dioxane, 0.050 mL, 0.20 mmol). The reaction was stirred at rt for 3 h, and HCl (4M HCl in dioxane, 0.60 mL, 2.4 mmol) was added. After 2 h, the mixture was concentrated and subjected to Prep HPLC purification (0-100% MeCN in $H_2O$, 0.1% HCl modifier) to afford rel-(1R,2R,6S)-2-((4-(trifluoromethyl)phenoxy)methyl)-6-(4-((N,1,2-trimethyl-7-((R)-piperidin-3-yl)-1H-benzo[d]imidazole)-5-sulfonamido)phenyl)cyclohexane-1-carboxylic acid, hydrochloride ISOMER 1 (35 mg, 0.050 mmol, 63% yield) as an off-white solid. $^1$H NMR (400 MHz, DMSO-$d_6$) δ 9.27 (d, J=10.4 Hz, 1H), 8.91 (d, J=9.6 Hz, 1H), 7.66-7.60 (m, 3H), 7.20 (d, J=8.4 Hz, 2H), 7.11-7.08 (m, 3H), 6.94 (d, J=8.8 Hz, 2H), 4.05 (s, 3H), 3.98-3.94 (m, 4H), 3.37 (d, J=11.2 Hz, 1H), 3.22 (d, J=11.2 Hz, 1H), 3.05 (s, 3H), 2.93-2.90 (m, 2H), 2.76-2.73 (m, 1H), 2.67 (s, 3H), 2.11-2.10 (m, 1H), 1.94-1.87 (m, 5H), 1.75-1.68 (m, 2H), 1.56-1.50 (m, 2H), 1.48-1.38 (m, 1H). ES-LCMS m/z 699.2 $[M+H]^+$.

The following compounds were synthesized in an analogous manner to the preparation described above (Example 207) using the relevant BOC-protected precursors.

| Ex | Structure/Name | $^1$H NMR | LCMS |
|---|---|---|---|
| 208 | 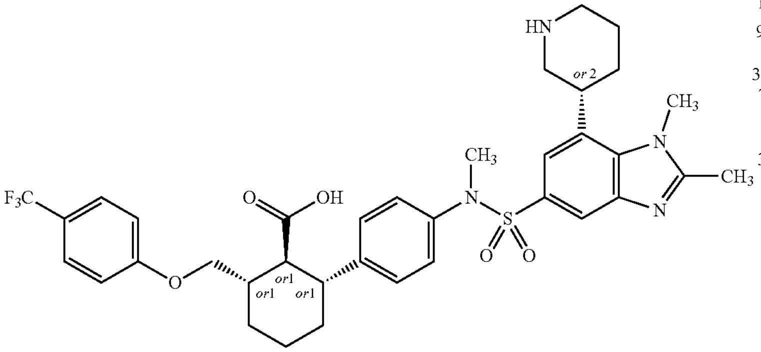 ISOMER 2 rel-(1R,2R,6S)-2-((4-(trifluoromethyl)phenoxy)methyl)-6-(4-((N,1,2-trimethyl-7-((R)-piperidin-3-yl)-1H-benzo[d]imidazole)-5-sulfonamido)phenyl)cyclohexane-1-carboxylic acid, hydrochloride ISOMER 2 | $^1$H NMR (400 MHz, DMSO-$d_6$) δ 9.27 (d, J = 10.4 Hz, 1H), 8.91 (d, J = 9.6 Hz, 1H), 7.66-7.60 (m, 3H), 7.20 (d, J = 8.4 Hz, 2H), 7.11-7.08 (m, 3H), 6.94 (d, J = 8.8 Hz, 2H), 4.05 (s, 3H), 3.98-3.94 (m, 4H), 3.37 (d, J = 11.2 Hz, 1H), 3.22 (d, J = 11.2 Hz, 1H), 3.05 (s, 3H), 2.93-2.90 (m, 2H), 2.76-2.73 (m, 1H), 2.67 (s, 3H), 2.11-2.10 (m, 1H), 1.94-1.87 (m, 5H), 1.75-1.68 (m, 2H), 1.56-1.50 (m, 2H), 1.48-1.38 (m, 1H) | ES-LCMS m/z 699.2 $[M + H]^+$. |
| 209 | 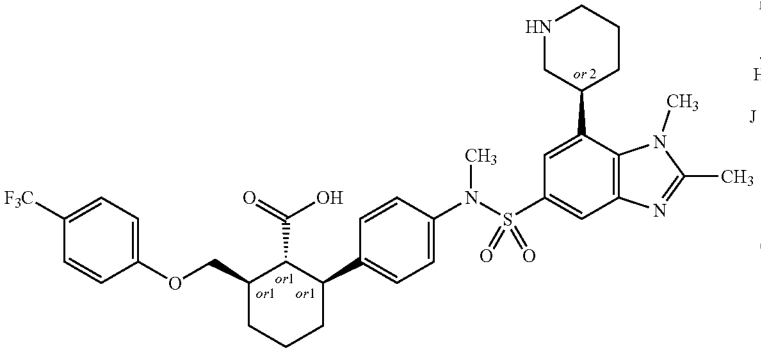 ISOMER 3 rel-(1R,2R,6S)-2-((4-(trifluoromethyl)phenoxy)methyl)-6-(4-((N,1,2-trimethyl-7-((S)-piperidin-3-yl)-1H-benzo[d]imidazole)-5-sulfonamido)phenyl)cyclohexane-1-carboxylic acid, hydrochloride ISOMER 3 | $^1$H NMR (400 MHz, DMSO-$d_6$) δ 9.45 (d, J = 6.4 Hz, 1H), 9.23 (d, J = 10.8 Hz, 1H), 7.65 (d, J = 8.4 Hz, 2H), 7.61 (s, 1H), 7.34 (s, 1H), 7.22 (d, J = 8.0 Hz, 2H), 7.08 (d, J = 8.4 Hz, 2H), 6.94 (d, J = 8.4 Hz, 2H), 4.06 (s, 3H), 3.99-3.93 (m, 2H), 3.14 (d, J = 12.8 Hz, 1H), 3.02 (s, 3H), 2.95-2.89 (m, 2H), 2.76-2.73 (m, 1H), 2.67-2.62 (m, 2H), 2.51 (s, 3H), 2.12-2.08 (m, 1H), 1.93-1.84 (m, 4H), 1.75-1.74 (m, 2H), 1.57-1.38 (m, 3H), 1.38-1.35 (m, 1H), one proton obscured by solvent peak | ES-LCMS m/z 698.8 $[M + H]^+$. |

-continued

| Ex | Structure/Name | $^1$H NMR | LCMS |
| --- | --- | --- | --- |
| 210 | 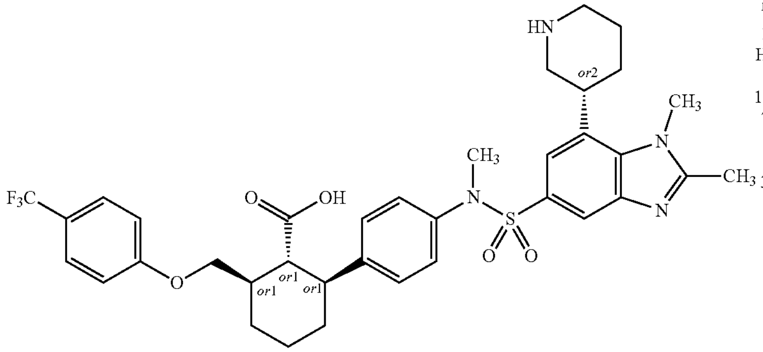 ISOMER 4 rel-(1R,2R,6S)-2-((4-(trifluoromethyl)phenoxy)methyl)-6-(4-((N,1,2-trimethyl-7-((S)-piperidin-3-yl)-1H-benzo[d]imidazole)-5-sulfonamido)phenyl)cyclohexane-1-carboxylic acid, hydrochloride ISOMER 4 | $^1$H NMR (400 MHz, DMSO-$d_6$) δ 11.96 (br s, 1H), 9.23 (d, J = 10.8 Hz, 1H), 8.90 (d, J = 10.4 Hz, 1H), 7.65 (d, J = 8.8 Hz, 2H), 7.57 (s, 1H), 7.20 (d, J = 8.8 Hz, 2H), 7.21-7.19 (m, 3H), 6.93 (d, J = 8.8 Hz, 2H), 4.04 (s, 3H), 3.49-3.43 (m, 2H), 3.37 (d, J = 12.0 Hz, 1H), 3.22 (d, J = 11.6 Hz, 1H), 3.04 (s, 3H), 2.96-2.86 (m, 2H), 2.79-2.73 (m, 1H), 2.65 (s, 3H), 2.16-2.04 (m, 1H), 1.96-1.73 (m, 5H), 1.78-1.62 (m, 2H), 1.55-1.46 (m, 2H), 1.39-1.32 (m, 1H), two protons obscured by solvent peaks | ES-LCMS m/z 699.3 [M + H]$^+$. |

Example 211 rel-(1R,2R,6S)-2-((4-(trifluoromethyl)phenoxy)methyl)-6-(4-((N,1,2-trimethyl-7-((R)-1-methylpiperidin-3-yl)-1H-benzo[d]imidazole)-5-sulfonamido)phenyl)cyclohexane-1-carboxylic acid, formic acid salt, ISOMER 1

ISOMER 1

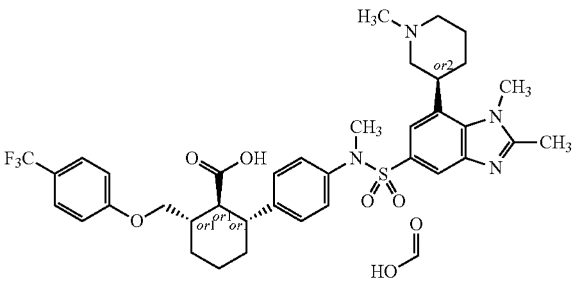

To a mixture of rel-(1R,2R,6S)-2-((4-(trifluoromethyl)phenoxy)methyl)-6-(4-((N,1,2-trimethyl-7-((R)-piperidin-3-yl)-1H-benzo[d]imidazole)-5-sulfonamido)phenyl)cyclohexane-1-carboxylic acid hydrochloride Example 207 (13.6 mg, 0.0200 mmol) in 1,2-dichloroethane (1 mL) was added triethyl amine (0.01 mL, 0.09 mmol) and formaldehyde (37% in $H_2O$, 0.01 mL, 0.18 mmol). After 16 h, sodium cyanoborohydride (17.4 mg, 0.280 mmol) was added. After 2 h the reaction was quenched with water (0.1 mL), concentrated and subjected to Prep HPLC purification (0-100% MeCN in $H_2O$, 0.1% formic acid modifier) to afford rel-(1R,2R,6S)-2-((4-(trifluoromethyl)phenoxy)methyl)-6-(4-((N,1,2-trimethyl-7-((R)-1-methylpiperidin-3-yl)-1H-benzo[d]imidazole)-5-sulfonamido)phenyl)cyclohexane-1-carboxylic acid, formic acid salt ISOMER 1 (8.5 mg, 0.010 mmol, 62% yield) as an off-white solid. $^1$H NMR (400 MHz, DMSO-$d_6$) δ7.65-7.61 (m, 3H), 7.19 (d, J=8.8 Hz, 2H), 7.09 (d, J=8.8 Hz, 2H), 6.90 (d, J=8.0 Hz, 2H), 6.77 (s, 1H), 3.96 (s, 3H), 3.94 (m, 2H), 3.68-3.66 (m, 1H), 2.99 (s, 3H), 2.85-2.78 (m, 2H), 2.68 (t, J=2.0 Hz, 1H), 2.58 (s, 3H), 2.41 (s, 3H), 2.18-2.08 (m, 2H), 1.96 (br d, J=12.8 Hz, 1H), 1.88-1.65 (m, 5H), 1.55-1.46 (m, 2H), 1.32-1.24 (m, 2H), three protons obscured by solvent peaks. ES-LCMS m/z 713.2 [M+H]$^+$.

The following compound was synthesized in an analogous manner to the preparation described above (Example 211) using the relevant amine precursor.

| Ex | Structure/Name | $^1$H NMR | LCMS |
|---|---|---|---|
| 212 | 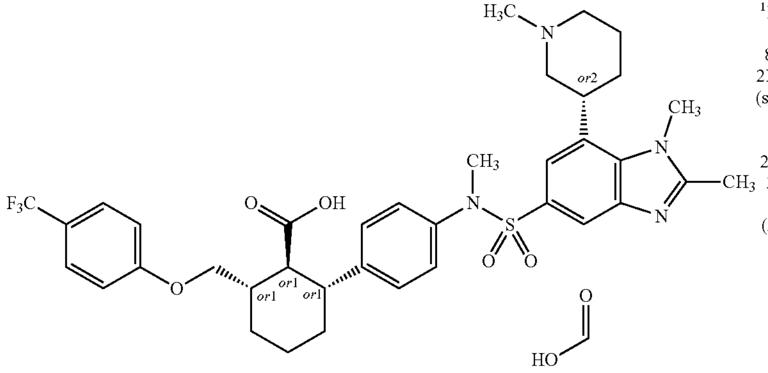 ISOMER 2 rel-(1R,2R,6S)-2-((4-(trifluoromethyl)phenoxy)methyl)-6-(4-((N,1,2-trimethyl-7-((R)-1-methylpiperidin-3-yl)-1H-benzo[d]imidazole)-5-sulfonamido)phenyl)cyclohexane-1-carboxylic acid, formic acid salt ISOMER 2 | $^1$H NMR (400 MHz, DMSO-$d_6$) δ 7.65-7.61 (m,3H), 7.19 (d, J = 8.8 Hz, 2H), 7.09 (d, J = 8.8 Hz, 2H), 6.90 (d, J = 8.0 Hz, 2H), 6.77 (s, 1H), 3.96 (s, 3H), 3.94 (m, 2H), 3.68-3.66 (m, 1H), 2.99 (s, 3H), 2.85-2.78 (m, 2H), 2.68 (t, J = 2.0 Hz, 1H), 2.58 (s, 3H), 2.41 (s, 3H), 2.18-2.08 (m, 2H), 1.96 (br d, J = 12.8 Hz, 1H), 1.88-1.65 (m, 5H), 1.55-1.46 (m, 2H), 1.32-1.24 (m, 2H), three protons obscured by solvent peaks | ES-LCMS m/z 713.2 $[M + H]^+$. |

The following compound was synthesized in an analogous manner to the preparation described above (Example 205) using the relevant sulfonyl chloride precursor.

| Ex | Structure/Name | $^1$H NMR | LCMS |
|---|---|---|---|
| 213 | 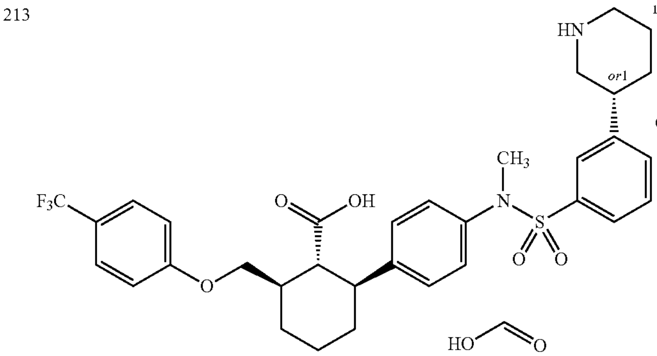 ISOMER 1 (1R,2S,6R)-2-(4-((N-methyl-3-((R*)-piperidin-3-yl)phenyl)sulfonamido)phenyl)-6-((4-(trifluoromethyl)phenoxy)methyl)cyclohexane-1-carboxylic acid, formic acid salt ISOMER 1 | $^1$H NMR (400 MHz, DMSO-$d_6$) δ 7.72 (d, J = 7.6 Hz, 1H), 7.65-7.58 (m, 4H), 7.22 (d, J = 8.4 Hz, 2H), 7.09 (d, J = 8.4 Hz, 2H), 6.90 (d, J = 8.0 Hz, 2H), 6.40 (s, 1H), 4.10 (d, J = 8.0 Hz, 1H), 3.90 (t, J = 8.0 Hz, 2H), 3.13-3.10 (m, 1H), 2.97 (s, 3H), 2.89-2.72 (m, 3H), 2.26-2.17 (m, 2H), 2.01-1.99 (m, 2H), 1.78-1.71(m, 2H), 1.68-1.63 (m, 3H), 1.45-1.35 (m, 4H), two protons obscured by solvent peaks | ES-LCMS m/z 631.2 $[M + H]^+$. |

-continued

| Ex | Structure/Name | $^1H$ NMR | LCMS |
|---|---|---|---|
| 214 | 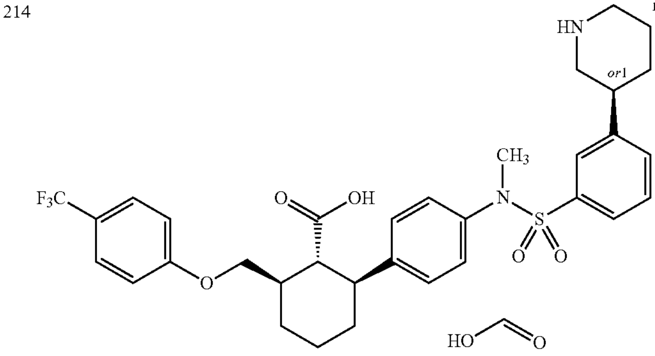 ISOMER 2 (1R,2S,6R)-2-(4-((N-methyl-3-((R*)-piperidin-3-yl)phenyl)sulfonamido)phenyl)-6-((4-(trifluoromethyl)phenoxy)methyl)cyclohexane-1-carboxylic acid, formic acid salt ISOMER 2 | $^1H$ NMR (400 MHz, DMSO-$d_6$) δ 7.72 (d, J = 7.6 Hz, 1H), 7.65-7.58 (m, 4H), 7.22 (d, J = 8.4 Hz, 2H), 7.09 (d, J = 8.4 Hz, 2H), 6.90 (d, J = 8.0 Hz, 2H), 6.40 (s, 1H), 4.10 (d, J = 8.0 Hz, 1H), 3.90 (t, J = 8.0 Hz, 2H), 3.13-3.10 (m, 1H), 2.97 (s, 3H), 2.89-2.72 (m, 3H), 2.26-2.17 (m, 2H), 2.01-1.99 (m, 2H), 1.78-1.71(m, 2H), 1.68-1.63 (m, 3H), 1.45-1.35 (m, 4H), two protons obscured by solvent peaks | ES-LCMS m/z 631.2 $[M + H]^+$. |

Example 215

(1R,2R,6S)-2-((((1 r,4R)-4-(trifluoromethyl)cyclohexyl)oxy)methyl)-6-(4-((N,1,2-trimethyl-1H-benzo[d]imidazole)-5-sulfonamido)phenyl)cyclohexane-1-carboxylic acid

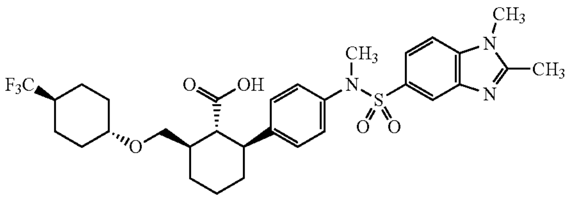 [SMILES: Cc1nc2cc(S(=O)(=O)N(C)c3ccc([C@H]4CCC[C@@H](CO[C@H]5CC[C@H](C(F)(F)F)CC5)[C@@H]4C(=O)O)cc3)ccc2n1C]

To a suspension of (1R,2S,6R)-2-(4-(methylamino)phenyl)-6-((((1r,4R)-4-(trifluoromethyl)cyclohexyl)oxy)methyl)cyclohexane-1-carboxylic acid Intermediate 31 (0.010 mg, 0.024 mmol) and 1,2-dimethyl-1H-benzo[d]imidazole-5-sulfonyl chloride (17.8 mg, 0.0730 mmol) in dichloromethane (1 mL) was added pyridine (0.012 mL, 0.15 mmol), dropwise over 1 min. After 1 h, the mixture was concentrated and subjected to reverse phase purification (40-100% MeCN in $H_2O$, 0.1% ammonium bicarbonate modifier) to afford (1R,2R,6S)-2-((((1r,4R)-4-(trifluoromethyl)cyclohexyl)oxy)methyl)-6-(4-((N,1,2-trimethyl-1H-benzo[d]imidazole)-5-sulfonamido)phenyl)cyclohexane-1-carboxylic acid (7.0 mg, 11 μmol, 45% yield) as a white solid. $^1H$ NMR (400 MHz, DMSO-$d_6$) δ 12.04 (br s, 1H), 7.68 (d, J=8.5 Hz, 1H), 7.52 (s, 1H), 7.28 (dd, J=8.5, 1.5 Hz, 1H), 7.13 (d, J=8.5 Hz, 2H), 6.94 (d, J=8.5 Hz, 2H), 3.80 (s, 3H), 3.22-3.09 (m, 2H), 3.05 (s, 3H), 2.60 (s, 3H), 2.30-2.20 (m, 2H), 2.01 (t, J=11.0 Hz, 2H), 1.91-1.65 (m, 7H), 1.41-1.39 (s, 2H), 1.33-1.08 (m, 6H). ES-LCMS m/z 620.2 $[M-H]^-$.

Example 216

(1R,2S,6R)-2-(4-((1-(2-aminoethyl)-N,2-dimethyl-1H-benzo[d]imidazole)-5-sulfonamido)phenyl)-6-((4-(trifluoromethyl)phenoxy)methyl)cyclohexane-1-carboxylic acid, 0.41 formic acid salt

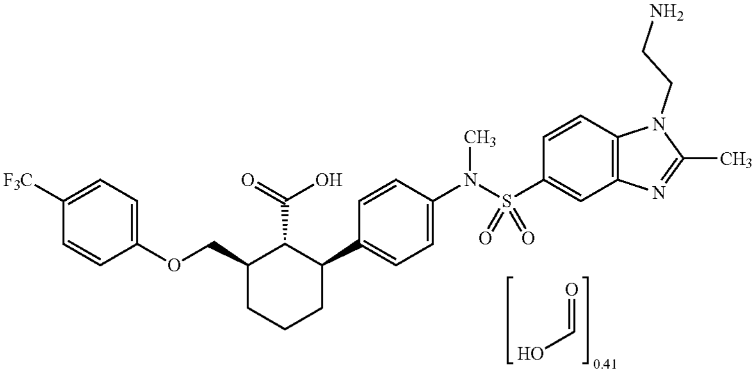

To a mixture of (1R,2S,6R)-2-(4-((1-(2-((tert-butoxycarbonyl)amino)ethyl)-N,2-dimethyl-1H-benzo[d]imidazole)-5-sulfonamido)phenyl)-6-((4-trifluoromethyl)phenoxy) methyl)cyclohexane-1-carboxylic acid Intermediate 32 (70 mg, 0.09 mmol)) in dioxane (1 mL) at 0° C. was added HCl (4M in dioxane, 0.85 mL, 3.38 mmol). The reaction was stirred at rt for 1 h, concentrated and subjected to Prep HPLC purification (0-100% MeCN in $H_2O$, with 0.1% formic acid modifier) to afford (1R,2S,6R)-2-(4-((1-(2-aminoethyl)-N,2-dimethyl-1H-benzo[d]imidazole)-5-sulfonamido)phenyl)-6-((4-(trifluoromethyl) phenoxy)methyl)cyclohexane-1-carboxylic acid, 0.41 formic acid salt (30 mg, 0.04 mmol, 47% yield) as white solid. $^1$H NMR (400 MHz, DMSO-$d_6$) δ 7.69 (d, J=8.4 Hz, 1H), 7.64 (d, J=8.8 Hz, 2H), 7.50 (d, J=1.2 Hz, 1H), 7.24 (dd, J=8.6, 2.0 Hz, 1H), 7.18 (d, J=8.8 Hz, 2H), 7.09 (d, J=8.4 Hz, 2H), 6.97 (d, J=8.4 Hz, 2H), 4.22 (t, J=6.4 Hz, 2H), 3.95 (d, J=5.2 Hz, 2H), 3.07 (s, 3H), 2.92 (t, J=6.4 Hz, 2H), 2.74-2.68 (m, 1H), 2.57 (2, 3H), 2.56-2.55 (m, 1H), 2.50-2.49 (m, 1H), 2.09-2.08 (s, 1H), 1.95 (br d, J=11.6 Hz, 1H), 1.85 (d, J=6.8 Hz, 1H), 1.75 (d, J=8.8 Hz, 1H), 1.54-1.51 (m, 2H), 1.49-1.32 (m, 1H), two protons obscured by solvent peaks. ES-L(MS m/z 645.0 $[M+H]^-$.

The following compounds were synthesized in an analogous manner to the methylation procedure described above (Example 211) using the relevant amine precursors.

| Ex | Structure/Name | $^1$H NMR | LCMS |
|---|---|---|---|
| 217 | 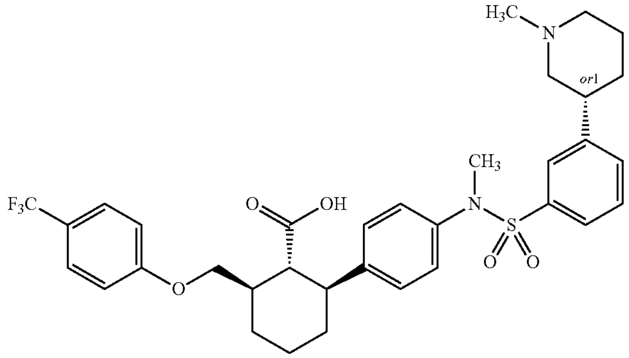 [SMILES: CN1CCC[C@H](c2cccc(S(=O)(=O)N(C)c3ccc([C@H]4CCC[C@@H](COc5ccc(C(F)(F)F)cc5)[C@@H]4C(=O)O)cc3)c2)C1] ISOMER 2 rel-(1R,2S,6R)-2-(4-((N-methyl-3-((S*)-1-methylpiperidin-3-yl)phenyl)sulfonamido)phenyl)-6-((4-(trifluoromethyl)phenoxy)methyl)cyclohexane-1-carboxylic acid ISOMER 2 | $^1$H NMR (400 MHz, DMSO-$d_6$) δ 7.65 (m, 2H), 7.57 (m, 3H), 7.22 (m, 2H), 7.10 (m, 2H), 6.93 (d, 2H), 6.90 (s, 1H), 3.99-3.91 (m, 2H), 3.80-3.5 (bs, 3H), 2.99 (s, 2H), 2.88- 2.75 (m, 3H), 2.70-2.67 (m, 2H), 2.51-2.50 (m, 3H), 2.46-2.41 (m, 1H), 2.40-2.33 (m, 4H), 1.82-1.72 (m, 2H), 1.48-1.33 (m, 3H) | ES-LCMS m/z 645.2 $[M + H]^+$. |
| 218 | 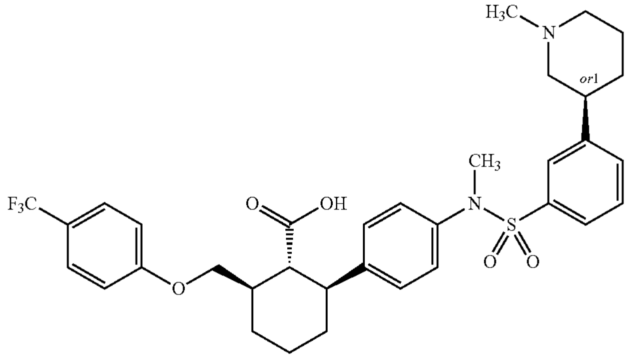 [SMILES: CN1CCC[C@@H](c2cccc(S(=O)(=O)N(C)c3ccc([C@H]4CCC[C@@H](COc5ccc(C(F)(F)F)cc5)[C@@H]4C(=O)O)cc3)c2)C1] ISOMER 1 rel-(1R,2S,6R)-2-(4-((N-methyl-3-((R*)-1-methylpiperidin-3-yl)phenyl)sulfonamido)phenyl)-6-((4-(trifluoromethyl)phenoxy)methyl)cyclohexane-1-carboxylic acid ISOMER 1 | $^1$H NMR (400 MHz, DMSO-$d_6$) δ 7.50-7.49 (m, 5H), 7.20 (d, J = 8.40 Hz, 2H), 7.09 (d, J = 8.40 Hz, 2H), 6.90 (d, J = 7.60 Hz, 3H), 4.10 (s, 1H), 3.84 (s, 1H), 3.03 (s, 3H), 2.68 (m, 3H), 2.23 (s, 3H), 2.01-1.98 (m, 3H), 1.79 (s, 2H), 1.69-1.63 (m, 3H), 1.42 (s, 3H), 1.24 (s, 3H), 0.86-0.84 (m, 2H) | ES-LCMS m/z 645.4 $[M + H]^+$. |

-continued

| Ex | Structure/Name | $^1H$ NMR | LCMS |
|---|---|---|---|
| 219 | 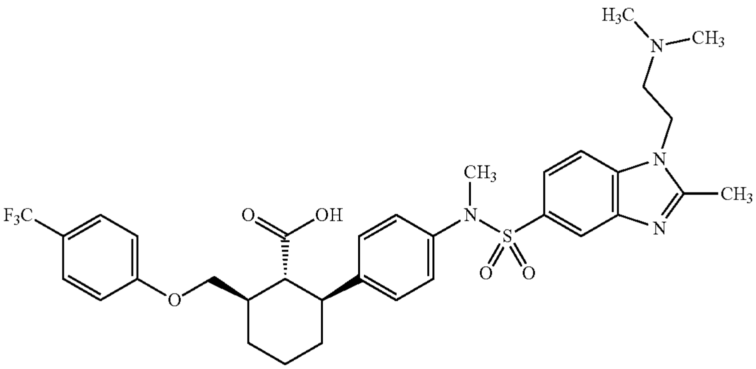 [SMILES: Cc1nc2cc(S(=O)(=O)N(C)c3ccc([C@H]4CCC[C@@H](COc5ccc(C(F)(F)F)cc5)[C@@H]4C(=O)O)cc3)ccc2n1CCN(C)C] (1R,2S,6R)-2-(4-((1-(2-(dimethylamino)ethyl)-N,2-dimethyl-1H-benzo[d]imidazole)-5-sulfonamido)phenyl)-6-((4-(trifluoromethyl)phenoxy)methyl)cyclohexane-1-carboxylic acid | $^1H$ NMR (400 MHz, DMSO-$d_6$) δ 7.70 (d, J = 8.0 Hz, 1H), 7.65 (d, J = 8.8 Hz, 2H), 7.51 (s, 1H), 7.30 (d, J = 7.6 Hz, 1H), 7.18 (d, J = 8.4 Hz, 2H), 7.09 (d, J = 8.8 Hz, 2H), 6.98 (d, J = 8.8 Hz, 2H), 4.39 (s, 2H), 3.95 (d, J = 5.2 Hz, 2H), 3.17 (s, 3H), 2.77-2.71 (m, 2H), 2.61 (s, 3H), 2.50-2.45 (m, 2H), 2.14-2.04 (m, 1H), 1.94 (d, J = 13.6 Hz, 1H), 1.85 (d, J = 6.0 Hz, 1H), 1.79-1.74 (m, 1H), 1.54-1.31 (m, 3H), seven protons obscured by solvent peaks | ES-LCMS m/z 673.2 $[M + H]^+$. |

The following compounds were synthesized in an analogous manner to the preparation described above (Example 205) using the relevant benzyl ester-protected precursors.

| Ex | Structure/Name | $^1H$ NMR | LCMS |
|---|---|---|---|
| 220 | 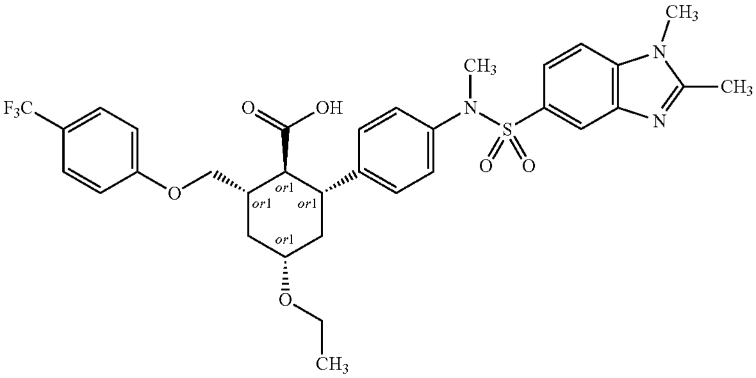 [SMILES: CCO[C@@H]1C[C@H](COc2ccc(C(F)(F)F)cc2)[C@@H](C(=O)O)[C@H](c2ccc(N(C)S(=O)(=O)c3ccc4c(c3)nc(C)n4C)cc2)C1] ISOMER 1 rel-(1R,2R,4R,6S)-4-ethoxy-2-((4-(trifluoromethyl)phenoxy)methyl)-6-(4-((N,1,2-trimethyl-1H-benzo[d]imidazole)-5-sulfonamido)phenyl)cyclohexane-1-carboxylic acid ISOMER 1 | $^1H$ NMR (400 MHz, DMSO-$d_6$) δ 12.29 (s, 1H), 7.66-7.63 (m, 3H), 7.48 (d, J = 1.2 Hz, 1H), 7.27 (dd, J = 8.6, 1.6 Hz, 1H), 7.19 (d, J = 8.8 Hz, 2H), 7.10 (d, J = 8.8 Hz, 2H), 6.97 (d, J = 8.8 Hz, 2H), 4.03-3.94 (m, 2H), 3.79 (s, 3H), 3.54-3.47 (m, 3H), 3.06 (s, 3H), 2.85-2.77 (m, 1H), 2.58 (s, 3H), 2.45 (t, J = 11.6 Hz, 1H), 2.28-2.13 (m, 2H), 2.06 (d, J = 12.0 Hz, 1H), 1.47 (q, J = 11.2 Hz, 1H), 1.30 (q, J = 11.6 Hz, 1H), 1.10 (t, J = 7.2 Hz, 3H) | ES-LCMS m/z 660.0 $[M + H]^+$. |

-continued

| Ex | Structure/Name | $^1$H NMR | LCMS |
|---|---|---|---|
| 221 | 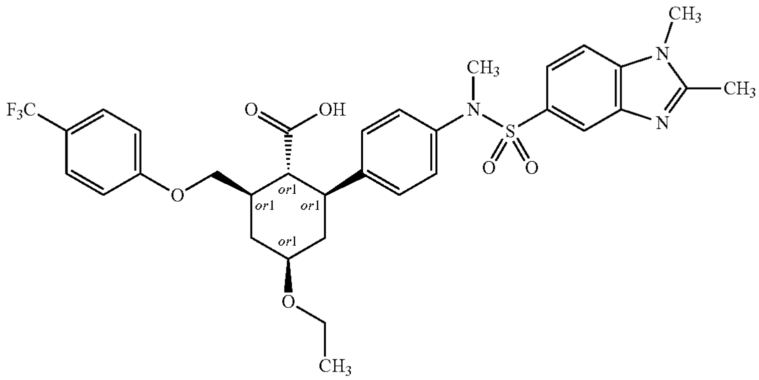 [SMILES: CCO[C@H]1C[C@@H](COc2ccc(C(F)(F)F)cc2)[C@H](C(=O)O)[C@@H](c2ccc(N(C)S(=O)(=O)c3ccc4c(c3)nc(C)n4C)cc2)C1] ISOMER 2 rel-(1R,2R,4R,6S)-4-ethoxy-2-((4-(trifluoromethyl)phenoxy)methyl)-6-(4-((N,1,2-trimethyl-1H-benzo[d]imidazole)-5-sulfonamido)phenyl)cyclohexane-1-carboxylic acid ISOMER 2 | $^1$H NMR (400 MHz, DMSO-$d_6$) δ 12.29 (br s, 1H), 7.66-7.63 (m, 3H), 7.48 (d, J = 1.2 Hz, 1H), 7.27 (dd, J = 8.6, 1.6 Hz, 1H), 7.19 (d, J = 8.8 Hz, 2H), 7.10 (d, J = 8.8 Hz, 2H), 6.97 (d, J = 8.8 Hz, 2H), 4.03-3.94 (m, 2H), 3.79 (s, 3H), 3.54-3.47 (m, 3H), 3.06 (s, 3H), 2.85-2.77 (m, 1H), 2.58 (s, 3H), 2.45 (t, J = 11.6 Hz, 1H), 2.28-2.13 (m, 2H), 2.06 (d, J = 12.0 Hz, 1H), 1.47 (q, J = 11.2 Hz, 1H), 1.30 (q, J = 11.6 Hz, 1H), 1.10 (t, J = 7.2 Hz, 3H) | ES-LCMS m/z 660.2 [M + H]$^+$. |

Example 222 rac-(1R,2R,6S)-2-((2-fluoro-4-(trifluoromethyl)phenyl)carbamoyl)-6-(4-(piperidin-1-yl)phenyl)cyclohexane-1-carboxylic acid

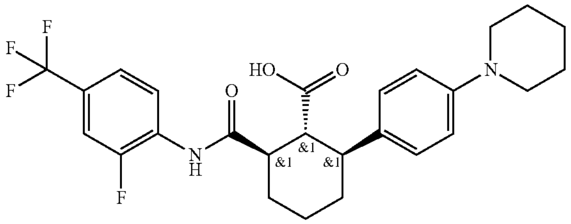 [SMILES: O=C(O)[C@@H]1[C@@H](c2ccc(N3CCCCC3)cc2)CCC[C@H]1C(=O)Nc1ccc(C(F)(F)F)cc1F]

To a mixture of rac-(1R,2S,6R)-2-(4-bromophenyl)-6-((2-fluoro-4-(trifluoromethyl)phenyl)carbamoyl)cyclohexane-1-carboxylic acid Intermediate 6 Step 1 (0.050 g, 0.10 mmol) and sodium tert-butoxide (25 mg, 0.26 mmol) in dioxane (1.0 mL) was added piperidine (87 mg, 1.0 mmol). After degassing for 5 min, tBuXPhos PdG3 (16 mg, 0.02 mmol) was added. The reaction was microwaved at 100° C. for 1 h, concentrated and purified by prep HPLC using (X Bridge C8 column), eluting with 20-100% MeCN in 10 mM ammonium bicarbonate in water to afford rac-(1R,2R,6S)-2-((2-fluoro-4-(trifluoromethyl)phenyl)carbamoyl)-6-(4-(piperidin-1-yl)phenyl)cyclohexane-1-carboxylic acid (10 mg, 0.02 mmol, 20% yield) as a white solid. $^1$H-NMR (400 MHz, DMSO-$d_6$): δ 11.70 (br s, 1H), 10.07 (s, 1H), 8.21 (t, J=8.0 Hz, 1H), 7.71 (dd, J=11.2, 1.6 Hz, 1H), 7.55 (d, J=8.4 Hz, 1H), 7.25-7.09 (m, 2H), 6.99-6.84 (m, 2H), 3.33-2.97 (m, 5H), 2.76-2.69 (m, 1H), 2.68-2.67 (m, 1H), 2.08-1.99 (m, 1H), 1.87-1.71 (m, 1H), 1.64-1.54 (m, 5H), 1.52-1.40 (m, 5H). ES-LCMS m/z 493.2 [M+H]$^+$.

The following compounds were synthesized in an analogous manner to the preparation described above (Example 79 and Example 80) using the relevant arylamine and sulphonyl chloride precursors. Compounds were purified using reverse phase chromatography (MeCN/$H_2O$, basic or acidic modifiers) and resolution on a Chiral column.

| Ex | Structure/Name | $^1$H NMR | LCMS |
|---|---|---|---|
| 223 | 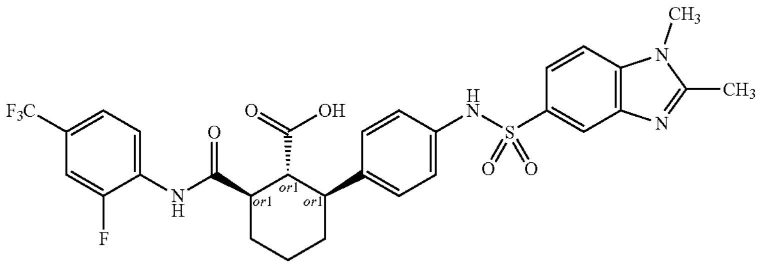 [SMILES: Cc1nc2cc(S(=O)(=O)Nc3ccc([C@H]4CCC[C@@H](C(=O)Nc5ccc(C(F)(F)F)cc5F)[C@@H]4C(=O)O)cc3)ccc2n1C] ISOMER 1 rel-(1R,2S,6R)-2-(4-((1,2-dimethyl-1H-benzo[d]imidazole)-5-sulfonamido)phenyl)-6-((2-fluoro-4-(trifluoromethyl)phenyl)carbamoyl)cyclohexane-1-carboxylic acid ISOMER 1 | $^1$H NMR (400 MHz, DMSO-$d_6$) δ 11.68 (br s, 1H), 10.12 (br s, 2H), 8.19 (t, J = 8.3 Hz, 1H), 7.85 (d, J = 1.0 Hz, 1H), 7.69 (dd, J = 10.8, 1.3 Hz, 1H), 7.63-7.50 (m, 3H), 7.05 (d, J = 8.5 Hz, 2H), 6.94 (d, J = 8.0 Hz, 2H), 3.73 (s, 3H), 2.91 (br t, J = 9.3 Hz, 1H), 2.69-2.58 (m, 2H), 2.53 (s, 3H), 2.00-1.77 (m, 2H), 1.61 (br s, 1H), 1.53-1.36 (m, 3H) | ES-LCMS m/z 633.0 [M + H]+. |

-continued

| Ex | Structure/Name | $^1$H NMR | LCMS |
|---|---|---|---|
| 224 | 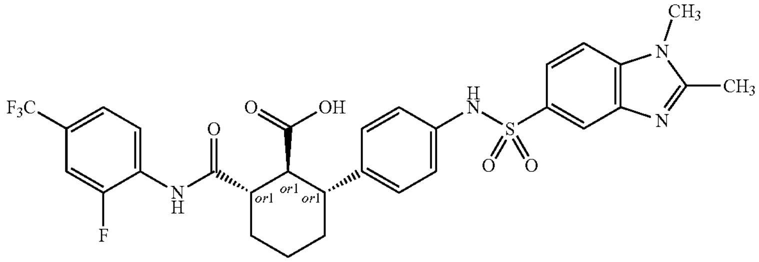 [SMILES: Cc1nc2cc(S(=O)(=O)Nc3ccc([C@@H]4CCC[C@H](C(=O)Nc5ccc(C(F)(F)F)cc5F)[C@H]4C(=O)O)cc3)ccc2n1C] ISOMER 2 rel-(1R,2S,6R)-2-(4-((1,2-dimethyl-1H-benzo[d]imidazole)-5-sulfonamido)phenyl)-6-((2-fluoro-4-(trifluoromethyl)phenyl)carbamoyl)cyclohexane-1-carboxylic acid ISOMER 2 | $^1$H NMR (400 MHz, DMSO-$d_6$) δ 11.73 (br s, 1H), 10.20 (br s, 1H), 8.21 (br t, J = 8.5 Hz, 1H), 7.85 (s, 1H), 7.71-7.46 (m, 4H), 7.05 (br d, J = 8.0 Hz, 2H), 6.93 (d, J = 8.5 Hz, 2H), 5.39 (br s, 1H), 3.73 (s, 3H), 2.95-2.83 (m, 1H), 2.58 (br s, 2H), 2.53 (s, 3H), 1.99-1.76 (m, 2H), 1.61 (br d, J = 5.0 Hz, 1H), 1.53-1.33 (m, 3H) | ES-LCMS m/z 633.0 [M + H]+. |
| 225 | 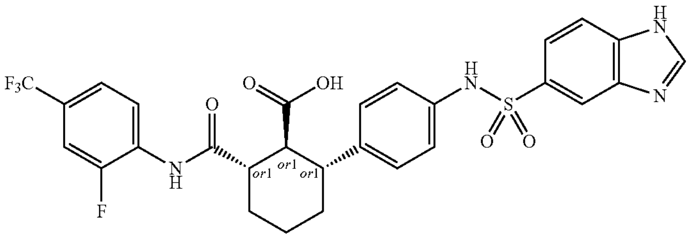 [SMILES: O=C(O)[C@@H]1[C@@H](C(=O)Nc2ccc(C(F)(F)F)cc2F)CCC[C@H]1c1ccc(NS(=O)(=O)c2ccc3[nH]cnc3c2)cc1] ISOMER 2 rel-(1R,2S,6R)-2-(4-(1H-benzo[d]imidazole-5-sulfonamido)phenyl)-6-((2-fluoro-4-(trifluoromethyl)phenyl)carbamoyl)cyclohexane-1-carboxylic acid ISOMER 2 | $^1$H NMR (400 MHz, DMSO-$d_6$) δ 12.06 (br,s, 1H), 10.06 (s, 1H), 8.41 (s, 1H), 8.20 (t, J = 8.0 Hz, 1H), 7.92 (s, 1H), 7.72 (d, J = 1.6 Hz, 2H), 7.58-7.53 (m, 2H), 7.08 (d, J = 8.4 Hz, 2H), 6.97 (d, J = 8.4 Hz, 2H), 3.18 (s, 1H), 2.97-2.91 (m, 1H), 2.70-2.53 (m, 3H), 2.09-1.64 (m, 6H) | ES-LCMS m/z 605.0 [M + H]+. |

Example 227 rac-(1R,2R,6S)-2-((2-fluoro-4-(trifluoromethyl)phenyl) carbamoyl)-6-(4-(2-fluoroacrylamido)phenyl) cyclohexane-1-carboxylic acid

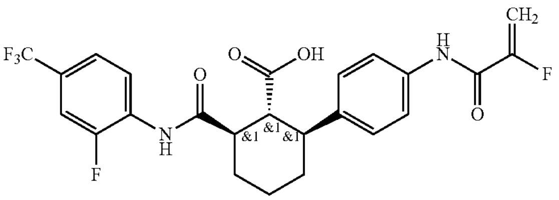 [SMILES: C=C(F)C(=O)Nc1ccc([C@H]2CCC[C@@H](C(=O)Nc3ccc(C(F)(F)F)cc3F)[C@@H]2C(=O)O)cc1]

To a mixture of rac-(1R,2S,6R)-2-(4-aminophenyl)-6-((2-fluoro-4-(trifluoromethyl)phenyl)carbamoyl)cyclohexane-1-carboxylic acid Intermediate 35 (0.060 g, 0.14 mmol) and 2-fluoroacrylic acid (127 mg, 1.41 mmol) in DMF (3 mL) at 0° C. were added DIPEA (0.049 mL, 0.28 mmol) and $T_3P$ (0.180 g, 0.283 mmol). The reaction was stirred at rt for 1 h, concentrated and subjected to reverse phase purification (0-100% MeCN in $H_2O$, 0.1% ammonium bicarbonate modifier) to afford rac-(1R,2R,6S)-2-((2-fluoro-4-(trifluoromethyl)phenyl)carbamoyl)-6-(4-(2-fluoroacrylamido) phenyl)cyclohexane-1-carboxylic acid (28 mg, 0.060 mmol, 39% yield) as a white solid. $^1$H NMR (400 MHz, DMSO-$d_6$) δ 10.21 (br s, 1H), 10.15 (d, J=1.0 Hz, 1H), 8.22 (t, J=7.5 Hz, 1H), 7.73-7.51 (m, 4H), 7.21 (d, J=8.0 Hz, 2H), 5.77-5.61 (m, 1H), 5.40 (dd, J=15.5, 3.5 Hz, 1H), 3.03-2.91 (m, 1H), 2.80-2.67 (m, 2H), 2.02-1.69 (m, 3H), 1.62-1.42 (m, 3H), one proton obscured by solvent peaks. ES-LCMS m/z 495.0 $[M-H]^-$.

Example 228 rac-(1R,2S,6R)-2-(4-(1-oxa-6-azaspiro[2.5]octan-6-yl)phenyl)-6-((2-fluoro-4-(trifluoromethyl)phenyl) carbamoyl)cyclohexane-1-carboxylic acid

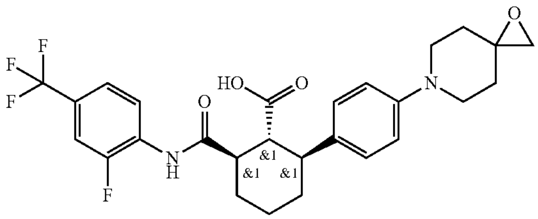 [SMILES: O=C(O)[C@@H]1[C@@H](c2ccc(N3CCC4(CC3)CO4)cc2)CCC[C@H]1C(=O)Nc1ccc(C(F)(F)F)cc1F]

To a mixture of trimethylsulfoxonium iodide (98 mg, 0.44 mmol) in DMSO (2 mL) was added potassium 2-methylpropan-2-olate (0.36 mL, 0.35 mmol). After 30 min, a solution of rac-(1R,2R,6S)-2-((2-fluoro-4-(trifluoromethyl) phenyl)carbamoyl)-6-(4-(4-oxopiperidin-1-yl)phenyl)cyclohexane-1-carboxylic acid Intermediate 37 (0.090 g, 0.18 mmol) in DMSO (1 mL). After 3 h, the reaction was concentrated and subjected to reverse phase purification (10-100% MeCN in $H_2O$, 0.1% ammonium bicarbonate modifier) to afford rac-(1R,2S,6R)-2-(4-(1-oxa-6-azaspiro [2.5]octan-6-yl)phenyl)-6-((2-fluoro-4-(trifluoromethyl) phenyl)carbamoyl)cyclohexane-1-carboxylic acid (40 mg, 0.07 mmol, 42% yield) as an off-white solid. $^1$H NMR (400 MHz, DMSO-$d_6$) δ 11.43 (br s, 1H), 10.15 (br s, 1H), 8.21 (t, J=8.3 Hz, 1H), 7.69 (dd, J=11.0, 1.5 Hz, 1H), 7.53 (d, J=8.5 Hz, 1H), 7.08 (d, J=8.5 Hz, 2H), 6.87 (d, J=8.5 Hz, 2H), 3.29-3.19 (m, 4H), 2.95 (t, J=10.5 Hz, 1H), 2.79-2.57 (m, 4H), 2.02-1.66 (m, 5H), 1.61-1.42 (m, 5H). ES-LCMS m/z 521.2 $[M-H]^-$.

The following compound was synthesized in an analogous manner to the preparation described above (Example 227) using the relevant carboxylic acid precursor.

| Ex | Structure/Name | $^1$H NMR | LCMS |
|---|---|---|---|
| 229 | 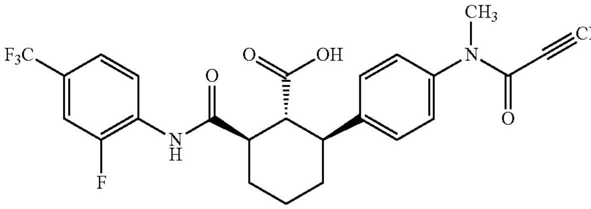 (1R,2R,6S)-2-((2-fluoro-4-(trifluoromethyl)phenyl)carbamoyl)-6-(4-(N-methylpropiolamido)phenyl)cyclohexane-1-carboxylic acid | $^1$H NMR (400 MHz, DMSO-$d_6$) δ 11.78 (br s, 1H), 10.10 (s, 1H), 8.21 (t, J = 8.0 Hz, 1H), 7.72 (dd, J = 11.0, 1.6 Hz, 1H), 7.55 (d, J = 8.4 Hz, 1H), 7.36-7.27 (m, 4H), 4.12 (s, 1H), 3.51 (s, 1H), 3.19 (s, 2H), 3.07-2.98 (m, 1H), 2.83 (t, J = 10.4 Hz, 1H), 2.75 (t, J = 11.2 Hz, 1H), 2.06-1.98 (m, 1H), 1.92-1.86 (m, 1H), 1.74-1.80 (m, 1H), 1.48-1.63 (m, 3H) | ES-LCMS m/z 491.0 $[M + H]^+$. |

Example 230 rel-(1R,2S,6R)-2-(4-bromo-3-cyanophenyl)-6-((2-fluoro-4-(trifluoromethyl)phenyl)carbamoyl)cyclohexane-1-carboxylic acid ISOMER 1

ISOMER 1

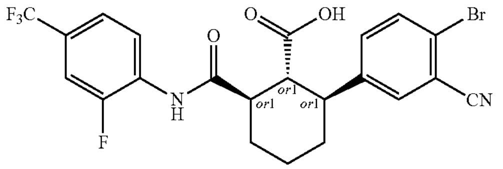

rac-(1R,2S,6R)-2-(4-bromo-3-cyanophenyl)-6-((2-fluoro-4-(trifluoromethyl)phenyl)carbamoyl)cyclohexane-1-carboxylic acid Intermediate 19 Step 7 was separated by Chiral-Prep-SFC (Column: Chiralpak IG 250×30 mm, 5 μm; 85:15 $CO_2$:IPA) to afford the second-eluting compound rel-(1R,2S,6R)-2-(4-bromo-3-cyanophenyl)-6-((2-fluoro-4-(trifluoromethyl)phenyl)carbamoyl)cyclohexane-1-carboxylic acid ISOMER 1 (14 mg, 0.030 mmol, 17% yield) as off-white solid. $^1$H NMR (400 MHz, DMSO-$d_6$) δ 10.13 (s, 1H), 8.22 (t, J=8.0 Hz, 1H), 7.94 (d, J=2.0 Hz, 1H), 7.80 (d, J=8.4 Hz, 1H), 7.72 (d, J=9.6 Hz, 1H), 7.60-7.54 (m, 2H), 3.02-2.97 (m, 1H), 2.83-2.76 (m, 2H), 2.04-2.01 (m, 1H), 1.89-1.87 (m, 1H), 1.76-1.73 (m, 1H), 1.67-1.64 (m, 1H), 1.56-1.48 (m, 2H). ES-LCMS m/z 512.8 $[M-H]^-$.

Example 231

(1R,2S,6R)-2-(4-((R*)-1,1-dioxidotetrahydrothiophen-3-yl)phenyl)-6-((2-fluoro-4-(trifluoromethyl)phenyl)carbamoyl)cyclohexane-1-carboxylic acid ISOMER 1

ISOMER 1

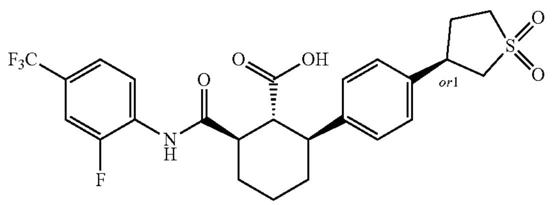

To a mixture of (1R,2S,6R)-2-(4-(1,1-dioxido-2,5-dihydrothiophen-3-yl)phenyl)-6-((2-fluoro-4-(trifluoromethyl)phenyl)carbamoyl)cyclohexane-1-carboxylic acid Example 58 (95 mg, 0.18 mmol) in methanol (3 mL) was added Pd/C (58 mg, 0.054 mmol). The reaction was hydrogenated using bladder at 1 atm pressure for 16 h, filtered through Celite, concentrated and subjected to reverse phase purification (0-100% MeCN in $H_2O$, 0.1% ammonium bicarbonate modifier) to afford rac-(1R,2S,6R)-2-(4-((R*)-1,1-dioxidotetrahydrothiophen-3-yl)phenyl)-6-((2-fluoro-4-(trifluoromethyl)phenyl)carbamoyl)cyclohexane-1-carboxylic acid (0.070 g, 0.13 mmol, 69% yield) as an off-white solid. The racemic compound was separated by Chiral-Prep-SFC (Column: Lux Cellulose-C2, 250×30 mm, 5 μm; 60:40 $CO_2$:methanol) to afford the first-eluting compound (1R,2S,6R)-2-(4-((R*)-1,1-dioxidotetrahydrothiophen-3-yl)phenyl)-6-((2-fluoro-4-(trifluoromethyl)phenyl)carbamoyl)cyclohexane-1-carboxylic acid ISOMER 1 (25 mg, 0.046 mmol, 35% yield) as a white solid. $^1$H NMR (400 MHz, DMSO-$d_6$) δ 11.52 (br s, 1H), 10.14 (s, 1H), 8.21 (t, J=8.0 Hz, 1H), 7.70 (dd, J=11.0, 1.5 Hz, 1H), 7.54 (d, J=8.5 Hz, 1H), 7.32-7.18 (m, 4H), 3.62-3.47 (m, 2H), 3.23-3.11 (m, 2H), 3.02-2.89 (m, 1H), 2.85-2.68 (m, 2H), 2.47-2.38 (m, 2H), 2.23-2.09 (m, 1H), 2.02-1.69 (m, 3H), 1.60-1.45 (m, 3H). ES-LCMS m/z 526.0 $[M-H]^-$.

Example 232 rac-(3R,4S,5R)-3-((2-fluoro-4-(trifluoromethyl)phenyl)carbamoyl)-5-(4-((N,1,2-trimethyl-1H-benzo[d]imidazole)-5-sulfonamido)phenyl)tetrahydro-2H-pyran-4-carboxylic acid

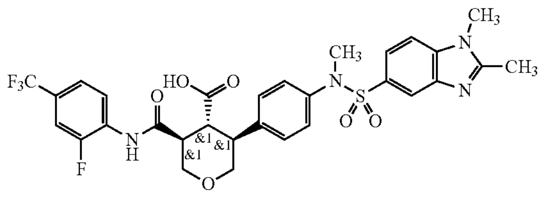 [SMILES: Cc1nc2cc(S(=O)(=O)N(C)c3ccc([C@H]4COC[C@@H](C(=O)Nc5ccc(C(F)(F)F)cc5F)[C@@H]4C(=O)O)cc3)ccc2n1C]

To a mixture of rac-(3R,4S,5R)-3-((2-fluoro-4-(trifluoromethyl)phenyl)carbamoyl)-5-(4-(methylamino)phenyl) tetrahydro-2H-pyran-4-carboxylic acid (8.00 mg, 18.2 μmol) in DCM (1 mL) at 0° C. was added 1,2-dimethyl-1H-benzo[d]imidazole-5-sulfonyl chloride (4.89 mg, 20.0 μmol) and pyridine (8.08 mg, 0.00813 mL, 5.62 Eq, 102 μmol). After 2 h, the reaction was quenched with ice water (2 mL), concentrated and subjected to reverse phase purification, eluting with 10-100% MeCN in $H_2O$, 0.1% formic acid modifier, to afford rac-(3R,4S,5R)-3-((2-fluoro-4-(trifluoromethyl)phenyl)carbamoyl)-5-(4-((N,1,2-trimethyl-1H-benzo[d]imidazole)-5-sulfonamido)phenyl)tetrahydro-2H-pyran-4-carboxylic acid (5.6 mg, 8.5 μmol, 47% yield) as a white solid. $^{1}$H NMR (400 MHz, DMSO-$d_6$) δ 10.43 (d, J=1.0 Hz, 1H), 8.19 (t, J=8.0 Hz, 1H), 7.76-7.70 (m, 1H), 7.63 (d, J=8.5 Hz, 1H), 7.60-7.53 (m, 2H), 7.30-7.23 (m, 4H), 7.00 (d, J=8.5 Hz, 2H), 4.16 (dd, J=10.8, 4.3 Hz, 1H), 3.81 (d, J=4.5 Hz, 1H), 3.78 (s, 3H), 3.56-3.51 (m, 1H), 3.50-3.45 (m, 1H), 3.30-3.20 (m, 3H), 3.11 (t, J=11.0 Hz, 1H), 2.99-2.91 (m, 1H), 2.57 (s, 3H), one proton obscured by solvent peak. ES-LCMS m/z 649.2 $[M+1]^+$ The following compound was synthesized in an analogous manner to the preparation described above (Example 83, second preparation method), substituting ethylamine for methylamine.

Example 234 rac-(1R,2R,6S)-2-((2-fluoro-4-(trifluoromethyl)phenyl)carbamoyl)-6-(3-(2-methoxyethoxy)-4-(trifluoromethyl)phenyl)cyclohexane-1-carboxylic acid

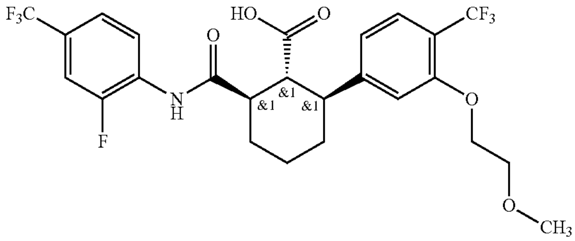

To a mixture of rac-(1R,2S,6R)-2-(3-bromo-4-(trifluoromethyl)phenyl)-6-((2-fluoro-4-(trifluoromethyl)phenyl) carbamoyl)cyclohexane-1-carboxylic acid Intermediate 38 (0.070 g, 0.13 mmol) and 2-methoxyethan-1-ol (0.2 mL, 2.52 mmol) in degassed dioxane (0.9 mL) was added sodium tert-butoxide (30.2 mg, 0.315 mmol). The reaction was degassed for 5 min, and tBuXPhos Pd G3 (0.020 g, 0.025 mmol) was added. The mixture was microwaved at 100° C. for 1 h, concentrated and subjected to reverse phase purification (45-75% MeCN in $H_2O$, 0.1% formic acid modifier) to afford rac-(1R,2R,6S)-2-((2-fluoro-4-(trifluoromethyl) phenyl)carbamoyl)-6-(3-(2-methoxyethoxy)-4-(trifluoromethyl)phenyl)cyclohexane-1-carboxylic acid (17 mg, 0.032 mmol, 25% yield) as a white solid. $^{1}$H NMR (400 MHz, DMSO-$d_6$) δ 11.86 (s, 1H), 10.15 (s, 1H), 8.22 (t, J=8.4 Hz, 1H), 7.72 (d, J=10.8 Hz, 1H), 7.65 (d, J=8.0 Hz, 1H), 7.55 (d, J=8.8 Hz, 1H), 7.49 (d, J=8.0 Hz, 1H), 7.20 (s, 1H), 6.97 (d, J=8.0 Hz, 1H), 4.24 (dd, J=5.2, 3.2 Hz, 1H), 3.69 (t, J=4.8 Hz, 1H), 3.00 (t, J=8.4 Hz, 1H), 2.89 (t, J=11.2 Hz, 1H), 2.84-2.76 (m, 1H), 2.03 (d, J=10.0 Hz, 1H), 1.89 (d, J=11.6 Hz, 1H), 1.77 (d, J=11.2 Hz, 1H), 1.70-1.46 (m, 4H), three protons obscured by solvent peaks. ES-LCMS m/z 550.0 $[M-H]^-$.

The following compounds were synthesized in an analogous manner to the preparation described above (Example 82 and Example 83) using the relevant arylamine precursor and Chiral chromatographic resolution.

| Ex | Structure/Name | $^{1}$H NMR | LCMS |
|---|---|---|---|
| 233 | 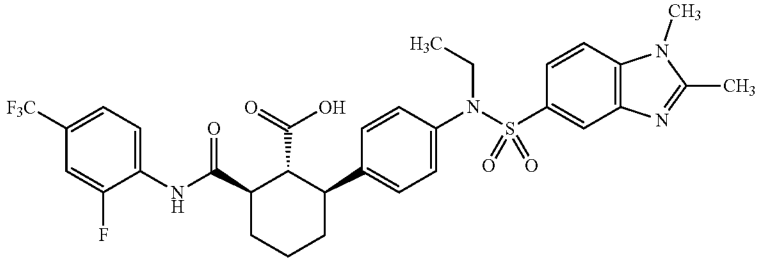 [SMILES: CCN(c1ccc([C@H]2CCC[C@@H](C(=O)Nc3ccc(C(F)(F)F)cc3F)[C@@H]2C(=O)O)cc1)S(=O)(=O)c1ccc2c(c1)nc(C)n2C] (1R,2S,6R)-2-(4-((N-ethyl-1,2-dimethyl-1H-benzo[d]imidazole)-5-sulfonamido)phenyl)-6-((2-fluoro-4-(trifluoromethyl)phenyl)carbamoyl)cyclohexane-1-carboxylic acid | 1H NMR (400 MHz, DMSO-$d_6$) δ 11.66 (br s, 1H), 10.13 (br s, 1H), 8.22 (t, J = 8.0 Hz, 1H), 7.76-7.49 (m, 4H), 7.33 (dd, J = 8.5, 1.5 Hz, 1H), 7.20 (d, J = 8.5 Hz, 2H), 6.89 (d, J = 8.5 Hz, 2H), 3.78 (s, 3H), 3.52 (q, J = 6.8 Hz, 2H), 3.07-2.93 (m, 1H), 2.79-2.64 (m, 2H), 2.57 (s, 3H), 2.06-1.72 (m, 3H), 1.66-1.45 (m, 3H), 0.93 (t, J = 7.0 Hz, 3H) | ES-LCMS m/z 661.2 $[M + H]^+$. |

| Ex | Structure/Name | $^1$H NMR | LCMS |
|---|---|---|---|
| 235 | 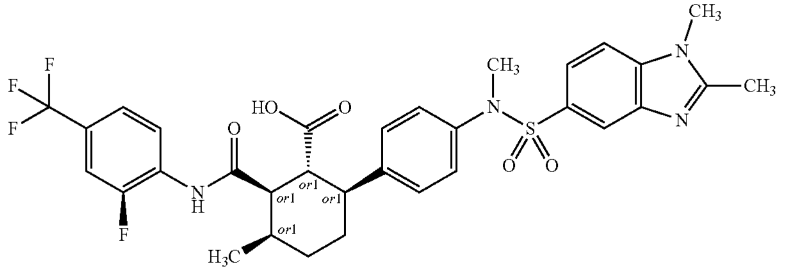 ISOMER 1 rel-(1R,2R,3R,6S)-2-((2-fluoro-4-(trifluoromethyl)phenyl)carbamoyl)-3-methyl-6-(4-((N,1,2-trimethyl-1H-benzo[d]imidazole)-5-sulfonamido)phenyl)cyclohexane-1-carboxylic acid, ISOMER 1 | $^1$H NMR (400 MHz, DMSO-d$_6$) δ 11.94 (br s, 1H), 10.14 (br s, 1H), 8.20 (t, J = 8.0 Hz, 1H), 7.78-7.68 (m, 1H), 7.64 (d, J = 8.5 Hz, 1H), 7.55 (d, J = 9.0 Hz, 1H), 7.51-7.44 (m, 1H), 7.36-7.13 (m, 3H), 6.96 (d, J = 8.5 Hz, 2H), 3.79 (s, 3H), 3.24-3.12 (m, 1H), 3.06 (s, 3H), 2.90 (t, J = 11.5 Hz, 1H), 2.61-2.54 (m, 4H), 2.49-2.39 (m, 1H), 1.88-1.64 (m, 3H), 1.56 (s, 1H), 0.98 (d, J = 7.0 Hz, 3H) | ES-LCMS m/z 658.8 [M − H]$^-$. |
| 236 | 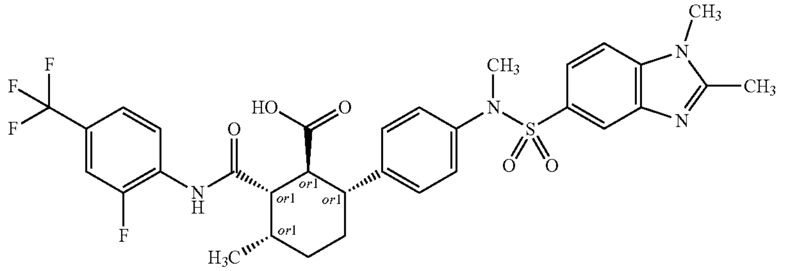 [SMILES: Cc1nc2cc(S(=O)(=O)N(C)c3ccc([C@@H]4CC[C@H](C)[C@H](C(=O)Nc5ccc(C(F)(F)F)cc5F)[C@H]4C(=O)O)cc3)ccc2n1C] ISOMER 2 rel-(1R,2R,3R,6S)-2-((2-fluoro-4-(trifluoromethyl)phenyl)carbamoyl)-3-methyl-6-(4-((N,1,2-trimethyl-1H-benzo[d]imidazole)-5-sulfonamido)phenyl)cyclohexane-1-carboxylic acid, ISOMER 2 | $^1$H NMR (400 MHz, DMSO-d$_6$) δ 11.94 (br s, 1H), 10.14 (br s, 1H), 8.20 (t, J = 8.0 Hz, 1H), 7.78-7.68 (m, 1H), 7.64 (d, J = 8.5 Hz, 1H), 7.55 (d, J = 9.0 Hz, 1H), 7.51-7.44 (m, 1H), 7.36-7.13 (m, 3H), 6.96 (d, J = 8.5 Hz, 2H), 3.79 (s, 3H), 3.24-3.12 (m, 1H), 3.06 (s, 3H), 2.90 (t, J = 11.5 Hz, 1H), 2.61-2.54 (m, 4H), 2.49-2.39 (m, 1H), 1.88-1.64 (m, 3H), 1.56 (s, 1H), 0.98 (d, J = 7.0 Hz, 3H) | ES-LCMS m/z 660.8 [M + H]$^+$. |

Example 237 rac-(1R,2R,6S)-2-((2-fluoro-4-(trifluoromethyl)phenyl)carbamoyl)-6-(2-methoxy-4-(trifluoromethyl)phenyl)cyclohexane-1-carboxylic acid

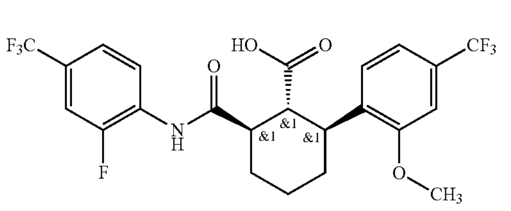 [SMILES: COc1cc(C(F)(F)F)ccc1[C@H]1CCC[C@@H](C(=O)Nc2ccc(C(F)(F)F)cc2F)[C@@H]1C(=O)O]

To a mixture of rac-(1R,2S,6R)-2-(2-bromo-4-(trifluoromethyl)phenyl)-6-((2-fluoro-4-(trifluoromethyl)phenyl)carbamoyl)cyclohexane-1-carboxylic acid Intermediate 40 (100 mg, 0.180 mmol) in methanol (0.5 mL) was added copper(II) chloride (19 mg, 0.14 mmol), sodium methoxide (0.290 mL, 1.44 mmol) and methyl formate (0.010 mL, 0.18 mmol). The reaction was stirred at 115° C. for 2 h, filtered through a Celite pad, concentrated and subjected to reverse phase purification (10-55% MeCN in $H_2O$, 0.1% ammonium bicarbonate modifier) to afford rac-(1R,2R,6S)-2-((2-fluoro-4-(trifluoromethyl)phenyl)carbamoyl)-6-(2-methoxy-4-(trifluoromethyl)phenyl)cyclohexane-1-carboxylic acid (7.5 mg, 0.014 mmol, 8.0% yield) as a white solid. $^1$H NMR (400 MHz, DMSO-d$_6$) δ 11.77 (br s, 1H), 10.12 (br s, 1H), 8.22 (t, J=8.0 Hz, 1H), 7.71 (d, J=11.0 Hz, 1H), 7.61-7.44 (m, 2H), 7.33-7.11 (m, 2H), 3.85 (s, 3H), 3.26-3.12 (m, 1H), 3.06-2.90 (m, 2H), 2.05-1.65 (m, 3H), 1.63-1.34 (m, 3H). ES-LCMS m/z 505.8 [M−H]$^-$ The following compound was synthesized in an analogous manner to the preparation described above (Example 83, second preparation method), substituting cyclopropylamine for methylamine.

| Ex | Structure/Name | $^1$H NMR | LCMS |
|---|---|---|---|
| 238 | 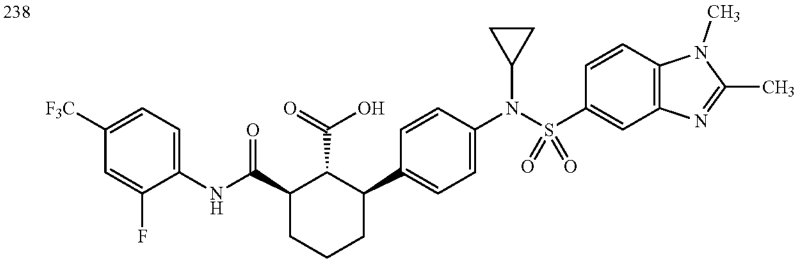 (1R,2S,6R)-2-(4-((N-cyclopropyl-1,2-dimethyl-1H-benzo[d]imidazole)-5-sulfonamido)phenyl)-6-((2-fluoro-4-(trifluoromethyl)phenyl)carbamoyl)cyclohexane-1-carboxylic acid | $^1$H NMR (400 MHz, DMSO-$d_6$) δ 10.23 (br s, 1H), 8.25 (t, J = 8.0 Hz, 1H), 7.71 (dd, J= 11.0, 2.0 Hz, 1H), 7.66 (d, J = 8.4 Hz, 1H), 7.58-7.54 (m, 2H), 7.33 (dd, J = 8.4, 1.6 Hz, 1H), 7.18 (d, J = 8.4 Hz, 2H), 6.92 (d, J = 8.4 Hz, 2H), 3.79 (s, 3H), 2.99-2.92 (m, 1H), 2.76-2.67 (m, 2H), 2.58 (s, 3H), 2.06-1.99 (m, 1H), 1.90-1.83 (m, 1H), 1.81-1.74 (m, 1H), 1.63-1.48 (m, 3H), 0.81-0.74 (m, 2H), 0.68-0.55 (m, 2H), two protons obscured by solvent peaks | ES-LCMS m/z 672.8 [M + H]$^+$. |

Example 239 rac-(1R,2R,6S)-2-((2-fluoro-4-(trifluoromethyl)phenyl)carbamoyl)-6-(3-(3-hydroxy-3-methylbut-1-yn-1-yl)-4-(trifluoromethyl)phenyl)cyclohexane-1-carboxylic acid

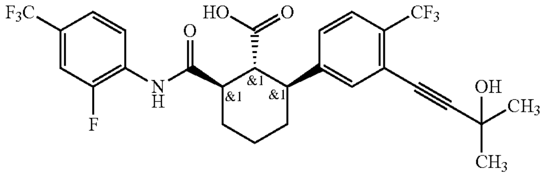 [SMILES: CC(C)(O)C#Cc1cc([C@H]2CCC[C@@H](C(=O)Nc3ccc(C(F)(F)F)cc3F)[C@@H]2C(=O)O)ccc1C(F)(F)F]

A mixture of rac-(1R,2S,6R)-2-(3-bromo-4-(trifluoromethyl)phenyl)-6-((2-fluoro-4-(trifluoromethyl)phenyl)carbamoyl)cyclohexane-1-carboxylic acid Intermediate 38 (50 mg, 0.09 mmol), 2-methylbut-3-yn-2-ol (0.176 mL, 1.80 mmol), triethylamine (0.050 mL, 0.360 mmol) and copper (1) iodide (3.42 mg, 0.018 mmol) in DMF (0.5 mL) was degassed with nitrogen for 2 min. Bis(triphenylphosphine) palladium(II) chloride (12.6 mg, 0.0180 mmol) was added, and the reaction was stirred at 80° C. overnight. The mixture was concentrated and subjected to reverse phase purification (MeCN in $H_2O$, 0.1% formic acid modifier) to afford rac-(1R,2R,6S)-2-((2-fluoro-4-(trifluoromethyl)phenyl)carbamoyl)-6-(3-(3-hydroxy-3-methylbut-1-yn-1-yl)-4-(trifluoromethyl)phenyl)cyclohexane-1-carboxylic acid (22 mg, 0.038 mmol, 42% yield) as an off-white solid. $^1$H NMR (400 MHz, DMSO-$d_6$) δ 11.92 (br s, 1H), 1015 (s, 1H), 8.21 (t, J=8.0 Hz, 1H), 7.72 (d, J=11.2 Hz, 1H), 7.67 (d, J=8.4 Hz, 1H), 7.59-7.52 (m, 2H), 7.46 (d, J=8.0 Hz, 1H), 5.54 (s, 1H), 3.15-2.96 (m, 1H), 2.91-2.75 (m, 2H), 2.08-1.97 (m, 1H), 1.91-1.82 (m, 1H), 180-1.72 (m, 1H), 1.70-1.52 (m, 3H), 1.47 (s, 6H). ES-LCMS m/z 558.0 [M−H]$^-$.

Example 240 rac-(1R,2R,6S)-2-((2-fluoro-4-(trifluoromethyl)phenyl)carbamoyl)-6-(3-(prop-1-yn-1-yl)-4-(trifluoromethyl)phenyl)cyclohexane-1-carboxylic acid

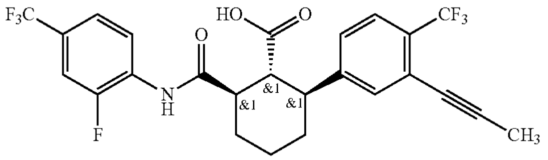 [SMILES: CC#Cc1cc([C@H]2CCC[C@@H](C(=O)Nc3ccc(C(F)(F)F)cc3F)[C@@H]2C(=O)O)ccc1C(F)(F)F]

A mixture of rac-(1R,2S,6R)-2-(3-bromo-4-(trifluoromethyl)phenyl)-6-((2-fluoro-4-(trifluoromethyl)phenyl)carbamoyl)cyclohexane-1-carboxylic acid Intermediate 38 (0.050 g, 0.090 mmol), but-2-ynoic acid (37.8 mg, 0.449 mmol), DBU (0.041 mL, 0.27 mmol), bis(triphenylphosphine)palladium(II) chloride (1.89 mg, 2.70 μmol) and 1,4-bis(diphenylphosphino)butane (1.92 mg, 4.49 μmol) in DMSO (0.5 mL) was degassed with nitrogen for 1 min. The reaction was stirred at 80° C. overnight, concentrated and subjected to reverse phase purification (MeCN in $H_2O$, 0.1% formic acid modifier) to afford rac-(1R,2R,6S)-2-((2-fluoro-4-(trifluoromethyl)phenyl)carbamoyl)-6-(3-(prop-1-yn-1-yl)-4-(trifluoromethyl)phenyl)cyclohexane-1-carboxylic acid (34 mg, 0.066 mmol, 74% yield) as an off-white solid. $^1$H NMR (400 MHz, DMSO-$d_6$) δ 11.89 (br s, 1H), 10.13 (s, 1H), 8.21 (d, J=8.0 Hz, 1H), 7.72 (dd, J=10.8, 1.6 Hz, 1H), 7.65 (d, J=8.0 Hz, 1H), 7.58-7.52 (m, 2H), 7.44 (d, J=8.0 Hz, 1H), 3.05-2.96 (m, 1H), 2.86 (t, J=11.2 Hz, 1H), 2.78 (td, J=11.2, 2.8 Hz, 1H), 2.10 (s, 3H), 2.06-1.98 (m, 1H), 1.92-1.83 (m, 1H), 1.80-1.72 (m, 1H), 1.70-1.43 (m, 3H). ES-LCMS m/z 514.0 [M−H]$^-$.

The following compounds were synthesized in an analogous manner to the preparation described above (Example 83 and Example 84) using the relevant arylamine precursor. Compounds were purified using reverse phase chromatography (MeCN/$H_2O$, basic or acidic modifiers) and resolution on a Chiral column.

| Ex | Structure/Name | $^1$H NMR | LCMS |
|---|---|---|---|
| 241 | 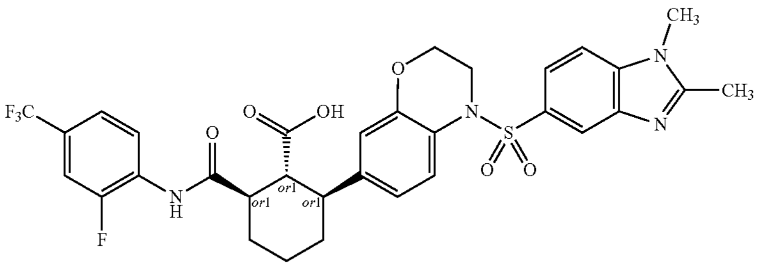 [SMILES: Cc1nc2cc(S(=O)(=O)N3CCOc4cc([C@H]5CCC[C@@H](C(=O)Nc6ccc(C(F)(F)F)cc6F)[C@@H]5C(=O)O)ccc43)ccc2n1C] ISOMER 1 rel-(1R,2S,6R)-2-(4-((1,2-dimethyl-1H-benzo[d]imidazol-5-yl)sulfonyl)-3,4-dihydro-2H-benzo[b][1,4]oxazin-7-yl)-6-((2-fluoro-4-(trifluoromethyl)phenyl)carbamoyl) cyclohexane-1-carboxylic acid ISOMER 1 | $^1$H NMR (400 MHz, DMSO-$d_6$) δ 12.03 (br s, 1H), 10.11 (s, 1H), 8.22 (t, J = 8.0 Hz, 1H), 7.73 (dd, J = 10.8, 1.6 Hz, 1H), 7.67-7.64 (m, 3H), 7.56 (d, J = 8.4 Hz, 1H), 7.38 (dd, J = 8.6, 1.6 Hz, 1H), 6.91 (dd, J = 8.6, 1.6 Hz, 1H), 6.62 (d, J = 2.0 Hz, 1H), 3.94-3.87 (m, 1H), 3.83-3.76 (m, 1H), 3.76 (s, 3H), 3.58-3.54 (m, 1H), 3.46-3.41 (m, 1H), 3.01-2.93 (m, 1H), 2.74 (t, J = 11.2 Hz, 1H), 2.62-2.55 (m, 1H), 2.55 (s, 3H), 2.06-1.98 (m, 1H), 1.89-1.83 (m, 1H), 1.78-1.70 (m, 1H), 1.66-1.46 (m, 3H) | ES-LCMS m/z 675.2 [M + H]+. |
| 242 | 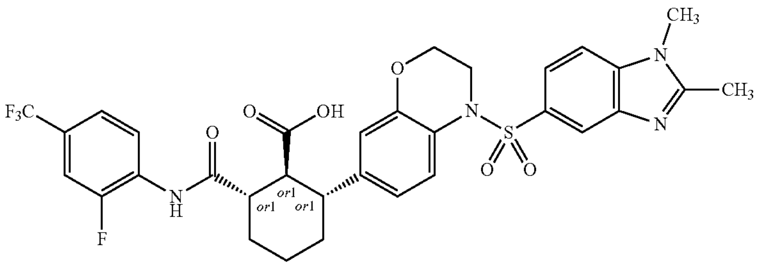 [SMILES: Cc1nc2cc(S(=O)(=O)N3CCOc4cc([C@@H]5CCC[C@H](C(=O)Nc6ccc(C(F)(F)F)cc6F)[C@H]5C(=O)O)ccc43)ccc2n1C] ISOMER 2 rel-(1R,2R,6S)-2-((5-(trifluoromethyl)pyridin-2-yl)carbamoyl)-6-(4-((N,1,2-trimethyl-1H-benzo[d]imidazole)-5-sulfonamido)phenyl)cyclohexane-1-carboxylic acid, ISOMER 2 | $^1$H NMR (400 MHz, DMSO-$d_6$) δ 12.03 (br s, 1H), 10.11 (s, 1H), 8.22 (t, J = 8.0 Hz, 1H), 7.73 (dd, J = 10.8, 1.6 Hz, 1H), 7.67-7.64 (m, 3H), 7.56 (d, J = 8.4 Hz, 1H), 7.38 (dd, J = 8.6, 1.6 Hz, 1H), 6.91 (dd, J = 8.6, 1.6 Hz, 1H), 6.62 (d, J = 2.0 Hz, 1H), 3.94-3.87 (m, 1H), 3.83-3.76 (m, 1H), 3.76 (s, 3H), 3.58-3.54 (m, 1H), 3.46 -3.41 (m, 1H), 3.01-2.93 (m, 1H), 2.74 (t, J = 11.2 Hz, 1H), 2.62-2.55 (m, 1H), 2.55 (s, 3H), 2.06-1.98 (m, 1H), 1.89-1.83 (m, 1H), 1.78-1.70 (m, 1H), 1.66-1.46 (m, 3H) | ES-LCMS m/z 675.4 [M + H]+. |

Example 243 rac-(1R,2S,6R)-2-(4-bromophenyl)-1-fluoro-6-((4-(trifluoromethyl)phenyl)carbamoyl)cyclohexane-1-carboxylic acid

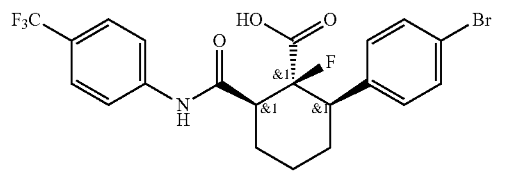 [SMILES: O=C(Nc1ccc(C(F)(F)F)cc1)[C@@H]1CCC[C@H](c2ccc(Br)cc2)[C@@]1(F)C(=O)O]

To a mixture of rac-methyl (1R,2R,6R)-6-(4-bromophenyl)-2-fluoro-2-((4-(trifluoromethyl)phenyl)carbamoyl)cyclohexane-1-carboxylate compound with rac-methyl (1R,2S,6R)-2-(4-bromophenyl)-1-fluoro-6-((4-(trifluoromethyl)phenyl)carbamoyl)cyclohexane-1-carboxylate Intermediate 42 (150 mg, 0.086 mmol) in acetonitrile (10 ml) was added TMS-I (0.12 ml, 0.86 mmol). The reaction was heated to 80° C. for 5 h, diluted with EtOAc (50 mL), washed with 10% sodium thiosulfate (2×20 mL) and brine (20 mL), dried over anhydrous sodium sulfate, filtered, concentrated and subjected to reverse phase purification (0-100% MeCN in $H_2O$, 0.1% ammonium bicarbonate modifier) to afford 40 mg crude compound. This material was purified by Achiral-Prep-SFC (Column: YMC EP-2; 80:20 $CO_2$:IPA with isopropylamine additive) to afford rac-(1R,2S,6R)-2-(4-bromophenyl)-1-fluoro-6-((4-(trifluoromethyl)phenyl)carbamoyl)cyclohexane-1-carboxylic acid (13 mg, 0.026 mmol, 30% yield) as an off-white solid. $^1H$ NMR (400 MHz, DMSO-$d_6$) δ 13.08 (s, 1H), 10.15 (s, 1H), 7.76 (d, J=8.40 Hz, 2H), 7.65-7.63 (m, 2H), 7.48 (d, J=8.00 Hz, 2H), 7.21 (d, J=8.0 Hz, 2H), 3.13 (td, J=20.0, 12.4 Hz, 2H), 2.00-1.89 (m, 4H), 1.69-1.59 (m, 2H). ES-LCMS m/z 488.0 $[M+H]^+$.

Example 245 rel-(1R,2R,6S)-2-((2-fluoro-4-(trifluoromethyl)phenyl)carbamoyl)-6-(3-(5-methyl-1,3,4-oxadiazol-2-yl)-4-(trifluoromethyl)phenyl)cyclohexane-1-carboxylic acid, ISOMER 2

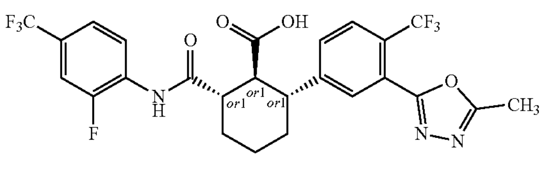 [SMILES: Cc1nnc(-c2cc([C@@H]3CCC[C@H](C(=O)Nc4ccc(C(F)(F)F)cc4F)[C@H]3C(=O)O)ccc2C(F)(F)F)o1]

To a mixture of rac-(1R,2S,6R)-2-(3-bromo-4-(trifluoromethyl)phenyl)-6-((2-fluoro-4-(trifluoromethyl)phenyl)carbamoyl)cyclohexane-1-carboxylic acid Intermediate 38 (85 mg, 0.15 mmol) in toluene (2.4 mL) were added $K_2CO_3$ (211 mg, 1.53 mmol), pivalic acid (4.4 µl, 0.038 mmol), Ruphos Pd G2 (17.80 mg, 0.023 mmol) and 2-methyl-1,3,4-oxadiazole (64.2 mg, 0.764 mmol). The reaction was stirred at 110° C. overnight and subjected to reverse phase purification (40-60% MeCN in $H_2O$, 10 mM ammonium bicarbonate modifier) to afford rac-(1R,2R,6S)-2-((2-fluoro-4-(trifluoromethyl)phenyl)carbamoyl)-6-(3-(5-methyl-1,3,4-oxadiazol-2-yl)-4-(trifluoromethyl)phenyl)cyclohexane-1-carboxylic acid (0.040 g, 0.069 mmol, 45% yield). The racemic material was separated by Chiral-Prep-SFC (Column: Chiralpak IB—N; 85:15 $CO_2$:methanol) to afford the second-eluting compound rel-(1R,2R,6S)-2-((2-fluoro-4-(trifluoromethyl)phenyl)carbamoyl)-6-(3-(5-methyl-1,3,4-oxadiazol-2-yl)-4-(trifluoromethyl)phenyl)cyclohexane-1-carboxylic acid, ISOMER 2. $^1H$ NMR (400 MHz, METHANOL-$d_4$) δ 8.25 (t, J=8.1 Hz, 1H), 7.96-7.85 (m, 2H), 7.77 (d, J=8.3 Hz, 1H), 7.56-7.40 (m, 2H), 3.03 (br s, 3H), 2.65 (s, 3H), 2.21-2.11 (m, 1H), 2.09-1.93 (m, 2H), 1.84-1.62 (m, 3H). ES-LCMS m/z 560.1 $[M+H]^+$.

Example 246 rac-(1R,2R,6S)-2-((2-fluoro-4-(trifluoromethyl)phenyl)carbamoyl)-6-(2-(hydroxymethyl)-4-(trifluoromethyl)phenyl)cyclohexane-1-carboxylic acid

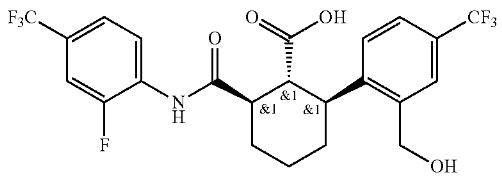 [SMILES: O=C(O)[C@@H]1[C@@H](c2ccc(C(F)(F)F)cc2CO)CCC[C@H]1C(=O)Nc1ccc(C(F)(F)F)cc1F]

To a mixture of rac-(1R,2R,6S)-2-((2-fluoro-4-(trifluoromethyl)phenyl)carbamoyl)-6-(2-formyl-4-(trifluoromethyl)phenyl)cyclohexane-1-carboxylic acid Intermediate 43 (0.030 g, 0.059 mmol) in methanol (1 mL) at 0° C. was added $NaBH_4$ (5.61 mg, 0.148 mmol). The reaction was stirred at rt for 30 min, concentrated and subjected to reverse phase purification (10-100% MeCN in $H_2O$, 0.1% ammonium bicarbonate modifier) to afford rac-(1R,2R,6S)-2-((2-fluoro-4-(trifluoromethyl)phenyl)carbamoyl)-6-(2-(hydroxymethyl)-4-(trifluoromethyl)phenyl)cyclohexane-1-carboxylic acid (7.0 mg, 0.014 mmol, 23% yield) was isolated as a white solid. $^1H$ NMR (400 MHz, DMSO-$d_6$) δ 10.19 (s, 1H), 8.23 (t, J=8.5 Hz, 1H), 7.77-7.48 (m, 5H), 6.60 (br s, 1H), 4.61 (br s, 2H), 3.10-3.02 (m, 1H), 2.99-2.82 (m, 2H), 2.01 (d, J=11.5 Hz, 1H), 1.91-1.80 (m, 1H), 1.76-1.31 (m, 5H). ES-LCMS m/z 506.0 $[M-H]^-$.

Example 247 rac-(1R,2R,6S)-2-((2-fluoro-4-(trifluoromethyl)phenyl)carbamoyl)-6-(4-(trifluoromethyl)phenyl)cyclohexane-1-carboxylic acid

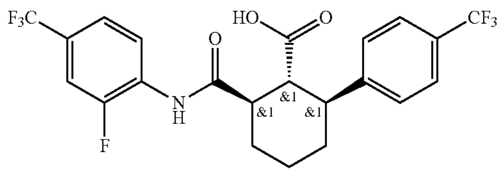 [SMILES: O=C(O)[C@@H]1[C@@H](c2ccc(C(F)(F)F)cc2)CCC[C@H]1C(=O)Nc1ccc(C(F)(F)F)cc1F]

To a mixture of rac-(1R,2S,6R)-2-(3-bromo-4-(trifluoromethyl)phenyl)-6-((2-fluoro-4-(trifluoromethyl)phenyl)carbamoyl)cyclohexane-1-carboxylic acid Intermediate 38 (50 mg, 0.09 mmol) in methanol (5 mL) was added Pd/C (48 mg, 0.045 mmol) at 25° C. under nitrogen atmosphere. The reaction was degassed via vacuum evacuation, then backfilling with hydrogen, and this process was repeated three times. The mixture was placed under hydrogen atmosphere with a tiny clave (5 Kg). After 16 h, the reaction was filtered, concentrated and subjected to reverse phase purification (0-100% MeCN in $H_2O$, 0.1% ammonium bicarbonate modifier) to afford rac-(1R,2R,6S)-2-((2-fluoro-4-(trifluoromethyl)phenyl)carbamoyl)-6-(4-(trifluoromethyl)phenyl) cyclohexane-1-carboxylic acid (0.030 g, 0.063 mmol, 70% yield) as a white solid. $^1$H NMR (400 MHz, DMSO-$d_6$) δ 11.84 (br s, 1H), 10.13 (s, 1H), 8.21 (t, J=8.3 Hz, 1H), 7.72 (dd, J=11.0, 1.5 Hz, 1H), 7.64 (d, J=8.5 Hz, 2H), 7.57-7.47 (m, 3H), 3.08-2.97 (m, 1H), 2.91-2.75 (m, 2H), 2.08-1.72 (m, 3H), 1.68-1.46 (m, 3H). ES-LCMS m/z 475.7 $[M-H]^-$.

The following compound was synthesized in an analogous manner to the preparation described above (Example 93) using the relevant sulfonyl chloride precursor. Compounds were purified using reverse phase chromatography (MeCN/$H_2O$, basic or acidic modifiers).

| Ex | Structure/Name | $^1$H NMR | LCMS |
|---|---|---|---|
| 248 | 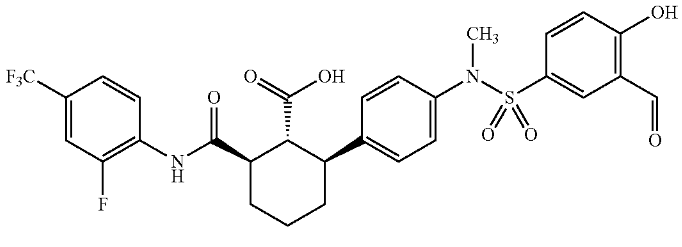 [SMILES: CN(c1ccc([C@H]2CCC[C@@H](C(=O)Nc3ccc(C(F)(F)F)cc3F)[C@@H]2C(=O)O)cc1)S(=O)(=O)c1ccc(O)c(C=O)c1] (1R,2R,6S)-2-((2-fluoro-4-(trifluoromethyl)phenyl)carbamoyl)-6-(4-((3-formyl-4-hydroxy-N-methylphenyl)sulfonamido)phenyl)cyclohexane-1-carboxylic acid | $^1$H NMR (400 MHz, DMSO-$d_6$) δ 11.80 (s, 2H), 10.27 (s, 1H), 10.12 (s, H), 8.22 (t, J = 8.00 Hz, 1H), 7.77 - 7.71 (m, 2H), 7.56 (d, J = 8.40 Hz, 1H), 7.32 (dd, J = 8.80, 2.20 Hz, 1H), 7.22 (d, J = 8.40 Hz, 2H), 7.05 - 7.07 (m, 3H), 3.11 - 2.98 (m, 4H), 2.78 (t, J = 10.80 Hz, 1H), 2.68 - 2.66 (m, 1H), 2.09 - 1.75 (m, 3H), 1.60 - 1.52 (m, 3H) | ES-LCMS m/z 621.0 $[M-H]^-$. |

Example 249 rac-(1R,2S,3R,6R)-3-(ethylamino)-6-((4-isopropylphenyl)carbamoyl)-2-(4-((N,1,2-trimethyl-1H-benzo[d]imidazole)-5-sulfonamido)phenyl)cyclohexane-1-carboxylic acid

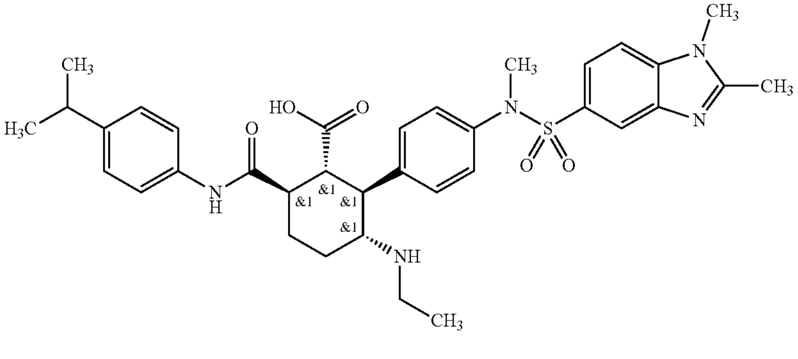 [SMILES: CCN[C@@H]1CC[C@@H](C(=O)Nc2ccc(C(C)C)cc2)[C@H](C(=O)O)[C@H]1c1ccc(N(C)S(=O)(=O)c2ccc3c(c2)nc(C)n3C)cc1]

To a mixture of rac-methyl (1R,2S,3R,6R)-3-(ethylamino)-6-((4-isopropylphenyl)carbamoyl)-2-(4-((N,1,2-trimethyl-1H-benzo[d]imidazole)-5-sulfonamido)phenyl) cyclohexane-1-carboxylate Intermediate 55 (20 mg, 0.030 mmol) in dichloromethane (2 mL) was added $BBr_3$ (1M in DCM, 0.30 mL, 0.30 mmol). After 5 h, the reaction was cooled to 0° C., quenched with ice water (1 mL) concentrated and purified by Prep HPLC (0-100% MeCN in $H_2O$, with 0.1% ammonium bicarbonate) to afford rac-(1R,2S,3R,6R)-3-(ethylamino)-6-((4-isopropylphenyl)carbamoyl)-2-(4-((N,1,2-trimethyl-1H-benzo[d]imidazole)-5-sulfonamido)phenyl)cyclohexane-1-carboxylic acid (7.5 mg, 0.010 mmol, 38% yield) as an off-white solid. $^1$H NMR (400 MHz, DMSO-$d_6$) δ 9.89 (s, 1H), 7.58 (d, J=8.8 Hz, 1H), 7.49-7.46 (m, 3H), 7.22-7.13 (m, 5H), 6.99 (d, J=8.4 Hz, 2H), 3.78 (s, 3H), 3.07 (s, 3H),), 2.90-2.80 (m, 2H), 2.79-2.63 (m, 3H), 2.56 (s, 3H), 2.27-2.03 (m, 2H), 2.02-1.90 (m, 1H), 1.75-1.50 (m, 1H), 1.30-1.10 (m, 6H), 0.79 (t, J=6.8 Hz, 3H), two protons obscured by solvent peaks. ES-LCMS m/z 646.2 $[M+H]^+$.

Example 250

(1R,2R,4R,6S)-2-((2-fluoro-4-(trifluoromethyl)phenyl)carbamoyl)-4-(methoxymethyl)-6-(4-((N,1,2-trimethyl-1H-benzo[d]imidazole)-5-sulfonamido)phenyl)cyclohexane-1-carboxylic acid

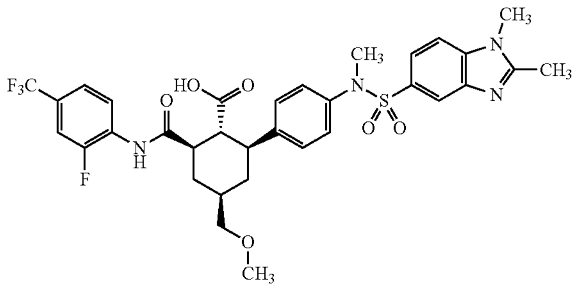 [SMILES: COC[C@@H]1C[C@H](c2ccc(N(C)S(=O)(=O)c3ccc4c(c3)nc(C)n4C)cc2)[C@@H](C(=O)O)[C@H](C(=O)Nc2ccc(C(F)(F)F)cc2F)C1]

To a suspension of rac-(1R,2R,6S)-2-((2-fluoro-4-(trifluoromethyl)phenyl)carbamoyl)-4-(methoxymethyl)-6-(4-(methylamino)phenyl)cyclohexane-1-carboxylic acid Intermediate 45 (325 mg, 0.674 mmol) and 1,2-dimethyl-1H-benzo[d]imidazole-5-sulfonyl chloride (0.330 g, 1.35 mmol) in dichloromethane (0.5 mL) at 0° C. was added pyridine (0.272 mL, 3.37 mmol). After 10 min the reaction was stirred at rt for 1 h, the mixture was concentrated and subjected to reverse phase purification (25-75% MeCN in $H_2O$, 10 nM ammonium bicarbonate modifier) to afford rac-(1R,2R,4R,6S)-2-((2-fluoro-4-(trifluoromethyl)phenyl)carbamoyl)-4-(methoxymethyl)-6-(4-((N,1,2-trimethyl-1H-benzo[d]imidazole)-5-sulfonamido)phenyl)cyclohexane-1-carboxylic acid (0.150 g, 0.206 mmol, 30.6% yield) as an off-white solid. The racemic compound was separated by Chiral-Prep-SFC (Column: YMC Amylose-SA 250×20 mm, 5 μm; 1:1 $CO_2$: 0.5% isopropylamine in IPA) to afford the fourth-eluting peak (1R,2R,4R,6S)-2-((2-fluoro-4-(trifluoromethyl)phenyl)carbamoyl)-4-(methoxymethyl)-6-(4-((N,1,2-trimethyl-1H-benzo[d]imidazole)-5-sulfonamido)phenyl)cyclohexane-1-carboxylic acid (16 mg, 0.023 mmol, 11% yield) as a white solid. $^1$H NMR (400 MHz, DMSO-$d_6$) δ 12.05 (br s, 1H), 10.15 (s, 1H), 8.21 (t, J=8.0 Hz, 1H), 7.72 (dd, J=11.0, 2.0 Hz, 1H), 7.63 (d, J=8.5 Hz, 1H), 7.55 (d, J=8.5 Hz, 1H), 7.50 (d, J=1.5 Hz, 1H), 7.25 (dd, J=8.5, 1.5 Hz, 1H), 7.19 (d, J=8.5 Hz, 2H), 6.96 (d, J=8.5 Hz, 2H), 3.78 (s, 3H), 3.27-3.20 (m, 5H), 3.08-3.00 (m, 4H), 2.79-2.71 (m, 2H), 2.56 (s, 3H), 2.07 (d, J=12.5 Hz, 1H), 1.95-1.83 (m, 1H), 1.80-1.69 (m, 1H), 1.36-1.23 (m, 2H). ES-LCMS m/z 691.2 $[M+H]^+$. Relative Stereochemistry was assigned by 2D NMR structure elucidation, and absolute stereochemistry was assigned by known SAR correlation.

The following compounds were synthesized in an analogous manner to the preparation described above (Example 183) using the relevant benzyl ester-protected precursors.

| Ex | Structure/Name | $^1$H NMR | LCMS |
|---|---|---|---|
| 251 | 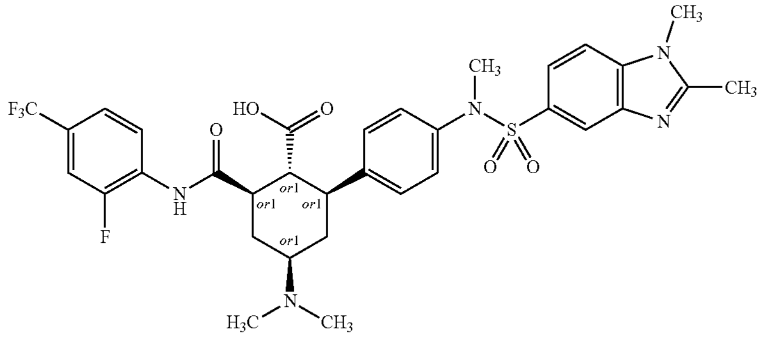 [SMILES: Cc1nc2cc(S(=O)(=O)N(C)c3ccc([C@H]4C[C@@H](N(C)C)C[C@@H](C(=O)Nc5ccc(C(F)(F)F)cc5F)[C@@H]4C(=O)O)cc3)ccc2n1C] ISOMER 1 rel-(1R,2R,4R,6S)-4-(dimethylamino)-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylic acid ISOMER 1 | $^1$H NMR (400 MHz, DMSO-$d_6$) δ 12.06 (s, 1H), 10.16 (s, 1H), 8.25 (t, J = 8.0 Hz, 1H), 7.73 (dd, J = 11.0, 1.6 Hz, 1H), 7.64 (d, J = 8.4 Hz, 1H), 7.56 (d, J = 8.8 Hz, 1H), 7.51 (d, J = 1.2 Hz, 1H), 7.27 - 7.21 (m, 3H), 6.97 (d, J = 8.4 Hz, 2H), 3.78 (s, 3H), 3.06 (s, 3H), 3.05 (m, 1H), 2.74 (d, J = 9.6 Hz, 2H), 2.57 (s, 3H), 2.54 - 2.53 (m, 1H), 2.21 (s, 6H), 2.09 (d, J = 6.4 Hz, 1H), 1.82 (d, J = 12.0 Hz, 1H), 1.60 (q, J = 11.2 Hz, 1H), 1.50 (q, J = 12.0 Hz, 1H) | ES-LCMS m/z 688.2 [M + H]+. |
| 252 | 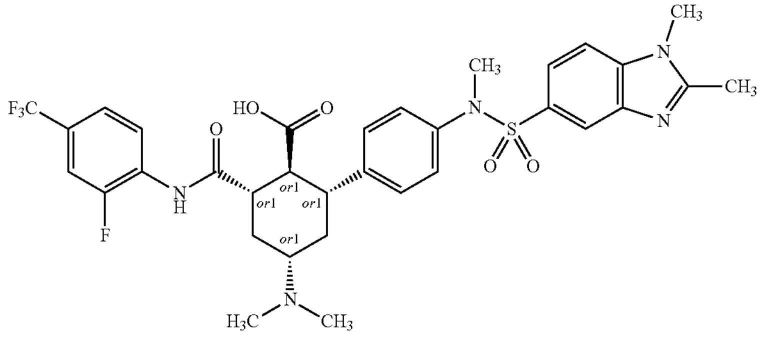 [SMILES: Cc1nc2cc(S(=O)(=O)N(C)c3ccc([C@@H]4C[C@H](N(C)C)C[C@H](C(=O)Nc5ccc(C(F)(F)F)cc5F)[C@H]4C(=O)O)cc3)ccc2n1C] ISOMER 2 rel-(1R,2R,4R,6S)-4-(dimethylamino)-2-((2- | $^1$H NMR (400 MHz, DMSO-$d_6$) δ 12.06 (s, 1H), 10.16 (s, 1H), 8.25 (t, J = 8.0 Hz, 1H), 7.73 (dd, J = 11.0, 1.6 Hz, 1H), 7.64 (d, J = 8.4 Hz, 1H), 7.56 (d, J = 8.8 Hz, 1H), 7.51 (d, J = 1.2 Hz, 1H), 7.27 - 7.21 (m, 3H), 6.97 (d, J = 8.4 Hz, 2H), 3.78 (s, 3H), 3.06 (s, 3H), 3.05 (m, 1H), 2.74 (d, J = 9.6 Hz, 2H), 2.57 (s, 3H), 2.54 - 2.53 (m, 1H), 2.21 (s, 6H), 2.09 (d, J = 6.4 Hz, 1H), 1.82 (d, J = 12.0 Hz, 1H), 1.60 (q, J = 11.2 Hz, 1H), 1.50 (q, J = 12.0 Hz, 1H) | ES-LCMS m/z 688.2 [M + H]+. |

-continued

| Ex | Structure/Name | $^1$H NMR | LCMS |
|---|---|---|---|
| | fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylic acid ISOMER 1 | | |
| 253 | 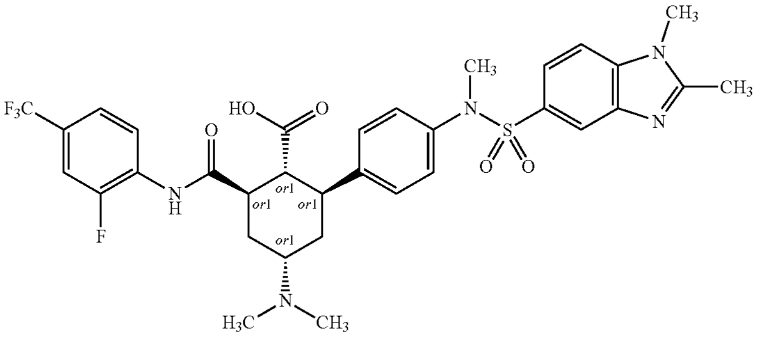 [SMILES: Cc1nc2cc(S(=O)(=O)N(C)c3ccc([C@H]4C[C@H](N(C)C)C[C@@H](C(=O)Nc5ccc(C(F)(F)F)cc5F)[C@@H]4C(=O)O)cc3)ccc2n1C] ISOMER 1 rel-(1R,2R,4S,6S)-4-(dimethylamino)-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylic acid ISOMER 1 | $^1$H NMR (400 MHz, DMSO-$d_6$) δ 12.16 (s, 1H), 10.20 (s, 1H), 8.09 (t, J = 8.00 Hz, 1H), 7.72 (d, J = 1.60 Hz, 1H), 7.69 (d, J = 1.60 Hz, 1H), 7.60 - 7.48 (m, 2H), 7.26 (d, J = 2.00 Hz, 1H), 7.24 (d, J = 1.60 Hz, 2H), 6.97 (d, J = 8.40 Hz, 2H), 3.79 (s, 3H), 3.50 - 3.40 (m, 3H), 3.20 - 3.10 (m, 1H), 3.06 (s, 3H), 2.84 - 2.78 (m, 1H), 2.57 (s, 3H), 2.26 (s, 5.55H), 2.23 - 2.10 (m,2.5H), 2.00 - 1.90 (m, 1H), 1.78 - 1.65 (m, 2H) | ES-LCMS m/z 690.2 [M + H]+. |
| 254 | 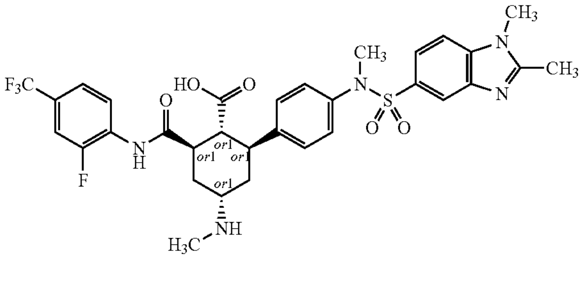 [SMILES: CN[C@H]1C[C@H](c2ccc(N(C)S(=O)(=O)c3ccc4c(c3)nc(C)n4C)cc2)[C@@H](C(=O)O)[C@H](C(=O)Nc2ccc(C(F)(F)F)cc2F)C1] ISOMER 1 rel-(1R,2R,4S,6S)-4-(dimethylamino)-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylic acid ISOMER 1 | $^1$H NMR (400 MHz, DMSO-$d_6$) δ 10.07 (s, 1H), 8.15 (t, J = 8.4 Hz, 1H), 7.72 (dd, J = 10.8, 1.6 Hz, 1H), 7.64 (d, J = 8.4 Hz, 1H), 7.56 - 7.51 (m, 2H), 7.26 - 7.24 (m, 1H), 7.18 (d, J = 8.4 Hz, 2H), 6.97 (d, J = 8.8 Hz, 2H), 3.78 (s, 3H), 3.38 - 3.32 (m, 2H), 3.19 - 3.14 (m, 1H), 3.08 (s, 3H), 2.92 (m, 1H), 2.77 (t, J = 11.6 Hz, 1H), 2.57 (s, 3H), 2.04 (d, J = 13.2 Hz, 1H), 1.78 - 1.69 (m, 3H), four protons obscured by solvent peaks | ES-LCMS m/z 676.0 [M + H]+. |
| 255 | 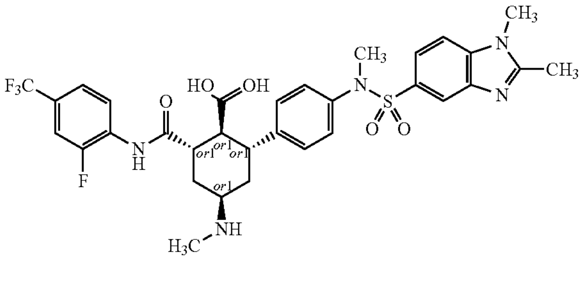 [SMILES: CN[C@H]1C[C@H](C(=O)Nc2ccc(C(F)(F)F)cc2F)[C@@H](C(=O)O)[C@H](c2ccc(N(C)S(=O)(=O)c3ccc4c(c3)nc(C)n4C)cc2)C1] ISOMER 2 rel-(1R,2R,4S,6S)-4-(dimethylamino)-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylic acid ISOMER 1 | $^1$H NMR (400 MHz, DMSO-$d_6$) δ 10.07 (s, 1H), 8.15 (t, J = 8.4 Hz, 1H), 7.72 (dd, J = 10.8, 1.6 Hz, 1H), 7.64 (d, J = 8.4 Hz, 1H), 7.56 - 7.51 (m, 2H), 7.26 - 7.24 (m, 1H), 7.18 (d, J = 8.4 Hz, 2H), 6.97 (d, J = 8.8 Hz, 2H), 3.78 (s, 3H), 3.38 - 3.32 (m, 2H), 3.19 - 3.14 (m, 1H), 3.08 (s, 3H), 2.92 (m, 1H), 2.77 (t, J = 11.6 Hz, 1H), 2.57 (s, 3H), 2.04 (d, J = 13.2 Hz, 1H), 1.78 - 1.69 (m, 3H), four protons obscured by solvent peaks | ES-LCMS m/z 676.0 [M + H]+. |

-continued

| Ex | Structure/Name | $^1$H NMR | LCMS |
| --- | --- | --- | --- |
| 256 | 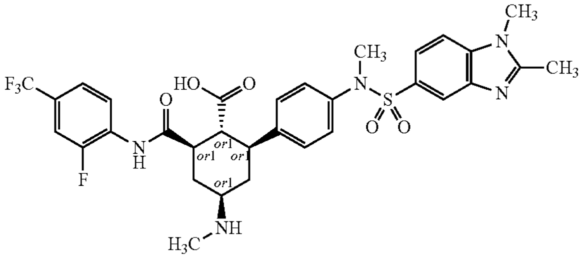 [SMILES: CN[C@@H]1C[C@H](c2ccc(N(C)S(=O)(=O)c3ccc4c(c3)nc(C)n4C)cc2)[C@@H](C(=O)O)[C@H](C(=O)Nc2ccc(C(F)(F)F)cc2F)C1] ISOMER 1 rel-(1R,2R,4R,6S)-4-(dimethylamino)-2-((2-fluoro-4-(trifluoromethyl)phenyl)carbamoyl)-6-(4-((N,1,2-trimethyl-1H-benzo[ d] imidazole)-5-sulfonamido)phenyl)cyclohexane-1-carboxylic acid ISOMER 1 | $^1$H NMR (400 MHz, DMSO-$d_6$) δ 10.23 (br s, 1H), 8.23 (t, J = 8.0 Hz, 1H), 7.72 (d, J = 5.2 Hz, 1H), 7.65 (d, J = 8.4 Hz, 1H), 7.57 (d, J = 8.4 Hz, 1H), 7.50 (s, 1H), 7.27 (dd, J = 8.6, 1.6 Hz, 1H), 7.20 (d, J = 8.0 Hz, 1H), 6.99 (d, J = 8.4 Hz, 2H), 4.58 (s, 1H), 3.78 (s, 3H), 3.49 - 3.43 (m, 2H), 3.11 - 3.08 (m, 1H), 3.05 (s, 3H), 2.88 - 2.79 (m, 1H), 2.79 - 2.71 (m, 2H), 2.51 (m, 3H), 2.43 (s, 3H), 2.33 - 2.28 (m, 1H), 2.08 - 2.03 (m, 1H), 1.53 - 1.46 (m, 2H) | ES-LCMS m/z 676.0 [M + H]+. |
| 257 | 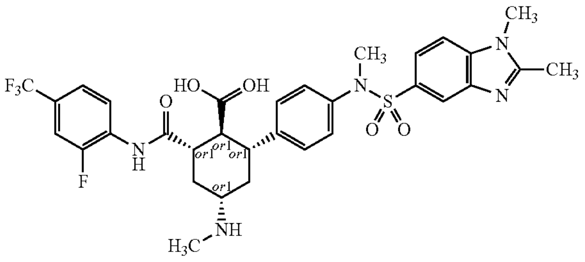 [SMILES: CN[C@@H]1C[C@H](C(=O)Nc2ccc(C(F)(F)F)cc2F)[C@@H](C(=O)O)[C@H](c2ccc(N(C)S(=O)(=O)c3ccc4c(c3)nc(C)n4C)cc2)C1] ISOMER 2 rel-(1R,2R,4R,6S)-4-(dimethylamino)-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylic acid ISOMER 2 | $^1$H NMR (400 MHz, DMSO-$d_6$) δ 10.23 (br s, 1H), 8.23 (t, J = 8.0 Hz, 1H), 7.72 (d, J = 5.2 Hz, 1H), 7.65 (d, J = 8.4 Hz, 1H), 7.57 (d, J = 8.4 Hz, 1H), 7.50 (s, 1H), 7.27 (dd, J = 8.6, 1.6 Hz, 1H), 7.20 (d, J = 8.0 Hz, 1H), 6.99 (d, J = 8.4 Hz, 2H), 4.58 (s, 1H), 3.78 (s, 3H), 3.49 - 3.43 (m, 2H), 3.11 - 3.08 (m, 1H), 3.05 (s, 3H), 2.88 - 2.79 (m, 1H), 2.79 - 2.71 (m, 2H), 2.51 (m, 3H), 2.43 (s, 3H), 2.33 - 2.28 (m, 1H), 2.08 - 2.03 (m, 1H), 1.53 - 1.46 (m, 2H) | ES-LCMS m/z 676.0 [M + H]+. |

Example 258 and Example 259 rel-(1R,2R,6S)-2-((2-fluoro-4-(trifluoromethyl)phenyl)carbamoyl)-6-(4-((2-methyl-1H-benzo[d]imidazole)-5-sulfonamido)phenyl)cyclohexane-1-carboxylic acid ISOMER 1 and ISOMER 2

ISOMER 1 and ISOMER 2

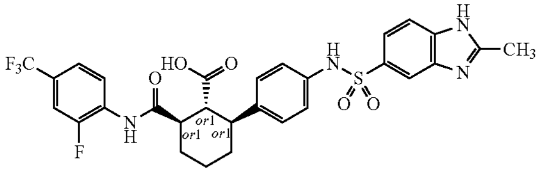

To a mixture of rac-(1R,2S,6R)-2-(4-aminophenyl)-6-((2-fluoro-4-(trifluoromethyl)phenyl)carbamoyl)cyclohexane-1-carboxylic acid Intermediate 35 (110 mg, 0.26 mmol) in dichloromethane (2 mL) at 0° C. were added pyridine (0.060 mL, 0.78 mmol) and 2-methyl-1H-benzo[d]imidazole-5-sulfonyl chloride hydrochloride (104 mg, 0.389 mmol). The reaction was stirred at 0° C. for 1 h and then stirred at rt. After 16 h, the mixture was concentrated and purified by reverse phase chromatography (0-100% MeCN in $H_2O$, 0.1% formic acid modifier) to afford (rac-(1R,2R,6S)-2-((2-fluoro-4-(trifluoromethyl)phenyl)carbamoyl)-6-(4-((2-methyl-1H-benzo[d]imidazole)-5-sulfonamido)phenyl)cyclohexane-1-carboxylic acid (0.11 g, 0.16 mmol, 60% yield) as a off-white solid. $^1$H-NMR (400 MHz, DMSO-$d_6$): δ 12.59 (br s, 1H), 12.02 (br s, 1H), 10.06 (s, 2H), 8.19 (t, J=9.20 Hz, 1H), 7.82 (s, 1H), 7.72 (d, J=1.60 Hz, 1H), 7.55-7.49 (m, 3H), 7.08 (d, J=8.80 Hz, 2H), 6.96 (d, J=8.80 Hz, 2H), 2.95 (t, J=8.80 Hz, 1H), 1.99-1.94 (m, 1H), 1.85-1.78 (m, 1H), 1.68-1.63 (m, 1H), 1.50-1.43 (m, 3H), five protons obscured by solvent peaks. The racemic compound was purified by chiral SFC (YMC Amylose-C 250×30 mm, 5 μm; 70:30 $CO_2$: 0.5% isopropyl amine in IPA) to afford:

Example 258, the first-eluting isomer: rel-(1R,2R,6S)-2-((2-fluoro-4-(trifluoromethyl)phenyl)carbamoyl)-6-(4-((2-methyl-1H-benzo[d]imidazole)-5-sulfonamido)phenyl)cyclohexane-1-carboxylic acid ISOMER 1 (81 mg, 0.10 mmol, 45% yield). ES-LCMS m/z 619.0 $[M+H]^+$.

Example 259, the second-eluting isomer: rel-(1R,2R,6S)-2-((2-fluoro-4-(trifluoromethyl)phenyl)carbamoyl)-6-(4-((2-methyl-1H-benzo[d]imidazole)-5-sulfonamido)phenyl) cyclohexane-1-carboxylic acid ISOMER 2 (23.0 mg, 0.040 mmol, 22% yield). ES-LCMS m/z 619.0 $[M+H]^+$.

Example 260

(1R,2R,6S)-2-((2-fluoro-4-(trifluoromethyl)phenyl) carbamoyl)-6-(4-((N-methyl-1,2,3,4-tetrahydroisoquinoline)-7-sulfonamido)phenyl)cyclohexane-1-carboxylic aid hydrochloride

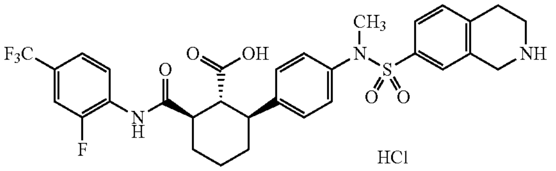 [SMILES: CN(c1ccc([C@H]2CCC[C@@H](C(=O)Nc3ccc(C(F)(F)F)cc3F)[C@@H]2C(=O)O)cc1)S(=O)(=O)c1ccc2c(c1)CNCC2 ; Cl]

HCl

To a mixture of (1R,2R,6S)-2-((2-fluoro-4-(trifluoromethyl)phenyl)carbamoyl)-6-(4-((N-methyl-2-(2,2,2-trifluoroacetyl)-1,2,3,4-tetrahydroisoquinoline)-7-sulfonamido) phenyl)cyclohexane-1-carboxylic acid Example 108 (55 mg, 0.060 mmol) in methanol (2 mL) was added a solution of potassium carbonate (17 mg, 0.12 mmol) in water (0.7 mL). After 1 h, the reaction was concentrated to remove methanol, and 1M aq HCl was added dropwise until pH ~3. The resulting solid was collected by filtration, rinsed with water and triturated with DMSO (1 mL). This material was rinsed with MeCN to give (1R,2R,6S)-2-((2-fluoro-4-(trifluoromethyl)phenyl)carbamoyl)-6-(4-((N-methyl-1,2,3,4-tetrahydroisoquinoline)-7-sulfonamido)phenyl)cyclohexane-1-carboxylic acid hydrochloride (23 mg, 0.034 mmol, 54% yield) as a white solid. $^1$H NMR (400 MHz, DMSO-$d_6$) δ 8.27 (br t, J=8.3 Hz, 1H), 7.69 (br d, J=11.2 Hz, 1H), 7.54 (br d, J=8.8 Hz, 1H), 7.28-7.13 (m, 4H), 7.06-6.92 (m, 3H), 3.81 (br s, 2H), 3.12-3.07 (m, 3H), 3.01-2.85 (m, 3H), 2.79-2.62 (m, 4H), 2.02-1.95 (m, 1H), 1.85 (br d, J=3.9 Hz, 1H), 1.74-1.67 (m, 1H), 1.56-1.42 (m, 3H). ES-LCMS m/z 634.2 [M+H]$^+$.

Example 261

(1R,2R,6S)-2-((2-fluoro-4-(trifluoromethyl)phenyl) carbamoyl)-6-(4-((N-methyl-3-(piperidin-4-yl)phenyl)sulfonamido)phenyl)cyclohexane-1-carboxylic acid

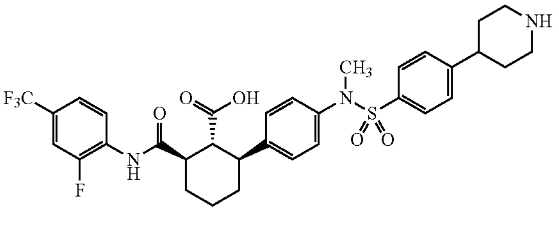 [SMILES: CN(c1ccc([C@H]2CCC[C@@H](C(=O)Nc3ccc(C(F)(F)F)cc3F)[C@@H]2C(=O)O)cc1)S(=O)(=O)c1ccc(C2CCNCC2)cc1]

To a mixture of (1R,2S,6R)-2-(4-((3-(1-(tert-butoxycarbonyl)piperidin-4-yl)-N-methylphenyl)sulfonamido)phenyl)-6-((2-fluoro-4-(trifluoromethyl)phenyl)carbamoyl)cyclohexane-1-carboxylic acid Example 115 (198 mg, 234 μmol) in dichloromethane (5 mL) at 0° C. was added TFA (1 mL), and the reaction was stirred at 22° C. After 1 hour, the mixture was diluted with methanol (50 mL), concentrated and purified by reverse phase chromatography (25-65% MeCN in $H_2O$, 0.1% formic acid modifier) to afford (1R,2R,6S)-2-((2-fluoro-4-(trifluoromethyl)phenyl)carbamoyl)-6-(4-((N-methyl-3-(piperidin-4-yl)phenyl)sulfonamido)phenyl)cyclohexane-1-carboxylic acid (71 mg, 0.11 mmol, 46% yield) as a white solid. $^1$H NMR (400 MHz, DMSO-$d_6$) δ 9.97 (s, 1H), 8.32 (t, J=8.1 Hz, 1H), 8.18 (s, 1H), 7.72-7.66 (m, 2H), 7.60 (t, J=7.6 Hz, 1H), 7.57-7.51 (m, 2H), 7.22 (d, J=8.3 Hz, 2H), 6.90 (br d, J=7.8 Hz, 2H), 6.51 (s, 1H), 3.33 (br d, J=10.8 Hz, 1H), 3.18 (br d, J=11.7 Hz, 1H), 2.98 (s, 3H), 2.95-2.87 (m, 1H), 2.82-2.67 (m, 4H), 2.66-2.56 (m, 1H), 1.97 (br d, J=9.8 Hz, 1H), 1.88-1.77 (m, 1H), 1.71-1.43 (m, 8H), 1.40-1.22 (m, 1H). ES-LCMS m/z 662.3 [M+H]$^+$.

Example 262

(1R,2R,6S)-2-((2-fluoro-4-(trifluoromethyl)phenyl) carbamoyl)-6-(4-((N-methyl-3-((S)-piperidin-3-yl) phenyl)sulfonamido)phenyl)cyclohexane-1-carboxylic acid

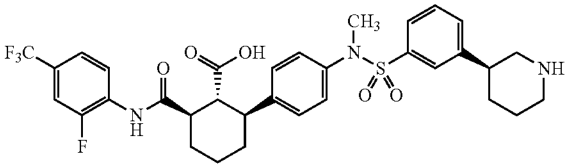 [SMILES: CN(c1ccc([C@H]2CCC[C@@H](C(=O)Nc3ccc(C(F)(F)F)cc3F)[C@@H]2C(=O)O)cc1)S(=O)(=O)c1cccc([C@@H]2CCCNC2)c1]

To a mixture of (1R,2R,6S)-2-((2-fluoro-4-(trifluoromethyl)phenyl)carbamoyl)-6-(4-(methylamino)phenyl)cyclohexane-1-carboxylic acid Intermediate 7, alternate route, Step 3 (118 mg, 0.270 mmol) and pyridine (64.1 mg, 0.810 mmol) in dichloromethane (3 mL) at 0° C. was added tert-butyl (S)-3-(3-(chlorosulfonyl)phenyl)piperidine-1-carboxylate (0.180 g, 0.387 mmol) in dichloromethane (3 mL). After 19 h, the reaction was warmed to 22° C. over 30 min. After 3 h, the mixture was diluted with sat. aq. $NaHCO_3$ and DCM. The phases were separated, and the aqueous phase was extracted with DCM (2 X). The combined organic phases were dried over $MgSO_4$, filtered, concentrated, suspended in dichloromethane (3 mL) and cooled to 0° C. TFA (1 mL) was added, and the reaction mixture was stirred at 22° C. After 1 h, the mixture was diluted with methanol (20 mL), concentrated and subjected to reverse phase purification (25-65% gradient acetonitrile in water with 0.1% formic acid) to afford (1R,2R,6S)-2-((2-fluoro-4-(trifluoromethyl) phenyl)carbamoyl)-6-(4-((N-methyl-3-((S)-piperidin-3-yl) phenyl)sulfonamido)phenyl)cyclohexane-1-carboxylic acid (35 mg, 48 μmol, 18% yield) as a white solid. $^1$H NMR (400 MHz, DMSO-$d_6$) δ 9.81 (s, 1H), 8.37 (t, J=8.1 Hz, 1H), 7.77-7.51 (m, 6H), 7.19 (br d, J=8.3 Hz, 2H), 6.82 (br d, J=7.8 Hz, 2H), 6.43 (s, 1H), 2.97 (s, 3H), 2.93-2.60 (m, 6H), 2.38 (br t, J=12.7 Hz, 1H), 1.96-1.38 (m, 11H), 1.37-1.20 (m, 1H). ES-LCMS m/z 662.2 [M+H]$^+$.

The following compound was synthesized in an analogous manner to the preparation described above (Example 262) using the relevant BOC-protected sulfonyl chloride precursor.

| Ex | Structure/Name | $^1$H NMR | LCMS |
|---|---|---|---|
| 263 | 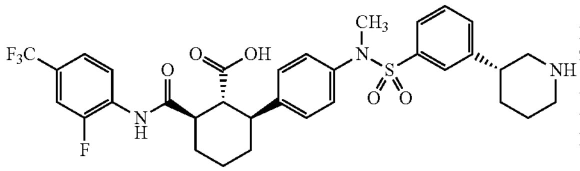 (1R,2R,6S)-2-((2-fluoro-4-(trifluoromethyl)phenyl)carbamoyl)-6-(4-((N-methyl-3-((R)-piperidin-3-yl)phenyl)sulfonamido)phenyl)cyclohexane-1-carboxylic acid | 1H NMR (400 MHz, DMSO-$d_6$) δ 9.84 (s, 1H), 8.35 (t, J = 8.1 Hz, 1H), 7.74 - 7.67 (m, 2H), 7.63(t, J = 7.6 Hz, 1H), 7.60 - 7.57 (m, 1H), 7.56 - 7.50 (m, 1H), 7.22 (d,J = 8.3 Hz, 2H), 6.89 (d, J = 8.3 Hz, 2H), 6.42 (s, 1H), 3.05 (br d, J = 12.2 Hz, 1H), 2.98 (s, 3H), 2.95 - 2.65 (m, 6H), 2.60 - 2.54 (m, 1H), 2.18 (br t, J = 12.5 Hz, 1H), 1.94 - 1.78 (m, 3H), 1.78 - 1.63 (m, 3H), 1.63 - 1.36 (m, 5H) | ES-LCMS m/z 666.2 [M + H]+. |

Example 265

(1R,2R,6S)-2-((2-fluoro-4-(trifluoromethyl)phenyl)carbamoyl)-6-(4-((N-methyl-7-(4-methylpiperazin-1-yl)benzofuran)-5-sulfonamido)phenyl)cyclohexane-1-carboxylic acid

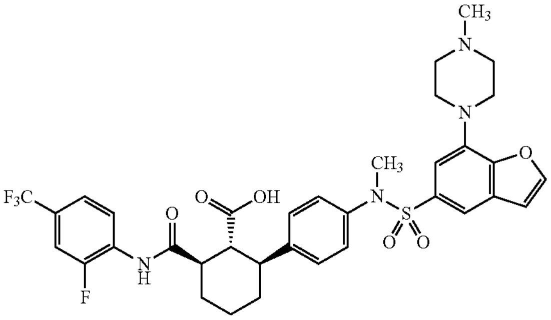 [SMILES: CN1CCN(c2cc(S(=O)(=O)N(C)c3ccc([C@H]4CCC[C@@H](C(=O)Nc5ccc(C(F)(F)F)cc5F)[C@@H]4C(=O)O)cc3)cc3ccoc23)CC1]

A mixture of (1R,2R,6S)-2-((2-fluoro-4-(trifluoromethyl)phenyl)carbamoyl)-6-(4-((7-iodo-N-methylbenzofuran)-5-sulfonamido)phenyl)cyclohexane-1-carboxylic acid Example 117 (42.0 mg, 56.4 μmol) in DMF (10 mL) was degassed with nitrogen, then treated with cesium carbonate (55.1 mg, 169 μmol), 1-methylpiperazine (5.65 mg, 56.4 μmol) and tBuBrettPhos Pd G3 (2.89 mg, 3.38 μmol). The reaction was heated at 60° C. for 2 hours, concentrated and subjected to reverse phase purification (30-85% gradient acetonitrile in water with 0.1% formic acid) to afford (1R,2R,6S)-2-((2-fluoro-4-(trifluoromethyl)phenyl)carbamoyl)-6-(4-((N-methyl-7-(4-methylpiperazin-1-yl)benzofuran)-5-sulfonamido)phenyl)cyclohexane-1-carboxylic acid (4.0 mg, 5.6 μmol, 9.9% yield) as a pale yellow solid. $^1$H NMR (400 MHz, METHANOL-$d_4$) δ=8.38 (t, J=8.3 Hz, 1H), 7.94 (d, J=2.4 Hz, 1H), 7.90 (d, J=1.5 Hz, 1H), 7.54-7.47 (m, 2H), 7.27 (d, J=8.8 Hz, 2H), 7.07 (d, J=2.4 Hz, 1H), 6.96 (d, J=8.8 Hz, 2H), 6.21 (d, J=2.0 Hz, 1H), 3.34 (d, J=1.5 Hz, 4H), 3.27-3.18 (m, 3H), 3.08 (s, 4H), 2.99-2.93 (m, 2H), 2.85 (br d, J=3.4 Hz, 1H), 2.56 (s, 3H), 2.03 (br dd, J=3.7, 12.5 Hz, 1H), 1.94 (td, J=2.9, 12.8 Hz, 1H), 1.84-1.73 (m, 2H), 1.63 (td, J=3.4, 12.8 Hz, 1H), 1.43-1.35 (m, 1H). ES-LCMS m/z 717.4 $[M+H]^+$.

The following compounds were synthesized in an analogous manner to the preparation described above (Example 207) using the relevant BOC-protected sulfonyl chloride precursors, followed by, where necessary, chiral separation.

| Ex | Structure/Name | $^1$H NMR | LCMS |
|---|---|---|---|
| 266 | 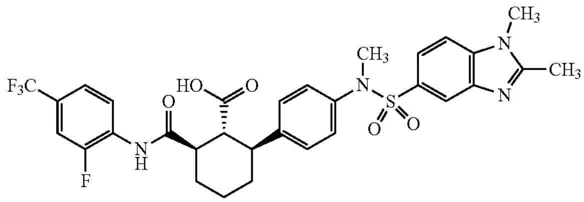 [SMILES: Cc1nc2cc(S(=O)(=O)N(C)c3ccc([C@H]4CCC[C@@H](C(=O)Nc5ccc(C(F)(F)F)cc5F)[C@@H]4C(=O)O)cc3)ccc2n1C] (1R,2S,6R)-2-(4-((2-amino-N,1-dimethyl-1H-benzo[ d] imidazole)-5-sulfonamido)phenyl)-6-((2-fluoro-4-(trifluoromethyl)phenyl)carbamoyl)cyclohexane-1-carboxylic acid | $^1$H NMR (400 MHz, DMSO-$d_6$) δ 12.3 (br s, 1H), 10.12 (s, 1H), 8.7 (br s, 2H), 8.21 (t, J = 8.0 Hz, 1H), 7.73 (dd, J = 11.0, 1.6 Hz, 1H), 7.56 (d, J = 8.4 Hz, 2H), 7.46 (s, 1H), 7.24 (d, J = 2.4 Hz, 3H), 7.00 (d, J = 8.4 Hz, 2H), 3.64 (s, 3H), 3.10 (s, 3H), 3.05 - 2.98 (m, 1H), 2.79 (t, J = 10.8 Hz, 1H), 2.72 - 2.67 (m, 1H), 2.10 - 1.95 (m, 1H), 1.92 - 1.81 (m, 1H), 1.80 - 1.72 (m, 1H), 1.68 - 1.50 (m, 3H) | ES-LCMS m/z 646.0 $[M - H]^-$. |

-continued

| Ex | Structure/Name | $^1$H NMR | LCMS |
| --- | --- | --- | --- |
| 267 | 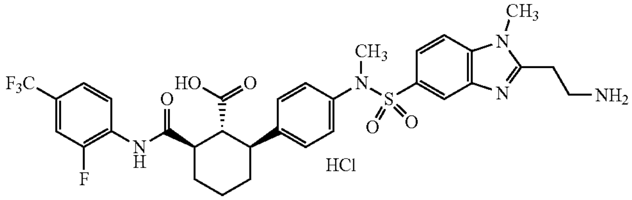 [SMILES: CN(c1ccc([C@H]2CCC[C@@H](C(=O)Nc3ccc(C(F)(F)F)cc3F)[C@@H]2C(=O)O)cc1)S(=O)(=O)c1ccc2c(c1)nc(CCN)n2C ; Cl] (1R,2S,6R)-2-(4-((2-(2-aminoethyl)-N,1-dimethyl-1H-benzo[ d] imidazole)-5-sulfonamido)phenyl)-6-((2-fluoro-4-(trifluoromethyl)phenyl) carbamoyl)cyclohexane-1-carboxylic acid hydrochloride | $^1$H NMR (400 MHz, DMSO-$d_6$) δ 10.14 (s, 1H), 8.20 - 8.17 (m, 4H), 7.79 (d, J = 1.6 Hz, 1H), 7.76 (d, J = 8.4 Hz, 1H), 7.72 (dd, J = 10.8, 1.6 Hz, 1H), 7.55 (d, J = 8.4 Hz, 1H), 7.26 (dd, J = 8.6, 1.6 Hz, 1H), 7.21 (d, J = 8.4 Hz, 2H), 6.98 (d, J = 8.4 Hz, 2H), 3.85 (s, 3H), 3.34 (m, 4H), 3.08 (s, 3H), 2.99 - 2.96 (m, 1H), 2.78 (t, J = 10.8 Hz, 1H), 2.69 - 2.65 (m, 1H), 2.02 (br d, J = 7.6 Hz, 1H), 1.88 ( br d, J = 3.2 Hz, 1H), 1.75 (br d, J = 10.4 Hz, 1H), 1.56 - 1.51 (m, 3H) | ES-LCMS m/z 676.2 [M + H]$^+$. |
| 268 | 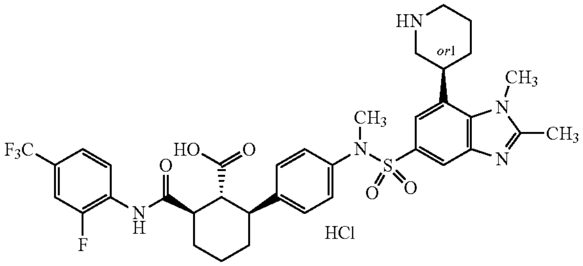 [SMILES: Cc1nc2cc(S(=O)(=O)N(C)c3ccc([C@H]4CCC[C@@H](C(=O)Nc5ccc(C(F)(F)F)cc5F)[C@@H]4C(=O)O)cc3)cc([C@@H]3CCCNC3)c2n1C ; Cl] ISOMER 1 (1R,2R,6S)-2-((2-fluoro-4-(trifluoromethyl)phenyl)carbamoyl)-6-(4-((N,1,2-trimethyl-7-((S*)-piperidin-3-yl)-1H-benzo[d]imidazole)-5-sulfonamido)phenyl)cyclohexane-1-carboxylic acid hydrochloride, ISOMER 1 | $^1$H NMR (400 MHz, DMSO-$d_6$) δ 10.12 (s, 1H), 8.80 (d, J = 9.0 Hz, 1H), 8.23 - 8.13 (m, 1H), 7.72 (d, J = 11.0 Hz, 1H), 7.61 - 7.50 (m, 2H), 7.23 (d, J = 8.5 Hz, 2H), 6.94 (d, J = 8.5 Hz, 2H), 4.01 (s, 3H), 3.97 - 3.87 (m, 1H), 3.02 (s, 3H), 3.01 - 2.93 (m, 2H), 2.85 - 2.77 (m, 1H), 2.75 - 2.68 (m, 1H), 2.62 (s, 3H), 2.10 - 1.99 (m, 2H), 1.93 - 1.75 (m, 6H), 1.70 - 1.48 (m, 5H) | ES LCMS m/z 730.4 [M + H]$^+$. |
| 269 | 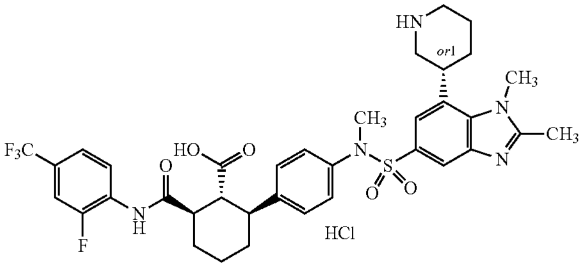 [SMILES: Cc1nc2cc(S(=O)(=O)N(C)c3ccc([C@H]4CCC[C@@H](C(=O)Nc5ccc(C(F)(F)F)cc5F)[C@@H]4C(=O)O)cc3)cc([C@H]3CCCNC3)c2n1C ; Cl] ISOMER 2 (1R,2R,6S)-2-((2-fluoro-4-(trifluoromethyl)phenyl)carbamoyl)-6-(4-((N,1,2-trimethyl-7-((R*)-piperidin-3-yl)-1H-benzo[d]imidazole)-5-sulfonamido)phenyl)cyclohexane-1-carboxylic acid hydrochloride, ISOMER 2 | $^1$H NMR (400 MHz, DMSO-$d_6$) δ 10.12 (s, 1H), 8.80 (d, J = 9.0 Hz, 1H), 8.23 - 8.13 (m, 1H), 7.72 (d, J = 11.0 Hz, 1H), 7.61 - 7.50 (m, 2H), 7.23 (d, J = 8.5 Hz, 2H), 6.94 (d, J = 8.5 Hz, 2H), 4.01 (s, 3H), 3.97 - 3.87 (m, 1H), 3.02 (s, 3H), 3.01 - 2.93 (m, 2H), 2.85 - 2.77 (m, 1H), 2.75 - 2.68 (m, 1H), 2.62 (s, 3H), 2.10 - 1.99 (m, 2H), 1.93 - 1.75 (m, 6H), 1.70 - 1.48 (m, 5H) | ES-LCMS m/z 730.4 [M + H]$^+$. |

The following compounds were synthesized in an analogous manner to the preparation described above (Example 211) using the relevant amine precursors, followed by, where necessary, chiral separation.

| Ex | Structure/Name |
|---|---|
| 270 | 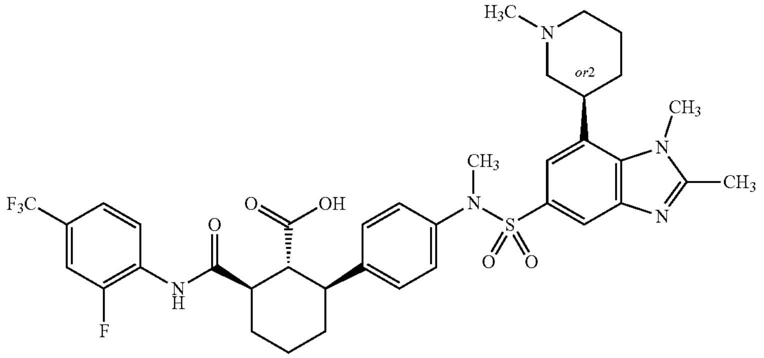 [SMILES: Cc1nc2cc(S(=O)(=O)N(C)c3ccc([C@H]4CCC[C@@H](C(=O)Nc5ccc(C(F)(F)F)cc5F)[C@@H]4C(=O)O)cc3)cc([C@@H]3CCCN(C)C3)c2n1C] ISOMER 1 (1R,2R,6S)-2-((2-fluoro-4-(trifluoromethyl)phenyl)carbamoyl)-6-(4-((N,1,2-trimethyl-7-((S*)-1-methylpiperidin-3-yl)-1H-benzo[d]imidazole)-5-sulfonamido)phenyl)cyclohexane-1-carboxylic acid, ISOMER 1 |
| 271 | 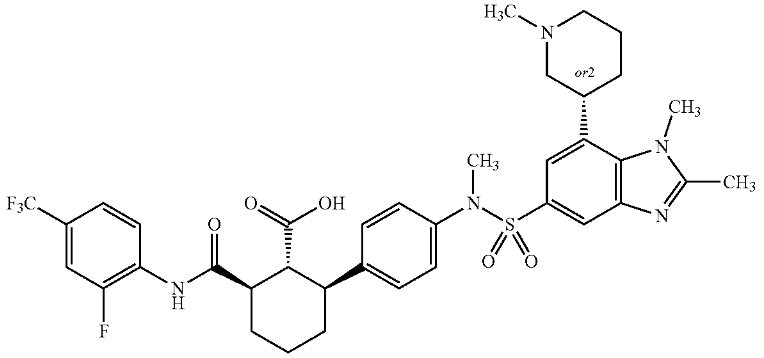 [SMILES: Cc1nc2cc(S(=O)(=O)N(C)c3ccc([C@H]4CCC[C@@H](C(=O)Nc5ccc(C(F)(F)F)cc5F)[C@@H]4C(=O)O)cc3)cc([C@H]3CCCN(C)C3)c2n1C] ISOMER 2 (1R,2R,6S)-2-((2-fluoro-4-(trifluoromethyl)phenyl)carbamoyl)-6-(4-((N,1,2-trimethyl-7-((R*)-1-methylpiperidin-3-yl)-1H-benzo[d]imidazole)-5-sulfonamido)phenyl)cyclohexane-1-carboxylic acid, ISOMER 2 |
| 272 | 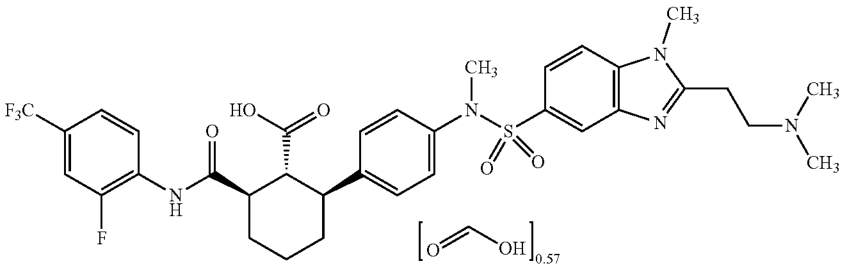 (1R,2S,6R)-2-(4-((2-(2-(dimethylamino)ethyl)-N, 1-dimethyl-1H-benzo[d]imidazole)-5-sulfonamido)phenyl)-6-((2-fluoro-4-(trifluoromethyl)phenyl)carbamoyl)cyclohexane-1-carboxylic acid, 0.57 formic acid salt |

| Ex | $^1H$ NMR | LCMS |
|---|---|---|
| 270 | $^1H$ NMR (400 MHz, DMSO-$d_6$) δ 10.02 (s, 1H), 8.25 (t, J = 8.00 Hz, 3H), 7.72 (dd, J = 11.20, 1.60 Hz, 1H), 7.57 (d, J = 8.80, 2H), 7.21 (d, J = 8.40 Hz, 2H), 6.91 (d, J = 8.00 Hz, 2H), 6.83 | ES-LCMS m/z 742.2 $[M + H]^+$. |

-continued

| | | |
|---|---|---|
| | (s, 1H), 3.95 (s, 3H), 3.63 - 3.60 (m, 1H), 3.00 - 2.96 (m, 4H), 2.68 - 2.67 (m, 4H), 2.58 (s, 3H), 2.32 (s, 3H), 2.04 - 2.01 (m, 1H), 1.83 - 1.76 (m, 2H), 1.75 - 1.73 (m, 2H), 1.68 - 1.64 (m, 1H), 1.57 - 1.54 (m, 1H), 1.51 - 1.49 (m, 3H), 1.25 - 1.24 (m, 1H) | |
| 271 | $^1$H NMR (400 MHz, DMSO-$d_6$) δ 12.00 (s, 1H), 10.084 (s, 1H), 8.21 (dd, J = 7.20, 15.60 Hz, 1H), 7.72 (d, J = 9.60 Hz, 1H), 7.54 (dd, J = 1.60, 10.40 Hz, 2H), 7.22 (d, J = 8.40 Hz, 2H), 6.95 (d, J = 8.40 Hz, 2H), 6.90 (s, 1H), 3.94 (s, 3H), 3.57 - 3.60 (m, 1H), 2.92 - 2.98 (m, 4H), 2.79 - 2.82 (m, 1H), 2.71 - 2.73 (m, 2H), 2.67 - 2.68 (m, 1H), 2.57 (s, 3H), 2.25 (s, 3H), 1.95 - 1.98 (m, 2H), 1.86 - 1.89 (m, 2H), 1.81 - 1.83 (m, 2H), 1.77 - 1.79 (m, 2H), 1.69 (s, 3H), 1.24 - 1.25 (m, 1H) | ES-LCMS m/z 742.2 $[M + H]^+$. |
| 272 | $^1$H NMR (400 MHz, DMSO-$d_6$) δ 10.1 (s, 1H), 8.23 (t, J = 8.0 Hz, 1H), 7.73 (d, J = 1.6 Hz, 1H), 7.70 (d, J = 1.2 Hz, 1H), 7.66 (d, J = 8.8 Hz, 1H), 7.55 (d, J = 8.4 Hz, 1H), 7.45 (d, J = 1.6 Hz, 1H), 7.27 (dd, J = 8.6, 2.0 Hz, 1H), 7.20 (d, J = 8.4 Hz, 1H), 6.98 (d, J = 8.4 Hz, 2H), 3.81 (s, 3H), 3.06 (s, 3H), 3.04 - 3.02 (m, 3H), 2.80 - 2.69 (m, 4H), 2.16 (s, 6H), 2.16 - 2.03 (m, 1H), 2.01 - 1.90 (m, 1H), 1.75 - 1.62 (m, 1H), 1.55 - 1.51 (m, 3H) | ES-LCMS m/z 704.2 $[M + H]^+$. |

The following compound was synthesized in an analogous manner to the preparation described above (Example 183) using the relevant benzyl ester-protected precursor.

| Ex | Structure/Name |
|---|---|
| 273 | 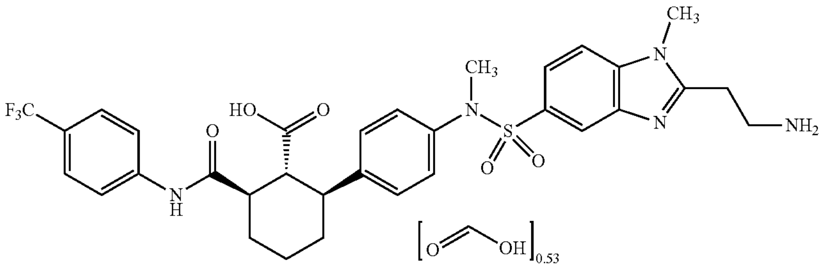<br>(1R,2S,6R)-2-(4-((2-(2-aminoethyl)-N,1-dimethyl-1H-benzo[d]imidazole)-5-sulfonamido)phenyl)-6-((4-(trifluoromethyl)phenoxy)methyl)cyclohexane-1-carboxylic acid, 0.53 formic acid salt |

| Ex | $^1$H NMR | LCMS |
|---|---|---|
| 273 | $^1$H NMR (400 MHz, DMSO-$d_6$) δ 7.67 - 7.55 (m, 4H), 7.27 (d, J = 7.6 Hz, 1H), 7.17 - 7.07 (m, 4H), 6.97 - 6.95 (m, 2H), 3.99 - 3.91 (m, 2H), 3.78 (s, 3H), 3.05 (s, 3H), 3.09 - 3.07 (m, 4H), 2.73 - 2.62 (m, 1H), 2.41 - 2.38 (m, 1H), 1.96 | ES-LCMS m/z 645.2 [M + H]+. |

-continued

| |
|---|
| (d, J = 11.6 Hz, 1H), 2.07 – 2.03 (m, 1H), 1.82 – 1.72 (m, 2H), 1.31 – 1.24 (m, 3H), three protons were obscured by solvent peaks |

Example 274

(1R,2S,6R)-2-(4-((4-bromo-3-hydroxy-N-methyl phenyl) sulfonamido)phenyl)-6-((2-fluoro-4-(trifluoromethyl)phenyl)carbamoyl)cyclohexane-1-carboxylic acid

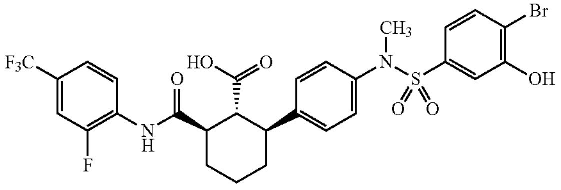 [SMILES: CN(c1ccc([C@H]2CCC[C@@H](C(=O)Nc3ccc(C(F)(F)F)cc3F)[C@@H]2C(=O)O)cc1)S(=O)(=O)c1ccc(Br)c(O)c1]

To a mixture of (1R,2S,6R)-2-(4-((4-bromo-3-methoxy-N-methyl phenyl) sulfonamido)phenyl)-6-((2-fluoro-4-(trifluoromethyl)phenyl)carbamoyl)cyclohexane-1-carboxylic acid Example 136 (40 mg, 0.06 mmol) in dichloromethane (4 mL) at 0° C. was added $BBr_3$ (1M solution in dichloromethane, 0.29 mL, 0.29 mmol). After 16 h, the reaction was quenched with water (1.0 mL), concentrated and subjected to reverse phase purification (0-100% MeCN in $H_2O$, 0.1% ammonium bicarbonate modifier) to afford (1R,2S,6R)-2-(4-((4-bromo-3-hydroxy-N-methylphenyl)sulfonamido)phenyl)-6-((2-fluoro-4-(trifluoromethyl)phenyl)carbamoyl)cyclohexane-1-carboxylic acid (7.5 mg, 0.011 mmol, 19% yield) as a white solid. $^1$H NMR (400 MHz, DMSO-$d_6$) δ 12.00 (br s, 1H), 11.81 (br s, 1H), 10.08 (s, 1H), 8.23 (s, 1H), 7.72 (d, J=10.00 Hz, 1H), 7.62-7.54 (m, 2H), 7.23-7.03 (m, 5H), 6.66 (s, 1H), 3.08 (s, 3H), 3.00-2.98 (m, 2H), 2.69-2.67 (m, 1H), 1.99-1.76 (m, 3H), 1.59-1.51 (m, 3H). ES-LCMS m/z 670.8 $[M-H]^-$.

The following compound was synthesized in an analogous manner to the preparation described above (Example 211) using the relevant amine precursor.

| Ex | Structure/Name |
|---|---|
| 275 | 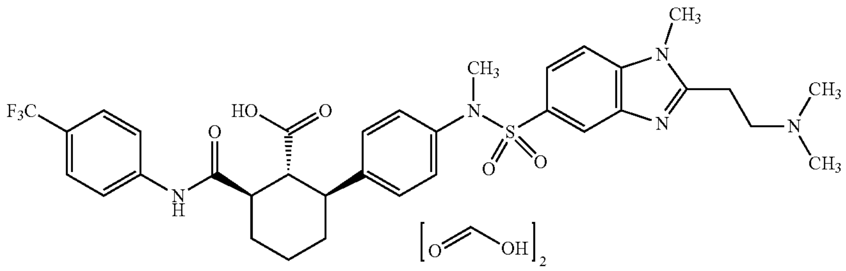<br>(1R,2S,6R)-2-(4-((2-(2-(dimethylamino)ethyl)-N, 1-dimethyl-1H-benzo[d]imidazole)-5-sulfonamido)phenyl)-6-((4-(trifluoromethyl)phenoxy)methyl)cyclohexane-1-carboxylic acid, 2 formic acid salt |

| Ex | $^1$H NMR | LCMS |
|---|---|---|
| 275 | $^1$H NMR (400 MHz, DMSO-$d_6$) δ 8.37 (s, 2H), 7.67 – 7.64 (m, 3H), 7.50 (s, 1H), 7.28 (dd, J = 8.4, 1.6 Hz, 1H), 7.17 (d, J = 8.4 Hz, 2H), 7.09 (d, J = 8.8 Hz, 2H), 6.96 (d, J = 8.4 Hz, 2H), 4.00 – 3.99 (m, 1H), 3.93 – 3.89 (m, 1H), 3.79 (s, 3H), 3.07 (s, 6H), 2.75 (t, J = 6.8 Hz, 3H), 2.50 – 2.41 (m, 1H), 2.33 (s, 3H), 2.19 – 2.10 (m, 2H), 1.95 (d, J = 11.6 Hz, 1H), 1.84 – 1.73 (m, 3H), 1.47 – 1.33 (m, 3H) | ES-LCMS m/z 673.2 $[M + H]^+$. |

Example 276

(1R,2R,6S)-2-((2-fluoro-4-(trifluoromethyl)phenyl) carbamoyl)-6-(4-((4-formyl-3-hydroxy-N-methylphenyl)sulfonamido)phenyl)cyclohexane-1-carboxylic acid

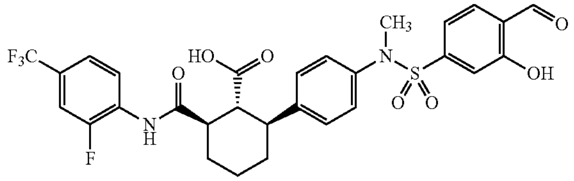 [SMILES: CN(c1ccc([C@H]2CCC[C@@H](C(=O)Nc3ccc(C(F)(F)F)cc3F)[C@@H]2C(=O)O)cc1)S(=O)(=O)c1ccc(C=O)c(O)c1]

To a mixture of (1R,2R,6S)-2-((2-fluoro-4-(trifluoromethyl)phenyl)carbamoyl)-6-(4-((3-hydroxy-N-methyl-4-vinylphenyl)sulfonamido)phenyl)cyclohexane-1-carboxylic acid Intermediate 56 (35 mg, 0.060 mmol) in tert-butanol (1.05 mL), tetrahydrofuran (0.35 mL) and water (0.11 mL) was added N-methylmorpholine N-oxide (7.9 mg, 0.070 mmol), followed by osmium tetroxide (4.0% solution in water, 0.020 mL, 2.8 μmol). After 16 h, sodium bicarbonate (56.9 mg, 0.677 mmol), sodium periodate (37 mg, 0.18 mmol) and water (2.45 mL) were added. After (h, the reaction was concentrated and subjected to reverse phase purification (MeCN in $H_2O$, 0.1% formic acid modifier) to afford (1R,2R,6S)-2-((2-fluoro-4-(trifluoromethyl)phenyl) carbamoyl)-6-(4-((4-formyl-3-hydroxy-N-methyl phenyl) sulfonamido)phenyl)cyclohexane-1-carboxylic acid (10 mg, 0.020 mmol, 28% yield) as an off-white solid. $^1$H NMR (400 MHz, DMSO-$d_6$) δ 11.77 (br, 1H), 10.34 (s, 1H), 10.08 (s, 1H), 8.23 (t, J=8.4 Hz, 1H), 7.74-17.68 (m, 2H), 7.55 (d, J=8.0 Hz, 1H), 7.24 (d, J=8.4 Hz, 2H), 7.05 (d, J=8.0 Hz, 2H), 6.80 (dd, J=8.2, 0.8 Hz, 1H), 3.35 (s, 3H), 3.13-2.98 (m, 1H), 2.74-2.65 (m, 2H), 2.08-1.75 (m, 3H), 1.64-1.51 (n, 3H). ES-LCMS m/z 620.8 [M−H]$^-$.

The following compound was synthesized in an analogous manner to the preparation described above (Example 207) using the relevant BOO-protected sulfonyl chloride precursor.

| Ex | Structure/Name | $^1$H NMR | LCMS |
|---|---|---|---|
| 277 | 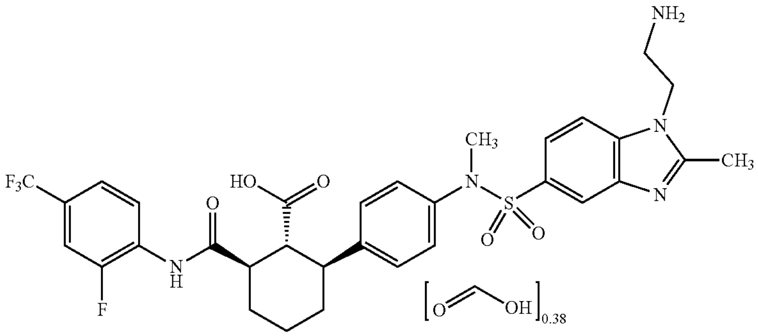 (1R,2S,6R)-2-(4-((1-(2-aminoethyl)-N,2-dimethyl-1H-benzo[d]imidazole)-5-sulfonamido)phenyl)-6-((2-fluoro-4-(trifluoromethyl)phenyl) carbamoyl)cyclohexane-1-carboxylic acid, 0.38 formic acid salt | $^1$H NMR (400 MHz, DMSO-$d_6$) δ 10.11 (s, 1H), 8.22 (t, J = 7.6 Hz, 1H), 7.73 (dd, J = 11.0, 2.0 Hz, 1H), 7.68 (d, J = 8.8 Hz, 1H), 7.56 (d, J = 8.4 Hz, 1H), 7.51 (d, J = 1.6 Hz, 1H), 7.25 (dd, J = 8.4, 1.6 Hz, 1H), 7.20 (d, J = 8.4 Hz, 2H), 6.98 (d, J = 8.8 Hz, 2H), 4.23 (t, J = 6.0 Hz, 2H), 3.06 (s, 3H), 3.05 − 2.96 (m, 1H), 2.94 (t, J = 6.4 Hz, 2H), 2.78 (t, J = 10.8 Hz, 1H), 2.72 − 2.65 (m, 1H), 2.60 (s, 3H), 2.02 (d, J = 8.40 Hz, 1H), 1.91 − 1.83 (m, 1H), 1.76 (d, J = 12.8 Hz, 1H), 1.67 − 1.48 (m, 3H), three protons obscured by solvent peaks | ES-LCMS m/z 676.0 [M + H]$^+$. |

-

The following compound was synthesized in an analogous manner to the preparation described above (Example 211) using the relevant amine precursor.

| Ex | Structure/Name | $^1$H NMR | LCMS |
|---|---|---|---|
| 278 | 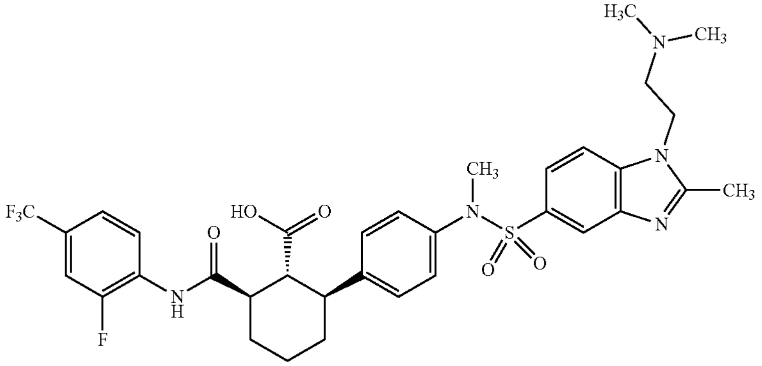 [SMILES: Cc1nc2cc(S(=O)(=O)N(C)c3ccc([C@H]4CCC[C@@H](C(=O)Nc5ccc(C(F)(F)F)cc5F)[C@@H]4C(=O)O)cc3)ccc2n1CCN(C)C] | $^1$H NMR (400 MHz, DMSO-$d_6$) δ 8.26 (t, J = 8.0 Hz, 1H), 7.63 (d, J = 8.4 Hz, 1H), 7.57 (d, J = 1.2 Hz, 1H), 7.52-7.47 (m, 2H), 7.38 (dd, J = 8.4, 1.6 Hz, 1H), 7.19 (d, J = 8.4 Hz, 2H), 6.98 (d, J = 8.4 Hz, 1H), 4.48 (t, J = 7.2 Hz, 2H), 3.14 (s, 3H), 3.04 − 2.97 (m, 3H), 2.89 (t, J = 10.4 Hz, 1H), 2.81 − 2.80 (m, 1H), 2.68 (s, 3H), 2.57 (s, 6H), 2.14 − 2.11 (m, 1H), 2.02 (m, 1H), 1.91 − 1.89 (m, 1H), 1.72 − 1.67 (m, 3H) | ES-LCMS m/z 704.2 [M + H]$^+$. |

-continued

| Ex | Structure/Name | $^1$H NMR | LCMS |
|---|---|---|---|
| | (1R,2S,6R)-2-(4-((1-(2-(dimethylamino)ethyl)-N,2-dimethyl-1H-benzo[d]imidazole)-5-sulfonamido)phenyl)-6-((2-fluoro-4-(trifluoromethyl)phenyl)carbamoyl)cyclohexane-1-carboxylic acid | | |

The following compound was synthesized in an analogous manner to the preparation described above (Example 139) using the relevant sulfonyl chloride precursor.

| Ex | Structure/Name | $^1$H NMR | LCMS |
|---|---|---|---|
| 279 | 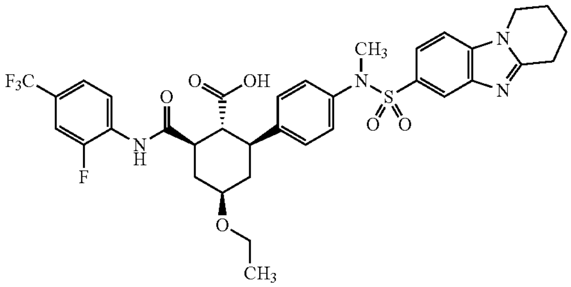 [SMILES: CCO[C@@H]1C[C@H](c2ccc(N(C)S(=O)(=O)c3ccc4c(c3)nc3n4CCCC3)cc2)[C@@H](C(=O)O)[C@H](C(=O)Nc2ccc(C(F)(F)F)cc2F)C1] (1R,2R,4R,6S)-4-ethoxy-2-((2-fluoro-4-(trifluoromethyl)phenyl)carbamoyl)-6-(4-((N-methyl-1,2,3,4-tetrahydrobenzo[4,5]imidazo[1,2-a]pyridine)-7-sulfonamido)phenyl)cyclohexane-1-carboxylic acid | $^1$H NMR (400 MHz, DMSO-$d_6$) δ 10.15 (s, 1H), 8.25 (t, J = 9.6 Hz, 1H), 7.73 (d, J = 11.2 Hz, 1H), 7.61 (d, J = 8.8 Hz, 1H), 7.56 (d, J = 7.6 Hz, 1H), 7.51 (s, 1H), 7.26 - 7.21 (m, 3H), 6.97 (d, J = 8.4 Hz, 2H), 4.17 (t, J = 6.0 Hz, 2H), 3.52 (q, J = 7.2 Hz, 3H), 3.06 (s, 3H), 3.05 (m, 1H), 3.01 (t, J = 6.0 Hz, 3H), 2.75 (d, J = 9.6 Hz, 1H), 2.06 - 2.05 (m, 3H), 1.96 - 1.94 (m, 2H), 1.53 - 1.43 (m, 2H), 1.11 (t, J = 6.8 Hz, 3H) | ES-LCMS m/z 717.2 [M + H]$^+$. |
| 281 | 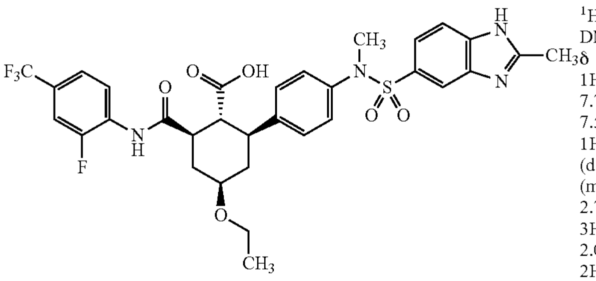 (1R,2S,4R,6R)-2-(4-((N,2-dimethyl-1H-benzo[d]imidazole)-5-sulfonamido)phenyl)-4-ethoxy-6-((2-fluoro-4-(trifluoromethyl)phenyl)carbamoyl)cyclohexane-1-carboxylic acid | $^1$H NMR (400 MHz, DMSO-$d_6$) δ 12.55 (br s, 1H), 10.12 (s, 1H), 8.23 (t, J = 8.3 Hz, 1H), 7.73 (dd, J = 11.0, 1.5 Hz, 1H), 7.55 (t, J = 7.8 Hz, 2H), 7.45 (s, 1H), 7.25 - 7.12 (m, 3H), 6.96 (d, J = 8.5 Hz, 2H), 3.59 - 3.45 (m, 3H), 3.11 - 2.98 (m, 4H), 2.79 - 2.71 (m, 2H), 2.53 (s, 3H), 2.37 - 2.25 (m, 1H), 2.10 - 2.00 (m, 1H), 1.61 - 1.37 (m, 2H), 1.10 (t, J = 7.0 Hz, 3H) | ES-LCMS m/z 675.0 [M - H]$^-$. |

The following compounds were synthesized in an analogous manner to the preparation described above (Example 137 and Example 138), substituting the relevant base (sodium sulfate for Example 283 and Example 284), alkylating group (2,2-difluoro-2-(fluorosulfonyl)acetic acid for Example 283 and Example 284, tosylate for Example 282) and Chiral chromatographic resolution.

| Ex | Structure/Name | $^1$H NMR | LCMS |
|---|---|---|---|
| 282 | 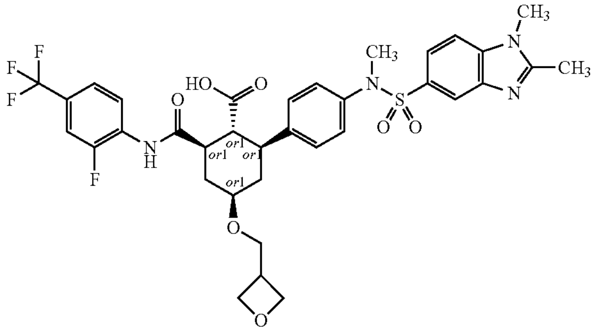 [SMILES: Cc1nc2cc(S(=O)(=O)N(C)c3ccc([C@H]4C[C@@H](OCC5COC5)C[C@@H](C(=O)Nc5ccc(C(F)(F)F)cc5F)[C@@H]4C(=O)O)cc3)ccc2n1C] ISOMER 1 rel-(1R,2R,4R,6S)-2-((2-fluoro-4-(trifluoromethyl)phenyl)carbamoyl)-4-(oxetan-3-ylmethoxy)-6-(4-((N,1,2-trimethyl-1H-benzo[d]imidazole)-5-sulfonamido)phenyl)cyclohexane-1-carboxylic acid, ISOMER 1 | $^1$H NMR (400 MHz, DMSO-$d_6$) δ 10.27 (br s, 1H), 8.24 (t, J = 8.0 Hz, 1H), 7.72 (dd, J = 11.0, 1.5 Hz, 1H), 7.63 (d, J = 8.5 Hz, 1H), 7.55 (d, J = 8.5 Hz, 1H), 7.51 (d, J = 1.5 Hz, 1H), 7.26 - 7.19 (m, 3H), 6.95 (d, J = 8.5 Hz, 2H), 4.60 (ddd, J = 7.8, 5.8, 1.0 Hz, 2H), 4.28 (t, J = 6.0 Hz, 2H), 3.78 (s, 3H), 3.69 (dd, J = 6.8, 1.3 Hz, 2H), 3.57 - 3.48 (m, 1H), 3.17 - 2.97 (m, 6H), 2.83 - 2.68 (m, 2H), 2.56 (s, 3H), 2.38 - 2.33 (m, 1H), 2.13 - 2.01 (m, 1H), 1.61 - 1.39 (m, 2H) | ES-LCMS m/z 733.2 [M + H]$^+$. |
| 283 | 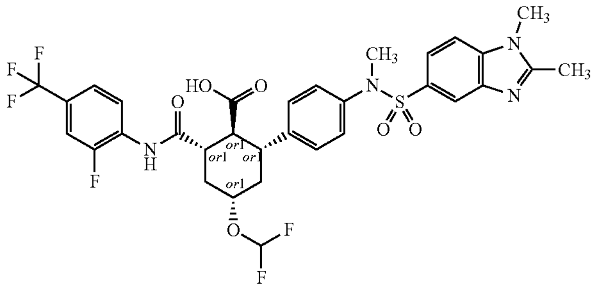 [SMILES: Cc1nc2cc(S(=O)(=O)N(C)c3ccc([C@@H]4C[C@H](OC(F)F)C[C@H](C(=O)Nc5ccc(C(F)(F)F)cc5F)[C@H]4C(=O)O)cc3)ccc2n1C] ISOMER 1 rel-(1R,2R,4R,6S)-4-(difluoromethoxy)-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylic acid, ISOMER 1 | $^1$H NMR (400 MHz, DMSO-$d_6$) δ 10.38 (bs, 1H), 8.25 (t, J = 8.0 Hz, 1H), 7.71 (dd, J = 11.0, 1.5 Hz, 1H), 7.63 (d, J = 8.5 Hz, 1H), 7.58 - 7.52 (m, 2H), 7.29 - 7.20 (m, 3H), 6.98 - 6.94 (m, 2H), 6.78 - 6.55 (m, 1H), 4.34 - 4.24 (m, 1H), 3.77 (s, 3H), 3.11 - 2.98 (m, 4H), 2.83 (td, J = 12.1, 2.8 Hz, 1H), 2.73 - 2.66 (m, 1H), 2.56 (s, 3H), 2.34 - 2.25 (m, 1H), 2.03 (d, J = 12.0 Hz, 1H), 1.83 - 1.63 (m, 2H) | ES-LCMS m/z 713.0 [M + H]$^+$. |
| 284 | 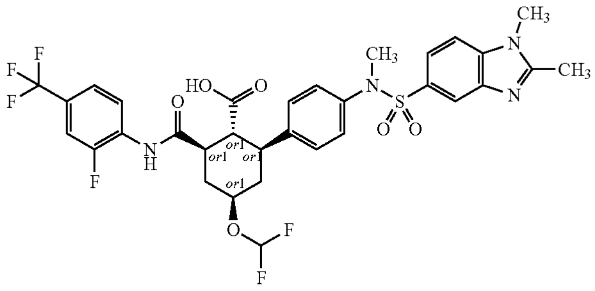 [SMILES: Cc1nc2cc(S(=O)(=O)N(C)c3ccc([C@H]4C[C@@H](OC(F)F)C[C@@H](C(=O)Nc5ccc(C(F)(F)F)cc5F)[C@@H]4C(=O)O)cc3)ccc2n1C] ISOMER 2 rel-(1R,2R,4R,6S)-4-(difluoromethoxy)-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylic acid, ISOMER 2 | $^1$H NMR (400 MHz, DMSO-$d_6$) δ 10.35 (br s, 1H), 8.24 (t, J = 8.0 Hz, 1H), 7.72 (dd, J = 11.3, 1.8 Hz, 1H), 7.63 (d, J = 8.5 Hz, 1H), 7.57 - 7.51 (m, 2H), 7.26 - 7.21 (m, 3H), 6.96 (d, J = 8.5 Hz, 2H), 6.78 - 6.56 (m, 1H), 4.29 (ddd, J = 15.4, 10.9, 4.3 Hz, 1H), 3.78 (s, 3H), 3.11 - 3.01 (m, 4H), 2.83 (td, J = 12.1, 2.8 Hz, 1H), 2.75 - 2.68 (m, 1H), 2.56 (s, 3H), 2.33 - 2.27 (m, 1H), 2.03 (br d, J = 11.0 Hz, 1H), 1.85 - 1.63 (m, 2H) | ES-LCMS m/z 713.0 [M + H]$^+$. |

The following compound was synthesized in an analogous manner to the preparation described above (Example 93) using the relevant sulfonyl chloride precursor.

| Ex | Structure/Name | $^1$H NMR | LCMS |
|---|---|---|---|
| 285 | 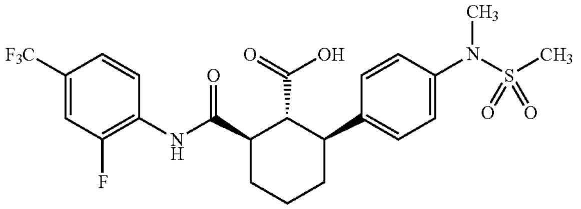 [SMILES: CN(c1ccc([C@H]2CCC[C@@H](C(=O)Nc3ccc(C(F)(F)F)cc3F)[C@@H]2C(=O)O)cc1)S(C)(=O)=O] (1R,2R,6S)-2-((2-fluoro-4-(trifluoromethyl)phenyl)carbamoyl)-6-(4-(N-methylmethylsulfonamido)phenyl) cyclohexane-1-carboxylic acid | $^1$H NMR (400 MHz, DMSO-$d_6$) δ 10.21 (br s, 1H), 8.23 (t, J = 8.0 Hz, 1H), 7.70 (dd, J = 11.0, 1.5 Hz, 1H), 7.54 (d, J = 9.5 Hz, 1H), 7.29 (d, J = 1.5 Hz, 4H), 3.20 (s, 3H), 3.00 - 2.93 (m, 1H), 2.90 (s, 3H), 2.81 - 2.69 (m, 2H), 2.04 - 1.96 (m, 1H), 1.87 (s, 1H), 1.74 (d, J = 11.0 Hz, 1H), 1.61 - 1.44 (m, 3H) | ES-LCMS m/z 515.0 $[M - H]^-$. |

The following compounds were synthesized in an analogous manner to the preparation described above (Example 160) using Intermediate 57 for Example 286, Intermediate 58 for Example 287 and Intermediate 59 for Example 288:

| Ex | Structure/Name | $^1$H NMR | LCMS |
|---|---|---|---|
| 286 | 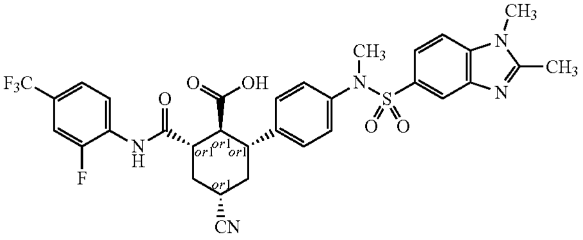 [SMILES: Cc1nc2cc(S(=O)(=O)N(C)c3ccc([C@@H]4C[C@H](C#N)C[C@H](C(=O)Nc5ccc(C(F)(F)F)cc5F)[C@H]4C(=O)O)cc3)ccc2n1C] ISOMER 1 rel-(1R,2R,4R,6S)-4-cyano-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylic acid, ISOMER 1 | $^1$H NMR (400 MHz, DMSO-$d_6$) δ 10.22 (br s, 1H), 8.22 (t, J = 8.3 Hz, 1H), 7.73 (dd, J = 11.0, 2.0 Hz, 1H), 7.63 (d, J = 8.5 Hz, 1H), 7.56 (d, J = 8.0 Hz, 1H), 7.50 (d, J = 1.5 Hz, 1H), 7.27 - 7.18 (m, 3H), 6.98 (d, J = 8.5 Hz, 2H), 3.78 (s, 3H), 3.10 - 2.97 (m, 5H), 2.87 - 2.74 (m, 2H), 2.56 (s, 3H), 2.36 (br s, 1H), 2.09 - 1.96 (m, 2H), 1.92 - 1.80 (m, 1H) | ES-LCMS m/z 670.0 $[M - H]^-$. |
| 287 | 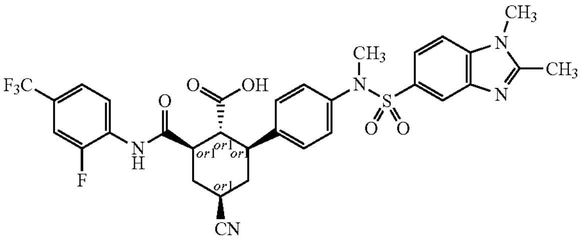 [SMILES: Cc1nc2cc(S(=O)(=O)N(C)c3ccc([C@H]4C[C@@H](C#N)C[C@@H](C(=O)Nc5ccc(C(F)(F)F)cc5F)[C@@H]4C(=O)O)cc3)ccc2n1C] ISOMER 2 rel-(1R,2R,4R,6S)-4-cyano-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylic acid, ISOMER 2 | $^1$H NMR (400 MHz, DMSO-$d_6$) δ 10.22 (br s, 1H), 8.22 (t, J = 8.3 Hz, 1H), 7.73 (dd, J = 11.0, 2.0 Hz, 1H), 7.63 (d, J = 8.5 Hz, 1H), 7.56 (d, J = 8.0 Hz, 1H), 7.50 (d, J = 1.5 Hz, 1H), 7.27 - 7.18 (m, 3H), 6.98 (d, J = 8.5 Hz, 2H), 3.78 (s, 3H), 3.10 - 2.97 (m, 5H), 2.87 - 2.74 (m, 2H), 2.56 (s, 3H), 2.36 (br s, 1H), 2.09 - 1.96 (m, 2H), 1.92 - 1.80 (m, 1H) | ES-LCMS m/z 670.0 $[M - H]^-$. |

-continued

| Ex | Structure/Name | $^1$H NMR | LCMS |
|---|---|---|---|
| 288 | 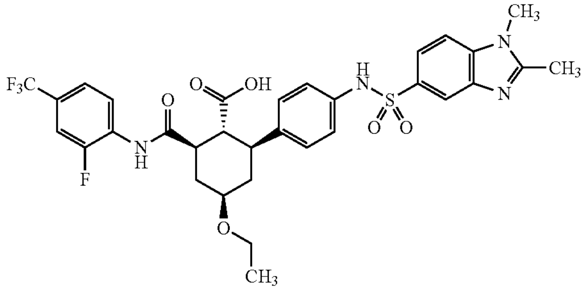 [SMILES: CCO[C@@H]1C[C@H](c2ccc(NS(=O)(=O)c3ccc4c(c3)nc(C)n4C)cc2)[C@@H](C(=O)O)[C@H](C(=O)Nc2ccc(C(F)(F)F)cc2F)C1] (1R,2S,4R,6R)-2-(4-((1,2-dimethyl-1H-benzo[d]imidazole)-5-sulfonamido)phenyl)-4-ethoxy-6-((2-fluoro-4-(trifluoromethyl)phenyl)carbamoyl)cyclohexane-1-carboxylic acid | $^1$H NMR (400 MHz, DMSO-$d_6$) δ 10.22 (br s, 1H), 8.22 (t, J = 8.3 Hz, 11.84 (br s, 1H), 10.11 - 10.00 (m, 2H), 8.19 (t, J = 8.3 Hz, 1H), 7.84 (d, J = 1.5 Hz, 1H), 7.71 (dd, J = 11.0, 1.5 Hz, 1H), 7.64 - 7.60 (m, 1H), 7.58 - 7.51 (m, 2H), 7.09 (d, J = 8.5 Hz, 2H), 6.95 (d, J = 8.5 Hz, 2H), 3.73 (s, 3H), 3.51 - 3.41 (m, 3H), 3.06 - 2.94 (m, 1H), 2.66 - 2.59 (m, 2H), 2.53 (s, 3H), 2.27 (d, J = 12.5 Hz, 1H), 1.93 (d, J = 10.5 Hz, 1H), 1.48 - 1.30 (m, 2H), 1.06 (t, J = 7.0 Hz, 3H) | ES-LCMS m/z 675.2 [M − H]$^-$. |

The following compound was synthesized in an analogous manner to the preparation described above (Example 216) using the relevant BOO-protected precursor.

| Ex | Structure/Name | $^1$H NMR | LCMS |
|---|---|---|---|
| 289 | 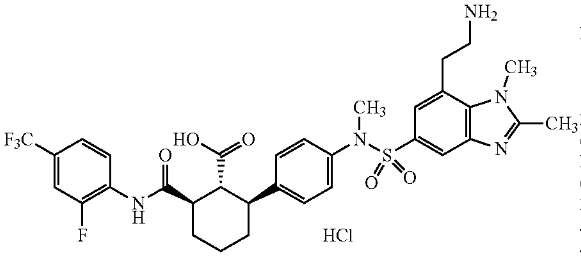 [SMILES: Cc1nc2cc(S(=O)(=O)N(C)c3ccc([C@H]4CCC[C@@H](C(=O)Nc5ccc(C(F)(F)F)cc5F)[C@@H]4C(=O)O)cc3)cc(CCN)c2n1C ; Cl] (1R,2S,6R)-2-(4-((7-(2-aminoethyl)-N,1,2-trimethyl-1H-benzo[d]imidazole)-5-sulfonamido)phenyl)-6-((2-fluoro-4-(trifluoromethyl)phenyl)carbamoyl) cyclohexane-1-carboxylic acid, hydrochloride | $^1$H NMR (400 MHz, DMSO-$d_6$) δ 10.15 (s, 1H), 8.20 (t, J = 8.3 Hz, 1H), 8.06 (br s, 3H), 7.73 (dd, J = 10.8, 1.8 Hz, 1H), 7.58 - 7.50 (m, 2H), 7.22 (d, J = 8.5 Hz, 2H), 7.09 (d, J = 1.5 Hz, 1H), 6.98 (d, J = 8.5 Hz, 2H), 4.01 (s, 3H), 3.38 - 3.30 (m, 2H), 3.07 (s, 3H), 2.09-3.03 (m, 3H), 2.84 - 2.76 (m, 1H), 2.70 (d, J = 3.0 Hz, 1H), 2.67 (s, 3H), 2.03 (d, J = 8.5 Hz, 1H), 1.94 - 1.74 (m, 2H), 1.66 - 1.46 (m, 3H) | ES-LCMS m/z 690.2 [M + H]$^+$. |

Example 290

(1R,2S,6R)-2-(4-((7-(2-(dimethylamino)ethyl)-N,1,2-trimethyl-1H-benzo[d]imidazole)-5-sulfonamido)phenyl)-6-((2-fluoro-4-(trifluoromethyl)phenyl)carbamoyl)cyclohexane-1-carboxylic acid, 0.21 formic acid salt

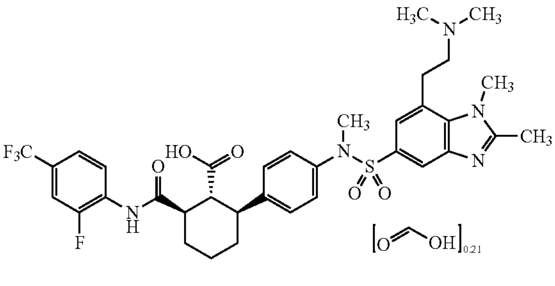

To a mixture of (1R,2S,6R)-2-(4-((7-(2-aminoethyl)-N,1,2-trimethyl-1H-benzo[d]imidazole)-5-sulfonamido)phenyl)-6-((2-fluoro-4-(trifluoromethyl)phenyl)carbamoyl)cyclohexane-1-carboxylic acid, hydrochloride (0.10 g, 0.14 mmol) in methanol (1.5 mL) was added formaldehyde (0.10 mL, 1.3 mmol) and DIEA (0.040 mL, 0.22 mmol). After 10 min, the reaction was cooled to 0° C., and sodium cyanoborohydride (48 mg, 0.76 mmol) was added. The mixture was stirred at rt for 1 h, then the reaction was subjected to reverse phase purification (MeCN in $H_2O$, 0.1% formic acid modifier, 0 to 100% gradient) to afford (1R,2S,6R)-2-(4-((7-(2-(dimethylamino)ethyl)-N,1,2-trimethyl-1H-benzo[d]imidazole)-5-sulfonamido)phenyl)-6-((2-fluoro-4-(trifluoromethyl)phenyl)carbamoyl)cyclohexane-1-carboxylic acid, 0.21 formic acid salt (65 mg, 0.090 mmol, 63% yield) as a white solid. $^1$H NMR (400 MHz, METHANOL-$d_4$) δ 8.37-8.27 (m, 1H), 7.86 (d, J=2.0 Hz, 1H), 7.56-7.43 (m, 2H), 7.27 (d, J=8.5 Hz, 2H), 7.01 (d, J=8.5 Hz, 2H), 6.38 (d, J=1.5 Hz, 1H), 4.01 (s, 3H), 3.50-3.39 (m, 1H), 3.25-3.12 (m, 2H), 3.09-3.07 (m, 1H) 3.04 (s, 3H), 2.95 (d, J=2.5 Hz, 1H), 2.86 (s, 6H), 2.84-2.81 (m, 1H), 2.75 (d, J=11.0 Hz, 1H), 2.65 (s, 3H), 2.10 (d, J=11.0 Hz, 1H), 2.03-1.94 (m, 1H), 1.88-1.86 (m, 1H), 1.75-1.68 (m, 3H). ES-LCMS m/z 718.2 [M+H]$^+$.

The following compounds were synthesized in an analogous manner to the preparation described above (Example 183) using the relevant benzyl-protected precursors.

| Ex | Structure/Name | $^1$H NMR | LCMS |
|---|---|---|---|
| 291 | 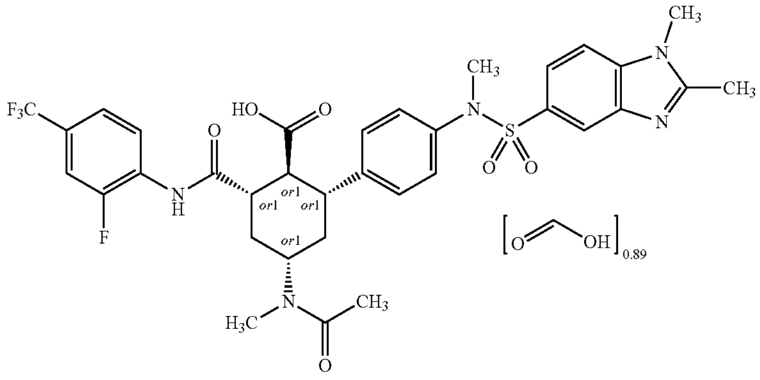 ISOMER 1 rel-(1R,2R,4R,6S)-2-((2-fluoro-4-(trifluoromethyl)phenyl)carbamoyl)-4-(N-methylacetamido)-6-(4-((N,1,2-trimethyl-1H-benzo[d]imidazole)-5-sulfonamido)phenyl)cyclohexane-1-carboxylic acid ISOMER 1, 0.89 formic acid salt | $^1$H NMR (400 MHz, DMSO-$d_6$) δ 10.3 (s, 1H), 8.25 (t, J = 8.0 Hz, 1H), 7.77 – 7.68 (m, 1H), 7.64 (d, J = 8.5 Hz, 1H), 7.58 – 7.48 (m, 2H), 7.31 – 7.19 (m, 3H), 7.00 – 6.90 (m, 2H), 4.68 – 4.51 (m, 1H), 3.79 (s, 3H), 3.15-3.12 (m, 1H), 3.06 (s, 3H), 2.92-2.89 (m, 1H), 2.86 (s, 3H), 2.78 ( d, J = 9.5 Hz, 1H), 2.57 (s, 3H), 1.99 (s, 3H), 1.90 – 1.72 (m, 3H), 1.52 ( d, J = 11.5 Hz, 1H) | ES-LCMS m/z 718.0 $[M + H]^+$. |
| 292 | 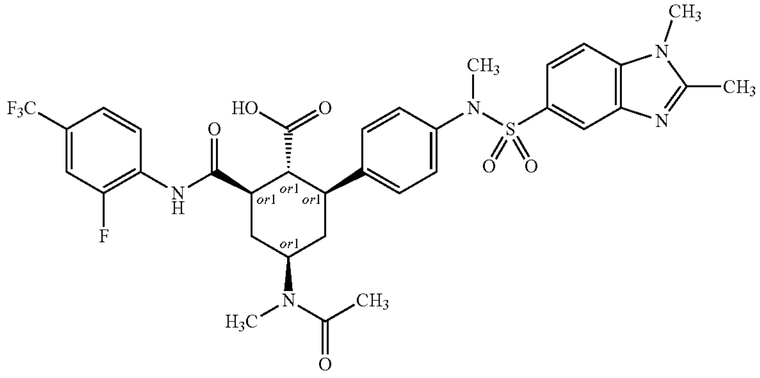 ISOMER 2 rel-(1R,2R,4R,6S)-2-((2-fluoro-4-(trifluoromethyl)phenyl)carbamoyl)-4-(N-methylacetamido)-6-(4-((N,1,2-trimethyl-1H-benzo[d]imidazole)-5-sulfonamido)phenyl)cyclohexane-1-carboxylic acid ISOMER 2 | $^1$H NMR (400 MHz, DMSO-$d_6$) δ 10.26 (s, 1H), 8.24 (t, J = 8.0 Hz, 1H), 7.78 – 7.68 (m, 1H), 7.63 (d, J = 8.5 Hz, 1H), 7.55 (br d, J = 8.5 Hz, 1H), 7.49 (s, 1H), 7.31 – 7.19 (m, 3H), 7.00 – 6.92 (m, 2H), 4.67 – 4.55 (m, 1H), 3.78 (s, 3H), 3.19 – 3.10 (m, 1H), 3.05 (s, 3H), 2.92-2.89 (m, 1H), 2.85 (s, 3H), 2.80 ( d, J = 9.5 Hz, 1H), 2.56 (s, 3H), 1.98 (s, 3H), 1.87 – 1.64 (m, 3H), 1.52 ( d, J = 12.0 Hz, 1H) | ES-LCMS m/z 718.2 $[M + H]^+$. |
| 293 | 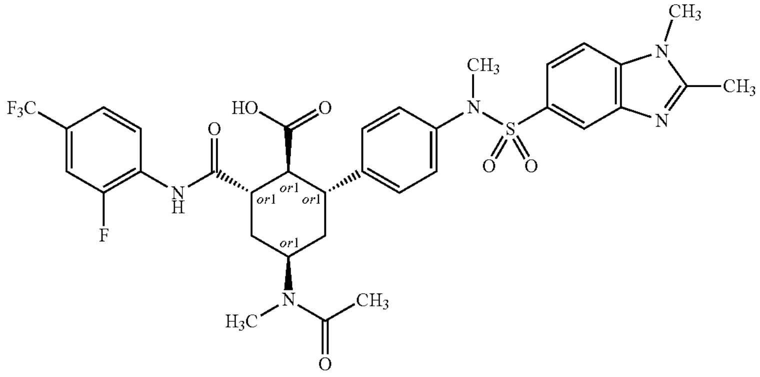 [SMILES: CC(=O)N(C)[C@H]1C[C@H](C(=O)Nc2ccc(C(F)(F)F)cc2F)[C@@H](C(=O)O)[C@H](c2ccc(N(C)S(=O)(=O)c3ccc4c(c3)nc(C)n4C)cc2)C1] | $^1$H NMR (400 MHz, DMSO-$d_6$) δ 8.18 (t, J = 8.0 Hz, 1H), 7.72 (d, J = 10.0 Hz, 1H), 7.63 (d, J = 8.5 Hz, 1H), 7.59 – 7.52 (m, 2H), 7.24 (d, J = 8.5 Hz, 3H), 6.95 (d, J = 8.5 Hz, 2H), 4.64 – 4.53 (m, 1H), 3.78 (s, 3H), 3.19 – 3.08 (m, 2H), 3.04 (s, 6H), 2.86 – 2.82 (m, 1H), 2.57 (s, 3H), 2.04 (s, 3H), 2.06 – 2.03 (m, 1H), 1.99 – 1.81 (m, 3H) | ES-LCMS m/z 718.2 $[M + H]^+$. |

-continued

| Ex | Structure/Name | $^1$H NMR | LCMS |
|---|---|---|---|
| | ISOMER 1<br>rel-(1R,2R,4S,6S)-2-((2-fluoro-4-(trifluoromethyl)phenyl)carbamoyl)-4-(N-methylacetamido)-6-(4-((N,1,2-trimethyl-1H-benzo[d]imidazole)-5-sulfonamido)phenyl)cyclohexane-1-carboxylic acid<br>ISOMER 1 | | |
| 294 | 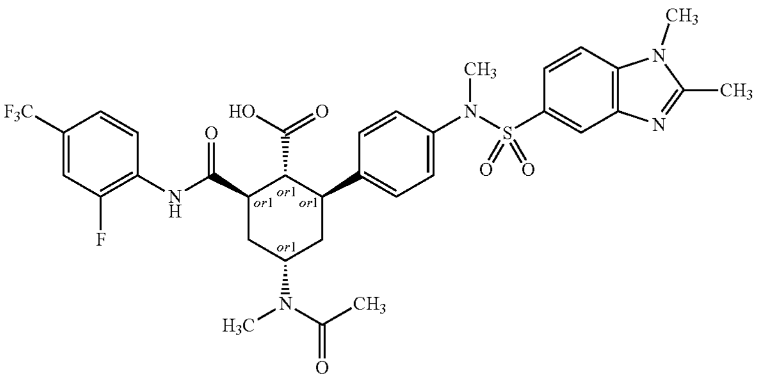<br>ISOMER 2<br>rel-(1R,2R,4S,6S)-2-((2-fluoro-4-(trifluoromethyl)phenyl)carbamoyl)-4-(N-methylacetamido)-6-(4-((N,1,2-trimethyl-1H-benzo[d]imidazole)-5-sulfonamido)phenyl)cyclohexane-1-carboxylic acid<br>ISOMER 2 | $^1$H NMR (400 MHz, DMSO-$d_6$) δ 8.27 - 8.19 (m, 1H), 7.72 - 7.58 (m, 3H), 7.52 (d, J = 8.5 Hz, 1H), 7.27 - 7.18 (m, 3H), 6.92 (d, J = 7.0 Hz, 2H), 4.70 - 4.15 (m, 1H), 3.78 (s, 3H), 3.24-3.21 (m, 1H), 3.03 (s, 6H), 2.89 - 2.73 (m, 2H), 2.57 (s, 3H), 2.03 (s, 3H), 1.93 - 1.82 (m, 4H) | ES-LCMS m/z 718.2 [M + H]$^+$. |

Example 295

(1R,2R,6S)-2-((2-fluoro-4-(trifluoromethyl)phenyl)carbamoyl)-6-(3-methyl-4-((N,1,2-trimethyl-1H-benzo[d]imidazole)-5-sulfonamido)phenyl)cyclohexane-1-carboxylic acid

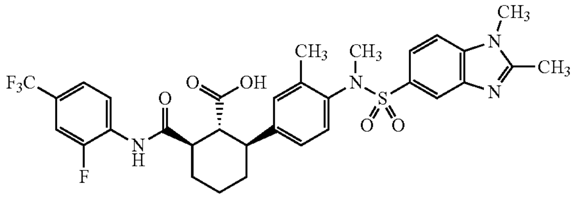 [SMILES: Cc1cc([C@H]2CCC[C@@H](C(=O)Nc3ccc(C(F)(F)F)cc3F)[C@@H]2C(=O)O)ccc1N(C)S(=O)(=O)c1ccc2c(c1)nc(C)n2C]

A mixture of (1R,2S,6R)-2-(3-bromo-4-((N,1,2-trimethyl-1H-benzo[d]imidazole)-5-sulfonamido)phenyl)-6-((2-fluoro-4-(trifluoromethyl)phenyl)carbamoyl)cyclohexane-1-carboxylic acid Example 166 (120 mg, 0.17 mmol), 2,4,6-trimethyl-1,3,5,2,4,6-trioxatriborinane (42 mg, 0.33 mmol) and potassium carbonate (57 mg, 0.41 mmol) in dioxane (1 mL) and water (0.13 mL) was purged with $N_2$ for 10 min. Tetrakis(triphenylphosphine)palladium(0) (15.1 mg, 0.0300 mmol) was added, and the reaction was again purged with $N_2$ for 10 mins. The mixture was heated to 100° C. for 16 h, concentrated and subjected to Prep HPLC purification (MeCN in $H_2O$, 0.1% formic acid modifier, 0-100% gradient) to afford (1R,2R,6S)-2-((2-fluoro-4-(trifluoromethyl)phenyl)carbamoyl)-6-(3-methyl-4-((N,1,2-trimethyl-1H-benzo[d]imidazole)-5-sulfonamido)phenyl)cyclohexane-1-carboxylic acid (20 mg, 0.03 mmol, 18% yield) as a white solid. $^1$H NMR (400 MHz, DMSO-$d_6$) δ 12.33-11.47 (m, 1H), 10.14 (brs, 1H), 8.22 (t, J=8.2 Hz, 1H), 7.85-7.67 (m, 3H), 7.55 (br d, J=8.5 Hz, 1H), 7.46 (br d, J=8.6 Hz, 1H), 7.19 (s, 1H), 7.03-6.87 (m, 1H), 6.45 (d, J=8.3 Hz, 1H), 3.82 (s, 3H), 3.03 (s, 3H), 2.98 (br d, J=11.1 Hz, 1H), 2.77 (br t, J=11.0 Hz, 1H), 2.68 (dt, J=3.6, 1.8 Hz, 1H), 2.60 (s, 3H), 2.27 (s, 3H), 2.00 (br d, J=8.9 Hz, 1H), 1.87 (br s, 1H), 1.75 (br d, J=11.1 Hz, 1H), 1.63-1.43 (m, 3H) ES-LCMS m/z 661.2 [M+H]$^+$.

The following compound was synthesized in an analogous manner to the preparation described above (Example 72) using the relevant arylamine precursor.

| Ex | Structure/Name | $^{1}H$ NMR |
|---|---|---|
| 296 | 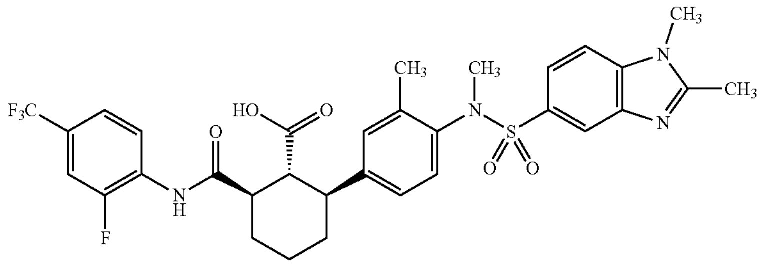 [SMILES: Cc1cc([C@H]2CCC[C@@H](C(=O)Nc3ccc(C(F)(F)F)cc3F)[C@@H]2C(=O)O)ccc1N(C)S(=O)(=O)c1ccc2c(c1)nc(C)n2C] (1R,2S,6R)-2-(3-chloro-4-((N,1,2-trimethyl-1H-benzo[d]imidazole)-5-sulfonamido)phenyl)-6-((2-fluoro-4-(trifluoromethyl)phenyl)carbamoyl) cyclohexane-1-carboxylic acid | $^{1}H$ NMR (400 MHz, DMSO-$d_6$) δ 11.95 (br s, 1H), 10.11 (s, 1H), 8.21 (t, J = 8.0 Hz, 1H), 7.85 (d, J = 1.2 Hz, 1H), 7.78 - 7.71 (m, 2H), 7.56 (dd, J = 8.6, 1.6 Hz, 2H), 7.47 (d, J = 1.6 Hz, 1H), 7.22 (dd, J = 8.2, 2.0 Hz, 1H), 6.91 (d, J = 8.0 Hz, 1H), 3.84 (s, 3H), 3.09 (s, 3H), 2.99 (t, J = 8.0 Hz, 1H), 2.83 (t, J = 10.8 Hz, 1H), 2.77 - 2.73 (m, 1H), 2.62 (s, 3H), 2.03 - 2.02 (m, 1H), 1.91 - 1.89 (m, 1H), 1.87 - 1.78 (m, 1H), 1.59 - 1.47 (m, 3H). |

| Ex | LCMS |
|---|---|
| 296 | ES-LCMS m/z 681.0 $[M + H]^+$. |

Example 297 rel-(1R,2R,4S,6S)-4-acetamido-2-((4-(trifluoromethyl)phenoxy)methyl)-6-(4-((N,1,2-trimethyl-1H-benzo[d]imidazole)-5-sulfonamido)phenyl)cyclohexane-1-carboxylic acid ISOMER 1

ISOMER 1

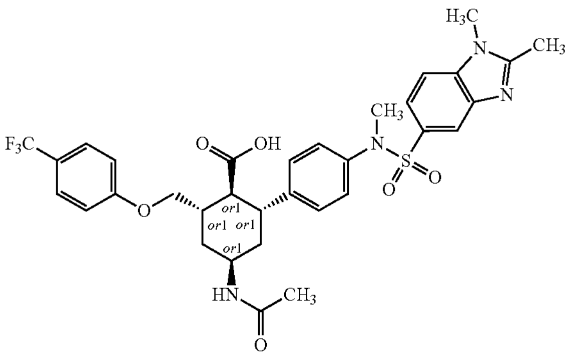

A mixture of rel-(1R,2R,4S,6S)-4-amino-2-((4-(trifluoromethyl)phenoxy)methyl)-6-(4-((N,1,2-trimethyl-1H-benzo[d]imidazole)-5-sulfonamido)phenyl)cyclohexane-1-carboxylic acid ISOMER 1 (60 mg, 0.1 mmol) and acetic anhydride (1 mL, 10.60 mmol) was stirred for 5 h and subjected to reverse phase purification (0-100% MeCN in $H_2O$, 0.1% ABC modifier) to afford rel-(1R,2R,4S,6S)-4-acetamido-2-((4-(trifluoromethyl)phenoxy)methyl)-6-(4-((N,1,2-trimethyl-1H-benzo[d]imidazole)-5-sulfonamido) phenyl)cyclohexane-1-carboxylic acid ISOMER 1 (48 mg, 0.070 mmol, 75% yield) as white solid. CH NMR (400 MHz, DMSO-$d_6$) δ 12.08 (s, 1H), 8.11 (d, J=6.5 Hz, 1H), 7.64 (dd, J=8.5, 2.0 Hz, 3H), 7.52 (d, J=1.5 Hz, 1H), 7.25 (dd, J=8.5, 1.5 Hz, 1H), 7.18 (d, J=8.5 Hz, 2H), 7.09 (d, J=8.5 Hz, 2H), 6.98 (d, J=8.5 Hz, 2H), 4.11 (s, 1H), 3.94 (d, J=3.5 Hz, 2H), 3.78 (O, 3H), 3.13 (td, J=11.1, 4.3 Hz, 1H), 3.06 (s, 3H), 2.57 (s, 3H), 2.51-2.47 (m, 2H), 1.95-1.91 (m, 1H), 1.89 (s, 3H), 1.74-1.71 (m, 2H), 1.62-1.58 (in, 1H). ES-LCMS m/z 673.2 $[M+H]^+$.

The following compound was synthesized in an analogous manner to the preparation described above (Example 297):

| Ex | Structure/Name | $^1$H NMR | LCMS |
|---|---|---|---|
| 298 | 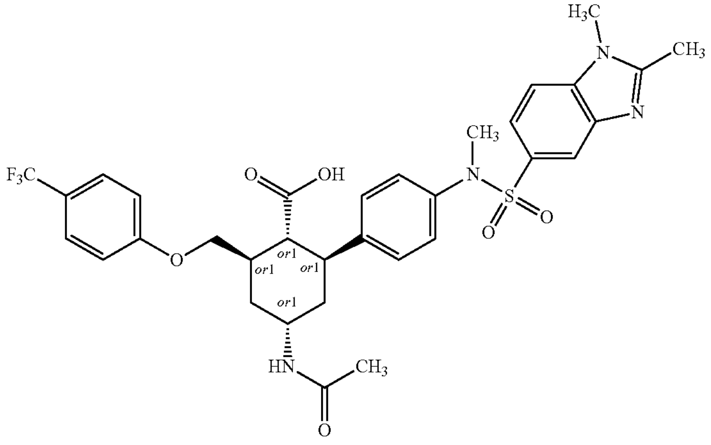 [SMILES: CC(=O)N[C@@H]1C[C@@H](COc2ccc(C(F)(F)F)cc2)[C@H](C(=O)O)[C@@H](c2ccc(N(C)S(=O)(=O)c3ccc4c(c3)nc(C)n4C)cc2)C1] ISOMER 2 rel-(1R,2R,4S,6S)-4-acetamido-2-((4-(trifluoromethyl)phenoxy)methyl)-6-(4-((N,1,2-trimethyl-1H-benzo[d]imidazole)-5-sulfonamido)phenyl)cyclohexane-1-carboxylic acid ISOMER 2 | $^1$H NMR (400 MHz, DMSO-$d_6$) δ 12.26 (s, 1H), 8.10 (d, J = 6.5 Hz, 1H), 7.63 (dd, J = 8.8, 1.8 Hz, 3H), 7.51 (d, J = 1.5 Hz, 1H), 7.24 (dd, J = 8.5, 2.0 Hz, 1H), 7.18 (d, J = 9.0 Hz, 2H), 7.08 (d, J = 8.5 Hz, 2H), 6.97 (d, J = 8.5 Hz, 2H), 4.10 (d, J = 3.5 Hz, 1H), 3.93 (d, J = 3.5 Hz, 2H), 3.77 (s, 3H), 3.19 - 3.06 (m, 1H), 3.05 (s, 3H), 2.56 (s, 3H), 2.45 - 2.42 (m, 2H), 1.92 - 1.89 (m, 1H), 1.87 (s, 3H), 1.79 - 1.70 (m, 2H), 1.65 - 1.51 (m, 1H) | ES-LCMS m/z 673.2 $[M + H]^+$. |

The following compounds were synthesized from intermediates 69-71 in an analogous manner to the preparation described above (Example 200), changing the temperature to rt and using acetic acid as the solvent:

| Ex | Structure/Name | $^1$H NMR | LCMS |
|---|---|---|---|
| 299 | 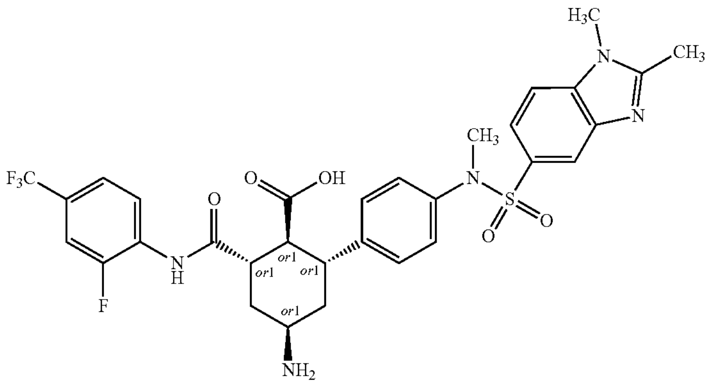 [SMILES: Cc1nc2cc(S(=O)(=O)N(C)c3ccc([C@@H]4C[C@@H](N)C[C@H](C(=O)Nc5ccc(C(F)(F)F)cc5F)[C@H]4C(=O)O)cc3)ccc2n1C] ISOMER 1 rel-(1R,2R,4S,6S)-4-amino-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylic acid ISOMER 1 | $^1$H NMR (400 MHz, DMSO-$d_6$) δ 10.13 (s, 1H), 8.17 (t, J = 8.0 Hz, 1H), 7.70 (dd, J = 11.0, 1.5 Hz, 1H), 7.62 (d, J = 8.5 Hz, 1H), 7.56 - 7.47 (m, 2H), 7.24 (dd, J = 8.5, 2.0 Hz, 1H), 7.17 (d, J = 8.5 Hz, 2H), 6.94 (d, J = 8.5 Hz, 2H), 3.82 (s, 3H), 3.49 - 3.45 (m, 1H), 3.23 - 3.17 (m, 2H), 3.04 (s, 3H), 2.76 - 2.61 (m, 1H), 2.56 (s, 3H), 1.92 - 1.88 (m, 1H), 1.81 - 1.55 (m, 3H) | ES-LCMS m/z 662.2 $[M + H]^+$. |

-continued

| Ex | Structure/Name | $^1H$ NMR | LCMS |
|---|---|---|---|
| 300 | 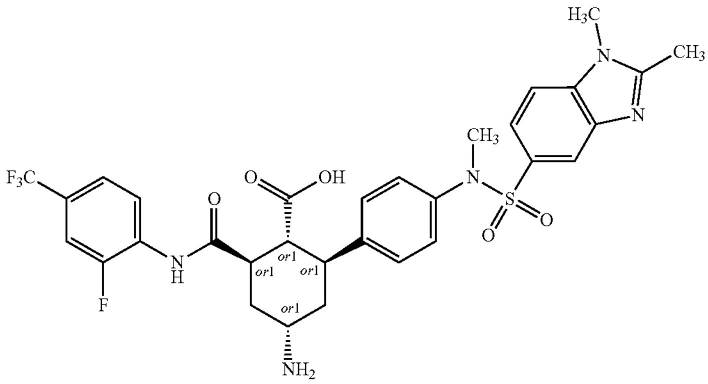 [SMILES: Cc1nc2cc(S(=O)(=O)N(C)c3ccc([C@H]4C[C@H](N)C[C@@H](C(=O)Nc5ccc(C(F)(F)F)cc5F)[C@@H]4C(=O)O)cc3)ccc2n1C] ISOMER 2 rel-(1R,2R,4S,6S)-4-amino-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylic acid ISOMER 2 | $^1H$ NMR (400 MHz, DMSO-$d_6$) δ 10.13 (s, 1H), 8.18 (t, J = 7.8 Hz, 1H), 7.75 - 7.67 (m, 1H), 7.64 (d, J = 8.5 Hz, 1H), 7.58 - 7.47 (m, 2H), 7.26 (dd, J = 8.5, 1.5 Hz, 1H), 7.18 (d, J = 8.5 Hz, 2H), 6.96 (d, J = 8.5 Hz, 2H), 3.79 (s, 3H), 3.49 - 3.45 (m, 1H), 3.23 - 3.17 (m, 2H), 3.06 (s, 3H), 2.73 (t, J = 11.3 Hz, 1H), 2.57 (s, 3H), 1.92 (d, J = 13.0 Hz, 1H), 1.86 - 1.70 (m, 2H), 1.64 (d, J = 12.5 Hz, 1H) | ES-LCMS m/z 662.2 $[M + H]^+$. |
| 301 | 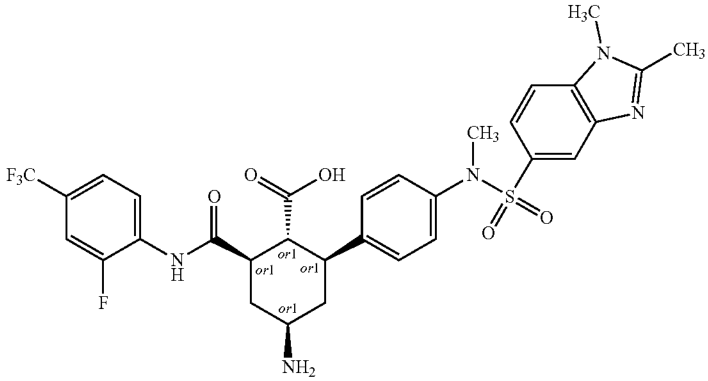 [SMILES: Cc1nc2cc(S(=O)(=O)N(C)c3ccc([C@H]4C[C@@H](N)C[C@@H](C(=O)Nc5ccc(C(F)(F)F)cc5F)[C@@H]4C(=O)O)cc3)ccc2n1C] rel-(1R,2R,4R,6S)-4-amino-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylic acid ISOMER 1 | $^1H$ NMR (400 MHz, DMSO-$d_6$) δ 10.16 (s, 1H), 8.23 (t, J = 8.3 Hz, 1H), 7.76 - 7.67 (m, 1H), 7.64 (d, J = 8.5 Hz, 1H), 7.58 - 7.48 (m, 2H), 7.27 (dd, J = 8.5, 1.5 Hz, 1H), 7.18 (d, J = 8.5 Hz, 2H), 6.97 (d, J = 8.5 Hz, 2H), 3.79 (s, 3H), 3.09 (s, 1H), 3.06 (s, 3H), 2.98-2.88 (m, 1H), 2.84 - 2.72 (m, 1H), 2.70 - 2.64 (m, 1H), 2.57 (s, 3H), 2.16 - 2.08 (m, 1H), 1.88 (d, J = 13.0 Hz, 1H), 1.50 - 1.33 (m, 2H) | ES-LCMS m/z 662.2 $[M + H]^+$. |
| 302 | 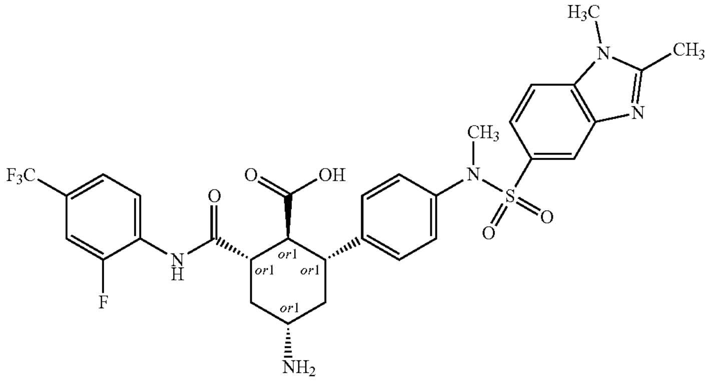 [SMILES: Cc1nc2cc(S(=O)(=O)N(C)c3ccc([C@@H]4C[C@H](N)C[C@H](C(=O)Nc5ccc(C(F)(F)F)cc5F)[C@H]4C(=O)O)cc3)ccc2n1C] ISOMER 2 rel-(1R,2R,4R,6S)-4-amino-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylic acid ISOMER 2 | $^1H$ NMR (400 MHz, DMSO-$d_6$) δ 10.16 (s, 1H), 8.22 (t, J = 8.0 Hz, 1H), 7.71 (dd, J = 11.0, 2.0 Hz, 1H), 7.63 (d, J = 8.5 Hz, 1H), 7.57 - 7.47 (m, 2H), 7.25 (dd, J = 8.5, 1.5 Hz, 1H), 7.16 (d, J = 8.5 Hz, 2H), 6.95 (d, J = 8.5 Hz, 2H), 3.78 (s, 3H), 3.05 (s, 4H), 2.92 - 2.83 (m, 1H), 2.81 - 2.72 (m, 1H), 2.68 - 2.60 (m, 1H), 2.57 (s, 3H), 2.10 (d, J = 12.0 Hz, 1H), 1.89 - 1.80 (m, 1H), 1.45 - 1.30 (m, 2H) | ES-LCMS m/z 662.2 $[M + H]^+$. |

Example 303 rel-(1R,2R,4S,6S)-4-(3,3-difluoropyrrolidin-1-yl)-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylic acid ISOMER 1

ISOMER 1

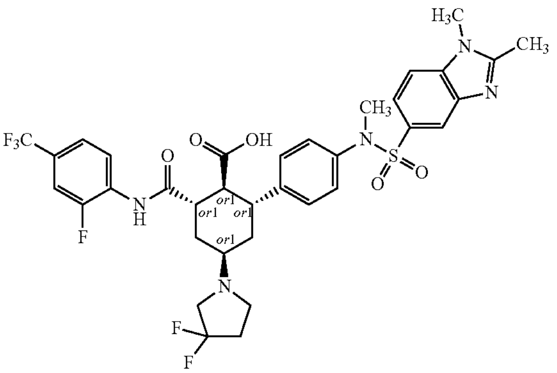

To a mixture of rel-benzyl (1R,2R,4S,6S)-4-(3,3-difluoropyrrolidin-1-yl)-2-((2-fluoro-4-(trifluoromethyl)phenyl) carbamoyl)-6-(4-((N,1,2-trimethyl-1H-benzo[d]imidazole)-5-sulfonamido)phenyl)cyclohexane-1-carboxylate ISOMER 1 Intermediate 72 (46 mg, 0.055 mmol) in dichloromethane (2 mL) at 0° C. was added boron trichloride (1M in DCM, 0.16 mL, 0.16 mmol). After 2 h at rt, the reaction was quenched with water (1 mL), concentrated and subjected to reverse phase purification (MeCN in 10 mM aq ammonium bicarbonate, 40-100% gradient) to afford rel-(1R,2R,4S,6S)-4-(3,3-difluoropyrrolidin-1-yl)-2-((2-fluoro-4-(trifluoromethyl)phenyl)carbamoyl)-6-(4-((N,1,2-trimethyl-1H-benzo[d]imidazole)-5-sulfonamido)phenyl) cyclohexane-1-carboxylic acid ISOMER 1 (28 mg, 0.037 mmol, 67% yield) as a white solid. $^1H$ NMR (400 MHz, DMSO-$d_6$) δ 10.19 (s, 1H), 8.09 (t, J=8.3 Hz, 1H), 7.71 (dd, J=10.8, 1.8 Hz, 1H), 7.63 (d, J=8.5 Hz, 1H), 7.58-7.51 (m, 2H), 7.27-7.16 (m, 3H), 6.97 (d, J=9.0 Hz, 2H), 3.78 (s, 3H), 3.38-3.37 (m, 1H), 3.18-3.07 (m, 2H), 3.05 (s, 3H), 2.98-2.69 (m, 4H), 2.58 (s, 3H), 2.53 (s, 1H), 2.42-2.25 (m, 2H), 2.09-2.00 (m, 1H), 1.90-1.69 (m, 3H). ES-LCMS m/z 752.2 $[M+H]^+$.

Example 304 rel-(1R,2R,4S,6S)-4-(3,3-difluoropyrrolidin-1-yl)-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylic acid ISOMER 2

ISOMER 2

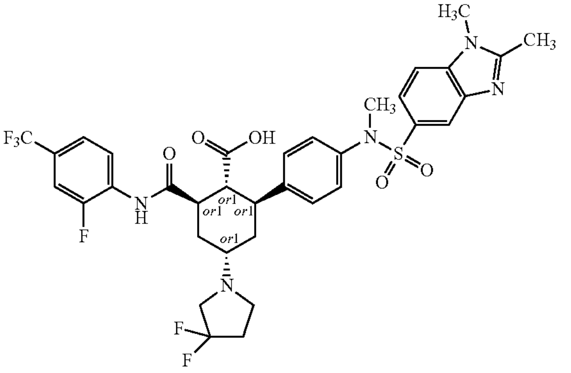

To a mixture of rel-benzyl (1R,2R,4S,6S)-4-(3,3-difluoropyrrolidin-1-yl)-2-((2-fluoro-4-(trifluoromethyl)phenyl) carbamoyl)-6-(4-((N,1,2-trimethyl-1H-benzo[d]imidazole)-5-sulfonamido)phenyl)cyclohexane-1-carboxylate ISOMER 2 Intermediate 73 (42 mg, 0.050 mmol) in dichloromethane (2 mL) at 0° C. was added boron trichloride (1M in DCM, 0.15 mL, 0.15 mmol). After 2 h at rt, the reaction was quenched with water (2 mL), concentrated and subjected to reverse phase purification (MeCN in 10 mM aq ammonium bicarbonate, 30-100% gradient) to afford rel-(1R,2R,4S,6S)-4-(3,3-difluoropyrrolidin-1-yl)-2-((2-fluoro-4-(trifluoromethyl)phenyl)carbamoyl)-6-(4-((N,1,2-trimethyl-1H-benzo[d]imidazole)-5-sulfonamido)phenyl) cyclohexane-1-carboxylic acid ISOMER 2 (20 mg, 0.027 mmol, 53% yield) as a white solid. $^1H$ NMR (400 MHz, DMSO-$d_6$) δ 12.16 (s, 1H), 10.20 (s, 1H), 8.09 (t, J=8.5 Hz, 1H), 7.70 (dd, J=10.8, 1.8 Hz, 1H), 7.62 (d, J=8.5 Hz, 1H), 7.58-7.49 (m, 2H), 7.27-7.16 (m, 3H), 6.96 (d, J=8.5 Hz, 2H), 3.77 (s, 3H), 3.38-3.37 (m, 1H), 3.10 (dd, J=12.0, 8.0 Hz, 2H), 3.04 (s, 3H), 2.98-2.70 (m, 4H), 2.55 (s, 3H), 2.53 (s, 1H), 2.40-2.26 (m, 2H), 2.06-1.99 (m, 1H), 1.88-1.68 (m, 3H). ES-LCMS m/z 752.2 $[M+H]^+$.

Example 305

(1S,2S,4S,6R)-4-(3,3-difluoropyrrolidin-1-yl)-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylic acid

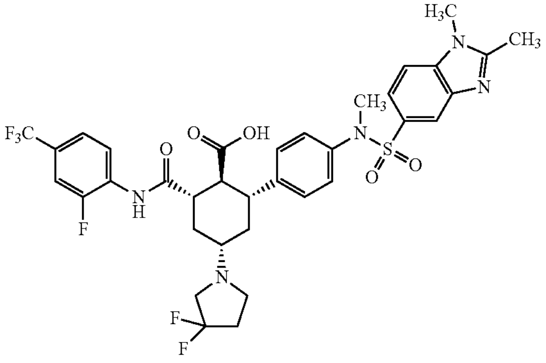 [SMILES: Cc1nc2cc(S(=O)(=O)N(C)c3ccc([C@@H]4C[C@H](N5CCC(F)(F)C5)C[C@H](C(=O)Nc5ccc(C(F)(F)F)cc5F)[C@H]4C(=O)O)cc3)ccc2n1C]

To a mixture of benzyl (1 S,2S,4S,6R)-4-(3,3-difluoropyrrolidin-1-yl)-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylate Intermediate 74 (74 mg, 0.088 mmol) in dichloromethane (2 mL) at 0° C. was added boron trichloride (1M in DCM, 0.30 mL, 0.30 mmol). After 2 h at rt, the reaction was quenched with water (2 mL), concentrated and subjected to reverse phase purification to afford (1 S,2S,4S,6R)-4-(3,3-difluoropyrrolidin-1-yl)-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylic acid (40 mg, 0.053 mmol, 60% yield) as a white solid. $^{1}$H NMR (400 MHz, DMSO-$d_6$) δ 12.18 (s, 1H), 10.15 (s, 1H), 8.24 (t, J=8.0 Hz, 1H), 7.72 (dd, J=10.8, 1.8 Hz, 1H), 7.62 (d, J=8.5 Hz, 1H), 7.55 (d, J=9.0 Hz, 1H), 7.49 (d, J=1.5 Hz, 1H), 7.27-7.18 (m, 3H), 6.96 (d, J=8.5 Hz, 2H), 3.77 (s, 3H), 3.05 (s, 4H), 3.01-2.92 (m, 2H), 2.85-2.71 (m, 5H), 2.56 (s, 3H), 2.26-2.14 (m, 3H), 1.98-1.89 (m, 1H), 1.63-1.39 (m, 2H). ES-LCMS m/z 752.2 $[M+H]^+$. Absolute stereochemistry was assigned based on Example 305 being the enantiomer of Example 306.

Example 306

(1R,2R,4R,6S)-4-(3,3-difluoropyrrolidin-1-yl)-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylic acid

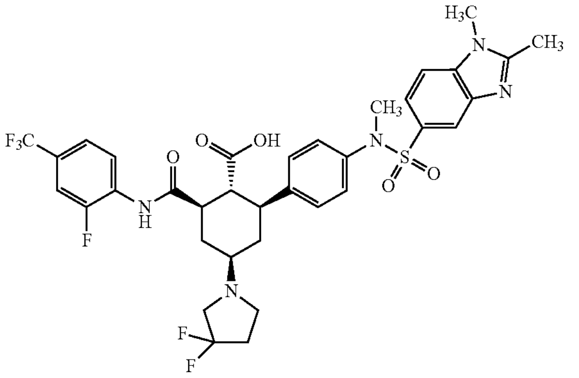 [SMILES: Cc1nc2cc(S(=O)(=O)N(C)c3ccc([C@H]4C[C@@H](N5CCC(F)(F)C5)C[C@@H](C(=O)Nc5ccc(C(F)(F)F)cc5F)[C@@H]4C(=O)O)cc3)ccc2n1C]

To a mixture of benzyl (1R,2R,4R,6S)-4-(3,3-difluoropyrrolidin-1-yl)-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylate Intermediate 75 (64 mg, 0.076 mmol) in dichloromethane (2 mL) at 0° C. was added boron trichloride (1M in DCM, 0.30 mL, 0.30 mmol). After 2 h at rt, the reaction was quenched with water (2 mL), concentrated and subjected to reverse phase purification to afford (1R,2R,4R,6S)-4-(3,3-difluoropyrrolidin-1-yl)-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylic acid (22 mg, 0.028 mmol, 37% yield) as a white solid. $^{1}$H NMR (400 MHz, DMSO-$d_6$) δ 12.21 (s, 1H), 10.18 (s, 1H), 8.24 (t, J=8.0 Hz, 1H), 7.75-7.69 (m, 1H), 7.63 (d, J=8.5 Hz, 1H), 7.57-7.47 (m, 2H), 7.28-7.18 (m, 3H), 6.96 (d, J=8.5 Hz, 2H), 3.78 (s, 3H), 3.05 (s, 4H), 3.02-2.91 (m, 2H), 2.85-2.68 (m, 5H), 2.56 (s, 3H), 2.28-2.12 (m, 3H), 1.94 (d, J=11.5 Hz, 1H), 1.61-1.36 (m, 2H). ES-LCMS m/z 752.2 $[M+H]^+$. Absolute stereochemistry was assigned by co-crystallization with WRN protein.

Example 307 rel-(3R,4S,5R)-3-((2-fluoro-4-(trifluoromethyl)phenyl)carbamoyl)-5-(4-((N,1,2-trimethyl-1H-benzo[d]imidazole)-5-sulfonamido)phenyl)piperidine-4-carboxylic acid ISOMER 1

ISOMER 1

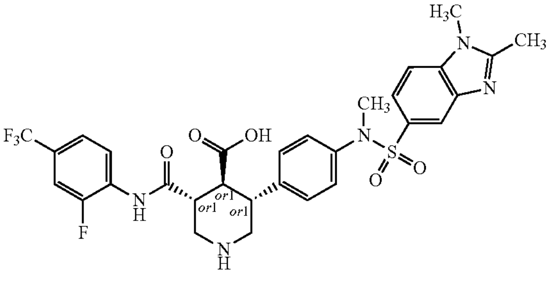

To a mixture of rel-methyl (3R,4S,5R)-3-((2-fluoro-4-(trifluoromethyl)phenyl)carbamoyl)-5-(4-((N,1,2-trimethyl-1H-benzo[d]imidazole)-5-sulfonamido)phenyl)piperidine-4-carboxylate (50 mg, 0.08 mmol) in dichloromethane (2 mL) at 0° C. was added tribromoborane in DCM (0.11 mL, 0.11 mmol). The reaction was stirred at rt for 1 h, quenched with water (1 ml), concentrated and purified by Prep HPLC (MeCN in $H_2O$, 0.1% ABC modifier, 0 to 100% gradient) to afford rel-(3R,4S,5R)-3-((2-fluoro-4-(trifluoromethyl)phenyl)carbamoyl)-5-(4-((N,1,2-trimethyl-1H-benzo[d]imidazole)-5-sulfonamido)phenyl)piperidine-4-carboxylic acid ISOMER 1 (15 mg, 0.020 mmol, 31% yield) as an off-white solid. $^1H$ NMR (400 MHz, DMSO-$d_6$) δ 8.31-8.17 (m, 1H), 7.72-7.61 (m, 2H), 7.61 (br s, 1H), 7.53 (d, J=10.5 Hz, 1H), 7.25 (dd, J=8.5, 1.5 Hz, 1H), 7.18 (d, J=9.0 Hz, 2H), 6.94 (d, J=8.0 Hz, 2H), 3.79 (s, 3H), 3.27-3.24 (m, 2H), 3.07 (s, 4H), 2.92-2.73 (m, 4H), 2.58 (s, 3H). ES-LCMS m/z 648.1 $[M+H]^+$.

The following compounds were synthesized in an analogous manner to the preparation described above (Example 307) from the appropriate methyl ester:

| Ex | Structure/Name | $^1H$ NMR | LCMS |
|---|---|---|---|
| 308 | 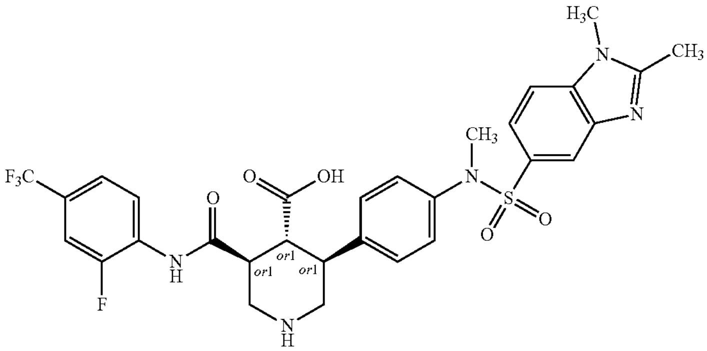 [SMILES: Cc1nc2cc(S(=O)(=O)N(C)c3ccc([C@H]4CNC[C@@H](C(=O)Nc5ccc(C(F)(F)F)cc5F)[C@@H]4C(=O)O)cc3)ccc2n1C]<br>ISOMER 2<br>rel-(3R,4S,5R)-3-((2-fluoro-4-(trifluoromethyl)phenyl)carbamoyl)-5-(4-((N,1,2-trimethyl-1H-benzo[d]imidazole)-5-sulfonamido)phenyl)piperidine-4-carboxylic acid<br>ISOMER 2 | $^1H$ NMR (400 MHz, DMSO-$d_6$) δ 8.17 (t, J = 7.5 Hz, 1H), 7.71 (dd, J = 11.0, 2.0 Hz, 1H), 7.63 (d, J = 8.5 Hz, 1H), 7.58 - 7.51 (m, 2H), 7.26 - 7.17 (m, 3H), 6.97 (d, J = 8.5 Hz, 2H), 3.89 - 3.81 (m, 1H), 3.78 (s, 3H), 3.23 (d, J = 3.5 Hz, 1H), 3.06 (s, 3H), 3.03 - 2.88 (m, 3H), 2.82 - 2.70 (m, 2H), 2.57 (s, 3H) | ES-LCMS m/z 648.2 $[M + H]^+$. |
| 309 | 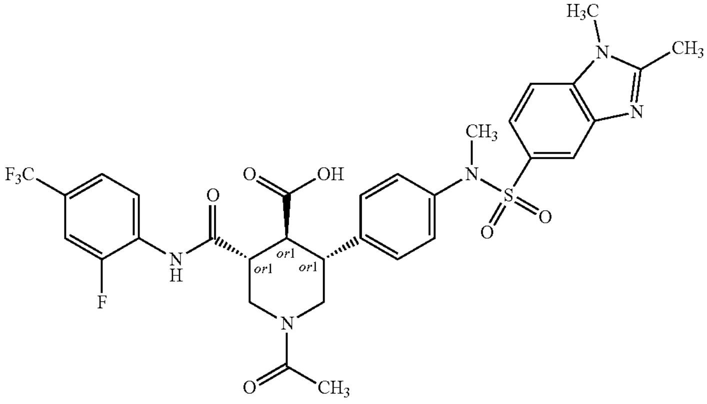 [SMILES: CC(=O)N1C[C@H](C(=O)Nc2ccc(C(F)(F)F)cc2F)[C@@H](C(=O)O)[C@H](c2ccc(N(C)S(=O)(=O)c3ccc4c(c3)nc(C)n4C)cc2)C1]<br>ISOMER 1<br>rel-(3R,4S,5R)-1-acetyl-3-((2-fluoro-4-(trifluoromethyl)phenyl)carbamoyl)-5-(4-((N,1,2-trimethyl-1H-benzo[d]imidazole)-5-sulfonamido)phenyl)piperidine-4-carboxylic acid<br>ISOMER 1 | $^1H$ NMR (400 MHz, DMSO-$d_6$) δ 12.25 (s, 1H), 10.43 - 10.28 (m, 1H), 8.27 - 8.09 (m, 1H), 7.78 - 7.70 (m, 1H), 7.65 - 7.50 (m, 3H), 7.34 - 7.19 (m, 3H), 7.06 - 6.98 (m, 2H), 4.71 (dd, J = 12.3, 3.8 Hz, 1H), 4.38 - 4.04 (m, 1H), 3.77 (d, J = 2.5 Hz, 3H), 3.21 - 3.10 (m, 2H), 3.06 (s, 3H), 2.95 - 2.69 (m, 3H), 2.56 (s, 3H), 2.18 - 2.04 (m, 3H) | ES-LCMS m/z 690.2 $[M + H]^+$. |

-continued

| Ex | Structure/Name | $^1H$ NMR | LCMS |
|---|---|---|---|
| 310 | 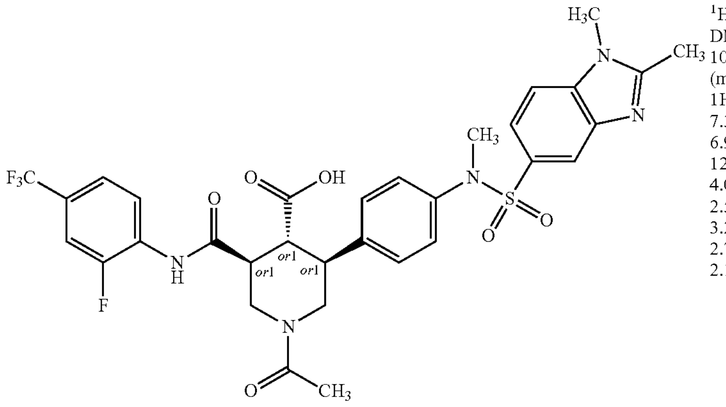<br>ISOMER 2<br>rel-(3R,4S,5R)-1-acetyl-3-((2-fluoro-4-(trifluoromethyl)phenyl)carbamoyl)-5-(4-((N,1,2-trimethyl-1H-benzo[d]imidazole)-5-sulfonamido)phenyl)piperidine-4-carboxylic acid ISOMER 2 | $^1H$ NMR (400 MHz, DMSO-$d_6$) δ 10.45 - 10.32 (m, 1H), 8.29 - 8.10 (m, 1H), 7.81 - 7.70 (m, 1H), 7.67 - 7.52 (m, 3H), 7.37 - 7.19 (m, 3H), 7.06 - 6.98 (m, 2H), 4.73 (dd, J = 12.8, 3.3 Hz, 1H), 4.40 - 4.08 (m, 1H), 3.79 (d, J = 2.5 Hz, 3H), 3.06 (s, 3H), 3.20 - 3.11 (m, 2H), 3.03 - 2.73 (m, 3H), 2.57 (s, 3H), 2.19 - 2.06 (m, 3H) | ES-LCMS m/z 690.0 $[M + H]^+$. |

The following compounds were synthesized in an analogous manner to the preparation described above (Example 81), using the relevant sulfonyl chloride and arylamine precursors, followed by chiral separation for Examples 313-316.

| Ex | Structure/Name | $^1H$ NMR | LCMS |
|---|---|---|---|
| 311 | 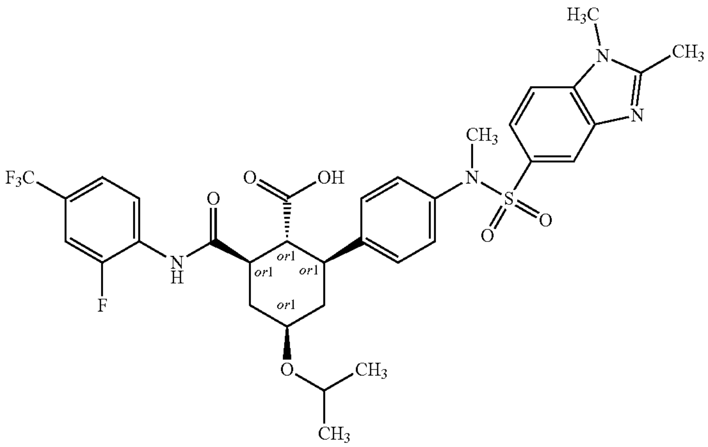 [SMILES: Cc1nc2cc(S(=O)(=O)N(C)c3ccc([C@H]4C[C@@H](OC(C)C)C[C@@H](C(=O)Nc5ccc(C(F)(F)F)cc5F)[C@@H]4C(=O)O)cc3)ccc2n1C]<br>ISOMER 1<br>rel-(1R,2R,4R,6S)-2-((2-fluoro-4-(trifluoromethyl)phenyl)carbamoyl)-4-isopropoxy-6-(4-((N,1,2-trimethyl-1H-benzo[d]imidazole)-5-sulfonamido)phenyl)cyclohexane-1-carboxylic acid ISOMER 1 | $^1H$ NMR (400 MHz, DMSO-$d_6$) δ 12.11 (br s, 1H), 10.10 (s, 1H), 8.22 (t, J = 8.0 Hz, 1H), 7.73 (dd, J = 11.3, 1.8 Hz, 1H), 7.63 (d, J = 8.5 Hz, 1H), 7.55 (d, J = 8.0 Hz, 1H), 7.48 (d, J = 1.5 Hz, 1H), 7.28 - 7.18 (m, 3H), 6.96 (d, J = 9.0 Hz, 2H), 3.81 - 3.71 (m, 4H), 3.62 - 3.51 (m, 1H), 3.11 - 3.01 (m, 4H), 2.80 - 2.72 (m, 2H), 2.56 (s, 3H), 2.26 (d, J = 12.0 Hz, 1H), 1.98 (d, J = 11.5 Hz, 1H), 1.55 (q, J = 12.0 Hz, 1H), 1.41 (q, J = 12.0 Hz, 1H), 1.08 (dd, J = 6.0, 5.0 Hz, 6H) | ES-LCMS m/z 703.2 $[M - H]^-$. |

-continued

| Ex | Structure/Name | $^1$H NMR | LCMS |
|---|---|---|---|
| 312 | 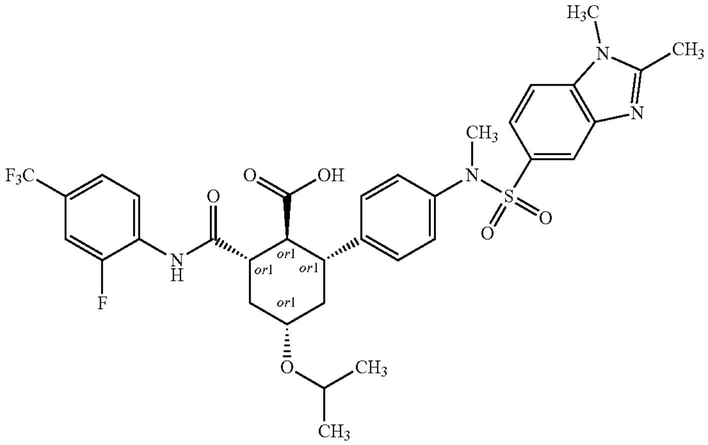 [SMILES: Cc1nc2cc(S(=O)(=O)N(C)c3ccc([C@@H]4C[C@H](OC(C)C)C[C@H](C(=O)Nc5ccc(C(F)(F)F)cc5F)[C@H]4C(=O)O)cc3)ccc2n1C] ISOMER 2 rel-(1R,2R,4R,6S)-2-((2-fluoro-4-(trifluoromethyl)phenyl)carbamoyl)-4-isopropoxy-6-(4-((N,1,2-trimethyl-1H-benzo[d]imidazole)-5-sulfonamido)phenyl)cyclohexane-1-carboxylic acid ISOMER 2 | $^1$H NMR (400 MHz, DMSO-$d_6$) δ 12.12 (br s, 1H), 10.11 (s, 1H), 8.22 (t, J = 8.3 Hz, 1H), 7.73 (dd, J = 11.0, 1.5 Hz, 1H), 7.63 (d, J = 8.5 Hz, 1H), 7.55 (d, J = 8.5 Hz, 1H), 7.48 (d, J = 2.0 Hz, 1H), 7.27 - 7.19 (m, 3H), 6.96 (d, J = 8.5 Hz, 2H), 3.81 - 3.72 (m, 4H), 3.64 - 3.51 (m, 1H), 3.11 - 3.01 (m, 4H), 2.81 - 2.72 (m, 2H), 2.56 (s, 3H), 2.26 (d, J = 12.0 Hz, 1H), 1.98 (d, J = 11.0 Hz, 1H), 1.55 (q, J = 11.8 Hz, 1H), 1.41 (q, J = 12.0 Hz, 1H), 1.08 (t, J = 5.5 Hz, 6H) | ES-LCMS m/z 705.2 $[M + H]^+$. |
| 313 | 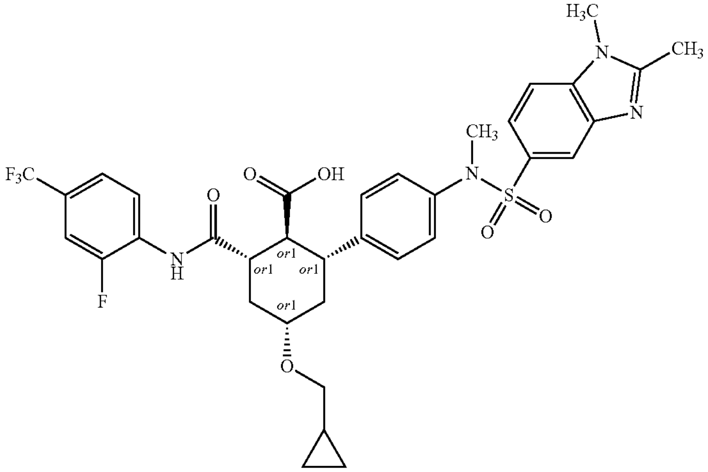 [SMILES: Cc1nc2cc(S(=O)(=O)N(C)c3ccc([C@@H]4C[C@H](OCC5CC5)C[C@H](C(=O)Nc5ccc(C(F)(F)F)cc5F)[C@H]4C(=O)O)cc3)ccc2n1C] ISOMER 1 rel-(1R,2R,4R,6S)-4-(cyclopropylmethoxy)-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylic acid ISOMER 1 | $^1$H NMR (400 MHz, DMSO-$d_6$) δ 12.11 (br s, 1H), 10.12 (br s, 1H), 8.22 (t, J = 8.0 Hz, 1H), 7.72 (dd, J = 11.0, 2.0 Hz, 1H), 7.62 (d, J = 8.5 Hz, 1H), 7.55 (br d, J = 9.5 Hz, 1H), 7.49 (d, J = 1.5 Hz, 1H), 7.26 - 7.19 (m, 3H), 6.96 (d, J = 8.5 Hz, 2H), 3.78 (s, 3H), 3.60 - 3.46 (m, 1H), 3.30 (br s, 2H), 3.10 - 2.99 (m, 4H), 2.78 - 2.72 (m, 2H), 2.56 (s, 3H), 2.33 - 2.28 (m, 1H), 2.04 (br s, 1H), 1.61 - 1.51 (m, 1H), 1.48 - 1.38 (m, 1H), 1.03 - 0.93 (m, 1H), 0.47 - 0.41 (m, 2H), 0.18 - 0.13 (m, 2H) | ES-LCMS m/z 715.2 $[M - H]^-$. |

-continued

| Ex | Structure/Name | $^1$H NMR | LCMS |
|---|---|---|---|
| 314 | 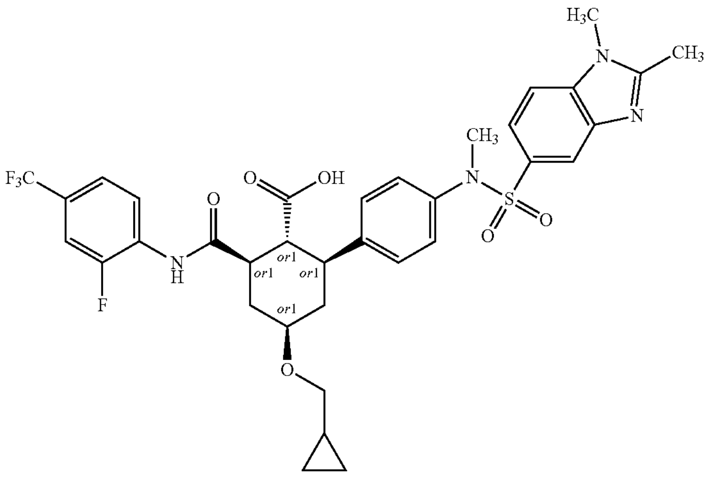 [SMILES: Cc1nc2cc(S(=O)(=O)N(C)c3ccc([C@H]4C[C@@H](OCC5CC5)C[C@@H](C(=O)Nc5ccc(C(F)(F)F)cc5F)[C@@H]4C(=O)O)cc3)ccc2n1C] ISOMER 2 rel-(1R,2R,4R,6S)-4-(cyclopropylmethoxy)-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylic acid ISOMER 2 | $^1$H NMR (400 MHz, DMSO-$d_6$) δ 12.13 (br s, 1H), 10.11 (br s, 1H), 8.22 (t, J = 8.3 Hz, 1H), 7.72 (dd, J = 11.0, 1.5 Hz, 1H), 7.62 (d, J = 8.5 Hz, 1H), 7.58 - 7.53 (m, 1H), 7.49 (d, J = 1.5 Hz, 1H), 7.27 - 7.18 (m, 3H), 6.96 (d, J = 8.5 Hz, 2H), 3.78 (s, 3H), 3.61 - 3.49 (m, 1H), 3.30 - 3.25 (m, 2H), 3.12 - 2.98 (m, 4H), 2.81 - 2.70 (m, 2H), 2.56 (s, 3H), 2.33 - 2.26 (m, 1H), 2.08 - 2.00 (m, 1H), 1.63 - 1.52 (m, 1H), 1.49 - 1.36 (m, 1H), 1.05 - 0.93 (m, 1H), 0.49 - 0.39 (m, 2H), 0.21 - 0.09 (m, 2H) | ES-LCMS m/z 715.2 [M - H]$^-$. |
| 315 | 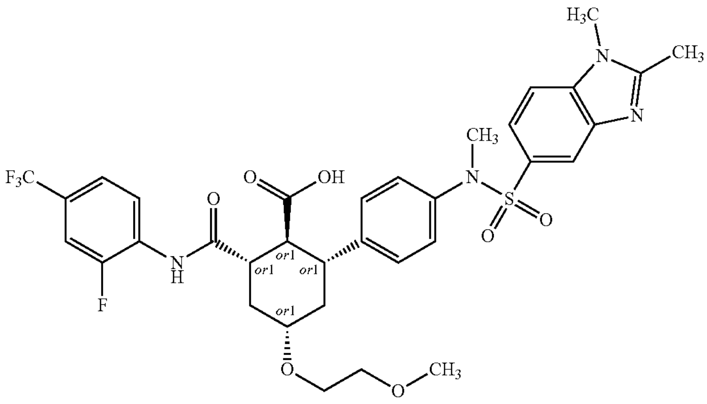 [SMILES: COCCO[C@@H]1C[C@H](C(=O)Nc2ccc(C(F)(F)F)cc2F)[C@@H](C(=O)O)[C@H](c2ccc(N(C)S(=O)(=O)c3ccc4c(c3)nc(C)n4C)cc2)C1] ISOMER 1 rel-(1R,2R,4R,6S)-2-((2-fluoro-4-(trifluoromethyl)phenyl)carbamoyl)-4-(2-methoxyethoxy)-6-(4-((N,1,2-trimethyl-1H-benzo[d]imidazole)-5-sulfonamido)phenyl)cyclohexane-1-carboxylic acid ISOMER 1 | $^1$H NMR (400 MHz, DMSO-$d_6$) δ 12.14 (br s, 1H), 10.13 (s, 1H), 8.22 (t, J = 8.0 Hz, 1H), 7.73 (dd, J = 11.0, 1.5 Hz, 1H), 7.63 (d, J = 8.5 Hz, 1H), 7.56 (d, J = 9.0 Hz, 1H), 7.49 (d, J = 1.5 Hz, 1H), 7.26 - 7.20 (m, 3H), 6.96 (d, J = 8.5 Hz, 2H), 3.78 (s, 3H), 3.59 (dd, J = 6.0, 4.0 Hz, 2H), 3.56 - 3.48 (m, 1H), 3.42 (dd, J = 5.5, 4.0 Hz, 2H), 3.24 (s, 3H), 3.10 - 3.00 (m, 4H), 2.79 - 2.71 (m, 2H), 2.56 (s, 3H), 2.33 (td, J = 4.0, 2.5 Hz, 1H), 2.11 - 2.02 (m, 1H), 1.62 - 1.51 (m, 1H), 1.43 (q, J = 12.0 Hz, 1H) | ES-LCMS m/z 719.2 [M - H]$^-$. |
| 316 | 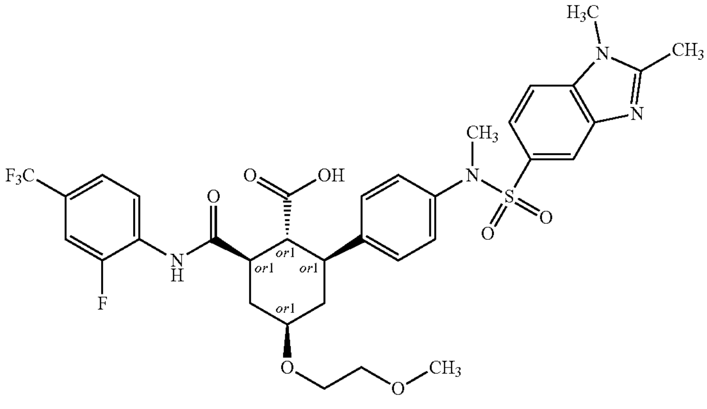 | $^1$H NMR (400 MHz, DMSO-$d_6$) δ 12.14 (br s, 1H), 10.14 (br s, 1H), 8.23 (t, J = 8.0 Hz, 1H), 7.73 (dd, J = 11.0, 2.0 Hz, 1H), 7.63 (d, J = 8.5 Hz, 1H), 7.56 (d, J = 8.5 Hz, 1H), 7.49 (d, J = 1.5 Hz, 1H), 7.29 - 7.13 (m, 3H), 6.96 (d, J = 8.5 Hz, 2H), 3.78 (s, 3H), 3.59 (dd, J = 5.5, 4.0 Hz, 2H), 3.56 - 3.48 (m, 1H), 3.42 (dd, J = 5.8, 4.3 Hz, 2H), 3.24 (s, 3H), 3.10 - 3.00 (m, 4H), 2.81 - 2.69 (m, 2H), 2.56 (s, 3H), 2.33 (td, J = 4.0, 2.5 Hz, 1H), 2.06 (d, J = 11.5 Hz, 1H), 1.62 - 1.51 (m, 1H), 1.43 (q, J = 12.0 Hz, 1H) | ES-LCMS m/z 715.2 [M - H]$^-$. |

-continued

| Ex | Structure/Name | $^1$H NMR | LCMS |
|---|---|---|---|
| | ISOMER 2<br>rel-(1R,2R,4R,6S)-2-((2-fluoro-4-(trifluoromethyl)phenyl)carbamoyl)-4-(2-methoxyethoxy)-6-(4-((N,1,2-trimethyl-1H-benzo[d]imidazole)-5-sulfonamido)phenyl)cyclohexane-1-carboxylic acid ISOMER 2 | | |
| 317 | 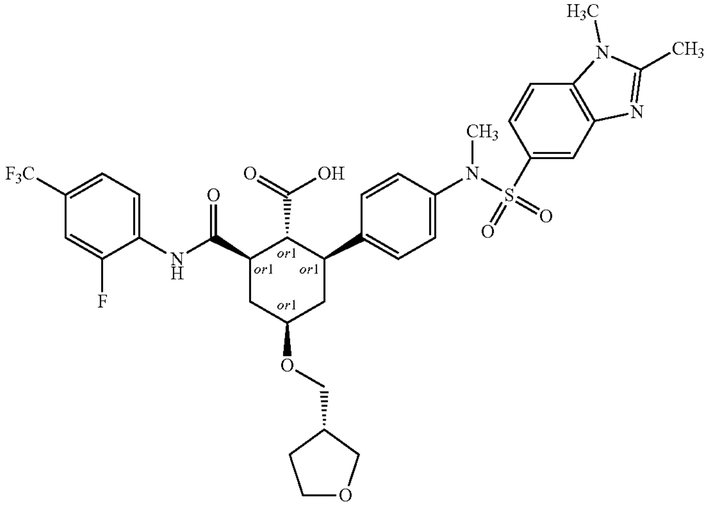 [SMILES: Cc1nc2cc(S(=O)(=O)N(C)c3ccc([C@H]4C[C@@H](OC[C@H]5CCOC5)C[C@@H](C(=O)Nc5ccc(C(F)(F)F)cc5F)[C@@H]4C(=O)O)cc3)ccc2n1C]<br>ISOMER 1<br>(1R*,2R*,4R*,6S*)-2-((2-fluoro-4-(trifluoromethyl)phenyl) carbamoyl)-4-(((S)-tetrahydrofuran-3-yl)methoxy)-6-(4-((N,1,2-trimethyl-1H-benzo[d]imidazole)-5-sulfonamido)phenyl)cyclohexane-1-carboxylic acid ISOMER 1 | $^1$H NMR (400 MHz, DMSO-$d_6$) δ 12.14 (br s, 1H), 10.13 (br s, 1H), 8.22 (t, J = 8.3 Hz, 1H), 7.73 (dd, J = 11.3, 1.8 Hz, 1H), 7.63 (d, J = 8.5 Hz, 1H), 7.56 (d, J = 8.5 Hz, 1H), 7.49 (d, J = 1.5 Hz, 1H), 7.28 - 7.20 (m, 3H), 6.96 (d, J = 8.5 Hz, 2H), 3.78 (s, 3H), 3.71 - 3.64 (m, 2H), 3.62 - 3.55 (m, 1H), 3.54 - 3.37 (m, 4H), 3.10 - 3.00 (m, 4H), 2.80 - 2.73 (m, 2H), 2.56 (s, 3H), 2.47 - 2.34 (m, 2H), 2.06 (d, J = 11.5 Hz, 1H), 1.95 - 1.84 (m, 1H), 1.62 - 1.40 (m, 3H) | ES-LCMS m/z 745.2 [M - H]$^-$. |
| 318 | 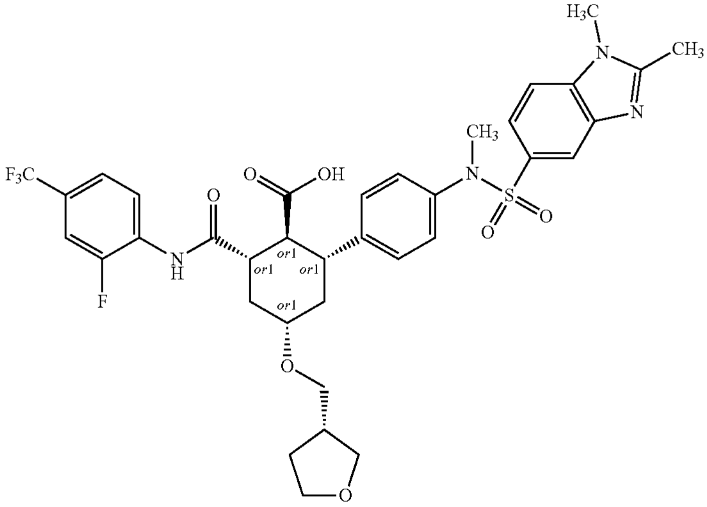 [SMILES: Cc1nc2cc(S(=O)(=O)N(C)c3ccc([C@@H]4C[C@H](OC[C@H]5CCOC5)C[C@H](C(=O)Nc5ccc(C(F)(F)F)cc5F)[C@H]4C(=O)O)cc3)ccc2n1C]<br>ISOMER 2<br>(1R*,2R*,4R*,6S*)-2-((2-fluoro-4-(trifluoromethyl)phenyl)carbamoyl)-4-(((S)-tetrahydrofuran-3-yl)methoxy)-6-(4-((N,1,2-trimethyl-1H-benzo[d]imidazole)-5-sulfonamido)phenyl)cyclohexane-1-carboxylic acid ISOMER 2 | $^1$H NMR (400 MHz, DMSO-$d_6$) δ 12.13 (br s, 1H), 10.14 (br s, 1H), 8.22 (t, J = 8.0 Hz, 1H), 7.73 (dd, J = 11.0, 1.5 Hz, 1H), 7.63 (d, J = 8.5 Hz, 1H), 7.55 (d, J = 8.5 Hz, 1H), 7.49 (d, J = 1.5 Hz, 1H), 7.28 - 7.19 (m, 3H), 6.96 (d, J = 8.5 Hz, 2H), 3.78 (s, 3H), 3.71 - 3.65 (m, 2H), 3.62 - 3.55 (m, 1H), 3.54 - 3.47 (m, 1H), 3.47 - 3.36 (m, 3H), 3.09 - 3.01 (m, 4H), 2.80 - 2.71 (m, 2H), 2.56 (s, 3H), 2.38 (dd, J = 14.3, 6.8 Hz, 2H), 2.09 - 2.02 (m, 1H), 1.94 - 1.84 (m, 1H), 1.62 - 1.39 (m, 3H) | ES-LCMS m/z 745.2 [M - H]$^-$. |

The following compounds were synthesized in an analogous manner to the preparation described above (Example 317 and Example 318), using the relevant alcohol.

| Ex | Structure/Name | $^1$H NMR | LCMS |
|---|---|---|---|
| 319 | 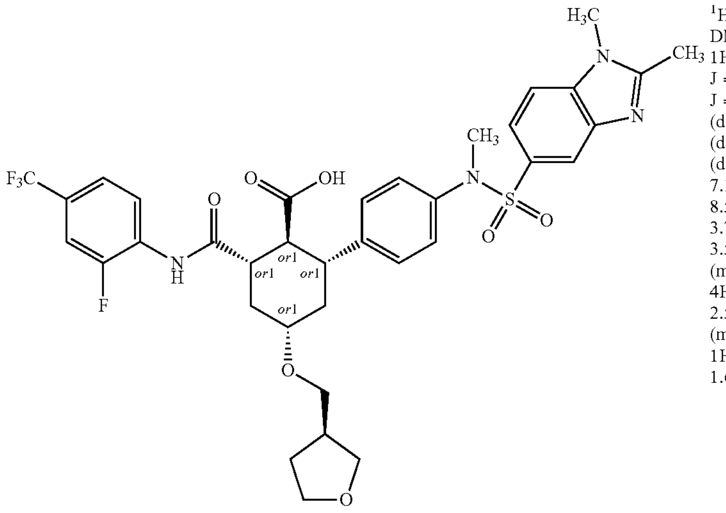 ISOMER 1 (1R*,2R*,4R*,6S*)-2-((2-fluoro-4-(trifluoromethyl) phenyl) carbamoyl)-4-(((R)-tetrahydrofuran-3-yl)methoxy)-6-(4-((N,1,2-trimethyl-1H-benzo[d]imidazole)-5-sulfonamido)phenyl)cyclohexane-1-carboxylic acid ISOMER 1 | $^1$H NMR (400 MHz, DMSO-$d_6$) δ 12.12 (br s, 1H), 10.14 (s, 1H), 8.22 (t, J = 8.0 Hz, 1H), 7.73 (dd, J = 11.0, 2.0 Hz, 1H), 7.63 (d, J = 8.5 Hz, 1H), 7.56 (d, J = 9.0 Hz, 1H), 7.49 (d, J = 1.5 Hz, 1H), 7.28 - 7.19 (m, 3H), 6.96 (d, J = 8.5 Hz, 2H), 3.78 (s, 3H), 3.71 - 3.64 (m, 2H), 3.62 - 3.56 (m, 1H), 3.54 - 3.36 (m, 5H), 3.09 - 3.00 (m, 4H), 2.80 - 2.71 (m, 2H), 2.56 (s, 3H), 2.45 - 2.34 (m, 1H), 2.09 - 2.02 (m, 1H), 1.95 - 1.84 (m, 1H), 1.62 - 1.37 (m, 3H) | ES-LCMS m/z 745.2 [M - H]$^-$. |
| 320 | 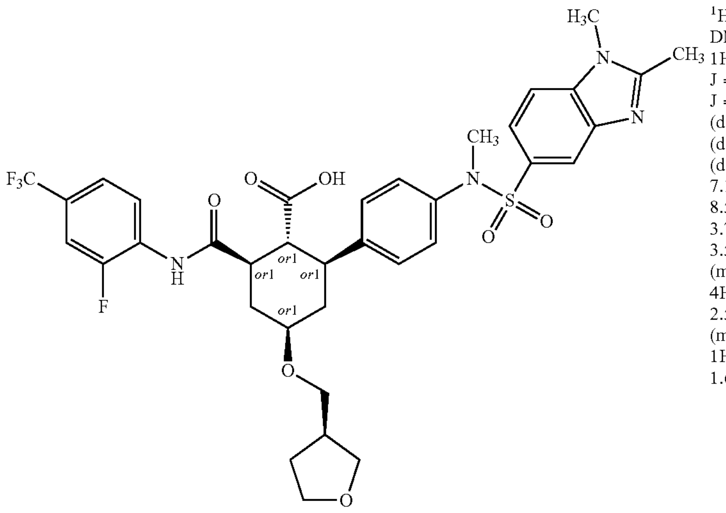 ISOMER 2 (1R*,2R*,4R*,6S*)-2-((2-fluoro-4-(trifluoromethyl) phenyl) carbamoyl)-4-(((R)-tetrahydrofuran-3-yl)methoxy)-6-(4-((N,1,2-trimethyl-1H-benzo[d]imidazole)-5-sulfonamido)phenyl)cyclohexane-1-carboxylic acid ISOMER 2 | $^1$H NMR (400 MHz, DMSO-$d_6$) δ 12.14 (br s, 1H), 10.13 (s, 1H), 8.22 (t, J = 8.0 Hz, 1H), 7.73 (dd, J = 11.0, 2.0 Hz, 1H), 7.63 (d, J = 8.5 Hz, 1H), 7.56 (d, J = 9.0 Hz, 1H), 7.48 (d, J = 1.5 Hz, 1H), 7.28 - 7.19 (m, 3H), 6.96 (d, J = 8.5 Hz, 2H), 3.78 (s, 3H), 3.71 - 3.64 (m, 2H), 3.62 - 3.55 (m, 1H), 3.54 - 3.36 (m, 5H), 3.10 - 3.01 (m, 4H), 2.80 - 2.71 (m, 2H), 2.56 (s, 3H), 2.43 - 2.34 (m, 1H), 2.09 - 2.02 (m, 1H), 1.94 - 1.84 (m, 1H), 1.63 - 1.37 (m, 3H) | ES-LCMS m/z 745.2 [M - H]$^-$. |

-continued

| Ex | Structure/Name | $^1$H NMR | LCMS |
|---|---|---|---|
| 321 | 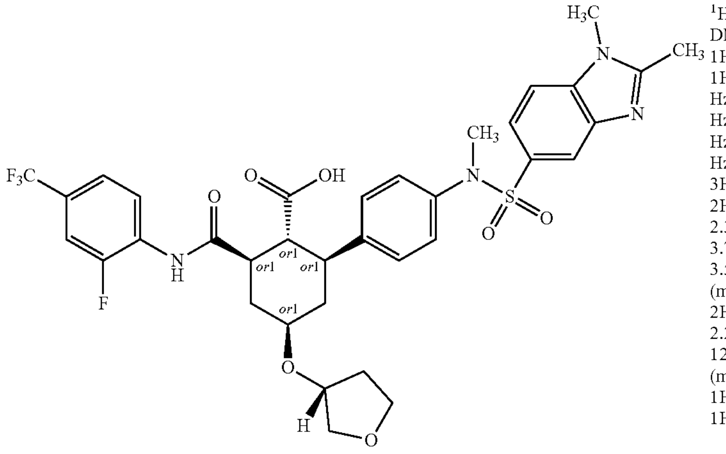 ISOMER 1 (1R*,2R*,4R*,6S*)-2-((2-fluoro-4-(trifluoromethyl)phenyl)carbamoyl)-4-(((R)-tetrahydrofuran-3-yl)oxy)-6-(4-((N,1,2-trimethyl-1H-benzo[d]imidazole)-5-sulfonamido)phenyl)cyclohexane-1-carboxylic acid ISOMER 1 | $^1$H NMR (400 MHz, DMSO-$d_6$) δ 10.22 (br s, 1H), 8.23 (t, J = 8.0 Hz, 1H), 7.72 (dd, J = 11.0, 1.5 Hz, 1H), 7.63 (d, J = 8.5 Hz, 1H), 7.55 (d, J = 8.5 Hz, 1H), 7.50 (d, J = 1.5 Hz, 1H), 7.29 - 7.17 (m, 3H), 6.95 (d, J = 9.0 Hz, 2H), 4.33 (ddt, J = 6.4, 4.5, 2.3 Hz, 1H), 3.78 (s, 3H), 3.73 - 3.62 (m, 3H), 3.62 - 3.53 (m, 2H), 3.07 - 2.97 (m, 4H), 2.82 - 2.65 (m, 2H), 2.56 (s, 3H), 2.35 - 2.26 (m, 1H), 2.02 (d, J = 12.5 Hz, 1H), 1.98 - 1.89 (m, 1H), 1.87 - 1.78 (m, 1H), 1.56 (q, J = 11.7 Hz, 1H), 1.48 - 1.37 (m, 1H) | ES-LCMS m/z 731.2 $[M - H]^-$. |
| 322 | 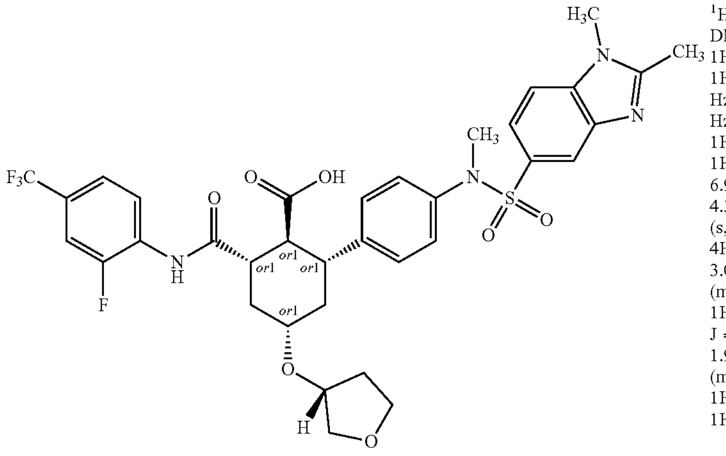 ISOMER 2 (1R*,2R*,4R*,6S*)-2-((2-fluoro-4-(trifluoromethyl)phenyl)carbamoyl)-4-(((R)-tetrahydrofuran-3-yl)oxy)-6-(4-((N,1,2-trimethyl-1H-benzo[d]imidazole)-5-sulfonamido)phenyl)cyclohexane-1-carboxylic acid ISOMER 2 | $^1$H NMR (400 MHz, DMSO-$d_6$) δ 10.24 (br s, 1H), 8.24 (t, J = 8.3 Hz, 1H), 7.72 (dd, J = 11.0, 1.5 Hz, 1H), 7.63 (d, J = 8.5 Hz, 1H), 7.58 - 7.53 (m, 1H), 7.50 (d, J = 1.5 Hz, 1H), 7.27 - 7.19 (m, 3H), 6.95 (d, J = 8.5 Hz, 2H), 4.37 - 4.29 (m, 1H), 3.78 (s, 3H), 3.74 - 3.62 (m, 4H), 3.62 - 3.50 (m, 3H), 3.05 (s, 3H), 3.03 - 2.95 (m, 1H), 2.83 - 2.73 (m, 1H), 2.56 (s, 3H), 2.29 (d, J = 8.5 Hz, 1H), 2.06 - 1.99 (m, 1H), 1.98 - 1.89 (m, 1H), 1.87 - 1.78 (m, 1H), 1.55 (q, J = 12.0 Hz, 1H), 1.42 (q, J = 12.0 Hz, 1H) | ES-LCMS m/z 731.2 $[M - H]^-$. |

-continued

| Ex | Structure/Name | $^1$H NMR | LCMS |
|---|---|---|---|
| 323 | 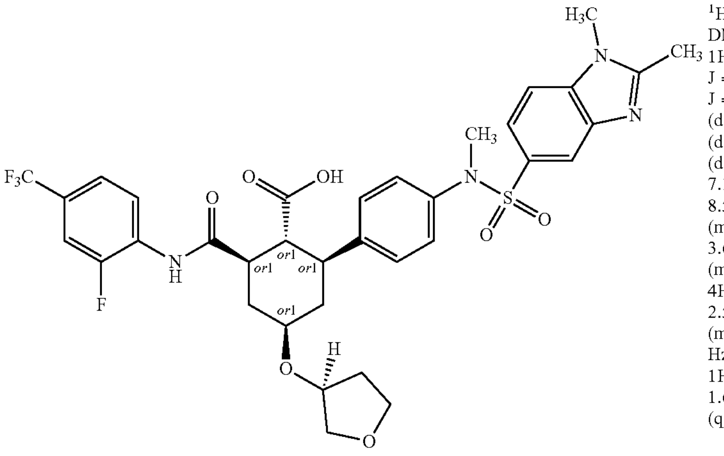 ISOMER 1 (1R*,2R*,4R*,6S*)-2-((2-fluoro-4-(trifluoromethyl)phenyl)carbamoyl)-4-(((S)-tetrahydrofuran-3-yl)oxy)-6-(4-((N,1,2-trimethyl-1H-benzo[d]imidazole)-5-sulfonamido)phenyl)cyclohexane-1-carboxylic acid ISOMER 1 | $^1$H NMR (400 MHz, DMSO-$d_6$) δ 12.13 (br s, 1H), 10.11 (s, 1H), 8.22 (t, J = 8.3 Hz, 1H), 7.73 (dd, J = 11.0, 2.0 Hz, 1H), 7.63 (d, J = 8.5 Hz, 1H), 7.56 (d, J = 8.0 Hz, 1H), 7.48 (d, J = 1.5 Hz, 1H), 7.27 - 7.19 (m, 3H), 6.96 (d, J = 8.5 Hz, 2H), 4.36 - 4.30 (m, 1H), 3.78 (s, 3H), 3.73 - 3.63 (m, 3H), 3.62 - 3.52 (m, 2H), 3.10 - 3.01 (m, 4H), 2.80 - 2.72 (m, 2H), 2.56 (s, 3H), 2.37 - 2.27 (m, 1H), 2.04 (d, J = 11.5 Hz, 1H), 1.99 - 1.89 (m, 1H), 1.88 - 1.79 (m, 1H), 1.65 - 1.54 (m, 1H), 1.43 (q, J = 12.0 Hz, 1H) | ES-LCMS m/z 731.2 $[M - H]^-$. |
| 324 | 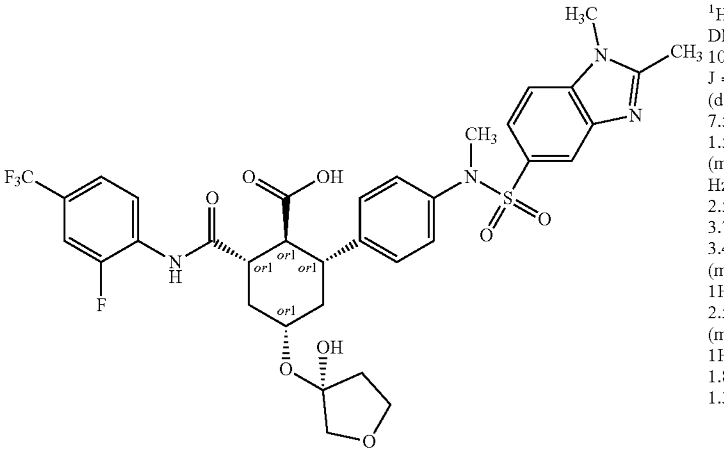 ISOMER 2 (1R*,2R*,4R*,6S*)-2-((2-fluoro-4-(trifluoromethyl)phenyl)carbamoyl)-4-(((S)-tetrahydrofuran-3-yl)oxy)-6-(4-((N,1,2-trimethyl-1H-benzo[d]imidazole)-5-sulfonamido)phenyl)cyclohexane-1-carboxylic acid ISOMER 2 | $^1$H NMR (400 MHz, DMSO-$d_6$) δ 12.77 (s, 1H), 10.26 (br s, 1H), 7.72 (dd, J = 11.0, 1.5 Hz, 1H), 7.63 (d, J = 8.5 Hz, 1H), 7.57 - 7.53 (m, 1H), 7.51 (d, J = 1.5 Hz, 1H), 7.27 - 7.17 (m, 3H), 6.95 (d, J = 8.5 Hz, 2H), 4.32 (qd, J = 4.3, 2.5 Hz, 1H), 3.78 (s, 3H), 3.75 - 3.63 (m, 3H), 3.62 - 3.47 (m, 2H), 3.07 - 2.96 (m, 4H), 2.83 - 2.73 (m, 1H), 2.71 - 2.63 (m, 1H), 2.56 (s, 3H), 2.53 - 2.52 (m, 1H), 2.33 - 2.25 (m, 1H), 2.08 - 1.90 (m, 2H), 1.87 - 1.76 (m, 1H), 1.60 - 1.38 (m, 2H) | ES-LCMS m/z 731.2 $[M - H]^-$. |

-continued

| Ex | Structure/Name | $^1$H NMR | LCMS |
|---|---|---|---|
| 325 | 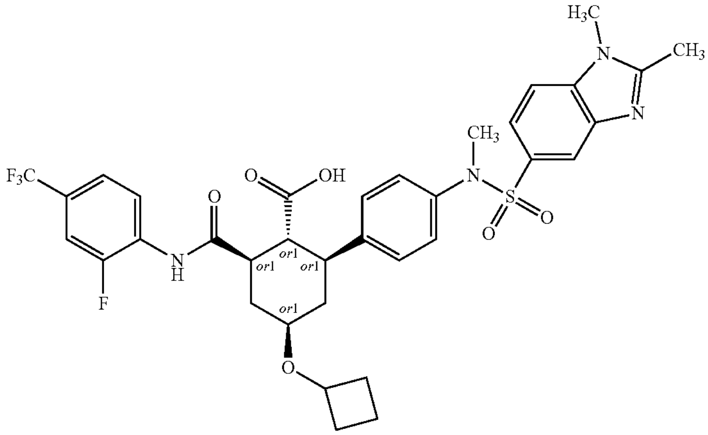 [SMILES: Cc1nc2cc(S(=O)(=O)N(C)c3ccc([C@H]4C[C@@H](OC5CCC5)C[C@@H](C(=O)Nc5ccc(C(F)(F)F)cc5F)[C@@H]4C(=O)O)cc3)ccc2n1C] ISOMER 1 rel-(1R,2R,4R,6S)-4-cyclobutoxy-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylic acid ISOMER 1 | $^1$H NMR (400 MHz, DMSO-$d_6$) δ 12.14 (br s, 1H), 10.13 (br s, 1H), 8.22 (t, J = 8.0 Hz, 1H), 7.76 - 7.70 (m, 1H), 7.62 (d, J = 8.5 Hz, 1H), 7.55 (d, J = 8.5 Hz, 1H), 7.48 (d, J = 1.5 Hz, 1H), 7.26 - 7.18 (m, 3H), 6.96 (d, J = 8.5 Hz, 2H), 4.13 - 4.02 (m, 1H), 3.78 (s, 3H), 3.57 - 3.44 (m, 1H), 3.10 - 2.98 (m, 4H), 2.79 - 2.70 (m, 2H), 2.56 (s, 3H), 2.29 - 2.22 (m, 1H), 2.19 - 2.10 (m, 2H), 2.01 - 1.93 (m, 1H), 1.86 - 1.77 (m, 2H), 1.64 - 1.54 (m, 2H), 1.49 - 1.37 (m, 2H) | ES-LCMS m/z 715.0 $[M - H]^-$. |
| 326 | 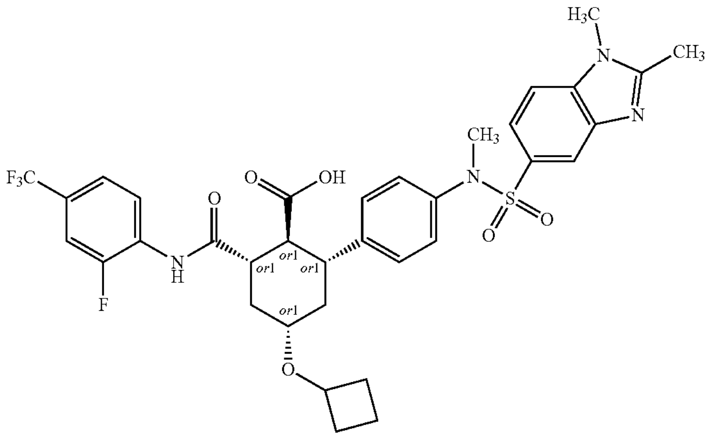 [SMILES: Cc1nc2cc(S(=O)(=O)N(C)c3ccc([C@@H]4C[C@H](OC5CCC5)C[C@H](C(=O)Nc5ccc(C(F)(F)F)cc5F)[C@H]4C(=O)O)cc3)ccc2n1C] ISOMER 2 rel-(1R,2R,4R,6S)-4-cyclobutoxy-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylic acid ISOMER 2 | $^1$H NMR (400 MHz, DMSO-$d_6$) δ 12.15 (br s, 1H), 10.12 (s, 1H), 8.22 (t, J = 8.0 Hz, 1H), 7.73 (dd, J = 11.0, 1.5 Hz, 1H), 7.62 (d, J = 8.5 Hz, 1H), 7.56 (d, J = 8.0 Hz, 1H), 7.47 (d, J = 1.5 Hz, 1H), 7.27 - 7.18 (m, 3H), 6.96 (d, J = 8.5 Hz, 2H), 4.11 - 4.01 (m, 1H), 3.78 (s, 3H), 3.55 - 3.47 (m, 1H), 3.10 - 3.00 (m, 4H), 2.79 - 2.71 (m, 2H), 2.56 (s, 3H), 2.25 (d, J = 11.5 Hz, 1H), 2.20 - 2.08 (m, 2H), 2.02 - 1.93 (m, 1H), 1.90 - 1.75 (m, 2H), 1.64 - 1.50 (m, 2H), 1.49 - 1.37 (m, 2H) | ES-LCMS m/z 715.0 $[M - H]^-$. |

-continued

| Ex | Structure/Name | $^1$H NMR | LCMS |
|---|---|---|---|
| 327 | 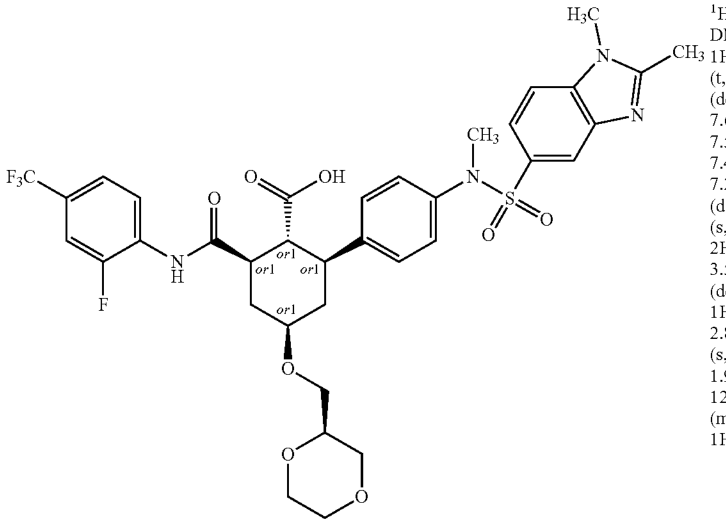 ISOMER 1 (1R*,2R*,4R*,6S*)-4-(((R)-1,4-dioxan-2-yl)methoxy)-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylic acid ISOMER 1 | $^1$H NMR (400 MHz, DMSO-$d_6$) δ 12.14 (br s, 1H), 10.14 (br s, 1H), 8.22 (t, J = 8.3 Hz, 1H), 7.73 (dd, J = 11.3, 1.8 Hz, 1H), 7.63 (d, J = 8.5 Hz, 1H), 7.56 (d, J = 9.0 Hz, 1H), 7.49 (d, J = 1.5 Hz, 1H), 7.27 - 7.19 (m, 3H), 6.96 (d, J = 9.0 Hz, 2H), 3.78 (s, 3H), 3.73 - 3.66 (m, 2H), 3.65 - 3.57 (m, 2H), 3.56 - 3.38 (m, 5H), 3.25 (dd, J = 11.5, 10.0 Hz, 1H), 3.14 - 2.96 (m, 4H), 2.82 - 2.69 (m, 2H), 2.56 (s, 3H), 2.33 (dt, J = 3.6, 1.9 Hz, 1H), 2.04 (d, J = 12.0 Hz, 1H), 1.61 - 1.50 (m, 1H), 1.47 - 1.36 (m, 1H) | ES-LCMS m/z 763.2 [M + H]$^+$. |
| 328 | 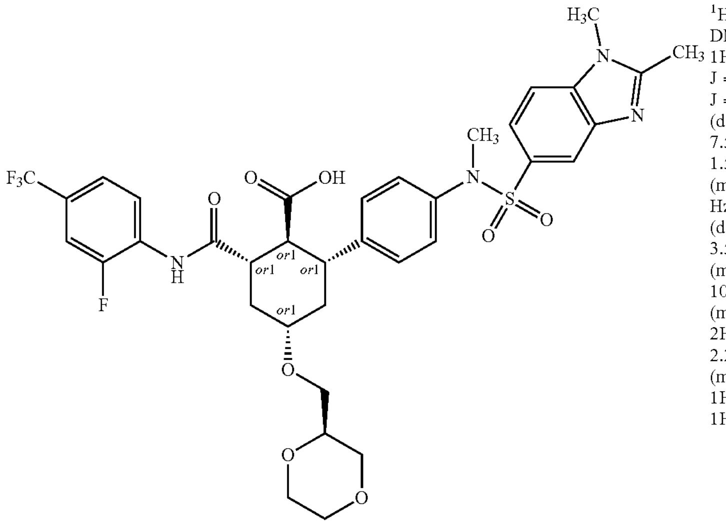 ISOMER 2 (1R*,2R*,4R*,6S*)-4-(((R)-1,4-dioxan-2-yl)methoxy)-2-((2-fluoro-4-(trifluoromethyl)phenyl)carbamoyl)-6-(4-((N,1,2-trimethyl-1H-benzo[d]imidazole)-5-sulfonamido) phenyl)cyclohexane-1-carboxylic acid ISOMER 2 | $^1$H NMR (400 MHz, DMSO-$d_6$) δ 12.12 (br s, 1H), 10.14 (s, 1H), 8.22 (t, J = 8.0 Hz, 1H), 7.73 (dd, J = 11.0, 1.5 Hz, 1H), 7.63 (d, J = 8.5 Hz, 1H), 7.58 - 7.54 (m, 1H), 7.49 (d, J = 1.5 Hz, 1H), 7.26 - 7.19 (m, 3H), 6.96 (d, J = 8.5 Hz, 2H), 3.78 (s, 3H), 3.69 (d, J = 11.5 Hz, 2H), 3.64 - 3.51 (m, 3H), 3.50 - 3.39 (m, 4H), 3.25 (dd, J = 11.5, 10.0 Hz, 1H), 3.09 - 2.99 (m, 4H), 2.77 - 2.71 (m, 2H), 2.56 (s, 3H), 2.35 - 2.29 (m, 1H), 2.09 - 2.02 (m, 1H), 1.60 - 1.50 (m, 1H), 1.42 (q, J = 12.0 Hz, 1H) | ES-LCMS m/z 763.0 [M + H]$^+$. |

-continued

| Ex | Structure/Name | $^1$H NMR | LCMS |
| --- | --- | --- | --- |
| 329 | 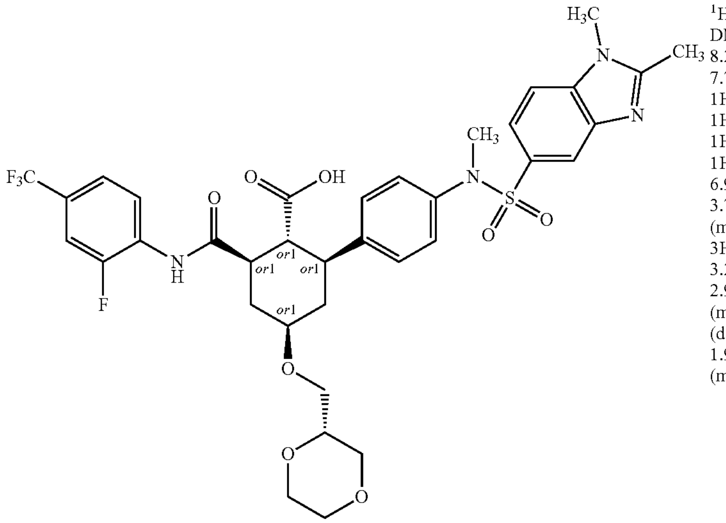 ISOMER 1 (1R*,2R*,4R*,6S*)-4-(((S)-1,4-dioxan-2-yl)methoxy)-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylic acid ISOMER 1 | $^1$H NMR (400 MHz, DMSO-$d_6$) δ 10.17 (s, 1H), 8.23 (t, J = 8.0 Hz, 1H), 7.73 (dd, J = 11.0, 2.0 Hz, 1H), 7.63 (d, J = 9.0 Hz, 1H), 7.56 (d, J = 8.0 Hz, 1H), 7.50 (d, J = 1.5 Hz, 1H), 7.29 - 7.18 (m, 3H), 6.96 (d, J = 8.5 Hz, 2H), 3.78 (s, 3H), 3.73 - 3.65 (m, 2H), 3.63 - 3.53 (m, 3H), 3.52 - 3.39 (m, 4H), 3.28 - 3.21 (m, 1H), 3.08 - 2.99 (m, 4H), 2.77 - 2.70 (m, 2H), 2.57 (s, 3H), 2.31 (d, J = 7.5 Hz, 1H), 2.09 - 1.98 (m, 1H), 1.61 - 1.33 (m, 2H) | ES-LCMS m/z 763.0 [M + H]$^+$. |
| 330 | 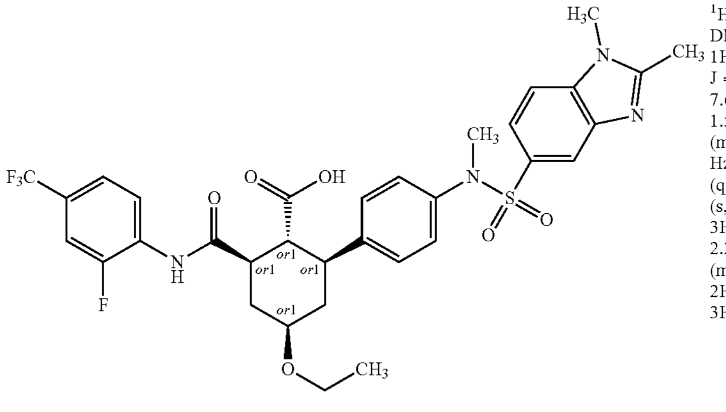 ISOMER 1 rel-(1R,2R,4R,6S)-4-ethoxy-2-((4-(trifluoromethyl)phenyl)carbamoyl)-6-(4-((N,1,2-trimethyl-1H-benzo[d]imidazole)-5-sulfonamido)phenyl)cyclohexane-1-carboxylic acid ISOMER 1 | $^1$H NMR (400 MHz, DMSO-$d_6$) δ 12.14 (br s, 1H), 10.38 (s, 1H), 7.79 (d, J = 8.5 Hz, 2H), 7.69 - 7.60 (m, 3H), 7.49 (d, J = 1.5 Hz, 1H), 7.26 - 7.19 (m, 3H), 6.96 (d, J = 8.5 Hz, 2H), 3.78 (s, 3H), 3.51 (q, J = 7.0 Hz, 3H), 3.05 (s, 3H), 2.89 - 2.71 (m, 3H), 2.56 (s, 3H), 2.36 - 2.26 (m, 1H), 2.11 - 1.99 (m, 1H), 1.65 - 1.38 (m, 2H), 1.10 (t, J = 7.0 Hz, 3H) | ES-LCMS m/z 673.0 [M + H]$^+$. |

-continued

| Ex | Structure/Name | $^1$H NMR | LCMS |
|---|---|---|---|
| 331 | 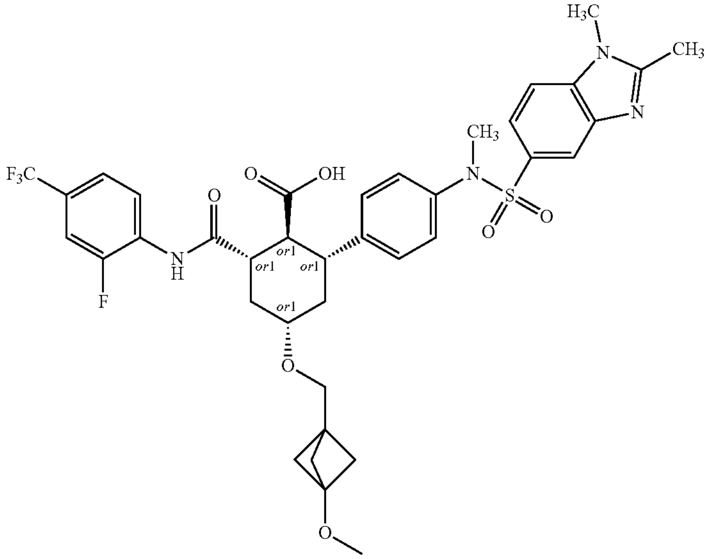 [SMILES: COC12CC(CO[C@@H]3C[C@H](C(=O)Nc4ccc(C(F)(F)F)cc4F)[C@@H](C(=O)O)[C@H](c4ccc(N(C)S(=O)(=O)c5ccc6c(c5)nc(C)n6C)cc4)C3)(C1)C2] ISOMER 1 rel-(1R,2R,4R,6S)-2-((2-fluoro-4-(trifluoromethyl)phenyl)carbamoyl)-4-((3-methoxybicyclo[1.1.1]pentan-1-yl)methoxy)-6-(4-((N,1,2-trimethyl-1H-benzo[d]imidazole)-5-sulfonamido)phenyl)cyclohexane-1-carboxylic acid ISOMER 1 | $^1$H NMR (400 MHz, DMSO-$d_6$) δ 12.17 (br s, 1H), 10.21 (br s, 1H), 8.23 (t, J = 8.0 Hz, 1H), 7.72 (dd, J = 11.0, 1.5 Hz, 1H), 7.63 (d, J = 9.0 Hz, 1H), 7.57 - 7.50 (m, 2H), 7.28 - 7.18 (m, 3H), 6.95 (d, J = 8.5 Hz, 2H), 3.78 (s, 3H), 3.62 (s, 2H), 3.55 - 3.45 (m, 1H), 3.16 (s, 3H), 3.08 - 2.94 (m, 4H), 2.79 - 2.69 (m, 2H), 2.56 (s, 3H), 2.30 (dd, J = 12.0, 2.5 Hz, 1H), 2.07 - 1.98 (m, 1H), 1.72 (s, 6H), 1.53 (d, J = 11.5 Hz, 1H), 1.46 - 1.35 (m, 1H) | ES-LCMS m/z 771.2 [M - H]$^-$. |
| 332 | 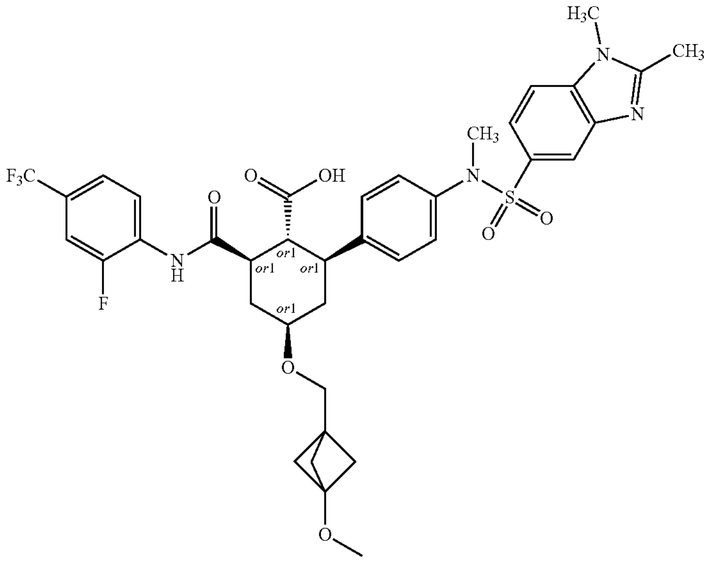 [SMILES: COC12CC(CO[C@@H]3C[C@H](c4ccc(N(C)S(=O)(=O)c5ccc6c(c5)nc(C)n6C)cc4)[C@@H](C(=O)O)[C@H](C(=O)Nc4ccc(C(F)(F)F)cc4F)C3)(C1)C2] ISOMER 2 rel-(1R,2R,4R,6S)-2-((2-fluoro-4-(trifluoromethyl)phenyl)carbamoyl)-4-((3-methoxybicyclo[1.1.1]pentan-1-yl)methoxy)-6-(4-((N,1,2-trimethyl-1H-benzo[d]imidazole)-5-sulfonamido)phenyl)cyclohexane-1-carboxylic acid ISOMER 2 | $^1$H NMR (400 MHz, DMSO-$d_6$) δ 12.15 (br s, 1H), 10.19 (br s, 1H), 8.24 (t, J = 8.3 Hz, 1H), 7.72 (d, J = 10.5 Hz, 1H), 7.64 (d, J = 8.5 Hz, 1H), 7.59 - 7.50 (m, 2H), 7.28 - 7.19 (m, 3H), 6.96 (d, J = 8.5 Hz, 2H), 3.79 (s, 3H), 3.63 (s, 2H), 3.56 - 3.45 (m, 1H), 3.17 (s, 3H), 3.06 (s, 3H), 3.04 - 2.94 (m, 1H), 2.82 - 2.71 (m, 2H), 2.57 (s, 3H), 2.30 (br s, 1H), 2.04 (dd, J = 11.8, 1.8 Hz, 1H), 1.73 (s, 6H), 1.60 - 1.50 (m, 1H), 1.49 - 1.37 (m, 1H) | ES-LCMS m/z 771.0 [M - H]$^-$. |

The following compounds were synthesized in an analogous manner to the preparation described above (Example 254-257) using the relevant alkylamine.

| Ex | Structure/Name | $^1$H NMR | LCMS |
|---|---|---|---|
| 333 | 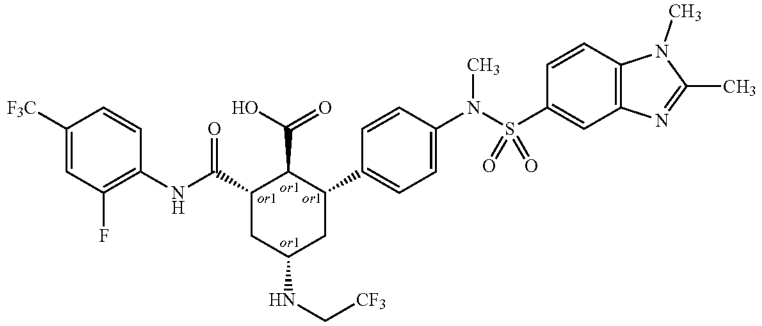 [SMILES: Cc1nc2cc(S(=O)(=O)N(C)c3ccc([C@@H]4C[C@H](NCC(F)(F)F)C[C@H](C(=O)Nc5ccc(C(F)(F)F)cc5F)[C@H]4C(=O)O)cc3)ccc2n1C] ISOMER 1 rel-(1R,2R,4R,6S)-2-((2-fluoro-4-(trifluoromethyl)phenyl)carbamoyl)-4-((2,2,2-trifluoroethyl)amino)-6-(4-((N,1,2-trimethyl-1H-benzo[d]imidazole)-5-sulfonamido)phenyl)cyclohexane-1-carboxylic acid ISOMER 1 | $^1$H NMR (400 MHz, DMSO-$d_6$) δ 10.18 (s, 1H), 8.23 (t, J = 8.3 Hz, 1H), 7.73 (dd, J = 11.0, 1.5 Hz, 1H), 7.64 (d, J = 8.5 Hz, 1H), 7.58 - 7.49 (m, 2H), 7.25 - 7.18 (m, 3H), 6.97 (d, J = 8.5 Hz, 2H), 3.78 (s, 3H), 3.28 - 3.25 (m, 2H), 3.06 (s, 3H), 3.03 - 2.99 (m, 1H), 2.75 - 2.69 (m, 3H), 2.57 (s, 3H), 2.45 (br s, 1H), 2.21 (d, J = 12.0 Hz, 1H), 1.98 (r d, J = 12.0 Hz, 1H), 1.33 (d, J = 11.5 Hz, 2H) | ES-LCMS m/z 744.1 [M + H]$^+$. |
| 334 | 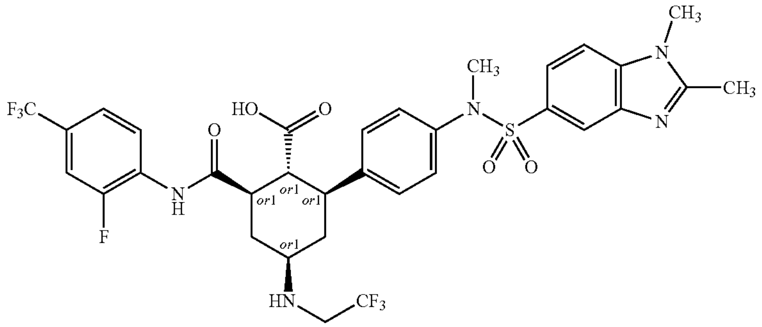 [SMILES: Cc1nc2cc(S(=O)(=O)N(C)c3ccc([C@H]4C[C@@H](NCC(F)(F)F)C[C@@H](C(=O)Nc5ccc(C(F)(F)F)cc5F)[C@@H]4C(=O)O)cc3)ccc2n1C] ISOMER 2 rel-(1R,2R,4R,6S)-2-((2-fluoro-4-(trifluoromethyl)phenyl) carbamoyl)-4-((2,2,2-trifluoroethyl)amino)-6-(4-((N,1,2-trimethyl-1H-benzo[d]imidazole)-5-sulfonamido)phenyl)cyclohexane-1-carboxylic acid ISOMER 2 | $^1$H NMR (400 MHz, DMSO-$d_6$) δ 12.17 (s, 1H), 10.15 (s, 1H), 8.23 (t, J = 8.0 Hz, 1H), 7.74 (dd, J = 11.0, 2.0 Hz, 1H), 7.63 (d, J = 8.5 Hz, 1H), 7.59 - 7.48 (m, 2H), 7.29 - 7.15 (m, 3H), 6.98 (d, J = 8.5 Hz, 2H), 3.78 (s, 3H), 3.28 - 3.25 (m, 2H), 3. 06 (s, 3H), 3.03 - 2.99 (m, 1H), 2.76 - 2.70 (m, 3H), 2.57 (s, 3H), 2.45 (br s, 1H), 2.21 (d, J = 11.5 Hz, 1H), 1.98 (d, J = 11.5 Hz, 1H), 1.43 - 1.30 (m, 2H) | ES-LCMS m/z 744.1 [M + H]$^+$. |
| 335 | 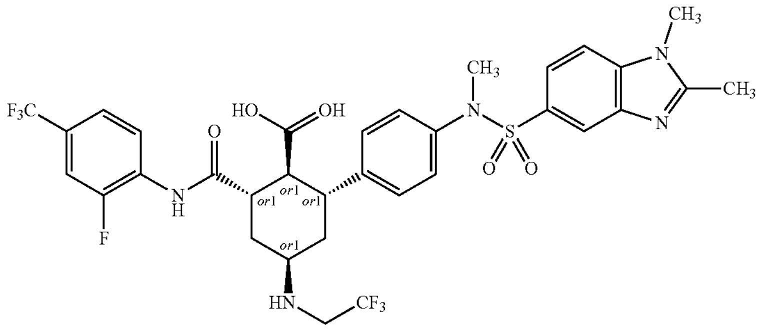 [SMILES: Cc1nc2cc(S(=O)(=O)N(C)c3ccc([C@@H]4C[C@@H](NCC(F)(F)F)C[C@H](C(=O)Nc5ccc(C(F)(F)F)cc5F)[C@H]4C(=O)O)cc3)ccc2n1C] ISOMER 1 rel-(1R,2R,4S,6S)-2-((2-fluoro-4-(trifluoromethyl)phenyl)carbamoyl)-4-((2,2,2-trifluoroethyl)amino)-6-(4-((N,1,2-trimethyl-1H-benzo[d]imidazole)-5-sulfonamido)phenyl)cyclohexane-1-carboxylic acid ISOMER 1 | $^1$H NMR (400 MHz, DMSO-$d_6$) δ 12.10 (s, 1H), 10.02 (s, 1H), 8.17 (t, J = 8.0 Hz, 1H), 7.72 (dd, J = 11.3, 1.8 Hz, 1H), 7.62 (d, J = 8.5 Hz, 1H), 7.57 - 7.48 (m, 2H), 7.25 (dd, J = 8.5, 1.5 Hz, 1H), 7.16 (d, J = 8.5 Hz, 1H), 6.96 (d, J = 8.5 Hz, 2H), 3.77 (s, 3H), 3.48 - 3.37 (m, 1H), 3.25 - 3.12 (m, 3H), 3.07 (s, 3H), 2.77 (t, J = 11.5 Hz, 1H), 2.56 (s, 3H), 2.39 (t, J = 7.8 Hz, 1H), 2.03 ( d, J = 12.5 Hz, 1H), 1.85 - 1.67 (m, 3H) | ES-LCMS m/z 744.1 [M + H]$^+$. |

-continued

| Ex | Structure/Name | $^1$H NMR | LCMS |
|---|---|---|---|
| 336 | 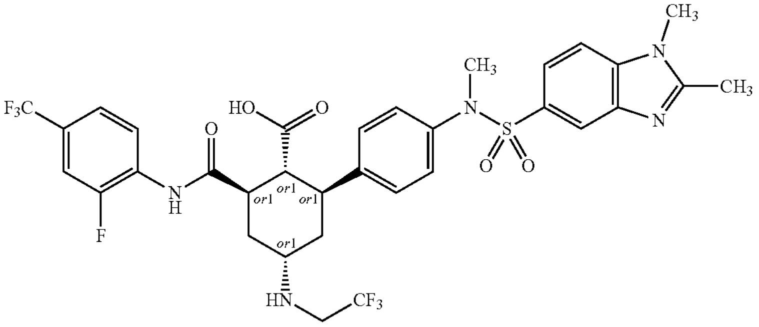 [SMILES: Cc1nc2cc(S(=O)(=O)N(C)c3ccc([C@H]4C[C@H](NCC(F)(F)F)C[C@@H](C(=O)Nc5ccc(C(F)(F)F)cc5F)[C@@H]4C(=O)O)cc3)ccc2n1C] ISOMER 2 rel-(1R,2R,4S,6S)-2-((2-fluoro-4-(trifluoromethyl)phenyl)carbamoyl)-4-((2,2,2-trifluoroethyl)amino)-6-(4-((N,1,2-trimethyl-1H-benzo[d]imidazole)-5-sulfonamido)phenyl)cyclohexane-1-carboxylic acid ISOMER 2 | $^1$H NMR (400 MHz, DMSO-$d_6$) δ 12.08 (s, 1H), 10.02 (s, 1H), 8.18 (t, J = 8.3 Hz, 1H), 7.76 - 7.70 (m, 1H), 7.63 (d, J = 8.5 Hz, 1H), 7.59 - 7.50 (m, 2H), 7.26 (dd, J = 8.5, 1.5 Hz, 1H), 7.17 (d, J = 8.5 Hz, 2H), 6.97 (d, J = 8.5 Hz, 2H), 3.78 (s, 3H), 3.48 - 3.37 (m, 1H), 3.24 - 3.10 (m, 3H), 3.05 (s, 3H), 2.78 (t, J = 11.5 Hz, 1H), 2.57 (s, 3H), 2.43 - 2.35 (m, 1H), 2.04 (d, J = 13.0 Hz, 1H), 1.84 - 1.66 (m, 3H) | ES-LCMS m/z 744.1 [M + H]$^+$. |
| 337 | 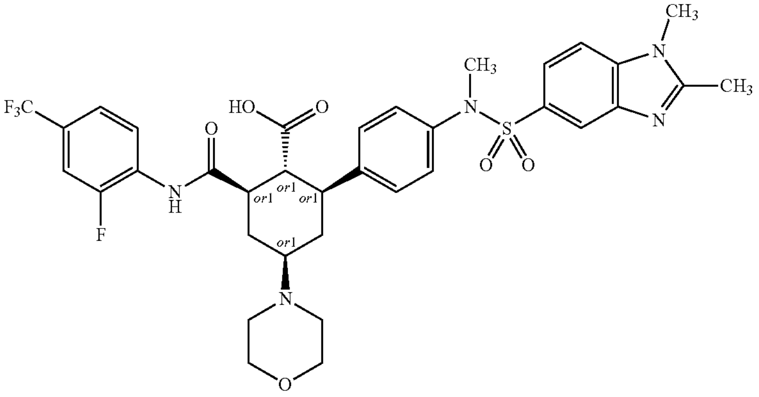 [SMILES: Cc1nc2cc(S(=O)(=O)N(C)c3ccc([C@H]4C[C@@H](N5CCOCC5)C[C@@H](C(=O)Nc5ccc(C(F)(F)F)cc5F)[C@@H]4C(=O)O)cc3)ccc2n1C] ISOMER 1 rel-(1R,2R,4R,6S)-2-((2-fluoro-4-(trifluoromethyl)phenyl)carbamoyl)-4-morpholino-6-(4-((N,1,2-trimethyl-1H-benzo[d]imidazole)-5-sulfonamido)phenyl)cyclohexane-1-carboxylic acid ISOMER 1 | $^1$H NMR (400 MHz, DMSO-$d_6$) δ 12.20 (br s, 1H), 10.15 (br s, 1H), 8.23 (t, J = 8.3 Hz, 1H), 7.72 (d, J = 11.0 Hz, 1H), 7.63 (d, J = 8.5 Hz, 1H), 7.55 (d, J = 9.0 Hz, 1H), 7.49 (d, J = 1.5 Hz, 1H), 7.29 - 7.19 (m, 3H), 6.96 (d, J = 8.5 Hz, 2H), 3.78 (s, 3H), 3.54 (t, J = 4.0 Hz, 4H), 3.22 (d, J = 3.0 Hz, 2H), 3.10 - 2.99 (m, 4H), 2.78 - 2.70 (m, 2H), 2.56 (s, 4H), 2.48 - 2.38 (m, 2H), 2.15 (d, J = 12.0 Hz, 1H), 1.85 (d, J = 12.5 Hz, 1H), 1.70 - 1.60 (m, 1H), 1.52 (q, J = 12.0 Hz, 1H) | ES-LCMS m/z 730.2 [M - H]$^-$. |
| 338 | 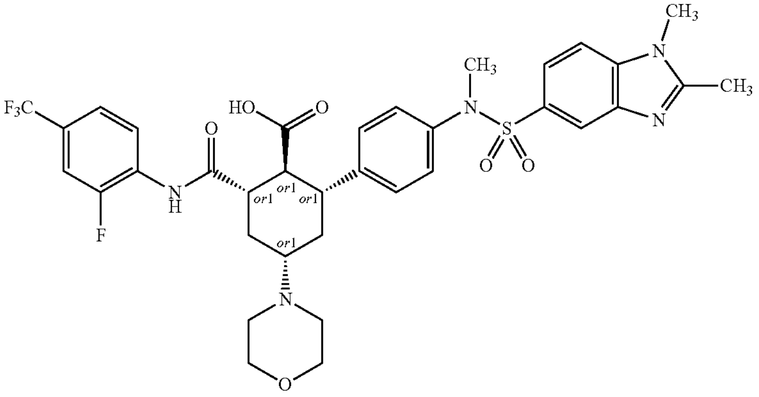 [SMILES: Cc1nc2cc(S(=O)(=O)N(C)c3ccc([C@@H]4C[C@H](N5CCOCC5)C[C@H](C(=O)Nc5ccc(C(F)(F)F)cc5F)[C@H]4C(=O)O)cc3)ccc2n1C] ISOMER 2 rel-(1R,2R,4R,6S)-2-((2-fluoro-4-(trifluoromethyl)phenyl)carbamoyl)-4-morpholino-6-(4-((N,1,2-trimethyl-1H-benzo[d]imidazole)-5-sulfonamido)phenyl)cyclohexane-1-carboxylic acid ISOMER 2 | $^1$H NMR (400 MHz, DMSO-$d_6$) δ 12.10 (br s, 1H), 10.14 (s, 1H), 8.23 (t, J = 8.0 Hz, 1H), 7.76 - 7.70 (m, 1H), 7.63 (d, J = 8.5 Hz, 1H), 7.56 (d, J = 8.0 Hz, 1H), 7.48 (d, J = 1.5 Hz, 1H), 7.27 - 7.20 (m, 3H), 6.96 (d, J = 8.5 Hz, 2H), 3.78 (s, 3H), 3.54 (t, J = 4.5 Hz, 4H), 3.43 - 3.35 (m, 3H), 3.05 (s, 4H), 2.78 - 2.71 (m, 2H), 2.62 - 2.54 (m, 4H), 2.64 - 2.54 (m, 1H), 2.15 (d, J = 11.0 Hz, 1H), 1.85 (d, J = 12.5 Hz, 1H), 1.72 - 1.59 (m, 1H), 1.53 (q, J = 12.5 Hz, 1H) | ES-LCMS m/z 730.2 [M - H]$^-$. |

-continued

| Ex | Structure/Name | $^1$H NMR | LCMS |
|---|---|---|---|
| 339 | 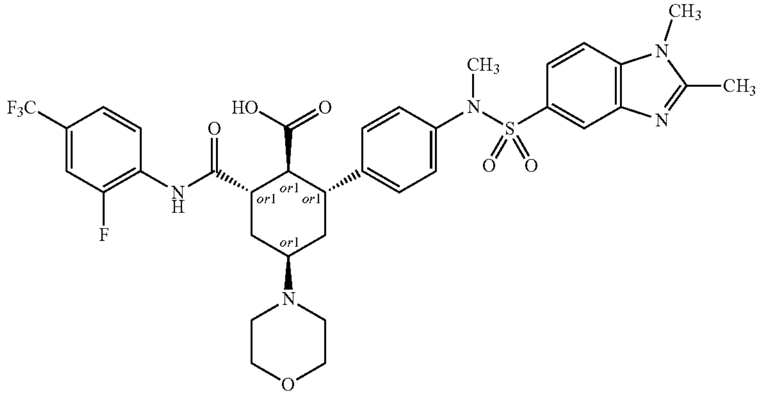 ISOMER 1 rel-(1R,2R,4S,6S)-2-((2-fluoro-4-(trifluoromethyl)phenyl)carbamoyl)-4-morpholino-6-(4-((N,1,2-trimethyl-1H-benzo[d]imidazole)-5-sulfonamido)phenyl)cyclohexane-1-carboxylic acid ISOMER 1 | $^1$H NMR (400 MHz, DMSO-$d_6$) δ 12.04 (br s, 1H), 10.13 (br s, 1H), 8.06 (t, J = 8.0 Hz, 1H), 7.71 (d, J = 10.0 Hz, 1H), 7.63 (d, J = 8.5 Hz, 1H), 7.59 – 7.51 (m, 2H), 7.24 (dd, J = 8.5, 1.5 Hz, 1H), 7.18 (d, J = 8.5 Hz, 2H), 6.96 (d, J = 8.5 Hz, 2H), 3.78 (s, 3H), 3.70 (br s, 4H), 3.30 – 3.23 (m, 1H), 3.16 – 3.01 (m, 5H), 2.91 – 2.79 (m, 1H), 2.56 (s, 3H), 2.45 – 2.30 (m, 4H), 2.25 – 2.15 (m, 1H), 1.97 (d, J = 12.5 Hz, 1H), 1.82 – 1.64 (m, 2H) | ES-LCMS m/z 730.2 [M − H]$^-$. |
| 340 | 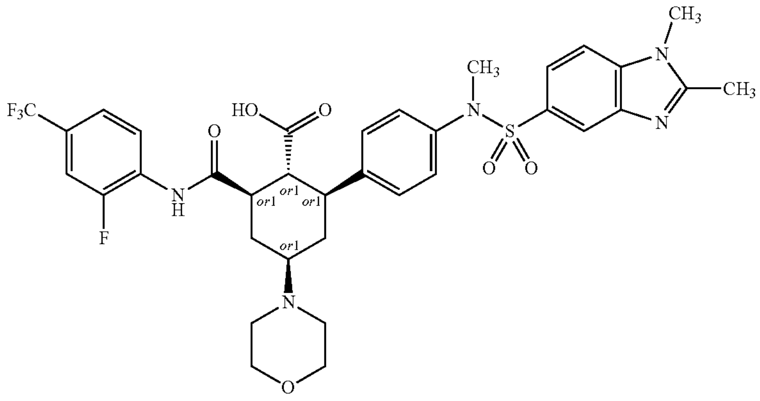 [SMILES: Cc1nc2cc(S(=O)(=O)N(C)c3ccc([C@H]4C[C@@H](N5CCOCC5)C[C@@H](C(=O)Nc5ccc(C(F)(F)F)cc5F)[C@@H]4C(=O)O)cc3)ccc2n1C] ISOMER 2 rel-(1R,2R,4S,6S)-2-((2-fluoro-4-(trifluoromethyl)phenyl)carbamoyl)-4-morpholino-6-(4-((N,1,2-trimethyl-1H-benzo[d]imidazole)-5-sulfonamido)phenyl)cyclohexane-1-carboxylic acid ISOMER 2 | $^1$H NMR (400 MHz, DMSO-$d_6$) δ 12.09 (br s, 1H), 10.12 (s, 1H), 8.06 (t, J = 8.0 Hz, 1H), 7.71 (dd, J = 10.8, 1.8 Hz, 1H), 7.63 (d, J = 8.5 Hz, 1H), 7.56 (d, J = 8.5 Hz, 1H), 7.53 (d, J = 1.5 Hz, 1H), 7.24 (dd, J = 8.5, 1.5 Hz, 1H), 7.18 (d, J = 8.5 Hz, 2H), 6.96 (d, J = 8.5 Hz, 2H), 3.78 (s, 3H), 3.70 (d, J = 2.0 Hz, 4H), 3.28 (br s, 1H), 3.16 – 3.02 (m, 4H), 2.90 – 2.80 (m, 1H), 2.56 (s, 3H), 2.48 – 2.30 (m, 5H), 2.19 (d, J = 12.0 Hz, 1H), 1.97 (d, J = 12.5 Hz, 1H), 1.81 – 1.65 (m, 2H) | ES-LCMS m/z 730.2 [M − H]$^-$. |
| 341 | 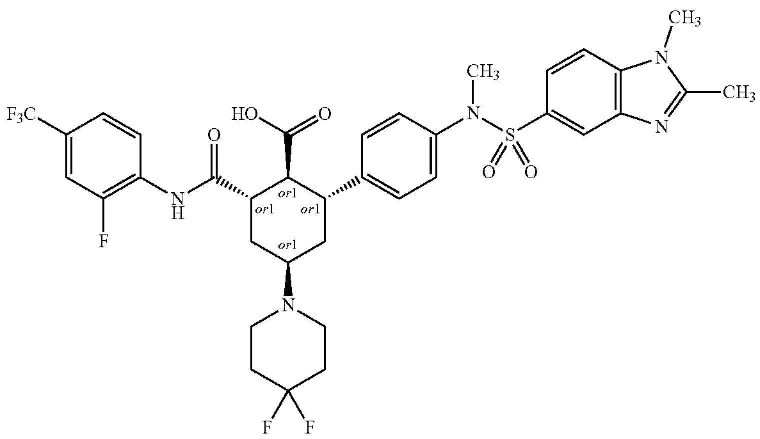 [SMILES: Cc1nc2cc(S(=O)(=O)N(C)c3ccc([C@@H]4C[C@@H](N5CCC(F)(F)CC5)C[C@H](C(=O)Nc5ccc(C(F)(F)F)cc5F)[C@H]4C(=O)O)cc3)ccc2n1C] ISOMER 1 rel-(1R,2R,4S,6S)-4-(4,4-difluoropiperidin-1-yl)-2-((2-fluoro-4-(trifluoromethyl)phenyl)carbamoyl)-6- | $^1$H NMR (400 MHz, DMSO-$d_6$) δ 10.19 – 10.09 (m, 1H), 8.13 – 8.07 (m, 1H), 7.72 (d, J = 10.5 Hz, 1H), 7.64 (d, J = 8.5 Hz, 1H), 7.55 (s, 1H), 7.27 – 7.17 (m, 4H), 6.97 (d, J = 8.5 Hz, 2H), 3.78 (s, 3H), 3.31 – 3.25 (m, 1H), 3.10 (d, J = 10.5 Hz, 1H), 3.06 (s,3H), 2.83 (t, J = 10.3 Hz, 1H), 2.69 – 2.58 (m, 5H), 2.57 (s, 3H), 2.21 (d, J = 13.0 Hz, 1H), 2.11 – 1.93 (m, 5H), 1.84 – 1.70 (m, 2H) | ES-LCMS m/z 766.2 [M + H]$^+$. |

-continued

| Ex | Structure/Name | $^1H$ NMR | LCMS |
|---|---|---|---|
| | (4-((N,1,2-trimethyl-1H-benzo[d]imidazole)-5-sulfonamido)phenyl)cyclohexane-1-carboxylic acid ISOMER 1 | | |
| 342 | 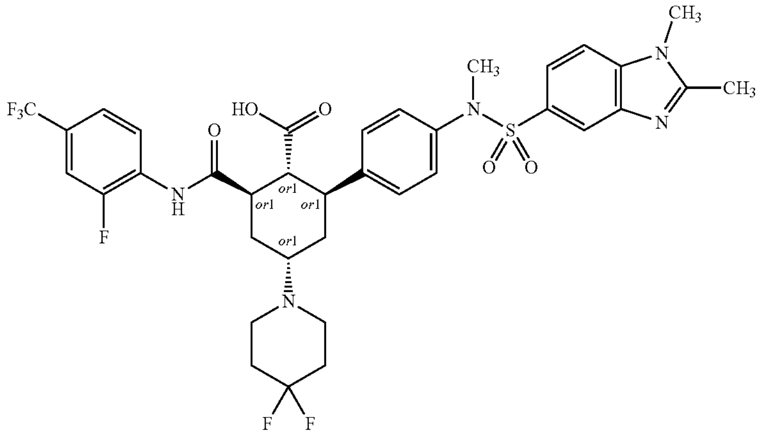 [SMILES: Cc1nc2cc(S(=O)(=O)N(C)c3ccc([C@H]4C[C@H](N5CCC(F)(F)CC5)C[C@@H](C(=O)Nc5ccc(C(F)(F)F)cc5F)[C@@H]4C(=O)O)cc3)ccc2n1C] ISOMER 2 rel-(1R,2R,4S,6S)-4-(4,4-difluoropiperidin-1-yl)-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylic acid ISOMER 2 | $^1H$ NMR (400 MHz, DMSO-$d_6$) δ 12.16 (s, 1H), 10.16 (m, 1H), 8.09 (t, J = 8.0 Hz, 1H), 7.72 (dd, J = 10.5, 1.5 Hz, 1H), 7.63 (d, J = 8.5 Hz, 1H), 7.58 - 7.51 (m, 2H), 7.27 - 7.16 (m, 3H), 6.97 (d, J = 8.5 Hz, 2H), 3.78 (s, 3H), 3.31 - 3.25 (m, 1H), 3.16 - 3.06 (m, 1H), 3.05 (s, 3H), 2.87 - 2.78 (m, 1H), 2.68 - 2.57 (m, 5H), 2.56 (s, 3H), 2.21 (d, J = 13.5 Hz, 1H), 2.13 - 1.96 (m, 5H), 1.83 - 1.69 (m, 2H) | ES-LCMS m/z 766.2 [M + H]$^+$. |
| 343 | 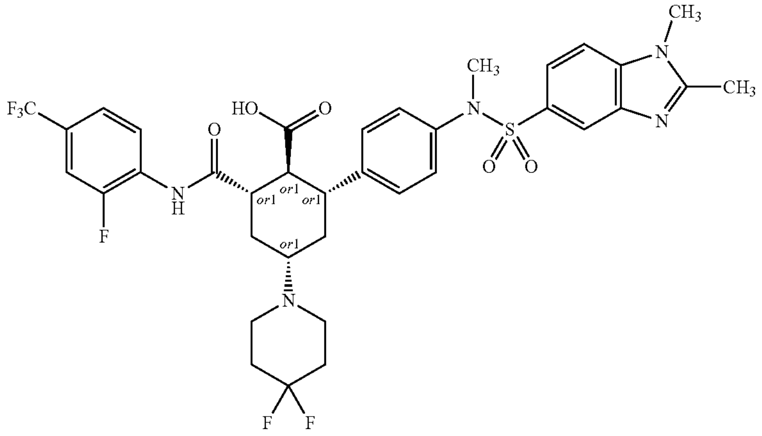 [SMILES: Cc1nc2cc(S(=O)(=O)N(C)c3ccc([C@@H]4C[C@H](N5CCC(F)(F)CC5)C[C@H](C(=O)Nc5ccc(C(F)(F)F)cc5F)[C@H]4C(=O)O)cc3)ccc2n1C] ISOMER 1 rel-(1R,2R,4R,6S)-2-((2-fluoro-4-(trifluoromethyl)phenyl)carbamoyl)-4-morpholino-6-(4-((N,1,2-trimethyl-1H-benzo[d]imidazole)-5-sulfonamido)phenyl)cyclohexane-1-carboxylic acid ISOMER 1 | $^1H$ NMR (400 MHz, DMSO-$d_6$) δ 12.10 (s, 1H), 10.13 (s, 1H), 8.23 (t, J = 8.0 Hz, 1H), 7.73 (dd, J = 11.3, 1.8 Hz, 1H), 7.64 (d, J = 8.5 Hz, 1H), 7.56 (d, J = 8.5 Hz, 1H), 7.49 (d, J = 1.5 Hz, 1H), 7.30 - 7.19 (m, 3H), 6.97 (d, J = 8.5 Hz, 2H), 3.78 (s, 3H), 3.06 (s, 4H), 2.79 - 2.72 (m, 3H), 2.70 - 2.61 (m, 4H), 2.57 (s, 3H), 2.14 - 2.07 (m, 1H), 1.98 - 1.84 (m, 4H), 1.81 - 1.55 (m, 3H) | ES-LCMS m/z 766.2 [M + H]$^+$. |

-continued

| Ex | Structure/Name | $^1H$ NMR | LCMS |
|---|---|---|---|
| 344 | 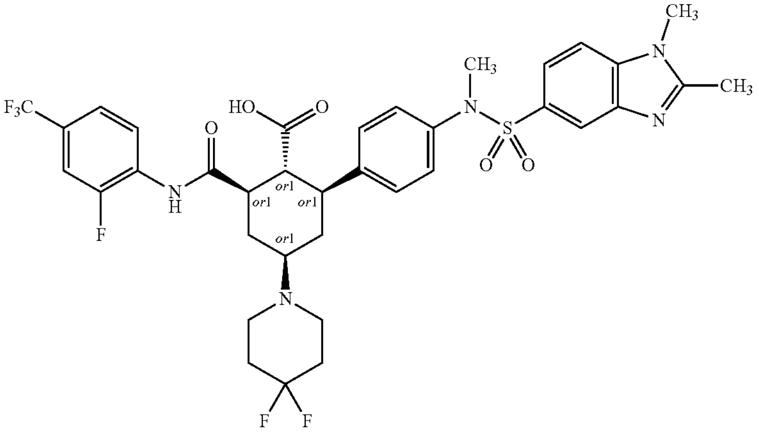 [SMILES: Cc1nc2cc(S(=O)(=O)N(C)c3ccc([C@H]4C[C@@H](N5CCC(F)(F)CC5)C[C@@H](C(=O)Nc5ccc(C(F)(F)F)cc5F)[C@@H]4C(=O)O)cc3)ccc2n1C] ISOMER 2 rel-(1R,2R,4R,6S)-2-((2-fluoro-4-(trifluoromethyl)phenyl)carbamoyl)-4-morpholino-6-(4-((N,1,2-trimethyl-1H-benzo[d]imidazole)-5-sulfonamido)phenyl)cyclohexane-1-carboxylic acid ISOMER 2 | $^1H$ NMR (400 MHz, DMSO-$d_6$) δ 12.15 (s, 1H), 10.15 (m, 1H), 8.23 (t, J = 8.3 Hz, 1H), 7.71 (dd, J = 11.0, 1.5 Hz, 1H), 7.63 (d, J = 8.5 Hz, 1H), 7.57 - 7.48 (m, 2H), 7.29 - 7.17 (m, 3H), 6.95 (d, J = 8.5 Hz, 2H), 3.77 (s, 3H), 3.05 (s, 4H), 2.79 - 2.72 (m, 3H), 2.69 - 2.60 (m, 4H), 2.56 (s, 3H), 2.09 (dd, J = 8.5, 3.0 Hz, 1H), 1.97 - 1.83 (m, 4H), 1.82 - 1.54 (m, 3H) | ES-LCMS m/z 766.2 [M + H]$^+$. |
| 345 | 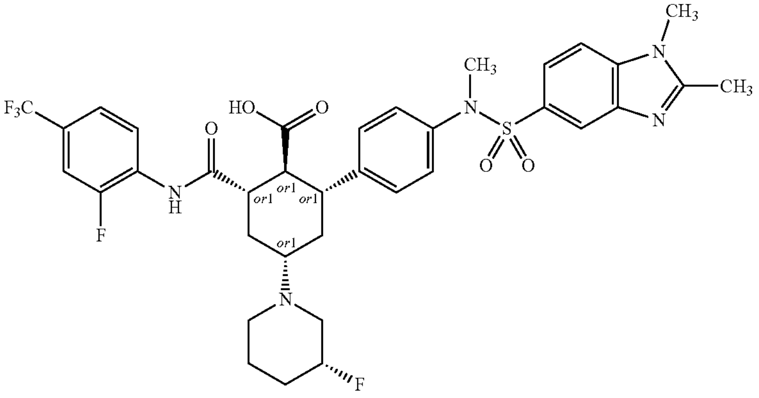 [SMILES: Cc1nc2cc(S(=O)(=O)N(C)c3ccc([C@@H]4C[C@H](N5CCC[C@@H](F)C5)C[C@H](C(=O)Nc5ccc(C(F)(F)F)cc5F)[C@H]4C(=O)O)cc3)ccc2n1C] ISOMER 1 rel-(1R*,2R*,4R*,6S*)-2-((2-fluoro-4-(trifluoromethyl)phenyl)carbamoyl)-4-((R)-3-fluoropiperidin-1-yl)-6-(4-((N,1,2-trimethyl-1H-benzo[d]imidazole)-5-sulfonamido)phenyl)cyclohexane-1-carboxylic acid ISOMER 1 | $^1H$ NMR (400 MHz, DMSO-$d_6$) δ 12.07 (br s, 1H), 10.15 (br s, 1H), 8.23 (t, J = 8.0 Hz, 1H), 7.72 (dd, J = 11.0, 1.5 Hz, 1H), 7.63 (d, J = 8.5 Hz, 1H), 7.55 (d, J = 9.5 Hz, 1H), 7.50 (d, J = 1.5 Hz, 1H), 7.29 - 7.20 (m, 3H), 6.96 (d, J = 8.5 Hz, 2H), 4.67 - 4.46 (m, 1H), 3.78 (s, 3H), 3.11 - 2.97 (m, 4H), 2.95 - 2.82 (m, 1H), 2.79 - 2.68 (m, 3H), 2.56 (s, 5H), 2.47 - 2.35 (m, 1H), 2.07 (d, J = 10.5 Hz, 1H), 1.90 - 1.53 (m, 5H), 1.52 - 1.33 (m, 2H) | ES-LCMS m/z 748.0 [M + H]$^+$. |
| 346 | 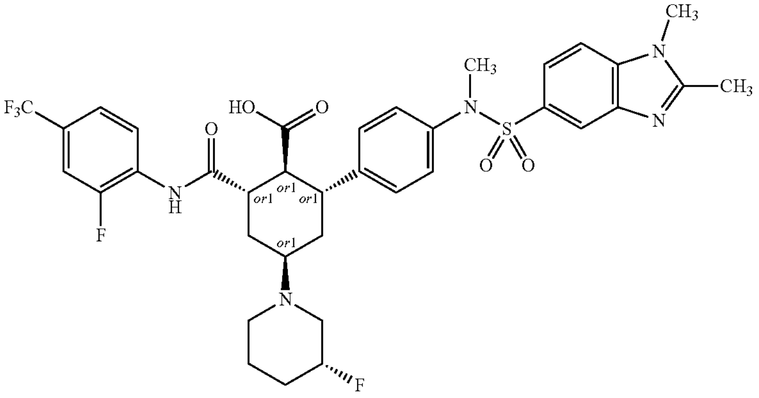 [SMILES: Cc1nc2cc(S(=O)(=O)N(C)c3ccc([C@@H]4C[C@@H](N5CCC[C@@H](F)C5)C[C@H](C(=O)Nc5ccc(C(F)(F)F)cc5F)[C@H]4C(=O)O)cc3)ccc2n1C] ISOMER 1 rel-(1R*,2R*,4S*,6S*)-2-((2-fluoro-4- | $^1H$ NMR (400 MHz, DMSO-$d_6$) δ 12.09 (br s, 1H), 10.16 (s, 1H), 8.07 (t, J = 8.0 Hz, 1H), 7.72 (dd, J = 10.8, 1.3 Hz, 1H), 7.63 (d, J = 8.5 Hz, 1H), 7.56 (d, J = 8.5 Hz, 1H), 7.53 (d, J = 1.5 Hz, 1H), 7.24 (dd, J = 8.5, 1.5 Hz, 1H), 7.16 (d, J = 8.5 Hz, 2H), 6.97 (d, J = 8.5 Hz, 2H), 4.87 - 4.67 (m, 1H), 3.78 (s, 3H), 3.13 - 3.07 (m, 1H), 3.05 (s, 3H), 3.00 - 2.89 (m, 1H), 2.87 - 2.80 (m, 1H), 2.56 (s, 3H), 2.48 - 2.38 (m, 2H), 2.32 - 2.16 (m, 3H), 2.05 - 1.68 (m, 6H), 1.60 - 1.46 (m, 2H) | ES-LCMS m/z 748.0 [M + H]$^+$. |

-continued

| Ex | Structure/Name | $^1$H NMR | LCMS |
|---|---|---|---|
| | (trifluoromethyl)phenyl)carbamoyl)-4-((R)-3-fluoropiperidin-1-yl)-6-(4-((N,1,2-trimethyl-1H-benzo[d]imidazole)-5-sulfonamido)phenyl)cyclohexane-1-carboxylic acid ISOMER 1 | | |
| 347 | 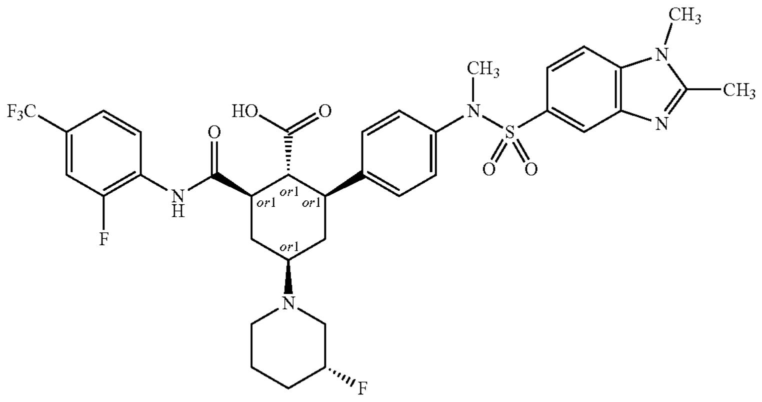 ISOMER 2 rel-(1R*,2R*,4S*,6S*)-2-((2-fluoro-4-(trifluoromethyl)phenyl)carbamoyl)-4-((R)-3-fluoropiperidin-1-yl)-6-(4-((N,1,2-trimethyl-1H-benzo[d]imidazole)-5-sulfonamido)phenyl)cyclohexane-1-carboxylic acid ISOMER 2 | $^1$H NMR (400 MHz, DMSO-$d_6$) δ 10.12 (br s, 1H), 8.03 (t, J = 8.3 Hz, 1H), 7.71 (dd, J = 10.8, 1.8 Hz, 1H), 7.63 (d, J = 8.5 Hz, 1H), 7.58 - 7.52 (m, 2H), 7.24 (dd, J = 8.5, 1.5 Hz, 1H), 7.19 (d, J = 8.5 Hz, 2H), 6.97 (d, J = 8.5 Hz, 2H), 4.81 - 4.57 (m, 1H), 3.78 (s, 3H), 3.28 - 3.20 (m, 1H), 3.09 (br s, 1H), 3.05 (s, 3H), 2.98 (t, J = 11.5 Hz, 1H), 2.89 - 2.77 (m, 2H), 2.56 (s, 3H), 2.46 (d, J = 1.5 Hz, 2H), 2.21 (d, J = 12.0 Hz, 2H), 2.11 - 1.91 (m, 3H), 1.84 - 1.70 (m, 3H), 1.66 - 1.42 (m, 2H) | ES-LCMS m/z 748.0 [M + H]$^+$. |
| 348 | 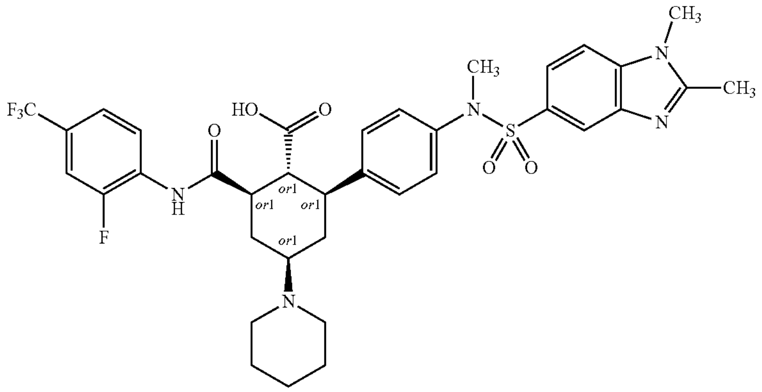 [SMILES: Cc1nc2cc(S(=O)(=O)N(C)c3ccc([C@H]4C[C@@H](N5CCCCC5)C[C@@H](C(=O)Nc5ccc(C(F)(F)F)cc5F)[C@@H]4C(=O)O)cc3)ccc2n1C] ISOMER 2 rel-(1R,2R,4R,6S)-2-((2-fluoro-4-(trifluoromethyl)phenyl)carbamoyl)-4-(piperidin-1-yl)-6-(4-((N,1,2-trimethyl-1H-benzo[d]imidazole)-5-sulfonamido)phenyl)cyclohexane-1-carboxylic acid ISOMER 2 | $^1$H NMR (400 MHz, DMSO-$d_6$) δ 12.15 (s, 1H), 10.14 (s, 1H), 8.24 (t, J = 8.0 Hz, 1H), 7.73 (dd, J = 11.0, 1.5 Hz, 1H), 7.64 (d, J = 8.5 Hz, 1H), 7.56 (d, J = 9.0 Hz, 1H), 7.50 (d, J = 1.5 Hz, 1H), 7.30 - 7.16 (m, 3H), 6.97 (d, J = 8.5 Hz, 2H), 3.79 (s, 3H), 3.06 (s, 4H), 2.76 - 2.69 (m, 2H), 2.62 (d, J = 12.0 Hz, 1H), 2.57 (s, 3H), 2.15 - 2.01 (m, 1H), 1.83 - 1.73 (m, 1H), 1.70 - 1.52 (m, 2H), 1.50 - 1.31 (m, 7H), three protons obscured by solvent peaks | ES-LCMS m/z 730.3 [M + H]$^+$. |

-continued

| Ex | Structure/Name | $^1$H NMR | LCMS |
|---|---|---|---|
| 349 | 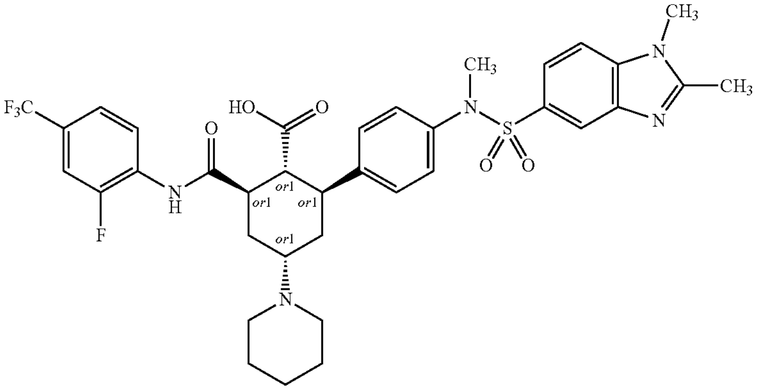 [SMILES: Cc1nc2cc(S(=O)(=O)N(C)c3ccc([C@H]4C[C@H](N5CCCCC5)C[C@@H](C(=O)Nc5ccc(C(F)(F)F)cc5F)[C@@H]4C(=O)O)cc3)ccc2n1C]<br>ISOMER 2<br>rel-(1R,2R,4S,6S)-2-((2-fluoro-4-(trifluoromethyl)phenyl)carbamoyl)-4-(piperidin-1-yl)-6-(4-((N,1,2-trimethyl-1H-benzo[d]imidazole)-5-sulfonamido)phenyl)cyclohexane-1-carboxylic acid<br>ISOMER 2 | $^1$H NMR (400 MHz, DMSO-$d_6$) δ 10.33 – 10.07 (m, 1H), 8.07 (br s, 1H), 7.70 (d, J = 10.0 Hz, 1H), 7.63 (d, J = 9.0 Hz, 1H), 7.59 – 7.51 (m, 2H), 7.24 (dd, J = 8.5, 2.0 Hz, 1H), 7.16 (d, J = 8.5 Hz, 2H), 6.95 (d, J = 8.5 Hz, 2H), 3.78 (s, 3H), 3.28 – 3.24 (m, 2H), 3.09 (d, J = 13.0 Hz, 1H), 3.05 (s, 3H), 2.84 – 2.73 (m, 1H), 2.56 (s, 3H), 2.43 – 2.31 (m, 5H), 2.22 (d, J = 12.5 Hz, 1H), 2.03 –1.55 (m, 6H), 1.42 (br d, J = 5.5 Hz, 2H) | ES-LCMS m/z 730.2 [M + H]$^+$. |
| 350 | 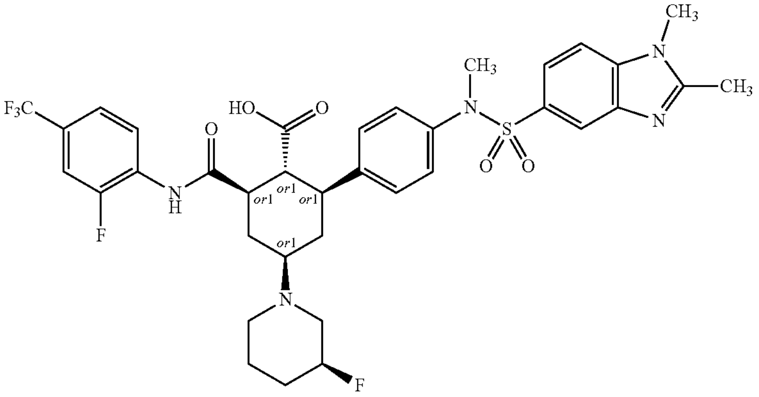 [SMILES: Cc1nc2cc(S(=O)(=O)N(C)c3ccc([C@H]4C[C@@H](N5CCC[C@H](F)C5)C[C@@H](C(=O)Nc5ccc(C(F)(F)F)cc5F)[C@@H]4C(=O)O)cc3)ccc2n1C]<br>ISOMER 2<br>rel-(1R*,2R*,4R*,6S*)-2-((2-fluoro-4-(trifluoromethyl)phenyl)carbamoyl)-4-((S)-3-fluoropiperidin-1-yl)-6-(4-((, 1,2-trimethyl-1H-benzo[d]imidazole)-5-sulfonamido)phenyl)cyclohexane-1-carboxylic acid<br>ISOMER 2 | $^1$H NMR (400 MHz, DMSO-$d_6$) δ 12.10 (br s, 1H), 10.16 (br s, 1H), 8.24 (t, J = 8.3 Hz, 1H), 7.73 (d, J = 11.0 Hz, 1H), 7.64 (d, J = 8.5 Hz, 1H), 7.55 (d, J = 8.0 Hz, 1H), 7.50 (s, 1H), 7.29 – 7.19 (m, 3H), 6.96 (d, J = 8.5 Hz, 2H), 4.68 – 4.45 (m, 1H), 3.78 (s, 3H), 3.47 – 3.37 (m, 1H), 3.12 – 2.98 (m, 5H), 2.95 – 2.82 (m, 1H), 2.79 – 2.69 (m, 3H), 2.56 (s, 3H), 2.43 – 2.35 (m, 1H), 2.12 – 2.02 (m, 1H), 1.90 – 1.53 (m, 5H), 1.51 – 1.33 (m, 2H) | ES-LCMS m/z 748.2 [M + H]$^+$. |
| 351 | 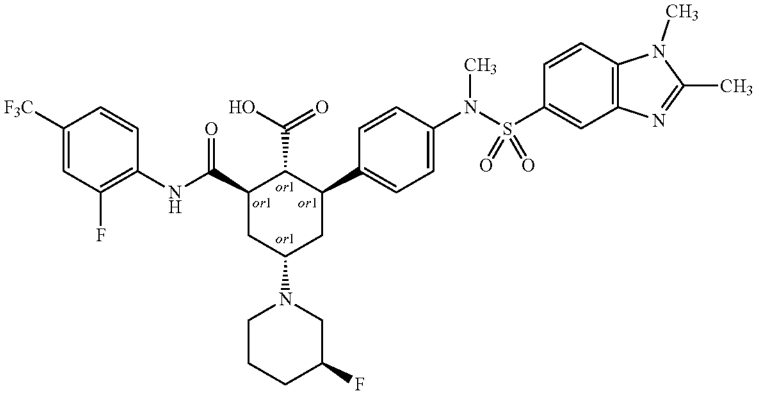 [SMILES: Cc1nc2cc(S(=O)(=O)N(C)c3ccc([C@H]4C[C@H](N5CCC[C@H](F)C5)C[C@@H](C(=O)Nc5ccc(C(F)(F)F)cc5F)[C@@H]4C(=O)O)cc3)ccc2n1C]<br>ISOMER 2<br>rel-(1R*,2R*,4S*,6S*)-2-((2-fluoro-4-(trifluoromethyl)phenyl)carbamoyl)-4-((S)-3-fluoropiperidin-1-yl)-6-(4-((N,1,2-trimethyl-1H- | $^1$H NMR (400 MHz, DMSO-$d_6$) δ 12.07 (br s, 1H), 10.17 (s, 1H), 8.48 – 8.41 (m, 1H), 8.07 (t, J = 8.0 Hz, 1H), 7.75 – 7.70 (m, 1H), 7.63 (d, J = 9.0 Hz, 1H), 7.58 – 7.52 (m, 2H), 7.24 (dd, J = 8.5, 1.5 Hz, 1H), 7.16 (d, J = 8.5 Hz, 2H), 6.97 (d, J = 8.5 Hz, 2H), 4.82 (br s, 1H), 3.78 (s, 3H), 3.05 (s, 3H), 2.87 – 2.80 (m, 1H), 2.56 (s, 3H), 2.36 – 2.20 (m, 4H), 2.06 – 1.67 (m, 7H), 1.54 (d, J = 7.0 Hz, 3H) | ES-LCMS m/z 748.2 [M + H]$^+$. |

-continued

| Ex | Structure/Name | $^1$H NMR | LCMS |
| --- | --- | --- | --- |
| | benzo[d]imidazole)-5-sulfonamido)phenyl)cyclohexane-1-carboxylic acid ISOMER 2 | | |
| 352 | 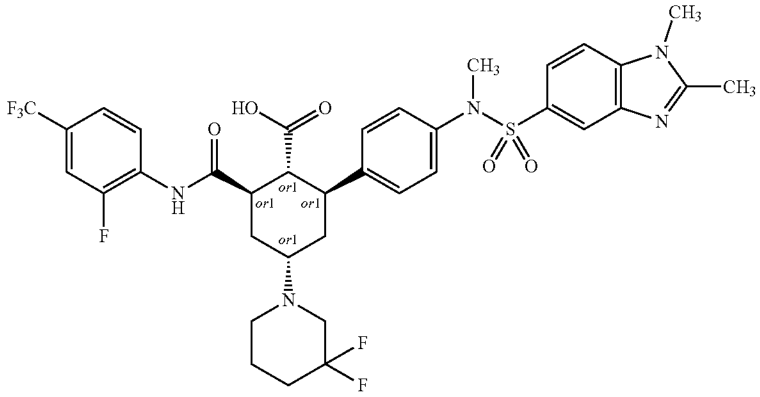 [SMILES: Cc1nc2cc(S(=O)(=O)N(C)c3ccc([C@H]4C[C@H](N5CCCC(F)(F)C5)C[C@@H](C(=O)Nc5ccc(C(F)(F)F)cc5F)[C@@H]4C(=O)O)cc3)ccc2n1C] ISOMER 1 rel-(1R,2R,4S,6S)-4-(3,3-difluoropiperidin-1-yl)-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylic acid ISOMER 1 | $^1$H NMR (400 MHz, DMSO-$d_6$) δ 12.12 (br s, 1H), 10.17 (br s, 1H), 8.04 (t, J = 8.0 Hz, 1H), 7.71 (dd, J = 10.8, 1.8 Hz, 1H), 7.63 (d, J = 8.5 Hz, 1H), 7.59 - 7.52 (m, 2H), 7.25 (dd, J = 8.5, 1.5 Hz, 1H), 7.16 (d, J = 8.5 Hz, 2H), 6.98 (d, J = 8.5 Hz, 2H), 3.78 (s, 3H), 3.31 - 3.21 (m, 1H), 3.15 - 3.02 (m, 4H), 2.90 - 2.74 (m, 3H), 2.63 - 2.53 (m, 5H), 2.32 - 2.18 (m, 2H), 1.98 (d, J = 12.5 Hz, 2H), 1.89 - 1.68 (m, 5H) | ES-LCMS m/z 766.2 [M + H]$^+$. |
| 353 | 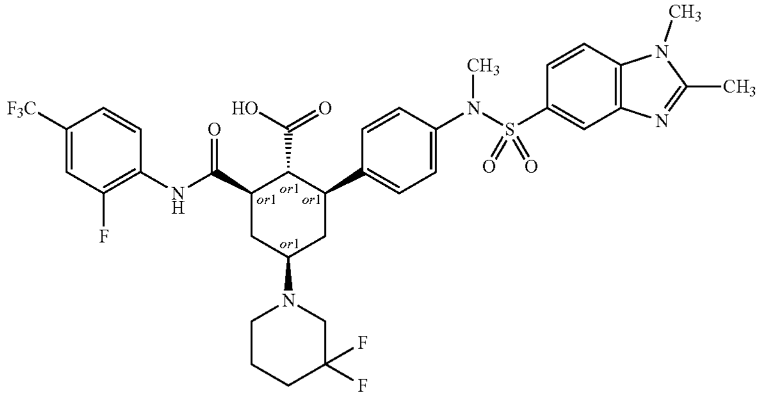 [SMILES: Cc1nc2cc(S(=O)(=O)N(C)c3ccc([C@H]4C[C@@H](N5CCCC(F)(F)C5)C[C@@H](C(=O)Nc5ccc(C(F)(F)F)cc5F)[C@@H]4C(=O)O)cc3)ccc2n1C] ISOMER 1 rel-(1R,2R,4R,6S)-4-(3,3-difluoropiperidin-1-yl)-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylic acid ISOMER 1 | $^1$H NMR (400 MHz, DMSO-$d_6$) δ 12.08 (br s, 1H), 10.13 (s, 1H), 8.23 (t, J = 8.3 Hz, 1H), 7.73 (dd, J = 11.3, 1.8 Hz, 1H), 7.63 (d, J = 8.5 Hz, 1H), 7.56 (d, J = 9.0 Hz, 1H), 7.49 (d, J = 2.0 Hz, 1H), 7.29 - 7.20 (m, 3H), 6.96 (d, J = 8.5 Hz, 2H), 3.78 (s, 3H), 3.09 - 3.00 (m, 4H), 2.86 - 2.71 (m, 5H), 2.56 (s, 5H), 2.13 - 2.05 (m, 1H), 1.92 - 1.69 (m, 4H), 1.66 - 1.55 (m, 3H) | ES-LCMS m/z 766.2 [M + H]$^+$. |

The following compounds were synthesized in an analogous manner to the preparation described above (Example 81), using the relevant sulfonyl chloride and arylamine precursors.

| Ex | Structure/Name | $^1H$ NMR | LCMS |
|---|---|---|---|
| 354 | 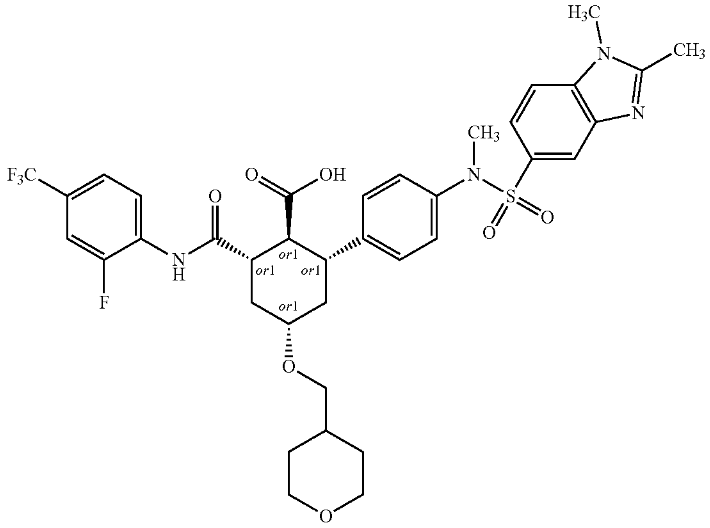 [SMILES: Cc1nc2cc(S(=O)(=O)N(C)c3ccc([C@@H]4C[C@H](OCC5CCOCC5)C[C@H](C(=O)Nc5ccc(C(F)(F)F)cc5F)[C@H]4C(=O)O)cc3)ccc2n1C] ISOMER 1 rel-(1R,2R,4R,6S)-2-((2-fluoro-4-(trifluoromethyl)phenyl)carbamoyl)-4-((tetrahydro-2H-pyran-4-yl)methoxy)-6-(4-((N,1,2-trimethyl-1H-benzo[d]imidazole)-5-sulfonamido)phenyl)cyclohexane-1-carboxylic acid ISOMER 1 | $^1H$ NMR (400 MHz, DMSO-$d_6$) δ 12.20 (s, 1H), 10.13 (s, 1H), 8.23 (t, J = 8.0 Hz, 1H), 7.74 (dd, J = 11.0, 2.0 Hz, 1H), 7.65 (d, J = 8.5 Hz, 1H), 7.57 - 7.49 (m, 2H), 7.31 - 7.17 (m, 3H), 6.97 (d, J = 9.0 Hz, 2H), 3.85 - 3.79 (m, 5H), 3.54 - 3.43 (m, 2H), 3.29 - 3.21 (m, 3H), 3.06 (s, 4H), 2.78 - 2.73 (m, 2H), 2.58 (s, 3H), 2.39 - 2.34 (m, 1H), 2.07 (d, J = 12.0 Hz, 1H), 1.78 - 1.67 (m, 1H), 1.61 - 1.38 (m, 4H), 1.24 - 1.13 (m, 2H) | ES-LCMS m/z 761.2 $[M - H]^-$. |
| 355 | 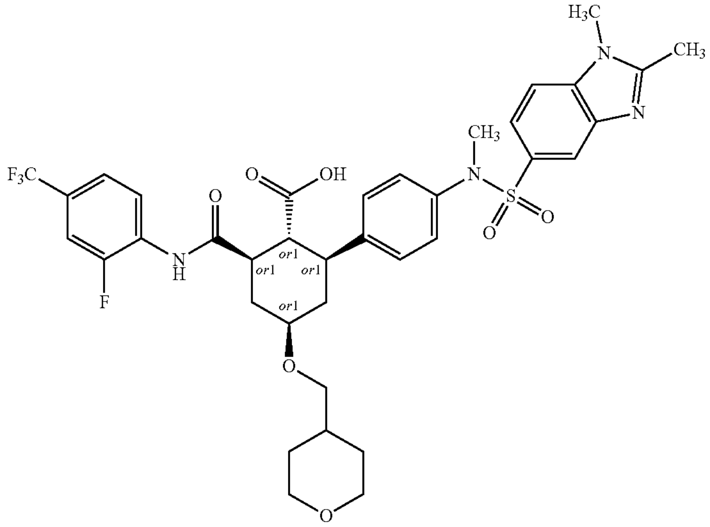 [SMILES: Cc1nc2cc(S(=O)(=O)N(C)c3ccc([C@H]4C[C@@H](OCC5CCOCC5)C[C@@H](C(=O)Nc5ccc(C(F)(F)F)cc5F)[C@@H]4C(=O)O)cc3)ccc2n1C] ISOMER 2 rel-(1R,2R,4R,6S)-2-((2-fluoro-4-(trifluoromethyl)phenyl)carbamoyl)-4-((tetrahydro-2H-pyran-4-yl)methoxy)-6-(4-((N,1,2-trimethyl-1H-benzo[d]imidazole)-5-sulfonamido)phenyl)cyclohexane-1-carboxylic acid ISOMER 2 | $^1H$ NMR (400 MHz, DMSO-$d_6$) δ 12.18 (s, 1H), 10.14 (s, 1H), 8.23 (t, J = 8.0 Hz, 1H), 7.74 (dd, J = 11.0, 1.5 Hz, 1H), 7.64 (d, J = 8.5 Hz, 1H), 7.58 - 7.47 (m, 2H), 7.29 - 7.18 (m, 3H), 6.97 (d, J = 9.0 Hz, 2H), 3.86 - 3.80 (m, 2H), 3.79 (s, 3H), 3.53 - 3.43 (m, 1H), 3.29 - 3.21 (m, 4H), 3.06 (s, 4H), 2.80 - 2.73 (m, 2H), 2.57 (s, 3H), 2.34 (dt, J = 4.0, 2.0 Hz, 1H), 2.10 - 2.00 (m, 1H), 1.80 - 1.66 (m, 1H), 1.62 - 1.53 (m, 3H), 1.43 (q, J = 11.7 Hz, 1H), 1.27 - 1.08 (m, 2H) | ES-LCMS m/z 761.2 $[M + H]^+$. |

Example 356 and Example 357 rac-(1R,2R,4R,6S)-2-((2-fluoro-4-(trifluoromethyl)phenyl)carbamoyl)-4-hydroxy-4-methyl-6-(4-((N,1,2-trimethyl-1H-benzo[d]imidazole)-5-sulfonamido)phenyl)cyclohexane-1-carboxylic acid and rac-(1R,2R,4S,6S)-2-((2-fluoro-4-(trifluoromethyl)phenyl)carbamoyl)-4-hydroxy-4-methyl-6-(4-((N,1,2-trimethyl-1H-benzo[d]imidazole)-5-sulfonamido)phenyl)cyclohexane-1-carboxylic acid

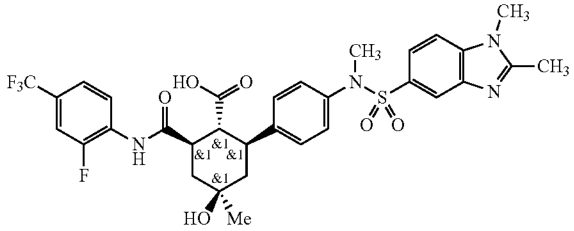

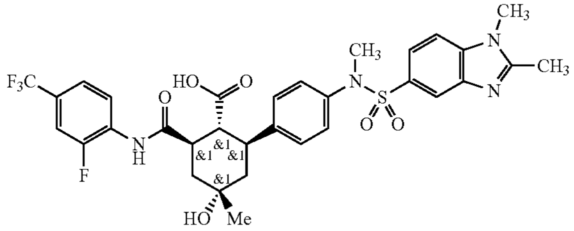

To a mixture of rel-(1R,2R,6S)-2-((2-fluoro-4-(trifluoromethyl)phenyl)carbamoyl)-4-oxo-6-(4-((N,1,2-trimethyl-1H-benzo[d]imidazole)-5-sulfonamido)phenyl)cyclohexane-1-carboxylic acid Intermediate 97 (0.150 g, 0.227 mmol) in THF (4 mL) at 0° C. was added methylmagnesium bromide (3M in diethyl ether, 3 mL, 9.00 mmol). The reaction was stirred at rt for 16 h, quenched with ammonium chloride solution (6 mL), diluted with water (10 mL) and extracted with ethyl acetate (3×15 mL). The combined organic layers were washed with brine (10 mL), dried over anhydrous sodium sulfate, concentrated and subjected to Prep HPLC (MeCN in $H_2O$, with 0.1% ABC modifier, 0 to 100% gradient) to afford:

Example 356, the first-eluting compound: rac-(1R,2R,4R,6S)-2-((2-fluoro-4-(trifluoromethyl)phenyl)carbamoyl)-4-hydroxy-4-methyl-6-(4-((N,1,2-trimethyl-1H-benzo[d]imidazole)-5-sulfonamido)phenyl)cyclohexane-1-carboxylic acid (4.2 mg, 6.2 μmol, 3.0% yield) as a white solid. $^1H$ NMR (400 MHz, DMSO-$d_6$) δ 12.15 (s, 1H), 10.14 (s, 1H), 8.24 (br s, 1H), 7.72-7.47 (m, 4H), 7.25 (d, J=7.0 Hz, 1H), 7.16 (d, J=8.0 Hz, 2H), 6.93 (d, J=8.0 Hz, 2H), 4.63-4.48 (m, 1H), 3.77 (s, 3H), 3.51-3.37 (m, 1H), 3.29-3.26 (m, 1H), 3.05 (s, 3H), 2.88-2.73 (m, 1H), 2.56 (s, 3H), 1.84 (d, J=11.0 Hz, 1H), 1.65-1.50 (m, 3H), 1.28 (s, 3H). ES-LCMS m/z 675.2 $[M-H]^-$.

Example 357, the second-eluting compound: rac-(1R,2R,4S,6S)-2-((2-fluoro-4-(trifluoromethyl)phenyl)carbamoyl)-4-hydroxy-4-methyl-6-(4-((N,1,2-trimethyl-1H-benzo[d]imidazole)-5-sulfonamido)phenyl)cyclohexane-1-carboxylic acid (7.5 mg, 0.010 mmol, 5.0% yield) as a white solid. $^1H$ NMR (400 MHz, DMSO-$d_6$) δ 12.09 (s, 1H), 10.06 (s, 1H), 8.08 (t, J=7.8 Hz, 1H), 7.70 (dd, J=10.5, 1.5 Hz, 1H), 7.63 (d, J=8.5 Hz, 1H), 7.57-7.46 (m, 2H), 7.25 (dd, J=8.5, 1.5 Hz, 1H), 7.17 (d, J=8.5 Hz, 2H), 6.95 (d, J=8.5 Hz, 2H), 4.43 (s, 1H), 3.78 (s, 3H), 3.41-3.36 (m, 1H), 3.15 (td, J=11.6, 4.3 Hz, 1H), 3.05 (s, 3H), 2.74-2.69 (m, 1H), 2.56 (s, 3H), 1.85 (d, J=11.5 Hz, 1H), 1.72-1.55 (m, 3H), 1.19 (s, 3H). ES-LCMS m/z 677.2 $[M+H]^+$.

The following compound was synthesized in an analogous manner to the preparation described above (Example 309), using 2,2,2-trifluoroethyl trifluoromethanesulfonate as the electrophile.

| Ex | Structure/Name | $^1H$ NMR | LCMS |
|---|---|---|---|
| 358 | 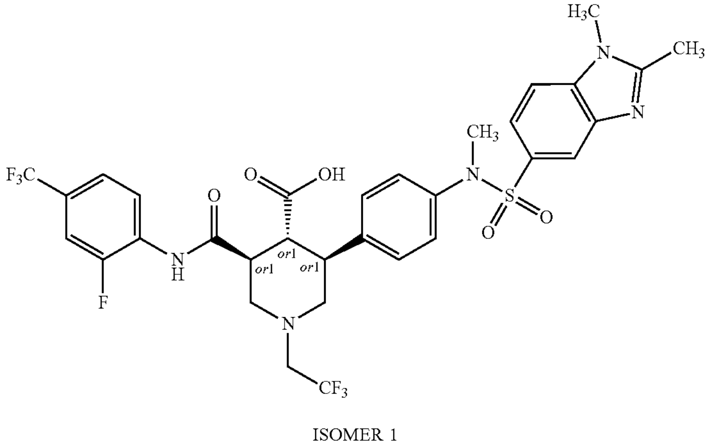 ISOMER 1 rel-(3R,4S,5R)-3-((2-fluoro-4-(trifluoromethyl)phenyl)carbamoyl)-1-(2,2,2-trifluoroethyl)-5-(4-((N,1,2-trimethyl-1H-benzo[d]imidazole)-5-sulfonamido)phenyl)piperidine-4-carboxylic acid ISOMER 1 | $^1H$ NMR (400 MHz, DMSO-$d_6$) δ 12.18 (1, 1H), 10.30 (s, 1H), 8.18 (t, J = 8.0 Hz, 1H), 7.74 (d, J = 11.0 Hz, 1H), 7.63 (d, J = 8.5 Hz, 1H), 7.58 - 7.47 (m, 2H), 7.24 (d, J = 8.5 Hz, 3H), 6.99 (d, J = 8.5 Hz, 2H), 3.77 (s, 3H), 3.37 - 3.36 (m, 2H), 3.24 - 3.21 (m, 2H), 3.05 (s, 3H), 2.95 - 2.83 (m, 3H), 2.76 - 2.67 (m, 2H), 2.56 (s, 3H) | ES-LCMS m/z 730.2 $[M-H]^-$. |

-

The following compounds were synthesized in an analogous manner to the preparation described above (Example 137 and Example 138), using the relevant amine precursor:

| Ex | Structure/Name | $^1$H NMR | LCMS |
|---|---|---|---|
| 359 | 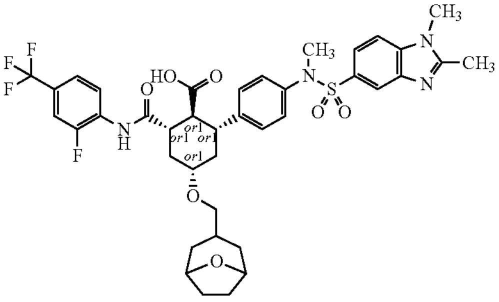 [SMILES: Cc1nc2cc(S(=O)(=O)N(C)c3ccc([C@@H]4C[C@H](OCC5CC6CCC(C5)O6)C[C@H](C(=O)Nc5ccc(C(F)(F)F)cc5F)[C@H]4C(=O)O)cc3)ccc2n1C] ISOMER 1 rel-(1R,2R,4R,6S)-4-((8-oxabicyclo[3.2.1]octan-3-yl)methoxy)-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylic acid, ISOMER 1 | $^1$H NMR (400 MHz, DMSO-$d_6$) δ 12.13 (br s, 1H), 10.11 (s, 1H), 8.22 (t, J = 8.3 Hz, 1H), 7.73 (dd, J = 11.0, 2.0 Hz, 1H), 7.63 (d, J = 8.5 Hz, 1H), 7.55 (d, J = 9.0 Hz, 1H), 7.48 (d, J = 1.5 Hz, 1H), 7.27 - 7.18 (m, 3H), 6.96 (d, J = 8.5 Hz, 2H), 4.26 (br s, 2H), 3.78 (s, 3H), 3.45 (ddd, J = 14.8, 10.5, 3.8 Hz, 1H), 3.26 (d, J = 6.0 Hz, 2H), 3.09 - 2.99 (m, 4H), 2.77 - 2.71 (m, 2H), 2.58 - 2.54 (m, 3H), 2.31 (d, J = 6.0 Hz, 1H), 2.04 (d, J = 11.5 Hz, 1H), 1.95 (ddd, J = 17.4, 11.6, 5.5 Hz, 1H), 1.80 - 1.74 (m, 2H), 1.70 - 1.64 (m, 2H), 1.48 - 1.38 (m, 3H), 1.33 - 1.22 (m, 3H) | ES-LCMS m/z 785.2 [M - H]$^-$. |
| 360 | 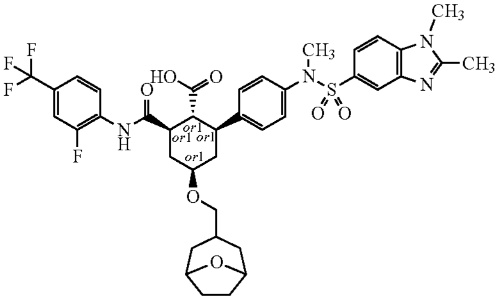 [SMILES: Cc1nc2cc(S(=O)(=O)N(C)c3ccc([C@H]4C[C@@H](OCC5CC6CCC(C5)O6)C[C@@H](C(=O)Nc5ccc(C(F)(F)F)cc5F)[C@@H]4C(=O)O)cc3)ccc2n1C] ISOMER 2 rel-(1R,2R,4R,6S)-4-((8-oxabicyclo[3.2.1]octan-3-yl)methoxy)-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylic acid, ISOMER 2 | $^1$H NMR (400 MHz, DMSO-$d_6$) δ 12.13 (br s, 1H), 10.11 (s, 1H), 8.22 (t, J = 8.0 Hz, 1H), 7.73 (dd, J = 11.0, 1.5 Hz, 1H), 7.63 (d, J = 8.5 Hz, 1H), 7.56 (d, J = 8.5 Hz, 1H), 7.48 (d, J = 1.5 Hz, 1H), 7.28 - 7.19 (m, 3H), 6.96 (d, J = 8.5 Hz, 2H), 4.26 (br s, 2H), 3.78 (s, 3H), 3.50 - 3.40 (m, 1H), 3.26 (d, J = 6.5 Hz, 2H), 3.09 - 3.00 (m, 4H), 2.77 - 2.71 (m, 2H), 2.56 (s, 3H), 2.30 (br s, 1H), 2.04 (d, J = 11.5 Hz, 1H), 1.98 - 1.89 (m, 1H), 1.80 - 1.74 (m, 2H), 1.69 - 1.64 (m, 2H), 1.48 - 1.38 (m, 3H), 1.33 - 1.22 (m, 3H) | ES-LCMS m/z 785.2 [M - H]$^-$. |

The following compound was synthesized in an analogous manner to the preparation described above (Example 139) using the relevant sulfonyl chloride precursor.

| Ex | Structure/Name | $^1$H NMR | LCMS |
|---|---|---|---|
| 361 | 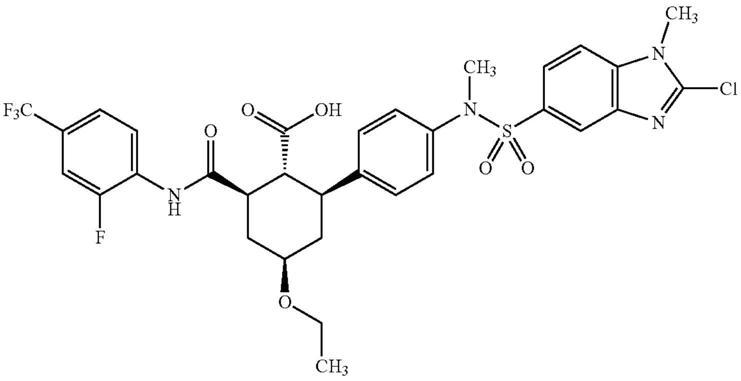 [SMILES: CCO[C@@H]1C[C@H](c2ccc(N(C)S(=O)(=O)c3ccc4c(c3)nc(Cl)n4C)cc2)[C@@H](C(=O)O)[C@H](C(=O)Nc2ccc(C(F)(F)F)cc2F)C1] ISOMER 1 rel-(1R,2S,4R,6R)-2-(4-((2-chloro-N,1-dimethyl-1H-benzo[d]imidazole)-5-sulfonamido)phenyl)-4-ethoxy-6-((2-fluoro-4- | $^1$H NMR (400 MHz, DMSO-$d_6$) δ 11.88 (br s, 1H), 10.12 (s, 1H), 8.22 (t, J = 8.3 Hz, 1H), 7.78 - 7.69 (m, 3H), 7.55 (d, J = 9.0 Hz, 1H), 7.30 - 7.20 (m, 3H), 6.99 (d, J = 8.5 Hz, 2H), 3.84 (s, 3H), 3.56 - 3.44 (m, 3H), 3.13 - 3.00 (m, 4H), 2.81 - 2.73 (m, 2H), 2.36 - 2.28 (m, 1H), 2.11 - 2.01 (m, 1H), 1.61 - 1.50 (m, 1H), 1.48 - 1.36 (m, 1H), 1.10 (t, J = 7.0 Hz, 3H) | ES-LCMS m/z 709.2 [M - H]$^-$. |

-continued

| Ex | Structure/Name | $^1$H NMR | LCMS |
|---|---|---|---|
| | (trifluoromethyl)phenyl) carbamoyl)cyclohexane-1-carboxylic acid ISOMER 1 | | |

The following compounds were synthesized in an analogous manner to the preparation described above (Example 254-257) using the relevant alkylamine.

| Ex | Structure/Name | $^1$H NMR | LCMS |
|---|---|---|---|
| 362 | 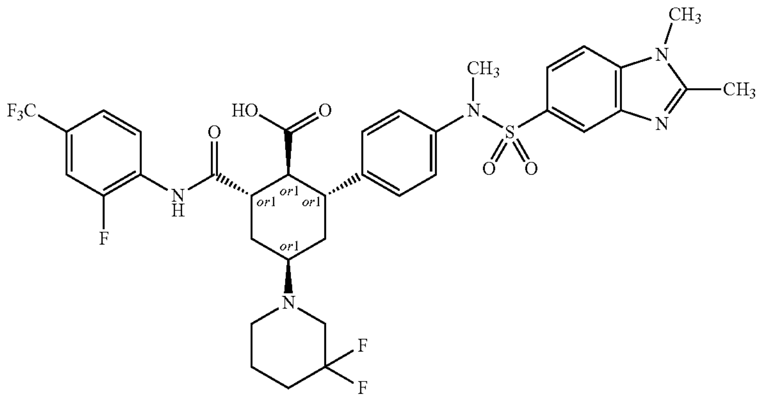 [SMILES: Cc1nc2cc(S(=O)(=O)N(C)c3ccc([C@@H]4C[C@@H](N5CCCC(F)(F)C5)C[C@H](C(=O)Nc5ccc(C(F)(F)F)cc5F)[C@H]4C(=O)O)cc3)ccc2n1C] ISOMER 1 rel-(1R,2R,4S,6S)-4-(3,3-difluoropiperidin-1-yl)-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylic acid ISOMER 1 | $^1$H NMR (400 MHz, DMSO-$d_6$) δ 12.26 (s, 1H), 10.23 (br s, 1H), 8.06 (t, J = 8.0 Hz, 1H), 7.74 - 7.68 (m, 1H), 7.63 (d, J = 8.5 Hz, 1H), 7.58 - 7.51 (m, 2H), 7.24 (d, J = 8.5 Hz, 1H), 7.15 (d, J = 8.5 Hz, 2H), 6.97 (d, J = 8.5 Hz, 2H), 3.77 (s, 3H), 3.29 - 3.18 (m, 3H), 3.13 - 3.01 (m, 4H), 2.88 2.72 (m, 3H), 2.56 (s, 3H), 2.31 - 2.16 (m, 2H), 1.97 (d, J = 14.0 Hz, 2H), 1.88 - 1.70 (m, 5H) | ES-LCMS m/z 766.2 [M + H]$^+$. |

The following compounds were synthesized in an analogous manner to the preparation described above (Example 72) using the relevant arylamine and sulfonyl chloride precursors.

| Ex | Structure/Name | $^1$H NMR | LCMS |
|---|---|---|---|
| 363 | 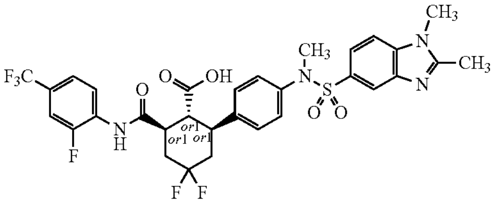 [SMILES: Cc1nc2cc(S(=O)(=O)N(C)c3ccc([C@H]4CC(F)(F)C[C@@H](C(=O)Nc5ccc(C(F)(F)F)cc5F)[C@@H]4C(=O)O)cc3)ccc2n1C] ISOMER 1 rel-(1R,2R,6S)-4,4-difluoro-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylic acid ISOMER 1 | $^1$H NMR (400 MHz, DMSO-$d_6$) δ 12.41 (br s, 1H), 10.37 (br s, 1H), 8.17 (t, J = 8.0 Hz, 1H), 7.73 (dd, J = 10.8, 1.8 Hz, 1H), 7.62 (d, J = 8.5 Hz, 1H), 7.60 - 7.55 (m, 1H), 7.50 (d, J = 1.5 Hz, 1H), 7.29 (d, J = 8.5 Hz, 2H), 7.24 (dd, J = 8.5, 1.5 Hz, 1H), 7.00 (d, J = 9.0 Hz, 2H), 3.78 (s, 3H), 3.27 (br s, 1H), 3.06 (s, 3H), 3.00 - 2.93 (m, 2H), 2.56 (s, 3H), 2.44 - 2.34 (m, 2H), 2.30 - 2.12 (m, 2H) | ES-LCMS m/z 680.5 [M - H]$^-$. |

-continued

| Ex | Structure/Name | $^1$H NMR | LCMS |
|---|---|---|---|
| 364 | 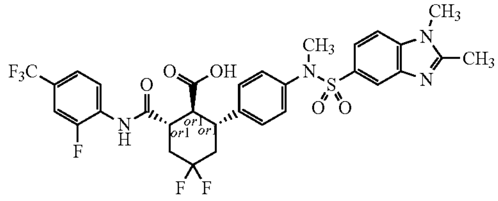 [SMILES: Cc1nc2cc(S(=O)(=O)N(C)c3ccc([C@@H]4CC(F)(F)C[C@H](C(=O)Nc5ccc(C(F)(F)F)cc5F)[C@H]4C(=O)O)cc3)ccc2n1C] ISOMER 2 rel-(1R,2R,6S)-4,4-difluoro-2-((2-fluoro-4-(trifluoromethyl)phenyl)carbamoyl)-6-(4-((N,1,2-trimethyl-1H-benzo[d]imidazole)-5-sulfonamido)phenyl)cyclohexane-1-carboxylic acid ISOMER 2 | $^1$H NMR (400 MHz, DMSO-$d_6$) δ 12.42 (br s, 1H), 10.36 (br s, 1H), 8.17 (t, J = 8.0 Hz, 1H), 7.73 (dd, J = 11.0, 2.0 Hz, 1H), 7.62 (d, J = 8.5 Hz, 1H), 7.57 (d, J = 8.5 Hz, 1H), 7.49 (d, J = 1.5 Hz, 1H), 7.29 (d, J = 8.5 Hz, 2H), 7.24 (dd, J = 8.5, 2.0 Hz, 1H), 7.00 (d, J = 8.5 Hz, 2H), 3.78 (s, 3H), 3.27 (br s, 1H), 3.06 (s, 3H), 2.97 (d, J = 10.5 Hz, 2H), 2.56 (s, 3H), 2.44 - 2.34 (m, 2H), 2.30 - 2.10 (m, 2H) | ES-LCMS m/z 681.0 [M − H]$^-$. |
| 365 | 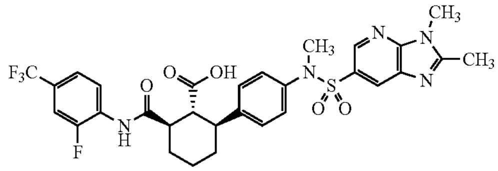 (1R,2S,6R)-2-(4-((2-chloro-N,1-dimethyl-1H-benzo[d] imidazole)-5-sulfonamido)phenyl)-6-((2-fluoro-4-(trifluoromethyl)phenyl)carbamoyl)cyclohexane-1-carboxylic acid | $^1$H NMR (400 MHz, DMSO-$d_6$) δ 11.80 (br s, 1H), 10.09 (s, 1H), 8.25 - 8.18 (m, 1H), 7.77 - 7.69 (m, 3H), 7.55 (d, J = 8.5 Hz, 1H), 7.27 (dd, J = 8.5, 1.5 Hz, 1H), 7.21 (d, J = 8.5 Hz, 2H), 6.98 (d, J = 8.5 Hz, 2H), 3.84 (s, 3H), 3.09 (s, 3H), 3.03 - 2.95 (m, 1H), 2.82 - 2.75 (m, 1H), 2.56 - 2.54 (m, 1H), 2.05 - 1.97 (m, 1H), 1.91 - 1.84 (m, 1H), 1.80 - 1.69 (m, 1H), 1.64 - 1.48 (m, 3H) | ES-LCMS m/z 667.0 [M + H]$^+$. |

The following compounds were synthesized in an analogous manner to the preparation described above (Example 83 and Example 84) using the relevant arylamine precursors. Compounds were purified using reverse phase chromatography (MeCN/$H_2O$, basic or acidic modifiers) and resolution on a Chiral column.

| Ex | Structure/Name | $^1$H NMR | LCMS |
|---|---|---|---|
| 366 | 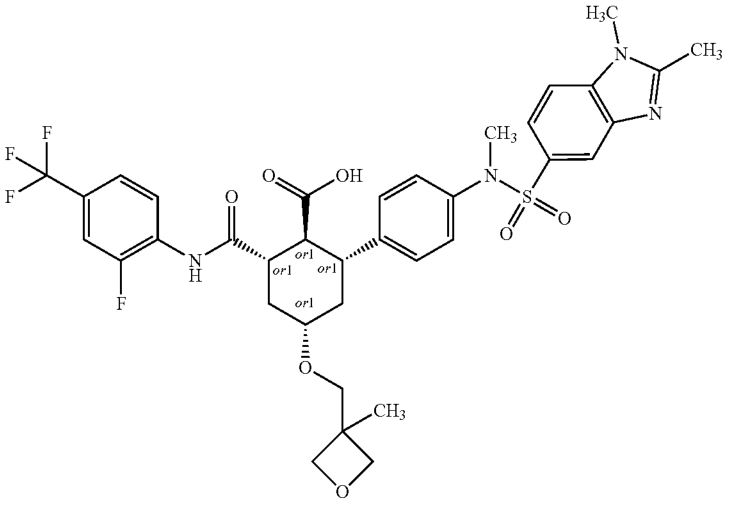 [SMILES: Cc1nc2cc(S(=O)(=O)N(C)c3ccc([C@@H]4C[C@H](OCC5(C)COC5)C[C@H](C(=O)Nc5ccc(C(F)(F)F)cc5F)[C@H]4C(=O)O)cc3)ccc2n1C] ISOMER 3 rel-(1R,2R,4R,6S)-2-((2-fluoro-4-(trifluoromethyl)phenyl)carbamoyl)-4-((3-methyloxetan-3-yl)methoxy)-6-(4-((N,1,2-trimethyl-1H-benzo[d]imidazole)-5-sulfonamido)phenyl)cyclohexane-1-carboxylic acid ISOMER 3 | $^1$H NMR (400 MHz, DMSO-$d_6$) δ 12.09 (br s, 1H), 10.13 (s, 1H), 8.22 (t, J = 8.0 Hz, 1H), 7.72 (dd, J = 11.0, 2.0 Hz, 1H), 7.63 (d, J = 8.5 Hz, 1H), 7.56 (d, J = 8.5 Hz, 1H), 7.50 (d, J = 1.5 Hz, 1H), 7.28 - 7.20 (m, 3H), 6.97 (d, J = 8.5 Hz, 2H), 4.35 (d, J = 5.5 Hz, 2H), 4.19 (d, J = 5.5 Hz, 2H), 3.78 (s, 3H), 3.55 (d, J = 1.5 Hz, 3H), 3.14 - 3.01 (m, 4H), 2.84 - 2.74 (m, 2H), 2.56 (s, 3H), 2.38 (d, J = 11.0 Hz, 1H), 2.15 - 2.06 (m, 1H), 1.67 - 1.55 (m, 1H), 1.53 - 1.41 (m, 1H), 1.22 (s, 3H) | ES-LCMS m/z 745.2 [M − H]$^-$. |

-continued

| Ex | Structure/Name | $^1$H NMR | LCMS |
| --- | --- | --- | --- |
| 367 | 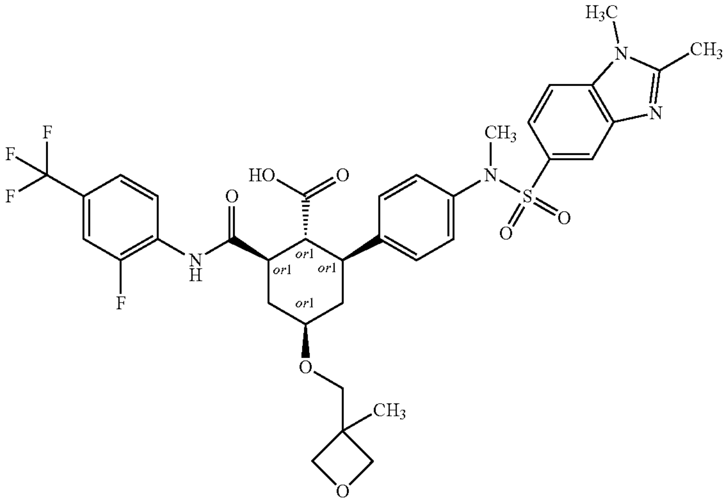 [SMILES: Cc1nc2cc(S(=O)(=O)N(C)c3ccc([C@H]4C[C@@H](OCC5(C)COC5)C[C@@H](C(=O)Nc5ccc(C(F)(F)F)cc5F)[C@@H]4C(=O)O)cc3)ccc2n1C] ISOMER 4 rel-(1R,2R,4R,6S)-2-((2-fluoro-4-(trifluoromethyl)phenyl) carbamoyl)-4-((3-methyloxetan-3-yl)methoxy)-6-(4-((N,1,2-trimethyl-1H-benzo[d]imidazole)-5-sulfonamido)phenyl)cyclohexane-1-carboxylic acid ISOMER 4 | $^1$H NMR (400 MHz, DMSO-d$_6$) δ 11.89 (s, 1H), 10.17 (br s, 1H), 8.23 (t, J = 8.0 Hz, 1H), 7.72 (dd, J = 11.0, 1.5 Hz, 1H), 7.63 (d, J = 8.5 Hz, 1H), 7.56 (d, J = 8.5 Hz, 1H), 7.50 (d, J = 1.5 Hz, 1H), 7.27 – 7.21 (m, 3H), 6.97 (d, J = 8.5 Hz, 2H), 4.34 (d, J = 5.5 Hz, 2H), 4.18 (d, J = 5.5 Hz, 2H), 3.78 (s, 3H), 3.55 (d, J = 1.0 Hz, 3H), 3.05 (s, 4H), 2.80 – 2.74 (m, 2H), 2.56 (s, 3H), 2.38 (d, J = 12.5 Hz, 1H), 2.09 (d, J = 10.5 Hz, 1H), 1.65 – 1.54 (m, 1H), 1.47 (q, J = 11.7 Hz, 1H), 1.22 (s, 3H) | ES-LCMS m/z 745.2 [M − H]$^-$. |
| 368 | 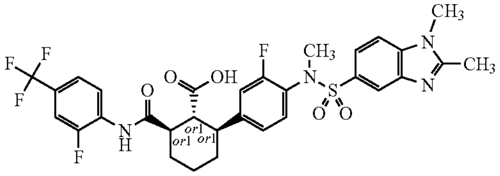 [SMILES: Cc1nc2cc(S(=O)(=O)N(C)c3ccc([C@H]4CCC[C@@H](C(=O)Nc5ccc(C(F)(F)F)cc5F)[C@@H]4C(=O)O)cc3F)ccc2n1C] ISOMER 1 rel-(1R,2S,6R)-2-(3-fluoro-4-((N,1,2-trimethyl-1H-benzo[d]imidazole)-5-sulfonamido)phenyl)-6-((2-fluoro-4-(trifluoromethyl)phenyl)carbamoyl)cyclohexane-1-carboxylic acid ISOMER 1 | $^1$H NMR (400 MHz, DMSO-d$_6$) δ 10.14 (s, 1H), 8.22 (t, J = 8.3 Hz, 1H), 7.75 – 7.66 (m, 3H), 7.55 (d, J = 8.5 Hz, 1H), 7.41 (dd, J = 8.5, 2.0 Hz, 1H), 7.17 (dd, J= 12.0, 2.0 Hz, 1H), 7.10 – 6.94 (m, 2H), 3.81 (s, 3H), 3.08 (s, 3H), 3.02 – 2.93 (m, 1H), 2.84 – 2.66 (m, 2H), 2.59 (s, 3H), 2.02 ( d, J = 9.0 Hz, 1H), 1.92 – 1.83 (m, 1H), 1.80 – 1.71 (m, 1H), 1.68 – 1.45 (m, 3H) | ES-LCMS m/z 665.2 [M + H]$^+$. |
| 369 | 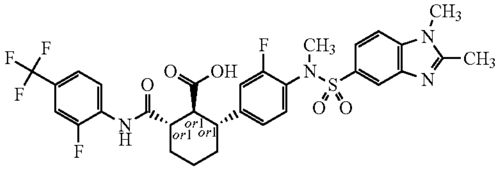 [SMILES: Cc1nc2cc(S(=O)(=O)N(C)c3ccc([C@@H]4CCC[C@H](C(=O)Nc5ccc(C(F)(F)F)cc5F)[C@H]4C(=O)O)cc3F)ccc2n1C] ISOMER 2 rel-(1R,2S,6R)-2-(3-fluoro-4-((N,1,2-trimethyl-1H-benzo[d]imidazole)-5-sulfonamido)phenyl)-6-((2-fluoro-4-(trifluoromethyl)phenyl)carbamoyl)cyclohexane-1-carboxylic acid ISOMER 2 | $^1$H NMR (400 MHz, DMSO-d$_6$) δ 10.16 (s, 1H), 8.22 (t, J = 8.3 Hz, 1H), 7.73 – 7.64 (m, 3H), 7.58 – 7.51 (m, 1H), 7.40 (dd, J = 8.5, 1.5 Hz, 1H), 7.16 (dd, J = 12.0, 1.5 Hz, 1H), 7.09 – 6.92 (m, 2H), 3.80 (s, 3H), 3.07 (s, 3H), 3.00 – 2.91 (m, 1H), 2.84 – 2.68 (m, 2H), 2.58 (s, 3H), 2.01 ( d, J = 9.0 Hz, 1H), 1.89 – 1.82 (m, 1H), 1.75 ( d, J = 3.5 Hz, 1H), 1.65 – 1.43 (m, 3H) | ES-LCMS m/z 665.2 [M + H]$^+$. |

Example 370 rac-methyl (1R,2S,3R,6R)-3-ethoxy-6-((2-fluoro-4-(trifluoromethyl)phenyl)carbamoyl)-2-(4-(N,1,2-trimethyl-1H-benzo[d]imidazole-5-sulfonamido)phenyl)cyclohexane-1-carboxylate

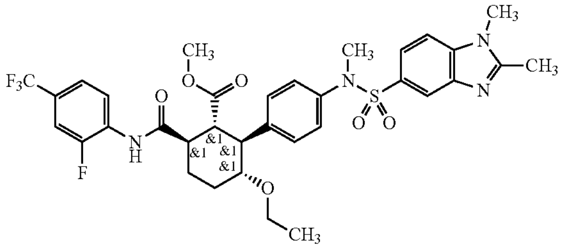 [SMILES: CCO[C@@H]1CC[C@@H](C(=O)Nc2ccc(C(F)(F)F)cc2F)[C@H](C(=O)OC)[C@H]1c1ccc(N(C)S(=O)(=O)c2ccc3c(c2)nc(C)n3C)cc1]

To a mixture of rac-methyl (1R,2S,3R,6R)-6-(chlorocarbonyl)-3-ethoxy-2-(4-((N,1,2-trimethyl-1H-benzo[d]imidazole)-5-sulfonamido)phenyl)cyclohexane-1-carboxylate Intermediate 109 (0.450 g, 800 μmol) in DCM (5 mL) at 0° C. was added 2-fluoro-4-(trifluoromethyl)aniline (172 mg, 961 μmol) and pyridine (63.3 mg 800 μmol). The reaction was stirred at RT for 1 h, concentrated, diluted water (100 mL) and extracted with ethyl acetate (300 mL). The organic layer was washed with brine (50 mL), dried over sodium sulphate, concentrated, dissolved in 5 mL DCM, adsorbed on of silica gel (5 g, 60-120 mesh) and purified by column chromatography, eluting with 15% methanol in DCM to afford rac-methyl (1R,2S,3R,6R)-3-ethoxy-6-((2-fluoro-4-(trifluoromethyl)phenyl)carbamoyl)-2-(4-((N,1,2-trimethyl-1H-benzo[d]imidazole)-5-sulfonamido)phenyl)cyclohexane-1-carboxylate (0.50 g, 700 μmol, 87%) as a pale yellow solid. $^1$H NMR (400 MHz, DMSO-$d_6$) δ10.13 (s, 1H), 8.14 (t, J=8.0 Hz, 1H), 7.73 (dd, J=11.0, 1.5 Hz, 1H), 7.62 (d, J=8.5 Hz, 1H), 7.58-7.51 (m, 2H), 7.30-7.20 (m, 3H), 6.97 (d, J=8.5 Hz, 2H), 3.78 (s, 3H), 3.49 (br s, 1H), 3.47-3.36 (m, 1H), 3.28 (d, J=12.0 Hz, 1H), 3.21 (s, 3H), 3.10 (s, 3H), 2.98 (dd, J=9.5, 7.0 Hz, 2H), 2.89 (dd, J=12.3, 1.8 Hz, 1H), 2.56 (s, 3H), 2.11-2.01 (m, 1H), 1.85-1.76 (m, 2H), 1.66-1.48 (m, 1H), 0.98 (t, J=7.0 Hz, 3H). ES-LCMS m/z 705.2 [M+H]$^+$.

Example 371 rac-(1R,2S,3R,6R)-3-ethoxy-6-((2-fluoro-4-(trifluoromethyl)phenyl)carbamoyl)-2-(4-((N,1,2-trimethyl-1H-benzo[d]imidazole)-5-sulfonamido)phenyl)cyclohexane-1-carboxylic acid

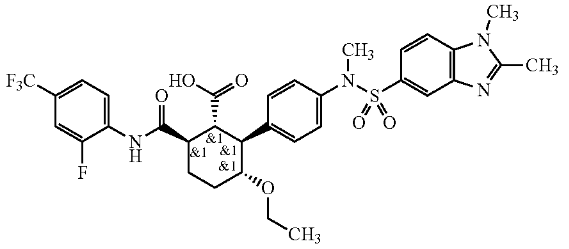 [SMILES: CCO[C@@H]1CC[C@@H](C(=O)Nc2ccc(C(F)(F)F)cc2F)[C@H](C(=O)O)[C@H]1c1ccc(N(C)S(=O)(=O)c2ccc3c(c2)nc(C)n3C)cc1]

To a mixture of 2-methylpropan-2-olate potassium (111 mg, 993 μmol) in THF (1 mL) at 0° C. was added water (5.114 mg, 0.005114 mL, 2.000 Eq, 283.8 μmol). After 15 min rac-methyl (1R,2S,3R,6R)-3-ethoxy-6-((2-fluoro-4-(trifluoromethyl)phenyl)carbamoyl)-2-(4-((N,1,2-trimethyl-1H-benzo[d]imidazole)-5-sulfonamido)phenyl)cyclohexane-1-carboxylate Example 370 (0.100 g, 142 μmol) in THF (0.5 mL) was added. After 20 h, the reaction was concentrated and subjected to reverse phase purification (0-100% MeCN in $H_2O$, with 0.1% ABC modifier) to afford rac-(1R,2S,3R,6R)-3-ethoxy-6-((2-fluoro-4-(trifluoromethyl)phenyl)carbamoyl)-2-(4-((N,1,2-trimethyl-1H-benzo[d]imidazole)-5-sulfonamido)phenyl)cyclohexane-1-carboxylic acid (0.010 g, 14 μmol, 10%) as a white solid. $^1$H NMR (400 MHz, DMSO-$d_6$) δ 10.11 (s, 1H), 8.20 (t, J=8.3 Hz, 1H), 7.70 (dd, J=11.0, 1.5 Hz, 1H), 7.60-7.49 (m, 3H), 7.27-7.18 (m, 3H), 6.94 (d, J=8.4 Hz, 2H), 3.76 (s, 3H), 3.44 (br s, 1H), 3.41-3.34 (m, 1H), 3.21 (t, J=11.5 Hz, 1H), 3.07 (s, 3H) 3.01-2.81 (m, 3H), 2.55 (s, 3H), 2.04 (dd, J=13.5, 3.0 Hz, 1H), 1.84-1.73 (m, 2H), 1.58-1.53 (m, 1H), 0.93 (t, J=7.0 Hz, 3H). ES-LCMS m/z 691.2 [M+H]$^+$.

The following compounds were synthesized in an analogous manner to the preparation described above (Example 72) using the relevant arylamine and sulfonyl chloride precursors.

| Ex | Structure/Name | $^1$H NMR | LCMS |
|---|---|---|---|
| 372 | 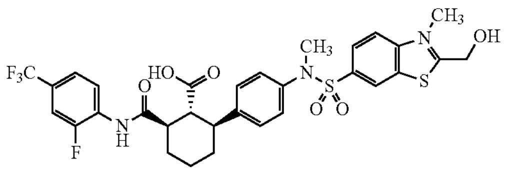 (1R,2R,6S)-2-((2-fluoro-4-(trifluoromethyl)phenyl)carbamoyl)-6-(4-((2-(hydroxymethyl)-N,1-dimethyl-1H-benzo[d]imidazole)-5-sulfonamido)phenyl)cyclohexane-1-carboxylic acid | 1H NMR (400 MHz, DMSO-$d_6$) δ 11.93 (br s, 1H), 10.09 (s, 1H), 8.21 (t, J = 8.0 Hz, 1H), 7.77 - 7.65 (m, 3H), 7.55 (d, J = 9.0 Hz, 1H), 7.27 (dd, J = 8.8, 1.8 Hz, 1H), 7.20 (d, J = 8.5 Hz, 2H), 6.97 (d, J = 8.5 Hz, 2H), 5.69 (t, J = 5.8 Hz, 1H), 4.75 (d, J = 6.0 Hz, 2H), 3.88 (s, 3H), 3.07 (s, 3H), 3.00 (br s, 1H), 2.78 (t, J = 11.3 Hz, 1H), 2.73 - 2.67 (m, 1H), 2.06 - 1.98 (m, 1H), 1.93 - 1.82 (m, 1H), 1.80 - 1.71 (m, 1H), 1.59 - 1.45 (m, 3H) | ES-LCMS m/z 663.3 [M + H]$^+$. |

-continued

| Ex | Structure/Name | $^1H$ NMR | LCMS |
|---|---|---|---|
| 373 | 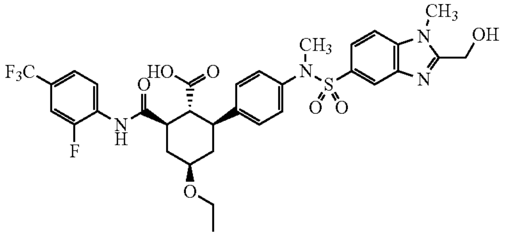 [SMILES: CCO[C@@H]1C[C@H](c2ccc(N(C)S(=O)(=O)c3ccc4c(c3)nc(CO)n4C)cc2)[C@@H](C(=O)O)[C@H](C(=O)Nc2ccc(C(F)(F)F)cc2F)C1] (1R,2R,4R,6S)-4-ethoxy-2-((2-fluoro-4-(trifluoromethyl)phenyl)carbamoyl)-6-(4-((2-(hydroxymethyl)-N,1-dimethyl-1H-benzo[d]imidazole)-5-sulfonamido)phenyl)cyclohexane-1-carboxylic acid | $^1H$ NMR (400 MHz, DMSO-$d_6$) δ 12.01 (s, 1H), 10.12 (s, 1H), 8.22 (t, J = 8.0 Hz, 1H), 7.73 (dd, J = 11.0, 1.5 Hz, 1H), 7.70 - 7.64 (m, 2H), 7.55 (d, J = 8.5 Hz, 1H), 7.27 (dd, J = 8.5, 1.5 Hz, 1H), 7.22 (d, J = 8.5 Hz, 2H), 6.97 (d, J = 8.5 Hz, 2H), 5.69 (t, J = 5.8 Hz, 1H), 4.75 (d, J = 5.5 Hz, 2H), 3.88 (s, 3H), 3.57 - 3.45 (m, 3H), 3.11 - 3.00 (m, 4H), 2.82 - 2.71 (m, 2H), 2.36 - 2.30 (m, 1H), 2.12 - 2.00 (m, 1H), 1.61 - 1.49 (m, 1H), 1.48 - 1.37 (m, 1H), 1.10 (t, J = 7.0 Hz, 3H) | ES-LCMS m/z 707.2 $[M + H]^+$. |
| 374 | 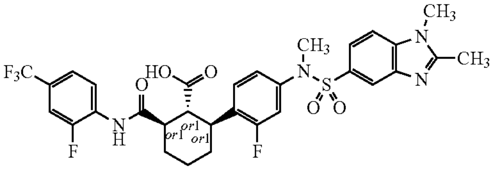 [SMILES: Cc1nc2cc(S(=O)(=O)N(C)c3ccc([C@H]4CCC[C@@H](C(=O)Nc5ccc(C(F)(F)F)cc5F)[C@@H]4C(=O)O)c(F)c3)ccc2n1C] ISOMER 1 rel-(1R,2S,6R)-2-(2-fluoro-4-((N,1,2-trimethyl-1H-benzo[ d] imidazole)-5-sulfonamido)phenyl)-6-((2-fluoro-4-(trifluoromethyl)phenyl) carbamoyl) cyclohexane-1-carboxylic acid ISOMER 1 | $^1H$ NMR (400 MHz, DMSO-$d_6$) δ 12.08 (br s, 1H), 10.12 (s, 1H), 8.22 (t, J = 8.3 Hz, 1H), 7.72 (dd, J = 11.0, 2.0 Hz, 1H), 7.66 (d, J = 9.0 Hz, 1H), 7.61 (d, J = 1.5 Hz, 1H), 7.55 (d, J = 8.5 Hz, 1H), 7.36 (t, J = 8.5 Hz, 1H), 7.25 (dd, J = 8.5, 2.0 Hz, 1H), 6.92 - 6.84 (m, 2H), 3.79 (s, 3H), 3.07 (s, 3H), 3.03 - 2.93 (m, 2H), 2.90 (d, J = 11.0 Hz, 1H), 2.58 (s, 3H), 2.11 - 2.00 (m, 1H), 1.94 - 1.86 (m, 1H), 1.80 - 1.60 (m, 2H), 1.57 - 1.43 (m, 2H) | ES-LCMS m/z 663.2 $[M - H]^-$. |
| 375 | 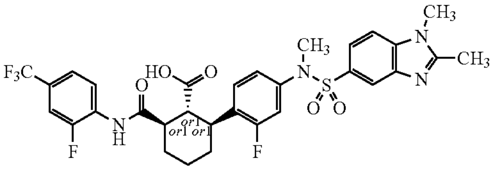 [SMILES: Cc1nc2cc(S(=O)(=O)N(C)c3ccc([C@H]4CCC[C@@H](C(=O)Nc5ccc(C(F)(F)F)cc5F)[C@@H]4C(=O)O)c(F)c3)ccc2n1C] ISOMER 1 rel-(1R,2S,6R)-2-(2-fluoro-4-((N,1,2-trimethyl-1H-benzo[ d] imidazole)-5-sulfonamido)phenyl)-6-((2-fluoro-4-(trifluoromethyl)phenyl)carbamoyl) cyclohexane-1-carboxylic acid ISOMER 2 | $^1H$ NMR (400 MHz, DMSO-$d_6$) δ 12.09 (br s, 1H), 10.13 (br s, 1H), 8.29 - 8.18 (m, 1H), 7.71 (d, J = 11.0 Hz, 1H), 7.64 (d, J = 9.0 Hz, 1H), 7.59 (s, 1H), 7.55 (d, J = 8.0 Hz, 1H), 7.40 - 7.32 (m, 1H), 7.24 (dd, J = 8.5, 2.0 Hz, 1H), 6.91 - 6.83 (m, 2H), 3.78 (s, 3H), 3.06 (s, 3H), 3.03 - 2.94 (m, 2H), 2.91 - 2.83 (m, 1H), 2.57 (s, 3H), 2.02 (d, J = 7.0 Hz, 1H), 1.88 (d, J = 7.5 Hz, 1H), 1.78 - 1.71 (m, 1H), 1.68 - 1.60 (m, 1H), 1.56 - 1.46 (m, 2H) | ES-LCMS m/z 663.0 $[M - H]^-$. |

The following compounds were synthesized in an analogous manner to the preparation described above (Example 183) using the relevant benzyl-protected precursor.

| Ex | Structure/Name | $^1$H NMR | LCMS |
|---|---|---|---|
| 376 | 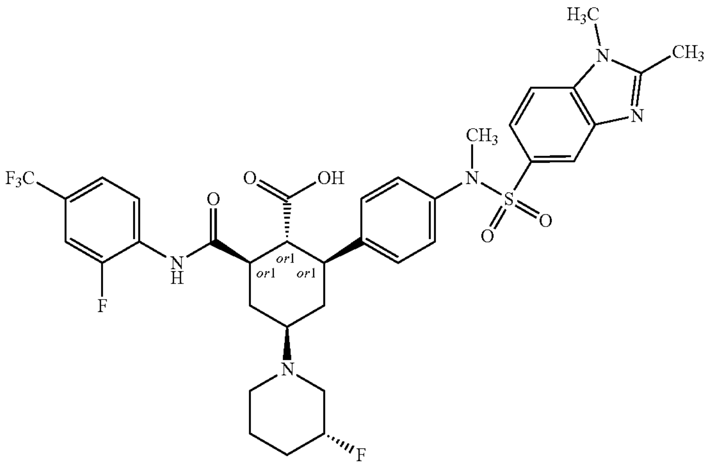 [SMILES: Cc1nc2cc(S(=O)(=O)N(C)c3ccc([C@H]4C[C@@H](N5CCC[C@@H](F)C5)C[C@@H](C(=O)Nc5ccc(C(F)(F)F)cc5F)[C@@H]4C(=O)O)cc3)ccc2n1C] rel-(1R*,2R*,4R*,6S*)-2-((2-fluoro-4-(trifluoromethyl)phenyl)carbamoyl)-4-((R)-3-fluoropiperidin-1-yl)-6-(4-((N,1,2-trimethyl-1H-benzo[d]imidazole)-5-sulfonamido)phenyl)cyclohexane-1-carboxylic acid | $^1$H NMR (400 MHz, DMSO-$d_6$) δ 12.15 (br s, 1H), 10.19 (br s, 1H), 8.24 (t, J = 8.5 Hz, 1H), 7.71 (d, J = 11.0 Hz, 1H), 7.64 (d, J = 8.5 Hz, 1H), 7.59 - 7.49 (m, 2H), 7.31 - 7.17 (m, 3H), 6.95 (d, J = 8.5 Hz, 2H), 4.67 - 4.42 (m, 2H), 3.78 (s, 3H), 3.11 - 2.86 (m, 5H), 2.80 - 2.68 (m, 3H), 2.56 (s, 3H), 2.47 - 2.36 (m, 2H), 2.14 - 2.02 (m, 1H), 1.90 - 1.59 (m, 4H), 1.58 - 1.31 (m, 3H) | ES-LCMS m/z 748.2 [M + H]$^+$. |
| 377 | 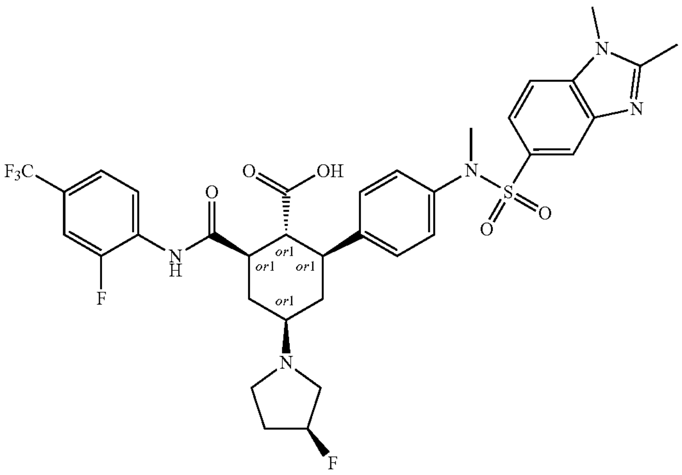 [SMILES: Cc1nc2cc(S(=O)(=O)N(C)c3ccc([C@H]4C[C@@H](N5CC[C@H](F)C5)C[C@@H](C(=O)Nc5ccc(C(F)(F)F)cc5F)[C@@H]4C(=O)O)cc3)ccc2n1C] ISOMER 1 rel-(1R*,2R*,4R*,6S*)-2-((2-fluoro-4-(trifluoromethyl)phenyl)carbamoyl)-4-((S)-3-fluoropyrrolidin-1-yl)-6-(4-((N,1,2-trimethyl-1H-benzo[d]imidazole)-5-sulfonamido)phenyl)cyclohexane-1-carboxylic acid ISOMER 1 | $^1$H NMR (400 MHz, DMSO-$d_6$) δ 12.11 (br s, 1H), 10.13 (s, 1H), 8.24 (t, J = 8.0 Hz, 1H), 7.73 (dd, J = 11.0, 1.5 Hz, 1H), 7.63 (d, J = 8.5 Hz, 1H), 7.56 (d, J = 9.0 Hz, 1H), 7.49 (d, J = 1.5 Hz, 1H), 7.26 (dd, J = 8.5, 2.0 Hz, 1H), 7.22 (d, J = 8.5 Hz, 2H), 6.97 (d, J = 8.5 Hz, 2H), 5.27 - 5.07 (m, 1H), 3.78 (s, 3H), 3.14 - 3.01 (m, 4H), 2.94 - 2.75 (m, 4H), 2.56 (s, 3H), 2.44 (d, J = 7.5 Hz, 2H), 2.25 (d, J = 12.5 Hz, 1H), 2.15 - 1.75 (m, 4H), 1.67 - 1.53 (m, 1H), 1.52 - 1.39 (m, 1H) | ES-LCMS m/z 734.2 [M + H]$^+$. |

-continued

| Ex | Structure/Name | $^1H$ NMR | LCMS |
|---|---|---|---|
| 378 | 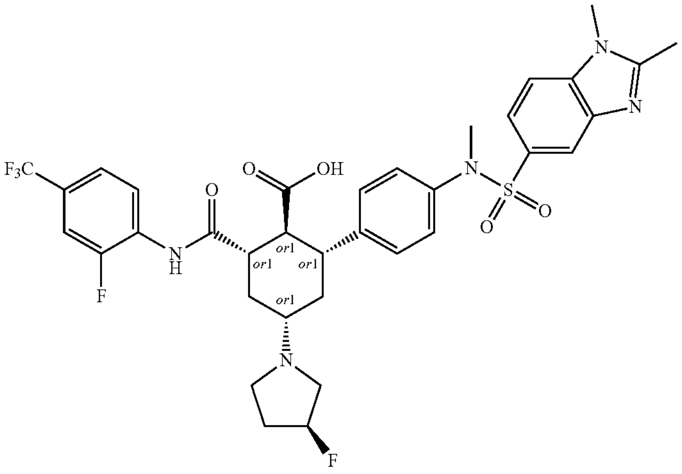 [SMILES: Cc1nc2cc(S(=O)(=O)N(C)c3ccc([C@@H]4C[C@H](N5CC[C@H](F)C5)C[C@H](C(=O)Nc5ccc(C(F)(F)F)cc5F)[C@H]4C(=O)O)cc3)ccc2n1C] ISOMER 2 rel-(1R*,2R*,4R*,6S*)-2-((2-fluoro-4-(trifluoromethyl)phenyl)carbamoyl)-4-((S)-3-fluoropyrrolidin-1-yl)-6-(4-((N,1,2-trimethyl-1H-benzo[d]imidazole)-5-sulfonamido)phenyl)cyclohexane-1-carboxylic acid ISOMER 2 | $^1H$ NMR (400 MHz, DMSO-$d_6$) δ 12.11 (br s, 1H), 10.14 (s, 1H), 8.24 (t, J = 8.3 Hz, 1H), 7.73 (dd, J = 11.0, 1.5 Hz, 1H), 7.63 (d, J = 8.5 Hz, 1H), 7.56 (d, J = 8.5 Hz, 1H), 7.50 (d, J = 1.5 Hz, 1H), 7.29 - 7.20 (m, 3H), 6.97 (d, J = 8.5 Hz, 2H), 5.26 - 5.08 (m, 1H), 3.78 (s, 3H), 3.13 - 3.01 (m, 4H), 2.96 - 2.72 (m, 5H), 2.56 (s, 3H), 2.47 - 2.38 (m, 2H), 2.25 (d, J = 12.0 Hz, 1H), 2.05 - 1.76 (m, 3H), 1.65 - 1.53 (m, 1H), 1.46 (q, J = 12.2 Hz, 1H) | ES-LCMS m/z 734.2 $[M + H]^+$. |
| 379 | 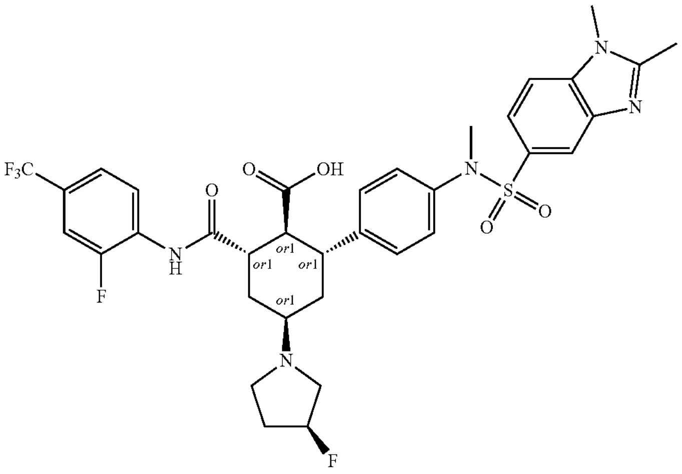 [SMILES: Cc1nc2cc(S(=O)(=O)N(C)c3ccc([C@@H]4C[C@@H](N5CC[C@H](F)C5)C[C@H](C(=O)Nc5ccc(C(F)(F)F)cc5F)[C@H]4C(=O)O)cc3)ccc2n1C] ISOMER 1 rel-(1R*,2R*,4S*,6S*)-2-((2-fluoro-4-(trifluoromethyl)phenyl)carbamoyl)-4-((S)-3-fluoropyrrolidin-1-yl)-6-(4-((N,1,2-trimethyl-1H-benzo[d]imidazole)-5-sulfonamido)phenyl)cyclohexane-1-carboxylic acid ISOMER 1 | $^1H$ NMR (400 MHz, DMSO-$d_6$) δ 12.09 (br s, 1H), 10.17 (s, 1H), 8.14 - 8.06 (m, 1H), 7.70 (d, J = 10.0 Hz, 1H), 7.63 (d, J = 9.0 Hz, 1H), 7.59 - 7.51 (m, 2H), 7.24 (dd, J = 8.3, 1.8 Hz, 1H), 7.18 (d, J = 8.5 Hz, 2H), 7.01 - 6.94 (m, 2H), 5.39 - 5.18 (m, 1H), 3.78 (s, 3H), 3.45 - 3.35 (m, 1H), 3.20 - 3.10 (m, 1H), 3.09 - 2.95 (m, 4H), 2.90 - 2.71 (m, 3H), 2.56 (s, 3H), 2.45 (d, J = 1.5 Hz, 2H), 2.42 - 2.33 (m, 1H), 2.29 - 2.12 (m, 1H), 2.06 (d, J = 12.0 Hz, 1H), 1.93 - 1.72 (m, 3H) | ES-LCMS m/z 734.3 $[M + H]^+$. |

-continued

| Ex | Structure/Name | $^1H$ NMR | LCMS |
|---|---|---|---|
| 380 | 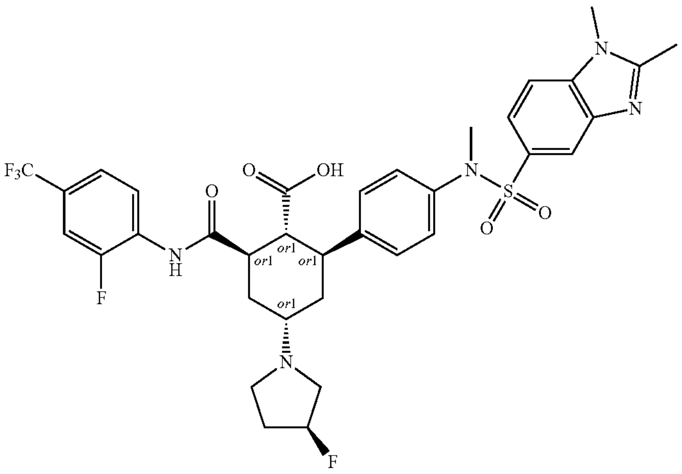 [SMILES: Cc1nc2cc(S(=O)(=O)N(C)c3ccc([C@H]4C[C@H](N5CC[C@H](F)C5)C[C@@H](C(=O)Nc5ccc(C(F)(F)F)cc5F)[C@@H]4C(=O)O)cc3)ccc2n1C] ISOMER 2 rel-(1R*,2R*,4S*,6S*)-2-((2-fluoro-4-(trifluoromethyl)phenyl)carbamoyl)-4-((S)-3-fluoropyrrolidin-1-yl)-6-(4-((N,1,2-trimethyl-1H-benzo[d]imidazole)-5-sulfonamido)phenyl)cyclohexane-1-carboxylic acid ISOMER 2 | $^1H$ NMR (400 MHz, DMSO-$d_6$) δ 12.10 (br s, 1H), 10.20 (br s, 1H), 8.06 (t, J = 8.0 Hz, 1H), 7.72 (d, J = 11.0 Hz, 1H), 7.64 (d, J = 8.5 Hz, 1H), 7.59 - 7.52 (m, 2H), 7.25 (dd, J = 8.5, 1.5 Hz, 1H), 7.21 (d, J = 8.5 Hz, 2H), 6.98 (d, J = 8.5 Hz, 2H), 5.38 - 5.21 (m, 1H), 3.79 (s, 3H), 3.37 (d, J = 3.5 Hz, 1H), 3.23 - 3.12 (m, 1H), 3.10 - 2.92 (m, 4H), 2.89 - 2.73 (m, 3H), 2.57 (s, 3H), 2.27 - 1.94 (m, 4H), 1.92 - 1.72 (m, 4H) | ES-LCMS m/z 734.3 $[M + H]^+$. |
| 381 | 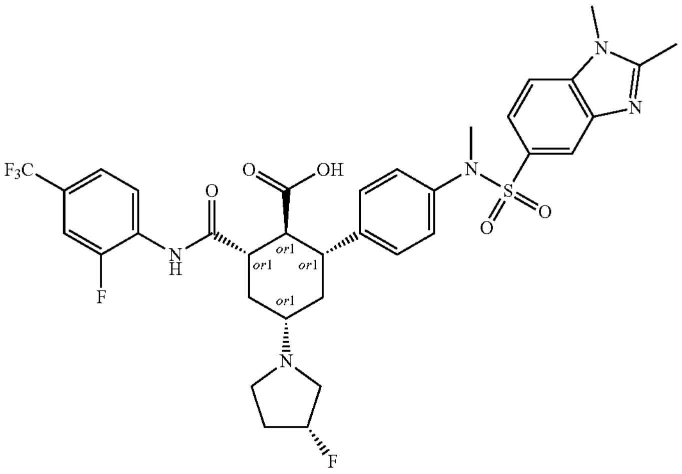 [SMILES: Cc1nc2cc(S(=O)(=O)N(C)c3ccc([C@@H]4C[C@H](N5CC[C@@H](F)C5)C[C@H](C(=O)Nc5ccc(C(F)(F)F)cc5F)[C@H]4C(=O)O)cc3)ccc2n1C] ISOMER 1 rel-(1R*,2R*,4R*,6S*)-2-((2-fluoro-4-(trifluoromethyl)phenyl)carbamoyl)-4-((R)-3-fluoropyrrolidin-1-yl)-6-(4-((N,1,2-trimethyl-1H-benzo[d]imidazole)-5-sulfonamido)phenyl)cyclohexane-1-carboxylic acid ISOMER 1 | $^1H$ NMR (400 MHz, DMSO-$d_6$) δ 12.11 (br s, 1H), 10.14 (s, 1H), 8.24 (t, J = 8.3 Hz, 1H), 7.73 (dd, J = 11.3, 1.8 Hz, 1H), 7.63 (d, J = 8.5 Hz, 1H), 7.56 (d, J = 8.0 Hz, 1H), 7.49 (d, J = 1.5 Hz, 1H), 7.28 - 7.20 (m, 3H), 6.97 (d, J = 9.0 Hz, 2H), 5.26 - 5.10 (m, 1H), 3.78 (s, 3H), 3.12 - 3.01 (m, 4H), 2.93 - 2.81 (m, 2H), 2.79 - 2.69 (m, 3H), 2.56 (s, 3H), 2.25 (d, J = 11.0 Hz, 1H), 2.14 - 1.94 (m, 3H), 1.93 - 1.75 (m, 2H), 1.65 - 1.53 (m, 1H), 1.52 - 1.39 (m, 1H) | ES-LCMS m/z 734.1 $[M + H]^+$. |

-continued

| Ex | Structure/Name | $^1$H NMR | LCMS |
|---|---|---|---|
| 382 | 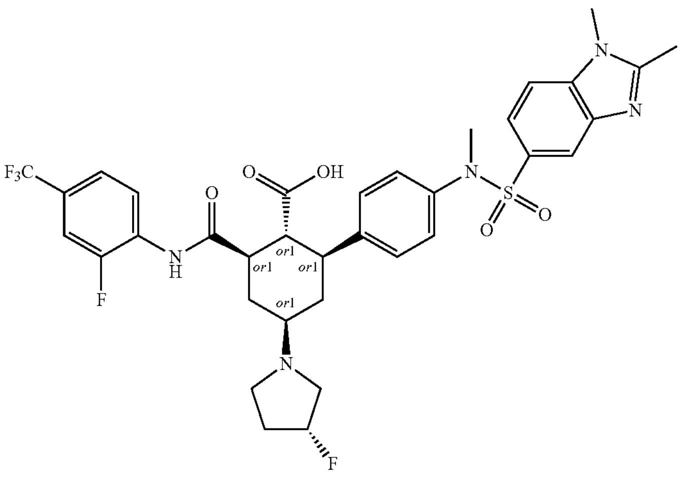 [SMILES: Cc1nc2cc(S(=O)(=O)N(C)c3ccc([C@H]4C[C@@H](N5CC[C@@H](F)C5)C[C@@H](C(=O)Nc5ccc(C(F)(F)F)cc5F)[C@@H]4C(=O)O)cc3)ccc2n1C] ISOMER 2 rel-(1R*,2R*,4R*,6S*)-2-((2-fluoro-4-(trifluoromethyl)phenyl)carbamoyl)-4-((R)-3-fluoropyrrolidin-1-yl)-6-(4-((N,1,2-trimethyl-1H-benzo[d]imidazole)-5-sulfonamido)phenyl)cyclohexane-1-carboxylic acid ISOMER 2 | $^1$H NMR (400 MHz, DMSO-$d_6$) δ 12.11 (br s, 1H), 10.14 (s, 1H), 8.24 (t, J = 8.0 Hz, 1H), 7.73 (dd, J = 11.3, 1.3 Hz, 1H), 7.63 (d, J = 8.5 Hz, 1H), 7.56 (d, J = 8.0 Hz, 1H), 7.50 (d, J = 1.5 Hz, 1H), 7.28 - 7.18 (m, 3H), 6.96 (d, J = 8.5 Hz, 2H), 5.27 - 5.07 (m, 1H), 3.78 (s, 3H), 3.13 - 3.02 (m, 4H), 2.96 - 2.72 (m, 5H), 2.56 (s, 3H), 2.46 - 2.37 (m, 2H), 2.25 (d, J = 12.0 Hz, 1H), 2.14 - 1.75 (m, 3H), 1.65 - 1.53 (m, 1H), 1.46 (q, J = 12.3 Hz, 1H) | ES-LCMS m/z 734.1 [M + H]$^+$. |
| 383 | 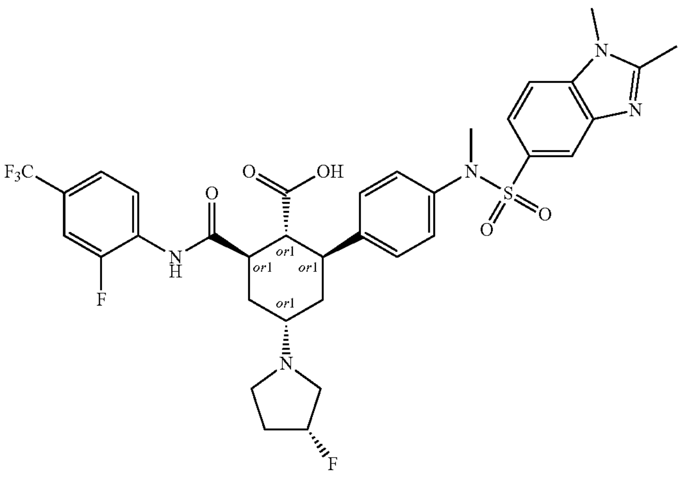 [SMILES: Cc1nc2cc(S(=O)(=O)N(C)c3ccc([C@H]4C[C@H](N5CC[C@@H](F)C5)C[C@@H](C(=O)Nc5ccc(C(F)(F)F)cc5F)[C@@H]4C(=O)O)cc3)ccc2n1C] ISOMER 1 rel-(1R*,2R*,4S*,6S*)-2-((2-fluoro-4-(trifluoromethyl)phenyl)carbamoyl)-4-((R)-3-fluoropyrrolidin-1-yl)-6-(4-((N,1,2-trimethyl-1H-benzo[d]imidazole)-5-sulfonamido)phenyl)cyclohexane-1-carboxylic acid ISOMER 1 | $^1$H NMR (400 MHz, DMSO-$d_6$) δ 12.08 (br s, 1H), 10.16 (s, 1H), 8.10 (t, J = 8.0 Hz, 1H), 7.74 - 7.67 (m, 1H), 7.63 (d, J = 8.5 Hz, 1H), 7.59 - 7.51 (m, 2H), 7.24 (dd, J = 8.5, 1.5 Hz, 1H), 7.18 (d, J = 8.5 Hz, 2H), 6.97 (d, J = 8.5 Hz, 2H), 5.36 - 5.18 (m, 1H), 3.78 (s, 3H), 3.45 - 3.35 (m, 2H), 3.15 (td, J = 11.8, 3.5 Hz, 1H), 3.09 - 2.96 (m, 4H), 2.91 - 2.74 (m, 3H), 2.56 (s, 3H), 2.37 (d, J = 6.5 Hz, 1H), 2.30 - 2.13 (m, 1H), 2.10 - 2.01 (m, 2H), 1.95 - 1.71 (m, 3H) | ES-LCMS m/z 734.2 [M + H]$^+$. |

-continued

| Ex | Structure/Name | $^1$H NMR | LCMS |
| --- | --- | --- | --- |
| 384 | 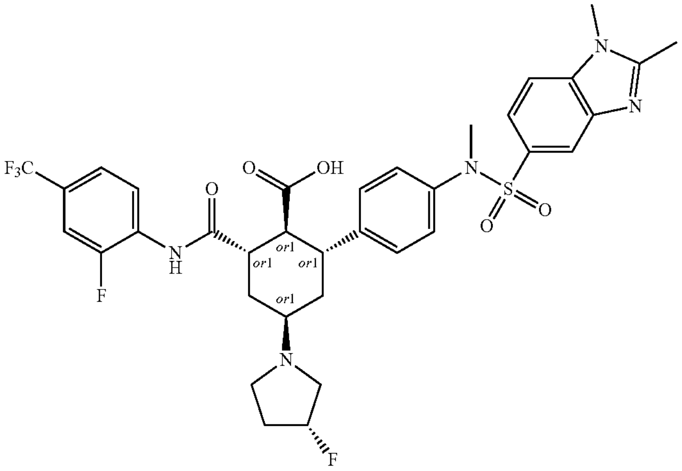 [SMILES: Cc1nc2cc(S(=O)(=O)N(C)c3ccc([C@@H]4C[C@@H](N5CC[C@@H](F)C5)C[C@H](C(=O)Nc5ccc(C(F)(F)F)cc5F)[C@H]4C(=O)O)cc3)ccc2n1C] ISOMER 2 rel-(1R*,2R*,4S*,6S*)-2-((2-fluoro-4-(trifluoromethyl)phenyl)carbamoyl)-4-((R)-3-fluoropyrrolidin-1-yl)-6-(4-((N,1,2-trimethyl-1H-benzo[d]imidazole)-5-sulfonamido)phenyl)cyclohexane-1-carboxylic acid ISOMER 2 | $^1$H NMR (400 MHz, DMSO-$d_6$) δ 12.09 (br s, 1H), 10.18 (s, 1H), 8.05 (t, J = 7.5 Hz, 1H), 7.75 - 7.68 (m, 1H), 7.63 (d, J = 9.0 Hz, 1H), 7.59 - 7.51 (m, 2H), 7.25 (dd, J = 8.5, 1.5 Hz, 1H), 7.20 (d, J = 8.5 Hz, 2H), 6.97 (d, J = 8.5 Hz, 2H), 5.38 - 5.19 (m, 1H), 3.78 (s, 3H), 3.36 (br s, 2H), 3.20 - 3.11 (m, 1H), 3.05 (s, 3H), 2.99 - 2.89 (m, 1H), 2.87 - 2.72 (m, 4H), 2.56 (s, 3H), 2.26 - 1.95 (m, 3H), 1.90 - 1.72 (m, 3H) | ES-LCMS m/z 734.2 [M + H]$^+$. |

Example 385 and Example 386 rel-(1R,2R,6S)-2-((2-fluoro-4-(trifluoromethyl)phenyl) carbamoyl)-6-(2-methyl-4-((N,1,2-trimethyl-1H-benzo[d]imidazole)-5-sulfonamido)phenyl)cyclohexane-1-carboxylic acid ISOMER 1 and rel-(1R,2R,6S)-2-((2-fluoro-4-(trifluoromethyl)phenyl) carbamoyl)-6-(2-methyl-4-((N,1,2-trimethyl-1H-benzo[d]imidazole)-5-sulfonamido)phenyl) cyclohexane-1-carboxylic acid ISOMER 2

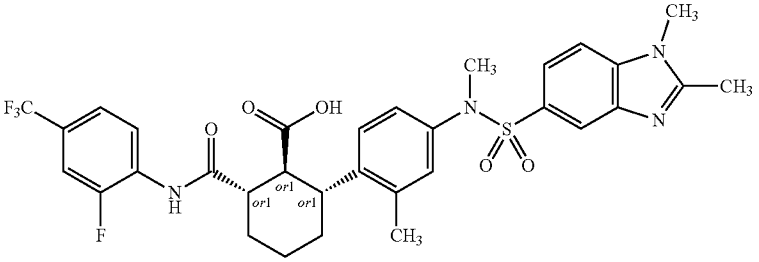

ISOMER 1

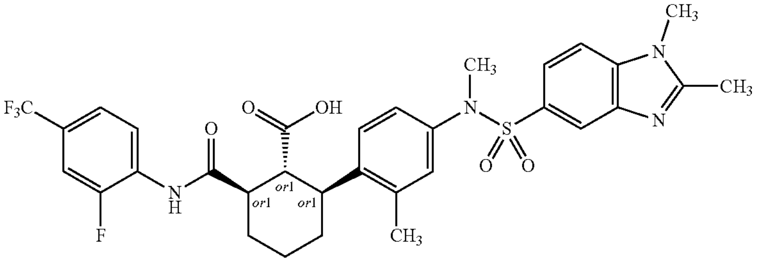

ISOMER 2

In a microwave vial, to a suspension of rac-(1R,2S,6R)-2-(2-bromo-4-((N,1,2-trimethyl-1H-benzo[d]imidazole)-5-sulfonamido)phenyl)-6-((2-fluoro-4-(trifluoromethyl)phenyl)carbamoyl)cyclohexane-1-carboxylic acid Intermediate 124 (60.00 mg, 82.70 μmol) in dioxane (3 mL) was added cesium carbonate (40.42 mg, 124.0 μmol) and 2,4,6-trimethyl-1,3,5,2,4,6-trioxatriborinane (83.1 mg, 0.0928 mL, 25% wt, 165 μmol). The suspension was purged with $N_2$ twice, and [1,1'-bis(diphenylphosphino)ferrocene]dichloropalladium(II)-DCM complex (13.51 mg, 16.54 μmol) was added. The reaction vessel was sealed and heated at 120° C. in a Biotage Initiator for 2 h. The mixture was concentrated and subjected to reverse phase purification (MeCN/$H_2O$, 0.1% ammonium bicarbonate modifier, 0-100%) to afford rac-(1R,2R,6S)-2-((2-fluoro-4-(trifluoromethyl)phenyl)carbamoyl)-6-(2-methyl-4-((N,1,2-trimethyl-1H-benzo[d]imidazole)-5-sulfonamido)phenyl)cyclohexane-1-carboxylic acid (0.40 g, 56 μmol, 67% yield) as an off-white solid. This material was subjected to separation by Chiral-Prep-SFC (Column: YMC Cellulose-SB [250×20] mm, 5 μm; Mobile Phase: 70:30 $CO_2$: 0.5% Isopropylamine in MeOH) to afford:

Example 385, the first-eluting compound: rel-(1R,2R,6S)-2-((2-fluoro-4-(trifluoromethyl)phenyl)carbamoyl)-6-(2-methyl-4-((N,1,2-trimethyl-1H-benzo[d]imidazole)-5-sulfonamido)phenyl)cyclohexane-1-carboxylic acid ISOMER 1 (15 mg, 22 μmol, 32% yield) as a white solid. $^1H$ NMR (400 MHz, DMSO-$d_6$) δ 11.98 (br s, 1H), 10.08 (br s, 1H), 8.21 (t, J=8.3 Hz, 1H), 7.71 (dd, J=11.0, 2.0 Hz, 1H), 7.65-7.58 (m, 2H), 7.55 (d, J=8.5 Hz, 1H), 7.32-7.21 (m, 2H), 6.88-6.78 (m, 2H), 3.78 (s, 3H), 3.11-2.91 (m, 5H), 2.90-2.78 (m, 1H), 2.57 (s, 3H), 2.20 (s, 3H), 2.06-1.96 (m, 1H), 1.91-1.84 (m, 1H), 1.71 (d, J=9.0 Hz, 1H), 1.62-1.40 (m, 3H). ES-LCMS m/z 661.2 $[M+H]^+$;

Example 386, the second-eluting compound: rel-(1R,2R,6S)-2-((2-fluoro-4-(trifluoromethyl)phenyl)carbamoyl)-6-(2-methyl-4-((N,1,2-trimethyl-1H-benzo[d]imidazole)-5-sulfonamido)phenyl)cyclohexane-1-carboxylic acid ISOMER 2 (16 mg, 0.024 mmol, 34% yield) as a white solid. $^1H$ NMR (400 MHz, DMSO-$d_6$) δ 11.98 (br s, 1H), 10.07 (s, 1H), 8.21 (t, J=8.0 Hz, 1H), 7.71 (dd, J=11.0, 2.0 Hz, 1H), 7.65-7.59 (m, 2H), 7.55 (dd, J=8.5, 1.0 Hz, 1H), 7.33-7.20 (m, 2H), 6.90-6.77 (m, 2H), 3.78 (s, 3H), 3.10-2.94 (m, 5H), 2.89-2.77 (m, 1H), 2.57 (s, 3H), 2.20 (s, 3H), 2.06-1.97 (m, 1H), 1.88 (d, J=6.0 Hz, 1H), 1.71 (d, J=10.0 Hz, 1H), 1.64-1.41 (in, 3H). ES-LCMS m/z 661.2 $[M+H]^+$.

The following compounds were synthesized in an analogous manner to the preparation described above (Example 81), using the relevant sulfonyl chloride and arylamine precursors, followed by chiral separation.

| Ex | Structure/Name | $^1H$ NMR | LCMS |
|---|---|---|---|
| 387 | 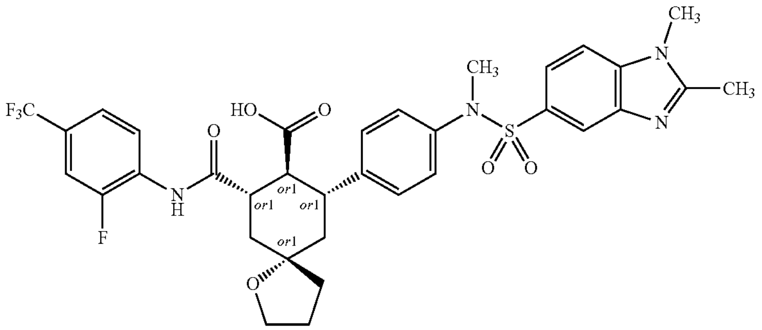 [SMILES: Cc1nc2cc(S(=O)(=O)N(C)c3ccc([C@@H]4C[C@@]5(CCCO5)C[C@H](C(=O)Nc5ccc(C(F)(F)F)cc5F)[C@H]4C(=O)O)cc3)ccc2n1C] ISOMER 1 rel-(5R,7R,8R,9S)-7-((2-fluoro-4-(trifluoromethyl)phenyl)carbamoyl)-9-(4-((N,1,2-trimethyl-1H-benzo[d]imidazole)-5-sulfonamido)phenyl)-1-oxaspiro[4.5]decane-8-carboxylic acid, ISOMER 1 | $^1H$ NMR (400 MHz, DMSO-$d_6$) δ 12.01 (br s, 1H), 10.19 (s, 1H), 8.06 (t, J = 8.0 Hz, 2H), 7.73 - 7.67 (m, 1H), 7.63 (d, J = 8.5 Hz, 1H), 7.55 (d, J = 9.0 Hz, 1H), 7.50 (d, J = 1.5 Hz, 1H), 7.25 (dd, J = 8.5, 2.0 Hz, 1H), 7.18 (d, J = 8.5 Hz, 2H), 6.96 (d, J = 8.5 Hz, 2H), 3.89 - 3.75 (m, 4H), 3.11 - 2.99 (m, 4H), 2.77 (t, J = 11.5 Hz, 2H), 2.56 (s, 3H), 1.97 - 1.80 (m, 4H), 1.74 - 1.62 (m, 4H) | ES-LCMS m/z 703.2 [M + H]+. |
| 388 | 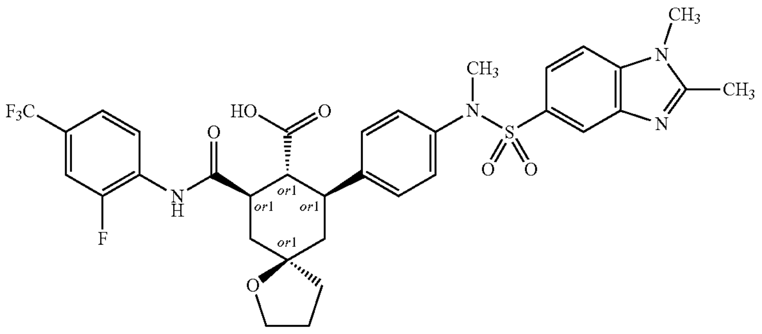 [SMILES: Cc1nc2cc(S(=O)(=O)N(C)c3ccc([C@H]4C[C@]5(CCCO5)C[C@@H](C(=O)Nc5ccc(C(F)(F)F)cc5F)[C@@H]4C(=O)O)cc3)ccc2n1C] ISOMER 2 rel-(5R,7R,8R,9S)-7-((2-fluoro-4-(trifluoromethyl)phenyl)carbamoyl)-9-(4-((N,1,2-trimethyl-1H-benzo[d]imidazole)-5-sulfonamido)phenyl)-1-oxaspiro[4.5]decane-8-carboxylic acid, ISOMER 2 | $^1H$ NMR (400 MHz, DMSO-$d_6$) δ 10.29 (br s, 1H), 8.14 - 8.06 (m, 1H), 7.69 (d, J = 11.0 Hz, 1H), 7.64 (d, J = 8.5 Hz, 1H), 7.57 - 7.50 (m, 2H), 7.25 (d, J = 7.5 Hz, 1H), 7.18 (d, J = 8.0 Hz, 2H), 6.95 (d, J = 8.5 Hz, 2H), 3.82 - 3.76 (m, 4H), 3.25 - 3.18 (m, 2H), 3.10 - 3.00 (m, 4H), 2.72 (d, J = 11.0 Hz, 1H), 2.56 (s, 3H), 2.46 - 2.40 (m, 1H), 1.96 - 1.82 (m, 3H), 1.74 - 1.61 (m, 5H). | ES-LCMS m/z 703.2 [M + H]+. |

Example 389 rel-(3aR,4S,5S,6S,7aR)-4-((2-fluoro-4-(trifluoromethyl)phenyl)carbamoyl)-6-(4-((N,1,2-trimethyl-1H-benzo[d]imidazole)-5-sulfonamido)phenyl)octahydroisobenzofuran-5-carboxylic acid ISOMER 1

ISOMER 1

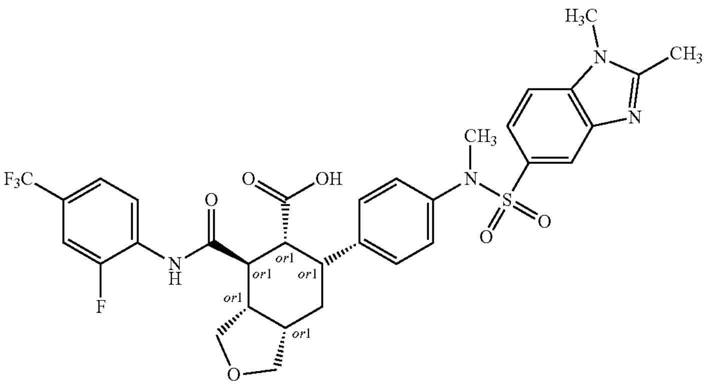 [SMILES: Cc1nc2cc(S(=O)(=O)N(C)c3ccc([C@@H]4C[C@@H]5COC[C@@H]5[C@@H](C(=O)Nc5ccc(C(F)(F)F)cc5F)[C@@H]4C(=O)O)cc3)ccc2n1C]

To a mixture of rel-methyl (3aR,4S,5S,6S,7aR)-4-((2-fluoro-4-(trifluoromethyl)phenyl)carbamoyl)-6-(4-((N,1,2-trimethyl-1H-benzo[d]imidazole)-5-sulfonamido)phenyl) octahydroisobenzofuran-5-carboxylate ISOMER 1 Intermediate 129 (250.0 mg, 355.8 μmol) in THF (3 mL) and water (3 mL) at 0° C. was added lithium hydroxide monohydrate (59.71 mg, 1.423 mmol). The reaction was stirred at 100° C. for 2 h, concentrated and subjected to reverse phase purification (MeCN in $H_2O$, 0.1% ammonium bicarbonate modifier, 0-100% gradient) to afford rel-(3aR,4S,5S,6S,7aR)-4-((2-fluoro-4-(trifluoromethyl)phenyl)carbamoyl)-6-(4-((N,1,2-trimethyl-1H-benzo[d]imidazole)-5-sulfonamido)phenyl)octahydroisobenzofuran-5-carboxylic acid ISOMER 1 (45 mg, 65 μmol, 18% yield) as a white solid. $^1H$ NMR (400 MHz, DMSO-$d_6$) δ 12.24 (br s, 1H), 10.15 (br s, 1H), 8.26 (t, J=8.0 Hz, 1H), 7.71 (dd, J=11.0, 1.5 Hz, 1H), 7.63 (d, J=8.5 Hz, 1H), 7.60-7.53 (m, 2H), 7.29-7.18 (m, 3H), 6.96 (d, J=8.5 Hz, 2H), 3.86 (t, J=8.0 Hz, 1H), 3.81-3.73 (m, 4H), 3.66 (t, J=8.3 Hz, 1H), 3.51-3.35 (m, 3H), 3.13-3.01 (m, 4H), 2.60 (d, J=4.5 Hz, 1H), 2.55 (s, 3H), 2.46-2.35 (m, 1H), 1.79-1.63 (m, 1H), 1.43 (q, J=12.7 Hz, 1H). ES-LCMS m/z 689.2 $[M+H]^+$.

The following compound was synthesized in an analogous manner to the preparation described above (Example 389), using the relevant ester precursor.

| Ex | Structure/Name | $^1H$ NMR | LCMS |
| --- | --- | --- | --- |
| 390 | 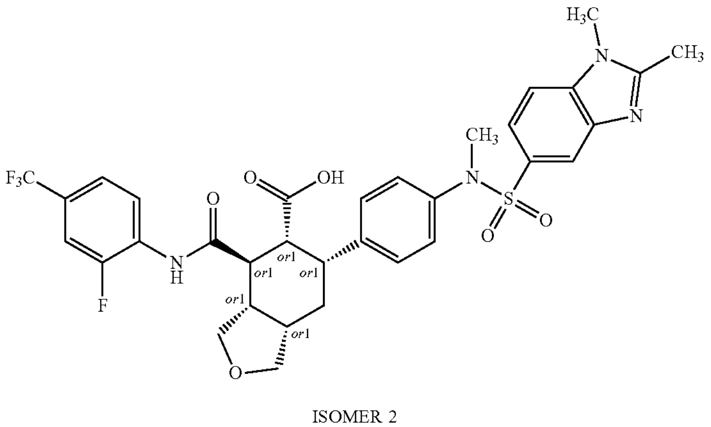 ISOMER 2 rel-(3aR,4S,5S,6S,7aR)-4-((2-fluoro-4-(trifluoromethyl)phenyl)carbamoyl)-6-(4-((N,1,2-trimethyl-1H-benzo[d]imidazole)-5-sulfonamido)phenyl)octahydroisobenzofuran-5-carboxylic acid ISOMER 2 | $^1H$ NMR (400 MHz, DMSO-$d_6$) δ 12.23 (br s, 1H), 10.06 (s, 1H), 8.25 (t, J = 8.3 Hz, 1H), 7.71 (dd, J = 11.0, 2.0 Hz, 1H), 7.64 (d, J = 8.5 Hz, 1H), 7.60 - 7.54 (m, 2H), 7.26 (dd, J = 8.5, 2.0 Hz, 1H), 7.21 (d, J = 8.5 Hz, 2H), 6.96 (d, J = 8.5 Hz, 2H), 3.91 - 3.84 (m, 1H), 3.81 - 3.74 (m, 4H), 3.66 (t, J = 8.3 Hz, 1H), 3.52 - 3.37 (m, 4H), 3.13 - 3.01 (m, 4H), 2.64 - 2.58 (m, 1H), 2.56 (s, 3H), 1.72 (dt, J = 8.1, 4.2 Hz, 1H), 1.50 - 1.35 (m, 1H) | ES-LCMS m/z 689.2 [M + H]+. |

-

The following compounds were synthesized in an analogous manner to the preparation described above (Example 307) from the appropriate methyl ester:

| Ex | Structure/Name | $^1H$ NMR | LCMS |
|---|---|---|---|
| 391 | 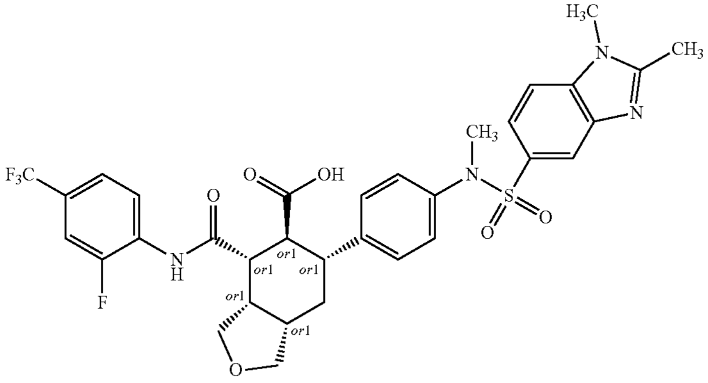 [SMILES: Cc1nc2cc(S(=O)(=O)N(C)c3ccc([C@@H]4C[C@@H]5COC[C@@H]5[C@H](C(=O)Nc5ccc(C(F)(F)F)cc5F)[C@H]4C(=O)O)cc3)ccc2n1C]<br>ISOMER 1<br>rel-(3aR,4R,5R,6S,7aR)-4-((2-fluoro-4-(trifluoromethyl)phenyl)carbamoyl)-6-(4-((N,1,2-trimethyl-1H-benzo[d]imidazole)-5-sulfonamido)phenyl)octahydroisobenzofuran-5-carboxylic acid ISOMER 1 | $^1H$ NMR (400 MHz, DMSO-$d_6$) δ 12.16 (br s, 1H), 10.22 (s, 1H), 8.14 (t, J = 8.0 Hz, 1H), 7.74 (dd, J = 11.0, 1.5 Hz, 1H), 7.63 (d, J = 8.5 Hz, 1H), 7.56 (d, J = 10.0 Hz, 1H), 7.49 (d, J = 1.5 Hz, 1H), 7.29 - 7.21 (m, 3H), 6.97 (d, J = 8.5 Hz, 2H), 3.90 (dd, J = 11.0, 9.0 Hz, 1H), 3.82 - 3.73 (m, 4H), 3.63 - 3.49 (m, 3H), 3.06 (s, 3H), 2.95 (t, J = 11.5 Hz, 1H), 2.89 - 2.79 (m, 1H), 2.77 - 2.70 (m, 1H), 2.57 (s, 3H), 2.43 - 2.35 (m, 1H), 1.73 - 1.61 (m, 2H) | ES-LCMS m/z 689.2 $[M + H]^+$. |
| 392 | 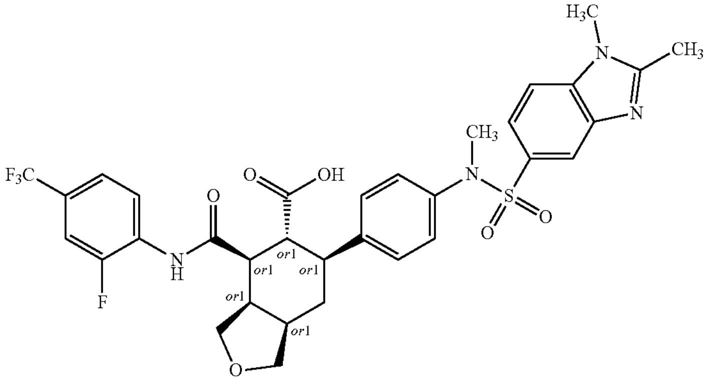 [SMILES: Cc1nc2cc(S(=O)(=O)N(C)c3ccc([C@H]4C[C@H]5COC[C@H]5[C@@H](C(=O)Nc5ccc(C(F)(F)F)cc5F)[C@@H]4C(=O)O)cc3)ccc2n1C]<br>ISOMER 2<br>rel-(3aR,4R,5R,6S,7aR)-4-((2-fluoro-4-(trifluoromethyl)phenyl)carbamoyl)-6-(4-((N,1,2-trimethyl-1H-benzo[d]imidazole)-5-sulfonamido)phenyl)octahydroisobenzofuran-5-carboxylic acid ISOMER 2 | $^1H$ NMR (400 MHz, DMSO-$d_6$) δ 12.15 (br s, 1H), 10.21 (s, 1H), 8.13 (t, J = 8.0 Hz, 1H), 7.73 (dd, J = 11.0, 1.5 Hz, 1H), 7.63 (d, J = 8.5 Hz, 1H), 7.55 (d, J = 8.5 Hz, 1H), 7.48 (d, J = 1.5 Hz, 1H), 7.29 - 7.20 (m, 3H), 7.00 - 6.93 (m, 2H), 3.89 (dd, J= 10.8, 8.8 Hz, 1H), 3.81 - 3.73 (m, 4H), 3.63 - 3.48 (m, 3H), 3.05 (s, 3H), 2.94 (t, J = 11.5 Hz, 1H), 2.88 - 2.78 (m, 1H), 2.75 - 2.69 (m, 1H), 2.56 (s, 3H), 2.39 (dd, J = 11.0, 5.5 Hz, 1H), 1.72 - 1.60 (m, 2H) | ES-LCMS m/z 689.2 $[M + H]^+$. |

The following compounds were synthesized in an analogous manner to the preparation described above (Example 389) from the appropriate methyl ester:

| Ex | Structure/Name | $^1H$ NMR | LCMS |
|---|---|---|---|
| 393 | 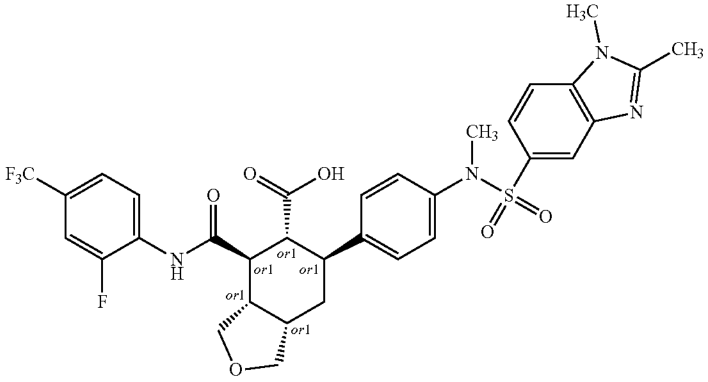 [SMILES: Cc1nc2cc(S(=O)(=O)N(C)c3ccc([C@H]4C[C@@H]5COC[C@@H]5[C@@H](C(=O)Nc5ccc(C(F)(F)F)cc5F)[C@@H]4C(=O)O)cc3)ccc2n1C] | $^1H$ NMR (400 MHz, DMSO-$d_6$) δ 12.43 (br s, 1H), 9.26 (br s, 1H), 7.83 (t, J = 8.0 Hz, 1H), 7.62 - 7.56 (m, 2H), 7.49 - 7.41 (m, 2H), 7.19 - 7.10 (m, 3H), 6.90 (d, J = 8.5 Hz, 2H), 4.39 (t, J = 8.8 Hz, 1H), 3.81 - 3.70 (m, 5H), 3.57 (d, J = 8.0 Hz, 1H), 3.54 - 3.50 (m, 1H), 3.41 (t, J = 6.3 Hz, 1H), 3.12 - 3.05 (m, 1H), 2.97 (s, 3H), 2.78 - 2.69 (m, 1H), 2.56 (s, 3H), 2.37 - 2.25 (m, 2H), 1.51 (d, J = 8.0 Hz, 1H) | ES-LCMS m/z 689.2 $[M + H]^+$. |

-continued

| Ex | Structure/Name | $^1$H NMR | LCMS |
|---|---|---|---|
| | ISOMER 1 rel-(3aR,4S,5S,6R,7aR)-4-((2-fluoro-4-(trifluoromethyl)phenyl) carbamoyl)-6-(4-((N,1,2-trimethyl-1H-benzo[d]imidazole)-5-sulfonamido)phenyl)octahydroisobenzofuran-5-carboxylic acid ISOMER 1 | | |
| 394 | 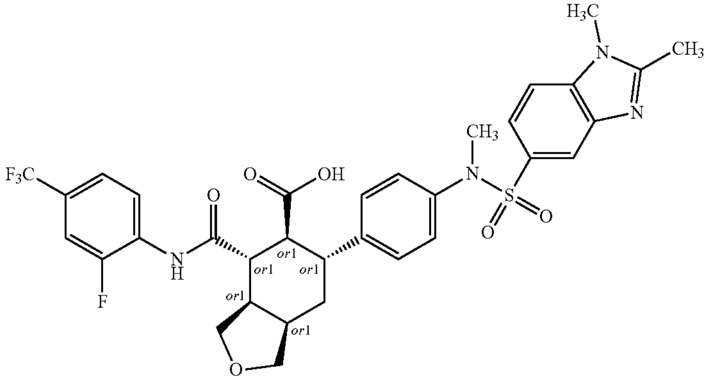 [SMILES: Cc1nc2cc(S(=O)(=O)N(C)c3ccc([C@@H]4C[C@H]5COC[C@H]5[C@H](C(=O)Nc5ccc(C(F)(F)F)cc5F)[C@H]4C(=O)O)cc3)ccc2n1C] | $^1$H NMR (400 MHz, DMSO-$d_6$) δ 12.42 (br s, 1H), 9.21 (s, 1H), 7.82 (t, J = 8.0 Hz, 1H), 7.62 - 7.56 (m, 2H), 7.49 - 7.41 (m, 2H), 7.19 - 7.11 (m, 3H), 6.90 (d, J = 8.5 Hz, 2H), 4.41 (dd, J = 10.0, 8.0 Hz, 1H), 3.80 - 3.70 (m, 5H), 3.57 (d, J = 8.0 Hz, 1H), 3.52 (t, J = 5.8 Hz, 1H), 3.41 (t, J = 6.5 Hz, 1H), 3.13 - 3.04 (m, 1H), 2.97 (s, 3H), 2.77 - 2.69 (m, 1H), 2.56 (s, 3H), 2.35 - 2.26 (m, 2H), 1.56 - 1.47 (m, 1H) | ES-LCMS m/z 689.2 $[M + H]^+$. |
| | ISOMER 2 rel-(3aR,4S,5S,6R,7aR)-4-((2-fluoro-4-(trifluoromethyl)phenyl)carbamoyl)-6-(4-((N,1,2-trimethyl-1H-benzo[d]imidazole)-5-sulfonamido)phenyl)octahydroisobenzofuran-5-carboxylic acid ISOMER 2 | | |

Example 395 rel-(1R,2R,4R,6S)-2-((2-fluoro-4-(trifluoromethyl)phenyl)carbamoyl)-4-((methyl sulfonyl)methyl)-6-(4-((N,1,2-trimethyl-1H-benzo[d]imidazole)-5-sulfonamido)phenyl)cyclohexane-1-carboxylic acid

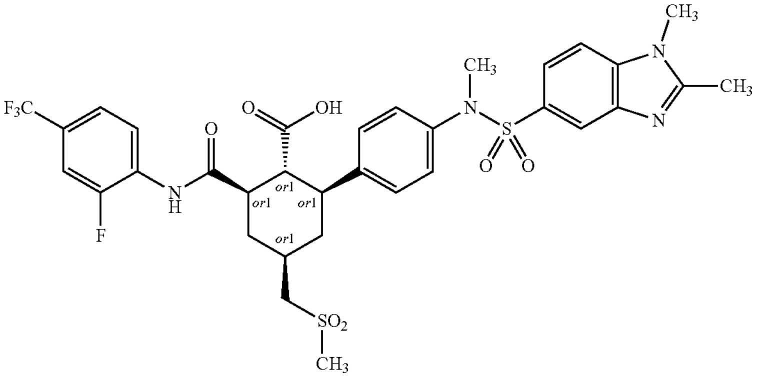 [SMILES: Cc1nc2cc(S(=O)(=O)N(C)c3ccc([C@H]4C[C@@H](CS(C)(=O)=O)C[C@@H](C(=O)Nc5ccc(C(F)(F)F)cc5F)[C@@H]4C(=O)O)cc3)ccc2n1C]

To a mixture of rac-benzyl (1R,2R,6S,E)-2-((2-fluoro-4-(trifluoromethyl)phenyl)carbamoyl)-4-((methylsulfonyl)methylene)-6-(4-((N,1,2-trimethyl-1H-benzo[d]imidazole)-5-sulfonamido)phenyl)cyclohexane-1-carboxylate Intermediate 135 (320.0 mg, 387.0 μmol) in THF (10 mL) was added palladium on carbon (82.37 mg, 10% wt, 77.40 μmol). The reaction was hydrogenated under tiny clave at 5 kg pressure for 32 hours, filtered through Celite (washing with DCM), concentrated and subjected to reverse phase purification (MeCN in $H_2O$, 0.1% formic acid modifier, 0-100% gradient) to afford rac-(1R,2R,6S)-2-((2-fluoro-4-(trifluoromethyl)phenyl)carbamoyl)-4-((methylsulfonyl)methyl)-6-(4-((N,1,2-trimethyl-1H-benzo[d]imidazole)-5-sulfonamido)phenyl)cyclohexane-1-carboxylic acid (0.12 g, 0.15 mmol, 39% yield) as a white solid. $^1$H NMR (400 MHz, DMSO-$d_6$) δ 12.13 (br s, 1H), 10.19 (s, 1H), 8.22 (t, J=8.3 Hz, 1H), 7.73 (d, J=11.0 Hz, 1H), 7.65 (d, J=8.5 Hz, 1H), 7.60-7.51 (m, 2H), 7.26 (dd, J=8.5, 1.5 Hz, 1H), 7.20 (d, J=8.5 Hz, 2H), 6.98 (d, J=8.5 Hz, 2H), 3.79 (s, 3H), 3.19-3.13 (m, 2H), 3.06 (s, 3H), 3.00 (s, 3H), 2.81-2.74 (m, 2H), 2.58 (s, 3H), 2.24 (d, J=11.5 Hz, 2H), 1.99 (d, J=11.0 Hz, 1H), 1.57-1.41 (m, 3H). ES-LCMS m/z 737.0 [M−H]$^-$.

The racemic compound was separated by Chiral-Prep-SFC (Column: Chiralpak-IA (250×20) mm, 5 μm; Mobile Phase $CO_2$: 0.5% IPAm in IPA (50:50)) to afford a mixture of three enantiomers (this mixture was not further analyzed) followed by the fourth-eluting peak rel-(1R,2R,4R,6S)-2-((2-fluoro-4-(trifluoromethyl)phenyl)carbamoyl)-4-((methylsulfonyl)methyl)-6-(4-((N,1,2-trimethyl-1H-benzo[d]imidazole)-5-sulfonamido)phenyl)cyclohexane-1-carboxylic acid (36 mg, 49 μmol, 16% yield) as a white solid. $^1$H NMR (400 MHz, DMSO-$d_6$) δ 12.03 (br s, 1H), 10.19 (s, 1H), 8.22 (t, J=8.3 Hz, 1H), 7.78-7.70 (m, 2H), 7.65 (s, 1H), 7.56 (d, J=9.0 Hz, 1H), 7.32 (dd, J=8.5, 1.5 Hz, 1H), 7.25-7.17 (m, 2H), 6.99 (d, J=8.5 Hz, 2H), 3.83 (s, 3H), 3.15 (dd, J=14.8, 7.8 Hz, 3H), 3.08 (s, 3H), 3.00 (s, 3H), 2.85-2.75 (m, 2H), 2.64 (s, 3H), 2.23 (d, J=12.5 Hz, 2H), 1.99 (d, J=12.0 Hz, 1H), 1.58-1.41 (m, 2H). ES-LCMS m/z 739.2 [M+H]$^+$. Relative Stereochemistry was assigned by NMR structure elucidation, and absolute stereochemistry was assigned by known SAR correlation.

The following compound was synthesized in an analogous manner to the preparation described above (Example 72) using the relevant arylamine precursor.

| Ex | Structure/Name | $^1$H NMR | LCMS |
|---|---|---|---|
| 396 | 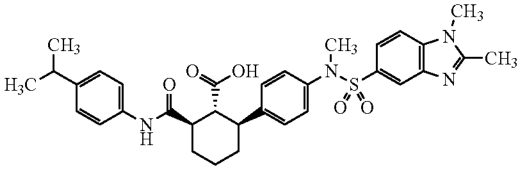 [SMILES: Cc1nc2cc(S(=O)(=O)N(C)c3ccc([C@H]4CCC[C@@H](C(=O)Nc5ccc(C(C)C)cc5)[C@@H]4C(=O)O)cc3)ccc2n1C] (1R,2R,6S)-2-((4-isopropylphenyl)carbamoyl)-6-(4-((N,1,2-trimethyl-1H-benzo[d]imidazole)-5-sulfonamido)phenyl)cyclohexane-1-carboxylic acid | $^1$H NMR (400 MHz, DMSO-$d_6$) δ 11.97 (br s, 1H), 9.85 (s, 1H), 7.62 (d, J = 8.5 Hz, 1H), 7.52 – 7.46 (m, 3H), 7.24 (dd, J = 8.5, 2.0 Hz, 1H), 7.18 (d, J = 8.5 Hz, 2H), 7.14 (d, J = 8.5 Hz, 2H), 6.96 (d, J = 8.5 Hz, 2H), 3.78 (s, 3H), 3.05 (s, 3H), 2.82 (quin, J = 6.9 Hz, 1H), 2.77 – 2.66 (m, 3H), 2.56 (s, 3H), 2.00 – 1.84 (m, 2H), 1.79 – 1.71 (m, 1H), 1.65 – 1.43 (m, 3H), 1.16 (d, J = 7.0 Hz, 6H) | ES-LCMS m/z 603.3 [M + H]$^+$. |

The following compounds were synthesized in an analogous manner to the preparation described above (Example 251) using the relevant alkylamine precursor and chiral purification.

| Ex | Structure/Name | $^1$H NMR | LCMS |
|---|---|---|---|
| 397 | 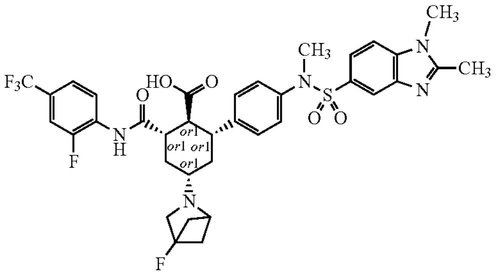 [SMILES: Cc1nc2cc(S(=O)(=O)N(C)c3ccc([C@@H]4C[C@H](N5CC6(F)CC5C6)C[C@H](C(=O)Nc5ccc(C(F)(F)F)cc5F)[C@H]4C(=O)O)cc3)ccc2n1C] rel-(1R,2R,4R,6S)-2-((2-fluoro-4-(trifluoromethyl)phenyl)carbamoyl)-4-(4-fluoro-2-azabicyclo[2.1.1]hexan-2-yl)-6-(4-((N,1,2-trimethyl-1H-benzo[d]imidazole)-5-sulfonamido)phenyl)cyclohexane-1-carboxylic acid | $^1$H NMR (400 MHz, DMSO-$d_6$) δ 10.26 (br s, 1H), 8.26 (t, J = 8.3 Hz, 1H), 7.76 – 7.70 (m, 1H), 7.63 (d, J = 8.5 Hz, 1H), 7.55 (d, J = 9.5 Hz, 1H), 7.26 (dd, J = 8.5, 1.5 Hz, 1H), 7.20 (d, J = 8.5 Hz, 2H), 6.95 (d, J = 8.5 Hz, 2H), 3.78 (s, 3H), 3.58 – 3.50 (m, 1H), 3.13 (t, J = 6.5 Hz, 1H), 3.07 – 2.94 (m, 4H), 2.79 – 2.67 (m, 4H), 2.56 (s, 4H), 2.23 (d, J = 13.0 Hz, 1H), 2.00 – 1.88 (m, 3H), 1.80 (br s, 2H), 1.44 – 1.25 (m, 2H) | ES-LCMS m/z 746.3 [M + H]+. |
| 398 | 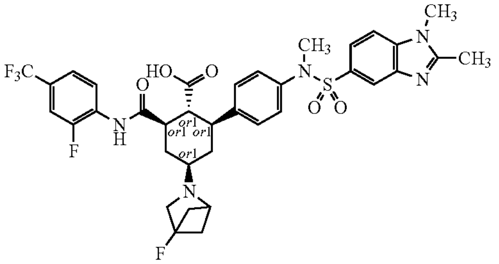 [SMILES: Cc1nc2cc(S(=O)(=O)N(C)c3ccc([C@H]4C[C@@H](N5CC6(F)CC5C6)C[C@@H](C(=O)Nc5ccc(C(F)(F)F)cc5F)[C@@H]4C(=O)O)cc3)ccc2n1C] rel-(1R,2R,4R,6S)-2-((2-fluoro-4-(trifluoromethyl)phenyl)carbamoyl)-4-(4-fluoro-2-azabicyclo[2.1.1]hexan-2-yl)-6-(4-((N,1,2-trimethyl-1H-benzo[d]imidazole)-5- | $^1$H NMR (400 MHz, DMSO-$d_6$) δ 10.26 (br s, 1H), 8.26 (t, J = 8.0 Hz, 1H), 7.72 (d, J = 9.0 Hz, 1H), 7.63 (d, J = 8.5 Hz, 1H), 7.57 – 7.47 (m, 2H), 7.29 – 7.13 (m, 3H), 6.95 (d, J = 8.5 Hz, 2H), 3.78 (s, 3H), 3.58 – 3.49 (m, 1H), 3.15 – 3.08 (m, 1H), 3.08 – 2.95 (m, 4H), 2.83 – 2.73 (m, 1H), 2.72 – 2.66 (m, 3H), 2.56 (s, 3H), 2.26 – 2.19 (m, 1H), 2.01 – 1.89 (m, 3H), 1.80 (br d, J = 1.0 Hz, 2H), 1.44 – 1.27 (m, 2H) | ES-LCMS m/z 746.3 [M + H]+. |

-continued

| Ex | Structure/Name | $^1$H NMR | LCMS |
|---|---|---|---|
| | sulfonamido)phenyl)cyclohexane-1-carboxylic acid | | |
| 399 | 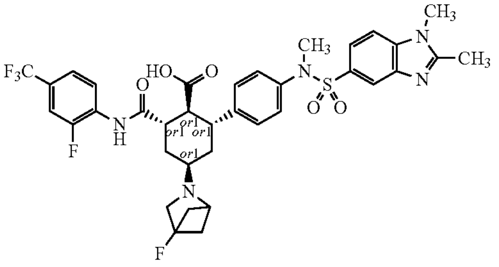 [SMILES: Cc1nc2cc(S(=O)(=O)N(C)c3ccc([C@@H]4C[C@@H](N5CC6(F)CC5C6)C[C@H](C(=O)Nc5ccc(C(F)(F)F)cc5F)[C@H]4C(=O)O)cc3)ccc2n1C] rel-(1R,2R,4S,6S)-2-((2-fluoro-4-(trifluoromethyl)phenyl)carbamoyl)-4-(4-fluoro-2-azabicyclo[2.1.1]hexan-2-yl)-6-(4-((N,1,2-trimethyl-1H-benzo[d]imidazole)-5-sulfonamido)phenyl)cyclohexane-1-carboxylic acid | $^1$H NMR (400 MHz, DMSO-$d_6$) δ 12.04 (br s, 1H), 10.12 (s, 1H), 8.07 (t, J = 8.3 Hz, 1H), 7.70 (dd, J = 10.8, 1.8 Hz, 1H), 7.63 (d, J = 8.5 Hz, 1H), 7.58 - 7.51 (m, 2H), 7.25 (dd, J = 8.5, 2.0 Hz, 1H), 7.19 (d, J = 8.5 Hz, 2H), 6.97 (d, J = 8.5 Hz, 2H), 3.78 (s, 3H), 3.65 - 3.56 (m, 1H), 3.43 - 3.32 (m, 2H), 3.24 - 3.14 (m, 1H), 3.05 (s, 3H), 2.87 - 2.73 (m, 3H), 2.56 (s, 3H), 2.07 - 1.98 (m, 3H), 1.93 - 1.66 (m, 5H) | ES-LCMS m/z 746.3 [M + H]+. |
| 400 | 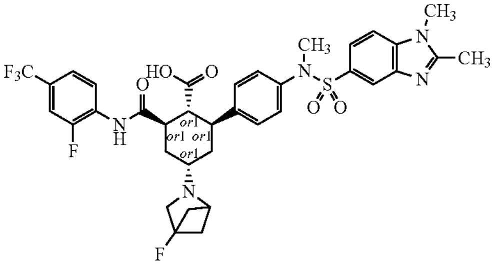 [SMILES: Cc1nc2cc(S(=O)(=O)N(C)c3ccc([C@H]4C[C@H](N5CC6(F)CC5C6)C[C@@H](C(=O)Nc5ccc(C(F)(F)F)cc5F)[C@@H]4C(=O)O)cc3)ccc2n1C] rel-(1R,2R,4S,6S)-2-((2-fluoro-4-(trifluoromethyl)phenyl)carbamoyl)-4-(4-fluoro-2-azabicyclo[2.1.1]hexan-2-yl)-6-(4-((N,1,2-trimethyl-1H-benzo[d]imidazole)-5-sulfonamido)phenyl)cyclohexane-1-carboxylic acid | $^1$H NMR (400 MHz, DMSO-$d_6$) δ 12.04 (br s, 1H), 10.12 (s, 1H), 8.07 (t, J = 8.0 Hz, 1H), 7.74 - 7.68 (m, 1H), 7.63 (d, J = 8.5 Hz, 1H), 7.58 - 7.51 (m, 2H), 7.25 (dd, J = 8.5, 2.0 Hz, 1H), 7.19 (d, J = 8.5 Hz, 2H), 6.97 (d, J = 8.5 Hz, 2H), 3.78 (s, 3H), 3.65 - 3.56 (m, 1H), 3.44 - 3.33 (m, 2H), 3.22 - 3.11 (m, 1H), 3.05 (s, 3H), 2.89 - 2.73 (m, 3H), 2.56 (s, 3H), 2.08 - 1.97 (m, 3H), 1.93 - 1.68 (m, 5H) | ES-LCMS m/z 746.3 [M + H]+. |

LIST OF SELECTED ABBREVIATIONS 4,4'-dtbbpy)$NiCl_2$+[4,4'-Bis(1,1-dimethylethyl)-2,2'-bipyridine]nickel (II) dichloride Aminosupersilane—N-(Adamantan-1-yl)-1,1,1,3,3,3-hexamethyl-2-(trimethylsilyl)trisilan-2-amine APhos Pd G3—palladium G3-(4-(N,N-Dimethylamino)phenyl)di-tert-butylphosphine, [4-(Di-tert-butylphosphino)-N,N-dimethylaniline-2-(2'-aminobiphenyl)]palladium(II) methanesulfonate DBU—1,8-diazabicyclo(5.4.0)undec-7-ene DCM—dichloromethane DMF—N,N-dimethylformamide dppf Pd G3—methanesulfonato 1,1-ferrocenediyl-bis(diphenylphosphino) (2'-amino-1,1'-biphenyl-2-yl) palladium(II)

EtOAc—ethyl acetate i-PrOH—isopropanol

IPAm—isopropylamine $[Ir(dtbbpy)(ppy)_2]PF_6$—[4,4'-Bis(1,1-dimethylethyl)-2,2'-bipyridine-N1,N1']bis[2-(2-pyridinyl-N)phenyl-C]iridium(II) hexafluorophosphate $K_2CO_3$—potassium carbonate MeCN—acetonitrile MeOH—methanol $Na_2CO_3$—sodium carbonate NaH—sodium hydride $NH_4Cl$—ammonium chloride NMI—N-methylimidazole $PdCl_2$(dppf)-DCM adduct—palladium chloride-1,1-ferrocenediyl-bis(diphenylphosphino)-dichloromethane adduct PE—petroleum ether TCFH—N,N,N',N'-tetramethylchloroformamidinium hexafluorophosphate TFA—trifluoroacetic acid THF—tetrahydrofuran TIPSOTf—Triisopropylsilyl trifluoromethanesulfonate TsOH—p-Toluenesulfonic acid

BIOLOGICAL EXAMPLES

Example A

Functional WRN unwinding activity can be measured using a fluorogenic plate based 384 well assay configured to measure the separation of labeled double stranded DNA substrate. Compounds were dosed out in neat DMSO with a 1:3 serial dilution scheme. 100 nL of compound was stamped into Greiner low volume black assay plates (Greiner Cat #784076) using the Echo Acoustic Dispenser to generate assay ready plates. All solutions were prepared in assay buffer (25 mM TRIS (pH8.0), 5 mM NaCl, 2 mM $MgCl_2$, 1 mM DTT, 0.05% BSA) for this 10 μL low volume reaction. To prepare the solutions, a 2×WRN Enzyme cocktail was made containing 200 pM of recombinant full-length WRN protein (1-1432). A 2× Substrate cocktail was made to consist of both 200 μM ATP (any ultrapure ATP sample) and 12 nM of the fluorescent quenched labeled double stranded DNA oligomer (IDT Custom synthesis; 5'-5IABkFQ (SEQ ID NO. 1)/GCA CTG GCC GTC GTT TTA CGG TCG TGA CT-3' (SEQ ID NO. 2): 5'-TTT TTT ACT TAA CGA CGG CCA GTG C (SEQ ID NO. 3)/36-TAMTSP/-3' (SEQ ID NO. 4)). To start the reaction, 5 μL of assay buffer was added to a single column to serve as the low control. Following this, 5 μL of 2×WRN Enzyme was added in all wells except the buffer low control wells. The reaction plate was covered and incubated at ambient temperature for 4 hours to allow for time dependent inhibition if it existed. After 4 hours, the addition of 5 μL of 2×-ATP/DNA substrate cocktail was added across all wells of the assay plate. This initiated the reaction, as the plate was incubated at ambient temperature for 60 minutes for the unwinding reaction to occur. A 10 mM EDTA solution was prepared and added at 5 μL across the entire plate after 60 minutes to quench the samples for an endpoint measurement. Fluorescent intensity was measured using excitation and emission wavelengths of 525 nm and 598 nm, respectively. High florescent intensity (DMSO with buffer) represents full inhibition of unwinding activity and low florescent intensity (DMSO with enzyme) represents no inhibition of unwinding activity. The potency of the compounds was determined using a four-parameter inhibition model to generate $pIC_{50}$, Hill Slope, maximum inhibition (see Table 2).

Example B

SW48 human colorectal cancer cells (MSI-H cancer cells) were obtained from the American Type Culture Collection and maintained in growth medium composed of RPMI-1640 supplemented with 10% fetal bovine serum. Cells were maintained in a humidified 5% CO2 incubator at 37° C. Cell dissociation was conducted using TrypLE Select to detach cells from culture flasks. Following dissociation, cells were centrifuged briefly and resuspended in assay medium RPMI-1640+10% fetal bovine serum. Black 384-well assay plates were prepared from source plates of DMSO and compounds dissolved in DMSO prior to cell dispensation. These source plates were prepared in eleven point, 3-fold serial dilutions from 10 mM stocks stored at 4° C. Compounds and DMSO controls were dispensed into assay plates at 150 nanoliters per well from source plates using Labcyte Echo 555 or Echo 655T dispensers with Column 6 and Column 18 containing DMSO only. Cells were then seeded into prepared assay plates in 50 microliters assay medium at 250 cells per well into Columns 1 thru 17 and Columns 19-24. Assay medium without cells was added to column 18 to serve as a surrogate for 100% cell cytotoxicity. Following incubation for 120 hours in a humidified 5% CO2 incubator at 37° C., cellular ATP concentration of each well was measured and used as a surrogate of cell viability. This was performed by adding 50 microliters of CellTiter-Glo reagent to each well followed by a 10-minute incubation at room temperature. Luminescence was measured on a Synergy Neo or Synergy Neo2 multimode plate reader. Compound cytotoxic response (% C) was normalized to the robust means of column 6 (Control 1, 0% Cytotoxicity) and column 18 (Control 2, 100% Cytotoxicity) and normalized % cytotoxicity (% C) calculated. % C=100−100*((Compound−Control 2)/(Control1−Control2)). These normalized data were then used to determine a 50% cytotoxic response (CC50) using 4-parameter logistic curve model 201 in Activity Base XE:

$$\text{Four (4) Parameter Logistic Model fit} = A + (B - A)/(1 + (10^{\wedge}C/x)^{\wedge}D),$$

where A=minimum asymptote (% cytotoxicity), B=maximum asymptote (% cytotoxicity), C=Log CC50 (pCC50), D=Hill slope, and x=[inhibitor], (M). WRN unwinding activity data and cell viability data are shown in Table 2.

TABLE 2

| Example No. | 4 hr UNW $pIC_{50}$ | SW48 $pCC_{50}$ |
|---|---|---|
| 1 | 6.0 | 5.0 |
| 2 | 5.9 | 4.9 |
| 3 | 8.4 | 5.0 |
| 4 | 6.0 | |
| 5 | 7.7 | |
| 6 | 8.2 | 5.0 |
| 7 | 7.0 | |
| 8 | 8.4 | 5.1 |
| 9 | 6.1 | 4.6 |
| 10 | 7.0 | 4.9 |
| 11 | 6.8 | 4.8 |
| 12 | 7.2 | |
| 13 | 7.2 | |
| 14 | 8.1 | 4.5 |
| 15 | 6.8 | 4.7 |
| 16 | 8.4 | 5.4 |
| 17 | 7.7 | |
| 18 | 8.3 | 4.9 |
| 19 | 6.5 | |
| 20 | 5.2 | |
| 21 | 5.1 | |
| 22 | 6.0 | |
| 23 | 6.9 | |
| 24 | 7.1 | 4.8 |
| 25 | 8.8 | 5.3 |
| 26 | 5.0 | |
| 27 | 7.9 | 5.4 |
| 28 | 7.5 | |
| 29 | 5.4 | |
| 30 | 5.2 | |
| 31 | 7.0 | 5.0 |
| 32 | 7.1 | 5.0 |
| 33 | 6.9 | |
| 34 | 5.6 | |
| 35 | 5.7 | 5.2 |
| 36 | 6.2 | 5.3 |
| 37 | 8.7 | 5.6 |
| 38 | 8.8 | |
| 39 | 5.7 | |
| 40 | 5.0 | |
| 41 | 8.3 | 5.4 |
| 42 | 6.0 | |
| 43 | 8.0 | |
| 44 | 5.2 | |
| 45 | 6.9 | |
| 46 | 7.5 | |
| 47 | 8.0 | |
| 48 | 7.8 | 5.3 |
| 49 | 6.0 | |
| 50 | 8.1 | |
| 51 | 8.0 | |
| 52 | 6.1 | |
| 53 | 7.8 | 5.1 |
| 54 | 8.3 | 5.1 |
| 55 | 8.6 | 5.0 |
| 56 | 8.8 | |
| 57 | 7.0 | |
| 58 | 7.5 | 4.8 |
| 59 | 6.1 | 4.5 |
| 60 | 5.6 | 4.5 |
| 61 | 5.5 | 4.5 |

TABLE 2-continued

| Example No. | 4 hr UNW $pIC_{50}$ | SW48 $pCC_{50}$ |
|---|---|---|
| 62 | 6.9 | |
| 63 | 5.8 | 4.5 |
| 64 | 7.6 | 4.8 |
| 65 | 7.3 | |
| 66 | 5.6 | |
| 67 | 5.7 | |
| 68 | 5.8 | |
| 69 | 5.2 | |
| 70 | 4.8 | |
| 71 | 4.0 | |
| 72 | 8.5 | |
| 73 | 8.9 | 5.4 |
| 74 | 6.6 | |
| 75 | 8.2 | 5.3 |
| 76 | 5.9 | |
| 77 | 8.4 | 5.4 |
| 78 | 8.7 | 6.0 |
| 79 | 6.3 | |
| 80 | 8.8 | 6.3 |
| 81 | 8.1 | 5.9 |
| 82 | 8.3 | 5.3 |
| 83 | 8.6 | 6.6 |
| 84 | 6.8 | 5.3 |
| 85 | 6.6 | |
| 86 | 8.8 | 5.6 |
| 87 | 6.5 | |
| 88 | 8.6 | 6.4 |
| 89 | 6.7 | 4.5 |
| 90 | 8.4 | 5.9 |
| 91 | 6.9 | |
| 92 | 8.8 | 6.1 |
| 93 | 8.6 | 5.6 |
| 94 | 7.3 | 5.4 |
| 95 | 8.6 | 5.5 |
| 96 | 9.3 | |
| 97 | 8.7 | 6.0 |
| 98 | 8.6 | 5.5 |
| 99 | 8.6 | 6.1 |
| 100 | 8.3 | 5.4 |
| 101 | 8.3 | 5.9 |
| 102 | 8.2 | 5.0 |
| 103 | 8.8 | 4.9 |
| 104 | 7.4 | 5.4 |
| 105 | 8.8 | |
| 106 | 8.5 | 5.8 |
| 107 | 8.3 | 6.1 |
| 108 | 8.5 | 5.7 |
| 109 | 9.0 | 5.9 |
| 110 | 8.4 | 5.9 |
| 111 | 8.6 | 5.8 |
| 112 | 8.6 | 6.1 |
| 113 | 8.8 | 6.2 |
| 114 | 8.1 | 5.6 |
| 115 | 8.3 | 5.9 |
| 116 | 8.8 | 6.3 |
| 117 | 7.2 | 5.4 |
| 118 | 8.7 | 5.9 |
| 119 | 8.8 | 6.0 |
| 120 | 8.0 | 5.5 |
| 121 | 8.5 | 6.5 |
| 122 | 8.1 | 6.0 |
| 123 | 8.4 | 6.3 |
| 124 | 8.4 | 6.3 |
| 125 | 8.7 | 5.8 |
| 126 | 8.2 | 6.2 |
| 127 | 8.4 | 6.0 |
| 128 | 8.4 | 6.0 |
| 129 | 7.7 | 6.2 |
| 130 | 8.2 | 6.3 |
| 131 | 8.2 | 5.4 |
| 132 | 7.9 | 6.2 |
| 133 | 8.4 | 4.9 |
| 134 | 8.1 | 4.9 |
| 135 | 8.6 | 5.6 |
| 136 | 7.4 | 5.5 |
| 137 | 6.6 | |
| 138 | 8.5 | 6.6 |

TABLE 2-continued

| Example No. | 4 hr UNW $pIC_{50}$ | SW48 $pCC_{50}$ |
|---|---|---|
| 139 | 8.8 | 7.0 |
| 140 | 8.6 | 6.8 |
| 141 | 8.5 | 6.2 |
| 142 | 5.7 | |
| 143 | 7.8 | |
| 144 | 7.3 | |
| 145 | 8.8 | 5.9 |
| 146 | 7.0 | |
| 147 | 7.1 | 4.9 |
| 148 | 8.9 | 6.7 |
| 149 | 8.8 | 6.7 |
| 150 | 5.4 | 4.5 |
| 151 | 8.5 | 6.3 |
| 152 | 8.0 | 5.7 |
| 153 | 5.5 | 4.5 |
| 154 | 8.4 | 6.4 |
| 155 | 6.1 | |
| 156 | 6.9 | 4.6 |
| 157 | 8.6 | 6.9 |
| 158 | 7.5 | 5.4 |
| 159 | 8.6 | 6.7 |
| 160 | 7.3 | 4.8 |
| 161 | 8.6 | 6.1 |
| 162 | 8.7 | 5.5 |
| 163 | 7.7 | |
| 164 | 8.9 | 5.6 |
| 165 | 7.6 | 4.6 |
| 166 | 8.1 | 5.6 |
| 167 | 8.3 | 4.7 |
| 168 | 8.6 | 6.2 |
| 169 | 5.1 | |
| 170 | 7.1 | |
| 171 | 8.5 | 6.1 |
| 172 | 8.4 | 5.9 |
| 173 | 8.3 | 6.2 |
| 174 | 7.7 | 5.0 |
| 175 | 8.5 | 5.8 |
| 176 | 8.9 | 5.9 |
| 177 | 8.8 | 5.8 |
| 178 | 5.3 | |
| 179 | 8.6 | 6.0 |
| 180 | 8.4 | 6.2 |
| 181 | 8.8 | 5.7 |
| 182 | 8.6 | 5.8 |
| 183 | 8.2 | 4.5 |
| 184 | 6.2 | 4.5 |
| 185 | 7.2 | 4.5 |
| 186 | 5.5 | 4.5 |
| 187 | 8.2 | 5.4 |
| 188 | 8.6 | 5.6 |
| 189 | 6.4 | 4.5 |
| 190 | 8.8 | 5.4 |
| 191 | 6.4 | |
| 192 | 4.4 | 4.5 |
| 193 | 4.7 | 4.5 |
| 194 | 8.1 | 5.0 |
| 195 | 7.7 | |
| 196 | 8.5 | 5.8 |
| 197 | 5.6 | 4.5 |
| 198 | 8.3 | 4.5 |
| 199 | 8.6 | 6.3 |
| 200 | 7.9 | |
| 201 | 4.6 | |
| 202 | 4.0 | |
| 203 | | |
| 204 | | |
| 205 | 7.6 | |
| 206 | 7.8 | 5.4 |
| 207 | 8.8 | 5.1 |
| 208 | 8.8 | 5.9 |
| 209 | 5.7 | |
| 210 | 5.7 | 4.9 |
| 211 | 8.7 | 5.5 |
| 212 | 8.8 | 5.7 |
| 213 | 7.4 | 4.5 |
| 214 | 7.2 | |
| 215 | 7.1 | 4.7 |

TABLE 2-continued

| Example No. | 4 hr UNW $pIC_{50}$ | SW48 $pCC_{50}$ |
|---|---|---|
| 216 | 8.3 | 4.9 |
| 217 | 6.9 | 5.0 |
| 218 | 7.4 | 4.8 |
| 219 | 8.3 | 5.2 |
| 220 | 6.5 | 4.8 |
| 221 | 8.4 | 5.7 |
| 222 | 6.3 | 4.5 |
| 223 | 6.8 | 4.5 |
| 224 | 8.9 | 6.3 |
| 225 | 9.6 | 5.1 |
| 227 | 7.1 | 4.8 |
| 228 | 5.2 | |
| 229 | 6.5 | |
| 230 | 7.0 | 5.1 |
| 231 | 6.5 | |
| 232 | 8.8 | 5.9 |
| 233 | 7.9 | 5.3 |
| 234 | 6.0 | |
| 235 | 8.7 | 6.6 |
| 236 | 6.2 | 5.1 |
| 237 | 6.7 | |
| 238 | 8.4 | 5.7 |
| 239 | 6.6 | 4.5 |
| 240 | 5.4 | |
| 241 | 8.3 | 5.9 |
| 242 | 6.1 | |
| 243 | 5.3 | |
| 244 | | |
| 245 | 8.1 | 5.1 |
| 246 | 6.9 | 4.5 |
| 247 | 7.1 | 4.5 |
| 248 | 8.5 | 5.4 |
| 249 | 8.8 | 4.5 |
| 250 | 8.2 | 6.5 |
| 251 | 9.0 | 6.3 |
| 252 | 7.2 | 4.5 |
| 253 | 8.7 | |
| 254 | 7.6 | 5.0 |
| 255 | 6.8 | 5.1 |
| 256 | 8.9 | 5.2 |
| 257 | 6.6 | 4.5 |
| 258 | 6.2 | |
| 259 | 9.2 | 5.4 |
| 260 | 8.7 | 5.8 |
| 261 | 8.8 | 6.0 |
| 262 | 8.8 | 6.0 |
| 263 | 8.8 | 6.7 |
| 264 | | |
| 265 | 8.2 | 6.1 |
| 266 | 8.9 | 6.4 |
| 267 | 9.0 | 6.1 |
| 268 | 9.1 | 4.8 |
| 269 | 9.1 | 5.6 |
| 270 | 9.0 | 6.5 |
| 271 | 8.8 | 7.1 |
| 272 | 8.8 | 6.8 |
| 273 | 8.3 | 5.1 |
| 274 | 7.8 | 4.8 |
| 275 | 8.7 | 5.3 |
| 276 | 8.2 | |
| 277 | 9.2 | 5.8 |
| 278 | 9.2 | 6.9 |
| 279 | 8.7 | 6.9 |
| 280 | | |
| 281 | 8.8 | 6.1 |
| 282 | 8.8 | 7.2 |
| 283 | 6.2 | 4.7 |
| 284 | 8.5 | 6.7 |
| 285 | 7.5 | 5.2 |
| 286 | 7.0 | 4.9 |
| 287 | 8.8 | 6.4 |
| 288 | 8.3 | 6.0 |
| 289 | 8.8 | 5.0 |
| 290 | 8.8 | 6.4 |
| 291 | 7.5 | 4.9 |
| 292 | 8.8 | 6.1 |
| 293 | 7.5 | 4.5 |

TABLE 2-continued

| Example No. | 4 hr UNW $pIC_{50}$ | SW48 $pCC_{50}$ |
|---|---|---|
| 294 | 8.8 | 5.2 |
| 295 | 8.8 | 5.8 |
| 296 | 8.8 | 5.8 |
| 297 | 5.6 | 4.5 |
| 298 | 6.3 | 5.0 |
| 299 | 7.2 | 4.5 |
| 300 | 8.8 | 4.9 |
| 301 | 8.8 | 5.4 |
| 302 | 6.9 | 4.5 |
| 303 | 5.4 | 4.6 |
| 304 | 7.8 | 4.9 |
| 305 | 6.5 | |
| 306 | 8.3 | 7.0 |
| 307 | 6.2 | 4.5 |
| 308 | 8.8 | 4.5 |
| 309 | 6.7 | 4.5 |
| 310 | 8.8 | 5.8 |
| 311 | 8.6 | 6.6 |
| 312 | 6.8 | 4.9 |
| 313 | 6.6 | 4.7 |
| 314 | 8.8 | 6.8 |
| 315 | 7.2 | 5.0 |
| 316 | 8.8 | 6.8 |
| 317 | 8.8 | 7.1 |
| 318 | 6.7 | 4.9 |
| 319 | 6.5 | 4.9 |
| 320 | 8.4 | 7.1 |
| 321 | 8.8 | 6.7 |
| 322 | 7.7 | 5.0 |
| 323 | 8.8 | 7.0 |
| 324 | 7.2 | 5.1 |
| 325 | 8.7 | 6.7 |
| 326 | 6.2 | 4.5 |
| 327 | 8.6 | 6.7 |
| 328 | 6.9 | 4.8 |
| 329 | 8.8 | 7.2 |
| 330 | 8.3 | 6.4 |
| 331 | 6.6 | 4.7 |
| 332 | 8.4 | 7.0 |
| 333 | 6.9 | 5.0 |
| 334 | 8.8 | 6.6 |
| 335 | 5.6 | |
| 336 | 8.8 | 5.5 |
| 337 | 8.8 | 6.8 |
| 338 | 7.1 | 4.8 |
| 339 | 6.2 | |
| 340 | 8.1 | 5.1 |
| 341 | 5.1 | 4.5 |
| 342 | | 5.2 |
| 343 | 7.0 | 5.3 |
| 344 | 8.3 | 6.9 |
| 345 | 6.4 | 4.9 |
| 346 | 5.4 | 5.0 |
| 347 | 8.0 | 5.2 |
| 348 | 8.8 | 6.4 |
| 349 | 6.6 | 4.9 |
| 350 | 8.8 | 7.2 |
| 351 | | 5.0 |
| 352 | 8.4 | 5.4 |
| 353 | 8.8 | 7.4 |
| 354 | 5.8 | 4.7 |
| 355 | 8.4 | 7.0 |
| 356 | 7.9 | 5.9 |
| 357 | 8.0 | 6.0 |
| 358 | | 6.2 |
| 359 | 5.8 | 4.9 |
| 360 | 8.3 | 7.2 |
| 361 | 8.8 | 6.3 |
| 362 | 5.8 | 5.0 |
| 363 | 8.5 | 7.1 |
| 364 | 6.2 | 5.0 |
| 365 | 8.5 | 6.4 |
| 366 | 6.9 | 4.8 |
| 367 | 8.8 | 7.1 |
| 368 | 8.3 | 6.1 |
| 369 | 6.2 | 4.9 |
| 370 | | |

TABLE 2-continued

| Example No. | 4 hr UNW $pIC_{50}$ | SW48 $pCC_{50}$ |
|---|---|---|
| 371 | 8.2 | 6.0 |
| 372 | 8.8 | 6.7 |
| 373 | 8.8 | 7.0 |
| 374 | 8.4 | 6.4 |
| 375 | 7.0 | 4.7 |
| 376 | 8.6 | 7.1 |
| 377 | 8.3 | 6.9 |
| 378 | 7.3 | 5.4 |
| 379 | 6.3 | 4.7 |
| 380 | 7.4 | 5.0 |
| 381 | 7.1 | 5.1 |
| 382 | 8.8 | 7.2 |
| 383 | 8.1 | 5.1 |
| 384 | 6.4 | 4.6 |
| 385 | 5.9 | 4.5 |
| 386 | 8.4 | 5.7 |
| 387 | 7.2 | 5.0 |
| 388 | 8.4 | |
| 389 | 8.3 | 5.6 |
| 390 | 8.2 | 5.7 |
| 391 | | 4.7 |
| 392 | 8.8 | 6.6 |
| 393 | 6.6 | 4.5 |
| 394 | 6.3 | 4.5 |
| 395 | 8.8 | 6.0 |
| 396 | 8.8 | 6.2 |
| 397 | 8.8 | 6.5 |
| 398 | 7.0 | 4.6 |
| 399 | 4.9 | 4.5 |
| 400 | 7.7 | 5.1 |

Example C

It was observed that the compounds of the present disclosure are bound to cell assay media to various degrees, which would affect the cellular potency analysis in Example B. To measure free drug potency, concentrations used in the cell assays were corrected with the measured free fraction determined in the cell assay media. Compounds were incubated in a rapid equilibrium dialysis (RED) at a nominal concentration of 1 μM, using a dialysis buffer of phosphate-buffered saline (PBS, 100 mM sodium phosphate+150 mM sodium chloride, pH 7.4). The test compound was spiked into the medium. Aliquots were added to the donor wells of a RED plate in triplicate, and blank PBS was added to each receiver well, at volumes recommended by the manufacturer. Plates were incubated with shaking at 200 rpm for 4 hours at 37° C. The resultant samples were analysed by LC-MS/MS using a specific and sensitive method. Results were reported as analyte:internal standard peak area ratios (PARs), and the percent unbound was calculated with the following equation:

$$\%\,\text{Unbound} = 100\times((1/D))/\{[(1/\text{Apparent } F_u))-1]+1/D\},$$

where D=the matrix dilution factor (D=1 for media); Apparent $F_u=C_{rec}/C_{don}$; $C_{rec}$=PAR in receiver samples; $C_{don}$=PAR in donor samples.

Percent stability was calculated by:

$$\%\,\text{Stability} = 100\times C_{final}/C_{initial},$$

where $C_{final}$=PAR in the T=240 minute sample; $C_{initial}$=PAR in the T=0 minute sample. Cell culture media unbound percentage and calculated free drug potency of selected compounds along with their measured potency from Example B are shown in Table 3.

TABLE 3

| Example No. | SW48 $pCC_{50}$ | Cell Culture Media Binding (% unbound) | Free Drug SW48 $pCC_{50}$ |
|---|---|---|---|
| 16 | 5.4 | 4.99 | 6.70 |
| 82 | 5.3 | 1.47 | 7.13 |
| 83 | 6.6 | 6.5 | 7.89 |
| 88 | 6.4 | 2.97 | 7.93 |
| 90 | 5.9 | 5.53 | 7.16 |
| 94 | 5.4 | 0.14 | 8.25 |
| 97 | 6.0 | 24.06 | 6.62 |
| 99 | 6.1 | 2.14 | 7.77 |
| 101 | 5.9 | 3.49 | 7.36 |
| 107 | 6.1 | 2.45 | 7.71 |
| 109 | 5.9 | 8.29 | 6.98 |
| 110 | 5.9 | 0.85 | 7.97 |
| 112 | 6.1 | 4.05 | 7.49 |
| 113 | 6.2 | 8.99 | 7.25 |
| 116 | 6.3 | 28.6 | 6.84 |
| 117 | 5.4 | 0.11 | 8.36 |
| 119 | 6.0 | 23.07 | 6.64 |
| 120 | 5.5 | 1.07 | 7.47 |
| 121 | 6.5 | 1.95 | 8.21 |
| 122 | 6.0 | 0.56 | 8.25 |
| 123 | 6.3 | 0.71 | 8.45 |
| 124 | 6.3 | 9.7 | 7.31 |
| 125 | 5.8 | 4.33 | 7.16 |
| 126 | 6.2 | 5.8 | 7.44 |
| 127 | 6.0 | 4.43 | 7.35 |
| 128 | 6.0 | 4.52 | 7.34 |
| 129 | 6.2 | 1.43 | 8.04 |
| 130 | 6.3 | 3.26 | 7.79 |
| 132 | 6.2 | 3.49 | 7.66 |
| 138 | 6.6 | 6.7 | 7.77 |
| 139 | 7.0 | 5.18 | 8.29 |
| 140 | 6.8 | 10.1 | 7.80 |
| 141 | 6.2 | 11.2 | 7.15 |
| 148 | 6.7 | 12.92 | 7.59 |
| 151 | 6.3 | 2.33 | 7.93 |
| 154 | 6.4 | 1.27 | 8.30 |
| 157 | 6.9 | 24.2 | 7.50 |
| 158 | 5.4 | 23.6 | 6.03 |
| 159 | 6.7 | 9.91 | 7.70 |
| 161 | 6.1 | 4.81 | 7.42 |
| 168 | 6.2 | 5.85 | 7.43 |
| 171 | 6.1 | 6.34 | 7.30 |
| 172 | 5.9 | 17.55 | 6.66 |
| 173 | 6.2 | 1.63 | 7.99 |
| 177 | 5.8 | 23.7 | 6.43 |
| 179 | 6.0 | 14.55 | 6.84 |
| 180 | 6.2 | 3.57 | 7.65 |
| 181 | 5.7 | 30.27 | 6.22 |
| 194 | 5.0 | 11.36 | 5.94 |
| 196 | 5.8 | 6.06 | 7.02 |
| 199 | 6.3 | 16 | 7.10 |
| 206 | 5.4 | 0.32 | 7.89 |
| 207 | 5.1 | 1.38 | 6.96 |
| 208 | 5.9 | 2.89 | 7.44 |
| 211 | 5.5 | 2.08 | 7.18 |
| 212 | 5.7 | 2.05 | 7.39 |
| 219 | 5.2 | 0.31 | 7.71 |
| 221 | 5.7 | 4.11 | 7.09 |
| 224 | 6.3 | 3.55 | 7.75 |
| 235 | 6.6 | 3.32 | 8.08 |
| 245 | 5.1 | 9.71 | 6.11 |
| 250 | 6.5 | 2.7 | 8.07 |
| 251 | 6.3 | 27.4 | 6.86 |
| 254 | 5.0 | 23.4 | 5.63 |
| 255 | 5.1 | 43.9 | 5.46 |
| 256 | 5.2 | 28.4 | 5.75 |
| 261 | 6.0 | 31.11 | 6.51 |
| 262 | 6.0 | 24.15 | 6.62 |
| 263 | 6.7 | 27.76 | 7.26 |

TABLE 3-continued

| Example No. | SW48 $pCC_{50}$ | Cell Culture Media Binding (% unbound) | Free Drug SW48 $pCC_{50}$ |
|---|---|---|---|
| 265 | 6.1 | 11.54 | 7.04 |
| 266 | 6.4 | 14.14 | 7.25 |
| 267 | 6.1 | 22.63 | 6.75 |
| 269 | 5.6 | 25.65 | 6.19 |
| 270 | 6.5 | 20.71 | 7.18 |
| 271 | 7.1 | 22.38 | 7.75 |
| 272 | 6.8 | 23.6 | 7.43 |
| 273 | 5.1 | 0.82 | 7.19 |
| 275 | 5.3 | 0.83 | 7.38 |
| 277 | 5.8 | 19.7 | 6.51 |
| 278 | 6.9 | 20.8 | 7.58 |
| 279 | 6.9 | 7.9 | 8.00 |
| 281 | 6.1 | 14.8 | 6.93 |
| 284 | 6.7 | 6.8 | 7.87 |
| 285 | 5.2 | 54.9 | 5.46 |
| 287 | 6.4 | 15.6 | 7.21 |
| 288 | 6.0 | 2.14 | 7.67 |
| 289 | 5.0 | 41.2 | 5.39 |
| 290 | 6.4 | 41.1 | 6.79 |
| 292 | 6.1 | 22.3 | 6.75 |
| 294 | 5.2 | 25.6 | 5.79 |
| 295 | 5.8 | 11.8 | 6.73 |
| 296 | 5.8 | 9.79 | 6.81 |
| 298 | 5.0 | 15.1 | 5.82 |
| 301 | 5.4 | 40.6 | 5.79 |
| 306 | 7.0 | 10.3 | 7.99 |
| 310 | 5.8 | 27.3 | 6.36 |
| 311 | 6.6 | 8.56 | 7.67 |
| 314 | 6.8 | 7.95 | 7.90 |
| 315 | 5.0 | 38.4 | 5.42 |
| 316 | 6.8 | 19 | 7.52 |
| 317 | 7.1 | 15 | 7.92 |
| 320 | 7.1 | 11.2 | 8.05 |
| 321 | 6.7 | 16 | 7.50 |
| 322 | 5.0 | 36.2 | 5.44 |
| 323 | 7.0 | 14.4 | 7.84 |
| 324 | 5.1 | 31.8 | 5.60 |
| 325 | 6.7 | 8.62 | 7.76 |
| 327 | 6.7 | 29.6 | 7.23 |
| 329 | 7.2 | 20.5 | 7.89 |
| 330 | 6.4 | 10.2 | 7.39 |
| 332 | 7.0 | 12.2 | 7.91 |
| 333 | 5.0 | 32.6 | 5.49 |
| 334 | 6.6 | 18.3 | 7.34 |
| 336 | 5.5 | 4.91 | 6.81 |
| 337 | 6.8 | 22.4 | 7.45 |
| 340 | 5.1 | 12.9 | 5.99 |
| 342 | 5.2 | 6.23 | 6.41 |
| 343 | 5.3 | 23.7 | 5.93 |
| 344 | 6.9 | 11.8 | 7.83 |
| 346 | 5.0 | 41.9 | 5.38 |
| 347 | 5.2 | 10.7 | 6.17 |
| 350 | 7.2 | 21.8 | 7.86 |
| 352 | 5.4 | 2.8 | 6.95 |
| 353 | 7.4 | 11.3 | 8.35 |
| 355 | 7.0 | 12.8 | 7.89 |
| 360 | 7.2 | 9.42 | 8.23 |
| 361 | 6.3 | 6.32 | 7.50 |
| 362 | 5.0 | 16.9 | 5.77 |
| 363 | 7.1 | 21.6 | 7.77 |
| 364 | 5.0 | 11.3 | 5.95 |
| 365 | 6.4 | 6.58 | 7.58 |
| 367 | 7.1 | 14.5 | 7.94 |
| 368 | 6.1 | 12.8 | 6.99 |
| 372 | 6.7 | 20.8 | 7.38 |
| 373 | 7.0 | 17.5 | 7.76 |
| 374 | 6.4 | 11.3 | 7.35 |
| 376 | 7.1 | 25.0 | 7.70 |
| 377 | 6.9 | 7.1 | 8.05 |
| 378 | 5.4 | 20.8 | 6.08 |
| 380 | 5.0 | 3.34 | 6.48 |
| 381 | 5.1 | 30.8 | 5.61 |
| 382 | 7.2 | 13.6 | 8.07 |
| 383 | 5.1 | 5.89 | 6.33 |
| 386 | 5.7 | 10 | 6.70 |
| 389 | 5.6 | 23.5 | 6.23 |

TABLE 3-continued

| Example No. | SW48 $pCC_{50}$ | Cell Culture Media Binding (% unbound) | Free Drug SW48 $pCC_{50}$ |
|---|---|---|---|
| 390 | 5.7 | 16.3 | 6.49 |
| 392 | 6.6 | 9.93 | 7.60 |
| 395 | 6.0 | 8.75 | 7.06 |
| 396 | 6.2 | 7.17 | 7.34 |
| 397 | 6.5 | 5.27 | 7.78 |
| 400 | 5.1 | 4.9 | 6.41 |

Example D

In Viva Efficacy Study of Test Compounds in Mouse Model Bearing SW48 Human Colorectal Cancer Cell Line Xenografts Experiments were performed with female Crl:Nu-Foxn1$^{nu}$ nude mice. Animals were housed under optimized hygienic condition with food and water at libitum and a 12 h:12 h light:dark cycle. Animals were allowed to acclimatize for at least 4 days before being enrolled in the experimental design.

SW48 human colorectal cancer cells (RRID:CVCL1724) were obtained from ATCC. The cells were cultured in RPMI 1640 with 10% Fetal Bovine Serum at 37° C. in atmosphere of 5% $CO_2$ in air. To establish SW48 xenografts, cells were harvested and resuspended in serum free RPM11640 and Matrigel before inoculation and 5×10^6 SW48 tumor cells were injected subcutaneously in 100 μL volume using 27G1/2 needle. Cells were inoculated in the right hind flank of the animals.

Post cell inoculation, tumor growth was monitored daily, and animals were randomized into treatment groups (n=10/group) once the tumor volume reached an appropriate size (80-150 $mm^3$). Throughout the treatment period, both tumor volume and body weight were measured approximately twice a week. The tumor size, in $mm^3$, was computed using the formula: 0.5×L×W^2, where W=width and L=length of the tumor. To prepare a test compound for oral administration, between 30-120 mg of the test compound was dissolved in a vehicle solution consisting of 0.5% Methycellulose (cp 400) and 0.5% Tween 80. The compound was freshly prepared one hour prior to daily administration. If turbidity was observed, the solution was vortexed at over 2000 rpm for 10 minutes and mixed with a 1 mL syringe. The resulting solution formulation was utilized for in vivo studies.

Animals received either a vehicle or test compounds at dosage of 30 or 100 mg/kg daily through oral gavage (10 ml/kg). Body weight was measured twice a week using the Ohaus electronic scale (STX421) and the data was automatically added to the study log. Moreover, daily clinical observations were performed to closely monitor the animals. Tumor growth inhibition was computed using the following formula:

$$\text{Mean \% } \Delta \text{ Inhinition} = [(\text{Mean}(C) - \text{Mean}(C_0)) - (\text{Mean}(T) - \text{Mean}(T_0))] / (\text{Mean}(C) - \text{Mean}(C_0)) * 100\%,$$

where T=current group value; $T_0$=Current group initial value; C=Control group Value; $C_0$=control group initial value.

Data of tumor volume were exported and analyzed in GraphPad Prism (9.5). The analysis included a two-way ANOVA test, comparing the vehicle control vs. treatments at different time points, followed by a Tukey HSD post hoc test.

The calculation of tumor regression was conducted as per the following formula:

$$\text{Tumor Regression} = (\Delta\ \text{tumor volume}/\text{tumor volume at Day 0}) * 100,$$

where Day 0=treatment start day; Δ tumor volume=mean tumor volume on the evaluation day—mean tumor volume Day 0.

Treatment commenced using the compound of Example 138 at a dosage of 30 mpk, which was administered orally once a day when the average tumor volume reached 117.6 $mm^3$ (n=10/group). The course of treatment with Example 138 lasted for 21 days, after which its overall efficacy was evaluated based on changes in tumor volume, as illustrated in FIG. 1. On the 21st day, a mean tumor regression of −74.26% was observed.

Figure 2:
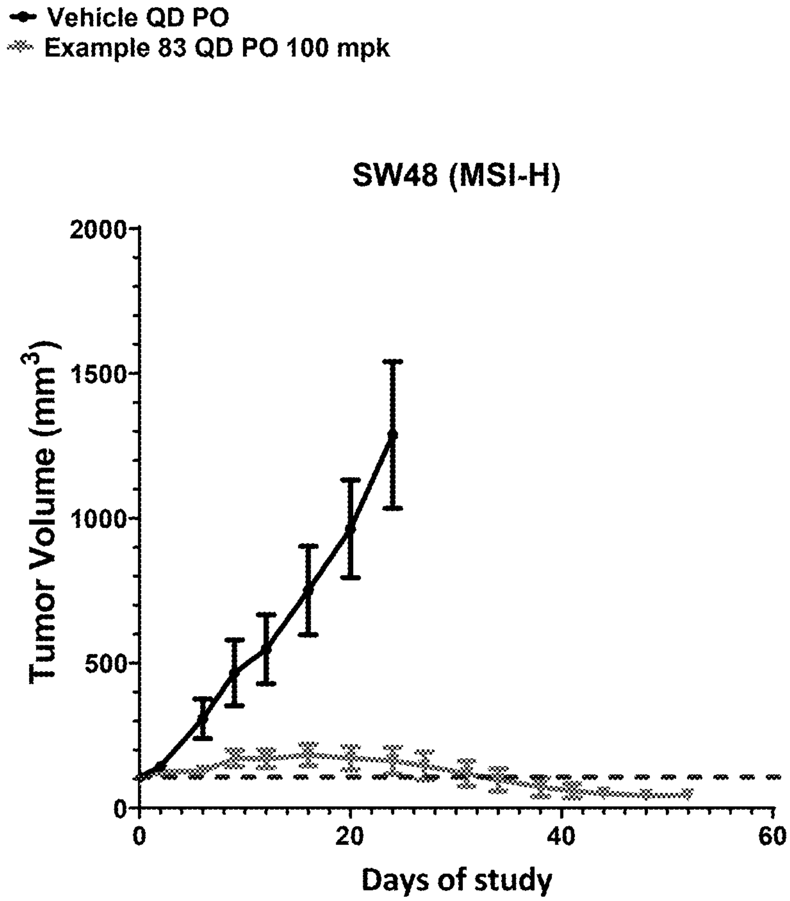
FIG. 2 shows an efficacy study of the compound of Example 83 in mouse model bearing SW48 human colorectal cancer cell line xenografts.
Figure 3:
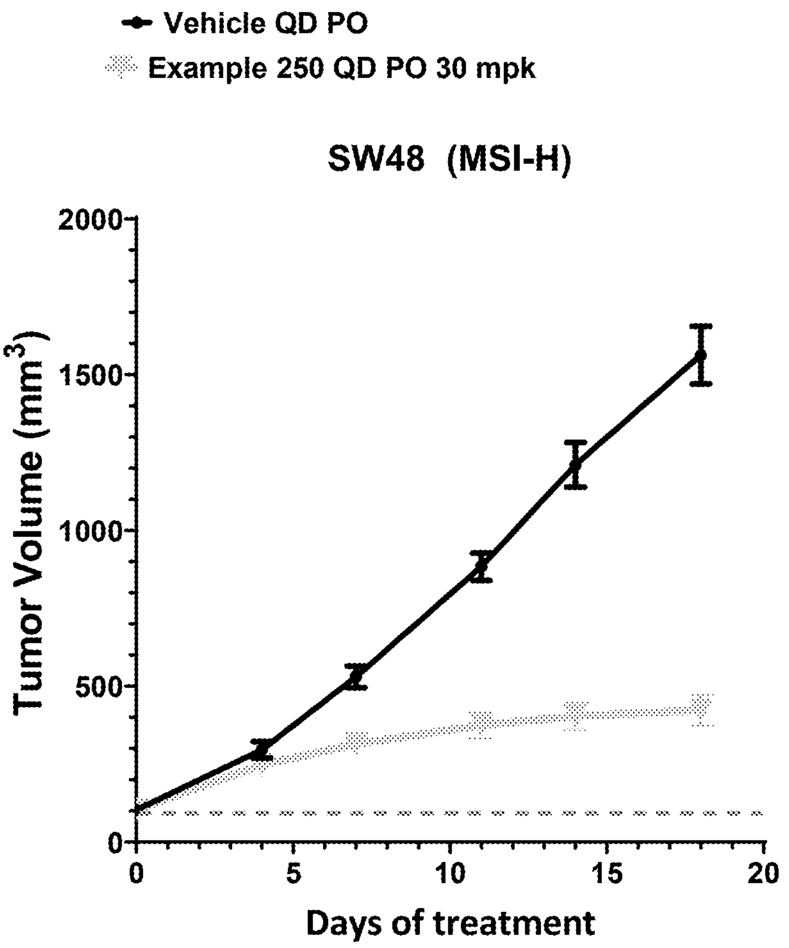
FIG. 3 shows an efficacy study of the compound of Example 250 in mouse model bearing SW48 human colorectal cancer cell line xenografts.

The efficacy data associated with the compound of Example 83 is depicted in FIG. 2. Treatment was initiated with a daily oral administration of the compound at a dosage of 100 mpk, once the average tumor volume reached 97.2 $mm^3$ (n=10/group). By the 55th day, a significant mean tumor regression of −24.01% was observed in the SW48 tumor. The efficacy data for the compound of Example 250 is depicted in FIG. 3. Daily oral administration of the compound at a dosage of 30 mpk was initiated when the average tumor volume reached 103.18 $mm^3$ (n=10/group). By the 21st day, a significant tumor growth inhibition of 72.95% compared to the vehicle control was observed in the SW48 tumors ($p<0.0001$).

Figure 4:
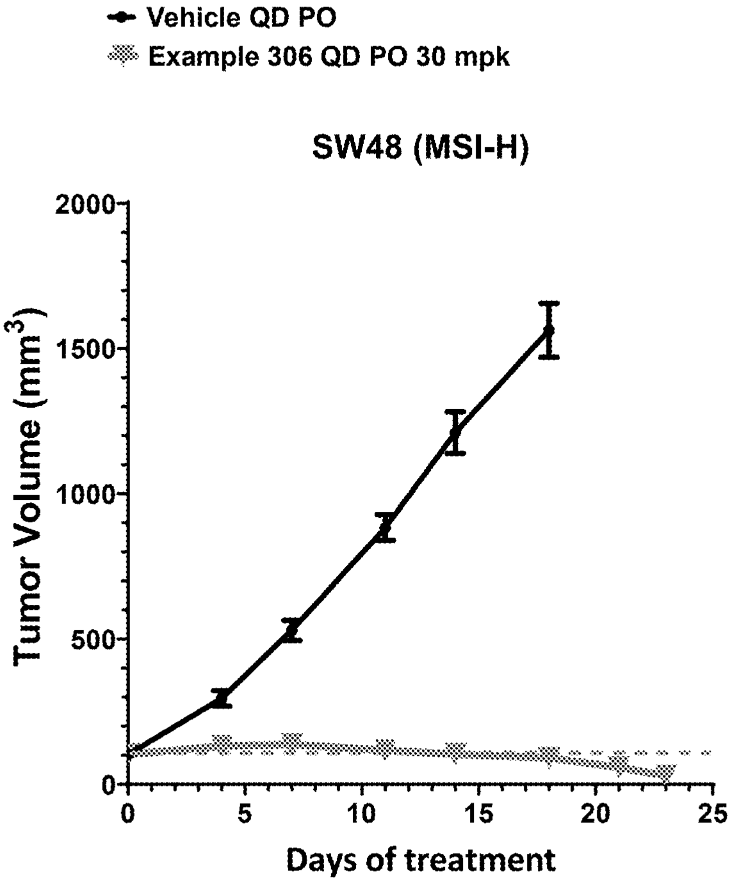
FIG. 4 shows an efficacy study of the compound of Example 306 in mouse model bearing SW48 human colorectal cancer cell line xenografts.

The efficacy data for the compound of Example 306 is depicted in FIG. 4. Daily oral administration of the compound at a dosage of 30 mpk was initiated when the average tumor volume was 103.13 $mm^3$ (n=10/group). By the 23rd day, a significant mean tumor regression of −73.2% was observed in the SW48 tumor.

All patent applications, patents, and printed publications cited herein are incorporated herein by reference in the entireties, except for any definitions, subject matter disclaimers or disavowals, and except to the extent that the incorporated material is inconsistent with the express disclosure herein, in which case the language in this disclosure controls.

EMBODIMENTS OF THE INVENTION

1. A compound of Formula (I-aa):

(I-aa)

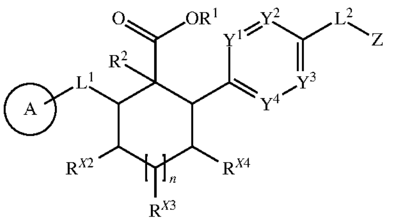

wherein:

ring A is aryl, heteroaryl, $C_{3-10}$ cycloalkyl, or 3- to 10-membered heterocycloalkyl ring containing one, two, or three heteroatoms independently selected from N, O, and S, wherein ring A is mono- or bicyclic and ring A is optionally substituted with up to three substituents independently selected from halo, cyano, nitro, hydroxy, $—NR^aR^b$, carboxy, $—CONR^aR^b$, $C_{1-3}$ alkyl, $C_{1-3}$ alkoxy, halo($C_{1-3}$)alkyl, halo($C_{1-3}$)alkoxy, hydroxy($C_{1-3}$)alkyl, cyano($C_{1-3}$)alkyl, $C_{1-3}$ alkylsulfonyl, —C(O)O($C_{1-4}$)alkyl, and $C_{3-7}$ cycloalkyl;

$L^1$ is $—NR^o—C(O)—$, $—OCH_2—$, $—NR^o—CH_2—$, or $—CH_2—$;

n is 0, 1, or 2;

$R^1$ is hydrogen or $C_{1-3}$ alkyl;

$R^2$ is hydrogen, halo, or $C_{1-3}$ alkyl;

$R^{X2}$, $R^{X3}$, and $R^{X4}$ are each independently selected from hydrogen, halo, $—NR^dR^e$, hydroxy, carboxy, phenoxy, phenyl, $C_{1-3}$ alkyl, halo($C_{1-3}$)alkyl, hydroxy($C_{1-3}$)alkyl, methoxy($C_{1-3}$)alkyl, $C_{1-3}$ alkoxy, and halo($C_{1-3}$)alkoxy, wherein $C_{1-3}$ alkoxy is optionally substituted with $C_{3-7}$ cycloalkyl; or any two of $R^{X2}$, $R^{X3}$, or $R^{X4}$ taken together with the carbon atoms to which they are attached form a 5- or 6-membered ring which optionally contains one or two heteroatoms independently selected from N, O, and S;

$Y^1$, $Y^2$, $Y^3$, and $Y^4$ are each independently N or CRY, and at most two of $Y^1$, $Y^2$, $Y^3$, and $Y^4$ are N;

$L^2$ is a bond, $—NR—S(O)_2—$, —NR—C(O)—, or $—(CH_2)_p—$;

Z is hydrogen, halo, cyano, hydroxy, $—NR^gR^h$, nitro, carboxy, $C_{1-3}$ alkyl, $C_{1-3}$alkoxy, halo($C_{1-3}$)alkyl, halo ($C_{1-3}$)alkoxy, hydroxy($C_{1-3}$)alkyl, cyano($C_{1-3}$)alkyl, $C_{2-5}$ alkenyl, halo($C_{2-5}$)alkenyl, $C_{2-5}$ alkynyl, or halo ($C_{2-5}$)alkynyl; or Z is ring B, wherein ring B is aryl, heteroaryl, $C_{3-10}$ cycloalkyl, or 3- to 10-membered heterocycloalkyl ring containing one, two, or three heteroatoms independently selected from N, O, and S, wherein ring B is mono- or bicyclic and ring B is optionally substituted with up to three substituents independently selected from halo, cyano, nitro, hydroxy, carboxy, $C_{1-3}$alkyl, $C_{1-3}$ alkoxy, halo($C_{1-3}$)alkyl, halo($C_{1-3}$)alkoxy, hydroxy($C_{1-3}$)alkyl, $C_{2-5}$ alkenyl, $C_{2-5}$ alkynyl, $—C_{1-3}$ alkylene-$NR^gR^h$, $—CONR^gR^h$, $—NR^gR^h$, $—NR^gC(O)R^h$, $SO_2NR^gR^h$, and $L^B$-W, or two substituents of ring B taken together with the atoms to which they are attached form a 5- or 6-membered ring which optionally contains one or two heteroatoms independently selected from N, O, and S;

$L^B$ is independently selected from a bond, $—(CH_2)_p—$, $—CH_2O—$, —C(O)—NH—, —C(O)—, and $—CH_2C(O)NH—$;

W is independently selected from hydrogen, $C_{1-3}$ alkyl, —O($C_{1-4}$)alkyl, $C_{3-7}$ cycloalkyl, 5- or 6-membered heteroaryl, and 4- to 6-membered heterocycloalkyl ring containing one, two, or three heteroatoms independently selected from N, O, and S, wherein W is optionally substituted with up to three substituents independently selected from halo, cyano, nitro, hydroxy, $—NR^mR^n$, carboxy, $—CONR^mR^n$, $C_{1-3}$ alkyl, $C_{1-3}$ alkoxy, halo($C_{1-3}$)alkyl, halo($C_{1-3}$)alkoxy, hydroxy($C_{1-3}$)alkyl, cyano($C_{1-3}$)alkyl, sulfonyl($C_{1-3}$) alkyl, —C(O)O($C_{1-4}$)alkyl, and $C_{3-7}$ cycloalkyl;

each $R^y$ is independently hydrogen, halo, cyano, nitro, hydroxy, $—NR^jR^k$, carboxy, $C_{1-3}$ alkyl, halo($C_{1-3}$)alkyl, hydroxy($C_{1-3}$)alkyl, cyano($C_{1-3}$)alkyl, $C_{1-3}$ alkoxy, halo($C_{1-3}$)alkoxy, methoxy($C_{1-3}$)alkoxy, $C_{2-5}$ alkenyl, halo($C_{2-5}$)alkenyl, hydroxy($C_{2-5}$)alkenyl, $C_{2-5}$ alkynyl, halo($C_{2-5}$)alkynyl, hydroxy($C_{2-5}$)alkynyl, or 5- or 6-membered heteroaryl containing one, two, or three heteroatoms independently selected from N, O, and S, wherein the heteroaryl is optionally substituted with up to three $C_{1-3}$ alkyl; or $R^y$ and $R^f$ taken together with the atoms to which they are attached form a 5- or 6-membered ring which contains one or two heteroatoms independently selected from N, O, and S;

each p is independently 1 or 2; and $R^a$, $R^b$, $R^c$, $R^d$, $R^e$, $R^f$, $R^g$, $R^h$, $R^i$, $R^k$, $R^m$, and $R^n$ are each independently hydrogen, $C_{1-3}$ alkyl, or $C_{3-7}$ cycloalkyl;

or a pharmaceutically acceptable salt thereof.

2. A compound of embodiment 1 or a pharmaceutically acceptable salt thereof, wherein ring A is phenyl, 2-azaspiro[3.3]heptyl, tetrahydropyranyl, pyridinyl, bicyclo[1.1.1]pentyl, cyclohexyl, spiro[4.5]decyl, (3as,6as)-octahydropentalenyl, bicyclo[2.2.1]heptyl, or 2,3-dihydroindenyl, wherein ring A is optionally substituted with up to three substituents independently selected from halo, cyano, nitro, hydroxy, —$NR^aR^b$, carboxy, —$CONR^aR^b$, $C_{1-3}$ alkyl, $C_{1-3}$ alkoxy, halo($C_{1-3}$)alkyl, halo($C_{1-3}$)alkoxy, hydroxy($C_{1-3}$)alkyl, cyano($C_{1-3}$)alkyl, sulfonyl($C_{1-3}$)alkyl, —C(O)O($C_{1-4}$)alkyl, and $C_{3-7}$ cycloalkyl.

3. A compound of embodiment 1 or embodiment 2 or a pharmaceutically acceptable salt thereof, wherein ring A is phenyl, bicyclo[1.1.1]pentyl, or cyclohexyl, wherein ring A is optionally substituted with up to three substituents independently selected from halo, cyano, nitro, hydroxy, —$NR^aR^b$, carboxy, —$CONR^aR^b$, $C_{1-3}$alkyl, $C_{1-3}$alkoxy, halo($C_{1-3}$)alkyl, halo($C_{1-3}$)alkoxy, hydroxy($C_{1-3}$)alkyl, cyano($C_{1-3}$)alkyl, sulfonyl($C_{1-3}$)alkyl, —C(O)O($C_{1-4}$)alkyl, and $C_{3-7}$ cycloalkyl.

4. A compound of any one of the preceding embodiments or a pharmaceutically acceptable salt thereof, wherein ring A is optionally substituted with up to three substituents independently selected from halo, hydroxy, $C_{1-3}$ alkyl, halo($C_{1-3}$)alkyl, hydroxy($C_{1-3}$)alkyl, and $C_{3-7}$ cycloalkyl.

5. A compound of any one of the preceding embodiments or a pharmaceutically acceptable salt thereof, wherein ring A is phenyl, optionally substituted with one or two substituents independently selected from halo, hydroxy, $C_{1-3}$ alkyl, and halo($C_{1-3}$)alkyl.

6. A compound of any one of the preceding embodiments or a pharmaceutically acceptable salt thereof, wherein ring A is phenyl substituted with fluoro and trifluoromethyl.

7. A compound of any one of the preceding embodiments or a pharmaceutically acceptable salt thereof, wherein $L^1$ is —$NR^c$—C(O)—or —$OCH_2$—.

8. A compound of any one of the preceding embodiments or a pharmaceutically acceptable salt thereof, wherein $L^1$ is —NH—C(O)—.

9. A compound of any one of the preceding embodiments or a pharmaceutically acceptable salt thereof, wherein n is 1.

10. A compound of any one of the preceding embodiments or a pharmaceutically acceptable salt thereof, wherein $R^1$ is hydrogen.

11. A compound of any one of the preceding embodiments or a pharmaceutically acceptable salt thereof, wherein $R^2$ is hydrogen.

12. A compound of any one of the preceding embodiments or a pharmaceutically acceptable salt thereof, wherein $L^2$ is —$NR^f$—$S(O)_2$—.

13. A compound of any one of the preceding embodiments or a pharmaceutically acceptable salt thereof, wherein $L^2$ is —$N(CH_3)$—$S(O)_2$—.

14. A compound of any one of the preceding embodiments or a pharmaceutically acceptable salt thereof, wherein $R^{X2}$, $R^{X3}$, and $R^{X4}$ are each independently selected from hydrogen, —$NR^dR^e$, hydroxy, phenoxy, $C_{1-3}$ alkyl, methoxy($C_{1-3}$)alkyl, halo($C_{1-3}$)alkoxy, and $C_{1-3}$ alkoxy, wherein $C_{1-3}$ alkoxy is optionally substituted with $C_{3-7}$ cycloalkyl; or $R^{X2}$ and $R^{X3}$ taken together with the carbon atoms to which they are attached form a 5-membered ring which optionally contains one O.

15. A compound of any one of the preceding embodiments, wherein $R^{X2}$, $R^{X3}$, and $R^{X4}$ are each independently selected from hydrogen and $C_{1-3}$ alkoxy.

16. A compound of any one of the preceding embodiments, wherein $R^{X2}$ and $R^{X4}$ are hydrogen and $R^{X3}$ is selected from $C_{1-3}$ alkoxy and hydrogen.

17. A compound of any one of the preceding embodiments, wherein $R^{X2}$, $R^{X3}$, and $R^{X4}$ are hydrogen.

18. A compound of any one of the preceding embodiments or a pharmaceutically acceptable salt thereof, wherein $Y^1$, $Y^2$, $Y^3$, and $Y^4$ are CRY.

19. A compound of any one of the preceding embodiments or a pharmaceutically acceptable salt thereof, wherein each $R^y$ is independently selected from hydrogen, halo, cyano, $C_{1-3}$ alkoxy, methoxy($C_{1-3}$)alkoxy, hydroxy($C_{2-5}$)alkyl, hydroxy($C_{2-5}$)alkynyl, $C_{2-5}$ alkynyl, and a 5-membered heteroaryl containing up to three heteroatoms independently selected from N, O, and S, wherein the 5-membered heteroaryl is optionally substituted with up to three $C_{1-3}$ alkyl; or $R^y$ and $R^f$ taken together with the atoms to which they are attached form a 6-membered ring which optionally contains an oxygen atom.

20. A compound of any one of the preceding embodiments or a pharmaceutically acceptable salt thereof, wherein each $R^y$ is hydrogen.

21. A compound of any one of the preceding embodiments or a pharmaceutically acceptable salt thereof, wherein Z is halo, halo($C_{1-3}$)alkyl, $C_{2-5}$ alkenyl, halo($C_{2-5}$)alkenyl, or $C_{2-5}$ alkynyl.

22. A compound of any one of embodiments 1 to 21, wherein Z is ring B, wherein ring B is phenyl, benzimidazolyl, 3-azabicycloheptyl, 1,2,3,4-tetrahydroisoquinolinyl, 1,2,3,4-tetrahydroquinoxalinyl, 1,3,4-thiadiazolyl, 1,3-dihydroisobenzofuranyl, indazolyl, indolyl, 1-oxa-6-azaspirooctyl, 2,3-dihydrobenzofuranyl, 2,5-dihydrofuranyl, 2,5-dihydrothienyl 1,1-dioxide, 3,4-dihydrobenzooxazinyl, 3,4-dihydropyranyl, imidazopyridinyl, 1,2,4-triazolyl, 5,6,7,8-tetrahydropyridopyridazinyl, 5,6-dihydropyrrolopyrazolyl, 6-oxaspirooctyl, benzothienyl, benzoisothiazolyl, benzooxazolyl-2-one, benzooxazolyl, benzothiazolyl, benzofuranyl, cyclohexyl, cyclopentyl, cyclopropyl, furanyl, furopyridazinyl, imidazopyridazinyl, imidazolidinyl-2-one, indolinyl, isoquinolinyl, isothiazolyl, isoxazolyl, oxepanyl, oxetyl, piperidinyl, pyrazolyl, pyridazinyl, pyridinyl, pyrimidinyl, tetrahydrofuranyl, tetrahydrothienyl 1,1-dioxide, tetrazolopyridazinyl, thiazolyl, thienopyrimidinyl, thienopyridinyl, or thienyl, wherein ring B is optionally substituted with up to three substituents independently selected from halo, cyano, nitro, hydroxy, carboxy, $C_{1-3}$alkyl, $C_{1-3}$alkoxy, halo($C_{1-3}$)alkyl, halo($C_{1-3}$)alkoxy, hydroxy($C_{1-3}$)alkyl, $C_{2-5}$ alkenyl, $C_{2-5}$ alkynyl, —$C_{1-3}$alkylene-$NR^gR^h$, —$CONR^gR^h$, —$NR^gR^h$, —$NR^gC(O)R^h$, $SO_2NR^gR^h$, and $L^B$-W, or two substituents of ring B taken together with the atoms to which they are attached form a 5- or 6-membered ring which optionally contains one or two heteroatoms independently selected from N, O, and S.

23. A compound of any one of the preceding embodiments or a pharmaceutically acceptable salt thereof, wherein ring B is optionally substituted with up to three substituents independently selected from halo, cyano, hydroxy, $C_{1-3}$ alkyl, $C_{1-3}$ alkoxy, halo($C_{1-3}$)alkyl, hydroxy($C_{1-3}$)alkyl, $C_{2-5}$ alkenyl, —$C_{1-3}$alkylene-$NR^gR^h$, —$NR^gR^h$, —$NR^gC(O)R^h$, $SO_2NR^gR^h$, and $L^B$-W, or two substituents of ring B taken together with the atoms to which they are attached form a 5- or 6-membered ring which optionally contains one or two heteroatoms independently selected from N, O, and S;

$L^B$ is independently selected from a bond, —$(CH_2)_p$—, —$CH_2O$—, —C(O)—, and —$CH_2C(O)NH$—;

W is independently selected from hydrogen, $C_{1-3}$ alkyl, —O($C_{1-4}$)alkyl, $C_{3-7}$ cycloalkyl, 5- or 6-membered heteroaryl, and 4- to 6-membered heterocycloalkyl ring containing one, two, or three heteroatoms independently selected from N, O, and S, wherein W is optionally substituted with up to three substituents independently selected from halo, $C_{1-3}$ alkyl, and —C(O)O($C_{1-4}$)alkyl;

p is 1; and $R^g$ and $R^h$ are each independently hydrogen or $C_{1-3}$ alkyl.

24. A compound of embodiment 22 or a pharmaceutically acceptable salt thereof, wherein Z is ring B, wherein ring B is phenyl, benzimidazolyl, 1,2,3,4-tetrahydroisoquinolinyl, 1,2,3,4-tetrahydroquinoxalinyl, 1,3,4-thiadiazolyl, 1,3-dihydroisobenzofuranyl, indazolyl, indolyl, 2,3-dihydrobenzofuranyl, 2,5-dihydrofuranyl, 2,5-dihydrothienyl 1,1-dioxide, 3,4-dihydrobenzooxazinyl, 3,4-dihydropyranyl, imidazopyridinyl, 1,2,4-triazolyl, 5,6-dihydropyrrolopyrazolyl, 6-oxaspirooctyl, benzoisothiazolyl, benzooxazolyl-2-one, benzooxazolyl, benzothiazolyl, benzofuranyl, cyclohexyl, cyclopentyl, furanyl, furopyridazinyl, imidazopyridazinyl, indolinyl, isothiazolyl, isoxazolyl, oxepanyl, piperidinyl, pyrazolyl, pyridazinyl, pyridinyl, pyrimidinyl, tetrahydrothienyl 1,1-dioxide, thiazolyl, orthienyl, wherein ring B is optionally substituted with up to three substituents independently selected from halo, cyano, nitro, hydroxy, carboxy, $C_{1-3}$ alkyl, $C_{1-3}$ alkoxy, halo($C_{1-3}$)alkyl, halo($C_{1-3}$)alkoxy, hydroxy($C_{1-3}$)alkyl, $C_{2-5}$alkenyl, $C_{2-5}$alkynyl, —$C_{1-3}$alkylene-$NR^gR^h$, —$CONR^gR^h$, —$NR^gR^h$, —$NR^gC(O)R^h$, —$SO_2NR^gR^h$, and $L^B$-W; and $R^g$ and $R^h$ are each independently hydrogen or $C_{1-3}$ alkyl.

25. A compound of any one of the preceding embodiments or a pharmaceutically acceptable salt thereof, wherein ring B is benzimidazolyl optionally substituted with up to three substituents independently selected from halo, $C_{1-3}$ alkyl, $C_{3-7}$ cycloalkyl, —$C_{1-3}$ alkylene-$NR^gR^h$, —$NR^gR^h$ and a 4- to 6-membered heterocycloalkyl ring containing one or two heteroatoms independently selected from N, O, and S, wherein the heterocycloalkyl ring is optionally substituted with $C_{1-3}$ alkyl; and wherein $R^g$ and $R^h$ are each independently hydrogen or $C_{1-3}$ alkyl.

26. A compound of any one of the preceding embodiments having the structure of Formula (I-b):

(I-b)

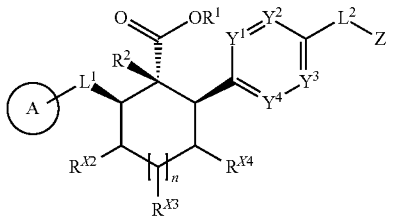

or a pharmaceutically acceptable salt thereof.

27. A compound of embodiment 1, having the structure of Formula (II):

(II)

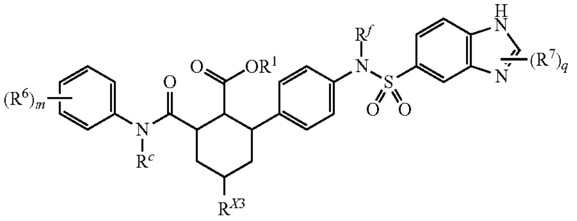

wherein:

m is an integer from 1 to 3;

q is an integer from 1 to 3;

each $R^6$ is independently selected from halo, cyano, nitro, hydroxy, —$NR^aR^b$, carboxy, —$CONR^aR^b$, $C_{1-3}$ alkyl, $C_{1-3}$ alkoxy, halo($C_{1-3}$)alkyl, halo($C_{1-3}$)alkoxy, hydroxy($C_{1-3}$)alkyl, cyano($C_{1-3}$)alkyl, sulfonyl($C_{1-3}$)alkyl, —C(O)O($C_{1-4}$)alkyl, and $C_{3-7}$ cycloalkyl; each $R^7$ is independently selected from halo, cyano, nitro, hydroxy, carboxy, $C_{1-3}$alkyl, $C_{1-3}$ alkoxy, halo($C_{1-3}$)alkyl, halo($C_{1-3}$)alkoxy, hydroxy($C_{1-3}$)alkyl, $C_{2-5}$ alkenyl, $C_{2-5}$ alkynyl, —$C_{1-3}$ alkylene-$NR^gR^h$, —$CONR^gR^h$, —$NR^gR^h$, —$NR^gC(O)R^h$, $SO_2NR^gR^h$, and $L^B$-W, or two $R^7$ taken together with the atoms to which they are attached form a 5- or 6-membered ring which optionally contains one or two heteroatoms independently selected from N, O, and S;

$L^B$ is independently selected from a bond, —$(CH_2)_p$—, —$CH_2O$—, —C(O)—NH—, —C(O)—, and —$CH_2C(O)NH$—;

W is independently selected from hydrogen, $C_{1-3}$ alkyl, —O($C_{1-4}$)alkyl, $C_{3-7}$ cycloalkyl, 5- or 6-membered heteroaryl, and 4- to 6-membered heterocycloalkyl ring containing one, two, or three heteroatoms independently selected from N, O, and S, wherein W is optionally substituted with up to three substituents independently selected from halo, cyano, nitro, hydroxy, —$NR^mR^n$, carboxy, —$CONR^mR^n$, $C_{1-3}$ alkyl, $C_{1-3}$ alkoxy, halo($C_{1-3}$)alkyl, halo($C_{1-3}$)alkoxy, hydroxy($C_{1-3}$)alkyl, cyano($C_{1-3}$)alkyl, sulfonyl($C_{1-3}$)alkyl, —C(O)O($C_{1-4}$)alkyl, and $C_{3-7}$ cycloalkyl;

p is 1 or 2;

$R^a$, $R^b$, $R^g$, $R^h$, $R^m$, and $R^n$ are each independently hydrogen, $C_{1-3}$ alkyl, or $C_{3-7}$ cycloalkyl;

$R^1$ is hydrogen or $C_{1-3}$ alkyl;

$R^{X3}$ is hydrogen or $C_{1-3}$ alkoxy; and $R^c$ and $R^f$ are each independently hydrogen, $C_{1-3}$ alkyl, or $C_{3-7}$ cycloalkyl;

or a pharmaceutically acceptable salt thereof.

28. A compound of embodiment 27 or a pharmaceutically acceptable salt thereof, wherein:

each $R^6$ is independently selected from halo, hydroxy, $C_{1-3}$ alkyl, and halo($C_{1-3}$)alkyl;

each $R^7$ is independently selected from halo, $C_{1-3}$alkyl, $—C_{1-3}$alkylene-$NR^gR^h$, $—NR^gR^h$ and $L^B$-W;

$L^B$ is a bond;

W is independently selected from $C_{3-7}$ cycloalkyl and 4- to 6-membered heterocycloalkyl ring containing one, two, or three heteroatoms independently selected from N, O, and S, wherein W is optionally substituted with $C_{1-3}$ alkyl; and $R^g$ and $R^h$ are each independently hydrogen or $C_{1-3}$ alkyl.

29. A compound of embodiments 27 or 28, having the structure of Formula (II-a):

(II-a)

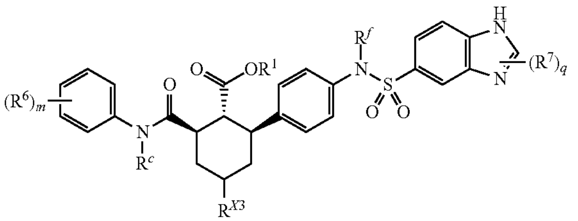

or a pharmaceutically acceptable salt thereof.

30. A compound of embodiment 29 or a pharmaceutically acceptable salt thereof, wherein m is 2;

q is 2;

$R^1$ is hydrogen;

$R^c$ is hydrogen;

$R^f$ is methyl;

$R^6$ is selected from trifluoromethyl and fluoro;

$R^7$ is methyl.

31. A compound or a pharmaceutically acceptable salt thereof selected from the compounds of Table 1.

32. A compound which is

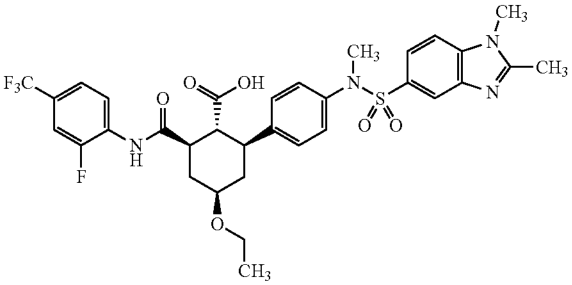

or a pharmaceutically acceptable salt thereof.

33. A compound which is

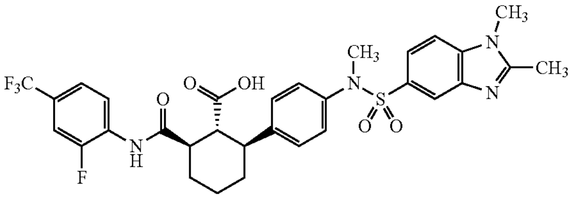 [SMILES: Cc1nc2cc(S(=O)(=O)N(C)c3ccc([C@H]4CCC[C@@H](C(=O)Nc5ccc(C(F)(F)F)cc5F)[C@@H]4C(=O)O)cc3)ccc2n1C]

or a pharmaceutically acceptable salt thereof.

34. A pharmaceutical composition comprising a compound or pharmaceutically acceptable salt thereof of any one of the preceding embodiments and a pharmaceutically acceptable excipient.

35. A compound or pharmaceutically acceptable salt thereof of any one of embodiments 1 to 33 or a pharmaceutical composition of embodiment 34, for use in therapy.

36. A compound or pharmaceutically acceptable salt thereof of any one of embodiments 1 to 33 or a pharmaceutical composition of embodiment 34, for use in the treatment of cancer.

37. A method of treatment of cancer in a subject in need thereof comprising administering to said subject a therapeutically effective amount of a compound or pharmaceutically acceptable salt thereof of any one of embodiments 1 to 33 or a pharmaceutical composition of embodiment 34.

38. A method of treatment of cancer of embodiment 37, wherein the cancer is characterised by MSI-H and/or dMMR.

39. A method of treatment of cancer of embodiment 37, wherein the cancer is treatable by inhibition of WRN.

40. Use of a compound or pharmaceutically acceptable salt thereof of any one of embodiments 1 to 33 or a pharmaceutical composition of embodiment 34, in the manufacture of a medicament for use in the treatment of cancer.

SEQUENCE LISTING

```
Sequence total quantity: 4
SEQ ID NO: 1           moltype = AA  length = 5
FEATURE                Location/Qualifiers
REGION                 1..5
                       note = IDT Custom synthesis
source                 1..5
                       mol_type = protein
                       organism = synthetic construct
SEQUENCE: 1
```

-continued

| | | |
|---|---|---|
| IABFQ | | 5 |
| SEQ ID NO: 2 | moltype = DNA length = 29 | |
| FEATURE | Location/Qualifiers | |
| misc_feature | 1..29 | |
| | note = IDT Custom synthesis | |
| source | 1..29 | |
| | mol_type = other DNA | |
| | organism = synthetic construct | |
| SEQUENCE: 2 | | |
| gcactggccg tcgttttacg gtcgtgact | | 29 |
| SEQ ID NO: 3 | moltype = DNA length = 25 | |
| FEATURE | Location/Qualifiers | |
| misc_feature | 1..25 | |
| | note = IDT Custom synthesis | |
| source | 1..25 | |
| | mol_type = other DNA | |
| | organism = synthetic construct | |
| SEQUENCE: 3 | | |
| tttttactt aacgacggcc agtgc | | 25 |
| SEQ ID NO: 4 | moltype = AA length = 6 | |
| FEATURE | Location/Qualifiers | |
| REGION | 1..6 | |
| | note = IDT Custom synthesis | |
| source | 1..6 | |
| | mol_type = protein | |
| | organism = synthetic construct | |
| SEQUENCE: 4 | | |
| TAMTSP | | 6 |

What is claimed:

1. A compound which is selected from the group consisting of:

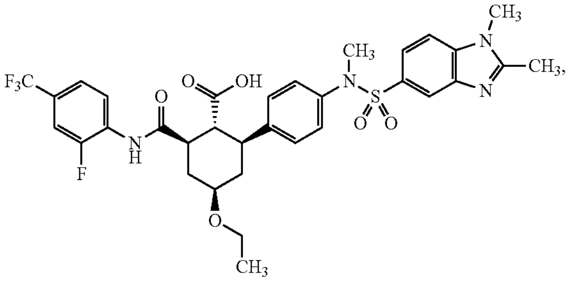

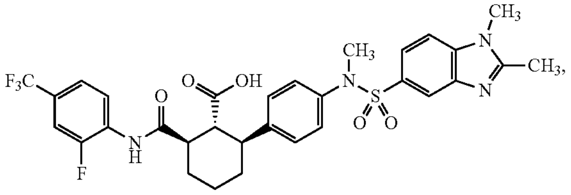 [SMILES: Cc1nc2cc(S(=O)(=O)N(C)c3ccc([C@H]4CCC[C@@H](C(=O)Nc5ccc(C(F)(F)F)cc5F)[C@@H]4C(=O)O)cc3)ccc2n1C]

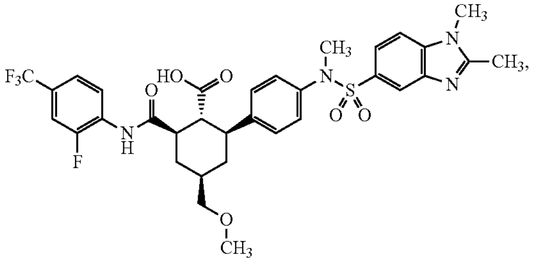

and

-continued

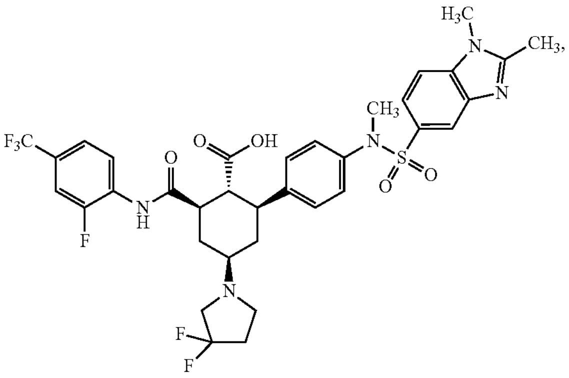

or a pharmaceutically acceptable salt thereof.

2. A compound which is selected from the group consisting of

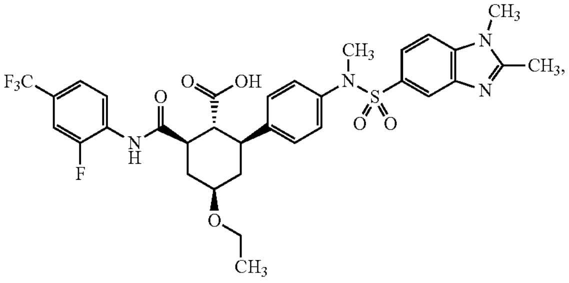

-continued

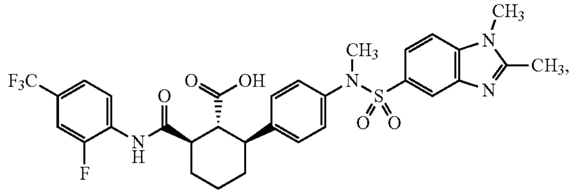 [SMILES: Cc1nc2cc(S(=O)(=O)N(C)c3ccc([C@H]4CCC[C@@H](C(=O)Nc5ccc(C(F)(F)F)cc5F)[C@@H]4C(=O)O)cc3)ccc2n1C]

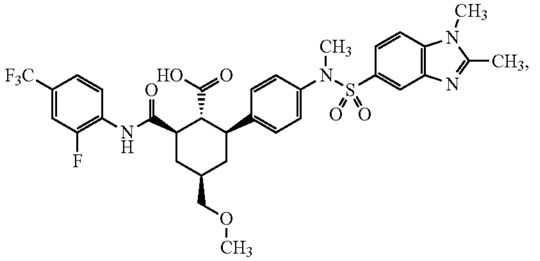

and

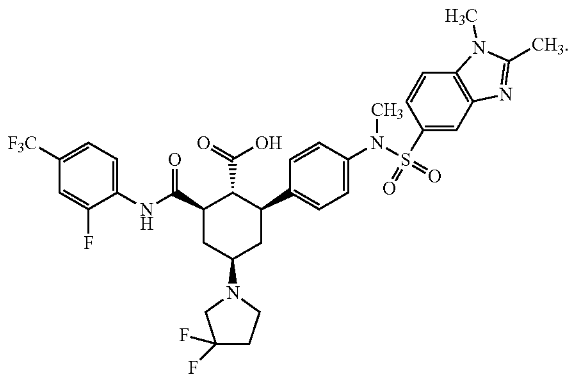 [SMILES: Cc1nc2cc(S(=O)(=O)N(C)c3ccc([C@H]4C[C@@H](N5CCC(F)(F)C5)C[C@@H](C(=O)Nc5ccc(C(F)(F)F)cc5F)[C@@H]4C(=O)O)cc3)ccc2n1C]

3. A compound

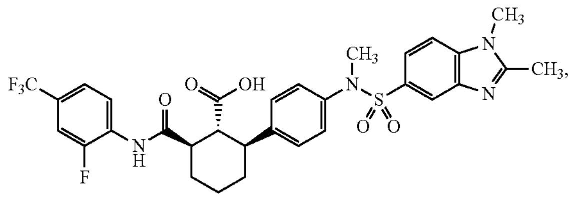

or a pharmaceutically acceptable salt thereof.

4. A compound

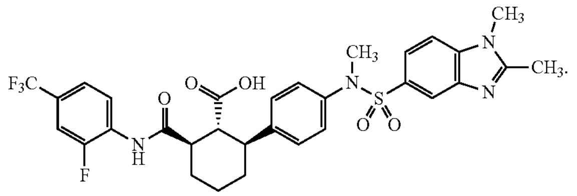

5. A compound

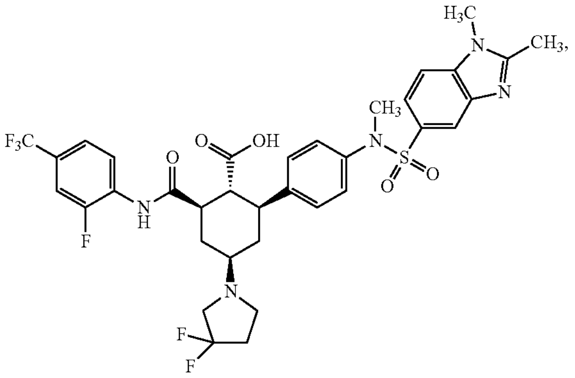

or a pharmaceutically acceptable salt thereof.

6. A compound

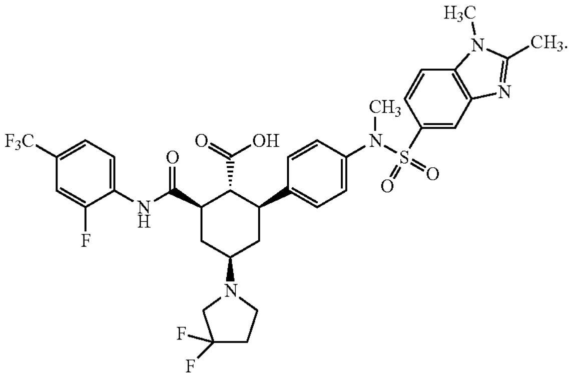 [SMILES: Cc1nc2cc(S(=O)(=O)N(C)c3ccc([C@H]4C[C@@H](N5CCC(F)(F)C5)C[C@@H](C(=O)Nc5ccc(C(F)(F)F)cc5F)[C@@H]4C(=O)O)cc3)ccc2n1C]

7. A pharmaceutical composition comprising a compound or pharmaceutically acceptable salt thereof of claim 1 and a pharmaceutically acceptable excipient.

8. A pharmaceutical composition comprising a compound or pharmaceutically acceptable salt thereof of claim 3 and a pharmaceutically acceptable excipient.

9. A pharmaceutical composition comprising a compound or pharmaceutically acceptable salt thereof of claim 5 and a pharmaceutically acceptable excipient.

10. A method of treatment of colorectal cancer in a human subject in need thereof comprising administering to said human subject a therapeutically effective amount of a compound or pharmaceutically acceptable salt thereof of claim 1.

11. A method of treatment of colorectal cancer in a human subject in need thereof comprising administering to said human subject a therapeutically effective amount of a pharmaceutical composition of claim 7.

12. A method of treatment of colorectal cancer in a human subject in need thereof comprising administering to said human subject a therapeutically effective amount of a compound or pharmaceutically acceptable salt thereof of claim 3.

13. A method of treatment of colorectal cancer of claim 10, wherein the cancer is characterised by MSI-H and/or dMMR.

14. A method of treatment of colorectal cancer of claim 12, wherein the cancer is characterised by MSI-H and/or dMMR.

* * * * *